United States Patent
Chen et al.

(10) Patent No.: US 7,186,564 B2
(45) Date of Patent: Mar. 6, 2007

(54) POLYNUCLEOTIDES ENCODING NOVEL CYSTEINE PROTEASES OF THE CALPAIN SUPERFAMILY, CAN-12V1 AND CAN-12V2.

(75) Inventors: Jian Chen, Princeton, NJ (US); Thomas C. Nelson, Lawrenceville, NJ (US); Roy J. Vaz, North Branch, NJ (US); Franck Duclos, Washington Crossing, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/116,519

(22) Filed: Apr. 3, 2002

(65) Prior Publication Data

US 2003/0114373 A1   Jun. 19, 2003

Related U.S. Application Data

(60) Provisional application No. 60/300,620, filed on Jun. 25, 2001, provisional application No. 60/296,180, filed on Jun. 6, 2001, provisional application No. 60/288,768, filed on May 4, 2001, provisional application No. 60/281,253, filed on Apr. 3, 2001.

(51) Int. Cl.
C12N 15/57    (2006.01)
C12N 9/64     (2006.01)
C12N 15/74    (2006.01)
C12N 15/79    (2006.01)

(52) U.S. Cl. ............... 436/23.2; 435/69.1; 435/226; 435/252.3; 435/320.1

(58) Field of Classification Search ............. 435/69.1, 435/226, 252.3, 320.1, 69.7, 471; 536/23.2, 536/23.4
See application file for complete search history.

(56) References Cited

U.S. PATENT DOCUMENTS 6,943,241 B2 * 9/2005 Isogai et al. ............ 536/23.1

(Continued)

FOREIGN PATENT DOCUMENTS

EP    1308459 A2    5/2003

(Continued)

OTHER PUBLICATIONS

Busquets, et al. "Calpain-3 gene expression is decreased during experimental cancer cachexia", Biochimica et Biophysica Acta, vol. 1475, pp. 5-9 (2000).

(Continued)

*Primary Examiner*—Nashaat T. Nashed
*Assistant Examiner*—William W. Moore
(74) *Attorney, Agent, or Firm*—Stephen C. D'Amico

(57) ABSTRACT

The present invention provides novel polynucleotides encoding CAN-12 polypeptides, fragments and homologues thereof. The present invention also provides polynucleotides encoding variants of CAN-12 polypeptides, CAN-12v1 and CAN-12v2. Also provided are vectors, host cells, antibodies, and recombinant and synthetic methods for producing said polypeptides. The invention further relates to diagnostic and therapeutic methods for applying these novel CAN-12, CAN-12v1, and CAN-12v2 polypeptides to the diagnosis, treatment, and/or prevention of various diseases and/or disorders related to these polypeptides, particularly neuro- and musculo-degenerative conditions. The invention further relates to screening methods for identifying agonists and antagonists of the polynucleotides and polypeptides of the present invention.

Figure 3:
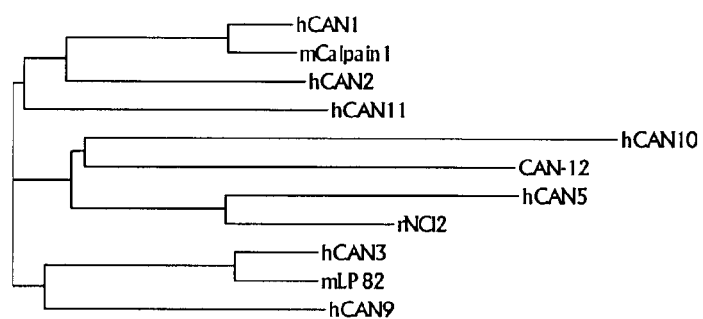

18 Claims, 27 Drawing Sheets
(2 of 27 Drawing Sheet(s) Filed in Color)

U.S. PATENT DOCUMENTS

| | | | | |
|---|---|---|---|---|
| 2003/0204070 | A1* | 10/2003 | Chen et al. | 536/23.2 |
| 2004/0014093 | A1* | 1/2004 | Duclos et al. | 435/6 |
| 2004/0029249 | A1* | 2/2004 | Lee et al. | 435/226 |
| 2004/0063107 | A1* | 4/2004 | Plowman et al. | 435/6 |

FOREIGN PATENT DOCUMENTS

| | | |
|---|---|---|
| WO | WO 96/14067 | 5/1996 |
| WO | WO 96/25403 | 8/1996 |
| WO | WO 98/11134 | 3/1998 |
| WO | WO0175067 | 10/2001 |
| WO | WO0183782 | 11/2001 |
| WO | WO0238744 | 5/2002 |

OTHER PUBLICATIONS

Huang, et al. "The calpin family and human disease", TRENDS in Mol. Med., vol. 7, No. 8, pp. 355-362 (2001).

NCBI Entrez Accession No. AC015980 (gi:17647083), Sulston, et al., Jan. 10, 2002.

NCBI Entrez Accession No. 1CFZF (gi:7546423), Fritsche, E. et al., Mar. 23, 1999.

NCBI Entrez Accession No. AAC61764 (gi:3661585), Ma, H. et al., Sep. 29, 1998.

NCBI Entrez Accession No. AL133246 (gi:7594587), Hazan, J. et al., Apr. 18, 2002.

NCBI Entrez Accession No. AL540944 (gi:45716538), Li, W.B. et al., Mar. 24, 2004.

NCBI Entrez Accession No. BM554389 (gi:18793945), NIH-MGC, Feb. 20, 2002.

NCBI Entrez Accession No. $NP_{13}000061$ (gi:4557405), Diaz, B.G. et al., Oct. 26, 2004.

NCBI Entrez Accession No. $NP_{13}001739$ (gi:4502563), Alexa, A. et al., Oct. 26, 2004.

NCBI Entrez Accession No. $NP_{13}004046$ (gi:37577157), Waghray, A. et al., Mar. 2, 2005.

NCBI Entrez Accession No. $NP_{13}005177$ (gi:12408656), Kulkarni, S. et al., Oct. 26, 2004.

NCBI Entrez Accession No. $NP_{13}006606$ (gi:5729758), Huang, Y. et al., Mar. 2, 2005.

NCBI Entrez Accession No. $NP_{13}008989$ (gi:5901916), Dear, T.N. et al., Jan. 26, 2005.

NCBI Entrez Accession No. $NP_{13}075571$ (gi:13186302), Carlsson, E. et al., Oct. 26, 2004.

NCBI Entrez Accession No. $NP_{13}075574$ (gi:13186308), Carlsson, E. et al., Mar. 2, 2005.

NCBI Entrez Accession No. O35350 (gi:12643550), Poirier, C. et al., May 1, 2005.

NCBI Entrez Accession No. $XP_{13}351430$ (gi:37546876), Oct. 17, 2003.

Swiss-Prot Accession No. Q64698, Release 01, Nov. 1996.

Altschul, S.F. et al., "Basic Local Alignment Search Tool", J. Mol. Biol., vol. 215, pp. 403-410 (1990).

Arnold, D. et al., "Substrate specificity of cathepsins D and E determined by N-terminal and C-terminal sequencing of peptide pools", Eur. J. Biochem., vol. 249, pp. 171-179 (1997).

Arora, A.S. et al., "Hepatocellular Carcinoma Cells Resist Necrosis During Anoxia by Preventing Phospholipase-Mediated Calpain Activation", Journal of Cellular Physiology, vol. 167, pp. 434-442 (1996).

Azuma, M. et al., "Cysteine protease inhibitor E64 reduces the rate of formation of selenite cataract in the whole animal", Current Eye Research, vol. 10, No. 7, pp. 657-666 (1991).

Backes, B.J. et al., "Synthesis of positional-scanning libraries of fluorogenic peptide substrates to define the extended substrate specificity of plasmin and thrombin", Nature Biotechnology, vol. 18, pp. 187-193 (2000).

Baier, L.J. et al., "A calpain-10 gene polymorphism is associated with reduced muscle mRNA levels and insulin resistance", The Journal of Clinical Investigation, vol. 106, pp. R69-R73 (2000).

Bairoch, A. et al., "EF-hand mofits in inositol phospholipid-specific phospholipase C", FEBS Letters, vol. 269, No. 2, pp. 454-456 (1990).

Balasubramanian, N. et al., "Active Site-Directed Synthetic Thrombin Inhibitors: Synthesis, in Vitro and in Vivo Activity Profile of BMY 44621 and Analogs. An Examination of the Role of the Amino Group in the D-Phe-Pro-Arg-H Series", J. Med. Chem., vol. 36, No. 2, pp. 300-303 (1993).

Banik, N.L. et al., "Role of Calpain and Its Inhibitors in Tissue Degeneration and Neuroprotection in Spinal Cord Injury", Annals New York Academy of Sciences, vol. 825, pp. 120-127 (1997).

Banik, N.L. et al., "Role of Calpain in Spinal Cord Injury: Effects of Calpain and Free Radical Inhibitors", Annals New York Academy of Sciences, vol. 844, pp. 131-137 (1998).

Bartlett, P.A. et al., "CAVEAT: A Program to Facilitate the Structure-derived Design of Biologically Active Molecules", Molecular Recognition: Chemical and Biochemical Problems, The Proceedings of an International Symposium, University of Exeter, Special Publication No. 78, The Royal Society of Chemistry, publ., Roberts, S.M., ed., pp. 182-196 (1989).

Bernstein, F.C. et al., "The Protein Data Bank: A Computer-based Archival File for Macromolecular Structures", J. Mol. Biol., vol. 112, pp. 535-542 (1977).

Böhm, H.-J., "The computer program LUDI: A new method for the de novo design of enzyme inhibitors", Journal of Computer-Aided Molecular Design, vol. 6, pp. 61-78 (1992).

Bradbury, A.F. et al., "Biosynthesis of the C-Terminal Amide in Peptide Hormones", Bioscience Reports, vol. 7, No. 12, pp. 907-916 (1987).

Carafoli, E. et al., "Calpain: A Protease in Search of a Function?", Biochemical and Biophysical Research Communications, vol. 247, No. 2, pp. 193-203 (1998).

Cardozo, T. et al., "Homology Modeling by the ICM Method", Proteins: Structure, Function, and Genetics, vol. 23, pp. 403-414 (1995).

Chapot-Cartier, M.-P. et al., "Cloning and Sequencing of PepC, a Cysteine Aminopeptidase Gene from Lactococcus lactis subsp. cremoris AM2", Applied and Environmental Microbiology, vol. 59, No. 1, pp. 330-333 (1993).

Chauvaux, S. et al., "Calcium-binding affinity and calcium-enhanced activity of Clostridium thermocellum endoglucanase D", Biochem. J., vol. 265, pp. 261-265 (1990).

Combrink, K.D. et al., "1,2-Benzisothiazol-3-one 1,1-Dioxide Inhibitors of Human Mast Cell Tryptase", J. Med. Chem., vol. 41, No. 24, pp. 4854-4860 (1998).

Cuzzocrea, S. et al., "Calpain Inhibitor I Reduces the Development of Acute and Chronic Inflammation", American Journal of Pathology, vol. 157, No. 6, pp. 2065-2079 (2000).

David, L.L. et al., "Buthionine sulfoximine induced cataracts in mice contain insolubilized crystallins with calpain II cleavage sites", Exp. Eye Res., vol. 59, pp. 501-504 (1994).

DeBiasi, R.L. et al., "Calpain Inhibition Protects against Virus-Induced Apoptotic Myocardial Injury", Journal of Virology, vol. 75, No. 1, pp. 351-361 (2001).

D'Souza, S.E. et al., "Arginyl-glycyl-aspartic acid (RGD): a cell adhesion motif", Trends in Biochemical Sciences, vol. 16, pp. 246-250 (1991).

Dufour, E., "Sequence homologies, hydrophobic profiles and secondary structures of cathepsins B, H and L: comparison with papain and actinidin", Biochimie, vol. 70, pp. 1335-1342 (1988).

Ebers, G.C. et al., "A full genome search in multiple sclerosis", Nature Genetics, vol. 13, pp. 472-476 (1996).

Elce, J.S., ed., Methods in Molecular Biology: Calpain Methods and Protocols, Humana Press Inc., publ., pp. ix-xii (table of contents) (2000).

Fox, J.E.B., "On the Role of Calpain and Rho Proteins in Regulating Integrin-induced Signaling", Thrombosis and Haemostasis, vol. 82, No. 2, pp. 385-391 (1999).

Goodford, P.J., "A Computational Procedure for Determining Energetically Favorable Binding Sites on Biologically Important Macromolecules", J. Med. Chem., vol. 28, No. 7, pp. 849-857 (1985).

Goodsell, D.S. et al., "Automated Docking of Substrates to Proteins by Simulated Annealing", Proteins: Structure, Function, and Genetics, vol. 8, pp. 195-202 (1990).

Greer, J., "Comparative Modeling of Homologous Proteins", Methods in Enzymology, vol. 202, pp. 239-252 (1991).

Grynspan, F. et al., "Active site-directed antibodies identify calpain II as an early-appearing and pervasive component of neurofibrillary pathology in Alzheimer's disease", Brain Research, vol. 763, pp. 145-158 (1997).

Haiech, J. et al. "Computer search of calcium binding sites in a gene data blank: use of learning techniques to build an expert system", Biochimie, vol. 67, pp. 555-560 (1985).

Hayes, R.L. et al., "Potential Contribution of Proteases to Neuronal Damage", Drug News Perspect., vol. 11, No. 4, pp. 215-222 (1998).

Heizmann, C.W. et al., "Intracellular calcium-binding proteins: more sites than insights", Trends in Biochemical Sciences, vol. 16, pp. 98-103 (1991).

Hendlich, M. et al., "Idenification of Native Protein Folds Amongst a Large Number of Incorrect Models: The Calculation of Low Energy Conformations from Potential of Mean Force", J. Mol. Biol., vol. 216, pp. 167-180 (1990).

Higgins, D.G. et al., "Malarial proteinase?", Nature, vol. 340, p. 604 (1989).

Horikawa, Y. et al., "Genetic variation in the gene encoding calpain-10 is associated with type 2 diabetes mellitus", Nature Genetics, vol. 26, pp. 163-175 (2000).

Hosfield, C.M. et al., "Crystal structure of calpain reveals the structural basis for $Ca^{2+}$-dependent protease activity and a novel mode of enzyme activation", The EMBO Journal, vol. 18, No. 24, pp. 6880-6889 (1999).

Houghten, R.A. et al., "Generation and use of synthetic peptide combinatorial libraries for basic research and drug discovery", Nature, vol. 354, pp. 84-86 (1991).

Inomata, M. et al., "Evidence for the involvement of calpain in cataractogenesis in Shumiya cataract rat (SCR)", Biochimica et Biophysica Acta, vol. 1362, pp. 11-23 (1997).

Iwamoto, H. et al., "Calpain Inhibitor-1 Reduces Infarct Size and DNA Fragmentation of Myocardium in Ischemic/Reperfused Rat Heart", Journal of Cardiovascular Pharmacology, vol. 33, pp. 580-586 (1999).

Iwamoto, N. et al., "Localization of calpain immunoreactivity in senile plaques and in neurones undergoing neurofibrillary degeneration in Alzheimer's disease", Brain Research, vol. 561, pp. 177-180 (1991).

Kadoya, K. et al., "Role of calpain in hydrogen peroxide induced cataract", Current Eye Research, vol. 12, No. 4, pp. 341-346 (1993).

Kawasaki, H. et al., Protein Profile: Calcium Binding Proteins 1—EF hands, vol. 2, No. 4, pp. 305-490 (1995).

Kirschke, H. et al., Protein Profile: Lysosomal Cysteine Proteinases, vol. 2, pp. 1587-1643 (1995).

Kishimoto, A. et al., "Studies on the Phosphorylation of Myelin Basic Protein by Protein Kinase C and Adenosine 3':5'-Monophosphate-dependent Protein Kinase", The Journal of Biological Chemistry, vol. 260, No. 23, pp. 12492-12499 (1985).

Kligman, D. et al., "The S100 protein family", Trends in Biochemical Sciences, vol. 13, pp. 437-443 (1988).

Knight, C.G., "Fluorimetric Assays of Proteolytic Enzymes", Methods in Enzymology, vol. 248, pp. 18-34 (1995).

Kreil, G., "Occurrence, Detection, and Biosynthesis of Carboxy-Terminal Amides", Methods in Enzymology, vol. 106, pp. 218-223 (1984).

Kretsinger, R.H., "Calcium Coordination and the Calmodulin Fold: Divergent versus Convergent Evolution", Cold Spring Harbor Symposia on Quantitative Biology, vol. LII, pp. 499-510 (1987).

Kuntz, I.D. et al., "A Geometric Approach to Macromolecule-Ligand Interactions", J. Mol. Biol., vol. 161, pp. 269-288 (1982).

Lam, K.S. et al. "A new type of synthetic peptide library for identifying ligand-binding activity", Nature, vol. 354, pp. 82-84 (1991).

Lee, H.-J. et al., "Molecular Cloning and Characterization of a Novel Tissue-Specific Calpain Predominantly Expressed in the Digestive Tract", Biol. Chem., vol. 379, pp. 175-183 (1998).

Lee, K.S. et al., "Calcium-Activated Proteolysis as a Therapeutic Target in Cerebrovascular Disease", Annals New York Academy of Sciences, vol. 825, pp. 95-103 (1997).

Lee, K.S. et al., "Inhibition of proteolysis protects hippocampal neurons from ischemia", Proc. Natl. Acad. Sci. USA, vol. 88, pp. 7233-7237 (1991).

Lee, M.-S. et al., "Neurotoxicity induces cleavage of p35 to p25 by calpain", Nature, vol. 405, pp. 360-364 (2000).

Lesk, A.M. et al., "Homology modelling: inferences from tables of aligned sequences", Current Opinion in Structural Biology, vol. 2, pp. 242-247 (1992).

Martin, Y.C., "3D Database Searching in Drug Design", Journal of Medicinal Chemistry, vol. 35, No. 12, pp. 2145-2154 (1992).

McGeehan, G.M. et al., "Defined Substrate Mixtures for Mapping of Proteinase Specificities", Methods in Enzymology, vol. 248, pp. 35-46 (1995).

Moncrief, N.D. et al., "Evolution of EF-Hand Calcium-Modulated Proteins. I. Relationships Based on Amino Acid Sequences", Journal of Molecular Evolution, vol. 30, pp. 522-562 (1990).

Nakayama, S. et al., "Evolution of EF-Hand Calcium-Modulated Proteins. II. Domains of Several Subfamilies Have Diverse Evolutionary Histories", Journal of Molecular Evolution. vol. 34, pp. 416-448 (1992).

Nixon, R.A. et al., "Calcium-Activated Neutral Proteinase (Calpain) System in Aging and Alzheimer's Disease", Annals New York Academy of Sciences, vol. 747, pp. 77-91 (1994).

Pearson, W.R., "Rapid and Sensitive Sequence Comparison with FASTP and FASTA", Methods in Enzymology, vol. 183, pp. 63-98 (1990).

Rami, A. et al., "Protective effects of calpain inhibitors against neuronal damage caused by cytotoxic hypoxia in vitro and ischemia in vivo", Brain Research, vol. 609, pp. 67-70 (1993).

Rawlings, N.D. et al., "Families of Cysteine Peptidases", Methods in Enzymology, vol. 244, pp. 461-486 (1994).

Ray, S.K. et al., "Increased Calpain Expression Is Associated with Apoptosis in Rat Spinal Cord Injury: Calpain Inhibitor Provides Neuroprotection", Neurochemical Research, vol. 25, Nos. 9/10, pp. 1191-1198 (2000).

Richard, I. et al., "Mutations in Proteolytic Enzyme Calpain 3 Cause Limb-Girdle Muscular Dystrophy Type 2A", Cell, vol. 81, pp. 27-40 (1995).

Ruoslahti, E. et al., "Arg-Gly-Asp: A Versatile Cell Recognition Signal", Cell, vol. 44, pp. 517-518 (1986).

Saito, K.-I, et al., "Widespread activation of calcium-activated neutral proteinase (calpain) in the brain in Alzheimer disease: A potential molecular basis for neuronal degeneration", Proc. Natl. Acad. Sci. USA, vol. 90, pp. 2628-2632 (1993).

Šali, A. et al., "Evaluation of Comparative Protein Modeling by MODELLER", Proteins: Structure, Function, and Genetics, vol. 23, pp. 318-326 (1995).

Shearer, T.R. et al., "Review of selenite cataract", Current Eye Research, vol. 11, No. 4, pp. 357-369 (1992).

Shi, G.-P. et al., "Molecular cloning of human cathepsin O, a novel endoproteinase and homologue of rabbit OC2", FEBS Letters, vol. 357, pp. 129-134 (1995).

Shields, D.C. et al., "A putative mechanism of demyelination in multiple sclerosis by a proteolytic enzyme, calpain", Proc. Natl. Acad. Sci. USA, vol. 96, pp. 11486-11491 (1999).

Sipple, M.J., "Boltzmann's principle, knowledge-based mean fields and protein folding. An approach to the computational determination of protein structures", Journal of Computer-Aided Molecular Design, vol. 7, pp. 473-501 (1993).

Songyang, Z. et al., "SH2 Domains Recognize Specific Phosphopeptide Sequences", Cell, vol. 72, pp. 767-778 (1993).

Sorimachi, H. et al., "Structure and physiological function of calpains", Biochem. J., vol. 328, pp. 721-732 (1997).

Stracher, A., "Calpain Inhibitors as Therapeutic Agents in Nerve and Muscle Degeneration", Annals New York Academy of Sciences, vol. 884, pp. 52-59 (1999).

Strobl, S. et al., "The crystal structure of calcium-free human m-calpain suggests an electrostatic switch mechanism for activation by calcium", Proc. Natl. Acad. Sci., vol. 97, No. 2, pp. 588-592 (2000).

Strynadka, N.C.J. et al., "Crystal Structures of the Helix-Loop-Helix Calcium-Binding Proteins", Annu. Rev. Biochem., vol. 58, pp. 951-958 (1989).

Turk, B.E. et al., "Determination of protease cleavage site motifs using mixture-based oriented peptide libraries", Nature Biotechnology, vol. 19, pp. 661-667 (2001).

Udenfriend, S. et al., "Fluorescamine: A Reagent for Assay of Amino Acids, Peptides, Proteins, and Primary Amines in the Picomole Range", Science, vol. 178, pp. 871-872 (1972).

Velasco, G. et al., "Human Cathepsin O: Molecular Cloning from a Breast Carcinoma, Production of the Active Enzyme in *Escherichia Coli*, and Expression Analysis in Human Tissues", The Journal of Biological Chemistry, vol. 269, No. 43, pp. 27136-27142 (1994).

Wang, K.K.W. et al., "An alpha-mercaptoacrylic acid derivative is a selective nonpeptide cell-permeable calpain inhibitor and is neuroprotective", Proc. Natl. Acad. Sci. USA, vol. 93, pp. 6687-6692 (1996).

Wang, K.K.W. et al., "Calpain inhibition: an overview of its therapeutic potential", Trends in Pharmacological Sciences, vol. 15, pp. 412-419 (1994).

Wang, K.K.W. et al., Calpain: Pharmacology and Toxicology of Calcium-Dependent Protease, Taylor & Francis, publ., pp. v-vi (table of contents) (1999).

Woodgett, J.R. et al., "Substrate specificity of protein kinase C: Use of synthetic peptides corresponding to physiological sites as probes for substrate recognition requirements", Eur. J. Biochem., vol. 161, pp. 177-184 (1986).

Yoshikawa, Y. et al., "Isolation of Two Novel Genes, Down-regulated in Gastric Cancer", Jpn. J. Cancer Res., vol. 91, pp. 459-463 (2000).

\* cited by examiner

Figure 1A

```
  1 GAAAAATCCATGCTGAAGGACCCCAGGACCAGCACCAGTTCCTGAGCATCTTTCCCGGGC    60

61 TGAGCAGCAGAGACTCCTCAGGAAGACTCACTGGACTGTACCCACCACCTGCCATGTCTC   120
  1                                                        M  S  L   3

121 TGTGGCCACCTTTCCGATGCAGATGGAAGCTGGCGCCAAGGTACTCTAGGAGGGCGTCTC   180
  4  W  P  P  F  R  C  R  W  K  L  A  P  R  Y  S  R  R  A  S  P    23

181 CACAGCAACCCCAACAGGACTTTGAGGCCCTGCTGGCAGAGTGCCTGAGGAATGGCTGCC   240
 24  Q  Q  P  Q  Q  D  F  E  A  L  L  A  E  C  L  R  N  G  C  L    43

241 TCTTTGAAGACACCAGCTTCCCGGCCACCCTGAGCTCCATCGGCAGTGGCTCCCTGCTGC   300
 44  F  E  D  T  S  F  P  A  T  L  S  S  I  G  S  G  S  L  L  Q    63

301 AGAAGCTGCCACCCCGCCTGCAGTGGAAGAGGCCCCCGGAGCTGCACAGCAATCCCCAGT   360
 64  K  L  P  P  R  L  Q  W  K  R  P  P  E  L  H  S  N  P  Q  F    83

361 TTTATTTTGCCAAGGCCAAAAGGCTGGATCTGTGCCAGGGGATAGTAGGAGACTGCTGGT   420
 84  Y  F  A  K  A  K  R  L  D  L  C  Q  G  I  V  G  D  C  W  F   103

421 TCTTGGCTGCTTTGCAAGCTCTGGCCTTGCACCAGGACATCCTGAGCCGGGTTGTTCCCC   480
104  L  A  A  L  Q  A  L  A  L  H  Q  D  I  L  S  R  V  V  P  L   123

481 TGAATCAGAGTTTCACTGAGAAGTATGCTGGCATCTTCCGGTTCTGGTTCTGGCACTATG   540
124  N  Q  S  F  T  E  K  Y  A  G  I  F  R  F  W  F  W  H  Y  G   143

541 GGAACTGGGTTCCTGTGGTGATCGATGACCGTCTGCCTGTGAATGAGGCTGGCCAGCTGG   600
144  N  W  V  P  V  V  I  D  D  R  L  P  V  N  E  A  G  Q  L  V   163

601 TCTTTGTCTCCTCCACCTATAAGAACTTGTTCTGGGGAGCACTTCTGGAAAAGGCCTATG   660
164  F  V  S  S  T  Y  K  N  L  F  W  G  A  L  L  E  K  A  Y  A   183

661 CCAAGCTCTCTGGTTCCTATGAAGACTTGCAGTCAGGACAGGTGTCTGAAGCCCTTGTAG   720
184  K  L  S  G  S  Y  E  D  L  Q  S  G  Q  V  S  E  A  L  V  D   203

721 ACTTCACTGGAGGGGTGACAATGACCATCAACCTGGCAGAAGCCCATGGCAACCTCTGGG   780
204  F  T  G  G  V  T  M  T  I  N  L  A  E  A  H  G  N  L  W  D   223

781 ACATCCTCATCGAAGCCACCTACAACAGAACCCTCATTGGCTGCCAGACCCACTCAGGGA   840
224  I  L  I  E  A  T  Y  N  R  T  L  I  G  C  Q  T  H  S  G  K   243
```

Figure 1B

```
 841  AGATTCTGGAGAATGGGCTGGTGGAAGGCCATGCCTATACTCTCACAGGAATCAGGAAGG   900
 244    I   L   E   N   G   L   V   E   G   H   A   Y   T   L   T   G   I   R   K   V    263
                                          ↑

901  TGACCTGCAAACATAGACCTGAATATCTCGTCAAGCTACGGAACCCCTGGGGAAAGGTGG   960
 264    T   C   K   H   R   P   E   Y   L   V   K   L   R   N   P   W   G   K   V   E    283
                                                            ↑

961  AATGGAAAGGAGACTGGAGTGACAGTTCAAGTAAATGGGAGCTGCTGAGCCCCAAGGAGA  1020
 284    W   K   G   D   W   S   D   S   S   S   K   W   E   L   L   S   P   K   E   K    303

1021  AGATTCTGCTTCTGAGGAAAGACAATGACGGAGAATTCTGGATGACGCTGCAGGACTTTA  1080
 304    I   L   L   L   R   K   D   N   D   G   E   F   W   M   T   L   Q   D   F   K    323

1081  AAACACATTTCGTGCTCCTGGTTATCTGTAAACTGACCCCAGGCCTGTTGAGCCAGGAGG  1140
 324    T   H   F   V   L   L   V   I   C   K   L   T   P   G   L   L   S   Q   E   A    343

1141  CGGCCCAGAAGTGGACGTACACCATGCGGGAGGGGAGATGGGAGAAGCGGAGCACAGCTG  1200
 344    A   Q   K   W   T   Y   T   M   R   E   G   R   W   E   K   R   S   T   A   G    363

1201  GTGGCCAGAGGCAGTTGCTGCAGGACACATTTTGGAAGAACCCGCAGTTCCTGCTGTCTG  1260
 364    G   Q   R   Q   L   L   Q   D   T   F   W   K   N   P   Q   F   L   L   S   V    383

1261  TCTGGAGGCCCGAGGAGGGCAGGAGATCCCTGAGGCCCTGCAGCGTGCTGGTGTCCCTGC  1320
 384    W   R   P   E   E   G   R   R   S   L   R   P   C   S   V   L   V   S   L   L    403

1321  TCCAGAAGCCCAGGCACAGGTGCCGCAAGCGGAAGCCTCTCCTCGCCATTGGCTTCTACC  1380
 404    Q   K   P   R   H   R   C   R   K   R   K   P   L   L   A   I   G   F   Y   L    423

1381  TCTATAGGATGAACAAGTGAAATTGGCAGCAATTCTGGTGTCGTCTTCTCAAAGGAGATA  1440
 424    Y   R   M   N   K                                                                428

1441  GAAGACCAAAATGAAAGGCAGGATGAATTCTTCACCAAATTCTTTGAAAAGCATCCAGAG  1500

1501  ATTAATGCAGTTCAACTTCAGAACCTCCTGAACCAGATGACCTGGTCAAGTCTGGGGAGC  1560
 429                                                M   T   W   S   S   L   G   S        436

1561  AGACAGCCCTTCTTTAGCCTGGAAGCCTGCCAGGGGATCCTGGCCTTACTGGACCTTAAT  1620
 437    R   Q   P   F   F   S   L   E   A   C   Q   G   I   L   A   L   L   D   L   N    456

1621  GCATCAGGTACTATGAGCATCCAGGAATTCAGGGACCTGTGGAAGCAGCTGAAGCTCTCT  1680
 457    A   S   G   T   M   S   I   Q   E   F   R   D   L   W   K   Q   L   K   L   S    476

1681  CAGAAGGTTTTCCACAAGCAAGACCGTGGGTCAGGATACCTGAACTGGGAGCAGCTGCAC  1740
 477    Q   K   V   F   H   K   Q   D   R   G   S   G   Y   L   N   W   E   Q   L   H    496
```

Figure 1C

```
1741  GCTGCCATGAGGGAGGCAGGTAGGCACAGGAAGAGCTGGAGCTGTGGGCACACACGGGCA  1800
497    A   A   M   R   E   A   G   R   H   R   K   S   W   S   C   G   H   T   R   A    516

1801  GGGTGCACACTCATCAGGCAGAGGAGAGGGGATGTGTGGCATGCTGAAGTAACTCTAATA  1860
517    G   C   T   L   I   R   Q   R   R   G   D   V   W   H   A   E   V   T   L   I    536

1861  CGCAGTGTTACTCTCAAAGACGTAGATCTGCAGTCAACTCCAACATTTTTTATGATTGTC  1920
537    R   S   V   T   L   K   D   V   D   L   Q   S   T   P   T   F   F   M   I   V    556

1921  CCTGTGATCCTAGCCAACATTGATGGAGGGGTGGCACATTCAACTTCTTATTTAATCTTC  1980
557    P   V   I   L   A   N   I   D   G   G   V   A   H   S   T   S   Y   L   I   F    576

1981  AACACCACCTTGTTATAATCCTCACTTCACAGAGGAAGAAATTGAAGCTCAATTGCCTGG  2040
577    N   T   T   L   L                                                                581

2041  GGTTTAAATTCAGGACTGCCGGGCTCCCAAGCAGGTACTTTTGAGCACTTAGCAGACTGC  2100

2101  CTCCTTCATTGAAGGCTGGTAACATACTTGATGAAAACAGCCTCATGCTGGTTGCCTTAA  2160

2161  CAGACAGGGGTGAAGAGTAGGGATTAAATAAAATAAATTGGTTAAACAATTAAACCATTC  2220

2221  AAAATGAACCCTATAAAAGAAGATTTCCATGCTATCAGGATTCAGGTCCCTAAACTGGAG  2280

2281  GGACATTTGAAGGGGCCTTGAGCAGGAGGGGAGCTGGGTGCAAGCCCCCAATACCCACAG  2340

2341  CAGGAGCTTGTGCTCAATGCAGGAATCATGCTCAGTGATGACGTCTGTCAGCTGATGCTC  2400

2401  ATCCGCTACGGCGGCCCCCGCCTCCAGATGGACTTTGTCAGTTTCATCCACTTGATGCTG  2460

2461  CGTGTAGAGAACATGGAGGGTAAGCTGGCGGGAAGCTGGGGAGGGCCAGGTCTTCCTCTG  2520

2521  CTGCCCCATGACTTCCCACCTGTCCCTAGTTTAAGCACAAGGGAGGACAGCCGCCATCCC  2580

2581  AGAAACAGCAGACCAGGGAAGCTGTGGGACCTCCAGCCAAGTGCCTGTGAACCCTGGCT  2640

2641  GCAGATATCCAAACTCATCTTTTCCTGACTTGTTCCAGAGACAAAGGCTTGAAGTGGCTC  2700

2701  ACTTATCATAGATGTGGCTGCGTGTGGTCACATGTAGGCTGACACTGGGTTCCCTCACGT  2760

2761  TTTCAGAATGGATGTGGTTAAGGTGAGACATATGGGAGGAACTAATTCATAATGTTTCCA  2820
```

Figure 1D

```
2821  ATAGACACATTAGCTGTATTCCTTTCTGCTGCATTTTCACAGATGTCTTCCAAAACTTAA  2880

2881  CCCAAGATGGCAAAGGGATATACCTCCAGAAGCCAGAGTGGATGATGATGGCACTGTACT  2940

2941  CCTGAGAAGGCTGAGTCTCACCTGCCCTCACTGAAGACTCTGCATGTGGCCCAAGAGCAG  3000

3001  CCTTTGGCTGAGACCAACCCATGCCCACCCTACTTACTGATCTTCAGGACAGCCTCACTA  3060

3061  GCCGTCACCTTCTCAGCTGGGAAGGTTTCTCTTCTGCAGCCCTCCCCGTGCATGGCCAGC  3120

3121  ATGCAGAAAGGGAAGGGAGGAAGTAAAGATTACATCAGATTTGTAAAAGCTAGCCATCCT  3180

3181  TCCCTGAGGCCACAACCTTGTCACAAGCGGAGATGTTACCTGACATGGCCTAAGCATTCT  3240

3241  GACTCCAGAGCTGGTGTGGTTAGCCTCCATACAACACTGCCTCTGTGGCTGCAAACTCAA  3300

3301  GTGACTTTAGACATGCCACATGTTCTCACATGGTGGGTAATCATCTAGGTTTTAAGGTC  3360

3361  TGAAATGGGAATGATATATCCTTAGACATTTAGTCCCAGCATCTGCAAATTGATAGAGAC  3420

3421  ATAGGCTAAGTTTCAGCTGTTTGGGGATGGGGTCAGGGATATAGTGGGCTTTCAGAAACA  3480

3481  CAGACAGTAAGAGAATTGGCAGAGTCCAGGTGGGGTGGGCTGGCTCTGGCATCTGAGGTC  3540

3541  ATGGGGTAGTCTTCTTCTGACAATATCTCCGTATGATTGGATCTGGGGCAACCTAGTAGA  3600

3601  TTTAAAACACCTGAGTTCTCAAAGGGCTTCCTGCTTGTGACAGGTGTGTCTATTTGCTTG  3660

3661  ATATATAGACTATCAGATCCATTTCAAATCTGTCCAGAAATTCTCTGTCTATCTACTTCA  3720

3721  AAGGACAAAAACAAACCCATGCTAAATTATAGAGTCAATCAGTGGGTGGTTGGTATATCT  3780

3781  GATTTTTTGAACTACCATGAAACACCTTGTTTATGTCATCCCTCTCAACCAAGAATACAG  3840

3841  GTGCAAAACCAGAACAATGGCCTTTTTCCAAAGTCTATGCAATTTATTCATAAGTTAGCA  3900

3901  CCTCAGAGCCATTTATTACTACAGGTTGAGCATCCCAAATCTGAAAACCCCAAATCTGAA  3960
```

Figure 1E

```
3961  ATACTCCAAAATCTAAAATTTCTGAGAGTAGACATGAAACTCAAAGGAAATAGGGGCATT  4020

4021  TTGGATTTTGAATTTTTGGGTTTGAGGTGTTCAACTGACAAGTCTATAATGCAGATATCC  4080

4081  TGAAATCTGAAACACTTCTGGTCCCAAGCATTTTAGTTAAGAGATAGTCAACCTGTATTC  4140

4141  TATTTAATCTTAATTTACAAACAATTCTAACAAACATGGCTGTTTGATTTCCAACTCCAT  4200

4201  AGCAGACTCAGGAAGGAAGCTGAATGAAGAGATAAAAGTGTGTCCATTGGCAGAGGACTA  4260

4261  AAGGAGATTTGAGCACCTGTCAGATGGGTACTGTACCAGAAGAAAGGAGCACTTTGAAAG  4320

4321  CGTAGCTTATGGGGTAGGAAAGTATTTTATTTAGGAAAAAAAACCCTTCATTTATTCCAA  4380

4381  ATGATAAAATGTAAAATGGGTTTCCATAAAGTGCCAGATACATGAGATGTTGTTGATTTT  4440

4441  ATAAATGATGATCATGTATTTACAGCCTTTTACAGTTTTTTATATCCATTGACTTATTTG  4500

4501  TGTCTTTGTCTTTAAAATCTGCCATTGCAAATAGCTGTTTTAATAAACCAATTTTGCCTT  4560

4561  GGCCCCTGAAAAAAAAAAAAAAAA  4584
```

Figure 2A

```
                 1                                                50
   hCAN1    (1)  MSEEIITPVYCTGVSAQVQKQRARELG--------------LGRHEN---
   hCAN10   (1)  --------------------------------------------------
   hCAN11   (1)  --------------MVAHINNSRLKAKG--------------VGQHDN---
   hCAN2    (1)  ----------MAGIAAKLAKDREAAEG---------------LGSHER---
   hCAN3    (1)  ------MPTVISASVAPRTAAEPRSPGPVPHPAQSKATEAGGGNPSGIYS
   hCAN5    (1)  ----------------------------------------------MFSC---
   hCAN9    (1)  ------MPYLYRAPGPQAHPVPKDARI---------------THS----
mCalpain1   (1)  MTEELITPVYCTGVSAQVQKKRDKELG---------------LGRHEN---
   mLP82    (1)  ------MPYLLPGFFCDRVIRERDRRN-----GE--------GTVS----
   rNC12    (1)  ----------MAALAAGVSKQRAVAEG---------------LGSNQN---
   CAN-12   (1)  --MSLWPPFRCRWKLAPRYSRRASPQQ----------------------
   CAN-12v1 (1)  --MSLWPPFRCRWKLAPRYSRRASPQQ----------------------
   CAN-12v2 (1)  --MSLWPPFRCRWKLAPRYSRRASPQQ----------------------

51                                               100
   hCAN1   (34)  --------AIKYLGQDYEQLRVRCLQSGTLFRDEAFPPVPQSLGYKDLGP
   hCAN10   (1)  -------------------MRAGRGATPARELFRDAAFPAADSSLFCDLSTP
   hCAN11  (21)  --------AQNFGNQSFEELRAACLRKGELFEDPLFPAEPSSLGFKDLGP
   hCAN2   (24)  --------AIKYLNQDYEALRNECLEAGTLFQDPSFPAIPSALGFKELGP
   hCAN3   (45)  AIISRNFPIIGVKEKTFEQLHKKCLEKKVLYVDPEFPPDETSL----FYS
   hCAN5    (5)  --------VKPYEDQNYSALRQDCRRRKVLFEDPLFPATDDSLYYKGT-P
   hCAN9   (25)  --------SG----QSFEQMRQECLQRGTLFEDADFPASNSSL----FYS
mCalpain1  (34)  --------AIKYLGQDYETLRARCLQSGVLFQDEAFPPVSHSLGFKELGP
   mLP82   (28)  -------QPLKFEGQDFVVLKQRCLAQKCLFEDRVFPAGVQALGSHELSQ
   rNC12   (24)  --------AVKYLGQDFETLRKQCLNSGVLFKDPEFPACPSALGYKDLGP
   CAN-12  (26)  ------------PQQDFEALLAECLRNGCLFEDTSFPATLSSIGSG--SL
   CAN-12v1 (26) ------------PQQDFEALLAECLRNGCLFEDTSFPATLSSIGSG--SL
   CAN-12v2 (26) ------------PQQDFEALLAECLRNGCLFEDTSFPATLSSIGSG--SL 101                                              150
   hCAN1   (76)  NSSKTYGIKWKRPTELLSNPQFIVDGATRTDICQGALGDCWLLAAIASLT
   hCAN10  (34)  LAQFREDLTWRRPQEICATPRLFPDDPREGQVKQGLLGDCWFLACAAALQ
   hCAN11  (63)  NSKNVQNISWQRPKDIINNPLFIMDGISPTDICQGILGDCWLLAAIGSLT
   hCAN2   (66)  YSSKTRGMRWKRPTEICADPQFIIGGATRTDICQGALGDCWLLAAIASLT
   hCAN3   (91)  QK-FPIQFVWKRPPEICENPRFIIDGANRTDICQGELGDCWFLAAIACLT
   hCAN5   (46)  G----PAVRWKRPKGICEDPRLFVDGISSHDLHQGQVGNCWFVAACSSLA
   hCAN9   (59)  ER-PQIPFVWKRPGEIVKNPEFILGGATRTDICQGELGDCWLLAAIASLT
mCalpain1  (76)  HSSKTYGIKWKRPTELMSNPQFIVDGATRTDICQGALGDCWLLAAIASLT
   mLP82   (71)  KA-KMKAITWKKPKEICENPGFIIGGANRTDICQGDLGDCWLLAAIACLT
   rNC12   (66)  GSPDTQGIVWKRPTELCPNPQFIVGGAKRTDIRQGGLGDCWLLAAIQALA
   CAN-12  (62)  LQKLPPRLQWKRPPELHSNPQFYFAKAKRLDLCQGIVGDCWFLAALQALA
   CAN-12v1 (62) LQKLPPRLQWKRPPELHSNPQFYFAKAKRLDLCQGIVGDCWFLAALQALA
   CAN-12v2 (62) LQKLPPRLQWKRPPELHSNPQFYFAKAKRLDLCQGIVGDCWFLAALQALA 151                                              200
   hCAN1  (126)  LNDTLLHRVVPHG--QS----FQNGYAGIFHFQLWQFGEWVDVVVDDLLP
   hCAN10  (84)  KSRHLLDQVIPPG--QP--SWADQEYRGSFTCRIWQFGRWVEVTTDDRLP
   hCAN11 (113)  TCPKLLYRVVPRG--QS----FKKNYAGIFHFQIWQFGQWVNVVVDDRLP
   hCAN2  (116)  LNEEILARVVPLN--QS----FQENYAGIFHFQFWQFGEWVDVVVDDRLP
   hCAN3  (140)  LNQHLLFRVIPHD--QS----FIENYAGIFHFQFWRYGEWVDVVVIDDCLP
   hCAN5   (92)  SRESLWQKVIPDWKEQEWDPRKAQAYAGIFHFHFWRLG-MVDVVIDERLP
   hCAN9  (108)  LNQKALARVIPQD--QS----FGPGYAGIFHFQFWQHSEWLDVVIDDRLP
mCalpain1 (126)  LNETILHRVVPYG--QS----FQDGYAGIFHFQLWQFGEWVDVVIDDLLP
   mLP82  (120)  LNERLLFRVIPHD--QS----FTENYAGIFHFQFWRYGDWVDVVIDDCLP
   rNC12  (116)  LNEKLLYRVLPRD--QS----FQKDYAGIFHFQFWQYGEWVEVVIDDRLP
   CAN-12 (112)  LHQDILSRVVPLN--QS----FTEKYAGIFRFWFWHYGNWVPVVIDDRLP
   CAN-12v1 (112) LHQDILSRVVPLN--QS----FTEKYAGIFRFWFWHYGNWVPVVIDDRLP
   CAN-12v2 (112) LHQDILSRVVPLN--QS----FTEKYAGIFRFWFWHYGNWVPVVIDDRLP
```

Figure 2B

```
              201                                                  250
hCAN1    (170) IKDG-KLVFVHSAEGNEFWSALLEKAYAKVNGSYEALSGGSTSEGFEDFT
hCAN10   (130) CLAG-RLCFSRCQREDVFWLPLLEKVYAKVHGSYEHLWAGQVADALVDLT
hCAN11   (157) TKND-KLVFVHSTERSEFWSALLEKAYAKLSGSYEALSGGSTMEGLEDFT
hCAN2    (160) TKDG-ELLFVHSAEGSEFWSALLEKAYAKINGCYEALSGGATTEGFEDFT
hCAN3    (184) TYNN-QLVFTKSNHRNEFWSALLEKAYAKLHGSYEALKGGNTTEAMEDFT
hCAN5    (141) TVNN-QLIYCHSNSRNEFWCALVEKAYAKLAGCYQALDGGNTADALVDFT
hCAN9    (152) TFRD-RLVFLHSADHNEFWSALLEKAYAKLNGSYEALKGGSAIEAMEDFT
mCalpain1(170) TKDG-KLVFVHSAQGNEFWSALLEKAYAKVNGSYEALSGGCTSEAFEDFT
mLP82    (164) TYNN-QLVFTKSNHRNEFWSALLEKAYAKLHGSYEALKGGNTTEAMEDFT
rNC12    (160) TKNG-QLLFLHSEEGNEFWSALLEKAYAKLNGSYEALVGGSTIEGFEDFT
CAN-12   (156) VNEAGQLVFVSSTYKNLFWGALLEKAYAKLSGSYEDLQSGQVSEALVDFT
CAN-12v1 (156) VNEAGQLVFVSSTYKNLFWGALLEKAYAKLSGSYEDLQSGQVSEALVDFT
CAN-12v2 (156) VNEAGQLVFVSSTYKNLFWGALLEKAYAKLSGSYEDLQSGQVSEALVDFT 251                                                  300
hCAN1    (219) GGVTEWYELRK--------APSDLYQIILKALERGSLLGCSID------
hCAN10   (179) GGLAERWNLKGVAGSGGQQDRPGRWEHRTCRQLLHLKDQCLIS------
hCAN11   (206) GGVAQSFQLQR--------PPQNLLRLLRKAVERSSLMGCSIE------
hCAN2    (209) GGIAEWYELKK--------PPPNLFKIIQKALQKGSLLGCSID------
hCAN3    (233) GGVAEFFEIRD--------APSDMYKIMKKAIERGSLMGCSIDDGTNMTY
hCAN5    (190) GGVSEPIDLTEGDFANDETKRNQLFERMLKVHSRGGLISASIK------
hCAN9    (201) GGVAETFQTKE--------APENFYEILEKALKRGSLLGCFID------
mCalpain1(219) GGVTEWYDLQK--------APSDLYQIILKALERGSLLGCSIN------
mLP82    (213) GGVIEFFEIKD--------APSDMYKIMRKALERGSLMGCSID------
rNC12    (209) GGISEFYDLKK--------PPENLYYIIQKALRKGSLLGCSID------
CAN-12   (206) GGVTMTINLAE--------AHGNLWDILIEATYNRTLIGCQTHSG----
CAN-12v1 (206) GGVTMTINLAE--------AHGNLWDILIEATYNRTLIGCQTHSGE---
CAN-12v2 (206) GGVTMTINLAE--------AHGNLWDILIEATYNRTLIGCQTHSGE---

301                                                  350
hCAN1    (254) ------------------------------ISSVLDMEA
hCAN10   (222) ------------------------------CCVLSPR
hCAN11   (241) ------------------------------VTSDSELES
hCAN2    (244) ------------------------------ITSAADSEA
hCAN3    (275) GTSPSGLNMGELIARMVRNMDNSLLQDSDLDPRGSDERPTRTIIPVQYET
hCAN5    (233) ------------------------------AVTAADMEA
hCAN9    (236) ------------------------------TRSAAESEA
mCalpain1(254) ------------------------------ISDIRDLEA
mLP82    (248) ------------------------------TIVPVQYET
rNC12    (244) ------------------------------VSTAAEAEA
CAN-12   (243) ----------------------------------K
CAN-12v1 (244) ----------------------------------K
CAN-12v2 (244) ----------------------------------K 351                                                  400
hCAN1    (263) ITFKKLVKGHAYSVTGAKQVNYRG--------QVWSLIRMRNPWGEVEWT
hCAN10   (229) AGARELGEFHAFIVSDLRELQGQAG-------QCLLLRIQNPWGRRCWQ
hCAN11   (250) MTDKMLVRGHAYSVTGLQDVHYRG--------KMETLIRVRNPWGRIEWN
hCAN2    (253) LTFQKLVKGHAYSVTGAEEVESNG--------SLQKLIRIRNPWGEVEWT
hCAN3    (325) RMACGLVRGHAYSVTGLDEVPFKG--------EKVKLVRLRNPWGQVEWN
hCAN5    (242) RLACGLVKGHAYAVTDVRKVRLGHGLLAFFKSEKLDMIRLRNPWGEREWN
hCAN9    (245) RTPFGLIKGHAYSVTCIDQVSFRG--------QRIELIRIRNPWGQVEWN
mCalpain1(263) LTFKNLVRGHAYSVTGAKQVTYQG--------QRVNLIRMRNPWGEVEWN
mLP82    (257) RMACGLVKGHAYSVTGLEEALFKG--------EKVKLIRLRNPWGQVEWK
rNC12    (253) TTRQKLVKGHAYSVTGVEEVNFHG-----RP-E--KLIRLRNPWGEVEWS
CAN-12   (244) ILENGLVEGHAYTLTGIRKVTCKH--------RPEYLVKLRNPWGKVEWK
CAN-12v1 (245) ILENGLVEGHAYTLTGIRKVTCKH--------RPEYLVKLRNPWGKVEWK
CAN-12v2 (245) ILENGLVEGHAYTLTGIRKVTCKH--------RPEYLVKLRNPWGKVEWK
```

Figure 2C

```
                401                                                450
hCAN1     (305) GAWSDSSSEWNNVDPYER-DQLRVKMEDGEFWMSFRDFMREFTRLEICNL
hCAN10    (272) GLWREGGEGWSQVDAAVASELLSQLQE-GEFWVEEEEFLREEDELIVGYP
hCAN11    (292) GAWSDSAREWEEVASDIQ-MQLLHKTEDGEFWMSYQDFLNNETLLEICNL
hCAN2     (295) GRWNDNCPSWNTIDEEER-ERLTRRHEDGEFWMSFSDFLRHYSRLEICNL
hCAN3     (367) GSWSDRWKDWSFVDKDEKARLQHQVTEDGEFWMSYEDFIYHFTKLEICNL
hCAN5     (292) GPWSDTSEEWQKVSKSEREKMGVTVQDDGEFWMTFEDVCRYFTDIIKCRV
hCAN9     (287) GSWSDSSPEWRSVGPAEQKRLCHTALDDGEFWMAFKDEKAHFDKVEICNL
mCalpain1 (305) GPWSDSSYEWNKVDPYER-EQLRVKMEDGEFWMSFRDFIREFTKLEICNL
mLP82     (299) GSWSDGWKDWSFVDKDEKARLQHQVTEDGEFWMSYDDFVYHFTKLEICNL
rNCl2     (295) GAWSDNAPEWNYIDP-RRKEELDKKAEDGEFWMSFSDFLKQYSRLEICNL
CAN-12    (286) GDWSDSSSKWELLSPKEK-ILLLRKDNDGEFWMTLQDFKTHFVLLVICKL
CAN-12v1  (287) GDWSDSSSKWELLSPKEK-ILLLRKDNDGEFWMTLQDFKTHFVLLVICKL
CAN-12v2  (287) GDWSDSSSKWELLSPKEK-ILLLRKDNDGEFWMTLQDFKTHFVLLVICKL 451                                                500
hCAN1     (354) TPDALKSRTIRKWNTTLYE----GTWRRGST----AGGCR-NYPATFWVN
hCAN10    (321) VTEAGHLQSLYTERLLCHTRALPGAWVKGQS----AGGCR--NNSGFPSN
hCAN11    (341) TPDTLSGDYKSYWHTTFYE----GSWRRGSS----AGGCR-NHPGTFWTN
hCAN2     (344) TPDTLTSDTYKKWKLTKMD----GNWRRGST----AGGCR-NYPNTFWMN
hCAN3     (417) TADALQSDKLQTWTVSVNE----GRWVRGCS----AGGCR-NFPDTFWTN
hCAN5     (342) INTSHLS-IHKTWEEARLH----GAWTLHEDPRQNRGGCINHKDTFFQN
hCAN9     (337) TPDALEEDAIHKWEVTVHQ----GSWVRGST----AGGCR-NFLDTFWTN
mCalpain1 (354) TPDALKSRTLRNWNTTFYE----GTWRRGST----AGGCR-NYPATFWVN
mLP82     (349) TADALESDKLQTWTVSVNE----GRWVRGCS----AGGCR-NFPDTFWTN
rNCl2     (344) SPDSLSSEETHKWNLVLFN----GRWTRGST-----AGGCLNYPGTYWTN
CAN-12    (335) TPGLLSQEAAQKWTYTMRE----GRWEKRST----AGGQRQLLQDTFWKN
CAN-12v1  (336) TPGLLSQEAAQKWTYTMRE----GRWEKRST----AGGQRQLLQDTFWKN
CAN-12v2  (336) TPGLLSQEAAQKWTYTMRE----GRWEKRST----AGGQRQLLQDTFWKN 501                                                550
hCAN1     (395) PQFKIRLDETDDPDDYGD---------RESGCSFVLALMQKHRRRERRFG
hCAN10    (365) PKFWLRVSEPSEVYIAVLQRSRLHAADWAGRARALVGDSHTSWSPASIPG
hCAN11    (382) PQFKISLPEGDDPEDDAEG-------NVVVCTCLVALMQKNWRHARQQG
hCAN2     (385) PQYLIKLEEEDEDEEDG----------ESGCTFLVGLIQKHRRRQRKMG
hCAN3     (458) PQYRIKLLEFDDDPDDSE-----------VICSFLVALMQKNRRKDRKLG
hCAN5     (387) PQYIFEVKKPEDE--------------------VLICIQQRPKRSTRREG
hCAN9     (378) PQIKLSLTEKDEGQEE------------CSFLVALMQKHRRRERRFG
mCalpain1 (395) PQFKIRLEEVDDADDYDN---------RESGCSFLLALMQKHRRRERRFG
mLP82     (390) PQYRLKLLKEDDDPEDSE-----------VICSFLVALMQKDRRKDRKLG
rNCl2     (385) PQFKIHLDEVDEDQEEGT--------SEPCCTVLLGLMQKNRRRQKRIG
CAN-12    (377) PQFLLSVWRPEEGRRS----------LRPCSVLVSLLQKPRHRCRKR-
CAN-12v1  (378) PQFLLSVWRPEEGRRS----------LRPCSVLVSLLQKPRHRCRKR-
CAN-12v2  (378) PQFLLSVWRPEEGRRS----------LRPCSVLVSLLQKPRHRCRKR- 551                                                600
hCAN1     (436) -RDMETIGFAVYEVPPELVGQPAVHLKRDFFLANASRARSEQFINLREVS
hCAN10    (415) -KHYQAVCLHLWKVEK----R---RVNLPRVLSMPPVAGTACHAYDREVH
hCAN11    (424) -AQLQTIGFVLYAVPKEFQNIQDVHLKKEFFTKYQDHGFSEIFTNSREVS
hCAN2     (424) -EDMHTIGFGIYEVPPKEMHGNK-QHLSKNFFLTNRARERSDTFINLREVL
hCAN3     (497) -ASLFTIGFAIYEVPKEMHGNK-QHLQKDFFLYNASKARSKTYINMREVS
hCAN5     (417) KGENLAIGFDIYKVEEN---RQ------YRMHSLQHKAASSIYINSRSVF
hCAN9     (413) -ANVLTIGYAIYECP---DKD-EHLNKDFFRYHASRARSKTFINLREVS
mCalpain1 (436) -RDMETIGFAVYQVPRELAGQP-VHLKRDFFLANASRAQSEHFINLREVS
mLP82     (429) -ANLFTIGFAIYEVPKEMHGNK-QHLQKDFFLYNASKARSKTYINMREVS
rNCl2     (426) QG-MLAIGFDIYKVEEN---RQ------YRMHSLQHKAASSIYINSRSVF
CAN-12    (414) -KPLLAIGFYLV----------R---------------------------
CAN-12v1  (415) -KPLLAIGFYLY---R--YHDDQRRLPPEFFQRNTPLSQPDRFLKEKEVS
CAN-12v2  (415) -KPLLAIGFYLYRMNK--YHDDQRRLPPEFFQRNTPLSQPDRFLKEKEVS
```

Figure 2D

```
            601                                                  650
hCAN1    (485) TRFRLPPGEYVVVPSTFEPNKEGDFVLRFFSEKSAGTVELDDQIQANLPD
hCAN10   (457) LRCELSPGYYLAVPSTFLKDAPGEFLLRVFSTGRVSLSAIRAVAKNTTPG
hCAN11   (473) SQLRLPPGEYITIPSTFEPHRDADFLLRVFTEKHSESWELDEVNYAEQLQ
hCAN2    (473) NRFKLPPGEYILVPSTFEPNKDGDFCIRVFSEKKADYQAVDDEIEANLEE
hCAN3    (545) QRFRLPPSEYVIVPSTYEPHQEGEFILRVFSEKRNLSEEVENTISVDRPV
hCAN5    (458) LRTDQPEGRYVIIPTTFEPGHTGEFLLRVFTDVPSNCRELRLDKPPHTCW
hCAN9    (457) DRFKLPPGEYILIPSTFEPHQEADFCLRIFSEKKAITRDMDGNVDIDLPE
mCalpain1(484) NRIRLPPGEYIVVPSTFEPNKEGDFLLRFFSEKKAGTQELDDQIQANLPD
mLP82    (477) QRFRLPPSEYVIVPSTYEPHQEGEFILRVFSEKRNLSEEAENTISVDRPV
rNC12    (466) LRTDQPEGRYVIIPTTFEPGHTGEFLLRVFTDVPSNCRELRLDKPPHTCW
CAN-12   (426) --------------------------------------------------
CAN-12v1 (459) QELCLEPGTYLIVPCILEAHQKSEFVLRVFSRKHIFYEIGSNSGVVFSKE
CAN-12v2 (462) QELCLEPGTYLIVPCILEAHQKSEFVLRVFSRKHIFYEIGSNSGVVFSKE 651                                                  700
hCAN1    (535) EQVLS---------------------------------------------
hCAN10   (507) AALPAG--------------------------------------------
hCAN11   (523) EEKVS---------------------------------------------
hCAN2    (523) FDIS----------------------------------------------
hCAN3    (595) KKKKTKPIIFVSDRANSNKELGVDQESEEGKGKTSPDKQKQSPQPQPGSS
hCAN5    (508) SSLCG---------------------------------------------
hCAN9    (507) PPK-------------------------------------------PTPP
mCalpain1(534) EKVLS---------------------------------------------
mLP82    (527) PR--------------------------------------------PGHT
rNC12    (516) SSLCG---------------------------------------------
CAN-12   (426) --------------------------------------------------
CAN-12v1 (509) IE------------------------------------------------
CAN-12v2 (512) IE------------------------------------------------

701                                                  750
hCAN1    (540) --EEEIDENFKALFRQLAGEDMEISVKELRTILNRIISKHKD-LRTKGFS
hCAN10   (513) -EWGTVQLRGSWRVGQTAGGSRNFASYPTNPCFPFSVPEGPGPRCVRITL
hCAN11   (528) --EDDMDQDFLHLEKIVAGEGKEIGVYELQRLLNRMAIKFKS-FKTKGFG
hCAN2    (527) --EDDIDDGVRRLEAQLAGEDAEISAFELQTILRRVLAKRQD-IKSDGFS
hCAN3    (645) DQESEEQQQFRNIFKQIAGDDMEICADELKKVLNTVVNKHKD-LKTHGFT
hCAN5    (513) ----YPQLVTQVHVLGAAGLKDSPTGANSYVIIKCEGDKVRS-AVQKGTS
hCAN9    (514) DQETEEEQRFRALFEQVAGEDMEVTAEELEYVLNAVLQKKKD-IKFKKLS
mCalpain1(539) --EEEIDDNFKTLFSKLAGDDMEISVKELQTILNRIISKHKD-LRTNGFS
mLP82    (533) DQESEEQQQFRNIFRQIAGDDMEICADELKNVLNTVVNKHKD-LKTQGFT
rNC12    (521) ----YPQLVTQVHVLGAAGLKDSPTGANSYVIIKCEGDKVRS-AVQKGTS
CAN-12   (426) ------------------------------MNKMTWSSLG-SRQPFFS
CAN-12v1 (511) ----DQNERQDEFFTKFFEKHPEINAVQLQNLLNQMTWSSLG-SRQPFFS
CAN-12v2 (514) ----DQNERQDEFFTKFFEKHPEINAVQLQNLLNQMTWSSLG-SRQPFFS 751                                                  800
hCAN1    (587) LESCRSMVNLMDRDGNGKLGLVEFNILWNRIRNYLSIFRKFDLDKSGSMS
hCAN10   (562) HQHCRPSDTEFHPIGFHIFQVPEGGRSQDAPPLLLQFFLLSCVPHRYAQE
hCAN11   (575) LDACRCMINLMKDGSGKIGLLEFKILWKKLKKWMDIFRECDQDHSGTLN
hCAN2    (574) IETCKIMVDMLSDGSGKIGLKEFYILWTKIQKYQKIYREIDVDRSGTMN
hCAN3    (694) LESCRSMIALMDTDGSGKLNLQEFHHLWNKIKAWQKIFKHYDTDQSGTIN
hCAN5    (558) TPEYNVKGIFYRKKLSQPITVQVWNHRVLKDEFLGQVHLKADPDNLQALH
hCAN9    (563) IISCKNIISLMDTSCNGKLEFDEFKVFWDKLKQWINLFLRFDADKSGTMS
mCalpain1(586) LESCRSMVNLMDRDCNGKLGLVEFNILWNRIRNYLTIFRKFDLDKSGSMS
mLP82    (582) LESCRSMIALMDTDGSCRLNLQEFHHLWKKIKAWQKIFKHYDTDHSGTIN
rNC12    (566) TPEYNVKGIFYRKKLSQPITVQVWNHRVLKDEFLGQVHLKADPDNLQALH
CAN-12   (443) LEACQGTILALLDLNASGTMSIQEFRDLWKQLKLSQKVFHKQDRG-SGYLN
CAN-12v1 (556) LEACQGTILALLDLNASGTMSIQEFRDLWKQLKLSQKVFHKQDRG-SGYLN
CAN-12v2 (559) LEACQGTILALLDLNASGTMSIQEFRDLWKQLKLSQKVFHKQDRG-SGYLN
```

Figure 2E

```
              801                                                    850
hCAN1     (637) AYEMRMAIESAG-----FKINKKLYELIITR-------YSEPDLAVDFDN
hCAN10    (612) VSRLCLLPAG-------------------------------TYKVVPST
hCAN11    (625) SYEMRLVIEKAG-----IKLNNKVMQVLVAR-------YADDDLIIDFDS
hCAN2     (624) SYEMRKALEEAG-----FKMPCQLHQVIVAR-------FADDQLIIDFDN
hCAN3     (744) SYEMRNAVNDAG-----FHLNNQLYDIITMR-------YADKHMNIDFDS
hCAN5     (608) TLHLRDRNSRQP--------------------------------------
hCAN9     (613) IYELRTALKAAG-----FQLSSHLLQLIVLR-------YADEELQLDFDD
mCalpain1 (636) AYEMRMAIEAAG-----FKLNKKLHELIITR-------YSEPDLAVDFDN
mLP82     (632) SYEMRNAVNDAG-----FHLNSQLYDIITMR-------YADKHMNIDFDS
rNC12     (616) TLHLRDRNSRQP--------------------------------------
CAN-12    (492) WEQLHAAMREAGRHRKSWSCGHTRAGCTLIRQRRGDVWHAEVTLIRSVTL
CAN-12v1  (605) WEQLHAAMREAGRHRKSWSCGHTRAGCTLIRQRRGDVWHAEVTLIRSVTL
CAN-12v2  (608) WEQLHAAMREAGRHRKSWSCGHTRAGCTLIRQRRGDVWHAEVTLIRSVTL 851                              892
hCAN1     (675) FVCCLVRLETMFRFFKTIDTDLDGVVTFDLFKWLQLIMFA--
hCAN10    (630) YLPDTEGAFIVTIATRIDPSIHSQEMLGQFLQEVSVMAVMKT
hCAN11    (663) FISCFLRLKIMFTFFLTMDPKNTGHICLSLEQWLQMIMWG--
hCAN2     (662) FVRCLVRLEILFKIFKQLDPENTGTLELDLISWLCFSVL---
hCAN3     (782) FICCFVRLEGMERAFHAFDKDGDGIIKLNVLEWLQLIMYA--
hCAN5     (620) ------------------SNLPGTVAVHILSSTSLMAV---
hCAN9     (651) FLNCLVRLENASRVFQALSTKNKEFIHLNINEFIHLIMNI--
mCalpain1 (674) FVCCLVRLETMFRFFKLLDTDLDGVVTFDLFKWLQLIMFA--
mLP82     (670) FICCFVRLEGMERAFNAFDKDGDGIIKLNVLEWLQLIMYA--
rNC12     (628) ------------------SNLPGTVAVHILSSTSLMAV---
CAN-12    (542) KDVDLQSTPIFFMIVPVILANIDGGVAHSTSYLIFNTTLL--
CAN-12v1  (655) KDVDLQSTPIFFMIVPVILANIDGGVAHSTSYLIFNTTLL--
CAN-12v2  (658) KDVDLQSTPIFFMIVPVILANIDGGVAHSTSYLIFNTTLL--
```

Figure 5A

CAN-12+ (SEQ ID NO:2)

| Protein | Genbank ID | Identities | Similarities |
|---|---|---|---|
| human CAN10 protein | gi|NP_075574 | 30.7% | 38.0% |
| human CAN5 protein | gi|NP_004046 | 34.2% | 45.4% |
| the large catalytic subunit of the human CALPAIN 1 protein | gi|12408656 | 37.9% | 47.4% |
| the large subunit of the human calpain 3 protein | gi|4557405 | 36.3% | 43.6% |
| the large catalytic subunit of the mouse CALPAIN 1 protein | gi|O88666 | 39.0% | 47.6% |
| mouse CALPAIN LP82 | gi|3661585 | 37.8% | 45.3% |
| rat stomach-specific calcium-activated neutral protease large subunit, NCL2 protein | gi|NP_006606 | 34.2% | 45.4% |
| human CAN11 protein | gi|NP_008989 | 40.4% | 47.3% |
| human CAN2 protein | gi|4502563 | 36.8% | 45.8% |
| human CAN9 protein | gi|5729758 | 39.4% | 47.2% |

CAN-12v1 (SEQ ID NO:54)

| Protein | Genbank ID | Identities | Similarities |
|---|---|---|---|
| human CAN10 protein | gi|NP_075574 | 28.7% | 35.6% |
| human CAN5 protein | gi|NP_004046 | 33.3% | 45.1% |
| the large catalytic subunit of the human CALPAIN 1 protein | gi|12408656 | 38.3% | 46.8% |
| the large subunit of the human calpain 3 protein | gi|4557405 | 40.4% | 49.1% |
| the large catalytic subunit of the mouse CALPAIN 1 protein | gi|O88666 | 39.8% | 47.8% |
| mouse CALPAIN LP82 | gi|3661585 | 40.6% | 48.8% |
| rat stomach-specific calcium-activated neutral protease large subunit, NCL2 protein | gi|NP_006606 | 36.3% | 44.9% |
| human CAN11 protein | gi|NP_008989 | 38.8% | 47.4% |
| human CAN2 protein | gi|4502563 | 37.9% | 47.6% |
| human CAN9 protein | gi|5729758 | 40.7% | 49.8% |

CAN-12v2 (SEQ ID NO:56)

| Protein | Genbank ID | Identities | Similarities |
|---|---|---|---|
| human CAN10 protein | gi|NP_075574 | 28.8% | 35.7% |
| human CAN5 protein | gi|NP_004046 | 33.3% | 45.1% |
| the large catalytic subunit of the human CALPAIN 1 protein | gi|12408656 | 38.3% | 46.6% |
| the large subunit of the human calpain 3 protein | gi|4557405 | 41.3% | 49.8% |
| the large catalytic subunit of the mouse CALPAIN 1 protein | gi|O88666 | 39.6% | 47.6% |
| mouse CALPAIN LP82 | gi|3661585 | 40.6% | 48.8% |
| rat stomach-specific calcium-activated neutral protease large subunit, NCL2 protein | gi|NP_006606 | 36.3% | 44.9% |
| human CAN11 protein | gi|NP_008989 | 38.8% | 47.3% |
| human CAN2 protein | gi|4502563 | 37.9% | 47.3% |
| human CAN9 protein | gi|5729758 | 40.7% | 49.8% |

Figure 5B

CAN-12 (SEQ ID NO:24)

| Protein | Genbank ID | Identities | Similarities |
|---|---|---|---|
| human CAN10 protein | gi|NP_075574 | 34.3% | 42.3% |
| human CAN5 protein | gi|NP_004046 | 40.5% | 51.9% |
| the large catalytic subunit of the human CALPAIN 1 protein | gi|12408656 | 44.3% | 51.9% |
| the large subunit of the human calpain 3 protein | gi|4557405 | 44.9% | 51.8% |
| the large catalytic subunit of the mouse CALPAIN 1 protein | gi|O88666 | 46.1% | 52.7% |
| mouse CALPAIN LP82 | gi|3661585 | 46.2% | 53.5% |
| rat stomach-specific calcium-activated neutral protease large subunit, NCL2 protein | gi|NP_006606 | 44.6% | 51.4% |
| human CAN11 protein | gi|NP_008989 | 45.5% | 51.7% |
| human CAN2 protein | gi|4502563 | 46.2% | 53.5% |
| human CAN9 protein | gi|5729758 | 44.3% | 51.9% |

Figure 7

>AC015980_27.[9107:987].spCAGGACTTTGAGGCCCTGCTGGCAGAGTGCCTGAGGAATGGC
TGCCTCTTTGAAGACACCAGCTTCCCGGCCACCCTGAGCTCCATCGGCAGTGGCTCCCTGC
TGCAGAAGCTGCCACCCCGCCTGCAGTGGAAGAGGCCCCCGGAGCTGCACAGCAATCCCC
AGTTTTATTTTGCCAAGGCCAAAAGGCTGGATCTGTGCCAGGGGATAGTAGGAGACTGCTGG
TTCTTGGCTGCTTTGCAAGCTCTGGCCTTGCACCAGGACATCCTGAGCCGGGTTGTTCCCCT
GAATCAGAGTTTCACTGAGAAGTATGCTGGCATCTTCCGGTTCTGGTTCTGGCACTATGGGA
ACTGGGTTCCTGTGGTGATCGATGACCGTCTGCCTGTGAATGAGGCTGGCCAGCTGGTCTT
TGTCTCCTCCACCTATAAGAACTTGTTCTGGGGAGCACTTCTGGAAAAGGCCTATGCCAAGC
TCTCTGGTTCCTATGAAGACTTGCAGTCAGGACAGGTGTCTGAAGCCCTTGTAGACTTCACT
GGAGGGGTGACAATGACCATCAACCTGGCAGAAGCCCATGGCAACCTCTGGGACATCCTCA
TCGAAGCCACCTACAACAGAACCCTCATTGGCTGCCAGACCCACTCAGGGGAGAAGATTCT
GGAGAATGGGCTGGTGGAAGGCCATGCCTATACTCTCACAGGAATCAGGAAGGTGACCTGC
AAACATAGACCTGAATATCTCGTCAAGCTACGGAACCCCTGGGGAAAGGTGGAATGGAAAG
GAGACTGGAGTGAC (SEQ ID NO:13).

>AC015980_22.[6610:2602].spATGACGCTGCAGGACTTTAAAACACATTTCGTGCTCCTGGTT
ATCTGTAAACTGACCCCAGGCCTGTTGAGCCAGGAGGCGGCCCAGAAGTGGACGTACACCA
TGCGGGAGGGGAGATGGGAGAAGCGGAGCACAGCTGGTGGCCAGAGGCAGTTGCTGCAG
GACACATTTTGGAAGAACCCGCAGTTCCTGCTGTCTGTCTGGAGGCCCGAGGAGGGCAGGA
GATCCCTGAGGCCCTGCAGCGTGCTGGTGTCCCTGCTCCAGAAGCCCAGGCACAGGTGCC
GCAAGCGGAAGCCTCTCCTCGCCATTGGCTTCTACCTGTATAGGGTAGCCATAAAATGGAAG
GCACAGGGACATTCCTCACATCATTTAGTGCTGGTGTTGTTTTTAAGAAACACTCCTCTGAGC
CAGCCTGATAGGTTTCTCAAGGAGAAAGAAGTGAGTCAGGAGCTGTGTCTGGAACCAGGGA
CGTACCTCATCGTGCCCTGCATATTGGAGGCCCACCAGAAGTCAGAGTTCGTCCTCAGGGT
CTTCTCCAGGAAG (SEQ ID NO:14).

>AC015980_2.[21:86].spAAATGGGAACTCTTTAGAATAGATGGATCCTTGAGGCACACAAGTA
CTCAAATGTCAGCAAGGAAT (SEQ ID NO:15).

>AC015980_27.[4504:4554].spTTCCAATACCATACCCATCCTGAATGGCTCCAGCTGGTGGTC
ATAGATAAA (SEQ ID NO:16).

>AC015980_29.[395:433].spGAGTGGTTCCTTCTGAAAGCTCCAAGGAAGAACCTATTT (SEQ
ID NO:17).

>AC015980.[195:1397]
CAGGACTTTGAGGCCCTGCTGGCAGAGTGCCTGAGGAATGGCTGCCTCTTTGAAGACACCA
GCTTCCCGGCCACCCTGAGCTCCATCGGCAGTGGCTCCCTGCTGCAGAAGCTGCCACCCC
GCCTGCAGTGGAAGAGGCCCCCGGAGCTGCACAGCAATCCCCAGTTTTATTTTGCCAAGGC
CAAAAGGCTGGATCTGTGCCAGGGGATAGTAGGAGACTGCTGGTTCTTGGCTGCTTTGCAA
GCTCTGGCCTTGCACCAGGACATCCTGAGCCGGGTTGTTCCCCTGAATCAGAGTTTCACTGA
GAAGTATGCTGGCATCTTCCGGTTCTGGTTCTGGCACTATGGGAACTGGGTTCCTGTGGTGA
TCGATGACCGTCTGCCTGTGAATGAGGCTGGCCAGCTGGTCTTTGTCTCCTCCACCTATAAG
AACTTGTTCTGGGGAGCACTTCTGGAAAAGGCCTATGCCAAGCTCTCTGGTTCCTATGAAGA
CTTGCAGTCAGGACAGGTGTCTGAAGCCCTTGTAGACTTCACTGGAGGGGTGACAATGACC
ATCAACCTGGCAGAAGCCCATGGCAACCTCTGGGACATCCTCATCGAAGCCACCTACAACA
GAACCCTCATTGGCTGCCAGACCCACTCAGGGAAGATTCTGGAGAATGGGCTGGTGGAAGG
CCATGCCTATACTCTCACAGGAATCAGGAAGGTGACCTGCAAACATAGACCTGAATATCTCG
TCAAGCTACGGAACCCCTGGGGAAAGGTGGAATGGAAAGGAGACTGGAGTGACAGTTCAAG
TAAATGGGAGCTGCTGAGCCCCAAGGAGAAGATTCTGCTTCTGAGGAAAGACAATGACGGA
GAATTCTGGATGACGCTGCAGGACTTTAAAACACATTTCGTGCTCCTGGTTATCTGTAAACTG
ACCCCAGGCCTGTTGAGCCAGGAGGCGGCCCAGAAGTGGACGTACACCATGCGGGAGGGG
AGATGGGAGAAGCGGAGCACAGCTGGTGGCCAGAGGCAGTTGCTGCAGGACACATTTTGG
AAGAACCCGCAGTTCCTGCTGTCTGTCTGGAGGCCCGAGGAGGGCAGGAGATCCCTGAGG
CCCTGCAGCGTGCTGGTGTCCCTGCTCCAGAAGCCCAGGCACAGGTGCCGCAAGCGGAAG
CCTCTCCTCGCCATTGGCTTCTACCTCTATAGGATGAACAAG (SEQ ID NO:26).

Figure 8A

```
  1  CACCTGCCATGTCTCTGTGGCCACCTTTCCGATGCAGATGGAAGCTGGCGCCAAGGTACT   60
  1            M  S  L  W  P  P  F  R  C  R  W  K  L  A  P  R  Y  S   18

61  CTAGGAGGGCGTCTCCACAGCAACCCCAACAGGACTTTGAGGCCCTGCTGGCAGAGTGCC  120
 19   R  R  A  S  P  Q  Q  P  Q  Q  D  F  E  A  L  L  A  E  C  L   38

121  TGAGGAATGGCTGCCTCTTTGAAGACACCAGCTTCCCGGCCACCCTGAGCTCCATCGGCA  180
 39   R  N  G  C  L  F  E  D  T  S  F  P  A  T  L  S  S  I  G  S   58

181  GTGGCTCCCTGCTGCAGAAGCTGCCACCCCGCCTGCAGTGGAAGAGGCCCCCGGAGCTGC  240
 59   G  S  L  L  Q  K  L  P  P  R  L  Q  W  K  R  P  P  E  L  H   78

241  ACAGCAATCCCCAGTTTTATTTTGCCAAGGCCAAAAGGCTGGATCTGTGCCAGGGGATAG  300
 79   S  N  P  Q  F  Y  F  A  K  A  K  R  L  D  L  C  Q  G  I  V   98

301  TAGGAGACTGCTGGTTCTTGGCTGCTTTGCAAGCTCTGGCCTTGCACCAGGACATCCTGA  360
 99   G  D  C  W  F  L  A  A  L  Q  A  L  A  L  H  Q  D  I  L  S  118
                 ↑

361  GCCGGGTTGTTCCCCTGAATCAGAGTTTCACTGAGAAGTATGCTGGCATCTTCCGGTTCT  420
119   R  V  V  P  L  N  Q  S  F  T  E  K  Y  A  G  I  F  R  F  W  138

421  GGTTCTGGCACTATGGGAACTGGGTTCCTGTGGTGATCGATGACCGTCTGCCTGTGAATG  480
139   F  W  H  Y  G  N  W  V  P  V  V  I  D  D  R  L  P  V  N  E  158

481  AGGCTGGCCAGCTGGTCTTTGTCTCCTCCACCTATAAGAACTTGTTCTGGGGAGCACTTC  540
159   A  G  Q  L  V  F  V  S  S  T  Y  K  N  L  F  W  G  A  L  L  178

541  TGGAAAAGGCCTATGCCAAGCTCTCTGGTTCCTATGAAGACTTGCAGTCAGGACAGGTGT  600
179   E  K  A  Y  A  K  L  S  G  S  Y  E  D  L  Q  S  G  Q  V  S  198

601  CTGAAGCCCTTGTAGACTTCACTGGAGGGGTGACAATGACCATCAACCTGGCAGAAGCCC  660
199   E  A  L  V  D  F  T  G  G  V  T  M  T  I  N  L  A  E  A  H  218

661  ATGGCAACCTCTGGGACATCCTCATCGAAGCCACCTACAACAGAACCCTCATTGGCTGCC  720
219   G  N  L  W  D  I  L  I  E  A  T  Y  N  R  T  L  I  G  C  Q  238

721  AGACCCACTCAGGGGAGAAGATTCTGGAGAATGGGCTGGTGGAAGGCCATGCCTATACTC  780
239   T  H  S  G  E  K  I  L  E  N  G  L  V  E  G  H  A  Y  T  L  258
                                                     ↑

781  TCACAGGAATCAGGAAGGTGACCTGCAAACATAGACCTGAATATCTCGTCAAGCTACGGA  840
259   T  G  I  R  K  V  T  C  K  H  R  P  E  Y  L  V  K  L  R  N  278
                                                                 ↑

841  ACCCCTGGGGAAAGGTGGAATGGAAAGGAGACTGGAGTGACAGTTCAAGTAAATGGGAGC  900
279   P  W  G  K  V  E  W  K  G  D  W  S  D  S  S  K  W  E  L  298
```

Figure 8B

```
 901  TGCTGAGCCCCAAGGAGAAGATTCTGCTTCTGAGGAAAGACAATGACGGAGAATTCTGGA   960
 299    L  S  P  K  E  K  I  L  L  L  R  K  D  N  D  G  E  F  W  M   318

961  TGACGCTGCAGGACTTTAAAACACATTTCGTGCTCCTGGTTATCTGTAAACTGACCCCAG  1020
 319    T  L  Q  D  F  K  T  H  F  V  L  L  L  V  I  C  K  L  T  P  G  338

1021  GCCTGTTGAGCCAGGAGGCGGCCCAGAAGTGGACGTACACCATGCGGGAGGGGAGATGGG  1080
 339    L  L  S  Q  E  A  A  Q  K  W  T  Y  T  M  R  E  G  R  W  E   358

1081  AGAAGCGGAGCACAGCTGGTGGCCAGAGGCAGTTGCTGCAGGACACATTTTGGAAGAACC  1140
 359    K  R  S  T  A  G  G  Q  R  Q  L  L  Q  D  T  F  W  K  N  P   378

1141  CGCAGTTCCTGCTGTCTGTCTGGAGGCCCGAGGAGGGCAGGAGATCCCTGAGGCCCTGCA  1200
 379    Q  F  L  L  S  V  W  R  P  E  E  G  R  R  S  L  R  P  C  S   398

1201  GCGTGCTGGTGTCCCTGCTCCAGAAGCCCAGGCACAGGTGCCGCAAGCGGAAGCCTCTCC  1260
 399    V  L  V  S  L  L  Q  K  P  R  H  R  C  R  K  R  K  P  L  L   418

1261  TCGCCATTGGCTTCTACCTCTATAGGTACCATGATGACCAGAGGAGACTGCCCCCTGAGT  1320
 419    A  I  G  F  Y  L  Y  R  Y  H  D  D  Q  R  R  L  P  P  E  F   438

1321  TCTTCCAGAGAAACACTCCTCTGAGCCAGCCTGATAGGTTTCTCAAGGAGAAAGAAGTGA  1380
 439    F  Q  R  N  T  P  L  S  Q  P  D  R  F  L  K  E  K  E  V  S   458

1381  GTCAGGAGCTGTGTCTGGAACCAGGGACGTACCTCATCGTGCCCTGCATATTGGAGGCCC  1440
 459    Q  E  L  C  L  E  P  G  T  Y  L  I  V  P  C  I  L  E  A  H   478

1441  ACCAGAAGTCAGAGTTCGTCCTCAGGGTCTTCTCCAGGAAGCACATCTTTTATGAAATTG  1500
 479    Q  K  S  E  F  V  L  R  V  F  S  R  K  H  I  F  Y  E  I  G   498

1501  GCAGCAATTCTGGTGTCGTCTTCTCAAAGGAGATAGAAGACCAAAATGAAAGGCAGGATG  1560
 499    S  N  S  G  V  V  F  S  K  E  I  E  D  Q  N  E  R  Q  D  E   518

1561  AATTCTTCACCAAATTCTTTGAAAAGCATCCAGAGATTAATGCAGTTCAACTTCAGAACC  1620
 519    F  F  T  K  F  F  E  K  H  P  E  I  N  A  V  Q  L  Q  N  L   538

1621  TCCTGAACCAGATGACCTGGTCAAGTCTGGGGAGCAGACAGCCCTTCTTTAGCCTGGAAG  1680
 539    L  N  Q  M  T  W  S  S  L  G  S  R  Q  P  F  F  S  L  E  A   558

1681  CCTGCCAGGGGATCCTGGCCTTACTGGACCTTAATGCATCAGGTACTATGAGCATCCAGG  1740
 559    C  Q  G  I  L  A  L  L  D  L  N  A  S  G  T  M  S  I  Q  E   578

1741  AATTCAGGGACCTGTGGAAGCAGCTGAAGCTCTCTCAGAAGGTTTTCCACAAGCAAGACC  1800
 579    F  R  D  L  W  K  Q  L  K  L  S  Q  K  V  F  H  K  Q  D  R   598
```

Figure 8C

```
1801  GTGGGTCAGGATACCTGAACTGGGAGCAGCTGCACGCTGCCATGAGGGAGGCAGGTAGGC  1860
599     G   S   G   Y   L   N   W   E   Q   L   H   A   A   M   R   E   A   G   R   H    618

1861  ACAGGAAGAGCTGGAGCTGTGGGCACACACGGGCAGGGTGCACACTCATCAGGCAGAGGA  1920
619     R   K   S   W   S   C   G   H   T   R   A   G   C   T   L   I   R   Q   R   R    638

1921  GAGGGGATGTGTGGCATGCTGAAGTAACTCTAATACGCAGTGTTACTCTCAAAGACGTAG  1980
639     G   D   V   W   H   A   E   V   T   L   I   R   S   V   T   L   K   D   V   D    658

1981  ATCTGCAGTCAACTCCAACATTTTTTATGATTGTCCCTGTGATCCTAGCCAACATTGATG  2040
659     L   Q   S   T   P   T   F   F   M   I   V   P   V   I   L   A   N   I   D   G    678

2041  GAGGGGTGGCACATTCAACTTCTTATTTAATCTTCAACACCACCTTGTTATAATC  2095
679     G   V   A   H   S   T   S   Y   L   I   F   N   T   T   L   L              694
```

Figure 9A

```
  1  CACCTGCCATGTCTCTGTGGCCACCTTTCCGATGCAGATGGAAGCTGGCGCCAAGGTACT   60
  1             M  S  L  W  P  P  F  R  C  R  W  K  L  A  P  R  Y  S    18

61  CTAGGAGGGCGTCTCCACAGCAACCCCAACAGGACTTTGAGGCCCTGCTGGCAGAGTGCC  120
 19   R  R  A  S  P  Q  Q  P  Q  Q  D  F  E  A  L  L  A  E  C  L    38

121  TGAGGAATGGCTGCCTCTTTGAAGACACCAGCTTCCCGGCCACCCTGAGCTCCATCGGCA  180
 39   R  N  G  C  L  F  E  D  T  S  F  P  A  T  L  S  S  I  G  S    58

181  GTGGCTCCCTGCTGCAGAAGCTGCCACCCCGCCTGCAGTGGAAGAGGCCCCCGGAGCTGC  240
 59    G  S  L  L  Q  K  L  P  P  R  L  Q  W  K  R  P  P  E  L  H    78

241  ACAGCAATCCCCAGTTTTATTTTGCCAAGGCCAAAAGGCTGGATCTGTGCCAGGGGATAG  300
 79    S  N  P  Q  F  Y  F  A  K  A  K  R  L  D  L  C  Q  G  I  V    98

301  TAGGAGACTGCTGGTTCTTGGCTGCTTTGCAAGCTCTGGCCTTGCACCAGGACATCCTGA  360
 99    G  D  C  W  F  L  A  A  L  Q  A  L  H  Q  D  I  L  S   118

361  GCCGGGTTGTTCCCCTGAATCAGAGTTTCACTGAGAAGTATGCTGGCATCTTCCGGTTCT  420
119    R  V  V  P  L  N  Q  S  F  T  E  K  Y  A  G  I  F  R  F  W   138

421  GGTTCTGGCACTATGGGAACTGGGTTCCTGTGGTGATCGATGACCGTCTGCCTGTGAATG  480
139    F  W  H  Y  G  N  W  V  P  V  V  I  D  D  R  L  P  V  N  E   158

481  AGGCTGGCCAGCTGGTCTTTGTCTCCTCCACCTATAAGAACTTGTTCTGGGGAGCACTTC  540
159    A  G  Q  L  V  F  V  S  S  T  Y  K  N  L  F  W  G  A  L  L   178

541  TGGAAAAGGCCTATGCCAAGCTCTCTGGTTCCTATGAAGACTTGCAGTCAGGACAGGTGT  600
179    E  K  A  Y  A  K  L  S  G  S  Y  E  D  L  Q  S  G  Q  V  S   198

601  CTGAAGCCCTTGTAGACTTCACTGGAGGGGTGACAATGACCATCAACCTGGCAGAAGCCC  660
199    E  A  L  V  D  F  T  G  G  V  T  M  T  I  N  L  A  E  A  H   218

661  ATGGCAACCTCTGGGACATCCTCATCGAAGCCACCTACAACAGAACCCTCATTGGCTGCC  720
219    G  N  L  W  D  I  L  I  E  A  T  Y  N  R  T  L  I  G  C  Q   238

721  AGACCCACTCAGGGGAGAAGATTCTGGAGAATGGGCTGGTGGAAGGCCATGCCTATACTC  780
239    T  H  S  G  E  K  I  L  E  N  G  L  V  E  G  H  A  Y  T  L   258

781  TCACAGGAATCAGGAAGGTGACCTGCAAACATAGACCTGAATATCTCGTCAAGCTACGGA  840
259    T  G  I  R  K  V  T  C  K  H  R  P  E  Y  L  V  K  L  R  N   278
```

Figure 9B

```
 841  ACCCCTGGGGAAAGGTGGAATGGAAAGGAGACTGGAGTGACAGTTCAAGTAAATGGGAGC   900
 279   P  W  G  K  V  E  W  K  G  D  W  S  D  S  S  S  K  W  E  L   298

901  TGCTGAGCCCCAAGGAGAAGATTCTGCTTCTGAGGAAAGACAATGACGGAGAATTCTGGA   960
 299   L  S  P  K  E  K  I  L  L  L  R  K  D  N  D  G  E  F  W  M   318

961  TGACGCTGCAGGACTTTAAAACACATTTCGTGCTCCTGGTTATCTGTAAACTGACCCCAG  1020
 319   T  L  Q  D  F  K  T  H  F  V  L  L  V  I  C  K  L  T  P  G   338

1021  GCCTGTTGAGCCAGGAGGCGGCCCAGAAGTGGACGTACACCATGCGGGAGGGGAGATGGG  1080
 339   L  L  S  Q  E  A  A  Q  K  W  T  Y  T  M  R  E  G  R  W  E   358

1081  AGAAGCGGAGCACAGCTGGTGGCCAGAGGCAGTTGCTGCAGGACACATTTTGGAAGAACC  1140
 359   K  R  S  T  A  G  G  Q  R  Q  L  L  Q  D  T  F  W  K  N  P   378

1141  CGCAGTTCCTGCTGTCTGTCTGGAGGCCCGAGGAGGGCAGGAGATCCCTGAGGCCCTGCA  1200
 379   Q  F  L  L  S  V  W  R  P  E  E  G  R  R  S  L  R  P  C  S   398

1201  GCGTGCTGGTGTCCCTGCTCCAGAAGCCCAGGCACAGGTGCCGCAAGCGGAAGCCTCTCC  1260
 399   V  L  V  S  L  L  Q  K  P  R  H  R  C  R  K  R  K  P  L  L   418

1261  TCGCCATTGGCTTCTACCTCTATAGGATGAACAAGTACCATGATGACCAGAGGAGACTGC  1320
 419   A  I  G  F  Y  L  Y  R  M  N  K  Y  H  D  D  Q  R  R  L  P   438

1321  CCCCTGAGTTCTTCCAGAGAAACACTCCTCTGAGCCAGCCTGATAGGTTTCTCAAGGAGA  1380
 439   P  E  F  F  Q  R  N  T  P  L  S  Q  P  D  R  F  L  K  E  K   458

1381  AAGAAGTGAGTCAGGAGCTGTGTCTGGAACCAGGGACGTACCTCATCGTGCCCTGCATAT  1440
 459   E  V  S  Q  E  L  C  L  E  P  G  T  Y  L  I  V  P  C  I  L   478

1441  TGGAGGCCCACCAGAAGTCAGAGTTCGTCCTCAGGGTCTTCTCCAGGAAGCACATCTTTT  1500
 479   E  A  H  Q  K  S  E  F  V  L  R  V  F  S  R  K  H  I  F  Y   498

1501  ATGAAATTGGCAGCAATTCTGGTGTCGTCTTCTCAAAGGAGATAGAAGACCAAAATGAAA  1560
 499   E  I  G  S  N  S  G  V  V  F  S  K  E  I  E  D  Q  N  E  R   518

1561  GGCAGGATGAATTCTTCACCAAATTCTTTGAAAAGCATCCAGAGATTAATGCAGTTCAAC  1620
 519   Q  D  E  F  F  T  K  F  F  E  K  H  P  E  I  N  A  V  Q  L   538

1621  TTCAGAACCTCCTGAACCAGATGACCTGGTCAAGTCTGGGGAGCAGACAGCCCTTCTTTA  1680
 539   Q  N  L  L  N  Q  M  T  W  S  S  L  G  S  R  Q  P  F  F  S   558

1681  GCCTGGAAGCCTGCCAGGGGATCCTGGCCTTACTGGACCTTAATGCATCAGGTACTATGA  1740
 559   L  E  A  C  Q  G  I  L  A  L  L  D  L  N  A  S  G  T  M  S   578
```

Figure 9C

```
1741   GCATCCAGGAATTCAGGGACCTGTGGAAGCAGCTGAAGCTCTCTCAGAAGGTTTTCCACA   1800
 579     I   Q   E   F   R   D   L   W   K   Q   L   K   L   S   Q   K   V   F   H   K    598

1801   AGCAAGACCGTGGGTCAGGATACCTGAACTGGGAGCAGCTGCACGCTGCCATGAGGGAGG   1860
 599     Q   D   R   G   S   G   Y   L   N   W   E   Q   L   H   A   A   M   R   E   A    618

1861   CAGGTAGGCACAGGAAGAGCTGGAGCTGTGGGCACACACGGGCAGGGTGCACACTCATCA   1920
 619     G   R   H   R   K   S   W   S   C   G   H   T   R   A   G   C   T   L   I   R    638

1921   GGCAGAGGAGAGGGGATGTGTGGCATGCTGAAGTAACTCTAATACGCAGTGTTACTCTCA   1980
 639     Q   R   R   G   D   V   W   H   A   E   V   T   L   I   R   S   V   T   L   K    658

1981   AAGACGTAGATCTGCAGTCAACTCCAACATTTTTTATGATTGTCCCTGTGATCCTAGCCA   2040
 659     D   V   D   L   Q   S   T   P   T   F   F   M   I   V   P   V   I   L   A   N    678

2041   ACATTGATGGAGGGGTGGCACATTCAACTTCTTATTTAATCTTCAACACCACCTTGTTAT   2100
 679     I   D   G   G   V   A   H   S   T   S   Y   L   I   F   N   T   T   L   L        697

2101   AATC   2104
```

Figure 10A

```
              1                                                  50
CAN-12    (1) MSLWPPFRCRWKLAPRYSRRASPQQPQQDFEALLAECLRNGCLFEDTSFP
CAN-12+   (1) MSLWPPFRCRWKLAPRYSRRASPQQPQQDFEALLAECLRNGCLFEDTSFP
CAN-12v1  (1) MSLWPPFRCRWKLAPRYSRRASPQQPQQDFEALLAECLRNGCLFEDTSFP
CAN-12v2  (1) MSLWPPFRCRWKLAPRYSRRASPQQPQQDFEALLAECLRNGCLFEDTSFP 51                                                100
CAN-12   (51) ATLSSIGSGSLLQKLPPRLQWKRPPELHSNPQFYFAKAKRLDLCQGIVGD
CAN-12+  (51) ATLSSIGSGSLLQKLPPRLQWKRPPELHSNPQFYFAKAKRLDLCQGIVGD
CAN-12v1 (51) ATLSSIGSGSLLQKLPPRLQWKRPPELHSNPQFYFAKAKRLDLCQGIVGD
CAN-12v2 (51) ATLSSIGSGSLLQKLPPRLQWKRPPELHSNPQFYFAKAKRLDLCQGIVGD 101                                               150
CAN-12  (101) CWFLAALQALALHQDILSRVVPLNQSFTEKYAGIFRFWFWHYGNWVPVVI
CAN-12+ (101) CWFLAALQALALHQDILSRVVPLNQSFTEKYAGIFRFWFWHYGNWVPVVI
CAN-12v1(101) CWFLAALQALALHQDILSRVVPLNQSFTEKYAGIFRFWFWHYGNWVPVVI
CAN-12v2(101) CWFLAALQALALHQDILSRVVPLNQSFTEKYAGIFRFWFWHYGNWVPVVI 151                                               200
CAN-12  (151) DDRLPVNEAGQLVFVSSTYKNLFWGALLEKAYAKLSGSYEDLQSGQVSEA
CAN-12+ (151) DDRLPVNEAGQLVFVSSTYKNLFWGALLEKAYAKLSGSYEDLQSGQVSEA
CAN-12v1(151) DDRLPVNEAGQLVFVSSTYKNLFWGALLEKAYAKLSGSYEDLQSGQVSEA
CAN-12v2(151) DDRLPVNEAGQLVFVSSTYKNLFWGALLEKAYAKLSGSYEDLQSGQVSEA 201                                               250
CAN-12  (201) LVDFTGGVTMTINLAEAHGNLWDILIEATYNRTLIGCQTHSG-KILENGL
CAN-12+ (201) LVDFTGGVTMTINLAEAHGNLWDILIEATYNRTLIGCQTHSG-KILENGL
CAN-12v1(201) LVDFTGGVTMTINLAEAHGNLWDILIEATYNRTLIGCQTHSGEKILENGL
CAN-12v2(201) LVDFTGGVTMTINLAEAHGNLWDILIEATYNRTLIGCQTHSGEKILENGL 251                                               300
CAN-12  (250) VEGHAYTLTGIRKVTCKHRPEYLVKLRNPWGKVEWKGDWSDSSSKWELLS
CAN-12+ (250) VEGHAYTLTGIRKVTCKHRPEYLVKLRNPWGKVEWKGDWSDSSSKWELLS
CAN-12v1(251) VEGHAYTLTGIRKVTCKHRPEYLVKLRNPWGKVEWKGDWSDSSSKWELLS
CAN-12v2(251) VEGHAYTLTGIRKVTCKHRPEYLVKLRNPWGKVEWKGDWSDSSSKWELLS 301                                               350
CAN-12  (300) PKEKILLLRKDNDGEFWMTLQDFKTHFVLLVICKLTPGLLSQEAAQKWTY
CAN-12+ (300) PKEKILLLRKDNDGEFWMTLQDFKTHFVLLVICKLTPGLLSQEAAQKWTY
CAN-12v1(301) PKEKILLLRKDNDGEFWMTLQDFKTHFVLLVICKLTPGLLSQEAAQKWTY
CAN-12v2(301) PKEKILLLRKDNDGEFWMTLQDFKTHFVLLVICKLTPGLLSQEAAQKWTY 351                                               400
CAN-12  (350) TMREGRWEKRSTAGGQRQLLQDTFWKNPQFLLSVWRPEEGRRSLRPCSVL
CAN-12+ (350) TMREGRWEKRSTAGGQRQLLQDTFWKNPQFLLSVWRPEEGRRSLRPCSVL
CAN-12v1(351) TMREGRWEKRSTAGGQRQLLQDTFWKNPQFLLSVWRPEEGRRSLRPCSVL
CAN-12v2(351) TMREGRWEKRSTAGGQRQLLQDTFWKNPQFLLSVWRPEEGRRSLRPCSVL 401                                               450
CAN-12  (400) VSLLQKPRHRCRKRKPLLAIGFYLYRMNK---------------------
CAN-12+ (400) VSLLQKPRHRCRKRKPLLAIGFYLYRMNKM--------------------
CAN-12v1(401) VSLLQKPRHRCRKRKPLLAIGFYLYRYHDDQR---RLPPEFFQRNTPLSQ
CAN-12v2(401) VSLLQKPRHRCRKRKPLLAIGFYLYRMNKYHDDQRRLPPEFFQRNTPLSQ
```

Figure 10B

```
               451                                                500
CAN-12   (429) --------------------------------------------------
CAN-12+  (430) --------------------------------------------------
CAN-12v1 (448) PDRFLKEKEVSQELCLEPGTYLIVPCILEAHQKSEFVLRVFSRKHIFYEI
CAN-12v2 (451) PDRFLKEKEVSQELCLEPGTYLIVPCILEAHQKSEFVLRVFSRKHIFYEI 501                                                550
CAN-12   (429) --------------------------------------------------
CAN-12+  (430) ---------------------------------------------TWSSL
CAN-12v1 (498) GSNSGVVFSKEIEDQNERQDEFFTKFFEKHPEINAVQLQNLLNQMTWSSL
CAN-12v2 (501) GSNSGVVFSKEIEDQNERQDEFFTKFFEKHPEINAVQLQNLLNQMTWSSL 551                                                600
CAN-12   (429) --------------------------------------------------
CAN-12+  (435) GSRQPFFSLEACQGILALLDLNASGTMSIQEFRDLWKQLKLSQKVFHKQD
CAN-12v1 (548) GSRQPFFSLEACQGILALLDLNASGTMSIQEFRDLWKQLKLSQKVFHKQD
CAN-12v2 (551) GSRQPFFSLEACQGILALLDLNASGTMSIQEFRDLWKQLKLSQKVFHKQD 601                                                650
CAN-12   (429) --------------------------------------------------
CAN-12+  (485) RGSGYLNWEQLHAAMREAGRHRKSWSCGHTRAGCTLIRQRRGDVWHAEVT
CAN-12v1 (598) RGSGYLNWEQLHAAMREAGRHRKSWSCGHTRAGCTLIRQRRGDVWHAEVT
CAN-12v2 (601) RGSGYLNWEQLHAAMREAGRHRKSWSCGHTRAGCTLIRQRRGDVWHAEVT 651                                          697
CAN-12   (429) -----------------------------------------------
CAN-12+  (535) LIRSVTLKDVDLQSTPTFFMIVPVILANIDGGVAHSTSYLIFNTTLL
CAN-12v1 (648) LIRSVTLKDVDLQSTPTFFMIVPVILANIDGGVAHSTSYLIFNTTLL
CAN-12v2 (651) LIRSVTLKDVDLQSTPTFFMIVPVILANIDGGVAHSTSYLIFNTTLL
```

POLYNUCLEOTIDES ENCODING NOVEL CYSTEINE PROTEASES OF THE CALPAIN SUPERFAMILY, CAN-12V1 AND CAN-12V2.

This application claims benefit to provisional application U.S. Ser. No. 60/281,253 filed Apr. 3, 2001; to provisional application U.S. Ser. No. 60/288,768, filed May 4, 2001; to provisional application U.S. Ser. No. 60/296,180, filed Jun. 6, 2001; to provisional application U.S. Ser. No. 60/300,620, filed Jun. 25, 2001. The entire teachings of the referenced applications are incorporated herein by reference.

FIELD OF THE INVENTION

The present invention provides novel polynucleotides encoding CAN-12 polypeptides, fragments and homologues thereof. The present invention also provides polynucleotides encoding variants of CAN-12 polypeptides, CAN-12v1 and CAN-12v2. Also provided are vectors, host cells, antibodies, and recombinant and synthetic methods for producing said polypeptides. The invention further relates to diagnostic and therapeutic methods for applying these novel CAN-12, CAN-12v1, and CAN-12v2 polypeptides to the diagnosis, treatment, and/or prevention of various diseases and/or disorders related to these polypeptides, particularly neuro- and musculo-degenerative conditions. The invention further relates to screening methods for identifying agonists and antagonists of the polynucleotides and polypeptides of the present invention.

BACKGROUND OF THE INVENTION

Cysteine or thiol proteases contain a reactive sulphydral moiety activated by an adjacent histidine. Hydrolysis of the substrates peptide bond is initiated when the cysteine sulfur attacks the carbon in the peptide bond forming a thiol-enzyme intermediate, liberating the amino portion of the peptide. The thiol-enzyme intermediate is hydrolyzed by water releasing the substrates C-terminus and restoring the enzyme. There are over 20 some families of cysteine proteases. [Rawlings N. D., & Barrett A. J. Families of cysteine peptidases. Methods in Enzymol. 244 461–486 (1994)]. The present invention relates to a thiol protease of the C2 family that includes the calpain superfamily.

Calpains are calcium-activated intracellular neutral cysteine proteases (EC 3.4.22.17)(for reviews see Sorimachi et al., Structure and physiological function of calpains. Biochem J. 328:721–32, 1997; Carafoli E and Molinari M. Calpain: a protease in search of a function? Biochem Biophys Res Commun 247:193–203, 1998). Some calpains are expressed ubiquitously while others are tissue-specific. μ-Calpain and m-calpains appear in all tissues, p94 is skeletal muscle specific while nCL-2 is stomach specific. (Sorimachi et al., Structure and physiological function of calpains. Biochem J. 328:721–32, 1997). The best characterized are μ-calpain and m-calpains which consist of two subunits. An 80 kDa large subunit contains both $Ca^{2+}$ binding sites and the catalytic activity and small 30 kDa subunit with a separate set of $Ca^{2+}$ binding sites. All the proteolytic activity is contained in the larger subunit of both μ- and m-calpain. In the presence of PEG or chaperones the large subunit is catalytically activated in the absence of the smaller subunit. Other calpains, for example nCL-2 and p94, are proteolytically active monomers with homology to the μ-calpain and m-calpains large subunit.

The large (catalytic) subunit has four domains (I–IV) (Hosfield et al., Crystal structure of calpain reveals the structural basis for Ca(2+)-dependent protease activity and a novel mode of enzyme activation. EMBO J. 18:6880–9, 1999; Strobl et al., The crystal structure of calcium-free human m-calpain suggests an electrostatic switch mechanism for activation by calcium. Proc Natl Acad Sci USA. 97:588–92, 2000). The N-terminus (domain I) contains an alpha helical region and a site of autocatalytic cleavage. Domain II contains the catalytically active domain with the active site amino acids (m-calpain residues Cys105, His262, & Asn286). Domain III contains the linker between the $Ca^{2+}$ binding domain (in domain IV) and links $Ca^{2+}$ binding to proteolytic activity. Domain IV contains a calmodulin-like $Ca^{2+}$ binding regions with EF hands. p94 (also called calpain 3) is similarly organized with domains I–IV, but, also contains a proline-rich N-terminus and two unique insertion loops (IS1 and IS2). nCL-2 is also active as a large monomer with domains I–IV; however, a splice variant (nCL-2') lacks domains III & IV, but maintains proteolytic activity.

Calpains are responsible for limited intracellular proteolytic cleavage, as opposed to complete proteolytic digestion. The proteolysis modifies protein function both specifically and irreversibly. Numerous proteins have been identified as calpain substrates (Carafoli E and Molinari M Calpain: a protease in search of a function? Biochem Biophys Res Commun 247:193–203, 1998; Hayes et al., Drug News Perspect 11:215–222, 1998). The best-characterized substrates are large cytostructural and/or membrane associated proteins, calmodulin-binding proteins and transcriptional factors. Physiologically significant substrates for calpain include kinases, phosphatases, channel proteins and cytoskeletal proteins that link transmembrane receptors to the membrane skeleton. Proteolytic modification of these proteins may have fundamental roles in development, differentiation, and cellular transformation in response to cell signaling, cell-cell and/or cell-extracellular matrix interactions. In platelets, calpain activation appears to be linked to clustering of the integrin receptor aIIb3 (Fox JE On the role of calpain and Rho proteins in regulating integrin-induced signaling. Thromb Haemost 82:385–91, 1999).

Calpains have been implicated in cell signaling through activation of protein kinases and phosphatases (cleaving between regulatory and catalytic domains resulting in changes in activity after hydrolysis) and modulation of their intracellular localization. Calpains have been shown to modify specific enzymes and cytoskeletal proteins as part of calcium-mediated signal pathways. They are also involved in remodeling and disassembling the cytoskeleton, especially where the cytoskeleton attaches to membranes or other subcellular structures.

Several nuclear transcription factors have been suggested as calpain substrates. Calpains are also involved in the progression of cells through the cell cycle (Carafoli E and Molinari M Calpain: a protease in search of a function? Biochem Biophys Res Commun 247:193–203, 1998) in that calpain activity accelerates some cells through the cell cycle by cleavage of p53. Calpain is also thought to play a role in long term potentiation (memory) and rat strains deficient in the endogenous calpain inhibitor, calpastatin, have increased long term potentiation.

Calpains in Disease:

Several diseases have been associated with calpain deficiencies. For example, limb-girdle muscular dystrophy (LGMD) is a group of disorders that primarily cause weakness of the shoulder and pelvic regions. A subtype of LGMD called LGMD2A is caused by defects in the gene for p94 (also called calpain 3)(Richard et al., Mutations in the proteolytic enzyme calpain 3 cause limb-girdle muscular dystrophy type 2A. Cell 81:27–40, 1995).

Positional cloning has recently identified single-nucleotide polymorphisms (SNPs) in an intron of the gene coding for calpain-10 that appears to confer insulin resistance in diabetics. Presence of this mutation correlates with reduced levels of calpain 10 in patients susceptible to type II diabetes (Horikawa et al., Genetic variation in the gene encoding calpain-10 is associated with type 2 diabetes mellitus. Nat Genet. 26:163–75, 2000). The same calpain-10 SNP also correlates with type II diabetes in a high-risk population of Pima Indians (Baier et al., A calpain-10 gene polymorphism is associated with reduced muscle mRNA levels and insulin resistance. J Clin Invest. 106:R69–73, 2000).

Over Activation of Calpain—Ischemic and Traumatic Damage

Intracellular calcium levels and calpain activity are normally tightly regulated. Under stress, such as follows neuronal excitotoxicity, ischemic stroke, hemoragic stroke, hypoxic stress and/or trauma, intracellular calcium levels rise causing inappropriate calpain proteolytic activity. Calpain activity has been implicated in further cell destruction and non-specific calpain inhibitors have been shown to be protective in animal models (Lee et al., Proc. Natl. Acad. Sci. USA, 88:7233–7237, 1991; Wang K K and Yuen P W. Calpain inhibition: an overview of its therapeutic potential. Trends Pharmacol. Sci. 15:412–9, 1994; Lee, K S, et al., Calcium-activated proteolysis as a therapeutic target in cerebrovascular disease. Annal NY Acad Sci. 825, 95–103, 1997).

Calpains are activated in neurons following ischemia-induced damage in animal models of stroke. (Lee et al., Proc. Natl. Acad. Sci. USA, 88:7233–7237, 1991). Inhibition of calcium-activated proteolysis by means of high doses of (usually non-specific) calpain inhibitors protect against the degeneration of vulnerable hippocampal neurons after ischemia (Rami et al., Brain Research, 609:67–70, 1993; Wang et al., An alpha-mercaptoacrylic acid derivative is a selective nonpeptide cell-permeable calpain inhibitor and is neuroprotective. Proc Natl Acad Sci USA. 93:6687–92, 1996). After an ischemic insult, neuronal death is delayed for hours to days. This time interval represents a potential therapeutic window in which to apply effective therapies to minimize brain damage after stroke.

In addition to neuronal damage, calpains are thought to contribute to cardiac ischemic damage (Iwamoto H et al., Calpain inhibitor-1 reduces infarct size and DNA fragmentation of myocardium in ischemic/reperfused rat heart.J Cardiovasc Pharmacol 33:580–6, 1999) and hepatocyte necrosis during and following anoxia (Arora A S et al., Hepatocellular carcinoma cells resist necrosis during anoxia by preventing phospholipase-mediated calpain activation. J Cell Physiol 167:434–42, 1996).

Neurodegenerative Diseases

Calpains have been implicated in neurodegenerative diseases ncluding, Alzheimer's disease, Multiple sclerosis, Huntington's disease, Parkinson's disease and amyotrophy. Calpain activation is increased during normal aging and a strong case can be made for the involvement of calpain in the abnormal proteolysis underlying the accumulation of plaque and neurofibriles in brain tissue from people who suffered Alzheimer-type dementia (Iwamoto et al., Brain Research, 561:177–180 1991; Nixon et al., Calcium-activated neutral proteinase (calpain) system in aging and Alzheimer's disease. Ann NY Acad Sci ;747:77–91, 1994; Grynspan et al., Active site-directed antibodies identify calpain II as an early-appearing and pervasive component of neurofibrillary pathology in Alzheimer's disease. Brain Res 763:145–58, 1997). Calpains are significantly activated in human postmortem brain from patients with Alzheimer's disease, and the degree of activation correlated with those regions of the brain showing the greatest amount of degeneration (Saito et al., Proc. Natl. Acad. Sci. USA, 90:2628–2632, 1993). More recently, it has been recognized that in Alzheimer's disease cyclin-dependent kinase 5 (cdk5) and its neuron-specific activator p3[5] are involved in neurite outgrowth and cortical lamination. Calpain cleavage of p35 produces p25, which accumulates in the brains of patients with Alzheimers disease. Conversion of p35 to p25 causes prolonged activation and mislocalization of cdk5 which hyperphosphorylates tau, disrupts the cytoskeleton and promotes the death (apoptosis) of primary neurons (Lee et al., Neurotoxicity induces cleavage of p35 to p25 by calpain. Nature. 18;405:360–4, 2000). Compounds that inhibit calpain activity could prove useful in reducing or delaying neurodegeneration caused to Alzheimer's disease.

Damage Following Trauma

Traumatic injury also causes calpain activation associated with further cell death, atrophy and shrinkage of the brain. A forceful blow trigger cell damage and increased calpain activity that can cleave structural proteins in the brain for up to weeks afterward (Hayes et al., Potential Contribution of Proteases to Neuronal Damage Drug News & Perspectives 11, 1998).

Calpain activation has also been implicated in spinal cord injury following trauma (for reviews see: Banik et al., Role of calpain and its inhibitors in tissue degeneration and neuroprotection in spinal cord injury. Ann. N.Y. Acad. Sci. 825:120–7 1997; Banik et al., Role of calpain in spinal cord injury: effects of calpain and free radical inhibitors. Ann. N.Y. Acad. Sci. 844:131–7, 1998). Analogous to brain trauma, secondary pathophysiological alterations occur in the traumatized spinal cord well after the initiating insult. These secondary events ultimately cause cell death and tissue damage. Non-specific calpain inhibitors have shown utility in preventing further damage due to spinal chord injury in animal models (Ray et al., Increased calpain expression is associated with apoptosis in rat spinal cord injury: calpain inhibitor provides neuroprotection. Neurochem Res. 25:1191–8, 2000).

These studies indicate the potential utility of calpain inhibitors (especially those calpains located in the spinal cord) in treating traumatic injury resulting from automobile crashes, gunshot wounds, and sports accidents.

Degeneration of Cochlear Tissues Following Noise Exposure

Calpains are activated during acoustic trauma and calpain inhibitors protect against hearing loss caused by noise (Stracher A Calpain inhibitors as therapeutic agents in nerve and muscle degeneration. Ann NY Acad Sci 884:52–9, 1999).

Inflammation

Calpains also regulate integrin-mediated interaction of T-cells with the extracellular matrix (ECM) and calpain inhibitors prevent acute and chronic inflammation in animal models (Cuzzocrea S et al., Calpain inhibitor I reduces the development of acute and chronic inflammation Am J Pathol 157:2065–79, 2000).

Multiple Sclerosis

Multiple sclerosis is characterized by the progressive loss of the myelin of the brain and spinal cord. In autoimmune demyelinating diseases such as multiple sclerosis and experimental allergic encephalomyelitis, the degradation of myelin proteins results in the destabilization of the myelin sheath. Calpains have been implicated in that calpain degrades all major myelin proteins and increased calpain activity is observed in multiple sclerosis (Shields D C et al., A putative mechanism of demyelination in multiple sclerosis by a proteolytic enzyme, calpain. Proc. Natl. Acad. Sci. USA 96:11486–91, 1999).

Cataract Formation

In the lens, crystallins prevent thermal denaturation and aggregation of other proteins. Crystallins are also substrates for calpains and cataract formation in a rat model of selenite-induced cataract formation is thought to result from calpain activation and cleavage of crystallins (Shearer T R, David L L, Anderson R S, Azuma M. Review of selenite cataract. Curr Eye Res 1992; 11:357–369). In this model the crystallin cleavage could be blocked by calpain inhibitors (Azuma M et al., Cysteine protease inhibitor E64 reduces the rate of formation of selenite cataract in the whole animal. Curr Eye Res 10:657–666, 1991). In a genetic model cataract-prone rats also showed enhanced proteolysis of crystallins and lens cytoskeleton proteins thought to be mediated by calpain (Inomata M et al., Evidence for the involvement of calpain in cataractogenesis in Shumiya cataract rat (SCR). Biochim Biophys Acta 1362:11–23 1997). Calpain activation is also thought to play a role in cataracts induced by buthionine sulfoximine, calcium ionophore A23187, hydrogen peroxide, diamide, xylose, galactose and streptozotocin (Kadoya et al., Role of calpain in hydrogen peroxide cataract. Curr Eye Res 1993; 12:341–346; David et al., Buthionine sulfoximine induced cataracts in mice contain insolubilized crystallins with calpain II cleavage sites, Exp Eye Res 1994; 59:501–504.). These models of cataract formation in rats suggest that calpain-induced proteolysis is a common underlying mechanism. Fragments of alpha-crystallin, consistent with calpain cleavage, have been also observed in cataractous human lens.

Reovirus Induced Myocarditis

Infection of neonatal mice with reovirus produces histological myocarditis. This is due to a direct viral injury and apoptosis of myocytes. Calpain inhibitors block reovirus-induced apoptosis in vitro and prevented viral-induced induced myocarditis (DeBiasi et al., Calpain inhibition protects against virus-induced apoptotic myocardial injury. Virol 75:351–61, 2001).

The inventors of the present invention describe herein, the polynucleotides corresponding to the full-length novel CAN-12 calpain gene, its encoded polypeptide, in addition to the variants CAN-12v1 and CAN-12v2. Also provided are polypeptide alignments illustrating the strong conservation of the CAN-12, CAN-12v1, and CAN-12v2 polypeptides to known proteases and a model of the active conformation of CAN-12. Based on this strong conservation, the inventors have ascribed the CAN-12, CAN-12v1, and CAN-12v2 polypeptides as having calpain proteolytic activity. Data is also provided illustrating the unique tissue expression profile of the CAN-12 polypeptide in esophagus, lymph node, and spinal cord tissues.

In fact, calpains have been the subject of significant research and development programs designed to identify inhibitors of this disease associated protein class. For example, the following, non-limiting examples of drugs, therapies, or regimens directed to inhibiting calpains are currently known: BDA 410 (Mitsubishi Tokyo); AK 295 (Alkermes; CAS® Registry Number: 160399-35-9, 144231-82-3, and 145731-49-3; (1-(((1-ethyl-3-((3-(4-morpholinyl) propyl)amino)-2,3-dioxopropyl)amino)carbonyl)-3-methylbutyl)carbamic acid phenylmethyl ester stereois); AK 275 (Alkermes; CAS® Registry Number: 158798-83-5, and 150519-08-7; N-((phenylmethoxy)carbonyl)-L-leucyl-N-ethyl-L-2-aminobutanamide); inhibitor 1 (University of Indiana; acetyl-leu-leu-norleucinal); calpeptin (University of Indiana; benzyloxycarbonyl-leu-norleucinal); VASOLEX (Cortex); RESTENEX (Cortex); MDL 28170 (Aventis; CBZ-Val-Phe-H); PI (Sankyo; CAS® Registry Number: 128102-74-9, and 128102-75-0; L-phenylalanyl-L-glutaminyl-L-valyl-L-valyl-3-((3-nitro-2-pyridinyl)dithio)-L-alanylglycinamide); MDL 28170 (Hoechst Marion Roussel); BDA-410 (Mitsubishi-Tokyo); SJA-6017 (Senju; CAS® Registry Number: 190274-53-4; Butanamide,2-(((4-fluorophenyl)sulfonyl)amino)-N-((1S)-1-formyl-3-methylbutyl.).-3-methyl-, (2S)-); Pharmaprojects No. 5123 (Pfizer; 2-Chloro-acetic acid(3-oxo-4-phenyl-3,4-dihydro-1H-quinoxalin-2-ylidene)hydrazide; WO96-25403); CEP-4143 (Cephalon; WO96-14067); MDL-104903 (Aventis; CAS® Registry Number: 180799-56-8; Carbamic acid, ((1S)-1-(((4S,5R)-5-hydroxy-4-(phenylmethyl)-3-oxazolidinyl)carbonyl)-2-methylpropyl)-, phenylmethyl ester)); MDL-28170 (Aventis; CAS® Registry Number: 19542-51-9; Alanine, N-(N-carboxy-L-valyl)-3-phenyl-N-benzyl ester, L-); CX-275 (Cortex Pharmaceuticals; PhenylmethylN-((1R)-1-((((1S)-1-ethyl-3-(ethylamino)-2,3-dioxopropyl)amino)carbonyl)-3-methylbutyl)carbamate); NS 7 (Nippon Shinyaku; 4-(4-Fluorophenyl)-2-methyl-6-(5-piperidinopentyloxy)pyrimidine hydrochloride); Calpain inhibitor 1 (Suntory; N-Acetyl-L-leucinyl-L-leucinyl-L-norleucinal); E64 (Taisho Pharmaceutical (; CAS® Registry Number: 66701-25-5); CEP 4143 (Cephalon); SJA 6017 (Senju; N-(4-Fluorophenylsulfonyl)-L-valyl-L-leucinal); The present invention is directed to antagonists specific to the CAN-12, CAN-12v1, and/or CAN-12v2 polypeptides. Modulating the activity of the calpain polypeptides of the present invention may result in fewer toxicities than the drugs, therapies, or regimens presently known to regulate other known calpains.

The present invention also relates to recombinant vectors, which include the isolated nucleic acid molecules of the present invention, and to host cells containing the recombinant vectors, as well as to methods of making such vectors and host cells, in addition to their use in the production of CAN-12, CAN-12v1, and CAN-12v2 polypeptides or peptides using recombinant techniques. Synthetic methods for producing the polypeptides and polynucleotides of the present invention are provided. Also provided are diagnostic methods for detecting diseases, disorders, and/or conditions related to the CAN-12, CAN-12v1, and CAN-12v2 polypeptides and polynucleotides, and therapeutic methods for treating such diseases, disorders, and/or conditions. The invention further relates to screening methods for identifying binding partners of the polypeptides, particularly activators and inhibitors of the novel CAN-12, CAN-12v1, and CAN-12v2 polypeptides of the present invention.

BRIEF SUMMARY OF THE INVENTION

The present invention provides isolated nucleic acid molecules, that comprise, or alternatively consist of, a polynucleotide encoding the CAN-12 protein having the amino acid sequence shown in FIGS. 1A–E (SEQ ID NO:24) or the amino acid sequence encoded by the cDNA clone, CAN-12 (also referred to as protease 5, clone 70).

The present invention provides isolated nucleic acid molecules, that comprise, or alternatively consist of, a polynucleotide encoding the CAN-12+ polypeptide sequence having the amino acid sequence shown in FIGS. 1A–E (SEQ ID NO:2) or the amino acid sequence encoded by the cDNA clone, CAN-12+ (also referred to as protease 5, clone 70; + splice amino acids).

The present invention provides isolated nucleic acid molecules, that comprise, or alternatively consist of, a polynucleotide encoding the CAN-12v1 protein having the amino acid sequence shown in FIGS. 8A–C (SEQ ID NO:54) or the amino acid sequence encoded by the cDNA clone, CAN-12v1 (also referred to as protease 5, clone 1e), deposited as ATCC Deposit Number PTA-3434 on Jun. 7, 2001.

The present invention provides isolated nucleic acid molecules, that comprise, or alternatively consist of, a polynucleotide encoding the CAN-12v2 protein having the amino acid sequence shown in FIGS. 9A-C (SEQ ID NO:56) or the amino acid sequence encoded by the cDNA clone, CAN-12v2 (also referred to as protease 5, clone 1e1b-1), deposited as ATCC Deposit Number PTA-3434 on Jun. 7, 2001.

The present invention also relates to recombinant vectors, which include the isolated nucleic acid molecules of the present invention, and to host cells containing the recombinant vectors, as well as to methods of making such vectors and host cells, in addition to their use in the production of CAN-12, CAN-12v1, and CAN-12v1 polypeptides or peptides using recombinant techniques. Synthetic methods for producing the polypeptides and polynucleotides of the present invention are provided. Also provided are diagnostic methods for detecting diseases, disorders, and/or conditions related to the CAN-12, CAN-12v1, and CAN-12v1 polypeptides and polynucleotides, and therapeutic methods for treating such diseases, disorders, and/or conditions. The invention further relates to screening methods for identifying binding partners of the polypeptides.

The invention further provides an isolated CAN-12 polypeptide having an amino acid sequence encoded by a polynucleotide described herein.

The invention further provides an isolated CAN-12v1 polypeptide having an amino acid sequence encoded by a polynucleotide described herein.

The invention further provides an isolated CAN-12v2 polypeptide having an amino acid sequence encoded by a polynucleotide described herein.

The invention also provides a machine readable storage medium which comprises the structure coordinates of CAN-12, including all or any parts conserved calpain regions. Such storage medium encoded with these data are capable of displaying on a computer screen or similar viewing device, a three-dimensional graphical representation of a molecule or molecular complex which comprises said regions or similarly shaped homologous regions.

The invention also provides methods for designing, evaluating and identifying compounds which bind to all or parts of the aforementioned regions. The methods include three dimensional model building (homology modeling) and methods of computer assisted-drug design which can be used to identify compounds which bind or modulate the forementioned regions of the CAN-12 polypeptide. Such compounds are potential inhibitors of CAN-12 or its homologues.

The invention also provides novel classes of compounds, and pharmaceutical compositions thereof, that are useful as inhibitors of CAN-12 or its homologues.

The invention also provides novel classes of compounds, and pharmaceutical compositions thereof, that are useful as inhibitors of CAN-12v1 or its homologues.

The invention also provides novel classes of compounds, and pharmaceutical compositions thereof, that are useful as inhibitors of CAN-12v2 or its homologues.

The invention further relates to a polynucleotide encoding a polypeptide fragment of SEQ ID NO:2, 24, 54, and/or 56, or a polypeptide fragment encoded by the cDNA sequence included in the deposited clone, which is hybridizable to SEQ ID NO:1, 23, 53, and/or 55.

The invention further relates to a polynucleotide encoding a polypeptide domain of SEQ ID NO:2, 24, 54, and/or 56 or a polypeptide domain encoded by the cDNA sequence included in the deposited clone, which is hybridizable to SEQ ID NO:1, 23, 53, and/or 55.

The invention further relates to a polynucleotide encoding a polypeptide epitope of SEQ ID NO:2, 24, 54, and/or 56 or a polypeptide epitope encoded by the cDNA sequence included in the deposited clone, which is hybridizable to SEQ ID NO:1, 23, 53, and/or 55.

The invention further relates to a polynucleotide encoding a polypeptide of SEQ ID NO:2, 24, 54, and/or 56 or the cDNA sequence included in the deposited clone, which is hybridizable to SEQ ID NO:1, 23, 53, and/or 55, having biological activity.

The invention further relates to a polynucleotide which is a variant of SEQ ID NO:1, 23, 53, and/or 55.

The invention further relates to a polynucleotide which is an allelic variant of SEQ ID NO:1, 23, 53, and/or 55.

The invention further relates to a polynucleotide which encodes a species homologue of the SEQ ID NO:2, 24, 54, and/or 56.

The invention further relates to a polynucleotide which represents the complimentary sequence (antisense) of SEQ ID NO:1, 23, 53, and/or 55.

The invention further relates to a polynucleotide capable of hybridizing under stringent conditions to any one of the polynucleotides specified herein, wherein said polynucleotide does not hybridize under stringent conditions to a nucleic acid molecule having a nucleotide sequence of only A residues or of only T residues.

The invention further relates to an isolated nucleic acid molecule of SEQ ID NO:2, 24, 54, and/or 56, wherein the polynucleotide fragment comprises a nucleotide sequence encoding a calpain protein.

The invention further relates to an isolated nucleic acid molecule of SEQ ID NO:1, 23, 53, and/or 55 wherein the polynucleotide fragment comprises a nucleotide sequence encoding the sequence identified as SEQ ID NO:2, 24, 54, and/or 56 or the polypeptide encoded by the cDNA sequence included in the deposited clone, which is hybridizable to SEQ ID NO:1, 23, 53, and/or 55.

The invention further relates to an isolated nucleic acid molecule of of SEQ ID NO:1, 23, 53, and/or 55 wherein the polynucleotide fragment comprises the entire nucleotide sequence of SEQ ID NO:1, 23, 53, and/or 55 or the cDNA sequence included in the deposited clone, which is hybridizable to SEQ ID NO:1, 23, 53, and/or 55.

The invention further relates to an isolated nucleic acid molecule of SEQ ID NO:1, 23, 53, and/or 55, wherein the nucleotide sequence comprises sequential nucleotide deletions from either the C-terminus or the N-terminus.

The invention further relates to an isolated polypeptide comprising an amino acid sequence that comprises a polypeptide fragment of SEQ ID NO:2, 24, 54, and/or 56 or the encoded sequence included in the deposited clone.

The invention further relates to a polypeptide fragment of SEQ ID NO:2, 24, 54, and/or 56 or the encoded sequence included in the deposited clone, having biological activity.

The invention further relates to a polypeptide domain of SEQ ID NO:2, 24, 54, and/or 56 or the encoded sequence included in the deposited clone.

The invention further relates to a polypeptide epitope of SEQ ID NO:2, 24, 54, and/or 56 or the encoded sequence included in the deposited clone.

The invention further relates to a full length protein of SEQ ID NO:2, 24, 54, and/or 56 or the encoded sequence included in the deposited clone.

The invention further relates to a variant of SEQ ID NO:2, 24, 54, and/or 56.

The invention further relates to an allelic variant of SEQ ID NO:2, 24, 54, and/or 56. The invention further relates to a species homologue of SEQ ID NO:2, 24, 54, and/or 56.

The invention further relates to the isolated polypeptide of of SEQ ID NO:2, 24, 54, and/or 56, wherein the full length protein comprises sequential amino acid deletions from either the C-terminus or the N-terminus.

The invention further relates to an isolated antibody that binds specifically to the isolated polypeptide of SEQ ID NO:2, 24, 54, and/or 56.

The invention further relates to a method for preventing, treating, or ameliorating a medical condition, comprising administering to a mammalian subject a therapeutically effective amount of the polypeptide of SEQ ID NO:2, 24, 54, and/or 56 or the polynucleotide of SEQ ID NO:1, 23, 53, and/or 55.

The invention further relates to a method of diagnosing a pathological condition or a susceptibility to a pathological condition in a subject comprising the steps of (a) determining the presence or absence of a mutation in the polynucleotide of SEQ ID NO:1, 23, 53, and/or 55; and (b) diagnosing a pathological condition or a susceptibility to a pathological condition based on the presence or absence of said mutation.

The invention further relates to a method of diagnosing a pathological condition or a susceptibility to a pathological condition in a subject comprising the steps of (a) determining the presence or amount of expression of the polypeptide of of SEQ ID NO:2, 24, 54, and/or 56 in a biological sample; and diagnosing a pathological condition or a susceptibility to a pathological condition based on the presence or amount of expression of the polypeptide.

The invention further relates to a method for identifying a binding partner to the polypeptide of SEQ ID NO:2, 24, 54, and/or 56 comprising the steps of (a) contacting the polypeptide of SEQ ID NO:2, 24, 54, and/or 56 with a binding partner; and (b) determining whether the binding partner effects an activity of the polypeptide.

The invention further relates to a gene corresponding to the cDNA sequence of SEQ ID NO:1, 23, 53, and/or 55.

The invention further relates to a method of identifying an activity in a biological assay, wherein the method comprises the steps of expressing SEQ ID NO:1, 23, 53, and/or 55 in a cell, (b) isolating the supernatant; (c) detecting an activity in a biological assay; and (d) identifying the protein in the supernatant having the activity.

The invention further relates to a process for making polynucleotide sequences encoding gene products having altered activity selected from the group consisting of SEQ ID NO:2, 24, 54, and/or 56 activity comprising the steps of (a) shuffling a nucleotide sequence of SEQ ID NO:1, 23, 53, and/or 55, (b) expressing the resulting shuffled nucleotide sequences and, (c) selecting for altered activity selected from the group consisting of SEQ ID NO:2, 24, 54, and/or 56 activity as compared to the activity selected from the group consisting of SEQ ID NO:2, 24, 54, and/or 56 activity of the gene product of said unmodified nucleotide sequence.

The invention further relates to a shuffled polynucleotide sequence produced by a shuffling process, wherein said shuffled DNA molecule encodes a gene product having enhanced tolerance to an inhibitor of any one of the activities selected from the group consisting of SEQ ID NO:2, 24, 54, and/or 56 activity.

The invention further relates to a method for preventing, treating, or ameliorating a medical condition with the polypeptide provided as SEQ ID NO:2, 24, 54, and/or 56, in addition to, its encoding nucleic acid, wherein the medical condition is a gastrointenstinal disorder.

The invention further relates to a method for preventing, treating, or ameliorating a medical condition with the polypeptide provided as SEQ ID NO:2, 24, 54, and/or 56, in addition to, its encoding nucleic acid, wherein the medical condition is a neural disorder.

The invention further relates to a method for preventing, treating, or ameliorating a medical condition with the polypeptide provided as SEQ ID NO:2, 24, 54, and/or 56, in addition to, its encoding nucleic acid, wherein the medical condition is an inflammatory disease.

The invention further relates to a method for preventing, treating, or ameliorating a medical condition with the polypeptide provided as SEQ ID NO:2, 24, 54, and/or 56, in addition to, its encoding nucleic acid, wherein the medical condition is an inflammatory disease where proteases, either directly or indirectly, are involved in disease progression.

The invention further relates to a method for preventing, treating, or ameliorating a medical condition with the polypeptide provided as SEQ ID NO:2, 24, 54, and/or 56, in addition to, its encoding nucleic acid, wherein the medical condition is a degenerative disease wherein proteases, either directly or indirectly, are involved in disease progression.

The invention further relates to a method for preventing, treating, or ameliorating a medical condition with the polypeptide provided as SEQ ID NO:2, 24, 54, and/or 56, in addition to, its encoding nucleic acid, wherein the medical condition is multiple sclerosis.

The invention further relates to a method for preventing, treating, or ameliorating a medical condition with the polypeptide provided as SEQ ID NO:2, 24, 54, and/or 56, in addition to, its encoding nucleic acid, wherein the medical condition is a cancer.

The invention further relates to a method for preventing, treating, or ameliorating a medical condition with the polypeptide provided as SEQ ID NO:2, 24, 54, and/or 56, in addition to, its encoding nucleic acid, wherein the medical condition is a blood disorder.

The invention further relates to a method for preventing, treating, or ameliorating a medical condition with the polypeptide provided as SEQ ID NO:2, 24, 54, and/or 56, in addition to, its encoding nucleic acid, wherein the medical condition is an immune disorder.

The invention further relates to a method for preventing, treating, or ameliorating a medical condition with the polypeptide provided as SEQ ID NO:2, 24, 54, and/or 56, in addition to, its encoding nucleic acid, wherein the medical condition is a hematopoietic disorder.

The invention further relates to a method for preventing, treating, or ameliorating a medical condition with the polypeptide provided as SEQ ID NO:2, 24, 54, and/or 56, in addition to, its encoding nucleic acid, wherein the medical condition is a disorder related to aberrant protease regulation.

The invention further relates to a method for preventing, treating, or ameliorating a medical condition with the polypeptide provided as SEQ ID NO:2, 24, 54, and/or 56, in addition to, its encoding nucleic acid, wherein the medical condition is a condition associated with tissue damage caused by calpain activation, either directly or indirectly.

The invention further relates to a method of identifying a compound that modulates the biological activity of CAN-12, comprising the steps of, (a) combining a candidate modulator compound with CAN-12 having the sequence set forth in one or more of SEQ ID NO:2, 24, 54, and/or 56; and measuring an effect of the candidate modulator compound on the activity of CAN-12.

The invention further relates to a method of identifying a compound that modulates the biological activity of a calpain, comprising the steps of, (a) combining a candidate modulator compound with a host cell expressing CAN-12 having the sequence as set forth in SEQ ID NO:2, 24, 54, and/or 56; and, (b) measuring an effect of the candidate modulator compound on the activity of the expressed CAN-12.

The invention further relates to a method of identifying a compound that modulates the biological activity of CAN-12, comprising the steps of, (a) combining a candidate modulator compound with a host cell containing a vector described herein, wherein CAN-12 is expressed by the cell; and, (b) measuring an effect of the candidate modulator compound on the activity of the expressed CAN-12.

The invention further relates to a method of screening for a compound that is capable of modulating the biological activity of CAN-12, comprising the steps of: (a) providing a host cell described herein; (b) determining the biological activity of CAN-12 in the absence of a modulator compound; (c) contacting the cell with the modulator compound; and (d) determining the biological activity of CAN-12 in the presence of the modulator compound; wherein a difference between the activity of CAN-12 in the presence of the modulator compound and in the absence of the modulator compound indicates a modulating effect of the compound.

The invention further relates to a compound that modulates the biological activity of human CAN-12 as identified by the methods described herein.

The invention also provides a machine readable storage medium which comprises the structure coordinates of CAN-12, including all or any parts conserved calpain regions. Such storage medium encoded with these data are capable of displaying on a computer screen or similar viewing device, a three-dimensional graphical representation of a molecule or molecular complex which comprises said regions or similarly shaped homologous regions.

The invention also provides a machine-readable data storage medium, comprising a data storage material encoded with machine readable data, wherein the data is defined by the structure coordinates of the model CAN-12 according to Table IV or a homologue of said model, wherein said homologue comprises any kind of surrogate atoms that have a root mean square deviation from the backbone atoms of the complex of not more than about 5.0 Å.

The invention also provides a machine-readable data storage medium, comprising a data storage material encoded with machine readable data, wherein the data is defined by the structure coordinates of the model CAN-12 according to Table IV or a homologue of said model, wherein said homologue comprises any kind of surrogate atoms that have a root mean square deviation from the backbone atoms of the complex of not more than about 5.0 Å, preferably not more than about 4.0 Å, or less.

The invention also provides a model comprising all or any part of the model defined by structure coordinates of CAN-12 according to Table IV, or a mutant or homologue of said molecule or molecular complex.

The invention also provides a method for identifying a mutant of CAN-12 with altered biological properties, function, or reactivity, the method comprising one or more of the following steps: (a) use of the model or a homologue of said model according to Table IV, for the design of protein mutants with altered biological function or properties which exhibit any combination of therapeutic effects described herein; and/or (b) use of the model or a homologue of said model, for the design of a protein with mutations in the active site region comprised of the amino acids from about amino acid R90 to about amino acid C94, from about amino acid G99 to about amino acid L104, from about amino acid Q196 to about amino acid S198, from about amino acid M210 to about amino acid I212, from about amino acid G236 to about amino acid H240, from about amino acid E251 to about amino acid Y255, from about amino acid N277 to about amino acid K281, from about amino acid V327 to about amino acid V330 of SEQ ID NO:2 according to Table IV with altered biological function or properties which exhibit any combination of therapeutic effects described herein.

The invention also provides methods for designing, evaluating and identifying compounds which bind to all or parts of the aforementioned regions. The methods include three dimensional model building (homology modeling) and methods of computer assisted-drug design which can be used to identify compounds which bind or modulate the forementioned regions of the CAN-12 polypeptide. Such compounds are potential inhibitors of CAN-12 or its homologues.

The invention also relates to method for identifying modulators of CAN-12 biological properties, function, or reactivity, the method comprising the step of modeling test compounds that fit spatially into the EF-hand calcium binding region defined by I449-K471 of SEQ ID NO:2 using a homologue or portion thereof or analogue in which the original C, N, and O atoms have been replaced with other elements.

The invention also relates to a method of using said structure coordinates as set forth in Table IV to identify structural and chemical features of CAN-12; employing identified structural or chemical features to design or select compounds as potential CAN-12 modulators; employing the three-dimensional structural model to design or select compounds as potential CAN-12 modulators; synthesizing the potential CAN-12 modulators; screening the potential CAN-12 modulators in an assay characterized by binding of a protein to the CAN-12. The invention also relates to said method wherein the potential CAN-12 modulator is selected from a database. The invention further relates to said method wherein the potential CAN-12 modulator is designed de novo. The invention further relates to a method wherein the potential CAN-12 modulator is designed from a known modulator of activity.

The invention also provides a machine-readable data storage medium, comprising a data storage material encoded with machine readable data, wherein the data is defined by the structure coordinates of the model CAN-12v2v2 according to Table V or a homologue of said model, wherein said homologue comprises any kind of surrogate atoms that have a root mean square deviation from the backbone atoms of the complex of not more than 5.0 Å.

The invention also provides a machine-readable data storage medium, comprising a data storage material encoded with machine readable data, wherein the data is defined by the structure coordinates of the model CAN-12v2 according to Table V or a homologue of said model, wherein said homologue comprises any kind of surrogate atoms that have a root mean square deviation from the backbone atoms of the complex of not more than 5.0 Å, preferabbly not more than 4.0A, or less The invention also provides a model comprising all or any part of the model defined by structure coordinates of CAN-12v2 according to Table V, or a mutant or homologue of said molecule or molecular complex.

The invention also provides a method for identifying a mutant of CAN-12v2 with altered biological properties, function, or reactivity, the method comprising one or more of the following steps: (a) use of the model or a homologue of said model according to Table V, for the design of protein mutants with altered biological function or properties which exhibit any combination of therapeutic effects described herein; and/or (b) use of the model or a homologue of said model, for the design of a protein with mutations in the active site region comprised of the amino acids from about amino acid R90 to about amino acid C94, from about amino acid G99 to about amino acid L104, from about amino acid Q196 to about amino acid S198, from about amino acid M210 to about amino acid I212, from about amino acid G236 to about amino acid H240, from about amino acid E252 to about amino acid Y256, from about amino acid N278 to about amino acid K282, from about amino acid V328 to about amino acid V331 of SEQ ID NO:56 according to Table V with altered biological function or properties which exhibit any combination of therapeutic effects described herein.

The invention also provides methods for designing, evaluating and identifying compounds which bind to all or parts of the aforementioned regions. The methods include three dimensional model building (homology modeling) and methods of computer assisted-drug design which can be used to identify compounds which bind or modulate the forementioned regions of the CAN-12v2 polypeptide. Such compounds are potential inhibitors of CAN-12v2 or its homologues.

The invention also relates to method for identifying modulators of CAN-12v2 biological properties, function, or reactivity, the method comprising the step of modeling test compounds that fit spatially into the EF-hand calcium binding regions defined by amino acids I565 to K587 of SEQ ID NO:56, using a homologue or portion thereof or analogue in which the original C, N, and O atoms have been replaced with other elements.

The invention also relates to a method of using said structure coordinates as set forth in Table V to identify structural and chemical features of CAN-12v2; employing identified structural or chemical features to design or select compounds as potential CAN-12v2 modulators; employing the three-dimensional structural model to design or select compounds as potential CAN-12v2 modulators; synthesizing the potential CAN-12v2 modulators; screening the potential CAN-12v2 modulators in an assay characterized by binding of a protein to the CAN-12v2. The invention also relates to said method wherein the potential CAN-12v2 modulator is selected from a database. The invention further relates to said method wherein the potential CAN-12v2 modulator is designed de novo. The invention further relates to a method wherein the potential CAN-12v2 modulator is designed from a known modulator of activity.

The present invention also relates to an isolated polynucleotide consisting of a portion of the human CAN-12 gene consisting of at least 8 bases, specifically excluding Genbank Accession Nos. gilAL540944, and/or gilBM554389.

The present invention also relates to an isolated polynucleotide consisting of a nucleotide sequence encoding a fragment of the human CAN-12 protein, wherein said fragment displays one or more functional activities specifically excluding Genbank Accession Nos. gilAL540944, and/or gilBM554389.

The present invention also relates to the polynucleotide of SEQ ID NO:1, 23, 53, and/or 55 consisting of at least 10 to 50 bases, wherein said at least 10 to 50 bases specifically exclude the polynucleotide sequence of Genbank Accession Nos. gilAL540944, and/or gilBM554389.

The present invention also relates to the polynucleotide of SEQ ID NO:1, 23, 53, and/or 55 consisting of at least 15 to 100 bases, wherein said at least 15 to 100 bases specifically exclude the polynucleotide sequence of Genbank Accession Nos. gilAL540944, and/or gilBM554389.

The present invention also relates to the polynucleotide of SEQ ID NO:1, 23, 53, and/or 55 consisting of at least 100 to 1000 bases, wherein said at least 100 to 1000 bases specifically exclude the polynucleotide sequence of Genbank Accession Nos. gilAL540944, and/or gilBM554389.

The present invention also relates to an isolated polypeptide fragment of the human CAN-12 protein, wherein said polypeptide fragment does not consist of the polypeptide encoded by the polynucleotide sequence of Genbank Accession Nos. gilAL540944, and/or gilBM554389.

BRIEF DESCRIPTION OF THE FIGURES/DRAWINGS

The file of this patent contains at least one Figure executed in color. Copies of this patent with color Figure(s) will be provided by the Patent and Trademark Office upon request and payment of the necessary fee.

FIGS. 1A–E show the polynucleotide sequence (SEQ ID NO:1) and deduced amino acid sequence (SEQ ID NO:24) of the novel human calpain, CAN-12, of the present invention. The standard one-letter abbreviation for amino acids is used to illustrate the deduced amino acid sequence. The polynucleotide sequence contains a sequence of 4584 nucleotides (SEQ ID NO:1), encoding a polypeptide of about 428 amino acids (SEQ ID NO:24). The polynucleotide sequence of CAN-12 is believed to represent a short splice variant form. As a result, the alternative splicing introduces a stop codon truncating the open reading frame to end at amino acid 428. Additional amino acids beyond amino acid 428 of SEQ ID NO:24 are shown and are represented in bold (beginning at nucleotide 1537 to 1995 of SEQ ID NO:1). These additional amino acids likely corresponde to the polypeptide sequence of alternative splice forms of CAN-12 as evidenced by the presence of the EF-hand calcium binding domain. However, these additional amino acids are not considered to be a part of this splice form (SEQ ID NO:24). Additional splice forms of CAN-12 have been identified and are described herein (CAN-12v1 and CAN-12v2). The CAN-12 polypeptide sequence comprising these additional amino acids is provided as SEQ ID NO:2 to serve as a reference for the CAN-12v1 and CAN12-v2 splice variants. An analysis of the CAN-12 polypeptide determined that it comprised the following features: predicted active site domain amino acids located from about amino acid R90 to about amino acid C94, from about amino acid G99 to about amino acid L104, from about amino acid Q196 to about amino acid S198, from about amino acid M210 to about amino acid I212, from about amino acid G236 to about amino acid H240, from about amino acid E251 to about amino acid Y255, from about amino acid N277 to about amino acid K281, and/or from about amino acid V327 to about amino acid V330 of SEQ ID NO:24 (FIGS. 1A–E) represented by shading; and a predicted eukaryotic thiol (cysteine) protease active site domain located from about amino acid 90 to about amino acid 111 of SEQ ID NO:24 (FIGS. 1A–E) represented by double underlining. The predicted active site domain amino acids are believed to form the active site binding pocket of the CAN-12 polypeptide and facilitate catalysis of appropriate calpain substrates. The predicted catalytic amino acid residues within the CAN-12 active site are located at amino acid C101, H253, and N277 residues of SEQ ID NO:24 (FIGS. 1A–E) and are denoted by an arrow ("↑"). The additional amino acids beyond amino acid 428 of SEQ ID NO:24 depicted in the Figure were predicted to comprise an EF-hand calcium-binding domain located from about amino acid 439 to about amino acid 471 of SEQ ID NO:24 (FIGS. 1A–E) represented by dotted underlining; and a predicted cell attachment sequence located from about amino acid 520 to about amino acid 532 of SEQ ID NO:24 (FIGS. 1A–E) represented in italics. The presence of the eukaryotic thiol (cysteine) protease active site domain in the additional translated amino acids supports the notion that additional splice variants of CAN-12 exist, at least two of which are described herein.

FIGS. 2A–E show the regions of identity and similarity between the encoded CAN-12 (SEQ ID NO:2), CAN-12v1 (SEQ ID NO:54), and CAN-12v2 polypeptides (SEQ ID NO:56) to other calpains, specifically, the human CAN10 protein (type II diabetes linked) (hCAN10; Genbank Accession No: gi|NP_075574; SEQ ID NO:3); the human CAN5 protein (hCAN5; Genbank Accession No: gi|NP_004046; SEQ ID NO:4); the large catalytic subunit of the human CALPAIN1 protein (also referred to as Calcium-Activated Neutral Proteinase, CANP, µ-TYPE) (hCAN1; Genbank Accession No: gi|12408656; SEQ ID NO:5); the large subunit of the human calpain 3 protein (EC 3.4.22.17) (also referred to as CALPAIN L3, CALPAIN P94, Calcium-Activated Neutral Proteinase 3, CANP3; muscle-specific calcium-activated neutral protease 3 large subunit) (hCAN3; Genbank Accession No: gi|4557405; SEQ ID NO:6); the large catalytic subunit of the mouse CALPAIN 1 protein (also referred to as Calcium-Activated Neutral Proteinase) (CANP) µ-TYPE) (mCALPAIN1; Genbank Accession No: gi|O88666; SEQ ID NO:7); the mouse CALPAIN LP82 (mLP82; Genbank Accession No: gi|3661585; SEQ ID NO:8); the rat stomach-specific calcium-activated neutral protease large subunit, NCL2 protein (rNCL2; Genbank Accession No: gi|NP_006606; SEQ ID NO:9); the human CAN11 protein (hCAN11; Genbank Accession No: gi|NP_008989; SEQ ID NO:10); the human CAN2 protein (hCAN2; Genbank Accession No: gi|4502563; SEQ ID NO:11); and the human CAN9 protein (hCAN9; Genbank Accession No: gi|5729758; SEQ ID NO:12). The alignment was performed using the CLUSTALW algorithm described elsewhere herein. The darkly shaded amino acids represent regions of matching identity. The lightly shaded amino acids represent regions of matching similarity. Lines between residues indicate gapped regions for the aligned polypeptides. The asterisk ("↑") denotes the characteristic active site cysteine (C101), histidine (H253), and asparagine (N277) residues of calpain proteases. The CAN-12 polypeptide sequence shown (CAN12+; SEQ ID NO:2) includes the additional translated amino acids beyond amino acid 428 of SEQ ID NO:24 (shown in FIGS. 1A–E) to illustrate their identity with the CAN-12v1 and CAN-12v2 splice variants.

FIG. 3 shows a phylogenetic tree organization of various calpain family members with respect to the CAN-12 polypeptide of the present invention. The organization was created using the Vector NTI AlignX algorithm, based upon the CLUSTALW alignment described in FIGS. 2A–E above. As shown, CAN-12 is most closely related, phylogenetically, to the human CAN5 and CAN10 proteins.

Figure 4:
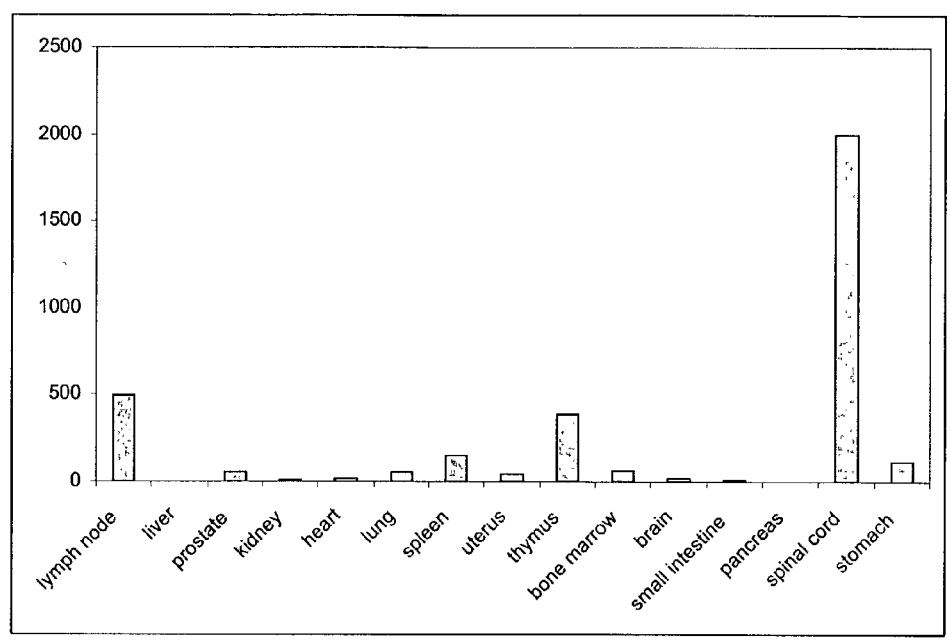

FIG. 4 shows an expression profile of the novel human calpain, CAN-12. The figure illustrates the relative expression level of CAN-12 amongst various mRNA tissue sources. As shown, transcripts corresponding to CAN-12 expressed highly in spinal cord. The CAN-12 polypeptide was also expressed significantly in lymph node, thymus, and to a lesser extent, in spleen. Expression data was obtained by measuring the steady state CAN-12 mRNA levels by quantitative PCR using the PCR primer pair provided as SEQ ID NO:21 and 22 as described herein.

FIGS. 5A–B show a table illustrating the percent identity and percent similarity values between the CAN-12+ (SEQ ID NO:2), CAN-12v1 (SEQ ID NO:54), CAN-12v2 (SEQ ID NO:56), and CAN-12 (SEQ ID NO:24) polypeptides of the present invention with other calpains, specifically, the human CAN10 protein (type II diabetes linked) (hCAN10; Genbank Accession No: gi|NP_075574; SEQ ID NO:3); the human CAN5 protein (hCAN5; Genbank Accession No: gi|NP_004046; SEQ ID NO:4); the large catalytic subunit of the human CALPAIN 1 protein (also referred to as Calcium-Activated Neutral Proteinase, CANP, µ-TYPE) (hCAN1; Genbank Accession No: gi|12408656; SEQ ID NO:5); the large subunit of the human calpain 3 protein (EC 3.4.22.17) (also referred to as CALPAIN L3, CALPAIN P94, Calcium-Activated Neutral Proteinase 3, CANP 3; muscle-specific calcium-activated neutral protease 3 large subunit) (hCAN3; Genbank Accession No: gi|4557405; SEQ ID NO:6); the large catalytic subunit of the mouse CALPAIN 1 protein (also referred to as Calcium-Activated Neutral Proteinase) (CANP) µ-TYPE) (mCALPAIN1; Genbank Accession No: gi|O88666; SEQ ID NO:7); the mouse CALPAIN LP82 (nLP82; Genbank Accession No: gi|3661585; SEQ ID NO:8); the rat stomach-specific calcium-activated neutral protease large subunit, NCL2 protein (rNCL2; Genbank Accession No: gi|NP_006606; SEQ ID NO:9); the human CAN11 protein (hCAN11; Genbank Accession No: gi|NP_008989; SEQ ID NO:10); the human CAN2 protein (hCAN2; Genbank Accession No: gi|4502563; SEQ ID NO:11); and the human CAN9 protein (hCAN9; Genbank Accession No: gi|5729758; SEQ ID NO:12). The alignment was performed using the CLUSTALW algorithm described elsewhere herein. The darkly shaded amino acids represent regions of matching identity. The lightly shaded amino acids represent regions of matching similarity. Lines between residues indicate gapped regions for the aligned polypeptides.

Figure 6:
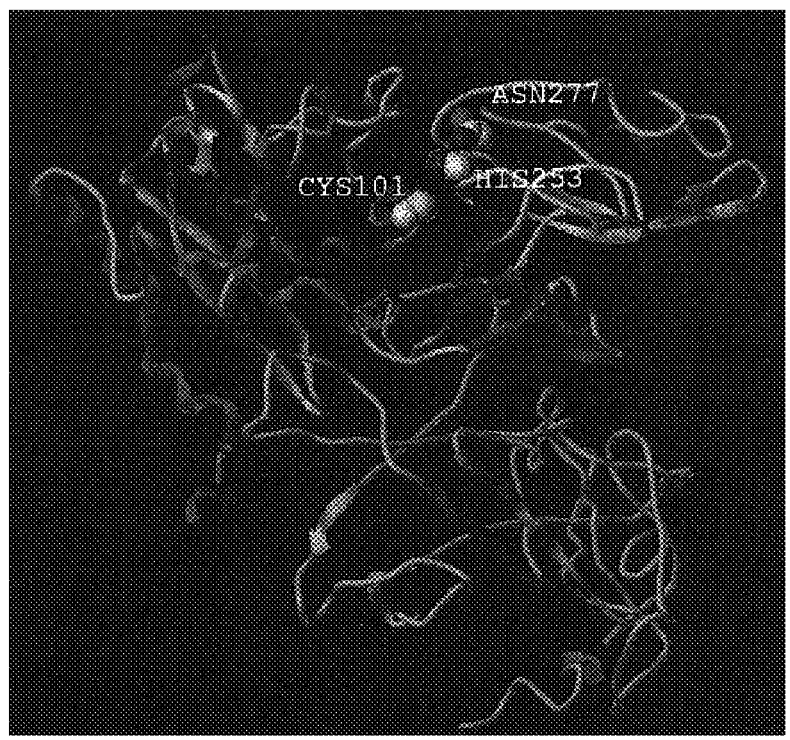

FIG. 6 shows a three-dimensional homology model of the CAN-12 polypeptide based upon the homologous structure of a portion of the human m-calpain, also referred to as, CAN2 (hCAN2; Genbank Accession No. gi|4502563; SEQ ID NO:11). The predicted catalytic active site amino acids of the human CAN-12 polypeptide are labeled. The predicted regions of alpha helix structure are represented in magenta; the predicted regions of beta sheet structure are represented in yellow; the predicted regions of flexible loop structure are represented in cyan; the catalytic amino acid residues are shown in a CPK/space filled rendering of the side chain atoms wherein carbon atoms are represented in white, the sulfur atoms are represented in yellow, and the nitrogen atoms are represented in blue. The structural coordinates of the CAN-12 polypeptide are provided in Table IV herein. The homology model of CAN-12 was derived from generating a sequence alignment with the human m-calpain, CAN2 protein (hCAN2; Genbank Accession No. gil4502563; SEQ ID NO:11) using the Proceryon suite of software (Proceryon Biosciences, Inc. N.Y., N.Y.), and the overall atomic model including plausible sidechain orientations using the program LOOK (V3.5.2, Molecular Applications Group).

FIGS. 8A–C show the polynucleotide sequence (SEQ ID NO: 53) and deduced amino acid sequence (SEQ ID NO:54) of the novel human calpain, CAN-12v1, of the present invention. The standard one-letter abbreviation for amino acids is used to illustrate the deduced amino acid sequence. The polynucleotide sequence contains a sequence of 2095 nucleotides (SEQ ID NO:53), encoding a polypeptide of about 694 amino acids (SEQ ID NO:54). The polynucleotide sequence of CAN-12v1 is believed to represent a novel splice variant of the CAN-12 polynucleotide described herein. An analysis of the CAN-12v1 polypeptide determined that it comprised the following features: predicted active site domain amino acids located from about amino acid R90 to about amino acid C94, from about amino acid G99 to about amino acid L104, from about amino acid Q196 to about amino acid S198, from about amino acid M210 to about amino acid I212, from about amino acid G236 to about amino acid H240, from about amino acid E252 to about amino acid Y256, from about amino acid N278 to about amino acid K282, and/or from about amino acid V328 to about amino acid V331 of SEQ ID NO:54 (FIGS. 8A–C) represented by shading; a predicted eukaryotic thiol (cysteine) protease active site domain located from about amino acid 90 to about amino acid 111 of SEQ ID NO:54 (FIGS. 8A–C) represented by double underlining; a predicted EF-hand calcium-binding domain located from about amino acid 567 to about amino acid 584 of SEQ ID NO:54 (FIGS. 8A–C) represented by dotted underlining; and a predicted cell attachment sequence located from about amino acid 633 to about amino acid 532 of SEQ ID NO:54 (FIGS. 8A–C) represented in italics. The presence of the eukaryotic thiol (cysteine) protease active site domain, in addition to, the EF-hand calcium binding domain is consistent with the CAN-12v1 polypeptide representing a member of the calpain family of proteases. The predicted active site domain amino acids are believed to form the active site binding pocket of the CAN-12v1 polypeptide and facilitate catalysis of appropriate calpain substrates. The predicted catalytic amino acid residues within the CAN-12v1 active site are located at amino acid C101, H254, and N278 residues of SEQ ID NO:54 (FIGS. 8A–C) and are denoted by an arrow ("↑").

FIGS. 9A–C show the polynucleotide sequence (SEQ ID NO: 55) and deduced amino acid sequence (SEQ ID NO:56) of the novel human calpain, CAN-12v2, of the present invention. The standard one-letter abbreviation for amino acids is used to illustrate the deduced amino acid sequence. The polynucleotide sequence contains a sequence of 2104 nucleotides (SEQ ID NO:53), encoding a polypeptide of about 694 amino acids (SEQ ID NO:56). The polynucleotide sequence of CAN-12v2 is believed to represent a novel splice variant of the CAN-12 polynucleotide described herein and likely represents the physiologically relevant splice form. An analysis of the CAN-12v2 polypeptide determined that it comprised the following features: predicted active site domain amino acids located from about amino acid R90 to about amino acid C94, from about amino acid G99 to about amino acid L104, from about amino acid Q196 to about amino acid S198, from about amino acid M210 to about amino acid I212, from about amino acid G236 to about amino acid H240, from about amino acid E252 to about amino acid Y256, from about amino acid N278 to about amino acid K282, and/or from about amino acid V328 to about amino acid V331 of SEQ ID NO:56 (FIGS. 9A–C) represented by shading; a predicted eukaryotic thiol (cysteine) protease active site domain located from about amino acid 90 to about amino acid 111 of SEQ ID NO:56 (FIGS. 9A–C) represented by double underlining; a predicted EF-hand calcium-binding domain located from about amino acid 565 to about amino acid 587 of SEQ ID NO:56 (FIGS. 9A–C) represented by dotted underlining; and a predicted cell attachment sequence located from about amino acid 636 to about amino acid 648 of SEQ ID NO:56 (FIGS. 9A–C) represented by italics. The presence of the eukaryotic thiol (cysteine) protease active site domain, in addition to, the EF-hand calcium binding domain is consistent with the CAN-12v2 polypeptide representing a member of the calpain family of proteases. The predicted active site domain amino acids are believed to form the active site binding pocket of the CAN-12v2 polypeptide and facilitate catalysis of appropriate calpain substrates. The predicted catalytic amino acid residues within the CAN-12v2 active site are located at amino acid C101, H254, and N278 residues of SEQ ID NO:56 (FIGS. 9A–C) and are denoted by an arrow ("↑").CAN-12v2 is believed to represent the true physioligical form of CAN-12.

FIGS. 10A–B show the regions of identity and similarity between the encoded CAN-12+ (SEQ ID NO:2), CAN-12v1 (SEQ ID NO:54), CAN-12v2 polypeptides (SEQ ID NO:56), and CAN-12 (SEQ ID NO:24) The alignment was performed using the CLUSTALW algorithm described elsewhere herein. The darkly shaded amino acids represent regions of matching identity. The lightly shaded amino acids represent regions of matching similarity. Lines between residues indicate gapped regions for the aligned polypeptides.

Figure 11:
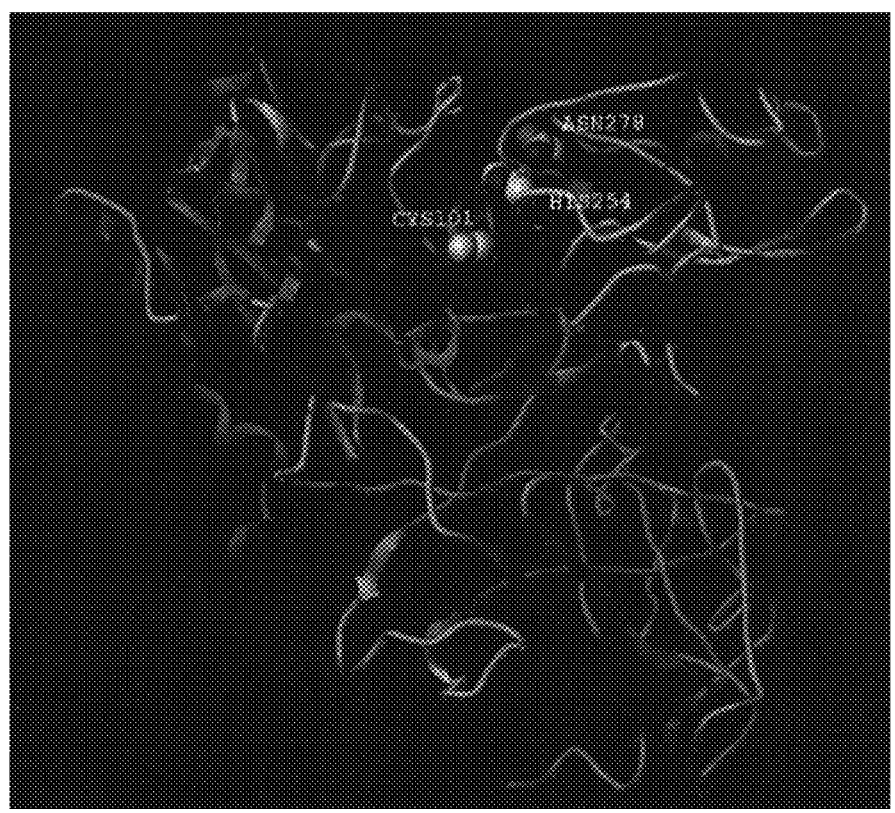

FIG. 11 shows a three-dimensional homology model of the CAN-12v2 polypeptide based upon the homologous structure of a portion of the human m-calpain, also referred to as, CAN2 (hCAN2; Genbank Accession No. gil4502563; SEQ ID NO:11). The predicted catalytic active site amino acids of the human CAN-12v2 polypeptide are labeled. The predicted regions of alpha helix structure are represented in magenta; the predicted regions of beta sheet structure are represented in yellow; the predicted regions of flexible loop structure are represented in cyan; the catalytic amino acid residues are shown in a CPK/space filled rendering of the side chain atoms wherein carbon atoms are represeted in white, the sulfur atoms are represented in yellow, and the nitrogen atoms are represented in blue. The structural coordinates of the CAN-12v2 polypeptide are provided in Table V herein. The homology model of CAN-12v2 was derived from generating a sequence alignment with the human m-calpain, CAN2 protein (hCAN2; Genbank Accession No. gil4502563; SEQ ID NO:11) using the SYBYL suite of software (Tripos, Inc., St. Louis, Mo.), and the overall atomic model including plausible sidechain orientations using the program COMPOSER (Tripos, Inc., St. Louis, Mo.).

Figure 12:
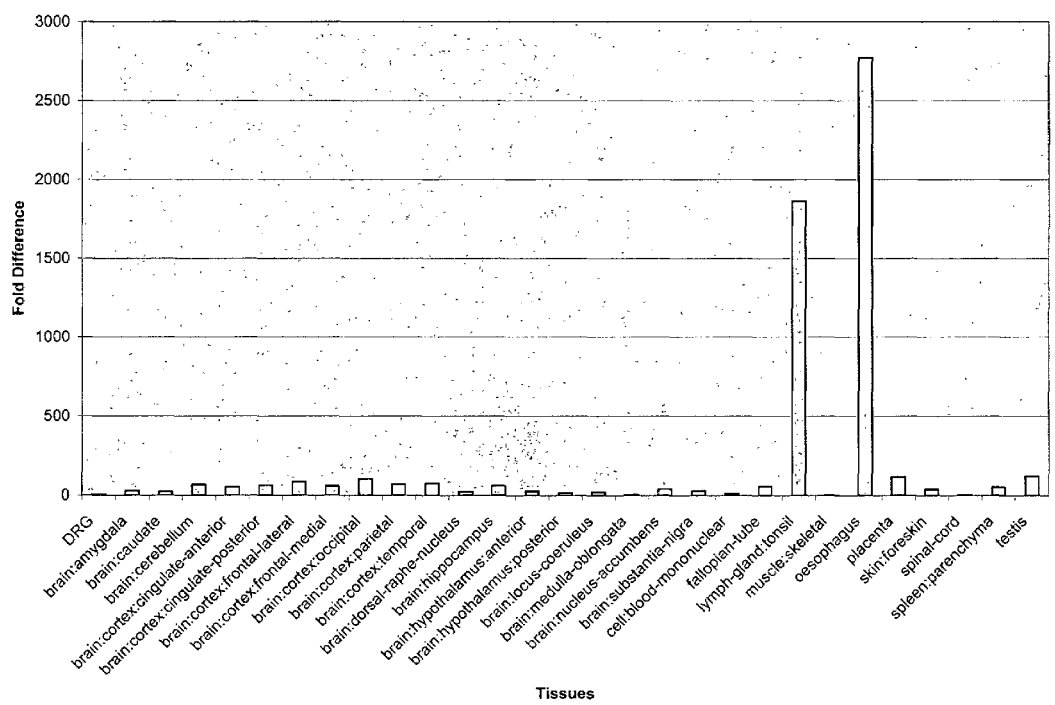

FIG. 12 shows an expanded expression profile of the novel human calpains, CAN-12v2 and CAN-12v1. The figure illustrates the relative expression level of CAN-12v2 and CAN-12v1 amongst various mRNA tissue sources. As shown, the CAN-12v2 and CAN-12v1 polypeptides were expressed at relatively low levels, though predominately in esophagus, lymph node, and to a lesser extent in other tissues as shown. Expression data was obtained by measuring the steady state CAN-12v2 and CAN-12v1 mRNA levels by quantitative PCR using the PCR primer pair provided as SEQ ID NO:143 and 144, and TAQMAN™ probe (SEQ ID NO:145) as described in Example 6 herein. These primers are specific to both CAN-12v1 and CAN-12v2.

Figure 13:
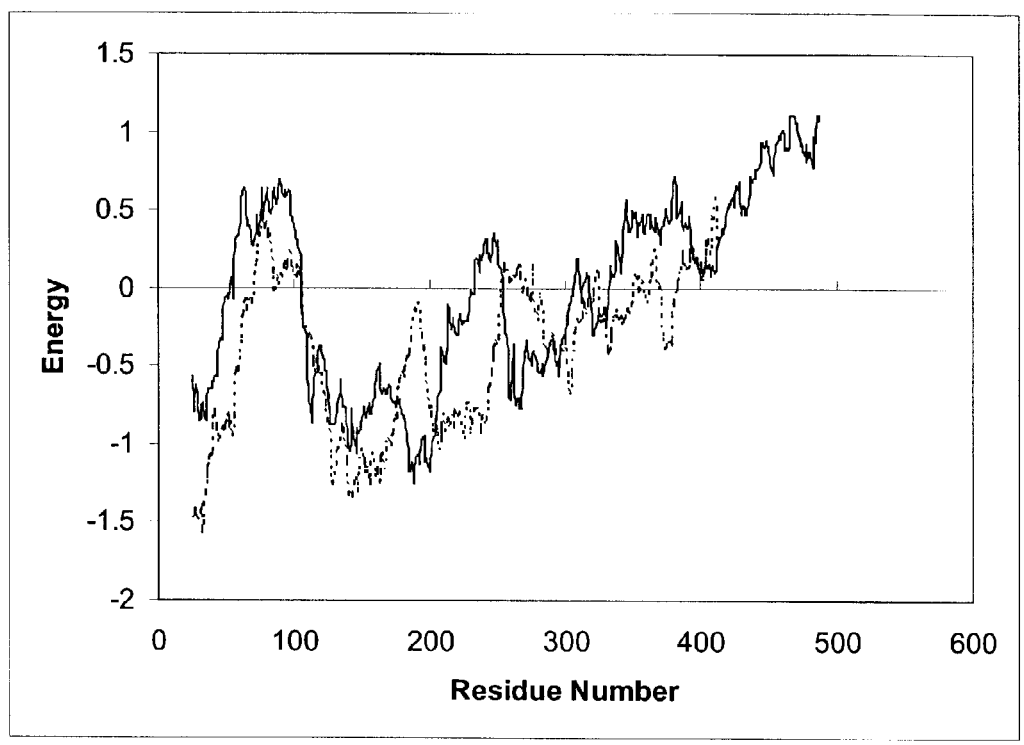

FIG. 13 shows an energy graph for the CAN-12.v2 model (see FIG. 11) of the present invention (solid line) and the human m-calpain template (PDB code 1dkv) (dotted line) from which the model was generated. The energy distribution for each protein fold is displayed on the y-axis, while the amino acid residue position of the protein fold is displayed on the x-axis. As shown, the CAN-12.v2 model and 1dkv template have similar energies over the aligned region, suggesting that the structural model of CAN-12.v2 represents a "native-like" conformation of the CAN-12.v2 polypeptide. This graph supports the motif and sequence alignments in confirming that the three-dimensional structure coordinates of CAN-12.v2 are an accurate and useful representation of the structure of the CAN-12.v2 polypeptide.

Table I provides a summary of the novel polypeptides and their encoding polynucleotides of the present invention.

Table II illustrates the preferred hybridization conditions for the polynucleotides of the present invention. Other hybridization conditions may be known in the art or are described elsewhere herein.

Table III provides a summary of various conservative substitutions encompassed by the present invention.

Table IV provides the structural coordinates of the homology model of the CAN-12 polypeptide provided in FIG. 6. A description of the headings are as follows: "Atom No" refers to the atom number within the CAN-12 homology model; "Atom Name" refers to the element whose coordinates are measured, the first letter in the column defines the element; "Residue" refers to the amino acid of the CAN-12 polypeptide within which the atom resides, in addition to the amino acid position in which the atom resides; "X Coord", "Y Coord", and "Z Coord" structurally define the atomic position of the element measured in three dimensions.

Table V provides the structural coordinates of the homology model of the CAN-12v2 polypeptide provided in FIG. 11. A description of the headings are as follows: "Atom No" refers to the atom number within the CAN-12v2 homology model; "Atom Name" refers to the element whose coordinates are measured, the first letter in the column defines the element; "Residue" refers to the amino acid of the CAN-12v2 polypeptide within which the atom resides, in addition to the amino acid position in which the atom resides; "X Coord", "Y Coord", and "Z Coord" structurally define the atomic position of the element measured in three dimensions.

DETAILED DESCRIPTION OF THE INVENTION

The present invention may be understood more readily by reference to the following detailed description of the preferred embodiments of the invention and the Examples included herein. All references to "CAN-12" shall be construed to apply to CAN-12+, CAN-12, CAN-12v1, and/or CAN-12v2 unless otherwise specified herein.

The invention provides a novel human sequence that encodes a calpain with substantial homology to the large subunits of a variety of known calpains. Calpains affect a variety of cellular processes based upon their involvement in modulating signal transduction. Aberrations in the large subunit polypeptides of calpains have been implicated in a number of diseases and disorders which include, for example, incidence of type II diabetes (Horikawa et al., Nat Genet. 26:163–75 (2000)), limb-girdle muscular dystrophy (Richard et al., Cell 81:27–40 (1995)), ischemia-induced damage in neurons and heart tissue, neurodegenerative disorders such as Alzheimer's disease, Multiple sclerosis, Huntington's disease, Parkinson's disease and amyotrophy, inflammatory disorders, susceptibility to infectious diseases, etc. CAN-12 polynucleotides and polypeptides, including agonists and antagonists thereof are expected to be useful in ameliorating at least some of these disorders. In addition, expression analysis indicates the CAN-12 has strong preferential expression in esophagus, lymph node, spinal cord, and to a lesser extent, in thymus, and spleen. Based on this information, we have provisionally named the gene and protein CAN-12.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention.

In specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the gene of interest in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

As used herein, a "polynucleotide" refers to a molecule having a nucleic acid sequence contained in SEQ ID NO:1, SEQ ID NO:53, SEQ ID NO:55, SEQ ID NO:23 or the cDNA contained within the clone(s) deposited with the ATCC. For example, the polynucleotide can contain the nucleotide sequence of the full length cDNA sequence, including the 5' and 3' untranslated sequences, the coding region, with or without a signal sequence, the secreted protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

In the present invention, the full length sequence identified as SEQ ID NO:1, SEQ ID NO:53, SEQ ID NO:55, and SEQ ID NO:23 was often generated by overlapping sequences contained in one or more clones (contig analysis). A representative clone containing all or most of the sequence for SEQ ID NO:1, SEQ ID NO:53, SEQ ID NO:55, and/or, SEQ ID NO:23 was deposited with the American Type Culture Collection ("ATCC"). As shown in Table I, each clone is identified by a cDNA Clone ID (Identifier) and the ATCC Deposit Number. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure. The deposited clone is inserted in the pSport1 plasmid (Life Technologies) using the NotI and SalI restriction endonuclease cleavage sites.

Unless otherwise indicated, all nucleotide sequences determined by sequencing a DNA molecule herein were determined using an automated DNA sequencer (such as the Model 373, preferably a Model 3700, from Applied Biosystems, Inc.), and all amino acid sequences of polypeptides encoded by DNA molecules determined herein were predicted by translation of a DNA sequence determined above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in FIGS. 1A–E (SEQ ID NO:1), a nucleic acid molecule of the present invention encoding the CAN-12 polypeptide may be obtained using standard cloning and screening procedures, such as those for cloning cDNAs using mRNA as starting material. Illustrative of the invention, the nucleic acid molecule described in FIGS. 1A–E (SEQ ID NO:1) was discovered in a cDNA library derived from human liver, brain and testis and spleen.

The determined nucleotide sequence of the CAN-12 cDNA in FIGS. 1A–E (SEQ ID NO:1) contains an open reading frame encoding a protein of about 428 amino acid residues, with a deduced molecular weight of about 49.5 kDa. The amino acid sequence of the predicted CAN-12 polypeptide is shown in FIGS. 1A–E (SEQ ID NO:24).

Using the information provided herein, such as the nucleotide sequence in FIGS. 8A–C (SEQ ID NO:53), a nucleic acid molecule of the present invention encoding the CAN-12v1 polypeptide may be obtained using standard cloning and screening procedures, such as those for cloning cDNAs using mRNA as starting material. Illustrative of the invention, the nucleic acid molecule described in FIGS. 8A–C (SEQ ID NO:53) was discovered in a cDNA library derived from human liver, brain and testis and spleen.

The determined nucleotide sequence of the CAN-12v1 cDNA in FIGS. 8A–C (SEQ ID NO:53) contains an open reading frame encoding a protein of about 694 amino acid residues, with a deduced molecular weight of about 80.3 kDa. The amino acid sequence of the predicted CAN-12v1 polypeptide is shown in FIGS. 8A–C (SEQ ID NO:54).

Using the information provided herein, such as the nucleotide sequence in FIGS. 9A–C (SEQ ID NO:55), a nucleic acid molecule of the present invention encoding the CAN-12v2 polypeptide may be obtained using standard cloning and screening procedures, such as those for cloning cDNAs using mRNA as starting material. Illustrative of the invention, the nucleic acid molecule described in FIGS. 9A–C (SEQ ID NO:55) was discovered in a cDNA library derived from human liver, brain and testis and spleen.

The determined nucleotide sequence of the CAN-12v2 cDNA in FIGS. 9A–C (SEQ ID NO:55) contains an open reading frame encoding a protein of about 697 amino acid residues, with a deduced molecular weight of about 80.6 kDa. The amino acid sequence of the predicted CAN-12v2 polypeptide is shown in FIGS. 9A–C (SEQ ID NO:56).

A "polynucleotide" of the present invention also includes those polynucleotides capable of hybridizing, under stringent hybridization conditions, to sequences contained in SEQ ID NO:1, SEQ ID NO:53, SEQ ID NO:55, SEQ ID NO:23, the complement thereof, or the cDNA within the clone deposited with the ATCC. "Stringent hybridization conditions" refers to an overnight incubation at 42 degree C. in a solution comprising 50% formamide, 5×SSC (750 mM NaCl, 75 mM trisodium citrate), 50 mM sodium phosphate (pH 7.6), 5× Denhardt's solution, 10% dextran sulfate, and 20 μg/ml denatured, sheared salmon sperm DNA, followed by washing the filters in 0.1×SSC at about 65 degree C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37 degree C. in a solution comprising 6×SSPE (20×SSPE=3M NaCl; 0.2M NaH2PO4; 0.02M EDTA, pH 7.4), 0.5% SDS, 30% formamide, 100 ug/ml salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone generated using oligo dT as a primer).

The polynucleotide of the present invention can be composed of any polyribonucleotide or polydeoxribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins—Structure and Molecular Properties, 2nd Ed., T. E. Creighton, W. H. Freeman and Company, New York (1993); Posttranslational Covalent Modification of Proteins, B. C. Johnson, Ed., Academic Press, New York, pgs. 1–12 (1983); Seifter et al., Meth Enzymol 182:626–646 (1990); Rattan et al., Ann NY Acad Sci 663:48–62 (1992).)

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about tenfold less activity, and most preferably, not more than about three-fold less activity relative to the polypeptide of the present invention.)

The term "organism" as referred to herein is meant to encompass any organism referenced herein, though preferably to eukaryotic organisms, more preferably to mammals, and most preferably to humans.

As used herein the terms "modulate" or "modulates" refer to an increase or decrease in the amount, quality or effect of a particular activity, DNA, RNA, or protein. The definition of "modulate" or "modulates" as used herein is meant to encompass agonists and/or antagonists of a particular activity, DNA, RNA, or protein.

The present invention encompasses the identification of proteins, nucleic acids, or other molecules, that bind to polypeptides and polynucleotides of the present invention (for example, in a receptor-ligand interaction). The polynucleotides of the present invention can also be used in interaction trap assays (such as, for example, that described by Ozenberger and Young (Mol Endocrinol., 9(10):1321–9, (1995); and Ann. N.Y. Acad. Sci., 7;766:279–81, (1995)).

The polynucleotide and polypeptides of the present invention are useful as probes for the identification and isolation of full-length cDNAs and/or genomic DNA which correspond to the polynucleotides of the present invention, as probes to hybridize and discover novel, related DNA sequences, as probes for positional cloning of this or a related sequence, as probe to "subtract-out" known sequences in the process of discovering other novel polynucleotides, as probes to quantify gene expression, and as probes for microarrays.

In addition, polynucleotides and polypeptides of the present invention may comprise one, two, three, four, five, six, seven, eight, or more membrane domains.

Also, in preferred embodiments the present invention provides methods for further refining the biological function of the polynucleotides and/or polypeptides of the present invention.

Specifically, the invention provides methods for using the polynucleotides and polypeptides of the invention to identify orthologs, homologs, paralogs, variants, and/or allelic variants of the invention. Also provided are methods of using the polynucleotides and polypeptides of the invention to identify the entire coding region of the invention, non-coding regions of the invention, regulatory sequences of the invention, and secreted, mature, pro-, prepro-, forms of the invention (as applicable).

In preferred embodiments, the invention provides methods for identifying the glycosylation sites inherent in the polynucleotides and polypeptides of the invention, and the subsequent alteration, deletion, and/or addition of said sites for a number of desirable characteristics which include, but are not limited to, augmentation of protein folding, inhibition of protein aggregation, regulation of intracellular trafficking to organelles, increasing resistance to proteolysis, modulation of protein antigenicity, and mediation of intercellular adhesion.

In further preferred embodiments, methods are provided for evolving the polynucleotides and polypeptides of the present invention using molecular evolution techniques in an effort to create and identify novel variants with desired structural, functional, and/or physical characteristics.

The present invention further provides for other experimental methods and procedures currently available to derive functional assignments. These procedures include but are not limited to spotting of clones on arrays, micro-array technology, PCR based methods (e.g., quantitative PCR), anti-sense methodology, gene knockout experiments, and other procedures that could use sequence information from clones to build a primer or a hybrid partner.

Polynucleotides and Polypeptides of the Invention

Features of the Polypeptide Encoded by Gene No:1

The polypeptide of this gene provided as SEQ ID NO:24 (FIGS. 1A–E), encoded by the polynucleotide sequence according to SEQ ID NO:1 (FIGS. 1A–E), and/or encoded by the polynucleotide contained within the deposited clone, CAN-12, has significant homology at the nucleotide and amino acid level to a number of calpains, which include, for example, the human CAN10 protein (type II diabetes linked) (hCAN10; Genbank Accession No: gi|NP_075574; SEQ ID NO:3); the human CAN5 protein (hCAN5; Genbank Accession No: gi|NP_004046; SEQ ID NO:4); the large catalytic subunit of the human CALPAIN 1 protein (also referred to as Calcium-Activated Neutral Proteinase, CANP, μ-TYPE) (hCAN1; Genbank Accession No: gi|12408656; SEQ ID NO:5); the large subunit of the human calpain 3 protein (EC 3.4.22.17) (also referred to as CALPAIN L3, CALPAIN P94, Calcium-Activated Neutral Proteinase 3, CANP 3; muscle-specific calcium-activated neutral protease 3 large subunit) (hCAN3; Genbank Accession No: gi|4557405; SEQ ID NO:6); the large catalytic subunit of the mouse CALPAIN 1 protein (also referred to as Calcium-Activated Neutral Proteinase) (CANP) μ-TYPE) (mCALPAIN1; Genbank Accession No: gi|O88666; SEQ ID NO:7); the mouse CALPAIN LP82 (mLP82; Genbank Accession No: gi|3661585; SEQ ID NO:8); the rat stomach-specific calcium-activated neutral protease large subunit, NCL2 protein (rNCL2; Genbank Accession No: gi|NP_006606; SEQ ID NO:9); the human CAN11 protein (hCAN11; Genbank Accession No: gi|NP_008989; SEQ ID NO:10); the human CAN2 protein (hCAN2; Genbank Accession No: gi|4502563; SEQ ID NO:11); and the human CAN9 protein (hCAN9; Genbank Accession No: gi|5729758; SEQ ID NO:12). An alignment of the CAN-12 polypeptide with these proteins is provided in FIGS. 2A–E. Based upon such strong conservation, the inventors have ascribed the CAN-12 polypeptide as having proteolytic activity, preferably calpain activity.

The CAN-12+ (SEQ ID NO:2) polypeptide was determined to have 30.7% identity and 38.0% similarity with the human CAN10 protein (type II diabetes linked) (hCAN10; Genbank Accession No: gi|NP_075574; SEQ ID NO:3); to have 34.2% identity and 45.4% similarity with the human CAN5 protein (hCAN5; Genbank Accession No: gi|NP_004046; SEQ ID NO:4); to have 37.9% identity and 47.4% similarity with the large catalytic subunit of the human CALPAIN 1 protein (also referred to as Calcium-Activated Neutral Proteinase, CANP, μ-TYPE) (hCAN1; Genbank Accession No: gi|12408656; SEQ ID NO:5); to have 36.3% identity and 43.6% similarity with the large subunit of the human calpain 3 protein (EC 3.4.22.17) (also referred to as CALPAIN L3, CALPAIN P94, Calcium-Activated Neutral Proteinase 3, CANP 3; muscle-specific calcium-activated neutral protease 3 large subunit) (hCAN3; Genbank Accession No: gi|4557405; SEQ ID NO:6); to have 39.0% identity and 47.6% similarity with the large catalytic subunit of the mouse CALPAIN 1 protein (also referred to as Calcium-Activated Neutral Proteinase) (CANP) μ-TYPE ) (mCALPAIN1; Genbank Accession No: gi|O88666; SEQ ID NO:7); to have 37.8% identity and 45.3% similarity with the mouse CALPAIN LP82 (mLP82; Genbank Accession No: gi|3661585; SEQ ID NO:8); to have 34.2% identity and 45.4% similarity with the rat stomach-specific calcium-activated neutral protease large subunit, NCL2 protein (rNCL2; Genbank Accession No: gi|NP_006606; SEQ ID NO:9); to have 40.4% identity and 47.3% similarity with the human CAN11 protein (hCAN11; Genbank Accession No: gi|NP_008989; SEQ ID NO:10); to have 36.8% identity and 45.8% similarity with the human CAN2 protein (hCAN2; Genbank Accession No: gi|4502563; SEQ ID NO:11); and to have 39.4% identity and 47.2% similarity with the human CAN9 protein (hCAN9; Genbank Accession No: gi|5729758; SEQ ID NO:12). The polypeptide sequence used for these percent identity and similarity values comprised the additional amino acids that extend beyond amino acid 428 of SEQ ID NO:24—specifically, SEQ ID NO:2.

The CAN-12 polypeptide was determined to have 34.3% identity and 42.3% similarity with the human CAN10 protein (type II diabetes linked) (hCAN10; Genbank Accession No: gi|NP_075574; SEQ ID NO:3); to have 40.5% identity and 51.9% similarity with the human CAN5 protein (hCAN5; Genbank Accession No: gi|NP_004046; SEQ ID NO:4); to have 44.3% identity and 51.9% similarity with the large catalytic subunit of the human CALPAIN 1 protein (also referred to as Calcium-Activated Neutral Proteinase, CANP, μ-TYPE) (hCAN1; Genbank Accession No: gi|12408656; SEQ ID NO:5); to have 44.9% identity and 51.8% similarity with the large subunit of the human calpain 3 protein (EC 3.4.22.17) (also referred to as CALPAIN L3, CALPAIN P94, Calcium-Activated Neutral Proteinase 3, CANP 3; muscle-specific calcium-activated neutral protease 3 large subunit) (hCAN3; Genbank Accession No: gi|4557405; SEQ ID NO:6); to have 46.1% identity and 52.7% similarity with the large catalytic subunit of the mouse CALPAIN 1 protein (also referred to as Calcium-Activated Neutral Proteinase) (CANP) μ-TYPE ) (mCALPAIN1; Genbank Accession No: gi|O88666; SEQ ID NO:7); to have 46.2% identity and 53.5% similarity with the mouse CALPAIN LP82 (mLP82; Genbank Accession No: gi|3661585; SEQ ID NO:8); to have 44.6% identity and 51.4% similarity with the rat stomach-specific calcium-activated neutral protease large subunit, NCL2 protein (rNCL2; Genbank Accession No: gi|NP_006606; SEQ ID NO:9); to have 45.5% identity and 51.7% similarity with the human CAN11 protein (hCAN11; Genbank Accession No: gi|NP_008989; SEQ ID NO:10); to have 46.2% identity and 53.5% similarity with the human CAN2 protein (hCAN2; Genbank Accession No: gi|4502563; SEQ ID NO:11); and to have 44.3% identity and 51.9% similarity with the human CAN9 protein (hCAN9; Genbank Accession No: gi|5729758; SEQ ID NO:12). The polypeptide sequence used for these percent identity and similarity values was the full-length CAN-12 polypeptide (SEQ ID NO:24).

The human CAN10 protein (type II diabetes linked) (hCAN10; Genbank Accession No: gi|NP_075574; SEQ ID NO:3)is a human calpain gene that encodes a large calpain subunit. CAN10 is an atypical calpain in that it lacks the calmodulin-like calcium-binding domain and instead has a divergent C-terminal domain. CAN10 is similar in organization to calpains 5 and 6 and is associated with type 2 or non-insulin-dependent diabetes mellitus (NIDDM) and located within the NIDDM1 chromosomal region (Nat. Genet. 26 (2), 163–175 (2000)).

The large subunit of the human calpain 3 protein (EC 3.4.22.17) (also referred to as CALPAIN L3, CALPAIN P94, Calcium-Activated Neutral Proteinase 3, CANP 3; muscle-specific calcium-activated neutral protease 3 large subunit) (hCAN3; Genbank Accession No: gi|4557405; SEQ ID NO:6) is a muscle-specific member of the calpain large subunit family. Loss of CAPN3 function has been associated with limb-girdle muscular dystrophies type 2A (Cell 81 (1), 27–40 (1995)).

The human CAN9 protein (hCAN9; Genbank Accession No: gil5729758; SEQ ID NO:12) is a calpain that is expressed predominantly in stomach and small intestine and is thought to have specialized functions in the digestive tract, and be associated with gastric cancer.(Biol. Chem. 379 (2), 175–183 (1998); and Jpn. J. Cancer Res. 91 (5), 459–463 (2000)).

As described above, the CAN-12 polypeptide was found to have significant sequence homology with calpains, particularly members of the m-calpain family. A conserved peptide signature of Qx3(G,E)xC(Y,W)x2(S,T,A,G,C)(S,T,A,G,C,V) Qx{3} (G)xC(W)x{2} (A)(A) (referred to as a thiol (cysteine) protease active site domain) common to most calpain family members is found in the protein sequence of CAN-12 from amino acid 90 to amino acid 111 of SEQ ID NO:24 (FIGS. 1A–E). Protein threading and molecular modeling of CAN-12 suggests that CAN-12 has a structural fold similar to representative m-calpains. Moreover, the structural and threading alignments of the present invention suggest that amino acids 101 ("C"), 253 ("H"), and 277 ("N") of SEQ ID NO:24 (FIGS. 1A–E) may represent the catalytic amino acids within the active site domain. Thus, based upon the sequence and structural homology to known calpains, particularly the presence of the thiol cysteine protease active site domain, the novel CAN-12 is believed to represent a novel human calpain.

In an alternative embodiment, the following polypeptide is encompassed by the present invention: MSLWPPFRCR-WKLAPRYSRRASPQQPQQDFEALLAECL-RNGCLFEDTSFPAT LSSIGSGSLLQKLPPRLQWKRP-PELHSNPQFYFAKAKRLDLCQGIVGDCWFLA ALQALALHQDILSRVVPLNQSFTEKY-AGIFRFWFWHYGNWVPVVIDDRLPVN EAGQLVFVSSTYKNLFWGALLEKAY-AKLSGSYEDLQSGQVSEALVDFTGGVT MTINLAE-AHGNLWDILEATYNRTLIGCQTHS-GKILENGLVEGHAYTLTGIRKV TCKHRPEYLVKLRNPWGKVEWKGDWS-DSSSKWELLSPKEKILLLRKDNDGE FWMTLQDFK-THFVLLVICKLTPGLLSQEAAQKWTYTM-REGRWEKRSTAGGQ RQLLQDTFWKNPQFLLSVWRPEEGRRSL-RPCSVLVSLLQKPRHRCRKRKPLL AIGFYLYRMNK (SEQ ID NO:24). Polynucleotides encoding these polypeptides are also provided (SEQ ID NO:23).

In confirmation of the strong homology to known calpains, the CAN-12 polypeptide was determined to have several conserved catalytic amino acids at amino acid C101, H253, and N277 of SEQ ID NO:24 (FIGS. 1A–E). As discussed more particularly herein, calpains are a group of structurally diverse, high molecular weight (400 to 500 amino acids) proteins that have a catalytic cysteine amino acid and one or more calcium binding domains. Despite the structural heterogeneity, calpains share some well defined structural-functional characteristics, particularly in their active site domains.

In preferred embodiments, the CAN-12 polypeptide of the present invention is directed to a polypeptide having structural similarity to calpains.

Based upon the strong homology to members of the calpain family, the CAN-12 polypeptide is expected to share at least some biological activity with calpains, preferably with m-calpain family members, and more preferable to the large subunits of m-calpain family members, in addition to other calpains and calpain subunits referenced herein and/or otherwise known in the art.

Expression profiling designed to measure the steady state mRNA levels encoding the CAN-12 polypeptide showed predominately high expression levels in spinal cord tissue; significantly high expression in lymph node and thymus, and to a lesser extent, in spleen tissue (See FIG. 4).

Expanded analysis of CAN-12v1 and CAN-12v2 expression levels by TAQMAN™ quantitative PCR (see FIG. 12) confirmed that the CAN-12 polypeptide is expressed in the lymph gland. However, the TAQMAN™ quantitative PCR determined that the CAN-12v1 and CAN-12v2 polypeptide is primarily expressed in the esophagus. In fact, with the exception of the lymph gland, the steady state mRNA level of CAN-12v1 and CAN-12v2 was approximately 2700 times higher in the esophagus than in all other tissues tested. These data suggest modulators of the CAN-12 polynucleotides and polypeptides may be useful for the treatment, detection, and/or amelioration of the following, non-limiting diseases and disorders associated with the esophagus: dysphagia, cricoharyngeal in coordination, esophageal carcinoma, esophageal webs, achalasia, symptomatic diffuse esophageal spasm; gastroesophageal reflux, and/or corrosive esophagitis.

The polynucleotides encoding the CAN-12 polypeptide of the present invention were used to determine the chromosomal localization of the calpain12 gene. which encodes the CAN-12, CAN-12v1, and CAN-12v2 polypeptides of the present invention. Polynucleotides corresponding to CAN-12 (SEQ ID NO:1) were shown to localize to chromosome 2, specifically 2p16-p21. The comparison of the chromosomal location of the calpain12 gene with the location of chromosomal regions which have been shown to be associated with specific diseases or conditions, e.g. by linkage analysis, can be indicative of diseases in which calpain12 may play a role. Interestingly, a whole-genome linkage scan in multiple sclerosis families (Ebers et al. A full genome search in multiple sclerosis. Nature Genet. 13: 472–476, 1996.) identified 5 susceptibility loci on chromosomes 2, 3, 5, 11, and X. In particular, an association was identified with marker D2S119 on chromosome 2 and MS. The localization of the D2S119 marker was further delineated to 2p16-p21 based on a radiation hybrid linkage map retrieved from an online query at an NCBI web site. Since the map of calpain 12 and the susceptibility marker D2S119 overlaps, it is reasonable to postulate that calpain 12 may contribute to MS. Furthermore, the transcription profile of calpain12 indicated a prominent expression in spinal cord, and implication of calpains in MS has been suggested (Shields DC et al. A putative mechanism of demyelination in multiple sclerosis by a proteolytic enzyme, calpain. Proc Nati Acad Sci U S A. 96:11486–91.1999).

The CAN-12 polynucleotides and polypeptides of the present invention, including agonists, antagonists, and/or fragments thereof, have uses that include modulating cellular adhesion events, cellular proliferation, and inflammation, in various cells, tissues, and organisms, and particularly in mammalian spinal cord tissue, lymph node, thymus, and spleen tissue, preferably human tissue. CAN-12 polynucleotides and polypeptides of the present invention, including agonists and/or fragments thereof, may be useful in diagnosing, treating, prognosing, and/or preventing neural, immune, hematopoietic, and/or proliferative diseases or disorders.

The strong homology to human calpains, particularly m-calpains, combined with the predominate localized expression in esophagus tissue suggests the CAN-12 polynucleotides and polypeptides may be useful in treating, diagnosing, prognosing, and/or preventing gastrointestinal diseases, particularly esophageal diseases and/or disorders which include the following non-limiting examples: aberrant transport of food bolus from the mouth to the stomach, aberrant prevention of retrograde flow of gastrointestinal contents, aberrant esophageal peristaltic contractions, pyrosis, painful swallowing, reflux esophagitis, esophageal motility disorders, esophageal spasms, diffuse esophageal spasm, atypical chest pain, regurgitation, oropharyngeal paralysis, nasal regurgitation, dysphagia, cricopharyngeal bar, globus pharyngeus, achalasia, motor disorders of the esophageal smooth muscle, scleroderma esophagus, gastroesophageal reflux disease (GERD), esophagitis, Barrett's esophagus, viral esophagitis, Herpes simplex virus mediated viral esophagitis, Varicella-zoster virus mediated viral esophagitis, Cytomegalovirus mediated viral esophagitis, bacterial esophagitis, *Lactobacillus* mediated bacterial esophagitis, *Candida* mediated esophagitis, radiation esophagitis, corrosive esophagitis, pill-induced esophagitis, esophagitis associated with mucocutaneous and systemic diseases, diverticula, lower esophageal mucosal ring, lower esophageal muscular ring, hiatal hernia, paraesophageal hernia, esophageal rupture, and/or Mallory-Weiss Syndrome.

Although calpains are typically associated primarily with neurogenerative conditions, their association in gastrointestinal tissues has precedence. For example, the human CAN9 protein (hCAN9; Genbank Accession No: gil5729758; SEQ ID NO:12) is predominately expressed in the stomach and small intestine and is thought to be associated with gastric cancers.

The strong homology to human calpains, particularly m-calpains, combined with the predominate expression in spinal cord tissue suggests the CAN-12 polynucleotides and polypeptides may be useful in treating, diagnosing, prognosing, and/or preventing neural diseases, neurodegenerative disease states, behavioral disorders, or inflammatory conditions. Representative uses are described in the "Neurological Diseases", "Regeneration" and "Hyperproliferative Disorders" sections below, in the Examples, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Alternatively, the strong homology to human calpains, particularly m-calpains, combined with the localized expression in lymph node, thymus, and spleen tissue suggests the CAN-12 polynucleotides and polypeptides may be useful in treating, diagnosing, prognosing, ameliorating, and/or preventing immune diseases and/or disorders. Representative uses are described in the "Immune Activity" and "Infectious Disease" sections below, and elsewhere herein. Briefly, the strong expression in immune tissue indicates a role in regulating the proliferation; survival; differentiation; and/or activation of hematopoietic cell lineages, including blood stem cells. The CAN-12 polypeptide may also be useful as a preventative agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product may be useful in the expansion of stem cells and committed progenitors of various blood lineages, and in the differentiation and/or proliferation of various cell types.

Moreover, the protein would be useful in the detection, treatment, and/or prevention of a variety of vascular disorders and conditions, which include, but are not limited to miscrovascular disease, vascular leak syndrome, aneurysm, stroke, embolism, thrombosis, coronary artery disease, arteriosclerosis, and/or atherosclerosis. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

In addition, antagonists of the CAN-12 polynucleotides and polypeptides may have uses that include diagnosing, treating, prognosing, and/or preventing diseases or disorders related to hyper calpain activity, which may include immune and/or proliferative diseases or disorders, particularly thrombosis, embolism, and other blood disorders. Therapeutic and/or pharmaceutical compositions comprising the CAN-12 polypeptides may be formulated to comprise heparin.

In addition, antagonists of the CAN-12 polynucleotides and polypeptides may have uses that include diagnosing, treating, ameliorating, prognosing, and/or preventing diseases or disorders related to hyper calpain activity, which may include neuronal excitotoxicity, ischemic stroke, hemoragic stroke, hypoxic stress, trauma, cell destruction, spinal cord injury following trauma, degeneration of vulnerable hippocampal neurons after ischemia, reovirus-induced apoptosis, viral-induced induced myocarditis, acute and chronic inflammation, cataract formation, multiple sclerosis, demylenating disorders, acoustic trauma, hearing loss caused by noise, neuronal damage, cardiac ischemic damage, and/or hepatocyte necrosis during and following anoxia CAN-12 polynucleotides and polypeptides, including fragments and/or antagonists thereof, may have uses which include modulating development, differentiation, cellular transformation in response to cell signaling, cell-cell and/or cell-extracellular matrix interactions, clustering of the integrin receptor aIIb3, modulating in long term potentiation (memory), modulating neurite outgrowth, modulating cortical lamination activation of protein kinases and phosphatases, remodeling and disassembling the cytoskeleton, cell cycle modulation, in addition, to ameliorating, preventing, and/or treating limb-girdle muscular dystrophy (LGMD), insulin resistance in diabetics, Alzheimer's disease, Multiple sclerosis, Huntington's disease, Parkinson's disease and amyotrophy.

Moreover, CAN-12 polynucleotides and polypeptides, including fragments and agonists thereof, may have uses which include treating, diagnosing, prognosing, and/or preventing hyperproliferative disorders, particularly of the neural and immune systems. Such disorders may include, for example, cancers, and metastatic conditions.

CAN-12 polynucleotides and polypeptides, including fragments and/or antagonsists thereof, may have uses which include identification of modulators of CAN-12 function including antibodies (for detection or neutralization), naturally-occurring modulators and small molecule modulators. Antibodies to domains (including CAN-12 epitopes provided herein) of the CAN-12 protein could be used as diagnostic agents of inflammatory conditions in patients, are useful in monitoring the activation and presence of cognate proteases, and can be used as a biomarker for the protease involvement in disease states and in the evaluation of inhibitors of the cognate protease in vivo.

CAN-12 polypeptides and polynucleotides are useful for diagnosing diseases related to over or under expression of CAN-12 proteins by identifying mutations in the CAN-12 gene using CAN-12 probes, or determining CAN-12 protein or mRNA expression levels. CAN-12 polypeptides are also useful for screening for compounds, which affect activity of the protein. Diseases that can be treated with CAN-12 include, the following, non-limiting examples: neuro-regeneration, neuropathic pain, obesity, anorexia, HIV infections, cancers, bulimia, asthma, Parkinson's disease, acute heart failure, hypotension, hypertension, osteoporosis, angina pectoris, myocardial infarction, psychotic, immune, metabolic, cardiovascular, and neurological disorders.

The predominate expression in neural tissues, combined with the significant expression in a number of other tissues, suggests the CAN-12 polynucleotide and polypeptide of the present invention may be involved in modulating nerve invasion, innervation, nerve maintenance, and potentially myeline sheath maintenance and integrity.

The CAN-12 polynucleotides and polypeptides, including fragments and antagonists thereof, may have uses which include detecting, diagnosing, treating, ameliorating, and/or preventing diseases and disorders of the neural system, particularly Alzheimer's disease, either directly or indirectly, in addition to other neural disorders known in the art or provided in the "Neurological Diseases" section herein, such as modulating nerve invasion, innervation, nerve maintenance, potentially myelin sheath maintenance and integrity, encephalomyelitis, autoimmune encephalomyelitis, human T cell leukemia virus type I (HTLV-I)-associated myelopathy/tropical spastic paraparesis (HAM/TSP), and neuro-inflammatory diseases.

Molecular genetic manipulation of the structure of the active site domain, particularly the predicted catalytic amino acids, and of other functional domains in the calpain family (e.g., active site domain binding pocket) enables the production of calpains with tailor-made activities. Thus, the CAN-12 polypeptides, and fragments thereof, as well as any homologous product resulting from genetic manipulation of the structure, are useful for NMR-based design of modulators of CAN-12 biological activity, and calpains, in general.

CAN-12 polypeptides and polynucleotides have additional uses which include diagnosing diseases related to the over and/or under expression of CAN-12 by identifying mutations in the CAN-12 gene by using CAN-12 sequences as probes or by determining CAN-12 protein or mRNA expression levels. CAN-12 polypeptides may be useful for screening compounds that affect the activity of the protein. CAN-12 peptides can also be used for the generation of specific antibodies and as bait in yeast two hybrid screens to find proteins the specifically interact with CAN-12 (described elsewhere herein).

The CAN-12 polynucleotides and polypeptides, including fragments and agonists thereof, may have uses which include detecting, diagnosing, treating, ameliorating, and/or preventing metabolic diseases and disorders, such as diabetes. Moreover, expressed human CAN-12 may be useful in the detection of patients susceptible to diabetes. Also paradigms that would simulate intracellular CAN-12 activity would be useful in treating diabetes.

The CAN-12 polynucleotides and polypeptides, including fragments thereof, may have uses which include identifying inhibitors of intracellular calpain inhibitors (calpastatins) leading to an effective increase in calpain activity.

Various approaches to detect alterations or allelic variants at the genomic or mRNA level of CAN-12, could be used as a diagnostic for identifying MS patients, or individuals susceptible to have MS. It is likely that the calpain12 gene comprises polymorphic sites (i.e. SNPs), with specific alleles which may be associated with MS or other neurodegenerative disorders, or associated with an increased likelihood of developing these diseases. Therefore, the invention provides the calpain12 sequence that can be used to design specific primers for the identification of polymorphisms or mutations in calpain12 of patients affected with MS. The presence of a specific allele variant, such as a SNP allele or SNPs haplotype that renders the subject carrying it more susceptible to develop MS or other related diseases could be identified (e.g. a variant in the can12 promoter region that increased transcript levels of can12, or mutations in the coding sequence that increased the stability or half-life of the can12 protein). Other methods such as Northern-blot analysis could be performed to measure transcript levels using a can12 cDNA probe derived from the sequence of the invention.

Although it is believed the encoded polypeptide may share at least some biological activities with human calpains (particularly m-calpains), a number of methods of determining the exact biological function of this clone are either known in the art or are described elsewhere herein. Briefly, the function of this clone may be determined by applying microarray methodology. Nucleic acids corresponding to the CAN-12 polynucleotides, in addition to, other clones of the present invention, may be arrayed on microchips for expression profiling. Depending on which polynucleotide probe is used to hybridize to the slides, a change in expression of a specific gene may provide additional insight into the function of this gene based upon the conditions being studied. For example, an observed increase or decrease in expression levels when the polynucleotide probe used comes from diseased neural tissue, as compared to, normal tissue might indicate a function in modulating neural function, for example. In the case of CAN-12, spinal cord, lymph node, thymus, and/or spleen tissue should be used to extract RNA to prepare the probe.

In addition, the function of the protein may be assessed by applying quantitative PCR methodology, for example. Real time quantitative PCR would provide the capability of following the expression of the CAN-12 gene throughout development, for example. Quantitative PCR methodology requires only a nominal amount of tissue from each developmentally important step is needed to perform such experiments. Therefore, the application of quantitative PCR methodology to refining the biological function of this polypeptide is encompassed by the present invention. In the case of CAN-12, a disease correlation related to CAN-12 may be made by comparing the mRNA expression level of CAN-12 in normal tissue, as compared to diseased tissue (particularly diseased tissue isolated from the following: esophagus, spinal cord, lymph node, thymus, and/or spleen tissue). Significantly higher or lower levels of CAN-12 expression in the diseased tissue may suggest CAN-12 plays a role in disease progression, and antagonists against CAN-12 polypeptides would be useful therapeutically in treating, preventing, and/or ameliorating the disease. Alternatively, significantly higher or lower levels of CAN-12 expression in the diseased tissue may suggest CAN-12 plays a defensive role against disease progression, and agonists of CAN-12 polypeptides may be useful therapeutically in treating, preventing, and/or ameliorating the disease. Also encompassed by the present invention are quantitative PCR probes corresponding to the polynucleotide sequence provided as SEQ ID NO:1 (FIGS. 1A–E).

The function of the protein may also be assessed through complementation assays in yeast. For example, in the case of the CAN-12, transforming yeast deficient in calpain activity, particularly m-calpain activity, and assessing their ability to grow would provide convincing evidence the CAN-12 polypeptide has calpain activity, and possibly m-calpain activity. Additional assay conditions and methods that may be used in assessing the function of the polynucleotides and polypeptides of the present invention are known in the art, some of which are disclosed elsewhere herein.

Alternatively, the biological function of the encoded polypeptide may be determined by disrupting a homologue of this polypeptide in Mice and/or rats and observing the resulting phenotype. Such knock-out experiments are known in the art, some of which are disclosed elsewhere herein.

Moreover, the biological function of this polypeptide may be determined by the application of antisense and/or sense methodology and the resulting generation of transgenic mice and/or rats. Expressing a particular gene in either sense or antisense orientation in a transgenic mouse or rat could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., an esophagus, spinal cord, lymph node, thymus, or spleen specific promoter), or it can be expressed at a specified time of development using an inducible and/or a developmentally regulated promoter.

In the case of CAN-12 transgenic mice or rats, if no phenotype is apparent in normal growth conditions, observing the organism under diseased conditions (neural, immune, hematopoietic diseases or disorders, cancers, etc.) may lead to understanding the function of the gene. Therefore, the application of antisense and/or sense methodology to the creation of transgenic mice or rats to refine the biological function of the polypeptide is encompassed by the present invention.

In preferred embodiments, the following N-terminal CAN-12 deletion polypeptides are encompassed by the present invention: M1-L581, S2-L581, L3-L581, W4-L581, P5-L581, P6-L581, F7-L581, R8-L581, C9-L581, R10-L581, W11-L581, K12-L581, L13-L581, A14-L581, P15-L581, R16-L581, Y17-L581, S18-L581, R19-L581, R20-L581, A21-L581, S22-L581, P23-L581, Q24-L581, Q25-L581, P26-L581, Q27-L581, Q28-L581, D29-L581, F30-L581, E31-L581, A32-L581, L33-L581, L34-L581, A35-L581, E36-L581, C37-L581, L38-L581, R39-L581, N40-L581, G41-L581, C42-L581, L43-L581, F44-L581, E45-L581, D46-L581, T47-L581, S48-L581, F49-L581, P50-L581, A51-L581, T52-L581, L53-L581, S54-L581, S55-L581, I56-L581, G57-L581, S58-L581, G59-L581, S60-L581, L61-L581, L62-L581, Q63-L581, K64-L581, L65-L581, P66-L581, P67-L581, R68-L581, L69-L581, Q70-L581, W71-L581, K72-L581, R73-L581, P74-L581, P75-L581, E76-L581, L77-L581, H78-L581, S79-L581, N80-L581, P81-L581, Q82-L581, F83-L581, Y84-L581, F85-L581, A86-L581, K87-L581, A88-L581, K89-L581, R90-L581, L91-L581, D92-L581, L93-L581, C94-L581, Q95-L581, G96-L581, I97-L581, V98-L581, G99-L581, D100-L581, C101-L581, W102-L581, F103-L581, L104-L581, A105-L581, A106-L581, L107-L581, Q108-L581, A109-L581, L110-L581, A111-L581, L112-L581, H113-L581, Q114-L581, D115-L581, I116-L581, L117-L581, S118-L581, R119-L581, V120-L581, V121-L581, P122-L581, L123-L581, N124-L581, Q125-L581, S126-L581, F127-L581, T128-L581, E129-L581, K130-L581, Y131-L581, A132-L581, G133-L581, I134-L581, F135-L581, R136-L581, F137-L581, W138-L581, F139-L581, W140-L581, H141-L581, Y142-L581, G143-L581, N144-L581, W145-L581, V146-L581, P147-L581, V148-L581, V149-L581, I150-L581, D151-L581, D152-L581, R153-L581, L154-L581, P155-L581, V156-L581, N157-L581, E158-L581, A159-L581, G160-L581, Q161-L581, L162-L581, V163-L581, F164-L581, V165-L581, S166-L581, S167-L581, T168-L581, Y169-L581, K170-L581, N171-L581, L172-L581, F173-L581, W174-L581, G175-L581, A176-L581, L177-L581, L178-L581, E179-L581, K180-L581, A181-L581, Y182-L581, A183-L581, K184-L581, L185-L581, S186-L581, G187-L581, S188-L581, Y189-L581, E190-L581, D191-L581, L192-L581, Q193-L581, S194-L581, G195-L581, Q196-L581, V197-L581, S198-L581, E199-L581, A200-L581, L201-L581, V202-L581, D203-L581, F204-L581, T205-L581, G206-L581, G207-L581, V208-L581, T209-L581, M210-L581, T211-L581, I212-L581, N213-L581, L214-L581, A215-L581, E216-L581, A217-L581, H218-L581, G219-L581, N220-L581, L221-L581, W222-L581, D223-L581, I224-L581, L225-L581, I226-L581, E227-L581, A228-L581, T229-L581, Y230-L581, N231-L581, R232-L581, T233-L581, L234-L581, I235-L581, G236-L581, C237-L581, Q238-L581, T239-L581, H240-L581, S241-L581, G242-L581, K243-L581, I244-L581, L245-L581, E246-L581, N247-L581, G248-L581, L249-L581, V250-L581, E251-L581, G252-L581, H253-L581, A254-L581, Y255-L581, T256-L581, L257-L581, T258-L581, G259-L581, I260-L581, R261-L581, K262-L581, V263-L581, T264-L581, C265-L581, K266-L581, H267-L581, R268-L581, P269-L581, E270-L581, Y271-L581, L272-L581, L273-L581, V273-L581, K274-L581, L275-L581, R276-L581, N277-L581, P278-L581, W279-L581, G280-L581, K281-L581, V282-L581, E283-L581, W284-L581, K285-L581, G286-L581, D287-L581, W288-L581, S289-

L581, D290-L581, S291-L581, S292-L581, S293-L581, K294-L581, W295-L581, E296-L581, L297-L581, L298-L581, S299-L581, P300-L581, K301-L581, E302-L581, K303-L581, I304-L581, L305-L581, L306-L581, L307-L581, R308-L581, K309-L581, D310-L581, N311-L581, D312-L581, G313-L581, E314-L581, F315-L581, W316-L581, M317-L581, T318-L581, L319-L581, Q320-L581, D321-L581, F322-L581, K323-L581, T324-L581, H325-L581, F326-L581, V327-L581, L328-L581, L329-L581, V330-L581, I331-L581, C332-L581, K333-L581, L334-L581, T335-L581, P336-L581, G337-L581, L338-L581, L339-L581, S340-L581, Q341-L581, E342-L581, A343-L581, A344-L581, Q345-L581, K346-L581, W347-L581, T348-L581, Y349-L581, T350-L581, M351-L581, R352-L581, E353-L581, G354-L581, R355-L581, W356-L581, E357-L581, K358-L581, R359-L581, S360-L581, T361-L581, A362-L581, G363-L581, G364-L581, Q365-L581, R366-L581, Q367-L581, L368-L581, L369-L581, Q370-L581, D371-L581, T372-L581, F373-L581, W374-L581, K375-L581, N376-L581, P377-L581, Q378-L581, F379-L581, L380-L581, L381-L581, S382-L581, V383-L581, W384-L581, R385-L581, P386-L581, E387-L581, E388-L581, G389-L581, R390-L581, R391-L581, S392-L581, L393-L581, R394-L581, P395-L581, C396-L581, S397-L581, V398-L581, L399-L581, V400-L581, S401-L581, L402-L581, L403-L581, Q404-L581, K405-L581, P406-L581, R407-L581, H408-L581, R409-L581, C410-L581, R411-L581, K412-L581, R413-L581, K414-L581, P415-L581, L416-L581, L417-L581, A418-L581, I419-L581, G420-L581, F421-L581, Y422-L581, L423-L581, Y424-L581, R425-L581, M426-L581, N427-L581, K428-L581, M429-L581, T430-L581, W431-L581, S432-L581, S433-L581, L434-L581, G435-L581, S436-L581, R437-L581, Q438-L581, P439-L581, F440-L581, F441-L581, S442-L581, L443-L581, E444-L581, A445-L581, C446-L581, Q447-L581, G448-L581, I449-L581, L450-L581, A451-L581, L452-L581, L453-L581, D454-L581, L455-L581, N456-L581, A457-L581, S458-L581, G459-L581, T460-L581, M461-L581, S462-L581, I463-L581, Q464-L581, E465-L581, F466-L581, R467-L581, D468-L581, L469-L581, W470-L581, K471-L581, Q472-L581, L473-L581, K474-L581, L475-L581, S476-L581, Q477-L581, K478-L581, V479-L581, F480-L581, H481-L581, K482-L581, Q483-L581, D484-L581, R485-L581, G486-L581, S487-L581, G488-L581, Y489-L581, L490-L581, N491-L581, W492-L581, E493-L581, Q494-L581, L495-L581, H496-L581, A497-L581, A498-L581, M499-L581, R500-L581, E501-L581, A502-L581, G503-L581, R504-L581, H505-L581, R506-L581, K507-L581, S508-L581, W509-L581, S510-L581, C511-L581, G512-L581, H513-L581, T514-L581, R515-L581, A516-L581, G517-L581, C518-L581, T519-L581, L520-L581, I521-L581, R522-L581, Q523-L581, R524-L581, R525-L581, G526-L581, D527-L581, V528-L581, W529-L581, H530-L581, A531-L581, E532-L581, V533-L581, T534-L581, L535-L581, I536-L581, R537-L581, S538-L581, V539-L581, T540-L581, L541-L581, K542-L581, D543-L581, V544-L581, D545-L581, L546-L581, Q547-L581, S548-L581, T549-L581, P550-L581, T551-L581, F552-L581, F553-L581, M554-L581, I555-L581, V556-L581, P557-L581, V558-L581, I559-L581, L560-L581, A561-L581, N562-L581, I563-L581, D564-L581, G565-L581, G566-L581, V567-L581, A568-L581, H569-L581, S570-L581, T571-L581, S572-L581, Y573-L581, L574-L581, and/or I575-L581 of SEQ ID NO:2. Polynucleotide sequences encoding these polypeptides are also provided. The present invention also encompasses the use of these N-terminal CAN-12 deletion polypeptides as immunogenic and/or antigenic epitopes as described elsewhere herein. The invention specifically encompasses the N-terminal deletions from amino acid 1 to amino acid 421 of SEQ ID NO:2.

In preferred embodiments, the following C-terminal CAN-12 deletion polypeptides are encompassed by the present invention: M1-L581, M1-L580, M1-T579, M1-T578, M1-N577, MI-F576, M1-1575, M1-L574, M1-Y573, M1-S572, M1-T571, M1-S570, M1-H569, M1-A568, M1-V567, M1-G566, M1-G565, M1-D564, M1-1563, M1-N562, MI-A561, M1-L560, M1-1559, M1-V558, M1-P557, M1-V556, M1-1555, M1-M554, M1-F553, M1-F552, M1-T551, M1-P550, M1-T549, M1-S548, M1-Q547, M1-L546, MI-D545, M1-V544, M1-D543, M1-K542, M1-L541, M1-T540, M1-V539, M1-S538, M1-R537, M1-1536, M1-L535, M1-T534, M1-V533, M1-E532, M1-A531, M1-H530, M1-W529, M1-V528, M1-D527, M1-G526, M1-R525, M1-R524, M1-Q523, M1-R522, M1-1521, M1-L520, M1-T519, M1-C518, M1-G517, M1-A516, M1-R515, M1-T514, M1-H513, M1-G512, M1-C511, M1-S510, M1-W509, M1-S508, M1-K507, M1-R506, M1-H505, M1-R504, M1-G503, M1-A502, M1-E501, M1-R500, M1-M499, M1-A498, M1-A497, M1-H496, M1-L495, M1-Q494, M1-E493, M1-W492, M1-N491, M1-L490, M1-Y489, M1-G488, M1-S487, M1-G486, M1-R485, M1-D484, M1-Q483, M1-K482, M1-H481, M1-F480, M1-V479, M1-K478, M1-Q477, M1-S476, M1-L475, M1-K474, M1-L473, M1-Q472, M1-K471, M1-W470, M1-L469, M1-D468, M1-R467, M1-F466, M1-E465, M1-Q464, M1-1463, M1-S462, M1-M461, M1-T460, M1-G459, M1-S458, M1-A457, M1-N456, M1-L455, M1-D454, M1-L453, M1-L452, M1-A451, M1-L450, M1-1449, M1-G448, M1-Q447, M1-C446, M1-A445, M1-E444, M1-L443, M1-S442, M1-F441, M1-F440, M1-P439, M1-Q438, M1-R437, M1-S436, M1-G435, M1-L434, M1-S433, M1-S432, M1-W431, M1-T430, M1-M429, M1-K428, M1-N427, M1-M426, M1-R425, M1-Y424, M1-L423, M1-Y422, M1-F421, M1-G420, M1-1419, M1-A418, M1-L417, M1-L416, M1-P415, M1-K414, M1-R413, M1-K412, M1-R411, M1-C410, M1-R409, M1-H408, M1-R407, M1-P406, M1-K405, M1-Q404, M1-L403, M1-L402, M1-S401, M1-V400, M1-L399, M1-V398, M1-S397, M1-C396, M1-P395, M1-R394, M1-L393, M1-S392, M1-R391, M1-R390, M1-G389, M1-E388, M1-E387, M1-P386, M1-R385, M1-W384, M1-V383, M1-S382, M1-L381, M1-L380, M1-F379, M1-Q378, M1-P377, M1-N376, M1-K375, M1-W374, M1-F373, M1-T372, M1-D371, M1-Q370, M1-L369, M1-L368, M1-Q367, M1-R366, M1-Q365, M1-G364, M1-G363, M1-A362, M1-T361, M1-S360, M1-R359, M1-K358, M1-E357, M1-W356, M1-R355, M1-G354, M1-E353, M1-R352, M1-M351, M1-T350, M1-Y349, M1-T348, M1-W347, M1-K346, M1-Q345, M1-A344, M1-A343, M1-E342, M1-Q341, M1-S340, M1-L339, M1-L338, M1-G337, M1-P336, M1-T335, M1-L334, M1-K333, M1-C332, M1-I331, M1-V330, M1-L329, M1-L328, M1-V327, M1-F326, M1-H325, M1-T324, M1-K323, M1-F322, M1-D321, M1-Q320, M1-L319, M1-T318, M1-M317, M1-W316, M1-F315, M1-E314, M1-G313, M1-D312, M1-N311, M1-D310, M1-K309, M1-R308, M1-L307, M1-L306, M1-L305, M1-304, M1-K303, M1-E302, M1-K301, M1-P300, M1-S299, M1-L298, M1-L297, M1-E296, M1-W295, M1-K294, M1-S293, M1-S292, M1-S291, M1-D290, M1-S289, M1-W288, M1-D287, M1-G286, M1-K285, M1-W284, M1-E283, M1-V282, M1-K281, M1-G280, M1-W279, M1-P278, M1-N277, M1-R276, M1-L275, M1-K274, M1-V273, M1-L272, M1-Y271, M1-E270, M1-P269, M1-R268, M1-H267, M1-K266, M1-C265, M1-T264, M1-V263, M1-K262, M1-R261, M1-I260, M1-G259, M1-T258, M1-L257, M1-T256, M1-Y255, M1-A254, M1-H253, M1-G252, M1-E251, M1-V250, M1-L249, M1-G248, M1-N247, M1-E246, M1-L245, M1-I244, M1-K243, M1-G242, M1-S241, M1-H240, M1-T239, M1-Q238, M1-C237, M1-G236, M1-I235, M1-L234, M1-T233, M1-R232, M1-N231, M1-Y230, M1-T229, M1-A228, M1-E227, M1-I226, M1-L225, M1-I224, M1-D223, M1-W222, M1-L221, M1-N220, M1-G219, M1-H218, M1-A217, M1-E216, M1-A215, M1-L214, M1-N213, M1-I212, M1-T211, M1-M210, M1-T209, M1-V208, M1-G207, M1-G206, M1-T205, M1-F204, M1-D203, M1-V202, M1-L201, M1-A200, M1-E199, M1-S198, M1-V197, M1-Q196, M1-G195, M1-S194, M1-Q193, M1-L192, M1-D191, M1-E190, M1-Y189, M1-S188, M1-G187, M1-S186, M1-L185, M1-K184, M1-A183, M1-Y182, M1-A181, M1-K180, M1-E179, M1-L178, M1-L177, M1-A176, M1-G175, M1-W174, M1-F173, M1-L172, M1-N171, M1-K170, M1-Y169, M1-T168, M1-S167, M1-S166, M1-V165, M1-F164, M1-V163, M1-L162, M1-Q161, M1-G160, M1-A159, M1-E158, M1-N157, M1-V156, M1-P155, M1-L154, M1-R153, M1-D152, M1-D151, M1-I150, M1-V149, M1-V148, M1-P147, M1-V146, M1-W145, M1-N144, M1-G143, M1-Y142, M1-H141, M1-W140, M1-F139, M1-W138, M1-F137, M1-R136, M1-F135, M1-I134, M1-G133, M1-A132, M1-Y131, M1-K130, M1-E129, M1-T128, M1-F127, M1-S126, M1-Q125, M1-N124, M1-L123, M1-P122, M1-V121, M1-V120, M1-R119, M1-S118, M1-L117, M1-I116, M1-D115, M1-Q114, M1-H113, M1-L112, M1-A111, M1-L111, M1-A109, M1-Q108, M1-L107, M1-A106, M1-A105, M1-L104, M1-F103, M1-W102, M1-C101, M1-D100, M1-G99, M1-V98, M1-I97, M1-G96, M1-Q95, M1-C94, M1-L93, M1-D92, M1-L91, M1-R90, M1-K89, M1-A88, M1-K87, M1-A86, M1-F85, M1-Y84, M1-F83, M1-Q82, M1-P81, M1-N80, M1-S79, M1-H78, M1-L77, M1-E76, M1-P75, M1-P74, M1-R73, M1-K72, M1-W71, M1-Q70, M1-L69, M1-R68, M1-P67, M1-P66, M1-L65, M1-K64, M1-Q63, M1-L62, M1-L61, M1-S60, M1-G59, M1-S58, M1-G57, M1-I56, M1-S55, M1-S54, M1-L53, M1-T52, M1-A51, M1-P50, M1-F49, M1-S48, M1-T47, M1-D46, M1-E45, M1-F44, M1-L43, M1-C42, M1-G41, M1-N40, M1-R39, M1-L38, M1-C37, M1-E36, M1-A35, M1-L34, M1-L33, M1-A32, M1-E31, M1-F30, M1-D29, M1-Q28, M1-Q27, M1-P26, M1-Q25, M1-Q24, M1-P23, M1-S22, M1-A21, M1-R20, M1-R19, M1-S18, M1-Y17, M1-R16, M1-P15, M1-A14, M1-L13, M1-K12, M1-W11, M1-R10, M1-C9, M1-R8, and/or M1-F7 of SEQ ID NO:2. Polynucleotide sequences encoding these polypeptides are also provided. The present invention also encompasses the use of these C-terminal CAN-12 deletion polypeptides as immunogenic and/or antigenic epitopes as described elsewhere herein. The invention specifically encompasses the C-terminal deletions from amino acid 428 to amino acid 7 of SEQ ID NO:2.

Alternatively, preferred polypeptides of the present invention may comprise polypeptide sequences corresponding to, for example, internal regions of the CAN-12 polypeptide (e.g., any combination of both N- and C-terminal CAN-12 polypeptide deletions) of SEQ ID NO:2. For example, internal regions could be defined by the equation: amino acid NX to amino acid CX, wherein NX refers to any N-terminal deletion polypeptide amino acid of CAN-12 (SEQ ID NO:2), and where CX refers to any C-terminal deletion polypeptide amino acid of CAN-12 (SEQ ID NO:2). Polynucleotides encoding these polypeptides are also provided. The present invention also encompasses the use of these polypeptides as an immunogenic and/or antigenic epitope as described elsewhere herein.

The present invention also encompasses immunogenic and/or antigenic epitopes of the CAN-12 polypeptide.

The CAN-12 polypeptides of the present invention were determined to comprise several phosphorylation sites based upon the Motif algorithm (Genetics Computer Group, Inc.). The phosphorylation of such sites may regulate some biological activity of the CAN-12 polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the CAN-12 polypeptide to associate with other polypeptides, particularly the serine protease substrate for CAN-12, or its ability to modulate serine protease function.

The CAN-12 polypeptide was predicted to comprise eleven PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177–184(1986), and Kishimoto A., Nishiyama K., Nakanishi H., Uratsuji Y., Nomura H., Takeyama Y., Nishizuka Y., J. Biol. Chem. . . . 260:12492–12499(1985); which are hereby incorporated by reference herein.

In preferred embodiments, the following PKC phosphorylation site polypeptides are encompassed by the present invention: LAPRYSRRASPQQ (SEQ ID NO:27), LNQSFTEKYAGIF (SEQ ID NO:28), VFVSSTYKNLFWG (SEQ ID NO:29), GCQTHSGKILENG (SEQ ID NO:30), GIRKVTCKHRPEY (SEQ ID NO:31), DWSDSSSKWELLS (SEQ ID NO:32), KWELLSPKEKILL (SEQ ID NO:33), QKWTYTMREGRWE (SEQ ID NO:34), EEGRRSLRPCSVL (SEQ ID NO:35), KQLKLSQKVFHKQ (SEQ ID NO:36), and/or LIRSVTLKDVDLQ (SEQ ID NO:37). Polynucleotides encoding these polypeptides are also provided. The present invention also encompasses the use of the CAN-12 PKC phosphorylation site polypeptides as immunogenic and/or antigenic epitopes as described elsewhere herein.

The CAN-12 polypeptide has been shown to comprise four glycosylation site according to the Motif algorithm (Genetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

In preferred embodiments, the following asparagine glycosylation site polypeptide is encompassed by the present invention: RVVPLNQSFTEKYA (SEQ ID NO:38), IEATYNRTLIGCQT (SEQ ID NO:39), ALLDLNASGTMSIQ (SEQ ID NO:40), and/or SYLIFNTTLL (SEQ ID NO:41). Polynucleotides encoding this polypeptide are also provided. The present invention also encompasses the use of the CAN-12 asparagine glycosylation site polypeptides as immunogenic and/or antigenic epitopes as described elsewhere herein.

The CAN-12 polypeptide has been shown to comprise one amidation site according to the Motif algorithm (Genetics Computer Group, Inc.). The precursor of hormones and other active peptides which are C-terminally amidated is always directly followed by a glycine residue which provides the amide group, and most often by at least two consecutive basic residues (Arg or Lys) which generally function as an active peptide precursor cleavage site. Although all amino acids can be amidated, neutral hydrophobic residues such as Val or Phe are good substrates, while charged residues such as Asp or Arg are much less reactive. A consensus pattern for amidation sites is the following: x-G-[RK]-[RK] (SEQ ID NO:146), wherein "X" represents the amidation site. Additional information relating to asparagine glycosylation may be found in reference to the following publications, which are hereby incorporated by reference herein: Kreil G., Meth. Enzymol. 106:218–223(1984); and Bradbury A. F., Smyth D. G., Biosci. Rep. 7:907–916(1987).

In preferred embodiments, the following amidation site polypeptide is encompassed by the present invention: VWRPEEGRRSLRPC (SEQ ID NO:42). Polynucleotides encoding these polypeptides are also provided. The present invention also encompasses the use of this CAN-12 amidation site polypeptide as an immunogenic and/or antigenic epitope as described elsewhere herein.

The CAN-12 polypeptide has been shown to comprise one RGD cell attachment site domain according to the Motif algorithm (Genetics Computer Group, Inc.). The sequence Arg-Gly-Asp, found in fibronectin, is crucial for its interaction with its cell surface receptor, an integrin. What has been called the 'RGD' tripeptide is also found in the sequences of a number of other proteins, where it has been shown to play a role in cell adhesion. Non-limiting examples of these proteins are the following: some forms of collagens, fibrinogen, vitronectin, von Willebrand factor (VWF), snake disintegrins, and slime mold discoidins. The 'RGD' tripeptide is also found in other proteins where it may serve the same purpose. A consensus pattern for RGD cell attachment sites is the following: R-G-D. Additional information relating to RGD cell attachment site domains may be found in reference to the following publications, which are hereby incorporated by reference herein: Ruoslahti E., Pierschbacher M. D., Cell 44:517–518(1986); and d'Souza S. E., Ginsberg M. H., Plow E. F., Trends Biochem. Sci. 16:246–250(1991).

In preferred embodiments, the following RGD cell attachment site domain polypeptide is encompassed by the present invention: LIRQRRGDVWHAE (SEQ ID NO:43). Polynucleotides encoding these polypeptides are also provided. The present invention also encompasses the use of this RGD cell attachment site domain polypeptide as an immunogenic and/or antigenic epitope as described elsewhere herein.

In confirmation of the CAN-12 polypeptide being a calpain, it has been shown to comprise one EF-hand calcium-binding domain according to the Motif algorithm (Genetics Computer Group, Inc.). Many calcium-binding proteins belong to the same evolutionary family and share a type of calcium-binding domain known as the EF-hand. This type of domain consists of a twelve residue loop flanked on both side by a twelve residue alpha-helical domain. In an EF-hand loop the calcium ion is coordinated in a pentagonal bipyramidal configuration. The six residues involved in the binding are in positions 1, 3, 5, 7, 9 and 12; these residues are denoted by X, Y, Z, -Y, -X and -Z. The invariant Glu or Asp at position 12 provides two oxygens for liganding Ca (bidentate ligand). Several representative proteins containing EF-hand regions are provided below: For each type of protein, the total number of EF-hand regions known or supposed to exist are provided in parenthesis: *Aequorin* and *Renilla luciferin* binding protein (LBP) (Ca=3); Alpha actinin (Ca=2); Calbindin (Ca=4); Calcineurin B subunit (protein phosphatase 2B regulatory subunit) (Ca=4); Calcium-binding protein from *Streptomyces erythraeus* (Ca=3?); Calcium-binding protein from *Schistosoma mansoni* (Ca=2?); Calcium-binding proteins TCBP-23 and TCBP-25 from *Tetrahymena thermophila* (Ca=4?); Calcium-dependent protein kinases (CDPK) from plants (Ca=4); Calcium vector protein from amphoxius (Ca=2); Calcyphosin (thyroid protein p24) (Ca=4?); Calmodulin (Ca=4, except in yeast where Ca=3); Calpain small and large chains (Ca=2); Calretinin (Ca=6); Calcyclin (prolactin receptor associated protein) (Ca=2); Caltractin (centrin) (Ca=2 or 4); Cell Division Control protein 31 (gene CDC31) from yeast (Ca=2?); Diacylglycerol kinase (EC 2.7.1.107) (DGK) (Ca=2); FAD-dependent glycerol-3-phosphate dehydrogenase (EC 1.1.99.5) from mammals (Ca=1); Fimbrin (plastin) (Ca=2); Flagellar calcium-binding protein (1f8) from *Trypanosoma cruzi* (Ca=1 or 2); Guanylate cyclase activating protein (GCAP) (Ca=3); Inositol phospholipid-specific phospholipase C isozymes gamma-1 and delta-1 (Ca=2) [10]; Intestinal calcium-binding protein (ICaBPs) (Ca=2); MIF related proteins 8 (MRP-8 or CFAG) and 14 (MRP-14) (Ca=2); Myosin regulatory light chains (Ca=1); Oncomodulin (Ca=2); Osteonectin (basement membrane protein BM-40) (SPARC) and proteins that contains an 'osteonectin' domain (QR1, matrix glycoprotein SC1) (Ca=1); Parvalbumins alpha and beta (Ca=2); Placental calcium-binding protein (18a2) (nerve growth factor induced protein 42a) (p9k) (Ca=2); Recoverins (visinin, hippocalcin, neurocalcin, S-modulin) (Ca=2 to 3); Reticulocalbin (Ca=4); S-100 protein, alpha and beta chains (Ca=2); Sarcoplasmic calcium-binding protein (SCPs) (Ca=2 to 3); Sea urchin proteins Spec 1 (Ca=4), Spec 2 (Ca=4?), Lps-1 (Ca=8); Serine/threonine protein phosphatase rdgc (EC 3.1.3.16) from *Drosophila* (Ca=2); Sorcin V19 from hamster (Ca=2); Spectrin alpha chain (Ca=2); Squidulin (optic lobe calcium-binding protein) from squid (Ca=4); and Troponins C; from skeletal muscle (Ca=4), from cardiac muscle (Ca=3), from arthropods and molluscs (Ca=2).

A consensus pattern for EF hand calcium binding domains is the following:

(SEQ ID NO:147)

```
1 2 3   4     5        6         7  8    9       10   12    13
X   Y   Z              -Y        -X       -Z
D-x-[DNS]-{ILVFYW}-[DENSTG]-[DNQGHRK]-{GP}-[LIVMC]-[DENQSTAGC]-x(2)-[DE]-[LIVMFYW],
``` wherein X, Y, Z, -Y, -X, and -Z are as defined above, and wherein "x" represents any amino acid. Amino acid residues within the consensus at positions 1 (X), 3 (Y) and 12 (-Z) are the most conserved. The 6th residue in an EF-hand loop is in most cases a Gly.

Additional information relating to RGD cell attachment site domains may be found in reference to the following publications, which are hereby incorporated by reference herein: Kawasaki H., Kretsinger R. H., Protein Prof. 2:305–490(1995); Kretsinger R. H., Cold Spring Harbor Symp. Quant. Biol. 52:499–510(1987); Moncrief N. D., Kretsinger R. H., Goodman M., J. Mol. Evol. 30:522–562 (1990); Nakayama S., Moncrief N. D., Kretsinger R. H., J. Mol. Evol. 34:416–448(1992); Heizmann C. W., Hunziker W., Trends Biochem. Sci. 16:98–103(1991); Kligman D., Hilt D. C., Trends Biochem. Sci. 13:437–443(1988); Strynadka N. C. J., James M. N. G., Annu. Rev. Biochem. 58:951–98(1989); Haiech J., Sallantin J., Biochimie 67:555–560(1985); Chauvaux S., Beguin P., Aubert J.-P., Bhat K. M., Gow L. A., Wood T. M., Bairoch A., Biochem. J. 265:261–265(1990); Bairoch A., Cox J. A., FEBS Lett. 269:454–456(1990).

In preferred embodiments, the following EF-hand calcium binding domain polypeptide is encompassed by the present invention: ILALLDLNASGTMSIQEFRDLWK (SEQ ID NO:44). Polynucleotides encoding these polypeptides are also provided. The present invention also encompasses the use of this EF-hand calcium binding domain polypeptide as an immunogenic and/or antigenic epitope as described elsewhere herein.

In further confirmation of the CAN-12 polypeptide being a calpain, it has been shown to comprise one eukaryotic thiol (cysteine) protease active site domain according to the Motif algorithm (Genetics Computer Group, Inc.). Eukaryotic thiol proteases (EC 3.4.22.-) are a family of proteolytic enzymes which contain an active site cysteine. Catalysis proceeds through a thioester intermediate and is facilitated by a nearby histidine side chain; an asparagine completes the essential catalytic triad. Non-limiting examples of proteases which are known to belong to this family are provided below: Vertebrate lysosomal cathepsins B (EC 3.4.22.1), H (EC 3.4.22.16), L (EC 3.4.22.15), and S (EC 3.4.22.27); Vertebrate lysosomal dipeptidyl peptidase I (EC 3.4.14.1) (also known as cathepsin C); Vertebrate calpains (EC 3.4.22.17) (Calpains are intracellular calcium-activated thiol protease that contain both a N-terminal catalytic domain and a C-terminal calcium-binding domain; Mammalian cathepsin K, which seems involved in osteoclastic bone resorption; Human cathepsin O; Bleomycin hydrolase (An enzyme that catalyzes the inactivation of the antitumor drug BLM (a glycopeptide); Plant enzymes: barley aleurain (EC 3.4.22.16), EP-B1/B4; kidney bean EP-C1, rice bean SH-EP; kiwi fruit actinidin (EC 3.4.22.14); papaya latex papain (EC 3.4.22.2), chymopapain (EC 3.4.22.6), caricain (EC 3.4.22.30), and proteinase IV (EC 3.4.22.25); pea turgor-responsive protein 15A; pineapple stem bromelain (EC 3.4.22.32); rape COT44; rice oryzain alpha, beta, and gamma; tomato low-temperature induced, *Arabidopsis thaliana* A494, RD19A and RD21A; House-dust mites allergens DerP1 and EurM1; Cathepsin B-like proteinases from the worms *Caenorhabditis elegans* (genes gcp-1, cpr-3, cpr-4, cpr-5 and cpr-6), *Schistosoma mansoni* (antigen SM31) and *Japonica* (antigen SJ31), *Haemonchus contortus* (genes AC-1 and AC-2), and *Ostertagia ostertagi* (CP-1 and CP-3); Slime mold cysteine proteinases CP1 and CP2; Cruzipain from *Trypanosoma cruzi* and *brucei*; Throphozoite cysteine proteinase (TCP) from various *Plasmodium* species; Proteases from *Leishmania mexicana*, *Theileria annulata* and *Theileria parva*; Baculoviruses cathepsin-like enzyme (v-cath); *Drosophila* small optic lobes protein (gene sol), a neuronal protein that contains a calpain-like domain; Yeast thiol protease BLH1I/YCP1/LAP3; and *Caenorhabditis elegans* hypothetical protein C06G4.2, a calpain-like protein; Two bacterial peptidases are also part of this family—Aminopeptidase C from *Lactococcus lactis* (gene pepC), and Thiol protease tpr from *Porphyromonas gingivalis*.

A consensus pattern for eukaryotic thiol (cysteine) protease active site domains is the following: Q-x(3)-[GE]-x-C-[YW]-x(2)-[STAGC]-[STAGCV] (SEQ ID NO:148), wherein C is the active site residue, and "x" represents any amino acid. The residue in position 4 of the pattern is almost always cysteine; the only exceptions are calpains (Leu), bleomycin hydrolase (Ser) and yeast YPC1 (Ser); while the residue in position 5 of the pattern is always Gly except in papaya protease IV where it is Glu.

An additional consensus pattern for eukaryotic thiol (cysteine) protease active site domains is the following: [LIVMGSTAN]-x-H-[GSACE]-[LIVM]-x-[LIVMAT](2)-G-x-[GSADNH] (SEQ ID NO:149), wherein H is the active site residue, and "x" represents any amino acid.

An additional consensus pattern for eukaryotic thiol (cysteine) protease active site domains is the following: [FYCH]-[WI]-[LIVT]-x-[KRQAG]-N-[ST]-W-x(3)-[FYW]-G-x(2)-G-[LFYW]-[LIVMFYG]-x-[LIVMF] (SEQ ID NO:150), wherein N is the active site residue, and "x" represents any amino acid.

Additional information relating to for eukaryotic thiol (cysteine) protease active site domains may be found in reference to the following publications, which are hereby incorporated by reference herein: Dufour E., Biochimie 70:1335–1342(1988); Kirschke H., Barrett A.J., Rawlings N. D., Protein Prof. 2:1587–1643(1995); Shi G.-P., Chapman H. A., Bhairi S. M., Deleeuw C., Reddy V. Y., Weiss S. J., FEBS Lett. 357:129–134(1995); Velasco G., Ferrando A. A., Puente X. S., Sanchez L. M., Lopez-Otin C., J. Biol. Chem. . . . 269:27136–27142(1994); Chapot-Chartier M. P., Nardi M., Chopin M. C., Chopin A., Gripon J. C., Appl. Environ. Microbiol. 59:330–333(1993); Higgins D. G., McConnell D. J., Sharp P. M., Nature 340:604–604(1989); Rawlings N. D., Barrett A. J., Meth. Enzymol. 244:461–486 (1994), which are hereby incorporated by reference in their entirety herein.

In preferred embodiments, the following for eukaryotic thiol (cysteine) protease active site domain polypeptide is encompassed by the present invention: RLDLCQGIVGD-CWFLAALQALA (SEQ ID NO:45). Polynucleotides encoding these polypeptides are also provided. The present invention also encompasses the use of this for eukaryotic thiol (cysteine) protease active site domain polypeptide as an immunogenic and/or antigenic epitope as described elsewhere herein.

The present invention also provides a three-dimensional homology model of the CAN-12 polypeptide (see FIG. 6) representing amino acids 12 to 524 of CAN-12 (SEQ ID NO:2). As referenced herein, SEQ ID NO:2 comprises additoinal amino acids that are not part of the CAN-12 polypeptide sequence but have been added to the sequence for reference to the CAN-12 splice variants referenced herein. The inclusion of the additional amino acids also helps for a more complete homology model. A three-dimensional homology model can be constructed on the basis of the known structure of a homologous protein (Greer et al, 1991, Lesk, et al, 1992, Cardozo, et al, 1995, Yuan, et al, 1995). The homology model of the CAN-12 polypeptide, corresponding to amino acid residues 12 to 524 of SEQ ID NO:2, was based upon the homologous structure of CAN2, a m-calpain family member (Strobl et al, 2000; hCAN2; Genbank Accession No. gil7546423; SEQ ID NO:11) and is defined by the set of structural coordinates set forth in Table IV herein.

The CAN-12 homology model of the present invention may provide one basis for designing rational stimulators (agonists) and/or inhibitors (antagonists) of one or more of the biological functions of CAN-12, or of CAN-12 mutants having altered specificity (e.g., molecularly evolved CAN-12 polypeptides, engineered site-specific CAN-12 mutants, CAN-12 allelic variants, etc.).

Homology models are not only useful for designing rational agonists and/or antagonists, but are also useful in predicting the function of a particular polypeptide. The functional predictions from homology models are typically more accurate than the functional attributes derived from traditional polypeptide sequence homology alignments (e.g., CLUSTALW), particularly when the three dimensional structure of a related polypeptide is known (e.g., m-calpain family member CAN2 protein; Genbank Accession No. gil7546423; SEQ ID NO:11). The increased prediction accuracy is based upon the fact that homology models approximate the three-dimensional structure of a protein, while homology based alignments only take into account the one dimension polypeptide sequence. Since the function of a particular polypeptide is determined not only by its primary, secondary, and tertiary structure, functional assignments derived solely upon homology alignments using the one dimensional protein sequence may be less reliable. A 3-dimensional model can be constructed on the basis of the known structure of a homologous protein (Greer et al, 1991, Lesk, et al, 1992, Cardozo, et al, 1995, Yuan, et al, 1995).

Prior to developing a homology model, those of skill in the art would appreciate that a template of a known protein, or model protein, must first be identified which will be used as a basis for constructing the homology model for the protein of unknown structure (query template). In the case of the CAN-12 polypeptide of the present invention, the model protein template used in constructing the CAN-12 homology model was the m-calpain family member CAN2 protein; Genbank Accession No. gil7546423; SEQ ID NO:11).

Identifying a template can be accomplished using pairwise alignment of protein sequences using such programs as FASTA (Pearson, et al 1990) and BLAST (Altschul, et al, 1990). In cases where sequence similarity is high (greater than 30%), such pairwise comparison methods may be adequate for identifying an appropriate template. Likewise, multiple sequence alignments or profile-based methods can be used to align a query sequence to an alignment of multiple (structurally and biochemically) related proteins. When the sequence similarity is low, more advanced techniques may be used. Such techniques, include, for example, protein fold recognition (protein threading; Hendlich, et al, 1990), where the compatibility of a particular polypeptide sequence with the 3-dimensional fold of a potential template protein is gauged on the basis of a knowledge-based potential.

Following the initial sequence alignment, the second step would be to optimally align the query template to the model template by manual manipulation and/or by the incorporation of features specific to the polypeptides (e.g., motifs, secondary structure predictions, and allowed conservations). Preferably, the incorporated features are found within both the model and query template.

The third step would be to identify structurally conserved regions that could be used to construct secondary core structure (Sali, et al, 1995). Loops could be added using knowledge-based techniques, and by performing forcefield calculations (Sali, et al, 1995).

The term "structure coordinates" refers to Cartesian coordinates generated from the building of a homology model. In this invention, the homology model of residues 12 to 524 of CAN-12 (SEQ ID NO:2) was derived from generating a sequence alignment with m-calpain (Strobl et al, 2000; hCAN2; Genbank Accession No. gil7546423; SEQ ID NO:11) using the COMPOSER suite of software within SYBYL6.6 (Tripos Associates, St. Louis, Mo.) and then generating the backbone and side chain conformations. In the original crystal structure (pdb code 1dkv) as well as the crystal structure reported elsewhere (Hosfield et al, 1999), the active site of the enzyme comprising a cysteine, a histidine and an asparagine residue was not "formed". The helix that contains the active site C101 was altered by moving the helix down one pitch so that the active site geometry could match that found in Papain (pdb code 1b4). This modified structure of human m-calpain was used as the template for construction of the homology model (illustrated in FIG. 6 herein).

The skilled artisan would appreciate that a set of structure coordinates for a protein represents a relative set of points that define a shape in three dimensions. Thus, it is possible that an entirely different set of coordinates could define a similar or identical shape. Moreover, slight variations in the individual coordinates, as emanate from the generation of similar homology models using different alignment templates (i.e., other than the m-calpain (Strobl et al, 2000; hCAN2; Genbank Accession No. gil7546423; SEQ ID NO:11), and/or using different methods in generating the homology model, will likely have minor effects on the overall shape. Variations in coordinates may also be generated because of mathematical manipulations of the structure coordinates. For example, the structure coordinates set forth in Table IV could be manipulated by fractionalization of the structure coordinates; integer additions, or integer subtractions to sets of the structure coordinates, inversion of the structure coordinates or any combination of the above.

Therefore, various computational analyses are necessary to determine whether a template molecule or a portion thereof is sufficiently similar to all or part of a query template (e.g., CAN-12) in order to be considered the same. Such analyses may be carried out in current software applications, such as SYBYL version 6.6 or INSIGHTII (Molecular Simulations Inc., San Diego, Calif.) version 2000 and as described in the accompanying User's Guides.

Using the superimposition tool in the program SYBYL, comparisons can be made between different structures and different conformations of the same structure. The procedure used in SYBYL to compare structures is divided into four steps: 1) load the structures to be compared; 2) define the atom equivalencies in these structures; 3) perform a fitting operation; and 4) analyze the results. Each structure is identified by a name. One structure is identified as the target (i.e., the fixed structure); the second structure (i.e., moving structure) is identified as the source structure. The atom equivalency within SYBYL is defined by user input. For the purpose of this invention, we will define equivalent atoms as protein backbone atoms (N, Cα, C and O) for all conserved residues between the two structures being compared. We will also consider only rigid fitting operations. When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atoms is an absolute minimum. This number, given in angstroms, is reported by the SYBYL program. For the purpose of the present invention, any homology model of a CAN-12 that has a root mean square deviation of conserved residue backbone atoms (N, Cα, C, O) of less than 3.0 Å when superimposed on the relevant backbone atoms described by structure coordinates listed in Table IV are considered identical. More preferably, the root mean square deviation for the CAN-12 polypeptide is less than 2.0 Å.

The homology model of the present invention is useful for the structure-based design of modulators of the CAN-12 biological function, as well as mutants with altered biological function and/or specificity.

In accordance with the structural coordinates provided in Table IV and the three dimensional homology model of CAN-12, the CAN-12 polypeptide has been shown to comprise a an active site region embodied by the following amino acids: from about amino acid R90 to about amino acid C94, from about amino acid G99 to about amino acid L104, from about amino acid Q196 to about amino acid S198, from about amino acid M210 to about amino acid I212, from about amino acid G236 to about amino acid H240, from about amino acid E251 to about amino acid Y255, from about amino acid N277 to about amino acid K281, from about amino acid V327 to about amino acid V330 of SEQ ID NO:2 or SEQ ID NO:24 (FIGS. 1A–E). In this context, the term "about" may be construed to mean 1, 2, 3, 4, 5, 6, 7, 8, 9 or 10 amino acids more in either the N- or C-terminal direction of the above referenced amino acids.

Also more preferred are polypeptides comprising all or any part of the CAN-12 active site domain, or a mutant or homologue of said polypeptide or molecular complex. By mutant or homologue of the molecule is meant a molecule that has a root mean square deviation from the backbone atoms of said CAN-12 amino acids of not more than about 4.5 Angstroms, and preferably not more than about 3.5 Angstroms.

In preferred embodiments, the following CAN-12 active site domain polypeptide is encompassed by the present invention: RLDLCQGIVGDCWFLAALQALAL-HQDILSRVVPLNQSFTEKYAGIFRFWFWH YGN-WVPVVIDDRLPVNEAGQLVFVSSTYKN-LFWGALLEKAYAKLSGSYEDL QSGQVSEALVDFTGGVTMTINLAEAHGN-LWDILIEATYNRTLIGCQTHSGKIL ENGLVEGHAY-TLTGIRKVTCKHRPEYLVKLRNP-WGKVEWKGDWSDSSSKW ELLSPKEKILLLRKDNDGEFWMTLQDFKTHFVLLV (SEQ ID NO:46). Polynucleotides encoding this polypeptide are also provided. The present invention also encompasses the use of the CAN-12 active site domain polypeptide as an immunogenic and/or antigenic epitope as described elsewhere herein.

The present invention also encompasses polypeptides comprising at least a portion of the CAN-12 active site domain (SEQ ID NO:46). Such polypeptides may correspond, for example, to the N- and/or C-terminal deletions of the active site domain.

In preferred embodiments, the following N-terminal CAN-12 active site domain deletion polypeptides are encompassed by the present invention: R1-V241, L2-V241, D3-V241, L4-V241, C5-V241, Q6-V241, G7-V241, I8-V241, V9-V241, G10-V241, D11-V241, C12-V241, W13-V241, F14-V241, L15-V241, A16-V241, A17-V241, L18-V241, Q19-V241, A20-V241, L21-V241, A22-V241, L23-V241, H24-V241, Q25-V241, D26-V241, I27-V241, L28-V241, S29-V241, R30-V241, V31-V241, V32-V241, P33-V241, L34-V241, N35-V241, Q36-V241, S37-V241, F38-V241, T39-V241, E40-V241, K41-V241, Y42-V241, A43-V241, G44-V241, I45-V241, F46-V241, R47-V241, F48-V241, W49-V241, F50-V241, W51-V241, H52-V241, Y53-V241, G54-V241, N55-V241, W56-V241, V57-V241, P58-V241, V59-V241, V60-V241, I61-V241, D62-V241, D63-V241, R64-V241, L65-V241, P66-V241, V67-V241, N68-V241, E69-V241, A70-V241, G71-V241, Q72-V241, L73-V241, V74-V241, F75-V241, V76-V241, S77-V241, S78-V241, T79-V241, Y80-V241, K81-V241, N82-V241, L83-V241, F84-V241, W85-V241, G86-V241, A87-V241, L88-V241, L89-V241, E90-V241, K91-V241, A92-V241, Y93-V241, A94-V241, K95-V241, L96-V241, S97-V241, G98-V241, S99-V241, Y100-V241, E101-V241, D102-V241, L103-V241, Q104-V241, S105-V241, G106-V241, Q107-V241, V108-V241, S109-V241, E110-V241, A111-V241, L112-V241, V113-V241, D114-V241, F115-V241, T116-V241, G117-V241, G118-V241, V119-V241, T120-V241, M121-V241, T122-V241, I123-V241, N124-V241, L125-V241, A126-V241, E127-V241, A128-V241, H129-V241, G130-V241, N131-V241, L132-V241, W133-V241, D134-V241, I135-V241, L136-V241, I137-V241, E138-V241, A139-V241, T140-V241, Y141-V241, N142-V241, R143-V241, T144-V241, L145-V241, I146-V241, G147-V241, C148-V241, Q149-V241, T150-V241, H151-V241, S152-V241, G153-V241, K154-V241, I155-V241, L156-V241, E157-V241, N158-V241, G159-V241, L160-V241, V161-V241, E162-V241, G163-V241, H164-V241, A165-V241, Y166-V241, T167-V241, L168-V241, T169-V241, G170-V241, I171-V241, R172-V241, K173-V241, V174-V241, T175-V241, C176-V241, K177-V241, H178-V241, R179-V241, P180-V241, E181-V241, Y182-V241, L183-V241, V184-V241, K185-V241, L186-V241, R187-V241, N188-V241, P189-V241, W190-V241, G191-V241, K192-V241, V193-V241, E194-V241, W195-V241, K196-V241, G197-V241, D198-V241, W199-V241, S200-V241, D201-V241, S202-V241, S203-V241, S204-V241, K205-V241, W206-V241, E207-V241, L208-V241, L209-V241, S210-V241, P211-V241, K212-V241, E213-V241, K214-V241, I215-V241, L216-V241, L217-V241, L218-V241, R219-V241, K220-V241, D221-V241, N222-V241, D223-V241, G224-V241, E225-V241, F226-V241, W227-V241, M228-V241, T229-V241, L230-V241, Q231-V241, D232-V241, F233-V241, K234-V241, and/or T235-V241 of SEQ ID NO:46. Polynucleotide sequences encoding these polypeptides are also provided. The present invention also encompasses the use of these N-terminal CAN-12 active site domain deletion polypeptides as immunogenic and/or antigenic epitopes as described elsewhere herein.

In preferred embodiments, the following C-terminal CAN-12 active site domain deletion polypeptides are encompassed by the present invention: R1-V241, R1-L240, R1-L239, R1-V238, R1-F237, R1-H236, R1-T235, R1-K234, R1-F233, R1-D232, R1-Q231, R1-L230, R1-T229, R1-M228, R1-W227, R1-F226, R1-E225, R1-G224, R1-D223, R1-N222, R1-D221, R1-K220, R1-R219, R1-L218, R1-L217, R1-L216, R1-I215, R1-K214, R1-E213, R1-K212, R1-P211, R1-S210, R1-L209, R1-L208, R1-E207, R1-W206, R1-K205, R1-S204, R1-S203, R1-S202, R1-D201, R1-S200, R1-W199, R1-D198, R1-G197, R1-K196, R1-W195, R1-E194, R1-V193, R1-K192, R1-G191, R1-W190, R1-P189, R1-N188, R1-R187, R1-L186, R1-K185, R1-V184, R1-L183, R1-Y182, R1-E181, R1-P180, R1-R179, R1-H178, R1-K177, R1-C176, R1-T175, R1-V174, R1-K173, R1-R172, R1-I171, R1-G170, R1-T169, R1-L168, R1-T167, R1-Y166, R1-A165, R1-H164, R1-G163, R1-E162, R1-V161, R1-L160, R1-G159, R1-N158, R1-E157, R1-L156, R1-I155, R1-K154, R1-G153, R1-S152, R1-H151, R1-T150, R1-Q149, R1-C148, R1-G147, R1-I146, R1-L145, R1-T144, R1-R143, R1-N142, R1-Y141, R1-T140, R1-A139, R1-E138, R1-I137, R1-L136, R1-I135, R1-D134, R1-W133, R1-L132, R1-N131, R1-G130, R1-H129, R1-A128, R1-E127, R1-A126, R1-L125, R1-N124, R1-I123, R1-T122, R1-M121, R1-T120, R1-V119, R1-G118, R1-G117, R1-T116, R1-F115, R1-D114, R1-V113, R1-L112, R1-A111, R1-E110, R1-S109, R1-V108, R1-Q107, R1-G106, R1-S105, R1-Q104, R1-L103, R1-D102, R1-E101, R1-Y100, R1-S99, R1-G98, R1-S97, R1-L96, R1-K95, R1-A94, R1-Y93, R1-A92, R1-K91, R1-E90, R1-L89, R1-L88, R1-A87, R1-G86, R1-W85, R1-F84, R1-L83, R1-N82, R1-K81, R1-Y80, R1-T79, R1-S78, R1-S77, R1-V76, R1-F75, R1-V74, R1-L73, R1-Q72, R1-G71, R1-A70, R1-E69, R1-N68, R1-V67, R1-P66, R1-L65, R1-R64, R1-D63, R1-D62, R1-I61, R1-V60, R1-V59, R1-P58, R1-V57, R1-W56, R1-N55, R1-G54, R1-Y53, R1-H52, R1-W51, R1-F50, R1-W49, R1-F48, R1-R47, R1-F46, R1-I45, R1-G44, R1-A43, R1-Y42, R1-K41, R1-E40, R1-T39, R1-F38, R1-S37, R1-Q36, R1-N35, R1-L34, R1-P33, R1-V32, R1-V31, R1-R30, R1-S29, R1-L28, R1-I27, R1-D26, R1-Q25, R1-H24, R1-L23, R1-A22, R1-L21, R1-A20, R1-Q19, R1-L18, R1-A17, R1-A16, R1-L15, R1-F14, R1-W13, R1-C12, R1-D11, R1-G10, R1-V9, R1-I8, and/or R1-G7 of SEQ ID NO:46. Polynucleotide sequences encoding these polypeptides are also provided. The present invention also encompasses the use of these C-terminal CAN-12 active site domain deletion polypeptides as immunogenic and/or antigenic epitopes as described elsewhere herein.

Alternatively, such polypeptides may comprise polypeptide sequences corresponding, for example, to internal regions of the CAN-12 active site domain (e.g., any combination of both N- and C-terminal CAN-12 active site domain deletions) of SEQ ID NO:46. For example, internal regions could be defined by the equation NX to CX, where NX refers to any N-terminal amino acid position of the CAN-12 active site domain (SEQ ID NO:46), and where CX refers to any C-terminal amino acid position of the CAN-12 active site domain (SEQ ID NO:46). Polynucleotides encoding these polypeptides are also provided. The present invention also encompasses the use of these polypeptides as an immunogenic and/or antigenic epitope as described elsewhere herein.

In preferred embodiments, the following CAN-12 active site domain amino acid substitutions are encompassed by the present invention: wherein R90 is substituted with either an A, C, D, E, F, G, H, I, K, L, M, N, P, Q, S, T, V, W, or Y; wherein L91 is substituted with either an A, C, D, E, F, G, H, I, K, M, N, P, Q, R, S, T, V, W, or Y; wherein D92 is substituted with either an A, C, E, F, G, H, I, K, L, M, N, P, Q, R, S, T, V, W, or Y; wherein L93 is substituted with either an A, C, D, E, F, G, H, I, K, M, N, P, Q, R, S, T, V, W, or Y; wherein C94 is substituted with either an A, D, E, F, G, H, I, K, L, M, N, P, Q, R, S, T, V, W, or Y; wherein Q95 is substituted with either an A, C, D, E, F, G, H, I, K, L, M, N, P, R, S, T, V, W, or Y; wherein G96 is substituted with either an A, C, D, E, F, H, I, K, L, M, N, P, Q, R, S, T, V, W, or Y; wherein I97 is substituted with either an A, C, D, E, F, G, H, K, L, M, N, P, Q, R, S, T, V, W, or Y; wherein V98 is substituted with either an A, C, D, E, F, G, H, I, K, L, M, N, P, Q, R, S, T, W, or Y; wherein G99 is substituted with either an A, C, D, E, F, H, I, K, L, M, N, P, Q, R, S, T, V, W, or Y; wherein D100 is substituted with either an A, C, E, F, G, H, I, K, L, M, N, P, Q, R, S, T, V, W, or Y; wherein C101 is substituted with either an A, D, E, F, G, H, I, K, L, M, N, P, Q, R, S, T, V, W, or Y; wherein W102 is substituted with either an A, C, D, E, F, G, H, I, K, L, M, N, P, Q, R, S, T, V, or Y; wherein F103 is substituted with either an A, C, D, E, G, H, I, K, L, M, N, P, Q, R, S, T, V, W, or Y; wherein L104 is substituted with either an A, C, D, E, F, G, H, I, K, M, N, P, Q, R, S, T, V, W, or Y; wherein A105 is substituted with either a C, D, E, F, G, H, I, K, L, M, N, P, Q, R, S, T, V, W, or Y; wherein A106 is substituted with either a C, D, E, F, G, H, I, K, L, M, N, P, Q, R, S, T, V, W, or Y; wherein L107 is substituted with either an A, C, D, E, F, G, H, I, K, M, N, P, Q, R, S, T, V, W, or Y; wherein Q108 is substituted with either an A, C, D, E, F, G, H, I, K, L, M, N, P, R, S, T, V, W, or Y; wherein A109 is substituted with either a C, D, E, F, G, H, I, K, L, M, N, P, Q, R, S, T, V, W, or Y; wherein L110 is substituted with either an A, C, D, E, F, G, H, I, K, M, N, P, Q, R, S, T, V, W, or Y; wherein A111 is substituted with either a C, D, E, F, G, H, I, K, L, M, N, P, Q, R, S, T, V, W, or Y; wherein L112 is substituted with either an A, C, D, E, F, G, H, I, K, M, N, P, Q, R, S, T, V, W, or Y; wherein H113 is substituted with either an A, C, D, E, F, G, I, K, L, M, N, P, Q, R, S, T, V, W, or Y; wherein Q114 is substituted with either an A, C, D, E, F, G, H, I, K, L, M, N, P, R, S, T, V, W, or Y; wherein D115 is substituted with either an A, C, E, F, G, H, I, K, L, M, N, P, Q, R, S, T, V, W, or Y; wherein I116 is substituted with either an A, C, D, E, F, G, H, K, L, M, N, P, Q, R, S, T, V, W, or Y; wherein L117 is substituted with either an A, C, D, E, F, G, H, I, K, M, N, P, Q, R, S, T, V, W, or Y; wherein S118 is substituted with either an A, C, D, E, F, G, H, I, K, L, M, N, P, Q, R, T, V, W, or Y; wherein R119 is substituted with either an A, C, D, E, F, G, H, I, K, L, M, N, P, Q, S, T, V, W, or Y; wherein V120 is substituted with either an A, C, D, E, F, G, H, I, K, L, M, N, P, Q, R, S, T, W, or Y; wherein V121 is substituted with either an A, C, D, E, F, G, H, I, K, L, M, N, P, Q, R, S, T, W, or Y; wherein P122 is substituted with either an A, C, D, E, F, G, H, I, K, L, M, N, Q, R, S, T, V, W, or Y; wherein L123 is substituted with either an A, C, D, E, F, G, H, I, K, M, N, P, Q, R, S, T, V, W, or Y; wherein N124 is substituted with either an A, C, D, E, F, G, H, I, K, L, M, P, Q, R, S, T, V, W, or Y; wherein Q125 is substituted with either an A, C, D, E, F, G, H, I, K, L, M, N, P, R, S, T, V, W, or Y; wherein S126 is substituted with either an A, C, D, E, F, G, H, I, K, L, M, N, P, Q, R, T, V, W, or Y; wherein F127 is substituted with either an A, C, D, E, G, H, I, K, L, M, N, P, Q, R, S, T, V, W, or Y; wherein T128 is substituted with either an A, C, D, E, F, G, H, I, K, L, M, N, P, Q, R, S, V, W, or Y; wherein E129 is substituted with either an A, C, D, F, G, H, I, K, L, M, N, P, Q, R, S, T, V, W, or Y; wherein K130 is substituted with either an A, C, D, E, F, G, H, I, L, M, N, P, Q, R, S, T, V, W, or Y; wherein Y131 is substituted with either an A, C, D, E, F, G, H, I, K, L, M, N, P, Q, R, S, T, V, or W; wherein A132 is substituted with either a C, D, E, F, G, H, I, K, L, M, N, P, Q, R, S, T, V, W, or Y; wherein G133 is substituted with either an A, C, D, E, F, H, I, K, L, M, N, P, Q, R, S, T, V, W, or Y; wherein I134 is substituted with either an A, C, D, E, F, G, H, K, L, M, N, P, Q, R, S, T, V, W, or Y; wherein F135 is substituted with either an A, C, D, E, G, H, I, K, L, M, N, P, Q, R, S, T, V, W, or Y; wherein R136 is substituted with either an A, C, D, E, F, G, H, I, K, L, M, N, P, Q, S, T, V, W, or Y; wherein F137 is substituted with either an A, C, D, E, G, H, I, K, L, M, N, P, Q, R, S, T, V, W, or Y; wherein W138 is substituted with either an A, C, D, E, F, G, H, I, K, L, M, N, P, Q, R, S, T, V, or Y; wherein F139 is substituted with either an A, C, D, E, G, H, I, K, L, M, N, P, Q, R, S, T, V, W, or Y; wherein W140 is substituted with either an A, C, D, E, F, G, H, I, K, L, M, N, P, Q, R, S, T, V, or Y; wherein H141 is substituted with either an A, C, D, E, F, G, I, K, L, M, N, P, Q, R, S, T, V, W, or Y; wherein Y142 is substituted with either an A, C, D, E, F, G, H, I, K, L, M, N, P, Q, R, S, T, V, or W; wherein G143 is substituted with either an A, C, D, E, F, H, I, K, L, M, N, P, Q, R, S, T, V, W, or Y; wherein N144 is substituted with either an A, C, D, E, F, G, H, I, K, L, M, P, Q, R, S, T, V, W, or Y; wherein W145 is substituted with either an A, C, D, E, F, G, H, I, K, L, M, N, P, Q, R, S, T, V, or Y; wherein V146 is substituted with either an A, C, D, E, F, G, H, I, K, L, M, N, P, Q, R, S, T, W, or Y; wherein P147 is substituted with either an A, C, D, E, F, G, H, I, K, L, M, N, Q, R, S, T, V, W, or Y; wherein V148 is substituted with either an A, C, D, E, F, G, H, I, K, L, M, N, P, Q, R, S, T, W, or Y; wherein V149 is substituted with either an A, C, D, E, F, G, H, I, K, L, M, N, P, Q, R, S, T, W, or Y; wherein I150 is substituted with either an A, C, D, E, F, G, H, K, L, M, N, P, Q, R, S, T, V, W, or Y; wherein D151 is substituted with either an A, C, E, F, G, H, I, K, L, M, N, P, Q, R, S, T, V, W, or Y; wherein D152 is substituted with either an A, C, E, F, G, H, I, K, L, M, N, P, Q, R, S, T, V, W, or Y; wherein R153 is substituted with either an A, C, D, E, F, G, H, I, K, L, M, N, P, Q, S, T, V, W, or Y; wherein L154 is substituted with either an A, C, D, E, F, G, H, 1, K, M, N, P, Q, R, S, T, V, W, or Y; wherein P155 is substituted with either an A, C, D, E, F, G, H, I, K, L, M, N, Q, R, S, T, V, W, or Y; wherein V156 is substituted with either an A, C, D, E, F, G, H, I, K, L, M, N, P, Q, R, S, T, W, or Y; wherein N157 is substituted with either an A, C, D, E, F, G, H, I, K, L, M, P, Q, R, S, T, V, W, or Y; wherein E158 is substituted with either an A, C, D, F, G, H, I, K, L, M, N, P, Q, R, S, T, V, W, or Y; wherein A159 is substituted with either a C, D, E, F, G, H, I, K, L, M, N, P, Q, R, S, T, V, W, or Y; wherein G160 is substituted with either an A, C, D, E, F, H, I, K, L, M, N, P, Q, R, S, T, V, W, or Y; wherein Q161 is substituted with either an A, C, D, E, F, G, H, I, K, L, M, N, P, R, S, T, V, W, or Y; wherein L162 is substituted with either an A, C, D, E, F, G, H, I, K, M, N, P, Q, R, S, T, V, W, or Y; wherein V163 is substituted with either an A, C, D, E, F, G, H, I, K, L, M, N, P, Q, R, S, T, W, or Y; wherein F164 is substituted with either an A, C, D, E, G, H, I, K, L, M, N, P, Q, R, S, T, V, W, or Y; wherein V165 is substituted with either an A, C, D, E, F, G, H, I, K, L, M, N, P, Q, R, S, T, W, or Y; wherein S166 is substituted with either an A, C, D, E, F, G, H, I, K, L, M, N, P, Q, R, T, V, W, or Y; wherein S167 is substituted with either an A, C, D, E, F, G, H, I, K, L, M, N, P, Q, R, T, V, W, or Y; wherein T168 is substituted with either an A, C, D, E, F, G, H, I, K, L, M, N, P, Q, R, S, V, W, or Y; wherein Y169 is substituted with either an A, C, D, E, F, G, H, I, K, L, M, N, P, Q, R, S, T, V, or W; wherein K170 is substituted with either an A, C, D, E, F, G, H, I, L, M, N, P, Q, R, S, T, V, W, or Y; wherein N171 is substituted with either an A, C, D, E, F, G, H, I, K, L, M, P, Q, R, S, T, V, W, or Y; wherein L172 is substituted with either an A, C, D, E, F, G, H, I, K, M, N, P, Q, R, S, T, V, W, or Y; wherein F173 is substituted with either an A, C, D, E, G, H, I, K, L, M, N, P, Q, R, S, T, V, W, or Y; wherein W174 is substituted with either an A, C, D, E, F, G, H, I, K, L, M, N, P, Q, R, S, T, V, or Y; wherein G175 is substituted with either an A, C, D, E, F, H, I, K, L, M, N, P, Q, R, S, T, V, W, or Y; wherein A176 is substituted with either a C, D, E, F, G, H, I, K, L, M, N, P, Q, R, S, T, V, W, or Y; wherein L177 is substituted with either an A, C, D, E, F, G, H, I, K, M, N, P, Q, R, S, T, V, W, or Y; wherein L178 is substituted with either an A, C, D, E, F, G, H, I, K, M, N, P, Q, R, S, T, V, W, or Y; wherein E179 is substituted with either an A, C, D, F, G, H, I, K, L, M, N, P, Q, R, S, T, V, W, or Y; wherein K180 is substituted with either an A, C, D, E, F, G, H, I, L, M, N, P, Q, R, S, T, V, W, or Y; wherein A181 is substituted with either a C, D, E, F, G, H, I, K, L, M, N, P, Q, R, S, T, V, W, or Y; wherein Y182 is substituted with either an A, C, D, E, F, G, H, I, K, L, M, N, P, Q, R, S, T, V, or W; wherein A183 is substituted with either a C, D, E, F, G, H, I, K, L, M, N, P, Q, R, S, T, V, W, or Y; wherein K184 is substituted with either an A, C, D, E, F, G, H, I, L, M, N, P, Q, R, S, T, V, W, or Y; wherein L185 is substituted with either an A, C, D, E, F, G, H, I, K, M, N, P, Q, R, S, T, V, W, or Y; wherein S186 is substituted with either an A, C, D, E, F, G, H, I, K, L, M, N, P, Q, R, T, V, W, or Y; wherein G187 is substituted with either an A, C, D, E, F, H, I, K, L, M, N, P, Q, R, S, T, V, W, or Y; wherein S188 is substituted with either an A, C, D, E, F, G, H, I, K, L, M, N, P, Q, R, T, V, W, or Y; wherein Y189 is substituted with either an A, C, D, E, F, G, H, I, K, L, M, N, P, Q, R, S, T, V, or W; wherein E190 is substituted with either an A, C, D, F, G, H, I, K, L, M, N, P, Q, R, S, T, V, W, or Y; wherein D191 is substituted with either an A, C, E, F, G, H, I, K, L, M, N, P, Q, R, S, T, V, W, or Y; wherein L192 is substituted with either an A, C, D, E, F, G, H, I, K, M, N, P, Q, R, S, T, V, W, or Y; wherein Q193 is substituted with either an A, C, D, E, F, G, H, I, K, L, M, N, P, R, S, T, V, W, or Y; wherein S194 is substituted with either an A, C, D, E, F, G, H, I, K, L, M, N, P, Q, R, T, V, W, or Y; wherein G195 is substituted with either an A, C, D, E, F, H, I, K, L, M, N, P, Q, R, S, T, V, W, or Y; wherein Q196 is substituted with either an A, C, D, E, F, G, H, I, K, L, M, N, P, R, S, T, V, W, or Y; wherein V197 is substituted with either an A, C, D, E, F, G, H, I, K, L, M, N, P, Q, R, S, T, W, or Y; wherein S198 is substituted with either an A, C, D, E, F, G, H, I, K, L, M, N, P, Q, R, T, V, W, or Y; wherein E199 is substituted with either an A, C, D, F, G, H, I, K, L, M, N, P, Q, R, S, T, V, W, or Y; wherein A200 is substituted with either a C, D, E, F, G, H, I, K, L, M, N, P, Q, R, S, T, V, W, or Y; wherein L201 is substituted with either an A, C, D, E, F, G, H, I, K, M, N, P, Q, R, S, T, V, W, or Y; wherein V202 is substituted with either an A, C, D, E, F, G, H, I, K, L, M, N, P, Q, R, S, T, W, or Y; wherein D203 is substituted with either an A, C, E, F, G, H, I, K, L, M, N, P, Q, R, S, T, V, W, or Y; wherein F204 is substituted with either an A, C, D, E, G, H, I, K, L, M, N, P, Q, R, S, T, V, W, or Y; wherein T205 is substituted with either an A, C, D, E, F, G, H, I, K, L, M, N, P, Q, R, S, V, W, or Y; wherein G206 is substituted with either an A, C, D, E, F, H, I, K, L, M, N, P, Q, R, S, T, V, W, or Y; wherein G207 is substituted with either an A, C, D, E, F, H, I, K, L, M, N, P, Q, R, S, T, V, W, or Y; wherein V208 is substituted with either an A, C, D, E, F, G, H, I, K, L, M, N, P, Q, R, S, T, W, or Y; wherein T209 is substituted with either an A, C, D, E, F, G, H, I, K, L, M, N, P, Q, R, S, V, W, or Y; wherein M210 is substituted with either an A, C, D, E, F, G, H, I, K, L, N, P, Q, R, S, T, V, W, or Y; wherein T211 is substituted with either an A, C, D, E, F, G, H, I, K, L, M, N, P, Q, R, S, V, W, or Y; wherein I212 is substituted with either an A, C, D, E, F, G, H, K, L, M, N, P, Q, R, S, T, V, W, or Y; wherein N213 is substituted with either an A, C, D, E, F, G, H, I, K, L, M, P, Q, R, S, T, V, W, or Y; wherein L214 is substituted with either an A, C, D, E, F, G, H, I, K, M, N, P, Q, R, S, T, V, W, or Y; wherein A215 is substituted with either a C, D, E, F, G, H, I, K, L, M, N, P, Q, R, S, T, V, W, or Y; wherein E216 is substituted with either an A, C, D, F, G, H, I, K, L, M, N, P, Q, R, S, T, V, W, or Y; wherein A217 is substituted with either a C, D, E, F, G, H, I, K, L, M, N, P, Q, R, S, T, V, W, or Y; wherein H218 is substituted with either an A, C, D, E, F, G, I, K, L, M, N, P, Q, R, S, T, V, W, or Y; wherein G219 is substituted with either an A, C, D, E, F, H, I, K, L, M, N, P, Q, R, S, T, V, W, or Y; wherein N220 is substituted with either an A, C, D, E, F, G, H, I, K, L, M, P, Q, R, S, T, V, W, or Y; wherein L221 is substituted with either an A, C, D, E, F, G, H, I, K, M, N, P, Q, R, S, T, V, W, or Y; wherein W222 is substituted with either an A, C, D, E, F, G, H, I, K, L, M, N, P, Q, R, S, T, V, or Y; wherein D223 is substituted with either an A, C, E, F, G, H, I, K, L, M, N, P, Q, R, S, T, V, W, or Y; wherein I224 is substituted with either an A, C, D, E, F, G, H, K, L, M, N, P, Q, R, S, T, V, W, or Y; wherein L225 is substituted with either an A, C, D, E, F, G, H, I, K, M, N, P, Q, R, S, T, V, W, or Y; wherein I226 is substituted with either an A, C, D, E, F, G, H, K, L, M, N, P, Q, R, S, T, V, W, or Y; wherein E227 is substituted with either an A, C, D, F, G, H, I, K, L, M, N, P, Q, R, S, T, V, W, or Y; wherein A228 is substituted with either a C, D, E, F, G, H, I, K, L, M, N, P, Q, R, S, T, V, W, or Y; wherein T229 is substituted with either an A, C, D, E, F, G, H, I, K, L, M, N, P, Q, R, S, V, W, or Y; wherein Y230 is substituted with either an A, C, D, E, F, G, H, I, K, L, M, N, P, Q, R, S, T, V, or W; wherein N231 is substituted with either an A, C, D, E, F, G, H, 1, K, L, M, P, Q, R, S, T, V, W, or Y; wherein R232 is substituted with either an A, C, D, E, F, G, H, I, K, L, M, N, P, Q, S, T, V, W, or Y; wherein T233 is substituted with either an A, C, D, E, F, G, H, I, K, L, M, N, P, Q, R, S, V, W, or Y; wherein L234 is substituted with either an A, C, D, E, F, G, H, I, K, M, N, P, Q, R, S, T, V, W, or Y; wherein I235 is substituted with either an A, C, D, E, F, G, H, K, L, M, N, P, Q, R, S, T, V, W, or Y; wherein G236 is substituted with either an A, C, D, E, F, H, I, K, L, M, N, P, Q, R, S, T, V, W, or Y; wherein C237 is substituted with either an A, D, E, F, G, H, I, K, L, M, N, P, Q, R, S, T, V, W, or Y; wherein Q238 is substituted with either an A, C, D, E, F, G, H, I, K, L, M, N, P, R, S, T, V, W, or Y; wherein T239 is substituted with either an A, C, D, E, F, G, H, I, K, L, M, N, P, Q, R, S, V, W, or Y; wherein H240 is substituted with either an A, C, D, E, F, G, I, K, L, M, N, P, Q, R, S, T, V, W, or Y; wherein S241 is substituted with either an A, C, D, E, F, G, H, I, K, L, M, N, P, Q, R, T, V, W, or Y; wherein G242 is substituted with either an A, C, D, E, F, H, I, K, L, M, N, P, Q, R, S, T, V, W, or Y; wherein K243 is substituted with either an A, C, D, E, F, G, H, I, L, M, N, P, Q, R, S, T, V, W, or Y; wherein I244 is substituted with either an A, C, D, E, F, G, H, K, L, M, N, P, Q, R, S, T, V, W, or Y; wherein L245 is substituted with either an A, C, D, E, F, G, H, I, K, M, N, P, Q, R, S, T, V, W, or Y; wherein E246 is substituted with either an A, C, D, F, G, H, I, K, L, M, N, P, Q, R, S, T, V, W, or Y; wherein N247 is substituted with either an A, C, D, E, F, G, H, I, K, L, M, P, Q, R, S, T, V, W, or Y; wherein G248 is substituted with either an A, C, D, E, F, H, I, K, L, M, N, P, Q, R, S, T, V, W, or Y; wherein L249 is substituted with either an A, C, D, E, F, G, H, I, K, M, N, P, Q, R, S, T, V, W, or Y; wherein V250 is substituted with either an A, C, D, E, F, G, H, I, K, L, M, N, P, Q, R, S, T, W, or Y; wherein E251 is substituted with either an A, C, D, F, G, H, I, K, L, M, N, P, Q, R, S, T, V, W, or Y; wherein G252 is substituted with either an A, C, D, E, F, H, I, K, L, M, N, P, Q, R, S, T, V, W, or Y; wherein H253 is substituted with either an A, C, D, E, F, G, I, K, L, M, N, P, Q, R, S, T, V, W, or Y; wherein A254 is substituted with either a C, D, E, F, G, H, I, K, L, M, N, P, Q, R, S, T, V, W, or Y; wherein Y255 is substituted with either an A, C, D, E, F, G, H, I, K, L, M, N, P, Q, R, S, T, V, or W; wherein T256 is substituted with either an A, C, D, E, F, G, H, I, K, L, M, N, P, Q, R, S, V, W, or Y; wherein L257 is substituted with either an A, C, D, E, F, G, H, I, K, M, N, P, Q, R, S, T, V, W, or Y; wherein T258 is substituted with either an A, C, D, E, F, G, H, I, K, L, M, N, P, Q, R, S, V, W, or Y; wherein G259 is substituted with either an A, C, D, E, F, H, I, K, L, M, N, P, Q, R, S, T, V, W, or Y; wherein I260 is substituted with either an A, C, D, E, F, G, H, K, L, M, N, P, Q, R, S, T, V, W, or Y; wherein R261 is substituted with either an A, C, D, E, F, G, H, I, K, L, M, N, P, Q, S, T, V, W, or Y; wherein K262 is substituted with either an A, C, D, E, F, G, H, I, L, M, N, P, Q, R, S, T, V, W, or Y; wherein V263 is substituted with either an A, C, D, E, F, G, H, I, K, L, M, N, P, Q, R, S, T, W, or Y; wherein T264 is substituted with either an A, C, D, E, F, G, H, I, K, L, M, N, P, Q, R, S, V, W, or Y; wherein C265 is substituted with either an A, D, E, F, G, H, I, K, L, M, N, P, Q, R, S, T, V, W, or Y; wherein K266 is substituted with either an A, C, D, E, F, G, H, I, L, M, N, P, Q, R, S, T, V, W, or Y; wherein H267 is substituted with either an A, C, D, E, F, G, I, K, L, M, N, P, Q, R, S, T, V, W, or Y; wherein R268 is substituted with either an A, C, D, E, F, G, H, I, K, L, M, N, P, Q, S, T, V, W, or Y; wherein P269 is substituted with either an A, C, D, E, F, G, H, I, K, L, M, N, Q, R, S, T, V, W, or Y; wherein E270 is substituted with either an A, C, D, F, G, H, I, K, L, M, N, P, Q, R, S, T, V, W, or Y; wherein Y271 is substituted with either an A, C, D, E, F, G, H, I, K, L, M, N, P, Q, R, S, T, V, or W; wherein L272 is substituted with either an A, C, D, E, F, G, H, I, K, M, N, P, Q, R, S, T, V, W, or Y; wherein V273 is substituted with either an A, C, D, E, F, G, H, I, K, L, M, N, P, Q, R, S, T, W, or Y; wherein K274 is substituted with either an A, C, D, E, F, G, H, I, L, M, N, P, Q, R, S, T, V, W, or Y; wherein L275 is substituted with either an A, C, D, E, F, G, H, I, K, M, N, P, Q, R, S, T, V, W, or Y; wherein R276 is substituted with either an A, C, D, E, F, G, H, I, K, L, M, N, P, Q, S, T, V, W, or Y; wherein N277 is substituted with either an A, C, D, E, F, G, H, I, K, L, M, P, Q, R, S, T, V, W, or Y; wherein P278 is substituted with either an A, C, D, E, F, G, H, I, K, L, M, N, Q, R, S, T, V, W, or Y; wherein W279 is substituted with either an A, C, D, E, F, G, H, I, K, L, M, N, P, Q, R, S, T, V, or Y; wherein G280 is substituted with either an A, C, D, E, F, H, I, K, L, M, N, P, Q, R, S, T, V, W, or Y; wherein K281 is substituted with either an A, C, D, E, F, G, H, I, L, M, N, P, Q, R, S, T, V, W, or Y; wherein V282 is substituted with either an A, C, D, E, F, G, H, I, K, L, M, N, P, Q, R, S, T, W, or Y; wherein E283 is substituted with either an A, C, D, F, G, H, I, K, L, M, N, P, Q, R, S, T, V, W, or Y; wherein W284 is substituted with either an A, C, D, E, F, G, H, I, K, L, M, N, P, Q, R, S, T, V, or Y; wherein K285 is substituted with either an A, C, D, E, F, G, H, I, L, M, N, P, Q, R, S, T, V, W, or Y; wherein G286 is substituted with either an A, C, D, E, F, H, I, K, L, M, N, P, Q, R, S, T, V, W, or Y; wherein D287 is substituted with either an A, C, E, F, G, H, I, K, L, M, N, P, Q, R, S, T, V, W, or Y; wherein W288 is substituted with either an A, C, D, E, F, G, H, I, K, L, M, N, P, Q, R, S, T, V, or Y; wherein S289 is substituted with either an A, C, D, E, F, G, H, I, K, L, M, N, P, Q, R, T, V, W, or Y; wherein D290 is substituted with either an A, C, E, F, G, H, I, K, L, M, N, P, Q, R, S, T, V, W, or Y; wherein S291 is substituted with either an A, C, D, E, F, G, H, I, K, L, M, N, P, Q, R, T, V, W, or Y; wherein S292 is substituted with either an A, C, D, E, F, G, H, I, K, L, M, N, P, Q, R, T, V, W, or Y; wherein S293 is substituted with either an A, C, D, E, F, G, H, I, K, L, M, N, P, Q, R, T, V, W, or Y; wherein K294 is substituted with either an A, C, D, E, F, G, H, I, L, M, N, P, Q, R, S, T, V, W, or Y; wherein W295 is substituted with either an A, C, D, E, F, G, H, I, K, L, M, N, P, Q, R, S, T, V, or Y; wherein E296 is substituted with either an A, C, D, F, G, H, I, K, L, M, N, P, Q, R, S, T, V, W, or Y; wherein L297 is substituted with either an A, C, D, E, F, G, H, I, K, M, N, P, Q, R, S, T, V, W, or Y; wherein L298 is substituted with either an A, C, D, E, F, G, H, I, K, M, N, P, Q, R, S, T, V, W, or Y; wherein S299 is substituted with either an A, C, D, E, F, G, H, I, K, L, M, N, P, Q, R, T, V, W, or Y; wherein P300 is substituted with either an A, C, D, E, F, G, H, I, K, L, M, N, Q, R, S, T, V, W, or Y; wherein K301 is substituted with either an A, C, D, E, F, G, H, I, L, M, N, P, Q, R, S, T, V, W, or Y; wherein E302 is substituted with either an A, C, D, F, G, H, I, K, L, M, N, P, Q, R, S, T, V, W, or Y; wherein K303 is substituted with either an A, C, D, E, F, G, H, I, L, M, N, P, Q, R, S, T, V, W, or Y; wherein I304 is substituted with either an A, C, D, E, F, G, H, K, L, M, N, P, Q, R, S, T, V, W, or Y; wherein L305 is substituted with either an A, C, D, E, F, G, H, I, K, M, N, P, Q, R, S, T, V, W, or Y; wherein L306 is substituted with either an A, C, D, E, F, G, H, I, K, M, N, P, Q, R, S, T, V, W, or Y; wherein L307 is substituted with either an A, C, D, E, F, G, H, I, K, M, N, P, Q, R, S, T, V, W, or Y; wherein R308 is substituted with either an A, C, D, E, F, G, H, I, K, L, M, N, P, Q, S, T, V, W, or Y; wherein K309 is substituted with either an A, C, D, E, F, G, H, I, L, M, N, P, Q, R, S, T, V, W, or Y; wherein D310 is substituted with either an A, C, E, F, G, H, I, K, L, M, N, P, Q, R, S, T, V, W, or Y; wherein N311 is substituted with either an A, C, D, E, F, G, H, 1, K, L, M, P, Q, R, S, T, V, W, or Y; wherein D312 is substituted with either an A, C, E, F, G, H, I, K, L, M, N, P, Q, R, S, T, V, W, or Y; wherein G313 is substituted with either an A, C, D, E, F, H, I, K, L, M, N, P, Q, R, S, T, V, W, or Y; wherein E314 is substituted with either an A, C, D, F, G, H, I, K, L, M, N, P, Q, R, S, T, V, W, or Y; wherein F315 is substituted with either an A, C, D, E, G, H, I, K, L, M, N, P, Q, R, S, T, V, W, or Y; wherein W316 is substituted with either an A, C, D, E, F, G, H, I, K, L, M, N, P, Q, R, S, T, V, or Y; wherein M317 is substituted with either an A, C, D, E, F, G, H, I, K, L, N, P, Q, R, S, T, V, W, or Y; wherein T318 is substituted with either an A, C, D, E, F, G, H, I, K, L, M, N, P, Q, R, S, V, W, or Y; wherein L319 is substituted with either an A, C, D, E, F, G, H, I, K, M, N, P, Q, R, S, T, V, W, or Y; wherein Q320 is substituted with either an A, C, D, E, F, G, H, I, K, L, M, N, P, R, S, T, V, W, or Y; wherein D321 is substituted with either an A, C, E, F, G, H, I, K, L, M, N, P, Q, R, S, T, V, W, or Y; wherein F322 is substituted with either an A, C, D, E, G, H, I, K, L, M, N, P, Q, R, S, T, V, W, or Y; wherein K323 is substituted with either an A, C, D, E, F, G, H, I, L, M, N, P, Q, R, S, T, V, W, or Y; wherein T324 is substituted with either an A, C, D, E, F, G, H, I, K, L, M, N, P, Q, R, S, V, W, or Y; wherein H325 is substituted with either an A, C, D, E, F, G, I, K, L, M, N, P, Q, R, S, T, V, W, or Y; wherein F326 is substituted with either an A, C, D, E, G, H, I, K, L, M, N, P, Q, R, S, T, V, W, or Y; wherein V327 is substituted with either an A, C, D, E, F, G, H, I, K, L, M, N, P, Q, R, S, T, W, or Y; wherein L328 is substituted with either an A, C, D, E, F, G, H, I, K, M, N, P, Q, R, S, T, V, W, or Y; wherein L329 is substituted with either an A, C, D, E, F, G, H, I, K, M, N, P, Q, R, S, T, V, W, or Y; and/or wherein V330 is substituted with either an A, C, D, E, F, G, HI, K, L, M, N, P, Q, R, S, T, W, or Y of SEQ ID NO:2 or SEQ ID NO:24, in addition to any combination thereof. The present invention also encompasses the use of these CAN-12 active site domain amino acid substituted polypeptides as immunogenic and/or antigenic epitopes as described elsewhere herein.

In preferred embodiments, the following CAN-12 active site domain conservative amino acid substitutions are encompassed by the present invention: wherein R90 is substituted with either a K, or H; wherein L91 is substituted with either an A, I, or V; wherein D92 is substituted with an E; wherein L93 is substituted with either an A, I, or V; wherein C94 is a C; wherein Q95 is substituted with a N; wherein G96 is substituted with either an A, M, S, or T; wherein I97 is substituted with either an A, V, or L; wherein V98 is substituted with either an A, I, or L; wherein G99 is substituted with either an A, M, S, or T; wherein D100is substituted with an E; wherein C101 is a C; wherein W102 is either an F, or Y; wherein F103 is substituted with either a W, or Y; wherein L104 is substituted with either an A, I, or V; wherein A105 is substituted with either a G, I, L, M, S, T, or V; wherein A106 is substituted with either a G, I, L, M, S, T, or V; wherein L107 is substituted with either an A, I, or V; wherein Q108 is substituted with a N; wherein A109 is substituted with either a G, I, L, M, S, T, or V; wherein L110 is substituted with either an A, I, or V; wherein A111 is substituted with either a G, I, L, M, S, T, or V; wherein L112 is substituted with either an A, I, or V; wherein H113 is substituted with either a K, or R; wherein Q114 is substituted with a N; wherein D115 is substituted with an E; wherein I116 is substituted with either an A, V, or L; wherein L117 is substituted with either an A, I, or V; wherein S118 is substituted with either an A, G, M, or T; wherein R119 is substituted with either a K, or H; wherein V120 is substituted with either an A, I, or L; wherein V121 is substituted with either an A, I, or L; wherein P122 is a P; wherein L123 is substituted with either an A, I, or V; wherein N124 is substituted with a Q; wherein Q125 is substituted with a N; wherein S126 is substituted with either an A, G, M, or T; wherein F127 is substituted with either a W, or Y; wherein T128 is substituted with either an A, G, M, or S; wherein E129 is substituted with a D; wherein K130 is substituted with either a R, or H; wherein Y131 is either an F, or W; wherein A132 is substituted with either a G, I, L, M, S, T, or V; wherein G133 is substituted with either an A, M, S, or T; wherein I134 is substituted with either an A, V, or L; wherein F135 is substituted with either a W, or Y; wherein R136 is substituted with either a K, or H; wherein F137 is substituted with either a W, or Y; wherein W138 is either an F, or Y; wherein F139 is substituted with either a W, or Y; wherein W140 is either an F, or Y; wherein H141 is substituted with either a K, or R; wherein Y142 is either an F, or W; wherein G143 is substituted with either an A, M, S, or T; wherein N144 is substituted with a Q; wherein W145 is either an F, or Y; wherein V146 is substituted with either an A, I, or L; wherein P147 is a P; wherein V148 is substituted with either an A, I, or L; wherein V149 is substituted with either an A, I, or L; wherein 1150 is substituted with either an A, V, or L; wherein D151 is substituted with an E; wherein D152 is substituted with an E; wherein R153 is substituted with either a K, or H; wherein L154 is substituted with either an A, I, or V; wherein P155 is a P; wherein V156 is substituted with either an A, I, or L; wherein N157 is substituted with a Q; wherein E158 is substituted with a D; wherein A159 is substituted with either a G, I, L, M, S, T, or V; wherein G160 is substituted with either an A, M, S, or T; wherein Q161 is substituted with a N; wherein L162 is substituted with either an A, I, or V; wherein V163 is substituted with either an A, I, or L; wherein F164 is substituted with either a W, or Y; wherein V165 is substituted with either an A, I, or L; wherein S166 is substituted with either an A, G, M, or T; wherein S167 is substituted with either an A, G, M, or T; wherein T168 is substituted with either an A, G, M, or S; wherein Y169 is either an F, or W; wherein K170 is substituted with either a R, or H; wherein N171 is substituted with a Q; wherein L172 is substituted with either an A, I, or V; wherein F173 is substituted with either a W, or Y; wherein W174 is either an F, or Y; wherein G175 is substituted with either an A, M, S, or T; wherein A176 is substituted with either a G, I, L, M, S, T, or V; wherein L177 is substituted with either an A, I, or V; wherein L178 is substituted with either an A, I, or V; wherein E179 is substituted with a D; wherein K180 is substituted with either a R, or H; wherein A181 is substituted with either a G, I, L, M, S, T, or V; wherein Y182 is either an F, or W; wherein A183 is substituted with either a G, I, L, M, S, T, or V; wherein K184 is substituted with either a R, or H; wherein L185 is substituted with either an A, I, or V; wherein S186 is substituted with either an A, G, M, or T; wherein G187 is substituted with either an A, M, S, or T; wherein S188 is substituted with either an A, G, M, or T; wherein Y189 is either an F, or W; wherein E190 is substituted with a D; wherein D191 is substituted with an E; wherein L192 is substituted with either an A, I, or V; wherein Q193 is substituted with a N; wherein S194 is substituted with either an A, G, M, or T; wherein G195 is substituted with either an A, M, S, or T; wherein Q196 is substituted with a N; wherein V197 is substituted with either an A, I, or L; wherein S198 is substituted with either an A, G, M, or T; wherein E199 is substituted with a D; wherein A200 is substituted with either a G, I, L, M, S, T, or V; wherein L201 is substituted with either an A, I, or V; wherein V202 is substituted with either an A, I, or L; wherein D203 is substituted with an E; wherein F204 is substituted with either a W, or Y; wherein T205 is substituted with either an A, G, M, or S; wherein G206 is substituted with either an A, M, S, or T; wherein G207 is substituted with either an A, M, S, or T; wherein V208 is substituted with either an A, I, or L; wherein T209 is substituted with either an A, G, M, or S; wherein M210 is substituted with either an A, G, S, or T; wherein T211 is substituted with either an A, G, M, or S; wherein I212 is substituted with either an A, V, or L; wherein N213 is substituted with a Q; wherein L214 is substituted with either an A, I, or V; wherein A215 is substituted with either a G, I, L, M, S, T, or V; wherein E216 is substituted with a D; wherein A217 is substituted with either a G, I, L, M, S, T, or V; wherein H218 is substituted with either a K, or R; wherein G219 is substituted with either an A, M, S, or T; wherein N220 is substituted with a Q; wherein L221 is substituted with either an A, I, or V; wherein W222 is either an F, or Y; wherein D223 is substituted with an E; wherein I224 is substituted with either an A, V, or L; wherein L225 is substituted with either an A, I, or V; wherein I226 is substituted with either an A, V, or L; wherein E227 is substituted with a D; wherein A228 is substituted with either a G, I, L, M, S, T, or V; wherein T229 is substituted with either an A, G, M, or S; wherein Y230 is either an F, or W; wherein N231 is substituted with a Q; wherein R232 is substituted with either a K, or H; wherein T233 is substituted with either an A, G, M, or S; wherein L234 is substituted with either an A, I, or V; wherein I235 is substituted with either an A, V, or L; wherein G236 is substituted with either an A, M, S, or T; wherein C237 is a C; wherein Q238 is substituted with a N; wherein T239 is substituted with either an A, G, M, or S; wherein H240 is substituted with either a K, or R; wherein S241 is substituted with either an A, G, M, or T; wherein G242 is substituted with either an A, M, S, or T; wherein K243 is substituted with either a R, or H; wherein I244 is substituted with either an A, V, or L; wherein L245 is substituted with either an A, I, or V; wherein E246 is substituted with a D; wherein N247 is substituted with a Q; wherein G248 is substituted with either an A, M, S, or T; wherein L249 is substituted with either an A, I, or V; wherein V250 is substituted with either an A, I, or L; wherein E251 is substituted with a D; wherein G252 is substituted with either an A, M, S, or T; wherein H253 is substituted with either a K, or R; wherein A254 is substituted with either a G, I, L, M, S, T, or V; wherein Y255 is either an F, or W; wherein T256 is substituted with either an A, G, M, or S; wherein L257 is substituted with either an A, I, or V; wherein T258 is substituted with either an A, G, M, or S; wherein G259 is substituted with either an A, M, S, or T; wherein I260 is substituted with either an A, V, or L; wherein R261 is substituted with either a K, or H; wherein K262 is substituted with either a R, or H; wherein V263 is substituted with either an A, I, or L; wherein T264 is substituted with either an A, G, M, or S; wherein C265 is a C; wherein K266 is substituted with either a R, or H; wherein H267 is substituted with either a K, or R; wherein R268 is substituted with either a K, or H; wherein P269 is a P; wherein E270 is substituted with a D; wherein Y271 is either an F, or W; wherein L272 is substituted with either an A, I, or V; wherein V273 is substituted with either an A, I, or L; wherein K274 is substituted with either a R, or H; wherein L275 is substituted with either an A, I, or V; wherein R276 is substituted with either a K, or H; wherein N277 is substituted with a Q; wherein P278 is a P; wherein W279 is either an F, or Y; wherein G280 is substituted with either an A, M, S, or T; wherein K281 is substituted with either a R, or H; wherein V282 is substituted with either an A, I, or L; wherein E283 is substituted with a D; wherein W284 is either an F, or Y; wherein K285 is substituted with either a R, or H; wherein G286 is substituted with either an A, M, S, or T; wherein D287 is substituted with an E; wherein W288 is either an F, or Y; wherein S289 is substituted with either an A, G, M, or T; wherein D290 is substituted with an E; wherein S291 is substituted with either an A, G, M, or T; wherein S292 is substituted with either an A, G, M, or T; wherein S293 is substituted with either an A, G, M, or T; wherein K294 is substituted with either a R, or H; wherein W295 is either an F, or Y; wherein E296 is substituted with a D; wherein L297 is substituted with either an A, I, or V; wherein L298 is substituted with either an A, I, or V; wherein S299 is substituted with either an A, G, M, or T; wherein P300 is a P; wherein K301 is substituted with either a R, or H; wherein E302 is substituted with a D; wherein K303 is substituted with either a R, or H; wherein I304 is substituted with either an A, V, or L; wherein L305 is substituted with either an A, I, or V; wherein L306 is substituted with either an A, I, or V; wherein L307 is substituted with either an A, I, or V; wherein R308 is substituted with either a K, or H; wherein K309 is substituted with either a R, or H; wherein D310 is substituted with an E; wherein N311 is substituted with a Q; wherein D312 is substituted with an E; wherein G313 is substituted with either an A, M, S, or T; wherein E314 is substituted with a D; wherein F315 is substituted with either a W, or Y; wherein W316 is either an F, or Y; wherein M317 is substituted with either an A, G, S, or T; wherein T318 is substituted with either an A, G, M, or S; wherein L319 is substituted with either an A, I, or V; wherein Q320 is substituted with a N; wherein D321 is substituted with an E; wherein F322 is substituted with either a W, or Y; wherein K323 is substituted with either a R, or H; wherein T324 is substituted with either an A, G, M, or S; wherein H325 is substituted with either a K, or R; wherein F326 is substituted with either a W, or Y; wherein V327 is substituted with either an A, I, or L; wherein L328 is substituted with either an A, I, or V; wherein L329 is substituted with either an A, I, or V; and/or wherein V330 is substituted with either an A, I, or L of SEQ ID NO:2 or SEQ ID NO:24 in addition to any combination thereof. Other suitable substitutions within the CAN-12 active site domain are encompassed by the present invention and are referenced elsewhere herein. The present invention also encompasses the use of these CAN-12 active site domain conservative amino acid substituted polypeptides as immunogenic and/or antigenic epitopes as described elsewhere herein.

For purposes of the present invention, by "at least a portion of" is meant all or any part of the CAN-12 active site domain defined by the structure coordinates according to Table IV (e.g., fragments thereof). More preferred are molecules comprising all or any parts of the CAN-12 active site domain, according to Table IV, or a mutant or homologue of said molecule or molecular complex. By mutant or homologue of the molecule it is meant a molecule that has a root mean square deviation from the backbone atoms of said CAN-12 amino acids of not more than 4.5 Angstroms, and preferably not more than 3.5 Angstroms.

The term "root mean square deviation" means the square root of the arithmetic mean of the squares of the deviations from the mean. It is a term that expresses the deviation or variation from a trend or object. For the purposes of the present invention, the "root mean square deviation" defines the variation in the backbone of a protein from the relevant portion of the backbone of the AR portion of the complex as defined by the structure coordinates described herein.

A preferred embodiment is a machine-readable data storage medium that is capable of displaying a graphical three-dimensional representation of a molecule or molecular complex that is defined by the structure coordinates of all of the amino acids in Table IV +/− a root mean square deviation from the backbone atoms of those amino acids of not more than 4.0 ANG, preferably 3.0 ANG.

The structure coordinates of a CAN-12 homology model, including portions thereof, is stored in a machine-readable storage medium. Such data may be used for a variety of purposes, such as drug discovery.

Accordingly, in one embodiment of this invention is provided a machine-readable data storage medium comprising a data storage material encoded with the structure coordinates set forth in Table IV.

One embodiment utilizes System 10 as disclosed in WO 98/11134, the disclosure of which is incorporated herein by reference in its entirety. Briefly, one version of these embodiments comprises a computer comprising a central processing unit ("CPU"), a working memory which may be, e.g, RAM (random-access memory) or "core" memory, mass storage memory (such as one or more disk drives or CD-ROM drives), one or more cathode-ray tube ("CRT") display terminals, one or more keyboards, one or more input lines, and one or more output lines, all of which are interconnected by a conventional bidirectional system bus.

Input hardware, coupled to the computer by input lines, may be implemented in a variety of ways. Machine-readable data of this invention may be inputted via the use of a modem or modems connected by a telephone line or dedicated data line. Alternatively or additionally, the input hardware may comprise CD-ROM drives or disk drives. In conjunction with a display terminal, keyboard may also be used as an input device.

Output hardware, coupled to the computer by output lines, may similarly be implemented by conventional devices. By way of example, output hardware may include a CRT display terminal for displaying a graphical representation of a region or domain of the present invention using a program such as QUANTA as described herein. Output hardware might also include a printer, so that hard copy output may be produced, or a disk drive, to store system output for later use.

In operation, the CPU coordinates the use of the various input and output devices, coordinates data accesses from mass storage, and accesses to and from the working memory, and determines the sequence of data processing steps. A number of programs may be used to process the machine-readable data of this invention. Such programs are discussed in reference to the computational methods of drug discovery as described herein. Specific references to components of the hardware system are included as appropriate throughout the following description of the data storage medium.

For the purpose of the present invention, any magnetic data storage medium which can be encoded with machine-readable data would be sufficient for carrying out the storage requirements of the system. The medium could be a conventional floppy diskette or hard disk, having a suitable substrate, which may be conventional, and a suitable coating, which may be conventional, on one or both sides, containing magnetic domains whose polarity or orientation could be altered magnetically, for example. The medium may also have an opening for receiving the spindle of a disk drive or other data storage device.

The magnetic domains of the coating of a medium may be polarized or oriented so as to encode in a manner which may be conventional, machine readable data such as that described herein, for execution by a system such as the system described herein.

Another example of a suitable storage medium which could also be encoded with such machine-readable data, or set of instructions, which could be carried out by a system such as the system described herein, could be an optically-readable data storage medium. The medium could be a conventional compact disk read only memory (CD-ROM) or a rewritable medium such as a magneto-optical disk which is optically readable and magneto-optically writable. The medium preferably has a suitable substrate, which may be conventional, and a suitable coating, which may be conventional, usually of one side of substrate.

In the case of a CD-ROM, as is well known, the coating is reflective and is impressed with a plurality of pits to encode the machine-readable data. The arrangement of pits is read by reflecting laser light off the surface of the coating. A protective coating, which preferably is substantially transparent, is provided on top of the reflective coating.

In the case of a magneto-optical disk, as is well known, the coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

Thus, in accordance with the present invention, data capable of displaying the three dimensional structure of the CAN-12 homology model, or portions thereof and their structurally similar homologues is stored in a machine-readable storage medium, which is capable of displaying a graphical three-dimensional representation of the structure. Such data may be used for a variety of purposes, such as drug discovery.

For the first time, the present invention permits the use of structure-based or rational drug design techniques to design, select, and synthesize chemical entities that are capable of modulating the biological function of CAN-12.

Accordingly, the present invention is also directed to the design of small molecules which imitates the structure of the CAN-12 active site domain (SEQ ID NO:46), or a portion thereof, in accordance with the structure coordinates provided in Table IV. Alternatively, the present invention is directed to the design of small molecules which may bind to at least part of the CAN-12 active site domain (SEQ ID NO:25), or some portion thereof. For purposes of this invention, by CAN-12 active site domain, it is also meant to include mutants or homologues thereof. In a preferred embodiment, the mutants or homologues have at least 25% identity, more preferably 50% identity, more preferably 75% identity, and most preferably 90% identity to SEQ ID NO:46. In this context, the term "small molecule" may be construed to mean any molecule described known in the art or described elsewhere herein, though may include, for example, peptides, chemicals, carbohydrates, nucleic acids, PNAs, and any derivatives thereof.

The three-dimensional model structure of the CAN-12 will also provide methods for identifying modulators of biological function. Various methods or combination thereof can be used to identify these compounds.

For example, test compounds can be modeled that fit spatially into the active site domain in CAN-12 embodied by the sequence from about R90 to about amino acid C94, from about amino acid G99 to about amino acid L104, from about amino acid Q196 to about amino acid S198, from about amino acid M210 to about amino acid I212, from about amino acid G236 to about amino acid H240, from about amino acid E251 to about amino acid Y255, from about amino acid N277 to about amino acid K281, from about amino acid V327 to about amino acid V330, or some portion thereof, of SEQ ID NO:2 or SEQ ID NO:24 (corresponding to SEQ ID NO:46), in accordance with the structural coordinates of Table IV.

Structure coordinates of the active site domain in CAN-12 defined by the amino acids from about R90 to about amino acid C94, from about amino acid G99 to about amino acid L104, from about amino acid Q196 to about amino acid S198, from about amino acid M210 to about amino acid I212, from about amino acid G236 to about amino acid H240, from about amino acid E251 to about amino acid Y255, from about amino acid N277 to about amino acid K281, from about amino acid V327 to about amino acid V330 of SEQ ID NO:2 or SEQ ID NO:24, can also be used to identify structural and chemical features. Identified structural or chemical features can then be employed to design or select compounds as potential CAN-12 modulators. By structural and chemical features it is meant to include, but is not limited to, van der Waals interactions, hydrogen bonding interactions, charge interaction, hydrophobic bonding interaction, and dipole interaction. Alternatively, or in conjunction with, the three-dimensional structural model can be employed to design or select compounds as potential CAN-12 modulators. Compounds identified as potential CAN-12 modulators can then be synthesized and screened in an assay characterized by binding of a test compound to the CAN-12, or in characterizing the ability of CAN-12 to modulate a protease target in the presence of a small molecule. Examples of assays useful in screening of potential CAN-12 modulators include, but are not limited to, screening in silico, in vitro assays and high throughput assays. Finally, these methods may also involve modifying or replacing one or more amino acids at amino acid positions, C101, H253, and/or N277 of SEQ ID NO:2 or SEQ ID NO:24 in accordance with the structure coordinates of Table IV.

However, as will be understood by those of skill in the art upon this disclosure, other structure based design methods can be used. Various computational structure based design methods have been disclosed in the art.

For example, a number computer modeling systems are available in which the sequence of the CAN-12 and the CAN-12 structure (i.e., atomic coordinates of CAN-12 and/or the atomic coordinates of the active site domain as provided in Table IV) can be input. This computer system then generates the structural details of one or more these regions in which a potential CAN-12 modulator binds so that complementary structural details of the potential modulators can be determined. Design in these modeling systems is generally based upon the compound being capable of physically and structurally associating with CAN-12. In addition, the compound must be able to assume a conformation that allows it to associate with CAN-12. Some modeling systems estimate the potential inhibitory or binding effect of a potential CAN-12 modulator prior to actual synthesis and testing.

Methods for screening chemical entities or fragments for their ability to associate with a given protein target are also well known. Often these methods begin by visual inspection of the binding site on the computer screen. Selected fragments or chemical entities are then positioned in the active site domain of CAN-12. Docking is accomplished using software such as INSIGHTII, QUANTA and SYBYL, following by energy minimization and molecular dynamics with standard molecular mechanic forcefields such as CHARMM and AMBER. Examples of computer programs which assist in the selection of chemical fragment or chemical entities useful in the present invention include, but are not limited to, GRID (Goodford, 1985), AUTODOCK (Goodsell, 1990), and DOCK (Kuntz et al. 1982).

Upon selection of preferred chemical entities or fragments, their relationship to each other and CAN-12 can be visualized and then assembled into a single potential modulator. Programs useful in assembling the individual chemical entities include, but are not limited to CAVEAT (Bartlett et al. 1989) and 3D Database systems (Martin1992).

Alternatively, compounds may be designed de novo using either an empty active site or optionally including some portion of a known inhibitor. Methods of this type of design include, but are not limited to LUDI (Bohm 1992) and LeapFrog (Tripos Associates, St. Louis Mo.).

In addition, CAN-12 is overall well suited to modern methods including combinatorial chemistry.

Programs such as DOCK (Kuntz et al. 1982) can be used with the atomic coordinates from the homology model to identify potential ligands from databases or virtual databases which potentially bind CAN-12 active site domain, and which may therefore be suitable candidates for synthesis and testing.

Additionally, the three-dimensional homology model of CAN-12 will aid in the design of mutants with altered biological activity.

The following are encompassed by the present invention: a machine-readable data storage medium, comprising a data storage material encoded with machine readable data, wherein the data is defined by the structure coordinates of the model CAN-12 according to Table IV or a homologue of said model, wherein said homologue comprises backbone atoms that have a root mean square deviation from the backbone atoms of the complex of not more than 4.5 Å, preferably not more than 4.0 Å, most preferably not more than 3.5 Å, and even more preferably not more than 3.0 Å; and a machine-readable data storage medium, wherein said molecule is defined by the set of structure coordinates of the model for CAN-12 according to Table IV, or a homologue of said molecule, said homologue having a root mean square deviation from the backbone atoms of said amino acids of not more than 4.5 Å, preferably not more than 4.0 Å, most preferably not more than 3.5 Å, and even more preferably not more than 3.0 Å; a model comprising all or any part of the model defined by structure coordinates of CAN-12 according to Table IV, or a mutant or homologue of said molecule or molecular complex.

In a further embodiment, the following are encompassed by the present invention: a method for identifying a mutant of CAN-12 with altered biological properties, function, or reactivity, the method comprising any combination of steps of: use of the model or a homologue of said model according to Table IV, for the design of protein mutants with altered biological function or properties which exhibit any combination of therapeutic effects provided elsewhere herein; and use of the model or a homologue of said model, for the design of a protein with mutations in the active site domain comprised of the amino acids from about R90 to about amino acid C94, from about amino acid G99 to about amino acid L104, from about amino acid Q196 to about amino acid S198, from about amino acid M210 to about amino acid I212, from about amino acid G236 to about amino acid H240, from about amino acid E251 to about amino acid Y255, from about amino acid N277 to about amino acid K281, from about amino acid V327 to about amino acid V330 of SEQ ID NO:2 or SEQ ID NO:24 according to Table IV with altered biological function or properties which exhibit any combination of therapeutic effects provided elsewhere herein.

In further preferred embodiments, the following are encompassed by the present invention: a method for identifying modulators of CAN-12 biological properties, function, or reactivity, the method comprising any combination of steps of: modeling test compounds that overlay spatially into the active site domain defined by all or any portion of residues from about R90 to about amino acid C94, from about amino acid G99 to about amino acid L104, from about amino acid Q196 to about amino acid S198, from about amino acid M210 to about amino acid I212, from about amino acid G236 to about amino acid H240, from about amino acid E251 to about amino acid Y255, from about amino acid N277 to about amino acid K281, from about amino acid V327 to about amino acid V330 of SEQ ID NO:2 or SEQ ID NO:24 and of the three-dimensional structural model according to Table IV, or using a homologue or portion thereof.

The present invention encompasses using the structure coordinates as set forth herein to identify structural and chemical features of the CAN-12 polypeptide; employing identified structural or chemical features to design or select compounds as potential CAN-12 modulators; employing the three-dimensional structural model to design or select compounds as potential CAN-12 modulators; synthesizing the potential CAN-12 modulators; screening the potential CAN-12 modulators in an assay characterized by binding of a protein to the CAN-12; selecting the potential CAN-12 modulator from a database; designing the CAN-12 modulator de novo; and/or designing said CAN-12 modulator from a known modulator activity.

Many polynucleotide sequences, such as EST sequences, are publicly available and accessible through sequence databases. Some of these sequences are related to SEQ ID NO: 1 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 4570 of SEQ ID NO:1, b is an integer between 15 to 4584, where both a and b correspond to the positions of nucleotide residues shown in SEQ ID NO:1, and where b is greater than or equal to a+14.

In one embodiment, a CAN12 polypeptide comprises a portion of the amino sequence depicted in FIGS. 1A–E. In another embodiment, a CAN12 polypeptide comprises at least 4, 5, 6, 7, 8, 9, 10, 11, 12, 13, 14, 15, 16, 17, 18, 19 or 20 amino acids of the amino sequence depicted in FIGS. 1A–E. In further embodiments, the CAN12 polypeptide does not consist of the sequence ALLEKAYAKL (SEQ ID NO:141), and/or ALLEKAYAKLSGSYE. (SEQ ID NO:142).

Features of the Polypeptide Encoded by Gene No:2

The polypeptide of this gene provided as SEQ ID NO:54 (FIGS. 8A–C), encoded by the polynucleotide sequence according to SEQ ID NO:53 (FIGS. 8A–C), and/or encoded by the polynucleotide contained within the deposited clone, CAN-12v1, has significant homology at the nucleotide and amino acid level to a number of calpains, which include, for example, the human CAN10 protein (type II diabetes linked) (hCAN10; Genbank Accession No: gi|NP_075574; SEQ ID NO:3); the human CAN5 protein (hCAN5; Genbank Accession No: gi|NP_004046; SEQ ID NO:4); the large catalytic subunit of the human CALPAIN 1 protein (also referred to as Calcium-Activated Neutral Proteinase, CANP, μ-TYPE) (hCAN1; Genbank Accession No: gi|12408656; SEQ ID NO:5); the large subunit of the human calpain 3 protein (EC 3.4.22.17) (also referred to as CALPAIN L3, CALPAIN P94, Calcium-Activated Neutral Proteinase 3, CANP 3; muscle-specific calcium-activated neutral protease 3 large subunit) (hCAN3; Genbank Accession No: gi|4557405; SEQ ID NO:6); the large catalytic subunit of the mouse CALPAIN 1 protein (also referred to as Calcium-Activated Neutral Proteinase) (CANP) μ-TYPE) (mCALPAIN1; Genbank Accession No: gi|O88666; SEQ ID NO:7); the mouse CALPAIN LP82 (mLP82; Genbank Accession No: gi|3661585; SEQ ID NO:8); the rat stomach-specific calcium-activated neutral protease large subunit, NCL2 protein (rNCL2; Genbank Accession No: gi|NP_006606; SEQ ID NO:9); the human CAN11 protein (hCAN11; Genbank Accession No: gi|NP_008989; SEQ ID NO:10); the human CAN2 protein (hCAN2; Genbank Accession No: gi|4502563; SEQ ID NO:11); and the human CAN9 protein (hCAN9; Genbank Accession No: gi|5729758; SEQ ID NO:12). An alignment of the CAN-12v1 polypeptide with these proteins is provided in FIGS. 2A–E. Based upon such strong conservation, the inventors have ascribed the CAN-12v1 polypeptide as having proteolytic activity, preferably calpain activity.

The CAN-12v1 polypeptide was determined to have 28.7% identity and 35.6% similarity with the human CAN10 protein (type II diabetes linked) (hCAN10; Genbank Accession No: gi|NP_075574; SEQ ID NO:3); to have 33.3% identity and 45.1% similarity with the human CAN5 protein (hCAN5; Genbank Accession No: gi|NP_004046; SEQ ID NO:4); to have 38.3% identity and 46.8% similarity with the large catalytic subunit of the human CALPAIN 1 protein (also referred to as Calcium-Activated Neutral Proteinase, CANP, μ-TYPE) (hCAN1; Genbank Accession No: gi|12408656; SEQ ID NO:5); to have 40.4% identity and 49.1% similarity with the large subunit of the human calpain 3 protein (EC 3.4.22.17) (also referred to as CALPAIN L3, CALPAIN P94, Calcium-Activated Neutral Proteinase 3, CANP 3; muscle-specific calcium-activated neutral protease 3 large subunit) (hCAN3; Genbank Accession No: gi|4557405; SEQ ID NO:6); to have 39.8% identity and 47.8% similarity with the large catalytic subunit of the mouse CALPAIN 1 protein (also referred to as Calcium-Activated Neutral Proteinase) (CANP) μ-TYPE ) (mCALPAIN1; Genbank Accession No: gilO88666; SEQ ID NO:7); to have 40.6% identity and 48.8% similarity with the mouse CALPAIN LP82 (mLP82; Genbank Accession No: gil3661585; SEQ ID NO:8); to have 36.3% identity and 44.9% similarity with the rat stomach-specific calcium-activated neutral protease large subunit, NCL2 protein (rNCL2; Genbank Accession No: gilNP_006606; SEQ ID NO:9); to have 38.8% identity and 47.4% similarity with the human CAN11 protein (hCAN11; Genbank Accession No: gilNP_008989; SEQ ID NO:10); to have 37.9% identity and 47.6% similarity with the human CAN2 protein (hCAN2; Genbank Accession No: gil4502563; SEQ ID NO:11); and to have 40.7% identity and 49.8% similarity with the human CAN9 protein (hCAN9; Genbank Accession No: gil5729758; SEQ ID NO:12).

The human CAN10 protein (type II diabetes linked) (hCAN10; Genbank Accession No: gilNP_075574; SEQ ID NO:3)is a human calpain gene that encodes a large calpain subunit. CAN10 is an atypical calpain in that it lacks the calmodulin-like calcium-binding domain and instead has a divergent C-terminal domain. CAN10 is similar in organization to calpains 5 and 6 and is associated with type 2 or non-insulin-dependent diabetes mellitus (NIDDM) and located within the NIDDM1 chromosomal region (Nat. Genet. 26 (2), 163–175 (2000)).

The large subunit of the human calpain 3 protein (EC 3.4.22.17) (also referred to as CALPAIN L3, CALPAIN P94, Calcium-Activated Neutral Proteinase 3, CANP 3; muscle-specific calcium-activated neutral protease 3 large subunit) (hCAN3; Genbank Accession No: gil4557405; SEQ ID NO:6) is a muscle-specific member of the calpain large subunit family. Loss of CAPN3 function has been associated with limb-girdle muscular dystrophies type 2A (Cell 81 (1), 27–40 (1995)).

The human CAN9 protein (hCAN9; Genbank Accession No: gil5729758; SEQ ID NO:12) is a calpain that is expressed predominantly in stomach and small intestine and is thought to have specialized functions in the digestive tract, and be associated with gastric cancer.(Biol. Chem. 379 (2), 175–183 (1998); and Jpn. J. Cancer Res. 91 (5), 459–463 (2000)).

As described above, the CAN-12v1 polypeptide was found to have significant sequence homology with calpains, particularly members of the m-calpain family. A conserved peptide signature of Qx3(G,E)xC(Y,W)x2(S,T,A,G,C)(S,T,A,G,C,V) Qx{3}(G)xC(W)x{2}(A)(A) (referred to as a thiol (cysteine) protease active site domain) common to most calpain family members is found in the protein sequence of CAN-12v1 from amino acid 90 to amino acid 111 of SEQ ID NO:54 (FIGS. 1A–C). Protein threading and molecular modeling of CAN-12v1 suggests that CAN-12v1 has a structural fold similar to representative m-calpains. Moreover, the structural and threading alignments of the present invention suggest that amino acids 101 ("C"), 254 ("H"), and 278 ("N") of SEQ ID NO:54 (FIGS. 8A–C) may represent the catalytic amino acids within the active site domain. Thus, based upon the sequence and structural homology to known calpains, particularly the presence of the thiol cysteine protease active site domain, the novel CAN-12v1 is believed to represent a novel human calpain.

In confirmation of the strong homology to known calpains, the CAN-12v1 polypeptide was determined to have several conserved catalytic amino acids at amino acid C101, H254, and N278 of SEQ ID NO:54 (FIGS. 8A–C). As discussed more particularly herein, calpains are a group of structurally diverse, high molecular weight (400 to 500 amino acids) proteins that have a catalytic cysteine amino acid and one or more calcium binding domains. Despite the structural heterogeneity, calpains share some well defined structural-functional characteristics, particularly in their active site domains.

In preferred embodiments, the CAN-12v1 polypeptide of the present invention is directed to a polypeptide having structural similarity to calpains.

Based upon the strong homology to members of the calpain family, the CAN-12v1 polypeptide is expected to share at least some biological activity with calpains, preferably with m-calpain family members, and more preferable to the large subunits of m-calpain family members, in addition to other calpains and calpain subunits referenced herein and/or otherwise known in the art.

Expression profiling designed to measure the steady state mRNA levels encoding the CAN-12 polypeptide showed predominately high expression levels in spinal cord tissue; significantly high expression in lymph node and thymus, and to a lesser extent, in spleen tissue (See FIG. 4).

Expanded analysis of CAN-12 expression levels by TAQ-MAN™ quantitative PCR (see FIG. 6) confirmed that the CAN-12 polypeptide is expressed in the lymph gland. However, the TAQMAN™ quantitative PCR determined that the CAN-12 polypeptide is primarily expressed in the esophagus. In fact, with the exception of the lymph gland, the steady state mRNA level of CAN-12 was approximately 2700 times higher in the esophagus than in all other tissues tested. These data suggest modulators of the CAN-12 polynucleotides and polypeptides may be useful for the treatment, detection, andior amelioration of the following, non-limiting diseases and disorders associated with the esophagus: dysphagia, cricoharyngeal incoordination, esophageal carcinoma, esophageal webs, achalasia, symptomatic diffuse esophageal spasm, gastroesophageal reflux, and/or corrosive esophagitis.

The polynucleotides encoding the CAN-12 polypeptide of the present invention were used to determine the chromosomal localization of the calpain12 gene, which encodes the CAN-12, CAN-12v1, and CAN-12v2 polypeptides of the present invention. Polynucleotides corresponding to CAN-12 (SEQ ID NO:1) were shown to localize to chromosome 2, specifically 2p16-p21. The comparison of the chromosomal location of the calpain 12 gene with the location of chromosomal regions which have been shown to be associated with specific diseases or conditions, e.g. by linkage analysis, can be indicative of diseases in which calpain12 may play a role. Interestingly, a whole-genome linkage scan in multiple sclerosis families (Ebers et al. A full genome search in multiple sclerosis. Nature Genet. 13: 472–476, 1996.) identified 5 susceptibility loci on chromosomes 2, 3, 5, 11, and X. In particular, an association was identified with marker D2S119 on chromosome 2 and MS. The localization of the D2S119 marker was further delineated to 2p16-p21based on a radiation hybrid linkage map retrieved from an online query at an NCBI web site. Since the map of calpain 12 and the susceptibility marker D2S119 overlaps, it is reasonable to postulate that calpain 12 may contribute to MS. Furthermore, the transcription profile of calpain12 indicated a prominent expression in spinal cord, and implication of calpains in MS has been suggested (Shields DC et al. A putative mechanism of demyelination in multiple sclerosis by a proteolytic enzyme, calpain. Proc Natl Acad Sci U S A. 96:11486–91.1999).

The CAN-12v1 polynucleotides and polypeptides of the present invention, including agonists and/or fragments thereof, have uses that include modulating cellular adhesion events, cellular proliferation, and inflammation, in various cells, tissues, and organisms, and particularly in mammalian spinal cord tissue, lymph node, thymus, and spleen tissue, preferably human tissue. CAN-12v1 polynucleotides and polypeptides of the present invention, including agonists and/or fragments thereof, may be useful in diagnosing, treating, prognosing, and/or preventing neural, immune, hematopoietic, and/or proliferative diseases or disorders.

The strong homology to human calpains, particularly m-calpains, combined with the predominate localized expression in esophagus tissue suggests the CAN-12v1 polynucleotides and polypeptides may be useful in treating, diagnosing, prognosing, and/or preventing gastrointestinal diseases, particularly esophageal diseases and/or disorders which include the following non-limiting examples: aberrant transport of food bolus from the mouth to the stomach, aberrant prevention of retrograde flow of gastrointestinal contents, aberrant esophageal peristaltic contractions, pyrosis, painful swallowing, reflux esophagitis, esophageal motility disorders, esophageal spasms, diffuse esophageal spasm, atypical chest pain, regurgitation, oropharyngeal paralysis, nasal regurgitation, dysphagia, cricopharyngeal bar, globus pharyngeus, achalasia, motor disorders of the esophageal smooth muscle, scleroderma esophagus, gastroesophageal reflux disease (GERD), esophagitis, Barrett's esophagus, viral esophagitis, Herpes simplex virus mediated viral esophagitis, Varicella-zoster virus mediated viral esophagitis, Cytomegalovirus mediated viral esophagitis, bacterial esophagitis, *Lactobacillus* mediated bacterial esophagitis, *Candida* mediated esophagitis, radiation esophagitis, corrosive esophagitis, pill-induced esophagitis, esophagitis associated with mucocutaneous and systemic diseases, diverticula, lower esophageal mucosal ring, lower esophageal muscular ring, hiatal hernia, paraesophageal hernia, esophageal rupture, and/or Mallory-Weiss Syndrome.

Although calpains are typically associated primarily with neurogenerative conditions, their association in gastrointenstinal tissues has precedence. For example, the human CAN9 protein (hCAN9; Genbank Accession No: gil5729758; SEQ ID NO:12) is predominately expressed in the stomach and small intestine and is thought to be associated with gastric cancers.

The strong homology to human calpains, particularly m-calpains, combined with the localized expression in spinal cord tissue suggests the CAN-12v1 polynucleotides and polypeptides may be useful in treating, diagnosing, prognosing, and/or preventing neural diseases, neurodegenerative disease states, behavioral disorders, or inflammatory conditions. Representative uses are described in the "Neurological Diseases", "Regeneration" and "Hyperproliferative Disorders" sections below, in the Examples, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Alternatively, the strong homology to human calpains, particularly m-calpains, combined with the localized expression in lymph node, thymus, and spleen tissue suggests the CAN-12v1 polynucleotides and polypeptides may be useful in treating, diagnosing, prognosing, ameliorating, and/or preventing immune diseases and/or disorders. Representative uses are described in the "Immune Activity" and "Infectious Disease" sections below, and elsewhere herein. Briefly, the strong expression in immune tissue indicates a role in regulating the proliferation; survival; differentiation; and/or activation of hematopoietic cell lineages, including blood stem cells. The CAN-12v1 polypeptide may also be useful as a preventative agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product may be useful in the expansion of stem cells and committed progenitors of various blood lineages, and in the differentiation and/or proliferation of various cell types.

Moreover, the protein would be useful in the detection, treatment, and/or prevention of a variety of vascular disorders and conditions, which include, but are not limited to miscrovascular disease, vascular leak syndrome, aneurysm, stroke, embolism, thrombosis, coronary artery disease, arteriosclerosis, and/or atherosclerosis. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

In addition, antagonists of the CAN-12v1 polynucleotides and polypeptides may have uses that include diagnosing, treating, prognosing, and/or preventing diseases or disorders related to hyper calpain activity, which may include immune and/or proliferative diseases or disorders, particularly thrombosis, embolism, and other blood disorders. Therapeutic and/or pharmaceutical compositions comprising the CAN-12v1 polypeptides may be formulated to comprise heparin.

In addition, antagonists of the CAN-12v1 polynucleotides and polypeptides may have uses that include diagnosing, treating, ameliorating, prognosing, and/or preventing diseases or disorders related to hyper calpain activity, which may include neuronal excitotoxicity, ischemic stroke, hemoragic stroke, hypoxic stress, trauma, cell destruction, spinal cord injury following trauma, degeneration of vulnerable hippocampal neurons after ischemia, reovirus-induced apoptosis, viral-induced induced myocarditis, acute and chronic inflammation, cataract formation, multiple sclerosis, demylenating disorders, acoustic trauma, hearing loss caused by noise, neuronal damage, cardiac ischemic damage, and/or hepatocyte necrosis during and following anoxia.

CAN-12v1 polynucleotides and polypeptides, including fragments and/or antagonsists thereof, may have uses which include modulating development, differentiation, cellular transformation in response to cell signaling, cell-cell and/or cell-extracellular matrix interactions, clustering of the integrin receptor aIIb3, modulating in long term potentiation (memory), modulating neurite outgrowth, modulating cortical lamination activation of protein kinases and phosphatases, remodeling and disassembling the cytoskeleton, cell cycle modulation, in addition, to ameliorating, preventing, and/or treating limb-girdle muscular dystrophy (LGMD), insulin resistance in diabetics, Alzheimer's disease, Multiple sclerosis, Huntington's disease, Parkinson's disease and amyotrophy.

Moreover, CAN-12v1 polynucleotides and polypeptides, including fragments and agonists thereof, may have uses which include treating, diagnosing, prognosing, and/or preventing hyperproliferative disorders, particularly of the neural and immune systems. Such disorders may include, for example, cancers, and metastatic conditions.

CAN-12v1 polynucleotides and polypeptides, including fragments and/or antagonsists thereof, may have uses which include identification of modulators of CAN-12v1 function including antibodies (for detection or neutralization), naturally-occurring modulators and small molecule modulators. Antibodies to domains (including CAN-12v1 epitopes provided herein) of the CAN-12v1 protein could be used as diagnostic agents of inflammatory conditions in patients, are useful in monitoring the activation and presence of cognate proteases, and can be used as a biomarker for the protease involvement in disease states and in the evaluation of inhibitors of the cognate protease in vivo.

CAN-12v1 polypeptides and polynucleotides are useful for diagnosing diseases related to over or under expression of CAN-12v1 proteins by identifying mutations in the CAN-12v1 gene using CAN-12v1 probes, or determining CAN-12v1 protein or mRNA expression levels. CAN-12v1 polypeptides are also useful for screening for compounds, which affect activity of the protein. Diseases that can be treated with CAN-12v1 include, the following, non-limiting examples: neuro-regeneration, neuropathic pain, obesity, anorexia, HIV infections, cancers, bulimia, asthma, Parkinson's disease, acute heart failure, hypotension, hypertension, osteoporosis, angina pectoris, myocardial infarction, psychotic, immune, metabolic, cardiovascular, and neurological disorders.

The predominate expression in neural tissues, combined with the significant expression in a number of other tissues, suggests the CAN-12v1 polynucleotide and polypeptide of the present invention may be involved in modulating nerve invasion, innervation, nerve maintenance, and potentially myeline sheath maintenance and integrity.

The CAN-12v1 polynucleotides and polypeptides, including fragments and antagonists thereof, may have uses which include detecting, diagnosing, treating, ameliorating, and/or preventing diseases and disorders of the neural system, particularly Alzheimer's disease, either directly or indirectly, in addition to other neural disorders known in the art or provided in the "Neurological Diseases" section herein, such as modulating nerve invasion, innervation, nerve maintenance, potentially myelin sheath maintenance and integrity, encephalomyelitis, autoimmune encephalomyelitis, human T cell leukemia virus type I (HTLV-I)-associated myelopathy/tropical spastic paraparesis (HAM/TSP), and neuro-inflammatory diseases.

Molecular genetic manipulation of the structure of the active site domain, particularly the predicted catalytic amino acids, and of other functional domains in the calpain family (e.g., active site domain binding pocket) enables the production of calpains with tailor-made activities. Thus, the CAN-12v1 polypeptides, and fragments thereof, as well as any homologous product resulting from genetic manipulation of the structure, are useful for NMR-based design of modulators of CAN-12v1 biological activity, and calpains, in general.

CAN-12v1 polypeptides and polynucleotides have additional uses which include diagnosing diseases related to the over and/or under expression of CAN-12v1 by identifying mutations in the CAN-12v1 gene by using CAN-12v1 sequences as probes or by determining CAN-12v1 protein or mRNA expression levels. CAN-12v1 polypeptides may be useful for screening compounds that affect the activity of the protein. CAN-12v1 peptides can also be used for the generation of specific antibodies and as bait in yeast two hybrid screens to find proteins the specifically interact with CAN-12v1 (described elsewhere herein).

The CAN-12v1 polynucleotides and polypeptides, including fragments and agonists thereof, may have uses which include detecting, diagnosing, treating, ameliorating, and/or preventing metabolic diseases and disorders, such as diabetes. Moreover, expressed human CAN-12v1 may be useful in the detection of patients susceptible to diabetes. Also paradigms that would simulate intracellular CAN-12v1 activity would be useful in treating diabetes.

The CAN-12v1 polynucleotides and polypeptides, including fragments thereof, may have uses which include identifying inhibitors of intracellular calpain inhibitors (calpastatins) leading to an effective increase in calpain activity.

Various approaches to detect alterations or allelic variants at the genomic or mRNA level of CAN-12v1, could be used as a diagnostic for identifying MS patients, or individuals susceptible to have MS. It is likely that the CAN-12v1 gene comprises polymorphic sites (i.e. SNPs), with specific alleles which may be associated with MS or other neurodegenerative disorders, or associated with an increased likelihood of developing these diseases. Therefore, the invention provides the CAN-12v1 sequence that can be used to design specific primers for the identification of polymorphisms or mutations in CAN-12v1 of patients affected with MS. The presence of a specific allele variant, such as a SNP allele or SNPs haplotype that renders the subject carrying it more susceptible to develop MS or other related diseases could be identified (e.g. a variant in the CAN-12v1 promoter region that increased transcript levels of CAN-12v1, or mutations in the coding sequence that increased the stability or half-life of the CAN-12v1 protein). Other methods such as Northern-blot analysis could be performed to measure transcript levels using a CAN-12v1 cDNA probe derived from the sequence of the invention.

Although it is believed the encoded polypeptide may share at least some biological activities with human calpains (particularly m-calpains), a number of methods of determining the exact biological function of this clone are either known in the art or are described elsewhere herein. Briefly, the function of this clone may be determined by applying microarray methodology. Nucleic acids corresponding to the CAN-12v1 polynucleotides, in addition to, other clones of the present invention, may be arrayed on microchips for expression profiling. Depending on which polynucleotide probe is used to hybridize to the slides, a change in expression of a specific gene may provide additional insight into the function of this gene based upon the conditions being studied. For example, an observed increase or decrease in expression levels when the polynucleotide probe used comes from diseased neural tissue, as compared to, normal tissue might indicate a function in modulating neural function, for example. In the case of CAN-12v1, spinal cord, lymph node, thymus, and/or spleen tissue should be used to extract RNA to prepare the probe.

In addition, the function of the protein may be assessed by applying quantitative PCR methodology, for example. Real time quantitative PCR would provide the capability of following the expression of the CAN-12v1 gene throughout development, for example. Quantitative PCR methodology requires only a nominal amount of tissue from each developmentally important step is needed to perform such experiments. Therefore, the application of quantitative PCR methodology to refining the biological function of this polypeptide is encompassed by the present invention. In the case of CAN-12v1, a disease correlation related to CAN-12v1 may be made by comparing the mRNA expression level of CAN-12v1 in normal tissue, as compared to diseased tissue (particularly diseased tissue isolated from the following: esophagus, spinal cord, lymph node, thymus, and/or spleen tissue). Significantly higher or lower levels of CAN-12v1 expression in the diseased tissue may suggest CAN-12v1 plays a role in disease progression, and antagonists against CAN-12v1 polypeptides would be useful therapeutically in treating, preventing, and/or ameliorating the disease. Alternatively, significantly higher or lower levels of CAN-12v1 expression in the diseased tissue may suggest CAN-12v1 plays a defensive role against disease progression, and agonists of CAN-12v1 polypeptides may be useful therapeutically in treating, preventing, and/or ameliorating the disease. Also encompassed by the present invention are quantitative PCR probes corresponding to the polynucleotide sequence provided as SEQ ID NO:53 (FIGS. 8A–C).

The function of the protein may also be assessed through complementation assays in yeast. For example, in the case of the CAN-12v1, transforming yeast deficient in calpain activity, particularly m-calpain activity, and assessing their ability to grow would provide convincing evidence the CAN-12v1 polypeptide has calpain activity, and possibly m-calpain activity. Additional assay conditions and methods that may be used in assessing the function of the polynucleotides and polypeptides of the present invention are known in the art, some of which are disclosed elsewhere herein.

Alternatively, the biological function of the encoded polypeptide may be determined by disrupting a homologue of this polypeptide in Mice and/or rats and observing the resulting phenotype. Such knock-out experiments are known in the art, some of which are disclosed elsewhere herein.

Moreover, the biological function of this polypeptide may be determined by the application of antisense and/or sense methodology and the resulting generation of transgenic mice and/or rats. Expressing a particular gene in either sense or antisense orientation in a transgenic mouse or rat could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., an esophagus, spinal cord, lymph node, thymus, or spleen specific promoter), or it can be expressed at a specified time of development using an inducible and/or a developmentally regulated promoter.

In the case of CAN-12v1 transgenic mice or rats, if no phenotype is apparent in normal growth conditions, observing the organism under diseased conditions (neural, immune, hematopoietic diseases or disorders, cancers, etc.) may lead to understanding the function of the gene. Therefore, the application of antisense and/or sense methodology to the creation of transgenic mice or rats to refine the biological function of the polypeptide is encompassed by the present invention.

In preferred embodiments, the following N-terminal CAN-12v1 deletion polypeptides are encompassed by the present invention: M1-L694, S2-L694, L3-L694, W4-L694, P5-L694, P6-L694, F7-L694, R8-L694, C9-L694, R10-L694, W11-L694, K12-L694, L13-L694, A14-L694, P15-L694, R16-L694, Y17-L694, S18-L694, R19-L694, R20-L694, A21-L694, S22-L694, P23-L694, Q24-L694, Q25-L694, P26-L694, Q27-L694, Q28-L694, D29-L694, F30-L694, E31-L694, A32-L694, L33-L694, L34-L694, A35-L694, E36-L694, C37-L694, L38-L694, R39-L694, N40-L694, G41-L694, C42-L694, L43-L694, F44-L694, E45-L694, D46-L694, T47-L694, S48-L694, F49-L694, P50-L694, A51-L694, T52-L694, L53-L694, S54-L694, S55-L694, I56-L694, G57-L694, S58-L694, G59-L694, S60-L694, L61-L694, L62-L694, Q63-L694, K64-L694, L65-L694, P66-L694, P67-L694, R68-L694, L69-L694, Q70-L694, W71-L694, K72-L694, R73-L694, P74-L694, P75-L694, E76-L694, L77-L694, H78-L694, S79-L694, N80-L694, P81-L694, Q82-L694, F83-L694, Y84-L694, F85-L694, A86-L694, K87-L694, A88-L694, K89-L694, R90-L694, L91-L694, D92-L694, L93-L694, C94-L694, Q95-L694, G96-L694, I97-L694, V98-L694, G99-L694, D100-L694, C101-L694, W102-L694, F103-L694, L104-L694, A105-L694, A106-L694, L107-L694, Q108-L694, A109-L694, L110-L694, A111-L694, L112-L694, H113-L694, Q114-L694, D115-L694, I116-L694, L117-L694, S118-L694, R119-L694, V120-L694, V121-L694, P122-L694, L123-L694, N124-L694, Q125-L694, S126-L694, F127-L694, T128-L694, E129-L694, K130-L694, Y131-L694, A132-L694, G133-L694, I134-L694, F135-L694, R136-L694, F137-L694, W138-L694, F139-L694, W140-L694, H141-L694, Y142-L694, G143-L694, N144-L694, W145-L694, V146-L694, P147-L694, V148-L694, V149-L694, I150-L694, D151-L694, D152-L694, R153-L694, L154-L694, P155-L694, V156-L694, N157-L694, E158-L694, A159-L694, G160-L694, Q161-L694, L162-L694, V163-L694, F164-L694, V165-L694, S166-L694, S167-L694, T168-L694, Y169-L694, K170-L694, N171-L694, L172-L694, F173-L694, W174-L694, G175-L694, A176-L694, L177-L694, L178-L694, E179-L694, K180-L694, A181-L694, Y182-L694, A183-L694, K184-L694, L185-L694, S186-L694, G187-L694, S188-L694, Y189-L694, E190-L694, D191-L694, L192-L694, Q193-L694, S194-L694, G195-L694, Q196-L694, V197-L694, S198-L694, E199-L694, A200-L694, L201-L694, V202-L694, D203-L694, F204-L694, T205-L694, G206-L694, G207-L694, V208-L694, T209-L694, M210-L694, T211-L694, I212-L694, N213-L694, L214-L694, A215-L694, E216-L694, A217-L694, H218-L694, G219-L694, N220-L694, L221-L694, W222-L694, D223-L694, I224-L694, L225-L694, I226-L694, E227-L694, A228-L694, T229-L694, Y230-L694, N231-L694, R232-L694, T233-L694, L234-L694, I235-L694, G236-L694, C237-L694, Q238-L694, T239-L694, H240-L694, S241-L694, G242-L694, E243-L694, K244-L694, I245-L694, L246-L694, E247-L694, N248-L694, G249-L694, L250-L694, V251-L694, E252-L694, G253-L694, H254-L694, A255-L694, Y256-L694, T257-L694, L258-L694, T259-L694, G260-L694, I261-L694, R262-L694, K263-L694, V264-L694, T265-L694, C266-L694, K267-L694, H268-L694, R269-L694, P270-L694, E271-L694, Y272-L694, L273-L694, V274-L694, K275-L694, L276-L694, R277-L694, N278-L694, P279-L694, W280-L694, G281-L694, K282-L694, V283-L694, E284-L694, W285-L694, K286-L694, G287-L694, D288-L694, W289-L694, S290-L694, D291-L694, S292-L694, S293-L694, S294-L694, K295-L694, W296-L694, E297-L694, L298-L694, L299-L694, S300-L694, P301-L694, K302-L694, E303-L694, K304-L694, I305-L694, L306-L694, L307-L694, L308-L694, R309-L694, K310-L694, D311-L694, N312-L694, D313-L694, G314-L694, E315-L694, F316-L694, W317-L694, M318-L694, T319-L694, L320-L694, Q321-L694, D322-L694, F323-L694, K324-L694, T325-L694, H326-L694, F327-L694, V328-L694, L329-L694, L330-L694, V331-L694, I332-L694, C333-L694, K334-L694, L335-L694, T336-L694, P337-L694, G338-L694, L339-L694, L340-L694, S341-L694, Q342-L694, E343-L694, A344-L694, A345-L694, Q346-L694, K347-L694, W348-L694, T349-L694, Y350-L694, T351-L694, M352-L694, R353-L694, E354-L694, G355-L694, R356-L694, W357-L694, E358-L694, K359-L694, R360-L694, S361-L694, T362-L694, A363-L694, G364-L694, G365-L694, Q366-L694, R367-L694, Q368-L694, L369-L694, L370-L694, Q371-L694, D372-L694, T373-L694, F374-L694, W375-L694, K376-L694, N377-L694, P378-L694, Q379-L694, F380-L694, L381-L694, L382-L694, S383-L694, V384-L694, W385-L694, R386-L694, P387-L694, E388-L694, E389-L694, G390-L694, R391-L694, R392-L694, S393-L694, L394-L694, R395-L694, P396-L694, C397-L694, S398-L694, V399-L694, L400-L694, V401-L694, S402-L694, L403-L694, L404-L694, Q405-L694, K406-L694, P407-L694, R408-L694, H409-L694, R410-L694, C411-L694, R412-L694, K413-L694, R414-L694, K415-L694, P416-L694, L417-L694, L418-L694, A419-L694, I420-L694, G421-L694, F422-L694, Y423-L694, L424-L694, Y425-L694, R426-L694, Y427-L694, H428-L694, D429-L694, D430-L694, Q431-L694, R432-L694, R433-L694, L434-L694, P435-L694, P436-L694, E437-L694, F438-L694, F439-L694, Q440-L694, R441-L694, N442-L694, T443-L694, P444-L694, L445-L694, S446-L694, Q447-L694, P448-L694, D449-L694, R450-L694, F451-L694, L452-L694, K453-L694, E454-L694, K455-L694, E456-L694, V457-L694, S458-L694, Q459-L694, E460-L694, L461-L694, C462-L694, L463-L694, E464-L694, P465-L694, G466-L694, T467-L694, Y468-L694, L469-L694, I470-L694, V471-L694, P472-L694, C473-L694, I474-L694, L475-L694, E476-L694, A477-L694, H478-L694, Q479-L694, K480-L694, S481-L694, E482-L694, F483-L694, V484-L694, L485-L694, R486-L694, V487-L694, F488-L694, S489-L694, R490-L694, K491-L694, H492-L694, I493-L694, F494-L694, Y495-L694, E496-L694, I497-L694, G498-L694, S499-L694, N500-L694, S501-L694, G502-L694, V503-L694, V504-L694, F505-L694, S506-L694, K507-L694, E508-L694, I509-L694, E510-L694, D511-L694, Q512-L694, N513-L694, E514-L694, R515-L694, Q516-L694, D517-L694, E518-L694, F519-L694, F520-L694, T521-L694, K522-L694, F523-L694, F524-L694, E525-L694, K526-L694, H527-L694, P528-L694, E529-L694, I530-L694, N531-L694, A532-L694, V533-L694, Q534-L694, L535-L694, Q536-L694, N537-L694, L538-L694, L539-L694, N540-L694, Q541-L694, and/or M542-L694 of SEQ ID NO:54. Polynucleotide sequences encoding these polypeptides are also provided. The present invention also encompasses the use of these N-terminal CAN -12v1 deletion polypeptides as immunogenic and/or antigenic epitopes as described elsewhere herein.

In preferred embodiments, the following C-terminal CAN-12v1 deletion polypeptides are encompassed by the present invention: M1-L694, M1-L693, M1-T692, M1-T691, M1-N690, M1-F689, M1-I688, M1-L687, M1-Y686, M1-S685, M1-T684, M1-S683, M1-H682, M1-A681, M1-V680, M1-G679, M1-G678, M1-D677, M1-I676, M1-N675, M1-A674, M1-L673, M1-I672, M1-V671, M1-P670, M1-V669, M1-I668, M1-M667, M1-F666, M1-F665, M1-T664, M1-P663, M1-T662, M1-S661, M1-Q660, M1-L659, M1-D658, M1-V657, M1-D656, M1-K655, M1-L654, M1-T653, M1-V652, M1-S651, M1-R650, M1-I649, M1-L648, M1-T647, M1-V646, M1-E645, M1-A644, M1-H643, M1-W642, M1-V641, M1-D640, M1-G639, M1-R638, M1-R637, M1-Q636, M1-R635, M1-I634, M1-L633, M1-T632, M1-C631, M1-G630, M1-A629, M1-R628, M1-T627, M1-H626, M1-G625, M1-C624, M1-S623, M1-W622, M1-S621, M1-K620, M1-R619, M1-H618, M1-R617, M1-G616, M1-A615, M1-E614, M1-R613, M1-M612, M1-A611, M1-A610, M1-H609, M1-L608, M1-Q607, M1-E606, M1-W605, M1-N604, M1-L603, M1-Y602, M1-G601, M1-S600, M1-G599, M1-R598, M1-D597, M1-Q596, M1-K595, M1-H594, M1-F593, M1-V592, M1-K591, M1-Q590, M1-S589, M1-L588, M1-K587, M1-L586, M1-Q585, M1-K584, M1-W583, M1-L582, M1-D581, M1-R580, M1-F579, M1-E578, M1-Q577, M1-I576, M1-S575, M1-M574, M1-T573, M1-G572, M1-S571, M1-A570, M1-N569, M1-L568, M1-D567, M1-L566, M1-L565, M1-A564, M1-L563, M1-I562, M1-G561, M1-Q560, M1-C559, M1-A558, M1-E557, M1-L556, M1-S555, M1-F554, M1-F553, M1-P552, M1-Q551, M1-R550, M1-S549, M1-G548, M1-L547, M1-S546, M1-S545, M1-W544, M1-T543, M1-M542, M1-Q541, M1-N540, M1-L539, M1-L538, M1-N537, M1-Q536, M1-L535, M1-Q534, M1-V533, M1-A532, M1-N531, M1-I530, M1-E529, M1-P528, M1-H527, M1-K526, M1-E525, M1-F524, M1-F523, M1-K522, M1-T521, M1-F520, M1-F519, M1-E518, M1-D517, M1-Q516, M1-R515, M1-E514, M1-N513, M1-Q512, M1-D511, M1-E510, M1-I509, M1-E508, M1-K507, M1-S506, M1-F505, M1-V504, M1-V503, M1-G502, M1-S501, M1-N500, M1-S499, M1-G498, M1-I497, M1-E496, M1-Y495, M1-F494, M1-I493, M1-H492, M1-K491, M1-R490, M1-S489, M1-F488, M1-V487, M1-R486, M1-L485, M1-V484, M1-F483, M1-E482, M1-S481, M1-K480, M1-Q479, M1-H478, M1-A477, M1-E476, M1-L475, M1-I474, M1-C473, M1-P472, M1-V471, M1-I470, M1-L469, M1-Y468, M1-T467, M1-G466, M1-P465, M1-E464, M1-L463, M1-C462, M1-L461, M1-E460, M1-Q459, M1-S458, M1-V457, M1-E456, M1-K455, M1-E454, M1-K453, M1-L452, M1-F451, M1-R450, M1-D449, M1-P448, M1-Q447, M1-S446, M1-L445, M1-P444, M1-T443, M1-N442, M1-R441, M1-Q440, M1-F439, M1-F438, M1-E437, M1-P436, M1-P435, M1-L434, M1-R433, M1-R432, M1-Q431, M1-D430, M1-D429, M1-H428, M1-Y427, M1-R426, M1-Y425, M1-L424, M1-Y423, M1-F422, M1-G421, M1-I420, M1-A419, M1-L418, M1-L417, M1-P416, M1-K415, M1-R414, M1-K413, M1-R412, M1-C411, M1-R410, M1-H409, M1-R408, M1-P407, M1-K406, M1-Q405, M1-L404, M1-L403, M1-S402, M1-V401, M1-L400, M1-V399, M1-S398, M1-C397, M1-P396, M1-R395, M1-L394, M1-S393, M1-R392, M1-R391, M1-G390, M1-E389, M1-E388, M1-P387, M1-R386, M1-W385, M1-V384, M1-S383, M1-L382, M1-L381, M1-F380, M1-Q379, M1-P378, M1-N377, M1-K376, M1-W375, M1-F374, M1-T373, M1-D372, M1-Q371, M1-L370, M1-L369, M1-Q368, M1-R367, M1-Q366, M1-G365, M1-G364, M1-A363, M1-T362, M1-S361, M1-R360, M1-K359, M1-E358, M1-W357, M1-R356, M1-G355, M1-E354; M1-R353, M1-M352, M1-T351, M1-Y350, M1-T349, M1-W348, M1-K347, M1-Q346, M1-A345, M1-A344, M1-E343, M1-Q342, M1-S341, M1-L340, M1-L339, M1-G338, M1-P337, M1-T336, M1-L335, M1-K334, M1-C333, M1-I332, M1-V331, M1-L330, M1-L329, M1-V328, M1-F327, M1-H326, M1-T325, M1-K324, M1-F323, M1-D322, M1-Q321, M1-L320, M1-T319, M1-M318, M1-W317, M1-F316, M1-E315, M1-G314, M1-D313, M1-N312, M1-D311, M1-K310, M1-R309, M1-L308, M1-L307, M1-L306, M1-I305, M1-K304, M1-E303, M1-K302, M1-P301, M1-S300, M1-L299, M1-L298, M1-E297, M1-W296, M1-K295, M1-S294, M1-S293, M1-S292, M1-D291, M1-S290, M1-W289, M1-D288, M1-G287, M1-K286, M1-W285, M1-E284, M1-V283, M1-K282, M1-G281, M1-W280, M1-P279, M1-N278, M1-R277, M1-L276, M1-K275, M1-V274, M1-L273, M1-Y272, M1-E271, M1-P270, M1-R269, M1-H268, M1-K267, M1-C266, M1-T265, M1-V264, M1-K263, M1-R262, M1-I261, M1-G260, M1-T259, M1-L258, M1-T257, M1-Y256, M1-A255, M1-H254, M1-G253, M1-E252, M1-V251, M1-L250, M1-G249, M1-N248, M1-E247, M1-L246, M1-I245, M1-K244, and/or M1-E243 of SEQ ID NO:54. Polynucleotide sequences encoding these polypeptides are also provided. The present invention also encompasses the use of these C-terminal CAN-12v1 deletion polypeptides as immunogenic and/or antigenic epitopes as described elsewhere herein.

Alternatively, preferred polypeptides of the present invention may comprise polypeptide sequences corresponding to, for example, internal regions of the CAN-12v1 polypeptide (e.g., any combination of both N- and C-terminal CAN-12v1 polypeptide deletions) of SEQ ID NO:54. For example, internal regions could be defined by the equation: amino acid NX to amino acid CX, wherein NX refers to any N-terminal deletion polypeptide amino acid of CAN-12v1 (SEQ ID NO:54), and where CX refers to any C-terminal deletion polypeptide amino acid of CAN-12v1 (SEQ ID NO:54). Polynucleotides encoding these polypeptides are also provided. The present invention also encompasses the use of these polypeptides as an immunogenic and/or antigenic epitope as described elsewhere herein.

The present invention also encompasses immunogenic and/or antigenic epitopes of the CAN-12v1 polypeptide.

The CAN-12v1 polypeptides of the present invention were determined to comprise several phosphorylation sites based upon the Motif algorithm (Genetics Computer Group, Inc.). The phosphorylation of such sites may regulate some biological activity of the CAN-12v1 polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the CAN-12v1 polypeptide to associate with other polypeptides, particularly the serine protease substrate for CAN-12v1, or its ability to modulate serine protease function.

The CAN-12v1 polypeptide was predicted to comprise eleven PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177–184(1986), and Kishimoto A., Nishiyama K., Nakanishi H., Uratsuji Y., Nomura H., Takeyama Y., Nishizuka Y., J. Biol. Chem. . . . 260:12492–12499(1985); which are hereby incorporated by reference herein.

In preferred embodiments, the following PKC phosphorylation site polypeptides are encompassed by the present invention: LAPRYSRRASPQQ (SEQ ID NO:58), LNQSFTEKYAGIF (SEQ ID NO:59), VFVSSTYKNLFWG (SEQ ID NO:60), GIRKVTCKHRPEY (SEQ ID NO:61), DWSDSSSKWELLS (SEQ ID NO:62), KWELLSPKEKILL (SEQ ID NO:63), QKWTYTMREGRWE (SEQ ID NO:64), EEGRRSLRPCSVL (SEQ ID NO:65), VLRVFSRKHIFYE (SEQ ID NO:66), KQLKLSQKVFHKQ (SEQ ID NO:67), and/or LIRSVTLKDVDLQ (SEQ ID NO:68). Polynucleotides encoding these polypeptides are also provided. The present invention also encompasses the use of the CAN-12v1 PKC phosphorylation site polypeptides as immunogenic and/or antigenic epitopes as described elsewhere herein.

The CAN-12v1 polypeptide has been shown to comprise four glycosylation site according to the Motif algorithm (Genetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

In preferred embodiments, the following asparagine glycosylation site polypeptide is encompassed by the present invention: RVVPLNQSFTEKYA (SEQ ID NO:69), IEATYNRTLIGCQT (SEQ ID NO:70), ALLDLNASGTMSIQ (SEQ ID NO:71), and/or SYLIFNTTLL (SEQ ID NO:72). Polynucleotides encoding this polypeptide are also provided. The present invention also encompasses the use of the CAN-12v1 asparagine glycosylation site polypeptides as immunogenic and/or antigenic epitopes as described elsewhere herein.

The CAN-12v2 polypeptide has been shown to comprise one amidation site according to the Motif algorithm (Genetics Computer Group, Inc.). The precursor of hormones and other active peptides which are C-terminally amidated is always directly followed by a glycine residue which provides the amide group, and most often by at least two consecutive basic residues (Arg or Lys) which generally function as an active peptide precursor cleavage site. Although all amino acids can be amidated, neutral hydrophobic residues such as Val or Phe are good substrates, while charged residues such as Asp or Arg are much less reactive. A consensus pattern for amidation sites isthe following: x-G-[RK]-[RK] (SEQ ID NO:146), wherein "X" represents the amidation site. Additional information relating to asparagine glycosylation may be found in reference to the following publications, which are hereby incorporated by reference herein: Kreil G., Meth. Enzymol. 106:218–223(1984); and Bradbury A. F., Smyth D. G., Biosci. Rep. 7:907–916(1987).

In preferred embodiments, the following amidation site polypeptide is encompassed by the present invention: VWRPEEGRRSLRPC (SEQ ID NO:73). Polynucleotides encoding these polypeptides are also provided. The present invention also encompasses the use of this CAN-12v1 amidation site polypeptide as an immunogenic and/or antigenic epitope as described elsewhere herein.

The CAN-12v1 polypeptide has been shown to comprise one RGD cell attachment site domain according to the Motif algorithm (Genetics Computer Group, Inc.). The sequence Arg-Gly-Asp, found in fibronectin, is crucial for its interaction with its cell surface receptor, an integrin. What has been called the 'RGD' tripeptide is also found in the sequences of a number of other proteins, where it has been shown to play a role in cell adhesion. Non-limiting examples of these proteins are the following: some forms of collagens, fibrinogen, vitronectin, von Willebrand factor (VWF), snake disintegrins, and slime mold discoidins. The 'RGD' tripeptide is also found in other proteins where it may serve the same purpose. A consensus pattern for RGD cell attachment sites is the following: R-G-D. Additional information relating to RGD cell attachment site domains may be found in reference to the following publications, which are hereby incorporated by reference herein: Ruoslahti E., Pierschbacher M. D., Cell 44:517–518(1986); and d'Souza S. E., Ginsberg M. H., Plow E. F., Trends Biochem. Sci. 16:246–250(1991).

In preferred embodiments, the following RGD cell attachment site domain polypeptide is encompassed by the present invention: LIRQRRGDVWHAE (SEQ ID NO:74). Polynucleotides encoding these polypeptides are also provided. The present invention also encompasses the use of this RGD cell attachment site domain polypeptide as an immunogenic and/or antigenic epitope as described elsewhere herein.

In confirmation of the CAN-12v1 polypeptide being a calpain, it has been shown to comprise one EF-hand calcium-binding domain according to the Motif algorithm (Genetics Computer Group, Inc.). Many calcium-binding proteins belong to the same evolutionary family and share a type of calcium-binding domain known as the EF-hand. This type of domain consists of a twelve residue loop flanked on both side by a twelve residue alpha-helical domain. In an EF-hand loop the calcium ion is coordinated in a pentagonal bipyramidal configuration. The six residues involved in the binding are in positions 1, 3, 5, 7, 9 and 12; these residues are denoted by X, Y, Z, -Y, -X and -Z. The invariant Glu or Asp at position 12 provides two oxygens for liganding Ca (bidentate ligand). Several representative proteins containing EF-hand regions are provided below: For each type of protein, the total number of EF-hand regions known or supposed to exist are provided in parenthesis: Aequorin and Renilla luciferin binding protein (LBP) (Ca=3); Alpha actinin (Ca=2); Calbindin (Ca=4); Calcineurin B subunit (protein phosphatase 2B regulatory subunit) (Ca=4); Calcium-binding protein from Streptomyces erythraeus (Ca=3?); Calcium-binding protein from Schistosoma mansoni (Ca=2?); Calcium-binding proteins TCBP-23 and TCBP-25 from Tetrahymena thermophila (Ca=4?); Calcium-dependent protein kinases (CDPK) from plants (Ca=4); Calcium vector protein from amphoxius (Ca=2); Calcyphosin (thyroid protein p24) (Ca=4?); Calmodulin (Ca=4, except in yeast where Ca=3); Calpain small and large chains (Ca=2); Calretinin (Ca=6); Calcyclin (prolactin receptor associated protein) (Ca=2); Caltractin (centrin) (Ca=2 or 4); Cell Division Control protein 31 (gene CDC31) from yeast (Ca=2?); Diacylglycerol kinase (EC 2.7.1.107) (DGK) (Ca=2); FAD-dependent glycerol-3-phosphate dehydrogenase (EC 1.1.99.5) from mammals (Ca=1); Fimbrin (plastin) (Ca=2); Flagellar calcium-binding protein (1f8) from Trypanosoma cruzi (Ca=1 or 2); Guanylate cyclase activating protein (GCAP) (Ca=3); Inositol phospholipid-specific phospholipase C isozymes gamma-1 and delta-1 (Ca=2) [10]; Intestinal calcium-binding protein (ICaBPs) (Ca=2); MIF related proteins 8 (MRP-8 or CFAG) and 14 (MRP-14) (Ca=2); Myosin regulatory light chains (Ca=1); Oncomodulin (Ca=2); Osteonectin (basement membrane protein BM-40) (SPARC) and proteins that contains an 'osteonectin' domain (QR1, matrix glycoprotein SCI) (Ca=1); Parvalbumins alpha and beta (Ca=2); Placental calcium-binding protein (18a2) (nerve growth factor induced protein 42a) (p9k) (Ca=2); Recoverins (visinin, hippocalcin, neurocalcin, S-modulin) (Ca=2 to 3); Reticulocalbin (Ca=4); S-100 protein, alpha and beta chains (Ca=2); Sarcoplasmic calcium-binding protein (SCPs) (Ca=2 to 3); Sea urchin proteins Spec 1 (Ca=4), Spec 2 (Ca=4?), Lps-1 (Ca=8); Serine/threonine protein phosphatase rdgc (EC 3.1.3.16) from Drosophila (Ca=2); Sorcin V19 from hamster (Ca=2); Spectrin alpha chain (Ca=2); Squidulin (optic lobe calcium-binding protein) from squid (Ca=4); and Troponins C; from skeletal muscle (Ca=4), from cardiac muscle (Ca=3), from arthropods and molluscs (Ca=2).

A consensus pattern for EF hand calcium binding domains is the following:

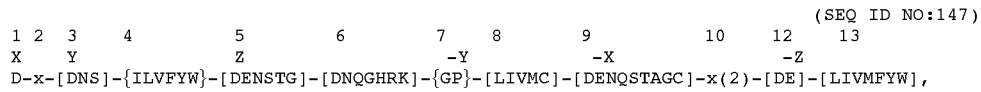

(SEQ ID NO:147)

```
1 2 3   4       5       6         7 8     9         10   12   13
X   Y           Z                 -Y      -X             -Z
D-x-[DNS]-{ILVFYW}-[DENSTG]-[DNQGHRK]-{GP}-[LIVMC]-[DENQSTAGC]-x(2)-[DE]-[LIVMFYW],
``` wherein X, Y, Z, -Y, -X, and -Z are as defined above, and wherein "x" represents any amino acid. Amino acid residues within the consensus at positions 1 (X), 3 (Y) and 12 (-Z) are the most conserved. The 6th residue in an EF-hand loop is in most cases a Gly.

Additional information relating to RGD cell attachment site domains may be found in reference to the following publications, which are hereby incorporated by reference herein: Kawasaki H., Kretsinger R. H., Protein Prof. 2:305–490(1995); Kretsinger R. H., Cold Spring Harbor Symp. Quant. Biol. 52:499–510(1987); Moncrief N. D., Kretsinger R. H., Goodman M., J. Mol. Evol. 30:522–562 (1990); Nakayama S., Moncrief N. D., Kretsinger R. H., J. Mol. Evol. 34:416–448(1992); Heizmann C. W., Hunziker W., Trends Biochem. Sci. 16:98–103(1991); Kligman D., Hilt D. C., Trends Biochem. Sci. 13:437–443(1988); Strynadka N. C. J., James M. N. G., Annu. Rev. Biochem. 58:951–98(1989); Haiech J., Sallantin J., Biochimie 67:555–560(1985); Chauvaux S., Beguin P., Aubert J.-P., Bhat K. M., Gow L. A., Wood T. M., Bairoch A., Biochem. J. 265:261–265(1990); Bairoch A., Cox J. A., FEBS Lett. 269:454–456(1990).

In preferred embodiments, the following EF-hand calcium binding domain polypeptide is encompassed by the present invention: ILALLDLNASGTMSIQEFRDLWK (SEQ ID NO:75). Polynucleotides encoding these polypeptides are also provided. The present invention also encompasses the use of this EF-hand calcium binding domain polypeptide as an immunogenic and/or antigenic epitope as described elsewhere herein.

In further confirmation of the CAN-12v1 polypeptide being a calpain, it has been shown to comprise one eukaryotic thiol (cysteine) protease active site domain according to the Motif algorithm (Genetics Computer Group, Inc.). Eukaryotic thiol proteases (EC 3.4.22.-) are a family of proteolytic enzymes which contain an active site cysteine. Catalysis proceeds through a thioester intermediate and is facilitated by a nearby histidine side chain; an asparagine completes the essential catalytic triad. Non-limiting examples of proteases which are known to belong to this family are provided below: Vertebrate lysosomal cathepsins B (EC 3.4.22.1), H (EC 3.4.22.16), L (EC 3.4.22.15), and S (EC 3.4.22.27); Vertebrate lysosomal dipeptidyl peptidase I (EC 3.4.14.1) (also known as cathepsin C); Vertebrate calpains (EC 3.4.22.17) (Calpains are intracellular calcium-activated thiol protease that contain both a N-terminal catalytic domain and a C-terminal calcium-binding domain; Mammalian cathepsin K, which seems involved in osteoclastic bone resorption; Human cathepsin O; Bleomycin hydrolase (An enzyme that catalyzes the inactivation of the antitumor drug BLM (a glycopeptide); Plant enzymes: barley aleurain (EC 3.4.22.16), EP-B1/B4; kidney bean EP-C1, rice bean SH-EP; kiwi fruit actinidin (EC 3.4.22.14); papaya latex papain (EC 3.4.22.2), chymopapain (EC 3.4.22.6), caricain (EC 3.4.22.30), and proteinase IV (EC 3.4.22.25); pea turgor-responsive protein 15A; pineapple stem bromelain (EC 3.4.22.32); rape COT44; rice oryzain alpha, beta, and gamma; tomato low-temperature induced, *Arabidopsis thaliana* A494, RD19A and RD21A; House-dust mites allergens DerP1 and EurM1; Cathepsin B-like proteinases from the worms *Caenorhabditis elegans* (genes gcp-1, cpr-3, cpr-4, cpr-5 and cpr-6), *Schistosoma mansoni* (antigen SM31) and *Japonica* (antigen SJ31), *Haemonchus contortus* (genes AC-1 and AC-2), and *Ostertagia ostertagi* (CP-1 and CP-3); Slime mold cysteine proteinases CP1 and CP2; Cruzipain from *Trypanosoma cruzi* and *brucei*; Throphozoite cysteine proteinase (TCP) from various *Plasmodium* species; Proteases from *Leishmania mexicana*, *Theileria annulata* and *Theileria parva*; Baculoviruses cathepsin-like enzyme (v-cath); *Drosophila* small optic lobes protein (gene sol), a neuronal protein that contains a calpain-like domain; Yeast thiol protease BLH1/YCP1/LAP3; and *Caenorhabditis elegans* hypothetical protein C06G4.2, a calpain-like protein; Two bacterial peptidases are also part of this family—Aminopeptidase C from *Lactococcus lactis* (gene pepC), and Thiol protease tpr from *Porphyromonas gingivalis*.

A consensus pattern for eukaryotic thiol (cysteine) protease active site domains is the following: Q-x(3)-[GE]-x-C-[YW]-x(2)-[STAGC]-[STAGCV] (SEQ ID NO:148), wherein C is the active site residue, and "x" represents any amino acid. The residue in position 4 of the pattern is almost always cysteine; the only exceptions are calpains (Leu), bleomycin hydrolase (Ser) and yeast YPC1 (Ser); while the residue in position 5 of the pattern is always Gly except in papaya protease IV where it is Glu.

An additional consensus pattern for eukaryotic thiol (cysteine) protease active site domains is the following: [LIVMGSTAN]-x-H-[GSACE]-[LIVM]-x-[LIVMAT](2)-G-x-[GSADNH] (SEQ ID NO:149), wherein H is the active site residue, and "x" represents any amino acid.

An additional consensus pattern for eukaryotic thiol (cysteine) protease active site domains is the following: [FYCH]-[WI]-[LIVT]-x-[KRQAG]-N-[ST]-W-x(3)-[FYW]-G-x(2)-G-[LFYW]-[LIVMFYG]-x-[LIVMF] (SEQ ID NO:150), wherein N is the active site residue, and "x" represents any amino acid.

Additional information relating to for eukaryotic thiol (cysteine) protease active site domains may be found in reference to the following publications, which are hereby incorporated by reference herein: Dufour E., Biochimie 70:1335–1342(1988); Kirschke H., Barrett A.J., Rawlings N. D., Protein Prof. 2:1587–1643(1995); Shi G.-P., Chapman H. A., Bhairi S. M., Deleeuw C., Reddy V. Y., Weiss S. J., FEBS Lett. 357:129–134(1995); Velasco G., Ferrando A. A., Puente X. S., Sanchez L. M., Lopez-Otin C., J. Biol. Chem. . . . 269:27136–27142(1994); Chapot-Chartier M. P., Nardi M., Chopin M. C., Chopin A., Gripon J. C., Appl. Environ. Microbiol. 59:330–333(1993); Higgins D. G., McConnell D. J., Sharp P. M., Nature 340:604–604(1989); Rawlings N. D., Barrett A. J., Meth. Enzymol. 244:461–486 (1994), which are hereby incorporated by reference in their entirety herein.

In preferred embodiments, the following for eukaryotic thiol (cysteine) protease active site domain polypeptide is encompassed by the present invention: RLDLCQGIVGD-CWFLAALQALA (SEQ ID NO:76). Polynucleotides encoding these polypeptides are also provided. The present invention also encompasses the use of this for eukaryotic thiol (cysteine) protease active site domain polypeptide as an immunogenic and/or antigenic epitope as described elsewhere herein.

As referenced elsewhere herein, calpains are organized in domains. As a point of reference, the larger catalytic subunit of the best characterized m-calpain is organized in four domains (I–IV)(Hosfield et al., Crystal structure of calpain reveals the structural basis for Ca(2+)-dependent protease activity and a novel mode of enzyme activation. EMBO J. 18:6880–9, 1999; Strobl et al., The crystal structure of calcium-free human m-calpain suggests an electrostatic switch mechanism for activation by calcium. Proc Natl Acad Sci USA. 97:588–92, 2000). The N-terminal domain I contains an alpha helical region. Domain II contains the catalytic active domain with the active site amino acids. Domain II contains the linker between the Ca2+ binding domain in domain IV to the active site domain II.

The CAN-12v1 calpain of the present invention has the same domain I and II as the CAN-12 calpain, but differ in domains III and IV. The N-terminal domain I consists of residues Met1-Arg20. Domain II of the present calpains (Ala21-Lys333) contain the catalytic active site residues acids (Cys101, His254 and Asn278). As can be seen in the sequence alignments (FIGS. 2A–E), there is high amino acid sequence homology in the amino acid residues bracketing the active site amino acids. Combined domains I and II of the calpains of the present invention are 42–45% homologous to m-calpain.

The CAN-12v1 calpain of the present invention, have the same domain I and II, although they differ in composition and content of domains III and IV. The CAN-12 and CAN-12v1 calpain contains the linker (domain III) and the C-terminal domain IV, though the CAN-12v1 calpain is lacking residues Met426, Asn427 and Lys428 of SEQ ID NO54) in the "linker" domain.

The present invention also provides a three-dimensional homology model of the CAN-12 polypeptide (see FIG. 6).

Although the CAN-12 polypeptide sequence is different than the CAN-12v1 polypeptide sequence, the fact that domain I and II are substantially the same suggests the homology model of CAN-12 may be used for designing potential ligands (including agonists and/or antagonists) for the CAN-12v1 polypeptide. A three-dimensional homology model can be constructed on the basis of the known structure of a homologous protein (Greer et al, 1991, Lesk, et al, 1992, Cardozo, et al, 1995, Yuan, et al, 1995). The homology model of the CAN-12 polypeptide, corresponding to amino acid residues 12 to 524 of SEQ ID NO:2, was based upon the homologous structure of CAN2, a m-calpain family member (Strobl et al, 2000; hCAN2; Genbank Accession No. gil7546423; SEQ ID NO:11) and is defined by the set of structural coordinates set forth in Table IV herein.

A description of the headings in Table IV are as follows: "Atom No" refers to the atom number within the CAN-12 homology model; "Atom name" refers to the element whose coordinates are measured, the first letter in the column defines the element; "Residue" refers to the amino acid within which the atom resides, and the provided number after the amino acid refers to the amino acid number of the "residue"; "X Coord", "Y Coord", and "Z Coord" structurally define the atomic position of the element measured in three dimensions.

The CAN-12 homology model of the present invention may provide one basis for designing rational stimulators (agonists) and/or inhibitors (antagonists) of one or more of the biological functions of CAN-12v1, or of CAN-12v1 mutants having altered specificity (e.g., molecularly evolved CAN-12v1 polypeptides, engineered site-specific CAN-12v1 mutants, CAN-12v1 allelic variants, etc.).

Homology models are not only useful for designing rational agonists and/or antagonists, but are also useful in predicting the function of a particular polypeptide. The functional predictions from homology models are typically more accurate than the functional attributes derived from traditional polypeptide sequence homology alignments (e.g., CLUSTALW), particularly when the three dimensional structure of a related polypeptide is known (e.g., m-calpain family member CAN2 protein; Genbank Accession No. gil7546423; SEQ ID NO:11). The increased prediction accuracy is based upon the fact that homology models approximate the three-dimensional structure of a protein, while homology based alignments only take into account the one dimension polypeptide sequence. Since the function of a particular polypeptide is determined not only by its primary, secondary, and tertiary structure, functional assignments derived solely upon homology alignments using the one dimensional protein sequence may be less reliable. A 3-dimensional model can be constructed on the basis of the known structure of a homologous protein (Greer et al, 1991, Lesk, et al, 1992, Cardozo, et al, 1995, Yuan, et al, 1995).

Prior to developing a homology model, those of skill in the art would appreciate that a template of a known protein, or model protein, must first be identified which will be used as a basis for constructing the homology model for the protein of unknown structure (query template). In the case of the CAN-12 polypeptide of the present invention, the model protein template used in constructing the CAN-12 homology model was the m-calpain family member CAN2 protein; Genbank Accession No. gil7546423; SEQ ID NO:11).

Identifying a template can be accomplished using pairwise alignment of protein sequences using such programs as FASTA (Pearson, et al 1990) and BLAST (Altschul, et al, 1990). In cases where sequence similarity is high (greater than 30%), such pairwise comparison methods may be adequate for identifying an appropriate template. Likewise, multiple sequence alignments or profile-based methods can be used to align a query sequence to an alignment of multiple (structurally and biochemically) related proteins. When the sequence similarity is low, more advanced techniques may be used. Such techniques, include, for example, protein fold recognition (protein threading; Hendlich, et al, 1990), where the compatibility of a particular polypeptide sequence with the 3-dimensional fold of a potential template protein is gauged on the basis of a knowledge-based potential.

Following the initial sequence alignment, the second step would be to optimally align the query template to the model template by manual manipulation and/or by the incorporation of features specific to the polypeptides (e.g., motifs, secondary structure predictions, and allowed conservations). Preferably, the incorporated features are found within both the model and query template.

The third step would be to identify structurally conserved regions that could be used to construct secondary core structure (Sali, et al, 1995). Loops could be added using knowledge-based techniques, and by performing forcefield calculations (Sali, et al, 1995).

The term "structure coordinates" refers to Cartesian coordinates generated from the building of a homology model. In this invention, the homology model of residues 12 to 524 of CAN-12 was derived from generating a sequence alignment with m-calpain (Strobl et al, 2000; hCAN2; Genbank Accession No. gil7546423; SEQ ID NO:11) using the COMPOSER suite of software within SYBYL6.6 (Tripos Associates, St. Louis, Mo.) and then generating the backbone and side chain conformations. In the original crystal structure (pdb code 1dkv) as well as the crystal structure reported elsewhere (Hosfield et al, 1999), the active site of the enzyme comprising a cysteine, a histidine and an asparagine residue was not "formed". The helix that contains the active site C101 was altered by moving the helix down one pitch so that the active site geometry could match that found in Papain (pdb code 1b4). This modified structure of human m-calpain was used as the template for construction of the homology model (illustrated in FIG. 6 herein).

The skilled artisan would appreciate that a set of structure coordinates for a protein represents a relative set of points that define a shape in three dimensions. Thus, it is possible that an entirely different set of coordinates could define a similar or identical shape. Moreover, slight variations in the individual coordinates, as emanate from the generation of similar homology models using different alignment templates (i.e., other than the m-calpain (Strobl et al, 2000; hCAN2; Genbank Accession No. gil7546423; SEQ ID NO:11), and/or using different methods in generating the homology model, will likely have minor effects on the overall shape. Variations in coordinates may also be generated because of mathematical manipulations of the structure coordinates. For example, the structure coordinates set forth in Table IV could be manipulated by fractionalization of the structure coordinates; integer additions, or integer subtractions to sets of the structure coordinates, inversion of the structure coordinates or any combination of the above.

Therefore, various computational analyses are necessary to determine whether a template molecule or a portion thereof is sufficiently similar to all or part of a query template (e.g., CAN-12) in order to be considered the same. Such analyses may be carried out in current software applications, such as SYBYL version 6.6 or INSIGHTII (Molecular Simulations Inc., San Diego, Calif.) version 2000 and as described in the accompanying User's Guides.

Using the superimposition tool in the program SYBYL, comparisons can be made between different structures and different conformations of the same structure. The procedure used in SYBYL to compare structures is divided into four steps: 1) load the structures to be compared; 2) define the atom equivalencies in these structures; 3) perform a fitting operation; and 4) analyze the results. Each structure is identified by a name. One structure is identified as the target (i.e., the fixed structure); the second structure (i.e., moving structure) is identified as the source structure. The atom equivalency within SYBYL is defined by user input. For the purpose of this invention, we will define equivalent atoms as protein backbone atoms (N, Cα, C and O) for all conserved residues between the two structures being compared. We will also consider only rigid fitting operations. When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atoms is an absolute minimum. This number, given in angstroms, is reported by the SYBYL program. For the purpose of the present invention, any homology model of a CAN-12 that has a root mean square deviation of conserved residue backbone atoms (N, Cα, C, O) of less than 3.0 Å when superimposed on the relevant backbone atoms described by structure coordinates listed in Table IV are considered identical. More preferably, the root mean square deviation for the CAN-12 polypeptide is less than 2.0 Å.

The homology model of the present invention is useful for the structure-based design of modulators of the CAN-12 biological function, as well as mutants with altered biological function and/or specificity.

In accordance with the structural coordinates provided in Table IV and the three dimensional homology model of CAN-12, the CAN-12v1 polypeptide has been shown to comprise a an active site region embodied by the following amino acids: from about amino acid R90 to about amino acid C94, from about amino acid G99 to about amino acid L104, from about amino acid Q196 to about amino acid S198, from about amino acid M210 to about amino acid I212, from about amino acid G236 to about amino acid H240, from about amino acid E252 to about amino acid Y256, from about amino acid N278 to about amino acid K282, from about amino acid V328 to about amino acid V331 of SEQ ID NO:54 (FIGS. 8A–C). In this context, the term "about" may be construed to mean 1, 2, 3, 4, 5, 6, 7, 8, 9 or 10 amino acids more in either the N- or C-terminal direction of the above referenced amino acids.

Also more preferred are polypeptides comprising all or any part of the CAN-12v1 active site domain, or a mutant or homologue of said polypeptide or molecular complex. By mutant or homologue of the molecule is meant a molecule that has a root mean square deviation from the backbone atoms of said CAN-12 amino acids of not more than about 4.5 Angstroms, and preferably not more than about 3.5 Angstroms.

In preferred embodiments, the following CAN-12v1 active site domain polypeptide is encompassed by the present invention: RLDLCQGIVGDCWFLAALQALAL-HQDILSRVVPLNQSFTEKYAGIFRFWFWH YGN-WVPVVIDDRLPVNEAGQLVFVSSTYKN-LFWGALLEKAYAKLSGSYEDL QSGQVSEALVDFTGGVTMTINLAEAHGN-LWDILIEATYNRTLIGCQTHSGKIL ENGLVEGHAY-TLTGIRKVTCKHRPEYLVKLRNP-WGKVEWKGDWSDSSSKW ELLSPKEKILLLRKDNDGEFWMTLQDFKTHFVLLV (SEQ ID NO:92). Polynucleotides encoding this polypeptide are also provided. The present invention also encompasses the use of the CAN-12v1 active site domain polypeptide as an immunogenic and/or antigenic epitope as described elsewhere herein.

The present invention also encompasses polypeptides comprising at least a portion of the CAN-12 active site domain (SEQ ID NO: 92). Such polypeptides may correspond, for example, to the N- and/or C-terminal deletions of the active site domain.

In preferred embodiments, the following N-terminal CAN-12v1 active site domain deletion polypeptides are encompassed by the present invention: R1-V242, L2-V242, D3-V242, L4-V242, C5-V242, Q6-V242, G7-V242, I8-V242, V9-V242, G10-V242, D11-V242, C12-V242, W13-V242, F14-V242, L15-V242, A16-V242, A17-V242, L18-V242, Q19-V242, A20-V242, L21-V242, A22-V242, L23-V242, H24-V242, Q25-V242, D26-V242, I27-V242, L28-V242, S29-V242, R30-V242, V31-V242, V32-V242, P33-V242, L34-V242, N35-V242, Q36-V242, S37-V242, F38-V242, T39-V242, E40-V242, K41-V242, Y42-V242, A43-V242, G44-V242, I45-V242, F46-V242, R47-V242, F48-V242, W49-V242, F50-V242, W51-V242, H52-V242, Y53-V242, G54-V242, N55-V242, W56-V242, V57-V242, P58-V242, V59-V242, V60-V242, I61-V242, D62-V242, D63-V242, R64-V242, L65-V242, P66-V242, V67-V242, N68-V242, E69-V242, A70-V242, G71-V242, Q72-V242, L73-V242, V74-V242, F75-V242, V76-V242, S77-V242, S78-V242, T79-V242, Y80-V242, K81-V242, N82-V242, L83-V242, F84-V242, W85-V242, G86-V242, A87-V242, L88-V242, L89-V242, E90-V242, K91-V242, A92-V242, Y93-V242, A94-V242, K95-V242, L96-V242, S97-V242, G98-V242, S99-V242, Y100-V242, E101-V242, D102-V242, L103-V242, Q104-V242, S105-V242, G106-V242, Q107-V242, V108-V242, S109-V242, E110-V242, A111-V242, L112-V242, V113-V242, D114-V242, F115-V242, T116-V242, G117-V242, G118-V242, V119-V242, T120-V242, M121-V242, T122-V242, I123-V242, N124-V242, L125-V242, A126-V242, E127-V242, A128-V242, H129-V242, G130-V242, N131-V242, L132-V242, W133-V242, D134-V242, I135-V242,-L136-V242, I137-V242, E138-V242, A139-V242, T140-V242, Y141-V242, N142-V242, R143-V242, T144-V242, L145-V242, I146-V242, G147-V242, C148-V242, Q149-V242, T150-V242, H151-V242, S152-V242, G153-V242, E154-V242, K155-V242, I156-V242, L157-V242, E158-V242, N159-V242, G160-V242, L161-V242, V162-V242, E163-V242, G164-V242, H165-V242, A166-V242, Y167-V242, T168-V242, L169-V242, T170-V242, G171-V242, I172-V242, R173-V242, K174-V242, V175-V242, T176-V242, C177-V242, K178-V242, H179-V242, R180-V242, P181-V242, E182-V242, Y183-V242, L184-V242, V185-V242, K186-V242, L187-V242, R188-V242, N189-V242, P190-V242, W191-V242, G192-V242, K193-V242, V194-V242, E195-V242, W196-V242, K197-V242, G198-V242, D199-V242, W200-V242, S201-V242, D202-V242, S203-V242, S204-V242, S205-V242, K206-V242, W207-V242, E208-V242, L209-V242, L210-V242, S211-V242, P212-V242, K213-V242, E214-V242, K215-V242, I216-V242, L217-V242, L218-V242, L219-V242, R220-V242, K221-V242, D222-V242, N223-V242, D224-V242, G225-V242, E226-V242, F227-V242, W228-V242, M229-V242, T230-V242, L231-V242, Q232-V242, D233-V242, F234-V242, K235-V242, and/or T236-V242 of SEQ ID NO:92. Polynucleotide sequences encoding these polypeptides are also provided. The present invention also encompasses the use of these N-terminal CAN-12v1 active site domain deletion polypeptides as immunogenic and/or antigenic epitopes as described elsewhere herein.

In preferred embodiments, the following C-terminal CAN-12v1 active site domain deletion polypeptides are encompassed by the present invention: R1-V242, R1-L241, R1-L240, R1-V239, R1-F238, R1-H237, R1-T236, R1-K235, R1-F234, R1-D233, R1-Q232, R1-L231, R1-T230, R1-M229, R1-W228, R1-F227, R1-E226, R1-G225, R1-D224, R1-N223, R1-D222, R1-K221, R1-R220, R1-L219, R1-L218, R1-L217, R1-I216, R1-K215, R1-E214, R1-K213, R1-P212, R1-S211, R1-L210, R1-L209, R1-E208, R1-W207, R1-K206, R1-S205, R1-S204, R1-S203, R1-D202, R1-S201, R1-W200, R1-D199, R1-G198, R1-K197, R1-W196, R1-E195, R1-V194, R1-K193, R1-G192, R1-W191, R1-P190, R1-N189, R1-R188, R1-L187, R1-K186, R1-V185, R1-L184, R1-Y183, R1-E182, R1-P181, R1-R180, R1-H179, R1-K178, R1-C177, R1-T176, R1-V175, R1-K174, R1-R173, R1-I172, R1-G171, R1-T170, R1-L169, R1-T168, R1-Y167, R1-A166, R1-H165, R1-G164, R1-E163, R1-V162, R1-L161, R1-G160, R1-N159, R1-E158, R1-L157, R1-I156, R1-K155, R1-E154, R1-G153, R1-S152, R1-H151, R1-T150, R1-Q149, R1-C148, R1-G147, R1-I146, R1-L145, R1-T144, R1-R143, R1-N142, R1-Y141, R1-T140, R1-A139, R1-E138, R1-I137, R1-L136, R1-I135, R1-D134, R1-W133, R1-L132, R1-N131, R1-G130, R1-H129, R1-A128, R1-E127, R1-A126, R1-L125, R1-N124, R1-I123, R1-T122, R1-M121, R1-T120, R1-V119, R1-G118, R1-G117, R1-T116, R1-F115, R1-D114, R1-V113, R1-L112, R1-A111, R1-E110, R1-S109, R1-V108, R1-Q107, R1-G106, R1-S105, R1-Q104, R1-L103, R1-D102, R1-E101, R1-Y100, R1-S99, R1-G98, R1-S97, R1-L96, R1-K95, R1-A94, R1-Y93, R1-A92, R1-K91, R1-E90, R1-L89, R1-L88, R1-A87, R1-G86, R1-W85, R1-F84, R1-L83, R1-N82, R1-K81, R1-Y80, R1-T79, R1-S78, R1-S77, R1-V76, R1-F75, R1-V74, R1-L73, R1-Q72, R1-G71, R1-A70, R1-E69, R1-N68, R1-V67, R1-P66, R1-L65, R1-R64, R1-D63, R1-D62, R1-I61, R1-V60, R1-V59, R1-P58, R1-V57, R1-W56, R1-N55, R1-G54, R1-Y53, R1-H52, R1-W51, R1-F50, R1-W49, R1-F48, R1-R47, R1-F46, R1-I45, R1-G44, R1-A43, R1-Y42, R1-K41, R1-E40, R1-T39, R1-F38, R1-S37, R1-Q36, R1-N35, R1-L34, R1-P33, R1-V32, R1-V31, R1-R30, R1-S29, R1-L28, R1-I27, R1-D26, R1-Q25, R1-H24, R1-L23, R1-A22, R1-L21, R1-A20, R1-Q19, R1-L18, R1-A17, R1-A16, R1-L15, R1-F14, R1-W13, R1-C12, R1-D11, R1-G10, R1-V9, R1-I8, and/or R1-G7 of SEQ ID NO:92. Polynucleotide sequences encoding these polypeptides are also provided. The present invention also encompasses the use of these C-terminal CAN-12v1 active site domain deletion polypeptides as immunogenic and/or antigenic epitopes as described elsewhere herein.

Alternatively, such polypeptides may comprise polypeptide sequences corresponding, for example, to internal regions of the CAN-12v1 active site domain (e.g., any combination of both N- and C-terminal CAN-12v1 active site domain deletions) of SEQ ID NO:92. For example, internal regions could be defined by the equation NX to CX, where NX refers to any N-terminal amino acid position of the CAN-12v1 active site domain (SEQ ID NO:92), and where CX refers to any C-terminal amino acid position of the CAN-12v1 active site domain (SEQ ID NO:92). Polynucleotides encoding these polypeptides are also provided. The present invention also encompasses the use of these polypeptides as an immunogenic and/or antigenic epitope as described elsewhere herein.

In preferred embodiments, the following CAN-12v1 active site domain amino acid substitutions are encompassed by the present invention: wherein R90 is substituted with either an A, C, D, E, F, G, H, I, K, L, M, N, P, Q, S, T, V, W, or Y; wherein L91 is substituted with either an A, C, D, E, F, G, H, I, K, M, N, P, Q, R, S, T, V, W, or Y; wherein D92 is substituted with either an A, C, E, F, G, H, I, K, L, M, N, P, Q, R, S, T, V, W, or Y; wherein L93 is substituted with either an A, C, D, E, F, G, H, I, K, M, N, P, Q, R, S, T, V, W, or Y; wherein C94 is substituted with either an A, D, E, F, G, H, I, K, L, M, N, P, Q, R, S, T, V, W, or Y; wherein Q95 is substituted with either an A, C, D, E, F, G, H, I, K, L, M, N, P, R, S, T, V, W, or Y; wherein G96 is substituted with either an A, C, D, E, F, H, I, K, L, M, N, P, Q, R, S, T, V, W, or Y; wherein I97 is substituted with either an A, C, D, E, F, G, H, K, L, M, N, P, Q, R, S, T, V, W, or Y; wherein V98 is substituted with either an A, C, D, E, F, G, H, I, K, L, M, N, P, Q, R, S, T, W, or Y; wherein G99 is substituted with either an A, C, D, E, F, H, I, K, L, M, N, P, Q, R, S, T, V, W, or Y; wherein D100 is substituted with either an A, C, E, F, G, H, I, K, L, M, N, P, Q, R, S, T, V, W, or Y; wherein C101 is substituted with either an A, D, E, F, G, H, I, K, L, M, N, P, Q, R, S, T, V, W, or Y; wherein W102 is substituted with either an A, C, D, E, F, G, H, I, K, L, M, N, P, Q, R, S, T, V, or Y; wherein F103 is substituted with either an A, C, D, E, G, H, I, K, L, M, N, P, Q, R, S, T, V, W, or Y; wherein L104 is substituted with either an A, C, D, E, F, G, H, I, K, M, N, P, Q, R, S, T, V, W, or Y; wherein A105 is substituted with either a C, D, E, F, G, H, I, K, L, M, N, P, Q, R, S, T, V, W, or Y; wherein A106 is substituted with either a C, D, E, F, G, H, I, K, L, M, N, P, Q, R, S, T, V, W, or Y; wherein L107 is substituted with either an A, C, D, E, F, G, H, I, K, M, N, P, Q, R, S, T, V, W, or Y; wherein Q108 is substituted with either an A, C, D, E, F, G, H, I, K, L, M, N, P, R, S, T, V, W, or Y; wherein A109 is substituted with either a C, D, E, F, G, H, I, K, L, M, N, P, Q, R, S, T, V, W, or Y; wherein L110 is substituted with either an A, C, D, E, F, G, H, I, K, M, N, P, Q, R, S, T, V, W, or Y; wherein A111 is substituted with either a C, D, E, F, G, H, I, K, L, M, N, P, Q, R, S, T, V, W, or Y; wherein L112 is substituted with either an A, C, D, E, F, G, H, I, K, M, N, P, Q, R, S, T, V, W, or Y; wherein H113 is substituted with either an A, C, D, E, F, G, I, K, L, M, N, P, Q, R, S, T, V, W, or Y; wherein Q114 is substituted with either an A, C, D, E, F, G, H, I, K, L, M, N, P, R, S, T, V, W, or Y; wherein D115 is substituted with either an A, C, E, F, G, H, I, K, L, M, N, P, Q, R, S, T, V, W, or Y; wherein I116 is substituted with either an A, C, D, E, F, G, H, K, L, M, N, P, Q, R, S, T, V, W, or Y; wherein L117 is substituted with either an A, C, D, E, F, G, H, I, K, M, N, P, Q, R, S, T, V, W, or Y; wherein S118 is substituted with either an A, C, D, E, F, G, H, I, K, L, M, N, P, Q, R, T, V, W, or Y; wherein R119 is substituted with either an A, C, D, E, F, G, H, I, K, L, M, N, P, Q, S, T, V, W, or Y; wherein V120 is substituted with either an A, C, D, E, F, G, H, I, K, L, M, N, P, Q, R, S, T, W, or Y; wherein V121 is substituted with either an A, C, D, E, F, G, H, I, K, L, M, N, P, Q, R, S, T, W, or Y; wherein P122 is substituted with either an A, C, D, E, F, G, H, I, K, L, M, N, Q, R, S, T, V, W, or Y; wherein L123 is substituted with either an A, C, D, E, F, G, H, I, K, M, N, P, Q, R, S, T, V, W, or Y; wherein N124 is substituted with either an A, C, D, E, F, G, H, I, K, L, M, P, Q, R, S, T, V, W, or Y; wherein Q125 is substituted with either an A, C, D, E, F, G, H, I, K, L, M, N, P, R, S, T, V, W, or Y; wherein S126 is substituted with either an A, C, D, E, F, G, H, I, K, L, M, N, P, Q, R, T, V, W, or Y; wherein F127 is substituted with either an A, C, D, E, G, H, I, K, L, M, N, P, Q, R, S, T, V, W, or Y; wherein T128 is substituted with either an A, C, D, E, F, G, H, I, K, L, M, N, P, Q, R, S, V, W, or Y; wherein E129 is substituted with either an A, C, D, F, G, H, I, K, L, M, N, P, Q, R, S, T, V, W, or Y; wherein K130 is substituted with either an A, C, D, E, F, G, H, I, L, M, N, P, Q, R, S, T, V, W, or Y; wherein Y131 is substituted with either an A, C, D, E, F, G, H, I, K, L, M, N, P, Q, R, S, T, V, or W; wherein A132 is substituted with either a C, D, E, F, G, H, I, K, L, M, N, P, Q, R, S, T, V, W, or Y; wherein G133 is substituted with either an A, C, D, E, F, H, I, K, L, M, N, P, Q, R, S, T, V, W, or Y; wherein I134 is substituted with either an A, C, D, E, F, G, H, K, L, M, N, P, Q, R, S, T, V, W, or Y; wherein F135 is substituted with either an A, C, D, E, G, H, I, K, L, M, N, P, Q, R, S, T, V, W, or Y; wherein R136 is substituted with either an A, C, D, E, F, G, H, I, K, L, M, N, P, Q, S, T, V, W, or Y; wherein F137 is substituted with either an A, C, D, E, G, H, I, K, L, M, N, P, Q, R, S, T, V, W, or Y; wherein W138 is substituted with either an A, C, D, E, F, G, H, I, K, L, M, N, P, Q, R, S, T, V, or Y; wherein F139 is substituted with either an A, C, D, E, G, H, I, K, L, M, N, P, Q, R, S, T, V, W, or Y; wherein W140 is substituted with either an A, C, D, E, F, G, H, I, K, L, M, N, P, Q, R, S, T, V, or Y; wherein H141 is substituted with either an A, C, D, E, F, G, I, K, L, M, N, P, Q, R, S, T, V, W, or Y; wherein Y142 is substituted with either an A, C, D, E, F, G, H, I, K, L, M, N, P, Q, R, S, T, V, or W; wherein G143 is substituted with either an A, C, D, E, F, H, I, K, L, M, N, P, Q, R, S, T, V, W, or Y; wherein N144 is substituted with either an A, C, D, E, F, G, H, I, K, L, M, P, Q, R, S, T, V, W, or Y; wherein W145 is substituted with either an A, C, D, E, F, G, H, I, K, L, M, N, P, Q, R, S, T, V, or Y; wherein V146 is substituted with either an A, C, D, E, F, G, H, I, K, L, M, N, P, Q, R, S, T, W, or Y; wherein P147 is substituted with either an A, C, D, E, F, G, H, I, K, L, M, N, Q, R, S, T, V, W, or Y; wherein V148 is substituted with either an A, C, D, E, F, G, H, I, K, L, M, N, P, Q, R, S, T, W, or Y; wherein V149 is substituted with either an A, C, D, E, F, G, H, I, K, L, M, N, P, Q, R, S, T, W, or Y; wherein I150 is substituted with either an A, C, D, E, F, G, H, K, L, M, N, P, Q, R, S, T, V, W, or Y; wherein D151 is substituted with either an A, C, E, F, G, H, I, K, L, M, N, P, Q, R, S, T, V, W, or Y; wherein D152 is substituted with either an A, C, E, F, G, H, I, K, L, M, N, P, Q, R, S, T, V, W, or Y; wherein R153 is substituted with either an A, C, D, E, F, G, H, I, K, L, M, N, P, Q, S, T, V, W, or Y; wherein L154 is substituted with either an A, C, D, E, F, G, H, I, K, M, N, P, Q, R, S, T, V, W, or Y; wherein P155 is substituted with either an A, C, D, E, F, G, H, I, K, L, M, N, Q, R, S, T, V, W, or Y; wherein V156 is substituted with either an A, C, D, E, F, G, H, I, K, L, M, N, P, Q, R, S, T, W, or Y; wherein N157 is substituted with either an A, C, D, E, F, G, H, I, K, L, M, P, Q, R, S, T, V, W, or Y; wherein E158 is substituted with either an A, C, D, F, G, H, I, K, L, M, N, P, Q, R, S, T, V, W, or Y; wherein A159 is substituted with either a C, D, E, F, G, H, I, K, L, M, N, P, Q, R, S, T, V, W, or Y; wherein G160 is substituted with either an A, C, D, E, F, H, I, K, L, M, N, P, Q, R, S, T, V, W, or Y; wherein Q161 is substituted with either an A, C, D, E, F, G, H, I, K, L, M, N, P, R, S, T, V, W, or Y; wherein L162 is substituted with either an A, C, D, E, F, G, H, I, K, M, N, P, Q, R, S, T, V, W, or Y; wherein V163 is substituted with either an A, C, D, E, F, G, H, I, K, L, M, N, P, Q, R, S, T, W, or Y; wherein F164 is substituted with either an A, C, D, E, G, H, I, K, L, M, N, P, Q, R, S, T, V, W, or Y; wherein V165 is substituted with either an A, C, D, E, F, G, H, I, K, L, M, N, P, Q, R, S, T, W, or Y; wherein S166 is substituted with either an A, C, D, E, F, G, H, I, K, L, M, N, P, Q, R, T, V, W, or Y; wherein S167 is substituted with either an A, C, D, E, F, G, H, I, K, L, M, N, P, Q, R, T, V, W, or Y; wherein T168 is substituted with either an A, C, D, E, F, G, H, I, K, L, M, N, P, Q, R, S, V, W, or Y; wherein Y169 is substituted with either an A, C, D, E, F, G, H, I, K, L, M, N, P, Q, R, S, T, V, or W; wherein K170 is substituted with either an A, C, D, E, F, G, H, I, L, M, N, P, Q, R, S, T, V, W, or Y; wherein N171 is substituted with either an A, C, D, E, F, G, H, I, K, L, M, P, Q, R, S, T, V, W, or Y; wherein L172 is substituted with either an A, C, D, E, F, G, H, I, K, M, N, P, Q, R, S, T, V, W, or Y; wherein F173 is substituted with either an A, C, D, E, G, H, I, K, L, M, N, P, Q, R, S, T, V, W, or Y; wherein W174 is substituted with either an A, C, D, E, F, G, H, I, K, L, M, N, P, Q, R, S, T, V, or Y; wherein G175 is substituted with either an A, C, D, E, F, H, I, K, L, M, N, P, Q, R, S, T, V, W, or Y; wherein A176 is substituted with either a C, D, E, F, G, H, I, K, L, M, N, P, Q, R, S, T, V, W, or Y; wherein L177 is substituted with either an A, C, D, E, F, G, H, I, K, M, N, P, Q, R, S, T, V, W, or Y; wherein L178 is substituted with either an A, C, D, E, F, G, H, I, K, M, N, P, Q, R, S, T, V, W, or Y; wherein E179 is substituted with either an A, C, D, F, G, H, I, K, L, M, N, P, Q, R, S, T, V, W, or Y; wherein K180 is substituted with either an A, C, D, E, F, G, H, I, L, M, N, P, Q, R, S, T, V, W, or Y; wherein A181 is substituted with either a C, D, E, F, G, H, I, K, L, M, N, P, Q, R, S, T, V, W, or Y; wherein Y182 is substituted with either an A, C, D, E, F, G, H, I, K, L, M, N, P, Q, R, S, T, V, or W; wherein A183 is substituted with either a C, D, E, F, G, H, I, K, L, M, N, P, Q, R, S, T, V, W, or Y; wherein K184 is substituted with either an A, C, D, E, F, G, H, I, L, M, N, P, Q, R, S, T, V, W, or Y; wherein L185 is substituted with either an A, C, D, E, F, G, H, I, K, M, N, P, Q, R, S, T, V, W, or Y; wherein S186 is substituted with either an A, C, D, E, F, G, H, I, K, L, M, N, P, Q, R, T, V, W, or Y; wherein G187 is substituted with either an A, C, D, E, F, H, I, K, L, M, N, P, Q, R, S, T, V, W, or Y; wherein S188 is substituted with either an A, C, D, E, F, G, H, I, K, L, M, N, P, Q, R, T, V, W, or Y; wherein Y189 is substituted with either an A, C, D, E, F, G, H, I, K, L, M, N, P, Q, R, S, T, V, or W; wherein E190 is substituted with either an A, C, D, F, G, H, I, K, L, M, N, P, Q, R, S, T, V, W, or Y; wherein D191 is substituted with either an A, C, E, F, G, H, I, K, L, M, N, P, Q, R, S, T, V, W, or Y; wherein L192 is substituted with either an A, C, D, E, F, G, H, I, K, M, N, P, Q, R, S, T, V, W, or Y; wherein Q193 is substituted with either an A, C, D, E, F, G, H, I, K, L, M, N, P, R, S, T, V, W, or Y; wherein S194 is substituted with either an A, C, D, E, F, G, H, I, K, L, M, N, P, Q, R, T, V, W, or Y; wherein G195 is substituted with either an A, C, D, E, F, H, I, K, L, M, N, P, Q, R, S, T, V, W, or Y; wherein Q196 is substituted with either an A, C, D, E, F, G, H, I, K, L, M, N, P, R, S, T, V, W, or Y; wherein V197 is substituted with either an A, C, D, E, F, G, H, I, K, L, M, N, P, Q, R, S, T, W, or Y; wherein S198 is substituted with either an A, C, D, E, F, G, H, I, K, L, M, N, P, Q, R, T, V, W, or Y; wherein E199 is substituted with either an A, C, D, F, G, H, I, K, L, M, N, P, Q, R, S, T, V, W, or Y; wherein A200 is substituted with either a C, D, E, F, G, H, I, K, L, M, N, P, Q, R, S, T, V, W, or Y; wherein L201 is substituted with either an A, C, D, E, F, G, H, I, K, M, N, P, Q, R, S, T, V, W, or Y; wherein V202 is substituted with either an A, C, D, E, F, G, H, I, K, L, M, N, P, Q, R, S, T, W, or Y; wherein D203 is substituted with either an A, C, E, F, G, H, I, K, L, M, N, P, Q, R, S, T, V, W, or Y; wherein F204 is substituted with either an A, C, D, E, G, H, I, K, L, M, N, P, Q, R, S, T, V, W, or Y; wherein T205 is substituted with either an A, C, D, E, F, G, H, I, K, L, M, N, P, Q, R, S, V, W, or Y; wherein G206 is substituted with either an A, C, D, E, F, H, I, K, L, M, N, P, Q, R, S, T, V, W, or Y; wherein G207 is substituted with either an A, C, D, E, F, H, I, K, L, M, N, P, Q, R, S, T, V, W, or Y; wherein V208 is substituted with either an A, C, D, E, F, G, H, I, K, L, M, N, P, Q, R, S, T, W, or Y; wherein T209 is substituted with either an A, C, D, E, F, G, H, I, K, L, M, N, P, Q, R, S, V, W, or Y; wherein M210 is substituted with either an A, C, D, E, F, G, H, I, K, L, N, P, Q, R, S, T, V, W, or Y; wherein T211 is substituted with either an A, C, D, E, F, G, H, I, K, L, M, N, P, Q, R, S, V, W, or Y; wherein I212 is substituted with either an A, C, D, E, F, G, H, K, L, M, N, P, Q, R, S, T, V, W, or Y; wherein N213 is substituted with either an A, C, D, E, F, G, H, I, K, L, M, P, Q, R, S, T, V, W, or Y; wherein L214 is substituted with either an A, C, D, E, F, G, H, I, K, M, N, P, Q, R, S, T, V, W, or Y; wherein A215 is substituted with either a C, D, E, F, G, H, I, K, L, M, N, P, Q, R, S, T, V, W, or Y; wherein E216 is substituted with either an A, C, D, F, G, H, I, K, L, M, N, P, Q, R, S, T, V, W, or Y; wherein A217 is substituted with either a C, D, E, F, G, H, I, K, L, M, N, P, Q, R, S, T, V, W, or Y; wherein H218 is substituted with either an A, C, D, E, F, G, I, K, L, M, N, P, Q, R, S, T, V, W, or Y; wherein G219 is substituted with either an A, C, D, E, F, H, I, K, L, M, N, P, Q, R, S, T, V, W, or Y; wherein N220 is substituted with either an A, C, D, E, F, G, H, I, K, L, M, P, Q, R, S, T, V, W, or Y; wherein L221 is substituted with either an A, C, D, E, F, G, H, I, K, M, N, P, Q, R, S, T, V, W, or Y; wherein W222 is substituted with either an A, C, D, E, F, G, H, I, K, L, M, N, P, Q, R, S, T, V, or Y; wherein D223 is substituted with either an A, C, E, F, G, H, I, K, L, M, N, P, Q, R, S, T, V, W, or Y; wherein I224 is substituted with either an A, C, D, E, F, G, H, K, L, M, N, P, Q, R, S, T, V, W, or Y; wherein L225 is substituted with either an A, C, D, E, F, G, H, I, K, M, N, P, Q, R, S, T, V, W, or Y; wherein I226 is substituted with either an A, C, D, E, F, G, H, K, L, M, N, P, Q, R, S, T, V, W, or Y; wherein E227 is substituted with either an A, C, D, F, G, H, I, K, L, M, N, P, Q, R, S, T, V, W, or Y; wherein A228 is substituted with either a C, D, E, F, G, H, I, K, L, M, N, P, Q, R, S, T, V, W, or Y; wherein T229 is substituted with either an A, C, D, E, F, G, H, I, K, L, M, N, P, Q, R, S, V, W, or Y; wherein Y230 is substituted with either an A, C, D, E, F, G, H, I, K, L, M, N, P, Q, R, S, T, V, or W; wherein N231 is substituted with either an A, C, D, E, F, G, H, I, K, L, P, Q, R, S, T, V, W, or Y; wherein R232 is substituted with either an A, C, D, E, F, G, H, I, K, L, M, N, P, Q, S, T, V, W, or Y; wherein T233 is substituted with either an A, C, D, E, F, G, H, I, K, L, M, N, P, Q, R, S, V, W, or Y; wherein L234 is substituted with either an A, C, D, E, F, G, H, I, K, M, N, P, Q, R, S, T, V, W, or Y; wherein I235 is substituted with either an A, C, D, E, F, G, H, K, L, M, N, P, Q, R, S, T, V, W, or Y; wherein G236 is substituted with either an A, C, D, E, F, H, I, K, L, M, N, P, Q, R, S, T, V, W, or Y; wherein C237 is substituted with either an A, D, E, F, G, H, I, K, L, M, N, P, Q, R, S, T, V, W, or Y; wherein Q238 is substituted with either an A, C, D, E, F, G, H, I, K, L, M, N, P, R, S, T, V, W, or Y; wherein T239 is substituted with either an A, C, D, E, F, G, H, I, K, L, M, N, P, Q, R, S, V, W, or Y; wherein H240 is substituted with either an A, C, D, E, F, G, I, K, L, M, N, P, Q, R, S, T, V, W, or Y; wherein S241 is substituted with either an A, C, D, E, F, G, H, I, K, L, M, N, P, Q, R, T, V, W, or Y; wherein G242 is substituted with either an A, C, D, E, F, H, I, K, L, M, N, P, Q, R, S, T, V, W, or Y; wherein E243 is substituted with either an A, C, D, F, G, H, I, K, L, M, N, P, Q, R, S, T, V, W, or Y; wherein K244 is substituted with either an A, C, D, E, F, G, H, I, L, M, N, P, Q, R, S, T, V, W, or Y; wherein I245 is substituted with either an A, C, D, E, F, G, H, K, L, M, N, P, Q, R, S, T, V, W, or Y; wherein L246 is substituted with either an A, C, D, E, F, G, H, I, K, M, N, P, Q, R, S, T, V, W, or Y; wherein E247 is substituted with either an A, C, D, F, G, H, I, K, L, M, N, P, Q, R, S, T, V, W, or Y; wherein N248 is substituted with either an A, C, D, E, F, G, H, I, K, L, M, P, Q, R, S, T, V, W, or Y; wherein G249 is substituted with either an A, C, D, E, F, H, I, K, L, M, N, P, Q, R, S, T, V, W, or Y; wherein L250 is substituted with either an A, C, D, E, F, G, H, 1, K, M, N, P, Q, R, S, T, V, W, or Y; wherein V251 is substituted with either an A, C, D, E, F, G, H, I, K, L, M, N, P, Q, R, S, T, W, or Y; wherein E252 is substituted with either an A, C, D, F, G, H, I, K, L, M, N, P, Q, R, S, T, V, W, or Y; wherein G253 is substituted with either an A, C, D, E, F, H, I, K, L, M, N, P, Q, R, S, T, V, W, or Y; wherein H254 is substituted with either an A, C, D, E, F, G, I, K, L, M, N, P, Q, R, S, T, V, W, or Y; wherein A255 is substituted with either a C, D, E, F, G, H, I, K, L, M, N, P, Q, R, S, T, V, W, or Y; wherein Y256 is substituted with either an A, C, D, E, F, G, H, I, K, L, M, N, P, Q, R, S, T, V, or W; wherein T257 is substituted with either an A, C, D, E, F, G, H, I, K, L, M, N, P, Q, R, S, V, W, or Y; wherein L258 is substituted with either an A, C, D, E, F, G, H, I, K, M, N, P, Q, R, S, T, V, W, or Y; wherein T259 is substituted with either an A, C, D, E, F, G, H, I, K, L, M, N, P, Q, R, S, V, W, or Y; wherein G260 is substituted with either an A, C, D, E, F, H, I, K, L, M, N, P, Q, R, S, T, V, W, or Y; wherein I261 is substituted with either an A, C, D, E, F, G, H, K, L, M, N, P, Q, R, S, T, V, W, or Y; wherein R262 is substituted with either an A, C, D, E, F, G, H, I, K, L, M, N, P, Q, S, T, V, W, or Y; wherein K263 is substituted with either an A, C, D, E, F, G, H, I, L, M, N, P, Q, R, S, T, V, W, or Y; wherein V264 is substituted with either an A, C, D, E, F, G, H, I, K, L, M, N, P, Q, R, S, T, W, or Y; wherein T265 is substituted with either an A, C, D, E, F, G, H, I, K, L, M, N, P, Q, R, S, V, W, or Y; wherein C266 is substituted with either an A, D, E, F, G, H, I, K, L, M, N, P, Q, R, S, T, V, W, or Y; wherein K267 is substituted with either an A, C, D, E, F, G, H, I, L, M, N, P, Q, R, S, T, V, W, or Y; wherein H268 is substituted with either an A, C, D, E, F, G, I, K, L, M, N, P, Q, R, S, T, V, W, or Y; wherein R269 is substituted with either an A, C, D, E, F, G, H, I, K, L, M, N, P, Q, S, T, V, W, or Y; wherein P270 is substituted with either an A, C, D, E, F, G, H, I, K, L, M, N, Q, R, S, T, V, W, or Y; wherein E271 is substituted with either an A, C, D, F, G, H, I, K, L, M, N, P, Q, R, S, T, V, W, or Y; wherein Y272 is substituted with either an A, C, D, E, F, G, H, I, K, L, M, N, P, Q, R, S, T, V, or W; wherein L273 is substituted with either an A, C, D, E, F, G, H, I, K, M, N, P, Q, R, S, T, V, W, or Y; wherein V274 is substituted with either an A, C, D, E, F, G, H, I, K, L, M, N, P, Q, R, S, T, W, or Y; wherein K275 is substituted with either an A, C, D, E, F, G, H, I, L, M, N, P, Q, R, S, T, V, W, or Y; wherein L276 is substituted with either an A, C, D, E, F, G, H, I, K, M, N, P, Q, R, S, T, V, W, or Y; wherein R277 is substituted with either an A, C, D, E, F, G, H, I, K, L, M, N, P, Q, S, T, V, W, or Y; wherein N278 is substituted with either an A, C, D, E, F, G, H, I, K, L, M, P, Q, R, S, T, V, W, or Y; wherein P279 is substituted with either an A, C, D, E, F, G, H, I, K, L, M, N, Q, R, S, T, V, W, or Y; wherein W280 is substituted with either an A, C, D, E, F, G, H, I, K, L, M, N, P, Q, R, S, T, V, or Y; wherein G281 is substituted with either an A, C, D, E, F, H, I, K, L, M, N, P, Q, R, S, T, V, W, or Y; wherein K282 is substituted with either an A, C, D, E, F, G, H, I, L, M, N, P, Q, R, S, T, V, W, or Y; wherein V283 is substituted with either an A, C, D, E, F, G, H, I, K, L, M, N, P, Q, R, S, T, W, or Y; wherein E284 is substituted with either an A, C, D, F, G, H, I, K, L, M, N, P, Q, R, S, T, V, W, or Y; wherein W285 is substituted with either an A, C, D, E, F, G, H, I, K, L, M, N, P, Q, R, S, T, V, or Y; wherein K286 is substituted with either an A, C, D, E, F, G, H, I, L, M, N, P, Q, R, S, T, V, W, or Y; wherein G287 is substituted with either an A, C, D, E, F, H, I, K, L, M, N, P, Q, R, S, T, V, W, or Y; wherein D288 is substituted with either an A, C, E, F, G, H, I, K, L, M, N, P, Q, R, S, T, V, W, or Y; wherein W289 is substituted with either an A, C, D, E, F, G, H, I, K, L, M, N, P, Q, R, S, T, V, or Y; wherein S290 is substituted with either an A, C, D, E, F, G, H, I, K, L, M, N, P, Q, R, T, V, W, or Y; wherein D291 is substituted with either an A, C, E, F, G, H, I, K, L, M, N, P, Q, R, S, T, V, W, or Y; wherein S292 is substituted with either an A, C, D, E, F, G, H, I, K, L, M, N, P, Q, R, T, V, W, or Y; wherein S293 is substituted with either an A, C, D, E, F, G, H, I, K, L, M, N, P, Q, R, T, V, W, or Y; wherein S294 is substituted with either an A, C, D, E, F, G, H, I, K, L, M, N, P, Q, R, T, V, W, or Y; wherein K295 is substituted with either an A, C, D, E, F, G, H, I, L, M, N, P, Q, R, S, T, V, W, or Y; wherein W296 is substituted with either an A, C, D, E, F, G, H, I, K, L, M, N, P, Q, R, S, T, V, or Y; wherein E297 is substituted with either an A, C, D, F, G, H, I, K, L, M, N, P, Q, R, S, T, V, W, or Y; wherein L298 is substituted with either an A, C, D, E, F, G, H, I, K, M, N, P, Q, R, S, T, V, W, or Y; wherein L299 is substituted with either an A, C, D, E, F, G, H, I, K, M, N, P, Q, R, S, T, V, W, or Y; wherein S300 is substituted with either an A, C, D, E, F, G, H, I, K, L, M, N, P, Q, R, T, V, W, or Y; wherein P301 is substituted with either an A, C, D, E, F, G, H, I, K, L, M, N, Q, R, S, T, V, W, or Y; wherein K302 is substituted with either an A, C, D, E, F, G, H, I, L, M, N, P, Q, R, S, T, V, W, or Y; wherein E303 is substituted with either an A, C, D, F, G, H, I, K, L, M, N, P, Q, R, S, T, V, W, or Y; wherein K304 is substituted with either an A, C, D, E, F, G, H, I, L, M, N, P, Q, R, S, T, V, W, or Y; wherein I305 is substituted with either an A, C, D, E, F, G, H, K, L, M, N, P, Q, R, S, T, V, W, or Y; wherein L306 is substituted with either an A, C, D, E, F, G, H, I, K, M, N, P, Q, R, S, T, V, W, or Y; wherein L307 is substituted with either an A, C, D, E, F, G, H, I, K, M, N, P, Q, R, S, T, V, W, or Y; wherein L308 is substituted with either an A, C, D, E, F, G, H, I, K, M, N, P, Q, R, S, T, V, W, or Y; wherein R309 is substituted with either an A, C, D, E, F, G, H, I, K, L, M, N, P, Q, S, T, V, W, or Y; wherein K310 is substituted with either an A, C, D, E, F, G, H, I, L, M, N, P, Q, R, S, T, V, W, or Y; wherein D311 is substituted with either an A, C, E, F, G, H, I, K, L, M, N, P, Q, R, S, T, V, W, or Y; wherein N312 is substituted with either an A, C, D, E, F, G, H, I, K, L, M, P, Q, R, S, T, V, W, or Y; wherein D313 is substituted with either an A, C, E, F, G, H, I, K, L, M, N, P, Q, R, S, T, V, W, or Y; wherein G314 is substituted with either an A, C, D, E, F, H, I, K, L, M, N, P, Q, R, S, T, V, W, or Y; wherein E315 is substituted with either an A, C, D, F, G, H, I, K, L, M, N, P, Q, R, S, T, V, W, or Y; wherein F316 is substituted with either an A, C, D, E, G, H, I, K, L, M, N, P, Q, R, S, T, V, W, or Y; wherein W317 is substituted with either an A, C, D, E, F, G, H, I, K, L, M, N, P, Q, R, S, T, V, or Y; wherein M318 is substituted with either an A, C, D, E, F, G, H, I, K, L, N, P, Q, R, S, T, V, W, or Y; wherein T319 is substituted with either an A, C, D, E, F, G, H, I, K, L, M, N, P, Q, R, S, V, W, or Y; wherein L320 is substituted with either an A, C, D, E, F, G, H, I, K, M, N, P, Q, R, S, T, V, W, or Y; wherein Q321 is substituted with either an A, C, D, E, F, G, H, I, K, L, M, N, P, R, S, T, V, W, or Y; wherein D322 is substituted with either an A, C, E, F, G, H, I, K, L, M, N, P, Q, R, S, T, V, W, or Y; wherein F323 is substituted with either an A, C, D, E, G, H, I, K, L, M, N, P, Q, R, S, T, V, W, or Y; wherein K324 is substituted with either an A, C, D, E, F, G, H, I, L, M, N, P, Q, R, S, T, V, W, or Y; wherein T325 is substituted with either an A, C, D, E, F, G, H, I, K, L, M, N, P, Q, R, S, V, W, or Y; wherein H326 is substituted with either an A, C, D, E, F, G, I, K, L, M, N, P, Q, R, S, T, V, W, or Y; wherein F327 is substituted with either an A, C, D, E, G, H, I, K, L, M, N, P, Q, R, S, T, V, W, or Y; wherein V328 is substituted with either an A, C, D, E, F, G, H, I, K, L, M, N, P, Q, R, S, T, W, or Y; wherein L329 is substituted with either an A, C, D, E, F, G, H, I, K, M, N, P, Q, R, S, T, V, W, or Y; wherein L330 is substituted with either an A, C, D, E, F, G, H, I, K, M, N, P, Q, R, S, T, V, W, or Y; and/or wherein V331 is substituted with either an A, C, D, E, F, G, H, I, K, L, M, N, P, Q, R, S, T, W, or Y of SEQ ID NO:54, in addition to any combination thereof. The present invention also encompasses the use of these CAN-12v1 active site domain amino acid substituted polypeptides as immunogenic and/or antigenic epitopes as described elsewhere herein.

In preferred embodiments, the following CAN-12v1 active site domain conservative amino acid substitutions are encompassed by the present invention: wherein R90 is substituted with either a K, or H; wherein L91 is substituted with either an A, I, or V; wherein D92 is substituted with an E; wherein L93 is substituted with either an A, I, or V; wherein C94 is a C; wherein Q95 is substituted with a N; wherein G96 is substituted with either an A, M, S, or T; wherein I97 is substituted with either an A, V, or L; wherein V98 is substituted with either an A, I, or L; wherein G99 is substituted with either an A, M, S, or T; wherein D100 is substituted with an E; wherein C101 is a C; wherein W102 is either an F, or Y; wherein F103 is substituted with either a W, or Y; wherein L104 is substituted with either an A, I, or V; wherein A105 is substituted with either a G, I, L, M, S, T, or V; wherein A106 is substituted with either a G, I, L, M, S, T, or V; wherein L107 is substituted with either an A, I, or V; wherein Q108 is substituted with a N; wherein A109 is substituted with either a G, I, L, M, S, T, or V; wherein L110 is substituted with either an A, I, or V; wherein A111 is substituted with either a G, I, L, M, S, T, or V; wherein L112 is substituted with either an A, I, or V; wherein H113 is substituted with either a K, or R; wherein Q114 is substituted with a N; wherein D115 is substituted with an E; wherein I116 is substituted with either an A, V, or L; wherein L117 is substituted with either an A, I, or V; wherein S118 is substituted with either an A, G, M, or T; wherein R119 is substituted with either a K, or H; wherein V120 is substituted with either an A, I, or L; wherein V121 is substituted with either an A, I, or L; wherein P122 is a P; wherein L123 is substituted with either an A, I, or V; wherein N124 is substituted with a Q; wherein Q125 is substituted with a N; wherein S126 is substituted with either an A, G, M, or T; wherein F127 is substituted with either a W, or Y; wherein T128 is substituted with either an A, G, M, or S; wherein E129 is substituted with a D; wherein K130 is substituted with either a R, or H; wherein Y131 is either an F, or W; wherein A132 is substituted with either a G, I, L, M, S, T, or V; wherein G133 is substituted with either an A, M, S, or T; wherein I134 is substituted with either an A, V, or L; wherein F135 is substituted with either a W, or Y; wherein R136 is substituted with either a K, or H; wherein F137 is substituted with either a W, or Y; wherein W138 is either an F, or Y; wherein F139 is substituted with either a W, or Y; wherein W140 is either an F, or Y; wherein H141 is substituted with either a K, or R; wherein Y142 is either an F, or W; wherein G143 is substituted with either an A, M, S, or T; wherein N144 is substituted with a Q; wherein W145 is either an F, or Y; wherein V146 is substituted with either an A, I, or L; wherein P147 is a P; wherein V148 is substituted with either an A, I, or L; wherein V149 is substituted with either an A, I, or L; wherein I150 is substituted with either an A, V, or L; wherein D151 is substituted with an E; wherein D152 is substituted with an E; wherein R153 is substituted with either a K, or H; wherein L154 is substituted with either an A, I, or V; wherein P155 is a P; wherein V156 is substituted with either an A, I, or L; wherein N157 is substituted with a Q; wherein E158 is substituted with a D; wherein A159 is substituted with either a G, I, L, M, S, T, or V; wherein G160 is substituted with either an A, M, S, or T; wherein Q161 is substituted with a N; wherein L162 is substituted with either an A, I, or V; wherein V163 is substituted with either an A, I, or L; wherein F164 is substituted with either a W, or Y; wherein V165 is substituted with either an A, I, or L; wherein S166 is substituted with either an A, G, M, or T; wherein S167 is substituted with either an A, G, M, or T; wherein T168 is substituted with either an A, G, M, or S; wherein Y169 is either an F, or W; wherein K170 is substituted with either a R, or H; wherein N171 is substituted with a Q; wherein L172 is substituted with either an A, I, or V; wherein F173 is substituted with either a W, or Y; wherein W174 is either an F, or Y; wherein G175 is substituted with either an A, M, S, or T; wherein A176 is substituted with either a G, I, L, M, S, T, or V; wherein L177 is substituted with either an A, I, or V; wherein L178 is substituted with either an A, I, or V; wherein E179 is substituted with a D; wherein K180 is substituted with either a R, or H; wherein A181 is substituted with either a G, I, L, M, S, T, or V; wherein Y182 is either an F, or W; wherein A183 is substituted with either a G, I, L, M, S, T, or V; wherein K184 is substituted with either a R, or H; wherein L185 is substituted with either an A, I, or V; wherein S186 is substituted with either an A, G, M, or T; wherein G187 is substituted with either an A, M, S, or T; wherein S188 is substituted with either an A, G, M, or T; wherein Y189 is either an F, or W; wherein E190 is substituted with a D; wherein D191 is substituted with an E; wherein L192 is substituted with either an A, I, or V; wherein Q193 is substituted with a N; wherein S194 is substituted with either an A, G, M, or T; wherein G195 is substituted with either an A, M, S, or T; wherein Q196 is substituted with a N; wherein V197 is substituted with either an A, I, or L; wherein S198 is substituted with either an A, G, M, or T; wherein E199 is substituted with a D; wherein A200 is substituted with either a G, I, L, M, S, T, or V; wherein L201 is substituted with either an A, I, or V; wherein V202 is substituted with either an A, I, or L; wherein D203 is substituted with an E; wherein F204 is substituted with either a W, or Y; wherein T205 is substituted with either an A, G, M, or S; wherein G206 is substituted with either an A, M, S, or T; wherein G207 is substituted with either an A, M, S, or T; wherein V208 is substituted with either an A, I, or L; wherein T209 is substituted with either an A, G, M, or S; wherein M210 is substituted with either an A, G, S, or T; wherein T211 is substituted with either an A, G, M, or S; wherein I212 is substituted with either an A, V, or L; wherein N213 is substituted with a Q; wherein L214 is substituted with either an A, I, or V; wherein A215 is substituted with either a G, I, L, M, S, T, or V; wherein E216 is substituted with a D; wherein A217 is substituted with either a G, I, L, M, S, T, or V; wherein H218 is substituted with either a K, or R; wherein G219 is substituted with either an A, M, S, or T; wherein N220 is substituted with a Q; wherein L221 is substituted with either an A, I, or V; wherein W222 is either an F, or Y; wherein D223 is substituted with an E; wherein I224 is substituted with either an A, V, or L; wherein L225 is substituted with either an A, I, or V; wherein I226 is substituted with either an A, V, or L; wherein E227 is substituted with a D; wherein A228 is substituted with either a G, I, L, M, S, T, or V; wherein T229 is substituted with either an A, G, M, or S; wherein Y230 is either an F, or W; wherein N231 is substituted with a Q; wherein R232 is substituted with either a K, or H; wherein T233 is substituted with either an A, G, M, or S; wherein L234 is substituted with either an A, I, or V; wherein I235 is substituted with either an A, V, or L; wherein G236 is substituted with either an A, M, S, or T; wherein C237 is a C; wherein Q238 is substituted with a N; wherein T239 is substituted with either an A, G, M, or S; wherein H240 is substituted with either a K, or R; wherein S241 is substituted with either an A, G, M, or T; wherein G242 is substituted with either an A, M, S, or T; wherein E243 is substituted with a D; wherein K244 is substituted with either a R, or H; wherein I245 is substituted with either an A, V, or L; wherein L246 is substituted with either an A, I, or V; wherein E247 is substituted with a D; wherein N248 is substituted with a Q; wherein G249 is substituted with either an A, M, S, or T; wherein L250 is substituted with either an A, I, or V; wherein V251 is substituted with either an A, I, or L; wherein E252 is substituted with a D; wherein G253 is substituted with either an A, M, S, or T; wherein H254 is substituted with either a K, or R; wherein A255 is substituted with either a G, I, L, M, S, T, or V; wherein Y256 is either an F, or W; wherein T257 is substituted with either an A, G, M, or S; wherein L258 is substituted with either an A, I, or V; wherein T259 is substituted with either an A, G, M, or S; wherein G260 is substituted with either an A, M, S, or T; wherein I261 is substituted with either an A, V, or L; wherein R262 is substituted with either a K, or H; wherein K263 is substituted with either a R, or H; wherein V264 is substituted with either an A, I, or L; wherein T265 is substituted with either an A, G, M, or S; wherein C266 is a C; wherein K267 is substituted with either a R, or H; wherein H268 is substituted with either a K, or R; wherein R269 is substituted with either a K, or H; wherein P270 is a P; wherein E271 is substituted with a D; wherein Y272 is either an F, or W; wherein L273 is substituted with either an A, I, or V; wherein V274 is substituted with either an A, I, or L; wherein K275 is substituted with either a R, or H; wherein L276 is substituted with either an A, I, or V; wherein R277 is substituted with either a K, or H; wherein N278 is substituted with a Q; wherein P279 is a P; wherein W280 is either an F, or Y; wherein G281 is substituted with either an A, M, S, or T; wherein K282 is substituted with either a R, or H; wherein V283 is substituted with either an A, I, or L; wherein E284 is substituted with a D; wherein W285 is either an F, or Y; wherein K286 is substituted with either a R, or H; wherein G287 is substituted with either an A, M, S, or T; wherein D288 is substituted with an E; wherein W289 is either an F, or Y; wherein S290 is substituted with either an A, G, M, or T; wherein D291 is substituted with an E; wherein S292 is substituted with either an A, G, M, or T; wherein S293 is substituted with either an A, G, M, or T; wherein S294 is substituted with either an A, G, M, or T; wherein K295 is substituted with either a R, or H; wherein W296 is either an F, or Y; wherein E297 is substituted with a D; wherein L298 is substituted with either an A, I, or V; wherein L299 is substituted with either an A, I, or V; wherein S300 is substituted with either an A, G, M, or T; wherein P301 is a P; wherein K302 is substituted with either a R, or H; wherein E303 is substituted with a D; wherein K304 is substituted with either a R, or H; wherein I305 is substituted with either an A, V, or L; wherein L306 is substituted with either an A, I, or V; wherein L307 is substituted with either an A, I, or V; wherein L308 is substituted with either an A, I, or V; wherein R309 is substituted with either a K, or H; wherein K310 is substituted with either a R, or H; wherein D311 is substituted with an E; wherein N312 is substituted with a Q; wherein D313 is substituted with an E; wherein G314 is substituted with either an A, M, S, or T; wherein E315 is substituted with a D; wherein F316 is substituted with either a W, or Y; wherein W317 is either an F, or Y; wherein M318 is substituted with either an A, G, S, or T; wherein T319 is substituted with either an A, G, M, or S; wherein L320 is substituted with either an A, I, or V; wherein Q321 is substituted with a N; wherein D322 is substituted with an E; wherein F323 is substituted with either a W, or Y; wherein K324 is substituted with either a R, or H; wherein T325 is substituted with either an A, G, M, or S; wherein H326 is substituted with either a K, or R; wherein F327 is substituted with either a W, or Y; wherein V328 is substituted with either an A, I, or L; wherein L329 is substituted with either an A, I, or V; wherein L330 is substituted with either an A, I, or V; and/or wherein V331 is substituted with either an A, I, or L of SEQ ID NO:54 in addition to any combination thereof. Other suitable substitutions within the CAN-12v1 active site domain are encompassed by the present invention and are referenced elsewhere herein. The present invention also encompasses the use of these CAN-12v1 active site domain conservative amino acid substituted polypeptides as immunogenic and/or antigenic epitopes as described elsewhere herein.

For purposes of the present invention, by "at least a portion of" is meant all or any part of the CAN-12v1 active site domain corresponding to the analogous amino acids of the CAN-12 active site domain defined by the structure coordinates according to Table IV (e.g., fragments thereof). More preferred are molecules comprising all or any parts of the CAN-12v1 active site domain, corresponding to the analogous amino acids of the CAN-12 active site domain defined by the structure coordinates according to Table IV, or a mutant or homologue of said molecule or molecular complex. By mutant or homologue of the molecule it is meant a molecule that has a root mean square deviation from the backbone atoms of said CAN-12v1 amino acids of not more than 4.5 Angstroms, and preferably not more than 3.5 Angstroms.

The term "root mean square deviation" means the square root of the arithmetic mean of the squares of the deviations from the mean. It is a term that expresses the deviation or variation from a trend or object. For the purposes of the present invention, the "root mean square deviation" defines the variation in the backbone of a protein from the relevant portion of the backbone of the AR portion of the complex as defined by the structure coordinates described herein.

A preferred embodiment is a machine-readable data storage medium that is capable of displaying a graphical three-dimensional representation of a molecule or molecular complex that is defined by the structure coordinates of all of the amino acids in Table IV +/− a root mean square deviation from the backbone atoms of those amino acids of not more than 4.0 HANG, preferably 3.0 HANG.

The structure coordinates of a CAN-12 homology model, including portions thereof, is stored in a machine-readable storage medium. Such data may be used for a variety of purposes, such as drug discovery.

Accordingly, in one embodiment of this invention is provided a machine-readable data storage medium comprising a data storage material encoded with the structure coordinates set forth in Table IV.

One embodiment utilizes System 10 as disclosed in WO 98/11134, the disclosure of which is incorporated herein by reference in its entirety. Briefly, one version of these embodiments comprises a computer comprising a central processing unit ("CPU"), a working memory which may be, e.g., RAM (random-access memory) or "core" memory, mass storage memory (such as one or more disk drives or CD-ROM drives), one or more cathode-ray tube ("CRT") display terminals, one or more keyboards, one or more input lines, and one or more output lines, all of which are interconnected by a conventional bisectional system bus.

Input hardware, coupled to the computer by input lines, may be implemented in a variety of ways. Machine-readable data of this invention may be inputted via the use of a modem or modems connected by a telephone line or dedicated data line. Alternatively or additionally, the input hardware may comprise CD-ROM drives or disk drives. In conjunction with a display terminal, keyboard may also be used as an input device.

Output hardware, coupled to the computer by output lines, may similarly be implemented by conventional devices. By way of example, output hardware may include a CRT display terminal for displaying a graphical representation of a region or domain of the present invention using a program such as QUANTA as described herein. Output hardware might also include a printer, so that hard copy output may be produced, or a disk drive, to store system output for later use.

In operation, the CPU coordinates the use of the various input and output devices, coordinates data accesses from mass storage, and accesses to and from the working memory, and determines the sequence of data processing steps. A number of programs may be used to process the machine-readable data of this invention. Such programs are discussed in reference to the computational methods of drug discovery as described herein. Specific references to components of the hardware system are included as appropriate throughout the following description of the data storage medium.

For the purpose of the present invention, any magnetic data storage medium which can be encoded with machine-readable data would be sufficient for carrying out the storage requirements of the system. The medium could be a conventional floppy diskette or hard disk, having a suitable substrate, which may be conventional, and a suitable coating, which may be conventional, on one or both sides, containing magnetic domains whose polarity or orientation could be altered magnetically, for example. The medium may also have an opening for receiving the spindle of a disk drive or other data storage device.

The magnetic domains of the coating of a medium may be polarized or oriented so as to encode in a manner which may be conventional, machine readable data such as that described herein, for execution by a system such as the system described herein.

Another example of a suitable storage medium which could also be encoded with such machine-readable data, or set of instructions, which could be carried out by a system such as the system described herein, could be an optically-readable data storage medium. The medium could be a conventional compact disk read only memory (CD-ROM) or a rentable medium such as a magneto-optical disk which is optically readable and magneto-optically writ able. The medium preferably has a suitable substrate, which may be conventional, and a suitable coating, which may be conventional, usually of one side of substrate.

In the case of a CD-ROM, as is well known, the coating is reflective and is impressed with a plurality of pits to encode the machine-readable data. The arrangement of pits is read by reflecting laser light off the surface of the coating. A protective coating, which preferably is substantially transparent, is provided on top of the reflective coating.

In the case of a magneto-optical disk, as is well known, the coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

Thus, in accordance with the present invention, data capable of displaying the three dimensional structure of the CAN-12 homology model, or portions thereof and their structurally similar homologues is stored in a machine-readable storage medium, which is capable of displaying a graphical three-dimensional representation of the structure. Such data may be used for a variety of purposes, such as drug discovery.

For the first time, the present invention permits the use of structure-based or rational drug design techniques to design, select, and synthesize chemical entities that are capable of modulating the biological function of CAN-12v1.

Accordingly, the present invention is also directed to the design of small molecules which imitates the structure of the CAN-12v1 active site domain (SEQ ID NO:92), or a portion thereof, corresponding to the analogous amino acids of the CAN-12 active site domain defined by the structure provided in Table IV. Alternatively, the present invention is directed to the design of small molecules which may bind to at least part of the CAN-12v1 active site domain (SEQ ID NO:92), or some portion thereof. For purposes of this invention, by CAN-12v1 active site domain, it is also meant to include mutants or homologues thereof. In a preferred embodiment, the mutants or homologues have at least 25% identity, more preferably 50% identity, more preferably 75% identity, and most preferably 90% identity to SEQ ID NO:92. In this context, the term "small molecule" may be construed to mean any molecule described known in the art or described elsewhere herein, though may include, for example, peptides, chemicals, carbohydrates, nucleic acids, PANS, and any derivatives thereof.

The three-dimensional model structure of CAN-12v1, corresponding to the structure coordinates of the analogous amino acids of the CAN-12 polypeptide, will also provide methods for identifying modulators of biological function. Various methods or combination thereof can be used to identify these compounds.

For example, test compounds can be modeled that fit spatially into the active site domain in CAN-12v1 embodied by the sequence from about R90 to about amino acid C94, from about amino acid G99 to about amino acid L104, from about amino acid Q196 to about amino acid S198, from about amino acid M210 to about amino acid I212, from about amino acid G236 to about amino acid H240, from about amino acid E252 to about amino acid Y256, from about amino acid N278 to about amino acid K282, from about amino acid V328 to about amino acid V331, or some portion thereof, of SEQ ID NO:54 (corresponding to SEQ ID NO:92), in accordance with the structural coordinates of the corresponding amino acids of the CAN-12 polypeptide of Table IV.

Structure coordinates of the active site domain in CAN-12v1 defined by the amino acids from about R90 to about amino acid C94, from about amino acid G99 to about amino acid L104, from about amino acid Q196 to about amino acid S198, from about amino acid M210 to about amino acid I212, from about amino acid G236 to about amino acid H240, from about amino acid E252 to about amino acid Y256, from about amino acid N278 to about amino acid K282, from about amino acid V328 to about amino acid V331 of SEQ ID NO:54, can also be used to identify structural and chemical features. Identified structural or chemical features can then be employed to design or select compounds as potential CAN-12v1 modulators. By structural and chemical features it is meant to include, but is not limited to, van dear Waals interactions, hydrogen bonding interactions, charge interaction, hydrophobic bonding interaction, and dipole interaction. Alternatively, or in conjunction with, the three-dimensional structural model can be employed to design or select compounds as potential CAN-12v1 modulators. Compounds identified as potential CAN-12v1 modulators can then be synthesized and screened in an assay characterized by binding of a test compound to the CAN-12v1, or in characterizing the ability of CAN-12v1 to modulate a protease target in the presence of a small molecule. Examples of assays useful in screening of potential CAN-12v1 modulators include, but are not limited to, screening in silico, in vitro assays and high throughput assays. Finally, these methods may also involve modifying or replacing one or more amino acids at amino acid positions, C101, H254, and/or N278 of SEQ ID NO:54 in accordance with the structure coordinates of the corresponding amino acids of CAN-12 as provided in Table IV.

However, as will be understood by those of skill in the art upon this disclosure, other structure based design methods can be used. Various computational structure based design methods have been disclosed in the art.

For example, a number of computer modeling systems are available in which the sequence of the CAN-12v1 and the CAN-12 structure (i.e., atomic coordinates of CAN-12 and/or the atomic coordinates of the active site domain as provided in Table IV, or the corresponding amino acids of CAN-12v1 which are identical to the same region of CAN-12 and for which the same coordinates may be relied thereon) can be input. This computer system then generates the structural details of one or more these regions in which a potential CAN-12v1 modulator binds so that complementary structural details of the potential modulators can be determined. Design in these modeling systems is generally based upon the compound being capable of physically and structurally associating with CAN-12v1. In addition, the compound must be able to assume a confirmation that allows it to associate with CAN-12v1. Some modeling systems estimate the potential inhibitory or binding effect of a potential CAN-12v1 modulator prior to actual synthesis and testing.

Methods for screening chemical entities or fragments for their ability to associate with a given protein target are also well known. Often these methods begin by visual inspection of the binding site on the computer screen. Selected fragments or chemical entities are then positioned in the active site domain of CAN-12v1. Docking is accomplished using software such as INSIGHTS, QUANTA and SYBYL, following by energy minimization and molecular dynamics with standard molecular mechanic forcefields such as CHARMM and AMBER. Examples of computer programs which assist in the selection of chemical fragment or chemical entities useful in the present invention include, but are not limited to, GRID (Good ford, 1985), AUTO DOCK (Goods ell, 1990), and DOCK (Kuntz et al. 1982).

Upon selection of preferred chemical entities or fragments, their relationship to each other and CAN-12v1 can be visualized and then assembled into a single potential modulator. Programs useful in assembling the individual chemical entities include, but are not limited to CAVEAT (Bartlett et al. 1989) and 3D Database systems (Martin1992).

Alternatively, compounds may be designed de novo using either an empty active site or optionally including some portion of a known inhibitor. Methods of this type of design include, but are not limited to LODI (Bohm 1992) and LeapFrog (Tripods Associates, St. Louis Mo.).

In addition, CAN-12v1 is overall well suited to modern methods including combinatorial chemistry.

Programs such as DOCK (Kuntz et al. 1982) can be used with the atomic coordinates from the homology model to identify potential ligands from databases or virtual databases which potentially bind CAN-12 active site domain, and which may therefore be suitable candidates for synthesis and testing.

Additionally, the three-dimensional homology model of CAN-12 will aid in the design of mutants with altered biological activity for the CAN-12v1 polypeptide.

The following are encompassed by the present invention: a machine-readable data storage medium, comprising a data storage material encoded with machine readable data, wherein the data is defined by the structure coordinates of the model CAN-12 according to Table IV or a homologue of said model, wherein said homologue comprises backbone atoms that have a root mean square deviation from the backbone atoms of the complex of not more than 4.5 Å, preferably not more than 4.0 Å, most preferably not more than 3.5 Å, and even more preferably not more than 3.0 Å; and a machine-readable data storage medium, wherein said molecule is defined by the set of structure coordinates of the model for CAN-12 according to Table IV, or a homologue of said molecule, said homologue having a root mean square deviation from the backbone atoms of said amino acids of not more than 4.5 Å, preferably not more than 4.0 Å, most preferably not more than 3.5 Å, and even more preferably not more than 3.0 Å; a model comprising all or any part of the model defined by structure coordinates of CAN-12 according to Table IV, or a mutant or homologue of said molecule or molecular complex.

In a further embodiment, the following are encompassed by the present invention: a method for identifying a mutant of CAN-12v1 with altered biological properties, function, or reactivity, the method comprising any combination of steps of: use of the model or a homologue of said model according to Table IV, for the design of protein mutants with altered biological function or properties which exhibit any combination of therapeutic effects provided elsewhere herein; and use of the model or a homologue of said model, for the design of a protein with mutations in the active site domain comprised of the amino acids from about R90 to about amino acid C94, from about amino acid G99 to about amino acid L104, from about amino acid Q196 to about amino acid S198, from about amino acid M210 to about amino acid I212, from about amino acid G236 to about amino acid H240, from about amino acid E252 to about amino acid Y256, from about amino acid N278 to about amino acid K282, from about amino acid V328 to about amino acid V331 of SEQ ID NO:54 according to the corresponding amino acids of CAN-12 as provided in Table IV with altered biological function or properties which exhibit any combination of therapeutic effects provided elsewhere herein.

In further preferred embodiments, the following are encompassed by the present invention: a method for identifying modulators of CAN-12v1 biological properties, function, or reactivity, the method comprising any combination of steps of: modeling test compounds that overlay spatially into the active site domain defined by all or any portion of residues from about R90 to about amino acid C94, from about amino acid G99 to about amino acid L104, from about amino acid Q196 to about amino acid S198, from about amino acid M210 to about amino acid I212, from about amino acid G236 to about amino acid H240, from about amino acid E252 to about amino acid Y256, from about amino acid N278 to about amino acid K282, from about amino acid V328 to about amino acid V331 of SEQ ID NO:54 in reference to the corresponding amino acids of CAN-12 according to Table IV, or using a homologue or portion thereof.

The present invention encompasses using the structure coordinates as set forth herein to identify structural and chemical features of the CAN-12v1 polypeptide; employing identified structural or chemical features to design or select compounds as potential CAN-12v1 modulators; employing the three-dimensional structural model to design or select compounds as potential CAN-12v1 modulators; synthesizing the potential CAN-12v1 modulators; screening the potential CAN-12v1 modulators in an assay characterized by binding of a protein to the CAN-12v1; selecting the potential CAN-12v1 modulator from a database; designing the CAN-12v1 modulator de novo; and/or designing said CAN-12v1 modulator from a known modulator activity.

Many polynucleotide sequences, such as EST sequences, are publicly available and accessible through sequence databases. Some of these sequences are related to SEQ ID NO: 53 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 2081 of SEQ ID NO:53, b is an integer between 15 to 2095, where both a and b correspond to the positions of nucleotide residues shown in SEQ ID NO:53, and where b is greater than or equal to a+14.

In one embodiment, a CAN12.v1 polypeptide comprises a portion of the amino sequence depicted in FIGS. 8A–C. In another embodiment, a CAN12.v1 polypeptide comprises at least 4, 5, 6, 7, 8, 9, 10, 11, 12, 13, 14, 15, 16, 17, 18, 19 or 20 amino acids of the amino sequence depicted in FIGS. 8A–C. In further embodiments, the CAN12.v1 polypeptide does not consist of the sequence ALLEKAYAKL (SEQ ID NO:141), and/or ALLEKAYAKLSGSYE. (SEQ ID NO:142).

Features of the Polypeptide Encoded by Gene No:3

The polypeptide of this gene provided as SEQ ID NO:56 (FIGS. 9A–C), encoded by the polynucleotide sequence according to SEQ ID NO:55 (FIGS. 9A–C), and/or encoded by the polynucleotide contained within the deposited clone, CAN-12v2, has significant homology at the nucleotide and amino acid level to a number of calpains, which include, for example, the human CAN10 protein (type II diabetes linked) (hCAN10; Genbank Accession No: gi|NP_075574; SEQ ID NO:3); the human CAN5 protein (hCAN5; Genbank Accession No: gi|NP_004046; SEQ ID NO:4); the large catalytic subunit of the human CALPAIN 1 protein (also referred to as Calcium-Activated Neutral Proteinase, CANP, μ-TYPE) (hCAN1; Genbank Accession No: gi|12408656; SEQ ID NO:5); the large subunit of the human calpain 3 protein (EC 3.4.22.17) (also referred to as CALPAIN L3, CALPAIN P94, Calcium-Activated Neutral Proteinase 3, CANP 3; muscle-specific calcium-activated neutral protease 3 large subunit) (hCAN3; Genbank Accession No: gi|4557405; SEQ ID NO:6); the large catalytic subunit of the mouse CALPAIN 1 protein (also referred to as Calcium-Activated Neutral Proteinase) (CANP) μ-TYPE) (mCALPAIN1; Genbank Accession No: gi|O88666; SEQ ID NO:7); the mouse CALPAIN LP82 (mLP82; Genbank Accession No: gil3661585; SEQ ID NO:8); the rat stomach-specific calcium-activated neutral protease large subunit, NCL2 protein (rNCL2; Genbank Accession No: gilNP_006606; SEQ ID NO:9); the human CAN11 protein (hCAN11; Genbank Accession No: gilNP_008989; SEQ ID NO:10); the human CAN2 protein (hCAN2; Genbank Accession No: gil4502563; SEQ ID NO:11); and the human CAN9 protein (hCAN9; Genbank Accession No: gil5729758; SEQ ID NO:12). An alignment of the CAN-12v2 polypeptide with these proteins is provided in FIGS. 2A–E. Based upon such strong conservation, the inventors have ascribed the CAN-12v2 polypeptide as having proteolytic activity, preferably calpain activity.

The CAN-12v2 polypeptide was determined to have 28.8% identity and 35.7% similarity with the human CAN10 protein (type, II diabetes linked) (hCAN10; Genbank Accession No: gilNP_075574; SEQ ID NO:3); to have 33.3% identity and 45.1% similarity with the human CAN5 protein (hCAN5; Genbank Accession No: gilNP_004046; SEQ ID NO:4); to have 38.3% identity and 46.6% similarity with the large catalytic subunit of the human CALPAIN 1 protein (also referred to as Calcium-Activated Neutral Proteinase, CANP, μ-TYPE) (hCAN1; Genbank Accession No: gil12408656; SEQ ID NO:5); to have 41.3% identity and 49.8% similarity with the large subunit of the human calpain 3 protein (EC 3.4.22.17) (also referred to as CALPAIN L3, CALPAIN P94, Calcium-Activated Neutral Proteinase 3, CANP 3; muscle-specific calcium-activated neutral protease 3 large subunit) (hCAN3; Genbank Accession No: gil4557405; SEQ ID NO:6); to have 39.6% identity and 47.6% similarity with the large catalytic subunit of the mouse CALPAIN 1 protein (also referred to as Calcium-Activated Neutral Proteinase) (CANP) μ-TYPE) (mCALPAIN1; Genbank Accession No: gilO88666; SEQ ID NO:7); to have 40.6% identity and 48.8% similarity with the mouse CALPAIN LP82 (mLP82; Genbank Accession No: gil3661585; SEQ ID NO:8); to have 36.3% identity and 44.9% similarity with the rat stomach-specific calcium-activated neutral protease large subunit, NCL2 protein (rNCL2; Genbank Accession No: gilNP_006606; SEQ ID NO:9); to have 38.8% identity and 47.3% similarity with the human CAN 11 protein (hCAN11; Genbank Accession No: gilNP_008989; SEQ ID NO:10); to have 37.9% identity and 47.3% similarity with the human CAN2 protein (hCAN2; Genbank Accession No: gil4502563; SEQ ID NO:11); and to have 40.7% identity and 49.8% similarity with the human CAN9 protein (hCAN9; Genbank Accession No: gil5729758; SEQ ID NO:12).

The human CAN10 protein (type II diabetes linked) (hCAN10; Genbank Accession No: gilNP_075574; SEQ ID NO:3) is a human calpain gene that encodes a large calpain subunit. CAN10 is an atypical calpain in that it lacks the calmodulin-like calcium-binding domain and instead has a divergent C-terminal domain. CAN10 is similar in organization to calpains 5 and 6 and is associated with type 2 or non-insulin-dependent diabetes mellitus (NIDDM) and located within the NIDDM1 chromosomal region (Nat. Genet. 26 (2), 163–175 (2000)).

The large subunit of the human calpain 3 protein (EC 3.4.22.17) (also referred to as CALPAIN L3, CALPAIN P94, Calcium-Activated Neutral Proteinase 3, CANP 3; muscle-specific calcium-activated neutral protease 3 large subunit) (hCAN3; Genbank Accession No: gil4557405; SEQ ID NO:6) is a muscle-specific member of the calpain large subunit family. Loss of CAPN3 function has been associated with limb-girdle muscular dystrophies type 2A (Cell 81 (1), 27–40 (1995)).

The human CAN9 protein (hCAN9; Genbank Accession No: gil5729758; SEQ ID NO:12) is a calpain that is expressed predominantly in stomach and small intestine and is thought to have specialized functions in the digestive tract, and be associated with gastric cancer.(Biol. Chem. 379 (2), 175–183 (1998); and Jpn. J. Cancer Res. 91 (5), 459–463 (2000)).

As described-above, the CAN-12v2 polypeptide was found to have significant sequence homology with calpains, particularly members of the m-calpain family. A conserved peptide signature of Qx3(G,E)xC(Y,W)x2(S,T,A,G,C)(S,T,A,G,C,V)Qx{3}(G)xC(W)x{2}(A)(A) (referred to as a thiol (cysteine) protease active site domain) common to most calpain family members is found in the protein sequence of CAN-12v2 from amino acid 90 to amino acid 111 of SEQ ID NO:56 (FIGS. 9A–C). Protein threading and molecular modeling of CAN-12v2 suggests that CAN-12v2 has a structural fold similar to representative m-calpains. Moreover, the structural and threading alignments of the present invention suggest that amino acids 101 ("C"), 254 ("H"), and 278 ("N") of SEQ ID NO:56 (FIGS. 9A–C) may represent the catalytic amino acids within the active site domain. Thus, based upon the sequence and structural homology to known calpains, particularly the presence of the thiol cysteine protease active site domain, the novel CAN-12v2 is believed to represent a novel human calpain.

In confirmation of the strong homology to known calpains, the CAN-12v2 polypeptide was determined to have several conserved catalytic amino acids at amino acid C101, H254, and N278 of SEQ ID NO:56 (FIGS. 9A–C). As discussed more particularly herein, calpains are a group of structurally diverse, high molecular weight (400 to 500 amino acids) proteins that have a catalytic cysteine amino acid and one or more calcium binding domains. Despite the structural heterogeneity, calpains share some well defined structural-functional characteristics, particularly in their active site domains.

In preferred embodiments, the CAN-12v2 polypeptide of the present invention is directed to a polypeptide having structural similarity to calpains.

Based upon the strong homology to members of the calpain family, the CAN-12v2 polypeptide is expected to share at least some biological activity with calpains, preferably with m-calpain family members, and more preferable to the large subunits of m-calpain family members, in addition to other calpains and calpain subunits referenced herein and/or otherwise known in the art.

Expression profiling designed to measure the steady state mRNA levels encoding the CAN-12 polypeptide showed predominately high expression levels in spinal cord tissue; significantly high expression in lymph node and thymus, and to a lesser extent, in spleen tissue (See FIG. 4).

Expanded analysis of CAN-12v1 and CAN-12v2 expression levels by TAQMAN™ quantitative PCR (see FIG. 12) confirmed that the CAN-12 polypeptide is expressed in the lymph gland. However, the TAQMAN™ quantitative PCR determined that the CAN-12v1 and CAN-12v2 polypeptides are primarily expressed in the esophagus. In fact, with the exception of the lymph gland, the steady state mRNA level of CAN-12v1 and CAN-12v2 was approximately 2700 times higher in the esophagus than in all other tissues tested. These data suggest modulators of the CAN-12v1 and CAN-12v2 polynucleotides and polypeptides may be useful for the treatment, detection, and/or amelioration of the following, non-limiting diseases and disorders associated with the esophagus: dysphagia, cricoharyngeal incoordination, esophageal carcinoma, esophageal webs, achalasia, symptomatic diffuse esophageal spasm, gastroesophageal reflux, and/or corrosive esophagitis.

The polynucleotides encoding the CAN-12 polypeptide of the present invention were used to determine the chromosomal localization of the calpain12 gene. which encodes the CAN-12, CAN-12v1, and CAN-12v2 polypeptides of the present invention. Polynucleotides corresponding to CAN-12 (SEQ ID NO:1) were shown to localize to chromosome 2, specifically 2p16-p21. The comparison of the chromosomal location of the calpain12 gene with the location of chromosomal regions which have been shown to be associated with specific diseases or conditions, e.g. by linkage analysis, can be indicative of diseases in which calpain12 may play a role. Interestingly, a whole-genome linkage scan in multiple sclerosis families (Ebers et al. A full genome search in multiple sclerosis. Nature Genet. 13: 472–476, 1996.) identified 5 susceptibility loci on chromosomes 2, 3, 5, 11, and X. In particular, an association was identified with marker D2S119 on chromosome 2 and MS. The localization of the D2S119 marker was further delineated to 2p16-p21 based on a radiation hybrid linkage map retrieved from an online query at an NCBI web site. Since the map of calpain 12 and the susceptibility marker D2S119 overlaps, it is reasonable to postulate that calpain 12 may contribute to MS. Furthermore, the transcription profile of calpain12 indicated a prominent expression in spinal cord, and implication of calpains in MS has been suggested (Shields DC et al. A putative mechanism of demyelination in multiple sclerosis by a proteolytic enzyme, calpain. Proc Nati Acad Sci U S A. 96:11486–91.1999).

The CAN-12v2 polynucleotides and polypeptides of the present invention, including agonists and/or fragments thereof, have uses that include modulating cellular adhesion events, cellular proliferation, and inflammation, in various cells, tissues, and organisms, and particularly in mammalian spinal cord tissue, lymph node, thymus, and spleen tissue, preferably human tissue. CAN-12v2 polynucleotides and polypeptides of the present invention, including agonists and/or fragments thereof, may be useful in diagnosing, treating, prognosing, and/or preventing neural, immune, hematopoietic, and/or proliferative diseases or disorders.

The strong homology to human calpains, particularly m-calpains, combined with the predominate localized expression in esophagus tissue suggests the CAN-12 polynucleotides and polypeptides may be useful in treating, diagnosing, prognosing, and/or preventing gastrointestinal diseases, particularly esophageal diseases and/or disorders which include the following non-limiting examples: aberrant transport of food bolus from the mouth to the stomach, aberrant prevention of retrograde flow of gastrointestinal contents, aberrant esophageal peristaltic contractions, pyrosis, painful swallowing, reflux esophagitis, esophageal motility disorders, esophageal spasms, diffuse esophageal spasm, atypical chest pain, regurgitation, oropharyngeal paralysis, nasal regurgitation, dysphagia, cricopharyngeal bar, globus pharyngeus, achalasia, motor disorders of the esophageal smooth muscle, scleroderma esophagus, gastroesophageal reflux disease (GERD), esophagitis, Barrett's esophagus, viral esophagitis, Herpes simplex virus mediated viral esophagitis, Varicella-zoster virus mediated viral esophagitis, Cytomegalovirus mediated viral esophagitis, bacterial esophagitis, *Lactobacillus* mediated bacterial esophagitis, *Candida* mediated esophagitis, radiation esophagitis, corrosive esophagitis, pill-induced esophagitis, esophagitis associated with mucocutaneous and systemic diseases, diverticula, lower esophageal mucosal ring, lower esophageal muscular ring, hiatal hernia, paraesophageal hernia, esophageal rupture, and/or Mallory-Weiss Syndrome.

Although calpains are typically associated primarily with neurogenerative conditions, their association in gastrointestinal tissues has precedence. For example, the human CAN9 protein (hCAN9; Genbank Accession No: gil5729758; SEQ ID NO:12) is predominately expressed in the stomach and small intestine and is thought to be associated with gastric cancers.

The strong homology to human calpains, particularly m-calpains, combined with the localized expression in spinal cord tissue suggests the CAN-12v2 polynucleotides and polypeptides may be useful in treating, diagnosing, prognosing, and/or preventing neural diseases, neurodegenerative disease states, behavioral disorders, or inflammatory conditions. Representative uses are described in the "Neurological Diseases", "Regeneration" and "Hyperproliferative Disorders" sections below, in the Examples, and elsewhere herein. Briefly, the uses include, but are not limited to the detection, treatment, and/or prevention of Alzheimer's Disease, Parkinson's Disease, Huntington's Disease, Tourette Syndrome, meningitis, encephalitis, demyelinating diseases, peripheral neuropathies, neoplasia, trauma, congenital malformations, spinal cord injuries, ischemia and infarction, aneurysms, hemorrhages, schizophrenia, mania, dementia, paranoia, obsessive compulsive disorder, depression, panic disorder, learning disabilities, ALS, psychoses, autism, and altered behaviors, including disorders in feeding, sleep patterns, balance, and perception. In addition, elevated expression of this gene product in regions of the brain indicates it plays a role in normal neural function. Potentially, this gene product is involved in synapse formation, neurotransmission, learning, cognition, homeostasis, or neuronal differentiation or survival. Furthermore, the protein may also be used to determine biological activity, to raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

Alternatively, the strong homology to human calpains, particularly m-calpains, combined with the localized expression in lymph node, thymus, and spleen tissue suggests the CAN-12v2 polynucleotides and polypeptides may be useful in treating, diagnosing, prognosing, ameliorating, and/or preventing immune diseases and/or disorders. Representative uses are described in the "Immune Activity" and "Infectious Disease" sections below, and elsewhere herein. Briefly, the strong expression in immune tissue indicates a role in regulating the proliferation; survival; differentiation; and/or activation of hematopoietic cell lineages, including blood stem cells. The CAN-12v2 polypeptide may also be useful as a preventative agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product may be useful in the expansion of stem cells and committed progenitors of various blood lineages, and in the differentiation and/or proliferation of various cell types.

Moreover, the protein would be useful in the detection, treatment, and/or prevention of a variety of vascular disorders and conditions, which include, but are not limited to miscrovascular disease, vascular leak syndrome, aneurysm, stroke, embolism, thrombosis, coronary artery disease, arteriosclerosis, and/or atherosclerosis. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

In addition, antagonists of the CAN-12v2 polynucleotides and polypeptides may have uses that include diagnosing, treating, prognosing, and/or preventing diseases or disorders related to hyper calpain activity, which may include immune and/or proliferative diseases or disorders, particularly thrombosis, embolism, and other blood disorders. Therapeutic and/or pharmaceutical compositions comprising the CAN-12v2 polypeptides may be formulated to comprise heparin.

In addition, antagonists of the CAN-12v2 polynucleotides and polypeptides may have uses that include diagnosing, treating, ameliorating, prognosing, and/or preventing diseases or disorders related to hyper calpain activity, which may include neuronal excitotoxicity, ischemic stroke, hemoragic stroke, hypoxic stress, trauma, cell destruction, spinal cord injury following trauma, degeneration of vulnerable hippocampal neurons after ischemia, reovirus-induced apoptosis, viral-induced induced myocarditis, acute and chronic inflammation, cataract formation, multiple sclerosis, demyelenating disorders, acoustic trauma, hearing loss caused by noise, neuronal damage, cardiac ischemic damage, and/or hepatocyte necrosis during and following anoxia.

CAN-12v2 polynucleotides and polypeptides, including fragments and/or antagonsists thereof, may have uses which include modulating development, differentiation, cellular transformation in response to cell signaling, cell-cell and/or cell-extracellular matrix interactions, clustering of the integrin receptor aIIb3, modulating in long term potentiation (memory), modulating neurite outgrowth, modulating cortical lamination activation of protein kinases and phosphatases, remodeling and disassembling the cytoskeleton, cell cycle modulation, in addition, to ameliorating, preventing, and/or treating limb-girdle muscular dystrophy (LGMD), insulin resistance in diabetics, Alzheimer's disease, Multiple sclerosis, Huntington's disease, Parkinson's disease and amyotrophy.

Moreover, CAN-12v2 polynucleotides and polypeptides, including fragments and agonists thereof, may have uses which include treating, diagnosing, prognosing, and/or preventing hyperproliferative disorders, particularly of the neural and immune systems. Such disorders may include, for example, cancers, and metastatic conditions.

CAN-12v2 polynucleotides and polypeptides, including fragments and/or antagonsists thereof, may have uses which include identification of modulators of CAN-12v2 function including antibodies (for detection or neutralization), naturally-occurring modulators and small molecule modulators. Antibodies to domains (including CAN-12v2 epitopes provided herein) of the CAN-12v2 protein could be used as diagnostic agents of inflammatory conditions in patients, are useful in monitoring the activation and presence of cognate proteases, and can be used as a biomarker for the protease involvement in disease states and in the evaluation of inhibitors of the cognate protease in vivo.

CAN-12v2 polypeptides and polynucleotides are useful for diagnosing diseases related to over or under expression of CAN-12v2 proteins by identifying mutations in the CAN-12v2 gene using CAN-12v2 probes, or determining CAN-12v2 protein or mRNA expression levels. CAN-12v2 polypeptides are also useful for screening for compounds, which affect activity of the protein. Diseases that can be treated with CAN-12v2 include, the following, non-limiting examples: neuro-regeneration, neuropathic pain, obesity, anorexia, HIV infections, cancers, bulimia, asthma, Parkinson's disease, acute heart failure, hypotension, hypertension, osteoporosis, angina pectoris, myocardial infarction, psychotic, immune, metabolic, cardiovascular, and neurological disorders.

The predominate expression in neural tissues, combined with the significant expression in a number of other tissues, suggests the CAN-12v2 polynucleotide and polypeptide of the present invention may be involved in modulating nerve invasion, innervation, nerve maintenance, and potentially myeline sheath maintenance and integrity.

The CAN-12v2 polynucleotides and polypeptides, including fragments and antagonists thereof, may have uses which include detecting, diagnosing, treating, ameliorating, and/or preventing diseases and disorders of the neural system, particularly Alzheimer's disease, either directly or indirectly, in addition to other neural disorders known in the art or provided in the "Neurological Diseases" section herein, such as modulating nerve invasion, innervation, nerve maintenance, potentially myelin sheath maintenance and integrity, encephalomyelitis, autoimmune encephalomyelitis, human T cell leukemia virus type I (HTLV-I)-associated myelopathy/tropical spastic paraparesis (HAM/TSP), and neuro-inflammatory diseases.

Molecular genetic manipulation of the structure of the active site domain, particularly the predicted catalytic amino acids, and of other functional domains in the calpain family (e.g., active site domain binding pocket) enables the production of calpains with tailor-made activities. Thus, the CAN-12v2 polypeptides, and fragments thereof, as well as any homologous product resulting from genetic manipulation of the structure, are useful for NMR-based design of modulators of CAN-12v2 biological activity, and calpains, in general.

CAN-12v2 polypeptides and polynucleotides have additional uses which include diagnosing diseases related to the over and/or under expression of CAN-12v2 by identifying mutations in the CAN-12v2 gene by using CAN-12v2 sequences as probes or by determining CAN-12v2 protein or mRNA expression levels. CAN-12v2 polypeptides may be useful for screening compounds that affect the activity of the protein. CAN-12v2 peptides can also be used for the generation of specific antibodies and as bait in yeast two hybrid screens to find proteins the specifically interact with CAN-12v2 (described elsewhere herein).

The CAN-12v2 polynucleotides and polypeptides, including fragments and agonists thereof, may have uses which include detecting, diagnosing, treating, ameliorating, and/or preventing metabolic diseases and disorders, such as diabetes. Moreover, expressed human CAN-12v2 may be useful in the detection of patients susceptible to diabetes. Also paradigms that would simulate intracellular CAN-12v2 activity would be useful in treating diabetes.

The CAN-12v2 polynucleotides and polypeptides, including fragments thereof, may have uses which include identifying inhibitors of intracellular calpain inhibitors (calpastatins) leading to an effective increase in calpain activity.

Various approaches to detect alterations or allelic variants at the genomic or mRNA level of CAN-12v2, could be used as a diagnostic for identifying MS patients, or individuals susceptible to have MS. It is likely that the CAN-12v2 gene comprises polymorphic sites (i.e. SNPs), with specific alleles which may be associated with MS or other neurodegenerative disorders, or associated with an increased likelihood of developing these diseases. Therefore, the invention provides the CAN-12v2 sequence that can be used to design specific primers for the identification of polymorphisms or mutations in CAN-12v2 of patients affected with MS. The presence of a specific allele variant, such as a SNP allele or SNPs haplotype that renders the subject carrying it more susceptible to develop MS or other related diseases could be identified (e.g. a variant in the CAN-12v2 promoter region that increased transcript levels of CAN-12v2, or mutations in the coding sequence that increased the stability or half-life of the CAN-12v2 protein). Other methods such as Northern-blot analysis could be performed to measure transcript levels using a CAN-12v2 cDNA probe derived from the sequence of the invention.

Although it is believed the encoded polypeptide may share at least some biological activities with human calpains (particularly m-calpains), a number of methods of determining the exact biological function of this clone are either known in the art or are described elsewhere herein. Briefly, the function of this clone may be determined by applying microarray methodology. Nucleic acids corresponding to the CAN-12v2 polynucleotides, in addition to, other clones of the present invention, may be arrayed on microchips for expression profiling. Depending on which polynucleotide probe is used to hybridize to the slides, a change in expression of a specific gene may provide additional insight into the function of this gene based upon the conditions being studied. For example, an observed increase or decrease in expression levels when the polynucleotide probe used comes from diseased neural tissue, as compared to, normal tissue might indicate a function in modulating neural function, for example. In the case of CAN-12v2, spinal cord, lymph node, thymus, and/or spleen tissue should be used to extract RNA to prepare the probe.

In addition, the function of the protein may be assessed by applying quantitative PCR methodology, for example. Real time quantitative PCR would provide the capability of following the expression of the CAN-12v2 gene throughout development, for example. Quantitative PCR methodology requires only a nominal amount of tissue from each developmentally important step is needed to perform such experiments. Therefore, the application of quantitative PCR methodology to refining the biological function of this polypeptide is encompassed by the present invention. In the case of CAN-12v2, a disease correlation related to CAN-12v2 may be made by comparing the mRNA expression level of CAN-I 2v2 in normal tissue, as compared to diseased tissue (particularly diseased tissue isolated from the following: esophagus, spinal cord, lymph node, thymus, and/or spleen tissue). Significantly higher or lower levels of CAN-12v2 expression in the diseased tissue may suggest CAN-12v2 plays a role in disease progression, and antagonists against CAN-12v2 polypeptides would be useful therapeutically in treating, preventing, and/or ameliorating the disease. Alternatively, significantly higher or lower levels of CAN-12v2 expression in the diseased tissue may suggest CAN-12v2 plays a defensive role against disease progression, and agonists of CAN-12v2 polypeptides may be useful therapeutically in treating, preventing, and/or ameliorating the disease. Also encompassed by the present invention are quantitative PCR probes corresponding to the polynucleotide sequence provided as SEQ ID NO:55 (FIGS. 9A–C).

The function of the protein may also be assessed through complementation assays in yeast. For example, in the case of the CAN-12v2, transforming yeast deficient in calpain activity, particularly m-calpain activity, and assessing their ability to grow would provide convincing evidence the CAN-12v2 polypeptide has calpain activity, and possibly m-calpain activity. Additional assay conditions and methods that may be used in assessing the function of the polynucleotides and polypeptides of the present invention are known in the art, some of which are disclosed elsewhere herein.

Alternatively, the biological function of the encoded polypeptide may be determined by disrupting a homologue of this polypeptide in Mice and/or rats and observing the resulting phenotype. Such knock-out experiments are known in the art, some of which are disclosed elsewhere herein.

Moreover, the biological function of this polypeptide may be determined by the application of antisense and/or sense methodology and the resulting generation of transgenic mice and/or rats. Expressing a particular gene in either sense or antisense orientation in a transgenic mouse or rat could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., an esophagus, spinal cord, lymph node, thymus, or spleen specific promoter), or it can be expressed at a specified time of development using an inducible and/or a developmentally regulated promoter.

In the case of CAN-12v2 transgenic mice or rats, if no phenotype is apparent in normal growth conditions, observing the organism under diseased conditions (neural, immune, hematopoietic diseases or disorders, cancers, etc.) may lead to understanding the function of the gene. Therefore, the application of antisense and/or sense methodology to the creation of transgenic mice or rats to refine the biological function of the polypeptide is encompassed by the present invention.

In preferred embodiments, the following N-terminal CAN-12v2 deletion polypeptides are encompassed by the present invention: M1-L697, S2-L697, L3-L697, W4-L697, P5-L697, P6-L697, F7-L697, R8-L697, C9-L697, R10-L697, W11-L697, K12-L697, L13-L697, A14-L697, P15-L697, R16-L697, Y17-L697, S18-L697, R19-L697, R20-L697, A21-L697, S22-L697, P23-L697, Q24-L697, Q25-L697, P26-L697, Q27-L697, Q28-L697, D29-L697, F30-L697, E31-L697, A32-L697, L33-L697, L34-L697, A35-L697, E36-L697, C37-L697, L38-L697, R39-L697, N40-L697, G41-L697, C42-L697, L43-L697, F44-L697, E45-L697, D46-L697, T47-L697, S48-L697, F49-L697, P50-L697, A51-L697, T52-L697, L53-L697, S54-L697, S55-L697, I56-L697, G57-L697, S58-L697, G59-L697, S60-L697, L61-L697, L62-L697, Q63-L697, K64-L697, L65-L697, P66-L697, P67-L697, R68-L697, L69-L697, Q70-

L697, W71-L697, K72-L697, R73-L697, P74-L697, P75-L697, E76-L697, L77-L697, H78-L697, S79-L697, N80-L697, P81-L697, Q82-L697, F83-L697, Y84-L697, F85-L697, A86-L697, K87-L697, A88-L697, K89-L697, R90-L697, L91-L697, D92-L697, L93-L697, C94-L697, Q95-L697, G96-L697, I97-L697, V98-L697, G99-L697, D100-L697, C101-L697, W102-L697, F103-L697, L104-L697, A105-L697, A106-L697, L107-L697, Q108-L697, A109-L697, L110-L697, A111-L697, L112-L697, H113-L697, Q114-L697, D115-L697, I116-L697, L117-L697, S118-L697, R119-L697, V120-L697, V121-L697, P122-L697, L123-L697, N124-L697, Q125-L697, S126-L697, F127-L697, T128-L697, E129-L697, K130-L697, Y131-L697, A132-L697, G133-L697, I134-L697, F135-L697, R136-L697, F137-L697, W138-L697, F139-L697, W140-L697, H141-L697, Y142-L697, G143-L697, N144-L697, W145-L697, V146-L697, P147-L697, V148-L697, V149-L697, I150-L697, D151-L697, D152-L697, R153-L697, L154-L697, P155-L697, V156-L697, N157-L697, E158-L697, A159-L697, G160-L697, Q161-L697, L162-L697, V163-L697, F164-L697, V165-L697, S166-L697, S167-L697, T168-L697, Y169-L697, K170-L697, N171-L697, L172-L697, F173-L697, W174-L697, G175-L697, A176-L697, L177-L697, L178-L697, E179-L697, K180-L697, A181-L697, Y182-L697, A183-L697, K184-L697, L185-L697, S186-L697, G187-L697, S188-L697, Y189-L697, E190-L697, D191-L697, L192-L697, Q193-L697, S194-L697, G195-L697, Q196-L697, V197-L697, S198-L697, E199-L697, A200-L697, L201-L697, V202-L697, D203-L697, F204-L697, T205-L697, G206-L697, G207-L697, V208-L697, T209-L697, M210-L697, T211-L697, I212-L697, N213-L697, L214-L697, A215-L697, E216-L697, A217-L697, H218-L697, G219-L697, N220-L697, L221-L697, W222-L697, D223-L697, I224-L697, L225-L697, I226-L697, E227-L697, A228-L697, T229-L697, Y230-L697, N231-L697, R232-L697, T233-L697, L234-L697, I235-L697, G236-L697, C237-L697, Q238-L697, T239-L697, H240-L697, S241-L697, G242-L697, E243-L697, K244-L697, I245-L697, L246-L697, E247-L697, N248-L697, G249-L697, L250-L697, V251-L697, E252-L697, G253-L697, H254-L697, A255-L697, Y256-L697, T257-L697, L258-L697, T259-L697, G260-L697, I261-L697, R262-L697, K263-L697, V264-L697, T265-L697, C266-L697, K267-L697, H268-L697, R269-L697, P270-L697, E271-L697, Y272-L697, L273-L697, V274-L697, K275-L697, L276-L697, R277-L697, N278-L697, P279-L697, W280-L697, G281-L697, K282-L697, V283-L697, E284-L697, W285-L697, K286-L697, G287-L697, D288-L697, W289-L697, S290-L697, D291-L697, S292-L697, S293-L697, S294-L697, K295-L697, W296-L697, E297-L697, L298-L697, L299-L697, S300-L697, P301-L697, K302-L697, E303-L697, K304-L697, I305-L697, L306-L697, L307-L697, L308-L697, R309-L697, K310-L697, D311-L697, N312-L697, D313-L697, G314-L697, E315-L697, F316-L697, W317-L697, M318-L697, T319-L697, L320-L697, Q321-L697, D322-L697, F323-L697, K324-L697, T325-L697, H326-L697, F327-L697, V328-L697, L329-L697, L330-L697, V331-L697, I332-L697, C333-L697, K334-L697, L335-L697, T336-L697, P337-L697, G338-L697, L339-L697, L340-L697, S341-L697, Q342-L697, E343-L697, A344-L697, A345-L697, Q346-L697, K347-L697, W348-L697, T349-L697, Y350-L697, T351-L697, M352-L697, R353-L697, E354-L697, G355-L697, R356-L697, W357-L697, E358-L697, K359-L697, R360-L697, S361-L697, T362-L697, A363-L697, G364-L697, G365-L697, Q366-L697, R367-L697, Q368-L697, L369-L697, L370-L697, Q371-L697, D372-L697, T373-L697, F374-L697, W375-L697, K376-L697, N377-L697, P378-L697, Q379-L697, F380-L697, L381-L697, L382-L697, S383-L697, V384-L697, W385-L697, R386-L697, P387-L697, E388-L697, E389-L697, G390-L697, R391-L697, R392-L697, S393-L697, L394-L697, R395-L697, P396-L697, C397-L697, S398-L697, V399-L697, L400-L697, V401-L697, S402-L697, L403-L697, L404-L697, Q405-L697, K406-L697, P407-L697, R408-L697, H409-L697, R410-L697, C411-L697, R412-L697, K413-L697, R414-L697, K415-L697, P416-L697, L417-L697, L418-L697, A419-L697, I420-L697, G421-L697, F422-L697, Y423-L697, L424-L697, Y425-L697, R426-L697, M427-L697, N428-L697, K429-L697, Y430-L697, H431-L697, D432-L697, D433-L697, Q434-L697, R435-L697, R436-L697, L437-L697, P438-L697, P439-L697, E440-L697, F441-L697, F442-L697, Q443-L697, R444-L697, N445-L697, T446-L697, P447-L697, L448-L697, S449-L697, Q450-L697, P451-L697, D452-L697, R453-L697, F454-L697, L455-L697, K456-L697, E457-L697, K458-L697, E459-L697, V460-L697, S461-L697, Q462-L697, E463-L697, L464-L697, C465-L697, L466-L697, E467-L697, P468-L697, G469-L697, T470-L697, Y471-L697, L472-L697, I473-L697, V474-L697, P475-L697, C476-L697, I477-L697, L478-L697, E479-L697, A480-L697, H481-L697, Q482-L697, K483-L697, S484-L697, E485-L697, F486-L697, V487-L697, L488-L697, R489-L697, V490-L697, F491-L697, S492-L697, R493-L697, K494-L697, H495-L697, I496-L697, F497-L697, Y498-L697, E499-L697, I500-L697, G501-L697, S502-L697, N503-L697, S504-L697, G505-L697, V506-L697, V507-L697, F508-L697, S509-L697, K510-L697, E511-L697, I512-L697, E513-L697, D514-L697, Q515-L697, N516-L697, E517-L697, R518-L697, Q519-L697, D520-L697, E521-L697, F522-L697, F523-L697, T524-L697, K525-L697, F526-L697, F527-L697, E528-L697, K529-L697, H530-L697, P531-L697, E532-L697, I533-L697, N534-L697, A535-L697, V536-L697, Q537-L697, L538-L697, Q539-L697, N540-L697, L541-L697, L542-L697, N543-L697, Q544-L697, and/or M545-L697 of SEQ ID NO:56. Polynucleotide sequences encoding these polypeptides are also provided. The present invention also encompasses the use of these N-terminal CAN-12v2 deletion polypeptides as immunogenic and/or antigenic epitopes as described elsewhere herein.

In preferred embodiments, the following C-terminal CAN-12v2 deletion polypeptides are encompassed by the present invention: M1-L697, M1-L696, M1-T695, M1-T694, M1-N693, M1-F692, M1-I691, M1-L690, M1-Y689, M1-S688, M1-T687, M1-S686, M1-H685, M1-A684, M1-V683, M1-G682, M1-G681, M1-D680, M1-I679, M1-N678, M1-A677, M1-L676, M1-I675, M1-V674, M1-P673, M1-V672, M1-I671, M1-M670, M1-F669, M1-F668, M1-T667, M1-P666, M1-T665, M1-S664, M1-Q663, M1-L662, M1-D661, M1-V660, M1-D659, M1-K658, M1-L657, M1-T656, M1-V655, M1-S654, M1-R653, M1-I652, M1-L651, M1-T650, M1-V649, M1-E648, M1-A647, M1-H646, M1-W645, M1-V644, M1-D643, M1-G642, M1-R641, M1-R640, M1-Q639, M1-R638, M1-I637, M1-L636, M1-T635, M1-C634, M1-G633, M1-A632, M1-R631, M1-T630, M1-H629, M1-G628, M1-C627, M1-S626, M1-W625, M1-S624, M1-K623, M1-R622, M1-H621, M1-R620, M1-G619, M1-A618, M1-E617, M1-R616, M1-M615, M1-A614, M1-A613, M1-H612, M1-L611, M1-Q610, M1-E609, M1-W608, M1-N607, M1-L606, M1-Y605, M1-G604, M1-S603, M1-G602, M1-R601, M1-D600, M1-Q599, M1-K598, M1-H597, M1-F596, M1-V595, M1-K594, M1-Q593, M1-S592, M1-L591, M1-K590, M1-L589, M1-Q588, M1-K587, M1-W586, M1-L585, M1-D584, M1-R583, M1-F582, M1-E581, M1-Q580, M1-I579, M1-S578, M1-M577, M1-T576, M1-G575, M1-S574, M1-A573, M1-N572, M1-L571, M1-D570, M1-L569, M1-L568, M1-A567, M1-L566, M1-I565, M1-G564, M1-Q563, M1-C562, M1-A561, M1-E560, M1-L559, M1-S558, M1-F557, M1-F556, M1-P555, M1-Q554, M1-R553, M1-S552, M1-G551, M1-L550, M1-S549, M1-S548, M1-W547, M1-T546, M1-M545, M1-Q544, M1-N543, M1-L542, M1-L541, M1-N540, M1-Q539, M1-L538, M1-Q537, M1-V536, M1-A535, M1-N534, M1-I533, M1-E532, M1-P531, M1-H530, M1-K529, M1-E528, M1-F527, M1-F526, M1-K525, M1-T524, M1-F523, M1-F522, M1-E521, M1-D520, M1-Q519, M1-R518, M1-E517, M1-N516, M1-Q515, M1-D514, M1-E513, M1-I512, M1-E511, M1-K510, M1-S509, M1-F508, M1-V507, M1-V506, M1-G505, M1-S504, M1-N503, M1-S502, M1-G501, M1-I500, M1-E499, M1-Y498, M1-F497, M1-I496, M1-H495, M1-K494, M1-R493, M1-S492, M1-F491, M1-V490, M1-R489, M1-L488, M1-V487, M1-F486, M1-E485, M1-S484, M1-K483, M1-Q482, M1-H481, M1-A480, M1-E479, M1-L478, M1-I477, M1-C476, M1-P475, M1-V474, M1-I473, M1-L472, M1-Y471, M1-T470, M1-G469, M1-P468, M1-E467, M1-L466, M1-C465, M1-L464, M1-E463, M1-Q462, M1-S461, M1-V460, M1-E459, M1-K458, M1-E457, M1-K456, M1-L455, M1-F454, M1-R453, M1-D452, M1-P451, M1-Q450, M1-S449, M1-L448, M1-P447, M1-T446, M1-N445, M1-R444, M1-Q443, M1-F442, M1-F441, M1-E440, M1-P439, M1-P438, M1-L437, M1-R436, M1-R435, M1-Q434, M1-D433, M1-D432, M1-H431, M1-Y430, M1-K429, M1-N428, and/or M1-M427 of SEQ ID NO:56. Polynucleotide sequences encoding these polypeptides are also provided. The present invention also encompasses the use of these C-terminal CAN-12v2 deletion polypeptides as immunogenic and/or antigenic epitopes as described elsewhere herein.

Alternatively, preferred polypeptides of the present invention may comprise polypeptide sequences corresponding to, for example, internal regions of the CAN-12v2 polypeptide (e.g., any combination of both N- and C-terminal CAN-12v2 polypeptide deletions) of SEQ ID NO:56. For example, internal regions could be defined by the equation: amino acid NX to amino acid CX, wherein NX refers to any N-terminal deletion polypeptide amino acid of CAN-12v2 (SEQ ID NO:56), and where CX refers to any C-terminal deletion polypeptide amino acid of CAN-12v2 (SEQ ID NO:56). Polynucleotides encoding these polypeptides are also provided. The present invention also encompasses the use of these polypeptides as an immunogenic and/or antigenic epitope as described elsewhere herein.

The present invention also encompasses immunogenic and/or antigenic epitopes of the CAN-12v2 polypeptide.

The CAN-12v2 polypeptides of the present invention were determined to comprise several phosphorylation sites based upon the Motif algorithm (Genetics Computer Group, Inc.). The phosphorylation of such sites may regulate some biological activity of the CAN-12v2 polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the CAN-12v2 polypeptide to associate with other polypeptides, particularly the serine protease substrate for CAN-12v2, or its ability to modulate serine protease function.

The CAN-12v2 polypeptide was predicted to comprise eleven PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177–184(1986), and Kishimoto A., Nishiyama K., Nakanishi H., Uratsuji Y., Nomura H., Takeyama Y., Nishizuka Y., J. Biol. Chem. . . . 260:12492–12499(1985); which are hereby incorporated by reference herein.

In preferred embodiments, the following PKC phosphorylation site polypeptides are encompassed by the present invention: LAPRYSRRASPQQ (SEQ ID NO:76), LNQSFTEKYAGIF (SEQ ID NO:77), VFVSSTYKNLFWG (SEQ ID NO:78), GIRKVTCKHRPEY (SEQ ID NO:79), DWSDSSSKWELLS (SEQ ID NO:80), KWELLSPKEKILL (SEQ ID NO:81), QKWTYTMREGRWE (SEQ ID NO:82), EEGRRSLRPCSVL (SEQ ID NO:83), VLRVFSRKHIFYE (SEQ ID NO:84), KQLKLSQKVFHKQ (SEQ ID NO:85), and/or LIRSVTLKDVDLQ (SEQ ID NO:86). Polynucleotides encoding these polypeptides are also provided. The present invention also encompasses the use of the CAN-12v2 PKC phosphorylation site polypeptides as immunogenic and/or antigenic epitopes as described elsewhere herein.

The CAN-12v2 polypeptide has been shown to comprise four glycosylation site according to the Motif algorithm (Genetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

In preferred embodiments, the following asparagine glycosylation site polypeptide is encompassed by the present invention: RVVPLNQSFTEKYA (SEQ ID NO:87), IEATYNRTLIGCQT (SEQ ID NO:102), ALLDLNASGTMSIQ (SEQ ID NO:103), and/or SYLIFNTTLL (SEQ ID NO:104). Polynucleotides encoding this polypeptide are also provided. The present invention also encompasses the use of the CAN-12v2 asparagine glycosylation site polypeptides as immunogenic and/or antigenic epitopes as described elsewhere herein.

The CAN-12v1 polypeptide has been shown to comprise one amidation site according to the Motif algorithm (Genetics Computer Group, Inc.). The precursor of hormones and other active peptides which are C-terminally amidated is always directly followed by a glycine residue which provides the amide group, and most often by at least two consecutive basic residues (Arg or Lys) which generally function as an active peptide precursor cleavage site. Although all amino acids can be amidated, neutral hydrophobic residues such as Val or Phe are good substrates, while charged residues such as Asp or Arg are much less reactive. A consensus pattern for amidation sites is the following: x-G-[RK]-[RK] (SEQ ID NO:146), wherein "X" represents the amidation site. Additional information relating to asparagine glycosylation may be found in reference to the following publications, which are hereby incorporated by reference herein: Kreil G., Meth. Enzymol. 106:218–223(1984); and Bradbury A. F., Smyth D. G., Biosci. Rep. 7:907–916(1987).

In preferred embodiments, the following amidation site polypeptide is encompassed by the present invention: VWRPEEGRRSLRPC (SEQ ID NO:88). Polynucleotides encoding these polypeptides are also provided. The present invention also encompasses the use of this CAN-12v2 amidation site polypeptide as an immunogenic and/or antigenic epitope as described elsewhere herein.

The CAN-12v2 polypeptide has been shown to comprise one RGD cell attachment site domain according to the Motif algorithm (Genetics Computer Group, Inc.). The sequence Arg-Gly-Asp, found in fibronectin, is crucial for its interaction with its cell surface receptor, an integrin. What has been called the 'RGD' tripeptide is also found in the sequences of a number of other proteins, where it has been shown to play a role in cell adhesion. Non-limiting examples of these proteins are the following: some forms of collagens, fibrinogen, vitronectin, von Willebrand factor (VWF), snake disintegrins, and slime mold discoidins. The 'RGD' tripeptide is also found in other proteins where it may serve the same purpose. A consensus pattern for RGD cell attachment sites is the following: R-G-D. Additional information relating to RGD cell attachment site domains may be found in reference to the following publications, which are hereby incorporated by reference herein: Ruoslahti E., Pierschbacher M. D., Cell 44:517–518(1986); and d'Souza S. E., Ginsberg M. H., Plow E. F., Trends Biochem. Sci. 16:246–250(1991).

In preferred embodiments, the following RGD cell attachment site domain polypeptide is encompassed by the present invention: LIRQRRGDVWHAE (SEQ ID NO:89). Polynucleotides encoding these polypeptides are also provided. The present invention also encompasses the use of this RGD cell attachment site domain polypeptide as an immunogenic and/or antigenic epitope as described elsewhere herein.

In confirmation of the CAN-12v2 polypeptide being a calpain, it has been shown to comprise one EF-hand calcium-binding domain according to the Motif algorithm (Genetics Computer Group, Inc.). Many calcium-binding proteins belong to the same evolutionary family and share a type of calcium-binding domain known as the EF-hand. This type of domain consists of a twelve residue loop flanked on both side by a twelve residue alpha-helical domain. In an EF-hand loop the calcium ion is coordinated in a pentagonal bipyramidal configuration. The six residues involved in the binding are in positions 1, 3, 5, 7, 9 and 12; these residues are denoted by X, Y, Z, -Y, -X and -Z. The invariant Glu or Asp at position 12 provides two oxygens for liganding Ca (bidentate ligand). Several representative proteins containing EF-hand regions are provided below: For each type of protein, the total number of EF-hand regions known or supposed to exist are provided in parenthesis: *Aequorin* and *Renilla luciferin* binding protein (LBP) (Ca=3); Alpha actinin (Ca=2); Calbindin (Ca=4); Calcineurin B subunit (protein phosphatase 2B regulatory subunit) (Ca=4); Calcium-binding protein from *Streptomyces erythraeus* (Ca=3?); Calcium-binding protein from *Schistosoma mansoni* (Ca=2?); Calcium-binding proteins TCBP-23 and TCBP-25 from *Tetrahymena thermophila* (Ca=4?); Calcium-dependent protein kinases (CDPK) from plants (Ca=4); Calcium vector protein from amphoxius (Ca=2); Calcyphosin (thyroid protein p24) (Ca=4?); Calmodulin (Ca=4, except in yeast where Ca=3); Calpain small and large chains (Ca=2); Calretinin (Ca=6); Calcyclin (prolactin receptor associated protein) (Ca=2); Caltractin (centrin) (Ca=2 or 4); Cell Division Control protein 31 (gene CDC31) from yeast (Ca=2?); Diacylglycerol kinase (EC 2.7.1.107) (DGK) (Ca=2); FAD-dependent glycerol-3-phosphate dehydrogenase (EC 1.1.99.5) from mammals (Ca=1); Fimbrin (plastin) (Ca=2); Flagellar calcium-binding protein (1f8) from *Trypanosoma cruzi* (Ca=1 or 2); Guanylate cyclase activating protein (GCAP) (Ca=3); Inositol phospholipid-specific phospholipase C isozymes gamma-1 and delta-1 (Ca=2) [10]; Intestinal calcium-binding protein (ICaBPs) (Ca=2); MIF related proteins 8 (MRP-8 or CFAG) and 14 (MRP-14) (Ca=2); Myosin regulatory light chains (Ca=1); Oncomodulin (Ca=2); Osteonectin (basement membrane protein BM-40) (SPARC) and proteins that contains an 'osteonectin' domain (QR1, matrix glycoprotein SCI) (Ca=1); Parvalbumins alpha and beta (Ca=2); Placental calcium-binding protein (18a2) (nerve growth factor induced protein 42a) (p9k) (Ca=2); Recoverins (visinin, hippocalcin, neurocalcin, S-modulin) (Ca=2 to 3); Reticulocalbin (Ca=4); S-100 protein, alpha and beta chains (Ca=2); Sarcoplasmic calcium-binding protein (SCPs) (Ca=2 to 3); Sea urchin proteins Spec 1 (Ca=4), Spec 2 (Ca=4?), Lps-1 (Ca=8); Serine/threonine protein phosphatase rdgc (EC 3.1.3.16) from *Drosophila* (Ca=2); Sorcin V19 from hamster (Ca=2); Spectrin alpha chain (Ca=2); Squidulin (optic lobe calcium-binding protein) from squid (Ca=4); and Troponins C; from skeletal muscle (Ca=4), from cardiac muscle (Ca=3), from arthropods and molluscs (Ca=2).

A consensus pattern for EF hand calcium binding domains is the following:

```
                                                                  (SEQ ID NO:147)
1 2  3    4          5         6         7    8        9          10    12    13
X    Y               Z                  -Y            -X                -Z
D-x-[DNS]-{ILVFYW}-[DENSTG]-[DNQGHRK]-{GP}-[LIVMC]-[DENQSTAGC]-x(2)-[DE]-[LIVMFYW],
``` wherein X, Y, Z, -Y, -X, and -Z are as defined above, and wherein "x" represents any amino acid. Amino acid residues within the consensus at positions 1 (X), 3 (Y) and 12 (-Z) are the most conserved. The 6th residue in an EF-hand loop is in most cases a Gly.

Additional information relating to RGD cell attachment site domains may be found in reference to the following publications, which are hereby incorporated by reference herein: Kawasaki H., Kretsinger R. H., Protein Prof. 2:305–490(1995); Kretsinger R. H., Cold Spring Harbor Symp. Quant. Biol. 52:499–510(1987); Moncrief N. D., Kretsinger R. H., Goodman M., J. Mol. Evol. 30:522–562 (1990); Nakayama S., Moncrief N. D., Kretsinger R. H., J. Mol. Evol. 34:416–448(1992); Heizmann C. W., Hunziker W., Trends Biochem. Sci. 16:98–103(1991); Kligman D., Hilt D. C., Trends Biochem. Sci. 13:437–443(1988); Strynadka N. C. J., James M. N. G., Annu. Rev. Biochem. 58:951–98(1989); Haiech J., Sallantin J., Biochimie 67:555–560(1985); Chauvaux S., Beguin P., Aubert J.-P., Bhat K. M., Gow L. A., Wood T. M., Bairoch A., Biochem. J. 265:261–265(1990); Bairoch A., Cox J. A., FEBS Lett. 269:454–456(1990).

In preferred embodiments, the following EF-hand calcium binding domain polypeptide is encompassed by the present invention: ILALLDLNASGTMSIQEFRDLWK (SEQ ID NO:90). Polynucleotides encoding these polypeptides are also provided. The present invention also encompasses the use of this EF-hand calcium binding domain polypeptide as an immunogenic and/or antigenic epitope as described elsewhere herein.

In further confirmation of the CAN-12v2 polypeptide being a calpain, it has been shown to comprise one eukaryotic thiol (cysteine) protease active site domain according to the Motif algorithm (Genetics Computer Group, Inc.). Eukaryotic thiol proteases (EC 3.4.22.-) are a family of proteolytic enzymes which contain an active site cysteine. Catalysis proceeds through a thioester intermediate and is facilitated by a nearby histidine side chain; an asparagine completes the essential catalytic triad. Non-limiting examples of proteases which are known to belong to this family are provided below: Vertebrate lysosomal cathepsins B (EC 3.4.22.1), H (EC 3.4.22.16), L (EC 3.4.22.15), and S (EC 3.4.22.27); Vertebrate lysosomal dipeptidyl peptidase I (EC 3.4.14.1) (also known as cathepsin C); Vertebrate calpains (EC 3.4.22.17) (Calpains are intracellular calcium-activated thiol protease that contain both a N-terminal catalytic domain and a C-terminal calcium-binding domain; Mammalian cathepsin K, which seems involved in osteoclastic bone resorption; Human cathepsin O; Bleomycin hydrolase (An enzyme that catalyzes the inactivation of the antitumor drug BLM (a glycopeptide); Plant enzymes: barley aleurain (EC 3.4.22.16), EP-B1/B4; kidney bean EP-C1, rice bean SH-EP; kiwi fruit actinidin (EC 3.4.22.14); papaya latex papain (EC 3.4.22.2), chymopapain (EC 3.4.22.6), caricain (EC 3.4.22.30), and proteinase IV (EC 3.4.22.25); pea turgor-responsive protein 15A; pineapple stem bromelain (EC 3.4.22.32); rape COT44; rice oryzain alpha, beta, and gamma; tomato low-temperature induced, *Arabidopsis thaliana* A494, RD19A and RD21A; House-dust mites allergens DerP1 and EurM1; Cathepsin B-like proteinases from the worms *Caenorhabditis elegans* (genes gcp-1, cpr-3, cpr-4, cpr-5 and cpr-6), *Schistosoma mansoni* (antigen SM31) and *Japonica* (antigen SJ31), *Haemonchus contortus* (genes AC-1 and AC-2), and *Ostertagia ostertagi* (CP-1 and CP-3); Slime mold cysteine proteinases CP1 and CP2; Cruzipain from *Trypanosoma cruzi* and *brucei*; Throphozoite cysteine proteinase (TCP) from various *Plasmodium* species; Proteases from *Leishmania mexicana*, *Theileria annulata* and *Theileria parva*; Baculoviruses cathepsin-like enzyme (v-cath); *Drosophila* small optic lobes protein (gene sol), a neuronal protein that contains a calpain-like domain; Yeast thiol protease BLH1/YCP1/LAP3; and *Caenorhabditis elegans* hypothetical protein C06G4.2, a calpain-like protein; Two bacterial peptidases are also part of this family—Aminopeptidase C from *Lactococcus lactis* (gene pepC), and Thiol protease tpr from *Porphyromonas gingivalis*.

A consensus pattern for eukaryotic thiol (cysteine) protease active site domains is the following: Q-x(3)-[GE]-x-C-[YW]-x(2)-[STAGC]-[STAGCV] (SEQ ID NO:148), wherein C is the active site residue, and "x" represents any amino acid. The residue in position 4 of the pattern is almost always cysteine; the only exceptions are calpains (Leu), bleomycin hydrolase (Ser) and yeast YCP1 (Ser); while the residue in position 5 of the pattern is always Gly except in papaya protease IV where it is Glu.

An additional consensus pattern for eukaryotic thiol (cysteine) protease active site domains is the following: [LIVMGSTAN]-x-H-[GSACE]-[LIVM]-x-[LIVMAT](2)-G-x-[GSADNH] (SEQ ID NO:149), wherein H is the active site residue, and "x" represents any amino acid.

An additional consensus pattern for eukaryotic thiol (cysteine) protease active site domains is the following: [FYCH]-[WI]-[LIVT]-x-[KRQAG]-N-[ST]-W-x(3)-[FYW]-G-x(2)-G-[LFYW]-[LIVMFYG]-x-[LIVMF] (SEQ ID NO:150), wherein N is the active site residue, and "x" represents any amino acid.

Additional information relating to for eukaryotic thiol (cysteine) protease active site domains may be found in reference to the following publications, which are hereby incorporated by reference herein: Dufour E., Biochimie 70:1335–1342(1988); Kirschke H., Barrett A.J., Rawlings N. D., Protein Prof. 2:1587–1643(1995); Shi G.-P., Chapman H. A., Bhairi S. M., Deleeuw C., Reddy V. Y., Weiss S. J., FEBS Lett. 357:129–134(1995); Velasco G., Ferrando A. A., Puente X. S., Sanchez L. M., Lopez-Otin C., J. Biol. Chem. . . . 269:27136–27142(1994); Chapot-Chartier M. P., Nardi M., Chopin M. C., Chopin A., Gripon J. C., Appl. Environ. Microbiol. 59:330–333(1993); Higgins D. G., McConnell D. J., Sharp P. M., Nature 340:604–604(1989); Rawlings N. D., Barrett A. J., Meth. Enzymol. 244:461–486 (1994), which are hereby incorporated by reference in their entirety herein.

In preferred embodiments, the following for eukaryotic thiol (cysteine) protease active site domain polypeptide is encompassed by the present invention: RLDLCQGIVGD-CWFLAALQALA (SEQ ID NO:91). Polynucleotides encoding these polypeptides are also provided. The present invention also encompasses the use of this for eukaryotic thiol (cysteine) protease active site domain polypeptide as an immunogenic and/or antigenic epitope as described elsewhere herein.

As referenced elsewhere herein, calpains are organized in domains. As a point of reference, the larger catalytic subunit of the best characterized m-calpain is organized in four domains (I–IV)(Hosfield et al., Crystal structure of calpain reveals the structural basis for Ca(2+)-dependent protease activity and a novel mode of enzyme activation. EMBO J. 18:6880–9, 1999; Strobl et al., The crystal structure of calcium-free human m-calpain suggests an electrostatic switch mechanism for activation by calcium. Proc Natl Acad Sci USA. 97:588–92, 2000). The N-terminal domain I contains an alpha helical region. Domain II contains the catalytic active domain with the active site amino acids. Domain III contains the linker between the Ca2+ binding domain in domain IV to the active site domain II.

The CAN-12v2 calpain of the present invention has the same domain I and II as the CAN-12 calpain, but differs in domains III and IV. The N-terminal domain I consists of residues Met1-Arg20. Domain II of the CAN-12v2 calpain (Ala21-Lys333) contain the catalytic active site residue acids (Cys101, His254 and Asn278). As can be seen in the sequence alignments (FIGS. 2A–E), there is high amino acid sequence homology in the amino acid residues bracketing the active site amino acids. Combined domains I and II of the calpains of the present invention are 42–45% homologous to m-calpain.

The CAN-12v2 calpain of the present invention, have the same domain I and II, although they differ in composition and content of domains III and IV. The CAN-12 and CAN-12v2 calpains contain both the linker (domain III) and C-terminal domain IV. The "linker" domain also contains residues Met426, Asn427 and Lys428 of SEQ ID NO56).

The present invention also provides a three-dimensional homology model of the CAN-12v2 polypeptide (see FIG. 11). The three-dimensional homology model of the CAN-12 polypeptide may also be applicable to the CAN-12v2 polypeptide. Although the CAN-12 polypeptide sequence is different than the CAN-12v2 polypeptide sequence, the fact that domain I and II are substantially the same suggests the homology model of CAN-12 may be used for designing potential ligands (including agonists and/or antagonists) for the CAN-12v2 polypeptide. A three-dimensional homology model can be constructed on the basis of the known structure of a homologous protein (Greer et al, 1991, Lesk, et al, 1992, Cardozo, et al, 1995, Yuan, et al, 1995). The homology model of the CAN-12v2 polypeptide, corresponding to amino acid residues 12 to 428 and from amino acid residues 543 to 639 of SEQ ID NO:56, was based upon the homologous structure of CAN2, a m-calpain family member (Strobl et al, 2000; hCAN2; Genbank Accession No. gil7546423; SEQ ID NO:11) and is defined by the set of structural coordinates set forth in Table V herein. Note that amino acids 429 to 542 of SEQ ID NO:56 were omitted from the homology model. As a result, the amino acid residue numbers in Table V do not correspond to the amino acid residue numbers as provided in SEQ ID NO:56 (FIGS. 9A–C). Rather, the amino acid residue numbers in Table V for amino acid residues 12 to 428 correspond to amino acid residues 12 to 428 of SEQ ID NO:56 (FIGS. 9A–C), while amino acid residue numbers in Table V for amino acid residues 429 to 512 correspond to amino acid residues 543 to 639 of SEQ ID NO:56 (FIGS. 9A–C).

A description of the headings in Table V are as follows: "Atom No" refers to the atom number within the CAN-12v2 homology model; "Atom name" refers to the element whose coordinates are measured, the first letter in the column defines the element; "Residue" refers to the amino acid within which the atom resides, and the provided number after the amino acid refers to the amino acid number of the "residue"; "X Coord", "Y Coord", and "Z Coord" structurally define the atomic position of the element measured in three dimensions.

The CAN-12v2 homology model of the present invention may provide one basis for designing rational stimulators (agonists) and/or inhibitors (antagonists) of one or more of the biological functions of CAN-12v2, or of CAN-12v2 mutants having altered specificity (e.g., molecularly evolved CAN-12v2 polypeptides, engineered site-specific CAN-12v2 mutants, CAN-12v2 allelic variants, etc.).

Homology models are not only useful for designing rational agonists and/or antagonists, but are also useful in predicting the function of a particular polypeptide. The functional predictions from homology models are typically more accurate than the functional attributes derived from traditional polypeptide sequence homology alignments (e.g., CLUSTALW), particularly when the three dimensional structure of a related polypeptide is known (e.g., m-calpain family member CAN2 protein; Genbank Accession No. gil7546423; SEQ ID NO:11). The increased prediction accuracy is based upon the fact that homology models approximate the three-dimensional structure of a protein, while homology based alignments only take into account the one dimension polypeptide sequence. Since the function of a particular polypeptide is determined not only by its primary, secondary, and tertiary structure, functional assignments derived solely upon homology alignments using the one dimensional protein sequence may be less reliable. A 3-dimensional model can be constructed on the basis of the known structure of a homologous protein (Greer et al, 1991, Lesk, et al, 1992, Cardozo, et al, 1995, Yuan, et al, 1995).

Prior to developing a homology model, those of skill in the art would appreciate that a template of a known protein, or model protein, must first be identified which will be used as a basis for constructing the homology model for the protein of unknown structure (query template). In the case of the CAN-12v2 polypeptide of the present invention, the model protein template used in constructing the CAN-12v2 homology model was the m-calpain family member CAN2 protein; Genbank Accession No. gil7546423; SEQ ID NO:11).

Identifying a template can be accomplished using pairwise alignment of protein sequences using such programs as FASTA (Pearson, et al 1990) and BLAST (Altschul, et al, 1990). In cases where sequence similarity is high (greater than 30%), such pairwise comparison methods may be adequate for identifying an appropriate template. Likewise, multiple sequence alignments or profile-based methods can be used to align a query sequence to an alignment of multiple (structurally and biochemically) related proteins. When the sequence similarity is low, more advanced techniques may be used. Such techniques, include, for example, protein fold recognition (protein threading; Hendlich, et al, 1990), where the compatibility of a particular polypeptide sequence with the 3-dimensional fold of a potential template protein is gauged on the basis of a knowledge-based potential.

Following the initial sequence alignment, the second step would be to optimally align the query template to the model template by manual manipulation and/or by the incorporation of features specific to the polypeptides (e.g., motifs, secondary structure predictions, and allowed conservations). Preferably, the incorporated features are found within both the model and query template.

The third step would be to identify structurally conserved regions that could be used to construct secondary core structure (Sali, et al, 1995). Loops could be added using knowledge-based techniques, and by performing forcefield calculations (Sali, et al, 1995).

In order to recognize errors in a three-dimensional structure, knowledge based mean fields can be used to judge the quality of protein folds (Sippl 1993). The methods can be used to recognize misfolded structures as well as faulty parts of structural models. The technique generates an energy graph where the energy distribution for a given protein fold is displayed on the y-axis and residue position in the protein fold is displayed on the x-axis. The knowledge based mean fields compose a force field derived from a set of globular protein structures taken as a subset from the Protein Data Bank (Bernstein et. al. 1977). To analyze the quality of a model the energy distribution is plotted and compared to the energy distribution of the template from which the model was generated. FIG. 13 shows the energy graph for the CAN-12.v2 model (dotted line) and the template (1dkv, m-calpain) from which the model was generated. This graph supports the motif and sequence alignments in confirming that the three dimensional structure coordinates of CAN-12.v2 are an accurate and useful representation for the polypeptide.

The term "structure coordinates" refers to Cartesian coordinates generated from the building of a homology model. In this invention, the homology model of residues 12 to 525 of CAN-12v2 was derived from generating a sequence alignment with m-calpain (Strobl et al, 2000; hCAN2; Genbank Accession No. gil7546423; SEQ ID NO:11) using the COMPOSER suite of software within SYBYL6.6 (Tripods Associates, St. Louis, Mo.) and then generating the backbone and side chain conformations. In the original crystal structure (pdb code 1dkv) as well as the crystal structure reported elsewhere (Hosfield et al, 1999), the active site of the enzyme comprising a cysteine, a histidine and an asparagine residue was not "formed". The helix that contains the active site C101 was altered by moving the helix down one pitch so that the active site geometry could match that found in Papain (pdb code 1b4). This modified structure of human m-calpain was used as the template for construction of the homology model (illustrated in FIG. 11 herein).

The skilled artisan would appreciate that a set of structure coordinates for a protein represents a relative set of points that define a shape in three dimensions. Thus, it is possible that an entirely different set of coordinates could define a similar or identical shape. Moreover, slight variations in the individual coordinates, as emanate from the generation of similar homology models using different alignment templates (i.e., other than the m-calpain (Strobl et al, 2000; hCAN2; Genbank Accession No. gil7546423; SEQ ID NO:11), and/or using different methods in generating the homology model, will likely have minor effects on the overall shape. Variations in coordinates may also be generated because of mathematical manipulations of the structure coordinates. For example, the structure coordinates set forth in Table V could be manipulated by fractionalization of the structure coordinates; integer additions, or integer subtractions to sets of the structure coordinates, inversion of the structure coordinates or any combination of the above.

Therefore, various computational analyses are necessary to determine whether a template molecule or a portion thereof is sufficiently similar to all or part of a query template (e.g., CAN-12v2) in order to be considered the same. Such analyses may be carried out in current software applications, such as SYBYL version 6.6 or INSIGHTS (Molecular Simulations Inc., San Diego, Calif.) version 2000 and as described in the accompanying User's Guides.

Using the superimposition tool in the program SYBYL, comparisons can be made between different structures and different conformations of the same structure. The procedure used in SYBYL to compare structures is divided into four steps: 1) load the structures to be compared; 2) define the atom equivalencies in these structures; 3) perform a fitting operation; and 4) analyze the results. Each structure is identified by a name. One structure is identified as the target (i.e., the fixed structure); the second structure (i.e., moving structure) is identified as the source structure. The atom equivalency within SYBYL is defined by user input. For the purpose of this invention, we will define equivalent atoms as protein backbone atoms (N, Cα, C and O) for all conserved residues between the two structures being compared. We will also consider only rigid fitting operations. When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atoms is an absolute minimum. This number, given in angstroms, is reported by the SYBYL program. For the purpose of the present invention, any homology model of a CAN-12v2 that has a root mean square deviation of conserved residue backbone atoms (N, Cα, C, O) of less than 3.0 Å when superimposed on the relevant backbone atoms described by structure coordinates listed in Table V are considered identical. More preferably, the root mean square deviation for the CAN-12v2 polypeptide is less than 2.0 Å.

The homology model of the present invention is useful for the structure-based design of modulators of the CAN-12v2 biological function, as well as mutants with altered biological function and/or specificity.

In accordance with the structural coordinates provided in Table V and the three dimensional homology model of CAN-12v2, the CAN-12v2 polypeptide has been shown to comprise a an active site region embodied by the following amino acids: from about amino acid R90 to about amino acid C94, from about amino acid G99 to about amino acid L104, from about amino acid Q196 to about amino acid S198, from about amino acid M210 to about amino acid I212, from about amino acid G236 to about amino acid H240, from about amino acid E252 to about amino acid Y256, from about amino acid N278 to about amino acid K282, from about amino acid V328 to about amino acid V331 of SEQ ID NO:56 (FIGS. 8A–C). In this context, the term "about" may be construed to mean 1, 2, 3, 4, 5, 6, 7, 8, 9 or 10 amino acids more in either the N- or C-terminal direction of the above referenced amino acids.

Also more preferred are polypeptides comprising all or any part of the CAN-12v2 active site domain, or a mutant or homologue of said polypeptide or molecular complex. By mutant or homologue of the molecule is meant a molecule that has a root mean square deviation from the backbone atoms of said CAN-12v2 amino acids of not more than about 4.5 Angstroms, and preferably not more than about 3.5 Angstroms.

In preferred embodiments, the following CAN-12v2 active site domain polypeptide is encompassed by the present invention: RLDLCQGIVGDCWFLAALQALAL-HQDILSRVVPLNQSFTEKYAGIFRFWFWH YGN-WVPVVIDDRLPVNEAGQLVFVSSTYKN-LFWGALLEKAYAKLSGSYEDL QSGQVSEALVDFTGGVTMTINLAEAHGN-LWDILIEATYNRTLIGCQTHSGEKI LENGLVEGHAY-TLTGIRKVTCKHRPEYLVKLRNP-WGKVEWKGDWSDSSSK WELLSPKEKILLLRKDNDGEFWMTLQDFKTHFVLLV (SEQ ID NO:93). Polynucleotides encoding this polypeptide are also provided. The present invention also encompasses the use of the CAN-12v2 active site domain polypeptide as an immunogenic and/or antigenic epitope as described elsewhere herein.

The present invention also encompasses polypeptides comprising at least a portion of the CAN-12v2 active site domain (SEQ ID NO: 93). Such polypeptides may correspond, for example, to the N- and/or C-terminal deletions of the active site domain.

In preferred embodiments, the following N-terminal CAN-12v2 active site domain deletion polypeptides are encompassed by the present invention: R1-V242, L2-V242, D3-V242, L4-V242, C5-V242, Q6-V242, G7-V242, I8-V242, V9-V242, G10-V242, D11-V242, C12-V242, W13-V242, F14-V242, L15-V242, A16-V242, A17-V242, L18-V242, Q19-V242, A20-V242, L21-V242, A22-V242, L23-V242, H24-V242, Q25-V242, D26-V242, I27-V242, L28-V242, S29-V242, R30-V242, V31-V242, V32-V242, P33-V242, L34-V242, N35-V242, Q36-V242, S37-V242, F38-V242, T39-V242, E40-V242, K41-V242, Y42-V242, A43-V242, G44-V242, I45-V242, F46-V242, R47-V242, F48-V242, W49-V242, F50-V242, W51-V242, H52-V242, Y53-V242, G54-V242, N55-V242, W56-V242, V57-V242, P58-V242, V59-V242, V60-V242, I61-V242, D62-V242, D63-V242, R64-V242, L65-V242, P66-V242, V67-V242, N68-V242, E69-V242, A70-V242, G71-V242, Q72-V242, L73-V242, V74-V242, F75-V242, V76-V242, S77-V242, S78-V242, T79-V242, Y80-V242, K81-V242, N82-V242, L83-V242, F84-V242, W85-V242, G86-V242, A87-V242, L88-V242, L89-V242, E90-V242, K91-V242, A92-V242, Y93-V242, A94-V242, K95-V242, L96-V242, S97-V242, G98-V242, S99-V242, Y100-V242, E101-V242, D102-V242, L103-V242, Q104-V242, S105-V242, G106-V242, Q107-V242, V108-V242, S109-V242, E110-V242, A111-V242, L112-V242, V113-V242, D114-V242, F115-V242, T116-V242, G117-V242, G118-V242, V119-V242, T120-V242, M121-V242, T122-V242, I123-V242, N124-V242, L125-V242, A126-V242, E127-V242, A128-V242, H129-V242, G130-V242, N131-V242, L132-V242, W133-V242, D134-V242, I135-V242, L136-V242, I137-V242, E138-V242, A139-V242, T140-V242, Y141-V242, N142-V242, R143-V242, T144-V242, L145-V242, I146-V242, G147-V242, C148-V242, Q149-V242, T150-V242, H151-V242, S152-V242, G153-V242, E154-V242, K155-V242, I156-V242, L157-V242, E158-V242, N159-V242, G160-V242, L161-V242, V162-V242, E163-V242, G164-V242, H165-V242, A166-V242, Y167-V242, T168-V242, L169-V242, T170-V242, G171-V242, I172-V242, R173-V242, K174-V242, V175-V242, T176-V242, C177-V242, K178-V242, H179-V242, R180-V242, P181-V242, E182-V242, Y183-V242, L184-V242, V185-V242, K186-V242, L187-V242, R188-V242, N189-V242, P190-V242, W191-V242, G192-V242, K193-V242, V194-V242, E195-V242, W196-V242, K197-V242, G198-V242, D199-V242, W200-V242, S201-V242, D202-V242, S203-V242, S204-V242, S205-V242, K206-V242, W207-V242, E208-V242, L209-V242, L210-V242, S211-V242, P212-V242, K213-V242, E214-V242, K215-V242, I216-V242, L217-V242, L218-V242, L219-V242, R220-V242, K221-V242, D222-V242, N223-V242, D224-V242, G225-V242, E226-V242, F227-V242, W228-V242, M229-V242, T230-V242, L231-V242, Q232-V242, D233-V242, F234-V242, K235-V242, and/or T236-V242 of SEQ ID NO:93. Polynucleotide sequences encoding these polypeptides are also provided. The present invention also encompasses the use of these N-terminal CAN-12v2 active site domain deletion polypeptides as immunogenic and/or antigenic epitopes as described elsewhere herein.

In preferred embodiments, the following C-terminal CAN-12v2 active site domain deletion polypeptides are encompassed by the present invention: R1-V242, R1-L241, R1-L240, R1-V239, R1-F238, R1-H237, R1-T236, R1-K235, R1-F234, R1-D233, R1-Q232, R1-L231, R1-T230, R1-M229, R1-W228, R1-F227, R1-E226, R1-G225, R1-D224, R1-N223, R1-D222, R1-K221, R1-R220, R1-L219, R1-L218, R1-L217, R1-I216, R1-K215, R1-E214, R1-K213, R1-P212, R1-S211, R1-L210, R1-L209, R1-E208, R1-W207, R1-K206, R1-S205, R1-S204, R1-S203, R1-D202, R1-S201, R1-W200, R1-D199, R1-G198, R1-K197, R1-W196, R1-E195, R1-V194, R1-K193, R1-G192, R1-W191, R1-P190, R1-N189, R1-R188, R1-L187, R1-K186, R1-V185, R1-L184, R1-Y183, R1-E182, R1-P181, R1-R180, R1-H179, R1-K178, R1-C177, R1-T176, R1-V175, R1-K174, R1-R173, R1-I172, R1-G171, R1-T170, R1-L169, R1-T168, R1-Y167, R1-A166, R1-H165, R1-G164, R1-E163, R1-V162, R1-L161, R1-G160, R1-N159, R1-E158, R1-L157, R1-I156, R1-K155, R1-E154, R1-G153, R1-S152, R1-H151, R1-T150, R1-Q149, R1-C148, R1-G147, R1-I146, R1-L145, R1-T144, R1-R143, R1-N142, R1-Y141, R1-T140, R1-A139, R1-E138, R1-I137, R1-L136, R1-I135, R1-D134, R1-W133, R1-L132, R1-N131, R1-G130, R1-H129, R1-A128, R1-E127, R1-A126, R1-L125, R1-N124, R1-I123, R1-T122, R1-M121, R1-T120, R1-V119, R1-G118, R1-G117, R1-T116, R1-F115, R1-D114, R1-V113, R1-L112, R1-A111, R1-E110, R1-S109, R1-V108, R1-Q107, R1-G106, R1-S105, R1-Q104, R1-L103, R1-D102, R1-E101, R1-Y100, R1-S99, R1-G98, R1-S97, R1-L96, R1-K95, R1-A94, R1-Y93, R1-A92, R1-K91, R1-E90, R1-L89, R1-L88, R1-A87, R1-G86, R1-W85, R1-F84, R1-L83, R1-N82, R1-K81, R1-Y80, R1-T79, R1-S78, R1-S77, R1-V76, R1-F75, R1-V74, R1-L73, R1-Q72, R1-G71, R1-A70, R1-E69, R1-N68, R1-V67, R1-P66, R1-L65, R1-R64, R1-D63, R1-D62, R1-I61, R1-V60, R1-V59, R1-P58, R1-V57, R1-W56, R1-N55, R1-G54, R1-Y53, R1-H52, R1-W51, R1-F50, R1-W49, R1-F48, R1-R47, R1-F46, R1-I45, R1-G44, R1-A43, R1-Y42, R1-K41, R1-E40, R1-T39, R1-F38, R1-S37, R1-Q36, R1-N35, R1-L34, R1-P33, R1-V32, R1-V31, R1-R30, R1-S29, R1-L28, R1-I27, R1-D26, R1-Q25, R1-H24, R1-L23, R1-A22, R1-L21, R1-A20, R1-Q19, R1-L18, R1-A17, R1-A16, R1-L15, R1-F14, R1-W13, R1-C12, R1-D11, R1-G10, R1-V9, R1-I8, and/or R1-G7 of SEQ ID NO:93. Polynucleotide sequences encoding these polypeptides are also provided. The present invention also encompasses the use of these C-terminal CAN-12v2 active site domain deletion polypeptides as immunogenic and/or antigenic epitopes as described elsewhere herein.

Alternatively, such polypeptides may comprise polypeptide sequences corresponding, for example, to internal regions of the CAN-12v2 active site domain (e.g., any combination of both N- and C-terminal CAN-12v2 active site domain deletions) of SEQ ID NO:93. For example, internal regions could be defined by the equation NX to CX, where NX refers to any N-terminal amino acid position of the CAN-12v2 active site domain (SEQ ID NO:93), and where CX refers to any C-terminal amino acid position of the CAN-12v2 active site domain (SEQ ID NO:93). Polynucleotides encoding these polypeptides are also provided. The present invention also encompasses the use of these polypeptides as an immunogenic and/or antigenic epitope as described elsewhere herein.

In preferred embodiments, the following CAN-I 2v2 active site domain amino acid substitutions are encompassed by the present invention: wherein R90 is substituted with either an A, C, D, E, F, G, H, I, K, L, M, N, P, Q, S, T, V, W, or Y; wherein L91 is substituted with either an A, C, D, E, F, G, H, I, K, M, N, P, Q, R, S, T, V, W, or Y; wherein D92 is substituted with either an A, C, E, F, G, H, I, K, L, M, N, P, Q, R, S, T, V, W, or Y; wherein L93 is substituted with either an A, C, D, E, F, G, H, I, K, M, N, P, Q, R, S, T, V, W, or Y; wherein C94 is substituted with either an A, D, E, F, G, H, I, K, L, M, N, P, Q, R, S, T, V, W, or Y; wherein Q95 is substituted with either an A, C, D, E, F, G, H, I, K, L, M, N, P, R, S, T, V, W, or Y; wherein G96 is substituted with either an A, C, D, E, F, H, I, K, L, M, N, P, Q, R, S, T, V, W, or Y; wherein I97 is substituted with either an A, C, D, E, F, G, H, K, L, M, N, P, Q, R, S, T, V, W, or Y; wherein V98 is substituted with either an A, C, D, E, F, G, H, I, K, L, M, N, P, Q, R, S, T, W, or Y; wherein G99 is substituted with either an A, C, D, E, F, H, I, K, L, M, N, P, Q, R, S, T, V, W, or Y; wherein D100 is substituted with either an A, C, E, F, G, H, I, K, L, M, N, P, Q, R, S, T, V, W, or Y; wherein C101 is substituted with either an A, D, E, F, G, H, I, K, L, M, N, P, Q, R, S, T, V, W, or Y; wherein W102 is substituted with either an A, C, D, E, F, G, H, I, K, L, M, N, P, Q, R, S, T, V, or Y; wherein F103 is substituted with either an A, C, D, E, G, H, I, K, L, M, N, P, Q, R, S, T, V, W, or Y; wherein L104 is substituted with either an A, C, D, E, F, G, H, I, K, M, N, P, Q, R, S, T, V, W, or Y; wherein A105 is substituted with either a C, D, E, F, G, H, I, K, L, M, N, P, Q, R, S, T, V, W, or Y; wherein A106 is substituted with either a C, D, E, F, G, H, I, K, L, M, N, P, Q, R, S, T, V, W, or Y; wherein L107 is substituted with either an A, C, D, E, F, G, H, I, K, M, N, P, Q, R, S, T, V, W, or Y; wherein Q108 is substituted with either an A, C, D, E, F, G, H, I, K, L, M, N, P, R, S, T, V, W, or Y; wherein A109 is substituted with either a C, D, E, F, G, H, I, K, L, M, N, P, Q, R, S, T, V, W, or Y; wherein L110 is substituted with either an A, C, D, E, F, G, H, I, K, M, N, P, Q, R, S, T, V, W, or Y; wherein A111 is substituted with either a C, D, E, F, G, H, I, K, L, M, N, P, Q, R, S, T, V, W, or Y; wherein L112 is substituted with either an A, C, D, E, F, G, H, I, K, M, N, P, Q, R, S, T, V, W, or Y; wherein H113 is substituted with either an A, C, D, E, F, G, I, K, L, M, N, P, Q, R, S, T, V, W, or Y; wherein Q114 is substituted with either an A, C, D, E, F, G, H, I, K, L, M, N, P, R, S, T, V, W, or Y; wherein D115 is substituted with either an A, C, E, F, G, H, I, K, L, M, N, P, Q, R, S, T, V, W, or Y; wherein I116 is substituted with either an A, C, D, E, F, G, H, K, L, M, N, P, Q, R, S, T, V, W, or Y; wherein L117 is substituted with either an A, C, D, E, F, G, H, I, K, M, N, P, Q, R, S, T, V, W, or Y; wherein S118 is substituted with either an A, C, D, E, F, G, H, I, K, L, M, N, P, Q, R, T, V, W, or Y; wherein R119 is substituted with either an A, C, D, E, F, G, H, I, K, L, M, N, P, Q, S, T, V, W, or Y; wherein V120 is substituted with either an A, C, D, E, F, G, H, I, K, L, M, N, P, Q, R, S, T, W, or Y; wherein V121 is substituted with either an A, C, D, E, F, G, H, I, K, L, M, N, P, Q, R, S, T, W, or Y; wherein P122 is substituted with either an A, C, D, E, F, G, H, I, K, L, M, N, Q, R, S, T, V, W, or Y; wherein L123 is substituted with either an A, C, D, E, F, G, H, I, K, M, N, P, Q, R, S, T, V, W, or Y; wherein N124 is substituted with either an A, C, D, E, F, G, H, I, K, L, M, P, Q, R, S, T, V, W, or Y; wherein Q125 is substituted with either an A, C, D, E, F, G, H, I, K, L, M, N, P, R, S, T, V, W, or Y; wherein S126 is substituted with either an A, C, D, E, F, G, H, I, K, L, M, N, P, Q, R, T, V, W, or Y; wherein F127 is substituted with either an A, C, D, E, G, H, I, K, L, M, N, P, Q, R, S, T, V, W, or Y; wherein T128 is substituted with either an A, C, D, E, F, G, H, I, K, L, M, N, P, Q, R, S, V, W, or Y; wherein E129 is substituted with either an A, C, D, F, G, H, I, K, L, M, N, P, Q, R, S, T, V, W, or Y; wherein K130 is substituted with either an A, C, D, E, F, G, H, I, L, M, N, P, Q, R, S, T, V, W, or Y; wherein Y131 is substituted with either an A, C, D, E, F, G, H, I, K, L, M, N, P, Q, R, S, T, V, or W; wherein A132 is substituted with either a C, D, E, F, G, H, I, K, L, M, N, P, Q, R, S, T, V, W, or Y; wherein G133 is substituted with either an A, C, D, E, F, H, I, K, L, M, N, P, Q, R, S, T, V, W, or Y; wherein I134 is substituted with either an A, C, D, E, F, G, H, K, L, M, N, P, Q, R, S, T, V, W, or Y; wherein F135 is substituted with either an A, C, D, E, G, H, I, K, L, M, N, P, Q, R, S, T, V, W, or Y; wherein R136 is substituted with either an A, C, D, E, F, G, H, I, K, L, M, N, P, Q, S, T, V, W, or Y; wherein F137 is substituted with either an A, C, D, E, G, H, I, K, L, M, N, P, Q, R, S, T, V, W, or Y; wherein W138 is substituted with either an A, C, D, E, F, G, H, I, K, L, M, N, P, Q, R, S, T, V, or Y; wherein F139 is substituted with either an A, C, D, E, G, H, I, K, L, M, N, P, Q, R, S, T, V, W, or Y; wherein W140 is substituted with either an A, C, D, E, F, G, H, I, K, L, M, N, P, Q, R, S, T, V, or Y; wherein H141 is substituted with either an A, C, D, E, F, G, I, K, L, M, N, P, Q, R, S, T, V, W, or Y; wherein Y142 is substituted with either an A, C, D, E, F, G, H, I, K, L, M, N, P, Q, R, S, T, V, or W; wherein G143 is substituted with either an A, C, D, E, F, H, I, K, L, M, N, P, Q, R, S, T, V, W, or Y; wherein N144 is substituted with either an A, C, D, E, F, G, H, I, K, L, M, P, Q, R, S, T, V, W, or Y; wherein W145 is substituted with either an A, C, D, E, F, G, H, I, K, L, M, N, P, Q, R, S, T, V, or Y; wherein V146 is substituted with either an A, C, D, E, F, G, H, I, K, L, M, N, P, Q, R, S, T, W, or Y; wherein P147 is substituted with either an A, C, D, E, F, G, H, I, K, L, M, N, Q, R, S, T, V, W, or Y; wherein V148 is substituted with either an A, C, D, E, F, G, H, I, K, L, M, N, P, Q, R, S, T, W, or Y; wherein V149 is substituted with either an A, C, D, E, F, G, H, I, K, L, M, N, P, Q, R, S, T, W, or Y; wherein I150 is substituted with either an A, C, D, E, F, G, H, K, L, M, N, P, Q, R, S, T, V, W, or Y; wherein D151 is substituted with either an A, C, E, F, G, H, I, K, L, M, N, P, Q, R, S, T, V, W, or Y; wherein D152 is substituted with either an A, C, E, F, G, H, I, K, L, M, N, P, Q, R, S, T, V, W, or Y; wherein R153 is substituted with either an A, C, D, E, F, G, H, I, K, L, M, N, P, Q, S, T, V, W, or Y; wherein L154 is substituted with either an A, C, D, E, F, G, H, I, K, M, N, P, Q, R, S, T, V, W, or Y; wherein P155 is substituted with either an A, C, D, E, F, G, H, I, K, L, M, N, Q, R, S, T, V, W, or Y; wherein V156 is substituted with either an A, C, D, E, F, G, H, I, K, L, M, N, P, Q, R, S, T, W, or Y; wherein N157 is substituted with either an A, C, D, E, F, G, H, I, K, L, M, P, Q, R, S, T, V, W, or Y; wherein E158 is substituted with either an A, C, D, F, G, H, I, K, L, M, N, P, Q, R, S, T, V, W, or Y; wherein A159 is substituted with either a C, D, E, F, G, H, I, K, L, M, N, P, Q, R, S, T, V, W, or Y; wherein G160 is substituted with either an A, C, D, E, F, H, I, K, L, M, N, P, Q, R, S, T, V, W, or Y; wherein Q161 is substituted with either an A, C, D, E, F, G, H, I, K, L, M, N, P, R, S, T, V, W, or Y; wherein L162 is substituted with either an A, C, D, E, F, G, H, I, K, M, N, P, Q, R, S, T, V, W, or Y; wherein V163 is substituted with either an A, C, D, E, F, G, H, I, K, L, M, N, P, Q, R, S, T, W, or Y; wherein F164 is substituted with either an A, C, D, E, G, H, I, K, L, M, N, P, Q, R, S, T, V, W, or Y; wherein V165 is substituted with either an A, C, D, E, F, G, H, I, K, L, M, N, P, Q, R, S, T, W, or Y; wherein S166 is substituted with either an A, C, D, E, F, G, H, 1, K, L, M, N, P, Q, R, T, V, W, or Y; wherein S167 is substituted with either an A, C, D, E, F, G, H, I, K, L, M, N, P, Q, R, T, V, W, or Y; wherein T168 is substituted with either an A, C, D, E, F, G, H, I, K, L, M, N, P, Q, R, S, V, W, or Y; wherein Y169 is substituted with either an A, C, D, E, F, G, H, I, K, L, M, N, P, Q, R, S, T, V, or W; wherein K170 is substituted with either an A, C, D, E, F, G, H, I, L, M, N, P, Q, R, S, T, V, W, or Y; wherein N171 is substituted with either an A, C, D, E, F, G, H, I, K, L, M, P, Q, R, S, T, V, W, or Y; wherein L172 is substituted with either an A, C, D, E, F, G, H, I, K, M, N, P, Q, R, S, T, V, W, or Y; wherein F173 is substituted with either an A, C, D, E, G, H, I, K, L, M, N, P, Q, R, S, T, V, W, or Y; wherein W174 is substituted with either an A, C, D, E, F, G, H, I, K, L, M, N, P, Q, R, S, T, V, or Y; wherein G175 is substituted with either an A, C, D, E, F, H, I, K, L, M, N, P, Q, R, S, T, V, W, or Y; wherein A176 is substituted with either a C, D, E, F, G, H, I, K, L, M, N, P, Q, R, S, T, V, W, or Y; wherein L177 is substituted with either an A, C, D, E, F, G, H, I, K, M, N, P, Q, R, S, T, V, W, or Y; wherein L178 is substituted with either an A, C, D, E, F, G, H, I, K, M, N, P, Q, R, S, T, V, W, or Y; wherein E179 is substituted with either an A, C, D, F, G, H, I, K, L, M, N, P, Q, R, S, T, V, W, or Y; wherein K180 is substituted with either an A, C, D, E, F, G, H, I, L, M, N, P, Q, R, S, T, V, W, or Y; wherein A181 is substituted with either a C, D, E, F, G, H, I, K, L, M, N, P, Q, R, S, T, V, W, or Y; wherein Y182 is substituted with either an A, C, D, E, F, G, H, I, K, L, M, N, P, Q, R, S, T, V, or W; wherein A183 is substituted with either a C, D, E, F, G, H, I, K, L, M, N, P, Q, R, S, T, V, W, or Y; wherein K184 is substituted with either an A, C, D, E, F, G, H, I, L, M, N, P, Q, R, S, T, V, W, or Y; wherein L185 is substituted with either an A, C, D, E, F, G, H, I, K, M, N, P, Q, R, S, T, V, W, or Y; wherein S186 is substituted with either an A, C, D, E, F, G, H, I, K, L, M, N, P, Q, R, T, V, W, or Y; wherein G187 is substituted with either an A, C, D, E, F, H, I, K, L, M, N, P, Q, R, S, T, V, W, or Y; wherein S188 is substituted with either an A, C, D, E, F, G, H, I, K, L, M, N, P, Q, R, T, V, W, or Y; wherein Y189 is substituted with either an A, C, D, E, F, G, H, I, K, L, M, N, P, Q, R, S, T, V, or W; wherein E190 is substituted with either an A, C, D, F, G, H, I, K, L, M, N, P, Q, R, S, T, V, W, or Y; wherein D191 is substituted with either an A, C, E, F, G, H, I, K, L, M, N, P, Q, R, S, T, V, W, or Y; wherein L192 is substituted with either an A, C, D, E, F, G, H, I, K, M, N, P, Q, R, S, T, V, W, or Y; wherein Q193 is substituted with either an A, C, D, E, F, G, H, I, K, L, M, N, P, R, S, T, V, W, or Y; wherein S194 is substituted with either an A, C, D, E, F, G, H, I, K, L, M, N, P, Q, R, T, V, W, or Y; wherein G195 is substituted with either an A, C, D, E, F, H, I, K, L, M, N, P, Q, R, S, T, V, W, or Y; wherein Q196 is substituted with either an A, C, D, E, F, G, H, I, K, L, M, N, P, R, S, T, V, W, or Y; wherein V197 is substituted with either an A, C, D, E, F, G, H, I, K, L, M, N, P, Q, R, S, T, W, or Y; wherein S198 is substituted with either an A, C, D, E, F, G, H, I, K, L, M, N, P, Q, R, T, V, W, or Y; wherein E199 is substituted with either an A, C, D, F, G, H, I, K, L, M, N, P, Q, R, S, T, V, W, or Y; wherein A200 is substituted with either a C, D, E, F, G, H, I, K, L, M, N, P, Q, R, S, T, V, W, or Y; wherein L201 is substituted with either an A, C, D, E, F, G, H, I, K, M, N, P, Q, R, S, T, V, W, or Y; wherein V202 is substituted with either an A, C, D, E, F, G, H, I, K, L, M, N, P, Q, R, S, T, W, or Y; wherein D203 is substituted with either an A, C, E, F, G, H, I, K, L, M, N, P, Q, R, S, T, V, W, or Y; wherein F204 is substituted with either an A, C, D, E, G, H, I, K, L, M, N, P, Q, R, S, T, V, W, or Y; wherein T205 is substituted with either an A, C, D, E, F, G, H, I, K, L, M, N, P, Q, R, S, V, W, or Y; wherein G206 is substituted with either an A, C, D, E, F, H, I, K, L, M, N, P, Q, R, S, T, V, W, or Y; wherein G207 is substituted with either an A, C, D, E, F, H, I, K, L, M, N, P, Q, R, S, T, V, W, or Y; wherein V208 is substituted with either an A, C, D, E, F, G, H, I, K, L, M, N, P, Q, R, S, T, W, or Y; wherein T209 is substituted with either an A, C, D, E, F, G, H, I, K, L, M, N, P, Q, R, S, V, W, or Y; wherein M210 is substituted with either an A, C, D, E, F, G, H, I, K, L, N, P, Q, R, S, T, V, W, or Y; wherein T211 is substituted with either an A, C, D, E, F, G, H, I, K, L, M, N, P, Q, R, S, V, W, or Y; wherein I212 is substituted with either an A, C, D, E, F, G, H, K, L, M, N, P, Q, R, S, T, V, W, or Y; wherein N213 is substituted with either an A, C, D, E, F, G, H, I, K, L, M, P, Q, R, S, T, V, W, or Y; wherein L214 is substituted with either an A, C, D, E, F, G, H, I, K, M, N, P, Q, R, S, T, V, W, or Y; wherein A215 is substituted with either a C, D, E, F, G, H, I, K, L, M, N, P, Q, R, S, T, V, W, or Y; wherein E216 is substituted with either an A, C, D, F, G, H, I, K, L, M, N, P, Q, R, S, T, V, W, or Y; wherein A217 is substituted with either a C, D, E, F, G, H, I, K, L, M, N, P, Q, R, S, T, V, W, or Y; wherein H218 is substituted with either an A, C, D, E, F, G, I, K, L, M, N, P, Q, R, S, T, V, W, or Y; wherein G219 is substituted with either an A, C, D, E, F, H, I, K, L, M, N, P, Q, R, S, T, V, W, or Y; wherein N220 is substituted with either an A, C, D, E, F, G, H, I, K, L, M, P, Q, R, S, T, V, W, or Y; wherein L221 is substituted with either an A, C, D, E, F, G, H, I, K, M, N, P, Q, R, S, T, V, W, or Y; wherein W222 is substituted with either an A, C, D, E, F, G, H, I, K, L, M, N, P, Q, R, S, T, V, or Y; wherein D223 is substituted with either an A, C, E, F, G, H, I, K, L, M, N, P, Q, R, S, T, V, W, or Y; wherein I224 is substituted with either an A, C, D, E, F, G, H, K, L, M, N, P, Q, R, S, T, V, W, or Y; wherein L225 is substituted with either an A, C, D, E, F, G, H, I, K, M, N, P, Q, R, S, T, V, W, or Y; wherein I226 is substituted with either an A, C, D, E, F, G, H, K, L, M, N, P, Q, R, S, T, V, W, or Y; wherein E227 is substituted with either an A, C, D, F, G, H, I, K, L, M, N, P, Q, R, S, T, V, W, or Y; wherein A228 is substituted with either a C, D, E, F, G, H, I, K, L, M, N, P, Q, R, S, T, V, W, or Y; wherein T229 is substituted with either an A, C, D, E, F, G, H, I, K, L, M, N, P, Q, R, S, V, W, or Y; wherein Y230 is substituted with either an A, C, D, E, F, G, H, I, K, L, M, N, P, Q, R, S, T, V, or W; wherein N231 is substituted with either an A, C, D, E, F, G, H, I, K, L, M, P, Q, R, S, T, V, W, or Y; wherein R232 is substituted with either an A, C, D, E, F, G, H, I, K, L, M, N, P, Q, S, T, V, W, or Y; wherein T233 is substituted with either an A, C, D, E, F, G, H, I, K, L, M, N, P, Q, R, S, V, W, or Y; wherein L234 is substituted with either an A, C, D, E, F, G, H, I, K, M, N, P, Q, R, S, T, V, W, or Y; wherein I235 is substituted with either an A, C, D, E, F, G, H, K, L, M, N, P, Q, R, S, T, V, W, or Y; wherein G236 is substituted with either an A, C, D, E, F, H, I, K, L, M, N, P, Q, R, S, T, V, W, or Y; wherein C237 is substituted with either an A, D, E, F, G, H, I, K, L, M, N, P, Q, R, S, T, V, W, or Y; wherein Q238 is substituted with either an A, C, D, E, F, G, H, I, K, L, M, N, P, R, S, T, V, W, or Y; wherein T239 is substituted with either an A, C, D, E, F, G, H, I, K, L, M, N, P, Q, R, S, V, W, or Y; wherein H240 is substituted with either an A, C, D, E, F, G, I, K, L, M, N, P, Q, R, S, T, V, W, or Y; wherein S241 is substituted with either an A, C, D, E, F, G, H, I, K, L, M, N, P, Q, R, T, V, W, or Y; wherein G242 is substituted with either an A, C, D, E, F, H, I, K, L, M, N, P, Q, R, S, T, V, W, or Y; wherein E243 is substituted with either an A, C, D, F, G, H, I, K, L, M, N, P, Q, R, S, T, V, W, or Y; wherein K244 is substituted with either an A, C, D, E, F, G, H, I, L, M, N, P, Q, R, S, T, V, W, or Y; wherein I245 is substituted with either an A, C, D, E, F, G, H, K, L, M, N, P, Q, R, S, T, V, W, or Y; wherein L246 is substituted with either an A, C, D, E, F, G, H, I, K, M, N, P, Q, R, S, T, V, W, or Y; wherein E247 is substituted with either an A, C, D, F, G, H, 1, K, L, M, N, P, Q, R, S, T, V, W, or Y; wherein N248 is substituted with either an A, C, D, E, F, G, H, I, K, L, M, P, Q, R, S, T, V, W, or Y; wherein G249 is substituted with either an A, C, D, E, F, H, I, K, L, M, N, P, Q, R, S, T, V, W, or Y; wherein L250 is substituted with either an A, C, D, E, F, G, H, I, K, M, N, P, Q, R, S, T, V, W, or Y; wherein V251 is substituted with either an A, C, D, E, F, G, H, I, K, L, M, N, P, Q, R, S, T, W, or Y; wherein E252 is substituted with either an A, C, D, F, G, H, I, K, L, M, N, P, Q, R, S, T, V, W, or Y; wherein G253 is substituted with either an A, C, D, E, F, H, I, K, L, M, N, P, Q, R, S, T, V, W, or Y; wherein H254 is substituted with either an A, C, D, E, F, G, I, K, L, M, N, P, Q, R, S, T, V, W, or Y; wherein A255 is substituted with either a C, D, E, F, G, H, I, K, L, M, N, P, Q, R, S, T, V, W, or Y; wherein Y256 is substituted with either an A, C, D, E, F, G, H, I, K, L, M, N, P, Q, R, S, T, V, or W; wherein T257 is substituted with either an A, C, D, E, F, G, H, I, K, L, M, N, P, Q, R, S, V, W, or Y; wherein L258 is substituted with either an A, C, D, E, F, G, H, I, K, M, N, P, Q, R, S, T, V, W, or Y; wherein T259 is substituted with either an A, C, D, E, F, G, H, I, K, L, M, N, P, Q, R, S, V, W, or Y; wherein G260 is substituted with either an A, C, D, E, F, H, I, K, L, M, N, P, Q, R, S, T, V, W, or Y; wherein I261 is substituted with either an A, C, D, E, F, G, H, K, L, M, N, P, Q, R, S, T, V, W, or Y; wherein R262 is substituted with either an A, C, D, E, F, G, H, I, K, L, M, N, P, Q, S, T, V, W, or Y; wherein K263 is substituted with either an A, C, D, E, F, G, H, I, L, M, N, P, Q, R, S, T, V, W, or Y; wherein V264 is substituted with either an A, C, D, E, F, G, H, I, K, L, M, N, P, Q, R, S, T, W, or Y; wherein T265 is substituted with either an A, C, D, E, F, G, H, I, K, L, M, N, P, Q, R, S, V, W, or Y; wherein C266 is substituted with either an A, D, E, F, G, H, I, K, L, M, N, P, Q, R, S, T, V, W, or Y; wherein K267 is substituted with either an A, C, D, E, F, G, H, I, L, M, N, P, Q, R, S, T, V, W, or Y; wherein H268 is substituted with either an A, C, D, E, F, G, I, K, L, M, N, P, Q, R, S, T, V, W, or Y; wherein R269 is substituted with either an A, C, D, E, F, G, H, I, K, L, M, N, P, Q, S, T, V, W, or Y; wherein P270 is substituted with either an A, C, D, E, F, G, H, I, K, L, M, N, Q, R, S, T, V, W, or Y; wherein E271 is substituted with either an A, C, D, F, G, H, I, K, L, M, N, P, Q, R, S, T, V, W, or Y; wherein Y272 is substituted with either an A, C, D, E, F, G, H, I, K, L, M, N, P, Q, R, S, T, V, or W; wherein L273 is substituted with either an A, C, D, E, F, G, H, I, K, M, N, P, Q, R, S, T, V, W, or Y; wherein V274 is substituted with either an A, C, D, E, F, G, H, I, K, L, M, N, P, Q, R, S, T, W, or Y; wherein K275 is substituted with either an A, C, D, E, F, G, H, I, L, M, N, P, Q, R, S, T, V, W, or Y; wherein L276 is substituted with either an A, C, D, E, F, G, H, I, K, M, N, P, Q, R, S, T, V, W, or Y; wherein R277 is substituted with either an A, C, D, E, F, G, H, I, K, L, M, N, P, Q, S, T, V, W, or Y; wherein N278 is substituted with either an A, C, D, E, F, G, H, I, K, L, M, P, Q, R, S, T, V, W, or Y; wherein P279 is substituted with either an A, C, D, E, F, G, H, I, K, L, M, N, Q, R, S, T, V, W, or Y; wherein W280 is substituted with either an A, C, D, E, F, G, H, I, K, L, M, N, P, Q, R, S, T, V, or Y; wherein G281 is substituted with either an A, C, D, E, F, H, I, K, L, M, N, P, Q, R, S, T, V, W, or Y; wherein K282 is substituted with either an A, C, D, E, F, G, H, I, L, M, N, P, Q, R, S, T, V, W, or Y; wherein V283 is substituted with either an A, C, D, E, F, G, H, I, K, L, M, N, P, Q, R, S, T, W, or Y; wherein E284 is substituted with either an A, C, D, F, G, H, I, K, L, M, N, P, Q, R, S, T, V, W, or Y; wherein W285 is substituted with either an A, C, D, E, F, G, H, I, K, L, M, N, P, Q, R, S, T, V, or Y; wherein K286 is substituted with either an A, C, D, E, F, G, H, I, L, M, N, P, Q, R, S, T, V, W, or Y; wherein G287 is substituted with either an A, C, D, E, F, H, I, K, L, M, N, P, Q, R, S, T, V, W, or Y; wherein D288 is substituted with either an A, C, E, F, G, H, I, K, L, M, N, P, Q, R, S, T, V, W, or Y; wherein W289 is substituted with either an A, C, D, E, F, G, H, I, K, L, M, N, P, Q, R, S, T, V, or Y; wherein S290 is substituted with either an A, C, D, E, F, G, H, I, K, L, M, N, P, Q, R, T, V, W, or Y; wherein D291 is substituted with either an A, C, E, F, G, H, I, K, L, M, N, P, Q, R, S, T, V, W, or Y; wherein S292 is substituted with either an A, C, D, E, F, G, H, I, K, L, M, N, P, Q, R, T, V, W, or Y; wherein S293 is substituted with either an A, C, D, E, F, G, H, I, K, L, M, N, P, Q, R, T, V, W, or Y; wherein S294 is substituted with either an A, C, D, E, F, G, H, I, K, L, M, N, P, Q, R, T, V, W, or Y; wherein K295 is substituted with either an A, C, D, E, F, G, H, I, L, M, N, P, Q, R, S, T, V, W, or Y; wherein W296 is substituted with either an A, C, D, E, F, G, H, I, K, L, M, N, P, Q, R, S, T, V, or Y; wherein E297 is substituted with either an A, C, D, F, G, H, I, K, L, M, N, P, Q, R, S, T, V, W, or Y; wherein L298 is substituted with either an A, C, D, E, F, G, H, I, K, M, N, P, Q, R, S, T, V, W, or Y; wherein L299 is substituted with either an A, C, D, E, F, G, H, I, K, M, N, P, Q, R, S, T, V, W, or Y; wherein S300 is substituted with either an A, C, D, E, F, G, H, I, K, L, M, N, P, Q, R, T, V, W, or Y; wherein P301 is substituted with either an A, C, D, E, F, G, H, I, K, L, M, N, Q, R, S, T, V, W, or Y; wherein K302 is substituted with either an A, C, D, E, F, G, H, I, L, M, N, P, Q, R, S, T, V, W, or Y; wherein E303 is substituted with either an A, C, D, F, G, H, I, K, L, M, N, P, Q, R, S, T, V, W, or Y; wherein K304 is substituted with either an A, C, D, E, F, G, H, I, L, M, N, P, Q, R, S, T, V, W, or Y; wherein I305 is substituted with either an A, C, D, E, F, G, H, K, L, M, N, P, Q, R, S, T, V, W, or Y; wherein L306 is substituted with either an A, C, D, E, F, G, H, I, K, M, N, P, Q, R, S, T, V, W, or Y; wherein L307 is substituted with either an A, C, D, E, F, G, H, I, K, M, N, P, Q, R, S, T, V, W, or Y; wherein L308 is substituted with either an A, C, D, E, F, G, H, I, K, M, N, P, Q, R, S, T, V, W, or Y; wherein R309 is substituted with either an A, C, D, E, F, G, H, I, K, L, M, N, P, Q, S, T, V, W, or Y; wherein K310 is substituted with either an A, C, D, E, F, G, H, I, L, M, N, P, Q, R, S, T, V, W, or Y; wherein D311 is substituted with either an A, C, E, F, G, H, I, K, L, M, N, P, Q, R, S, T, V, W, or Y; wherein N312 is substituted with either an A, C, D, E, F, G, H, I, K, L, M, P, Q, R, S, T, V, W, or Y; wherein D313 is substituted with either an A, C, E, F, G, H, I, K, L, M, N, P, Q, R, S, T, V, W, or Y; wherein G314 is substituted with either an A, C, D, E, F, H, I, K, L, M, N, P, Q, R, S, T, V, W, or Y; wherein E315 is substituted with either an A, C, D, F, G, H, I, K, L, M, N, P, Q, R, S, T, V, W, or Y; wherein F316 is substituted with either an A, C, D, E, G, H, I, K, L, M, N, P, Q, R, S, T, V, W, or Y; wherein W317 is substituted with either an A, C, D, E, F, G, H, I, K, L, M, N, P, Q, R, S, T, V, or Y; wherein M318 is substituted with either an A, C, D, E, F, G, H, I, K, L, N, P, Q, R, S, T, V, W, or Y; wherein T319 is substituted with either an A, C, D, E, F, G, H, I, K, L, M, N, P, Q, R, S, V, W, or Y; wherein L320 is substituted with either an A, C, D, E, F, G, H, I, K, M, N, P, Q, R, S, T, V, W, or Y; wherein Q321 is substituted with either an A, C, D, E, F, G, H, I, K, L, M, N, P, R, S, T, V, W, or Y; wherein D322 is substituted with either an A, C, E, F, G, H, I, K, L, M, N, P, Q, R, S, T, V, W, or Y; wherein F323 is substituted with either an A, C, D, E, G, H, I, K, L, M, N, P, Q, R, S, T, V, W, or Y; wherein K324 is substituted with either an A, C, D, E, F, G, H, I, L, M, N, P, Q, R, S, T, V, W, or Y; wherein T325 is substituted with either an A, C, D, E, F, G, H, 1, K, L, M, N, P, Q, R, S, V, W, or Y; wherein H326 is substituted with either an A, C, D, E, F, G, I, K, L, M, N, P, Q, R, S, T, V, W, or Y; wherein F327 is substituted with either an A, C, D, E, G, H, I, K, L, M, N, P, Q, R, S, T, V, W, or Y; wherein V328 is substituted with either an A, C, D, E, F, G, H, I, K, L, M, N, P, Q, R, S, T, W, or Y; wherein L329 is substituted with either an A, C, D, E, F, G, H, I, K, M, N, P, Q, R, S, T, V, W, or Y; wherein L330 is substituted with either an A, C, D, E, F, G, H, I, K, M, N, P, Q, R, S, T, V, W, or Y; and/or wherein V331 is substituted with either an A, C, D, E, F, G, H, I, K, L, M, N, P, Q, R, S, T, W, or Y of SEQ ID NO:56, in addition to any combination thereof. The present invention also encompasses the use of these CAN-12v2 active site domain amino acid substituted polypeptides as immunogenic and/or antigenic epitopes as described elsewhere herein.

In preferred embodiments, the following CAN-12v2 active site domain conservative amino acid substitutions are encompassed by the present invention: wherein R90 is substituted with either a K, or H; wherein L91 is substituted with either an A, I, or V; wherein D92 is substituted with an E; wherein L93 is substituted with either an A, I, or V; wherein C94 is a C; wherein Q95 is substituted with a N; wherein G96 is substituted with either an A, M, S, or T; wherein I97 is substituted with either an A, V, or L; wherein V98 is substituted with either an A, I, or L; wherein G99 is substituted with either an A, M, S, or T; wherein D100 is substituted with an E; wherein C101 is a C; wherein W102 is either an F, or Y; wherein F103 is substituted with either a W, or Y; wherein L104 is substituted with either an A, I, or V; wherein A105 is substituted with either a G, I, L, M, S, T, or V; wherein A106 is substituted with either a G, I, L, M, S, T, or V; wherein L107 is substituted with either an A, I, or V; wherein Q108 is substituted with a N; wherein A109 is substituted with either a G, I, L, M, S, T, or V; wherein L110 is substituted with either an A, I, or V; wherein A111 is substituted with either a G, I, L, M, S, T, or V; wherein L112 is substituted with either an A, I, or V; wherein H113 is substituted with either a K, or R; wherein Q114 is substituted with a N; wherein D115 is substituted with an E; wherein I116 is substituted with either an A, V, or L; wherein L117 is substituted with either an A, I, or V; wherein S118 is substituted with either an A, G, M, or T; wherein R119 is substituted with either a K, or H; wherein V120 is substituted with either an A, I, or L; wherein V121 is substituted with either an A, I, or L; wherein P122 is a P; wherein L123 is substituted with either an A, I, or V; wherein N124 is substituted with a Q; wherein Q125 is substituted with a N; wherein S126 is substituted with either an A, G, M, or T; wherein F127 is substituted with either a W, or Y; wherein T128 is substituted with either an A, G, M, or S; wherein E129 is substituted with a D; wherein K130 is substituted with either a R, or H; wherein Y131 is either an F, or W; wherein A132 is substituted with either a G, I, L, M, S, T, or V; wherein G133 is substituted with either an A, M, S, or T; wherein I134 is substituted with either an A, V, or L; wherein F135 is substituted with either a W, or Y; wherein R136 is substituted with either a K, or H; wherein F137 is substituted with either a W, or Y; wherein W138 is either an F, or Y; wherein F139 is substituted with either a W, or Y; wherein W140 is either an F, or Y; wherein H141 is substituted with either a K, or R; wherein Y142 is either an F, or W; wherein G143 is substituted with either an A, M, S, or T; wherein N144 is substituted with a Q; wherein W145 is either an F, or Y; wherein V146 is substituted with either an A, I, or L; wherein P147 is a P; wherein V148 is substituted with either an A, I, or L; wherein V149 is substituted with either an A, I, or L; wherein I150 is substituted with either an A, V, or L; wherein D151 is substituted with an E; wherein D152 is substituted with an E; wherein R153 is substituted with either a K, or H; wherein L154 is substituted with either an A, I, or V; wherein P155 is a P; wherein V156 is substituted with either an A, I, or L; wherein N157 is substituted with a Q; wherein E158 is substituted with a D; wherein A159 is substituted with either a G, I, L, M, S, T, or V; wherein G160 is substituted with either an A, M, S, or T; wherein Q161 is substituted with a N; wherein L162 is substituted with either an A, I, or V; wherein V163 is substituted with either an A, I, or L; wherein F164 is substituted with either a W, or Y; wherein V165 is substituted with either an A, I, or L; wherein S166 is substituted with either an A, G, M, or T; wherein S167 is substituted with either an A, G, M, or T; wherein T168 is substituted with either an A, G, M, or S; wherein Y169 is either an F, or W; wherein K170 is substituted with either a R, or H; wherein N171 is substituted with a Q; wherein L172 is substituted with either an A, I, or V; wherein F173 is substituted with either a W, or Y; wherein W174 is either an F, or Y; wherein G175 is substituted with either an A, M, S, or T; wherein A176 is substituted with either a G, I, L, M, S, T, or V; wherein L177 is substituted with either an A, I, or V; wherein L178 is substituted with either an A, I, or V; wherein E179 is substituted with a D; wherein K180 is substituted with either a R, or H; wherein A181 is substituted with either a G, I, L, M, S, T, or V; wherein Y182 is either an F, or W; wherein A183 is substituted with either a G, I, L, M, S, T, or V; wherein K184 is substituted with either a R, or H; wherein L185 is substituted with either an A, I, or V; wherein S186 is substituted with either an A, G, M, or T; wherein G187 is substituted with either an A, M, S, or T; wherein S188 is substituted with either an A, G, M, or T; wherein Y189 is either an F, or W; wherein E190 is substituted with a D; wherein D191 is substituted with an E; wherein L192 is substituted with either an A, I, or V; wherein Q193 is substituted with a N; wherein S194 is substituted with either an A, G, M, or T; wherein G195 is substituted with either an A, M, S, or T; wherein Q196 is substituted with a N; wherein V197 is substituted with either an A, I, or L; wherein S198 is substituted with either an A, G, M, or T; wherein E199 is substituted with a D; wherein A200 is substituted with either a G, I, L, M, S, T, or V; wherein L201 is substituted with either an A, I, or V; wherein V202 is substituted with either an A, I, or L; wherein D203 is substituted with an E; wherein F204 is substituted with either a W, or Y; wherein T205 is substituted with either an A, G, M, or S; wherein G206 is substituted with either an A, M, S, or T; wherein G207 is substituted with either an A, M, S, or T; wherein V208 is substituted with either an A, I, or L; wherein T209 is substituted with either an A, G, M, or S; wherein M210 is substituted with either an A, G, S, or T; wherein T211 is substituted with either an A, G, M, or S; wherein I212 is substituted with either an A, V, or L; wherein N213 is substituted with a Q; wherein L214 is substituted with either an A, I, or V; wherein A215 is substituted with either a G, I, L, M, S, T, or V; wherein E216 is substituted with a D; wherein A217 is substituted with either a G, I, L, M, S, T, or V; wherein H218 is substituted with either a K, or R; wherein G219 is substituted with either an A, M, S, or T; wherein N220 is substituted with a Q; wherein L221 is substituted with either an A, I, or V; wherein W222 is either an F, or Y; wherein D223 is substituted with an E; wherein I224 is substituted with either an A, V, or L; wherein L225 is substituted with either an A, I, or V; wherein I226 is substituted with either an A, V, or L; wherein E227 is substituted with a D; wherein A228 is substituted with either a G, I, L, M, S, T, or V; wherein T229 is substituted with either an A, G, M, or S; wherein Y230 is either an F, or W; wherein N231 is substituted with a Q; wherein R232 is substituted with either a K, or H; wherein T233 is substituted with either an A, G, M, or S; wherein L234 is substituted with either an A, I, or V; wherein I235 is substituted with either an A, V, or L; wherein G236 is substituted with either an A, M, S, or T; wherein C237 is a C; wherein Q238 is substituted with a N; wherein T239 is substituted with either an A, G, M, or S; wherein H240 is substituted with either a K, or R; wherein S241 is substituted with either an A, G, M, or T; wherein G242 is substituted with either an A, M, S, or T; wherein E243 is substituted with a D; wherein K244 is substituted with either a R, or H; wherein I245 is substituted with either an A, V, or L; wherein L246 is substituted with either an A, I, or V; wherein E247 is substituted with a D; wherein N248 is substituted with a Q; wherein G249 is substituted with either an A, M, S, or T; wherein L250 is substituted with either an A, I, or V; wherein V251 is substituted with either an A, I, or L; wherein E252 is substituted with a D; wherein G253 is substituted with either an A, M, S, or T; wherein H254 is substituted with either a K, or R; wherein A255 is substituted with either a G, I, L, M, S, T, or V; wherein Y256 is either an F, or W; wherein T257 is substituted with either an A, G, M, or S; wherein L258 is substituted with either an A, I, or V; wherein T259 is substituted with either an A, G, M, or S; wherein G260 is substituted with either an A, M, S, or T; wherein I261 is substituted with either an A, V, or L; wherein R262 is substituted with either a K, or H; wherein K263 is substituted with either a R, or H; wherein V264 is substituted with either an A, I, or L; wherein T265 is substituted with either an A, G, M, or S; wherein C266 is a C; wherein K267 is substituted with either a R, or H; wherein H268 is substituted with either a K, or R; wherein R269 is substituted with either a K, or H; wherein P270 is a P; wherein E271 is substituted with a D; wherein Y272 is either an F, or W; wherein L273 is substituted with either an A, I, or V; wherein V274 is substituted with either an A, I, or L; wherein K275 is substituted with either a R, or H; wherein L276 is substituted with either an A, I, or V; wherein R277 is substituted with either a K, or H; wherein N278 is substituted with a Q; wherein P279 is a P; wherein W280 is either an F, or Y; wherein G281 is substituted with either an A, M, S, or T; wherein K282 is substituted with either a R, or H; wherein V283 is substituted with either an A, I, or L; wherein E284 is substituted with a D; wherein W285 is either an F, or Y; wherein K286 is substituted with either a R, or H; wherein G287 is substituted with either an A, M, S, or T; wherein D288 is substituted with an E; wherein W289 is either an F, or Y; wherein S290 is substituted with either an A, G, M, or T; wherein D291 is substituted with an E; wherein S292 is substituted with either an A, G, M, or T; wherein S293 is substituted with either an A, G, M, or T; wherein S294 is substituted with either an A, G, M, or T; wherein K295 is substituted with either a R, or H; wherein W296 is either an F, or Y; wherein E297 is substituted with a D; wherein L298 is substituted with either an A, I, or V; wherein L299 is substituted with either an A, I, or V; wherein S300 is substituted with either an A, G, M, or T; wherein P301 is a P; wherein K302 is substituted with either a R, or H; wherein E303 is substituted with a D; wherein K304 is substituted with either a R, or H; wherein I305 is substituted with either an A, V, or L; wherein L306 is substituted with either an A, I, or V; wherein L307 is substituted with either an A, I, or V; wherein L308 is substituted with either an A, I, or V; wherein R309 is substituted with either a K, or H; wherein K310 is substituted with either a R, or H; wherein D311 is substituted with an E; wherein N312 is substituted with a Q; wherein D313 is substituted with an E; wherein G314 is substituted with either an A, M, S, or T; wherein E315 is substituted with a D; wherein F316 is substituted with either a W, or Y; wherein W317 is either an F, or Y; wherein M318 is substituted with either an A, G, S, or T; wherein T319 is substituted with either an A, G, M, or S; wherein L320 is substituted with either an A, I, or V; wherein Q321 is substituted with a N; wherein D322 is substituted with an E; wherein F323 is substituted with either a W, or Y; wherein K324 is substituted with either a R, or H; wherein T325 is substituted with either an A, G, M, or S; wherein H326 is substituted with either a K, or R; wherein F327 is substituted with either a W, or Y; wherein V328 is substituted with either an A, I, or L; wherein L329 is substituted with either an A, I, or V; wherein L330 is substituted with either an A, I, or V; and/or wherein V331 is substituted with either an A, I, or L of SEQ ID NO:56 in addition to any combination thereof. Other suitable substitutions within the CAN-12v2 active site domain are encompassed by the present invention and are referenced elsewhere herein. The present invention also encompasses the use of these CAN-12v2 active site domain conservative amino acid substituted polypeptides as immunogenic and/or antigenic epitopes as described elsewhere herein.

For purposes of the present invention, by "at least a portion of" is meant all or any part of the CAN-12v2 active site domain defined by the structure coordinates according to Table V (e.g., fragments thereof). More preferred are molecules comprising all or any parts of the CAN-12v2 active site domain defined by the structure coordinates according to Table V, or a mutant or homologue of said molecule or molecular complex. By mutant or homologue of the molecule it is meant a molecule that has a root mean square deviation from the backbone atoms of said CAN-12v2 amino acids of not more than 4.5 Angstroms, and preferably not more than 3.5 Angstroms.

The term "root mean square deviation" means the square root of the arithmetic mean of the squares of the deviations from the mean. It is a term that expresses the deviation or variation from a trend or object. For the purposes of the present invention, the "root mean square deviation" defines the variation in the backbone of a protein from the relevant portion of the backbone of the AR portion of the complex as defined by the structure coordinates described herein.

A preferred embodiment is a machine-readable data storage medium that is capable of displaying a graphical three-dimensional representation of a molecule or molecular complex that is defined by the structure coordinates of all of the amino acids in Table V +/– a root mean square deviation from the backbone atoms of those amino acids of not more than 4.0 HANG, preferably 3.0 HANG.

The structure coordinates of a CAN-12v2 homology model, including portions thereof, is stored in a machine-readable storage medium. Such data may be used for a variety of purposes, such as drug discovery.

Accordingly, in one embodiment of this invention is provided a machine-readable data storage medium comprising a data storage material encoded with the structure coordinates set forth in Table V.

One embodiment utilizes System 10 as disclosed in WO 98/11134, the disclosure of which is incorporated herein by reference in its entirety. Briefly, one version of these embodiments comprises a computer comprising a central processing unit ("CPU"), a working memory which may be, e.g., RAM (random-access memory) or "core" memory, mass storage memory (such as one or more disk drives or CD-ROM drives), one or more cathode-ray tube ("CRT") display terminals, one or more keyboards, one or more input lines, and one or more output lines, all of which are interconnected by a conventional bisectional system bus.

Input hardware, coupled to the computer by input lines, may be implemented in a variety of ways. Machine-readable data of this invention may be inputted via the use of a modem or modems connected by a telephone line or dedicated data line. Alternatively or additionally, the input hardware may comprise CD-ROM drives or disk drives. In conjunction with a display terminal, keyboard may also be used as an input device.

Output hardware, coupled to the computer by output lines, may similarly be implemented by conventional devices. By way of example, output hardware may include a CRT display terminal for displaying a graphical representation of a region or domain of the present invention using a program such as QUANTA as described herein. Output hardware might also include a printer, so that hard copy output may be produced, or a disk drive, to store system output for later use.

In operation, the CPU coordinates the use of the various input and output devices, coordinates data accesses from mass storage, and accesses to and from the working memory, and determines the sequence of data processing steps. A number of programs may be used to process the machine-readable data of this invention. Such programs are discussed in reference to the computational methods of drug discovery as described herein. Specific references to components of the hardware system are included as appropriate throughout the following description of the data storage medium.

For the purpose of the present invention, any magnetic data storage medium which can be encoded with machine-readable data would be sufficient for carrying out the storage requirements of the system. The medium could be a conventional floppy diskette or hard disk, having a suitable substrate, which may be conventional, and a suitable coating, which may be conventional, on one or both sides, containing magnetic domains whose polarity or orientation could be altered magnetically, for example. The medium may also have an opening for receiving the spindle of a disk drive or other data storage device.

The magnetic domains of the coating of a medium may be polarized or oriented so as to encode in a manner which may be conventional, machine readable data such as that described herein, for execution by a system such as the system described herein.

Another example of a suitable storage medium which could also be encoded with such machine-readable data, or set of instructions, which could be carried out by a system such as the system described herein, could be an optically-readable data storage medium. The medium could be a conventional compact disk read only memory (CD-ROM) or a rentable medium such as a magneto-optical disk which is optically readable and magneto-optically writ able. The medium preferably has a suitable substrate, which may be conventional, and a suitable coating, which may be conventional, usually of one side of substrate.

In the case of a CD-ROM, as is well known, the coating is reflective and is impressed with a plurality of pits to encode the machine-readable data. The arrangement of pits is read by reflecting laser light off the surface of the coating. A protective coating, which preferably is substantially transparent, is provided on top of the reflective coating.

In the case of a magneto-optical disk, as is well known, the coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

Thus, in accordance with the present invention, data capable of displaying the three dimensional structure of the CAN-12v2 homology model, or portions thereof and their structurally similar homologues is stored in a machine-readable storage medium, which is capable of displaying a graphical three-dimensional representation of the structure. Such data may be used for a variety of purposes, such as drug discovery.

For the first time, the present invention permits the use of structure-based or rational drug design techniques to design, select, and synthesize chemical entities that are capable of modulating the biological function of CAN-12v2.

Accordingly, the present invention is also directed to the design of small molecules which imitates the structure of the CAN-12v2 active site domain (SEQ ID NO:93), or a portion thereof defined by the structure provided in Table V. Alternatively, the present invention is directed to the design of small molecules which may bind to at least part of the CAN-12v2 active site domain (SEQ ID NO:93), or some portion thereof. For purposes of this invention, by CAN-12v2 active site domain, it is also meant to include mutants or homologues thereof. In a preferred embodiment, the mutants or homologues have at least 25% identity, more preferably 50% identity, more preferably 75% identity, and most preferably 90% identity to SEQ ID NO:93. In this context, the term "small molecule" may be construed to mean any molecule described known in the art or described elsewhere herein, though may include, for example, peptides, chemicals, carbohydrates, nucleic acids, PANS, and any derivatives thereof.

The three-dimensional model structure of CAN-12v2 will also provide methods for identifying modulators of biological function. Various methods or combination thereof can be used to identify these compounds.

For example, test compounds can be modeled that fit spatially into the active site domain in CAN-12v2 embodied by the sequence from about R90 to about amino acid C94, from about amino acid G99 to about amino acid L104, from about amino acid Q196 to about amino acid S198, from about amino acid M210 to about amino acid I212, from about amino acid G236 to about amino acid H240, from about amino acid E252 to about amino acid Y256, from about amino acid N278 to about amino acid K282, from about amino acid V328 to about amino acid V331, or some portion thereof, of SEQ ID NO:56 (corresponding to SEQ ID NO:93), in accordance with the structural coordinates of Table V.

Structure coordinates of the active site domain in CAN-12v2 defined by the amino acids from about R90 to about amino acid C94, from about amino acid G99 to about amino acid L104, from about amino acid Q196 to about amino acid S198, from about amino acid M210 to about amino acid I212, from about amino acid G236 to about amino acid H240, from about amino acid E252 to about amino acid Y256, from about amino acid N278 to about amino acid K282, from about amino acid V328 to about amino acid V331 of SEQ ID NO:56, can also be used to identify structural and chemical features. Identified structural or chemical features can then be employed to design or select compounds as potential CAN-12v2 modulators. By structural and chemical features it is meant to include, but is not limited to, van dear Waals interactions, hydrogen bonding interactions, charge interaction, hydrophobic bonding interaction, and dipole interaction. Alternatively, or in conjunction with, the three-dimensional structural model can be employed to design or select compounds as potential CAN-12v2 modulators. Compounds identified as potential CAN-12v2 modulators can then be synthesized and screened in an assay characterized by binding of a test compound to the CAN-12v2, or in characterizing the ability of CAN-12v2 to modulate a protease target in the presence of a small molecule. Examples of assays useful in screening of potential CAN-12v2 modulators include, but are not limited to, screening in silico, in vitro assays and high throughput assays. Finally, these methods may also involve modifying or replacing one or more amino acids at amino acid positions, C101, H254, and/or N278 of SEQ ID NO:56 in accordance with the structure coordinates of Table V.

However, as will be understood by those of skill in the art upon this disclosure, other structure based design methods can be used. Various computational structure based design methods have been disclosed in the art.

For example, a number of computer modeling systems are available in which the sequence of the CAN-12v2 and the CAN-12v2 structure (i.e., atomic coordinates of CAN-12v2 and/or the atomic coordinates of the active site domain as provided in Table V, can be input. This computer system then generates the structural details of one or more these regions in which a potential CAN-12v2 modulator binds so that complementary structural details of the potential modulators can be determined. Design in these modeling systems is generally based upon the compound being capable of physically and structurally associating with CAN-12v2. In addition, the compound must be able to assume a confirmation that allows it to associate with CAN-12v2. Some modeling systems estimate the potential inhibitory or binding effect of a potential CAN-12v2 modulator prior to actual synthesis and testing.

Methods for screening chemical entities or fragments for their ability to associate with a given protein target are also well known. Often these methods begin by visual inspection of the binding site on the computer screen. Selected fragments or chemical entities are then positioned in the active site domain of CAN-12v2. Docking is accomplished using software such as INSIGHTS, QUANTA and SYBYL, following by energy minimization and molecular dynamics with standard molecular mechanic forcefields such as CHARMM and AMBER. Examples of computer programs which assist in the selection of chemical fragment or chemical entities useful in the present invention include, but are not limited to, GRID (Good ford, 1985), AUTO DOCK (Goods ell, 1990), and DOCK (Kuntz et al. 1982).

Upon selection of preferred chemical entities or fragments, their relationship to each other and CAN-12v2 can be visualized and then assembled into a single potential modulator. Programs useful in assembling the individual chemical entities include, but are not limited to CAVEAT (Bartlett et al. 1989) and 3D Database systems (Martin 1992).

Alternatively, compounds may be designed de novo using either an empty active site or optionally including some portion of a known inhibitor. Methods of this type of design include, but are not limited to LODI (Bohm 1992) and LeapFrog (Tripods Associates, St. Louis Mo.).

In addition, CAN-12v2 is overall well suited to modern methods including combinatorial chemistry.

Programs such as DOCK (Kuntz et al. 1982) can be used with the atomic coordinates from the homology model to identify potential ligands from databases or virtual databases which potentially bind CAN-12v2 active site domain, and which may therefore be suitable candidates for synthesis and testing.

Additionally, the three-dimensional homology model of CAN-12v2 will aid in the design of mutants with altered biological activity for the CAN-12v2 polypeptide.

The following are encompassed by the present invention: a machine-readable data storage medium, comprising a data storage material encoded with machine readable data, wherein the data is defined by the structure coordinates of the model CAN-12v2 according to Table V or a homologue of said model, wherein said homologue comprises backbone atoms that have a root mean square deviation from the backbone atoms of the complex of not more than 4.5 Å, preferably not more than 4.0 Å, most preferably not more than 3.5 Å, and even more preferably not more than 3.0 Å; and a machine-readable data storage medium, wherein said molecule is defined by the set of structure coordinates of the model for CAN-12v2 according to Table V, or a homologue of said molecule, said homologue having a root mean square deviation from the backbone atoms of said amino acids of not more than 4.5 Å, preferably not more than 4.0 Å, most preferably not more than 3.5 Å, and even more preferably not more than 3.0 Å; a model comprising all or any part of the model defined by structure coordinates of CAN-12v2 according to Table V, or a mutant or homologue of said molecule or molecular complex.

In a further embodiment, the following are encompassed by the present invention: a method for identifying a mutant of CAN-12v2 with altered biological properties, function, or reactivity, the method comprising any combination of steps of: use of the model or a homologue of said model according to Table V, for the design of protein mutants with altered biological function or properties which exhibit any combination of therapeutic effects provided elsewhere herein; and use of the model or a homologue of said model, for the design of a protein with mutations in the active site domain comprised of the amino acids from about R90 to about amino acid C94, from about amino acid G99 to about amino acid L104, from about amino acid Q196 to about amino acid S198, from about amino acid M210 to about amino acid I212, from about amino acid G236 to about amino acid H240, from about amino acid E252 to about amino acid Y256, from about amino acid N278 to about amino acid K282, from about amino acid V328 to about amino acid V331 of SEQ ID NO:56 according to Table V with altered biological function or properties which exhibit any combination of therapeutic effects provided elsewhere herein.

In further preferred embodiments, the following are encompassed by the present invention: a method for identifying modulators of CAN-12v2 biological properties, function, or reactivity, the method comprising any combination of steps of: modeling test compounds that overlay spatially into the active site domain defined by all or any portion of residues from about R90 to about amino acid C94, from about amino acid G99 to about amino acid L104, from about amino acid Q196 to about amino acid S198, from about amino acid M210 to about amino acid I212, from about amino acid G236 to about amino acid H240, from about amino acid E252 to about amino acid Y256, from about amino acid N278 to about amino acid K282, from about amino acid V328 to about amino acid V331 of SEQ ID NO:56 according to Table V, or using a homologue or portion thereof.

The present invention encompasses using the structure coordinates as set forth herein to identify structural and chemical features of the CAN-12v2 polypeptide; employing identified structural or chemical features to design or select compounds as potential CAN-12v2 modulators; employing the three-dimensional structural model to design or select compounds as potential CAN-12v2 modulators; synthesizing the potential CAN-12v2 modulators; screening the potential CAN-12v2 modulators in an assay characterized by binding of a protein to the CAN-12v2; selecting the potential CAN-12v2 modulator from a database; designing the CAN-12v2 modulator de novo; and/or designing said CAN-12v2 modulator from a known modulator activity.

Many polynucleotide sequences, such as EST sequences, are publicly available and accessible through sequence databases. Some of these sequences are related to SEQ ID NO: 55 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 2090 of SEQ ID NO:55, b is an integer between 15 to 2104, where both a and b correspond to the positions of nucleotide residues shown in SEQ ID NO:55, and where b is greater than or equal to a+14.

In one embodiment, a CAN12.v2 polypeptide comprises a portion of the amino sequence depicted in FIGS. 9A–C. In another embodiment, a CAN12.v2 polypeptide comprises at least 4, 5, 6, 7, 8, 9, 10, 11, 12, 13, 14, 15, 16, 17, 18, 19 or 20 amino acids of the amino sequence depicted in FIGS. 9A–C. In further embodiments, the CAN12.v2 polypeptide does not consist of the sequence ALLEKAYAKL (SEQ ID NO:141), and/or ALLEKAYAKLSGSYE. (SEQ ID NO:142)

TABLE I

| Gene No. | CDNA CloneID | ATCC Deposit No. Z and Date | Vector | NT SEQ ID. No. X | Total NT Seq of Clone | 5' NT of Start Codon of ORF | 3' NT of ORF | AA Seq ID No. Y | Total AA of ORF |
|---|---|---|---|---|---|---|---|---|---|
| 1. | CAN-12 (protease 5, clone 70) | XXXXX Xx/Xx/Xx | pSport 1 | 1 and 23 | 4584 | 114 | 1397 | 24 | 428 |
| 1. | CAN-12 (protease 5, clone 70, CAN-12+) + splice amino acids | XXXXX Xx/Xx/Xx | pSport 1 | 1 | 4584 | 114 | 1995 | 2 | 581 |
| 2. | CAN-12v1 (protease 5, clone 1e) | PTA-3434 Jun. 07, 2001 | pSport 1 | 53 | 2095 | 9 | 2090 | 54 | 694 |
| 3. | CAN-12v2 (protease 5, clone 1e1b-1) | PTA-3434 Jun. 07, 2001 | pSport 1 | 55 | 2104 | 9 | 2099 | 56 | 697 |

Table I summarizes the information corresponding to each "Gene No." described above. The nucleotide sequence identified as "NT SEQ ID NO:X" was assembled from partially homologous ("overlapping") sequences obtained from the "cDNA clone ID" identified in Table I and, in some cases, from additional related DNA clones. The overlapping sequences were assembled into a single contiguous sequence of high redundancy (usually several overlapping sequences at each nucleotide position), resulting in a final sequence identified as SEQ ID NO:X.

The cDNA Clone ID was deposited on the date and given the corresponding deposit number listed in "ATCC Deposit No:Z and Date." "Vector" refers to the type of vector contained in the cDNA Clone ID.

"Total NT Seq. Of Clone" refers to the total number of nucleotides in the clone contig identified by "Gene No." The deposited clone may contain all or most of the sequence of SEQ ID NO:X. The nucleotide position of SEQ ID NO:X of the putative start codon (methionine) is identified as "5' NT of Start Codon of ORF."

The translated amino acid sequence, beginning with the methionine, is identified as "AA SEQ ID NO:Y," although other reading frames can also be easily translated using known molecular biology techniques. The polypeptides produced by these alternative open reading frames are specifically contemplated by the present invention.

The total number of amino acids within the open reading frame of SEQ ID NO:Y is identified as "Total AA of ORF".

SEQ ID NO:X (where X may be any of the polynucleotide sequences disclosed in the sequence listing) and the translated SEQ ID NO:Y (where Y may be any of the polypeptide sequences disclosed in the sequence listing) are sufficiently accurate and otherwise suitable for a variety of uses well known in the art and described further herein. For instance, SEQ ID NO:X is useful for designing nucleic acid hybridization probes that will detect nucleic acid sequences contained in SEQ ID NO:X or the cDNA contained in the deposited clone. These probes will also hybridize to nucleic acid molecules in biological samples, thereby enabling a variety of forensic and diagnostic methods of the invention. Similarly, polypeptides identified from SEQ ID NO:Y may be used, for example, to generate antibodies which bind specifically to proteins containing the polypeptides and the proteins encoded by the cDNA clones identified in Table I.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides may cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:1, 23, 53, and/or 55 and the predicted translated amino acid sequence identified as SEQ ID NO:2, 24, 54, and/or 56, but also a sample of plasmid DNA containing a cDNA of the invention deposited with the ATCC, as set forth in Table I. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell containing the deposited cDNA, collecting the protein, and determining its sequence.

The present invention also relates to the genes corresponding to SEQ ID NO:1, 23, 53, and/or 55, SEQ ID NO:2, 24, 54, or 56, or the deposited clone. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are species homologs, allelic variants, and/or orthologs. The skilled artisan could, using procedures well-known in the art, obtain the polynucleotide sequence corresponding to full-length genes (including, but not limited to the full-length coding region), allelic variants, splice variants, orthologs, and/or species homologues of genes corresponding to SEQ ID NO:1, 23, 53, and/or 55, SEQ ID NO:2, 24, 54, and/or 56, or a deposited clone, relying on the sequence from the sequences disclosed herein or the clones deposited with the ATCC. For example, allelic variants and/or species homologues may be isolated and identified by making suitable probes or primers which correspond to the 5', 3', or internal regions of the sequences provided herein and screening a suitable nucleic acid source for allelic variants and/or the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the protein, or may be a part of a larger protein, such as a fusion protein (see below). It is often advantageous to include an additional amino acid sequence which contains secretory or leader sequences, pro-sequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, can be substantially purified using techniques described herein or otherwise known in the art, such as, for example, by the one-step method described in Smith and Johnson, Gene 67:31–40 (1988). Polypeptides of the invention also can be purified from natural, synthetic or recombinant sources using protocols described herein or otherwise known in the art, such as, for example, antibodies of the invention raised against the full-length form of the protein.

The present invention provides a polynucleotide comprising, or alternatively consisting of, the sequence identified as SEQ ID NO:1, 23, 53, and/or 55, and/or a cDNA provided in ATCC Deposit No. Z:. The present invention also provides a polypeptide comprising, or alternatively consisting of, the sequence identified as SEQ ID NO:2, 24, 54, and/or 56, and/or a polypeptide encoded by the cDNA provided in ATCC Deposit NO:Z. The present invention also provides polynucleotides encoding a polypeptide comprising, or alternatively consisting of the polypeptide sequence of SEQ ID NO:2, 24, 54, and/or 56, and/or a polypeptide sequence encoded by the cDNA contained in ATCC Deposit No:Z.

Preferably, the present invention is directed to a polynucleotide comprising, or alternatively consisting of, the sequence identified as SEQ ID NO:1, 23, 53, and/or 55, and/or a cDNA provided in ATCC Deposit No.: that is less than, or equal to, a polynucleotide sequence that is 5 mega basepairs, 1 mega basepairs, 0.5 mega basepairs, 0.1 mega basepairs, 50,000 basepairs, 20,000 basepairs, or 10,000 basepairs in length.

The present invention encompasses polynucleotides with sequences complementary to those of the polynucleotides of the present invention disclosed herein. Such sequences may be complementary to the sequence disclosed as SEQ ID NO:1, 23, 53, and/or 55, the sequence contained in a deposit, and/or the nucleic acid sequence encoding the sequence disclosed as SEQ ID NO:2, 24, 54, and/or 56.

The present invention also encompasses polynucleotides capable of hybridizing, preferably under reduced stringency conditions, more preferably under stringent conditions, and most preferably under highly stringent conditions, to polynucleotides described herein. Examples of stringency conditions are shown in Table II below: highly stringent conditions are those that are at least as stringent as, for example, conditions A–F; stringent conditions are at least as stringent as, for example, conditions G–L; and reduced stringency conditions are at least as stringent as, for example, conditions M–R.

TABLE II

| Stringency Condition | Polynucleotide Hybrid ± | Hybrid Length (bp) ‡ | Hybridization Temperature and Buffer † | Wash Temperature and Buffer † |
|---|---|---|---|---|
| A | DNA:DNA | > or equal to 50 | 65° C.; 1xSSC - or- 42° C.; 1xSSC, 50% formamide | 65° C.; 0.3xSSC |
| B | DNA:DNA | <50 | Tb*; 1xSSC | Tb*; 1xSSC |
| C | DNA:RNA | > or equal to 50 | 67° C.; 1xSSC - or- 45° C.; 1xSSC, 50% formamide | 67° C.; 0.3xSSC |
| D | DNA:RNA | <50 | Td*; 1xSSC | Td*; 1xSSC |
| E | RNA:RNA | > or equal to 50 | 70° C.; 1xSSC - or- 50° C.; 1xSSC, 50% formamide | 70° C.; 0.3xSSC |
| F | RNA:RNA | <50 | Tf*; 1xSSC | Tf*; 1xSSC |
| G | DNA:DNA | > or equal to 50 | 65° C.; 4xSSC - or- 45° C.; 4xSSC, 50% formamide | 65° C.; 1xSSC |
| H | DNA:DNA | <50 | Th*; 4xSSC | Th*; 4xSSC |
| I | DNA:RNA | > or equal to 50 | 67° C.; 4xSSC - or- 45° C.; 4xSSC, 50% formamide | 67° C.; 1xSSC |
| J | DNA:RNA | <50 | Tj*; 4xSSC | Tj*; 4xSSC |
| K | RNA:RNA | > or equal to 50 | 70° C.; 4xSSC - or- 40° C.; 6xSSC, 50% formamide | 67° C.; 1xSSC |
| L | RNA:RNA | <50 | Tl*; 2xSSC | Tl*; 2xSSC |
| M | DNA:DNA | > or equal to 50 | 50° C.; 4xSSC - or- 40° C. 6xSSC, 50% formamide | 50° C.; 2xSSC |
| N | DNA:DNA | <50 | Tn*; 6xSSC | Tn*; 6xSSC |
| O | DNA:RNA | > or equal to 50 | 55° C.; 4xSSC - or- 42° C.; 6xSSC, 50% formamide | 55° C.; 2xSSC |
| P | DNA:RNA | <50 | Tp*; 6xSSC | Tp*; 6xSSC |

TABLE II-continued

| Stringency Condition Hybrid | Polynucleotide Hybrid ± | Hybrid Length (bp) ‡ | Hybridization Temperature and Buffer † | Wash Temperature and Buffer † |
|---|---|---|---|---|
| Q | RNA:RNA | > or equal to 50 | 60° C.; 4xSSC - or- 45° C.; 6xSSC, 50% formamide | 60° C.; 2xSSC |
| R | RNA:RNA | <50 | Tr*; 4xSSC | Tr*; 4xSSC |

‡ The "hybrid length" is the anticipated length for the hybridized region(s) of the hybridizing polynucleotides. When hybridizing a polynucleotide of unknown sequence, the hybrid is assumed to be that of the hybridizing plynucleotide of the present invention. When polynucletides of known sequence are hybridized, the hybrid length can be determined by aligning the sequences of the polynucleotides and identifying the region or regions of optimal sequence complementarity. Methods ofaligning two or more polynucleotide sequences and/or determining the percent identity between two polynucleotide sequences are well known in the art (e.g., MegAlign program of the DNA*Star suite of programs, etc).
† SSPE (1xSSPE is 0.15M NaCl, 10 mM NaH2PO4, and 1.25 mM EDTA, pH 7.4) can be substituted for SSC (1xSSC is 0.15 M NaCl and 15 mM sodium citrate) in the hybridization and wash buffers; washes are performed for 15 minutes after hybridization is complete. The hydridizations and washes may additionally include 5X Denhardt's reagent, .5–1.0% SDS, 100 ug/ml denatured, fragmented salmon sperm DNA, 0.5% sodium pyrophosphate, and up to 50% formamide.
*Tb–Tr: The hybridization temperature for hybrids anticipated to be less than 50 base pairs in length should be 5–10° C. less than the melting temperature Tm of the hybrids there Tm is determined according to the following equations. For hybrids less than 18 base pairs in length, Tm(° C.) = 2(# of A + T bases) + 4(# of G + C bases). For hybrids between 18 and 49 base pairs in length,Tm(° C.) = 81.5 + 16.6($\log_{10}$[Na+]) + 0.41(% G + C) − (600/N), where N is the number of bases in the hybrid, and [Na+] is the concentration of sodium ions in the hybridization buffer ([NA+] for 1xSSC = .165 M).
± The present invention encompasses the substitution of any one, or more DNA or RNA hybrid partners with either a PNA, or a modified polynucleotide. Such modified polynucleotides are known in the art and are more particularly described elsewhere herein.

Additional examples of stringency conditions for polynucleotide hybridization are provided, for example, in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M., Ausubel et al., eds, John Wiley and Sons, Inc., sections 2.10 and 6.3–6.4, which are hereby incorporated by reference herein.

Preferably, such hybridizing polynucleotides have at least 70% sequence identity (more preferably, at least 80% identity; and most preferably at least 90% or 95% identity) with the polynucleotide of the present invention to which they hybridize, where sequence identity is determined by comparing the sequences of the hybridizing polynucleotides when aligned so as to maximize overlap and identity while minimizing sequence gaps. The determination of identity is well known in the art, and discussed more specifically elsewhere herein.

The invention encompasses the application of PCR methodology to the polynucleotide sequences of the present invention, the clone deposited with the ATCC, and/or the cDNA encoding the polypeptides of the present invention. PCR techniques for the amplification of nucleic acids are described in U.S. Pat. No. 4,683,195 and Saiki et al., Science, 239:487–491 (1988). PCR, for example, may include the following steps, of denaturation of template nucleic acid (if double-stranded), annealing of primer to target, and polymerization. The nucleic acid probed or used as a template in the amplification reaction may be genomic DNA, cDNA, RNA, or a PNA. PCR may be used to amplify specific sequences from genomic DNA, specific RNA sequence, and/or cDNA transcribed from mRNA. References for the general use of PCR techniques, including specific method parameters, include Mullis et al., Cold Spring Harbor Symp. Quant. Biol., 51:263, (1987), Ehrlich (ed), PCR Technology, Stockton Press, NY, 1989; Ehrlich et al., Science, 252:1643–1650, (1991); and "PCR Protocols, A Guide to Methods and Applications", Eds., Innis et al., Academic Press, New York, (1990).

Signal Sequences

The present invention also encompasses mature forms of the polypeptide comprising, or alternatively consisting of, the polypeptide sequence of SEQ ID NO:2, 24, 54, and/or 56, the polypeptide encoded by the polynucleotide described as SEQ ID NO:1, 23, 53, and/or 55, and/or the polypeptide sequence encoded by a cDNA in the deposited clone. The present invention also encompasses polynucleotides encoding mature forms of the present invention, such as, for example the polynucleotide sequence of SEQ ID NO:1, 23, 53, and/or 55, and/or the polynucleotide sequence provided in a cDNA of the deposited clone.

According to the signal hypothesis, proteins secreted by eukaryotic cells have a signal or secretary leader sequence which is cleaved from the mature protein once export of the growing protein chain across the rough endoplasmic reticulum has been initiated. Most eukaryotic cells cleave secreted proteins with the same specificity. However, in some cases, cleavage of a secreted protein is not entirely uniform, which results in two or more mature species of the protein. Further, it has long been known that cleavage specificity of a secreted protein is ultimately determined by the primary structure of the complete protein, that is, it is inherent in the amino acid sequence of the polypeptide.

Methods for predicting whether a protein has a signal sequence, as well as the cleavage point for that sequence, are available. For instance, the method of McGeoch, Virus Res. 3:271–286 (1985), uses the information from a short N-terminal charged region and a subsequent uncharged region of the complete (uncleaved) protein. The method of von Heinje, Nucleic Acids Res. 14:4683–4690 (1986) uses the information from the residues surrounding the cleavage site, typically residues −13 to +2, where +1 indicates the amino terminus of the secreted protein. The accuracy of predicting the cleavage points of known mammalian secretory proteins for each of these methods is in the range of 75–80%. (von Heinje, supra.) However, the two methods do not always produce the same predicted cleavage point(s) for a given protein.

The established method for identifying the location of signal sequences, in addition, to their cleavage sites has been the SignalP program (v1.1) developed by Henrik Nielsen et al., Protein Engineering 10: 1–6 (1997). The program relies upon the algorithm developed by von Heinje, though provides additional parameters to increase the prediction accuracy.

More recently, a hidden Markov model has been developed (H. Neilson, et al., Ismb 1998;6: 122–30), which has been incorporated into the more recent SignalP (v2.0). This new method increases the ability to identify the cleavage site by discriminating between signal peptides and uncleaved signal anchors. The present invention encompasses the application of the method disclosed therein to the prediction of the signal peptide location, including the cleavage site, to any of the polypeptide sequences of the present invention.

As one of ordinary skill would appreciate, however, cleavage sites sometimes vary from organism to organism and cannot be predicted with absolute certainty. Accordingly, the polypeptide of the present invention may contain a signal sequence. Polypeptides of the invention which comprise a signal sequence have an N-terminus beginning within 5 residues (i.e., + or −5 residues, or preferably at the −5, −4, −3, −2, −1, +1, +2, +3, +4, or +5 residue) of the predicted cleavage point. Similarly, it is also recognized that in some cases, cleavage of the signal sequence from a secreted protein is not entirely uniform, resulting in more than one secreted species. These polypeptides, and the polynucleotides encoding such polypeptides, are contemplated by the present invention.

Moreover, the signal sequence identified by the above analysis may not necessarily predict the naturally occurring signal sequence. For example, the naturally occurring signal sequence may be further upstream from the predicted signal sequence. However, it is likely that the predicted signal sequence will be capable of directing the secreted protein to the ER. Nonetheless, the present invention provides the mature protein produced by expression of the polynucleotide sequence of SEQ ID NO:1, 23, 53, and/or 55 and/or the polynucleotide sequence contained in the cDNA of a deposited clone, in a mammalian cell (e.g., COS cells, as described below). These polypeptides, and the polynucleotides encoding such polypeptides, are contemplated by the present invention.

Polynucleotide and Polypeptide Variants

The present invention also encompasses variants (e.g., allelic variants, orthologs, etc.) of the polynucleotide sequence disclosed herein in SEQ ID NO:1, 23, 53, and/or 55, the complementary strand thereto, and/or the cDNA sequence contained in the deposited clone.

The present invention also encompasses variants of the polypeptide sequence, and/or fragments therein, disclosed in SEQ ID NO:2, 24, 54, and/or 56, a polypeptide encoded by the polynucleotide sequence in SEQ ID NO:1, 23, 53, and/or 55, and/or a polypeptide encoded by a cDNA in the deposited clone.

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

Thus, one aspect of the invention provides an isolated nucleic acid molecule comprising, or alternatively consisting of, a polynucleotide having a nucleotide sequence selected from the group consisting of: (a) a nucleotide sequence encoding a CAN-12 related polypeptide having an amino acid sequence as shown in the sequence listing and described in SEQ ID NO:1, 23, 53, and/or 55 or the cDNA contained in ATCC deposit No:PTA-3434; (b) a nucleotide sequence encoding a mature CAN-12 related polypeptide having the amino acid sequence as shown in the sequence listing and described in SEQ ID NO:1, 23, 53, and/or 55 or the cDNA contained in ATCC deposit No:PTA-3434; (c) a nucleotide sequence encoding a biologically active fragment of a CAN-12 related polypeptide having an amino acid sequence shown in the sequence listing and described in SEQ ID NO:1, 23, 53, and/or 55 or the cDNA contained in ATCC deposit No:PTA-3434; (d) a nucleotide sequence encoding an antigenic fragment of a CAN-12 related polypeptide having an amino acid sequence sown in the sequence listing and described in SEQ ID NO:1, 23, 53, and/or 55 or the cDNA contained in ATCC deposit No:PTA-3434; (e) a nucleotide sequence encoding a CAN-12 related polypeptide comprising the complete amino acid sequence encoded by a human cDNA plasmid contained in SEQ ID NO:1, 23, 53, and/or 55 or the cDNA contained in ATCC deposit No:PTA-3434; (f) a nucleotide sequence encoding a mature CAN-12 related polypeptide having an amino acid sequence encoded by a human cDNA plasmid contained in SEQ ID NO:1, 23, 53, and/or 55 or the cDNA contained in ATCC deposit No:PTA-3434; (g) a nucleotide sequence encoding a biologically active fragment of a CAN-12 related polypeptide having an amino acid sequence encoded by a human cDNA plasmid contained in SEQ ID NO:1, 23, 53, and/or 55 or the cDNA contained in ATCC deposit No:PTA-3434; (h) a nucleotide sequence encoding an antigenic fragment of a CAN-12 related polypeptide having an amino acid sequence encoded by a human cDNA plasmid contained in SEQ ID NO:1, 23, 53, and/or 55 or the cDNA contained in ATCC deposit No:PTA-3434; (I) a nucleotide sequence complimentary to any of the nucleotide sequences in (a), (b), (c), (d), (e), (f), (g), or (h), above.

The present invention is also directed to polynucleotide sequences which comprise, or alternatively consist of, a polynucleotide sequence which is at least about 80%, 85%, 90%, 91%, 92%, 92.4%, 93%, 94%, 95%, 96%, 97%, 98%, 99%, 99.1%, 99.2%, 99.3%, 99.4%, 99.5%, 99.6%, 99.7%, 99.8%, or 99.9% identical to, for example, any of the nucleotide sequences in (a), (b), (c), (d), (e), (f), (g), or (h), above. Polynucleotides encoded by these nucleic acid molecules are also encompassed by the invention. In another embodiment, the invention encompasses nucleic acid molecules which comprise, or alternatively, consist of a polynucleotide which hybridizes under stringent conditions, or alternatively, under lower stringency conditions, to a polynucleotide in (a), (b), (c), (d), (e), (f), (g), or (h), above. Polynucleotides which hybridize to the complement of these nucleic acid molecules under stringent hybridization conditions or alternatively, under lower stringency conditions, are also encompassed by the invention, as are polypeptides encoded by these polypeptides.

Another aspect of the invention provides an isolated nucleic acid molecule comprising, or alternatively, consisting of, a polynucleotide having a nucleotide sequence selected from the group consisting of: (a) a nucleotide sequence encoding a CAN-12 related polypeptide having an amino acid sequence as shown in the sequence listing and descried in Table I; (b) a nucleotide sequence encoding a mature CAN-12 related polypeptide having the amino acid sequence as shown in the sequence listing and descried in Table I; (c) a nucleotide sequence encoding a biologically active fragment of a CAN-12 related polypeptide having an amino acid sequence as shown in the sequence listing and descried in Table I; (d) a nucleotide sequence encoding an antigenic fragment of a CAN-12 related polypeptide having an amino acid sequence as shown in the sequence listing and descried in Table I; (e) a nucleotide sequence encoding a CAN-12 related polypeptide comprising the complete amino acid sequence encoded by a human cDNA in a cDNA plasmid contained in the ATCC Deposit and described in Table I; (f) a nucleotide sequence encoding a mature CAN-12 related polypeptide having an amino acid sequence encoded by a human cDNA in a cDNA plasmid contained in the ATCC Deposit and described in Table I: (g) a nucleotide sequence encoding a biologically active fragment of a CAN-12 related polypeptide having an amino acid sequence encoded by a human cDNA in a cDNA plasmid contained in the ATCC Deposit and described in Table I; (h) a nucleotide sequence encoding an antigenic fragment of a CAN-12 related polypeptide having an amino acid sequence encoded by a human cDNA in a cDNA plasmid contained in the ATCC deposit and described in Table I; (i) a nucleotide sequence complimentary to any of the nucleotide sequences in (a), (b), (c), (d), (e), (f), (g), or (h) above.

The present invention is also directed to nucleic acid molecules which comprise, or alternatively, consist of, a nucleotide sequence which is at least about 80%, 85%, 90%, 91%, 92%, 92.4%, 93%, 94%, 95%, 96%, 97%, 98%, 99%, 99.1%, 99.2%, 99.3%, 99.4%, 99.5%, 99.6%, 99.7%, 99.8%, or 99.9% identical to, for example, any of the nucleotide sequences in (a), (b), (c), (d), (e), (f), (g), or (h), above.

The present invention encompasses polypeptide sequences which comprise, or alternatively consist of, an amino acid sequence which is at least about 60.3%, 61.4%, 80%, 81.8%, 82.2%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, the following non-limited examples, the polypeptide sequence identified as SEQ ID NO:2, 24, 54, and/or 56, the polypeptide sequence encoded by a cDNA provided in the deposited clone, and/or polypeptide fragments of any of the polypeptides provided herein. Polynucleotides encoded by these nucleic acid molecules are also encompassed by the invention. In another embodiment, the invention encompasses nucleic acid molecules which comprise, or alternatively, consist of a polynucleotide which hybridizes under stringent conditions, or alternatively, under lower stringency conditions, to a polynucleotide in (a), (b), (c), (d), (e), (f), (g), or (h), above. Polynucleotides which hybridize to the complement of these nucleic acid molecules under stringent hybridization conditions or alternatively, under lower stringency conditions, are also encompassed by the invention, as are polypeptides encoded by these polypeptides.

The present invention is also directed to polypeptides which comprise, or alternatively consist of, an amino acid sequence which is at least about 60.3%, 61.4%, 80%, 81.8%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for example, the polypeptide sequence shown in SEQ ID NO:2, 24, 54, and/or 56, a polypeptide sequence encoded by the nucleotide sequence in SEQ ID NO:1, 23, 53, and/or 55, a polypeptide sequence encoded by the cDNA in cDNA plasmid:Z, and/or polypeptide fragments of any of these polypeptides (e.g., those fragments described herein). Polynucleotides which hybridize to the complement of the nucleic acid molecules encoding these polypeptides under stringent hybridization conditions or alternatively, under lower stringency conditions, are also encompasses by the present invention, as are the polypeptides encoded by these polynucleotides.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence referenced in Table I, the ORF (open reading frame), or any fragment specified as described herein.

As a practical matter, whether any particular nucleic acid molecule or polypeptide is at least about 60.3%, 61.4%, 80%, 81.8%, 80%, 85%, 90%, 91%, 92%, 92.4%, 93%, 94%, 95%, 96%, 97%, 98%, 99%, 99.1%, 99.2%, 99.3%, 99.4%, 99.5%, 99.6%, 99.7%, 99.8%, or 99.9% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):4673–4680, (1994)), which is based on the algorithm of Higgins, D. G., et al., Computer Applications in the Biosciences (CABIOS), 8(2):189–191, (1992). In a sequence alignment the query and subject sequences are both DNA sequences. An RNA sequence can be compared by converting U's to T's. However, the CLUSTALW algorithm automatically converts U's to T's when comparing RNA sequences to DNA sequences. The result of said global sequence alignment is in percent identity. Preferred parameters used in a CLUSTALW alignment of DNA sequences to calculate percent identity via pairwise alignments are: Matrix=IUB, k-tuple=1, Number of Top Diagonals=5, Gap Penalty=3, Gap Open Penalty 10, Gap Extension Penalty=0.1, Scoring Method=Percent, Window Size=5 or the length of the subject nucleotide sequence, whichever is shorter. For multiple alignments, the following CLUSTALW parameters are preferred: Gap Opening Penalty=10; Gap Extension Parameter=0.05; Gap Separation Penalty Range=8; End Gap Separation Penalty=Off; % Identity for Alignment Delay=40%; Residue Specific Gaps: Off; Hydrophilic Residue Gap=Off; and Transition Weighting=0. The pairwise and multple alignment parameters provided for CLUSTALW above represent the default parameters as provided with the AlignX software program (Vector NTI suite of programs, version 6.0).

The present invention encompasses the application of a manual correction to the percent identity results, in the instance where the subject sequence is shorter than the query sequence because of 5' or 3' deletions, not because of internal deletions. If only the local pairwise percent identity is required, no manual correction is needed. However, a manual correction may be applied to determine the global percent identity from a global polynucleotide alignment. Percent identity calculations based upon global polynucleotide alignments are often preferred since they reflect the percent identity between the polynucleotide molecules as a whole (i.e., including any polynucleotide overhangs, not just overlapping regions), as opposed to, only local matching polynucleotides. Manual corrections for global percent identity determinations are required since the CLUSTALW program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the CLUSTALW sequence alignment. This percentage is then subtracted from the percent identity, calculated by the above CLUSTALW program using the specified parameters, to arrive at a final percent identity score. This corrected score may be used for the purposes of the present invention. Only bases outside the 5' and 3' bases of the subject sequence, as displayed by the CLUSTALW alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the CLUSTALW alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the CLUSTALW program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by CLUSTALW is not manually corrected. Once again, only bases 5' and 3' of the subject sequence which are not matched/aligned with the query sequence are manually corrected for. No other manual corrections are required for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino- or carboxy-terminal positions of the reference amino acid sequence or anywhere between those terminal positions, interspersed either individually among residues in the reference sequence or in one or more contiguous groups within the reference sequence.

As a practical matter, whether any particular polypeptide is at least about 60.3%, 61.4%, 80%, 81.8%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for instance, an amino acid sequence referenced in Table 1 (SEQ ID NO:2) or to the amino acid sequence encoded by cDNA contained in a deposited clone, can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):4673–4680, (1994)), which is based on the algorithm of Higgins, D. G., et al., Computer Applications in the Biosciences (CABIOS), 8(2):189–191, (1992). In a sequence alignment the query and subject sequences are both amino acid sequences. The result of said global sequence alignment is in percent identity. Preferred parameters used in a CLUSTALW alignment of DNA sequences to calculate percent identity via pairwise alignments are: Matrix=BLOSUM, k-tuple=1, Number of Top Diagonals=5, Gap Penalty=3, Gap Open Penalty 10, Gap Extension Penalty=0.1, Scoring Method=Percent, Window Size=5 or the length of the subject nucleotide sequence, whichever is shorter. For multiple alignments, the following CLUSTALW parameters are preferred: Gap Opening Penalty=10; Gap Extension Parameter=0.05; Gap Separation Penalty Range=8; End Gap Separation Penalty=Off; % Identity for Alignment Delay=40%; Residue Specific Gaps:Off; Hydrophilic Residue Gap=Off; and Transition Weighting=0. The pairwise and multple alignment parameters provided for CLUSTALW above represent the default parameters as provided with the AlignX software program (Vector NTI suite of programs, version 6.0).

The present invention encompasses the application of a manual correction to the percent identity results, in the instance where the subject sequence is shorter than the query sequence because of N- or C-terminal deletions, not because of internal deletions. If only the local pairwise percent identity is required, no manual correction is needed. However, a manual correction may be applied to determine the global percent identity from a global polypeptide alignment. Percent identity calculations based upon global polypeptide alignments are often preferred since they reflect the percent identity between the polypeptide molecules as a whole (i.e., including any polypeptide overhangs, not just overlapping regions), as opposed to, only local matching polypeptides. Manual corrections for global percent identity determinations are required since the CLUSTALW program does not account for N- and C-terminal truncations of the subject sequence when calculating percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the CLUSTALW sequence alignment. This percentage is then subtracted from the percent identity, calculated by the above CLUSTALW program using the specified parameters, to arrive at a final percent identity score. This final percent identity score is what may be used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the CLUSTALW alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the CLUSTALW program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence, which are not matched/aligned with the query. In this case the percent identity calculated by CLUSTALW is not manually corrected. Once again, only residue positions outside the N- and C-terminal ends of the subject sequence, as displayed in the CLUSTALW alignment, which are not matched/aligned with the query sequence are manually corrected for. No other manual corrections are required for the purposes of the present invention.

In addition to the above method of aligning two or more polynucleotide or polypeptide sequences to arrive at a percent identity value for the aligned sequences, it may be desirable in some circumstances to use a modified version of the CLUSTALW algorithm which takes into account known structural features of the sequences to be aligned, such as for example, the SWISS-PROT designations for each sequence. The result of such a modifed CLUSTALW algorithm may provide a more accurate value of the percent identity for two polynucleotide or polypeptide sequences. Support for such a modified version of CLUSTALW is provided within the CLUSTALW algorithm and would be readily appreciated to one of skill in the art of bioinformatics.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. Polynucleotide variants can be produced for a variety of reasons, e.g., to optimize codon expression for a particular host (change codons in the mRNA to those preferred by a bacterial host such as $E. coli$).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the protein without substantial loss of biological function. The authors of Ron et al., J. Biol. Chem. 268: 2984–2988 (1993), reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein (Dobeli et al., J. Biotechnology 7:199–216 (1988)).

Moreover, ample evidence demonstrates that variants often retain a biological activity similar to that of the naturally occurring protein. For example, Gayle and coworkers (J. Biol. Chem. . . . 268:22105–22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the protein will likely be retained when less than the majority of the residues of the protein are removed from the N-terminus or C-terminus. Whether a particular polypeptide lacking N- or C-terminal residues of a protein retains such immunogenic activities can readily be determined by routine methods described herein and otherwise known in the art.

Alternatively, such N-terminus or C-terminus deletions of a polypeptide of the present invention may, in fact, result in a significant increase in one or more of the biological activities of the polypeptide(s). For example, biological activity of many polypeptides are governed by the presence of regulatory domains at either one or both termini. Such regulatory domains effectively inhibit the biological activity of such polypeptides in lieu of an activation event (e.g., binding to a cognate ligand or receptor, phosphorylation, proteolytic processing, etc.). Thus, by eliminating the regulatory domain of a polypeptide, the polypeptide may effectively be rendered biologically active in the absence of an activation event.

Thus, the invention further includes polypeptide variants that show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie et al., Science 247: 1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved.

The invention encompasses polypeptides having a lower degree of identity but having sufficient similarity so as to perform one or more of the same functions performed by the polypeptide of the present invention. Similarity is determined by conserved amino acid substitution. Such substitutions are those that substitute a given amino acid in a polypeptide by another amino acid of like characteristics (e.g., chemical properties). According to Cunningham et al above, such conservative substitutions are likely to be phenotypically silent. Additional guidance concerning which amino acid changes are likely to be phenotypically silent are found in Bowie et al., Science 247:1306–1310 (1990).

Tolerated conservative amino acid substitutions of the present invention involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

In addition, the present invention also encompasses the conservative substitutions provided in Table III below.

TABLE III

| For Amino Acid | Code | Replace with any of: |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-1-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Aside from the uses described above, such amino acid substitutions may also increase protein or peptide stability. The invention encompasses amino acid substitutions that contain, for example, one or more non-peptide bonds (which replace the peptide bonds) in the protein or peptide sequence. Also included are substitutions that include amino acid residues other than naturally occurring L-amino acids, e.g., D-amino acids or non-naturally occurring or synthetic amino acids, e.g., β or γ amino acids.

Both identity and similarity can be readily calculated by reference to the following publications: Computational Molecular Biology, Lesk, A. M., ed., Oxford University Press, New York, 1988; Biocomputing: Informatics and Genome Projects, Smith, D. W., ed., Academic Press, New York, 1993; Informatics Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991.

In addition, the present invention also encompasses substitution of amino acids based upon the probability of an amino acid substitution resulting in conservation of function. Such probabilities are determined by aligning multiple genes with related function and assessing the relative penalty of each substitution to proper gene function. Such probabilities are often described in a matrix and are used by some algorithms (e.g., BLAST, CLUSTALW, GAP, etc.) in calculating percent similarity wherein similarity refers to the degree by which one amino acid may substitute for another amino acid without lose of function. An example of such a matrix is the PAM250 or BLOSUM62 matrix.

Aside from the canonical chemically conservative substitutions referenced above, the invention also encompasses substitutions which are typically not classified as conservative, but that may be chemically conservative under certain circumstances. Analysis of enzymatic catalysis for proteases, for example, has shown that certain amino acids within the active site of some enzymes may have highly perturbed pKa's due to the unique microenvironment of the active site. Such perturbed pKa's could enable some amino acids to substitute for other amino acids while conserving enzymatic structure and function. Examples of amino acids that are known to have amino acids with perturbed pKa's are the Glu-35 residue of Lysozyme, the Ile-16 residue of Chymotrypsin, the His-159 residue of Papain, etc. The conservation of function relates to either anomalous protonation or anomalous deprotonation of such amino acids, relative to their canonical, non-perturbed pKa. The pKa perturbation may enable these amino acids to actively participate in general acid-base catalysis due to the unique ionization environment within the enzyme active site. Thus, substituting an amino acid capable of serving as either a general acid or general base within the microenvironment of an enzyme active site or cavity, as may be the case, in the same or similar capacity as the wild-type amino acid, would effectively serve as a conservative amino substitution.

Besides conservative amino acid substitution, variants of the present invention include, but are not limited to, the following: (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

Moreover, the invention further includes polypeptide variants created through the application of molecular evolution ("DNA Shuffling") methodology to the polynucleotide disclosed as SEQ ID NO:1, 23, 53, and/or 55, the sequence of the clone submitted in a deposit, and/or the cDNA encoding the polypeptide disclosed as SEQ ID NO:2, 24, 54, and/or 56. Such DNA Shuffling technology is known in the art and more particularly described elsewhere herein (e.g., WPC, Stemmer, PNAS, 91:10747, (1994)), and in the Examples provided herein).

A further embodiment of the invention relates to a polypeptide which comprises the amino acid sequence of the present invention having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of the present invention, which contains at least one, but not more than 10, 9, 8, 7, 6, 5, 4, 3, 2 or 1 amino acid substitutions. In specific embodiments, the number of additions, substitutions, and/or deletions in the amino acid sequence of the present invention or fragments thereof (e.g., the mature form and/or other fragments described herein), is 1–5,5–10, 5–25, 5–50, 10–50 or 50–150, conservative amino acid substitutions are preferable.

Polynucleotide and Polypeptide Fragments

The present invention is directed to polynucleotide fragments of the polynucleotides of the invention, in addition to polypeptides encoded therein by said polynucleotides and/or fragments.

In the present invention, a "polynucleotide fragment" refers to a short polynucleotide having a nucleic acid sequence which: is a portion of that contained in a deposited clone, or encoding the polypeptide encoded by the cDNA in a deposited clone; is a portion of that shown in SEQ ID NO:1, 23, 53, and/or 55 or the complementary strand thereto, or is a portion of a polynucleotide sequence encoding the polypeptide of SEQ ID NO:2, 24, 54, and/or 56. The nucleotide fragments of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A fragment "at least 20 nt in length," for example, is intended to include 20 or more contiguous bases from the cDNA sequence contained in a deposited clone or the nucleotide sequence shown in SEQ ID NO:1, 23, 53, and/or 55. In this context "about" includes the particularly recited value, a value larger or smaller by several (5, 4, 3, 2, or 1) nucleotides, at either terminus, or at both termini. These nucleotide fragments have uses that include, but are not limited to, as diagnostic probes and primers as discussed herein. Of course, larger fragments (e.g., 50, 150, 500, 600, 2000 nucleotides) are preferred.

Moreover, representative examples of polynucleotide fragments of the invention, include, for example, fragments comprising, or alternatively consisting of, a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1000, 1001–1050, 1051–1100, 1101–1150, 1151–1200, 1201–1250, 1251–1300, 1301–1350, 1351–1400, 1401–1450, 1451–1500, 1501–1550, 1551–1600, 1601–1650, 1651–1700, 1701–1750, 1751–1800, 1801–1850, 1851–1900, 1901–1950, 1951–2000, or 2001 to the end of SEQ ID NO:1, 23, 53, and/or 55, or the complementary strand thereto, or the cDNA contained in a deposited clone. In this context "about" includes the particularly recited ranges, and ranges larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein. Also encompassed by the present invention are polynucleotides which hybridize to these nucleic acid molecules under stringent hybridization conditions or lower stringency conditions, as are the polypeptides encoded by these polynucleotides.

In the present invention, a "polypeptide fragment" refers to an amino acid sequence which is a portion of that contained in SEQ ID NO:2, 24, 54, and/or 56 or encoded by the cDNA contained in a deposited clone. Protein (polypeptide) fragments may be "free-standing," or comprised within a larger polypeptide of which the fragment forms a part or region, most preferably as a single continuous region. Representative examples of polypeptide fragments of the invention, include, for example, fragments comprising, or alternatively consisting of, from about amino acid number 1–20, 21–40, 41–60, 61–80, 81–100, 102–120, 121–140, 141–160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges or values, and ranges or values larger or smaller by several (5, 4, 3, 2, or 1) amino acids, at either extreme or at both extremes. Polynucleotides encoding these polypeptides are also encompassed by the invention.

Preferred polypeptide fragments include the full-length protein. Further preferred polypeptide fragments include the full-length protein having a continuous series of deleted residues from the amino or the carboxy terminus, or both. For example, any number of amino acids, ranging from 1–60, can be deleted from the amino terminus of the full-length polypeptide. Similarly, any number of amino acids, ranging from 1–30, can be deleted from the carboxy terminus of the full-length protein. Furthermore, any combination of the above amino and carboxy terminus deletions are preferred. Similarly, polynucleotides encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:2, 24, 54, and/or 56 falling within conserved domains are specifically contemplated by the present invention. Moreover, polynucleotides encoding these domains are also contemplated.

Other preferred polypeptide fragments are biologically active fragments. Biologically active fragments are those exhibiting activity similar, but not necessarily identical, to an activity of the polypeptide of the present invention. The biological activity of the fragments may include an improved desired activity, or a decreased undesirable activity. Polynucleotides encoding these polypeptide fragments are also encompassed by the invention.

In a preferred embodiment, the functional activity displayed by a polypeptide encoded by a polynucleotide fragment of the invention may be one or more biological activities typically associated with the full-length polypeptide of the invention. Illustrative of these biological activities includes the fragments ability to bind to at least one of the same antibodies which bind to the full-length protein, the fragments ability to interact with at lease one of the same proteins which bind to the full-length, the fragments ability to elicit at least one of the same immune responses as the full-length protein (i.e., to cause the immune system to create antibodies specific to the same epitope, etc.), the fragments ability to bind to at least one of the same polynucleotides as the full-length protein, the fragments ability to bind to a receptor of the full-length protein, the fragments ability to bind to a ligand of the full-length protein, and the fragments ability to multimerize with the full-length protein. However, the skilled artisan would appreciate that some fragments may have biological activities which are desirable and directly inapposite to the biological activity of the full-length protein. The functional activity of polypeptides of the invention, including fragments, variants, derivatives, and analogs thereof can be determined by numerous methods available to the skilled artisan, some of which are described elsewhere herein.

The present invention encompasses polypeptides comprising, or alternatively consisting of, an epitope of the polypeptide having an amino acid sequence of SEQ ID NO:2, 24, 54, and/or 56, or an epitope of the polypeptide sequence encoded by a polynucleotide sequence contained in ATCC deposit No. Z or encoded by a polynucleotide that hybridizes to the complement of the sequence of SEQ ID NO:1, 23, 53, and/or 55 or contained in ATCC deposit No. Z under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:1), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131–5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids.

Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length, or longer. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767–778 (1984); Sutcliffe et al., Science 219:660–666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910–914; and Bittle et al., J. Gen. Virol. 66:2347–2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347–2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84–86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958–3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972–897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., Curr. Opinion Biotechnol. 8:724–33 (1997); Harayama, Trends Biotechnol. 16(2):76–82 (1998); Hansson, et al., J. Mol. Biol. 287:265–76 (1999); and Lorenzo and Blasco, Biotechniques 24(2):308–13 (1998) (each of these patents and publications are hereby incorporated by reference in its entirety). In one embodiment, alteration of polynucleotides corresponding to SEQ ID NO:1, 23, 53, and/or 55 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Antibodies

Further polypeptides of the invention relate to antibodies and T-cell antigen receptors (TCR) which immunospecifically bind a polypeptide, polypeptide fragment, or variant of SEQ ID NO:2, 24, 54, and/or 56, and/or an epitope, of the present invention (as determined by immunoassays well known in the art for assaying specific antibody-antigen binding). Antibodies of the invention include, but are not limited to, polyclonal, monoclonal, monovalent, bispecific, heteroconjugate, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Moreover, the term "antibody" (Ab) or "monoclonal antibody" (Mab) is meant to include intact molecules, as well as, antibody fragments (such as, for example, Fab and F(ab')2 fragments) which are capable of specifically binding to protein. Fab and F(ab')2 fragments lack the Fc fragment of intact antibody, clear more rapidly from the circulation of the animal or plant, and may have less non-specific tissue binding than an intact antibody (Wahl et al., J. Nucl. Med. . . . 24:316–325 (1983)). Thus, these fragments are preferred, as well as the products of a FAB or other immunoglobulin expression library. Moreover, antibodies of the present invention include chimeric, single chain, and humanized antibodies.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60–69 (1991); U.S.

Pat. Nos. 4,474,893; 4,714,681; 4,925,648; 5,573,920; 5,601,819; Kostelny et al., J. Immunol. 148:1547–1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homologue of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologues of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981–1988 (1998); Chen et al., Cancer Res. 58(16):3668–3678 (1998); Harrop et al., J. Immunol. 161 (4):1786–1794 (1998); Zhu et al., Cancer Res. 58(15): 3209–3214 (1998); Yoon et al., J. Immunol. 160(7):3170–3179 (1998); Prat et al., J. Cell. Sci. 111(Pt2): 237–247 (1998); Pitard et al., J. Immunol. Methods 205(2): 177–190 (1997); Liautard et al., Cytokine 9(4):233–241 (1997); Carlson et al., J. Biol. Chem. 272(17):11295–11301 (1997); Taryman et al., Neuron 14(4):755–762 (1995); Muller et al., Structure 6(9):1153–1167 (1998); Bartunek et al., Cytokine 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionucleotides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art.

The antibodies of the present invention may comprise polyclonal antibodies. Methods of preparing polyclonal antibodies are known to the skilled artisan (Harlow, et al., Antibodies: A Laboratory Manual, (Cold spring Harbor Laboratory Press, $2^{nd}$ ed. (1988); and Current Protocols, Chapter 2; which are hereby incorporated herein by reference in its entirety). In a preferred method, a preparation of the XXXXX protein is prepared and purified to render it substantially free of natural contaminants. Such a preparation is then introduced into an animal in order to produce polyclonal antisera of greater specific activity. For example, a polypeptide of the invention can be administered to various host animals including, but not limited to, rabbits, mice, rats, etc. to induce the production of sera containing polyclonal antibodies specific for the antigen. The administration of the polypeptides of the present invention may entail one or more injections of an immunizing agent and, if desired, an adjuvant. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art. For the purposes of the invention, "immunizing agent" may be defined as a polypeptide of the invention, including fragments, variants, and/or derivatives thereof, in addition to fusions with heterologous polypeptides and other forms of the polypeptides described herein.

Typically, the immunizing agent and/or adjuvant will be injected in the mammal by multiple subcutaneous or intraperitoneal injections, though they may also be given intramuscularly, and/or through IV). The immunizing agent may include polypeptides of the present invention or a fusion protein or variants thereof. Depending upon the nature of the polypeptides (i.e., percent hydrophobicity, percent hydrophilicity, stability, net charge, isoelectric point etc.), it may be useful to conjugate the immunizing agent to a protein known to be immunogenic in the mammal being immunized. Such conjugation includes either chemical conjugation by derivitizing active chemical functional groups to both the polypeptide of the present invention and the immunogenic protein such that a covalent bond is formed, or through fusion-protein based methodology, or other methods known to the skilled artisan. Examples of such immunogenic proteins include, but are not limited to keyhole limpet hemocyanin, serum albumin, bovine thyroglobulin, and soybean trypsin inhibitor. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Additional examples of adjuvants which may be employed includes the MPL-TDM adjuvant (monophosphoryl lipid A, synthetic trehalose dicorynomycolate). The immunization protocol may be selected by one skilled in the art without undue experimentation.

The antibodies of the present invention may comprise monoclonal antibodies. Monoclonal antibodies may be prepared using hybridoma methods, such as those described by Kohler and Milstein, Nature, 256:495 (1975) and U.S. Pat. No. 4,376,110, by Harlow, et al., Antibodies: A Laboratory Manual, (Cold spring Harbor Laboratory Press, $2^{nd}$ ed. (1988), by Hammerling, et al., Monoclonal Antibodies and T-Cell Hybridomas (Elsevier, N.Y., pp. 563–681 (1981); Köhler et al., Eur. J. Immunol. 6:511 (1976); Köhler et al., Eur. J. Immunol. 6:292 (1976), or other methods known to the artisan. Other examples of methods which may be employed for producing monoclonal antibodies includes, but are not limited to, the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In a hybridoma method, a mouse, a humanized mouse, a mouse with a human immune system, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include polypeptides of the present invention or a fusion protein thereof. Preferably, the immunizing agent consists of an XXXXX polypeptide or, more preferably, with a XXXXX polypeptide-expressing cell. Such cells may be cultured in any suitable tissue culture medium; however, it is preferable to culture cells in Earle's modified Eagle's medium supplemented with 10% fetal bovine serum (inactivated at about 56 degrees C.), and supplemented with about 10 g/l of nonessential amino acids, about 1,000 U/ml of penicillin, and about 100 ug/ml of streptomycin. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986), pp. 59–103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. More preferred are the parent myeloma cell line (SP2O) as provided by the ATCC. As inferred throughout the specification, human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, Marcel Dekker, Inc., New York, (1987) pp. 51–63).

The culture medium in which the hybridoma cells are cultured can then be assayed for the presence of monoclonal antibodies directed against the polypeptides of the present invention. Preferably, the binding specificity of monoclonal antibodies produced by the hybridoma cells is determined by immunoprecipitation or by an in vitro binding assay, such as radioimmunoassay (RIA) or enzyme-linked immunoabsorbant assay (ELISA). Such techniques are known in the art and within the skill of the artisan. The binding affinity of the monoclonal antibody can, for example, be determined by the Scatchard analysis of Munson and Pollart, Anal. Biochem., 107:220 (1980).

After the desired hybridoma cells are identified, the clones may be subcloned by limiting dilution procedures and grown by standard methods (Goding, supra, and/or according to Wands et al. (Gastroenterology 80:225–232 (1981)). Suitable culture media for this purpose include, for example, Dulbecco's Modified Eagle's Medium and RPMI-1640. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-sepharose, hydroxyapatite chromatography, gel exclusion chromatography, gel electrophoresis, dialysis, or affinity chromatography.

The skilled artisan would acknowledge that a variety of methods exist in the art for the production of monoclonal antibodies and thus, the invention is not limited to their sole production in hydridomas. For example, the monoclonal antibodies may be made by recombinant DNA methods, such as those described in U.S. Pat. No. 4,816,567. In this context, the term "monoclonal antibody" refers to an antibody derived from a single eukaryotic, phage, or prokaryotic clone. The DNA encoding the monoclonal antibodies of the invention can be readily isolated and sequenced using conventional procedures (e.g., by using oligonucleotide probes that are capable of binding specifically to genes encoding the heavy and light chains of murine antibodies, or such chains from human, humanized, or other sources). The hybridoma cells of the invention serve as a preferred source of such DNA. Once isolated, the DNA may be placed into expression vectors, which are then transformed into host cells such as Simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816, 567; Morrison et al, supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fe region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art. Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples described herein. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Inmunol. Methods 182: 41–50 (1995); Ames et al., J. Immunol. Methods 184: 177–186 (1995); Kettleborough et al., Eur. J. Immunol. 24:952–958 (1994); Persic et al., Gene 187 9–18 (1997); Burton et al., Advances in Immunology 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864–869 (1992); and Sawai et al., AJRI 34:26–34 (1995); and Better et al., Science 240:1041–1043 (1988) (said references incorporated by reference in their entireties). Examples of techniques which can be used to produce single-chain Fvs and antibodies include those described in U.S. Pat. Nos. 4,946,778 and 5,258,498; Huston et al., Methods in Enzymology 203:46–88 (1991); Shu et al., PNAS 90:7995–7999 (1993); and Skerra et al., Science 240:1038–1040 (1988).

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191–202; Cabilly et al., Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985); U.S. Pat. Nos. 5,807,715; 4,816,567; and 4,816397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489–498 (1991); Studnicka et al., Protein Engineering 7(6):805–814 (1994); Roguska. et al., PNAS 91:969–973 (1994)), and chain shuffling (U.S. Pat. No. 5,565,332). Generally, a humanized antibody has one or more amino acid residues introduced into it from a source that is non-human. These non-human amino acid residues are often referred to as "import" residues, which are typically taken from an "import" variable domain. Humanization can be essentially performed following the methods of Winter and co-workers (Jones et al., Nature, 321:522–525 (1986); Reichmann et al., Nature, 332:323–327 (1988); Verhoeyen et al., Science, 239:1534–1536 (1988), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possible some FR residues are substituted from analogous sites in rodent antibodies.

In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522–525 (1986); Riechmann et al., Nature 332:323–329 (1988)1 and Presta, Curr. Op. Struct. Biol., 2:593–596 (1992).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16,654, WO 96/34096, WO 96/33735, and WO 91/10741; each of which is incorporated herein by reference in its entirety. The techniques of cole et al., and Boerder et al., are also available for the preparation of human monoclonal antibodies (cole et al., Monoclonal Antibodies and Cancer Therapy, Alan R. Riss, (1985); and Boerner et al., J. Immunol., 147(1):86–95, (1991)).

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65–93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.), Genpharm (San Jose, Calif.), and Medarex, Inc. (Princeton, N.J.) can be engaged to provide human antibodies directed against a selected antigen using technology similar to that described above.

Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and creation of an antibody repertoire. This approach is described, for example, in U.S. Pat. Nos. 5,545,807; 5,545,806; 5,569,825; 5,625,126; 5,633,425; 5,661,106; and in the following scientific publications: Marks et al., Biotechnol., 10:779–783 (1992); Lonberg et al., Nature 368:856–859 (1994); Fishwild et al., Nature Biotechnol., 14:845–51 (1996); Neuberger, Nature Biotechnol., 14:826 (1996); Lonberg and Huszer, Intern. Rev. Immunol., 13:65–93 (1995).

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437–444; (1989) and Nissinoff, J. Immunol. 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Such anti-idiotypic antibodies capable of binding to the XXXXX polypeptide can be produced in a two-step procedure. Such a method makes use of the fact that antibodies are themselves antigens, and therefore, it is possible to obtain an antibody that binds to a second antibody. In accordance with this method, protein specific antibodies are used to immunize an animal, preferably a mouse. The splenocytes of such an animal are then used to produce hybridoma cells, and the hybridoma cells are screened to identify clones that produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

The antibodies of the present invention may be bispecific antibodies. Bispecific antibodies are monoclonal, Preferably human or humanized, antibodies that have binding specificities for at least two different antigens. In the present invention, one of the binding specificities may be directed towards a polypeptide of the present invention, the other may be for any other antigen, and preferably for a cell-surface protein, receptor, receptor subunit, tissue-specific antigen, virally derived protein, virally encoded envelope protein, bacterially derived protein, or bacterial surface protein, etc.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537–539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transformed into a suitable host organism. For further details of generating bispecific antibodies see, for example Suresh et al., Meth. In Enzym., 121:210 (1986).

Heteroconjugate antibodies are also contemplated by the present invention. Heteroconjugate antibodies are composed of two covalently joined antibodies. Such antibodies have, for example, been proposed to target immune system cells to unwanted cells (U.S. Pat. No. 4,676,980), and for the treatment of HIV infection (WO 91/00360; WO 92/20373; and EP03089). It is contemplated that the antibodies may be prepared in vitro using known methods in synthetic protein chemistry, including those involving crosslinking agents. For example, immunotoxins may be constructed using a disulfide exchange reaction or by forming a thioester bond. Examples of suitable reagents for this purpose include iminothiolate and methyl-4-mercaptobutyrimidate and those disclosed, for example, in U.S. Pat. No. 4,676,980.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2, 24, 54, and/or 56.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., Bio-Techniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties ), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851–855 (1984); Neuberger et al., Nature 312:604–608 (1984); Takeda et al., Nature 314:452–454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423–42 (1988); Huston et al., Proc. Natl. Acad. Sci. USA 85:5879–5883 (1988); and Ward et al., Nature 334:544–54 (1989)) can be adapted to produce single chain antibodies. Single chain antibodies are formed by linking the heavy and light chain fragments of the Fv region via an amino acid bridge, resulting in a single chain polypeptide.

Techniques for the assembly of functional Fv fragments in E. coli may also be used (Skerra et al., Science 242: 1038–1041 (1988)).

More preferably, a clone encoding an antibody of the present invention may be obtained according to the method described in the Example section herein.

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain, of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., E. coli, B. subtilis) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as Escherichia coli, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the E. coli expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101–3109 (1985); Van Heeke & Schuster, J. Biol. Chem. 24:5503–5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in Spodoptera frugiperda cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355–359 (1984)). Specific initiation signals may also be required for efficient translation of inserted antibody coding sequences. These signals include the ATG initiation codon and adjacent sequences: Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488–505; Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, 1993, TIB TECH 11(5): 155–215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535–10539 (1991); Zheng et al., J. Immunol. 154:5590–5600 (1995); and Vil et al., Proc. Natl. Acad. Sci. USA 89:11337–11341(1992) (said references incorporated by reference in their entireties).

As discussed, supra, the polypeptides corresponding to a polypeptide, polypeptide fragment, or a variant of SEQ ID NO:2, 24, 54, and/or 56 may be fused or conjugated to the above antibody portions to increase the in vivo half life of the polypeptides or for use in immunoassays using methods known in the art. Further, the polypeptides corresponding to SEQ ID NO:2, 24, 54, and/or 56 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52–58 (1995); Johanson et al., J. Biol. Chem. 270:9459–9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologues thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., Int. Immunol., 6:1567–1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev. 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

The present invention also encompasses the creation of synthetic antibodies directed against the polypeptides of the present invention. One example of synthetic antibodies is described in Radrizzani, M., et al., Medicina, (Aires), 59(6): 753–8, (1999)). Recently, a new class of synthetic antibodies has been described and are referred to as molecularly imprinted polymers (MIPs) (Semorex, Inc.). Antibodies, peptides, and enzymes are often used as molecular recognition elements in chemical and biological sensors. However, their lack of stability and signal transduction mechanisms limits their use as sensing devices. Molecularly imprinted polymers (MIPs) are capable of mimicking the function of biological receptors but with less stability constraints. Such polymers provide high sensitivity and selectivity while maintaining excellent thermal and mechanical stability. MIPs have the ability to bind to small molecules and to target molecules such as organics and proteins' with equal or greater potency than that of natural antibodies. These "super" MIPs have higher affinities for their target and thus require lower concentrations for efficacious binding.

During synthesis, the MIPs are imprinted so as to have complementary size, shape, charge and functional groups of the selected target by using the target molecule itself (such as a polypeptide, antibody, etc.), or a substance having a very similar structure, as its "print" or "template." MIPs can be derivatized with the same reagents afforded to antibodies. For example, fluorescent 'super' MIPs can be coated onto beads or wells for use in highly sensitive separations or assays, or for use in high throughput screening of proteins.

Moreover, MIPs based upon the structure of the polypeptide(s) of the present invention may be useful in screening for compounds that bind to the polypeptide(s) of the invention. Such a MIP would serve the role of a synthetic "receptor" by minimicking the native architecture of the polypeptide. In fact, the ability of a MIP to serve the role of a synthetic receptor has already been demonstrated for the estrogen receptor (Ye, L., Yu, Y., Mosbach, K, Analyst., 126(6):760–5, (2001); Dickert, F, L., Hayden, O., Halikias, K, P, Analyst., 126(6):766–71, (2001)). A synthetic receptor may either be mimicked in its entirety (e.g., as the entire protein), or mimicked as a series of short peptides corresponding to the protein (Rachkov, A., Minoura, N, Biochim, Biophys, Acta., 1544(1–2):255–66, (2001)). Such a synthetic receptor MIPs may be employed in any one or more of the screening methods described elsewhere herein.

MIPs have also been shown to be useful in "sensing" the presence of its mimicked molecule (Cheng, Z., Wang, E., Yang, X, Biosens, Bioelectron., 16(3): 179–85, (2001); Jenkins, A, L., Yin, R., Jensen, J. L, Analyst., 126(6): 798–802, (2001); Jenkins, A, L., Yin, R., Jensen, J. L, Analyst., 126(6):798–802, (2001)). For example, a MIP designed using a polypeptide of the present invention may be used in assays designed to identify, and potentially quantitate, the level of said polypeptide in a sample. Such a MIP may be used as a substitute for any component described in the assays, or kits, provided herein (e.g., ELISA, etc.).

A number of methods may be employed to create MIPs to a specific receptor, ligand, polypeptide, peptide, organic molecule. Several preferred methods are described by Esteban et al in J. Anal, Chem., 370(7):795–802, (2001), which is hereby incorporated herein by reference in its entirety in addition to any references cited therein. Additional methods are known in the art and are encompassed by the present invention, such as for example, Hart, B, R., Shea, K, J. J. Am. Chem, Soc., 123(9):2072–3, (2001); and Quaglia, M., Chenon, K., Hall, A, J., De, Lorenzi, E., Sellergren, B, J. Am. Chem, Soc., 123(10):2146–54, (2001); which are hereby incorporated by reference in their entirety herein.

Uses for Antibodies Directed Against Polypeptides of the Invention

The antibodies of the present invention have various utilities. For example, such antibodies may be used in diagnostic assays to detect the presence or quantification of the polypeptides of the invention in a sample. Such a diagnostic assay may be comprised of at least two steps. The first, subjecting a sample with the antibody, wherein the sample is a tissue (e.g., human, animal, etc.), biological fluid (e.g., blood, urine, sputum, semen, amniotic fluid, saliva, etc.), biological extract (e.g., tissue or cellular homogenate, etc.), a protein microchip (e.g., See Arenkov P, et al., Anal Biochem., 278(2):123–131 (2000)), or a chromatography column, etc. And a second step involving the quantification of antibody bound to the substrate. Alternatively, the method may additionally involve a first step of attaching the antibody, either covalently, electrostatically, or reversibly, to a solid support, and a second step of subjecting the bound antibody to the sample, as defined above and elsewhere herein.

Various diagnostic assay techniques are known in the art, such as competitive binding assays, direct or indirect sandwich assays and immunoprecipitation assays conducted in either heterogeneous or homogenous phases (Zola, Monoclonal Antibodies: A Manual of Techniques, CRC Press, Inc., (1987), pp 147–158). The antibodies used in the diagnostic assays can be labeled with a detectable moiety. The detectable moiety should be capable of producing, either directly or indirectly, a detectable signal. For example, the detectable moiety may be a radioisotope, such as $^{2}H$, $^{14}C$, $^{32}P$, or $^{125}I$, a florescent or chemiluminescent compound, such as fluorescein isothiocyanate, rhodamine, or luciferin, or an enzyme, such as alkaline phosphatase, beta-galactosidase, green fluorescent protein, or horseradish peroxidase. Any method known in the art for conjugating the antibody to the detectable moiety may be employed, including those methods described by Hunter et al., Nature, 144:945 (1962); Dafvid et al., Biochem., 13:1014 (1974); Pain et al., J. Immunol. Metho., 40:219(1981); and Nygren, J. Histochem. And Cytochem., 30:407 (1982).

Antibodies directed against the polypeptides of the present invention are useful for the affinity purification of such polypeptides from recombinant cell culture or natural sources. In this process, the antibodies against a particular polypeptide are immobilized on a suitable support, such as a Sephadex resin or filter paper, using methods well known in the art. The immobilized antibody then is contacted with a sample containing the polypeptides to be purified, and thereafter the support is washed with a suitable solvent that will remove substantially all the material in the sample except for the desired polypeptides, which are bound to the immobilized antibody. Finally, the support is washed with another suitable solvent that will release the desired polypeptide from the antibody.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., Cell, 96:737–49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays for Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or $^{125}$I) in the presence of increasing amounts of an unlabeled second antibody.

Therapeutic Uses of Antibodies

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than 5×10-2 M, 10-2 M, 5×10-3 M, 10-3 M, 5×10-4 M, 10-4 M, 5×10-5 M, 10-5 M, 5×10-6 M, 10-6 M, 5×10-7 M, 10-7 M, 5×10-8 M, 10-8 M, 5×10-9 M, 10-9 M, 5×10-10 M, 10-10 M, 5×10-11 M, 10-11 M, 5×10-12 M, 10-12 M, 5×10-13 M, 10-13 M, 5×10-14 M, 10-14 M, 5×10-15 M, and 10-15 M.

Antibodies directed against polypeptides of the present invention are useful for inhibiting allergic reactions in animals. For example, by administering a therapeutically acceptable dose of an antibody, or antibodies, of the present invention, or a cocktail of the present antibodies, or in combination with other antibodies of varying sources, the animal may not elicit an allergic response to antigens.

Likewise, one could envision cloning the gene encoding an antibody directed against a polypeptide of the present invention, said polypeptide having the potential to elicit an allergic and/or immune response in an organism, and transforming the organism with said antibody gene such that it is expressed (e.g., constitutively, inducibly, etc.) in the organism. Thus, the organism would effectively become resistant to an allergic response resulting from the ingestion or presence of such an immune/allergic reactive polypeptide. Moreover, such a use of the antibodies of the present invention may have particular utility in preventing and/or ameliorating autoimmune diseases and/or disorders, as such conditions are typically a result of antibodies being directed against endogenous proteins. For example, in the instance where the polypeptide of the present invention is responsible for modulating the immune response to auto-antigens, transforming the organism and/or individual with a construct comprising any of the promoters disclosed herein or otherwise known in the art, in addition, to a polynucleotide encoding the antibody directed against the polypeptide of the present invention could effective inhibit the organisms immune system from eliciting an immune response to the auto-antigen(s). Detailed descriptions of therapeutic and/or gene therapy applications of the present invention are provided elsewhere herein.

Alternatively, antibodies of the present invention could be produced in a plant (e.g., cloning the gene of the antibody directed against a polypeptide of the present invention, and transforming a plant with a suitable vector comprising said gene for constitutive expression of the antibody within the plant), and the plant subsequently ingested by an animal, thereby conferring temporary immunity to the animal for the specific antigen the antibody is directed towards (See, for example, U.S. Pat. Nos. 5,914,123 and 6,034,298).

In another embodiment, antibodies of the present invention, preferably polyclonal antibodies, more preferably monoclonal antibodies, and most preferably single-chain antibodies, can be used as a means of inhibiting gene expression of a particular gene, or genes, in a human, mammal, and/or other organism. See, for example, International Publication Number WO 00/05391, published Feb. 3, 2000, to Dow Agrosciences LLC. The application of such methods for the antibodies of the present invention are known in the art, and are more particularly described elsewhere herein.

In yet another embodiment, antibodies of the present invention may be useful for multimerizing the polypeptides of the present invention. For example, certain proteins may confer enhanced biological activity when present in a multimeric state (i.e., such enhanced activity may be due to the increased effective concentration of such proteins whereby more protein is available in a localized location).

Antibody-based Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488–505 (1993); Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, TIBTECH 11(5):155–215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932–8935 (1989); Zijlstra et al., Nature 342: 435–438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429–4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932–8935 (1989); Zijlstra et al., Nature 342:435–438 (1989)).

In a specific embodiment, viral vectors that contains nucleic acid sequences encoding an antibody of the invention are used. For example, a retroviral vector can be used (see Miller et al., Meth. Enzymol. 217:581–599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291–302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644–651 (1994); Kiem et al., Blood 83:1467–1473 (1994); Salmons and Gunzberg, Human Gene Therapy 4:129–141 (1993); and Grossman and Wilson, Curr. Opin. in Genetics and Devel. 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499–503 (1993) present a review of adenovirus-based gene therapy. Bout et al., Human Gene Therapy 5:3–10 (1994) demonstrated the use of adenovirus vectors to transfer genes to the respiratory epithelia of rhesus monkeys. Other instances of the use of adenoviruses in gene therapy can be found in Rosenfeld et al., Science 252:431–434 (1991); Rosenfeld et al., Cell 68:143–155 (1992); Mastrangeli et al., J. Clin. Invest. 91:225–234 (1993); PCT Publication WO94/12649; and Wang, et al., Gene Therapy 2:775–783 (1995). In a preferred embodiment, adenovirus vectors are used.

Adeno-associated virus (AAV) has also been proposed for use in gene therapy (Walsh et al., Proc. Soc. Exp. Biol. Med. 204:289–300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599–618 (1993); Cohen et al., Meth. Enzymol. 217:618–644 (1993); Cline, Pharmac. Ther. 29:69–92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973–985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription. Demonstration of Therapeutic or Prophylactic Activity.

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Compositions

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. . . . 262:4429–4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864–1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging with Antibodies

Labeled antibodies, and derivatives and analogs thereof, which specifically bind to a polypeptide of interest can be used for diagnostic purposes to detect, diagnose, or monitor diseases, disorders, and/or conditions associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the, expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976–985 (1985); Jalkanen, et al., J. Cell. Biol. 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (112In), and technetium (99Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or calorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because certain proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Peptide moieties may be added to the polypeptide to facilitate purification. Such regions may be removed prior to final preparation of the polypeptide. Similarly, peptide cleavage sites can be introduced in-between such peptide moieties, which could additionally be subjected to protease activity to remove said peptide(s)

from the protein of the present invention. The addition of peptide moieties, including peptide cleavage sites, to facilitate handling of polypeptides are familiar and routine techniques in the art.

Moreover, polypeptides of the present invention, including fragments, and specifically epitopes, can be combined with parts of the constant domain of immunoglobulins (IgA, IgE, IgG, IgM) or portions thereof (CH1, CH2, CH3, and any combination thereof, including both entire domains and portions thereof), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331: 84–86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958–3964 (1995).)

Similarly, EP-A-O 464 533 (Canadian counterpart 2045869) discloses fusion proteins comprising various portions of the constant region of immunoglobulin molecules together with another human protein or part thereof. In many cases, the Fe part in a fusion protein is beneficial in therapy and diagnosis, and thus can result in, for example, improved pharmacokinetic properties. (EP-A 0232 262.) Alternatively, deleting the Fe part after the fusion protein has been expressed, detected, and purified, would be desired. For example, the Fe portion may hinder therapy and diagnosis if the fusion protein is used as an antigen for immunizations. In drug discovery, for example, human proteins, such as hIL-5, have been fused with Fe portions for the purpose of high-throughput screening assays to identify antagonists of hIL-5. (See, D. Bennett et al., J. Molecular Recognition 8:52–58 (1995); K. Johanson et al., J. Biol. Chem. 270: 9459–9471 (1995).)

Moreover, the polypeptides of the present invention can be fused to marker sequences (also referred to as "tags"). Due to the availability of antibodies specific to such "tags", purification of the fused polypeptide of the invention, and/or its identification is significantly facilitated since antibodies specific to the polypeptides of the invention are not required. Such purification may be in the form of an affinity purification whereby an anti-tag antibody or another type of affinity matrix (e.g., anti-tag antibody attached to the matrix of a flow-thru column) that binds to the epitope tag is present. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984)).

The skilled artisan would acknowledge the existence of other "tags" which could be readily substituted for the tags referred to supra for purification and/or identification of polypeptides of the present invention (Jones C., et al., J Chromatogr A. 707(1):3–22 (1995)). For example, the c-myc tag and the 8F9, 3C7, 6E10, G4m B7 and 9E10 antibodies thereto (Evan et al., Molecular and Cellular Biology 5:3610–3616 (1985)); the Herpes Simplex virus glycoprotein D (gD) tag and its antibody (Paborsky et al., Protein Engineering, 3(6):547–553 (1990), the Flag-peptide—i.e., the octapeptide sequence DYKDDDDK (SEQ ID NO:47), (Hopp et al., Biotech. 6:1204–1210 (1988); the KT3 epitope peptide (Martin et al., Science, 255:192–194 (1992)); a-tubulin epitope peptide (Skinner et al., J. Biol. Chem., 266:15136–15166, (1991)); the T7 gene 10 protein peptide tag (Lutz-Freyermuth et al., Proc. Natl. Sci. USA, 87:6363–6397 (1990)), the FITC epitope (Zymed, Inc.), the GFP epitope (Zymed, Inc.), and the Rhodamine epitope (Zymed, Inc.).

The present invention also encompasses the attachment of up to nine codons encoding a repeating series of up to nine arginine amino acids to the coding region of a polynucleotide of the present invention. The invention also encompasses chemically derivitizing a polypeptide of the present invention with a repeating series of up to nine arginine amino acids. Such a tag, when attached to a polypeptide, has recently been shown to serve as a universal pass, allowing compounds access to the interior of cells without additional derivitization or manipulation (Wender, P., et al., unpublished data).

Protein fusions involving polypeptides of the present invention, including fragments and/or variants thereof, can be used for the following, non-limiting examples, subcellular localization of proteins, determination of protein-protein interactions via immunoprecipitation, purification of proteins via affinity chromatography, functional and/or structural characterization of protein. The present invention also encompasses the application of hapten specific antibodies for any of the uses referenced above for epitope fusion proteins. For example, the polypeptides of the present invention could be chemically derivatized to attach hapten molecules (e.g., DNP, (Zymed, Inc.)). Due to the availability of monoclonal antibodies specific to such haptens, the protein could be readily purified using immunoprecipation, for example.

Polypeptides of the present invention, including fragments and/or variants thereof, in addition to, antibodies directed against such polypeptides, fragments, and/or variants, may be fused to any of a number of known, and yet to be determined, toxins, such as ricin, saporin (Mashiba H, et al., Ann. N.Y. Acad. Sci. 1999;886:233–5), or HC toxin (Tonukari N J, et al., Plant Cell. 2000 February;12(2): 237–248), for example. Such fusions could be used to deliver the toxins to desired tissues for which a ligand or a protein capable of binding to the polypeptides of the invention exists.

The invention encompasses the fusion of antibodies directed against polypeptides of the present invention, including variants and fragments thereof, to said toxins for delivering the toxin to specific locations in a cell, to specific tissues, and/or to specific species. Such bifunctional antibodies are known in the art, though a review describing additional advantageous fusions, including citations for methods of production, can be found in P. J. Hudson, Curr. Opp. In. Imm. 11:548–557, (1999); this publication, in addition to the references cited therein, are hereby incorporated by reference in their entirety herein. In this context, the term "toxin" may be expanded to include any heterologous protein, a small molecule, radionucleotides, cytotoxic drugs, liposomes, adhesion molecules, glycoproteins, ligands, cell or tissue-specific ligands, enzymes, of bioactive agents, biological response modifiers, anti-fungal agents, hormones, steroids, vitamins, peptides, peptide analogs, anti-allergenic agents, anti-tubercular agents, anti-viral agents, antibiotics, anti-protozoan agents, chelates, radioactive particles, radioactive ions, X-ray contrast agents, monoclonal antibodies, polyclonal antibodies and genetic material. In view of the present disclosure, one skilled in the art could determine whether any particular "toxin" could be used in the compounds of the present invention. Examples of suitable "toxins" listed above are exemplary only and are not intended to limit the "toxins" that may be used in the present invention.

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, *Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE9, available from QIAGEN, Inc; pBluescript vectors, Phagescript vectors, pNH8A, pNH16a, pNH18A, pNH46A, available from Stratagene Cloning Systems, Inc; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/ GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlsbad, Calif.). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In one embodiment, the yeast *Pichia pastoris* is used to express the polypeptide of the present invention in a eukaryotic system. *Pichia pastoris* is a methylotrophic yeast which can metabolize methanol as its sole carbon source. A main step in the methanol metabolization pathway is the oxidation of methanol to formaldehyde using O2. This reaction is catalyzed by the enzyme alcohol oxidase. In order to metabolize methanol as its sole carbon source, *Pichia pastoris* must generate high levels of alcohol oxidase due, in part, to the relatively low affinity of alcohol oxidase for O2. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in *Pichia pastoris*. See, Ellis, S. B., et al., Mol. Cell. Biol. 5:1111–21 (1985); Koutz, P. J, et al., Yeast 5:167–77 (1989); Tschopp, J. F., et al., Nucl. Acids Res. 15:3859–76 (1987). Thus, a heterologous coding sequence, such as, for example, a polynucleotide of the present invention, under the transcriptional regulation of all or part of the AOX1 regulatory sequence is expressed at exceptionally high levels in *Pichia* yeast grown in the presence of methanol.

In one example, the plasmid vector pPIC9K is used to express DNA encoding a polypeptide of the invention, as set forth herein, in a Pichea yeast system essentially as described in "*Pichia* Protocols: Methods in Molecular Biology," D. R. Higgins and J. Cregg, eds. The Humana Press, Totowa, N.J., 1998. This expression vector allows expression and secretion of a protein of the invention by virtue of the strong AOX1 promoter linked to the *Pichia pastoris* alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG, as required.

In another embodiment, high-level expression of a heterologous coding sequence, such as, for example, a polynucleotide of the present invention, may be achieved by cloning the heterologous polynucleotide of the invention into an expression vector such as, for example, pGAPZ or pGAPZalpha, and growing the yeast culture in the absence of methanol.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination, resulting in the formation of a new transcription unit (see, e.g., U.S. Pat. No. 5,641,670, issued Jun. 24, 1997; U.S. Pat. No. 5,733,761, issued Mar. 31, 1998; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

In addition, polypeptides of the invention can be chemically synthesized using techniques known in the art (e.g., see Creighton, 1983, Proteins: Structures and Molecular Principles, W.H. Freeman & Co., N.Y., and Hunkapiller et al., Nature, 310:105–111 (1984)). For example, a polypeptide corresponding to a fragment of a polypeptide sequence of the invention can be synthesized by use of a peptide synthesizer. Furthermore, if desired, nonclassical amino acids or chemical amino acid analogs can be introduced as a substitution or addition into the polypeptide sequence. Nonclassical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The polypeptides may also be modified with a detectable label, such as an enzymatic, fluorescent, isotopic or affinity label to allow for detection and isolation of the protein, the addition of epitope tagged peptide fragments (e.g., FLAG, HA, GST, thioredoxin, maltose binding protein, etc.), attachment of affinity tags such as biotin and/or streptavidin, the covalent attachment of chemical moieties to the amino acid backbone, N- or C-terminal processing of the polypeptides ends (e.g., proteolytic processing), deletion of the N-terminal methionine residue, etc.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyinyl alcohol and the like. The polypeptides may be modified at random positions within the molecule, or at predetermined positions within the molecule and may include one, two, three or more attached chemical moieties.

The invention further encompasses chemical derivitization of the polypeptides of the present invention, preferably where the chemical is a hydrophilic polymer residue. Exemplary hydrophilic polymers, including derivatives, may be those that include polymers in which the repeating units contain one or more hydroxy groups (polyhydroxy polymers), including, for example, poly(vinyl alcohol); polymers in which the repeating units contain one or more amino groups (polyamine polymers), including, for example, peptides, polypeptides, proteins and lipoproteins, such as albumin and natural lipoproteins; polymers in which the repeating units contain one or more carboxy groups (polycarboxy polymers), including, for example, carboxymethylcellulose, alginic acid and salts thereof, such as sodium and calcium alginate, glycosaminoglycans and salts thereof, including salts of hyaluronic acid, phosphorylated and sulfonated derivatives of carbohydrates, genetic material, such as interleukin-2 and interferon, and phosphorothioate oligomers; and polymers in which the repeating units contain one or more saccharide moieties (polysaccharide polymers), including, for example, carbohydrates.

The molecular weight of the hydrophilic polymers may vary, and is generally about 50 to about 5,000,000, with polymers having a molecular weight of about 100 to about 50,000 being preferred. The polymers may be branched or unbranched. More preferred polymers have a molecular weight of about 150 to about 10,000, with molecular weights of 200 to about 8,000 being even more preferred.

For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

Additional preferred polymers which may be used to derivatize polypeptides of the invention, include, for example, poly(ethylene glycol) (PEG), poly(vinylpyrrolidine), polyoxomers, polysorbate and poly(vinyl alcohol), with PEG polymers being particularly preferred. Preferred among the PEG polymers are PEG polymers having a molecular weight of from about 100 to about 10,000. More preferably, the PEG polymers have a molecular weight of from about 200 to about 8,000, with PEG 2,000, PEG 5,000 and PEG 8,000, which have molecular weights of 2,000, 5,000 and 8,000, respectively, being even more preferred. Other suitable hydrophilic polymers, in addition to those exemplified above, will be readily apparent to one skilled in the art based on the present disclosure. Generally, the polymers used may include polymers that can be attached to the polypeptides of the invention via alkylation or acylation reactions.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartle acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminus) available for derivatization in a particular protein. Under the appropriate reaction conditions, substantially selective derivatization of the protein at the N-terminus with a carbonyl group containing polymer is achieved.

As with the various polymers exemplified above, it is contemplated that the polymeric residues may contain functional groups in addition, for example, to those typically involved in linking the polymeric residues to the polypeptides of the present invention. Such functionalities include, for example, carboxyl, amine, hydroxy and thiol groups. These functional groups on the polymeric residues can be further reacted, if desired, with materials that are generally reactive with such functional groups and which can assist in targeting specific tissues in the body including, for example, diseased tissue. Exemplary materials which can be reacted with the additional functional groups include, for example, proteins, including antibodies, carbohydrates, peptides, glycopeptides, glycolipids, lectins, and nucleosides.

In addition to residues of hydrophilic polymers, the chemical used to derivative the polypeptides of the present invention can be a saccharide residue. Exemplary saccharides which can be derived include, for example, monosaccharides or sugar alcohols, such as erythrose, threose, ribose, arabinose, xylose, lyxose, fructose, sorbitol, mannitol and sedoheptulose, with preferred monosaccharides being fructose, mannose, xylose, arabinose, mannitol and sorbitol; and disaccharides, such as lactose, sucrose, maltose and cellobiose. Other saccharides include, for example, inositol and ganglioside head groups. Other suitable saccharides, in addition to those exemplified above, will be readily apparent to one skilled in the art based on the present disclosure. Generally, saccharides which may be used for derivitization include saccharides that can be attached to the polypeptides of the invention via alkylation or acylation reactions.

Moreover, the invention also encompasses derivitization of the polypeptides of the present invention, for example, with lipids (including cationic, anionic, polymerized, charged, synthetic, saturated, unsaturated, and any combination of the above, etc.). stabilizing agents.

The invention encompasses derivitization of the polypeptides of the present invention, for example, with compounds that may serve a stabilizing function (e.g., to increase the polypeptides half-life in solution, to make the polypeptides more water soluble, to increase the polypeptides hydrophilic or hydrophobic character, etc.). Polymers useful as stabilizing materials may be of natural, semi-synthetic (modified natural) or synthetic origin. Exemplary natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthin gum, starch and various other natural homopolymer or heteropolymers, such as those containing one or more of the following aldoses, ketoses, acids or amines: erythose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof Accordingly, suitable polymers include, for example, proteins, such as albumin, polyalginates, and polylactide-coglycolide polymers. Exemplary semi-synthetic polymers include carboxymethylcellulose, hydroxymethylcellulose, hydroxypropylmethylcellulose, methylcellulose, and methoxycellulose. Exemplary synthetic polymers include polyphosphazenes, hydroxyapatites, fluoroapatite polymers, polyethylenes (such as, for example, polyethylene glycol (including for example, the class of compounds referred to as Pluronics.RTM., commercially available from BASF, Parsippany, N.J.), polyoxyethylene, and polyethylene terephthlate), polypropylenes (such as, for example, polypropylene glycol), polyurethanes (such as, for example, polyinyl alcohol (PVA), polyinyl chloride and polyinylpyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof. Methods for the preparation of derivatized polypeptides of the invention which employ polymers as stabilizing compounds will be readily apparent to one skilled in the art, in view of the present disclosure, when coupled with information known in the art, such as that described and referred to in Unger, U.S. Pat. No. 5,205,290, the disclosure of which is hereby incorporated by reference herein in its entirety.

Moreover, the invention encompasses additional modifications of the polypeptides of the present invention. Such additional modifications are known in the art, and are specifically provided, in addition to methods of derivitization, etc., in U.S. Pat. No. 6,028,066, which is hereby incorporated in its entirety herein.

The polypeptides of the invention may be in monomers or multimers (i.e., dimers, trimers, tetramers and higher multimers). Accordingly, the present invention relates to monomers and multimers of the polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of SEQ ID NO:2, 24, 54, and/or 56 or encoded by the cDNA contained in a deposited clone (including fragments, variants, splice variants, and fusion proteins, corresponding to these polypeptides as described herein). These homomers may contain polypeptides having identical or different amino acid sequences. In a specific embodiment, a homomer of the invention is a multimer containing only polypeptides having an identical amino acid sequence. In another specific embodiment, a homomer of the invention is a multimer containing polypeptides having different amino acid sequences. In specific embodiments, the multimer of the invention is a homodimer (e.g., containing polypeptides having identical or different amino acid sequences) or a homotrimer (e.g., containing polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., that recited in the sequence listing, or contained in the polypeptide encoded by a deposited clone). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein of the invention.

In one example, covalent associations are between the heterologous sequence contained in a fusion protein of the invention (see, e.g., U.S. Pat. No. 5,478,925). In a specific example, the covalent associations are between the heterologous sequence contained in an Fe fusion protein of the invention (as described herein). In another specific example, covalent associations of fusion proteins of the invention are between heterologous polypeptide sequence from another protein that is capable of forming covalently associated multimers, such as for example, osteoprotegerin (see, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between Flag® polypeptide sequence contained in fusion proteins of the invention containing Flag® polypeptide sequence. In a further embodiment, associations proteins of the invention are associated by interactions between heterologous polypeptide sequence contained in Flag® fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more intermolecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hydrophobic or signal peptide) and which can be incorporated by membrane reconstitution techniques into liposomes (see, e.g., U.S. Pat. No. 5,478,925, which is herein incorporated by reference in its entirety).

In addition, the polynucleotide insert of the present invention could be operatively linked to "artificial" or chimeric promoters and transcription factors. Specifically, the artificial promoter could comprise, or alternatively consist, of any combination of cis-acting DNA sequence elements that are recognized by trans-acting transcription factors. Preferably, the cis acting DNA sequence elements and trans-acting transcription factors are operable in mammals. Further, the trans-acting transcription factors of such "artificial" promoters could also be "artificial" or chimeric in design themselves and could act as activators or repressors to said "artificial" promoter.

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15–25 bp) from the sequences shown in SEQ ID NO:1, 23, 53, and/or 55. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:1, 23, 53, and/or 55 will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000–4,000 bp are preferred. For a review of this technique, see Verma et al., "Human Chromosomes: a Manual of Basic Techniques," Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. Disease mapping data are known in the art. Assuming 1 megabase mapping resolution and one gene per 20 kb, a cDNA precisely localized to a chromosomal region associated with the disease could be one of 50–500 potential causative genes.

Thus, once coinheritance is established, differences in the polynucleotide and the corresponding gene between affected and unaffected organisms can be examined. First, visible structural alterations in the chromosomes, such as deletions or translocations, are examined in chromosome spreads or by PCR. If no structural alterations exist, the presence of point mutations are ascertained. Mutations observed in some or all affected organisms, but not in normal organisms, indicates that the mutation may cause the disease. However, complete sequencing of the polypeptide and the corresponding gene from several normal organisms is required to distinguish the mutation from a polymorphism. If a new polymorphism is identified, this polymorphic polypeptide can be used for further linkage analysis.

Furthermore, increased or decreased expression of the gene in affected organisms as compared to unaffected organisms can be assessed using polynucleotides of the present invention. Any of these alterations (altered expression, chromosomal rearrangement, or mutation) can be used as a diagnostic or prognostic marker.

Thus, the invention also provides a diagnostic method useful during diagnosis of a disorder, involving measuring the expression level of polynucleotides of the present invention in cells or body fluid from an organism and comparing the measured gene expression level with a standard level of polynucleotide expression level, whereby an increase or decrease in the gene expression level compared to the standard is indicative of a disorder.

By "measuring the expression level of a polynucleotide of the present invention" is intended qualitatively or quantitatively measuring or estimating the level of the polypeptide of the present invention or the level of the mRNA encoding the polypeptide in a first biological sample either directly (e.g., by determining or estimating absolute protein level or mRNA level) or relatively (e.g., by comparing to the polypeptide level or mRNA level in a second biological sample). Preferably, the polypeptide level or mRNA level in the first biological sample is measured or estimated and compared to a standard polypeptide level or mRNA level, the standard being taken from a second biological sample obtained from an individual not having the disorder or being determined by averaging levels from a population of organisms not having a disorder. As will be appreciated in the art, once a standard polypeptide level or mRNA level is known, it can be used repeatedly as a standard for comparison.

By "biological sample" is intended any biological sample obtained from an organism, body fluids, cell line, tissue culture, or other source which contains the polypeptide of the present invention or mRNA. As indicated, biological samples include body fluids (such as the following non-limiting examples, sputum, amniotic fluid, urine, saliva, breast milk, secretions, interstitial fluid, blood, serum, spinal fluid, etc.) which contain the polypeptide of the present invention, and other tissue sources found to express the polypeptide of the present invention. Methods for obtaining tissue biopsies and body fluids from organisms are well known in the art. Where the biological sample is to include mRNA, a tissue biopsy is the preferred source.

The method(s) provided above may Preferably be applied in a diagnostic method and/or kits in which polynucleotides and/or polypeptides are attached to a solid support. In one exemplary method, the support may be a "gene chip" or a "biological chip" as described in U.S. Pat. Nos. 5,837,832, 5,874,219, and 5,856,174. Further, such a gene chip with polynucleotides of the present invention attached may be used to identify polymorphisms between the polynucleotide sequences, with polynucleotides isolated from a test subject. The knowledge of such polymorphisms (i.e. their location, as well as, their existence) would be beneficial in identifying disease loci for many disorders, including proliferative diseases and conditions. Such a method is described in U.S. Pat. Nos. 5,858,659 and 5,856,104. The US Patents referenced supra are hereby incorporated by reference in their entirety herein.

The present invention encompasses polynucleotides of the present invention that are chemically synthesized, or reproduced as peptide nucleic acids (PNA), or according to other methods known in the art. The use of PANS would serve as the preferred form if the polynucleotides are incorporated onto a solid support, or gene chip. For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PANS. As disclosed by P. E. Nielsen, M. Egholm, R. H. Berg and O. Buchardt, Science 254, 1497 (1991); and M. Egholm, O. Buchardt, L. Christensen, C. Behrens, S. M. Freier, D. A. Driver, R. H. Berg, S. K. Kim, B. Norden, and P. E. Nielsen, Nature 365, 666 (1993), PANS bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the stronger binding characteristics of PNA:DNA hybrids. In addition, it is more likely that single base mismatches can be determined with PNA/DNA hybridization because a single mismatch in a PNA/DNA 15-mer lowers the melting point (T.sub.m) by 8°–20° C., vs. 4°–16° C. for the DNA/DNA 15-mer duplex. Also, the absence of charge groups in PNA means that hybridization can be done at low ionic strengths and reduce possible interference by salt during the analysis.

In addition to the foregoing, a polynucleotide can be used to control gene expression through triple helix formation or antisense DNA or RNA. Antisense techniques are discussed, for example, in Okano, J. Neurochem. 56: 560 (1991); "Oligodeoxynucleotides as Antisense Inhibitors of Gene Expression, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). Both methods rely on binding of the polynucleotide to a complementary DNA or RNA. For these techniques, preferred polynucleotides are usually oligonucleotides 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxynucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat or prevent disease.

The present invention encompasses the addition of a nuclear localization signal, operably linked to the 5' end, 3' end, or any location therein, to any of the oligonucleotides, antisense oligonucleotides, triple helix oligonucleotides, ribozymes, PNA oligonucleotides, and/or polynucleotides, of the present invention. See, for example, G. Cutrona, et al., Nat. Biotech., 18:300–303, (2000); which is hereby incorporated herein by reference.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell. In one example, polynucleotide sequences of the present invention may be used to construct chimeric RNA/DNA oligonucleotides corresponding to said sequences, specifically designed to induce host cell mismatch repair mechanisms in an organism upon systemic injection, for example (Bartlett, R. J., et al., Nat. Biotech, 18:615–622 (2000), which is hereby incorporated by reference herein in its entirety). Such RNA/DNA oligonucleotides could be designed to correct genetic defects in certain host strains, and/or to introduce desired phenotypes in the host (e.g., introduction of a specific polymorphism within an endogenous gene corresponding to a polynucleotide of the present invention that may ameliorate and/or prevent a disease symptom and/or disorder, etc.). Alternatively, the polynucleotide sequence of the present invention may be used to construct duplex oligonucleotides corresponding to said sequence, specifically designed to correct genetic defects in certain host strains, and/or to introduce desired phenotypes into the host (e.g., introduction of a specific polymorphism within an endogenous gene corresponding to a polynucleotide of the present invention that may ameliorate and/or prevent a disease symptom and/or disorder, etc). Such methods of using duplex oligonucleotides are known in the art and are encompassed by the present invention (see EP1007712, which is hereby incorporated by reference herein in its entirety).

The polynucleotides are also useful for identifying organisms from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an organisms genome. These sequences can be used to prepare PCR primers for amplifying and isolating such selected DNA, which can then be sequenced. Using this technique, organisms can be identified because each organism will have a unique set of DNA sequences. Once an unique ID database is established for an organism, positive identification of that organism, living or dead, can be made from extremely small tissue samples. Similarly, polynucleotides of the present invention can be used as polymorphic markers, in addition to, the identification of transformed or non-transformed cells and/or tissues.

There is also a need for reagents capable of identifying the source of a particular tissue. Such need arises, for example, when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination. Moreover, as mentioned above, such reagents can be used to screen and/or identify transformed and non-transformed cells and/or tissues.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976–985 (1985); Jalkanen, M., et al., J. Cell. Biol. 105:3087–3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14C), sulfur (35S), tritium (3H), indium (112In), and technetium (99mTc), and fluorescent labels, such as fluorescein and rhodamine, and biotin.

In addition to assaying protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of a polypeptide of the present invention in cells or body fluid of an individual; (b) comparing the level of gene expression with a standard gene expression level, whereby an increase or decrease in the assayed polypeptide gene expression level compared to the standard expression level is indicative of a disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Moreover, polypeptides of the present invention can be used to treat, prevent, and/or diagnose disease. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B, SOD, catalase, DNA repair proteins), to inhibit the activity of a polypeptide (e.g., an oncogene or tumor suppressor), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth inhibition, enhancement of the immune response to proliferative cells or tissues).

Similarly, antibodies directed to a polypeptide of the present invention can also be used to treat, prevent, and/or diagnose disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Gene Therapy Methods

Another aspect of the present invention is to gene therapy methods for treating or preventing disorders, diseases and conditions. The gene therapy methods relate to the introduction of nucleic acid (DNA, RNA and antisense DNA or RNA) sequences into an animal to achieve expression of a polypeptide of the present invention. This method requires a polynucleotide which codes for a polypeptide of the invention that operatively linked to a promoter and any other genetic elements necessary for the expression of the polypeptide by the target tissue. Such gene therapy and delivery techniques are known in the art, see, for example, WO90/11092, which is herein incorporated by reference.

Thus, for example, cells from a patient may be engineered with a polynucleotide (DNA or RNA) comprising a promoter operably linked to a polynucleotide of the invention ex vivo, with the engineered cells then being provided to a patient to be treated with the polypeptide. Such methods are well-known in the art. For example, see Belldegrun et al., J. Natl. Cancer Inst., 85:207–216 (1993); Ferrantini et al., Cancer Research, 53:107–1112 (1993); Ferrantini et al., J. Immunology 153: 4604–4615 (1994); Kaido, T., et al., Int. J. Cancer 60: 221–229 (1995); Ogura et al., Cancer Research 50: 5102–5106 (1990); Santodonato, et al., Human Gene Therapy 7:1–10 (1996); Santodonato, et al., Gene Therapy 4:1246–1255 (1997); and Zhang, et al., Cancer Gene Therapy 3: 31–38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the polynucleotide constructs can be delivered by any method that delivers injectable materials to the cells of an animal, such as, injection into the interstitial space of tissues (heart, muscle, skin, lung, liver, and the like). The polynucleotide constructs may be delivered in a pharmaceutically acceptable liquid or aqueous carrier.

In one embodiment, the polynucleotide of the invention is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the polynucleotides of the invention can also be delivered in liposome forimulations and lipofectin formulations and the like can be prepared by methods well known to those skilled in the art. Such methods are described, for example, in U.S. Pat. Nos. 5,593,972, 5,589,466, and 5,580,859, which are herein incorporated by reference.

The polynucleotide vector constructs of the invention used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of polynucleotide sequence of the invention. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for the polynucleotides of the invention.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct of the invention can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked nucleic acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

The constructs may also be delivered with delivery vehicles such as viral sequences, viral particles, liposome formulations, lipofectin, precipitating agents, etc. Such methods of delivery are known in the art.

In certain embodiments, the polynucleotide constructs of the invention are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., Proc. Natl. Acad. Sci. USA, 84:7413–7416 (1987), which is herein incorporated by reference); mRNA (Malone et al., Proc. Natl. Acad. Sci. USA, 86:6077–6081 (1989), which is herein incorporated by reference); and purified transcription factors (Debs et al., J. Biol. Chem., 265:10189–10192 (1990), which is herein incorporated by reference), in functional form.

Cationic liposomes are readily available. For example, N-[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner et al., Proc. Natl. Acad. Sci. USA, 84:7413–7416 (1987), which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication NO: WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., Feigner et al., Proc. Natl. Acad. Sci. USA, 84:7413–7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., Methods of Immunology, 101:512–527 (1983), which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include Ca2+-EDTA chelation (Papahadjopoulos et al., Biochim. Biophys. Acta, 394:483 (1975); Wilson et al., Cell, 17:77 (1979)); ether injection (Deamer et al., Biochim. Biophys. Acta, 443:629 (1976); Ostro et al., Biochem. Biophys. Res. Commun., 76:836 (1977); Fraley et al., Proc. Natl. Acad. Sci. USA, 76:3348 (1979)); detergent dialysis (Enoch et al., Proc. Natl. Acad. Sci. USA, 76:145 (1979)); and reverse-phase evaporation (REV) (Fraley et al., J. Biol. Chem., 255:10431 (1980); Szoka et al., Proc. Natl. Acad. Sci. USA, 75:145 (1978); Schaefer-Ridder et al., Science, 215:166 (1982)), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication NO: WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication NO: WO 94/9469 (which are herein incorporated by reference) provide methods for delivering DNA-cationic lipid complexes to mammals.

In certain embodiments, cells are engineered, ex vivo or in vivo, using a retroviral particle containing RNA which comprises a sequence encoding polypeptides of the invention. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19-14x, VT-19-17-H2, RCRE, RCRIP, GP+E-86, GP+envAm12, and DAN cell lines as described in Miller, Human Gene Therapy, 1:5–14 (1990), which is incorporated herein by reference in its entirety. The vector may transduce the packaging cells through any means known in the art. Such means include, but are not limited to, electroporation, the use of liposomes, and CaPO4 precipitation. In one alternative, the retroviral plasmid vector may be encapsulated into a liposome, or coupled to a lipid, and then administered to a host.

The producer cell line generates infectious retroviral vector particles which include polynucleotide encoding polypeptides of the invention. Such retroviral vector particles then may be employed, to transduce eukaryotic cells, either in vitro or in vivo. The transduced eukaryotic cells will express polypeptides of the invention.

In certain other embodiments, cells are engineered, ex vivo or in vivo, with polynucleotides of the invention contained in an adenovirus vector. Adenovirus can be manipulated such that it encodes and expresses polypeptides of the invention, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartzet al., Am. Rev. Respir. Dis., 109:233–238 (1974)). Finally, adenovirus mediated gene transfer has been demonstrated in a number of instances including transfer of alpha-1-antitrypsin and CFTR to the lungs of cotton rats (Rosenfeld et al., Science, 252:431–434 (1991); Rosenfeld et al., Cell, 68:143–155 (1992)). Furthermore, extensive studies to attempt to establish adenovirus as a causative agent in human cancer were uniformly negative (Green et al. Proc. Natl. Acad. Sci. USA, 76:6606 (1979)).

Suitable adenoviral vectors useful in the present invention are described, for example, in Kozarsky and Wilson, Curr. Opin. Genet. Devel., 3:499–503 (1993); Rosenfeld et al., Cell, 68:143–155 (1992); Engelhardt et al., Human Genet. Ther., 4:759–769 (1993); Yang et al., Nature Genet., 7:362–369 (1994); Wilson et al., Nature , 365:691–692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, Curr. Topics in Microbiol. Immunol., 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The polynucleotide construct containing polynucleotides of the invention is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the polynucleotide construct of the invention. These viral particles are then used to transduce eukaryotic cells, either ex vivo or in vivo. The transduced cells will contain the polynucleotide construct integrated into its genome, and will express the desired gene product.

Another method of gene therapy involves operably associating heterologous control regions and endogenous polynucleotide, sequences (e.g. encoding the polypeptide sequence of interest) via homologous recombination (see, e.g., U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., Proc. Natl. Acad. Sci. USA, 86:8932–8935 (1989); and Zijlstra et al., Nature, 342:435–438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous sequence is placed under the control of the promoter. The promoter then drives the expression of the endogenous sequence.

The polynucleotides encoding polypeptides of the present invention may be administered along with other polynucleotides encoding angiogenic proteins. Angiogenic proteins include, but are not limited to, acidic and basic fibroblast growth factors, VEGF-1, VEGF-2 (VEGF-C), VEGF-3 (VEGF-B), epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

Preferably, the polynucleotide encoding a polypeptide of the invention contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers. (Kaneda et al., Science, 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA, 189:11277–11281 (1992), which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian. Therapeutic compositions of the present invention can be administered to any animal, preferably to mammals and birds. Preferred mammals include humans, dogs, cats, mice, rats, rabbits sheep, cattle, horses and pigs, with humans being particularly preferred.

Biological Activities

The polynucleotides or polypeptides, or agonists or antagonists of the present invention can be used in assays to test for one or more biological activities. If these polynucleotides and polypeptides do exhibit activity in a particular assay, it is likely that these molecules may be involved in the diseases associated with the biological activity. Thus, the polynucleotides or polypeptides, or agonists or antagonists could be used to treat the associated disease.

Immune Activity

The polynucleotides or polypeptides, or agonists or antagonists of the present invention may be useful in treating, preventing, and/or diagnosing diseases, disorders, and/or conditions of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune diseases, disorders, and/or conditions may be genetic, somatic, such as cancer or some autoimmune diseases, disorders, and/or conditions, acquired (e.g., by chemotherapy or toxins), or infectious. Moreover, a polynucleotides or polypeptides, or agonists or antagonists of the present invention can be used as a marker or detector of a particular immune system disease or disorder.

A polynucleotides or polypeptides, or agonists or antagonists of the present invention may be useful in treating, preventing, and/or diagnosing diseases, disorders, and/or conditions of hematopoietic cells. A polynucleotides or polypeptides, or agonists or antagonists of the present invention could be used to increase differentiation and proliferation of hematopoietic cells, including the pluripotent stem cells, in an effort to treat or prevent those diseases, disorders, and/or conditions associated with a decrease in certain (or many) types hematopoietic cells. Examples of immunologic deficiency syndromes include, but are not limited to: blood protein diseases, disorders, and/or conditions (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, a polynucleotides or polypeptides, or agonists or antagonists of the present invention could also be used to modulate hemostatic (the stopping of bleeding) or thrombolytic activity (clot formation). For example, by increasing hemostatic or thrombolytic activity, a polynucleotides or polypeptides, or agonists or antagonists of the present invention could be used to treat or prevent blood coagulation diseases, disorders, and/or conditions (e.g., afibrinogenemia, factor deficiencies, arterial thrombosis, venous thrombosis, etc.), blood platelet diseases, disorders, and/or conditions (e.g. thrombocytopenia), or wounds resulting from trauma, surgery, or other causes. Alternatively, a polynucleotides or polypeptides, or agonists or antagonists of the present invention that can decrease hemostatic or thrombolytic activity could be used to inhibit or dissolve clotting. Polynucleotides or polypeptides, or agonists or antagonists of the present invention are may also be useful for the detection, prognosis, treatment, and/or prevention of heart attacks (infarction), strokes, scarring, fibrinolysis, uncontrolled bleeding, uncontrolled coagulation, uncontrolled complement fixation, and/or inflammation.

A polynucleotides or polypeptides, or agonists or antagonists of the present invention may also be useful in treating, preventing, and/or diagnosing autoimmune diseases, disorders, and/or conditions. Many autoimmune diseases, disorders, and/or conditions result from inappropriate recognition of self as foreign material by immune cells. This inappropriate recognition results in an immune response leading to the destruction of the host tissue. Therefore, the administration of a polynucleotides or polypeptides, or agonists or antagonists of the present invention that inhibits an immune response, particularly the proliferation, differentiation, or chemotaxis of T-cells, may be an effective therapy in preventing autoimmune diseases, disorders, and/or conditions.

Examples of autoimmune diseases, disorders, and/or conditions that can be treated, prevented, and/or diagnosed or detected by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated, prevented, and/or diagnosed by polynucleotides or polypeptides, or agonists or antagonists of the present invention. Moreover, these molecules can be used to treat anaphylaxis, hypersensitivity to an antigenic molecule, or blood group incompatibility.

A polynucleotides or polypeptides, or agonists or antagonists of the present invention may also be used to treat, prevent, and/or diagnose organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of a polynucleotides or polypeptides, or agonists or antagonists of the present invention that inhibits an immune response, particularly the proliferation, differentiation, or chemotaxis of T-cells, may be an effective therapy in preventing organ rejection or GVHD.

Similarly, a polynucleotides or polypeptides, or agonists or antagonists of the present invention may also be used to modulate inflammation. For example, the polypeptide or polynucleotide or agonists or antagonist may inhibit the proliferation and differentiation of cells involved in an inflammatory response. These molecules can be used to treat, prevent, and/or diagnose inflammatory conditions, both chronic and acute conditions, including chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

A polynucleotides or polypeptides, or agonists or antagonists of the invention can be used to treat, prevent, and/or diagnose hyperproliferative diseases, disorders, and/or conditions, including neoplasms. A polynucleotides or polypeptides, or agonists or antagonists of the present invention may inhibit the proliferation of the disorder through direct or indirect interactions. Alternatively, a polynucleotides or polypeptides, or agonists or antagonists of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative diseases, disorders, and/or conditions can be treated, prevented, and/or diagnosed. This immune response may be increased by either enhancing an existing immune response, or by initiating a new immune response. Alternatively, decreasing an immune response may also be a method of treating, preventing, and/or diagnosing hyperproliferative diseases, disorders, and/or conditions, such as a chemotherapeutic agent.

Examples of hyperproliferative diseases, disorders, and/or conditions that can be treated, prevented, and/or diagnosed by polynucleotides or polypeptides, or agonists or antagonists of the present invention include, but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative diseases, disorders, and/or conditions can also be treated, prevented, and/or diagnosed by a polynucleotides or polypeptides, or agonists or antagonists of the present invention. Examples of such hyperproliferative diseases, disorders, and/or conditions include, but are not limited to: hypergammaglobulinemia, lymphoproliferative diseases, disorders, and/or conditions, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

One preferred embodiment utilizes polynucleotides of the present invention to inhibit aberrant cellular division, by gene therapy using the present invention, and/or protein fusions or fragments thereof.

Thus, the present invention provides a method for treating or preventing cell proliferative diseases, disorders, and/or conditions by inserting into an abnormally proliferating cell a polynucleotide of the present invention, wherein said polynucleotide represses said expression.

Another embodiment of the present invention provides a method of treating or preventing cell-proliferative diseases, disorders, and/or conditions in individuals comprising administration of one or more active gene copies of the present invention to an abnormally proliferating cell or cells. In a preferred embodiment, polynucleotides of the present invention is a DNA construct comprising a recombinant expression vector effective in expressing a DNA sequence encoding said polynucleotides. In another preferred embodiment of the present invention, the DNA construct encoding the polynucleotides of the present invention is inserted into cells to be treated utilizing a retrovirus, or more Preferably an adenoviral vector (See G J. Nabel, et. al., PNAS 1999 96: 324–326, which is hereby incorporated by reference). In a most preferred embodiment, the viral vector is defective and will not transform non-proliferating cells, only proliferating cells. Moreover, in a preferred embodiment, the polynucleotides of the present invention inserted into proliferating cells either alone, or in combination with or fused to other polynucleotides, can then be modulated via an external stimulus (i.e. magnetic, specific small molecule, chemical, or drug administration, etc.), which acts upon the promoter upstream of said polynucleotides to induce expression of the encoded protein product. As such the beneficial therapeutic affect of the present invention may be expressly modulated (i.e. to increase, decrease, or inhibit expression of the present invention) based upon said external stimulus.

Polynucleotides of the present invention may be useful in repressing expression of oncogenic genes or antigens. By "repressing expression of the oncogenic genes" is intended the suppression of the transcription of the gene, the degradation of the gene transcript (pre-message RNA), the inhibition of splicing, the destruction of the messenger RNA, the prevention of the post-translational modifications of the protein, the destruction of the protein, or the inhibition of the normal function of the protein.

For local administration to abnormally proliferating cells, polynucleotides of the present invention may be administered by any method known to those of skill in the art including, but not limited to transfection, electroporation, microinjection of cells, or in vehicles such as liposomes, lipofectin, or as naked polynucleotides, or any other method described throughout the specification. The polynucleotide of the present invention may be delivered by known gene delivery systems such as, but not limited to, retroviral vectors (Gilboa, J. Virology 44:845 (1982); Hocke, Nature 320:275 (1986); Wilson, et al., Proc. Natl. Acad. Sci. U.S.A. 85:3014), vaccinia virus system (Chakrabarty et al., Mol. Cell Biol. 5:3403 (1985) or other efficient DNA delivery systems (Yates et al., Nature 313:812 (1985)) known to those skilled in the art. These references are exemplary only and are hereby incorporated by reference. In order to specifically deliver or transfect cells which are abnormally proliferating and spare non-dividing cells, it is preferable to utilize a retrovirus, or adenoviral (as described in the art and elsewhere herein) delivery system known to those of skill in the art. Since host DNA replication is required for retroviral DNA to integrate and the retrovirus will be unable to self replicate due to the lack of the retrovirus genes needed for its life cycle. Utilizing such a retroviral delivery system for polynucleotides of the present invention will target said gene and constructs to abnormally proliferating cells and will spare the non-dividing normal cells.

The polynucleotides of the present invention may be delivered directly to cell proliferative disorder/disease sites in internal organs, body cavities and the like by use of imaging devices used to guide an injecting needle directly to the disease site. The polynucleotides of the present invention may also be administered to disease sites at the time of surgical intervention.

By "cell proliferative disease" is meant any human or animal disease or disorder, affecting any one or any combination of organs, cavities, or body parts, which is characterized by single or multiple local abnormal proliferations of cells, groups of cells, or tissues, whether benign or malignant.

Any amount of the polynucleotides of the present invention may be administered as long as it has a biologically inhibiting effect on the proliferation of the treated cells. Moreover, it is possible to administer more than one of the polynucleotide of the present invention simultaneously to the same site. By "biologically inhibiting" is meant partial or total growth inhibition as well as decreases in the rate of proliferation or growth of the cells. The biologically inhibitory dose may be determined by assessing the effects of the polynucleotides of the present invention on target malignant or abnormally proliferating cell growth in tissue culture, tumor growth in animals and cell cultures, or any other method known to one of ordinary skill in the art.

The present invention is further directed to antibody-based therapies which involve administering of anti-polypeptides and anti-polynucleotide antibodies to a mammalian, preferably human, patient for treating, preventing, and/or diagnosing one or more of the described diseases, disorders, and/or conditions. Methods for producing anti-polypeptides and anti-polynucleotide antibodies polyclonal and monoclonal antibodies are described in detail elsewhere herein. Such antibodies may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

In particular, the antibodies, fragments and derivatives of the present invention are useful for treating, preventing, and/or diagnosing a subject having or developing cell proliferative and/or differentiation diseases, disorders, and/or conditions as described herein. Such treatment comprises administering a single or multiple doses of the antibody, or a fragment, derivative, or a conjugate thereof.

The antibodies of this invention may be advantageously utilized in combination with other monoclonal or chimeric antibodies, or with lymphokines or hematopoietic growth factors, for example, which serve to increase the number or activity of effector cells which interact with the antibodies.

It is preferred to use high affinity and/or potent in vivo inhibiting and/or neutralizing antibodies against polypeptides or polynucleotides of the present invention, fragments or regions thereof, for both immunoassays directed to and therapy of diseases, disorders, and/or conditions related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than $5\times10^{-6}M$, $10^{-6}M$, $5\times10^{-7}M$, $10^{-7}M$, $5\times10^{-8}M$, $10^{-8}M$, $5\times10^{-9}M$, $10^{-9}M$, $5\times10^{-10}M$, $10^{-10}M$, $5\times10^{-11}M$, $10^{-11}M$, $5\times10^{-12}M$, $10^{-12}M$, $5\times10^{-13}M$, $10^{-13}M$, $5\times10^{-14}M$, $10^{-14}M$, $5\times10^{-15}M$, and $10^{-15}M$.

Moreover, polypeptides of the present invention may be useful in inhibiting the angiogenesis of proliferative cells or tissues, either alone, as a protein fusion, or in combination with other polypeptides directly or indirectly, as described elsewhere herein. In a most preferred embodiment, said anti-angiogenesis effect may be achieved indirectly, for example, through the inhibition of hematopoietic, tumor-specific cells, such as tumor-associated macrophages (See Joseph I B, et al. J Natl Cancer Inst, 90(21):1648–53 (1998), which is hereby incorporated by reference). Antibodies directed to polypeptides or polynucleotides of the present invention may also result in inhibition of angiogenesis directly, or indirectly (See Witte L, et al., Cancer Metastasis Rev. 17(2):155–61 (1998), which is hereby incorporated by reference)).

Polypeptides, including protein fusions, of the present invention, or fragments thereof may be useful in inhibiting proliferative cells or tissues through the induction of apoptosis. Said polypeptides may act either directly, or indirectly to induce apoptosis of proliferative cells and tissues, for example in the activation of a death-domain receptor, such as tumor necrosis factor (TNF) receptor-1, CD95 (Fas/APO-1), TNF-receptor-related apoptosis-mediated protein (TRAMP) and TNF-related apoptosis-inducing ligand (TRAIL) receptor-1 and -2 (See Schulze-Osthoff K, et al., Eur J Biochem 254(3):439–59 (1998), which is hereby incorporated by reference). Moreover, in another preferred embodiment of the present invention, said polypeptides may induce apoptosis through other mechanisms, such as in the activation of other proteins which will activate apoptosis, or through stimulating the expression of said proteins, either alone or in combination with small molecule drugs or adjuvants, such as apoptonin, galectins, thioredoxins, anti-inflammatory proteins (See for example, Mutat. Res. 400 (1–2):447–55 (1998), Med Hypotheses.50(5):423–33 (1998), Chem. Biol. Interact. April 24;111–112:23–34 (1998), J Mol Med.76(6):402–12 (1998), Int. J. Tissue React. 20(1):3–15 (1998), which are all hereby incorporated by reference).

Polypeptides, including protein fusions to, or fragments thereof, of the present invention are useful in inhibiting the metastasis of proliferative cells or tissues. Inhibition may occur as a direct result of administering polypeptides, or antibodies directed to said polypeptides as described elsewhere herein, or indirectly, such as activating the expression of proteins known to inhibit metastasis, for example alpha 4 integrins, (See, e.g., Curr Top Microbiol Inmunol 1998;231: 125–41, which is hereby incorporated by reference). Such therapeutic affects of the present invention may be achieved either alone, or in combination with small molecule drugs or adjuvants.

In another embodiment, the invention provides a method of delivering compositions containing the polypeptides of the invention (e.g., compositions containing polypeptides or polypeptide antibodies associated with heterologous polypeptides, heterologous nucleic acids, toxins, or prodrugs) to targeted cells expressing the polypeptide of the present invention. Polypeptides or polypeptide antibodies of the invention may be associated with heterologous polypeptides, heterologous nucleic acids, toxins, or prodrugs via hydrophobic, hydrophilic, ionic and/or covalent interactions.

Polypeptides, protein fusions to, or fragments thereof, of the present invention are useful in enhancing the immunogenicity and/or antigenicity of proliferating cells or tissues, either directly, such as would occur if the polypeptides of the present invention 'vaccinated' the immune response to respond to proliferative antigens and immunogens, or indirectly, such as in activating the expression of proteins known to enhance the immune response (e.g. chemokines), to said antigens and immunogens.

Cardiovascular Disorders

Polynucleotides or polypeptides, or agonists or antagonists of the invention may be used to treat, prevent, and/or diagnose cardiovascular diseases, disorders, and/or conditions, including peripheral artery disease, such as limb ischemia.

Cardiovascular diseases, disorders, and/or conditions include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular diseases, disorders, and/or conditions also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular diseases, disorders, and/or conditions, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular diseases, disorders, and/or conditions include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

Polynucleotides or polypeptides, or agonists or antagonists of the invention, are especially effective for the treatment of critical limb ischemia and coronary disease.

Polypeptides may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. Polypeptides of the invention may be administered as part of a Therapeutic, described in more detail below. Methods of delivering polynucleotides of the invention are described in more detail herein.

Diseases at the Cellular Level

Diseases associated with increased cell survival or the inhibition of apoptosis that could be treated, prevented, and/or diagnosed by the polynucleotides or polypeptides and/or antagonists or agonists of the invention, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, the polynucleotides or polypeptides, and/or agonists or antagonists of the invention are used to inhibit growth, progression, and/or metastasis of cancers, in particular those listed above.

Additional diseases or conditions associated with increased cell survival that could be treated, prevented or diagnosed by the polynucleotides or polypeptides, or agonists or antagonists of the invention, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated, prevented, and/or diagnosed by the polynucleotides or polypeptides, and/or agonists or antagonists of the invention, include AIDS; neurodegenerative diseases, disorders, and/or conditions (such as Alzheimer's disease, Parkinson's disease, Amyotrophic lateral sclerosis, Retinitis pigmentosa, Cerebellar degeneration and brain tumor or prior associated disease); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Wound Healing and Epithelial Cell Proliferation

In accordance with yet a further aspect of the present invention, there is provided a process for utilizing the polynucleotides or polypeptides, and/or agonists or antagonists of the invention, for therapeutic purposes, for example, to stimulate epithelial cell proliferation and basal keratinocytes for the purpose of wound healing, and to stimulate hair follicle production and healing of dermal wounds. Polynucleotides or polypeptides, as well as agonists or antagonists of the invention, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associated with systemic treatment with steroids, radiation therapy and antineoplastic drugs and antimetabolites. Polynucleotides or polypeptides, and/or agonists or antagonists of the invention, could be used to promote dermal reestablishment subsequent to dermal loss.

The polynucleotides or polypeptides, and/or agonists or antagonists of the invention, could be used to increase the adherence of skin grafts to a wound bed and to stimulate re-epithelialization from the wound bed. The following are a non-exhaustive list of grafts that polynucleotides or polypeptides, agonists or antagonists of the invention, could be used to increase adherence to a wound bed: autografts, artificial skin, allografts, autodermic graft, autoepidermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. The polynucleotides or polypeptides, and/or agonists or antagonists of the invention, can be used to promote skin strength and to improve the appearance of aged skin.

It is believed that the polynucleotides or polypeptides, and/or agonists or antagonists of the invention, will also produce changes in hepatocyte proliferation, and epithelial cell proliferation in the lung, breast, pancreas, stomach, small intestine, and large intestine. The polynucleotides or polypeptides, and/or agonists or antagonists of the invention, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. The polynucleotides or polypeptides, and/or agonists or antagonists of the invention, may promote proliferation of endothelial cells, keratinocytes, and basal keratinocytes.

The polynucleotides or polypeptides, and/or agonists or antagonists of the invention, could also be used to reduce the side effects of gut toxicity that result from radiation, chemotherapy treatments or viral infections. The polynucleotides or polypeptides, and/or agonists or antagonists of the invention, may have a cytoprotective effect on the small intestine mucosa. The polynucleotides or polypeptides, and/or agonists or antagonists of the invention, may also stimulate healing of mucositis (mouth ulcers) that result from chemotherapy and viral infections.

The polynucleotides or polypeptides, and/or agonists or antagonists of the invention, could further be used in full regeneration of skin in full and partial thickness skin defects, including burns, (i.e., repopulation of hair follicles, sweat glands, and sebaceous glands), treatment of other skin defects such as psoriasis. The polynucleotides or polypeptides, and/or agonists or antagonists of the invention, could be used to treat epidermolysis bullosa, a defect in adherence of the epidermis to the underlying dermis which results in frequent, open and painful blisters by accelerating reepithelialization of these lesions. The polynucleotides or polypeptides, and/or agonists or antagonists of the invention, could also be used to treat gastric and doudenal ulcers and help heal by scar formation of the mucosal lining and regeneration of glandular mucosa and duodenal mucosal lining more rapidly. Inflamamatory bowel diseases, such as Crohn's disease and ulcerative colitis, are diseases which result in destruction of the mucosal surface of the small or large intestine, respectively. Thus, the polynucleotides or polypeptides, and/or agonists or antagonists of the invention, could be used to promote the resurfacing of the mucosal surface to aid more rapid healing and to prevent progression of inflammatory bowel disease. Treatment with the polynucleotides or polypeptides, and/or agonists or antagonists of the invention, is expected to have a significant effect on the production of mucus throughout the gastrointestinal tract and could be used to protect the intestinal mucosa from injurious substances that are ingested or following surgery. The polynucleotides or polypeptides, and/or agonists or antagonists of the invention, could be used to treat diseases associate with the under expression of the polynucleotides of the invention.

Moreover, the polynucleotides or polypeptides, and/or agonists or antagonists of the invention, could be used to prevent and heal damage to the lungs due to various pathological states. A growth factor such as the polynucleotides or polypeptides, and/or agonists or antagonists of the invention, which could stimulate proliferation and differentiation and promote the repair of alveoli and brochiolar epithelium to prevent or treat acute or chronic lung damage. For example, emphysema, which results in the progressive loss of aveoli, and inhalation injuries, i.e., resulting from smoke inhalation and burns, that cause necrosis of the bronchiolar epithelium and alveoli could be effectively treated, prevented, and/or diagnosed using the polynucleotides or polypeptides, and/or agonists or antagonists of the invention. Also, the polynucleotides or polypeptides, and/or agonists or antagonists of the invention, could be used to stimulate the proliferation of and differentiation of type II pneumocytes, which may help treat or prevent disease such as hyaline membrane diseases, such as infant respiratory distress syndrome and bronchopulmonary displasia, in premature infants.

The polynucleotides or polypeptides, and/or agonists or antagonists of the invention, could stimulate the proliferation and differentiation of hepatocytes and, thus, could be used to alleviate or treat liver diseases and pathologies such as fulminant liver failure caused by cirrhosis, liver damage caused by viral hepatitis and toxic substances (i.e., acetaminophen, carbon tetraholoride and other hepatotoxins known in the art).

In addition, the polynucleotides or polypeptides, and/or agonists or antagonists of the invention, could be used treat or prevent the onset of diabetes mellitus. In patients with newly diagnosed Types I and II diabetes, where some islet cell function remains, the polynucleotides or polypeptides, and/or agonists or antagonists of the invention, could be used to maintain the islet function so as to alleviate, delay or prevent permanent manifestation of the disease. Also, the polynucleotides or polypeptides, and/or agonists or antagonists of the invention, could be used as an auxiliary in islet cell transplantation to improve or promote islet cell function.

Neurological Diseases

Nervous system diseases, disorders, and/or conditions, which can be treated, prevented, and/or diagnosed with the compositions of the invention (e.g., polypeptides, polynucleotides, and/or agonists or antagonists), include, but are not limited to, nervous system injuries, and diseases, disorders, and/or conditions which result in either a disconnection of axons, a diminution or degeneration of neurons, or demyelination. Nervous system lesions which may be treated, prevented, and/or diagnosed in a patient (including human and non-human mammalian patients) according to the invention, include but are not limited to, the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis; (5) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis (ALS); (6) lesions associated with nutritional diseases, disorders, and/or conditions, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

In a preferred embodiment, the polypeptides, polynucleotides, or agonists or antagonists of the invention are used to protect neural cells from the damaging effects of cerebral hypoxia. According to this embodiment, the compositions of the invention are used to treat, prevent, and/or diagnose neural cell injury associated with cerebral hypoxia. In one aspect of this embodiment, the polypeptides, polynucleotides, or agonists or antagonists of the invention are used to treat, prevent, and/or diagnose neural cell injury associated with cerebral ischemia. In another aspect of this embodiment, the polypeptides, polynucleotides, or agonists or antagonists of the invention are used to treat, prevent, and/or diagnose neural cell injury associated with cerebral infarction. In another aspect of this embodiment, the polypeptides, polynucleotides, or agonists or antagonists of the invention are used to treat, prevent, and/or diagnose or prevent neural cell injury associated with a stroke. In a further aspect of this embodiment, the polypeptides, polynucleotides, or agonists or antagonists of the invention are used to treat, prevent, and/or diagnose neural cell injury associated with a heart attack.

The compositions of the invention which are useful for treating or preventing a nervous system disorder may be selected by testing for biological activity in promoting the survival or differentiation of neurons. For example, and not by way of limitation, compositions of the invention which elicit any of the following effects may be useful according to the invention: (1) increased survival time of neurons in culture; (2) increased sprouting of neurons in culture or in vivo; (3) increased production of a neuron-associated molecule in culture or in vivo, e.g., choline acetyltransferase or acetylcholinesterase with respect to motor neurons; or (4) decreased symptoms of neuron dysfunction in vivo. Such effects may be measured by any method known in the art. In preferred, non-limiting embodiments, increased survival of neurons may routinely be measured using a method set forth herein or otherwise known in the art, such as, for example, the method set forth in Arakawa et al. (J. Neurosci. 10:3507–3515 (1990)); increased sprouting of neurons may be detected by methods known in the art, such as, for example, the methods set forth in Pestronk et al. (Exp. Neurol. 70:65–82 (1980)) or Brown et al. (Ann. Rev. Neurosci. 4:17–42 (1981)); increased production of neuron-associated molecules may be measured by bioassay, enzymatic assay, antibody binding, Northern blot assay, etc., using techniques known in the art and depending on the molecule to be measured; and motor neuron dysfunction may be measured by assessing the physical manifestation of motor neuron disorder, e.g., weakness, motor neuron conduction velocity, or functional disability.

In specific embodiments, motor neuron diseases, disorders, and/or conditions that may be treated, prevented, and/or diagnosed according to the invention include, but are not limited to, diseases, disorders, and/or conditions such as infarction, infection, exposure to toxin, trauma, surgical damage, degenerative disease or malignancy that may affect motor neurons as well as other components of the nervous system, as well as diseases, disorders, and/or conditions that selectively affect neurons such as amyotrophic lateral sclerosis, and including, but not limited to, progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

Infectious Disease

A polypeptide or polynucleotide and/or agonist or antagonist of the present invention can be used to treat, prevent, and/or diagnose infectious agents. For example, by increasing the immune response, particularly increasing the proliferation and differentiation of B and/or T cells, infectious diseases may be treated, prevented, and/or diagnosed. The immune response may be increased by either enhancing an existing immune response, or by initiating a new immune response. Alternatively, polypeptide or polynucleotide and/or agonist or antagonist of the present invention may also directly inhibit the infectious agent, without necessarily eliciting an immune response.

Viruses are one example of an infectious agent that can cause disease or symptoms that can be treated, prevented, and/or diagnosed by a polynucleotide or polypeptide and/or agonist or antagonist of the present invention. Examples of viruses, include, but are not limited to Examples of viruses, include, but are not limited to the following DNA and RNA viruses and viral families: Arbovirus, Adenoviridae, Arenaviridae, Arterivirus, Birnaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picornaviridae, Poxyiridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat, prevent, and/or diagnose: meningitis, Dengue, EBV, and/or hepatitis (e.g., hepatitis B). In an additional specific embodiment polynucleotides, polypeptides, or agonists or antagonists of the invention are used to treat patients nonresponsive to one or more other commercially available hepatitis vaccines. In a further specific embodiment polynucleotides, polypeptides, or agonists or antagonists of the invention are used to treat, prevent, and/or diagnose AIDS.

Similarly, bacterial or fungal agents that can cause disease or symptoms and that can be treated, prevented, and/or diagnosed by a polynucleotide or polypeptide and/or agonist or antagonist of the present invention include, but not limited to, include, but not limited to, the following Gram- Negative and Gram-positive bacteria and bacterial families and fungi: Actinomycetales (e.g., *Corynebacterium, Mycobacterium, Norcardia*), *Cryptococcus neoformans,* Aspergillosis, Bacillaceae (e.g., Anthrax, *Clostridium*), Bacteroidaceae, Blastomycosis, *Bordetella, Borrelia* (e.g., *Borrelia burgdorferi*), Brucellosis, Candidiasis, *Campylobacter,* Coccidioidomycosis, Cryptococcosis, Dermatocycoses, *E. coli* (e.g., Enterotoxigenic *E. coli* and Enterohemorrhagic *E. coli*), Enterobacteriaceae (*Klebsiella, Salmonella* (e.g., *Salmonella typhi,* and *Salmonella paratyphi*), *Serratia, Yersinia*), *Erysipelothrix, Helicobacter,* Legionellosis, Leptospirosis, *Listeria,* Mycoplasmatales, *Mycobacterium leprae, Vibrio cholerae,* Neisseriaceae (e.g., *Acinetobacter, Gonorrhea,* Menigococcal), *Meisseria mengitidis,* Pasteurellacea Infections (e.g., *Actinobacillus, Heamophilus* (e.g., *Heamophilus influenza* type B), *Pasteurella*), *Pseudomonas,* Rickettsiaceae, Chlamydiaceae, Syphilis, *Shigella* spp., Staphylococcal, Meningiococcal, Pneumococcal and Streptococcal (e.g., *Streptococcus pneumoniae* and Group B *Streptococcus*). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. Polynucleotides or polypeptides, agonists or antagonists of the invention, can be used to treat, prevent, and/or diagnose any of these symptoms or diseases. In specific embodiments, polynucleotides, polypeptides, agonists or antagonists of the invention are used to treat, prevent, and/or diagnose: tetanus, Diptheria, botulism, and/or meningitis type B.

Moreover, parasitic agents causing disease or symptoms that can be treated, prevented, and/or diagnosed by a polynucleotide or polypeptide and/or agonist or antagonist of the present invention include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. polynucleotides or polypeptides, or agonists or antagonists of the invention, can be used totreat, prevent, and/or diagnose any of these symptoms or diseases. In specific embodiments, polynucleotides, polypeptides, or agonists or antagonists of the invention are used to treat, prevent, and/or diagnose malaria.

Preferably, treatment or prevention using a polypeptide or polynucleotide and/or agonist or antagonist of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

A polynucleotide or polypeptide and/or agonist or antagonist of the present invention can be used to differentiate, proliferate, and attract cells, leading to the regeneration of tissues. (See, Science 276:59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, a polynucleotide or polypeptide and/or agonist or antagonist of the present invention may increase regeneration of tissues difficult to heal. For example, increased tendon/ligament regeneration would quicken recovery time after damage. A polynucleotide or polypeptide and/or agonist or antagonist of the present invention could also be used prophylactically in an effort to avoid damage. Specific diseases that could be treated, prevented, and/or diagnosed include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a polynucleotide or polypeptide and/or agonist or antagonist of the present invention to proliferate and differentiate nerve cells. Diseases that could be treated, prevented, and/or diagnosed using this method include central and peripheral nervous system diseases, neuropathies, or mechanical and traumatic diseases, disorders, and/or conditions (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated, prevented, and/or diagnosed using the polynucleotide or polypeptide and/or agonist or antagonist of the present invention.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors),or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide, either as a secreted protein or on the cell membrane. Preferred cells include cells from mammals, yeast, Drosophila, or E. coli. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

Additionally, the receptor to which a polypeptide of the invention binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labeled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of polypeptides of the invention thereby effectively generating agonists and antagonists of polypeptides of the invention. See generally, U.S. Pat. Nos. 5,605,793, 5,811,238, 5,830,721, 5,834,252, and 5,837,458, and Patten, P. A., et al., Curr. Opinion Biotechnol. 8:724–33 (1997); Harayama, S. Trends Biotechnol. 16(2):76–82 (1998); Hansson, L. O., et al., J. Mol. Biol. 287:265–76 (1999); and Lorenzo, M. M. and Blasco, R. Biotechniques 24(2):308–13 (1998) (each of these patents and publications are hereby incorporated by reference). In one embodiment, alteration of polynucleotides and corresponding polypeptides of the invention may be achieved by DNA shuffling. DNA shuffling involves the assembly of two or more DNA segments into a desired polynucleotide sequence of the invention molecule by homologous, or site-specific, recombination. In another embodiment, polynucleotides and corresponding polypeptides of the invention may be altered by being subjected to random mutagenesis by error-prone PCR, random nucleotide insertion or other methods prior to recombination. In another embodiment, one or more components, motifs, sections, parts, domains, fragments, etc., of the polypeptides of the invention may be recombined with one or more components, motifs, sections, parts, domains, fragments, etc. of one or more heterologous molecules. In preferred embodiments, the heterologous molecules are family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic(dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active fragments of the polypeptides of the invention. Biologically active fragments are those exhibiting activity similar, but not necessarily identical, to an activity of the polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and 3 [H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of 3[H] thymidine in each case. The amount of fibroblast cell proliferation is measured by liquid scintillation chromatography which measures the incorporation of 3[H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat, prevent, and/or diagnose disease or to bring about a particular result in a patient (e.g., blood vessel growth) by activating or inhibiting the polypeptide/molecule. Moreover, the assays can discover agents which may inhibit or enhance the production of the polypeptides of the invention from suitably manipulated cells or tissues. Therefore, the invention includes a method of identifying compounds which bind to the polypeptides of the invention comprising the steps of: (a) incubating a candidate binding compound with the polypeptide; and (b) determining if binding has occurred. Moreover, the invention includes a method of identifying agonists/antagonists comprising the steps of: (a) incubating a candidate compound with the polypeptide, (b) assaying a biological activity, and (b) determining if a biological activity of the polypeptide has been altered.

Also, one could identify molecules bind a polypeptide of the invention experimentally by using the beta-pleated sheet regions contained in the polypeptide sequence of the protein. Accordingly, specific embodiments of the invention are directed to polynucleotides encoding polypeptides which comprise, or alternatively consist of, the amino acid sequence of each beta pleated sheet regions in a disclosed polypeptide sequence. Additional embodiments of the invention are directed to polynucleotides encoding polypeptides which comprise, or alternatively consist of, any combination or all of contained in the polypeptide sequences of the invention. Additional preferred embodiments of the invention are directed to polypeptides which comprise, or alternatively consist of, the amino acid sequence of each of the beta pleated sheet regions in one of the polypeptide sequences of the invention. Additional embodiments of the invention are directed to polypeptides which comprise, or alternatively consist of, any combination or all of the beta pleated sheet regions in one of the polypeptide sequences of the invention.

Targeted Delivery

In another embodiment, the invention provides a method of delivering compositions to targeted cells expressing a receptor for a polypeptide of the invention, or cells expressing a cell bound form of a polypeptide of the invention.

As discussed herein, polypeptides or antibodies of the invention may be associated with heterologous polypeptides, heterologous nucleic acids, toxins, or prodrugs via hydrophobic, hydrophilic, ionic and/or covalent interactions. In one embodiment, the invention provides a method for the specific delivery of compositions of the invention to cells by administering polypeptides of the invention (including antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., polypeptides of the invention or antibodies of the invention) in association with toxins or cytotoxic prodrugs.

By "toxin" is meant compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, Pseudomonas exotoxin A, diphtheria toxin, saporin, momordin, gelonin, pokeweed antiviral protein, alpha-sarcin and cholera toxin. By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

Drug Screening

Further contemplated is the use of the polypeptides of the present invention, or the polynucleotides encoding these polypeptides, to screen for molecules which modify the activities of the polypeptides of the present invention. Such a method would include contacting the polypeptide of the present invention with a selected compound(s) suspected of having antagonist or agonist activity, and assaying the activity of these polypeptides following binding.

This invention is particularly useful for screening therapeutic compounds by using the polypeptides of the present invention, or binding fragments thereof, in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the present invention.

Thus, the present invention provides methods of screening for drugs or any other agents which affect activities mediated by the polypeptides of the present invention. These methods comprise contacting such an agent with a polypeptide of the present invention or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the present invention.

Another technique for drug screening provides high throughput screening for compounds having suitable binding affinity to the polypeptides of the present invention, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the present invention and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This invention also contemplates the use of competitive drug screening assays in which neutralizing antibodies capable of binding polypeptides of the present invention specifically compete with a test compound for binding to the polypeptides or fragments thereof. In this manner, the antibodies are used to detect the presence of any peptide which shares one or more antigenic epitopes with a polypeptide of the invention.

The human CAN-12 polypeptides and/or peptides of the present invention, or immunogenic fragments or oligopeptides thereof, can be used for screening therapeutic drugs or compounds in a variety of drug screening techniques. The fragment employed in such a screening assay may be free in solution, affixed to a solid support, borne on a cell surface, or located intracellularly. The reduction or abolition of activity of the formation of binding complexes between the ion channel protein and the agent being tested can be measured. Thus, the present invention provides a method for screening or assessing a plurality of compounds for their specific binding affinity with a CAN-12 polypeptide, or a bindable peptide fragment, of this invention, comprising providing a plurality of compounds, combining the CAN-12 polypeptide, or a bindable peptide fragment, with each of a plurality of compounds for a time sufficient to allow binding under suitable conditions and detecting binding of the CAN-12 polypeptide or peptide to each of the plurality of test compounds, thereby identifying the compounds that specifically bind to the CAN-12 polypeptide or peptide.

Methods of identifying compounds that modulate the activity of the novel human CAN-12 polypeptides and/or peptides are provided by the present invention and comprise combining a potential or candidate compound or drug modulator of calpain biological activity with an CAN-12 polypeptide or peptide, for example, the CAN-12 amino acid sequence as set forth in SEQ ID NOS:2, and measuring an effect of the candidate compound or drug modulator on the biological activity of the CAN-12 polypeptide or peptide. Such measurable effects include, for example, physical binding interaction; the ability to cleave a suitable calpain substrate; effects on native and cloned CAN-12-expressing cell line; and effects of modulators or other calpain-mediated physiological measures.

Another method of identifying compounds that modulate the biological activity of the novel CAN-12 polypeptides of the present invention comprises combining a potential or candidate compound or drug modulator of a calpain biological activity with a host cell that expresses the CAN-12 polypeptide and measuring an effect of the candidate compound or drug modulator on the biological activity of the CAN-12 polypeptide. The host cell can also be capable of being induced to express the CAN-12 polypeptide, e.g., via inducible expression. Physiological effects of a given modulator candidate on the CAN-12 polypeptide can also be measured. Thus, cellular assays for particular calpain modulators may be either direct measurement or quantification of the physical biological activity of the CAN-12 polypeptide, or they may be measurement or quantification of a physiological effect. Such methods preferably employ a CAN-12 polypeptide as described herein, or an overexpressed recombinant CAN-12 polypeptide in suitable host cells containing an expression vector as described herein, wherein the CAN-12 polypeptide is expressed, overexpressed, or undergoes upregulated expression.

Another aspect of the present invention embraces a method of screening for a compound that is capable of modulating the biological activity of a CAN-12 polypeptide, comprising providing a host cell containing an expression vector harboring a nucleic acid sequence encoding a CAN-12 polypeptide, or a functional peptide or portion thereof (e.g., SEQ ID NOS:2); determining the biological activity of the expressed CAN-12 polypeptide in the absence of a modulator compound; contacting the cell with the modulator compound and determining the biological activity of the expressed CAN-12 polypeptide in the presence of the modulator compound. In such a method, a difference between the activity of the CAN-12 polypeptide in the presence of the modulator compound and in the absence of the modulator compound indicates a modulating effect of the compound.

Essentially any chemical compound can be employed as a potential modulator or ligand in the assays according to the present invention. Compounds tested as calpain modulators can be any small chemical compound, or biological entity (e.g., protein, sugar, nucleic acid, lipid). Test compounds will typically be small chemical molecules and peptides. Generally, the compounds used as potential modulators can be dissolved in aqueous or organic (e.g., DMSO-based) solutions. The assays are designed to screen large chemical libraries by automating the assay steps and providing compounds from any convenient source. Assays are typically run in parallel, for example, in microtiter formats on microtiter plates in robotic assays. There are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland), for example. Also, compounds may be synthesized by methods known in the art.

High throughput screening methodologies are particularly envisioned for the detection of modulators of the novel CAN-12 polynucleotides and polypeptides described herein. Such high throughput screening methods typically involve providing a combinatorial chemical or peptide library containing a large number of potential therapeutic compounds (e.g., ligand or modulator compounds). Such combinatorial chemical libraries or ligand libraries are then screened in one or more assays to identify those library members (e.g., particular chemical species or subclasses) that display a desired characteristic activity. The compounds so identified can serve as conventional lead compounds, or can themselves be used as potential or actual therapeutics.

A combinatorial chemical library is a collection of diverse chemical compounds generated either by chemical synthesis or biological synthesis, by combining a number of chemical building blocks (i.e., reagents such as amino acids). As an example, a linear combinatorial library, e.g., a polypeptide or peptide library, is formed by combining a set of chemical building blocks in every possible way for a given compound length (i.e., the number of amino acids in a polypeptide or peptide compound). Millions of chemical compounds can be synthesized through such combinatorial mixing of chemical building blocks.

The preparation and screening of combinatorial chemical libraries is well known to those having skill in the pertinent art. Combinatorial libraries include, without limitation, peptide libraries (e.g. U.S. Pat. No. 5,010,175; Furka, 1991, *Int. J. Pept. Prot. Res.*, 37:487–493; and Houghton et al., 1991, *Nature*, 354:84–88). Other chemistries for generating chemical diversity libraries can also be used. Nonlimiting examples of chemical diversity library chemistries include, peptides (PCT Publication No. WO 91/019735), encoded peptides (PCT Publication No. WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., 1993, *Proc. Natl. Acad. Sci. USA*, 90:6909–6913), vinylogous polypeptides (Hagihara et al., 1992, *J. Amer. Chem. Soc.*, 114:6568), nonpeptidal peptidomimetics with glucose scaffolding (Hirschmann et al., 1992, *J. Amer. Chem. Soc.*, 114:9217–9218), analogous organic synthesis of small compound libraries (Chen et al., 1994, *J. Amer. Chem. Soc.*, 116:2661), oligocarbamates (Cho et al., 1993, *Science*, 261: 1303), and/or peptidyl phosphonates (Campbell et al., 1994, *J. Org. Chem.*, 59:658), nucleic acid libraries (see Ausubel, Berger and Sambrook, all supra), peptide nucleic acid libraries (U.S. Pat. No. 5,539,083), antibody libraries (e.g., Vaughn et al., 1996, *Nature Biotechnology*, 14(3):309–314) and PCT/US96/10287), carbohydrate libraries (e.g., Liang et al., 1996, *Science*, 274–1520–1522) and U.S. Pat. No. 5,593,853), small organic molecule libraries (e.g., benzodiazepines, Baum C&EN, Jan. 18, 1993, page 33; and U.S. Pat. No. 5,288,514; isoprenoids, U.S. Pat. No. 5,569,588; thiazolidinones and metathiazanones, U.S. Pat. No. 5,549, 974; pyrrolidines, U.S. Pat. Nos. 5,525,735 and 5,519,134; morpholino compounds, U.S. Pat. No. 5,506,337; and the like).

Devices for the preparation of combinatorial libraries are commercially available (e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, a large number of combinatorial libraries are commercially available (e.g., ComGenex, Princeton, N.J.; Asinex, Moscow, Russia; Tripods, Inc., St. Louis, Mo.; ChemStar, Ltd., Moscow, Russia; 3D Pharmaceuticals, Exton, Pa.; Martek Biosciences, Columbia, Md., and the like).

In one embodiment, the invention provides solid phase based in vitro assays in a high throughput format, where the cell or tissue expressing an ion channel is attached to a solid phase substrate. In such high throughput assays, it is possible to screen up to several thousand different modulators or ligands in a single day. In particular, each well of a microtiter plate can be used to perform a separate assay against a selected potential modulator, or, if concentration or incubation time effects are to be observed, every 5–10 wells can test a single modulator. Thus, a single standard microtiter plate can assay about 96 modulators. If 1536 well plates are used, then a single plate can easily assay from about 100 to about 1500 different compounds. It is possible to assay several different plates per day; thus, for example, assay screens for up to about 6,000–20,000 different compounds are possible using the described integrated systems.

In another of its aspects, the present invention encompasses screening and small molecule (e.g., drug) detection assays which involve the detection or identification of small molecules that can bind to a given protein, i.e., a CAN-12 polypeptide or peptide. Particularly preferred are assays suitable for high throughput screening methodologies.

In such binding-based detection, identification, or screening assays, a functional assay is not typically required. All that is needed is a target protein, preferably substantially purified, and a library or panel of compounds (e.g., ligands, drugs, small molecules) or biological entities to be screened or assayed for binding to the protein target. Preferably, most small molecules that bind to the target protein will modulate activity in some manner, due to preferential, higher affinity binding to functional areas or sites on the protein.

An example of such an assay is the fluorescence based thermal shift assay (3-Dimensional Pharmaceuticals, Inc., 3DP, Exton, Pa.) as described in U.S. Pat. Nos. 6,020,141 and 6,036,920 to Pantoliano et al.; see also, J. Zimmerman, 2000, *Gen. Eng. News*, 20(8)). The assay allows the detection of small molecules (e.g., drugs, ligands) that bind to expressed, and preferably purified, ion channel polypeptide based on affinity of binding determinations by analyzing thermal unfolding curves of protein-drug or ligand complexes. The drugs or binding molecules determined by this technique can be further assayed, if desired, by methods, such as those described herein, to determine if the molecules affect or modulate function or activity of the target protein.

To purify a CAN-12 polypeptide or peptide to measure a biological binding or ligand binding activity, the source may be a whole cell lysate that can be prepared by successive freeze-thaw cycles (e.g., one to three) in the presence of standard protease inhibitors. The CAN-12 polypeptide may be partially or completely purified by standard protein purification methods, e.g., affinity chromatography using specific antibody described infra, or by ligands specific for an epitope tag engineered into the recombinant CAN-12 polypeptide molecule, also as described herein. Binding activity can then be measured as described.

Compounds which are identified according to the methods provided herein, and which modulate or regulate the biological activity or physiology of the CAN-12 polypeptides according to the present invention are a preferred embodiment of this invention. It is contemplated that such modulatory compounds may be employed in treatment and therapeutic methods for treating a condition that is mediated by the novel CAN-12 polypeptides by administering to an individual in need of such treatment a therapeutically effective amount of the compound identified by the methods described herein.

In addition, the present invention provides methods for treating an individual in need of such treatment for a disease, disorder, or condition that is mediated by the CAN-12 polypeptides of the invention, comprising administering to the individual a therapeutically effective amount of the CAN-12-modulating compound identified by a method provided herein.

Antisense and Ribozyme (Antagonists)

In specific embodiments, antagonists according to the present invention are nucleic acids corresponding to the sequences contained in SEQ ID NO:1, 23, 53, and/or 55, or the complementary strand thereof, and/or to nucleotide sequences contained a deposited clone. In one embodiment, antisense sequence is generated internally by the organism, in another embodiment, the antisense sequence is separately administered (see, for example, O'Connor, Neurochem., 56:560 (1991). Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, Neurochem., 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research, 6:3073 (1979); Cooney et al., Science, 241:456 (1988); and Dervan et al., Science, 251:1300 (1991). The methods are based on binding of a polynucleotide to a complementary DNA or RNA.

For example, the use of c-myc and c-myb antisense RNA constructs to inhibit the growth of the non-lymphocytic leukemia cell line HL-60 and other cell lines was previously described. (Wickstrom et al. (1988); Anfossi et al. (1989)). These experiments were performed in vitro by incubating cells with the oligoribonucleotide. A similar procedure for in vivo use is described in WO 91/15580. Briefly, a pair of oligonucleotides for a given antisense RNA is produced as follows: A sequence complimentary to the first 15 bases of the open reading frame is flanked by an EcoR1 site on the 5 end and a HindIII site on the 3 end. Next, the pair of oligonucleotides is heated at 90° C. for one minute and then annealed in 2× ligation buffer (20 mM TRIS HCl pH 7.5, 10 mM MgCl2, 10MM dithiothreitol (DTT) and 0.2 mM ATP) and then ligated to the EcoR1/Hind III site of the retroviral vector PMV7 (WO 91/15580).

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the antisense nucleic acid of the invention. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding a polypeptide of the invention, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature, 29:304–310 (1981), the promoter contained in the 3' long terminal repeat of Rous sarcoma virus (Yamamoto et al., Cell, 22:787–797 (1980), the herpes thymidine promoter (Wagner et al., Proc. Natl. Acad. Sci. U.S.A., 78:1441–1445 (1981), the regulatory sequences of the metallothionein gene (Brinster et al., Nature, 296:39–42 (1982)), etc.

The antisense nucleic acids of the invention comprise a sequence complementary to at least a portion of an RNA transcript of a gene of interest. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded antisense nucleic acids of the invention, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a RNA sequence of the invention it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., Nature, 372: 333–335 (1994). Thus, oligonucleotides complementary to either the 5'- or 3'-non-translated, non-coding regions of a polynucleotide sequence of the invention could be used in an antisense approach to inhibit translation of endogenous mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., Proc. Natl. Acad. Sci. U.S.A. 86:6553–6556 (1989); Lemaitre et al., Proc. Natl. Acad. Sci., 84:648–652 (1987); PCT Publication NO: WO88/09810, published Dec. 15, 1988) or the blood-brain barrier (see, e.g., PCT Publication NO: WO89/10134, published Apr. 25, 1988), hybridization-triggered cleavage agents. (See, e.g., Krol et al., BioTechniques, 6:958–976 (1988)) or intercalating agents. (See, e.g., Zon, Pharm. Res., 5:539–549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine; 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., Nucl. Acids Res., 15:6625–6641 (1987)). The oligonucleotide is a 2-0-methylribonucleotide (Inoue et al., Nucl. Acids Res., 15:6131–6148 (1987)), or a chimeric RNA-DNA analogue (Inoue et al., FEBS Lett. 215:327–330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res., 16:3209 (1988)), methylphosphonate oligonucleotides can be prepared by use of controlled pore glass polymer supports (Sarin et al., Proc. Natl. Acad. Sci. U.S.A., 85:7448–7451 (1988)), etc.

While antisense nucleotides complementary to the coding region sequence of the invention could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science, 247:1222–1225 (1990). While ribozymes that cleave mRNA at site specific recognition sequences can be used to destroy mRNAs corresponding to the polynucleotides of the invention, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature, 334:585–591 (1988). There are numerous potential hammerhead ribozyme cleavage sites within each nucleotide sequence disclosed in the sequence listing. Preferably, the ribozyme is engineered so that the cleavage recognition site is located near the 5' end of the mRNA corresponding to the polynucleotides of the invention; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express the polynucleotides of the invention in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat, prevent, and/or diagnose the diseases described herein.

Thus, the invention provides a method of treating or preventing diseases, disorders, and/or conditions, including but not limited to the diseases, disorders, and/or conditions listed throughout this application, associated with overexpression of a polynucleotide of the present invention by administering to a patient (a) an antisense molecule directed to the polynucleotide of the present invention, and/or (b) a ribozyme directed to the polynucleotide of the present invention.

invention, and/or (b) a ribozyme directed to the polynucleotide of the present invention.

Biotic Associations

A polynucleotide or polypeptide and/or agonist or antagonist of the present invention may increase the organisms ability, either directly or indirectly, to initiate and/or maintain biotic associations with other organisms. Such associations may be symbiotic, nonsymbiotic, endosymbiotic, macrosymbiotic, and/or microsymbiotic in nature. In general, a polynucleotide or polypeptide and/or agonist or antagonist of the present invention may increase the organisms ability to form biotic associations with any member of the fungal, bacterial, lichen, mycorrhizal, cyanobacterial, dinoflaggellate, and/or algal, kingdom, phylums, families, classes, genuses, and/or species.

The mechanism by which a polynucleotide or polypeptide and/or agonist or antagonist of the present invention may increase the host organisms ability, either directly or indirectly, to initiate and/or maintain biotic associations is variable, though may include, modulating osmolarity to desirable levels for the symbiont, modulating pH to desirable levels for the symbiont, modulating secretions of organic acids, modulating the secretion of specific proteins, phenolic compounds, nutrients, or the increased expression of a protein required for host-biotic organisms interactions (e.g., a receptor, ligand, etc.). Additional mechanisms are known in the art and are encompassed by the invention (see, for example, "Microbial Signalling and Communication", eds., R. England, G. Hobbs, N. Bainton, and D. McL.

Roberts, Cambridge University Press, Cambridge, (1999); which is hereby incorporated herein by reference).

In an alternative embodiment, a polynucleotide or polypeptide and/or agonist or antagonist of the present invention may decrease the host organisms ability to form biotic associations with another organism, either directly or indirectly. The mechanism by which a polynucleotide or polypeptide and/or agonist or antagonist of the present invention may decrease the host organisms ability, either directly or indirectly, to initiate and/or maintain biotic associations with another organism is variable, though may include, modulating osmolarity to undesirable levels, modulating pH to undesirable levels, modulating secretions of organic acids, modulating the secretion of specific proteins, phenolic compounds, nutrients, or the decreased expression of a protein required for host-biotic organisms interactions (e.g., a receptor, ligand, etc.). Additional mechanisms are known in the art and are encompassed by the invention (see, for example, "Microbial Signalling and Communication", eds., R. England, G. Hobbs, N. Bainton, and D. McL. Roberts, Cambridge University Press, Cambridge, (1999); which is hereby incorporated herein by reference).

The hosts ability to maintain biotic associations with a particular pathogen has significant implications for the overall health and fitness of the host. For example, human hosts have symbiosis with enteric bacteria in their gastrointestinal tracts, particularly in the small and large intestine. In fact, bacteria counts in feces of the distal colon often approach $10^{12}$ per milliliter of feces. Examples of bowel flora in the gastrointestinal tract are members of the Enterobacteriaceae, Bacteriodes, in addition to a-hemolytic streptococci, *E. coli*, Bifobacteria, *Anaerobic cocci*, Eubacteria, Costridia, lactobacilli, and yeasts. Such bacteria, among other things, assist the host in the assimilation of nutrients by breaking down food stuffs not typically broken down by the hosts digestive system, particularly in the hosts bowel. Therefore, increasing the hosts ability to maintain such a biotic association would help assure proper nutrition for the host.

Aberrations in the enteric bacterial population of mammals, particularly humans, has been associated with the following disorders: diarrhea, ileus, chronic inflammatory disease, bowel obstruction, duodenal diverticula, biliary calculous disease, and malnutrition. A polynucleotide or polypeptide and/or agonist or antagonist of the present invention are useful for treating, detecting, diagnosing, prognosing, and/or ameliorating, either directly or indirectly, and of the above mentioned diseases and/or disorders associated with aberrant enteric flora population.

The composition of the intestinal flora, for example, is based upon a variety of factors, which include, but are not limited to, the age, race, diet, malnutrition, gastric acidity, bile salt excretion, gut motility, and immune mechanisms. As a result, the polynucleotides and polypeptides, including agonists, antagonists, and fragments thereof, may modulate the ability of a host to form biotic associations by affecting, directly or indirectly, at least one or more of these factors.

Although the predominate intestinal flora comprises anaerobic organisms, an underlying percentage represents aerobes (e.g., *E. coli*). This is significant as such aerobes rapidly become the predominate organisms in intraabdominal infections—effectively becoming opportunistic early in infection pathogenesis. As a result, there is an intrinsic need to control aerobe populations, particularly for immune compromised individuals.

In a preferred embodiment, a polynucleotides and polypeptides, including agonists, antagonists, and fragments thereof, are useful for inhibiting biotic associations with specific enteric symbiont organisms in an effort to control the population of such organisms.

Biotic associations occur not only in the gastrointestinal tract, but also on an in the integument. As opposed to the gastrointestinal flora, the cutaneous flora is comprised almost equally with aerobic and anaerobic organisms. Examples of cutaneous flora are members of the gram-positive cocci (e.g., *S. aureus*, coagulase-negative staphylococci, micrococcus, *M. sedentarius*), gram-positive bacilli (e.g., *Corynebacterium* species, *C. minutissimum, Brevibacterium* species, *Propoionibacterium* species, *P. acnes*), gram-negative bacilli (e.g., *Acinebacter* species), and fungi (*Pityrosporum orbiculare*). The relatively low number of flora associated with the integument is based upon the inability of many organisms to adhere to the skin. The organisms referenced above have acquired this unique ability. Therefore, the polynucleotides and polypeptides of the present invention may have uses which include modulating the population of the cutaneous flora, either directly or indirectly.

Aberrations in the cutaneous flora are associated with a number of significant diseases and/or disorders, which include, but are not limited to the following: impetigo, ecthyma, blistering distal dactulitis, pustules, folliculitis, cutaneous abscesses, pitted keratolysis, trichomycosis axcillaris, dermatophytosis complex, axillary odor, erthyrasma, cheesy foot odor, acne, tinea versicolor, seborrheic dermititis, and *Pityrosporum folliculitis,* to name a few. A polynucleotide or polypeptide and/or agonist or antagonist of the present invention are useful for treating, detecting, diagnosing, prognosing, and/or ameliorating, either directly or indirectly, and of the above mentioned diseases and/or disorders associated with aberrant cutaneous flora population.

Additional biotic associations, including diseases and disorders associated with the aberrant growth of such associations, are known in the art and are encompassed by the invention. See, for example, "Infectious Disease", Second Edition, Eds., S. L., Gorbach, J. G., Bartlett, and N. R., Blacklow, W. B. Saunders Company, Philadelphia, (1998); which is hereby incorporated herein by reference).

Pheromones

In another embodiment, a polynucleotide or polypeptide and/or agonist or antagonist of the present invention may increase the organisms ability to synthesize and/or release a pheromone. Such a pheromone may, for example, alter the organisms behavior and/or metabolism.

A polynucleotide or polypeptide and/or agonist or antagonist of the present invention may modulate the biosynthesis and/or release of pheromones, the organisms ability to respond to pheromones (e.g., behaviorally, and/or metabolically), and/or the organisms ability to detect pheromones. Preferably, any of the pheromones, and/or volatiles released from the organism, or induced, by a polynucleotide or polypeptide and/or agonist or antagonist of the invention have behavioral effects the organism.

Other Activities

The polypeptide of the present invention, as a result of the ability to stimulate vascular endothelial cell growth, may be employed in treatment for stimulating re-vascularization of ischemic tissues due to various disease conditions such as thrombosis, arteriosclerosis, and other cardiovascular conditions. These polypeptide may also be employed to stimulate angiogenesis and limb regeneration, as discussed above.

The polypeptide may also be employed for treating wounds due to injuries, burns, post-operative tissue repair, and ulcers since they are mitogenic to various cells of different origins, such as fibroblast cells and skeletal muscle cells, and therefore, facilitate the repair or replacement of damaged or diseased tissue.

The polypeptide of the present invention may also be employed stimulate neuronal growth and to treat, prevent, and/or diagnose neuronal damage which occurs in certain neuronal disorders or neuro-degenerative conditions such as Alzheimer's disease, Parkinson's disease, and AIDS-related complex. The polypeptide of the invention may have the ability to stimulate chondrocyte growth, therefore, they may be employed to enhance bone and periodontal regeneration and aid in tissue transplants or bone grafts.

The polypeptide of the present invention may be also be employed to prevent skin aging due to sunburn by stimulating keratinocyte growth.

The polypeptide of the invention may also be employed for preventing hair loss, since FGF family members activate hair-forming cells and promotes melanocyte growth. Along the same lines, the polypeptides of the present invention may be employed to stimulate growth and differentiation of hematopoietic cells and bone marrow cells when used in combination with other cytokines.

The polypeptide of the invention may also be employed to maintain organs before transplantation or for supporting cell culture of primary tissues.

The polypeptide of the present invention may also be employed for inducing tissue of mesodermal origin to differentiate in early embryos.

The polypeptide or polynucleotides and/or agonist or antagonists of the present invention may also increase or decrease the differentiation or proliferation of embryonic stem cells, besides, as discussed above, hematopoietic lineage.

The polypeptide or polynucleotides and/or agonist or antagonists of the present invention may also be used to modulate mammalian characteristics, such as body height, weight, hair color, eye color, skin, percentage of adipose tissue, pigmentation, size, and shape (e.g., cosmetic surgery). Similarly, polypeptides or polynucleotides and/or agonist or antagonists of the present invention may be used to modulate mammalian metabolism affecting catabolism, anabolism, processing, utilization, and storage of energy.

Polypeptide or polynucleotides and/or agonist or antagonists of the present invention may be used to change a mammal's mental state or physical state by influencing biorhythms, caricadic rhythms, depression (including depressive diseases, disorders, and/or conditions), tendency for violence, tolerance for pain, reproductive capabilities (preferably by Activin or Inhibin-like activity), hormonal or endocrine levels, appetite, libido, memory, stress, or other cognitive qualities.

Polypeptide or polynucleotides and/or agonist or antagonists of the present invention may also be used to increase the efficacy of a pharmaceutical composition, either directly or indirectly. Such a use may be administered in simultaneous conjunction with said pharmaceutical, or separately through either the same or different route of administration (e.g., intravenous for the polynucleotide or polypeptide of the present invention, and orally for the pharmaceutical, among others described herein.).

Polypeptide or polynucleotides and/or agonist or antagonists of the present invention may also be used to prepare individuals for extraterrestrial travel, low gravity environments, prolonged exposure to extraterrestrial radiation levels, low oxygen levels, reduction of metabolic activity, exposure to extraterrestrial pathogens, etc. Such a use may be administered either prior to an extraterrestrial event, during an extraterrestrial event, or both. Moreover, such a use may result in a number of beneficial changes in the recipient, such as, for example, any one of the following, non-limiting, effects: an increased level of hematopoietic cells, particularly red blood cells which would aid the recipient in coping with low oxygen levels; an increased level of B-cells, T-cells, antigen presenting cells, and/or macrophages, which would aid the recipient in coping with exposure to extraterrestrial pathogens, for example; a temporary (i.e., reversible) inhibition of hematopoietic cell production which would aid the recipient in coping with exposure to extraterrestrial radiation levels; increase and/or stability of bone mass which would aid the recipient in coping with low gravity environments; and/or decreased metabolism which would effectively facilitate the recipients ability to prolong their extraterrestrial travel by any one of the following, non-limiting means: (i) aid the recipient by decreasing their basal daily energy requirements; (ii) effectively lower the level of oxidative and/or metabolic stress in recipient (i.e., to enable recipient to cope with increased extraterrestrial radiation levels by decreasing the level of internal oxidative/metabolic damage acquired during normal basal energy requirements; and/or (iii) enabling recipient to subsist at a lower metabolic temperature (i.e., cryogenic, and/or sub-cryogenic environment).

Polypeptide or polynucleotides and/or agonist or antagonists of the present invention may also be used as a food additive or preservative, such as to increase or decrease storage capabilities, fat content, lipid, protein, carbohydrate, vitamins, minerals, cofactors or other nutritional components.

Other Preferred Embodiments

Further preferred is a method of making a recombinant vector comprising inserting any of the above isolated nucleic acid molecule(s) into a vector. Also preferred is the recombinant vector produced by this method. Also preferred is a method of making a recombinant host cell comprising introducing the vector into a host cell, as well as the recombinant host cell produced by this method.

Also preferred is a method of making an isolated polypeptide comprising culturing this recombinant host cell under conditions such that said polypeptide is expressed and recovering said polypeptide. Also preferred is this method of making an isolated polypeptide, wherein said recombinant host cell is a eukaryotic cell and said polypeptide is a protein comprising an amino acid sequence selected from the group consisting of: an amino acid sequence of SEQ ID NO:2, 24, 54, and/or 56 wherein Y is an integer set forth in Table I and said position of the "Total AA of ORF" of SEQ ID NO:2, 24, 54, and/or 56 is defined in Table I; and an amino acid sequence of a protein encoded by a cDNA clone identified by a cDNA Clone Identifier in Table I and contained in the deposit with the ATCC Deposit Number shown for said cDNA clone in Table I. The isolated polypeptide produced by this method is also preferred.

Also preferred is a method of treatment of an individual in need of an increased level of a protein activity, which method comprises administering to such an individual a pharmaceutical composition comprising an amount of an isolated polypeptide, polynucleotide, or antibody of the claimed invention effective to increase the level of said protein activity in said individual.

Having generally described the invention, the same will be more readily understood by reference to the following examples, which are provided by way of illustration and are not intended as limiting.

REFERENCES

Altschul S F; Gish W; Miller W; Myers E W; Lipman D J Basic local alignment search tool. J. Mol. Biol. 215: 403–10 (1990).

Bartlett et al. Molecular Recognition in Chemical and Biological Problems Special Publication, Royal Chem. Soc. 78:182–196 (1989).

Bohm H-J, LODI: rule-based automatic design of new substituents for enzyme inhibitor leads. J. Comp. Aid. Molec. Design 6:61–78 (1992)

Cardozo T; Totrov M; Abagyan R Homology modeling by the ICM method. Proteins 23:403–14 (1995).

Good ford, P. J. A computational procedure for determining energetically favorable binding sites on biologically important macromolecules. J. Med. Chem. 28:849–857 (1985)

Goods ell, D. S. and Olsen, A. J. Automated docking of substrates to proteins by simulated annealing. Proteins 8:195–202 (1990)

Greer J Comparative modeling of homologous proteins. Methods Enzymol 202:239–52 (1991).

Hendlich M; Lackner P; Weitckus S; Floeckner H; Froschauer R; Gottsbacher K; Casari G; Sippl M J Identification of native protein folds amongst a large number of incorrect models. The calculation of low energy conformations from potentials of mean force. J. Mol. Biol. 216:167–80 (1990).

Hosfield, C., Elce, J. S., Davies, P., Jia, Z., Crystal structure of calpain reveals the structural basis for $Ca^{2+}$-dependent protease activity and a novel mode of enzyme activation., EMBO J., 18, 6880–6889 (1999).

Kuntz I D, Blaney J M, Oatley S J, Langridge R, Ferrin T E. A geometric approach to macromolecule-ligand interactions. J. Mol. Biol. 161:269–288 (1982)

Lesk, A. M., Boswell, D. R., Homology Modeling: Inferences from Tables of Aligned Sequences. Curr. Op. Struc. Biol. 2:242–247 (1992)

Martin, Y. C. 3D database searching in drug design. J. Med. Chem. 35:2145–2154 (1992)

Pearson W R Rapid and sensitive sequence comparison with FASTP and FASTA. Methods Enzymol 183:63–98 (1990).

Sali A; Potterton L; Yuan F; van Vlijmen H; Karplus M Evaluation of comparative protein modeling by MODELLER. PROTEINS 23:318–26 (1995).

Strobl, S., Fernandez-Catalan, C., Braun, M., Huber, R., Masumoto, H., Nakagawa., K., Irie, A., Sorimachi, S., Bourenkow, G., Bartunik, H., Suzuki, K., Bode, W., The crystal structure of calcium-free human m-calpain suggests an electrostatic switch mechanism for activation by calcium. Proc. Natl. Acad. Sci., 2000, 97(2), 588–592.

EXAMPLES

Description of the Preferred Embodiments

Example 1

Bioinformatics Analysis

To search for novel protease inhibitors, a Hidden-Markov Model (HMM) of cysteine proteases (obtained from the Pfam database in Sanger center) was used to search against the human genomic sequence database using a computer program called GENEWISEDB. Genomic sequences that were found to have a GENEWISEDB matching score of more than 15 were selected for further analysis. The genomic sequence contained in BAC (bacteria artificial chromosome) AC015980 (Genbank Accession No. AC015980) was found to contain a putative exon sequence. The portion of the sequence from AC015980 that matched was extracted and back-searched against the Genbank non-redundant protein database using the BLASTX program (SEQ ID NO:26). The most similar protein sequence, the human CAN5 protein (SEQ ID NO:4), was used as a template to predict more exons from AC015980 using the GENEWISEDB program (see FIG. 7). The final predicted exons were assembled and a full length clone of the gene was obtained using the predicted exon sequences. The protein sequence was found to have significant sequence homology with a family of known proteases. Based on the sequence, structure and known calpain signature sequences, the novel gene was determined to represent a novel human calpain protease and have provisionally named the gene CAN-12 (calcium activated neutral protease 12) and the protease itself as calpain 12.

Example 2

Method for Constructing a Size Fractionated Brain and Testis cDNA Library

Brain and testis poly A+RNA was purchased from Clontech and converted into double stranded cDNA using the SuperScript™ Plasmid System for cDNA Synthesis and Plasmid Cloning (Life Technologies) except that no radioisotope was incorporated in either of the cDNA synthesis steps and that the cDNA was fractionated by HPLC. This was accomplished on a TransGenomics HPLC system equipped with a size exclusion column (TosoHass) with dimensions of 7.8 mm×30 cm and a particle size of 10 um. Tris buffered saline was used as the mobile phase and the column was run at a flow rate of 0.5 mL/min.

The resulting chromatograms were analyzed to determine which fractions should be pooled to obtain the largest cDNA's; generally fractions that eluted in the range of 12 to 15 minutes were pooled. The cDNA was precipitated prior to ligation into the Sal I/Not I sites in the pSport vector supplied with the kit. Using a combination of PCR with primers to the ends of the vector and Sal I/Not I restriction enzyme digestion of mini-prep DNA, it was determined that the average insert size of the library was greater the 3.5 Kb. The overall complexity of the library was greater that $10^7$ independent clones. The library was amplified in semi-solid agar for 2 days at 30° C. An aliquot (200 microliters) of the amplified library was inoculated into a 200 ml culture for single-stranded DNA isolation by super-infection with a f1 helper phage. After overnight growth, the released phage particles with precipitated with PEG and the DNA isolated with proteinase K, SDS and phenol extractions. The single stranded circular DNA was concentrated by ethanol precipitation and used for the cDNA capture experiments.

Example 3

Method of Cloning the Novel Human CAN-12 Calpain

Using the predicted exon genomic sequence from bac AC015980 (FIG. 7; SEQ ID NO:13, 14, 15, 16, 17, and 26) an antisense 80 bp oligonucleotide with biotin on the 5' end was designed with the following sequence;

5'bAGGGAGCCACTGCCGATGGAGCTCAGGGTGGCCGGGAAGCTGGTGTCTTCAAAGAGGCAGCCATTCCTCAGGCACTC-3'         (SEQ ID NO:18)

One microliter (one hundred and fifty nanograms) of the biotinylated oligonucleotide was added to six microliters (six micrograms) of a mixture of single-stranded covalently closed circular liver, brain, testis, and spleen cDNA libraries and seven microliters of 100% formamide in a 0.5 ml PCR tube. The library was a mixture of the brain and testis cDNA library referenced in Example 2, in addition to, commercially available liver and spleen cDNA libraries from Life Technologies (Rockville, Md.). The mixture was heated in a thermal cycler to 95° C. for 2 mins. Fourteen microliters of 2× hybridization buffer (50% formamide, 1.5 M NaCl, 0.04 M NaPO$_4$, pH 7.2, 5 mM EDTA, 0.2% SDS) was added to the heated probe/cDNA library mixture and incubated at 42° C. for 26 hours. Hybrids between the biotinylated oligonucleotide and the circular cDNA were isolated by diluting the hybridization mixture to 220 microliters in a solution containing 1 M NaCl, 10 mM Tris-HCl pH 7.5, 1 mM EDTA, pH 8.0 and adding 125 microliters of streptavidin magnetic beads. This solution was incubated at 42° C. for 60 mins, mixing every 5 mins to resuspend the beads. The beads were separated from the solution with a magnet and the beads washed three times in 200 microliters of 0.1× SSPE, 0.1% SDS at 45° C.

The single stranded cDNAs were released from the biotinlyated oligonucleotide/streptavidin magnetic bead complex by adding 50 microliters of 0.1 N NaOH and incubating at room temperature for 10 mins. Six microliters of 3 M Sodium Acetate was added along with 15 micrograms of glycogen and the solution ethanol precipitated with 120 microliters of 100% ethanol. The DNA was resuspended in 12 microliters of TE (10 mM Tris-HCl, pH 8.0), 1 mM EDTA, pH 8.0). The single stranded cDNA was converted into double strands in a thermal cycler by mixing 5 microliters of the captured DNA with 1.5 microliters 10 micromolar standard SP6 primer (homologous to a sequence on the cDNA cloning vector) and 1.5 microliters of 10×PCR buffer. The mixture was heated to 95° C. for 20 seconds then ramped down to 59° C. At this time 15 microliters of a repair mix, that was preheated to 70° C. (Repair mix contains 4 microliters of 5 mM dNTPs (1.25 mM each), 1.5 microliters of 10×PCR buffer, 9.25 microliters of water, and 0.25 microliters of Taq polymerase). The solution was ramped back to 73° C. and incubated for 23 mins. The repaired DNA was ethanol precipitate and resuspended in 10 microliters of TE. Two microliters were electroporated in *E. coli* DH12S cells and resulting colonies were screen by PCR, using a primer pair designed from the genomic exonic sequence to identify the proper cDNAs.

Oligonucleotides used to identity the cDNA by PCR.
AC015980-L1  GACTTTGAGGCCCTGCTG (SEQ ID NO:19)
AC015980-R1  ACAGGAACCCAGTTCCCATA (SEQ ID NO:20)

A single cDNA clone was positive by PCR. The insert was sized and the clone was sequenced. The sequence of the cDNA clone revealed an unspliced intron, in addition to a three base-pair deletion (SEQ ID NO:1). Further attempts to obtain more clones with this method were unsuccessful, so an RT-PCR cloning approach was applied.

The nucleotide sequence and the encoded polypeptide for CAN-12 containing the unspliced intron and three base-pair deletion is shown in FIGS. 1A–E (SEQ ID NO:1).

Example 4

Method of Cloning the Novel Human CAN-12 Calpain via RT-PCR

The cDNA was amplified from testis stranded cDNA and spinal cord first strand cDNA using the following RT-PCR primer pair in a standard PCR reaction (25 ng of DNA template were added to the reaction mixture along with each oligonucleotide primer at a final concentration of 0.2 μM each. The total volume of the reactions was 50 μL).

(SEQ ID NO:21)
RT-PCR Sense PRIMER      CACCTGCCATGTCTCTGTG (SEQ ID NO:22)
RT-PCR Antisense PRIMER  GATTATAACAAGGTGGTGTTGAAGA The thermal cycling conditions for the PCR were as follows:

| | |
|---|---|
| 96° C. | 2 minutes |
| Then 45 cycles of: | |
| 94° C. | 30 seconds |
| 55° C. | 30 seconds |
| 72° C. | 3 minutes |
| Then one cycle of: | |
| 72° C. | 10 minutes |
| 4° C. | hold |

The PCR was then subjected to electrophoresis on a 1% agarose gel. Bands on the gel were visualized of the predicted size. The bands were excised from the gel with a razor blade.

The PCR products were then extracted from the agarose gel slice using the Qiagen QIAquick™ Gel Extraction kit. Briefly, 3 volumes of buffer QG are added to the gel slice. The mixture is incubated at 50° C. until the agarose is melted. Then one volume of isopropanol is added. The sample is applied to a QIAquick spin column and centrifuged for 1 minute at high speed. The DNA binds to the column. The column is washed by applying 750 μL of buffer PE to and centrifuging for 1 minute. The column is then dried by spinning for an additional minute at high speed. The DNA is eluted from the column by applying 30 μL of elution buffer (buffer EB), letting the column stand for 1 minute, then centrifuging the column at high speed for 1 minute. The eluate is collected in a microcentrifuge tube.

Next, a 'TA' cloning procedure was used to insert the amplified fragment into a plasmid vector. In order to use the 'TA' cloning strategy, the PCR amplicon must have a 3' 'A' overhang which is generated by Taq polymerase. Since a high fidelity, proofreading enzyme was used for the PCR amplification, the proofreading properties of the enzyme mix cause the 'A' overhang to be removed. Therefore, before the 'TA' cloning could be done, 'A' overhangs had to be added to the PCR product. To do this, the PCR product was incubated for 15 minutes at 72° C. in a mixture containing 5 units of Taq polymerase, 1×PCR buffer and 0.2 mM dATP (all from Roche). The Taq polymerase is from *Thermus*

*aquaticus* BM, recombinant *E. coli*. The 10×PCR buffer contains 100 mM Tris-HCl, 15 mM $MgCl_2$, 500 mM KCl, pH 8.3.

The PCR products with added 3' 'A' overhangs was then immediately used for 'TA' cloning. To do this, the TOPO TA Cloning® Kit for Sequencing from Invitrogen was used.

The following reaction mixture was set up:
 4 µL PCR product
 1 µL Salt Solution
 1 µL pCR® 4-TOPO® vector This was incubated at room temperature for 5 minutes.

Then 2 µL of this reaction were added to a vial of TOP10 One Shot® chemically competent *E. Coli*. This was incubated on ice for 5 minutes. The cells were then heat shocked at 42° C. for 30 seconds. Cells were transferred to ice for another 5 minutes. 250 µL of room temperature S.O.C. medium was added to the cells. The cells were then incubated at 37° C. for 1 hour with shaking for aeration. 50 µL of cells were spread on selective plates containing 50 µg/µL carbenicillin and incubated at 37° C. overnight. A more detailed protocol for this kit from Invitrogen is available from their website.

The next step was to screen colonies that grew on the selective plates for positive clones. This was done by growing 7 colonies from the testis PCR and 7 from the spinal cord PCR overnight in 4 mL of LB broth containing 50 µg/µL carbenicillin. The plasmid DNA was then isolated from the bacteria using the Qiagen QIAquick Spin Miniprep Kit. Protocols for this are available from the Qiagen company web site.

Once the plasmid DNA was purified, a restriction digest analysis was performed to determine if the clones were correct. A restriction enzyme digestion was performed with NotI and SpeI restriction endonucleases, using the suggested buffer and 5 µL of the purified plasmid, 5 units of enzyme in a total volume of 20 µL. The mixture was incubated at 37° C. for 2 hours. The digest was visualized by electrophoretic separation on a 1% agarose gel stained with ethidium bromide. From this analysis it was apparent the plasmids contained one size insert corresponding to the predicted insert size of the transcript. Two clones from each PCR reaction were sequenced using Applied Biosystems Big-Dye™ dideoxy terminator cycle sequencing on an Applied Biosystems 3700 capillary array DNA sequencer.

The above method resulted in several positive clones. After sequencing, it was determined that all of them had an unspliced intron that introduced a stop codon, with the exception of clone 1e (CAN-12v1; FIGS. 8A–C; SEQ ID NO:53). Clone 1e was correct, except for it was missing 3 amino acids in the middle of the protein (See FIG. 10A–B). It is thought that these three amino acids may represent an exon of the CAN-12v1 polynucleotide.

Although the other clones contained the unspliced intron, one of the clones, clone 1b, had the missing 3 amino acids. Thus, clone 1e and clone 1b were recombinately combined together effectively cutting out the region of clone 1e that was missing the terminal three amino acids, and replacing it with the same region from clone 1b which did have the three amino acids. The resulting recombinant clone is named clone 1e1b (CAN-12v2), and is provided in FIGS. 9A–C (SEQ ID NO:55).

The method of recombinately combining clone 1e and clone 1b are provided below. The part of clone 1e that had the missing exon was excised by restriction digestion with unique cutting enzymes BamHI and AvaI. The corresponding fragment with the small exon (three amino acids) from clone 1b was excised with the same enzymes and inserted into clone 1e. This yielded the complete correct coding sequence that was predicted. The clone was called 1e1b (CAN-12v2; FIGS. 9A–C; SEQ ID NO:55). CAN-12v2 is believed to represent the true physioligical form of CAN-12.

Example 5

Expression Profiling of the Novel Human CAN-12 Calpain

The same PCR primer pair that was used to identify the novel CAN-12 cDNA clones via RT-PCR (SEQ ID NO: 21 and 22) was used to measure the steady state levels of mRNA by quantitative PCR. Briefly, first strand cDNA was made from commercially available mRNA. The relative amount of cDNA used in each assay was determined by performing a parallel experiment using a primer pair for a gene expressed in equal amounts in all tissues, cyclophilin. The cyclophilin primer pair detected small variations in the amount of cDNA in each sample and these data were used for normalization of the data obtained with the primer pair for the novel CAN-12. The PCR data was converted into a relative assessment of the difference in transcript abundance amongst the tissues tested and the data is presented in FIG. 4. Transcripts corresponding to CAN-12 were expressed highly in the spinal cord; significantly in lymph node, thymus, and to a lesser extent, in spleen.

Example 6

Method Of Assessing The Expression Profile of the Novel CAN-12v2 and CAN-12v1 Polypeptides of the Present Invention Using Expanded mRNA Tissue and Cell Sources Total RNA from tissues was isolated using the TriZol protocol (Invitrogen) and quantified by determining its absorbance at 260 nM. An assessment of the 18s and 28s ribosomal RNA bands was made by denaturing gel electrophoresis to determine RNA integrity.

The specific sequence to be measured was aligned with related genes found in GenBank to identity regions of significant sequence divergence to maximize primer and probe specificity. Gene-specific primers and probes were designed using the ABI primer express software to amplify small amplicons (150 base pairs or less) to maximize the likelihood that the primers function at 100% efficiency. All primer/probe sequences were searched against Public Genbank databases to ensure target specificity. Primers and probes were obtained from ABI.

For CAN-12v2 and CAN-12v1, the primer probe sequences were as follows
Forward Primer 5'-TCGTGCCCTGCATATTGGA-3' (SEQ ID NO:143)
Reverse Primer 5=-AAAAGATGTGCTTCCTGGAGAAGA-3' (SEQ ID NO:144)
TAQMAN™ Probe 5'-CCCACCAGAAGTCAGAGTTCGTCCTCAG-3' (SEQ IDNO:145)

DNA Contamination

To access the level, of contaminating genomic DNA in the RNA, the RNA was divided into 2 aliquots and one half was treated with Rnase-free Dnase (Invitrogen). Samples from both the Dnase-treated and non-treated were then subjected to reverse transcription reactions with (RT+) and without (RT−) the presence of reverse transcriptase. TAQMAN™ assays were carried out with gene-specific primers (see above) and the contribution of genomic DNA to the signal detected was evaluated by comparing the threshold cycles obtained with the RT+/RT− non-Dnase treated RNA to that on the RT+/RT− Dnase treated RNA. The amount of signal contributed by genomic DNA in the Dnased RT− RNA must be less that 10% of that obtained with Dnased RT+ RNA. If not the RNA was not used in actual experiments.

Reverse Transcription Reaction and Sequence Detection 100 ng of Dnase-treated total RNA was annealed to 2.5 µM of the respective gene-specific specific reverse primer in the presence of 5.5 mM Magnesium Chloride by heating the sample to 72° C. for 2 mm and then cooling to 55° C. for 30 mm. 1.25 U/µl of MuLv reverse transcriptase and 500 µM of each dNTP was added to the reaction and the tube was incubated at 37° C. for 30 min. The sample was then heated to 90° C. for 5 min to denature enzyme.

Quantitative sequence detection was carried out on an ABI PRISM 7700 by adding to the reverse transcribed reaction 2.5 µM forward and reverse primers, 500 µM of each dNTP, buffer and 5U AMPLITAQ GOLDυ. The PCR reaction was then held at 94° C. for 12 min, followed by 40 cycles of 94° C. for 15 sec and 60° C. for 30 sec.

Data Handling

The threshold cycle (Ct) of the lowest expressing tissue (the highest Ct value) was used as the baseline of expression and all other tissues were expressed as the relative abundance to that tissue by calculating the difference in Ct value between the baseline and the other tissues and using it as the exponent in $2^{(\alpha Ct)}$ The expanded expression profile of the CAN-12v2 and CAN-12v1 polypeptides, is provided in FIG. 12 and described elsewhere herein.

Example 7

Method of Measuring the Protease Activity of CAN-12 Polypeptides

Protease activity of the CAN-12 polypeptide are measured by following the inhibition of proteolytic activity in cells, tissues, and/or in in vitro assays. Cysteine proteases of the calpain family (of which the present invention is a member) catalyze the hydrolysis of peptide, amide, ester, thiol ester and thiono ester bonds. Any assay that measures cleavage of these bonds can be used to quantitate enzymatic activity. In vitro assays for measuring protease activity using synthetic peptide fluorescent, spectrophotometric either through the use of single substrates (see below for examples), and fluorescence resonance transfer assays are well described in the art, as single substrates or as part of substrate libraries (Backes et al., 2000; Knight, C. G. Fluorimetric Assays of Proteolytic Enzymes. Meth. Enzymol. 248: 18–34 (1995)). In addition proteolytic activity is measured by following production of peptide products. Such approaches are well known to those familiar with the art (reviewed in McGeehan, G. M., Bickett, D. M., Wiseman, J. S., Green, M., Berman, Meth. Enzymol. 248: 35–46 (1995))

A complete set of protocols that have been used to evaluate calpain activity and are provided in Calpain Methods and Protocols John Elce ed. In Meth. Mol. Biol. Volume 144, 2000 (Humana Press, Totowa, N.J.).

Inhibitor Identification

Early work on calpain inhibitors produced nonselective enzyme inhibitors. Peptidyl aldehydes such as leupeptin and antipain inhibit calpain but also other proteases including serine proteases. Irreversible inhibitors such as the E64 family have also been studied, and peptidyl halomethanes and diazomethanes have long been used as protease inhibitors (Hayes et al., Drug News Perspect 11:215–222, 1998). Given the multiple therapeutic indications for the inhibition of calpain it appears that the achievement of selective modulators including specific inhibitors of this enzyme is an important goal.

The CAN-12 may be incubated with potential inhibitors (preferably small molecule inhibitors or antibodies provided elsewhere herein) for different times and with varying concentrations. Residual protease activity could then be measured according to any appropriate means known in the art. Enzyme activity in the presence of control may be expressed as fraction of control and curve fit to pre-incubation time and serpin concentration to determine inhibitory parameters including concentration that half maximally inhibits the enzyme activity.

Non-limiting examples of in vitro protease assays are well described in the art. Non-limiting examples of a spectrophotometric protease assays are the thrombin and tryptase assays measuring time-dependent optical density change followed at 405 nm using a kinetic microplate reader (Molecular Devices UVmax)(Balasubramanian, et al., Active site-directed synthetic thrombin inhibitors: synthesis, in vitro and in vivo activity profile of BMY 44621 and analogs. an examination of the role of the amino group in the D-Phe-Pro-Arg-H series. J. Med. Chem. 36:300–303 (1993); and Combrink et al., Novel 1,2-Benzisothiazol-3-one-1,1-dioxide Inhibitors of Human Mast Cell Tryptase. J. Med. Chem. 41:4854–4860 (1998)).

An example of a fluorescence assay which may be used for the present invention is the Factor VIIa assay. Briefly, the Factor VIIa assay is measured in the presence of human recombinant tissue factor (INNOVIN from Dade Behring Cat.# B4212–100). Human Factor VIIa may be obtained from Enzyme Research Labs (Cat.# HFVIIA 1640). Enzymatic activity could be measured in a buffer containing 150 mM NaCl, 5 mM $CaCl_2$, 1 mM CHAPS and 1 mg/ml PEG 6000 (pH 7.4) with 1 nM FVIIa and 100 µM D-Ile-Pro-Arg-AFC (Enzyme Systems Products, Km>200 µM) 0.66% DMSO. The assay (302 µl total volume) may be incubated at room temperature for 2 hr prior to reading fluorometric signal (Ex 405/Em 535) using a Molecular Devices or Victor 2 (Wallac) fluorescent plate reader.

In addition to the methods described above, protease activity (and therefore serpin activity) can be measured using fluorescent resonance energy transfer (FRET with Quencher -$P_n$-$P_3$-$P_2$-$P_1$- -$P_1'$-$P_2'$-Fluorophore), fluorescent peptide bound to beads (Fluorophore -$P_n$-$P_3$-$P_2$-$P_1$- -$P_1'$-$P_2'$-Bead), dye-protein substrates and serpin-protease gel shifts. All of which are well known to those skilled in the art (see a non-limiting review in Knight, C. G. Fluorimetric Assays of Proteolytic Enzymes. Meth. Enzymol. 248: 18–34 (1995)).

Additional assay methods are known in the art and are encompassed by the present invention. See, for example, Backes B J, Harris J L, Leonetti F, Craik C S, Ellman J A. Synthesis of positional-scanning libraries of fluorogenic peptide substrates to define the extended substrate specificity of plasmin and thrombin. Nat Biotechnol. 18:187–93 (2000); Balasubramanian, et al., Active site-directed synthetic thrombin inhibitors: synthesis, in vitro and in vivo activity profile of BMY 44621 and analogs. an examination of the role of the amino group in the D-Phe-Pro-Arg-H series. J. Med. Chem. 36:300–303 (1993); and Combrink et al., Novel 1,2-Benzisothiazol-3-one-1,1-dioxide Inhibitors of Human Mast Cell Tryptase. J. Med. Chem. 41:4854–4860 (1998) and those methods described in: Calpain Methods and Protocols (ed J. S. Elce) Meth. Mol. Biol. 144, 2000 and Calpain: Pharmacology and Toxicology of a calcium-dependent protease (K. Wang & P.-W. Yuen editors) Taylor & Francis Philadelphia, Pa, 1999; which are hereby incorporated herein by reference in their entirety.

Example 8

Determination of the Preferred Substrate Sequence of the CAN-12 Protease

The preferred substrate sequence specificity of the CAN-12 of the present invention may be determined using two redundant peptide libraries mud Edman peptide sequencing (1-2) as described herein.

The first peptide library is random, can vary in length and incorporates a modification at the N-terminus to block Edman sequencing. In the example provided, biotin is used as the blocking group. Proteolytic cleavage of the library is allowed to proceed long enough to turn over approximately 5–10% of the library. Edman sequencing of the peptide mixture provides the preferred substrate residues for the P' sites on the protease. The second peptide library has fixed P' residues to restrict the proteolytic cleavage site and an affinity tag for removing the C-terminal product of the proteolysis leaving the N-terminal peptide product pool behind for Edman sequencing to determine the amino acid residues preferred in the P1, P2, P3 etc . . . sites of the protease.

Reagents.

The endoproteases Factor Xa (New England BioLabs, Inc., Beverly, Mass.) and human kidney Renin (Calbiochem, San Diego, Calif.) were purchased for validation experiments. A hexapeptide library containing $4.7 \times 10^7$ peptide species was synthesized by the Molecular Redesign group (Natarajan & Riexinger) at Bristol-Myers Squibb Company (Princeton, N.J.). The library contained equialent representation of 19 amino acid residues at each of the six degenerate positions and incorporated an N-terminal biotin group and a C-terminal amide. Cysteine residues were excluded from the peptide pool and Methionine residues were replaced with Norleucine.

Endoprotease Cleaage of the Peptide Library.

The following method may be used to determine the prefemd substrate sequence downstream of the cleavage site. A 1.88 mM peptide library solution is prepared in phosphate buffer (10 mM Sodium Phosphate (pH 7.6). 0.1 M NaCl, and 10% DMSO) and is incubated with 2–30 μg endoprotease at 37° C. Using a fluorescamine assay to estimate the extent of peptide cleavage, the reaction is stopped at 5–10% completion with incubation at 100° C. for 2.0 minutes. Peptide pools are subjected to Edman sequencing. The data obtained is normalized and corrected for differences in efficiency of cleavage and recovery in the sequencer.

Fluorescamine Assay to Monitor Peptide Cleavage.

Primary amines generated during peptide cleavage is measured by reaction with fluorescamine (Aldrich, St. Louis, Mo.), as described in reference 3. The relative fluorescence is determined by measuring signals at $\lambda^{ex}=355$ nm and $\lambda^{ex}=46$ O nm on a PerkinElmer Wallac 1420 Spectrofluorometer. Reactions are sampled at multiple time points and assayed in triplicate. The amount of cleavage product formed is determined using the relative fluorescence produced by varying concentrations of a peptide standard of known concentration.

REFERENCES (1) "Substrate Specificity of Cathepsins D and E Determined by N-Terminal and C-Terminal Sequencing of Peptide Pools" D. Arnold et al. (1997) Eur. J. Biochem. 249, 171.
(2) "Determination of Protease Cleavage Site Motifs Using Mixture-Based Oriented Peptide Libraries" B. E. Turk et al. (2001) Nature Biotech. 19, 661.
(3) "Fluorescamine: a Reagent for Assay of Amino Acids, Peptides, Proteins, and Primary Amines in tho Picomole Raugo" S. Udenfirend, S. Stein, P. Bohlen, W. Dairman, W. Leimgruber, and M. Weigele (1972) Science 178, 87.

Example 9

Chromosomal Mapping of Calpain 12 and Linkage to Neurodegenerative Disorders

The calpain12 polynucleotides of the present invention were used to determine the chromosomal localization of the calpain12 gene. The comparison of the chromosomal location of the calpain 12 gene with the location of chromosomal regions which have been shown to be associated with specific diseases or conditions, e.g. by linkage analysis, can be indicative of diseases in which calpain12 may play a role.

A chromosomal localization of the calpain12 gene was performed by using the nucleic acid sequence (SEQ ID NO:1) of the invention in a database search of the recently completed draft of human genome sequence. Using the Basic Local Alignment Search Tool 2 (BLAST2), the first 200 bp of calpain12 cDNA sequence showed a perfect alignment of nucleotides 62 to 200 with the minus strand of Homo sapiens chromosome 2 clone RP11-541A15 nucleotide 177952 to 177814, and a perfect alignment of nucleotide 1 to 62 of calpain 12 cDNA (SEQ ID NO:1) with the nucleotide 94118 to 94179 of the same clone, suggesting the likelihood of an intron intervening this 200 cDNA fragment. To confirm the map of calpain 12 gene, another BLAST2 search was done with a 300 pb fragment of calpain 12 cDNA sequence containing nucleotides 4251 up to poly A signal sequence at position 4550 (SEQ ID NO:1). An alignment with 97% identities (292/300) of this calpain 3' sequence was found with nucleotide 125724 to 126023 of the same Homo sapiens chromosome 2 clone RP11-541A15. In order to get a refined map of this clone containing the locus of calpain12, a map search of NCBI genome database was performed. RP11-541A15 (Acc# AC015980.2) was found within a BAC contig adjacent to clone 852C13 (AL133246.2) mapping in $^2$p21-p22.

A whole-genome linkage scan in multiple sclerosis families (Ebers et al. A full genome search in multiple sclerosis. Nature Genet. 13: 472–476, 1996.) identified 5 susceptibility loci on chromosomes 2, 3, 5, 11, and X. In particular, an association was identified with marker D2S119 on chromosome 2 and MS. We further delineated the localization of this marker, D2s119, on 2p16-p21 based on a radiation hybrid linkage map retrieved from an online query at an NCBI web site Since the map of calpain 12 and the susceptibility marker D2S119 overlaps, it is reasonable to postulate that calpain 12 may contribute to MS. Furthermore, the transcription profile of calpain12 indicated a prominent expression in spinal cord, and implication of calpains in MS has been suggested (Shields DC et al. A putative mechanism of demyelination in multiple sclerosis by a proteolytic enzyme, calpain. Proc Natl Acad Sci U S A. 96:11486–91.1999).

Example 10

Method of Screening for Compounds that Interact with the CAN-12 Polypeptide

The following assays are designed to identify compounds that bind to the CAN-12 polypeptide, bind to other cellular proteins that interact with the CAN-12 polypeptide, and to compounds that interfere with the interaction of the CAN-12 polypeptide with other cellular proteins.

Such compounds can include, but are not limited to, other cellular proteins. Specifically, such compounds can include, but are not limited to, peptides, such as, for example, soluble peptides, including, but not limited to Ig-tailed fusion peptides, comprising extracellular portions of CAN-12 polypeptide transmembrane receptors, and members of random peptide libraries (see, e.g., Lam, K. S. et al., 1991, Nature 354:82–84; Houghton, R. et al., 1991, Nature 354:84–86), made of D-and/or L-configuration amino acids, phosphopeptides (including, but not limited to, members of random or partially degenerate phosphopeptide libraries; see, e.g., Songyang, Z., et al., 1993, Cell 72:767–778), antibodies (including, but not limited to, polyclonal, monoclonal, humanized, anti-idiotypic, chimeric or single chain antibodies, and FAb, F(ab').sub.2 and FAb expression libary fragments, and epitope-binding fragments thereof), and small organic or inorganic molecules.

Compounds identified via assays such as those described herein can be useful, for example, in elaborating the biological function of the CAN-12 polypeptide, and for ameliorating symptoms of tumor progression, for example. In instances, for example, whereby a tumor progression state or disorder results from a lower overall level of CAN-12 expression, CAN-12 polypeptide, and/or CAN-12 polypeptide activity in a cell involved in the tumor progression state or disorder, compounds that interact with the CAN-12 polypeptide can include ones which accentuate or amplify the activity of the bound CAN-12 polypeptide. Such compounds would bring about an effective increase in the level of CAN-12 polypeptide activity, thus ameliorating symptoms of the tumor progression disorder or state. In instances whereby mutations within the CAN-12 polypeptide cause aberrant CAN-12 polypeptides to be made which have a deleterious effect that leads to tumor progression, compounds that bind CAN-12 polypeptide can be identified that inhibit the activity of the bound CAN-12 polypeptide. Assays for testing the effectiveness of such compounds are known in the art and discussed, elsewhere herein.

Example 11

Method of Screening, In Vitro, Compounds that Bind to the CAN-12 Polypeptide

In vitro systems can be designed to identify compounds capable of binding the CAN-12 polypeptide of the invention. Compounds identified can be useful, for example, in modulating the activity of wild type and/or mutant CAN-12 polypeptide, preferably mutant CAN-12 polypeptide, can be useful in elaborating the biological function of the CAN-12 polypeptide, can be utilized in screens for identifying compounds that disrupt normal CAN-12 polypeptide interactions, or can in themselves disrupt such interactions.

The principle of the assays used to identify compounds that bind to the CAN-12 polypeptide involves preparing a reaction mixture of the CAN-12 polypeptide and the test compound under conditions and for a time sufficient to allow the two components to interact and bind, thus forming a complex which can be removed and/or detected in the reaction mixture. These assays can be conducted in a variety of ways. For example, one method to conduct such an assay would involve anchoring CAN-12 polypeptide or the test substance onto a solid phase and detecting CAN-12 polypeptide/test compound complexes anchored on the solid phase at the end of the reaction. In one embodiment of such a method, the CAN-12 polypeptide can be anchored onto a solid surface, and the test compound, which is not anchored, can be labeled, either directly or indirectly.

In practice, microtitre plates can conveniently be utilized as the solid phase. The anchored component can be immobilized by non-covalent or covalent attachments. Non-covalent attachment can be accomplished by simply coating the solid surface with a solution of the protein and drying. Alternatively, an immobilized antibody, preferably a monoclonal antibody, specific for the protein to be immobilized can be used to anchor the protein to the solid surface. The surfaces can be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously immobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the immobilized component (the antibody, in turn, can be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for CAN-12 polypeptide or the test compound to anchor any complexes formed in solution, and a labeled antibody specific for the other component of the possible complex to detect anchored complexes.

Example 12

Method of Identifying Compounds that Interfere with CAN-12 Polypeptide/Cellular Product Interaction The CAN-12 polypeptide of the invention can, in vivo, interact with one or more cellular or extracellular macromolecules, such as proteins. Such macromolecules include, but are not limited to, nucleic acid molecules and those products identified via methods such as those described, elsewhere herein. For the purposes of this discussion, such cellular and extracellular macromolecules are referred to herein as "binding partner(s)". For the purpose of the present invention, "binding partner" may also encompass small molecule compounds, polysaccharides, lipids, and any other molecule or molecule type referenced herein. Compounds that disrupt such interactions can be useful in regulating the activity of the CAN-12 polypeptide, especially mutant CAN-12 polypeptide. Such compounds can include, but are not limited to molecules such as antibodies, peptides, and the like described in elsewhere herein.

The basic principle of the assay systems used to identify compounds that interfere with the interaction between the CAN-12 polypeptide and its cellular or extracellular binding partner or partners involves preparing a reaction mixture containing the CAN-12 polypeptide, and the binding partner under conditions and for a time sufficient to allow the two products to interact and bind, thus forming a complex. In order to test a compound for inhibitory activity, the reaction mixture is prepared in the presence and absence of the test compound. The test compound can be initially included in the reaction mixture, or can be added at a time subsequent to the addition of CAN-12 polypeptide and its cellular or extracellular binding partner. Control reaction mixtures are incubated without the test compound or with a placebo. The formation of any complexes between the CAN-12 polypeptide and the cellular or extracellular binding partner is then detected. The formation of a complex in the control reaction, but not in the reaction mixture containing the test compound, indicates that the compound interferes with the interaction of the CAN-12 polypeptide and the interactive binding partner. Additionally, complex formation within reaction mixtures containing the test compound and normal CAN-12 polypeptide can also be compared to complex formation within reaction mixtures containing the test compound and mutant CAN-12 polypeptide. This comparison can be important in those cases wherein it is desirable to identify compounds that disrupt interactions of mutant but not normal CAN-12 polypeptide.

The assay for compounds that interfere with the interaction of the CAN-12 polypeptide and binding partners can be conducted in a heterogeneous or homogeneous format. Heterogeneous assays involve anchoring either the CAN-12 polypeptide or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the CAN-12 polypeptide and the binding partners, e.g., by competition, can be identified by conducting the reaction in the presence of the test substance; i.e., by adding the test substance to the reaction mixture prior to or simultaneously with the CAN-12 polypeptide and interactive cellular or extracellular binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either the CAN-12 polypeptide or the interactive cellular or extracellular binding partner, is anchored onto a solid surface, while the non-anchored species is labeled, either directly or indirectly. In practice, microtitre plates are conveniently utilized. The anchored species can be immobilized by non-covalent or covalent attachments. Non-covalent attachment can be accomplished simply by coating the solid surface with a solution of the CAN-12 polypeptide or binding partner and drying. Alternatively, an immobilized antibody specific for the species to be anchored can be used to anchor the species to the solid surface. The surfaces can be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with a labeled anti-Ig antibody). Depending upon the order of addition of reaction components, test compounds, which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the CAN-12 polypeptide and the interactive cellular or extracellular binding partner product is prepared in which either the CAN-12 polypeptide or their binding partners are labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt CAN-12 polypeptide-cellular or extracellular binding partner interaction can be identified.

In a particular embodiment, the CAN-12 polypeptide can be prepared for immobilization using recombinant DNA techniques known in the art. For example, the CAN-12 polypeptide coding region can be fused to a glutathione-S-transferase (GST) gene using a fusion vector such as pGEX-5X-1, in such a manner that its binding activity is maintained in the resulting fusion product. The interactive cellular or extracellular product can be purified and used to raise a monoclonal antibody, using methods routinely practiced in the art and described above. This antibody can be labeled with the radioactive isotope .sup.125 I, for example, by methods routinely practiced in the art. In a heterogeneous assay, e.g., the GST-CAN-12 polypeptide fusion product can be anchored to glutathione-agarose beads. The interactive cellular or extracellular binding partner product can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the CAN-12 polypeptide and the interactive cellular or extracellular binding partner can be detected by measuring the amount of radioactivity that remains associated with the glutathione-agarose beads. A successful inhibition of the interaction by the test compound will result in a decrease in measured radioactivity.

Alternatively, the GST-CAN-12 polypeptide fusion product and the interactive cellular or extracellular binding partner product can be mixed together in liquid in the absence of the solid glutathione-agarose beads. The test compound can be added either during or after the binding partners are allowed to interact. This mixture can then be added to the glutathione-agarose beads and unbound material is washed away. Again the extent of inhibition of the binding partner interaction can be detected by adding the labeled antibody and measuring the radioactivity associated with the beads.

In another embodiment of the invention, these same techniques can be employed using peptide fragments that correspond to the binding domains of the CAN-12 polypeptide product and the interactive cellular or extracellular binding partner (in case where the binding partner is a product), in place of one or both of the full length products.

Any number of methods routinely practiced in the art can be used to identify and isolate the protein's binding site. These methods include, but are not limited to, mutagenesis of one of the genes encoding one of the products and screening for disruption of binding in a co-immunoprecipitation assay. Compensating mutations in the gene encoding the second species in the complex can be selected. Sequence analysis of the genes encoding the respective products will reveal the mutations that correspond to the region of the product involved in interactive binding. Alternatively, one product can be anchored to a solid surface using methods described in this Section above, and allowed to interact with and bind to its labeled binding partner, which has been treated with a proteolytic enzyme, such as trypsin. After washing, a short, labeled peptide comprising the binding domain can remain associated with the solid material, which can be isolated and identified by amino acid sequencing. Also, once the gene coding for the cellular or extracellular binding partner product is obtained, short gene segments can be engineered to express peptide fragments of the product, which can then be tested for binding activity and purified or synthesized.

Example 13

Isolation of a Specific Clone from the Deposited Sample

The deposited material in the sample assigned the ATCC Deposit Number cited in Table I for any given cDNA clone also may contain one or more additional plasmids, each comprising a cDNA clone different from that given clone. Thus, deposits sharing the same ATCC Deposit Number contain at least a plasmid for each cDNA clone identified in Table I. Typically, each ATCC deposit sample cited in Table I comprises a mixture of approximately equal amounts (by weight) of about 1–10 plasmid DNAs, each containing a different cDNA clone and/or partial cDNA clone; but such a deposit sample may include plasmids for more or less than 2 cDNA clones.

Two approaches can be used to isolate a particular clone from the deposited sample of plasmid DNA(s) cited for that clone in Table I. First, a plasmid is directly isolated by screening the clones using a polynucleotide probe corresponding to SEQ ID NO:1.

Particularly, a specific polynucleotide with 30–40 nucleotides is synthesized using an Applied Biosystems DNA synthesizer according to the sequence reported. The oligonucleotide is labeled, for instance, with 32P-(-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host, as indicated above (such as XL-1 Blue (Stratagene)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17–20 nucleotides derived from both ends of the SEQ ID NO:1 (i.e., within the region of SEQ ID NO:1 bounded by the 5' NT and the 3' NT of the clone defined in Table I) are synthesized and used to amplify the desired cDNA using the deposited cDNA plasmid as a template. The polymerase chain reaction is carried out under routine conditions, for instance, in 25 ul of reaction mixture with 0.5 ug of the above cDNA template. A convenient reaction mixture is 1.5–5 mM MgCl2, 0.01% (w/v) gelatin, 20 uM each of dATP, dCTP, dGTP, dTTP, 25 pmol of each primer and 0.25 Unit of Taq polymerase. Thirty five cycles of PCR (denaturation at 94 degree C. for 1 min; annealing at 55 degree C. for 1 min; elongation at 72 degree C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

The polynucleotide(s) of the present invention, the polynucleotide encoding the polypeptide of the present invention, or the polypeptide encoded by the deposited clone may represent partial, or incomplete versions of the complete coding region (i.e., full-length gene). Several methods are known in the art for the identification of the 5' or 3' non-coding and/or coding portions of a gene which may not be present in the deposited clone. The methods that follow are exemplary and should not be construed as limiting the scope of the invention. These methods include but are not limited to, filter probing, clone enrichment using specific probes, and protocols similar or identical to 5' and 3' "RACE" protocols that are well known in the art. For instance, a method similar to 5' RACE is available for generating the missing 5' end of a desired full-length transcript. (Fromont-Racine et al., Nucleic Acids Res. 21(7): 1683–1684 (1993)).

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full-length gene.

This above method starts with total RNA isolated from the desired source, although poly-A+ RNA can be used. The RNA preparation can then be treated with phosphatase if necessary to eliminate 5' phosphate groups on degraded or damaged RNA that may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene. Moreover, it may be advantageous to optimize the RACE protocol to increase the probability of isolating additional 5' or 3' coding or non-coding sequences. Various methods of optimizing a RACE protocol are known in the art, though a detailed description summarizing these methods can be found in B. C. Schaefer, Anal. Biochem., 227:255–273, (1995).

An alternative method for carrying out 5' or 3' RACE for the identification of coding or non-coding sequences is provided by Frohman, M. A., et al., Proc. Nat'l. Acad. Sci. USA, 85:8998–9002 (1988). Briefly, a cDNA clone missing either the 5' or 3' end can be reconstructed to include the absent base pairs extending to the translational start or stop codon, respectively. In some cases, cDNAs are missing the start of translation, therefor. The following briefly describes a modification of this original 5' RACE procedure. Poly A+ or total RNAs reverse transcribed with Superscript II (Gibco/BRL) and an antisense or I complementary primer specific to the cDNA sequence. The primer is removed from the reaction with a Microcon Concentrator (Amicon). The first-strand cDNA is then tailed with dATP and terminal deoxynucleotide transferase (Gibco/BRL). Thus, an anchor sequence is produced which is needed for PCR amplification. The second strand is synthesized from the dA-tail in PCR buffer, Taq DNA polymerase (Perkin-Elmer Cetus), an oligo-dT primer containing three adjacent restriction sites (XhoIJ SaiI and ClaI) at the 5' end and a primer containing just these restriction sites. This double-stranded cDNA is PCR amplified for 40 cycles with the same primers as well as a nested cDNA-specific antisense primer. The PCR products are size-separated on an ethidium bromide-agarose gel and the region of gel containing cDNA products the predicted size of missing protein-coding DNA is removed. cDNA is purified from the agarose with the Magic PCR Prep kit (Promega), restriction digested with XhoI or SalI, and ligated to a plasmid such as pBluescript SKII (Stratagene) at XhoI and EcoRV sites. This DNA is transformed into bacteria and the plasmid clones sequenced to identify the correct protein-coding inserts. Correct 5' ends are confirmed by comparing this sequence with the putatively identified homologue and overlap with the partial cDNA clone. Similar methods known in the art and/or commercial kits are used to amplify and recover 3' ends.

Several quality-controlled kits are commercially available for purchase. Similar reagents and methods to those above are supplied in kit form from Gibco/BRL for both 5' and 3' RACE for recovery of full length genes. A second kit is available from Clontech which is a modification of a related technique, SLIC (single-stranded ligation to single-stranded cDNA), developed by Dumas et al., Nucleic Acids Res., 19:5227–32(1991). The major differences in procedure are that the RNA is alkaline hydrolyzed after reverse transcription and RNA ligase is used to join a restriction site-containing anchor primer to the first-strand cDNA. This obviates the necessity for the dA-tailing reaction which results in a polyT stretch that is difficult to sequence past.

An alternative to generating 5' or 3' cDNA from RNA is to use cDNA library double-stranded DNA. An asymmetric PCR-amplified antisense cDNA strand is synthesized with an antisense cDNA-specific primer and a plasmid-anchored primer. These primers are removed and a symmetric PCR reaction is performed with a nested cDNA-specific antisense primer and the plasmid-anchored primer.

RNA Ligase Protocol for Generating the 5' or 3' End Sequences to Obtain full Length Genes Once a gene of interest is identified, several methods are available for the identification of the 5' or 3' portions of the gene which may not be present in the original cDNA plasmid. These methods include, but are not limited to, filter probing, clone enrichment using specific probes and protocols similar and identical to 5' and 3'RACE. While the full-length gene may be present in the library and can be identified by probing, a useful method for generating the 5' or 3' end is to use the existing sequence information from the original cDNA to generate the missing information. A method similar to 5'RACE is available for generating the missing 5' end of a desired full-length gene. (This method was published by Fromont-Racine et al., Nucleic Acids Res., 21(7): 1683–1684 (1993)). Briefly, a specific RNA oligonucleotide is ligated to the 5' ends of a population of RNA presumably 30 containing full-length gene RNA transcript and a primer set containing a primer specific to the ligated RNA oligonucleotide and a primer specific to a known sequence of the gene of interest, is used to PCR amplify the 5' portion of the desired full length gene which may then be sequenced and used to generate the full length gene. This method starts with total RNA isolated from the desired source, poly A RNA may be used but is not a prerequisite for this procedure. The RNA preparation may then be treated with phosphatase if necessary to eliminate 5' phosphate groups on degraded or damaged RNA which may interfere with the later RNA ligase step. The phosphatase if used is then inactivated and the RNA is treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase. This modified RNA preparation can then be used as a template for first strand cDNA synthesis using a gene specific oligonucleotide. The first strand synthesis reaction can then be used as a template for PCR amplification of the desired 5' end using a primer specific to the ligated RNA oligonucleotide and a primer specific to the known sequence of the apoptosis related of interest. The resultant product is then sequenced and analyzed to confirm that the 5' end sequence belongs to the relevant apoptosis related.

Example 14

Bacterial Expression of a Polypeptide

A polynucleotide encoding a polypeptide of the present invention is amplified using PCR oligonucleotide primers corresponding to the 5' and 3' ends of the DNA sequence, as outlined in Example 13, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance (Ampr), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the E. coli strain M15/rep4 (Qiagen, Inc.) which contains multiple copies of the plasmid pREP4, that expresses the lacI repressor and also confers kanamycin resistance (Kanr). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/mil) and Kan (25 ug/ml). The O/N culture is used to inoculate a large culture at a ratio of 1:100 to 1:250. The cells are grown to an optical density 600 (O.D.600) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000× g). The cell pellet is solubilized in the chaotropic agent 6 Molar Guanidine HCl by stirring for 3–4 hours at 4 degree C. The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 nM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM imidazole. Imidazole is removed by a final dialyzing step against PBS or 50 mM sodium acetate pH 6 buffer plus 200 mM NaCl. The purified protein is stored at 4 degree C. or frozen at −80 degree C.

Example 15

Purification of a Polypeptide from an Inclusion Body

The following alternative method can be used to purify a polypeptide expressed in E coli when it is present in the form of inclusion bodies. Unless otherwise specified, all of the following steps are conducted at 4–10 degree C.

Upon completion of the production phase of the E. coli fermentation, the cell culture is cooled to 4–10 degree C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfluidics, Corp. or APV Gaulin, Inc.) twice at 4000–6000 psi. The homogenate is then mixed with NaCl solution to a final concentration of 0.5 M NaCl, followed by centrifugation at 7000× g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000× g centrifugation for 15 min., the pellet is discarded and the polypeptide containing supernatant is incubated at 4 degree C. overnight to allow further GuHCl extraction.

Following high speed centrifugation (30,000× g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4 degree C. without mixing for 12 hours prior to further purification steps.

To clarify the refolded polypeptide solution, a previously prepared tangential filtration unit equipped with 0.16 um membrane filter with appropriate surface area (e.g., Filtron), equilibrated with 40 mM sodium acetate, pH 6.0 is employed. The filtered sample is loaded onto a cation exchange resin (e.g., Poros HS-50, Perceptive Biosystems). The column is washed with 40 mM sodium acetate, pH 6.0 and eluted with 250 mM, 500 mM, 1000 mM, and 1500 nM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perceptive Biosystems) and weak anion (Poros CM-20, Perceptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant A280 monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Coomassie blue stained 16% SDS-PAGE gel when 5 ug of purified protein is loaded. The purified protein can also be tested for endotoxin/LPS contamination, and typically the LPS content is less than 0.1 ng/ml according to LAL assays.

Example 16

Cloning and Expression of a Polypeptide in a Baculovirus Expression System

In this example, the plasmid shuttle vector pAc373 is used to insert a polynucleotide into a baculovirus to express a polypeptide. A typical baculovirus expression vector contains the strong polyhedrin promoter of the *Autographa californica* nuclear polyhedrosis virus (AcMNPV) followed by convenient restriction sites, which may include, for example BamHI, Xba I and Asp718. The polyadenylation site of the simian virus 40 ("SV40") is often used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (1989).

A polynucleotide encoding a polypeptide of the present invention is amplified using PCR oligonucleotide primers corresponding to the 5' and 3' ends of the DNA sequence, as outlined in Example 13, to synthesize insertion fragments. The primers used to amplify the cDNA insert should preferably contain restriction sites at the 5' end of the primers in order to clone the amplified product into the expression vector. Specifically, the cDNA sequence contained in the deposited clone, including the AUG initiation codon and the naturally associated leader sequence identified elsewhere herein (if applicable), is amplified using the PCR protocol described in Example 13. If the naturally occurring signal sequence is used to produce the protein, the vector used does not need a second signal peptide. Alternatively, the vector can be modified to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five ug of a plasmid containing the polynucleotide is co-transformed with 1.0 ug of a commercially available linearized baculovirus DNA ("BaculoGoldtm baculovirus DNA", Pharmingen, San Diego, Calif.), using the lipofection method described by Felgner et al., Proc. Natl. Acad. Sci. USA 84:7413–7417 (1987). One ug of BaculoGoldtm virus DNA and 5 ug of the plasmid are mixed in a sterile well of a microtiter plate containing 50 ul of serum-free Grace's medium (Life Technologies Inc., Gaithersburg, Md.). Afterwards, 10 ul Lipofectin plus 90 ul Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27 degrees C. The transfection solution is then removed from the plate and 1 ml of Grace's insect medium supplemented with 10% fetal calf serum is added. Cultivation is then continued at 27 degrees C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4 degree C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 uCi of 35S-methionine and 5 uCi 35S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 17

Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2dhfr (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The co-transformation with a selectable marker such as dhfr, gpt, neomycin, hygromycin allows the identification and isolation of the transformed cells.

The transformed gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem. . . . 253:1357–1370 (1978); Hamlin, J. L. and Ma, C., Biochem. et Biophys. Acta, 1097:107–143 (1990); Page, M. J. and Sydenham, M. A., Biotechnology 9:64–68 (1991).) Another useful selection marker is the enzyme glutamine synthase (GS) (Murphy et al., Biochem J. 227:277–279 (1991); Bebbington et al., Bio/Technology 10:169–175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

A polynucleotide of the present invention is amplified according to the protocol outlined in herein. If the naturally occurring signal sequence is used to produce the protein, the vector does not need a second signal peptide. Alternatively, if the naturally occurring signal sequence is not used, the vector can be modified to include a heterologous signal sequence. (See, e.g., WO 96/34891.) The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. E. coli HB101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transformation. Five µg of an expression plasmid is cotransformed with 0.5 ug of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 uM, 2 uM, 5 uM, 10 mM, 20 mM). The same procedure is repeated until clones are obtained which grow at a concentration of 100–200 uM.

Expression of the desired gene product is analyzed, for instance, by SDS-PAGE and Western blot or by reversed phase HPLC analysis.

Example 18

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example described herein; see also EP A 394,827; Traunecker, et al., Nature 331:84–86 (1988).) Similarly, fusion to IgG-1, IgG-3, and albumin increases the half-life time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector. Note that the polynucleotide is cloned without a stop codon, otherwise a fusion protein will not be produced.

The naturally occurring signal sequence may be used to produce the protein (if applicable). Alternatively, if the naturally occurring signal sequence is not used, the vector can be modified to include a heterologous signal sequence. (See, e.g., WO 96/34891 and/or U.S. Pat. No. 6,066,781, supra.)

```
Human IgG Fc region:                    (SEQ ID NO:48)
GGGATCCGGAGCCCAAATCTTCTGACAAAACTCACACATGCCCACCG

TGCCCAGCACCTGAATTCGAGGGTGCACCGTCAGTCTTCCTCTTCCCCCC

AAAACCCAAGGACACCCTCATGATCTCCCGGACTCCTGAGGTCACATGCG

TGGTGGTGGACGTAAGCCACGAAGACCCTGAGGTCAAGTTCAACTGGTAC

GTGGACGGCGTGGAGGTGCATAATGCCAAGACAAAGCCGCGGGAGGAGC

AGTACAACAGCACGTACCGTGTGGTCAGCGTCCTCACCGTCCTGCACCAG

GACTGGCTGAATGGCAAGGAGTACAAGTGCAAGGTCTCCAACAAAGCCCT

CCCAACCCCCATCGAGAAAACCATCTCCAAAGCCAAAGGGCAGCCCCGA

GAACCACAGGTGTACACCCTGCCCCCATCCCGGGATGAGCTGACCAAGAA

CCAGGTCAGCCTGACCTGCCTGGTCAAAGGCTTCTATCCAAGCGACATCG

CCGTGGAGTGGGAGAGCAATGGGCAGCCGGAGAACAACTACAAGACCAC

GCCTCCCGTGCTGGACTCCGACGGCTCCTTCTTCCTCTACAGCAAGCTCA

CCGTGGACAAGAGCAGGTGGCAGCAGGGGAACGTCTTCTCATGCTCCGTG

ATGCATGAGGCTCTGCACAACCACTACACGCAGAAGAGCCTCTCCCTGTC

TCCGGGTAAATGAGTGCGACGGCCGCGACTCTAGAGGAT
```

Example 19

Method of Creating N- and C-terminal Deletion Mutants Corresponding to the CAN-12, CAN-12v1, and CAN-12v2 Polypeptides of the Present Invention As described elsewhere herein, the present invention encompasses the creation of N- and C-terminal deletion mutants, in addition to any combination of N- and C-terminal deletions thereof, corresponding to the CAN-12, CAN-12v1, and CAN-12v2 polypeptides of the present invention. A number of methods are available to one skilled in the art for creating such mutants. Such methods may include a combination of PCR amplification and gene cloning methodology. Although one of skill in the art of molecular biology, through the use of the teachings provided or referenced herein, and/or otherwise known in the art as standard methods, could readily create each deletion mutant of the present invention, exemplary methods are described below.

Briefly, using the isolated cDNA clone encoding the full-length CAN-12, CAN-12v1, or CAN-12v2 polypeptide sequence (as described in Example 13, for example), appropriate primers of about 15–25 nucleotides derived from the desired 5' and 3' positions of SEQ ID NO:1, 53, or 55 may be designed to PCR amplify, and subsequently clone, the intended N- and/or C-terminal deletion mutant. Such primers could comprise, for example, an inititation and stop codon for the 5' and 3' primer, respectively. Such primers may also comprise restriction sites to facilitate cloning of the deletion mutant post amplification. Moreover, the primers may comprise additional sequences, such as, for example, flag-tag sequences, kozac sequences, or other sequences discussed and/or referenced herein.

For example, in the case of the P23 to L581 CAN-12 N-terminal deletion mutant, the following primers could be used to amplify a cDNA fragment corresponding to this deletion mutant:

```
5' Primer 5'-GCAGCA GCGGCCGC CCACAGCAACCCCAACAGGACTTTG-3'   (SEQ ID NO:49)
                   NotI NotI 3' Primer 5'-GCAGCA GTCGAC TAACAAGGTGGTGTTGAAGATTAAA-3'    (SEQ ID NO:50)
                   SalI SalI
```

For example, in the case of the M1 to L423 CAN-12 C-terminal deletion mutant, the following primers could be used to amplify a cDNA fragment corresponding to this deletion mutant:

```
5' Primer 5'-GCAGCA GCGGCCGC ATGTCTCTGTGGCCACCTTTCCG-3'    (SEQ ID NO:51)
                   NotI NotI 3' Primer 5'-GCAGCA GTCGAC GAGGTAGAAGCCAATGGCGAGGAG-3'     (SEQ ID NO:52)
                   SalI SalI
```

For example, in the case of the R90 to L694 CAN-12v1 N-terminal deletion mutant, the following primers could be used to amplify a cDNA fragment corresponding to this deletion mutant:

```
5' Primer 5'-GCAGCA GCGGCCGC AGGCTGGATCTGTGCCAGGGGATAG-3'  (SEQ ID NO:94)
                   NotI NotI 3' Primer 5'-GCAGCA GTCGAC TAACAAGGTGGTGTTGAAG-3'          (SEQ ID NO:95)
                   SalI SalI
```

For example, in the case of the M1 to G561 CAN-12v1 C-terminal deletion mutant, the following primers could be used to amplify a cDNA fragment corresponding to this deletion mutant:

```
5' Primer 5'-GCAGCA GCGGCCGC ATGTCTCTGTGGCCACCTTTCCG-3'    (SEQ ID NO:96)
                   NotI NotI 3' Primer 5'- GCAGCA GTCGAC CCCCTGGCAGGCTTCCAGGCTAAAG-3'   (SEQ ID NO:97)
                    SalI SalI
```

For example, in the case of the R90 to L697 CAN-12v2 N-terminal deletion mutant, the following primers could be used to amplify a cDNA fragment corresponding to this deletion mutant:

```
5' Primer 5'-GCAGCA GCGGCCGC AGGCTGGATCTGTGCCAGGGGATAG-3'   (SEQ ID NO:98)
                   NotINotI 3' Primer 5'-GCAGCA GTCGAC TAACAAGGTGGTGTTGAAG-3'           (SEQ ID NO:99)
                   SalISalI
```

For example, in the case of the M1 to G564 CAN-12v2 C-terminal deletion mutant, the following primers could be used to amplify a cDNA fragment corresponding to this deletion mutant:

```
5' Primer 5'-GCAGCA GCGGCCGC ATGTCTCTGTGGCCACCTTTCCG-3'     (SEQ ID NO:100)
                   NotINotI 3' Primer 5'-GCAGCA GTCGAC CCCCTGGCAGGCTTCCAGGCTAAAG-3'     (SEQ ID NO:101)
                   SalISalI
```

Representative PCR amplification conditions are provided below, although the skilled artisan would appreciate that other conditions may be required for efficient amplification. A 100 ul PCR reaction mixture may be prepared using long of the template DNA (cDNA clone of CAN-12), 200 uM 4dNTPs, 1 uM primers, 0.25U Taq DNA polymerase (PE), and standard Taq DNA polymerase buffer. Typical PCR cycling condition are as follows:

| 20–25 cycles: | 45 sec, 93 degrees |
|---|---|
|  | 2 min, 50 degrees |
|  | 2 min, 72 degrees |
| 1 cycle: | 10 min, 72 degrees |

After the final extension step of PCR, 5U Klenow Fragment may be added and incubated for 15 min at 30 degrees.

Upon digestion of the fragment with the NotI and SalI restriction enzymes, the fragment could be cloned into an appropriate expression and/or cloning vector which has been similarly digested (e.g., pSport1, among others). The skilled artisan would appreciate that other plasmids could be equally substituted, and may be desirable in certain circumstances. The digested fragment and vector are then ligated using a DNA ligase, and then used to transform competent E.coli cells using methods provided herein and/or otherwise known in the art.

The 5' primer sequence for amplifying any additional N-terminal deletion mutants may be determined by reference to the following formula:

(S+(X*3)) to ((S+(X*3))+25), wherein 'S' is equal to the nucleotide position of the initiating start codon of the CAN-12, CAN-12v1, or CAN12-v2 gene (SEQ ID NO:1, 53, or 55), and 'X' is equal to the most N-terminal amino acid of the intended N-terminal deletion mutant. The first term will provide the start 5' nucleotide position of the 5' primer, while the second term will provide the end 3' nucleotide position of the 5' primer corresponding to sense strand of SEQ ID NO:1, 53, or 55. Once the corresponding nucleotide positions of the primer are determined, the final nucleotide sequence may be created by the addition of applicable restriction site sequences to the 5' end of the sequence, for example. As referenced herein, the addition of other sequences to the 5' primer may be desired in certain circumstances (e.g., kozac sequences, etc.).

The 3' primer sequence for amplifying any additional N-terminal deletion mutants may be determined by reference to the following formula:

(S+(X*3)) to ((S+(X*3))−25), wherein 'S' is equal to the nucleotide position of the initiating start codon of the CAN-12, CAN-12v1, or CAN12-v2 gene (SEQ ID NO:1, 53, or 55), and 'X' is equal to the most C-terminal amino acid of the intended N-terminal deletion mutant. The first term will provide the start 5' nucleotide position of the 3' primer, while the second term will provide the end 3' nucleotide position of the 3' primer corresponding to the anti-sense strand of SEQ ID NO:1, 53, or 55. Once the corresponding nucleotide positions of the primer are determined, the final nucleotide sequence may be created by the addition of applicable restriction site sequences to the 5' end of the sequence, for example. As referenced herein, the addition of other sequences to the 3' primer may be desired in certain circumstances (e.g., stop codon sequences, etc.). The skilled artisan would appreciate that modifications of the above nucleotide positions may be necessary for optimizing PCR amplification.

The same general formulas provided above may be used in identifying the 5' and 3' primer sequences for amplifying any C-terminal deletion mutant of the present invention. Moreover, the same general formulas provided above may be used in identifying the 5' and 3' primer sequences for amplifying any combination of N-terminal and C-terminal deletion mutant of the present invention. The skilled artisan would appreciate that modifications of the above nucleotide positions may be necessary for optimizing PCR amplification.

Example 20

Site Directed/Site-Specific Mutagenesis

In vitro site-directed mutagenesis is an invaluable technique for studying protein structure-function relationships and gene expression, for example, as well as for vector modification. Site-directed mutagenesis can also be used for creating any of one or more of the mutants of the present invention, particularly the conservative and/or non-conservative amino acid substitution mutants of the prsent invention. Approaches utilizing single stranded DNA (ssDNA) as the template have been reported (e.g., T. A. Kunkel et al., 1985, *Proc. Natl. Acad. Sci. USA*), 82:488–492; M. A. Vandeyar et al., 1988, *Gene*, 65(1):129–133; M. Sugimoto et al., 1989, *Anal. Biochem.*, 179(2):309–311; and J. W. Taylor et al., 1985, *Nuc. Acids. Res.*, 13(24):8765–8785).

The use of PCR in site-directed mutagenesis accomplishes strand separation by using a denaturing step to separate the complementary strands and to allow efficient polymerization of the PCR primers. PCR site-directed mutagenesis methods thus permit site specific mutations to be incorporated in virtually any double stranded plasmid, thus eliminating the need for re-subcloning into M13-based bacteriophage vectors or single-stranded rescue. (M. P. Weiner et al., 1995, *Molecular Biology: Current Innovations and Future Trends*, Eds. A. M. Griffin and H. G. Griffin, Horizon Scientific Press, Norfolk, UK; and C. Papworth et al., 1996, *Strategies*, 9(3):3–4).

A protocol for performing site-directed mutagenesis, particularly employing the QuikChange™ site-directed mutagenesis kit (Stratagene, La Jolla, Calif.; U.S. Pat. Nos. 5,789,166 and 5,923,419) is provided for making point mutations, to switch or substitute amino acids, and to delete or insert single or multiple amino acids in the RATL1d6 amino acid sequence of this invention.

Primer Design

For primer design using this protocol, the mutagenic oligonucleotide primers are designed individually according to the desired mutation. The following considerations should be made for designing mutagenic primers: 1) Both of the mutagenic primers must contain the desired mutation and anneal to the same sequence on opposite strands of the plasmid; 2) Primers should be between 25 and 45 bases in length, and the melting temperature ($T_m$) of the primers should be greater than, or equal to, 78° C. The following formula is commonly used for estimating the Tm of primers: T=81.5+0.41 (%GC)–675/N-% mismatch. For calculating $T_m$, N is the primer length in bases; and values for % GC and % mismatch are whole numbers. For calculating $T_m$ for primers intended to introduce insertions or deletions, a modified version of the above formula is employed: T=81.5+0.41 (%GC)–675/N, where N does not include the bases which are being inserted or deleted; 3) The desired mutation (deletion or insertion) should be in the middle of the primer with approximately 10–15 bases of correct sequence on both sides; 4) The primers optimally should have a minimum GC content of 40%, and should terminate in one or more C or G bases; 5) Primers need not be 5'-phosphorylated, but must be purified either by fast polynucleotide liquid chromatography (FPLC) or by polyacrylamide gel electrophoresis (PAGE). Failure to purify the primers results in a significant decrease in mutation efficiency; and 6). It is important that primer concentration is in excess. It is suggested to vary the amount of template while keeping the concentration of the primers constantly in excess (QuikChange™ Site-Directed Mutagenesis Kit, Stratagene, La Jolla, Calif.).

Protocol for Setting Up the Reactions

Using the above-described primer design, two complimentary oligonucleotides containing the desired mutation, flanked by unmodified nucleic acid sequence, are synthesized. The resulting oligonucleotide primers are purified.

A control reaction is prepared using 5 µl 10× reaction buffer (100 mM KCl; 100 mM (NH$_4$)$_2$SO$_4$; 200 mM Tris-HCl, pH 8.8; 20 mM MgSO$_4$; 1% Triton® X-100; 1 mg/ml nuclease-free bovine serum albumin, BSA); 2 µl (10 ng) of pWhitescript™, 4.5-kb control plasmid (5 ng/µl); 1.25 µl (125 ng) of oligonucleotide control primer #1 (34-mer, 100 ng/µl); 1.25 µl (125 ng) of oligonucleotide control primer #2 (34-mer, 100 ng/µl); 1 µl of dNTP mix; double distilled H$_2$O; to a final volume of 50 µl. Thereafter, 1 µl of DNA polymerase (PfuTurbo® DNA Polymerase, Stratagene), (2.5U/µl) is added. PfuTurbo® DNA Polymerase is stated to have 6-fold higher fidelity in DNA synthesis than does Taq polymerase. To maximize temperature cycling performance, use of thin-walled test tubes is suggested to ensure optimum contact with the heating blocks of the temperature cycler.

The sample reaction is prepared by combining 5 µl of 10× reaction buffer; x µl (5–50 ng) of dsDNA template; x µl (125 ng) of oligonucleotide primer #1; x µl (5–50 ng) of dsDNA template; x µl (125 ng) of oligonucleotide primer #2; 1 µl of dNTP mix; and ddH$_2$O to a final volume of 50 µl. Thereafter, 1 µl of DNA polymerase (PfuTurbo DNA Polymerase, Stratagene), (2.5U/µl) is added.

It is suggested that if the thermal cycler does not have a hot-top assembly, each reaction should be overlaid with approximately 30 µl of mineral oil.

Cycling the Reactions

Each reaction is cycled using the following cycling parameters:

| Segment | Cycles | Temperature | Time |
| --- | --- | --- | --- |
| 1 | 1 | 95° C. | 30 seconds |
| 2 | 12–18 | 95° C. | 30 seconds |
|  |  | 55° C. | 1 minute |
|  |  | 68° C. | 2 minutes/kb of plasmid length |

For the control reaction, a 12-minute extension time is used and the reaction is run for 12 cycles. Segment 2 of the above cycling parameters is adjusted in accordance with the type of mutation desired. For example, for point mutations, 12 cycles are used; for single amino acid changes, 16 cycles are used; and for multiple amino acid deletions or insertions, 18 cycles are used. Following the temperature cycling, the reaction is placed on ice for 2 minutes to cool the reaction to <37° C.

Digesting the Products and Transforming Competent Cells

One µl of the DpnI restriction enzyme (10U/µl) is added directly (below mineral oil overlay) to each amplification reaction using a small, pointed pipette tip. The reaction mixture is gently and thoroughly mixed by pipetting the solution up and down several times. The reaction mixture is then centrifuged for 1 minute in a microcentrifuge. Immediately thereafter, each reaction is incubated at 37° C. for 1 hour to digest the parental (i.e., the non-mutated) supercoiled dsDNA.

Competent cells (i.e., XL1-Blue supercompetent cells, Stratagene) are thawed gently on ice. For each control and sample reaction to be transformed, 50 µl of the supercompetent cells are aliquotted to a prechilled test tube (Falcon 2059 polypropylene). Next, 1 µl of the DpnI-digested DNA is transferred from the control and the sample reactions to separate aliquots of the supercompetent cells. The transformation reactions are gently swirled to mix and incubated for 30 minutes on ice. Thereafter, the transformation reactions are heat-pulsed for 45 seconds at 42° C. for 2 minutes.

0.5 ml of NZY+ broth, preheated to 42° C. is added to the transformation reactions which are then incubated at 37° C.

for 1 hour with shaking at 225–250 rpm. An aliquot of each transformation reaction is plated on agar plates containing the appropriate antibiotic for the vector. For the mutagenesis and transformation controls, cells are spread on LB-ampicillin agar plates containing 80 µg/ml of X-gal and 20 mM MIPTG. Transformation plates are incubated for >16 hours at 37° C.

Example 21

Regulation of Protein Expression Via Controlled Aggregation in the Endoplasmic Reticulum As described more particularly herein, proteins regulate diverse cellular processes in higher organisms, ranging from rapid metabolic changes to growth and differentiation. Increased production of specific proteins could be used to prevent certain diseases and/or disease states. Thus, the ability to modulate the expression of specific proteins in an organism would provide significant benefits.

Numerous methods have been developed to date for introducing foreign genes, either under the control of an inducible, constitutively active, or endogenous promoter, into organisms. Of particular interest are the inducible promoters (see, M. Gossen, et al., Proc. Natl. Acad. Sci. USA., 89:5547 (1992); Y. Wang, et al., Proc. Natl. Acad. Sci. USA, 91:8180 (1994), D. No., et al., Proc. Natl. Acad. Sci. USA, 93:3346 (1996); and V. M. Rivera, et al., Nature Med, 2:1028 (1996); in addition to additional examples disclosed elsewhere herein). In one example, the gene for erthropoietin (Epo) was transferred into mice and primates under the control of a small molecule inducer for expression (e.g., tetracycline or rapamycin) (see, D. Bohl, et al., Blood, 92:1512, (1998); K. G. Rendahl, et al., Nat.,Biotech, 16:757, (1998); V. M. Rivera, et al., Proc. Natl. Acad. Sci. USA, 96:8657 (1999); and X. Ye et al., Science, 283:88 (1999). Although such systems enable efficient induction of the gene of interest in the organism upon addition of the inducing agent (i.e., tetracycline, rapamycin, etc,.), the levels of expression tend to peak at 24 hours and trail off to background levels after 4 to 14 days. Thus, controlled transient expression is virtually impossible using these systems, though such control would be desirable.

A new alternative method of controlling gene expression levels of a protein from a transgene (i.e., includes stable and transient transformants) has recently been elucidated (V. M. Rivera., et al., Science, 287:826–830, (2000)). This method does not control gene expression at the level of the mRNA like the aforementioned systems. Rather, the system controls the level of protein in an active secreted form. In the absence of the inducing agent, the protein aggregates in the ER and is not secreted. However, addition of the inducing agent results in dis-aggregation of the protein and the subsequent secretion from the ER. Such a system affords low basal secretion, rapid, high level secretion in the presence of the inducing agent, and rapid cessation of secretion upon removal of the inducing agent. In fact, protein secretion reached a maximum level within 30 minutes of induction, and a rapid cessation of secretion within 1 hour of removing the inducing agent. The method is also applicable for controlling the level of production for membrane proteins.

Detailed methods are presented in V. M. Rivera., et al., Science, 287:826–830, (2000)), briefly:

Fusion protein constructs are created using polynucleotide sequences of the present invention with one or more copies (preferably at least 2, 3, 4, or more) of a conditional aggregation domain (CAD) a domain that interacts with itself in a ligand-reversible manner (i.e., in the presence of an inducing agent) using molecular biology methods known in the art and discussed elsewhere herein. The CAD domain may be the mutant domain isolated from the human FKBP12 (Phe$^{36}$ to Met) protein (as disclosed in V. M. Rivera., et al., Science, 287:826–830, (2000), or alternatively other proteins having domains with similar ligand-reversible, self-aggregation properties. As a principle of design the fusion protein vector would contain a furin cleavage sequence operably linked between the polynucleotides of the present invention and the CAD domains. Such a cleavage site would enable the proteolytic cleavage of the CAD domains from the polypeptide of the present invention subsequent to secretion from the ER and upon entry into the trans-Golgi (J. B. Denault, et al., FEBS Lett., 379:113, (1996)). Alternatively, the skilled artisan would recognize that any proteolytic cleavage sequence could be substituted for the furin sequence provided the substituted sequence is cleavable either endogenously (e.g., the furin sequence) or exogenously (e.g., post secretion, post purification, post production, etc.). The preferred sequence of each feature of the fusion protein construct, from the 5' to 3' direction with each feature being operably linked to the other, would be a promoter, signal sequence, "X" number of (CAD)x domains, the furin sequence (or other proteolytic sequence), and the coding sequence of the polypeptide of the present invention. The artisan would appreciate that the promotor and signal sequence, independent from the other, could be either the endogenous promotor or signal sequence of a polypeptide of the present invention, or alternatively, could be a heterologous signal sequence and promotor.

The specific methods described herein for controlling protein secretion levels through controlled ER aggregation are not meant to be limiting are would be generally applicable to any of the polynucleotides and polypeptides of the present invention, including variants, homologues, orthologs, and fragments therein.

Example 22

Alteration of Protein Glycosylation Sites to Enhance Characteristics of Polypeptides of the Invention Many eukaryotic cell surface and proteins are post-translationally processed to incorporate N-linked and O-linked carbohydrates (Kornfeld and Kornfeld (1985) Annu. Rev. Biochem. 54:631–64; Rademacher et al., (1988) Annu. Rev. Biochem. 57:785–838). Protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion (Fieldler and Simons (1995) Cell, 81:309–312; Helenius (1994) Mol. Biol. Of the Cell 5:253–265; Olden et al., (1978) Cell, 13:461–473; Caton et al., (1982) Cell, 37:417–427; Alexamnder and Elder (1984), Science, 226:1328–1330; and Flack et al., (1994), J. Biol. Chem., 269:14015–14020). In higher organisms, the nature and extent of glycosylation can markedly affect the circulating half-life and bio-availability of proteins by mechanisms involving receptor mediated uptake and clearance (Ashwell and Morrell, (1974), Adv. Enzymol., 41:99–128; Ashwell and Harford (1982), Ann. Rev. Biochem., 51:531–54). Receptor systems have been identified that are thought to play a major role in the clearance of serum proteins through recognition of various carbohydrate structures on the glycoproteins (Stockert (1995), Physiol. Rev., 75:591–609; Kery et al., (1992), Arch. Biochem. Biophys., 298:49–55). Thus, production strategies resulting in incomplete attachment of terminal sialic acid residues might provide a means of shortening the bioavailability and half-life of glycoproteins. Conversely, expression strategies resulting in saturation of terminal sialic acid attachment sites might lengthen protein bioavailability and half-life.

In the development of recombinant glycoproteins for use as pharmaceutical products, for example, it has been speculated that the pharmacodynamics of recombinant proteins can be modulated by the addition or deletion of glycosylation sites from a glycoproteins primary structure (Berman and Lasky (1985a) Trends in Biotechnol., 3:51–53). However, studies have reported that the deletion of N-linked glycosylation sites often impairs intracellular transport and results in the intracellular accumulation of glycosylation site variants (Machamer and Rose (1988), J. Biol Chem., 263: 5955–5960; Gallagher et al., (1992), J. Virology., 66:7136–7145; Collier et al., (1993), Biochem., 32:7818–7823; Claffey et al., (1995) Biochemica et Biophysica Acta, 1246:1–9; Dube et al., (1988), J. Biol. Chem. 263:17516–17521). While glycosylation site variants of proteins can be expressed intracellularly, it has proved difficult to recover useful quantities from growth conditioned cell culture medium.

Moreover, it is unclear to what extent a glycosylation site in one species will be recognized by another species glycosylation machinery. Due to the importance of glycosylation in protein metabolism, particularly the secretion and/or expression of the protein, whether a glycosylation signal is recognized may profoundly determine a proteins ability to be expressed, either endogenously or recombinately, in another organism (i.e., expressing a human protein in E.coli, yeast, or viral organisms; or an E.coli, yeast, or viral protein in human, etc.). Thus, it may be desirable to add, delete, or modify a glycosylation site, and possibly add a glycosylation site of one species to a protein of another species to improve the proteins functional, bioprocess purification, and/or structural characteristics (e.g., a polypeptide of the present invention).

A number of methods may be employed to identify the location of glycosylation sites within a protein. One preferred method is to run the translated protein sequence through the PROSITE computer program (Swiss Institute of Bioinformatics). Once identified, the sites could be systematically deleted, or impaired, at the level of the DNA using mutagenesis methodology known in the art and available to the skilled artisan, Preferably using PCR-directed mutagenesis (See Maniatis, Molecular Cloning: A Laboratory Manual, Cold Spring Harbor Press, Cold Spring, N.Y. (1982)). Similarly, glycosylation sites could be added, or modified at the level of the DNA using similar methods, preferably PCR methods (See, Maniatis, supra). The results of modifying the glycosylation sites for a particular protein (e.g., solubility, secretion potential, activity, aggregation, proteolytic resistance, etc.) could then be analyzed using methods know in the art.

The skilled artisan would acknowledge the existence of other computer algorithms capable of predicting the location of glycosylation sites within a protein. For example, the Motif computer program (Genetics Computer Group suite of programs) provides this function, as well.

Example 23

Method of Enhancing the Biological Activity/Functional Characteristics of Invention through Molecular Evolution Although many of the most biologically active proteins known are highly effective for their specified function in an organism, they often possess characteristics that make them undesirable for transgenic, therapeutic, and/or industrial applications. Among these traits, a short physiological half-life is the most prominent problem, and is present either at the level of the protein, or the level of the proteins mRNA. The ability to extend the half-life, for example, would be particularly important for a proteins use in gene therapy, transgenic animal production, the bioprocess production and purification of the protein, and use of the protein as a chemical modulator among others. Therefore, there is a need to identify novel variants of isolated proteins possessing characteristics which enhance their application as a therapeutic for treating diseases of animal origin, in addition to the proteins applicability to common industrial and pharmaceutical applications.

Thus, one aspect of the present invention relates to the ability to enhance specific characteristics of invention through directed molecular evolution. Such an enhancement may, in a non-limiting example, benefit the inventions utility as an essential component in a kit, the inventions physical attributes such as its solubility, structure, or codon optimization, the inventions specific biological activity, including any associated enzymatic activity, the proteins enzyme kinetics, the proteins Ki, Kcat, Km, Vmax, Kd, protein-protein activity, protein-DNA binding activity, antagonist/inhibitory activity (including direct or indirect interaction), agonist activity (including direct or indirect interaction), the proteins antigenicity (e.g., where it would be desirable to either increase or decrease the antigenic potential of the protein), the immunogenicity of the protein, the ability of the protein to form dimers, trimers, or multimers with either itself or other proteins, the antigenic efficacy of the invention, including its subsequent use a preventative treatment for disease or disease states, or as an effector for targeting diseased genes. Moreover, the ability to enhance specific characteristics of a protein may also be applicable to changing the characterized activity of an enzyme to an activity completely unrelated to its initially characterized activity. Other desirable enhancements of the invention would be specific to each individual protein, and would thus be well known in the art and contemplated by the present invention.

For example, an engineered calpain may be constitutively active upon binding of its cognate substrate. Alternatively, an engineered calpain may be constitutively active in the absence of substrate binding, and/or may exhibit increased efficacy in inhibiting cysteine proteases. In yet another example, an engineered calpain may be capable of being activated with less than all of the regulatory factors and/or conditions typically required for calpain activation (e.g., substrate binding, phosphorylation, cofactor binding, Ca+ binding, Ca+ activation, conformational changes, etc.). Such calpain would be useful in screens to identify calpain modulators, among other uses described herein.

Directed evolution is comprised of several steps. The first step is to establish a library of variants for the gene or protein of interest. The most important step is to then select for those variants that entail the activity you wish to identify. The design of the screen is essential since your screen should be selective enough to eliminate non-useful variants, but not so stringent as to eliminate all variants. The last step is then to repeat the above steps using the best variant from the previous screen. Each successive cycle, can then be tailored as necessary, such as increasing the stringency of the screen, for example.

Over the years, there have been a number of methods developed to introduce mutations into macromolecules. Some of these methods include, random mutagenesis, "error-prone" PCR, chemical mutagenesis, site-directed mutagenesis, and other methods well known in the art (for a comprehensive listing of current mutagenesis methods, see Maniatis, Molecular Cloning: A Laboratory Manual, Cold Spring Harbor Press, Cold Spring, N.Y. (1982)). Typically, such methods have been used, for example, as tools for identifying the core functional region(s) of a protein or the function of specific domains of a protein (if a multi-domain protein). However, such methods have more recently been applied to the identification of macromolecule variants with specific or enhanced characteristics.

Random mutagenesis has been the most widely recognized method to date. Typically, this has been carried out either through the use of "error-prone" PCR (as described in Moore, J., et al, Nature Biotechnology 14:458, (1996), or through the application of randomized synthetic oligonucleotides corresponding to specific regions of interest (as described by Derbyshire, K. M. et al, Gene, 46:145–152, (1986), and Hill, D E, et al, Methods Enzymol., 55:559–568, (1987). Both approaches have limits to the level of mutagenesis that can be obtained. However, either approach enables the investigator to effectively control the rate of mutagenesis. This is particularly important considering the fact that mutations beneficial to the activity of the enzyme are fairly rare. In fact, using too high a level of mutagenesis may counter or inhibit the desired benefit of a useful mutation.

While both of the aforementioned methods are effective for creating randomized pools of macromolecule variants, a third method, termed "DNA Shuffling", or "sexual PCR" (WPC, Stemmer, PNAS, 91:10747, (1994)) has recently been elucidated. DNA shuffling has also been referred to as "directed molecular evolution", "exon-shuffling", "directed enzyme evolution", "in vitro evolution", and "artificial evolution". Such reference terms are known in the art and are encompassed by the invention. This new, preferred, method apparently overcomes the limitations of the previous methods in that it not only propagates positive traits, but simultaneously eliminates negative traits in the resulting progeny.

DNA shuffling accomplishes this task by combining the principal of in vitro recombination, along with the method of "error-prone" PCR. In effect, you begin with a randomly digested pool of small fragments of your gene, created by Dnase I digestion, and then introduce said random fragments into an "error-prone" PCR assembly reaction. During the PCR reaction, the randomly sized DNA fragments not only hybridize to their cognate strand, but also may hybridize to other DNA fragments corresponding to different regions of the polynucleotide of interest—regions not typically accessible via hybridization of the entire polynucleotide. Moreover, since the PCR assembly reaction utilizes "error-prone" PCR reaction conditions, random mutations are introduced during the DNA synthesis step of the PCR reaction for all of the fragments—further diversifying the potential hybridization sites during the annealing step of the reaction.

A variety of reaction conditions could be utilized to carry-out the DNA shuffling reaction. However, specific reaction conditions for DNA shuffling are provided, for example, in PNAS, 91:10747, (1994). Briefly:

Prepare the DNA substrate to be subjected to the DNA shuffling reaction. Preparation may be in the form of simply purifying the DNA from contaminating cellular material, chemicals, buffers, oligonucleotide primers, deoxynucleotides, RNAs, etc., and may entail the use of DNA purification kits as those provided by Qiagen, Inc., or by the Promega, Corp., for example.

Once the DNA substrate has been purified, it would be subjected to Dnase I digestion. About 2–4ug of the DNA substrate(s) would be digested with 0.0015 units of Dnase I (Sigma) per ul in 100 ul of 50 mM Tris-HCL, pH 7.4/1 mM MgCl2 for 10–20 min. at room temperature. The resulting fragments of 10–50 bp could then be purified by running them through a 2% low-melting point agarose gel by electrophoresis onto DE81 ion-exchange paper (Whatmann) or could be purified using Microcon concentrators (Amicon) of the appropriate molecular weight cutoff, or could use oligonucleotide purification columns (Qiagen), in addition to other methods known in the art. If using DE81 ion-exchange paper, the 10–50 bp fragments could be eluted from said paper using 1M NaCl, followed by ethanol precipitation.

The resulting purified fragments would then be subjected to a PCR assembly reaction by re-suspension in a PCR mixture containing: 2 mM of each dNTP, 2.2 mM MgCl2, 50 mM KCl, 10 mM Tris•HCL, pH 9.0, and 0.1% Triton X-100, at a final fragment concentration of 10–30 ng/ul. No primers are added at this point. Taq DNA polymerase (Promega) would be used at 2.5 units per 100 ul of reaction mixture. A PCR program of 94 C for 60 s; 94 C for 30 s, 50–55 C for 30 s, and 72 C for 30 s using 30–45 cycles, followed by 72 C for 5 min using an MJ Research (Cambridge, Mass.) PTC-150 thermocycler. After the assembly reaction is completed, a 1:40 dilution of the resulting primerless product would then be introduced into a PCR mixture (using the same buffer mixture used for the assembly reaction) containing 0.8 um of each primer and subjecting this mixture to 15 cycles of PCR (using 94 C for 30 s, 50 C for 30 s, and 72 C for 30 s). The referred primers would be primers corresponding to the nucleic acid sequences of the polynucleotide(s) utilized in the shuffling reaction. Said primers could consist of modified nucleic acid base pairs using methods known in the art and referred to else where herein, or could contain additional sequences (i.e., for adding restriction sites, mutating specific base-pairs, etc.).

The resulting shuffled, assembled, and amplified product can be purified using methods well known in the art (e.g., Qiagen PCR purification kits) and then subsequently cloned using appropriate restriction enzymes.

Although a number of variations of DNA shuffling have been published to date, such variations would be obvious to the skilled artisan and are encompassed by the invention. The DNA shuffling method can also be tailored to the desired level of mutagenesis using the methods described by Zhao, et al. (Nucl Acid Res., 25(6): 1307–1308, (1997).

As described above, once the randomized pool has been created, it can then be subjected to a specific screen to identify the variant possessing the desired characteristic(s). Once the variant has been identified, DNA corresponding to the variant could then be used as the DNA substrate for initiating another round of DNA shuffling. This cycle of shuffling, selecting the optimized variant of interest, and then re-shuffling, can be repeated until the ultimate variant is obtained. Examples of model screens applied to identify variants created using DNA shuffling technology may be found in the following publications: J. C., Moore, et al., J. Mol. Biol., 272:336–347, (1997), F. R., Cross, et al., Mol. Cell. Biol., 18:2923–2931, (1998), and A. Crameri., et al., Nat. Biotech., 15:436–438, (1997).

DNA shuffling has several advantages. First, it makes use of beneficial mutations. When combined with screening, DNA shuffling allows the discovery of the best mutational combinations and does not assume that the best combination contains all the mutations in a population. Secondly, recombination occurs simultaneously with point mutagenesis. An effect of forcing DNA polymerase to synthesize full-length genes from the small fragment DNA pool is a background mutagenesis rate. In combination with a stringent selection method, enzymatic activity has been evolved up to 16000 fold increase over the wild-type form of the enzyme. In essence, the background mutagenesis yielded the genetic variability on which recombination acted to enhance the activity.

A third feature of recombination is that it can be used to remove deleterious mutations. As discussed above, during the process of the randomization, for every one beneficial mutation, there may be at least one or more neutral or inhibitory mutations. Such mutations can be removed by including in the assembly reaction an excess of the wild-type random-size fragments, in addition to the random-size fragments of the selected mutant from the previous selection. During the next selection, some of the most active variants of the polynucleotide/polypeptide/enzyme, should have lost the inhibitory mutations.

Finally, recombination enables parallel processing. This represents a significant advantage since there are likely multiple characteristics that would make a protein more desirable (e.g. solubility, activity, etc.). Since it is increasingly difficult to screen for more than one desirable trait at a time, other methods of molecular evolution tend to be inhibitory. However, using recombination, it would be possible to combine the randomized fragments of the best representative variants for the various traits, and then select for multiple properties at once.

DNA shuffling can also be applied to the polynucleotides and polypeptides of the present invention to decrease their immunogenicity in a specified host. For example, a particular variant of the present invention may be created and isolated using DNA shuffling technology. Such a variant may have all of the desired characteristics, though may be highly immunogenic in a host due to its novel intrinsic structure. Specifically, the desired characteristic may cause the polypeptide to have a non-native structure which could no longer be recognized as a "self" molecule, but rather as a "foreign", and thus activate a host immune response directed against the novel variant. Such a limitation can be overcome, for example, by including a copy of the gene sequence for a xenobiotic ortholog of the native protein in with the gene sequence of the novel variant gene in one or more cycles of DNA shuffling. The molar ratio of the ortholog and novel variant DNAs could be varied accordingly. Ideally, the resulting hybrid variant identified would contain at least some of the coding sequence which enabled the xenobiotic protein to evade the host immune system, and additionally, the coding sequence of the original novel variant that provided the desired characteristics.

Likewise, the invention encompasses the application of DNA shuffling technology to the evolution of polynucleotides and polypeptides of the invention, wherein one or more cycles of DNA shuffling include, in addition to the gene template DNA, oligonucleotides coding for known allelic sequences, optimized codon sequences, known variant sequences, known polynucleotide polymorphism sequences, known ortholog sequences, known homologue sequences, additional homologous sequences, additional non-homologous sequences, sequences from another species, and any number and combination of the above.

In addition to the described methods above, there are a number of related methods that may also be applicable, or desirable in certain cases. Representative among these are the methods discussed in PCT applications WO 98/31700, and WO 98/32845, which are hereby incorporated by reference. Furthermore, related methods can also be applied to the polynucleotide sequences of the present invention in order to evolve invention for creating ideal variants for use in gene therapy, protein engineering, evolution of whole cells containing the variant, or in the evolution of entire enzyme pathways containing polynucleotides of the invention as described in PCT applications WO 98/13485, WO 98/13487, WO 98/27230, WO 98/31837, and Crameri, A., et al., Nat. Biotech., 15:436–438, (1997), respectively.

Additional methods of applying "DNA Shuffling" technology to the polynucleotides and polypeptides of the present invention, including their proposed applications, may be found in U.S. Pat. No. 5,605,793; PCT Application No. WO 95/22625; PCT Application No. WO 97/20078; PCT Application No. WO 97/35966; and PCT Application No. WO 98/42832; PCT Application No. WO 00/09727 specifically provides methods for applying DNA shuffling to the identification of herbicide selective crops which could be applied to the polynucleotides and polypeptides of the present invention; additionally, PCT Application No. WO 00/12680 provides methods and compositions for generating, modifying, adapting, and optimizing polynucleotide sequences that confer detectable phenotypic properties on plant species; each of the above are hereby incorporated in their entirety herein for all purposes.

Example 24

Method of Determining Alterations in a Gene Corresponding to a Polynucleotide

RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:1. Suggested PCR conditions consist of 35 cycles at 95 degrees C. for 30 seconds; 60–120 seconds at 52–58 degrees C.; and 60–120 seconds at 70 degrees C., using buffer solutions described in Sidransky et al., Science 252:706 (1991).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations is then cloned and sequenced to validate the results of the direct sequencing.

PCR products is cloned into T-tailed vectors as described in Holton et al., Nucleic Acids Research, 19:1156 (1991) and sequenced with T7 polymerase (United States Biochemical). Affected individuals are identified by mutations not present in unaffected individuals.

Genomic rearrangements are also observed as a method of determining alterations in a gene corresponding to a polynucleotide. Genomic clones isolated according to Example 2 are nick-translated with digoxigenindeoxy-uridine 5'-triphosphate (Boehringer Manheim), and FISH performed as described in Johnson et al., Methods Cell Biol. 35:73–99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 25

Method of Detecting Abnormal Levels of a Polypeptide in a Biological Sample

A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described elsewhere herein. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 26

Formulation

The invention also provides methods of treatment and/or prevention diseases, disorders, and/or conditions (such as, for example, any one or more of the diseases or disorders disclosed herein) by administration to a subject of an effective amount of a Therapeutic. By therapeutic is meant a polynucleotides or polypeptides of the invention (including fragments and variants), agonists or antagonists thereof, and/or antibodies thereto, in combination with a pharmaceutically acceptable carrier type (e.g., a sterile carrier).

The Therapeutic will be formulated and dosed in a fashion consistent with good medical practice, taking into account the clinical condition of the individual patient (especially the side effects of treatment with the Therapeutic alone), the site of delivery, the method of administration, the scheduling of administration, and other factors known to practitioners. The "effective amount" for purposes herein is thus determined by such considerations.

As a general proposition, the total pharmaceutically effective amount of the Therapeutic administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the Therapeutic is typically administered at a dose rate of about 1 ug/kg/hour to about 50 ug/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Therapeutics can be administered orally, rectally, parenterally, intracisternally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any. The term "parenteral" as used herein refers to modes of administration which include intravenous, intramuscular, intraperitoneal, intrasternal, subcutaneous and intraarticular injection and infusion.

In yet an additional embodiment, the Therapeutics of the invention are delivered orally using the drug delivery technology described in U.S. Pat. No. 6,258,789, which is hereby incorporated by reference herein.

Therapeutics of the invention are also suitably administered by sustained-release systems. Suitable examples of sustained-release Therapeutics are administered orally, rectally, parenterally, intracisternally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Therapeutics of the invention may also be suitably administered by sustained-release systems. Suitable examples of sustained-release Therapeutics include suitable polymeric materials (such as, for example, semi-permeable polymer matrices in the form of shaped articles, e.g., films, or microcapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman et al., Biopolymers 22:547–556 (1983)), poly (2-hydroxyethyl methacrylate) (Langer et al., J. Biomed. Mater. Res. 15:167–277 (1981), and Langer, Chem. Tech. 12:98–105 (1982)), ethylene vinyl acetate (Langer et al., Id.) or poly-D-(−)-3-hydroxybutyric acid (EP 133,988).

Sustained-release Therapeutics also include liposomally entrapped Therapeutics of the invention (see, generally, Langer, Science 249:1527–1533 (1990); Treat et al., in Liposomes in the Therapy of Infectious Disease and Cancer, Lopez-Berestein and Fidler (eds.), Liss, New York, pp. 317–327 and 353–365 (1989)). Liposomes containing the Therapeutic are prepared by methods known per se: DE 3,218,121; Epstein et al., Proc. Natl. Acad. Sci. (USA)

82:3688–3692 (1985); Hwang et al., Proc. Natl. Acad. Sci.(USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal Therapeutic.

In yet an additional embodiment, the Therapeutics of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (Science 249:1527–1533 (1990)).

For parenteral administration, in one embodiment, the Therapeutic is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to the Therapeutic.

Generally, the formulations are prepared by contacting the Therapeutic uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The Therapeutic will typically be formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any pharmaceutical used for therapeutic administration can be sterile. Sterility is readily accomplished by filtration through sterile filtration membranes (e.g., 0.2 micron membranes). Therapeutics generally are placed into a container having a sterile access port, for example, an intravenous solution bag or vial having a stopper pierceable by a hypodermic injection needle.

Therapeutics ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous Therapeutic solution, and the resulting mixture is lyophilized. The infusion solution is prepared by reconstituting the lyophilized Therapeutic using bacteriostatic Water-for-Injection.

The invention also provides a pharmaceutical pack or kit comprising one or more containers filled with one or more of the ingredients of the Therapeutics of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the Therapeutics may be employed in conjunction with other therapeutic compounds.

The Therapeutics of the invention may be administered alone or in combination with adjuvants. Adjuvants that may be administered with the Therapeutics of the invention include, but are not limited to, alum, alum plus deoxycholate (ImmunoAg), MTP-PE (Biocine Corp.), QS21 (Genentech, Inc.), BCG, and MPL. In a specific embodiment, Therapeutics of the invention are administered in combination with alum. In another specific embodiment, Therapeutics of the invention are administered in combination with QS-21. Further adjuvants that may be administered with the Therapeutics of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the Therapeutics of the invention include, but are not limited to, vaccines directed toward protection against MMR (measles, mumps, rubella), polio, varicella, tetanus/diptheria, hepatitis A, hepatitis B, haemophilus influenzae B, whooping cough, pneumonia, influenza, Lyme's Disease, rotavirus, cholera, yellow fever, Japanese encephalitis, poliomyelitis, rabies, typhoid fever, and pertussis. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The Therapeutics of the invention may be administered alone or in combination with other therapeutic agents. Therapeutic agents that may be administered in combination with the Therapeutics of the invention, include but not limited to, other members of the TNF family, chemotherapeutic agents, antibiotics, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the Therapeutics of the invention are administered in combination with members of the TNF family. TNF, TNF-related or TNF-like molecules that may be administered with the Therapeutics of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), and TR12, and soluble forms CD154, CD70, and CD153.

In certain embodiments, Therapeutics of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the Therapeutics of the invention, include, but are not limited to, RETROVIR (zidovudine/AZT), VIDEX (didanosine/ddI), HIVID (zalcitabine/ddC), ZERIT (stavudine/d4T), EPIVIR (lamivudine/3TC), and COMBIVIR (zidovudine/lamivudine). Non-nucleoside reverse transcriptase inhibitors that may be administered in combination with the Therapeutics of the invention, include, but are not limited to, VIRAMUNE (nevirapine), RESCRIPTOR (delavirdine), and SUSTIVA (efavirenz). Protease inhibitors that may be administered in combination with the Therapeutics of the invention, include, but are not limited to, CRIXIVAN (indinavir), NORVIR (ritonavir), INVIRASE (saquinavir), and VIRACEPT (nelfinavir). In a specific embodiment, antiretroviral agents, nucleoside reverse transcriptase inhibitors, non-nucleoside reverse transcriptase inhibitors, and/or protease inhibitors may be used in any combination with Therapeutics of the invention to treat AIDS and/or to prevent or treat HIV infection.

In other embodiments, Therapeutics of the invention may be administered in combination with anti-opportunistic infection agents. Anti-opportunistic agents that may be administered in combination with the Therapeutics of the invention, include, but are not limited to, TRIMETHOPRIM-SULFAMETHOXAZOLE, DAPSONE, PENTAMIDINE, ATOVAQUONE, ISONIAZID, RIFAMPIN, PYRAZINAMIDE, ETHAMBUTOL, RIFABUTIN, CLARITHROMYCIN, AZITHROMYCIN, GANCICLOVIR, FOSCARNET, CIDOFOVIR, FLUCONAZOLE, ITRACONAZOLE, KETOCONAZOLE, ACYCLOVIR, FAMCICOLVIR, PYRIMETHAMINE, LEUCOVORIN, NEUPOGEN (filgrastim/G-CSF), and LEUKINE (sargramostim/GM-CSF). In a specific embodiment, Therapeutics of the invention are used in any combination with TRIMETHOPRIM-SULFAMETHOXAZOLE, DAPSONE, PENTAMIDINE, and/or ATOVAQUONE to prophylactically treat or prevent an opportunistic *Pneumocystis carinii* pneumonia infection. In another specific embodiment, Therapeutics of the invention are used in any combination with ISONIAZID, RIFAMPIN, PYRAZINAMIDE, and/or ETHAMBUTOL to prophylactically treat or prevent an opportunistic *Mycobacterium avium* complex infection. In another specific embodiment, Therapeutics of the invention are used in any combination with RIFABUTIN, CLARITHROMYCIN, and/or AZITHROMYCIN to prophylactically treat or prevent an opportunistic *Mycobacterium tuberculosis* infection. In another specific embodiment, Therapeutics of the invention are used in any combination with GANCICLOVIR, FOSCARNET, and/or CIDOFOVIR to prophylactically treat or prevent an opportunistic cytomegalovirus infection. In another specific embodiment, Therapeutics of the invention are used in any combination with FLUCONAZOLE, ITRACONAZOLE, and/or KETOCONAZOLE to prophylactically treat or prevent an opportunistic fungal infection. In another specific embodiment, Therapeutics of the invention are used in any combination with ACYCLOVIR and/or FAMCICOLVIR to prophylactically treat or prevent an opportunistic herpes simplex virus type I and/or type II infection. In another specific embodiment, Therapeutics of the invention are used in any combination with PYRIMETHAMINE and/or LEUCOVORIN to prophylactically treat or prevent an opportunistic *Toxoplasma gondii* infection. In another specific embodiment, Therapeutics of the invention are used in any combination with LEUCOVORIN and/or NEUPOGEN to prophylactically treat or prevent an opportunistic bacterial infection.

In a further embodiment, the Therapeutics of the invention are administered in combination with an antiviral agent. Antiviral agents that may be administered with the Therapeutics of the invention include, but are not limited to, acyclovir, ribavirin, amantadine, and remantidine.

In a further embodiment, the Therapeutics of the invention are administered in combination with an antibiotic agent. Antibiotic agents that may be administered with the Therapeutics of the invention include, but are not limited to, amoxicillin, beta-lactamases, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the Therapeutics of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In specific embodiments, Therapeutics of the invention are administered in combination with immunosuppressants. Immunosuppressants preparations that may be administered with the Therapeutics of the invention include, but are not limited to, ORTHOCLONE (OKT3), SANDIMMUNE/NEORAL/SANGDYA (cyclosporin), PROGRAF (tacrolimus), CELLCEPT (mycophenolate), Azathioprine, glucorticosteroids, and RAPAMUNE (sirolimus). In a specific embodiment, immunosuppressants may be used to prevent rejection of organ or bone marrow transplantation.

In an additional embodiment, Therapeutics of the invention are administered alone or in combination with one or more intravenous immune globulin preparations. Intravenous immune globulin preparations that may be administered with the Therapeutics of the invention include, but not limited to, GAMMAR, IVEEGAM, SANDOGLOBULIN, GAMMAGARD S/D, and GAMIMUNE. In a specific embodiment, Therapeutics of the invention are administered in combination with intravenous immune globulin preparations in transplantation therapy (e.g., bone marrow transplant).

In an additional embodiment, the Therapeutics of the invention are administered alone or in combination with an anti-inflammatory agent. Anti-inflammatory agents that may be administered with the Therapeutics of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compositions of the invention are administered in combination with a chemotherapeutic agent. Chemotherapeutic agents that may be administered with the Therapeutics of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, Therapeutics of the invention are administered in combination with CHOP (cyclophosphamide, doxorubicin, vincristine, and prednisone) or any combination of the components of CHOP. In another embodiment, Therapeutics of the invention are administered in combination with Rituximab. In a further embodiment, Therapeutics of the invention are administered with Rituxmab and CHOP, or Rituxmab and any combination of the components of CHOP.

In an additional embodiment, the Therapeutics of the invention are administered in combination with cytokines. Cytokines that may be administered with the Therapeutics of the invention include, but are not limited to, IL2, IL3, IL4, IL5, IL6, IL7, IL10, IL12, IL13, IL15, anti-CD40, CD40L, IFN-gamma and TNF-alpha. In another embodiment, Therapeutics of the invention may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, and IL-21.

In an additional embodiment, the Therapeutics of the invention are administered in combination with angiogenic proteins. Angiogenic proteins that may be administered with the Therapeutics of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PIGF), as disclosed in International Publication Number WO 92/06194; Placental Growth Factor-2 (PIGF-2), as disclosed in Hauser et al., Gorwth Factors, 4:259–268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B (VEGF-3); Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the Therapeutics of the invention are administered in combination with hematopoietic growth factors. Hematopoietic growth factors that may be administered with the Therapeutics of the invention include, but are not limited to, LEUKINE (SARGRAMOSTIM) and NEUPOGEN (FILGRASTIM).

In an additional embodiment, the Therapeutics of the invention are administered in combination with Fibroblast Growth Factors. Fibroblast Growth Factors that may be administered with the Therapeutics of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In a specific embodiment, formulations of the present invention may further comprise antagonists of P-glycoprotein (also referred to as the multiresistance protein, or PGP), including antagonists of its encoding polynucleotides (e.g., antisense oligonucleotides, ribozymes, zinc-finger proteins, etc.). P-glycoprotein is well known for decreasing the efficacy of various drug administrations due to its ability to export intracellular levels of absorbed drug to the cell exterior. While this activity has been particularly pronounced in cancer cells in response to the administration of chemotherapy regimens, a variety of other cell types and the administration of other drug classes have been noted (e.g., T-cells and anti-HIV drugs). In fact, certain mutations in the PGP gene significantly reduces PGP function, making it less able to force drugs out of cells. People who have two versions of the mutated gene—one inherited from each parent—have more than four times less PGP than those with two normal versions of the gene. People may also have one normal gene and one mutated one. Certain ethnic populations have increased incidence of such PGP mutations. Among individuals from Ghana, Kenya, the Sudan, as well as African Americans, frequency of the normal gene ranged from 73% to 84%. In contrast, the frequency was 34% to 59% among British whites, Portuguese, Southwest Asian, Chinese, Filipino and Saudi populations. As a result, certain ethnic populations may require increased administration of PGP antagonist in the formulation of the present invention to arrive at the an efficacious dose of the therapeutic (e.g., those from African descent). Conversely, certain ethnic populations, particularly those having increased frequency of the mutated PGP (e.g., of Caucasian descent, or non-African descent) may require less pharmaceutical compositions in the formulation due to an effective increase in efficacy of such compositions as a result of the increased effective absorption (e.g., less PGP activity) of said composition.

Moreover, in another specific embodiment, formulations of the present invention may further comprise antagonists of OATP2 (also referred to as the multiresistance protein, or MRP2), including antagonists of its encoding polynucleotides (e.g., antisense oligonucleotides, ribozymes, zinc-finger proteins, etc.). The invention also further comprises any additional antagonists known to inhibit proteins thought to be attributable to a multidrug resistant phenotype in proliferating cells.

Preferred antagonists that formulations of the present may comprise include the potent P-glycoprotein inhibitor elacridar, and/or LY-335979. Other P-glycoprotein known in the art are also encompassed by the present invention.

In additional embodiments, the Therapeutics of the invention are administered in combination with other therapeutic or prophylactic regimens, such as, for example, radiation therapy.

Example 27

Method of Treating Decreased Levels of the Polypeptide

The present invention relates to a method for treating an individual in need of an increased level of a polypeptide of the invention in the body comprising administering to such an individual a composition comprising a therapeutically effective amount of an agonist of the invention (including polypeptides of the invention). Moreover, it will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a Therapeutic comprising an amount of the polypeptide to increase the activity level of the polypeptide in such an individual.

For example, a patient with decreased levels of a polypeptide receives a daily dose 0.1–100 ug/kg of the polypeptide for six consecutive days. Preferably, the polypeptide is in the secreted form. The exact details of the dosing scheme, based on administration and formulation, are provided herein.

Example 28

Method of Treating Increased Levels of the Polypeptide

The present invention also relates to a method of treating an individual in need of a decreased level of a polypeptide of the invention in the body comprising administering to such an individual a composition comprising a therapeutically effective amount of an antagonist of the invention (including polypeptides and antibodies of the invention).

In one example, antisense technology is used to inhibit production of a polypeptide of the present invention. This technology is one example of a method of decreasing levels of a polypeptide, preferably a secreted form, due to a variety of etiologies, such as cancer. For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided herein.

Example 29

Method of Treatment Using Gene Therapy—Ex Vivo

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 13 using primers and having appropriate restriction sites and initiation/stop codons, if necessary. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

Example 30

Gene Therapy Using Endogenous Genes Corresponding to Polynucleotides of the Invention Another method of gene therapy according to the present invention involves operably associating the endogenous polynucleotide sequence of the invention with a promoter via homologous recombination as described, for example, in U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., Proc. Natl. Acad. Sci. USA, 86:8932–8935 (1989); and Zijlstra et al., Nature, 342:435–438 (1989). This method involves the activation of a gene which is present in the target cells, but which is not expressed in the cells, or is expressed at a lower level than desired.

Polynucleotide constructs are made which contain a promoter and targeting sequences, which are homologous to the 5' non-coding sequence of endogenous polynucleotide sequence, flanking the promoter. The targeting sequence will be sufficiently near the 5' end of the polynucleotide sequence so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous polynucleotide sequence. This results in the expression of polynucleotide corresponding to the polynucleotide in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM Na2 HPO4, 6 mM dextrose). The cells are recentrifuged, the supernatant aspirated, and the cells resuspended in electroporation buffer containing 1 mg/ml acetylated bovine serum albumin. The final cell suspension contains approximately $3\times10^6$ cells/ml. Electroporation should be performed immediately following resuspension.

Plasmid DNA is prepared according to standard techniques. For example, to construct a plasmid for targeting to the locus corresponding to the polynucleotide of the invention, plasmid pUC 18 (MBI Fermentas, Amherst, N.Y.) is digested with HindIII. The CMV promoter is amplified by PCR with an XbaI site on the 5' end and a BamHI site on the 3'end. Two non-coding sequences are amplified via PCR: one non-coding sequence (fragment 1) is amplified with a HindIII site at the 5' end and an Xba site at the 3'end; the other non-coding sequence (fragment 2) is amplified with a BamHI site at the 5'end and a HindIII site at the 3'end. The CMV promoter and the fragments (1 and 2) are digested with the appropriate enzymes (CMV promoter—XbaI and BamHI; fragment 1—XbaI; fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 µg/ml. 0.5 ml of the cell suspension (containing approximately $1.5\times10^6$ cells) is then added to the cuvette, and the cell suspension and DNA solutions are gently mixed. Electroporation is performed with a Gene-Pulser apparatus (Bio-Rad). Capacitance and voltage are set at 960 µF and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37 degree C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 31

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) sequences into an animal to increase or decrease the expression of the polypeptide. The polynucleotide of the present invention may be operatively linked to a promoter or any other genetic elements necessary for the expression of the polypeptide by the target tissue. Such gene therapy and delivery techniques and methods are known in the art, see, for example, WO90/11092, WO98/11779; U.S. Pat. No. 5,693,622, 5,705,151, 5,580,859; Tabata et al., Cardiovasc. Res. 35(3):470–479 (1997); Chao et al., Pharmacol. Res. 35(6):517–522 (1997); Wolff, Neuromuscul. Disord. 7(5): 314–318 (1997); Schwartz et al., Gene Ther. 3(5):405–411 (1996); Tsurumi et al., Circulation 94(12):3281–3290 (1996) (incorporated herein by reference).

The polynucleotide constructs may be delivered by any method that delivers injectable materials to the cells of an animal, such as, injection into the interstitial space of tissues (heart, muscle, skin, lung, liver, intestine and the like). The polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the polynucleotides of the present invention may also be delivered in liposome formulations (such as those taught in Felgner P. L. et al. (1995) Ann. NY Acad. Sci. 772:126–139 and Abdallah B. et al. (1995) Biol. Cell 85(1):1–7) which can be prepared by methods well known to those skilled in the art.

The polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked polynucleotide constructs can be delivered to arteries during angioplasty by the catheter used in the procedure.

The dose response effects of injected polynucleotide in muscle in vivo is determined as follows. Suitable template DNA for production of mRNA coding for polypeptide of the present invention is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for protein expression. A time course for protein expression may be done in a similar fashion except that quadriceps from different mice are harvested at different times. Persistence of DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using naked DNA.

Example 32

Transgenic Animals

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691–698 (1994); Carver et al., Biotechnology (NY) 11:1263–1270 (1993); Wright et al., Biotechnology (NY) 9:830–834 (1991); and Hoppe et al., U.S. Pat. No. 4,873,191 (1989)); retrovirus mediated gene transfer into germ lines (Van dear Putten et al., Proc. Natl. Acad. Sci., USA 82:6148–6152 (1985)), blastocysts or embryos; gene targeting in embryonic stem cells (Thompson et al., Cell 56:313–321 (1989)); electroporation of cells or embryos (Lo, 1983, Mol Cell. Biol. 3:1803–1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717–723 (1989); etc. For a review of such techniques, see Gordon, "Transgenic Animals," Intl. Rev. Cytol. 115:171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64–66 (1996); Wilmut et al., Nature 385:810–813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103–106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR(RT-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 33

Knock-Out Animals

Endogenous gene expression can also be reduced by inactivating or "knocking out" the gene and/or its promoter using targeted homologous recombination. (E.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 34

Method of Isolating Antibody Fragments Directed Against CAN-12 from a Library of scFvs Naturally occurring V-genes isolated from human PBLs are constructed into a library of antibody fragments which contain reactivities against CAN-12 to which the donor may or may not have been exposed (see e.g., U.S. Pat. No. 5,885,793 incorporated herein by reference in its entirety).

Rescue of the Library. A library of scFvs is constructed from the RNA of human PBLs as described in PCT publication WO 92/01047. To rescue phage displaying antibody fragments, approximately 109 $E.$ $coli$ harboring the phagemid are used to inoculate 50 ml of 2×TY containing 1% glucose and 100 µg/ml of ampicillin (2×TY-AMP-GLU) and grown to an O.D. of 0.8 with shaking. Five ml of this culture is used to inoculate 50 ml of 2×TY-AMP-GLU, 2×108 TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 µg/ml ampicillin and 50 ug/ml kanamycin and grown overnight. Phage are prepared as described in PCT publication WO 92/01047.

M13 delta gene III is prepared as follows: M13 delta gene III helper phage does not encode gene III protein, hence, the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 µg ampicillin/ml and 25 µg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 µm filter (Minisart NML; Sartorius) to give a final concentration of approximately 1013 transducing units/mil (ampicillin-resistant clones).

Panning of the Library. Immunotubes (Nunc) are coated overnight in PBS with 4 ml of either 100 pg/ml or 10 pg/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 mil of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log $E.$ $coli$ TG1 by incubating eluted phage with bacteria for 30 minutes at 37° C. The $E.$ $coli$ are then plated on TYE plates containing 1% glucose and 100 µg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect $E.$ $coli$ HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., PCT publication WO 92/01047) and then by sequencing. These ELISA positive clones may also be further characterized by techniques known in the art, such as, for example, epitope mapping, binding affinity, receptor signal transduction, ability to block or competitively inhibit antibody/antigen binding, and competitive agonistic or antagonistic activity.

Moreover, in another preferred method, the antibodies directed against the polypeptides of the present invention may be produced in plants. Specific methods are disclosed in U.S. Pat. Nos. 5,959,177, and 6,080,560, which are hereby incorporated in their entirety herein. The methods not only describe methods of expressing antibodies, but also the means of assembling foreign multimeric proteins in plants (i.e., antibodies, etc,), and the subsequent secretion of such antibodies from the plant.

Example 35

Identification and Cloning of VH and VL Domains of Antibodies Directed Against the CAN-12 Polypeptide VH and VL domains may be identified and cloned from cell lines expressing an antibody directed against a CAN-12 epitope by performing PCR with VH and VL specific primers on cDNA made from the antibody expressing cell lines. Briefly, RNA is isolated from the cell lines and used as a template for RT-PCR designed to amplify the VH and VL domains of the antibodies expressed by the EBV cell lines. Cells may be lysed using the TRIzol reagent (Life Technologies, Rockville, Md.) and extracted with one fifth volume of chloroform. After addition of chloroform, the solution is allowed to incubate at room temperature for 10 minutes, and then centrifuged at 14,000 rpm for 15 minutes at 4 C in a tabletop centrifuge. The supernatant is collected and RNA is precipitated using an equal volume of isopropanol. Precipitated RNA is pelleted by centrifuging at 14,000 rpm for 15 minutes at 4 C in a tabletop centrifuge.

Following centrifugation, the supernatant is discarded and washed with 75% ethanol. Follwing the wash step, the RNA is centrifuged again at 800 rpm for 5 minutes at 4 C. The supernatant is discarded and the pellet allowed to air dry. RNA is the dissolved in DEPC water and heated to 60 C for 10 minutes. Quantities of RNA can be determined using optical density measurements. cDNA may be synthesized, according to methods well-known in the art and/or described herein, from 1.5–2.5 micrograms of RNA using reverse transcriptase and random hexamer primers. cDNA is then used as a template for PCR amplification of VH and VL domains.

Primers used to amplify VH and VL genes are shown below. Typically a PCR reaction makes use of a single 5'primer and a single 3'primer. Sometimes, when the amount of available RNA template is limiting, or for greater efficiency, groups of 5' and/or 3'primers may be used. For example, sometimes all five VH-5'primers and all JH3'primers are used in a single PCR reaction. The PCR reaction is carried out in a 50 microliter volume containing 1×PCR buffer, 2 mM of each dNTP, 0.7 units of High Fidelity Taq polymerse, 5'primer mix, 3'primer mix and 7.5 microliters of cDNA. The 5' and 3'primer mix of both VH and VL can be made by pooling together 22 pmole and 28 pmole, respectively, of each of the individual primers. PCR conditions are: 96 C for 5 minutes; followed by 25 cycles of 94 C for 1 minute, 50 C for 1 minute, and 72 C for 1 minute; followed by an extension cycle of 72 C for 10 minutes. After the reaction has been completed, sample tubes may be stored at 4 C.

| Primer name | Primer Sequence | SEQ ID NO: |
|---|---|---|
| Primer Sequences Used to Amplify VH domains. | | |
| Hu VH1-5' | CAGGTGCAGCTGGTGCAGTCTGG | 105 |
| Hu VH2-5' | CAGGTCAACTTAAGGGAGTCTGG | 106 |
| Hu VH3-5' | GAGGTGCAGCTGGTGGAGTCTGG | 107 |
| Hu VH4-5' | CAGGTGCAGCTGCAGGAGTCGGG | 108 |
| Hu VH5-5' | GAGGTGCAGCTGTTGCAGTCTGC | 109 |
| Hu VH6-5' | CAGGTACAGCTGCAGCAGTCAGG | 110 |
| Hu JH1-5' | TGAGGAGACGGTGACCAGGGTGCC | 111 |
| Hu JH3-5' | TGAAGAGACGGTGACCATTGTCCC | 112 |
| Hu JH4-5' | TGAGGAGACGGTGACCAGGGTTCC | 113 |
| Hu JH6-5' | TGAGGAGACGGTGACCGTGGTCCC | 114 |
| Primer Sequences Used to Amplify VL domains | | |
| Hu Vkappa1-5' | GACATCCAGATGACCCAGTCTCC | 115 |
| Hu Vkappa2a-5' | GATGTTGTGATGACTCAGTCTCC | 116 |
| Hu Vkappa2b-5' | GATATTGTGATGACTCAGTCTCC | 117 |
| Hu Vkappa3-5' | GAAATTGTGTTGACGCAGTCTCC | 118 |
| Hu Vkappa4-5' | GACATCGTGATGACCCAGTCTCC | 119 |
| Hu Vkappa5-5' | GAAACGACACTCACGCAGTCTCC | 120 |
| Hu Vkappa6-5' | GAAATTGTGCTGACTCAGTCTCC | 121 |
| Hu Vlambda1-5' | CAGTCTGTGTTGACGCAGCCGCC | 122 |
| Hu Vlambda2-5' | CAGTCTGCCCTGACTCAGCCTGC | 123 |
| Hu Vlambda3-5' | TCCTATGTGCTGACTCAGCCACC | 124 |
| Hu Vlambda3b-5' | TCTTCTGAGCTGACTCAGGACCC | 125 |
| Hu Vlambda4-5' | CACGTTATACTGACTCAACCGCC | 126 |
| Hu Vlambda5-5' | CAGGCTGTGCTCACTCAGCCGTC | 127 |
| Hu Vlambda6-5' | AATTTTATGCTGACTCAGCCCCA | 128 |
| Hu Jkappa1-3' | ACGTTTGATTTCCACCTTGGTCCC | 129 |
| Hu Jkappa2-3' | ACGTTTGATCTCCAGCTTGGTCCC | 130 |
| Hu Jkappa3-3' | ACGTTTGATATCCACTTTGGTCCC | 131 |
| Hu Jkappa4-3' | ACGTTTGATCTCCACCTTGGTCCC | 132 |
| Hu Jkappa5-3' | ACGTTTAATCTCCAGTCGTGTCCC | 133 |
| Hu Vlambda1-3' | CAGTCTGTGTTGACGCAGCCGCC | 134 |
| Hu Vlambda2-3' | CAGTCTGCCCTGACTCAGCCTGC | 135 |
| Hu Vlambda3-3' | TCCTATGTGCTGACTCAGCCACC | 136 |
| Hu Vlambda3b-3' | TCTTCTGAGCTGACTCAGGACCC | 137 |
| Hu Vlambda4-3' | CACGTTATACTGACTCAACCGCC | 138 |
| Hu Vlambda5-3' | CAGGCTGTGCTCACTCAGCCGTC | 139 |
| Hu Vlambda6-3' | AATTTTATGCTGACTCAGCCCCA | 140 |

PCR samples are then electrophoresed on a 1.3% agarose gel. DNA bands of the expected sizes (~506 base pairs for VH domains, and 344 base pairs for VL domains) can be cut out of the gel and purified using methods well known in the art and/or described herein.

Purified PCR products can be ligated into a PCR cloning vector (TA vector from Invitrogen Inc., Carlsbad, Calif.). Individual cloned PCR products can be isolated after transfection of E. coli and blue/white color selection. Cloned PCR products may then be sequenced using methods commonly known in the art and/or described herein.

The PCR bands containing the VH domain and the VL domains can also be used to create full-length Ig expression vectors. VH and VL domains can be cloned into vectors containing the nucleotide sequences of a heavy (e.g., human IgG1 or human IgG4) or light chain (human kappa or human ambda) constant regions such that a complete heavy or light chain molecule could be expressed from these vectors when transfected into an appropriate host cell. Further, when cloned heavy and light chains are both expressed in one cell line (from either one or two vectors), they can assemble into a complete functional antibody molecule that is secreted into the cell culture medium. Methods using polynucleotides encoding VH and VL antibody domain to generate expression vectors that encode complete antibody molecules are well known within the art.

Example 36

Assays Detecting Stimulation or Inhibition of B cell Proliferation and Differentiation Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL-4, IL-5, IL-6, IL-7, IL10, IL-13, IL-14 and IL-15. Interestingly, these signals are by themselves weak effectors but can, in combination with various co-stimulatory proteins, induce activation, proliferation, differentiation, homing, tolerance and death among B cell populations.

One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

In Vitro Assay—Purified polypeptides of the invention, or truncated forms thereof, is assessed for its ability to induce activation, proliferation, differentiation or inhibition and/or death in B-cell populations and their precursors. The activity of the polypeptides of the invention on purified human tonsillar B cells, measured qualitatively over the dose range from 0.1 to 10,000 ng/mL, is assessed in a standard B-lymphocyte co-stimulation assay in which purified tonsillar B cells are cultured in the presence of either formalin-fixed *Staphylococcus aureus* Cowan I (SAC) or immobilized anti-human IgM antibody as the priming agent. Second signals such as IL-2 and IL-15 synergize with SAC and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R(B220).

Various dilutions of each sample are placed into individual wells of a 96-well plate to which are added 105 B-cells suspended in culture medium (RPMI 1640 containing 10% FBS, 5×10-5M2ME, 100 U/ml penicillin, 10 ug/ml streptomycin, and 10-5 dilution of SAC) in a total volume of 150 ul. Proliferation or inhibition is quantitated by a 20 h pulse (1 uCi/well) with 3H-thymidine (6.7 Ci/mM) beginning 72 h post factor addition. The positive and negative controls are IL2 and medium respectively.

In Vivo Assay—BALB/c mice are injected (i.p.) twice per day with buffer only, or 2 mg/Kg of a polypeptide of the invention, or truncated forms thereof. Mice receive this treatment for 4 consecutive days, at which time they are sacrificed and various tissues and serum collected for analyses. Comparison of H&E sections from normal spleens and spleens treated with polypeptides of the invention identify the results of the activity of the polypeptides on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R(B220), are used to determine whether any physiological changes to splenic cells, such as splenic disorganization, are due to increased B-cell representation within loosely defined B-cell zones that infiltrate established T-cell regions.

Flow cytometric analyses of the spleens from mice treated with polypeptide is used to indicate whether the polypeptide specifically increases the proportion of ThB+, CD45R (B220)dull B cells over that which is observed in control mice.

Likewise, a predicted consequence of increased mature B-cell representation in vivo is a relative increase in serum Ig titers. Accordingly, serum IgM and IgA levels are compared between buffer and polypeptide-treated mice.

One skilled in the art could easily modify the exemplified-studies to test the activity of polynucleotides of the invention (e.g., gene therapy), agonists, and/or antagonists of polynucleotides or polypeptides of the invention.

Example 37

T Cell Proliferation Assay

A CD3-induced proliferation assay is performed on PBMCs and is measured by the uptake of 3H-thymidine. The assay is performed as follows. Ninety-six well plates are coated with 100 (l/well of mAb to CD3 (HIT3a, Pharmingen) or isotype-matched control mAb (B33.1) overnight at 4 degrees C. (1 (g/ml in 0.05M bicarbonate buffer, pH 9.5), then washed three times with PBS. PBMC are isolated by F/H gradient centrifugation from human peripheral blood and added to quadruplicate wells (5×104/well) of mAb coated plates in RPMI containing 10% FCS and P/S in the presence of varying concentrations of polypeptides of the invention (total volume 200 ul). Relevant protein buffer and medium alone are controls. After 48 hr. culture at 37 degrees C., plates are spun for 2 min. at 1000 rpm and 100 (1 of supernatant is removed and stored −20 degrees C. for measurement of IL-2 (or other cytokines) if effect on proliferation is observed. Wells are supplemented with 100 ul of medium containing 0.5 uCi of 3H-thymidine and cultured at 37 degrees C. for 18–24 hr. Wells are harvested and incorporation of 3H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative controls for the effects of polypeptides of the invention.

One skilled in the art could easily modify the exemplified studies to test the activity of polynucleotides of the invention (e.g., gene therapy), agonists, and/or antagonists of polynucleotides or polypeptides of the invention.

Example 38

Effect of Polypeptides of the Invention on the Expression of MHC Class II, Costimulatory and Adhesion Molecules and Cell Differentiation of Monocytes and Monocyte-Derived Human Dendritic Cells Dendritic cells are generated by the expansion of proliferating precursors found in the peripheral blood: adherent PBMC or elutriated monocytic fractions are cultured for 7–10 days with GM-CSF (50 ng/ml) and IL-4 (20 ng/ml). These dendritic cells have the characteristic phenotype of immature cells (expression of CD1, CD80, CD86, CD40 and MHC class II antigens). Treatment with activating factors, such as TNF-, causes a rapid change in surface phenotype (increased expression of MHC class I and II, costimulatory and adhesion molecules, downregulation of FC(RII, upregulation of CD83). These changes correlate with increased antigen-presenting capacity and with functional maturation of the dendritic cells.

FACS analysis of surface antigens is performed as follows. Cells are treated 1–3 days with increasing concentrations of polypeptides of the invention or LPS (positive control), washed with PBS containing 1% BSA and 0.02 mM sodium azide, and then incubated with 1:20 dilution of appropriate FITC- or PE-labeled monoclonal antibodies for 30 minutes at 4 degrees C. After an additional wash, the labeled cells are analyzed by flow cytometry on a FACScan (Becton Dickinson).

Effect on the production of cytokines. Cytokines generated by dendritic cells, in particular IL-12, are important in the initiation of T-cell dependent immune responses. IL-12 strongly influences the development of Th1 helper T-cell immune response, and induces cytotoxic T and NK cell function. An ELISA is used to measure the IL-12 release as follows. Dendritic cells (106/ml) are treated with increasing concentrations of polypeptides of the invention for 24 hours. LPS (100 ng/ml) is added to the cell culture as positive control. Supernatants from the cell cultures are then collected and analyzed for IL-12 content using commercial ELISA kit(e.g., R & D Systems (Minneapolis, Minn.)). The standard protocols provided with the kits are used.

Effect on the expression of MHC Class II, costimulatory and adhesion molecules. Three major families of cell surface antigens can be identified on monocytes: adhesion molecules, molecules involved in antigen presentation, and Fc receptor. Modulation of the expression of MHC class II antigens and other costimulatory molecules, such as B7 and ICAM-1, may result in changes in the antigen presenting capacity of monocytes and ability to induce T cell activation. Increase expression of Fc receptors may correlate with improved monocyte cytotoxic activity, cytokine release and phagocytosis.

FACS analysis is used to examine the surface antigens as follows. Monocytes are treated 1–5 days with increasing concentrations of polypeptides of the invention or LPS (positive control), washed with PBS containing 1% BSA and 0.02 mM sodium azide, and then incubated with 1:20 dilution of appropriate FITC- or PE-labeled monoclonal antibodies for 30 minutes at 4 degrees C. After an additional wash, the labeled cells are analyzed by flow cytometry on a FACScan (Becton Dickinson).

Monocyte activation and/or increased survival. Assays for molecules that activate (or alternatively, inactivate) monocytes and/or increase monocyte survival (or alternatively, decrease monocyte survival) are known in the art and may routinely be applied to determine whether a molecule of the invention functions as an inhibitor or activator of monocytes. Polypeptides, agonists, or antagonists of the invention can be screened using the three assays described below. For each of these assays, Peripheral blood mononuclear cells (PBMC) are purified from single donor leukopacks (American Red Cross, Baltimore, Md.) by centrifugation through a Histopaque gradient (Sigma). Monocytes are isolated from PBMC by counterflow centrifugal elutriation.

Monocyte Survival Assay. Human peripheral blood monocytes progressively lose viability when cultured in absence of serum or other stimuli. Their death results from internally regulated process (apoptosis). Addition to the culture of activating factors, such as TNF-alpha dramatically improves cell survival and prevents DNA fragmentation. Propidium iodide (PI) staining is used to measure apoptosis as follows. Monocytes are cultured for 48 hours in polypropylene tubes in serum-free medium (positive control), in the presence of 100 ng/ml TNF-alpha (negative control), and in the presence of varying concentrations of the compound to be tested. Cells are suspended at a concentration of 2×106/ml in PBS containing PI at a final concentration of 5 (g/ml, and then incubated at room temperature for 5 minutes before FACScan analysis. PI uptake has been demonstrated to correlate with DNA fragmentation in this experimental paradigm.

Effect on Cytokine Release. An important function of monocytes/macrophages is their regulatory activity on other cellular populations of the immune system through the release of cytokines after stimulation. An ELISA to measure cytokine release is performed as follows. Human monocytes are incubated at a density of 5×105 cells/ml with increasing concentrations of the a polypeptide of the invention and under the same conditions, but in the absence of the polypeptide. For IL-12 production, the cells are primed overnight with IFN (100 U/ml) in presence of a polypeptide of the invention. LPS (10 ng/ml) is then added. Conditioned media are collected after 24 h and kept frozen until use. Measurement of TNF-alpha, IL-10, MCP-1 and IL-8 is then performed using a commercially available ELISA kit(e.g., R & D Systems (Minneapolis, Minn.)) and applying the standard protocols provided with the kit.

Oxidative Burst. Purified monocytes are plated in 96-w plate at 2-1×105 cell/well. Increasing concentrations of polypeptides of the invention are added to the wells in a total volume of 0.2 ml culture medium (RPMI 1640+10% FCS, glutamine and antibiotics). After 3 days incubation, the plates are centrifuged and the medium is removed from the wells. To the macrophage monolayers, 0.2 ml per well of phenol red solution (140 mM NaCl, 10 mM potassium phosphate buffer pH 7.0, 5.5 mM dextrose, 0.56 mM phenol red and 19 U/ml of HRPO) is added, together with the stimulant (200 nM PMA). The plates are incubated at 37(C for 2 hours and the reaction is stopped by adding 20 µl 1N NaOH per well. The absorbance is read at 610 nm. To calculate the amount of H2O2 produced by the macrophages, a standard curve of a H2O2 solution of known molarity is performed for each experiment.

One skilled in the art could easily modify the exemplified studies to test the activity of polynucleotides of the invention (e.g., gene therapy), agonists, and/or antagonists of polynucleotides or polypeptides of the invention.

Example 39

Biological Effects of Polypeptides of the Invention

Astrocyte and Neuronal Assays

Recombinant polypeptides of the invention, expressed in *Escherichia coli* and purified as described above, can be tested for activity in promoting the survival, neurite outgrowth, or phenotypic differentiation of cortical neuronal cells and for inducing the proliferation of glial fibrillary acidic protein immunopositive cells, astrocytes. The selection of cortical cells for the bioassay is based on the prevalent expression of FGF-1 and FGF-2 in cortical structures and on the previously reported enhancement of cortical neuronal survival resulting from FGF-2 treatment. A thymidine incorporation assay, for example, can be used to elucidate a polypeptide of the invention's activity on these cells.

Moreover, previous reports describing the biological effects of FGF-2 (basic FGF) on cortical or hippocampal neurons in vitro have demonstrated increases in both neuron survival and neurite outgrowth (Walicke et al., "Fibroblast growth factor promotes survival of dissociated hippocampal neurons and enhances neurite extension." Proc. Natl. Acad. Sci. USA 83:3012–3016. (1986), assay herein incorporated by reference in its entirety). However, reports from experiments done on PC-12 cells suggest that these two responses are not necessarily synonymous and may depend on not only which FGF is being tested but also on which receptor(s) are expressed on the target cells. Using the primary cortical neuronal culture paradigm, the ability of a polypeptide of the invention to induce neurite outgrowth can be compared to the response achieved with FGF-2 using, for example, a thymidine incorporation assay.

Fibroblast and Endothelial Cell Assays.

Human lung fibroblasts are obtained from Clonetics (San Diego, Calif.) and maintained in growth media from Clonetics. Dermal microvascular endothelial cells are obtained from Cell Applications (San Diego, Calif.). For proliferation assays, the human lung fibroblasts and dermal microvascular endothelial cells can be cultured at 5,000 cells/well in a 96-well plate for one day in growth medium. The cells are then incubated for one day in 0.1% BSA basal medium. After replacing the medium with fresh 0.1% BSA medium, the cells are incubated with the test proteins for 3 days. Alamar Blue (Alamar Biosciences, Sacramento, Calif.) is added to each well to a final concentration of 10%. The cells are incubated for 4 hr. Cell viability is measured by reading in a CytoFluor fluorescence reader. For the PGE2 assays, the human lung fibroblasts are cultured at 5,000 cells/well in a 96-well plate for one day. After a medium change to 0.1% BSA basal medium, the cells are incubated with FGF-2 or polypeptides of the invention with or without IL-1(for 24 hours. The supernatants are collected and assayed for PGE2 by EIA kit (Cayman, Ann Arbor, Mich.). For the IL-6 assays, the human lung fibroblasts are cultured at 5,000 cells/well in a 96-well plate for one day. After a medium change to 0.1% BSA basal medium, the cells are incubated with FGF-2 or with or without polypeptides of the invention IL-1(for 24 hours. The supernatants are collected and assayed for IL-6 by ELISA kit (Endogen, Cambridge, Mass.).

Human lung fibroblasts are cultured with FGF-2 or polypeptides of the invention for 3 days in basal medium before the addition of Alamar Blue to assess effects on growth of the fibroblasts. FGF-2 should show a stimulation at 10–2500 ng/ml which can be used to compare stimulation with polypeptides of the invention.

Parkinson Models.

The loss of motor function in Parkinson's disease is attributed to a deficiency of striatal dopamine resulting from the degeneration of the nigrostriatal dopaminergic projection neurons. An animal model for Parkinson's that has been extensively characterized involves the systemic administration of 1-methyl-4 phenyl 1,2,3,6-tetrahydropyridine (MPTP). In the CNS, MPTP is taken-up by astrocytes and catabolized by monoamine oxidase B to 1-methyl-4-phenyl pyridine (MPP+) and released. Subsequently, MPP+ is actively accumulated in dopaminergic neurons by the high-affinity reuptake transporter for dopamine. MPP+ is then concentrated in mitochondria by the electrochemical gradient and selectively inhibits nicotidamide adenine disphosphate: ubiquinone oxidoreductionase (complex I), thereby interfering with electron transport and eventually generating oxygen radicals.

It has been demonstrated in tissue culture paradigms that FGF-2 (basic FGF) has trophic activity towards nigral dopaminergic neurons (Ferrari et al., Dev. Biol. 1989). Recently, Dr. Unsicker's group has demonstrated that administering FGF-2 in gel foam implants in the striatum results in the near complete protection of nigral dopaminergic neurons from the toxicity associated with MPTP exposure (Otto and Unsicker, J. Neuroscience, 1990).

Based on the data with FGF-2, polypeptides of the invention can be evaluated to determine whether it has an action similar to that of FGF-2 in enhancing dopaminergic neuronal survival in vitro and it can also be tested in vivo for protection of dopaminergic neurons in the striatum from the damage associated with MPTP treatment. The potential effect of a polypeptide of the invention is first examined in vitro in a dopaminergic neuronal cell culture paradigm. The cultures are prepared by dissecting the midbrain floor plate from gestation day 14 Wistar rat embryos. The tissue is dissociated with trypsin and seeded at a density of 200,000 cells/cm2 on polyorthinine-laminin coated glass coverslips. The cells are maintained in Dulbecco's Modified Eagle's medium and F12 medium containing hormonal supplements (Ni). The cultures are fixed with paraformaldehyde after 8 days in vitro and are processed for tyrosine hydroxylase, a specific marker for dopaminergic neurons, immunohistochemical staining. Dissociated cell cultures are prepared from embryonic rats. The culture medium is changed every third day and the factors are also added at that time.

Since the dopaminergic neurons are isolated from animals at gestation day 14, a developmental time which is past the stage when the dopaminergic precursor cells are proliferating, an increase in the number of tyrosine hydroxylase immunopositive neurons would represent an increase in the number of dopaminergic neurons surviving in vitro. Therefore, if a polypeptide of the invention acts to prolong the survival of dopaminergic neurons, it would suggest that the polypeptide may be involved in Parkinson's Disease.

One skilled in the art could easily modify the exemplified studies to test the activity of polynucleotides of the invention (e.g., gene therapy), agonists, and/or antagonists of polynucleotides or polypeptides of the invention.

Example 40

The Effect of Polypeptides of the Invention on the Growth of

Vascular Endothelial Cells

On day 1, human umbilical vein endothelial cells (HUVEC) are seeded at 2–5×104 cells/35 mm dish density in M199 medium containing 4% fetal bovine serum (FBS), 16 units/ml heparin, and 50 units/ml endothelial cell growth supplements (ECGS, Biotechnique, Inc.). On day 2, the medium is replaced with M199 containing 10% FBS, 8 units/ml heparin. A polypeptide having the amino acid sequence of SEQ ID NO:2, and positive controls, such as VEGF and basic FGF (bFGF) are added, at varying concentrations. On days 4 and 6, the medium is replaced. On day 8, cell number is determined with a Coulter Counter.

An increase in the number of HUVEC cells indicates that the polypeptide of the invention may proliferate vascular endothelial cells.

One skilled in the art could easily modify the exemplified studies to test the activity of polynucleotides of the invention (e.g., gene therapy), agonists, and/or antagonists of polynucleotides or polypeptides of the invention.

Example 41

Stimulatory Effect of Polypeptides of the Invention on the Proliferation of Vascular Endothelial Cells For evaluation of mitogenic activity of growth factors, the calorimetric MTS (3-(4,5-dimethylthiazol-2-yl)-5-(3-carboxymethoxyphenyl)-2-(4-sulfophenyl)2H-tetrazolium) assay with the electron coupling reagent PMS (phenazine methosulfate) was performed (CellTiter 96 AQ, Promega). Cells are seeded in a 96-well plate (5,000 cells/well) in 0.1 mL serum-supplemented medium and are allowed to attach overnight. After serum-starvation for 12 hours in 0.5% FBS, conditions (bFGF, VEGF165 or a polypeptide of the invention in 0.5% FBS) with or without Heparin (8 U/ml) are added to wells for 48 hours. 20 mg of MTS/PMS mixture (1:0.05) are added per well and allowed to incubate for 1 hour at 37° C. before measuring the absorbance at 490 nm in an ELISA plate reader. Background absorbance from control wells (some media, no cells) is subtracted, and seven wells are performed in parallel for each condition. See, Leak et al. In Vitro Cell. Dev. Biol. 30A:512–518 (1994).

One skilled in the art could easily modify the exemplified studies to test the activity of polynucleotides of the invention (e.g., gene therapy), agonists, and/or antagonists of polynucleotides or polypeptides of the invention.

Example 42

Inhibition of PDGF-induced Vascular Smooth Muscle Cell Proliferation Stimulatory Effect HAoSMC proliferation can be measured, for example, by BrdUrd incorporation. Briefly, subconfluent, quiescent cells grown on the 4-chamber slides are transfected with CRP or FITC-labeled AT2-3LP. Then, the cells are pulsed with 10% calf serum and 6 mg/mil BrdUrd. After 24 h, immunocytochemistry is performed by using BrdUrd Staining Kit (Zymed Laboratories). In brief, the cells are incubated with the biotinylated mouse anti-BrdUrd antibody at 4 degrees C. for 2 h after being exposed to denaturing solution and then incubated with the streptavidin-peroxidase and diaminobenzidine. After counterstaining with hematoxylin, the cells are mounted for microscopic examination, and the BrdUrd-positive cells are counted. The BrdUrd index is calculated as a percent of the BrdUrd-positive cells to the total cell number. In addition, the simultaneous detection of the BrdUrd staining (nucleus) and the FITC uptake (cytoplasm) is performed for individual cells by the concomitant use of bright field illumination and dark field-UV fluorescent illumination. See, Hayashida et al., J. Biol. Chem. 6:271(36): 21985–21992 (1996).

One skilled in the art could easily modify the exemplified studies to test the activity of polynucleotides of the invention (e.g., gene therapy), agonists, and/or antagonists of polynucleotides or polypeptides of the invention.

Example 43

Stimulation of Nitric Oxide Production by Endothelial Cells

Nitric oxide released by the vascular endothelium is believed to be a mediator of vascular endothelium relaxation. Thus, activity of a polypeptide of the invention can be assayed by determining nitric oxide production by endothelial cells in response to the polypeptide.

Nitric oxide is measured in 96-well plates of confluent microvascular endothelial cells after 24 hours starvation and a subsequent 4 hr exposure to various levels of a positive control (such as VEGF-1) and the polypeptide of the invention. Nitric oxide in the medium is determined by use of the Griess reagent to measure total nitrite after reduction of nitric oxide-derived nitrate by nitrate reductase. The effect of the polypeptide of the invention on nitric oxide release is examined on HUVEC.

Briefly, NO release from cultured HUVEC monolayer is measured with a NO-specific polarographic electrode connected to a NO meter (Iso-NO, World Precision Instruments Inc.) (1049). Calibration of the NO elements is performed according to the following equation:

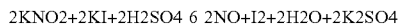

The standard calibration curve is obtained by adding graded concentrations of KNO2 (0, 5, 10, 25, 50, 100, 250, and 500 mmol/L) into the calibration solution containing KI and H2SO4. The specificity of the Iso-NO electrode to NO is previously determined by measurement of NO from authentic NO gas (1Q50). The culture medium is removed and HUVECs are washed twice with Dulbecco's phosphate buffered saline. The cells are then bathed in 5 ml of filtered Krebs-Henseleit solution in 6-well plates, and the cell plates are kept on a slide warmer (Lab Line Instruments Inc.) To maintain the temperature at 37° C. The NO sensor probe is inserted vertically into the wells, keeping the tip of the electrode 2 mm under the surface of the solution, before addition of the different conditions. S-nitroso acetyl penicillamin (SNAP) is used as a positive control. The amount of released NO is expressed as picomoles per 1×106 endothelial cells. All values reported are means of four to six measurements in each group (number of cell culture wells). See, Leak et al. Biochem. and Biophys. Res. Comm. 217: 96–105 (1995).

One skilled in the art could easily modify the exemplified studies to test the activity of polynucleotides of the invention (e.g., gene therapy), agonists, and/or antagonists of polynucleotides or polypeptides of the invention.

Example 44

Rescue of Ischemia in Rabbit Lower Limb Model

To study the in vivo effects of polynucleotides and polypeptides of the invention on ischemia, a rabbit hindlimb ischemia model is created by surgical removal of one femoral arteries as described previously (Takeshita et al., Am J. Pathol 147:1649–1660 (1995)). The excision of the femoral artery results in retrograde propagation of thrombus and occlusion of the external iliac artery. Consequently, blood flow to the ischemic limb is dependent upon collateral vessels originating from the internal iliac artery (Takeshitaet al. Am J. Pathol 147:1649–1660 (1995)). An interval of 10 days is allowed for post-operative recovery of rabbits and development of endogenous collateral vessels. At 10 day post-operatively (day 0), after performing a baseline angiogram, the internal iliac artery of the ischemic limb is transfected with 500 mg naked expression plasmid containing a polynucleotide of the invention by arterial gene transfer technology using a hydrogel-coated balloon catheter as described (Riessen et al. Hum Gene Ther. 4:749–758 (1993); Leclerc et al. J. Clin. Invest. 90: 936–944 (1992)). When a polypeptide of the invention is used in the treatment, a single bolus of 500 mg polypeptide of the invention or control is delivered into the internal iliac artery of the ischemic limb over a period of 1 min. through an infusion catheter. On day 30, various parameters are measured in these rabbits: (a) BP ratio—The blood pressure ratio of systolic pressure of the ischemic limb to that of normal limb; (b) Blood Flow and Flow Reserve—Resting FL: the blood flow during undilated condition and Max FL: the blood flow during fully dilated condition (also an indirect measure of the blood vessel amount) and Flow Reserve is reflected by the ratio of max FL: resting FL; (c) Angiographic Score— This is measured by the angiogram of collateral vessels. A score is determined by the percentage of circles in an overlaying grid that with crossing opacified arteries divided by the total number m the rabbit thigh; (d) Capillary density—The number of collateral capillaries determined in light microscopic sections taken from hindlimbs.

One skilled in the art could easily modify the exemplified studies to test the activity of polynucleotides of the invention (e.g., gene therapy), agonists, and/or antagonists of polynucleotides or polypeptides of the invention.

Example 45

Effect of Polypeptides of the Invention on Vasodilation

Since dilation of vascular endothelium is important in reducing blood pressure, the ability of polypeptides of the invention to affect the blood pressure in spontaneously hypertensive rats (SHR) is examined. Increasing doses (0, 10, 30, 100, 300, and 900 mg/kg) of the polypeptides of the invention are administered to 13–14 week old spontaneously hypertensive rats (SHR). Data are expressed as the mean +/− SEM. Statistical analysis are performed with a paired t-test and statistical significance is defined as $p<0.05$ vs. the response to buffer alone.

One skilled in the art could easily modify the exemplified studies to test the activity of polynucleotides of the invention (e.g., gene therapy), agonists, and/or antagonists of polynucleotides or polypeptides of the invention.

Example 46

Rat Ischemic Skin Flap Model

The evaluation parameters include skin blood flow, skin temperature, and factor VIII immunohistochemistry or endothelial alkaline phosphatase reaction. Expression of polypeptides of the invention, during the skin ischemia, is studied using in situ hybridization.

The study in this model is divided into three parts as follows:
  a) Ischemic skin
  b) Ischemic skin wounds
  c) Normal wounds The experimental protocol includes:
  a) Raising a 3×4 cm, single pedicle full-thickness random skin flap (myocutaneous flap over the lower back of the animal).
  b) An excisional wounding (4–6 mm in diameter) in the ischemic skin (skin-flap).
  c) Topical treatment with a polypeptide of the invention of the excisional wounds (day 0, 1, 2, 3, 4 post-wounding) at the following various dosage ranges: 1 mg to 100 mg.
  d) Harvesting the wound tissues at day 3, 5, 7, 10, 14 and 21 post-wounding for histological, immunohistochemical, and in situ studies.

One skilled in the art could easily modify the exemplified studies to test the activity of polynucleotides of the invention (e.g., gene therapy), agonists, and/or antagonists of polynucleotides or polypeptides of the invention.

Example 47

Peripheral Arterial Disease Model

Angiogenic therapy using a polypeptide of the invention is a novel therapeutic strategy to obtain restoration of blood flow around the ischemia in case of peripheral arterial diseases. The experimental protocol includes:
  a) One side of the femoral artery is ligated to create ischemic muscle of the hindlimb, the other side of hindlimb serves as a control.
  b) a polypeptide of the invention, in a dosage range of 20 mg–500 mg, is delivered intravenously and/or intramuscularly 3 times (perhaps more) per week for 2–3 weeks.
  c) The ischemic muscle tissue is collected after ligation of the femoral artery at 1, 2, and 3 weeks for the analysis of expression of a polypeptide of the invention and histology. Biopsy is also performed on the other side of normal muscle of the contralateral hindlimb.

One skilled in the art could easily modify the exemplified studies to test the activity of polynucleotides of the invention (e.g., gene therapy), agonists, and/or antagonists of polynucleotides or polypeptides of the invention.

Example 48

Ischemic Myocardial Disease Model

A polypeptide of the invention is evaluated as a potent mitogen capable of stimulating the development of collateral vessels, and restructuring new vessels after coronary artery occlusion. Alteration of expression of the polypeptide is investigated in situ. The experimental protocol includes:
  a) The heart is exposed through a left-side thoracotomy in the rat. Immediately, the left coronary artery is occluded with a thin suture (6-0) and the thorax is closed.
  b) a polypeptide of the invention, in a dosage range of 20 mg–500 mg, is delivered intravenously and/or intramuscularly 3 times (perhaps more) per week for 2–4 weeks.
  c) Thirty days after the surgery, the heart is removed and cross-sectioned for morphometric and in situ analyzes.

One skilled in the art could easily modify the exemplified studies to test the activity of polynucleotides of the invention (e.g., gene therapy), agonists, and/or antagonists of polynucleotides or polypeptides of the invention.

Example 49

Rat Corneal Wound Healing Model

This animal model shows the effect of a polypeptide of the invention on neovascularization. The experimental protocol includes:
  a) Making a 1–1.5 mm long incision from the center of cornea into the stromal layer.
  b) Inserting a spatula below the lip of the incision facing the outer corner of the eye.

c) Making a pocket (its base is 1–1.5 mm form the edge of the eye).

d) Positioning a pellet, containing 50 ng–5 ug of a polypeptide of the invention, within the pocket.

e) Treatment with a polypeptide of the invention can also be applied topically to the corneal wounds in a dosage range of 20 mg–500 mg (daily treatment for five days).

One skilled in the art could easily modify the exemplified studies to test the activity of polynucleotides of the invention (e.g., gene therapy), agonists, and/or antagonists of polynucleotides or polypeptides of the invention.

Example 50

Diabetic Mouse and Glucocorticoid-Impaired Wound Healing Models

A. Diabetic db+/db+ Mouse Model.

To demonstrate that a polypeptide of the invention accelerates the healing process, the genetically diabetic mouse model of wound healing is used. The full thickness wound healing model in the db+/db+ mouse is a well characterized, clinically relevant and reproducible model of impaired wound healing. Healing of the diabetic wound is dependent on formation of granulation tissue and re-epithelialization rather than contraction (Gartner, M. H. et al., J. Surg. Res. 52:389 (1992); Greenhalgh, D. G. et al., Am. J. Pathol. 136:1235 (1990)).

The diabetic animals have many of the characteristic features observed in Type II diabetes mellitus. Homozygous (db+/db+) mice are obese in comparison to their normal heterozygous (db+/+m) littermates. Mutant diabetic (db+/db+) mice have a single autosomal recessive mutation on chromosome 4 (db+) (Coleman et al. Proc. Natl. Acad. Sci. USA 77:283–293 (1982)). Animals show polyphagia, polydipsia and polyuria. Mutant diabetic mice (db+/db+) have elevated blood glucose, increased or normal insulin levels, and suppressed cell-mediated immunity (Mandel et al., J. Immunol. 120:1375 (1978); Debray-Sachs, M. et al., Clin. Exp. Immunol. 51(1):1–7 (1983); Leiter et al., Am. J. of Pathol. 114:46–55 (1985)). Peripheral neuropathy, myocardial complications, and microvascular lesions, basement membrane thickening and glomerular filtration abnormalities have been described in these animals (Norido, F. et al., Exp. Neurol. 83(2):221–232 (1984); Robertson et al., Diabetes 29(1):60–67 (1980); Giacomelli et al., Lab Invest. 40(4):460–473 (1979); Coleman, D. L., Diabetes 31 (Suppl): 1–6 (1982)). These homozygous diabetic mice develop hyperglycemia that is resistant to insulin analogous to human type II diabetes (Mandel et al., J. Immunol. 120:1375–1377 (1978)).

The characteristics observed in these animals suggests that healing in this model may be similar to the healing observed in human diabetes (Greenhalgh, et al., Am. J. of Pathol. 136:1235–1246 (1990)).

Genetically diabetic female C57BL/KsJ (db+/db+) mice and their non-diabetic (db+/+m) heterozygous littermates are used in this study (Jackson Laboratories). The animals are purchased at 6 weeks of age and are 8 weeks old at the beginning of the study. Animals are individually housed and received food and water ad libitum. All manipulations are performed using aseptic techniques. The experiments are conducted according to the rules and guidelines of Bristol-Myers Squibb Company's Institutional Animal Care and Use Committee and the Guidelines for the Care and Use of Laboratory Animals.

Wounding protocol is performed according to previously reported methods (Tsuboi, R. and Rifkin, D. B., J. Exp. Med. 172:245–251 (1990)). Briefly, on the day of wounding, animals are anesthetized with an intraperitoneal injection of Avertin (0.01 mg/mL), 2,2,2-tribromoethanol and 2-methyl-2-butanol dissolved in deionized water. The dorsal region of the animal is shaved and the skin washed with 70% ethanol solution and iodine. The surgical area is dried with sterile gauze prior to wounding. An 8 mm full-thickness wound is then created using a Keyes tissue punch. Immediately following wounding, the surrounding skin is gently stretched to eliminate wound expansion. The wounds are left open for the duration of the experiment. Application of the treatment is given topically for 5 consecutive days commencing on the day of wounding. Prior to treatment, wounds are gently cleansed with sterile saline and gauze sponges.

Wounds are visually examined and photographed at a fixed distance at the day of surgery and at two day intervals thereafter. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

A polypeptide of the invention is administered using at a range different doses, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology and immunohistochemistry. Tissue specimens are placed in 10% neutral buffered formalin in tissue cassettes between biopsy sponges for further processing.

Three groups of 10 animals each (5 diabetic and 5 non-diabetic controls) are evaluated: 1) Vehicle placebo control, 2) untreated group, and 3) treated group.

Wound closure is analyzed by measuring the area in the vertical and horizontal axis and obtaining the total square area of the wound. Contraction is then estimated by establishing the differences between the initial wound area (day 0) and that of post treatment (day 8). The wound area on day 1 is 64 mm2, the corresponding size of the dermal punch. Calculations are made using the following formula:

[Open area on day 8]–[Open area on day 1]/[Open area on day 1]

Specimens are fixed in 10% buffered formalin and paraffin embedded blocks are sectioned perpendicular to the wound surface (5 mm) and cut using a Reichert-Jung microtome. Routine hematoxylin-eosin (H&E) staining is performed on cross-sections of bisected wounds. Histologic examination of the wounds are used to assess whether the healing process and the morphologic appearance of the repaired skin is altered by treatment with a polypeptide of the invention. This assessment included verification of the presence of cell accumulation, inflammatory cells, capillaries, fibroblasts, re-epithelialization and epidermal maturity (Greenhalgh, D. G. et al., Am. J. Pathol. 136:1235 (1990)). A calibrated lens micrometer is used by a blinded observer.

Tissue sections are also stained immunohistochemically with a polyclonal rabbit anti-human keratin antibody using ABC Elite detection system. Human skin is used as a positive tissue control while non-immune IgG is used as a negative control. Keratinocyte growth is determined by evaluating the extent of reepithelialization of the wound using a calibrated lens micrometer.

Proliferating cell nuclear antigen/cyclin (PCNA) in skin specimens is demonstrated by using anti-PCNA antibody (1:50) with an ABC Elite detection system. Human colon cancer can serve as a positive tissue control and human brain tissue can be used as a negative tissue control. Each specimen includes a section with omission of the primary antibody and substitution with non-immune mouse IgG. Ranking of these sections is based on the extent of proliferation on a scale of 0–8, the lower side of the scale reflecting slight proliferation to the higher side reflecting intense proliferation.

Experimental data are analyzed using an unpaired t test. A p value of <0.05 is considered significant.

B. Steroid Impaired Rat Model

The inhibition of wound healing by steroids has been well documented in various in vitro and in vivo systems (Wahl, Glucocorticoids and Wound healing. In: Anti-Inflammatory Steroid Action: Basic and Clinical Aspects. 280–302 (1989); Wahl et al., J. Immunol. 115: 476–481 (1975); Werb et al., J. Exp. Med. 147:1684–1694 (1978)). Glucocorticoids retard wound healing by inhibiting angiogenesis, decreasing vascular permeability (Ebert et al., An. Intern. Med. 37:701–705 (1952)), fibroblast proliferation, and collagen synthesis (Beck et al., Growth Factors. 5: 295–304 (1991); Haynes et al., J. Clin. Invest. 61: 703–797 (1978)) and producing a transient reduction of circulating monocytes (Haynes et al., J. Clin. Invest. 61: 703–797 (1978); Wahl, "Glucocorticoids and wound healing", In: Antiinflammatory Steroid Action: Basic and Clinical Aspects, Academic Press, New York, pp. 280–302 (1989)). The systemic administration of steroids to impaired wound healing is a well establish phenomenon in rats (Beck et al., Growth Factors. 5: 295–304 (1991); Haynes et al., J. Clin. Invest. 61: 703–797 (1978); Wahl, "Glucocorticoids and wound healing", In: Antiinflammatory Steroid Action: Basic and Clinical Aspects, Academic Press, New York, pp. 280–302 (1989); Pierce et al., Proc. Natl. Acad. Sci. USA 86: 2229–2233 (1989)).

To demonstrate that a polypeptide of the invention can accelerate the healing process, the effects of multiple topical applications of the polypeptide on full thickness excisional skin wounds in rats in which healing has been impaired by the systemic administration of methylprednisolone is assessed.

Young adult male Sprague Dawley rats weighing 250–300 g (Charles River Laboratories) are used in this example. The animals are purchased at 8 weeks of age and are 9 weeks old at the beginning of the study. The healing response of rats is impaired by the systemic administration of methylprednisolone (17 mg/kg/rat intramuscularly) at the time of wounding. Animals are individually housed and received food and water ad libitum. All manipulations are performed using aseptic techniques. This study would be conducted according to the rules and guidelines of Bristol-Myers Squibb Corporations Guidelines for the Care and Use of Laboratory Animals.

The wounding protocol is followed according to section A, above. On the day of wounding, animals are anesthetized with an intramuscular injection of ketamine (50 mg/kg) and xylazine (5 mg/kg). The dorsal region of the animal is shaved and the skin washed with 70% ethanol and iodine solutions. The surgical area is dried with sterile gauze prior to wounding. An 8 mm full-thickness wound is created using a Keyes tissue punch. The wounds are left open for the duration of the experiment. Applications of the testing materials are given topically once a day for 7 consecutive days commencing on the day of wounding and subsequent to methylprednisolone administration. Prior to treatment, wounds are gently cleansed with sterile saline and gauze sponges.

Wounds are visually examined and photographed at a fixed distance at the day of wounding and at the end of treatment. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

The polypeptide of the invention is administered using at a range different doses, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology. Tissue specimens are placed in 10% neutral buffered formalin in tissue cassettes between biopsy sponges for further processing.

Four groups of 10 animals each (5 with methylprednisolone and 5 without glucocorticoid) are evaluated: 1) Untreated group 2) Vehicle placebo control 3) treated groups.

Wound closure is analyzed by measuring the area in the vertical and horizontal axis and obtaining the total area of the wound. Closure is then estimated by establishing the differences between the initial wound area (day 0) and that of post treatment (day 8). The wound area on day 1 is 64 mm2, the corresponding size of the dermal punch. Calculations are made using the following formula:

$$[\text{Open area on day 8}] - [\text{Open area on day 1}] / [\text{Open area on day 1}]$$

Specimens are fixed in 10% buffered formalin and paraffin embedded blocks are sectioned perpendicular to the wound surface (5 mm) and cut using an Olympus microtome. Routine hematoxylin-eosin (H&E) staining is performed on cross-sections of bisected wounds. Histologic examination of the wounds allows assessment of whether the healing process and the morphologic appearance of the repaired skin is improved by treatment with a polypeptide of the invention. A calibrated lens micrometer is used by a blinded observer to determine the distance of the wound gap.

Experimental data are analyzed using an unpaired t test. A p value of <0.05 is considered significant.

One skilled in the art could easily modify the exemplified studies to test the activity of polynucleotides of the invention (e.g., gene therapy), agonists, and/or antagonists of polynucleotides or polypeptides of the invention.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

TABLE IV

| Atom No | Residue | Atom name | x coord | y coord | z coord |
|---|---|---|---|---|---|
| 1 | LYS12 | N | −27.2159 | 19.7201 | −6.2824 |
| 2 | LYS12 | CA | −26.6971 | 18.4591 | −5.7744 |
| 3 | LYS12 | C | −27.7349 | 17.3482 | −5.7385 |
| 4 | LYS12 | O | −27.4109 | 16.2063 | −6.0352 |
| 5 | LYS12 | CB | −26.1266 | 18.6653 | −4.3594 |
| 6 | LYS12 | CG | −24.7332 | 18.0137 | −4.2714 |
| 7 | LYS12 | CD | −24.8483 | 16.4855 | −4.433 |
| 8 | LYS12 | CE | −23.4439 | 15.8647 | −4.5476 |
| 9 | LYS12 | NZ | −22.7011 | 16.0707 | −3.2959 |
| 10 | LEU13 | N | −28.9809 | 17.682 | −5.4127 |
| 11 | LEU13 | CA | −30.064 | 16.6951 | −5.4047 |
| 12 | LEU13 | C | −30.2537 | 16.2158 | −6.8405 |
| 13 | LEU13 | O | −30.3861 | 15.0234 | −7.0985 |
| 14 | LEU13 | CB | −31.3563 | 17.3552 | −4.8907 |
| 15 | LEU13 | CG | −31.1721 | 17.7804 | −3.421 |
| 16 | LEU13 | CD1 | −32.4543 | 18.4737 | −2.9249 |
| 17 | LEU13 | CD2 | −30.8835 | 16.5465 | −2.5441 |
| 18 | ALA14 | N | −30.2416 | 17.1744 | −7.7676 |
| 19 | ALA14 | CA | −30.3825 | 16.9101 | −9.195 |
| 20 | ALA14 | C | −29.2866 | 15.9587 | −9.6613 |
| 21 | ALA14 | O | −29.5553 | 14.9807 | −10.3628 |
| 22 | ALA14 | CB | −30.3313 | 18.232 | −9.9835 |
| 23 | PRO15 | N | −28.0569 | 16.2571 | −9.2419 |
| 24 | PRO15 | CA | −26.8772 | 15.4556 | −9.563 |
| 25 | PRO15 | C | −27.029 | 14.0783 | −8.9231 |
| 26 | PRO15 | O | −26.6765 | 13.0642 | −9.5273 |
| 27 | PRO15 | CB | −25.7231 | 16.2219 | −8.8922 |
| 28 | PRO15 | CG | −26.2623 | 17.6337 | −8.5936 |
| 29 | PRO15 | CD | −27.7987 | 17.5229 | −8.5821 |
| 30 | ARG16 | N | −27.58 | 14.0482 | −7.7102 |
| 31 | ARG16 | CA | −27.7908 | 12.7957 | −6.9958 |
| 32 | ARG16 | C | −28.7852 | 11.9184 | −7.7336 |
| 33 | ARG16 | O | −28.7192 | 10.6897 | −7.6578 |
| 34 | ARG16 | CB | −28.4328 | 13.1445 | −5.6398 |
| 35 | ARG16 | CG | −27.3904 | 13.7645 | −4.6917 |
| 36 | ARG16 | CD | −28.1224 | 14.4083 | −3.4996 |
| 37 | ARG16 | NE | −27.4893 | 15.6684 | −3.1552 |
| 38 | ARG16 | CZ | −26.8721 | 15.823 | −2.0196 |
| 39 | ARG16 | NH1 | −26.3196 | 16.9665 | −1.7426 |
| 40 | ARG16 | NH2 | −26.797 | 14.8537 | −1.1553 |
| 41 | TYR17 | N | −29.9822 | 12.8509 | −8.5832 |
| 42 | TYR17 | CA | −30.4267 | 11.5765 | −9.1118 |
| 43 | TYR17 | C | −29.9697 | 11.2849 | −10.5385 |
| 44 | TYR17 | O | −30.2553 | 10.2132 | −11.0727 |
| 45 | TYR17 | CB | −31.971 | 11.5383 | −9.0666 |
| 46 | TYR17 | CG | −32.529 | 12.9543 | −8.9375 |
| 47 | TYR17 | CD1 | −32.5301 | 13.8102 | −10.0419 |
| 48 | TYR17 | CD2 | −33.0158 | 13.3997 | −7.706 |
| 49 | TYR17 | CE1 | −32.8944 | 15.1493 | −9.8813 |
| 50 | TYR17 | CE2 | −33.3803 | 14.7389 | −7.5456 |
| 51 | TYR17 | CZ | −33.287 | 15.6204 | −8.6256 |
| 52 | TYR17 | OH | −33.5844 | 16.9663 | −8.4507 |
| 53 | GLN28 | N | −17.3167 | 19.6634 | −20.9577 |
| 54 | GLN28 | CA | −16.6717 | 19.1545 | −22.1761 |
| 55 | GLN28 | C | −17.6399 | 18.3959 | −23.1004 |
| 56 | GLN28 | O | −17.691 | 18.6208 | −24.3087 |
| 57 | GLN28 | CB | −15.9024 | 20.2732 | −22.9059 |
| 58 | GLN28 | CG | −16.8571 | 21.4214 | −23.2838 |
| 59 | GLN28 | CD | −16.0631 | 22.5632 | −23.8481 |
| 60 | GLN28 | OE1 | −16.2528 | 22.9559 | −24.9971 |
| 61 | GLN28 | NE2 | −15.1606 | 23.145 | −23.0375 |
| 62 | ASP29 | N | −17.812 | 18.2585 | −24.2329 |
| 63 | ASP29 | CA | −18.2937 | 17.1126 | −24.9955 |
| 64 | ASP29 | C | −17.3081 | 16.7493 | −26.0905 |
| 65 | ASP29 | O | −17.1225 | 17.4942 | −27.052 |
| 66 | ASP29 | CB | −19.7095 | 17.3082 | −25.5761 |
| 67 | ASP29 | CG | −20.2664 | 15.967 | −25.9577 |
| 68 | ASP29 | OD1 | −21.0819 | 15.42 | −25.1689 |
| 69 | ASP29 | OD2 | −19.8983 | 15.4607 | −27.0508 |
| 70 | PHE30 | N | −16.6686 | 15.5986 | −25.92 |
| 71 | PHE30 | CA | −15.6883 | 15.1073 | −26.876 |
| 72 | PHE30 | C | −16.2374 | 15.0541 | −28.2917 |
| 73 | PHE30 | O | −15.5848 | 15.4889 | −29.2215 |
| 74 | PHE30 | CB | −15.0913 | 13.7425 | −26.4865 |
| 75 | PHE30 | CG | −13.9312 | 13.4564 | −27.4363 |
| 76 | PHE30 | CD1 | −12.8189 | 14.302 | −27.4553 |
| 77 | PHE30 | CD2 | −13.9836 | 12.3569 | −28.2963 |
| 78 | PHE30 | CE1 | −11.7856 | 14.0734 | −28.367 |
| 79 | PHE30 | CE2 | −12.9192 | 12.0914 | −29.1615 |
| 80 | PHE30 | CZ | −11.8222 | 12.9557 | −29.2041 |
| 81 | GLU31 | N | −17.4227 | 14.4765 | −28.4391 |
| 82 | GLU31 | CA | −18.0695 | 14.3384 | −29.74 |
| 83 | GLU31 | C | −18.4961 | 15.6958 | −30.2978 |
| 84 | GLU31 | O | −18.1746 | 16.0281 | −31.4366 |
| 85 | GLU31 | CB | −19.3248 | 13.4596 | −29.5707 |
| 86 | GLU31 | CG | −18.9969 | 12.1952 | −28.7512 |
| 87 | GLU31 | CD | −19.1929 | 12.4724 | −27.2876 |
| 88 | GLU31 | OE1 | −20.3728 | 12.5627 | −26.8547 |
| 89 | GLU31 | OE2 | −18.1684 | 12.5927 | −26.5636 |
| 90 | ALA32 | N | −19.1724 | 16.4914 | −29.4728 |
| 91 | ALA32 | CA | −19.6256 | 17.817 | −29.8767 |
| 92 | ALA32 | C | −18.4792 | 18.7175 | −30.3487 |
| 93 | ALA32 | O | −18.5771 | 19.3496 | −31.4051 |
| 94 | ALA32 | CB | −20.3076 | 18.4749 | −28.6631 |
| 95 | LEU33 | N | −17.3954 | 18.7607 | −29.5751 |
| 96 | LEU33 | CA | −16.2231 | 19.5772 | −29.9031 |
| 97 | LEU33 | C | −15.4331 | 19.0228 | −31.0884 |
| 98 | LEU33 | O | −14.8897 | 19.7818 | −31.891 |
| 99 | LEU33 | CB | −15.3011 | 19.5611 | −28.6684 |
| 100 | LEU33 | CG | −16.0154 | 20.2097 | −27.4667 |
| 101 | LEU33 | CD1 | −15.182 | 19.9944 | −26.1896 |
| 102 | LEU33 | CD2 | −16.1953 | 21.7178 | −27.7216 |
| 103 | LEU34 | N | −15.3571 | 17.6969 | −31.1802 |
| 104 | LEU34 | CA | −14.6678 | 17.0334 | −32.2855 |
| 105 | LEU34 | C | −15.4723 | 17.3381 | −33.5408 |
| 106 | LEU34 | O | −14.9271 | 17.7085 | −34.5669 |
| 107 | LEU34 | CB | −14.7381 | 15.5166 | −32.0247 |
| 108 | LEU34 | CG | −14.4308 | 14.8282 | −32.4594 |
| 109 | LEU34 | CD1 | −13.4802 | 13.3423 | −32.0608 |
| 110 | LEU34 | CD2 | −13.2453 | 14.9435 | −33.9839 |
| 111 | ALA35 | N | −16.7854 | 17.2046 | −33.4234 |
| 112 | ALA35 | CA | −17.7074 | 17.4638 | −34.5157 |
| 113 | ALA35 | C | −17.5894 | 18.9123 | −34.9803 |
| 114 | ALA35 | O | −17.5165 | 19.1899 | −36.1781 |
| 115 | ALA35 | CB | −19.1407 | 17.2174 | −34.0109 |
| 116 | GLU36 | N | −17.5819 | 18.8209 | −34.0104 |
| 117 | GLU36 | CA | −17.4616 | 21.2591 | −34.2319 |
| 118 | GLU36 | C | −16.2171 | 21.5709 | −35.0692 |
| 119 | GLU36 | O | −16.2857 | 22.2732 | −36.0777 |
| 120 | GLU36 | CB | −17.5366 | 21.903 | −32.8349 |
| 121 | GLU36 | CG | −16.8291 | 23.3574 | −32.9143 |
| 122 | GLU36 | CD | −15.3265 | 23.3815 | −32.8896 |
| 123 | GLU36 | OE1 | −14.7352 | 22.8224 | −31.927 |
| 124 | GLU36 | OE2 | −14.7316 | 23.9054 | −33.8408 |
| 125 | CYS37 | N | −15.0851 | 21.0145 | −34.6518 |
| 126 | CYS37 | CA | −13.8228 | 21.2122 | −35.3467 |
| 127 | CYS37 | C | −13.8265 | 20.4262 | −36.6526 |
| 128 | CYS37 | O | −13.2082 | 20.8268 | −37.6325 |
| 129 | CYS37 | CB | −12.7031 | 20.6447 | −34.4549 |
| 130 | CYS37 | SG | −11.7988 | 22.0477 | −33.7396 |
| 131 | LEU38 | N | −14.5137 | 19.2872 | −36.6354 |
| 132 | LEU38 | CA | −14.6365 | 18.4176 | −37.7991 |
| 133 | LEU38 | C | −15.2427 | 19.2608 | −38.8935 |
| 134 | LEU38 | O | −14.7294 | 19.3257 | −40.0108 |
| 135 | LEU38 | CB | −15.5583 | 17.2359 | −37.4444 |
| 136 | LEU38 | CG | −14.8353 | 15.9028 | −37.7188 |
| 137 | LEU38 | CD1 | −13.5226 | 18.8275 | −36.9155 |
| 138 | LEU38 | CD2 | −15.7503 | 14.7352 | −37.3062 |
| 139 | ARG39 | N | −16.3056 | 19.9654 | −38.5243 |
| 140 | ARG39 | CA | −17.0297 | 20.8292 | −39.4381 |
| 141 | ARG39 | C | −16.244 | 22.0579 | −39.8902 |
| 142 | ARG39 | O | −15.9049 | 22.1629 | −41.0629 |
| 143 | ARG39 | CB | −18.3186 | 21.316 | −38.7483 |
| 144 | ARG39 | CG | −19.1868 | 20.1166 | −38.3268 |
| 145 | ARG39 | CD | −20.103 | 20.5459 | −37.1664 |
| 146 | ARG39 | NE | −20.3672 | 19.4053 | −36.3068 |
| 147 | ARG39 | CZ | −21.5716 | 18.9628 | −36.1218 |
| 148 | ARG39 | NH1 | −21.7652 | 17.9388 | −35.3449 |
| 149 | ARG39 | NH2 | −22.5913 | 19.5263 | −36.7005 |
| 150 | ASN40 | N | −15.8973 | 22.9463 | −38.9598 |
| 151 | ASN40 | CA | −15.158 | 24.169 | −39.2938 |
| 152 | ASN40 | C | −13.7759 | 23.9349 | −39.8974 |
| 153 | ASN40 | O | −13.082 | 24.8845 | −40.2596 |
| 154 | ASN40 | CB | −14.9873 | 25.0138 | −38.0155 |

TABLE IV-continued

| Atom No | Residue | Atom name | x coord | y coord | z coord |
|---|---|---|---|---|---|
| 155 | ASN40 | CG | −16.3169 | 25.3188 | −37.3873 |
| 156 | ASN40 | OD1 | −16.5252 | 25.0099 | −36.2256 |
| 157 | ASN40 | ND2 | −17.2341 | 25.9335 | −38.1556 |
| 158 | GLY41 | N | −13.3893 | 22.667 | −40.0176 |
| 159 | GLY41 | CA | −12.0967 | 22.3184 | −40.5824 |
| 160 | GLY41 | C | −10.9452 | 22.9275 | −39.8082 |
| 161 | GLY41 | O | −10.0967 | 23.6122 | −40.3791 |
| 162 | CYS42 | N | −10.9167 | 22.6693 | −38.5057 |
| 163 | CYS42 | CA | −9.8803 | 23.2064 | −37.6375 |
| 164 | CYS42 | C | −9.4616 | 22.2276 | −36.5439 |
| 165 | CYS42 | O | −9.9692 | 21.1126 | −36.4619 |
| 166 | CYS42 | CB | −10.4265 | 24.4707 | −36.9437 |
| 167 | CYS42 | SG | −10.753 | 25.7585 | −38.1837 |
| 168 | LEU43 | N | −8.5193 | 22.6577 | −35.7118 |
| 169 | LEU43 | CA | −8.0132 | 21.8337 | −34.6213 |
| 170 | LEU43 | C | −8.4703 | 22.3473 | −33.2651 |
| 171 | LEU43 | O | −8.5778 | 23.5611 | −33.0479 |
| 172 | LEU43 | CB | −6.4773 | 21.7117 | −34.6571 |
| 173 | LEU43 | CG | −5.9576 | 21.4349 | −36.0819 |
| 174 | LEU43 | CD1 | −4.4199 | 21.3664 | −36.0489 |
| 175 | LEU43 | CD2 | −6.5092 | 20.0994 | −36.615 |
| 176 | PHE44 | N | −8.6955 | 21.4162 | −32.3455 |
| 177 | PHE44 | CA | −9.1464 | 21.7627 | −31.0043 |
| 178 | PHE44 | C | −8.0883 | 22.4337 | −30.1214 |
| 179 | PHE44 | O | −6.9495 | 21.9754 | −29.9899 |
| 180 | PHE44 | CB | −9.8202 | 20.5294 | −30.3676 |
| 181 | PHE44 | CG | −9.882 | 20.6174 | −28.8472 |
| 182 | PHE44 | CD1 | −10.7478 | 21.5258 | −28.233 |
| 183 | PHE44 | CD2 | −9.0725 | 19.7821 | −28.073 |
| 184 | PHE44 | CE1 | −10.8371 | 21.5679 | −26.8396 |
| 185 | PHE44 | CE2 | −9.1608 | 19.8264 | −26.6796 |
| 186 | PHE44 | CZ | −10.0598 | 20.7022 | −26.0661 |
| 187 | GLU45 | N | −8.4811 | 23.5795 | −29.5902 |
| 188 | GLU45 | CA | −7.6634 | 24.3474 | −28.6926 |
| 189 | GLU45 | C | −8.5174 | 24.3954 | −27.4403 |
| 190 | GLU45 | O | −9.5537 | 25.0596 | −27.3985 |
| 191 | GLU45 | CB | −7.4462 | 25.7576 | −29.2734 |
| 192 | GLU45 | CG | −6.7926 | 25.6599 | −30.6663 |
| 193 | GLU45 | CD | −5.4031 | 25.1005 | −30.5591 |
| 194 | GLU45 | OE1 | −4.5005 | 25.842 | −30.0872 |
| 195 | GLU45 | OE2 | −5.2083 | 23.9213 | −30.9566 |
| 196 | ASP46 | N | −8.1279 | 23.5759 | −26.4713 |
| 197 | ASP46 | CA | −8.8271 | 23.4565 | −25.2064 |
| 198 | ASP46 | C | −8.9745 | 24.79 | −24.4679 |
| 199 | ASP46 | O | −7.9792 | 25.4257 | −24.1015 |
| 200 | ASP46 | CB | −7.9973 | 22.5011 | −24.3257 |
| 201 | ASP46 | CG | −8.8587 | 21.8017 | −23.3145 |
| 202 | ASP46 | OD1 | −9.4405 | 22.4985 | −22.4406 |
| 203 | ASP46 | OD2 | −8.9499 | 20.5471 | −23.39 |
| 204 | THR47 | N | −10.2319 | 25.236 | −24.2636 |
| 205 | THR47 | CA | −10.5788 | 26.4827 | −23.5731 |
| 206 | THR47 | C | −10.5448 | 26.3291 | −22.0414 |
| 207 | THR47 | O | −10.6702 | 27.3036 | −21.297 |
| 208 | THR47 | CB | −11.991 | 26.9051 | −24.0256 |
| 209 | THR47 | OG1 | −12.0685 | 26.8763 | −25.4538 |
| 210 | THR47 | CG2 | −12.2993 | 28.3333 | −23.5373 |
| 211 | SER48 | N | −10.3562 | 25.0947 | −21.5841 |
| 212 | SER48 | CA | −10.3202 | 24.7963 | −20.1625 |
| 213 | SER48 | C | −8.9327 | 24.3765 | −19.7007 |
| 214 | SER48 | O | −8.7044 | 24.1661 | −18.5061 |
| 215 | SER48 | CB | −11.3054 | 23.6448 | −19.8871 |
| 216 | SER48 | OG | −12.6213 | 24.0291 | −20.2945 |
| 217 | PHE49 | N | −8.0123 | 24.2454 | −20.6548 |
| 218 | PHE49 | CA | −6.6453 | 23.8505 | −20.3588 |
| 219 | PHE49 | C | −5.7089 | 24.3915 | −21.4418 |
| 220 | PHE49 | O | −5.1154 | 23.6305 | −22.2142 |
| 221 | PHE49 | CB | −6.5801 | 22.3116 | −20.2651 |
| 222 | PHE49 | CG | −5.3298 | 21.8633 | −19.5126 |
| 223 | PHE49 | CD1 | −5.3312 | 21.8194 | −18.1156 |
| 224 | PHE49 | CD2 | −4.1833 | 21.4888 | −20.2187 |
| 225 | PHE49 | CE1 | −4.1956 | 21.3837 | −17.4269 |
| 226 | PHE49 | CE2 | −3.047 | 21.0549 | −19.5305 |
| 227 | PHE49 | CZ | −3.0541 | 20.9974 | −18.1343 |
| 228 | PRO50 | N | −5.5643 | 25.7267 | −21.5041 |
| 229 | PRO50 | CA | −4.7293 | 26.4558 | −22.4561 |
| 230 | PRO50 | C | −3.2687 | 26.0165 | −22.478 |
| 231 | PRO50 | O | −2.7439 | 25.4808 | −21.4869 |
| 232 | PRO50 | CB | −4.8313 | 27.9279 | −22.0172 |
| 233 | PRO50 | CG | −5.8165 | 27.9803 | −20.831 |
| 234 | PRO50 | CD | −6.2821 | 26.5397 | −20.5405 |
| 235 | ALA51 | N | −2.6121 | 26.2739 | −23.6058 |
| 236 | ALA51 | CA | −1.2098 | 25.9377 | −23.7851 |
| 237 | ALA51 | C | −0.3497 | 26.9614 | −23.0391 |
| 238 | ALA51 | O | 0.7223 | 27.3612 | −23.5021 |
| 239 | ALA51 | CB | −0.8481 | 25.8622 | −25.281 |
| 240 | THR52 | N | −0.8405 | 27.3848 | −21.8767 |
| 241 | THR52 | CA | −0.1559 | 28.3625 | −21.0525 |
| 242 | THR52 | C | 0.6958 | 27.7065 | −19.9669 |
| 243 | THR52 | O | 0.709 | 26.4813 | −19.8398 |
| 244 | THR52 | CB | −1.2136 | 29.2515 | −20.369 |
| 245 | THR52 | OG1 | −2.0784 | 28.4487 | −19.5588 |
| 246 | THR52 | CG2 | −2.0467 | 29.9875 | −21.4353 |
| 247 | LEU53 | N | 1.5163 | 28.5131 | −19.2586 |
| 248 | LEU53 | CA | 2.3863 | 28.037 | −18.1786 |
| 249 | LEU53 | C | 1.5758 | 27.5585 | −16.9718 |
| 250 | LEU53 | O | 2.0681 | 26.7947 | −16.1515 |
| 251 | LEU53 | CB | 3.3336 | 29.1723 | −17.7501 |
| 252 | LEU53 | CG | 4.6099 | 29.1306 | −18.6121 |
| 253 | LEU53 | CD1 | 5.5137 | 30.3224 | −18.247 |
| 254 | LEU53 | CD2 | 5.3734 | 27.8177 | −18.3543 |
| 255 | SER54 | N | 0.3319 | 28.0127 | −16.8819 |
| 256 | SER54 | CA | −0.569 | 27.6427 | −15.7938 |
| 257 | SER54 | C | −0.9496 | 26.1564 | −15.8412 |
| 258 | SER54 | O | −1.2905 | 25.5583 | −14.8192 |
| 259 | SER54 | CB | −1.8575 | 28.4696 | −15.9596 |
| 260 | SER54 | OG | −1.5491 | 29.864 | −15.8839 |
| 261 | SER55 | N | −0.9164 | 25.584 | −17.0444 |
| 262 | SER55 | CA | −1.2204 | 24.1714 | −17.2571 |
| 263 | SER55 | C | −0.0414 | 23.3364 | −16.7588 |
| 264 | SER55 | O | −0.2092 | 22.2061 | −16.2832 |
| 265 | SER55 | CB | −1.469 | 23.9085 | −18.7566 |
| 266 | SER55 | OG | −0.2429 | 23.9254 | −19.4941 |
| 267 | ILE56 | N | 1.1563 | 23.8991 | −16.9025 |
| 268 | ILE56 | CA | 2.3905 | 23.2585 | −16.4678 |
| 269 | ILE56 | C | 2.5322 | 23.3656 | −14.9373 |
| 270 | ILE56 | O | 2.886 | 22.3901 | −14.2855 |
| 271 | ILE56 | CB | 3.5575 | 23.9946 | −17.1549 |
| 272 | ILE56 | CG1 | 3.3514 | 23.9704 | −18.6829 |
| 273 | ILE56 | CG2 | 4.8919 | 23.3115 | −16.798 |
| 274 | ILE56 | CD1 | 4.3716 | 24.8964 | −19.3715 |
| 275 | GLY57 | N | 2.2641 | 24.5079 | −14.3713 |
| 276 | GLY57 | CA | 2.3598 | 24.7298 | −12.9266 |
| 277 | GLY57 | C | 3.7996 | 24.4235 | −12.4989 |
| 278 | GLY57 | O | 4.2274 | 23.2821 | −12.5859 |
| 279 | LEU65 | N | 12.3115 | 25.9569 | −15.7051 |
| 280 | LEU65 | CA | 12.1314 | 24.6761 | −16.4042 |
| 281 | LEU65 | C | 11.0916 | 24.8704 | −17.538 |
| 282 | LEU65 | O | 11.2794 | 24.3854 | −18.6495 |
| 283 | LEU65 | CB | 11.5248 | 23.6404 | −15.4356 |
| 284 | LEU65 | CG | 12.5547 | 23.1647 | −14.3945 |
| 285 | LEU65 | CD1 | 11.8521 | 22.277 | −13.351 |
| 286 | LEU65 | CD2 | 13.6664 | 22.3566 | −15.0896 |
| 287 | PRO66 | N | 10.0696 | 25.653 | −17.3149 |
| 288 | PRO66 | CA | 9.0282 | 25.8331 | −18.322 |
| 289 | PRO66 | C | 9.2286 | 27.0866 | −19.1893 |
| 290 | PRO66 | O | 8.2609 | 27.7518 | −19.5641 |
| 291 | PRO66 | CB | 7.7834 | 26.0207 | −17.4333 |
| 292 | PRO66 | CG | 8.2941 | 26.5192 | −16.0641 |
| 293 | PRO66 | CD | 9.8033 | 26.2118 | −16.0068 |
| 294 | PRO67 | N | 10.4842 | 27.3788 | −19.5276 |
| 295 | PRO67 | CA | 10.8245 | 28.5473 | −20.3404 |
| 296 | PRO67 | C | 11.2929 | 28.1703 | −21.7447 |
| 297 | PRO67 | O | 12.161 | 27.3217 | −21.9075 |
| 298 | PRO67 | CB | 12.0302 | 29.1474 | −19.5952 |
| 299 | PRO67 | CG | 12.6726 | 27.9643 | −18.8471 |
| 300 | PRO67 | CD | 11.6812 | 26.7941 | −18.9858 |
| 301 | ARG68 | N | 10.701 | 28.7991 | −22.754 |
| 302 | ARG68 | CA | 11.0793 | 28.5286 | −24.135 |
| 303 | ARG68 | C | 10.7253 | 27.1529 | −24.6599 |
| 304 | ARG68 | O | 11.4609 | 26.5524 | −25.4496 |
| 305 | ARG68 | CB | 12.5578 | 28.8764 | −24.4017 |
| 306 | ARG68 | CG | 12.8181 | 30.3504 | −24.0425 |
| 307 | ARG68 | CD | 14.3237 | 30.6448 | −24.1658 |
| 308 | ARG68 | NE | 14.5854 | 31.9972 | −23.709 |

TABLE IV-continued

| Atom No | Residue | Atom name | x coord | y coord | z coord |
|---|---|---|---|---|---|
| 309 | ARG68 | CZ | 15.264 | 32.2199 | −22.6207 |
| 310 | ARG68 | NH1 | 15.4798 | 33.445 | −22.2438 |
| 311 | ARG68 | NH2 | 15.7293 | 31.2393 | −21.9035 |
| 312 | LEU69 | N | 9.5924 | 26.6432 | −24.2168 |
| 313 | LEU69 | CA | 9.1505 | 25.3393 | −24.6592 |
| 314 | LEU69 | C | 7.8526 | 25.4596 | −25.456 |
| 315 | LEU69 | O | 6.9058 | 26.1202 | −25.0331 |
| 316 | LEU69 | CB | 8.9084 | 24.3992 | −23.457 |
| 317 | LEU69 | CG | 8.7632 | 25.1657 | −22.1248 |
| 318 | LEU69 | CD1 | 7.4743 | 26.0088 | −22.1242 |
| 319 | LEU69 | CD2 | 8.7105 | 24.1644 | −20.9568 |
| 320 | GLN70 | N | 7.8405 | 24.8246 | −26.6228 |
| 321 | GLN70 | CA | 6.7115 | 24.8565 | −27.5489 |
| 322 | GLN70 | C | 5.7536 | 23.6717 | −27.4633 |
| 323 | GLN70 | O | 6.1667 | 22.5133 | −27.4887 |
| 324 | GLN70 | CB | 7.2115 | 24.9668 | −29.0024 |
| 325 | GLN70 | CG | 8.2553 | 26.0927 | −29.1291 |
| 326 | GLN70 | CD | 9.6245 | 25.5437 | −28.8497 |
| 327 | GLN70 | OE1 | 10.2487 | 25.9357 | −27.8779 |
| 328 | GLN70 | NE2 | 10.105 | 24.6265 | −29.7079 |
| 329 | TRP71 | N | 4.465 | 23.9829 | −27.3854 |
| 330 | TRP71 | CA | 3.4258 | 22.9642 | −27.3331 |
| 331 | TRP71 | C | 3.1746 | 22.4423 | −28.7393 |
| 332 | TRP71 | O | 2.4693 | 23.0698 | −29.5419 |
| 333 | TRP71 | CB | 2.1377 | 23.5984 | −26.7739 |
| 334 | TRP71 | CG | 2.312 | 23.8643 | −25.3078 |
| 335 | TRP71 | CD1 | 2.8263 | 24.9684 | −24.7439 |
| 336 | TRP71 | CD2 | 1.94 | 22.9265 | −24.192 |
| 337 | TRP71 | NE1 | 2.8321 | 24.8419 | −23.4397 |
| 338 | TRP71 | CE2 | 2.3239 | 23.6463 | −23.0764 |
| 339 | TRP71 | CE3 | 1.3639 | 21.6594 | −24.1194 |
| 340 | TRP71 | CZ2 | 2.1738 | 23.1341 | −21.788 |
| 341 | TRP71 | CZ3 | 1.2152 | 21.1334 | −22.8307 |
| 342 | TRP71 | CH2 | 1.6176 | 21.8522 | −21.6955 |
| 343 | LYS72 | N | 3.8006 | 21.3124 | −29.0428 |
| 344 | LYS72 | CA | 3.6586 | 20.6789 | −30.3357 |
| 345 | LYS72 | C | 2.6951 | 19.49 | −30.2769 |
| 346 | LYS72 | O | 2.6561 | 18.7499 | −29.2878 |
| 347 | LYS72 | CB | 5.0384 | 20.2965 | −30.9014 |
| 348 | LYS72 | CG | 5.9482 | 21.5389 | −30.8451 |
| 349 | LYS72 | CD | 7.3908 | 21.1728 | −31.2361 |
| 350 | LYS72 | CE | 8.3114 | 22.3529 | −30.8736 |
| 351 | LYS72 | NZ | 9.384 | 22.4688 | −31.8714 |
| 352 | ARG73 | N | 1.887 | 19.3481 | −31.3241 |
| 353 | ARG73 | CA | 0.9543 | 18.2391 | −31.4196 |
| 354 | ARG73 | C | 1.7324 | 17.134 | −32.1228 |
| 355 | ARG73 | O | 2.7467 | 17.4047 | −32.7786 |
| 356 | ARG73 | CB | −0.2282 | 18.6367 | −32.3243 |
| 357 | ARG73 | CG | −1.0143 | 19.8161 | −31.7239 |
| 358 | ARG73 | CD | −2.4537 | 19.344 | −31.4564 |
| 359 | ARG73 | NE | −3.4166 | 20.2295 | −32.081 |
| 360 | ARG73 | CZ | −4.5688 | 20.4563 | −31.5206 |
| 361 | ARG73 | NH1 | −4.888 | 19.8999 | −30.3895 |
| 362 | ARG73 | NH2 | −5.4157 | 21.2509 | −32.1024 |
| 363 | PRO74 | N | 1.299 | 15.8673 | −31.9654 |
| 364 | PRO74 | CA | 1.9489 | 14.7052 | −32.5823 |
| 365 | PRO74 | C | 2.1161 | 14.8143 | −34.1023 |
| 366 | PRO74 | O | 2.9741 | 14.1518 | −34.6932 |
| 367 | PRO74 | CB | 0.9333 | 13.5833 | −32.2893 |
| 368 | PRO74 | CG | −0.0003 | 14.0863 | −31.1698 |
| 369 | PRO74 | CD | 0.1523 | 15.6169 | −31.1164 |
| 370 | PRO75 | N | 1.2926 | 15.6575 | −34.7186 |
| 371 | PRO75 | CA | 1.316 | 15.8916 | −36.1551 |
| 372 | PRO75 | C | 2.6997 | 16.3246 | −36.5983 |
| 373 | PRO75 | O | 3.2238 | 15.8412 | −37.6031 |
| 374 | PRO75 | CB | 0.2915 | 17.0171 | −36.3851 |
| 375 | PRO75 | CG | −0.6163 | 17.027 | −35.1413 |
| 376 | PRO75 | CD | 0.1047 | 16.187 | −34.0712 |
| 377 | GLU76 | N | 3.2625 | 17.3134 | −35.8124 |
| 378 | GLU76 | CA | 4.4344 | 18.0945 | −36.1982 |
| 379 | GLU76 | C | 5.7322 | 17.2973 | −35.9839 |
| 380 | GLU76 | O | 6.7912 | 17.6086 | −36.527 |
| 381 | GLU76 | CB | 4.5004 | 19.329 | −35.2796 |
| 382 | GLU76 | CG | 3.3103 | 20.2616 | −35.5694 |
| 383 | GLU76 | CD | 2.2824 | 20.1052 | −34.4879 |
| 384 | GLU76 | OE1 | 2.3162 | 20.9111 | −33.5203 |
| 385 | GLU76 | OE2 | 1.4303 | 19.1867 | −34.6128 |
| 386 | LEU77 | N | 5.6511 | 16.3624 | −34.9705 |
| 387 | LEU77 | CA | 6.8391 | 15.8446 | −34.2955 |
| 388 | LEU77 | C | 7.4537 | 14.6814 | −35.0966 |
| 389 | LEU77 | O | 8.6507 | 14.4037 | −34.9876 |
| 390 | LEU77 | CB | 6.3855 | 15.2602 | −32.9414 |
| 391 | LEU77 | CG | 5.3161 | 16.1448 | −32.2704 |
| 392 | LEU77 | CD1 | 4.7594 | 15.4336 | −31.0233 |
| 393 | LEU77 | CD2 | 5.9284 | 17.4984 | −31.8652 |
| 394 | HIS78 | N | 6.5733 | 13.885 | −35.8006 |
| 395 | HIS78 | CA | 7.0516 | 12.7057 | −36.5296 |
| 396 | HIS78 | C | 6.221 | 12.4993 | −37.8079 |
| 397 | HIS78 | O | 5.1972 | 13.1305 | −38.0482 |
| 398 | HIS78 | CB | 6.9335 | 11.4315 | −35.6679 |
| 399 | HIS78 | CG | 7.2747 | 11.6999 | −34.231 |
| 400 | HIS78 | ND1 | 6.394 | 12.1963 | −33.3935 |
| 401 | HIS78 | CD2 | 8.4737 | 11.4727 | −33.6617 |
| 402 | HIS78 | CE1 | 6.9793 | 12.313 | −32.244 |
| 403 | HIS78 | NE2 | 8.1679 | 11.9184 | −32.3293 |
| 404 | SER79 | N | 6.744 | 11.5449 | −38.6654 |
| 405 | SER79 | CA | 6.2259 | 11.3421 | −40.0167 |
| 406 | SER79 | C | 4.9636 | 10.4715 | −40.0374 |
| 407 | SER79 | O | 4.1412 | 10.5656 | −40.9488 |
| 408 | SER79 | CB | 7.3217 | 10.6505 | −40.8505 |
| 409 | SER79 | OG | 7.6769 | 9.3977 | −40.2577 |
| 410 | ASN80 | N | 4.9115 | 9.4953 | −39.0614 |
| 411 | ASN80 | CA | 3.7097 | 8.6832 | −38.8418 |
| 412 | ASN80 | C | 3.3877 | 8.7954 | −37.3409 |
| 413 | ASN80 | O | 3.9182 | 8.0475 | −36.5135 |
| 414 | ASN80 | CB | 4.0308 | 7.2212 | −39.216 |
| 415 | ASN80 | CG | 2.8922 | 6.2781 | −38.9316 |
| 416 | ASN80 | OD1 | 1.8258 | 6.6843 | −38.4983 |
| 417 | ASN80 | ND2 | 3.1233 | 4.9769 | −39.1805 |
| 418 | PRO81 | N | 2.5675 | 9.8295 | −36.9434 |
| 419 | PRO81 | CA | 2.0432 | 9.8923 | −35.5806 |
| 420 | PRO81 | C | 0.9728 | 8.7992 | −35.4421 |
| 421 | PRO81 | O | −0.0481 | 8.7744 | −36.1332 |
| 422 | PRO81 | CB | 1.3513 | 11.2709 | −35.5758 |
| 423 | PRO81 | CG | 1.275 | 11.7676 | −37.0367 |
| 424 | PRO81 | CD | 2.1119 | 10.8087 | −37.9067 |
| 425 | GLN82 | N | 1.2765 | 7.8106 | −34.525 |
| 426 | GLN82 | CA | 0.2983 | 6.7865 | −34.207 |
| 427 | GLN82 | C | −0.3517 | 7.1645 | −32.8705 |
| 428 | GLN82 | O | 0.2082 | 7.817 | −31.9873 |
| 429 | GLN82 | CB | 1.0091 | 5.4307 | −34.0417 |
| 430 | GLN82 | CG | 1.6042 | 5.0014 | −35.3964 |
| 431 | GLN82 | CD | 0.583 | 4.3049 | −36.2521 |
| 432 | GLN82 | OE1 | −0.5485 | 4.1029 | −35.8418 |
| 433 | GLN82 | NE2 | 0.9893 | 3.9225 | −37.4754 |
| 434 | PHE83 | N | −1.6335 | 6.6481 | −32.7332 |
| 435 | PHE83 | CA | −2.2914 | 6.7368 | −31.4406 |
| 436 | PHE83 | C | −1.7335 | 5.594 | −30.5892 |
| 437 | PHE83 | O | −1.0996 | 5.8522 | −29.5679 |
| 438 | PHE83 | CB | −3.8224 | 6.6601 | −31.5886 |
| 439 | PHE83 | CG | −4.4571 | 7.7012 | −30.672 |
| 440 | PHE83 | CD1 | −4.1099 | 9.0492 | −30.7975 |
| 441 | PHE83 | CD2 | −5.3067 | 7.3067 | −29.7024 |
| 442 | PHE83 | CE1 | −4.6423 | 9.9939 | −29.9166 |
| 443 | PHE83 | CE2 | −5.929 | 8.2541 | −28.8324 |
| 444 | PHE83 | CZ | −5.5502 | 9.5954 | −28.9318 |
| 445 | ASP92 | N | 8.7138 | 1.3421 | −24.7856 |
| 446 | ASP92 | CA | 9.9333 | 2.1258 | −24.6143 |
| 447 | ASP92 | C | 11.0305 | 1.4805 | −25.5119 |
| 448 | ASP92 | O | 10.7546 | 0.699 | −26.4246 |
| 449 | ASP92 | CB | 10.407 | 2.1775 | −23.1449 |
| 450 | ASP92 | CG | 9.7248 | 3.2612 | −22.3582 |
| 451 | ASP92 | OD1 | 9.2374 | 4.2466 | −22.9756 |
| 452 | ASP92 | OD2 | 9.6647 | 3.1203 | −21.1075 |
| 453 | LEU93 | N | 12.3299 | 1.9183 | −25.302 |
| 454 | LEU93 | CA | 13.4513 | 1.2276 | −25.9597 |
| 455 | LEU93 | C | 13.9838 | 0.2162 | −24.9175 |
| 456 | LEU93 | O | 13.6738 | −0.9711 | −24.9345 |
| 457 | LEU93 | CB | 14.548 | 2.2237 | −26.3839 |
| 458 | LEU93 | CG | 13.9455 | 3.3288 | −27.2731 |
| 459 | LEU93 | CD1 | 15.0357 | 4.3611 | −27.6145 |
| 460 | LEU93 | CD2 | 13.3912 | 2.7184 | −28.5745 |
| 461 | CYS94 | N | 14.7737 | 0.7976 | −23.9419 |
| 462 | CYS94 | CA | 15.3553 | 0.0678 | −22.8027 |

TABLE IV-continued

| Atom No | Residue | Atom name | x coord | y coord | z coord | Atom No | Residue | Atom name | x coord | y coord | z coord |
|---|---|---|---|---|---|---|---|---|---|---|---|
| 463 | CYS94 | C | 15.5177 | 1.1607 | −21.7285 | 540 | LEU104 | C | 2.8276 | −1.3489 | −17.424 |
| 464 | CYS94 | O | 15.0841 | 1.0768 | −20.5819 | 541 | LEU104 | O | 2.6573 | −2.3938 | −18.0553 |
| 465 | CYS94 | CB | 16.7457 | −0.4768 | −23.1815 | 542 | LEU104 | CB | 5.1372 | −0.4506 | −17.0364 |
| 466 | CYS94 | SG | 16.5289 | −1.9599 | −24.2076 | 543 | LEU104 | CG | 6.3276 | 0.2252 | −17.7462 |
| 467 | GLN95 | N | 16.1911 | 2.2917 | −22.1814 | 544 | LEU104 | CD1 | 6.1177 | 1.7499 | −17.8154 |
| 468 | GLN95 | CA | 16.3642 | 3.4819 | −21.3572 | 545 | LEU104 | CD2 | 7.6261 | −0.0697 | −16.973 |
| 469 | GLN95 | C | 15.0323 | 4.2548 | −21.3495 | 546 | ALA105 | N | 2.1932 | −1.0749 | −16.2233 |
| 470 | GLN95 | O | 14.8373 | 5.2658 | −22.0181 | 547 | ALA105 | CA | 1.1276 | −1.9355 | −15.7244 |
| 471 | GLN95 | CB | 17.487 | 4.3453 | −21.962 | 548 | ALA105 | C | −0.1106 | −1.8301 | −16.6245 |
| 472 | GLN95 | CG | 18.8381 | 3.6285 | −21.7829 | 549 | ALA105 | O | −0.8567 | −2.7933 | −16.8042 |
| 473 | GLN95 | CD | 19.9443 | 4.4988 | −22.304 | 550 | ALA105 | CB | 0.7518 | −1.4414 | −14.3154 |
| 474 | GLN95 | OE1 | 20.6087 | 4.1307 | −23.2586 | 551 | ALA106 | N | −0.3581 | −0.5791 | −17.1656 |
| 475 | GLN95 | NE2 | 20.1536 | 5.6691 | −21.6745 | 552 | ALA106 | CA | −1.487 | −0.3921 | −18.0657 |
| 476 | GLY96 | N | 14.0855 | 3.7102 | −20.5023 | 553 | ALA106 | C | −1.22 | −1.1369 | −19.392 |
| 477 | GLY96 | CA | 12.7456 | 4.2719 | −20.3779 | 554 | ALA106 | O | −2.1309 | −1.6826 | −20.017 |
| 478 | GLY96 | C | 12.6237 | 5.1896 | −19.1601 | 555 | ALA106 | CB | −1.5879 | 1.1155 | −18.3643 |
| 479 | GLY96 | O | 11.5433 | 5.522 | −18.6759 | 556 | LEU107 | N | 0.0829 | −1.0988 | −19.8597 |
| 480 | ILE97 | N | 13.8142 | 5.7522 | −18.7335 | 557 | LEU107 | CA | 0.4617 | −1.7496 | −21.1241 |
| 481 | ILE97 | CA | 13.9329 | 6.3569 | −17.4039 | 558 | LEU107 | C | 0.418 | −3.2763 | −20.9538 |
| 482 | ILE97 | C | 13.1112 | 7.6447 | −17.1971 | 559 | LEU107 | O | 0.1156 | −4.0209 | −21.8892 |
| 483 | ILE97 | O | 12.9717 | 8.1418 | −16.0811 | 560 | LEU107 | CB | 1.8699 | −1.2468 | −21.4836 |
| 484 | ILE97 | CB | 15.428 | 6.6321 | −17.1406 | 561 | LEU107 | CG | 1.7736 | 0.2519 | −21.8284 |
| 485 | ILE97 | CG1 | 16.2594 | 5.3785 | −17.4804 | 562 | LEU107 | CD1 | 3.1721 | 0.8904 | −21.8436 |
| 486 | ILE97 | CG2 | 15.6462 | 7.0035 | −15.6609 | 563 | LEU107 | CD2 | 1.0896 | 0.4491 | −23.1921 |
| 487 | ILE97 | CD1 | 17.7616 | 5.7174 | −17.456 | 564 | GLN108 | N | 0.7506 | −3.7767 | −19.7065 |
| 488 | VAL98 | N | 12.6429 | 8.2331 | −18.3549 | 565 | GLN108 | CA | 0.7222 | −5.2282 | −19.4859 |
| 489 | VAL98 | CA | 11.7495 | 9.3858 | −18.3377 | 566 | GLN108 | C | −0.7099 | −5.7747 | −19.7101 |
| 490 | VAL98 | C | 10.252 | 8.9878 | −18.3753 | 567 | GLN108 | O | −0.933 | −6.9481 | −20.0032 |
| 491 | VAL98 | O | 9.3646 | 9.8424 | −18.3641 | 568 | GLN108 | CB | 1.1255 | −5.4721 | −18.0208 |
| 492 | VAL98 | CB | 12.0704 | 10.3188 | −19.5223 | 569 | GLN108 | CG | 2.6571 | −5.3768 | −17.8879 |
| 493 | VAL98 | CG1 | 13.5084 | 10.8545 | −19.3896 | 570 | GLN108 | CD | 3.0337 | −5.1535 | −16.4519 |
| 494 | VAL98 | CG2 | 11.9206 | 9.5627 | −20.8569 | 571 | GLN108 | OE1 | 3.7327 | −4.2021 | −16.1437 |
| 495 | GLY99 | N | 9.9718 | 7.6392 | −18.4239 | 572 | GLN108 | NE2 | 2.5673 | −6.0397 | −15.5542 |
| 496 | GLY99 | CA | 8.6184 | 7.1278 | −18.3169 | 573 | ALA109 | N | −1.6921 | −4.8226 | −19.5244 |
| 497 | GLY99 | C | 8.2272 | 6.8629 | −16.8609 | 574 | ALA109 | CA | −3.1166 | −5.0242 | −19.7711 |
| 498 | GLY99 | O | 9.0457 | 6.6416 | −15.9726 | 575 | ALA109 | C | −3.5236 | −4.8583 | −21.2595 |
| 499 | ASP100 | N | 6.8553 | 6.8641 | −16.6641 | 576 | ALA109 | O | −4.7013 | −4.7503 | −21.6008 |
| 500 | ASP100 | CA | 6.2623 | 6.5337 | −15.3641 | 577 | ALA109 | CB | −3.9504 | −4.0865 | −18.8771 |
| 501 | ASP100 | C | 5.831 | 5.0446 | −15.3993 | 578 | LEU110 | N | −2.5076 | −5.0135 | −22.1825 |
| 502 | ASP100 | O | 5.6976 | 4.4108 | −16.4423 | 579 | LEU110 | CA | −2.7165 | −5.3006 | −23.6053 |
| 503 | ASP100 | CB | 5.0095 | 7.4013 | −15.1404 | 580 | LEU110 | C | −2.2962 | −6.7648 | −23.8919 |
| 504 | ASP100 | CG | 4.7068 | 7.4901 | −13.6731 | 581 | LEU110 | O | −1.8484 | −7.1455 | −24.9707 |
| 505 | ASP100 | OD1 | 5.1626 | 8.4764 | −13.0357 | 582 | LEU110 | CB | −1.9913 | −4.2966 | −24.5207 |
| 506 | ASP100 | OD2 | 4.0011 | 6.5834 | −13.1557 | 583 | LEU110 | CG | −2.7136 | −2.9386 | −24.4503 |
| 507 | CYS101 | N | 5.6063 | 4.4998 | −14.1533 | 584 | LEU110 | CD1 | −2.133 | −2.0943 | −23.2995 |
| 508 | CYS101 | CA | 5.5167 | 3.0637 | −13.8994 | 585 | LEU110 | CD2 | −2.5442 | −2.1967 | −25.7885 |
| 509 | CYS101 | C | 4.1114 | 2.4834 | −14.084 | 586 | ALA111 | N | −2.6269 | −7.6359 | −22.8693 |
| 510 | CYS101 | O | 3.9375 | 1.2843 | −14.319 | 587 | ALA111 | CA | −2.5563 | −9.0971 | −23.007 |
| 511 | CYS101 | CB | 6.0579 | 2.7259 | −12.4996 | 588 | ALA111 | C | −3.8628 | −9.5213 | −23.7149 |
| 512 | CYS101 | SG | 6.8261 | 1.0845 | −12.6355 | 589 | ALA111 | O | −4.7955 | −8.7411 | −23.9273 |
| 513 | TRP102 | N | 3.0511 | 3.3388 | −13.8879 | 590 | ALA111 | CB | −2.5057 | −9.7403 | −21.6089 |
| 514 | TRP102 | CA | 1.6744 | 2.8555 | −14.0637 | 591 | LEU112 | N | −3.9772 | −10.8455 | −24.0885 |
| 515 | TRP102 | C | 1.3911 | 2.5082 | −15.5374 | 592 | LEU112 | CA | −5.1466 | −11.3563 | −24.8259 |
| 516 | TRP102 | O | 0.521 | 1.7013 | −15.8714 | 593 | LEU112 | C | −6.3949 | −11.5635 | −23.9092 |
| 517 | TRP102 | CB | 0.7186 | 3.986 | −13.6263 | 594 | LEU112 | O | −7.2128 | −12.4664 | −24.0847 |
| 518 | TRP102 | CG | 0.7217 | 5.1136 | −14.6207 | 595 | LEU112 | CB | −4.7856 | −12.6517 | −25.5768 |
| 519 | TRP102 | CD1 | 1.4421 | 6.2439 | −14.5577 | 596 | LEU112 | CG | −4.4419 | −12.3208 | −27.0409 |
| 520 | TRP102 | CD2 | −0.0869 | 5.1729 | −15.889 | 597 | LEU112 | CD1 | −3.8983 | −13.5827 | −27.7356 |
| 521 | TRP102 | NE1 | 1.1984 | 6.9888 | −15.6076 | 598 | LEU112 | CD2 | −5.7085 | −11.8411 | −27.7752 |
| 522 | TRP102 | CE2 | 0.3029 | 6.3884 | −16.4185 | 599 | ILE116 | N | −8.104 | −3.5179 | −19.3071 |
| 523 | TRP102 | CE3 | −1.0105 | 4.334 | −16.5113 | 600 | ILE116 | CA | −8.2759 | −2.3901 | −18.3846 |
| 524 | TRP102 | CZ2 | −0.2065 | 6.8568 | −17.6295 | 601 | ILE116 | C | −7.8945 | −1.0951 | −19.1202 |
| 525 | TRP102 | CZ3 | −1.5256 | 4.7953 | −17.7289 | 602 | ILE116 | O | −8.4238 | −0.0119 | −18.8715 |
| 526 | TRP102 | CH2 | −1.1332 | 6.0272 | −18.2731 | 603 | ILE116 | CB | −7.2846 | −2.5885 | −17.2211 |
| 527 | PHE103 | N | 2.1799 | 3.1817 | −16.4499 | 604 | ILE116 | CG1 | −7.3947 | −4.0199 | −16.6603 |
| 528 | PHE103 | CA | 1.97 | 3.0654 | −17.8948 | 605 | ILE116 | CG2 | −7.5752 | −1.5673 | −16.1043 |
| 529 | PHE103 | C | 2.26 | 1.6029 | −18.2845 | 606 | ILE116 | CD1 | −6.1486 | −4.3382 | −15.8139 |
| 530 | PHE103 | O | 1.6619 | 1.0124 | −19.1813 | 607 | LEU117 | N | −6.907 | −1.2245 | −20.0738 |
| 531 | PHE103 | CB | 2.9686 | 4.0053 | −18.5934 | 608 | LEU117 | CA | −6.3848 | −0.0669 | −20.8005 |
| 532 | PHE103 | CG | 2.3833 | 4.5108 | −19.9084 | 609 | LEU117 | C | −7.5499 | 0.6023 | −21.5521 |
| 533 | PHE103 | CD1 | 0.9999 | 4.5431 | −20.1068 | 610 | LEU117 | O | −7.6652 | 1.8281 | −21.6358 |
| 534 | PHE103 | CD2 | 3.2434 | 4.9646 | −20.9194 | 611 | LEU117 | CB | −5.3551 | −0.6028 | −21.8165 |
| 535 | PHE103 | CE1 | 0.4757 | 4.9946 | −21.3197 | 612 | LEU117 | CG | −4.3222 | 0.4745 | −22.206 |
| 536 | PHE103 | CE2 | 2.7199 | 5.416 | −22.1263 | 613 | LEU117 | CD1 | −4.997 | 1.6243 | −22.9783 |
| 537 | PHE103 | CZ | 1.3397 | 5.3971 | −22.3407 | 614 | LEU117 | CD2 | −3.6102 | 1.0177 | −20.9523 |
| 538 | LEU104 | N | 3.3014 | 1.0417 | −17.5789 | 615 | SER118 | N | −8.4382 | −0.2753 | −22.1503 |
| 539 | LEU104 | CA | 3.8472 | −0.2778 | −17.8623 | 616 | SER118 | CA | −9.527 | 0.208 | −22.9924 |

TABLE IV-continued

| Atom No | Residue | Atom name | x coord | y coord | z coord |
|---|---|---|---|---|---|
| 617 | SER118 | C | −10.6426 | 0.9255 | −22.2129 |
| 618 | SER118 | O | −11.551 | 1.5242 | −22.7887 |
| 619 | SER118 | CB | −10.1172 | −0.9766 | −23.7808 |
| 620 | SER118 | OG | −10.6208 | −1.9642 | −22.8771 |
| 621 | ARG119 | N | −10.569 | 0.8227 | −20.8375 |
| 622 | ARG119 | CA | −11.4775 | 1.5553 | −19.9688 |
| 623 | ARG119 | C | −11.0002 | 3.0022 | −19.7933 |
| 624 | ARG119 | O | −11.7956 | 3.914 | −19.5696 |
| 625 | ARG119 | CB | −11.4061 | 0.886 | −18.5811 |
| 626 | ARG119 | CG | −11.688 | −0.6251 | −18.6941 |
| 627 | ARG119 | CD | −11.0396 | −1.3648 | −17.5085 |
| 628 | ARG119 | NE | −11.8994 | −1.2975 | −16.3406 |
| 629 | ARG119 | CZ | −11.4917 | −0.7479 | −15.2328 |
| 630 | ARG119 | NH1 | −10.3021 | −0.2312 | −15.1306 |
| 631 | ARG119 | NH2 | −12.2908 | −0.7158 | −14.2078 |
| 632 | VAL120 | N | −9.631 | 3.1517 | −19.7311 |
| 633 | VAL120 | CA | −8.9808 | 4.4338 | −19.4573 |
| 634 | VAL120 | C | −8.8841 | 5.2185 | −20.7772 |
| 635 | VAL120 | O | −9.0856 | 6.4347 | −20.8279 |
| 636 | VAL120 | CB | −7.5615 | 4.1665 | −18.9181 |
| 637 | VAL120 | CG1 | −6.8398 | 5.5013 | −18.6496 |
| 638 | VAL120 | CG2 | −7.6483 | 3.366 | −17.6051 |
| 639 | VAL121 | N | −8.408 | 4.4728 | −21.8391 |
| 640 | VAL121 | CA | −8.1138 | 5.031 | −23.1509 |
| 641 | VAL121 | C | −9.1408 | 4.4303 | −24.128 |
| 642 | VAL121 | O | −9.0317 | 3.276 | −24.5517 |
| 643 | VAL121 | CB | −6.6705 | 4.6559 | −23.5399 |
| 644 | VAL121 | CG1 | −6.3261 | 5.265 | −24.9123 |
| 645 | VAL121 | CG2 | −5.6994 | 5.2154 | −22.4827 |
| 646 | PRO122 | N | −10.1876 | 5.2355 | −24.526 |
| 647 | PRO122 | CA | −11.1232 | 4.7921 | −25.5543 |
| 648 | PRO122 | C | −10.3369 | 4.6489 | −26.8664 |
| 649 | PRO122 | O | −9.7674 | 5.5885 | −27.4207 |
| 650 | PRO122 | CB | −12.0732 | 6.0025 | −25.6621 |
| 651 | PRO122 | CG | −11.4638 | 7.1599 | −24.8396 |
| 652 | PRO122 | CD | −10.3163 | 6.5757 | −23.9929 |
| 653 | LEU123 | N | −10.2932 | 3.3366 | −27.3276 |
| 654 | LEU123 | CA | −9.3386 | 2.9467 | −28.3737 |
| 655 | LEU123 | C | −9.728 | 3.5064 | −29.7541 |
| 656 | LEU123 | O | −8.9297 | 3.5627 | −30.6897 |
| 657 | LEU123 | CB | −9.2619 | 1.4084 | −28.4148 |
| 658 | LEU123 | CG | −8.9489 | 0.858 | −27.008 |
| 659 | LEU123 | CD1 | −8.9634 | −0.6812 | −27.0383 |
| 660 | LEU123 | CD2 | −7.5671 | 1.3497 | −26.5353 |
| 661 | ASN124 | N | −10.1556 | 3.8432 | −29.8956 |
| 662 | ASN124 | CA | −11.6259 | 4.3803 | −31.1327 |
| 663 | ASN124 | C | −11.1889 | 5.8395 | −31.3775 |
| 664 | ASN124 | O | −11.9811 | 6.7626 | −31.546 |
| 665 | ASN124 | CB | −13.1634 | 4.2757 | −31.0468 |
| 666 | ASN124 | CG | −13.7008 | 5.0409 | −29.8683 |
| 667 | ASN124 | OD1 | −14.4125 | 6.0144 | −30.0524 |
| 668 | ASN124 | ND2 | −13.3664 | 4.6068 | −28.6394 |
| 669 | GLN125 | N | −9.822 | 6.007 | −31.4634 |
| 670 | GLN125 | CA | −9.1814 | 7.3052 | −31.6147 |
| 671 | GLN125 | C | −7.9466 | 7.1256 | −32.5074 |
| 672 | GLN125 | O | −7.3304 | 6.0632 | −32.5861 |
| 673 | GLN125 | CB | −8.7584 | 7.8764 | −30.2481 |
| 674 | GLN125 | CG | −10.0007 | 8.1186 | −29.3703 |
| 675 | GLN125 | CD | −9.6273 | 8.9664 | −28.1894 |
| 676 | GLN125 | OE1 | −10.1086 | 10.0807 | −28.068 |
| 677 | GLN125 | NE2 | −8.7616 | 8.4413 | −27.3035 |
| 678 | SER126 | N | −7.5777 | 8.2638 | −33.2006 |
| 679 | SER126 | CA | −6.5795 | 8.2017 | −34.263 |
| 680 | SER126 | C | −6.11 | 9.618 | −34.6132 |
| 681 | SER126 | O | −6.7578 | 10.6218 | −34.3314 |
| 682 | SER126 | CB | −7.1575 | 7.5132 | −35.5138 |
| 683 | SER126 | OG | −6.1045 | 7.2436 | −36.4424 |
| 684 | PHE127 | N | −4.9112 | 9.6319 | −35.3035 |
| 685 | PHE127 | CA | −4.4128 | 10.8258 | −35.9869 |
| 686 | PHE127 | C | −4.7745 | 10.8026 | −37.4801 |
| 687 | PHE127 | O | −4.6802 | 11.8116 | −38.1782 |
| 688 | PHE127 | CB | −2.8721 | 10.8614 | −35.8505 |
| 689 | PHE127 | CG | −2.4867 | 11.0463 | −34.3877 |
| 690 | PHE127 | CD1 | −1.8966 | 9.9921 | −33.6854 |
| 691 | PHE127 | CD2 | −2.7169 | 12.2688 | −33.7507 |
| 692 | PHE127 | CE1 | −1.54 | 10.1607 | −32.345 |
| 693 | PHE127 | CE2 | −2.3612 | 12.4355 | −32.4099 |
| 694 | PHE127 | CZ | −1.7752 | 11.3805 | −31.7056 |
| 695 | TYR131 | N | −9.2595 | 13.5067 | −37.4336 |
| 696 | TYR131 | CA | −8.2461 | 13.9236 | −36.4549 |
| 697 | TYR131 | C | −8.6868 | 15.1692 | −35.6672 |
| 698 | TYR131 | O | −8.571 | 15.2393 | −34.441 |
| 699 | TYR131 | CB | −6.8845 | 14.1573 | −37.1456 |
| 700 | TYR131 | CG | −6.0123 | 15.0932 | −36.3094 |
| 701 | TYR131 | CD1 | −5.3854 | 14.636 | −35.1466 |
| 702 | TYR131 | CD2 | −5.8567 | 16.4228 | −36.7094 |
| 703 | TYR131 | CE1 | −4.671 | 15.5291 | −34.3426 |
| 704 | TYR131 | CE2 | −5.138 | 17.3139 | −35.9092 |
| 705 | TYR131 | CZ | −4.5609 | 16.8715 | −34.7166 |
| 706 | TYR131 | OH | −3.879 | 17.7694 | −33.9043 |
| 707 | ALA132 | N | −9.0168 | 16.2679 | −36.4355 |
| 708 | ALA132 | CA | −9.5328 | 17.5262 | −35.8823 |
| 709 | ALA132 | C | −8.5924 | 18.3499 | −34.9607 |
| 710 | ALA132 | O | −8.709 | 19.5738 | −34.8854 |
| 711 | ALA132 | CB | −10.8532 | 17.2515 | −35.1364 |
| 712 | GLY133 | N | −7.752 | 17.6291 | −34.1455 |
| 713 | GLY133 | CA | −6.9354 | 18.218 | −33.0956 |
| 714 | GLY133 | C | −7.6072 | 18.1022 | −31.7283 |
| 715 | GLY133 | O | −7.5639 | 19.0118 | −30.9002 |
| 716 | ILE134 | N | −8.1599 | 16.8637 | −31.4524 |
| 717 | ILE134 | CA | −8.9173 | 16.6142 | −30.2263 |
| 718 | ILE134 | C | −8.8182 | 15.1192 | −29.8913 |
| 719 | ILE134 | O | −8.8813 | 14.2514 | −30.7603 |
| 720 | ILE134 | CB | −10.3593 | 17.1524 | −30.3084 |
| 721 | ILE134 | CG1 | −11.0592 | 17.0133 | −28.9422 |
| 722 | ILE134 | CG2 | −11.1426 | 16.4052 | −31.4039 |
| 723 | ILE134 | CD1 | −12.4559 | 17.662 | −28.9913 |
| 724 | PHE135 | N | −8.7247 | 14.8401 | −28.5422 |
| 725 | PHE135 | CA | −8.6863 | 13.4695 | −28.0316 |
| 726 | PHE135 | C | −9.4508 | 13.4417 | −26.7029 |
| 727 | PHE135 | O | −9.6315 | 14.454 | −26.0215 |
| 728 | PHE135 | CB | −7.2428 | 12.9517 | −27.8844 |
| 729 | PHE135 | CG | −6.5844 | 12.915 | −29.2601 |
| 730 | PHE135 | CD1 | −5.5275 | 13.7812 | −29.5524 |
| 731 | PHE135 | CD2 | −7.0427 | 12.0197 | −30.2306 |
| 732 | PHE135 | CE1 | −4.95 | 13.7723 | −30.8247 |
| 733 | PHE135 | CE2 | −6.4702 | 12.0164 | −31.5053 |
| 734 | PHE135 | CZ | −5.4282 | 12.898 | −31.8044 |
| 735 | ARG136 | N | −9.8698 | 12.1836 | −26.3098 |
| 736 | ARG136 | CA | −10.6148 | 11.9962 | −25.0723 |
| 737 | ARG136 | C | −10.1408 | 10.7089 | −24.3312 |
| 738 | ARG136 | O | −9.6374 | 9.7405 | −24.9031 |
| 739 | ARG136 | CB | −12.1337 | 11.9063 | −25.3183 |
| 740 | ARG136 | CG | −12.4699 | 10.6748 | −26.1801 |
| 741 | ARG136 | CD | −13.9424 | 10.2825 | −25.9652 |
| 742 | ARG136 | NE | −14.3499 | 9.3766 | −27.0232 |
| 743 | ARG136 | CZ | −15.4376 | 9.5841 | −27.7076 |
| 744 | ARG136 | NH1 | −15.762 | 8.7525 | −28.6524 |
| 745 | ARG136 | NH2 | −16.2059 | 10.6056 | −27.4648 |
| 746 | PHE137 | N | −10.3449 | 10.7858 | −22.9627 |
| 747 | PHE137 | CA | −9.8043 | 9.8128 | −22.011 |
| 748 | PHE137 | C | −10.7722 | 9.7426 | −20.8275 |
| 749 | PHE137 | O | −11.4967 | 10.6948 | −20.5245 |
| 750 | PHE137 | CB | −8.4306 | 10.2588 | −21.4726 |
| 751 | PHE137 | CG | −7.3656 | 10.217 | −22.5633 |
| 752 | PHE137 | CD1 | −6.7371 | 11.3995 | −22.9629 |
| 753 | PHE137 | CD2 | −7.0118 | 9.0021 | −23.1568 |
| 754 | PHE137 | CE1 | −5.7247 | 11.363 | −23.9254 |
| 755 | PHE137 | CE2 | −6.0012 | 8.966 | −24.1212 |
| 756 | PHE137 | CZ | −5.3502 | 10.1442 | −24.4974 |
| 757 | TRP138 | N | −10.7345 | 8.5614 | −20.1081 |
| 758 | TRP138 | CA | −11.5544 | 8.3889 | −18.9132 |
| 759 | TRP138 | C | −10.6682 | 8.1648 | −17.6812 |
| 760 | TRP138 | O | −9.5891 | 7.5783 | −17.7445 |
| 761 | TRP138 | CB | −12.5733 | 7.2508 | −19.0873 |
| 762 | TRP138 | CG | −13.8737 | 7.8635 | −19.5123 |
| 763 | TRP138 | CD1 | −14.1925 | 8.302 | −20.7399 |
| 764 | TRP138 | CD2 | −15.0672 | 8.1022 | −18.628 |
| 765 | TRP138 | NE1 | −15.4138 | 8.7761 | −20.7391 |
| 766 | TRP138 | CE2 | −15.9622 | 8.6761 | −19.5107 |
| 767 | TRP138 | CE3 | −15.3643 | 7.8732 | −17.2856 |
| 768 | TRP138 | CZ2 | −17.2375 | 9.072 | −19.1083 |
| 769 | TRP138 | CZ3 | −16.6435 | 8.2685 | −16.8761 |
| 770 | TRP138 | CH2 | −17.5533 | 8.8666 | −17.7597 |

TABLE IV-continued

| Atom No | Residue | Atom name | x coord | y coord | z coord |
|---|---|---|---|---|---|
| 771 | PHE139 | N | −11.2525 | 8.5736 | −16.4965 |
| 772 | PHE139 | CA | −10.6047 | 8.4027 | −15.1966 |
| 773 | PHE139 | C | −11.6784 | 8.0116 | −14.1835 |
| 774 | PHE139 | O | −12.8384 | 8.4183 | −14.2702 |
| 775 | PHE139 | CB | −9.764 | 9.6274 | −14.7891 |
| 776 | PHE139 | CG | −8.9383 | 10.0973 | −15.9836 |
| 777 | PHE139 | CD1 | −9.3498 | 11.2112 | −16.7203 |
| 778 | PHE139 | CD2 | −7.7763 | 9.4121 | −16.3481 |
| 779 | PHE139 | CE1 | −8.6151 | 11.6229 | −17.8355 |
| 780 | PHE139 | CE2 | −7.043 | 9.8219 | −17.4648 |
| 781 | PHE139 | CZ | −7.4627 | 10.9269 | −18.2099 |
| 782 | TRP140 | N | −11.2181 | 7.2355 | −13.1403 |
| 783 | TRP140 | CA | −12.0124 | 7.0661 | −11.921 |
| 784 | TRP140 | C | −11.6556 | 8.2532 | −11.0208 |
| 785 | TRP140 | O | −10.5299 | 8.754 | −11.0265 |
| 786 | TRP140 | CB | −11.6066 | 5.7386 | −11.2498 |
| 787 | TRP140 | CG | −12.07 | 5.687 | −9.8235 |
| 788 | TRP140 | CD1 | −13.2049 | 5.1441 | −9.3567 |
| 789 | TRP140 | CD2 | −11.3253 | 6.2514 | −8.6444 |
| 790 | TRP140 | NE1 | −13.2639 | 5.2892 | −8.0555 |
| 791 | TRP140 | CE2 | −12.1694 | 5.9322 | −7.598 |
| 792 | TRP140 | CE3 | −10.1209 | 6.9325 | −8.4733 |
| 793 | TRP140 | CZ2 | −11.8562 | 6.2641 | −6.2802 |
| 794 | TRP140 | CZ3 | −9.8106 | 7.2898 | −7.1556 |
| 795 | TRP140 | CH2 | −10.6545 | 6.9571 | −6.0853 |
| 796 | HIS141 | N | −12.6722 | 8.7017 | −10.2057 |
| 797 | HIS141 | CA | −12.5073 | 9.8245 | −9.2918 |
| 798 | HIS141 | C | −13.4191 | 9.5704 | −8.0813 |
| 799 | HIS141 | O | −14.6246 | 9.8188 | −8.0798 |
| 800 | HIS141 | CB | −12.934 | 11.1155 | −10.0147 |
| 801 | HIS141 | CG | −12.0532 | 11.287 | −11.2152 |
| 802 | HIS141 | ND1 | −10.8127 | 11.7037 | −11.1111 |
| 803 | HIS141 | CD2 | −12.4213 | 11.027 | −12.4836 |
| 804 | HIS141 | CE1 | −10.3183 | 11.7319 | −12.3074 |
| 805 | HIS141 | NE2 | −11.1851 | 11.36 | −13.1359 |
| 806 | TYR142 | N | −12.795 | 8.9359 | −7.0187 |
| 807 | TYR142 | CA | −13.3433 | 9.0058 | −5.6555 |
| 808 | TYR142 | C | −14.7314 | 8.3527 | −5.5148 |
| 809 | TYR142 | O | −15.4898 | 8.5592 | −4.5781 |
| 810 | TYR142 | CB | −13.397 | 10.4616 | −5.1484 |
| 811 | TYR142 | CG | −12.0073 | 11.0876 | −5.0786 |
| 812 | TYR142 | CD1 | −11.2482 | 11.2589 | −6.2396 |
| 813 | TYR142 | CD2 | −11.4964 | 11.4996 | −3.8452 |
| 814 | TYR142 | CE1 | −9.9943 | 11.8714 | −6.1724 |
| 815 | TYR142 | CE2 | −10.2473 | 12.1222 | −3.7792 |
| 816 | TYR142 | CZ | −9.5014 | 12.319 | −4.9439 |
| 817 | TYR142 | OH | −8.2703 | 12.9606 | −4.8804 |
| 818 | GLY143 | N | −14.9795 | 7.3789 | −6.4539 |
| 819 | GLY143 | CA | −16.2053 | 6.619 | −6.5102 |
| 820 | GLY143 | C | −16.7664 | 6.5699 | −7.9246 |
| 821 | GLY143 | O | −17.2517 | 5.5321 | −8.3758 |
| 822 | ASN144 | N | −16.8015 | 7.7865 | −8.5793 |
| 823 | ASN144 | CA | −17.3743 | 7.914 | −9.9166 |
| 824 | ASN144 | C | −16.2826 | 7.8175 | −10.9978 |
| 825 | ASN144 | O | −15.0873 | 7.9838 | −10.7567 |
| 826 | ASN144 | CB | −18.1095 | 9.2584 | −10.0685 |
| 827 | ASN144 | CG | −19.2871 | 9.3093 | −9.1396 |
| 828 | ASN144 | OD1 | −19.3421 | 10.171 | −8.2779 |
| 829 | ASN144 | ND2 | −20.2454 | 8.3803 | −9.3069 |
| 830 | TRP145 | N | −16.775 | 7.5382 | −12.2662 |
| 831 | TRP145 | CA | −15.9231 | 7.6557 | −13.4515 |
| 832 | TRP145 | C | −16.1906 | 9.0373 | −14.058 |
| 833 | TRP145 | O | −17.311 | 9.5466 | −14.0413 |
| 834 | TRP145 | CB | −15.9475 | 6.4578 | −14.4157 |
| 835 | TRP145 | CG | −14.7551 | 5.6159 | −14.0635 |
| 836 | TRP145 | CD1 | −14.6017 | 4.8703 | −12.9577 |
| 837 | TRP145 | CD2 | −13.5001 | 5.4609 | −14.88 |
| 838 | TRP145 | NE1 | −13.4297 | 4.2851 | −12.9715 |
| 839 | TRP145 | CE2 | −12.7449 | 4.6195 | −14.0844 |
| 840 | TRP145 | CE3 | −13.0513 | 5.9493 | −16.1065 |
| 841 | TRP145 | CZ2 | −11.4595 | 4.2199 | −14.4501 |
| 842 | TRP145 | CZ3 | −11.7677 | 5.5395 | −16.4885 |
| 843 | TRP145 | CH2 | −10.9842 | 4.7093 | −15.6732 |
| 844 | VAL146 | N | −15.0943 | 9.6111 | −14.6657 |
| 845 | VAL146 | CA | −15.1323 | 10.9329 | −15.288 |
| 846 | VAL146 | C | −14.4039 | 10.7866 | −16.6377 |
| 847 | VAL146 | O | −13.3481 | 10.1608 | −16.7543 |
| 848 | VAL146 | CB | −14.5062 | 12.0252 | −14.4016 |
| 849 | VAL146 | CG1 | −14.5627 | 13.3836 | −15.1259 |
| 850 | VAL146 | CG2 | −15.2933 | 12.1222 | −13.0812 |
| 851 | PRO147 | N | −15.0407 | 11.4243 | −17.688 |
| 852 | PRO147 | CA | −14.4421 | 11.5445 | −19.0197 |
| 853 | PRO147 | C | −13.7611 | 12.9212 | −19.0753 |
| 854 | PRO147 | O | −14.2574 | 13.9182 | −18.5488 |
| 855 | PRO147 | CB | −15.7135 | 11.6846 | −19.8787 |
| 856 | PRO147 | CG | −16.8296 | 12.2116 | −18.9477 |
| 857 | PRO147 | CD | −16.3539 | 13.0027 | −17.496 |
| 858 | VAL148 | N | −12.5849 | 12.9549 | −19.7972 |
| 859 | VAL148 | CA | −11.8514 | 14.1932 | −20.0352 |
| 860 | VAL148 | C | −11.4656 | 14.2299 | −21.5245 |
| 861 | VAL148 | O | −11.0249 | 13.2515 | −22.1259 |
| 862 | VAL148 | CB | −10.5713 | 14.2143 | −19.1768 |
| 863 | VAL148 | CG1 | −9.8977 | 15.597 | −19.2662 |
| 864 | VAL148 | CG2 | −10.922 | 13.9061 | −17.7098 |
| 865 | VAL149 | N | −11.6336 | 16.541 | −22.0884 |
| 866 | VAL149 | CA | −11.3107 | 15.8132 | −23.4772 |
| 867 | VAL149 | C | −10.0416 | 16.689 | −23.4257 |
| 868 | VAL149 | O | −9.863 | 17.5286 | −22.5332 |
| 869 | VAL149 | CB | −12.4666 | 16.541 | −24.1919 |
| 870 | VAL149 | CG1 | −12.0679 | 16.8561 | −25.6467 |
| 871 | VAL149 | CG2 | −13.7176 | 15.6425 | −24.1975 |
| 872 | ILE150 | N | −9.1584 | 16.5193 | −24.4747 |
| 873 | ILE150 | CA | −7.8397 | 17.1654 | −24.4977 |
| 874 | ILE150 | C | −7.3708 | 17.3781 | −25.9591 |
| 875 | ILE150 | O | −7.7728 | 16.6718 | −26.8855 |
| 876 | ILE150 | CB | −6.8268 | 16.3699 | −23.645 |
| 877 | ILE150 | CG1 | −6.7359 | 14.8871 | −24.0676 |
| 878 | ILE150 | CG2 | −5.4384 | 17.0398 | −23.6387 |
| 879 | ILE150 | CD1 | −6.0369 | 14.7232 | −25.4318 |
| 880 | ASP151 | N | −6.4562 | 18.4073 | −26.1257 |
| 881 | ASP151 | CA | −5.7667 | 18.6717 | −27.3943 |
| 882 | ASP151 | C | −4.3473 | 18.0589 | −27.3541 |
| 883 | ASP151 | O | −3.8018 | 17.6815 | −26.3105 |
| 884 | ASP151 | CB | −5.6562 | 20.196 | −27.5904 |
| 885 | ASP151 | CG | −4.8288 | 20.8034 | −26.4927 |
| 886 | ASP151 | OD1 | −3.5843 | 20.8953 | −26.6713 |
| 887 | ASP151 | OD2 | −5.4241 | 21.2042 | −25.4574 |
| 888 | ASP152 | N | −3.6913 | 18.0528 | −28.5621 |
| 889 | ASP152 | CA | −2.4247 | 17.3595 | −28.815 |
| 890 | ASP152 | C | −1.2286 | 18.3059 | −28.9933 |
| 891 | ASP152 | O | −0.1476 | 17.9427 | −29.4503 |
| 892 | ASP152 | CB | −2.5075 | 16.1388 | −29.7539 |
| 893 | ASP152 | CG | −3.1537 | 16.4648 | −31.0697 |
| 894 | ASP152 | OD1 | −2.4711 | 16.2908 | −32.1139 |
| 895 | ASP152 | OD2 | −4.3413 | 16.8882 | −31.068 |
| 896 | ARG153 | N | −1.4181 | 19.5454 | −28.4233 |
| 897 | ARG153 | CA | −0.3124 | 20.46 | −28.1713 |
| 898 | ARG153 | C | 0.269 | 20.0286 | −26.8111 |
| 899 | ARG153 | O | −0.4419 | 19.9335 | −25.8052 |
| 900 | ARG153 | CB | −0.8267 | 21.9081 | −28.0912 |
| 901 | ARG153 | CG | −1.4103 | 22.3167 | −29.457 |
| 902 | ARG153 | CD | −2.9178 | 22.6007 | −29.3184 |
| 903 | ARG153 | NE | −3.1155 | 23.7076 | −28.3995 |
| 904 | ARG153 | CZ | −4.2574 | 23.8944 | −27.8041 |
| 905 | ARG153 | NH1 | −5.2654 | 23.1038 | −28.0233 |
| 906 | ARG153 | NH2 | −4.3959 | 24.8896 | −26.9796 |
| 907 | LEU154 | N | 1.6045 | 19.6786 | −26.8477 |
| 908 | LEU154 | CA | 2.3415 | 19.1173 | −25.7092 |
| 909 | LEU154 | C | 3.5418 | 20.0371 | −25.3873 |
| 910 | LEU154 | O | 3.993 | 20.806 | −26.2439 |
| 911 | LEU154 | CB | 2.8149 | 17.6876 | −26.038 |
| 912 | LEU154 | CG | 1.6904 | 16.8972 | −26.7388 |
| 913 | LEU154 | CD1 | 2.2113 | 15.5079 | −27.1503 |
| 914 | LEU154 | CD2 | 0.4791 | 16.7385 | −25.7994 |
| 915 | PRO155 | N | 4.1317 | 19.919 | −24.1174 |
| 916 | PRO155 | CA | 5.2572 | 20.7795 | −23.7535 |
| 917 | PRO155 | C | 6.5862 | 20.1545 | −24.2212 |
| 918 | PRO155 | O | 7.092 | 19.1556 | −23.7017 |
| 919 | PRO155 | CB | 5.1713 | 20.6814 | −22.217 |
| 920 | PRO155 | CG | 4.3153 | 19.4413 | −21.8727 |
| 921 | PRO155 | CD | 3.5972 | 18.9944 | −23.1615 |
| 922 | LEU162 | N | 9.1036 | 17.1652 | −22.7622 |
| 923 | LEU162 | CA | 9.5653 | 17.3634 | −21.3825 |
| 924 | LEU162 | C | 8.9453 | 16.3509 | −20.3944 |

TABLE IV-continued

| Atom No | Residue | Atom name | x coord | y coord | z coord |
|---|---|---|---|---|---|
| 925 | LEU162 | O | 9.3738 | 16.2255 | −19.2479 |
| 926 | LEU162 | CB | 9.1718 | 18.7986 | −20.9763 |
| 927 | LEU162 | CG | 9.5659 | 19.7972 | −22.085 |
| 928 | LEU162 | CD1 | 8.9469 | 21.1771 | −21.7988 |
| 929 | LEU162 | CD2 | 11.0986 | 19.9205 | −22.171 |
| 930 | VAL163 | N | 7.8059 | 15.7359 | −20.8548 |
| 931 | VAL163 | CA | 6.9001 | 14.9282 | −20.0167 |
| 932 | VAL163 | C | 6.8592 | 13.4935 | −20.5742 |
| 933 | VAL163 | O | 7.6291 | 13.1371 | −21.4753 |
| 934 | VAL163 | CB | 5.5354 | 15.6534 | −20.0225 |
| 935 | VAL163 | CG1 | 4.4405 | 14.9111 | −20.8157 |
| 936 | VAL163 | CG2 | 5.0723 | 15.9333 | −18.5813 |
| 937 | PHE164 | N | 5.9919 | 12.5981 | −19.9705 |
| 938 | PHE164 | CA | 6.0594 | 11.1646 | −20.2933 |
| 939 | PHE164 | C | 5.6914 | 10.9875 | −21.7803 |
| 940 | PHE164 | O | 4.8581 | 11.6769 | −22.3624 |
| 941 | PHE164 | CB | 5.033 | 10.3666 | −19.4641 |
| 942 | PHE164 | CG | 5.4169 | 10.3322 | −17.9883 |
| 943 | PHE164 | CD1 | 4.5025 | 10.7562 | −17.0208 |
| 944 | PHE164 | CD2 | 6.6779 | 9.8748 | −17.5988 |
| 945 | PHE164 | CE1 | 4.8585 | 10.7499 | −15.6698 |
| 946 | PHE164 | CE2 | 7.0391 | 9.8751 | −16.2491 |
| 947 | PHE164 | CZ | 6.1318 | 10.3218 | −15.2852 |
| 948 | VAL165 | N | 6.3903 | 9.9741 | −22.4123 |
| 949 | VAL165 | CA | 6.3353 | 9.7874 | −23.8582 |
| 950 | VAL165 | C | 6.8056 | 8.3647 | −24.1952 |
| 951 | VAL165 | O | 7.4217 | 7.6684 | −23.3901 |
| 952 | VAL165 | CB | 7.2052 | 10.8184 | −24.6081 |
| 953 | VAL165 | CG1 | 6.5458 | 12.2098 | −24.5778 |
| 954 | VAL165 | CG2 | 8.6119 | 10.8981 | −23.9844 |
| 955 | SER166 | N | 6.4785 | 7.9386 | −25.4751 |
| 956 | SER166 | CA | 7.1328 | 6.7639 | −26.0454 |
| 957 | SER166 | C | 6.838 | 6.5724 | −27.5437 |
| 958 | SER166 | O | 5.686 | 6.5221 | −27.96 |
| 959 | SER166 | CB | 6.7683 | 5.4809 | −25.2727 |
| 960 | SER166 | OG | 7.7074 | 4.4486 | −25.5853 |
| 961 | PHE173 | N | 2.2461 | 8.4031 | −28.877 |
| 962 | PHE173 | CA | 1.3314 | 9.4965 | −28.6476 |
| 963 | PHE173 | C | 0.336 | 9.3901 | −27.514 |
| 964 | PHE173 | O | −0.4975 | 10.2913 | −27.372 |
| 965 | PHE173 | CB | 0.6858 | 10.0229 | −29.9456 |
| 966 | PHE173 | CG | 1.7267 | 10.7609 | −30.7817 |
| 967 | PHE173 | CD1 | 1.8293 | 10.5041 | −32.1511 |
| 968 | PHE173 | CD2 | 2.5797 | 11.6915 | −30.1812 |
| 969 | PHE173 | CE1 | 2.8202 | 11.1379 | −32.9053 |
| 970 | PHE173 | CE2 | 3.5614 | 12.3352 | −30.9387 |
| 971 | PHE173 | CZ | 3.6865 | 12.0519 | −32.3009 |
| 972 | TRP174 | N | −0.2464 | 8.1445 | −27.29 |
| 973 | TRP174 | CA | −1.3832 | 8.0441 | −26.3625 |
| 974 | TRP174 | C | −0.9695 | 8.3698 | −24.9116 |
| 975 | TRP174 | O | −1.7629 | 8.8377 | −24.0928 |
| 976 | TRP174 | CB | −2.0615 | 6.6656 | −26.4833 |
| 977 | TRP174 | CG | −1.251 | 5.612 | −25.7898 |
| 978 | TRP174 | CD1 | −0.0053 | 5.2237 | −26.1002 |
| 979 | TRP174 | CD2 | −1.6945 | 4.7987 | −24.6045 |
| 980 | TRP174 | NE1 | 0.3806 | 4.2861 | −25.2719 |
| 981 | TRP174 | CE2 | −0.5919 | 3.9966 | −24.3848 |
| 982 | TRP174 | CE3 | −2.847 | 4.736 | −23.8226 |
| 983 | TRP174 | CZ2 | −0.5679 | 3.042 | −23.3686 |
| 984 | TRP174 | CZ3 | −2.8211 | 3.7981 | −22.7832 |
| 985 | TRP174 | CH2 | −1.7146 | 2.9625 | −22.5695 |
| 986 | GLY175 | N | 0.319 | 8.0074 | −24.5881 |
| 987 | GLY175 | CA | 0.8548 | 8.0482 | −23.229 |
| 988 | GLY175 | C | 0.924 | 9.5013 | −22.7643 |
| 989 | GLY175 | O | 0.4744 | 9.8591 | −21.6563 |
| 990 | ALA176 | N | 1.5527 | 10.3575 | −23.6355 |
| 991 | ALA176 | CA | 1.8162 | 11.7463 | −23.2667 |
| 992 | ALA176 | C | 0.4778 | 12.4832 | −23.1036 |
| 993 | ALA176 | O | 0.3087 | 13.3923 | −22.2917 |
| 994 | ALA176 | CB | 2.6081 | 12.4016 | −24.4134 |
| 995 | LEU177 | N | −0.4862 | 12.0977 | −24.0175 |
| 996 | LEU177 | CA | −1.8072 | 12.7043 | −24.039 |
| 997 | LEU177 | C | −2.6026 | 12.2801 | −22.7889 |
| 998 | LEU177 | O | −3.3645 | 13.0632 | −22.2149 |
| 999 | LEU177 | CB | −2.5591 | 12.1878 | −25.2811 |
| 1000 | LEU177 | CG | −2.1824 | 13.0175 | −26.5242 |
| 1001 | LEU177 | CD1 | −2.8503 | 12.4028 | −27.7689 |
| 1002 | LEU177 | CD2 | −2.6658 | 14.4711 | −26.3557 |
| 1003 | LEU178 | N | −2.4445 | 10.9664 | −22.3884 |
| 1004 | LEU178 | CA | −3.1132 | 10.4544 | −21.1906 |
| 1005 | LEU178 | C | −2.5251 | 11.1643 | −19.9513 |
| 1006 | LEU178 | O | −3.234 | 11.5138 | −19.0034 |
| 1007 | LEU178 | CB | −2.9177 | 8.9296 | −21.0891 |
| 1008 | LEU178 | CG | −3.8563 | 8.3476 | −20.0123 |
| 1009 | LEU178 | CD1 | −5.3264 | 8.6533 | −20.3596 |
| 1010 | LEU178 | CD2 | −3.6637 | 6.822 | −19.9332 |
| 1011 | GLU179 | N | −1.1524 | 11.3234 | −19.9572 |
| 1012 | GLU179 | CA | −0.4475 | 11.9849 | −18.8542 |
| 1013 | GLU179 | C | −0.9306 | 13.4538 | −18.7813 |
| 1014 | GLU179 | O | −1.217 | 13.995 | −17.7092 |
| 1015 | GLU179 | CB | 1.0603 | 11.9436 | −19.1576 |
| 1016 | GLU179 | CG | 1.836 | 12.3442 | −17.8903 |
| 1017 | GLU179 | CD | 2.7056 | 13.5265 | −18.1976 |
| 1018 | GLU179 | OE1 | 3.9506 | 13.3429 | −18.2297 |
| 1019 | GLU179 | OE2 | 2.1484 | 14.6392 | −18.399 |
| 1020 | LYS180 | N | −1.0611 | 14.1019 | −20.0001 |
| 1021 | LYS180 | CA | −1.5294 | 15.4849 | −20.058 |
| 1022 | LYS180 | C | −2.9863 | 15.5584 | −19.5596 |
| 1023 | LYS180 | O | −3.4062 | 16.527 | −18.9195 |
| 1024 | LYS180 | CB | −1.4866 | 15.9011 | −21.5416 |
| 1025 | LYS180 | CG | −1.9217 | 17.3697 | −21.7058 |
| 1026 | LYS180 | CD | −1.7157 | 17.8037 | −23.1693 |
| 1027 | LYS180 | CE | −2.086 | 19.2905 | −23.326 |
| 1028 | LYS180 | NZ | −3.4519 | 19.4078 | −23.8566 |
| 1029 | ALA181 | N | −3.8236 | 14.534 | −19.9589 |
| 1030 | ALA181 | CA | −5.227 | 14.5397 | −19.5633 |
| 1031 | ALA181 | C | −5.3504 | 14.3395 | −18.0377 |
| 1032 | ALA181 | O | −6.2726 | 14.8376 | −17.3882 |
| 1033 | ALA181 | CB | −5.9142 | 13.3553 | −20.2685 |
| 1034 | TYR182 | N | −4.3968 | 13.5147 | −17.4674 |
| 1035 | TYR182 | CA | −4.3378 | 13.3084 | −16.014 |
| 1036 | TYR182 | C | −3.911 | 14.6397 | −15.3604 |
| 1037 | TYR182 | O | −4.4286 | 15.0613 | −14.3233 |
| 1038 | TYR182 | CB | −3.2428 | 12.2534 | −15.7604 |
| 1039 | TYR182 | CG | −3.7672 | 11.0667 | −14.9534 |
| 1040 | TYR182 | CD1 | −2.8826 | 10.3532 | −14.1401 |
| 1041 | TYR182 | CD2 | −5.1102 | 10.6836 | −15.0169 |
| 1042 | TYR182 | CE1 | −3.3303 | 9.249 | −13.4101 |
| 1043 | TYR182 | CE2 | −5.5616 | 9.5844 | −14.2811 |
| 1044 | TYR182 | CZ | −4.6681 | 8.8552 | −13.4923 |
| 1045 | TYR182 | OH | −5.1083 | 7.7388 | −12.792 |
| 1046 | ALA183 | N | −2.9084 | 15.3364 | −16.0158 |
| 1047 | ALA183 | CA | −2.4983 | 16.6457 | −15.5238 |
| 1048 | ALA183 | C | −3.6901 | 17.6177 | −15.5866 |
| 1049 | ALA183 | O | −3.8643 | 18.4841 | −14.7264 |
| 1050 | ALA183 | CB | −1.384 | 17.1672 | −16.4469 |
| 1051 | LYS184 | N | −4.5087 | 17.4934 | −16.6977 |
| 1052 | LYS184 | CA | −5.611 | 18.422 | −16.9143 |
| 1053 | LYS184 | C | −6.6679 | 18.2596 | −15.8071 |
| 1054 | LYS184 | O | −7.2776 | 19.2443 | −15.383 |
| 1055 | LYS184 | CB | −6.2294 | 18.0837 | −18.2832 |
| 1056 | LYS184 | CG | −7.201 | 19.2001 | −18.7066 |
| 1057 | LYS184 | CD | −7.6414 | 18.9677 | −20.1633 |
| 1058 | LYS184 | CE | −8.7361 | 19.9852 | −20.5324 |
| 1059 | LYS184 | NZ | −10.0419 | 19.4944 | −20.0694 |
| 1060 | LEU185 | N | −6.9762 | 16.9651 | −15.4203 |
| 1061 | LEU185 | CA | −7.9755 | 16.7511 | −14.3701 |
| 1062 | LEU185 | C | −7.4202 | 17.1729 | −12.997 |
| 1063 | LEU185 | O | −8.1656 | 17.635 | −12.1312 |
| 1064 | LEU185 | CB | −8.3535 | 15.2591 | −14.3817 |
| 1065 | LEU185 | CG | −9.887 | 15.1102 | −14.4244 |
| 1066 | LEU185 | CD1 | −10.4851 | 15.9782 | −15.5488 |
| 1067 | LEU185 | CD2 | −10.2408 | 13.6361 | −14.6884 |
| 1068 | SER186 | N | −6.0696 | 16.9426 | −12.7748 |
| 1069 | SER186 | CA | −5.4961 | 17.2909 | −11.4717 |
| 1070 | SER186 | C | −5.3992 | 18.8264 | −11.3662 |
| 1071 | SER186 | O | −5.5294 | 19.4181 | −10.296 |
| 1072 | SER186 | CB | −4.0918 | 16.6661 | −11.3442 |
| 1073 | SER186 | OG | −3.2145 | 17.1663 | −12.3577 |
| 1074 | GLY187 | N | −5.0223 | 19.4634 | −12.5324 |
| 1075 | GLY187 | CA | −5.2652 | 20.8786 | −12.7556 |
| 1076 | GLY187 | C | −4.0857 | 21.5354 | −13.4597 |
| 1077 | GLY187 | O | −4.2258 | 22.4645 | −14.2511 |
| 1078 | SER188 | N | −2.8658 | 21.077 | −13.0129 |

TABLE IV-continued

| Atom No | Residue | Atom name | x coord | y coord | z coord |
|---|---|---|---|---|---|
| 1079 | SER188 | CA | −1.5882 | 21.562 | −13.5121 |
| 1080 | SER188 | C | −0.6525 | 20.3481 | −13.5519 |
| 1081 | SER188 | O | −0.7697 | 19.4057 | −12.7666 |
| 1082 | SER188 | CB | −0.9967 | 22.6529 | −12.6005 |
| 1083 | SER188 | OG | −1.8848 | 23.7722 | −12.5576 |
| 1084 | TYR189 | N | 0.4309 | 20.4751 | −14.4103 |
| 1085 | TYR189 | CA | 1.394 | 19.3635 | −14.5345 |
| 1086 | TYR189 | C | 2.1028 | 19.1407 | −13.1875 |
| 1087 | TYR189 | O | 2.5564 | 18.0528 | −12.8423 |
| 1088 | TYR189 | CB | 2.4205 | 19.6809 | −15.6392 |
| 1089 | TYR189 | CG | 1.7359 | 19.639 | −17.0026 |
| 1090 | TYR189 | CD1 | 1.6966 | 20.7877 | −17.7958 |
| 1091 | TYR189 | CD2 | 1.1439 | 18.4599 | −17.4631 |
| 1092 | TYR189 | CE1 | 0.9697 | 20.7938 | −18.9882 |
| 1093 | TYR189 | CE2 | 0.4434 | 18.4535 | −18.6726 |
| 1094 | TYR189 | CZ | 0.3372 | 19.627 | −19.4238 |
| 1095 | TYR189 | OH | −0.3958 | 19.6344 | −20.6038 |
| 1096 | GLU190 | N | 2.2353 | 20.2856 | −12.4271 |
| 1097 | GLU190 | CA | 2.9165 | 20.2945 | −11.1371 |
| 1098 | GLU190 | C | 2.0888 | 19.4928 | −10.1168 |
| 1099 | GLU190 | O | 2.6117 | 18.9198 | −9.1614 |
| 1100 | GLU190 | CB | 2.9576 | 21.7516 | −10.642 |
| 1101 | GLU190 | CG | 3.8849 | 21.8584 | −9.417 |
| 1102 | GLU190 | CD | 5.0422 | 22.7653 | −9.7201 |
| 1103 | GLU190 | OE1 | 5.8825 | 22.393 | −10.5826 |
| 1104 | GLU190 | OE2 | 5.1173 | 23.8523 | −9.0882 |
| 1105 | ASP191 | N | 0.7198 | 19.4753 | −10.3209 |
| 1106 | ASP191 | CA | −0.1724 | 18.7469 | −9.4237 |
| 1107 | ASP191 | C | −0.2456 | 17.2321 | −9.7198 |
| 1108 | ASP191 | O | −1.1273 | 16.5148 | −9.243 |
| 1109 | ASP191 | CB | −1.5988 | 19.355 | −9.455 |
| 1110 | ASP191 | CG | −1.6043 | 20.8365 | −9.5147 |
| 1111 | ASP191 | OD1 | −2.4983 | 21.3884 | −10.2095 |
| 1112 | ASP191 | OD2 | −0.7159 | 21.4698 | −8.8827 |
| 1113 | LEU192 | N | 0.819 | 16.7221 | −10.4365 |
| 1114 | LEU192 | CA | 1.1802 | 15.3111 | −10.4241 |
| 1115 | LEU192 | C | 2.3645 | 15.0764 | −9.4578 |
| 1116 | LEU192 | O | 2.6051 | 13.967 | −8.9756 |
| 1117 | LEU192 | CB | 1.606 | 14.9339 | −11.8584 |
| 1118 | LEU192 | CG | 0.6433 | 15.546 | −12.899 |
| 1119 | LEU192 | CD1 | 1.1591 | 15.2637 | −14.3222 |
| 1120 | LEU192 | CD2 | −0.7731 | 14.9614 | −12.7367 |
| 1121 | GLN193 | N | 3.2225 | 16.1521 | −9.2984 |
| 1122 | GLN193 | CA | 4.4874 | 16.0024 | −8.5836 |
| 1123 | GLN193 | C | 4.1847 | 15.9215 | −7.0888 |
| 1124 | GLN193 | O | 3.7016 | 16.8552 | −6.4531 |
| 1125 | GLN193 | CB | 5.4245 | 17.2036 | −8.8285 |
| 1126 | GLN193 | CG | 5.1253 | 17.9062 | −10.168 |
| 1127 | GLN193 | CD | 6.0074 | 19.112 | −10.3215 |
| 1128 | GLN193 | OE1 | 6.5849 | 19.3114 | −11.3772 |
| 1129 | GLN193 | NE2 | 6.126 | 19.9311 | −9.2612 |
| 1130 | SER194 | N | 4.4584 | 14.6824 | −6.5404 |
| 1131 | SER194 | CA | 4.1404 | 14.3758 | −5.1598 |
| 1132 | SER194 | C | 2.866 | 13.5587 | −4.9666 |
| 1133 | SER194 | O | 2.5222 | 13.2064 | −3.8381 |
| 1134 | SER194 | CB | 4.3567 | 15.493 | −4.1172 |
| 1135 | SER194 | OG | 3.1377 | 16.2063 | −3.8864 |
| 1136 | GLY195 | N | 2.176 | 13.2208 | −6.1141 |
| 1137 | GLY195 | CA | 1.1358 | 12.206 | −6.0658 |
| 1138 | GLY195 | C | 1.7882 | 10.822 | −6.0921 |
| 1139 | GLY195 | O | 2.8873 | 10.6093 | −6.6065 |
| 1140 | GLU199 | N | −2.5121 | 6.1465 | −5.8806 |
| 1141 | GLU199 | CA | −3.5773 | 7.0891 | −6.2252 |
| 1142 | GLU199 | C | −3.8566 | 6.9376 | −7.7303 |
| 1143 | GLU199 | O | −4.9993 | 6.8618 | −8.1812 |
| 1144 | GLU199 | CB | −3.046 | 8.5117 | −5.9794 |
| 1145 | GLU199 | CG | −2.8762 | 8.7261 | −4.4654 |
| 1146 | GLU199 | CD | −1.8341 | 9.7648 | −4.1654 |
| 1147 | GLU199 | OE1 | −1.63 | 10.6852 | −5.0024 |
| 1148 | GLU199 | OE2 | −1.2058 | 9.6511 | −3.0809 |
| 1149 | ALA200 | N | −2.7213 | 6.902 | −8.5278 |
| 1150 | ALA200 | CA | −2.842 | 6.7555 | −9.9605 |
| 1151 | ALA200 | C | −3.45 | 5.3988 | −10.3097 |
| 1152 | ALA200 | O | −4.3298 | 5.2754 | −11.1633 |
| 1153 | ALA200 | CB | −1.4357 | 6.8497 | −10.5805 |
| 1154 | LEU201 | N | −2.922 | 4.3129 | −9.635 |
| 1155 | LEU201 | CA | −3.3751 | 2.957 | −9.9427 |
| 1156 | LEU201 | C | −4.9075 | 2.8846 | −9.7547 |
| 1157 | LEU201 | O | −5.6129 | 2.2233 | −10.5246 |
| 1158 | LEU201 | CB | −2.7345 | 2.0008 | −8.9179 |
| 1159 | LEU201 | CG | −2.2696 | 0.7033 | −9.6083 |
| 1160 | LEU201 | CD1 | −1.7303 | −0.2762 | −8.5491 |
| 1161 | LEU201 | CD2 | −3.4383 | 0.0413 | −10.3625 |
| 1162 | VAL202 | N | −5.4127 | 3.5437 | −8.6455 |
| 1163 | VAL202 | CA | −6.8497 | 3.6253 | −8.4177 |
| 1164 | VAL202 | C | −7.5073 | 4.5069 | −9.4862 |
| 1165 | VAL202 | O | −8.4947 | 4.0924 | −10.1074 |
| 1166 | VAL202 | CB | −7.1239 | 4.2445 | −7.0323 |
| 1167 | VAL202 | CG1 | −8.6414 | 4.274 | −6.7649 |
| 1168 | VAL202 | CG2 | −6.4384 | 3.4126 | −5.9324 |
| 1169 | ASP203 | N | −6.9576 | 5.7508 | −9.7191 |
| 1170 | ASP203 | CA | −7.662 | 6.72 | −10.568 |
| 1171 | ASP203 | C | −7.7643 | 6.2123 | −12.0267 |
| 1172 | ASP203 | O | −8.6495 | 6.6136 | −12.7897 |
| 1173 | ASP203 | CB | −6.9312 | 8.0729 | −10.5074 |
| 1174 | ASP203 | CG | −7.5182 | 8.8924 | −9.3946 |
| 1175 | ASP203 | OD1 | −7.1833 | 8.6159 | −8.2117 |
| 1176 | ASP203 | OD2 | −8.3092 | 9.8239 | −9.7007 |
| 1177 | PHE204 | N | −6.7745 | 5.3288 | −12.4181 |
| 1178 | PHE204 | CA | −6.7787 | 4.6718 | −13.7209 |
| 1179 | PHE204 | C | −7.5039 | 3.3039 | −13.7173 |
| 1180 | PHE204 | O | −7.4301 | 2.5569 | −14.6962 |
| 1181 | PHE204 | CB | −5.3233 | 4.4568 | −14.1833 |
| 1182 | PHE204 | CG | −4.7906 | 5.6489 | −14.9755 |
| 1183 | PHE204 | CD1 | −5.63 | 6.3842 | −15.8175 |
| 1184 | PHE204 | CD2 | −3.4431 | 6.0012 | −14.8599 |
| 1185 | PHE204 | CE1 | −5.1116 | 7.4353 | −16.5787 |
| 1186 | PHE204 | CE2 | −2.9247 | 7.0537 | −15.619 |
| 1187 | PHE204 | CZ | −3.7573 | 7.7662 | −16.4858 |
| 1188 | THR205 | N | −8.3016 | 2.9986 | −12.63 |
| 1189 | THR205 | CA | −8.952 | 1.6829 | −12.5554 |
| 1190 | THR205 | C | −10.2705 | 1.7051 | −11.7627 |
| 1191 | THR205 | O | −11.295 | 1.18 | −12.1962 |
| 1192 | THR205 | CB | −7.9841 | 0.6757 | −11.8991 |
| 1193 | THR205 | OG1 | −6.7587 | 0.6175 | −12.6342 |
| 1194 | THR205 | CG2 | −8.6165 | −0.7291 | −11.8676 |
| 1195 | GLY206 | N | −10.175 | 2.1806 | −10.4697 |
| 1196 | GLY206 | CA | −11.3324 | 2.192 | −9.5885 |
| 1197 | GLY206 | C | −11.5494 | 0.908 | −8.7917 |
| 1198 | GLY206 | O | −12.5236 | 0.7578 | −8.0566 |
| 1199 | GLY207 | N | −10.5234 | −0.0067 | −8.9016 |
| 1200 | GLY207 | CA | −10.3755 | −1.0644 | −7.9225 |
| 1201 | GLY207 | C | −9.6759 | −0.488 | −6.6908 |
| 1202 | GLY207 | O | −9.3188 | 0.6865 | −6.6208 |
| 1203 | VAL208 | N | −9.4719 | −1.4096 | −5.6779 |
| 1204 | VAL208 | CA | −8.7137 | −1.0176 | −4.4842 |
| 1205 | VAL208 | C | −7.2252 | −1.2657 | −4.7591 |
| 1206 | VAL208 | O | −6.8341 | −2.3528 | −5.1916 |
| 1207 | VAL208 | CB | −9.1628 | −1.8 | −3.2434 |
| 1208 | VAL208 | CG1 | −8.4598 | −1.2244 | −1.9901 |
| 1209 | VAL208 | CG2 | −10.6865 | −1.6664 | −3.0526 |
| 1210 | ASN220 | N | 0.5391 | −14.5311 | 5.7482 |
| 1211 | ASN220 | CA | −0.345 | −15.0597 | 4.7114 |
| 1212 | ASN220 | C | −0.1301 | −14.4188 | 3.3248 |
| 1213 | ASN220 | O | −0.8992 | −14.5951 | 2.3761 |
| 1214 | ASN220 | CB | −1.8072 | −14.8271 | 5.1425 |
| 1215 | ASN220 | CG | −2.0916 | −13.3553 | 5.2608 |
| 1216 | ASN220 | OD1 | −2.825 | −12.8137 | 4.4512 |
| 1217 | ASN220 | ND2 | −1.5115 | −12.6891 | 6.2753 |
| 1218 | LEU221 | N | 1.0815 | −13.7713 | 3.1652 |
| 1219 | LEU221 | CA | 1.2715 | −12.8164 | 2.0571 |
| 1220 | LEU221 | C | 1.2799 | −13.5607 | 0.7046 |
| 1221 | LEU221 | O | 0.9346 | −13.036 | −0.3535 |
| 1222 | LEU221 | CB | 2.6218 | −12.1004 | 2.259 |
| 1223 | LEU221 | CG | 2.9041 | −11.0458 | 1.1678 |
| 1224 | LEU221 | CD1 | 3.4846 | −11.7071 | −0.0966 |
| 1225 | LEU221 | CD2 | 1.6457 | −10.2237 | 0.8287 |
| 1226 | TRP222 | N | 1.7467 | −14.8606 | 0.7729 |
| 1227 | TRP222 | CA | 1.8026 | −15.7229 | −0.4088 |
| 1228 | TRP222 | C | 0.3893 | −16.1528 | −0.8382 |
| 1229 | TRP222 | O | 0.1312 | −16.4911 | −1.9975 |
| 1230 | TRP222 | CB | 2.6551 | −16.9633 | −0.0895 |
| 1231 | TRP222 | CG | 3.514 | −17.3207 | −1.269 |
| 1232 | TRP222 | CD1 | 3.9296 | −18.551 | −1.6056 |

TABLE IV-continued

| Atom No | Residue | Atom name | x coord | y coord | z coord |
|---|---|---|---|---|---|
| 1233 | TRP222 | CD2 | 4.0798 | −16.3703 | −2.2906 |
| 1234 | TRP222 | NE1 | 4.6819 | −18.4953 | −2.6768 |
| 1235 | TRP222 | CE2 | 4.8057 | −17.2219 | −3.1023 |
| 1236 | TRP222 | CE3 | 4.0008 | −14.9958 | −2.5113 |
| 1237 | TRP222 | CZ2 | 5.5389 | −16.7516 | −4.1911 |
| 1238 | TRP222 | CZ3 | 4.7089 | −14.5196 | −3.6215 |
| 1239 | TRP222 | CH2 | 5.4654 | −15.3749 | −4.4357 |
| 1240 | ASP223 | N | −0.5353 | −16.2792 | 0.1887 |
| 1241 | ASP223 | CA | −1.9239 | −16.5685 | −0.1432 |
| 1242 | ASP223 | C | −2.5885 | −15.3166 | −0.7289 |
| 1243 | ASP223 | O | −3.4409 | −15.4233 | −1.6113 |
| 1244 | ASP223 | CB | −2.6696 | −16.9075 | 1.1623 |
| 1245 | ASP223 | CG | −1.9071 | −17.9206 | 1.9661 |
| 1246 | ASP223 | OD1 | −2.0616 | −19.1383 | 1.6831 |
| 1247 | ASP223 | OD2 | −1.1616 | −17.4999 | 2.8907 |
| 1248 | ILE224 | N | −2.193 | −14.0971 | −0.2059 |
| 1249 | ILE224 | CA | −2.7525 | −12.8492 | −0.744 |
| 1250 | ILE224 | C | −2.3698 | −12.7895 | −2.2384 |
| 1251 | ILE224 | O | −3.2148 | −12.5541 | −3.1062 |
| 1252 | ILE224 | CB | −1.9614 | −11.7006 | −0.08 |
| 1253 | ILE224 | CG1 | −2.0125 | −11.7554 | 1.4607 |
| 1254 | ILE224 | CG2 | −2.415 | −10.3245 | −0.6073 |
| 1255 | ILE224 | CD1 | −3.3687 | −11.2443 | 1.9805 |
| 1256 | LEU225 | N | −1.0318 | −13.0064 | −2.5371 |
| 1257 | LEU225 | CA | −0.5436 | −12.7541 | −3.9012 |
| 1258 | LEU225 | C | −1.2766 | −13.7007 | −4.8795 |
| 1259 | LEU225 | O | −1.6357 | −13.3264 | −5.9993 |
| 1260 | LEU225 | CB | 0.9715 | −13.0185 | −3.9213 |
| 1261 | LEU225 | CG | 1.7156 | −11.6713 | −3.8561 |
| 1262 | LEU225 | CD1 | 1.4854 | −10.9979 | −2.4897 |
| 1263 | LEU225 | CD2 | 3.2213 | −11.907 | −4.0649 |
| 1264 | ILE226 | N | −1.4518 | −15.0023 | −4.4456 |
| 1265 | ILE226 | CA | −2.0745 | −15.9965 | −5.3171 |
| 1266 | ILE226 | C | −3.5714 | −15.6726 | −5.5167 |
| 1267 | ILE226 | O | −4.1698 | −15.9481 | −6.5587 |
| 1268 | ILE226 | CB | −1.8899 | −17.3793 | −4.662 |
| 1269 | ILE226 | CG1 | −0.3862 | −17.718 | −4.6364 |
| 1270 | ILE226 | CG2 | −2.642 | −18.4549 | −5.4702 |
| 1271 | ILE226 | CD1 | −0.1398 | −18.9911 | −3.8053 |
| 1272 | GLU227 | N | −4.2228 | −15.1961 | −4.388 |
| 1273 | GLU227 | CA | −5.6282 | −14.8244 | −4.443 |
| 1274 | GLU227 | C | −5.8203 | −13.5496 | −5.2825 |
| 1275 | GLU227 | O | −6.8718 | −13.3538 | −5.8944 |
| 1276 | GLU227 | CB | −6.0543 | −14.5149 | −2.9947 |
| 1277 | GLU227 | CG | −6.7645 | −15.73 | −2.3659 |
| 1278 | GLU227 | CD | −5.8178 | −16.8723 | −2.1316 |
| 1279 | GLU227 | OE1 | −5.5349 | −17.1663 | −0.9395 |
| 1280 | GLU227 | OE2 | −5.3604 | −17.486 | −3.1329 |
| 1281 | ALA228 | N | −4.7777 | −12.6483 | −5.2521 |
| 1282 | ALA228 | CA | −4.776 | −11.455 | −6.0904 |
| 1283 | ALA228 | C | −4.5622 | −11.8767 | −7.5598 |
| 1284 | ALA228 | O | −5.1727 | −11.3474 | −8.4919 |
| 1285 | ALA228 | CB | −3.5912 | −10.5744 | −5.6525 |
| 1286 | THR229 | N | −3.6251 | −12.867 | −7.7922 |
| 1287 | THR229 | CA | −3.3162 | −13.2583 | −9.1709 |
| 1288 | THR229 | C | −4.5689 | −13.8572 | −9.8218 |
| 1289 | THR229 | O | −4.9097 | −13.5481 | −10.9646 |
| 1290 | THR229 | CB | −2.119 | −14.2272 | −9.2376 |
| 1291 | THR229 | OG1 | −2.3184 | −15.3492 | −8.3756 |
| 1292 | THR229 | CG2 | −0.825 | −13.4907 | −8.8429 |
| 1293 | TYR230 | N | −5.2918 | −14.763 | −9.0662 |
| 1294 | TYR230 | CA | −6.4583 | −15.4248 | −9.6547 |
| 1295 | TYR230 | C | −7.7072 | −14.5029 | −9.7559 |
| 1296 | TYR230 | O | −8.7519 | −14.8875 | −10.2748 |
| 1297 | TYR230 | CB | −6.8168 | −16.6984 | −8.8549 |
| 1298 | TYR230 | CG | −7.4666 | −16.426 | −7.4941 |
| 1299 | TYR230 | CD1 | −6.9898 | −17.0901 | −6.3609 |
| 1300 | TYR230 | CD2 | −8.5379 | −15.5367 | −7.3628 |
| 1301 | TYR230 | CE1 | −7.6126 | −16.9041 | −5.1237 |
| 1302 | TYR230 | CE2 | −9.1241 | −15.2992 | −6.118 |
| 1303 | TYR230 | CZ | −8.6664 | −15.9953 | −4.9973 |
| 1304 | TYR230 | OH | −9.2605 | −15.7837 | −3.7595 |
| 1305 | ASN231 | N | −7.5398 | −13.2328 | −9.2411 |
| 1306 | ASN231 | CA | −8.4707 | −12.1217 | −9.4628 |
| 1307 | ASN231 | C | −8.1441 | −11.3886 | −10.7844 |
| 1308 | ASN231 | O | −8.9255 | −10.5879 | −11.3015 |
| 1309 | ASN231 | CB | −8.3969 | −11.1441 | −8.2751 |
| 1310 | ASN231 | CG | −9.4706 | −11.4856 | −7.2813 |
| 1311 | ASN231 | OD1 | −9.169 | −11.7934 | −6.1402 |
| 1312 | ASN231 | ND2 | −10.7455 | −11.4325 | −7.7086 |
| 1313 | ARG232 | N | −6.8621 | −11.5676 | −11.2662 |
| 1314 | ARG232 | CA | −6.3853 | −10.8097 | −12.4064 |
| 1315 | ARG232 | C | −6.0159 | −9.4036 | −11.9561 |
| 1316 | ARG232 | O | −6.1526 | −8.4293 | −12.6958 |
| 1317 | ARG232 | CB | −7.3543 | −10.8028 | −13.6066 |
| 1318 | ARG232 | CG | −7.3407 | −12.1783 | −14.2961 |
| 1319 | ARG232 | CD | −8.3543 | −12.1759 | −15.4551 |
| 1320 | ARG232 | NE | −8.1377 | −13.349 | −16.2813 |
| 1321 | ARG232 | CZ | −7.7623 | −13.2361 | −17.5225 |
| 1322 | ARG232 | NH1 | −7.5672 | −14.3083 | −18.2308 |
| 1323 | ARG232 | NH2 | −7.5763 | −12.0707 | −18.0691 |
| 1324 | THR233 | N | −5.4344 | −9.3387 | −10.7042 |
| 1325 | THR233 | CA | −5.0346 | −8.0619 | −10.1287 |
| 1326 | THR233 | C | −3.7566 | −7.5873 | −10.8289 |
| 1327 | THR233 | O | −2.8805 | −8.3575 | −11.2235 |
| 1328 | THR233 | CB | −4.8108 | −8.1256 | −8.6048 |
| 1329 | THR233 | OG1 | −3.7279 | −9.0059 | −8.2917 |
| 1330 | THR233 | CG2 | −6.0987 | −8.5817 | −7.8934 |
| 1331 | LEU234 | N | −3.6383 | −6.2111 | −10.9129 |
| 1332 | LEU234 | CA | −2.4212 | −5.6082 | −11.4445 |
| 1333 | LEU234 | C | −1.4991 | −5.4025 | −10.2343 |
| 1334 | LEU234 | O | −1.7828 | −4.5966 | −9.3461 |
| 1335 | LEU234 | CB | −2.7335 | −4.2456 | −12.0927 |
| 1336 | LEU234 | CG | −3.805 | −4.3977 | −13.1899 |
| 1337 | LEU234 | CD1 | −4.1814 | −3.0033 | −13.7237 |
| 1338 | LEU234 | CD2 | −3.261 | −5.2597 | −14.3451 |
| 1339 | ILE235 | N | −0.4064 | −6.2504 | −10.1931 |
| 1340 | ILE235 | CA | 0.6017 | −6.192 | −9.1379 |
| 1341 | ILE235 | C | 1.7908 | −5.3356 | −9.6145 |
| 1342 | ILE235 | O | 2.2008 | −5.3498 | −10.779 |
| 1343 | ILE235 | CB | 1.1155 | −7.6203 | −8.8608 |
| 1344 | ILE235 | CG1 | −0.0599 | −8.5572 | −8.5186 |
| 1345 | ILE235 | CG2 | 2.1354 | −7.6114 | −7.7054 |
| 1346 | ILE235 | CD1 | 0.4306 | −10.0168 | −8.4676 |
| 1347 | GLY236 | N | 2.42 | −4.6484 | −8.592 |
| 1348 | GLY236 | CA | 3.6097 | −3.8503 | −8.8163 |
| 1349 | GLY236 | C | 4.4661 | −3.8751 | −7.556 |
| 1350 | GLY236 | O | 4.0494 | −3.4215 | −6.4864 |
| 1351 | CYS237 | N | 5.5388 | −4.1763 | −7.1446 |
| 1352 | CYS237 | CA | 6.8369 | −4.4386 | −7.1951 |
| 1353 | CYS237 | C | 7.4475 | −4.8061 | −5.8055 |
| 1354 | CYS237 | O | 7.484 | −3.758 | −5.1653 |
| 1355 | CYS237 | CB | 6.5137 | −6.2914 | −7.605 |
| 1356 | CYS237 | SG | 7.8892 | −6.9754 | −8.5747 |
| 1357 | VAL250 | N | 18.7837 | −1.06 | −3.8757 |
| 1358 | VAL250 | CA | 18.7728 | −1.6614 | −5.1968 |
| 1359 | VAL250 | C | 18.1563 | −0.7936 | −6.2755 |
| 1360 | VAL250 | O | 17.5799 | 0.2563 | −6.0141 |
| 1361 | VAL250 | CB | 20.2071 | −2.0544 | −5.6135 |
| 1362 | VAL250 | CG1 | 21.0983 | −0.8042 | −5.7459 |
| 1363 | VAL250 | CG2 | 20.1899 | −2.8323 | −6.9436 |
| 1364 | GLU251 | N | 18.3669 | −0.2148 | −7.3233 |
| 1365 | GLU251 | CA | 17.7665 | 0.993 | −7.8951 |
| 1366 | GLU251 | C | 16.217 | 0.9991 | −7.9433 |
| 1367 | GLU251 | O | 15.5217 | −0.0022 | −8.13 |
| 1368 | GLU251 | CB | 18.3563 | 1.2753 | −9.292 |
| 1369 | GLU251 | CG | 17.7693 | 0.3208 | −10.3534 |
| 1370 | GLU251 | CD | 18.039 | −1.1153 | −10.0041 |
| 1371 | GLU251 | OE1 | 17.0546 | −1.8468 | −9.7159 |
| 1372 | GLU251 | OE2 | 19.2333 | −1.5165 | −10.0181 |
| 1373 | GLY252 | N | 15.6734 | 2.2759 | −7.9118 |
| 1374 | GLY252 | CA | 14.2506 | 2.4954 | −7.6952 |
| 1375 | GLY252 | C | 13.3542 | 2.3126 | −8.9232 |
| 1376 | GLY252 | O | 12.4592 | 3.1102 | −9.1965 |
| 1377 | HIS253 | N | 13.5372 | 1.1273 | −9.6114 |
| 1378 | HIS253 | CA | 12.566 | 0.6781 | −10.6178 |
| 1379 | HIS253 | C | 11.4865 | −0.1559 | −9.8957 |
| 1380 | HIS253 | O | 11.7404 | −0.8619 | −8.9163 |
| 1381 | HIS253 | CB | 13.2764 | −0.2088 | −11.6594 |
| 1382 | HIS253 | CG | 12.3129 | −0.6933 | −12.7051 |
| 1383 | HIS253 | ND1 | 11.7376 | 0.1248 | −13.5563 |
| 1384 | HIS253 | CD2 | 11.9466 | −1.9771 | −12.8817 |
| 1385 | HIS253 | CE1 | 10.9773 | −0.5897 | −14.3244 |
| 1386 | HIS253 | NE2 | 11.0523 | −1.7983 | −13.9931 |

TABLE IV-continued

| Atom No | Residue | Atom name | x coord | y coord | z coord |
|---|---|---|---|---|---|
| 1387 | ALA254 | N | 10.2237 | −0.0612 | −10.4641 |
| 1388 | ALA254 | CA | 9.1262 | −0.9262 | −10.0465 |
| 1389 | ALA254 | C | 8.9691 | −2.0231 | −11.1058 |
| 1390 | ALA254 | O | 8.8789 | −1.772 | −12.3048 |
| 1391 | ALA254 | CB | 7.8177 | −0.1351 | −9.8715 |
| 1392 | TYR255 | N | 8.9631 | −3.2945 | −10.5799 |
| 1393 | TYR255 | CA | 8.7409 | −4.4746 | −11.4081 |
| 1394 | TYR255 | C | 7.2757 | −4.8968 | −11.1662 |
| 1395 | TYR255 | O | 6.6574 | −4.578 | −10.1462 |
| 1396 | TYR255 | CB | 9.7104 | −5.6038 | −11.0117 |
| 1397 | TYR255 | CG | 11.1349 | −5.06 | −11.0372 |
| 1398 | TYR255 | CD1 | 11.6245 | −4.3411 | −9.9433 |
| 1399 | TYR255 | CD2 | 11.9459 | −5.2746 | −12.1545 |
| 1400 | TYR255 | CE1 | 12.9031 | −3.7807 | −9.9923 |
| 1401 | TYR255 | CE2 | 13.2324 | −4.731 | −12.1946 |
| 1402 | TYR255 | CZ | 13.7027 | −3.9676 | −11.1225 |
| 1403 | TYR255 | OH | 14.9665 | −3.3926 | −11.1806 |
| 1404 | THR256 | N | 6.7032 | −5.6869 | −12.1463 |
| 1405 | THR256 | CA | 5.4017 | −6.3105 | −11.8927 |
| 1406 | THR256 | C | 5.62 | −7.7682 | −11.4666 |
| 1407 | THR256 | O | 6.704 | −8.3411 | −11.5791 |
| 1408 | THR256 | CB | 4.5349 | −6.2455 | −13.1674 |
| 1409 | THR256 | OG1 | 3.2634 | −6.8578 | −12.933 |
| 1410 | THR256 | CG2 | 5.2393 | −6.9521 | −14.3426 |
| 1411 | LEU257 | N | 4.4903 | −8.3735 | −10.956 |
| 1412 | LEU257 | CA | 4.4405 | −9.7992 | −10.6241 |
| 1413 | LEU257 | C | 3.3352 | −10.3492 | −11.5298 |
| 1414 | LEU257 | O | 2.3071 | −9.7058 | −11.7431 |
| 1415 | LEU257 | CB | 4.0719 | −9.97 | −9.1384 |
| 1416 | LEU257 | CG | 4.449 | −11.3805 | −8.6471 |
| 1417 | LEU257 | CD1 | 4.42 | −11.398 | −7.1079 |
| 1418 | LEU257 | CD2 | 3.4361 | −12.4093 | −9.1829 |
| 1419 | THR258 | N | 3.5695 | −11.6026 | −12.0657 |
| 1420 | THR258 | CA | 2.6236 | −12.1467 | −13.048 |
| 1421 | THR258 | C | 2.3296 | −13.6435 | −12.8472 |
| 1422 | THR258 | O | 1.6948 | −14.3054 | −13.6756 |
| 1423 | THR258 | CB | 3.0645 | −11.8512 | −14.4962 |
| 1424 | THR258 | OG1 | 4.2124 | −12.6355 | −14.8271 |
| 1425 | THR258 | CG2 | 3.3907 | −10.3551 | −14.6699 |
| 1426 | GLY259 | N | 2.8063 | −14.1799 | −11.6779 |
| 1427 | GLY259 | CA | 2.6734 | −15.5863 | −11.3513 |
| 1428 | GLY259 | C | 3.3389 | −15.854 | −10.0101 |
| 1429 | GLY259 | O | 4.304 | −15.195 | −9.6162 |
| 1430 | ILE260 | N | 2.7885 | −16.9007 | −9.3074 |
| 1431 | ILE260 | CA | 3.2533 | −17.2739 | −7.977 |
| 1432 | ILE260 | C | 2.7416 | −18.6858 | −7.7268 |
| 1433 | ILE260 | O | 1.5506 | −18.9623 | −7.8542 |
| 1434 | ILE260 | CB | 2.6632 | −16.3002 | −6.934 |
| 1435 | ILE260 | CG1 | 3.4254 | −14.9634 | −6.9743 |
| 1436 | ILE260 | CG2 | 2.7358 | −16.8838 | −5.5089 |
| 1437 | ILE260 | CD1 | 2.5596 | −13.8638 | −6.3365 |
| 1438 | LEU272 | N | 7.6295 | −20.2065 | −5.2267 |
| 1439 | LEU272 | CA | 8.2148 | −19.4305 | −6.3034 |
| 1440 | LEU272 | C | 7.2661 | −18.2935 | −6.6979 |
| 1441 | LEU272 | O | 6.0434 | −18.3602 | −6.5699 |
| 1442 | LEU272 | CB | 8.5888 | −20.3099 | −7.5079 |
| 1443 | LEU272 | CG | 9.6054 | −21.3716 | −7.0504 |
| 1444 | LEU272 | CD1 | 10.0036 | −22.2306 | −8.2604 |
| 1445 | LEU272 | CD2 | 10.8588 | −20.691 | −6.4681 |
| 1446 | VAL273 | N | 7.917 | −17.2324 | −7.2939 |
| 1447 | VAL273 | CA | 7.2358 | −16.0184 | −7.722 |
| 1448 | VAL273 | C | 7.8155 | −15.6174 | −9.0891 |
| 1449 | VAL273 | O | 9.0208 | −15.6826 | −9.3478 |
| 1450 | VAL273 | CB | 7.4182 | −14.8938 | −6.6832 |
| 1451 | VAL273 | CG1 | 6.7413 | −13.5994 | −7.1733 |
| 1452 | VAL273 | CG2 | 8.9137 | −14.6382 | −6.4113 |
| 1453 | LYS274 | N | 6.862 | −15.1989 | −10.0027 |
| 1454 | LYS274 | CA | 7.2322 | −14.6979 | −11.3118 |
| 1455 | LYS274 | C | 7.1133 | −13.1683 | −11.2835 |
| 1456 | LYS274 | O | 6.0599 | −12.5689 | −11.505 |
| 1457 | LYS274 | CB | 6.3006 | −15.2891 | −12.3851 |
| 1458 | LYS274 | CG | 7.1148 | −15.4963 | −13.6755 |
| 1459 | LYS274 | CD | 6.3157 | −14.9771 | −14.8844 |
| 1460 | LYS274 | CE | 7.0223 | −13.7456 | −15.4826 |
| 1461 | LYS274 | NZ | 6.9113 | −12.6067 | −14.5607 |
| 1462 | LEU275 | N | 8.3118 | −12.5555 | −10.9585 |
| 1463 | LEU275 | CA | 8.497 | −11.1202 | −11.1425 |
| 1464 | LEU275 | C | 8.6314 | −10.9281 | −12.6662 |
| 1465 | LEU275 | O | 9.183 | −11.7675 | −13.3771 |
| 1466 | LEU275 | CB | 9.7478 | −10.6015 | −10.4053 |
| 1467 | LEU275 | CG | 9.6452 | −10.8357 | −8.8828 |
| 1468 | LEU275 | CD1 | 8.3234 | −10.2695 | −8.3293 |
| 1469 | LEU275 | CD2 | 9.7528 | −12.336 | −8.5475 |
| 1470 | ARG276 | N | 8.1358 | −9.74 | −13.1543 |
| 1471 | ARG276 | CA | 8.3421 | −9.324 | −14.5331 |
| 1472 | ARG276 | C | 8.8047 | −7.8552 | −14.5295 |
| 1473 | ARG276 | O | 8.2417 | −6.9722 | −13.8836 |
| 1474 | ARG276 | CB | 7.0444 | −9.48 | −15.3455 |
| 1475 | ARG276 | CG | 7.3659 | −9.3005 | −16.8396 |
| 1476 | ARG276 | CD | 6.062 | −9.0872 | −17.6287 |
| 1477 | ARG276 | NE | 6.3734 | −8.4218 | −18.8805 |
| 1478 | ARG276 | CZ | 6.0922 | −7.1638 | −19.0603 |
| 1479 | ARG276 | NH1 | 5.5179 | −6.4638 | −18.1263 |
| 1480 | ARG276 | NH2 | 6.3917 | −6.5985 | −20.192 |
| 1481 | ASN277 | N | 9.9012 | −7.6359 | −15.3508 |
| 1482 | ASN277 | CA | 10.3016 | −6.298 | −15.783 |
| 1483 | ASN277 | C | 9.4382 | −6.0331 | −17.0268 |
| 1484 | ASN277 | O | 9.4635 | −6.8197 | −17.9793 |
| 1485 | ASN277 | CB | 11.7935 | −6.306 | −16.1691 |
| 1486 | ASN277 | CG | 12.2067 | −4.9569 | −16.6844 |
| 1487 | ASN277 | OD1 | 12.677 | −4.8526 | −17.8051 |
| 1488 | ASN277 | ND2 | 12.0325 | −3.9052 | −15.8638 |
| 1489 | PRO278 | N | 8.6591 | −4.8959 | −17.042 |
| 1490 | PRO278 | CA | 7.7978 | −4.6224 | −18.1928 |
| 1491 | PRO278 | C | 8.507 | −3.9806 | −19.3944 |
| 1492 | PRO278 | O | 7.9611 | −3.9586 | −20.4996 |
| 1493 | PRO278 | CB | 6.8446 | −3.5703 | −17.5903 |
| 1494 | PRO278 | CG | 7.4474 | −3.0849 | −16.2523 |
| 1495 | PRO278 | CD | 8.643 | −3.9952 | −15.9106 |
| 1496 | TRP279 | N | 9.717 | −3.3532 | −19.1338 |
| 1497 | TRP279 | CA | 10.5405 | −2.8672 | −20.2519 |
| 1498 | TRP279 | C | 11.0577 | −4.086 | −21.0245 |
| 1499 | TRP279 | O | 11.2024 | −4.0388 | −22.2464 |
| 1500 | TRP279 | CB | 11.702 | −2.029 | −19.6878 |
| 1501 | TRP279 | CG | 11.2019 | −0.672 | −19.2777 |
| 1502 | TRP279 | CD1 | 9.9671 | −0.1697 | −19.4439 |
| 1503 | TRP279 | CD2 | 12.0185 | 0.3875 | −18.5888 |
| 1504 | TRP279 | NE1 | 9.9044 | 1.0428 | −18.9516 |
| 1505 | TRP279 | CE2 | 11.0955 | 1.4041 | −18.4321 |
| 1506 | TRP279 | CE3 | 13.34 | 0.4865 | −18.1559 |
| 1507 | TRP279 | CZ2 | 11.43 | 2.606 | −17.8089 |
| 1508 | TRP279 | CZ3 | 13.6877 | 1.6954 | −17.5407 |
| 1509 | TRP279 | CH2 | 12.7518 | 2.7248 | −17.3612 |
| 1510 | GLY280 | N | 11.4159 | −5.1697 | −20.251 |
| 1511 | GLY280 | CA | 11.5344 | −6.5276 | −20.7606 |
| 1512 | GLY280 | C | 12.812 | −7.2554 | −20.3432 |
| 1513 | GLY280 | O | 12.8765 | −8.4845 | −20.3353 |
| 1514 | LYS281 | N | 13.8767 | −6.4156 | −20.0798 |
| 1515 | LYS281 | CA | 15.2169 | −6.9354 | −19.7943 |
| 1516 | LYS281 | C | 15.1794 | −7.7785 | −18.5004 |
| 1517 | LYS281 | O | 14.3936 | −7.5659 | −17.5749 |
| 1518 | LYS281 | CB | 16.1986 | −5.759 | −19.6333 |
| 1519 | LYS281 | CG | 16.1224 | −4.8304 | −20.8619 |
| 1520 | LYS281 | CD | 14.9288 | −3.865 | −20.7223 |
| 1521 | LYS281 | CE | 14.4474 | −3.4386 | −22.1215 |
| 1522 | LYS281 | NZ | 13.5748 | −2.261 | −22.0113 |
| 1523 | VAL282 | N | 16.105 | −8.809 | −18.4822 |
| 1524 | VAL282 | CA | 16.0955 | −9.8258 | −17.4338 |
| 1525 | VAL282 | C | 17.2642 | −9.5236 | −16.4779 |
| 1526 | VAL282 | O | 17.0861 | −9.1222 | −15.3283 |
| 1527 | VAL282 | CB | 16.1673 | −11.2512 | −18.0151 |
| 1528 | VAL282 | CG1 | 16.201 | −12.2832 | −16.8712 |
| 1529 | VAL282 | CG2 | 14.9202 | −11.505 | −18.8829 |
| 1530 | GLU283 | N | 18.5204 | −9.7489 | −17.0297 |
| 1531 | GLU283 | CA | 19.7139 | −9.1512 | −16.4335 |
| 1532 | GLU283 | C | 19.9054 | −9.6078 | −14.9743 |
| 1533 | GLU283 | O | 20.3128 | −8.8728 | −14.0762 |
| 1534 | GLU283 | CB | 19.699 | −7.6156 | −16.554 |
| 1535 | GLU283 | CG | 20.3208 | −7.2119 | −17.9031 |
| 1536 | GLU283 | CD | 19.2366 | −6.8709 | −18.8827 |
| 1537 | GLU283 | OE1 | 18.5651 | −7.8146 | −19.3787 |
| 1538 | GLU283 | OE2 | 19.0641 | −5.6559 | −19.1671 |
| 1539 | TRP284 | N | 19.711 | −10.9701 | −14.8076 |
| 1540 | TRP284 | CA | 19.6307 | −11.5979 | −13.4902 |

TABLE IV-continued

| Atom No | Residue | Atom name | x coord | y coord | z coord |
|---|---|---|---|---|---|
| 1541 | TRP284 | C | 20.32 | −12.9674 | −13.5704 |
| 1542 | TRP284 | O | 20.2535 | −13.6941 | −14.5633 |
| 1543 | TRP284 | CB | 18.1888 | −11.6225 | −12.9414 |
| 1544 | TRP284 | CG | 17.91 | −12.8763 | −12.1649 |
| 1545 | TRP284 | CD1 | 18.4357 | −13.2441 | −10.9858 |
| 1546 | TRP284 | CD2 | 16.9741 | −13.97 | −12.5976 |
| 1547 | TRP284 | NE1 | 17.9623 | −14.4142 | −10.6335 |
| 1548 | TRP284 | CE2 | 17.0959 | −14.874 | −11.5596 |
| 1549 | TRP284 | CE3 | 16.1459 | −14.1717 | −13.7001 |
| 1550 | TRP284 | CZ2 | 16.3837 | −16.0723 | −11.5488 |
| 1551 | TRP284 | CZ3 | 15.4287 | −15.3733 | −13.6977 |
| 1552 | TRP284 | CH2 | 15.5441 | −16.2952 | −12.6471 |
| 1553 | LYS285 | N | 21.0285 | −13.3247 | −12.4366 |
| 1554 | LYS285 | CA | 21.9632 | −14.4504 | −12.445 |
| 1555 | LYS285 | C | 21.1662 | −15.7417 | −12.2212 |
| 1556 | LYS285 | O | 21.0234 | −16.2627 | −11.1162 |
| 1557 | LYS285 | CB | 22.9755 | −14.2461 | −11.3019 |
| 1558 | LYS285 | CG | 23.8492 | −13.0142 | −11.6019 |
| 1559 | LYS285 | CD | 24.8293 | −12.7871 | −10.4367 |
| 1560 | LYS285 | CE | 25.6941 | −11.5475 | −10.7307 |
| 1561 | LYS28S | NZ | 26.6278 | −11.3271 | −9.6171 |
| 1562 | GLY286 | N | 20.6382 | −16.2482 | −13.3943 |
| 1563 | GLY286 | CA | 20.0064 | −17.545 | −13.4703 |
| 1564 | GLY286 | C | 18.5419 | −17.4677 | −13.887 |
| 1565 | GLY286 | O | 18.054 | −16.5184 | −14.4926 |
| 1566 | ASP287 | N | 17.8398 | −18.6115 | −13.5564 |
| 1567 | ASP287 | CA | 16.4395 | −18.815 | −13.9266 |
| 1568 | ASP287 | C | 15.7156 | −19.501 | −12.7544 |
| 1569 | ASP287 | O | 14.7632 | −20.2565 | −12.9279 |
| 1570 | ASP287 | CB | 16.3237 | −19.6363 | −15.2247 |
| 1571 | ASP287 | CG | 17.1292 | −18.977 | −16.3062 |
| 1572 | ASP287 | OD1 | 18.2282 | −19.5037 | −16.6247 |
| 1573 | ASP287 | OD2 | 16.665 | −17.9357 | −16.8427 |
| 1574 | TRP288 | N | 16.2054 | −19.094 | −11.5288 |
| 1575 | TRP288 | CA | 15.7924 | −19.5176 | −10.1793 |
| 1576 | TRP288 | C | 17.1337 | −19.6211 | −9.4095 |
| 1577 | TRP288 | O | 18.0766 | −20.2926 | −9.8253 |
| 1578 | TRP288 | CB | 15.2243 | −20.9457 | −10.3028 |
| 1579 | TRP288 | CG | 14.4441 | −21.4204 | −9.1144 |
| 1580 | TRP288 | CD1 | 14.2846 | −20.8147 | −7.9271 |
| 1581 | TRP288 | CD2 | 13.6849 | −22.7179 | −9.0621 |
| 1582 | TRP288 | NE1 | 13.5403 | −21.5602 | −7.1474 |
| 1583 | TRP288 | CE2 | 13.1744 | −22.655 | −7.779 |
| 1584 | TRP288 | CE3 | 13.4595 | −23.7651 | −9.9543 |
| 1585 | TRP288 | CZ2 | 12.4059 | −23.7469 | −7.2824 |
| 1586 | TRP288 | CZ3 | 12.6885 | −24.8255 | −9.4629 |
| 1587 | TRP288 | CH2 | 12.1814 | −24.8191 | −8.1553 |
| 1588 | PRO300 | N | 9.0722 | −32.1709 | −11.9449 |
| 1589 | PRO300 | CA | 8.8932 | −32.9359 | −13.178 |
| 1590 | PRO300 | C | 8.459 | −32.0578 | −14.3665 |
| 1591 | PRO300 | O | 8.001 | −30.9196 | −14.2469 |
| 1592 | PRO300 | CB | 7.7612 | −33.9139 | −12.8092 |
| 1593 | PRO300 | CG | 7.3326 | −33.6108 | −11.3554 |
| 1594 | PRO300 | CD | 8.2537 | −32.5064 | −10.7989 |
| 1595 | LYS301 | N | 8.4755 | −32.7272 | −15.5917 |
| 1596 | LYS301 | CA | 8.2126 | −31.983 | −16.8382 |
| 1597 | LYS301 | C | 6.7948 | −31.3758 | −16.8074 |
| 1598 | LYS301 | O | 6.4991 | −30.3471 | −17.4149 |
| 1599 | LYS301 | CB | 8.3182 | −32.9405 | −18.0382 |
| 1600 | LYS301 | CG | 8.4303 | −32.1066 | −19.3278 |
| 1601 | LYS301 | CD | 8.3916 | −33.0374 | −20.5528 |
| 1602 | LYS301 | CE | 8.5678 | −32.1989 | −21.8321 |
| 1603 | LYS301 | NZ | 8.4029 | −33.0622 | −23.01 |
| 1604 | GLU302 | N | 5.8877 | −32.1242 | −16.0797 |
| 1605 | GLU302 | CA | 4.4635 | −31.8098 | −16.0248 |
| 1606 | GLU302 | C | 4.2584 | −30.4583 | −15.3122 |
| 1607 | GLU302 | O | 3.2774 | −29.75 | −15.532 |
| 1608 | GLU302 | CB | 3.7449 | −32.9192 | −15.2313 |
| 1609 | GLU302 | CG | 4.1635 | −34.3169 | −15.7328 |
| 1610 | GLU302 | CD | 4.0107 | −34.4234 | −17.2234 |
| 1611 | GLU302 | OE1 | 5.0311 | −34.2282 | −17.9371 |
| 1612 | GLU302 | OE2 | 2.8745 | −34.7148 | −17.6831 |
| 1613 | LYS303 | N | 5.1878 | −30.1862 | −14.3216 |
| 1614 | LYS303 | CA | 5.2839 | −28.8544 | −13.7347 |
| 1615 | LYS303 | C | 6.181 | −27.9679 | −14.6161 |
| 1616 | LYS303 | O | 5.9116 | −26.7753 | −14.7922 |
| 1617 | LYS303 | CB | 5.9465 | −29.0006 | −12.3508 |
| 1618 | LYS303 | CG | 5.9219 | −27.6475 | −11.6131 |
| 1619 | LYS303 | CD | 6.4192 | −27.8209 | −10.165 |
| 1620 | LYS303 | CE | 7.945 | −28.0304 | −10.1462 |
| 1621 | LYS303 | NZ | 8.4058 | −28.1127 | −8.7527 |
| 1622 | ILE304 | N | 7.3301 | −28.5457 | −15.1282 |
| 1623 | ILE304 | CA | 8.3447 | −27.6959 | −15.7599 |
| 1624 | ILE304 | C | 7.7032 | −26.9572 | −16.9428 |
| 1625 | ILE304 | O | 7.8731 | −25.7468 | −17.1109 |
| 1626 | ILE304 | CB | 9.5889 | −28.5008 | −16.1894 |
| 1627 | ILE304 | CG1 | 10.7478 | −27.5181 | −16.4497 |
| 1628 | ILE304 | CG2 | 9.3053 | −29.3183 | −17.4652 |
| 1629 | ILE304 | CD1 | 12.0311 | −28.283 | −16.8261 |
| 1630 | LEU305 | N | 6.8641 | −27.6745 | −17.7763 |
| 1631 | LEU305 | CA | 6.3499 | −27.0252 | −18.9765 |
| 1632 | LEU305 | C | 5.2601 | −25.9522 | −18.6982 |
| 1633 | LEU305 | O | 4.7144 | −25.3199 | −19.6105 |
| 1634 | LEU305 | CB | 5.7725 | −28.0968 | −19.9225 |
| 1635 | LEU305 | CG | 6.7608 | −29.2675 | −20.0948 |
| 1636 | LEU305 | CD1 | 6.095 | −30.3824 | −20.9216 |
| 1637 | LEU305 | CD2 | 8.0414 | −28.7888 | −20.8042 |
| 1638 | LEU306 | N | 4.9626 | −25.7193 | −17.3707 |
| 1639 | LEU306 | CA | 4.19 | −24.5679 | −16.915 |
| 1640 | LEU306 | C | 5.1086 | −23.3267 | −16.7981 |
| 1641 | LEU306 | O | 4.6468 | −22.188 | −16.8894 |
| 1642 | LEU306 | CB | 3.6932 | −24.9148 | −15.4982 |
| 1643 | LEU306 | CG | 2.3333 | −24.2509 | −15.2081 |
| 1644 | LEU306 | CD1 | 1.7749 | −24.8107 | −13.8871 |
| 1645 | LEU306 | CD2 | 2.4939 | −22.7248 | −15.0753 |
| 1646 | GLU314 | N | 10.4436 | −13.0374 | −18.0961 |
| 1647 | GLU314 | CA | 9.8608 | −14.2598 | −17.5136 |
| 1648 | GLU314 | C | 10.4432 | −14.4897 | −16.0917 |
| 1649 | GLU314 | O | 9.7656 | −14.9325 | −15.1632 |
| 1650 | GLU314 | CB | 10.1254 | −15.473 | −18.426 |
| 1651 | GLU314 | CG | 9.5111 | −16.7608 | −17.8338 |
| 1652 | GLU314 | CD | 8.0669 | −16.6372 | −17.4286 |
| 1653 | GLU314 | OE1 | 7.4432 | −15.5794 | −17.7046 |
| 1654 | GLU314 | OE2 | 7.5444 | −17.6074 | −16.8192 |
| 1655 | PHE315 | N | 11.8166 | −14.3518 | −15.9765 |
| 1656 | PHE315 | CA | 12.5183 | −14.472 | −14.6901 |
| 1657 | PHE315 | C | 12.3189 | −15.866 | −14.031 |
| 1658 | PHE315 | O | 13.0269 | −16.8309 | −14.3115 |
| 1659 | PHE315 | CB | 12.1636 | −13.3303 | −13.7155 |
| 1660 | PHE315 | CG | 12.6233 | −11.9913 | −14.2807 |
| 1661 | PHE315 | CD1 | 11.6801 | −11.0594 | −14.7211 |
| 1662 | PHE315 | CD2 | 13.9865 | −11.6939 | −14.3555 |
| 1663 | PHE315 | CE1 | 12.0974 | −9.832 | −15.2422 |
| 1664 | PHE315 | CE2 | 14.4035 | −10.465 | −14.8729 |
| 1665 | PHE315 | CZ | 13.4607 | −9.5373 | −15.3237 |
| 1666 | TRP316 | N | 11.2462 | −15.886 | −13.1565 |
| 1667 | TRP316 | CA | 10.9705 | −16.8771 | −12.1173 |
| 1668 | TRP316 | C | 12.0455 | −16.8216 | −11.0225 |
| 1669 | TRP316 | O | 13.2421 | −16.9797 | −11.2594 |
| 1670 | TRP316 | CB | 10.7381 | −18.2895 | −12.6822 |
| 1671 | TRP316 | CG | 9.2689 | −18.4001 | −12.963 |
| 1672 | TRP316 | CD1 | 8.6753 | −18.4596 | −14.1651 |
| 1673 | TRP316 | CD2 | 8.1813 | −18.4517 | −11.9242 |
| 1674 | TRP316 | NE1 | 7.3755 | −18.5351 | −14.0157 |
| 1675 | TRP316 | CE2 | 7.0451 | −18.521 | −12.7075 |
| 1676 | TRP316 | CE3 | 8.1457 | −18.4409 | −10.5304 |
| 1677 | TRP316 | CZ2 | 5.7705 | −18.5613 | −12.1427 |
| 1678 | TRP316 | CZ3 | 6.8694 | −18.4933 | −9.9561 |
| 1679 | TRP316 | CH2 | 5.7095 | −18.5382 | −10.7435 |
| 1680 | MET317 | N | 11.5608 | −16.6275 | −9.7416 |
| 1681 | MET317 | CA | 12.4538 | −16.6791 | −8.585 |
| 1682 | MET317 | C | 11.7004 | −17.2206 | −7.3651 |
| 1683 | MET317 | O | 10.5025 | −17.5005 | −7.3973 |
| 1684 | MET317 | CB | 13.0084 | −15.2749 | −8.2814 |
| 1685 | MET317 | CG | 14.094 | −14.9049 | −9.309 |
| 1686 | MET317 | SD | 15.4463 | −14.1 | −8.4033 |
| 1687 | MET317 | CE | 15.699 | −12.6828 | −9.5119 |
| 1688 | THR318 | N | 12.492 | −17.4183 | −6.2542 |
| 1689 | THR318 | CA | 11.9454 | −17.9342 | −5.0041 |
| 1690 | THR318 | C | 11.1717 | −16.829 | −4.282 |
| 1691 | THR318 | O | 11.3504 | −15.634 | −4.5022 |
| 1692 | THR318 | CB | 13.0703 | −18.454 | −4.0877 |
| 1693 | THR318 | OG1 | 13.9732 | −17.3917 | −3.7649 |
| 1694 | THR318 | CG2 | 13.8342 | −19.5924 | −4.7897 |

TABLE IV-continued

| Atom No | Residue | Atom name | x coord | y coord | z coord |
|---|---|---|---|---|---|
| 1695 | LEU319 | N | 10.3978 | −17.2806 | −3.2302 |
| 1696 | LEU319 | CA | 9.7894 | −16.3701 | −2.2475 |
| 1697 | LEU319 | C | 10.7846 | −16.099 | −1.0834 |
| 1698 | LEU319 | O | 10.4341 | −15.8581 | 0.0692 |
| 1699 | LEU319 | CB | 8.4396 | −16.8786 | −1.7027 |
| 1700 | LEU319 | CG | 7.7041 | −15.7551 | −0.9471 |
| 1701 | LEU319 | CD1 | 7.3298 | −14.6195 | −1.9176 |
| 1702 | LEU319 | CD2 | 6.4304 | −16.3237 | −0.2959 |
| 1703 | GLN320 | N | 12.099 | −15.9985 | −1.4967 |
| 1704 | GLN320 | CA | 13.173 | −15.3505 | −0.75 |
| 1705 | GLN320 | C | 13.7063 | −14.1818 | −1.6072 |
| 1706 | GLN320 | O | 14.8386 | −13.7152 | −1.4908 |
| 1707 | GLN320 | CB | 14.2955 | −16.3545 | −0.4343 |
| 1708 | GLN320 | CG | 13.8084 | −17.3041 | 0.6748 |
| 1709 | GLN320 | CD | 14.5664 | −17.039 | 1.9426 |
| 1710 | GLN320 | OE1 | 15.1729 | −17.9483 | 2.4844 |
| 1711 | GLN320 | NE2 | 14.54 | −15.7854 | 2.4298 |
| 1712 | ASP321 | N | 12.7319 | −13.6055 | −2.4064 |
| 1713 | ASP321 | CA | 12.9573 | −12.3844 | −3.173 |
| 1714 | ASP321 | C | 13.1776 | −11.2013 | −2.2097 |
| 1715 | ASP321 | O | 13.9278 | −10.2725 | −2.5109 |
| 1716 | ASP321 | CB | 14.1028 | −12.5416 | −4.1915 |
| 1717 | ASP321 | CG | 13.7547 | −13.6243 | −5.1712 |
| 1718 | ASP321 | OD1 | 12.8643 | −13.3811 | −6.0284 |
| 1719 | ASP321 | OD2 | 14.3754 | −14.7177 | −5.0903 |
| 1720 | PHE322 | N | 12.475 | −11.3022 | −1.0119 |
| 1721 | PHE322 | CA | 12.3354 | −10.223 | −0.0218 |
| 1722 | PHE322 | C | 13.6416 | −9.511 | 0.3661 |
| 1723 | PHE322 | O | 13.64 | −8.4219 | 0.9499 |
| 1724 | PHE322 | CB | 11.4304 | −10.6181 | 1.1591 |
| 1725 | PHE322 | CG | 10.0585 | −11.0417 | 0.6353 |
| 1726 | PHE322 | CD1 | 9.2605 | −11.8954 | 1.4014 |
| 1727 | PHE322 | CD2 | 9.5925 | −10.5846 | −0.6018 |
| 1728 | PHE322 | CE1 | 7.9945 | −12.2709 | 0.9439 |
| 1729 | PHE322 | CE2 | 8.3347 | −10.9736 | −1.0689 |
| 1730 | PHE322 | CZ | 7.5274 | −11.8041 | −0.2875 |
| 1731 | LYS323 | N | 14.7997 | −10.2081 | 0.0947 |
| 1732 | LYS323 | CA | 16.1194 | −9.6218 | 0.2551 |
| 1733 | LYS323 | C | 16.1537 | −8.3235 | −0.5737 |
| 1734 | LYS323 | O | 16.3342 | −7.2263 | −0.029 |
| 1735 | LYS323 | CB | 17.1131 | −10.6095 | −0.3812 |
| 1736 | LYS323 | CG | 18.4795 | −9.9502 | −0.6458 |
| 1737 | LYS323 | CD | 19.1402 | −10.6292 | −1.8584 |
| 1738 | LYS323 | CE | 20.4432 | −11.3163 | −1.4133 |
| 1739 | LYS323 | NZ | 20.5091 | −12.6665 | −1.99 |
| 1740 | THR324 | N | 15.8967 | −8.4471 | −1.9344 |
| 1741 | THR324 | CA | 15.6988 | −7.2232 | −2.7145 |
| 1742 | THR324 | C | 14.1951 | −6.8837 | −2.728 |
| 1743 | THR324 | O | 13.3502 | −7.5502 | −2.1343 |
| 1744 | THR324 | CB | 16.624 | −6.0305 | −2.3844 |
| 1745 | THR324 | OG1 | 16.4994 | −5.0168 | −3.3859 |
| 1746 | THR324 | CG2 | 18.0017 | −6.4955 | −2.3306 |
| 1747 | HIS325 | N | 13.8893 | −5.7011 | −3.3613 |
| 1748 | HIS325 | CA | 12.5701 | −5.0806 | −3.2588 |
| 1749 | HIS325 | C | 12.3707 | −4.4943 | −1.8399 |
| 1750 | HIS325 | O | 13.062 | −4.7926 | −0.8612 |
| 1751 | HIS325 | CB | 11.4731 | −6.1791 | −3.1788 |
| 1752 | HIS325 | CG | 11.4857 | −7.5352 | −3.8442 |
| 1753 | HIS325 | ND1 | 11.8417 | −7.758 | −5.0868 |
| 1754 | HIS325 | CD2 | 11.1153 | −8.6655 | −3.2092 |
| 1755 | HIS325 | CE1 | 11.7254 | −9.0281 | −5.3105 |
| 1756 | HIS325 | NE2 | 11.3146 | −9.6062 | −4.2763 |
| 1757 | PHE326 | N | 11.3365 | −3.58 | −1.7799 |
| 1758 | PHE326 | CA | 11.0067 | −2.793 | −0.5818 |
| 1759 | PHE326 | C | 9.5505 | −2.7222 | −0.3591 |
| 1760 | PHE326 | O | 9.0613 | −2.9912 | 0.741 |
| 1761 | PHE326 | CB | 11.643 | −1.3757 | −0.7791 |
| 1762 | PHE326 | CG | 10.9725 | −0.3951 | 0.179 |
| 1763 | PHE326 | CD1 | 11.4 | −0.3051 | 1.506 |
| 1764 | PHE326 | CD2 | 9.9205 | 0.405 | −0.2744 |
| 1765 | PHE326 | CE1 | 10.7388 | 0.5484 | 2.393 |
| 1766 | PHE326 | CE2 | 9.2546 | 1.2522 | 0.6146 |
| 1767 | PHE326 | CZ | 9.659 | 1.3172 | 1.9505 |
| 1768 | VAL327 | N | 8.7986 | −2.2783 | −1.4285 |
| 1769 | VAL327 | CA | 7.3404 | −2.1816 | −1.3464 |
| 1770 | VAL327 | C | 6.7208 | −3.0375 | −2.455 |
| 1771 | VAL327 | O | 7.3013 | −3.2595 | −3.5218 |
| 1772 | VAL327 | CB | 6.9055 | −0.7062 | −1.473 |
| 1773 | VAL327 | CG1 | 7.4988 | −0.0788 | −2.749 |
| 1774 | VAL327 | CG2 | 5.3698 | −0.5854 | −1.5107 |
| 1775 | LEU328 | N | 5.4394 | −3.474 | −2.1761 |
| 1776 | LEU328 | CA | 4.5394 | −3.9376 | −3.218 |
| 1777 | LEU328 | C | 3.2176 | −3.1868 | −3.0694 |
| 1778 | LEU328 | O | 2.724 | −2.9298 | −1.9697 |
| 1779 | LEU328 | CB | 4.3597 | −5.4663 | −3.2082 |
| 1780 | LEU328 | CG | 4.3722 | −6.0073 | −4.6495 |
| 1781 | LEU328 | CD1 | 4.7594 | −7.4974 | −4.632 |
| 1782 | LEU328 | CD2 | 2.9671 | −5.859 | −5.2598 |
| 1783 | LEU329 | N | 2.6001 | −2.9333 | −4.2765 |
| 1784 | LEU329 | CA | 1.193 | −2.6048 | −4.3562 |
| 1785 | LEU329 | C | 0.5155 | −3.4931 | −5.4062 |
| 1786 | LEU329 | O | 1.1143 | −3.9316 | −6.3919 |
| 1787 | LEU329 | CB | 0.9461 | −1.1036 | −4.6129 |
| 1788 | LEU329 | CG | 1.0817 | −0.7385 | −6.1049 |
| 1789 | LEU329 | CD1 | 0.608 | 0.7114 | −6.3194 |
| 1790 | LEU329 | CD2 | 2.55 | −0.8685 | −6.5509 |
| 1791 | VAL330 | N | −0.8373 | −3.6758 | −5.1815 |
| 1792 | VAL330 | CA | −1.6764 | −4.2365 | −6.2131 |
| 1793 | VAL330 | C | −3.022 | −3.5331 | −6.2756 |
| 1794 | VAL330 | O | −3.6295 | −3.1734 | −5.2701 |
| 1795 | VAL330 | CB | −1.869 | −5.7582 | −6.0539 |
| 1796 | VAL330 | CG1 | −0.5085 | −6.4754 | −6.1294 |
| 1797 | VAL330 | CG2 | −2.5427 | −6.0744 | −4.7044 |
| 1798 | ILE331 | N | −3.4871 | −3.4207 | −7.5793 |
| 1799 | ILE331 | CA | −4.8617 | −3.0387 | −7.8651 |
| 1800 | ILE331 | C | −5.6687 | −4.3361 | −7.8171 |
| 1801 | ILE331 | O | −5.5087 | −5.2422 | −8.6338 |
| 1802 | ILE331 | CB | −5.0263 | −2.2262 | −9.166 |
| 1803 | ILE331 | CG1 | −6.3283 | −1.3981 | −9.1359 |
| 1804 | ILE331 | CG2 | −4.9675 | −3.1137 | −10.4239 |
| 1805 | ILE331 | CD1 | −7.5711 | −2.308 | −9.0729 |
| 1806 | CYS332 | N | −6.5239 | −4.4163 | −6.736 |
| 1807 | CYS332 | CA | −7.5339 | −5.4568 | −6.6303 |
| 1808 | CYS332 | C | −8.7833 | −4.897 | −7.3342 |
| 1809 | CYS332 | O | −9.3973 | −3.9144 | −6.9199 |
| 1810 | CYS332 | CB | −7.8548 | −5.6814 | −5.1396 |
| 1811 | CYS332 | SG | −6.3101 | −6.0673 | −4.2608 |
| 1812 | LYS333 | N | −9.0627 | −5.5952 | −8.5015 |
| 1813 | LYS333 | CA | −9.997 | −5.1317 | −9.5439 |
| 1814 | LYS333 | C | −11.4423 | −5.0121 | −9.0241 |
| 1815 | LYS333 | O | −11.8644 | −5.6915 | −8.0867 |
| 1816 | LYS333 | CB | −9.9678 | −6.077 | −10.7587 |
| 1817 | LYS333 | CG | −8.7072 | −5.8054 | −11.5994 |
| 1818 | LYS333 | CD | −8.75 | −6.6779 | −12.8672 |
| 1819 | LYS333 | CE | −7.6597 | −6.2085 | −13.8472 |
| 1820 | LYS333 | NZ | −7.6919 | −7.0471 | −15.0537 |
| 1821 | LEU334 | N | −12.2462 | −4.1357 | −9.7491 |
| 1822 | LEU334 | CA | −13.6898 | −4.1252 | −9.5381 |
| 1823 | LEU334 | C | −14.38 | −5.1407 | −10.4725 |
| 1824 | LEU334 | O | −13.8784 | −5.5852 | −11.5051 |
| 1825 | LEU334 | CB | −14.2489 | −2.7054 | −9.764 |
| 1826 | LEU334 | CG | −13.6956 | −2.0947 | −11.0682 |
| 1827 | LEU334 | CD1 | −14.4444 | −2.6689 | −12.2862 |
| 1828 | LEU334 | CD2 | −13.8664 | −0.5646 | −11.0349 |
| 1829 | THR335 | N | −15.6585 | −5.5113 | −10.0732 |
| 1830 | THR335 | CA | −16.2374 | −6.7494 | −10.6099 |
| 1831 | THR335 | C | −16.3599 | −6.7425 | −12.1466 |
| 1832 | THR335 | O | −16.076 | −7.7687 | −12.7772 |
| 1833 | THR335 | CB | −17.6125 | −6.9852 | −9.9543 |
| 1834 | THR335 | OG1 | −17.482 | −6.932 | −8.5303 |
| 1835 | THR335 | CG2 | −18.1496 | −8.3726 | −10.354 |
| 1836 | PRO336 | N | −16.8272 | −5.6156 | −12.7969 |
| 1837 | PRO336 | CA | −16.8699 | −5.5685 | −14.2567 |
| 1838 | PRO336 | C | −15.6067 | −4.9394 | −14.8805 |
| 1839 | PRO336 | O | −15.6777 | −4.3094 | −15.9435 |
| 1840 | PRO336 | CB | −18.0247 | −4.5626 | −14.4324 |
| 1841 | PRO336 | CG | −18.0624 | −3.6981 | −13.1509 |
| 1842 | PRO336 | CD | −17.2995 | −4.468 | −12.0539 |
| 1843 | GLY337 | N | −14.381 | −5.2228 | −14.289 |
| 1844 | GLY337 | CA | −13.1765 | −4.5548 | −14.8168 |
| 1845 | GLY337 | C | −12.9591 | −5.1022 | −16.2423 |
| 1846 | GLY337 | O | −12.8797 | −4.3511 | −17.2155 |
| 1847 | LEU338 | N | −12.8761 | −6.4767 | −16.2809 |
| 1848 | LEU338 | CA | −12.7619 | −7.2844 | −17.5043 |

TABLE IV-continued

| Atom No | Residue | Atom name | x coord | y coord | z coord | Atom No | Residue | Atom name | x coord | y coord | z coord |
|---|---|---|---|---|---|---|---|---|---|---|---|
| 1849 | LEU338 | C | −14.1606 | −7.3168 | −18.1368 | 1926 | ARG355 | NH2 | −24.5773 | 15.2885 | 1.3572 |
| 1850 | LEU338 | O | −15.1946 | −7.3322 | −17.4563 | 1927 | TRP356 | N | −18.603 | 14.6557 | 6.4408 |
| 1851 | LEU338 | CB | −12.3491 | −8.7238 | −17.1402 | 1928 | TRP356 | CA | −18.2124 | 14.9479 | 7.8044 |
| 1852 | LEU338 | CG | −11.1472 | −8.7229 | −16.1758 | 1929 | TRP356 | C | −18.4159 | 16.4559 | 7.8518 |
| 1853 | LEU338 | CD1 | −10.784 | −10.1731 | −15.8073 | 1930 | TRP356 | O | −17.8369 | 17.1917 | 7.0365 |
| 1854 | LEU338 | CD2 | −9.9384 | −8.0376 | −16.8396 | 1931 | TRP356 | CB | −16.7627 | 14.5146 | 8.0845 |
| 1855 | LEU339 | N | −14.2068 | −7.4401 | −19.5093 | 1932 | TRP356 | CG | −16.7726 | 13.0541 | 8.4347 |
| 1856 | LEU339 | CA | −15.4662 | −7.5266 | −20.2566 | 1933 | TRP356 | CD1 | −17.5396 | 12.4499 | 9.3559 |
| 1857 | LEU339 | C | −16.0264 | −8.9621 | −20.1133 | 1934 | TRP356 | CD2 | −15.9162 | 11.9884 | 7.8061 |
| 1858 | LEU339 | O | −16.1698 | −9.7391 | −21.05 | 1935 | TRP356 | NE1 | −17.2804 | 11.1661 | 9.3854 |
| 1859 | LEU339 | CB | −15.192 | −7.1854 | −21.7343 | 1936 | TRP356 | CE2 | −16.3253 | 10.8559 | 8.4849 |
| 1860 | LEU339 | CG | −16.5204 | −7.0397 | −22.5014 | 1937 | TRP356 | CE3 | −14.9384 | 11.9675 | 6.8125 |
| 1861 | LEU339 | CD1 | −17.3118 | −5.8347 | −21.9584 | 1938 | TRP356 | CZ2 | −15.7751 | 9.6027 | 8.2162 |
| 1862 | LEU339 | CD2 | −16.225 | −6.8256 | −23.9972 | 1939 | TRP356 | CZ3 | −14.3821 | 10.7126 | 6.5358 |
| 1863 | LYS346 | N | −13.6587 | −13.5204 | −9.0845 | 1940 | TRP356 | CH2 | −14.7886 | 9.5589 | 7.2227 |
| 1864 | LYS346 | CA | −14.0349 | −12.0861 | −9.0598 | 1941 | GLU357 | N | −19.3203 | 16.9044 | 8.7193 |
| 1865 | LYS346 | C | −14.753 | −11.721 | −7.7248 | 1942 | GLU357 | CA | −19.606 | 18.3352 | 8.86 |
| 1866 | LYS346 | O | −15.5288 | −12.4919 | −7.1579 | 1943 | GLU357 | C | −19.4842 | 18.8591 | 10.2964 |
| 1867 | LYS346 | CB | −14.8475 | −11.6676 | −10.2994 | 1944 | GLU357 | O | −19.9862 | 18.1955 | 11.2342 |
| 1868 | LYS346 | CG | −13.8718 | −11.3517 | −11.4487 | 1945 | GLU357 | CB | −20.9875 | 18.6842 | 8.2767 |
| 1869 | LYS346 | CD | −14.6375 | −11.2352 | −12.7799 | 1946 | GLU357 | CG | −20.9456 | 18.5321 | 6.7443 |
| 1870 | LYS346 | CE | −13.64 | −10.9981 | −13.9304 | 1947 | GLU357 | CD | −21.6577 | 17.277 | 6.3304 |
| 1871 | LYS346 | NZ | −12.7546 | −12.1634 | −14.0738 | 1948 | GLU357 | OE1 | −22.7097 | 17.3928 | 5.6473 |
| 1872 | TRP347 | N | −14.4396 | −10.4473 | −7.2103 | 1949 | GLU357 | OE2 | −21.1669 | 16.1715 | 6.6798 |
| 1873 | TRP347 | CA | −15.068 | −9.9379 | −5.9543 | 1950 | LYS358 | N | −18.8123 | 19.9638 | 10.4456 |
| 1874 | TRP347 | C | −16.5675 | −9.6711 | −6.1715 | 1951 | LYS358 | CA | −18.5784 | 20.596 | 11.7354 |
| 1875 | TRP347 | O | −17.1483 | −9.8828 | −7.2403 | 1952 | LYS358 | C | −19.8825 | 20.9007 | 12.4589 |
| 1876 | TRP347 | CB | −14.3837 | −8.615 | −5.5551 | 1953 | LYS358 | O | −20.7664 | 21.5584 | 11.8981 |
| 1877 | TRP347 | CG | −12.8879 | −8.754 | −5.5676 | 1954 | LYS358 | CB | −17.7647 | 21.8918 | 11.564 |
| 1878 | TRP347 | CD1 | −12.0729 | −8.5668 | −6.6177 | 1955 | LYS358 | CG | −16.3456 | 21.5481 | 11.0763 |
| 1879 | TRP347 | CD2 | −12.005 | −9.1279 | −4.3949 | 1956 | LYS358 | CD | −15.5385 | 22.8472 | 10.9012 |
| 1880 | TRP347 | NE1 | −10.8288 | −8.7702 | −6.2605 | 1957 | LYS358 | CE | −14.1201 | 22.5052 | 10.4097 |
| 1881 | TRP347 | CE2 | −10.7582 | −9.1 | −4.9544 | 1958 | LYS358 | NZ | −13.3483 | 23.7448 | 10.2417 |
| 1882 | TRP347 | CE3 | −12.2542 | −9.4434 | −3.0568 | 1959 | ARG359 | N | −19.988 | 20.4295 | 13.7038 |
| 1883 | TRP347 | CZ2 | −9.6518 | −9.3836 | −4.2033 | 1960 | ARG359 | CA | −21.1878 | 20.6504 | 14.4995 |
| 1884 | TRP347 | CZ3 | −11.1126 | −9.7177 | −2.2936 | 1961 | ARG359 | C | −22.3413 | 19.688 | 14.2599 |
| 1885 | TRP347 | CH2 | −9.8263 | −9.6862 | −2.8519 | 1962 | ARG359 | O | −23.4525 | 19.9153 | 14.7234 |
| 1886 | THR348 | N | −17.2311 | −9.2235 | −5.0483 | 1963 | ARG359 | CB | −21.6403 | 22.1238 | 14.5393 |
| 1887 | THR348 | CA | −18.4309 | −8.3907 | −5.139 | 1964 | ARG359 | CG | −20.4707 | 23.0073 | 15.0097 |
| 1888 | THR348 | C | −18.0481 | −7.0196 | −4.5307 | 1965 | ARG359 | CD | −20.7762 | 24.4776 | 14.6735 |
| 1889 | THR348 | O | −17.0874 | −6.9101 | −3.7678 | 1966 | ARG359 | NE | −19.57 | 25.2658 | 14.8468 |
| 1890 | THR348 | CB | −19.6085 | −9.0273 | −4.3772 | 1967 | ARG359 | CZ | −18.8966 | 25.6977 | 13.8199 |
| 1891 | THR348 | OG1 | −19.828 | −10.3548 | −4.8585 | 1968 | ARG359 | NH1 | −17.8225 | 26.4039 | 14.0137 |
| 1892 | THR348 | CG2 | −20.8846 | −8.1903 | −4.5859 | 1969 | ARG359 | NH2 | −19.2781 | 25.435 | 12.6043 |
| 1893 | TYR349 | N | −18.8199 | −5.9544 | −4.9677 | 1970 | SER360 | N | −22.4316 | 19.0681 | 13.2168 |
| 1894 | TYR349 | CA | −18.4601 | −4.5467 | −4.7233 | 1971 | SER360 | CA | −23.2043 | 17.8403 | 13.0915 |
| 1895 | TYR349 | C | −19.692 | −3.7778 | −4.2256 | 1972 | SER360 | C | −22.3742 | 16.6311 | 12.6699 |
| 1896 | TYR349 | O | −20.7812 | −3.8985 | −4.7855 | 1973 | SER360 | O | −22.0803 | 15.7688 | 13.4894 |
| 1897 | TYR349 | CB | −17.8732 | −3.949 | −6.0187 | 1974 | SER360 | CB | −24.3557 | 18.0463 | 12.0893 |
| 1898 | TYR349 | CG | −17.9756 | −2.4268 | −6.045 | 1975 | SER360 | OG | −23.823 | 18.3466 | 10.7957 |
| 1899 | TYR349 | CD1 | −17.1307 | −1.644 | −5.2536 | 1976 | THR361 | N | −21.9695 | 15.9826 | 11.893 |
| 1900 | TYR349 | CD2 | −18.9219 | −1.8173 | −6.8727 | 1977 | THR361 | CA | −21.462 | 14.6538 | 11.5505 |
| 1901 | TYR349 | CE1 | −17.1971 | −0.2503 | −5.3315 | 1978 | THR361 | C | −19.9422 | 14.4741 | 11.6396 |
| 1902 | TYR349 | CE2 | −18.9874 | −0.4242 | −6.9511 | 1979 | THR361 | O | −19.4294 | 13.4251 | 11.272 |
| 1903 | TYR349 | CZ | −18.1057 | 0.3584 | −6.2015 | 1980 | THR361 | CB | −21.9676 | 14.2128 | 10.1637 |
| 1904 | TYR349 | OH | −18.1316 | 1.7425 | −6.3246 | 1981 | THR361 | OG1 | −21.4778 | 15.2108 | 9.1653 |
| 1905 | THR350 | N | −19.4222 | −2.8685 | −3.2006 | 1982 | THR361 | CG2 | −23.5074 | 14.2041 | 10.1459 |
| 1906 | THR350 | CA | −20.5275 | −2.1332 | −2.5886 | 1983 | ALA362 | N | −19.2276 | 15.5002 | 12.0997 |
| 1907 | THR350 | C | −20.0198 | −0.8124 | −1.9808 | 1984 | ALA362 | CA | −17.7763 | 15.4321 | 12.2395 |
| 1908 | THR350 | O | −19.9987 | −0.6341 | −0.7551 | 1985 | ALA362 | C | −17.4367 | 14.8736 | 13.6251 |
| 1909 | THR350 | CB | −21.212 | −3.0091 | −1.5168 | 1986 | ALA362 | O | −16.9456 | 15.5913 | 14.5084 |
| 1910 | THR350 | OG1 | −21.5712 | −4.2818 | −2.0617 | 1987 | ALA362 | CB | −17.2028 | 16.8495 | 12.0477 |
| 1911 | THR350 | CG2 | −22.4841 | −2.3087 | −1.0023 | 1988 | GLY363 | N | −17.7217 | 13.5846 | 13.8023 |
| 1912 | GLY354 | N | −20.2194 | 9.6125 | 1.8171 | 1989 | GLY363 | CA | −17.4981 | 12.9106 | 15.0732 |
| 1913 | GLY354 | CA | −20.5803 | 10.3257 | 3.0207 | 1990 | GLY363 | C | −16.0507 | 12.7893 | 15.4886 |
| 1914 | GLY354 | C | −19.8737 | 11.6442 | 3.2219 | 1991 | GLY363 | O | −15.6953 | 13.0821 | 16.6239 |
| 1915 | GLY354 | O | −18.9396 | 12.0026 | 2.4973 | 1992 | GLY364 | N | −15.2455 | 12.2508 | 14.5819 |
| 1916 | ARG355 | N | −20.3337 | 12.3595 | 4.2427 | 1993 | GLY364 | CA | −13.8274 | 12.1014 | 14.8131 |
| 1917 | ARG355 | CA | −19.7915 | 13.6605 | 4.6068 | 1994 | GLY364 | C | −13.2913 | 11.0766 | 15.7932 |
| 1918 | ARG355 | C | −19.4816 | 13.7208 | 6.1058 | 1995 | GLY364 | O | −13.3416 | 11.273 | 17.0034 |
| 1919 | ARG355 | O | −20.0338 | 12.963 | 6.9176 | 1996 | GLN365 | N | −12.8872 | 10.5746 | 16.2587 |
| 1920 | ARG355 | CB | −20.7626 | 14.7857 | 4.2022 | 1997 | GLN365 | CA | −12.2177 | 9.3095 | 16.5323 |
| 1921 | ARG355 | CG | −21.0081 | 14.7491 | 2.6824 | 1998 | GLN365 | C | −12.7076 | 8.4801 | 17.7223 |
| 1922 | ARG355 | CD | −22.067 | 15.8029 | 2.3093 | 1999 | GLN365 | O | −13.2636 | 9.0032 | 18.6825 |
| 1923 | ARG355 | NE | −22.3912 | 15.6855 | 0.8987 | 2000 | GLN365 | CB | −10.6929 | 9.4905 | 16.6352 |
| 1924 | ARG355 | CZ | −23.607 | 15.4387 | 0.5038 | 2001 | GLN365 | CG | −10.134 | 9.9541 | 15.278 |
| 1925 | ARG355 | NH1 | −23.8574 | 15.3402 | −0.7679 | 2002 | GLN365 | CD | −8.6864 | 10.3147 | 15.4393 |

TABLE IV-continued

| Atom No | Residue | Atom name | x coord | y coord | z coord |
|---|---|---|---|---|---|
| 2003 | GLN365 | OE1 | −8.3248 | 11.4677 | 15.2723 |
| 2004 | GLN365 | NE2 | −7.8401 | 9.3218 | 15.7669 |
| 2005 | ARG366 | N | −12.561 | 7.1283 | 17.6094 |
| 2006 | ARG366 | CA | −13.1445 | 6.4723 | 18.781 |
| 2007 | ARG366 | C | −12.8896 | 7.1163 | 20.1587 |
| 2008 | ARG366 | O | −13.7738 | 7.0958 | 21.0315 |
| 2009 | ARG366 | CB | −12.7742 | 4.9759 | 18.7668 |
| 2010 | ARG366 | CG | −11.2472 | 4.7882 | 18.8446 |
| 2011 | ARG366 | CD | −10.8011 | 4.8256 | 20.3175 |
| 2012 | ARG366 | NE | −9.3898 | 5.1547 | 20.3869 |
| 2013 | ARG366 | CZ | −8.5786 | 4.479 | 21.1478 |
| 2014 | ARG366 | NH1 | −9.0032 | 3.4848 | 21.8713 |
| 2015 | ARG366 | NH2 | −7.3211 | 4.8053 | 21.1864 |
| 2016 | PHE373 | N | −17.8554 | 11.3119 | 17.8872 |
| 2017 | PHE373 | CA | −17.7516 | 9.8813 | 17.6262 |
| 2018 | PHE373 | C | −19.0308 | 9.2625 | 17.0505 |
| 2019 | PHE373 | O | −19.2568 | 8.0759 | 17.2172 |
| 2020 | PHE373 | CB | −16.9451 | 9.0389 | 18.6357 |
| 2021 | PHE373 | CG | −16.324 | 7.8476 | 17.9125 |
| 2022 | PHE373 | CD1 | −15.6237 | 8.036 | 16.7175 |
| 2023 | PHE373 | CD2 | −16.4628 | 6.5632 | 18.4445 |
| 2024 | PHE373 | CE1 | −15.099 | 6.9361 | 16.0341 |
| 2025 | PHE373 | CE2 | −15.9354 | 5.4632 | 17.7631 |
| 2026 | PHE373 | CZ | −15.2611 | 5.6491 | 16.5535 |
| 2027 | TRP374 | N | −19.9905 | 8.9731 | 17.9207 |
| 2028 | TRP374 | CA | −21.2595 | 8.3699 | 17.5252 |
| 2029 | TRP374 | C | −22.0245 | 9.1861 | 16.4926 |
| 2030 | TRP374 | O | −23.0368 | 8.7253 | 15.9713 |
| 2031 | TRP374 | CB | −22.1189 | 8.2192 | 18.7948 |
| 2032 | TRP374 | CG | −22.3328 | 9.5651 | 19.4249 |
| 2033 | TRP374 | CD1 | −21.6289 | 10.1063 | 20.4312 |
| 2034 | TRP374 | CD2 | −23.3884 | 10.5621 | 19.0313 |
| 2035 | TRP374 | NE1 | −22.1033 | 11.2936 | 20.7179 |
| 2036 | TRP374 | CE2 | −23.1461 | 11.5948 | 19.9167 |
| 2037 | TRP374 | CE3 | −24.4029 | 10.5999 | 18.0759 |
| 2038 | TRP374 | CZ2 | −23.9217 | 12.7536 | 19.9176 |
| 2039 | TRP374 | CZ3 | −25.1882 | 11.759 | 18.072 |
| 2040 | TRP374 | CH2 | −24.9569 | 12.8067 | 18.9757 |
| 2041 | LYS375 | N | −21.5275 | 10.3856 | 16.1942 |
| 2042 | LYS375 | CA | −22.1675 | 11.2789 | 15.2353 |
| 2043 | LYS375 | C | −21.7208 | 11.1765 | 13.7615 |
| 2044 | LYS375 | O | −22.3195 | 11.8173 | 12.8934 |
| 2045 | LYS375 | CB | −21.7945 | 12.7149 | 15.6462 |
| 2046 | LYS375 | CG | −22.7664 | 13.2608 | 16.7055 |
| 2047 | LYS375 | CD | −22.5243 | 14.7753 | 16.843 |
| 2048 | LYS375 | CE | −23.3317 | 15.3345 | 18.0282 |
| 2049 | LYS375 | NZ | −22.4946 | 15.3293 | 19.2364 |
| 2050 | ASN376 | N | −20.6742 | 10.3986 | 13.4772 |
| 2051 | ASN376 | CA | −20.2178 | 10.2068 | 12.0918 |
| 2052 | ASN376 | C | −21.271 | 9.3361 | 11.4082 |
| 2053 | ASN376 | O | −22.0253 | 8.6268 | 12.0802 |
| 2054 | ASN376 | CB | −18.8283 | 9.544 | 12.0305 |
| 2055 | ASN376 | CG | −17.8494 | 10.3106 | 12.8735 |
| 2056 | ASN376 | OD1 | −17.0336 | 11.0469 | 12.3438 |
| 2057 | ASN376 | ND2 | −17.9206 | 10.135 | 14.2054 |
| 2058 | PRO377 | N | −21.3361 | 9.3671 | 10.0661 |
| 2059 | PRO377 | CA | −22.3291 | 8.5243 | 9.388 |
| 2060 | PRO377 | C | −22.057 | 7.0623 | 9.8079 |
| 2061 | PRO377 | O | −20.9748 | 6.7568 | 10.3328 |
| 2062 | PRO377 | CB | −21.9825 | 8.734 | 7.9066 |
| 2063 | PRO377 | CG | −20.8463 | 9.8082 | 7.8403 |
| 2064 | PRO377 | CD | −20.4446 | 10.1914 | 9.2799 |
| 2065 | GLN378 | N | −23.0285 | 6.1737 | 9.6047 |
| 2066 | GLN378 | CA | −22.871 | 4.7658 | 9.9888 |
| 2067 | GLN378 | C | −23.3197 | 3.8135 | 8.888 |
| 2068 | GLN378 | O | −24.2184 | 4.1278 | 8.1139 |
| 2069 | GLN378 | CB | −23.5706 | 4.4419 | 11.321 |
| 2070 | GLN378 | CG | −22.6472 | 4.8381 | 12.4894 |
| 2071 | GLN378 | CD | −23.0559 | 6.1428 | 13.1145 |
| 2072 | GLN378 | OE1 | −24.035 | 6.7518 | 12.7144 |
| 2073 | GLN378 | NE2 | −22.2862 | 6.5883 | 14.1234 |
| 2074 | PHE379 | N | −22.6923 | 2.6423 | 8.8249 |
| 2075 | PHE379 | CA | −23.0117 | 1.663 | 7.7884 |
| 2076 | PHE379 | C | −23.1047 | 0.251 | 8.3362 |
| 2077 | PHE379 | O | −22.7774 | 0.007 | 9.4898 |
| 2078 | PHE379 | CB | −21.964 | 1.751 | 6.6627 |
| 2079 | PHE379 | CG | −21.9246 | 3.1751 | 6.118 |
| 2080 | PHE379 | CD1 | −20.9971 | 4.0886 | 6.6254 |
| 2081 | PHE379 | CD2 | −22.8168 | 3.5682 | 5.1172 |
| 2082 | PHE379 | CE1 | −20.9784 | 5.4026 | 6.1507 |
| 2083 | PHE379 | CE2 | −22.7849 | 4.8767 | 4.6284 |
| 2084 | PHE379 | CZ | −21.8707 | 5.796 | 5.1499 |
| 2085 | LEU380 | N | −23.5633 | −0.6734 | 7.5016 |
| 2086 | LEU380 | CA | −23.6919 | −2.0542 | 7.9269 |
| 2087 | LEU380 | C | −23.0878 | −3.0227 | 6.9376 |
| 2088 | LEU380 | O | −23.4873 | −3.0586 | 5.7696 |
| 2089 | LEU380 | CB | −25.1596 | −2.4145 | 8.2242 |
| 2090 | LEU380 | CG | −25.2241 | −3.7603 | 8.9722 |
| 2091 | LEU380 | CD1 | −24.5552 | −3.6241 | 10.3532 |
| 2092 | LEU380 | CD2 | −26.6953 | −4.1756 | 9.1552 |
| 2093 | LEU381 | N | −22.1021 | −3.782 | 7.3987 |
| 2094 | LEU381 | CA | −21.5005 | −4.808 | 6.5733 |
| 2095 | LEU381 | C | −21.4522 | −6.0765 | 7.4047 |
| 2096 | LEU381 | O | −21.1832 | −6.0301 | 8.6037 |
| 2097 | LEU381 | CB | −20.0819 | −4.4019 | 6.1319 |
| 2098 | LEU381 | CG | −20.1459 | −3.1452 | 5.2433 |
| 2099 | LEU381 | CD1 | −18.7168 | −2.6707 | 4.9222 |
| 2100 | LEU381 | CD2 | −20.8874 | −3.4641 | 3.931 |
| 2101 | LEU399 | N | −11.2797 | −5.5873 | 3.0256 |
| 2102 | LEU399 | CA | −11.0656 | −5.2862 | 1.7318 |
| 2103 | LEU399 | C | −11.7767 | −3.9423 | 1.8086 |
| 2104 | LEU399 | O | −13.0068 | −3.8811 | 1.7749 |
| 2105 | LEU399 | CB | −11.6931 | −6.1679 | 0.6362 |
| 2106 | LEU399 | CG | −10.8241 | −6.0892 | −0.6329 |
| 2107 | LEU399 | CD1 | −9.5321 | −6.9031 | −0.4288 |
| 2108 | LEU399 | CD2 | −11.6064 | −6.6564 | −1.8309 |
| 2109 | VAL400 | N | −11.7072 | −3.2732 | 2.9534 |
| 2110 | VAL400 | CA | −12.3614 | −1.9744 | 3.0903 |
| 2111 | VAL400 | C | −11.4375 | −0.7941 | 2.7835 |
| 2112 | VAL400 | O | −10.3307 | −0.6825 | 3.325 |
| 2113 | VAL400 | CB | −13.1588 | −1.7882 | 4.3968 |
| 2114 | VAL400 | CG1 | −13.8429 | −0.4074 | 4.412 |
| 2115 | VAL400 | CG2 | −14.2414 | −2.8795 | 4.4962 |
| 2116 | SER401 | N | −11.9045 | 0.062 | 1.8749 |
| 2117 | SER401 | CA | −11.1554 | 1.2383 | 1.489 |
| 2118 | SER401 | C | −11.992 | 2.4792 | 1.7104 |
| 2119 | SER401 | O | −13.1049 | 2.5887 | 1.1756 |
| 2120 | SER401 | CB | −10.6612 | 1.1333 | 0.0332 |
| 2121 | SER401 | OG | −11.7598 | 0.8699 | −0.8441 |
| 2122 | LEU402 | N | −11.4823 | 3.3815 | 2.5481 |
| 2123 | LEU402 | CA | −12.1437 | 4.6486 | 2.8585 |
| 2124 | LEU402 | C | −11.2989 | 5.7178 | 2.21 |
| 2125 | LEU402 | O | −10.1325 | 5.8508 | 2.551 |
| 2126 | LEU402 | CB | −12.0995 | 4.7962 | 4.3943 |
| 2127 | LEU402 | CG | −12.4102 | 6.2361 | 4.8492 |
| 2128 | LEU402 | CD1 | −13.8656 | 6.5997 | 4.5007 |
| 2129 | LEU402 | CD2 | −12.2011 | 6.3444 | 6.3717 |
| 2130 | LEU403 | N | −11.8967 | 6.5044 | 1.3209 |
| 2131 | LEU403 | CA | −11.1725 | 7.5474 | 0.6033 |
| 2132 | LEU403 | C | −11.7708 | 8.9329 | 0.8565 |
| 2133 | LEU403 | O | −12.9664 | 9.0696 | 1.0485 |
| 2134 | LEU403 | CB | −11.117 | 7.218 | −0.9012 |
| 2135 | LEU403 | CG | −9.8589 | 7.8275 | −1.5495 |
| 2136 | LEU403 | CD1 | −9.5662 | 7.0971 | −2.873 |
| 2137 | LEU403 | CD2 | −10.0937 | 9.3191 | −1.8493 |
| 2138 | GLN404 | N | −10.9207 | 9.9471 | 0.9415 |
| 2139 | GLN404 | CA | −11.3855 | 11.3051 | 1.1758 |
| 2140 | GLN404 | C | −11.3453 | 12.1121 | −0.1269 |
| 2141 | GLN404 | O | −10.3735 | 12.0411 | −0.8945 |
| 2142 | GLN404 | CB | −10.5112 | 12.0111 | 2.228 |
| 2143 | GLN404 | CG | −9.0183 | 11.8766 | 1.864 |
| 2144 | GLN404 | CD | −8.1937 | 12.9899 | 2.4457 |
| 2145 | GLN404 | OE1 | −8.7227 | 13.9938 | 2.8945 |
| 2146 | GLN404 | NE2 | −6.8613 | 12.8104 | 2.4463 |
| 2147 | LYS405 | N | −12.4222 | 12.8483 | −0.3878 |
| 2148 | LYS405 | CA | −12.518 | 13.6554 | −1.5974 |
| 2149 | LYS405 | C | −11.798 | 14.9875 | −1.4256 |
| 2150 | LYS405 | O | −11.5074 | 15.4054 | −0.2997 |
| 2151 | LYS405 | CB | −13.985 | 13.8319 | −2.0291 |
| 2152 | LYS405 | CG | −14.4537 | 12.5454 | −2.7338 |
| 2153 | LYS405 | CD | −15.9403 | 12.677 | −3.112 |
| 2154 | LYS405 | CE | −16.417 | 11.381 | −3.7939 |
| 2155 | LYS405 | NZ | −16.1861 | 11.4678 | −5.243 |
| 2156 | PRO406 | N | −11.5033 | 15.637 | −2.552 |

TABLE IV-continued

| Atom No | Residue | Atom name | x coord | y coord | z coord |
|---|---|---|---|---|---|
| 2157 | PRO406 | CA | −10.8137 | 16.9279 | −2.5722 |
| 2158 | PRO406 | C | −11.7236 | 18.0933 | −2.1786 |
| 2159 | PRO406 | O | −12.9466 | 18.0443 | −2.3818 |
| 2160 | PRO406 | CB | −10.4066 | 17.0777 | −4.0502 |
| 2161 | PRO406 | CG | −11.1618 | 15.9903 | −4.8462 |
| 2162 | PRO406 | CD | −11.8425 | 15.0486 | −3.833 |
| 2163 | ARG407 | N | −11.1004 | 19.1521 | −1.6506 |
| 2164 | ARG407 | CA | −11.8132 | 20.3502 | −1.2146 |
| 2165 | ARG407 | C | −10.9625 | 21.6281 | −1.3154 |
| 2166 | ARG407 | O | −10.4741 | 22.1387 | −0.3026 |
| 2167 | ARG407 | CB | −12.2986 | 20.1195 | 0.2285 |
| 2168 | ARG407 | CG | −13.75 | 20.6143 | 0.3605 |
| 2169 | ARG407 | CD | −14.5797 | 19.5414 | 1.0886 |
| 2170 | ARG407 | NE | −14.806 | 18.4195 | 0.1955 |
| 2171 | ARG407 | CZ | −14.1296 | 17.3139 | 0.3173 |
| 2172 | ARG407 | NH1 | −13.2197 | 17.1765 | 1.2366 |
| 2173 | ARG407 | NH2 | −14.3691 | 16.33 | −0.4971 |
| 2174 | HIS408 | N | −11.0014 | 22.2129 | −2.2375 |
| 2175 | HIS408 | CA | −9.8249 | 23.0234 | −2.5578 |
| 2176 | HIS408 | C | −9.1699 | 23.7237 | −1.3649 |
| 2177 | HIS408 | O | −8.391 | 24.3342 | −1.9958 |
| 2178 | HIS408 | CB | −10.163 | 23.9089 | −3.7771 |
| 2179 | HIS408 | CG | −9.6012 | 23.2388 | −4.9957 |
| 2180 | HIS408 | ND1 | −9.9112 | 22.0018 | −5.3088 |
| 2181 | HIS408 | CD2 | −8.7462 | 23.8055 | −5.8684 |
| 2182 | HIS408 | CE1 | −9.2706 | 21.7087 | −6.3952 |
| 2183 | HIS408 | NE2 | −8.5872 | 22.6943 | −6.7667 |
| 2184 | ARG409 | N | −8.5536 | 23.516 | −0.9303 |
| 2185 | ARG409 | CA | −7.3223 | 23.5699 | −0.1401 |
| 2186 | ARG409 | C | −6.0983 | 22.8344 | −0.7238 |
| 2187 | ARG409 | O | −4.9844 | 23.3773 | −0.7235 |
| 2188 | ARG409 | CB | −7.6311 | 22.9841 | 1.2506 |
| 2189 | ARG409 | CG | −6.5102 | 23.363 | 2.2356 |
| 2190 | ARG409 | CD | −6.7839 | 22.7001 | 3.5974 |
| 2191 | ARG409 | NE | −5.682 | 22.9836 | 4.4984 |
| 2192 | ARG409 | CZ | −4.9048 | 22.0328 | 4.9303 |
| 2193 | AR0409 | NH1 | −5.0867 | 20.7964 | 4.5691 |
| 2194 | ARG409 | NH2 | −3.9285 | 22.3251 | 5.7372 |
| 2195 | CYS410 | N | −6.305 | 21.6096 | −1.211 |
| 2196 | CYS410 | CA | −5.2291 | 20.8006 | −1.7878 |
| 2197 | CYS410 | C | −4.7437 | 21.339 | −3.1387 |
| 2198 | CYS410 | O | −5.4734 | 21.2892 | −4.1333 |
| 2199 | CYS410 | CB | −5.7726 | 19.3545 | −1.9733 |
| 2200 | CYS410 | SG | −6.1399 | 18.6764 | −0.3384 |
| 2201 | ARG411 | N | −3.5047 | 21.8272 | −3.1759 |
| 2202 | ARG411 | CA | −2.9217 | 22.3682 | −4.408 |
| 2203 | ARG411 | C | −2.3706 | 21.2465 | −5.2891 |
| 2204 | ARG411 | O | −2.334 | 21.365 | −6.521 |
| 2205 | ARG411 | CB | −1.8105 | 23.366 | −4.0351 |
| 2206 | ARG411 | CG | −2.2844 | 24.798 | −4.3547 |
| 2207 | ARG411 | CD | −3.3099 | 25.296 | −3.315 |
| 2208 | ARG411 | NE | −4.463 | 24.4149 | −3.2693 |
| 2209 | ARG411 | CZ | −5.5445 | 24.6704 | −3.946 |
| 2210 | ARG411 | NH1 | −5.6424 | 25.7334 | −4.689 |
| 2211 | ARG411 | NH2 | −6.5441 | 23.8429 | −3.8791 |
| 2212 | LYS412 | N | −2.0034 | 20.155 | −4.6818 |
| 2213 | LYS412 | CA | −1.3477 | 18.9915 | −5.2731 |
| 2214 | LYS412 | C | −2.2703 | 17.8226 | −5.6321 |
| 2215 | LYS412 | O | −1.8677 | 16.889 | −6.3285 |
| 2216 | LYS412 | CB | 0.1354 | 18.7248 | −4.9605 |
| 2217 | LYS412 | CG | 0.9794 | 19.5622 | −5.9387 |
| 2218 | LYS412 | CD | 2.4766 | 19.3549 | −5.6505 |
| 2219 | LYS412 | CE | 3.3033 | 20.2142 | −6.6246 |
| 2220 | LYS412 | NZ | 4.6200 | 19.5956 | −6.8299 |
| 2221 | ILE419 | N | −8.6232 | 9.5358 | 6.8454 |
| 2222 | ILE419 | CA | −8.7953 | 9.3093 | 8.2832 |
| 2223 | ILE419 | C | −8.8493 | 7.8239 | 8.5702 |
| 2224 | ILE419 | O | −9.1131 | 7.0324 | 7.6708 |
| 2225 | ILE419 | CB | −10.0831 | 9.9968 | 8.7935 |
| 2226 | ILE419 | CG1 | −11.3607 | 9.3761 | 8.1849 |
| 2227 | ILE419 | CG2 | −10.0433 | 11.5167 | 8.5429 |
| 2228 | ILE419 | CD1 | −11.4138 | 9.5647 | 6.6559 |
| 2229 | GLY420 | N | −9.4897 | 7.282 | 9.2986 |
| 2230 | GLY420 | CA | −9.5657 | 5.8953 | 9.7181 |
| 2231 | GLY420 | C | −11.0225 | 5.5333 | 9.9443 |
| 2232 | GLY420 | O | −11.8765 | 6.3862 | 9.9751 |
| 2233 | PHE421 | N | −11.2936 | 4.2932 | 10.0838 |
| 2234 | PHE421 | CA | −12.6684 | 3.8445 | 10.3389 |
| 2235 | PHE421 | C | −12.6373 | 2.6376 | 11.2691 |
| 2236 | PHE421 | O | −11.9166 | 1.7455 | 11.091 |
| 2237 | PHE421 | CB | −13.5136 | 3.6209 | 9.0676 |
| 2238 | PHE421 | CG | −12.8762 | 2.5907 | 8.1403 |
| 2239 | PHE421 | CD1 | −12.9824 | 1.2265 | 8.4257 |
| 2240 | PHE421 | CD2 | −12.1885 | 3.014 | 6.9999 |
| 2241 | PHE421 | CE1 | −12.3816 | 0.2863 | 7.5846 |
| 2242 | PHE421 | CE2 | −11.6042 | 2.0735 | 6.1476 |
| 2243 | PHE421 | CZ | −11.6955 | 0.7108 | 6.444 |
| 2244 | TYR422 | N | −13.3419 | 2.6273 | 12.2494 |
| 2245 | TYR422 | CA | −13.4014 | 1.4742 | 13.1552 |
| 2246 | TYR422 | C | −14.673 | 0.7253 | 12.8963 |
| 2247 | TYR422 | O | −15.7005 | 1.3588 | 12.6603 |
| 2248 | TYR422 | CB | −13.4225 | 1.896 | 14.6386 |
| 2249 | TYR422 | CG | −12.5988 | 3.1533 | 14.9 |
| 2250 | TYR422 | CD1 | −13.133 | 4.4116 | 14.6103 |
| 2251 | TYR422 | CD2 | −11.3139 | 3.0477 | 15.4382 |
| 2252 | TYR422 | CE1 | −12.3958 | 5.5657 | 14.8872 |
| 2253 | TYR422 | CE2 | −10.5773 | 4.2018 | 15.7175 |
| 2254 | TYR422 | CZ | −11.1209 | 5.4606 | 15.449 |
| 2255 | TYR422 | OH | −10.3932 | 6.6081 | 15.7404 |
| 2256 | LEU423 | N | −14.6042 | −0.5562 | 12.874 |
| 2257 | LEU423 | CA | −15.8179 | −1.3236 | 12.6719 |
| 2258 | LEU423 | C | −16.1001 | −2.2128 | 13.8968 |
| 2259 | LEU423 | O | −15.2057 | −2.8951 | 14.3503 |
| 2260 | LEU423 | CB | −15.6594 | −2.222 | 11.4302 |
| 2261 | LEU423 | CG | −17.0006 | −2.3612 | 10.6831 |
| 2262 | LEU423 | CD1 | −16.8092 | −3.278 | 9.4606 |
| 2263 | LEU423 | CD2 | −18.0756 | −2.9663 | 11.6055 |
| 2264 | TYR424 | N | −17.3096 | −2.1397 | 14.4203 |
| 2265 | TYR424 | CA | −17.6813 | −3.0385 | 15.5276 |
| 2266 | TYR424 | C | −18.874 | −3.8529 | 15.0155 |
| 2267 | TYR424 | O | −19.8515 | −3.2687 | 14.737 |
| 2268 | TYR424 | CB | −18.0616 | −2.1939 | 16.7602 |
| 2269 | TYR424 | CG | −17.0839 | −1.0307 | 16.913 |
| 2270 | TYR424 | CD1 | −17.3766 | 0.2036 | 16.3266 |
| 2271 | TYR424 | CD2 | −15.8977 | −1.1963 | 17.6328 |
| 2272 | TYR424 | CE1 | −16.4886 | 1.2738 | 16.4637 |
| 2273 | TYR424 | CE2 | −15.0125 | −0.1243 | 17.7756 |
| 2274 | TYR424 | CZ | −15.3148 | 1.115 | 17.2048 |
| 2275 | TYR424 | OH | −14.4498 | 2.1898 | 17.3759 |
| 2276 | SER18 | N | −29.219 | 12.2461 | −11.1118 |
| 2277 | SER18 | CA | −28.5696 | 11.9899 | −12.3855 |
| 2278 | SER18 | C | −27.2585 | 11.2838 | −12.1555 |
| 2279 | SER18 | O | −27.0026 | 10.8074 | −11.0608 |
| 2280 | SER18 | CB | −28.3112 | 13.3475 | −13.0696 |
| 2281 | SER18 | OG | −27.4242 | 14.143 | −12.2771 |
| 2282 | ARG19 | N | −26.4112 | 11.2244 | −13.2015 |
| 2283 | ARG19 | CA | −25.1037 | 10.6172 | −13.0182 |
| 2284 | ARG19 | C | −24.0502 | 11.6653 | −12.7938 |
| 2285 | ARG19 | O | −24.3376 | 12.8489 | −12.8706 |
| 2286 | ARG19 | CB | −24.7295 | 9.8228 | −14.2824 |
| 2287 | ARG19 | CG | −25.4163 | 8.4463 | −14.2455 |
| 2288 | ARG19 | CD | −24.9216 | 7.6042 | −15.4352 |
| 2289 | ARG19 | NE | −25.384 | 6.2371 | −15.2815 |
| 2290 | ARG19 | CZ | −26.1887 | 5.697 | −16.1504 |
| 2291 | ARG19 | NH1 | −26.5806 | 4.4696 | −15.9789 |
| 2292 | ARG19 | NH2 | −26.6077 | 6.3625 | −17.1867 |
| 2293 | ARG20 | N | −22.8103 | 11.2111 | −12.5208 |
| 2294 | ARG20 | CA | −21.7107 | 12.1564 | −12.4228 |
| 2295 | ARG20 | C | −21.2983 | 12.5578 | −13.8122 |
| 2296 | ARG20 | O | −20.9314 | 13.6994 | −14.038 |
| 2297 | ARG20 | CB | −20.5429 | 11.5144 | −11.6414 |
| 2298 | ARG20 | CG | −19.6366 | 10.6438 | −12.5364 |
| 2299 | ARG20 | CD | −20.4078 | 9.4148 | −13.0514 |
| 2300 | ARG20 | NE | −20.1989 | 8.3033 | −12.1436 |
| 2301 | ARG20 | CZ | −19.6059 | 7.215 | −12.5401 |
| 2302 | ARG20 | NH1 | −19.4299 | 6.2426 | −11.6956 |
| 2303 | ARG20 | NH2 | −19.1839 | 7.0845 | −13.764 |
| 2304 | ALA21 | N | −21.3829 | 11.5916 | −14.7481 |
| 2305 | ALA21 | CA | −21.0788 | 11.4988 | −16.1328 |
| 2306 | ALA21 | C | −22.0716 | 12.8888 | −16.6703 |
| 2307 | ALA21 | O | −21.7518 | 13.5873 | −16.7179 |
| 2308 | ALA21 | CB | −21.1798 | 10.5933 | −16.9424 |
| 2309 | SER22 | N | −23.2695 | 12.9551 | −16.0522 |
| 2310 | SER22 | CA | −24.2611 | 13.9176 | −16.5033 |

TABLE IV-continued

| Atom No | Residue | Atom name | x coord | y coord | z coord |
|---|---|---|---|---|---|
| 2311 | SER22 | C | -23.6822 | 15.3066 | -16.5316 |
| 2312 | SER22 | O | -23.6389 | 15.8754 | -17.6094 |
| 2313 | SER22 | CB | -25.5205 | 13.8526 | -15.6185 |
| 2314 | SER22 | OG | -26.0658 | 12.5317 | -15.6598 |
| 2315 | PRO23 | N | -23.2183 | 15.8635 | -15.3902 |
| 2316 | PRO23 | CA | -22.571 | 17.1607 | -15.4163 |
| 2317 | PRO23 | C | -21.2635 | 17.0693 | -16.1522 |
| 2318 | PRO23 | O | -20.8147 | 18.0635 | -16.6991 |
| 2319 | PRO23 | CB | -22.2752 | 17.4063 | -13.9234 |
| 2320 | PRO23 | CG | -22.6119 | 16.1125 | -13.1508 |
| 2321 | PRO23 | CD | -23.3322 | 15.1657 | -14.1283 |
| 2322 | GLN24 | N | -20.6603 | 15.8634 | -16.1775 |
| 2323 | GLN24 | CA | -19.433 | 15.6899 | -16.9365 |
| 2324 | GLN24 | C | -19.6586 | 16.0109 | -18.3889 |
| 2325 | GLN24 | O | -18.7296 | 16.44 | -19.0534 |
| 2326 | GLN24 | CB | -18.9822 | 14.2236 | -16.7999 |
| 2327 | GLN24 | CG | -17.8675 | 14.121 | -15.7416 |
| 2328 | GLN24 | CD | -18.1193 | 12.964 | -14.8176 |
| 2329 | GLN24 | OE1 | -18.1804 | 13.1523 | -13.6139 |
| 2330 | GLN24 | NE2 | -18.2685 | 11.7477 | -15.3715 |
| 2331 | GLN25 | N | -20.9014 | 15.8186 | -18.8769 |
| 2332 | GLN25 | CA | -21.1908 | 16.151 | -20.262 |
| 2333 | GLN25 | C | -20.9543 | 17.6163 | -20.5161 |
| 2334 | GLN25 | O | -20.1181 | 17.9192 | -21.352 |
| 2335 | GLN25 | CB | -22.6443 | 15.7729 | -20.6035 |
| 2336 | GLN25 | CG | -22.7804 | 14.244 | -20.7335 |
| 2337 | GLN25 | CD | -23.9393 | 13.7462 | -19.9172 |
| 2338 | GLN25 | OE1 | -23.8042 | 12.7627 | -19.2084 |
| 2339 | GLN25 | NE2 | -25.0992 | 14.4217 | -20.0082 |
| 2340 | PRO26 | N | -21.6509 | 18.5378 | -19.8106 |
| 2341 | PRO26 | CA | -21.3793 | 19.9524 | -19.9756 |
| 2342 | PRO26 | C | -19.9355 | 20.2396 | -19.6769 |
| 2343 | PRO26 | O | -19.3935 | 21.1953 | -20.2082 |
| 2344 | PRO26 | CB | -22.2515 | 20.5874 | -18.8742 |
| 2345 | PRO26 | CG | -23.0722 | 19.4644 | -18.2035 |
| 2346 | PRO26 | CD | -22.6617 | 18.1328 | -18.8588 |
| 2347 | GLN27 | N | -19.3128 | 19.3876 | -18.838 |
| 2348 | GLN27 | CA | -17.8868 | 19.5279 | -18.6092 |
| 2349 | GLN27 | C | -17.1497 | 18.9872 | -19.8049 |
| 2350 | GLN27 | O | -16.4509 | 17.9906 | -19.7081 |
| 2351 | GLN27 | CB | -17.5082 | 18.7621 | -17.3247 |
| 2352 | GLN27 | CG | -18.2592 | 19.3411 | -16.11 |
| 2353 | GLN27 | CD | -17.7275 | 20.7009 | -15.7592 |
| 2354 | GLN27 | OE1 | -17.1188 | 20.8629 | -14.7145 |
| 2355 | GLN27 | NE2 | -17.9586 | 21.6981 | -16.6322 |
| 2356 | TYR84 | N | -1.9756 | 4.3397 | -31.0125 |
| 2357 | TYR84 | CA | -1.4483 | 3.2203 | -30.2523 |
| 2358 | TYR84 | C | -1.5153 | 2.0149 | -31.1458 |
| 2359 | TYR84 | O | -2.2802 | 1.0942 | -30.904 |
| 2360 | TYR84 | CB | -2.2419 | 3.0353 | -28.9389 |
| 2361 | TYR84 | CG | -1.6037 | 2.0109 | -27.9974 |
| 2362 | TYR84 | CD1 | -1.8801 | 2.0732 | -26.6288 |
| 2363 | TYR84 | CD2 | -0.7562 | 1.0093 | -28.4802 |
| 2364 | TYR84 | CE1 | -1.3609 | 1.1086 | -25.7608 |
| 2365 | TYR84 | CE2 | -0.2246 | 0.0498 | -27.6157 |
| 2366 | TYR84 | CZ | -0.5326 | 0.0971 | -26.2544 |
| 2367 | TYR84 | OH | -0.0121 | -0.8597 | -25.3925 |
| 2368 | PHE85 | N | -0.6833 | 2.0379 | -32.2039 |
| 2369 | PHE85 | CA | -0.6605 | 0.8992 | -33.1028 |
| 2370 | PHE85 | C | -0.1316 | -0.33 | -32.4212 |
| 2371 | PHE85 | O | 0.8114 | -0.2439 | -31.6511 |
| 2372 | PHE85 | CB | 0.0502 | 1.1935 | -34.4406 |
| 2373 | PHE85 | CG | 1.4461 | 1.7991 | -34.2859 |
| 2374 | PHE85 | CD1 | 2.2748 | 1.8618 | -35.409 |
| 2375 | PHE85 | CD2 | 1.908 | 2.2915 | -33.0616 |
| 2376 | PHE85 | CE1 | 3.5469 | 2.4316 | -35.3173 |
| 2377 | PHE85 | CE2 | 3.1787 | 2.8638 | -32.9666 |
| 2378 | PHE85 | CZ | 4.0037 | 2.923 | -34.0921 |
| 2379 | ALA86 | N | -0.7817 | -1.4764 | -32.7076 |
| 2380 | ALA86 | CA | -0.3826 | -2.7278 | -32.0819 |
| 2381 | ALA86 | C | -0.6149 | -2.7582 | -30.596 |
| 2382 | ALA86 | O | -0.7942 | -1.7647 | -29.9715 |
| 2383 | ALA86 | CB | 1.0752 | -3.1029 | -32.4117 |
| 2384 | LYS87 | N | -0.6034 | -3.9801 | -30.027 |
| 2385 | LYS87 | CA | -0.671 | -4.0869 | -28.5799 |
| 2386 | LYS87 | C | 0.6572 | -3.6505 | -28.0358 |
| 2387 | LYS87 | O | 0.704 | -2.8939 | -27.0799 |
| 2388 | LYS87 | CB | -0.8607 | -5.5636 | -28.1861 |
| 2389 | LYS87 | CG | -2.293 | -6.028 | -28.5039 |
| 2390 | LYS87 | CD | -2.4255 | -7.5123 | -28.1168 |
| 2391 | LYS87 | CE | -3.8179 | -8.0329 | -28.5167 |
| 2392 | LYS87 | NZ | -3.8456 | -9.4955 | -28.374 |
| 2393 | ALA88 | N | 1.7382 | -4.1405 | -28.6778 |
| 2394 | ALA88 | CA | 3.0742 | -3.7712 | -28.2453 |
| 2395 | ALA88 | C | 3.3688 | -4.3514 | -26.8917 |
| 2396 | ALA88 | O | 3.2386 | -3.6715 | -25.8867 |
| 2397 | ALA88 | CB | 3.2728 | -2.2438 | -28.2909 |
| 2398 | LYS89 | N | 3.7874 | -5.6324 | -26.884 |
| 2399 | LYS89 | CA | 4.1863 | -6.2498 | -25.6303 |
| 2400 | LYS89 | C | 5.3313 | -5.4685 | -25.0515 |
| 2401 | LYS89 | O | 5.3175 | -5.1573 | -23.8715 |
| 2402 | LYS89 | CB | 4.6519 | -7.6849 | -25.942 |
| 2403 | LYS89 | CG | 5.1193 | -8.3944 | -24.6573 |
| 2404 | LYS89 | CD | 5.6894 | -9.7741 | -25.0329 |
| 2405 | LYS89 | CE | 6.2991 | -10.443 | -23.7881 |
| 2406 | LYS89 | NZ | 7.6382 | -10.9439 | -24.1273 |
| 2407 | ARG90 | N | 6.3187 | -5.1388 | -25.9065 |
| 2408 | ARG90 | CA | 7.4058 | -4.306 | -25.43 |
| 2409 | ARG90 | C | 6.9689 | -2.8753 | -25.2833 |
| 2410 | ARG90 | O | 5.8984 | -2.4983 | -25.7329 |
| 2411 | ARG90 | CB | 8.6259 | -4.4176 | -26.3627 |
| 2412 | ARG90 | CG | 9.4794 | -5.6297 | -25.944 |
| 2413 | ARG90 | CD | 10.1419 | -5.3493 | -24.582 |
| 2414 | ARG90 | NE | 10.8092 | -6.5457 | -24.1021 |
| 2415 | ARG90 | CZ | 12.0871 | -6.5553 | -23.854 |
| 2416 | ARG90 | NH1 | 12.8194 | -5.4944 | -24.0281 |
| 2417 | ARG90 | NH2 | 12.6424 | -7.6489 | -23.4233 |
| 2418 | LEU91 | N | 7.8313 | -2.0836 | -24.6216 |
| 2419 | LEU91 | CA | 7.4596 | -0.7216 | -24.2832 |
| 2420 | LEU91 | C | 8.727 | 0.0817 | -24.2932 |
| 2421 | LEU91 | O | 9.7323 | -0.4426 | -23.8379 |
| 2422 | LEU91 | CB | 7.0082 | -0.8199 | -22.8106 |
| 2423 | LEU91 | CG | 6.2327 | 0.4149 | -22.3125 |
| 2424 | LEU91 | CD1 | 5.823 | 0.1552 | -20.851 |
| 2425 | LEU91 | CD2 | 7.1128 | 1.6773 | -22.353 |
| 2426 | HIS113 | N | -6.4353 | -10.6403 | -22.9262 |
| 2427 | HIS113 | CA | -7.4859 | -10.5959 | -21.9252 |
| 2428 | HIS113 | C | -7.1733 | -9.4431 | -21.0038 |
| 2429 | HIS113 | O | -6.1033 | -8.8622 | -21.1001 |
| 2430 | HIS113 | CB | -7.5034 | -11.9014 | -21.1055 |
| 2431 | HIS113 | CG | -8.8663 | -12.5314 | -21.1377 |
| 2432 | HIS113 | ND1 | -9.3863 | -13.1002 | -20.0746 |
| 2433 | HIS113 | CD2 | -9.6792 | -12.5864 | -22.2107 |
| 2434 | HIS113 | CE1 | -10.5551 | -13.5481 | -20.4069 |
| 2435 | HIS113 | NE2 | -10.784 | -13.2858 | -21.6127 |
| 2436 | GLN114 | N | -8.1139 | -9.1025 | -20.0995 |
| 2437 | GLN114 | CA | -7.8701 | -8.0172 | -19.1592 |
| 2438 | GLN114 | C | -7.7198 | -6.6951 | -19.8615 |
| 2439 | GLN114 | O | -6.6331 | -6.1411 | -19.9172 |
| 2440 | GLN114 | CB | -6.6818 | -8.3332 | -18.2286 |
| 2441 | GLN114 | CG | -7.1246 | -9.3496 | -17.16 |
| 2442 | GLN114 | CD | -5.9534 | -9.736 | -16.3046 |
| 2443 | GLN114 | OE1 | -5.5315 | -10.8802 | -16.3337 |
| 2444 | GLN114 | NE2 | -5.4155 | -8.779 | -15.5274 |
| 2445 | ASP115 | N | -8.8445 | -6.1879 | -20.4018 |
| 2446 | ASP115 | CA | -8.7767 | -4.9376 | -21.1382 |
| 2447 | ASP115 | C | -9.0522 | -3.7711 | -20.2284 |
| 2448 | ASP115 | O | -10.0728 | -3.1112 | -20.3435 |
| 2449 | ASP115 | CB | -9.7649 | -5.0067 | -22.3186 |
| 2450 | ASP115 | CG | -9.3264 | -6.0903 | -23.2611 |
| 2451 | ASP115 | OD1 | -9.6038 | -7.2836 | -22.9664 |
| 2452 | ASP115 | OD2 | -8.7116 | -5.7495 | -24.3065 |
| 2453 | THR128 | N | -5.2098 | 9.6232 | -37.965 |
| 2454 | THR128 | CA | -5.5784 | 9.5422 | -39.3665 |
| 2455 | THR128 | C | -6.9869 | 10.0144 | -39.5951 |
| 2456 | THR128 | O | -7.1718 | 11.0374 | -40.2344 |
| 2457 | THR128 | CB | -5.3515 | 8.1277 | -39.9358 |
| 2458 | THR128 | OG1 | -6.1329 | 7.164 | -39.2253 |
| 2459 | THR128 | CG2 | -3.86 | 7.7591 | -39.8286 |
| 2460 | GLU129 | N | -7.9852 | 9.2654 | -39.0864 |
| 2461 | GLU129 | CA | -9.3583 | 9.6237 | -39.4022 |
| 2462 | GLU129 | C | -9.9398 | 10.5726 | -38.3948 |
| 2463 | GLU129 | O | -9.6855 | 10.4263 | -37.2097 |
| 2464 | GLU129 | CB | -10.2665 | 8.3833 | -39.5128 |

TABLE IV-continued

| Atom No | Residue | Atom name | x coord | y coord | z coord |
|---|---|---|---|---|---|
| 2465 | GLU129 | CG | −9.5043 | 7.2117 | −40.1622 |
| 2466 | GLU129 | CD | −9.12 | 6.2042 | −39.116 |
| 2467 | GLU129 | OE1 | −9.3115 | 4.9868 | −39.3768 |
| 2468 | GLU129 | OE2 | −8.6361 | 6.6199 | −38.0287 |
| 2469 | LYS130 | N | −10.7255 | 11.5496 | −38.8967 |
| 2470 | LYS130 | CA | −11.3809 | 12.5048 | −38.0141 |
| 2471 | LYS130 | C | −10.4409 | 13.0512 | −36.976 |
| 2472 | LYS130 | O | −10.7529 | 13.0495 | −35.7953 |
| 2473 | LYS130 | CB | −12.6455 | 11.888 | −37.3856 |
| 2474 | LYS130 | CG | −13.8196 | 12.0229 | −38.3713 |
| 2475 | LYS130 | CD | −15.1017 | 11.4827 | −37.7127 |
| 2476 | LYS130 | CE | −16.286 | 11.6603 | −38.6803 |
| 2477 | LYS130 | NZ | −17.5138 | 11.1586 | −38.0469 |
| 2478 | VAL156 | N | 7.1495 | 20.8156 | −25.2479 |
| 2479 | VAL156 | CA | 8.4489 | 20.3852 | −25.72 |
| 2480 | VAL156 | C | 9.3571 | 21.5798 | −25.7576 |
| 2481 | VAL156 | O | 9.3263 | 22.352 | −26.7025 |
| 2482 | VAL156 | CB | 8.3542 | 19.5969 | −27.0437 |
| 2483 | VAL156 | CG1 | 7.3527 | 18.4379 | −26.8884 |
| 2484 | VAL156 | CG2 | 7.9085 | 20.4856 | −28.2191 |
| 2485 | ASN157 | N | 10.171 | 21.7158 | −24.6912 |
| 2486 | ASN157 | CA | 11.0863 | 22.8404 | −24.6216 |
| 2487 | ASN157 | C | 11.9997 | 22.83 | −25.8116 |
| 2488 | ASN157 | O | 12.9363 | 22.049 | −25.8658 |
| 2489 | ASN157 | CB | 11.8895 | 22.7676 | −23.3092 |
| 2490 | ASN157 | CG | 12.0553 | 24.1436 | −22.7314 |
| 2491 | ASN157 | OD1 | 11.62 | 24.3951 | −21.62 |
| 2492 | ASN157 | ND2 | 12.6951 | 25.0339 | −23.4855 |
| 2493 | GLU158 | N | 11.693 | 23.7209 | −26.7747 |
| 2494 | GLU158 | CA | 12.4778 | 23.7633 | −27.9961 |
| 2495 | GLU158 | C | 12.3657 | 22.4554 | −28.7313 |
| 2496 | GLU158 | O | 13.3724 | 21.8341 | −29.0331 |
| 2497 | GLU158 | CB | 13.9391 | 24.1693 | −27.7137 |
| 2498 | GLU158 | CG | 13.9672 | 25.4183 | −26.8115 |
| 2499 | GLU158 | CD | 14.8271 | 25.1819 | −25.6025 |
| 2500 | GLU158 | OE1 | 14.7949 | 24.0494 | −25.0491 |
| 2501 | GLU158 | OE2 | 15.5511 | 26.1332 | −25.2057 |
| 2502 | ALA159 | N | 11.111 | 22.0446 | −29.0137 |
| 2503 | ALA159 | CA | 10.8855 | 20.7997 | −29.7342 |
| 2504 | ALA159 | C | 11.0809 | 19.5888 | −28.8664 |
| 2505 | ALA159 | O | 10.2895 | 18.6639 | −28.9558 |
| 2506 | ALA159 | CB | 11.7364 | 20.701 | −31.0156 |
| 2507 | GLY160 | N | 12.1317 | 19.5892 | −28.0226 |
| 2508 | GLY160 | CA | 12.365 | 18.4278 | −27.1826 |
| 2509 | GLY160 | C | 11.2963 | 18.3167 | −26.1341 |
| 2510 | GLY160 | O | 11.1203 | 19.2402 | −25.3565 |
| 2511 | GLN161 | N | 10.5857 | 17.1693 | −26.1209 |
| 2512 | GLN161 | CA | 9.5227 | 16.9887 | −25.1454 |
| 2513 | GLN161 | C | 10.032 | 17.0777 | −23.7338 |
| 2514 | GLN161 | O | 11.2329 | 17.0787 | −23.5131 |
| 2515 | GLN161 | CB | 8.8426 | 15.6214 | −25.3495 |
| 2516 | GLN161 | CG | 8.2536 | 15.5302 | −26.7698 |
| 2517 | GLN161 | CD | 7.5633 | 14.2099 | −26.952 |
| 2518 | GLN161 | OE1 | 6.3575 | 14.1746 | −27.1342 |
| 2519 | GLN161 | NE2 | 8.3294 | 13.105 | −26.907 |
| 2520 | GLN196 | N | 1.0418 | 9.8707 | −5.495 |
| 2521 | GLN196 | CA | 1.5364 | 8.5086 | −5.399 |
| 2522 | GLN196 | C | 1.1702 | 7.6878 | −6.6023 |
| 2523 | GLN196 | O | 0.4086 | 8.1229 | −7.4515 |
| 2524 | GLN196 | CB | 0.8757 | 7.8228 | −4.1892 |
| 2525 | GLN196 | CG | 1.6729 | 8.1168 | −2.9065 |
| 2526 | GLN196 | CD | 0.849 | 7.7169 | −1.7172 |
| 2527 | GLN196 | OE1 | 0.5058 | 8.5584 | −0.9035 |
| 2528 | GLN196 | NE2 | 0.5223 | 6.4166 | −1.6058 |
| 2529 | VAL197 | N | 1.7343 | 6.4652 | −6.6453 |
| 2530 | VAL197 | CA | 1.3872 | 5.552 | −7.7192 |
| 2531 | VAL197 | C | 0.0529 | 4.9215 | −7.4393 |
| 2532 | VAL197 | O | −0.7245 | 4.7517 | −8.3627 |
| 2533 | VAL197 | CB | 2.4636 | 4.454 | −7.8415 |
| 2534 | VAL197 | CG1 | 3.7945 | 5.0789 | −8.2996 |
| 2535 | VAL197 | CG2 | 2.6678 | 3.7271 | −6.4975 |
| 2536 | SER198 | N | −0.2035 | 4.5813 | −6.1611 |
| 2537 | SER198 | CA | −1.4755 | 3.9503 | −5.8222 |
| 2538 | SER198 | C | −2.6401 | 4.8349 | −6.17 |
| 2539 | SER198 | O | −3.6232 | 4.3419 | −6.6982 |
| 2540 | SER198 | CB | −1.4875 | 3.6546 | −4.31 |
| 2541 | SER198 | OG | −1.2465 | 4.856 | −3.5706 |
| 2542 | THR209 | N | −6.394 | −0.2325 | −4.529 |
| 2543 | THR209 | CA | −4.9737 | −0.4368 | −4.745 |
| 2544 | THR209 | C | −4.3568 | −0.8171 | −3.4284 |
| 2545 | THR209 | O | −3.5231 | −0.1004 | −2.8972 |
| 2546 | THR209 | CB | −4.3323 | 0.7936 | −5.4215 |
| 2547 | THR209 | OG1 | −4.9557 | 1.007 | −6.6915 |
| 2548 | THR209 | CG2 | −2.8285 | 0.5495 | −5.6524 |
| 2549 | MET210 | N | −4.7905 | −1.9815 | −2.9044 |
| 2550 | MET210 | CA | −4.2352 | −2.4464 | −1.6446 |
| 2551 | MET210 | C | −2.7662 | −2.7233 | −1.7981 |
| 2552 | MET210 | O | −2.3122 | −2.9945 | −2.8983 |
| 2553 | MET210 | CB | −4.9699 | −3.7096 | −1.1552 |
| 2554 | MET210 | CG | −6.4845 | −3.437 | −1.0776 |
| 2555 | MET210 | SD | −7.1137 | −4.1282 | 0.4811 |
| 2556 | MEI210 | CE | −8.7771 | −3.3982 | 0.4349 |
| 2557 | THR211 | N | −2.0041 | −2.6325 | −0.692 |
| 2558 | THR211 | CA | −0.5678 | −2.7725 | −0.8487 |
| 2559 | THR211 | C | 0.0522 | −3.5941 | 0.2431 |
| 2560 | THR211 | O | −0.4589 | −3.6484 | 1.3501 |
| 2561 | THR211 | CB | 0.1235 | −1.3971 | −0.9424 |
| 2562 | THR211 | OG1 | −0.0089 | −0.6997 | 0.2994 |
| 2563 | THR211 | CG2 | −0.5138 | −0.5555 | −2.064 |
| 2564 | ILE212 | N | 1.1822 | −4.2356 | −0.1071 |
| 2565 | ILE212 | CA | 1.9143 | −5.0079 | 0.8786 |
| 2566 | ILE212 | C | 3.3518 | −4.9831 | 0.448 |
| 2567 | ILE212 | O | 3.6862 | −5.6192 | −0.538 |
| 2568 | ILE212 | CB | 1.419 | −6.4711 | 0.8968 |
| 2569 | ILE212 | CG1 | −0.0541 | −6.5406 | 1.3449 |
| 2570 | ILE212 | CG2 | 2.2939 | −7.3081 | 1.8521 |
| 2571 | ILE212 | CD1 | −0.5911 | −7.9762 | 1.1884 |
| 2572 | ASN213 | N | 4.2062 | −4.2553 | 1.1941 |
| 2573 | ASN213 | CA | 5.6213 | −4.2737 | 0.8628 |
| 2574 | ASN213 | C | 6.1141 | −5.6779 | 1.0676 |
| 2575 | ASN213 | O | 6.4063 | −6.0634 | 2.1877 |
| 2576 | ASN213 | CB | 6.382 | −3.3112 | 1.7973 |
| 2577 | ASN213 | CG | 6.0491 | −1.8733 | 1.5174 |
| 2578 | ASN213 | OD1 | 4.928 | −1.5529 | 1.1578 |
| 2579 | ASN213 | ND2 | 7.0439 | −0.9828 | 1.6817 |
| 2580 | LEU214 | N | 6.1863 | −6.4488 | −0.0348 |
| 2581 | LEU214 | CA | 6.5039 | −7.8588 | 0.1037 |
| 2582 | LEU214 | C | 7.8453 | −8.0892 | 0.7358 |
| 2583 | LEU214 | O | 8.0269 | −9.1297 | 1.3458 |
| 2584 | LEU214 | CB | 6.4267 | −8.5505 | −1.2667 |
| 2585 | LEU214 | CG | 5.1616 | −9.4224 | −1.339 |
| 2586 | LEU214 | CD1 | 3.9038 | −8.532 | −1.3405 |
| 2587 | LEU214 | CD2 | 5.2104 | −10.2479 | −2.6365 |
| 2588 | ALA215 | N | 8.7748 | −7.1182 | 0.6196 |
| 2589 | ALA215 | CA | 10.0464 | −7.2635 | 1.3105 |
| 2590 | ALA215 | C | 9.7769 | −7.5799 | 2.7559 |
| 2591 | ALA215 | O | 10.3279 | −8.5342 | 3.2802 |
| 2592 | ALA215 | CB | 10.8273 | −5.9415 | 1.1907 |
| 2593 | GLU216 | N | 8.8848 | −6.7868 | 3.3804 |
| 2594 | GLU216 | CA | 8.3903 | −7.1675 | 4.6907 |
| 2595 | GLU216 | C | 6.9476 | −7.5615 | 4.5145 |
| 2596 | GLU216 | O | 6.0518 | −6.9214 | 5.0423 |
| 2597 | GLU216 | CB | 8.5538 | −5.9747 | 5.6525 |
| 2598 | GLU216 | CG | 8.2854 | −6.4355 | 7.0971 |
| 2599 | GLU216 | CD | 7.3825 | −5.4464 | 7.7742 |
| 2600 | GLU216 | OE1 | 6.1396 | −5.5673 | 7.6064 |
| 2601 | GLU216 | OE2 | 7.9134 | −4.5541 | 8.4878 |
| 2602 | ALA217 | N | 6.7323 | −8.6343 | 3.7284 |
| 2603 | ALA217 | CA | 5.374 | −8.9999 | 3.3618 |
| 2604 | ALA217 | C | 4.6093 | −9.6378 | 4.4887 |
| 2605 | ALA217 | O | 5.1317 | −9.8014 | 5.5798 |
| 2606 | ALA217 | CB | 5.4467 | −9.9884 | 2.1838 |
| 2607 | HIS218 | N | 3.3448 | −10.0049 | 4.1972 |
| 2608 | HIS218 | CA | 2.5306 | −10.6643 | 5.2054 |
| 2609 | HIS218 | C | 3.0285 | −12.0533 | 5.4931 |
| 2610 | HIS218 | O | 3.9116 | −12.551 | 4.8126 |
| 2611 | HIS218 | CB | 1.1008 | −10.8309 | 4.6532 |
| 2612 | HIS218 | CG | 0.3339 | −9.543 | 4.6987 |
| 2613 | HIS218 | ND1 | 0.8034 | −8.4292 | 4.186 |
| 2614 | HIS218 | CD2 | −0.8854 | −9.3962 | 5.2515 |
| 2615 | HIS218 | CE1 | −0.0876 | −7.51 | 4.3834 |
| 2616 | HIS218 | NE2 | −1.0761 | −7.9962 | 4.9856 |
| 2617 | GLY219 | N | 2.427 | −12.6904 | 6.5166 |
| 2618 | GLY219 | CA | 2.6988 | −14.1014 | 6.7225 |

TABLE IV-continued

| Atom No | Residue | Atom name | x coord | y coord | z coord |
|---|---|---|---|---|---|
| 2619 | GLY219 | C | 1.8493 | −14.8442 | 5.733 |
| 2620 | GLY219 | O | 2.3558 | −15.6498 | 4.9688 |
| 2621 | GLN238 | N | 8.1324 | −5.9044 | −5.4568 |
| 2622 | GLN238 | CA | 9.4731 | −5.6833 | −4.9464 |
| 2623 | GLN238 | C | 10.3999 | −5.3856 | −6.106 |
| 2624 | GLN238 | O | 9.9466 | −5.2424 | −7.2302 |
| 2625 | GLN238 | CB | 9.5334 | −4.5688 | −3.8746 |
| 2626 | GLN238 | CG | 9.065 | −5.0445 | −2.4777 |
| 2627 | GLN238 | CD | 8.29 | −6.3276 | −2.4983 |
| 2628 | GLN238 | OE1 | 8.8192 | −7.361 | −2.1257 |
| 2629 | GLN238 | NE2 | 7.0217 | −6.2661 | −2.9362 |
| 2630 | THR239 | N | 11.721 | −5.3061 | −5.8507 |
| 2631 | THR239 | CA | 12.6638 | −5.2142 | −6.9547 |
| 2632 | THR239 | C | 13.5003 | −6.4648 | −6.9995 |
| 2633 | THR239 | O | 14.0679 | −6.8369 | −5.9846 |
| 2634 | THR239 | CB | 13.5534 | −3.9622 | −6.8255 |
| 2635 | THR239 | OG1 | 14.3086 | −4.0071 | −5.6115 |
| 2636 | THR239 | CG2 | 12.6716 | −2.7002 | −6.8315 |
| 2637 | HIS240 | N | 13.555 | −7.1173 | −8.1813 |
| 2638 | HIS240 | CA | 14.163 | −8.4408 | −8.284 |
| 2639 | HIS240 | C | 15.4515 | −8.5949 | −7.5159 |
| 2640 | HIS240 | O | 16.24 | −7.6636 | −7.4811 |
| 2641 | HIS240 | CB | 13.1137 | −9.4858 | −7.8556 |
| 2642 | HIS240 | CG | 12.9509 | −10.5509 | −8.9012 |
| 2643 | HIS240 | ND1 | 12.9088 | −10.2764 | −10.1849 |
| 2644 | HIS240 | CD2 | 12.8277 | −11.8668 | −8.6425 |
| 2645 | HIS240 | CE1 | 12.7565 | −11.3982 | −10.8156 |
| 2646 | HIS240 | NE2 | 12.7006 | −12.3442 | −9.9931 |
| 2647 | SER241 | N | 15.6651 | −9.7692 | −6.8839 |
| 2648 | SER241 | CA | 16.8516 | −9.9218 | −6.0565 |
| 2649 | SER241 | C | 17.0666 | −11.3541 | −5.6464 |
| 2650 | SER241 | O | 16.3248 | −12.2304 | −6.0604 |
| 2651 | SER241 | CB | 16.6801 | −9.0557 | −4.7945 |
| 2652 | SER241 | OG | 17.9373 | −8.8969 | −4.1322 |
| 2653 | GLY242 | N | 18.1042 | −11.5854 | −4.8158 |
| 2654 | GLY242 | CA | 18.3714 | −12.9407 | −4.3647 |
| 2655 | GLY242 | C | 17.6696 | −13.2358 | −3.0682 |
| 2656 | GLY242 | O | 16.7701 | −12.5049 | −2.686 |
| 2657 | LYS243 | N | 18.1011 | −14.327 | −2.4015 |
| 2658 | LYS243 | CA | 17.4273 | −14.7712 | −1.1904 |
| 2659 | LYS243 | C | 17.4213 | −13.7439 | −0.0914 |
| 2660 | LYS243 | O | 18.3491 | −12.9592 | 0.0143 |
| 2661 | LYS243 | CB | 18.0192 | −16.1181 | −0.7284 |
| 2662 | LYS243 | CG | 17.3879 | −16.5818 | 0.5981 |
| 2663 | LYS243 | CD | 18.3077 | −16.1674 | 1.7608 |
| 2664 | LYS243 | CE | 17.5847 | −16.3813 | 3.1027 |
| 2665 | LYS243 | NZ | 18.4874 | −16.0221 | 4.2054 |
| 2666 | ILE244 | N | 16.3402 | −13.7602 | 0.7163 |
| 2667 | ILE244 | CA | 16.1453 | −12.7149 | 1.7103 |
| 2668 | ILE244 | C | 17.1361 | −12.8139 | 2.8396 |
| 2669 | ILE244 | O | 18.1547 | −13.4736 | 2.7099 |
| 2670 | ILE244 | CB | 14.7014 | −12.7747 | 2.2575 |
| 2671 | ILE244 | CG1 | 13.6943 | −13.0402 | 1.1243 |
| 2672 | ILE244 | CG2 | 14.3331 | −11.4383 | 2.9311 |
| 2673 | ILE244 | CD1 | 12.3433 | −13.4901 | 1.7111 |
| 2674 | LEU245 | N | 16.8305 | −12.1362 | 3.9958 |
| 2675 | LEU245 | CA | 17.7767 | −12.0954 | 5.0684 |
| 2676 | LEU245 | C | 19.0752 | −11.5053 | 4.5937 |
| 2677 | LEU245 | O | 20.1429 | −11.8815 | 5.0504 |
| 2678 | LEU245 | CB | 17.9564 | −13.4847 | 5.7113 |
| 2679 | LEU245 | CG | 17.7838 | −13.383 | 7.2384 |
| 2680 | LEU245 | CD1 | 17.8183 | −14.7962 | 7.8482 |
| 2681 | LEU245 | CD2 | 18.9207 | −12.5377 | 7.8437 |
| 2682 | GLU246 | N | 18.9479 | −10.5707 | 3.6328 |
| 2683 | GLU246 | CA | 20.1286 | −10.0014 | 3.0152 |
| 2684 | GLU246 | C | 19.7591 | −8.6028 | 2.6115 |
| 2685 | GLU246 | O | 19.5634 | −8.3168 | 1.4408 |
| 2686 | GLU246 | CB | 20.5101 | −10.8743 | 1.8014 |
| 2687 | GLU246 | CG | 21.0342 | −12.237 | 2.2939 |
| 2688 | GLU246 | CD | 21.314 | −13.1542 | 1.1397 |
| 2689 | GLU246 | OE1 | 20.5724 | −14.1619 | 0.9912 |
| 2690 | GLU246 | OE2 | 22.2844 | −12.8773 | 0.3853 |
| 2691 | ASN247 | N | 19.6554 | −7.7232 | 3.6269 |
| 2692 | ASN247 | CA | 19.1986 | −6.3703 | 3.359 |
| 2693 | ASN247 | C | 20.1145 | −5.6244 | 2.4312 |
| 2694 | ASN247 | O | 21.2558 | −6.0137 | 2.2406 |
| 2695 | ASN247 | CB | 19.0449 | −5.5882 | 4.6782 |
| 2696 | ASN247 | CG | 17.9811 | −6.1721 | 5.5668 |
| 2697 | ASN247 | OD1 | 17.3251 | −7.1387 | 5.2131 |
| 2698 | ASN247 | ND2 | 17.8028 | −5.571 | 6.7565 |
| 2699 | GLY248 | N | 19.5829 | −4.5368 | 1.8424 |
| 2700 | GLY248 | CA | 20.3934 | −3.7772 | 0.9097 |
| 2701 | GLY248 | C | 19.509 | −3.0448 | −0.0569 |
| 2702 | GLY248 | O | 18.429 | −3.5146 | −0.3793 |
| 2703 | LEU249 | N | 19.9903 | −1.8762 | −0.523 |
| 2704 | LEU249 | CA | 19.2109 | −1.1168 | −1.4862 |
| 2705 | LEU249 | C | 19.2242 | −1.7899 | −2.8314 |
| 2706 | LEU249 | O | 19.6245 | −2.9387 | −2.9378 |
| 2707 | LEU249 | CB | 19.8299 | 0.2894 | −1.6043 |
| 2708 | LEU249 | CG | 19.594 | 1.0806 | −0.3035 |
| 2709 | LEU249 | CD1 | 20.3173 | 2.4368 | −0.3936 |
| 2710 | LEU249 | CD2 | 18.0856 | 1.3192 | −0.1002 |
| 2711 | ARG261 | N | 3.7075 | −19.562 | −7.3982 |
| 2712 | ARG261 | CA | 3.3851 | −20.9648 | −7.232 |
| 2713 | ARG261 | C | 4.5578 | −21.6483 | −6.5934 |
| 2714 | ARG261 | O | 5.6844 | −21.4482 | −7.02 |
| 2715 | ARG261 | CB | 3.0626 | −21.6256 | −8.5898 |
| 2716 | ARG261 | CG | 4.1152 | −21.2544 | −9.6556 |
| 2717 | ARG261 | CD | 3.7549 | −21.9296 | −10.9934 |
| 2718 | ARG261 | NE | 4.2205 | −21.1202 | −12.1063 |
| 2719 | ARG261 | CZ | 4.8263 | −21.6535 | −13.1285 |
| 2720 | ARG261 | NH1 | 5.223 | −20.8915 | −14.1043 |
| 2721 | ARG261 | NH2 | 5.0417 | −22.9348 | −13.1953 |
| 2722 | LYS262 | N | 4.2857 | −22.4607 | −5.5544 |
| 2723 | LYS262 | CA | 5.3856 | −23.1774 | −4.9376 |
| 2724 | LYS262 | C | 5.8255 | −24.3186 | −5.8107 |
| 2725 | LYS262 | O | 5.1828 | −24.6312 | −6.8005 |
| 2726 | LYS262 | CB | 5.0152 | −23.6907 | −3.5336 |
| 2727 | LYS262 | CG | 6.3179 | −23.9676 | −2.7607 |
| 2728 | LYS262 | CD | 6.0206 | −24.5326 | −1.3622 |
| 2729 | LYS262 | CE | 7.3098 | −24.4656 | −0.5237 |
| 2730 | LYS262 | NZ | 7.0732 | −25.0873 | 0.7867 |
| 2731 | VAL263 | N | 6.9519 | −24.9407 | −5.421 |
| 2732 | VAL263 | CA | 7.4726 | −26.0424 | −6.208 |
| 2733 | VAL263 | C | 8.1395 | −26.9928 | −5.254 |
| 2734 | VAL263 | O | 7.6714 | −27.148 | −4.138 |
| 2735 | VAL263 | CB | 8.4965 | −25.4823 | −7.2192 |
| 2736 | VAL263 | CG1 | 7.793 | −24.6213 | −8.2849 |
| 2737 | VAL263 | CG2 | 9.5603 | −24.642 | −6.489 |
| 2738 | THR264 | N | 9.2483 | −27.6135 | −5.6989 |
| 2739 | THR264 | CA | 10.0418 | −28.4341 | −4.8006 |
| 2740 | THR264 | C | 11.2795 | −28.8729 | −5.5293 |
| 2741 | THR264 | O | 11.3053 | −28.8214 | −6.7478 |
| 2742 | THR264 | CB | 9.2501 | −29.5985 | −4.168 |
| 2743 | THR264 | OG1 | 10.1114 | −30.4496 | −3.4071 |
| 2744 | THR264 | CG2 | 8.5052 | −30.4127 | −5.2411 |
| 2745 | CYS265 | N | 12.3218 | −29.2873 | −4.785 |
| 2746 | CYS265 | CA | 13.5704 | −29.6047 | −5.4458 |
| 2747 | CYS265 | C | 14.2751 | −30.6831 | −4.6861 |
| 2748 | CYS265 | O | 15.0484 | −30.3903 | −3.7888 |
| 2749 | CYS265 | CB | 14.4239 | −28.3244 | −5.5279 |
| 2750 | CYS265 | SG | 14.0005 | −27.4808 | −7.0785 |
| 2751 | LYS266 | N | 13.9958 | −31.9498 | −5.0519 |
| 2752 | LYS266 | CA | 14.5391 | −33.0536 | −4.2768 |
| 2753 | LYS266 | C | 13.9713 | −32.9782 | −2.887 |
| 2754 | LYS266 | O | 14.7014 | −32.9772 | −1.9084 |
| 2755 | LYS266 | CB | 16.0807 | −33.0492 | −4.2688 |
| 2756 | LYS266 | CG | 16.6181 | −33.1531 | −5.7063 |
| 2757 | LYS266 | CD | 18.0988 | −32.7333 | −5.7235 |
| 2758 | LYS266 | CE | 18.6018 | −32.6909 | −7.1778 |
| 2759 | LYS266 | NZ | 19.5072 | −31.5454 | −7.3469 |
| 2760 | HIS267 | N | 12.6274 | −32.897 | −2.8274 |
| 2761 | HIS267 | CA | 11.9625 | −32.7559 | −1.5442 |
| 2762 | HIS267 | C | 12.337 | −31.4426 | −0.9165 |
| 2763 | HIS267 | O | 12.6154 | −31.3721 | 0.2699 |
| 2764 | HIS267 | CB | 12.2143 | −33.9712 | −0.6284 |
| 2765 | HIS267 | CG | 11.8724 | −35.2288 | −1.3735 |
| 2766 | HIS267 | ND1 | 12.6398 | −35.6975 | −2.3307 |
| 2767 | HIS267 | CD2 | 10.7805 | −35.9862 | −1.1556 |
| 2768 | HI8267 | CE1 | 12.0809 | −36.7767 | −2.7783 |
| 2769 | HIS267 | NE2 | 11.0167 | −36.9974 | −2.1501 |
| 2770 | ARG268 | N | 12.3454 | −30.3879 | −1.7539 |
| 2771 | ARG268 | CA | 12.6959 | −29.0768 | −1.2425 |
| 2772 | ARG268 | C | 11.7987 | −28.073 | −1.9135 |

TABLE IV-continued

| Atom No | Residue | Atom name | x coord | y coord | z coord |
|---|---|---|---|---|---|
| 2773 | ARG268 | O | 12.2499 | −27.365 | −2.7992 |
| 2774 | ARG268 | CB | 14.1807 | −28.7867 | −1.539 |
| 2775 | ARG268 | CG | 15.075 | −29.8563 | −0.8856 |
| 2776 | ARG268 | CD | 16.5401 | −29.5911 | −1.2753 |
| 2777 | ARG268 | NE | 17.2372 | −30.8544 | −1.429 |
| 2778 | ARG268 | CZ | 17.8507 | −31.1554 | −2.5371 |
| 2779 | ARG268 | NH1 | 18.4688 | −32.2949 | −2.6312 |
| 2780 | ARG268 | NH2 | 17.8589 | −30.3395 | −3.5505 |
| 2781 | PRO269 | N | 10.5143 | −27.9991 | −1.5013 |
| 2782 | PRO269 | CA | 9.5866 | −27.0874 | −2.1375 |
| 2783 | PRO269 | C | 10.0311 | −25.6531 | −2.0958 |
| 2784 | PRO269 | O | 10.8327 | −25.2856 | −1.2517 |
| 2785 | PRO269 | CB | 8.2973 | −27.2861 | −1.3184 |
| 2786 | PRO269 | CG | 8.542 | −28.4617 | −0.3464 |
| 2787 | PRO269 | CD | 10.0307 | −28.8527 | −0.437 |
| 2788 | GLU270 | N | 9.5086 | −24.8419 | −3.0367 |
| 2789 | GLU270 | CA | 9.9543 | −23.4606 | −3.0969 |
| 2790 | GLU270 | C | 8.8187 | −22.5727 | −3.5148 |
| 2791 | GLU270 | O | 8.3378 | −22.6901 | −4.6302 |
| 2792 | GLU270 | CB | 11.1188 | −23.3223 | −4.0978 |
| 2793 | GLU270 | CG | 12.3248 | −24.1506 | −3.6156 |
| 2794 | GLU270 | CD | 12.7022 | −25.1816 | −4.6395 |
| 2795 | GLU270 | OE1 | 13.9116 | −25.2456 | −4.9833 |
| 2796 | GLU270 | OE2 | 11.7987 | −25.9258 | −5.1071 |
| 2797 | TYR271 | N | 8.3949 | −21.6792 | −2.5981 |
| 2798 | TYR271 | CA | 7.3008 | −20.7762 | −2.9181 |
| 2799 | TYR271 | C | 7.7473 | −19.7883 | −3.9578 |
| 2800 | TYR271 | O | 8.189 | −18.6948 | −3.6512 |
| 2801 | TYR271 | CB | 6.8694 | −20.0676 | −1.6213 |
| 2802 | TYR271 | CG | 5.9845 | −21.0113 | −0.8158 |
| 2803 | TYR271 | CD1 | 6.4001 | −21.4533 | 0.4424 |
| 2804 | TYR271 | CD2 | 4.7584 | −21.4337 | −1.3361 |
| 2805 | TYR271 | CE1 | 5.5858 | −22.3144 | 1.1823 |
| 2806 | TYR271 | CE2 | 3.9429 | −22.2927 | −0.5958 |
| 2807 | TYR271 | CZ | 4.3602 | −22.7375 | 0.6613 |
| 2808 | TYR271 | OH | 3.5561 | −23.6022 | 1.3935 |
| 2809 | SER289 | N | 17.1658 | −18.93 | −8.2538 |
| 2810 | SER289 | CA | 18.3422 | −19.0254 | −7.408 |
| 2811 | SER289 | C | 18.4464 | −20.4103 | −6.8327 |
| 2812 | SER289 | O | 17.4627 | −21.1337 | −6.8167 |
| 2813 | SER289 | CB | 18.2595 | −17.9919 | −6.2689 |
| 2814 | SER289 | OG | 18.1295 | −16.678 | −6.8191 |
| 2815 | ASP290 | N | 19.658 | −20.783 | −6.3711 |
| 2816 | ASP290 | CA | 19.8478 | −22.1303 | −5.8561 |
| 2817 | ASP290 | C | 19.5131 | −23.1241 | −6.936 |
| 2818 | ASP290 | O | 18.616 | −23.9338 | −6.7705 |
| 2819 | ASP290 | CB | 19.0064 | −22.3277 | −4.577 |
| 2820 | ASP290 | CG | 19.3558 | −23.6273 | −3.9113 |
| 2821 | ASP290 | OD1 | 18.5143 | −24.5634 | −3.9658 |
| 2822 | ASP290 | OD2 | 20.4676 | −23.7127 | −3.3249 |
| 2823 | SER291 | N | 20.2476 | −23.0372 | −8.0632 |
| 2824 | SER291 | CA | 19.905 | −23.8381 | −9.229 |
| 2825 | SER291 | C | 18.8119 | −23.1601 | −10.0025 |
| 2826 | SER291 | O | 17.6878 | −23.0693 | −9.5349 |
| 2827 | SER291 | CB | 19.5625 | −25.3123 | −8.9314 |
| 2828 | SER291 | OG | 20.6095 | −25.9035 | −8.1578 |
| 2829 | SER292 | N | 19.1722 | −22.6698 | −11.2039 |
| 2830 | SER292 | CA | 18.195 | −21.9554 | −12.0051 |
| 2831 | SER292 | C | 17.2106 | −22.9225 | −12.5874 |
| 2832 | SER292 | O | 16.0318 | −22.843 | −12.2828 |
| 2833 | SER292 | CB | 18.9224 | −21.2063 | −13.1356 |
| 2834 | SER292 | OG | 19.8986 | −20.3309 | −12.5658 |
| 2835 | SER293 | N | 17.7122 | −23.8448 | −13.4301 |
| 2836 | SER293 | CA | 16.8111 | −24.8207 | −14.0092 |
| 2837 | SER293 | C | 16.5572 | −25.9456 | −13.0439 |
| 2838 | SER293 | O | 16.5136 | −27.0961 | −13.4508 |
| 2839 | SER293 | CB | 17.3567 | −25.3185 | −15.3625 |
| 2840 | SER293 | OG | 18.6298 | −25.9437 | −15.1757 |
| 2841 | LYS294 | N | 16.3779 | −25.616 | −11.7479 |
| 2842 | LYS294 | CA | 16.0064 | −26.6686 | −10.8191 |
| 2843 | LYS294 | C | 14.5559 | −27.0301 | −10.9887 |
| 2844 | LYS294 | O | 13.9326 | −27.5604 | −10.0834 |
| 2845 | LYS294 | CB | 16.4338 | −26.4047 | −9.3613 |
| 2846 | LYS294 | CG | 15.808 | −25.1066 | −8.8236 |
| 2847 | LYS294 | CD | 16.0614 | −25.0134 | −7.3086 |
| 2848 | LYS294 | CE | 15.7922 | −23.576 | −6.8301 |
| 2849 | LYS294 | NZ | 16.1052 | −23.4562 | −5.3993 |
| 2850 | TRP295 | N | 14.0282 | −26.7341 | −12.1931 |
| 2851 | TRP295 | CA | 12.6821 | −27.1618 | −12.5219 |
| 2852 | TRP295 | C | 12.7817 | −28.5945 | −12.97 |
| 2853 | TRP295 | O | 12.2805 | −28.9619 | −14.0205 |
| 2854 | TRP295 | CB | 12.1207 | −26.2722 | −13.6524 |
| 2855 | TRP295 | CG | 12.5239 | −24.8384 | −13.4586 |
| 2856 | TRP295 | CD1 | 13.5624 | −24.2088 | −14.0301 |
| 2857 | TRP295 | CD2 | 11.8326 | −23.8389 | −12.5722 |
| 2858 | TRP295 | NE1 | 13.6136 | −22.9662 | −13.6174 |
| 2859 | TRP295 | CE2 | 12.6152 | −22.7131 | −12.7465 |
| 2860 | TRP295 | CE3 | 10.7148 | −23.8688 | −11.7405 |
| 2861 | TRP295 | CZ2 | 12.3445 | −21.5215 | −12.0738 |
| 2862 | TRP295 | CZ3 | 10.4389 | −22.6751 | −11.0637 |
| 2863 | TRP295 | CH2 | 11.2391 | −21.5329 | −11.2145 |
| 2864 | GLU296 | N | 13.4637 | −29.41 | −12.1425 |
| 2865 | GLU296 | CA | 13.6738 | −30.7962 | −12.5123 |
| 2866 | GLU296 | C | 13.6457 | −31.6147 | −11.2556 |
| 2867 | GLU296 | O | 12.8159 | −32.5018 | −11.1372 |
| 2868 | GLU296 | CB | 15.0491 | −30.9523 | −13.1904 |
| 2869 | GLU296 | CG | 15.1797 | −29.9717 | −14.3715 |
| 2870 | GLU296 | CD | 16.5672 | −30.0476 | −14.9383 |
| 2871 | GLU296 | OE1 | 16.7082 | −30.5508 | −16.0845 |
| 2872 | GLU296 | OE2 | 17.5189 | −29.5994 | −14.2445 |
| 2873 | LEU297 | N | 14.5557 | −31.3013 | −10.3102 |
| 2874 | LEU297 | CA | 14.5168 | −31.9927 | −9.0331 |
| 2875 | LEU297 | C | 13.2502 | −31.6135 | −8.3246 |
| 2876 | LEU297 | O | 13.0172 | −30.4371 | −8.0988 |
| 2877 | LEU297 | CB | 15.7497 | −31.6707 | −8.1644 |
| 2878 | LEU297 | CG | 15.873 | −30.1595 | −7.8868 |
| 2879 | LEU297 | CD1 | 16.8503 | −29.9272 | −6.7201 |
| 2880 | LEU297 | CD2 | 16.3974 | −29.4396 | −9.1426 |
| 2881 | LEU298 | N | 12.4169 | −32.625 | −8.0092 |
| 2882 | LEU298 | CA | 11.1004 | −32.3273 | −7.4683 |
| 2883 | LEU298 | C | 10.3621 | −31.3525 | −8.3461 |
| 2884 | LEU298 | O | 9.5067 | −30.6151 | −7.8844 |
| 2885 | LEU298 | CB | 11.1792 | −31.8834 | −5.9944 |
| 2886 | LEU298 | CG | 10.8252 | −33.0547 | −5.057 |
| 2887 | LEU298 | CD1 | 9.3623 | −33.4862 | −5.2695 |
| 2888 | LEU298 | CD2 | 11.7632 | −34.252 | −5.3043 |
| 2889 | SER299 | N | 10.7258 | −31.3566 | −9.6423 |
| 2890 | SER299 | CA | 10.0974 | −30.4369 | −10.5692 |
| 2891 | SER299 | C | 9.9685 | −31.1633 | −11.8808 |
| 2892 | SER299 | O | 10.6607 | −30.836 | −12.8313 |
| 2893 | SER299 | CB | 10.9557 | −29.1635 | −10.7041 |
| 2894 | SER299 | OG | 11.1545 | −28.5444 | −9.4319 |
| 2895 | LEU307 | N | 6.3956 | −23.5665 | −16.4828 |
| 2896 | LEU307 | CA | 7.1931 | −22.4652 | −15.9735 |
| 2897 | LEU307 | C | 8.1083 | −21.8538 | −16.9929 |
| 2898 | LEU307 | O | 8.3851 | −22.46 | −18.0157 |
| 2899 | LEU307 | CB | 7.9177 | −22.8665 | −14.6752 |
| 2900 | LEU307 | CG | 8.3099 | −21.5991 | −13.8939 |
| 2901 | LEU307 | CD1 | 7.8988 | −21.7401 | −12.417 |
| 2902 | LEU307 | CD2 | 9.832 | −21.3982 | −13.9943 |
| 2903 | ARG308 | N | 8.5562 | −20.6166 | −16.6943 |
| 2904 | ARG308 | CA | 9.3351 | −19.8688 | −17.6684 |
| 2905 | ARG308 | C | 8.5562 | −19.7259 | −18.9476 |
| 2906 | ARG308 | O | 9.1174 | −19.6909 | −20.0309 |
| 2907 | ARG308 | CB | 10.7482 | −20.4495 | −17.8796 |
| 2908 | ARG308 | CG | 11.4783 | −20.6338 | −16.5325 |
| 2909 | ARG308 | CD | 11.4961 | −19.3378 | −15.6937 |
| 2910 | ARG308 | NE | 11.6184 | −18.1599 | −16.534 |
| 2911 | ARG308 | CZ | 12.7781 | −17.7454 | −16.9542 |
| 2912 | ARG308 | NH1 | 13.8705 | −18.3784 | −16.6421 |
| 2913 | ARG308 | NH2 | 12.8453 | −16.6798 | −17.6953 |
| 2914 | LYS309 | N | 7.2213 | −19.6664 | −18.7836 |
| 2915 | LYS309 | CA | 6.3417 | −19.6382 | −19.9366 |
| 2916 | LYS309 | C | 6.2972 | −18.2635 | −20.5374 |
| 2917 | LYS309 | O | 6.5442 | −18.1125 | −21.723 |
| 2918 | LYS309 | CB | 4.9278 | −20.0332 | −19.4624 |
| 2919 | LYS309 | CG | 4.57 | −19.2689 | −18.1717 |
| 2920 | LYS309 | CD | 3.2022 | −19.7298 | −17.6396 |
| 2921 | LYS309 | CE | 3.0136 | −19.1806 | −16.2137 |
| 2922 | LYS309 | NZ | 1.7878 | −19.7429 | −15.6295 |
| 2923 | ASP310 | N | 5.9687 | −17.2608 | −19.7008 |
| 2924 | ASP310 | CA | 5.7973 | −15.9166 | −20.2246 |
| 2925 | ASP310 | C | 7.1124 | −15.3194 | −20.6424 |
| 2926 | ASP310 | O | 8.1451 | −15.9616 | −20.5346 |

TABLE IV-continued

| Atom No | Residue | Atom name | x coord | y coord | z coord |
|---|---|---|---|---|---|
| 2927 | ASP310 | CB | 5.1166 | −15.0146 | −19.1735 |
| 2928 | ASP310 | CG | 4.1993 | −15.8056 | −18.2838 |
| 2929 | ASP310 | OD1 | 4.64 | −16.1806 | −17.1645 |
| 2930 | ASP310 | OD2 | 3.0342 | −16.0465 | −18.6978 |
| 2931 | ASN311 | N | 7.063 | −14.0653 | −21.1296 |
| 2932 | ASN311 | CA | 8.2916 | −13.436 | −21.579 |
| 2933 | ASN311 | C | 8.2891 | −11.9763 | −21.2219 |
| 2934 | ASN311 | O | 7.4456 | −11.544 | −20.4518 |
| 2935 | ASN311 | CB | 8.4266 | −13.6396 | −23.0999 |
| 2936 | ASN311 | CG | 8.7356 | −15.0815 | −23.3811 |
| 2937 | ASN311 | OD1 | 7.923 | −15.7738 | −23.9713 |
| 2938 | ASN311 | ND2 | 9.9227 | −15.549 | −22.9547 |
| 2939 | ASP312 | N | 9.2508 | −11.2127 | −21.7825 |
| 2940 | ASP312 | CA | 9.3773 | −9.8163 | −21.3949 |
| 2941 | ASP312 | C | 9.6773 | −9.7719 | −19.9227 |
| 2942 | ASP312 | O | 9.0169 | −9.0665 | −19.1788 |
| 2943 | ASP312 | CB | 8.0958 | −9.0254 | −21.7348 |
| 2944 | ASP312 | CG | 8.4216 | −7.784 | −22.5124 |
| 2945 | ASP312 | OD1 | 8.8258 | −6.7738 | −21.8768 |
| 2946 | ASP312 | OD2 | 8.2557 | −7.8116 | −23.7612 |
| 2947 | GLY313 | N | 10.6782 | −10.5659 | −19.4978 |
| 2948 | GLY313 | CA | 10.9737 | −10.6612 | −18.074 |
| 2949 | GLY313 | C | 10.2069 | −11.8465 | −17.5087 |
| 2950 | GLY313 | O | 9.4537 | −11.6938 | −16.5604 |
| 2951 | SER340 | N | −16.3887 | −9.2646 | −18.8495 |
| 2952 | SER340 | CA | −16.9789 | −10.5545 | −18.5298 |
| 2953 | SER340 | C | −16.0382 | −11.6865 | −18.8295 |
| 2954 | SER340 | O | −16.4224 | −12.6865 | −19.4149 |
| 2955 | SER340 | CB | −18.4188 | −10.7336 | −19.0575 |
| 2956 | SER340 | OG | −18.4344 | −10.989 | −20.4645 |
| 2957 | GLN341 | N | −14.7733 | −11.4999 | −18.409 |
| 2958 | GLN341 | CA | −13.7872 | −12.5328 | −18.6593 |
| 2959 | GLN341 | C | −13.9973 | −13.6595 | −17.6917 |
| 2960 | GLN341 | O | −13.8658 | −13.4705 | −16.4927 |
| 2961 | GLN341 | CB | −12.3744 | −11.9426 | −18.5055 |
| 2962 | GLN341 | CG | −12.2671 | −10.6679 | −19.3635 |
| 2963 | GLN341 | CD | −10.834 | −10.3784 | −19.6945 |
| 2964 | GLN341 | OE1 | −10.5296 | −10.0819 | −20.8379 |
| 2965 | GLN341 | NE2 | −9.9401 | −10.467 | −18.693 |
| 2966 | GLU342 | N | −14.334 | −14.842 | −18.2416 |
| 2967 | GLU342 | CA | −14.5771 | −15.9907 | −17.3859 |
| 2968 | GLU342 | C | −13.3583 | −16.3002 | −16.5657 |
| 2969 | GLU342 | O | −13.4924 | −16.6687 | −15.4098 |
| 2970 | GLU342 | CB | −14.8923 | −17.2033 | −18.2805 |
| 2971 | GLU342 | CG | −16.2407 | −16.984 | −18.991 |
| 2972 | GLU342 | CD | −16.5529 | −18.1797 | −19.8423 |
| 2973 | GLU342 | OE1 | −17.2257 | −19.1124 | −19.3278 |
| 2974 | GLU342 | OE2 | −16.1387 | −18.1828 | −21.0323 |
| 2975 | ALA343 | N | −12.1655 | −16.1326 | −17.171 |
| 2976 | ALA343 | CA | −10.9489 | −16.4186 | −16.4325 |
| 2977 | ALA343 | C | −10.8286 | −15.5741 | −15.1958 |
| 2978 | ALA343 | O | −11.2757 | −14.4382 | −15.1781 |
| 2979 | ALA343 | CB | −9.7128 | −16.2208 | −17.3284 |
| 2980 | ALA344 | N | −10.219 | −16.1722 | −14.1534 |
| 2981 | ALA344 | CA | −10.0489 | −15.4662 | −12.8946 |
| 2982 | ALA344 | C | −11.3061 | −15.3614 | −12.0785 |
| 2983 | ALA344 | O | −12.3777 | −15.1106 | −12.6066 |
| 2984 | ALA344 | CB | −9.3563 | −14.097 | −13.0367 |
| 2985 | GLN345 | N | −11.1378 | −15.5569 | −10.756 |
| 2986 | GLN345 | CA | −12.2396 | −15.3412 | −9.8354 |
| 2987 | GLN345 | C | −12.542 | −13.8713 | −9.7507 |
| 2988 | GLN345 | O | −11.7928 | −13.0625 | −10.2761 |
| 2989 | GLN345 | CB | −11.831 | −15.8247 | −8.4297 |
| 2990 | GLN345 | CG | −11.2853 | −17.2639 | −8.4949 |
| 2991 | GLN345 | CD | −11.6086 | −17.9922 | −7.2226 |
| 2992 | GLN345 | OE1 | −12.3591 | −18.9535 | −7.2488 |
| 2993 | GLN345 | NE2 | −11.0403 | −17.5418 | −6.0899 |
| 2994 | MET351 | N | −19.5867 | 0.1074 | −2.8647 |
| 2995 | MET351 | CA | −18.9917 | 1.333 | −2.3614 |
| 2996 | MET351 | C | −19.9682 | 2.156 | −1.5709 |
| 2997 | MET351 | O | −21.1705 | 2.0284 | −1.7395 |
| 2998 | MET351 | CB | −18.407 | 2.171 | −3.5126 |
| 2999 | MET351 | CG | −17.4789 | 3.2657 | −2.9539 |
| 3000 | MET351 | SD | −17.0298 | 4.3543 | −4.336 |
| 3001 | MET351 | CE | −16.091 | 5.592 | −3.3933 |
| 3002 | ARG352 | N | −19.4169 | 3.0104 | −0.69 |
| 3003 | ARG352 | CA | −20.2817 | 3.8805 | 0.083 |
| 3004 | ARG352 | C | −19.7783 | 5.2922 | −0.0036 |
| 3005 | ARG352 | O | −18.6784 | 5.5259 | −0.4795 |
| 3006 | ARG352 | CB | −20.3127 | 3.4321 | 1.5564 |
| 3007 | ARG352 | CG | −21.0796 | 2.1031 | 1.6878 |
| 3008 | ARG352 | CD | −21.145 | 1.7058 | 3.174 |
| 3009 | ARG352 | NE | −22.4189 | 1.0678 | 3.4523 |
| 3010 | ARG352 | CZ | −22.4939 | 0.0081 | 4.2047 |
| 3011 | ARG352 | NH1 | −23.6545 | −0.5309 | 4.4316 |
| 3012 | ARG352 | NH2 | −21.4306 | −0.5187 | 4.7369 |
| 3013 | GLU353 | N | −20.6069 | 6.243 | 0.4656 |
| 3014 | GLU353 | CA | −20.1771 | 7.6289 | 0.4297 |
| 3015 | GLU353 | C | −20.6351 | 8.3401 | 1.6712 |
| 3016 | GLU353 | O | −21.3374 | 7.7625 | 2.4861 |
| 3017 | GLU353 | CB | −20.7213 | 8.3284 | −0.8312 |
| 3018 | GLU353 | CG | −20.068 | 7.729 | −2.0919 |
| 3019 | GLU353 | CD | −18.7307 | 8.3669 | −2.3365 |
| 3020 | GLU353 | OE1 | −17.7195 | 7.8583 | −1.7831 |
| 3021 | GLU353 | OE2 | −18.6851 | 9.3703 | −3.097 |
| 3022 | SER58 | N | 4.5161 | 25.4695 | −12.0448 |
| 3023 | SER58 | CA | 5.8856 | 25.2609 | −11.6081 |
| 3024 | SER58 | C | 6.2426 | 26.247 | −10.5313 |
| 3025 | SER58 | O | 5.5046 | 27.1917 | −10.3003 |
| 3026 | SER58 | CB | 6.8662 | 25.352 | −12.7932 |
| 3027 | SER58 | OG | 6.8328 | 26.6638 | −13.3617 |
| 3028 | GLY59 | N | 7.3844 | 26.0176 | −9.8559 |
| 3029 | GLY59 | CA | 7.7292 | 26.9004 | −8.758 |
| 3030 | GLY59 | C | 9.2172 | 27.0021 | −8.6004 |
| 3031 | GLY59 | O | 9.8707 | 26.0045 | −8.3406 |
| 3032 | SER60 | N | 9.7354 | 28.2375 | −8.7523 |
| 3033 | SER60 | CA | 11.1556 | 28.4693 | −8.5488 |
| 3034 | SER60 | C | 12.0012 | 27.647 | −9.479 |
| 3035 | SER60 | O | 12.1356 | 28.0169 | −10.6331 |
| 3036 | SER60 | CB | 11.5573 | 28.3065 | −7.0694 |
| 3037 | SER60 | OG | 12.8944 | 28.7744 | −6.8761 |
| 3038 | LEU61 | N | 12.5734 | 26.5356 | −8.974 |
| 3039 | LEU61 | CA | 13.3703 | 25.6829 | −9.8388 |
| 3040 | LEU61 | C | 12.4744 | 25.0345 | −10.8529 |
| 3041 | LEU61 | O | 12.8547 | 24.9202 | −12.0066 |
| 3042 | LEU61 | CB | 14.0287 | 24.5946 | −8.9719 |
| 3043 | LEU61 | CG | 15.1543 | 25.2173 | −8.1245 |
| 3044 | LEU61 | CD1 | 15.6818 | 24.1691 | −7.1278 |
| 3045 | LEU61 | CD2 | 16.3056 | 25.6736 | −9.0407 |
| 3046 | LEU62 | N | 11.2662 | 24.634 | −10.4083 |
| 3047 | LEU62 | CA | 10.2797 | 24.1384 | −11.3521 |
| 3048 | LEU62 | C | 9.9899 | 25.2189 | −12.3535 |
| 3049 | LEU62 | O | 9.8158 | 24.9231 | −13.5236 |
| 3050 | LEU62 | CB | 8.9859 | 23.8371 | −10.5738 |
| 3051 | LEU62 | CG | 9.182 | 22.6054 | −9.6716 |
| 3052 | LEU62 | CD1 | 8.0821 | 22.5794 | −8.5947 |
| 3053 | LEU62 | CD2 | 9.0985 | 21.3253 | −10.5239 |
| 3054 | GLN63 | N | 9.9609 | 26.4803 | −11.8805 |
| 3055 | GLN63 | CA | 9.7744 | 27.5884 | −12.8005 |
| 3056 | GLN63 | C | 11.0014 | 27.8053 | −13.6448 |
| 3057 | GLN63 | O | 10.9047 | 28.4324 | −14.6872 |
| 3058 | GLN63 | CB | 9.4807 | 28.8481 | −11.9674 |
| 3059 | GLN63 | CG | 8.0421 | 28.7587 | −11.4255 |
| 3060 | GLN63 | CD | 7.7327 | 29.9547 | −10.5738 |
| 3061 | GLN63 | OE1 | 7.4182 | 29.8047 | −9.4048 |
| 3062 | GLN63 | NE2 | 7.817 | 31.1633 | −11.1583 |
| 3063 | LYS64 | N | 12.1588 | 27.2732 | −13.205 |
| 3064 | LYS64 | CA | 13.3597 | 27.3597 | −14.0352 |
| 3065 | LYS64 | C | 13.3802 | 26.1327 | −14.9053 |
| 3066 | LYS64 | O | 14.3184 | 25.3531 | −14.8528 |
| 3067 | LYS64 | CB | 14.5923 | 27.3962 | −13.124 |
| 3068 | LYS64 | CG | 14.4931 | 28.5556 | −12.1168 |
| 3069 | LYS64 | CD | 15.2394 | 28.156 | −10.8313 |
| 3070 | LYS64 | CE | 14.8604 | 29.1181 | −9.6912 |
| 3071 | LYS64 | NZ | 15.2794 | 28.5352 | −8.4089 |
| 3072 | SER167 | N | 7.9208 | 6.4674 | −28.337 |
| 3073 | SER167 | CA | 7.7436 | 6.2762 | −29.7669 |
| 3074 | SER167 | C | 7.2045 | 4.9046 | −30.0648 |
| 3075 | SER167 | O | 6.6653 | 4.6971 | −31.1401 |
| 3076 | SER167 | CB | 9.1172 | 6.4355 | −30.4468 |
| 3077 | SER167 | OG | 10.0458 | 5.4869 | −29.9125 |
| 3078 | THR168 | N | 7.3541 | 3.9725 | −29.1012 |
| 3079 | THR168 | CA | 6.9327 | 2.6017 | −29.3399 |
| 3080 | THR168 | C | 5.4961 | 2.4848 | −29.7688 |

TABLE IV-continued

| Atom No | Residue | Atom name | x coord | y coord | z coord |
|---|---|---|---|---|---|
| 3081 | THR168 | O | 4.7103 | 3.393 | −29.5518 |
| 3082 | THR168 | CB | 7.1788 | 1.756 | −28.0715 |
| 3083 | THR168 | OG1 | 6.9197 | 0.3739 | −28.3344 |
| 3084 | THR168 | CG2 | 6.2787 | 2.2329 | −26.9143 |
| 3085 | TYR169 | N | 5.1649 | 1.3297 | −30.3795 |
| 3086 | TYR169 | CA | 3.7747 | 1.0608 | −30.7045 |
| 3087 | TYR169 | C | 2.9715 | 1.1166 | −29.4396 |
| 3088 | TYR169 | O | 1.8501 | 1.5972 | −29.4459 |
| 3089 | TYR169 | CB | 3.6924 | −0.3845 | −31.2285 |
| 3090 | TYR169 | CG | 3.9609 | −0.4244 | −32.7279 |
| 3091 | TYR169 | CD1 | 5.1791 | 0.031 | −33.2386 |
| 3092 | TYR169 | CD2 | 2.9836 | −0.9252 | −33.5914 |
| 3093 | TYR169 | CE1 | 5.4261 | −0.0331 | −34.6122 |
| 3094 | TYR169 | CE2 | 3.2344 | −0.9998 | −34.9634 |
| 3095 | TYR169 | CZ | 4.4537 | −0.5472 | −35.4739 |
| 3096 | TYR169 | OH | 4.6986 | −0.6064 | −36.8403 |
| 3097 | LYS170 | N | 3.5939 | 0.6215 | −28.3524 |
| 3098 | LYS170 | CA | 2.9178 | 0.5885 | −27.0715 |
| 3099 | LYS170 | C | 2.4888 | 1.9565 | −26.6329 |
| 3100 | LYS170 | O | 1.4293 | 2.063 | −26.0395 |
| 3101 | LYS170 | CB | 3.9232 | 0.0584 | −26.0343 |
| 3102 | LYS170 | CG | 3.2029 | −0.8809 | −25.0516 |
| 3103 | LYS170 | CD | 4.1528 | −1.1913 | −23.8821 |
| 3104 | LYS170 | CE | 3.8263 | −2.5692 | −23.2794 |
| 3105 | LYS170 | NZ | 4.6894 | −2.8051 | −22.1133 |
| 3106 | ASN171 | N | 3.2958 | 3.0014 | −26.9052 |
| 3107 | ASN171 | CA | 2.9531 | 4.2881 | −26.3252 |
| 3108 | ASN171 | C | 3.0516 | 5.4378 | −27.2882 |
| 3109 | ASN171 | O | 3.275 | 6.5589 | −26.8592 |
| 3110 | ASN171 | CB | 3.7789 | 4.5344 | −25.0468 |
| 3111 | ASN171 | CG | 3.7314 | 3.3219 | −24.1631 |
| 3112 | ASN171 | OD1 | 4.7508 | 2.6909 | −23.9381 |
| 3113 | ASN171 | ND2 | 2.5327 | 2.9848 | −23.6566 |
| 3114 | LEU172 | N | 2.8874 | 5.1636 | −28.5976 |
| 3115 | LEU172 | CA | 3.054 | 6.2303 | −29.5703 |
| 3116 | LEU172 | C | 1.9448 | 7.2373 | −29.4526 |
| 3117 | LEU172 | O | 0.8427 | 6.9818 | −29.8769 |
| 3118 | LEU172 | CB | 3.1005 | 5.6355 | −30.9919 |
| 3119 | LEU172 | CG | 3.9739 | 6.524 | −31.8995 |
| 3120 | LEU172 | CD1 | 4.1502 | 5.8546 | −33.2738 |
| 3121 | LEU172 | CD2 | 3.3112 | 7.8991 | −32.0998 |
| 3122 | GLN367 | N | −11.6584 | 7.6284 | 20.3537 |
| 3123 | GLN367 | CA | −11.2992 | 8.0993 | 21.678 |
| 3124 | GLN367 | C | −11.1646 | 9.5941 | 21.7165 |
| 3125 | GLN367 | O | −10.6996 | 10.1277 | 22.7113 |
| 3126 | GLN367 | CB | −9.9796 | 7.4354 | 22.1105 |
| 3127 | GLN367 | CG | −10.0225 | 7.1421 | 23.6209 |
| 3128 | GLN367 | CD | −9.0236 | 6.071 | 23.9479 |
| 3129 | GLN367 | OE1 | −9.4052 | 4.9967 | 24.3819 |
| 3130 | GLN367 | NE2 | −7.7255 | 6.3572 | 23.7419 |
| 3131 | LEU368 | N | −11.5754 | 10.2737 | 20.6282 |
| 3132 | LEU368 | CA | −11.5262 | 11.7231 | 20.6468 |
| 3133 | LEU368 | C | −12.5936 | 12.2155 | 21.5826 |
| 3134 | LEU368 | O | −13.7453 | 12.3421 | 21.199 |
| 3135 | LEU368 | CB | −11.7396 | 12.2486 | 19.2157 |
| 3136 | LEU368 | CG | −10.4387 | 12.1409 | 18.3976 |
| 3137 | LEU368 | CD1 | −10.6866 | 12.677 | 16.9756 |
| 3138 | LEU368 | CD2 | −9.3312 | 12.9809 | 19.061 |
| 3139 | LEU369 | N | −12.1779 | 12.482 | 22.8363 |
| 3140 | LEU369 | CA | −13.138 | 12.8724 | 23.8552 |
| 3141 | LEU369 | C | −13.8092 | 14.1623 | 23.484 |
| 3142 | LEU369 | O | −15.0241 | 14.2483 | 23.5615 |
| 3143 | LEU369 | CB | −12.4024 | 13.0369 | 25.1993 |
| 3144 | LEU369 | CG | −11.5478 | 11.7894 | 25.5007 |
| 3145 | LEU369 | CD1 | −10.7853 | 11.9967 | 26.8221 |
| 3146 | LEU369 | CD2 | −12.4446 | 10.5419 | 25.6142 |
| 3147 | GLN370 | N | −13.0054 | 15.1578 | 23.0591 |
| 3148 | GLN370 | CA | −13.5889 | 16.3942 | 22.5661 |
| 3149 | GLN370 | C | −14.5276 | 16.0684 | 21.4381 |
| 3150 | GLN370 | O | −15.6099 | 16.6268 | 21.3618 |
| 3151 | GLN370 | CB | −12.4205 | 17.2626 | 22.0543 |
| 3152 | GLN370 | CG | −12.9717 | 18.3894 | 21.1269 |
| 3153 | GLN370 | CD | −12.7668 | 17.9562 | 19.697 |
| 3154 | GLN370 | OE1 | −13.7564 | 17.7562 | 19.0116 |
| 3155 | GLN370 | NE2 | −11.5136 | 17.8049 | 19.2321 |
| 3156 | ASP371 | N | −14.091 | 15.14 | 20.567 |
| 3157 | ASP371 | CA | −14.927 | 14.755 | 19.446 |
| 3158 | ASP371 | C | −16.1654 | 14.0217 | 19.8864 |
| 3159 | ASP371 | O | −16.2572 | 13.6014 | 21.0288 |
| 3160 | ASP371 | CB | −14.0746 | 13.845 | 18.5474 |
| 3161 | ASP371 | CG | −13.1204 | 14.6693 | 17.7345 |
| 3162 | ASP371 | OD1 | −13.3767 | 14.8343 | 16.5124 |
| 3163 | ASP371 | OD2 | −12.1057 | 15.1415 | 18.3128 |
| 3164 | THR372 | N | −17.1371 | 13.8795 | 18.9632 |
| 3165 | THR372 | CA | −18.3719 | 13.2085 | 19.3346 |
| 3166 | THR372 | C | −18.2847 | 11.727 | 19.0963 |
| 3167 | THR372 | O | −18.5994 | 10.9685 | 19.9991 |
| 3168 | THR372 | CB | −19.5853 | 13.834 | 18.6163 |
| 3169 | THR372 | OG1 | −20.7591 | 13.0569 | 18.8679 |
| 3170 | THR372 | CG2 | −19.3433 | 13.9323 | 17.0994 |
| 3171 | SER382 | N | −21.7125 | −7.2387 | 6.7774 |
| 3172 | SER382 | CA | −21.778 | −8.4416 | 7.5895 |
| 3173 | SER382 | C | −21.0627 | −9.6106 | 6.9768 |
| 3174 | SER382 | O | −20.601 | −9.5345 | 5.8495 |
| 3175 | SER382 | CB | −23.2573 | −8.7962 | 7.832 |
| 3176 | SER382 | OG | −23.8439 | −7.8212 | 8.6971 |
| 3177 | VAL383 | N | −20.9902 | −10.709 | 7.7553 |
| 3178 | VAL383 | CA | −20.4217 | −11.9392 | 7.2332 |
| 3179 | VAL383 | C | −20.6916 | −13.0827 | 8.177 |
| 3180 | VAL383 | O | −20.5488 | −12.9223 | 9.3776 |
| 3181 | VAL383 | CB | −18.9717 | −11.7586 | 6.7422 |
| 3182 | VAL383 | CG1 | −18.0495 | −11.3373 | 7.8991 |
| 3183 | VAL383 | CG2 | −18.4529 | −13.0195 | 6.0279 |
| 3184 | TRP384 | N | −21.1268 | −14.2369 | 7.6338 |
| 3185 | TRP384 | CA | −21.5699 | −15.3172 | 8.4986 |
| 3186 | TRP384 | C | −20.5212 | −16.3844 | 8.6219 |
| 3187 | TRP384 | O | −19.4864 | −16.2913 | 7.9853 |
| 3188 | TRP384 | CB | −22.9502 | −15.8666 | 8.0679 |
| 3189 | TRP384 | CG | −22.8699 | −16.9451 | 7.0232 |
| 3190 | TRP384 | CD1 | −22.4297 | −18.2021 | 7.1924 |
| 3191 | TRP384 | CD2 | −23.2752 | −16.8131 | 5.5799 |
| 3192 | TRP384 | NE1 | −22.4732 | −18.8513 | 6.0555 |
| 3193 | TRP384 | CE2 | −22.9321 | −18.0508 | 5.0717 |
| 3194 | TRP384 | CE3 | −23.8559 | −15.8137 | 4.8008 |
| 3195 | TRP384 | CZ2 | −23.0663 | −18.3452 | 3.7152 |
| 3196 | TRP384 | CZ3 | −23.9929 | −16.1 | 3.4379 |
| 3197 | TRP384 | CH2 | −23.5757 | −17.3263 | 2.9019 |
| 3198 | ARG385 | N | −20.7905 | −17.4056 | 9.4551 |
| 3199 | ARG385 | CA | −19.783 | −18.4237 | 9.6788 |
| 3200 | ARG385 | C | −20.499 | −19.7103 | 9.9672 |
| 3201 | ARG385 | O | −20.8957 | −19.9297 | 11.0998 |
| 3202 | ARG385 | CB | −19.0048 | −17.9882 | 10.929 |
| 3203 | ARG385 | CG | −17.802 | −18.8999 | 11.2165 |
| 3204 | ARG385 | CD | −17.0898 | −18.3609 | 12.4697 |
| 3205 | ARG385 | NE | −16.5758 | −17.0295 | 12.204 |
| 3206 | ARG385 | CZ | −16.7127 | −16.069 | 13.0714 |
| 3207 | ARG385 | NH1 | −16.2541 | −14.8854 | 12.7933 |
| 3208 | ARG385 | NH2 | −17.3001 | −16.2711 | 14.2137 |
| 3209 | PRO386 | N | −20.6675 | −20.5782 | 8.95 |
| 3210 | PRO386 | CA | −21.3959 | −21.8131 | 9.1558 |
| 3211 | PRO386 | C | −20.581 | −22.7837 | 9.9612 |
| 3212 | PRO386 | O | −19.5745 | −22.4162 | 10.546 |
| 3213 | PRO386 | CB | −21.4659 | −22.3502 | 7.7145 |
| 3214 | PRO386 | CG | −20.3189 | −21.6558 | 6.9529 |
| 3215 | PRO386 | CD | −20.1001 | −20.302 | 7.6479 |
| 3216 | GLU387 | N | −21.0369 | −24.0503 | 9.9733 |
| 3217 | GLU387 | CA | −20.2927 | −25.0616 | 10.6974 |
| 3218 | GLU387 | C | −19.1297 | −25.5457 | 9.8748 |
| 3219 | GLU387 | O | −19.0221 | −26.7281 | 9.5903 |
| 3220 | GLU387 | CB | −21.2503 | −26.2048 | 11.0833 |
| 3221 | GLU387 | CG | −22.2475 | −25.6974 | 12.1415 |
| 3222 | GLU387 | CD | −22.8692 | −26.8624 | 12.8554 |
| 3223 | GLU387 | OE1 | −24.1183 | −27.0029 | 12.7751 |
| 3224 | GLU387 | OE2 | −21.1147 | −27.6381 | 13.5014 |
| 3225 | GLU388 | N | −18.2392 | −24.6075 | 9.495 |
| 3226 | GLU388 | CA | −17.0442 | −25.0076 | 8.7712 |
| 3227 | GLU388 | C | −16.0882 | −25.7088 | 9.7019 |
| 3228 | GLU388 | O | −16.4578 | −26.0365 | 10.8183 |
| 3229 | GLU388 | CB | −16.4101 | −23.7532 | 8.1366 |
| 3230 | GLU388 | CG | −15.4454 | −24.1537 | 7.0037 |
| 3231 | GLU388 | CD | −14.086 | −23.5654 | 7.2516 |
| 3232 | GLU388 | OE1 | −13.8775 | −22.379 | 6.8856 |
| 3233 | GLU388 | OE2 | −13.2139 | −24.2894 | 7.8016 |
| 3234 | GLY389 | N | −14.8465 | −25.9491 | 9.2367 |

TABLE IV-continued

| Atom No | Residue | Atom name | x coord | y coord | z coord | Atom No | Residue | Atom name | x coord | y coord | z coord |
|---|---|---|---|---|---|---|---|---|---|---|---|
| 3235 | GLY389 | CA | −13.9185 | −26.7395 | 10.0294 | 3312 | ARG413 | CA | −4.5546 | 17.0011 | −5.6605 |
| 3236 | GLY389 | C | −13.4262 | −26.0583 | 11.2769 | 3313 | ARG413 | C | −4.175 | 15.563 | −5.4325 |
| 3237 | GLY389 | O | −14.1027 | −25.2136 | 11.8411 | 3314 | ARG413 | O | −4.4415 | 14.7133 | −6.2676 |
| 3238 | ARG390 | N | −12.2154 | −26.4654 | 11.7068 | 3315 | ARG413 | CB | −4.8684 | 17.2711 | −7.1488 |
| 3239 | ARG390 | CA | −11.6679 | −25.9396 | 12.9458 | 3316 | ARG413 | CG | −4.846 | 18.782 | −7.4541 |
| 3240 | ARG390 | C | −11.1701 | −24.5349 | 12.7423 | 3317 | ARG413 | CD | −6.0673 | 19.4646 | −6.8115 |
| 3241 | ARG390 | O | −9.9756 | −24.313 | 12.6198 | 3318 | ARG413 | NE | −6.5687 | 20.4804 | −7.7188 |
| 3242 | ARG390 | CB | −10.5192 | −26.8764 | 13.3736 | 3319 | ARG413 | CZ | −7.587 | 20.2434 | −8.4945 |
| 3243 | ARG390 | CG | −9.9781 | −26.4675 | 14.7567 | 3320 | ARG413 | NH1 | −8.0068 | 21.1749 | −9.298 |
| 3244 | ARG390 | CD | −10.9625 | −26.9213 | 15.8493 | 3321 | ARG413 | NH2 | −8.1897 | 19.0908 | −8.4829 |
| 3245 | ARG390 | NE | −10.6131 | −26.2863 | 17.1065 | 3322 | LYS414 | N | −3.5268 | 15.2994 | −4.2827 |
| 3246 | ARG390 | CZ | −11.4716 | −25.5413 | 17.74 | 3323 | LYS414 | CA | −3.097 | 13.9421 | −4.006 |
| 3247 | ARG390 | NH1 | −11.1289 | −24.9888 | 18.8657 | 3324 | LYS414 | C | −4.2566 | 13.1746 | −3.4316 |
| 3248 | ARG390 | NH2 | −12.6657 | −25.3433 | 17.2635 | 3325 | LYS414 | O | −4.6461 | 13.4592 | −2.3106 |
| 3249 | ARG391 | N | −12.1066 | −23.5686 | 12.7144 | 3326 | LYS414 | CB | −1.9473 | 14.0374 | −2.985 |
| 3250 | ARG391 | CA | −11.675 | −22.2004 | 12.5066 | 3327 | LYS414 | CG | −1.2538 | 12.6735 | −2.821 |
| 3251 | ARG391 | C | −11.4618 | −21.4903 | 13.8149 | 3328 | LYS414 | CD | −0.0276 | 12.8477 | −1.9063 |
| 3252 | ARG391 | O | −11.8324 | −20.3359 | 13.9572 | 3329 | LYS414 | CE | 0.6361 | 11.628 | −1.6484 |
| 3253 | ARG391 | CB | −12.6535 | −21.4511 | 11.5852 | 3330 | LYS414 | NZ | 1.2619 | 10.9927 | −2.8844 |
| 3254 | ARG391 | CG | −12.843 | −22.2182 | 10.2661 | 3331 | PRO415 | N | −4.8245 | 12.1984 | −4.1729 |
| 3255 | ARG391 | CD | −14.3048 | −22.0698 | 9.8165 | 3332 | PRO415 | CA | −5.9278 | 11.4283 | −3.6376 |
| 3256 | ARG391 | NE | −15.1209 | −22.9598 | 10.6179 | 3333 | PRO415 | C | −5.4305 | 10.5023 | −2.5651 |
| 3257 | ARG391 | CZ | −16.3317 | −22.6372 | 10.9653 | 3334 | PRO415 | O | −4.2473 | 10.2053 | −2.5311 |
| 3258 | ARG391 | NH1 | −17.0163 | −23.463 | 11.6969 | 3335 | PRO415 | CB | −6.3697 | 10.5929 | −4.8548 |
| 3259 | ARG391 | NH2 | −16.8663 | −21.511 | 10.597 | 3336 | PRO415 | CG | −5.305 | 10.7827 | −5.9589 |
| 3260 | SER392 | N | −10.8434 | −22.1905 | 14.7859 | 3337 | PRO415 | CD | −4.336 | 11.8912 | −5.4999 |
| 3261 | SER392 | CA | −10.515 | −21.5197 | 16.0313 | 3338 | LEU416 | N | −6.342 | 10.0587 | −1.676 |
| 3262 | SER392 | C | −9.222 | −20.7737 | 15.8405 | 3339 | LEU416 | CA | −5.9331 | 9.1489 | −0.6153 |
| 3263 | SER392 | O | −8.3233 | −20.8575 | 16.6623 | 3340 | LEU416 | C | −7.0039 | 9.0322 | 0.4323 |
| 3264 | SER392 | CB | −10.4051 | −22.5746 | 17.1487 | 3341 | LEU416 | O | −8.0493 | 9.6537 | 0.3288 |
| 3265 | SER392 | OG | −10.2618 | −21.9278 | 18.4149 | 3342 | LEU416 | CB | −4.619 | 9.587 | 0.0726 |
| 3266 | LEU393 | N | −9.1362 | −20.0478 | 14.7083 | 3343 | LEU416 | CG | −4.8195 | 10.827 | 0.9679 |
| 3267 | LEU393 | CA | −7.9112 | −19.3408 | 14.3803 | 3344 | LEU416 | CD1 | −3.5219 | 11.1125 | 1.7452 |
| 3268 | LEU393 | C | −8.1089 | −18.7172 | 13.0275 | 3345 | LEU416 | CD2 | −5.1887 | 12.0586 | 0.1214 |
| 3269 | LEU393 | O | −7.5096 | −19.1761 | 12.0691 | 3346 | LEU417 | N | −6.7043 | 8.2312 | 1.4723 |
| 3270 | LEU393 | CB | −6.6802 | −20.2771 | 14.4205 | 3347 | LEU417 | CA | −7.5794 | 8.2124 | 2.6286 |
| 3271 | LEU393 | CG | −6.7754 | −21.4227 | 13.3897 | 3348 | LEU417 | C | −7.3649 | 9.4743 | 3.4198 |
| 3272 | LEU393 | CD1 | −5.3984 | −22.0945 | 13.2432 | 3349 | LEU417 | O | −6.304 | 10.0736 | 3.3467 |
| 3273 | LEU393 | CD2 | −7.8166 | −22.4742 | 13.8166 | 3350 | LEU417 | CB | −7.2075 | 6.9839 | 3.4839 |
| 3274 | ARG394 | N | −8.9651 | −17.68 | 12.9082 | 3351 | LEU417 | CG | −7.7439 | 7.1108 | 4.9227 |
| 3275 | ARG394 | CA | −9.2458 | −17.2221 | 11.5567 | 3352 | LEU417 | CD1 | −9.2749 | 6.9509 | 4.9301 |
| 3276 | ARG394 | C | −9.8339 | −15.8452 | 11.3865 | 3353 | LEU417 | CD2 | −7.0885 | 6.0397 | 5.8121 |
| 3277 | ARG394 | O | −10.9908 | −15.7473 | 11.0116 | 3354 | ALA418 | N | −8.3933 | 9.879 | 4.1866 |
| 3278 | ARG394 | CB | −10.0227 | −18.2562 | 10.7129 | 3355 | ALA418 | CA | −8.2268 | 11.0604 | 5.0123 |
| 3279 | ARG394 | CG | −10.3857 | −19.5313 | 11.4973 | 3356 | ALA418 | C | −7.9996 | 10.6567 | 6.4381 |
| 3280 | ARG394 | CD | −9.5337 | −20.7126 | 10.9953 | 3357 | ALA418 | O | −7.305 | 11.3518 | 7.1618 |
| 3281 | ARG394 | NE | −9.860 | −20.9951 | 9.6108 | 3358 | ALA418 | CB | −9.5567 | 11.8355 | 5.0052 |
| 3282 | ARG394 | CZ | −10.0667 | −22.2112 | 9.1969 | 3359 | ARG425 | N | −18.6675 | −5.1801 | 14.9036 |
| 3283 | ARG394 | NH1 | −9.9769 | −23.2251 | 10.0066 | 3360 | ARG425 | CA | −19.6778 | −6.0328 | 14.305 |
| 3284 | ARG394 | NH2 | −10.3721 | −22.4142 | 7.9499 | 3361 | ARG425 | C | −20.1478 | −7.0639 | 15.2912 |
| 3285 | PRO395 | N | −9.0548 | −14.7611 | 11.5918 | 3362 | ARG425 | O | −19.5831 | −7.1842 | 16.3665 |
| 3286 | PRO395 | CA | −9.4903 | −13.4464 | 11.1559 | 3363 | ARG425 | CB | −19.0115 | −6.8061 | 13.1523 |
| 3287 | PRO395 | C | −9.5917 | −13.3885 | 9.6519 | 3364 | ARG425 | CG | −18.7297 | −5.8777 | 11.9577 |
| 3288 | PRO395 | O | −9.9065 | −14.3791 | 9.0115 | 3365 | ARG425 | CD | −17.818 | −6.6277 | 10.9718 |
| 3289 | PRO395 | CB | −8.2908 | −12.5759 | 11.5797 | 3366 | ARG425 | NE | −18.051 | −6.2043 | 9.6033 |
| 3290 | PRO395 | CG | −7.1218 | −13.5207 | 11.9251 | 3367 | ARG425 | CZ | −18.372 | −7.0629 | 8.6781 |
| 3291 | PRO395 | CD | −7.7492 | −14.8988 | 12.1934 | 3368 | ARG425 | NH1 | −18.5431 | −6.6498 | 7.4579 |
| 3292 | CYS396 | N | −9.3171 | −12.2055 | 9.0684 | 3369 | ARG425 | NH2 | −18.5244 | −8.3268 | 8.944 |
| 3293 | CYS396 | CA | −9.4524 | −12.0876 | 7.6277 | 3370 | MET426 | N | −21.1986 | −7.8127 | 14.8983 |
| 3294 | CYS396 | C | −8.5442 | −11.0416 | 7.0407 | 3371 | MET426 | CA | −21.719 | −8.856 | 15.767 |
| 3295 | CYS396 | O | −7.3374 | −11.1843 | 7.1501 | 3372 | MET426 | C | −22.8919 | −9.499 | 15.0809 |
| 3296 | CYS396 | CB | −10.9109 | −11.954 | 7.1431 | 3373 | MET426 | O | −23.8577 | −8.8107 | 14.7916 |
| 3297 | CYS396 | SG | −12.0989 | −11.6904 | 8.4891 | 3374 | MET426 | CB | −22.1868 | −8.2571 | 17.1093 |
| 3298 | SER397 | N | −9.1188 | −10.002 | 6.3994 | 3375 | MET426 | CG | −21.173 | −8.61 | 18.2132 |
| 3299 | SER397 | CA | −8.292 | −9.0079 | 5.7316 | 3376 | MET426 | SD | −21.2964 | −7.3602 | 19.5248 |
| 3300 | SER397 | C | −9.2078 | −8.0129 | 5.0712 | 3377 | MET426 | CE | −20.4539 | −8.2886 | 20.841 |
| 3301 | SER397 | O | −9.3854 | −8.057 | 3.8638 | 3378 | ASN427 | N | −22.806 | −10.8212 | 14.8188 |
| 3302 | SER397 | CB | −7.3971 | −9.7028 | 4.683 | 3379 | ASN427 | CA | −23.905 | −11.506 | 14.1492 |
| 3303 | SER397 | OG | −6.675 | −8.7363 | 3.9151 | 3380 | ASN427 | C | −24.0585 | −11.0112 | 12.7365 |
| 3304 | VAL398 | N | −9.8078 | −7.1174 | 5.8837 | 3381 | ASN427 | O | −24.7822 | −10.0552 | 12.5058 |
| 3305 | VAL398 | CA | −10.8301 | −6.221 | 5.3628 | 3382 | ASN427 | CB | −25.2258 | −11.3252 | 14.9271 |
| 3306 | VAL398 | C | −10.4519 | −5.596 | 4.0479 | 3383 | ASN427 | CG | −25.2255 | −12.1399 | 16.1864 |
| 3307 | VAL398 | O | −9.4642 | −4.8841 | 3.9578 | 3384 | ASN427 | OD1 | −25.405 | −11.5895 | 17.2602 |
| 3308 | VAL398 | CB | −11.2403 | −5.1829 | 6.4317 | 3385 | ASN427 | ND2 | −25.0267 | −13.4644 | 16.0609 |
| 3309 | VAL398 | CG1 | −12.403 | −5.6985 | 7.2958 | 3386 | LYS428 | N | −23.3755 | −11.6623 | 11.7736 |
| 3310 | VAL398 | CG2 | −11.6695 | −3.8377 | 5.8196 | 3387 | LYS428 | CA | −23.4068 | −11.1175 | 10.4257 |
| 3311 | ARG413 | N | −3.5361 | 17.9222 | −5.1779 | 3388 | LYS428 | C | −23.5166 | −12.1736 | 9.3602 |

TABLE IV-continued

| Atom No | Residue | Atom name | x coord | y coord | z coord |
|---|---|---|---|---|---|
| 3389 | LYS428 | O | −23.4093 | −13.3498 | 9.6638 |
| 3390 | LYS428 | CB | −22.1673 | −10.2258 | 10.2332 |
| 3391 | LYS428 | CG | −22.2938 | −9.0068 | 11.1642 |
| 3392 | LYS428 | CD | −21.2459 | −7.9416 | 10.8006 |
| 3393 | LYS428 | CE | −21.6234 | −6.6238 | 11.5019 |
| 3394 | LYS428 | NZ | −22.8771 | −6.1019 | 10.9393 |
| 3395 | GLU429 | N | −23.745 | −11.7541 | 8.0983 |
| 3396 | GLU429 | CA | −23.9137 | −12.747 | 7.0487 |
| 3397 | GLU429 | C | −22.9051 | −12.5924 | 5.9465 |
| 3398 | GLU429 | O | −22.5972 | −11.4855 | 5.5365 |
| 3399 | GLU429 | CB | −25.3542 | −12.7924 | 6.5111 |
| 3400 | GLU429 | CG | −26.2967 | −13.2913 | 7.6237 |
| 3401 | GLU429 | CD | −26.9033 | −14.6167 | 7.2596 |
| 3402 | GLU429 | OE1 | −27.0373 | −15.4729 | 8.1741 |
| 3403 | GLU429 | OE2 | −27.2415 | −14.815 | 6.0614 |
| 3404 | MET430 | N | −22.3773 | −13.7516 | 5.5091 |
| 3405 | MET430 | CA | −21.1515 | −13.7997 | 4.7279 |
| 3406 | MET430 | C | −21.1395 | −12.9922 | 3.4604 |
| 3407 | MET430 | O | −22.144 | −12.4203 | 3.0689 |
| 3408 | MET430 | CB | −20.8649 | −15.2791 | 4.4098 |
| 3409 | MET430 | CG | −19.7321 | −15.8442 | 5.2888 |
| 3410 | MET430 | SD | −19.858 | −17.6607 | 5.2326 |
| 3411 | MET430 | CE | −18.4284 | −18.1405 | 6.2421 |
| 3412 | THR431 | N | −19.9535 | −12.9534 | 2.8209 |
| 3413 | THR431 | CA | −19.8141 | −12.1439 | 1.6235 |
| 3414 | THR431 | C | −18.9606 | −12.8425 | 0.6023 |
| 3415 | THR431 | O | −19.3568 | −12.9109 | −0.5498 |
| 3416 | THR431 | CB | −19.1786 | −10.7891 | 1.993 |
| 3417 | THR431 | OG1 | −17.9959 | −10.9957 | 2.7711 |
| 3418 | THR431 | CG2 | −20.1824 | −9.9446 | 2.7992 |
| 3419 | TRP432 | N | −17.7884 | −13.3659 | 1.0154 |
| 3420 | TRP432 | CA | −16.9162 | −13.9906 | 0.0315 |
| 3421 | TRP432 | C | −16.2157 | −15.1928 | 0.5972 |
| 3422 | TRP432 | O | −16.0256 | −15.2741 | 1.7998 |
| 3423 | TRP432 | CB | −15.8778 | −13.0153 | −0.563 |
| 3424 | TRP432 | CG | −16.01 | −11.6374 | 0.0191 |
| 3425 | TRP432 | CD1 | −15.3432 | −11.1416 | 1.072 |
| 3426 | TRP432 | CD2 | −16.9314 | −10.5544 | −0.4726 |
| 3427 | TRP432 | NE1 | −15.7103 | −9.9077 | 1.3003 |
| 3428 | TRP432 | CE2 | −16.6595 | −9.5272 | 0.4111 |
| 3429 | TRP432 | CE3 | −17.862 | −10.4442 | −1.5046 |
| 3430 | TRP432 | CZ2 | −17.3132 | −8.298 | 0.3284 |
| 3431 | TRP432 | CZ3 | −18.5277 | −9.2155 | −1.589 |
| 3432 | TRP432 | CH2 | −18.2584 | −8.1672 | −0.6968 |
| 3433 | SER433 | N | −15.8397 | −16.141 | −0.2841 |
| 3434 | SER433 | CA | −15.2145 | −17.355 | 0.2126 |
| 3435 | SER433 | C | −13.7174 | −17.2481 | 0.2387 |
| 3436 | SER433 | O | −13.1583 | −16.9925 | 1.2919 |
| 3437 | SER433 | CB | −15.6441 | −18.5942 | −0.5969 |
| 3438 | SER433 | OG | −15.599 | −18.3117 | −1.9987 |
| 3439 | SER434 | N | −13.0628 | −17.4649 | −0.9199 |
| 3440 | SER434 | CA | −11.6091 | −17.4594 | −0.9335 |
| 3441 | SER434 | C | −11.0874 | −16.1277 | −0.4781 |
| 3442 | SER434 | O | −10.2951 | −16.0703 | 0.4479 |
| 3443 | SER434 | CB | −11.1082 | −17.7736 | −2.3567 |
| 3444 | SER434 | OG | −11.7692 | −16.9353 | −3.3093 |
| 3445 | LEU435 | N | −11.5575 | −15.0507 | −1.1328 |
| 3446 | LEU435 | CA | −11.1601 | −13.7259 | −0.6947 |
| 3447 | LEU435 | C | −11.8117 | −13.4319 | 0.6284 |
| 3448 | LEU435 | O | −11.2044 | −12.7876 | 1.4682 |
| 3449 | LEU435 | CB | −11.6284 | −12.7274 | −1.7707 |
| 3450 | LEU435 | CG | −10.9874 | −13.0944 | −3.1253 |
| 3451 | LEU435 | CD1 | −11.6377 | −12.2835 | −4.2611 |
| 3452 | LEU435 | CD2 | −9.4715 | −12.8205 | −3.0924 |
| 3453 | GLY436 | N | −13.0511 | −13.9301 | 0.8141 |
| 3454 | GLY436 | CA | −13.7463 | −13.6783 | 2.0645 |
| 3455 | GLY436 | C | −13.1259 | −14.3795 | 3.2413 |
| 3456 | GLY436 | O | −13.5195 | −14.0929 | 4.3606 |
| 3457 | SER437 | N | −12.1546 | −15.2873 | 3.0096 |
| 3458 | SER437 | CA | −11.4627 | −15.8787 | 4.1435 |
| 3459 | SER437 | C | −10.6472 | −14.7866 | 4.7693 |
| 3460 | SER437 | O | −10.7271 | −14.5724 | 5.9678 |
| 3461 | SER437 | CB | −10.5753 | −17.0588 | 3.6991 |
| 3462 | SER437 | OG | −9.4322 | −16.605 | 2.9694 |
| 3463 | ARG438 | N | −9.8934 | −14.0746 | 3.9088 |
| 3464 | ARG438 | CA | −9.3036 | −12.8255 | 4.3441 |
| 3465 | ARG438 | C | −10.3339 | −11.7506 | 4.1274 |
| 3466 | ARG438 | O | −10.0357 | −10.6992 | 3.5855 |
| 3467 | ARG438 | CB | −8.0394 | −12.5637 | 3.5059 |
| 3468 | ARG438 | CG | −6.799 | −12.675 | 4.4085 |
| 3469 | ARG438 | CD | −5.537 | −12.5279 | 3.5426 |
| 3470 | ARG438 | NE | −5.2563 | −13.78 | 2.8628 |
| 3471 | ARG438 | CZ | −5.3165 | −13.8747 | 1.5657 |
| 3472 | ARG438 | NH1 | −5.0562 | −15.0148 | 0.9988 |
| 3473 | ARG438 | NH2 | −5.633 | −12.8539 | 0.824 |
| 3474 | GLN439 | N | −11.5724 | −12.058 | 4.5619 |
| 3475 | GLN439 | CA | −12.6718 | −11.1177 | 4.4405 |
| 3476 | GLN439 | C | −12.5563 | −9.9071 | 5.3258 |
| 3477 | GLN439 | O | −11.6003 | −9.1648 | 5.1923 |
| 3478 | GLN439 | CB | −13.1032 | −10.8149 | 2.9912 |
| 3479 | GLN439 | CG | −12.3806 | −9.5842 | 2.4087 |
| 3480 | GLN439 | CD | −11.8279 | −9.9146 | 1.0526 |
| 3481 | GLN439 | OE1 | −10.6294 | −9.8213 | 0.8458 |
| 3482 | GLN439 | NE2 | −12.7032 | −10.308 | 0.1101 |
| 3483 | PRO440 | N | −13.5257 | −9.6736 | 6.2322 |
| 3484 | PRO440 | CA | −13.5102 | −8.454 | 7.0132 |
| 3485 | PRO440 | C | −12.5963 | −8.5337 | 8.2091 |
| 3486 | PRO440 | O | −13.0331 | −8.9057 | 9.2865 |
| 3487 | PRO440 | CB | −14.9903 | −8.3729 | 7.4378 |
| 3488 | PRO440 | CG | −15.6183 | −9.7669 | 7.2251 |
| 3489 | PRO440 | CD | −14.6348 | −10.5924 | 6.3754 |
| 3490 | PHE441 | N | −11.313 | −8.154 | 8.0356 |
| 3491 | PHE441 | CA | −10.4329 | −8.1481 | 9.1921 |
| 3492 | PHE441 | C | −9.3135 | −7.1499 | 9.079 |
| 3493 | PHE441 | O | −9.307 | −6.1968 | 9.8411 |
| 3494 | PHE441 | CB | −9.9065 | −9.5694 | 9.4543 |
| 3495 | PHE441 | CG | −8.8765 | −9.5947 | 10.5777 |
| 3496 | PHE441 | CD1 | −9.2572 | −9.3263 | 11.8948 |
| 3497 | PHE441 | CD2 | −7.5447 | −9.8939 | 10.2826 |
| 3498 | PHE441 | CE1 | −8.3156 | −9.4054 | 12.9238 |
| 3499 | PHE441 | CE2 | −6.598 | −9.9539 | 11.3085 |
| 3500 | PHE441 | CZ | −6.9871 | −9.7246 | 12.6308 |
| 3501 | PHE442 | N | −8.3614 | −7.3754 | 8.1492 |
| 3502 | PHE442 | CA | −7.2088 | −6.4892 | 8.0549 |
| 3503 | PHE442 | C | −7.6206 | −5.0488 | 7.9371 |
| 3504 | PHE442 | O | −7.2474 | −4.2463 | 8.7776 |
| 3505 | PHE442 | CB | −6.3572 | −6.8537 | 6.8211 |
| 3506 | PHE442 | CG | −5.5543 | −8.1401 | 7.0126 |
| 3507 | PHE442 | CD1 | −5.6384 | −8.883 | 8.1934 |
| 3508 | PHE442 | CD2 | −4.7192 | −8.374 | 5.9815 |
| 3509 | PHE442 | CE1 | −4.9145 | −10.0705 | 8.3302 |
| 3510 | PHE442 | CE2 | −4.0186 | −9.7817 | 6.1024 |
| 3511 | PHE442 | CZ | −4.1198 | −10.531 | 7.2771 |
| 3512 | SER443 | N | −8.4024 | −4.7357 | 6.8855 |
| 3513 | SER443 | CA | −8.8934 | −3.3779 | 6.7157 |
| 3514 | SER443 | C | −7.8833 | −2.4435 | 6.119 |
| 3515 | SER443 | O | −6.7567 | −2.3707 | 6.5828 |
| 3516 | SER443 | CB | −9.561 | −2.7648 | 7.9634 |
| 3517 | SER443 | OG | −10.3106 | −3.7529 | 8.6741 |
| 3518 | LEU444 | N | −8.3187 | −1.7202 | 5.0706 |
| 3519 | LEU444 | CA | −7.4518 | −0.7066 | 4.4982 |
| 3520 | LEU444 | C | −7.9637 | 0.6451 | 4.9117 |
| 3521 | LEU444 | O | −9.1482 | 0.7865 | 5.1681 |
| 3522 | LEU444 | CB | −7.4563 | −0.8342 | 2.9623 |
| 3523 | LEU444 | CG | −6.0403 | −0.638 | 2.3877 |
| 3524 | LEU444 | CD1 | −6.0698 | −0.9038 | 0.8713 |
| 3525 | LEU444 | CD2 | −5.5569 | 0.8034 | 2.6349 |
| 3526 | GLU445 | N | −7.0692 | 1.6498 | 4.9992 |
| 3527 | GLU445 | CA | −7.5102 | 2.9652 | 5.4428 |
| 3528 | GLU445 | C | −8.0475 | 2.9437 | 6.8497 |
| 3529 | GLU445 | O | −8.5261 | 3.9614 | 7.3251 |
| 3530 | GLU445 | CB | −8.5437 | 3.576 | 4.4742 |
| 3531 | GLU445 | CG | −7.8604 | 3.8923 | 3.1312 |
| 3532 | GLU445 | CD | −8.464 | 3.0583 | 2.0392 |
| 3533 | GLU445 | OE1 | −9.0241 | 3.6551 | 1.0816 |
| 3534 | GLU445 | OE2 | −8.378 | 1.8052 | 2.1324 |
| 3535 | ALA446 | N | −7.9729 | 1.7703 | 7.5121 |
| 3536 | ALA446 | CA | −8.5063 | 1.6526 | 8.8598 |
| 3537 | ALA446 | C | −8.4942 | 0.2083 | 9.2776 |
| 3538 | ALA446 | O | −7.7962 | −0.5946 | 8.679 |
| 3539 | ALA446 | CB | −9.9677 | 2.1342 | 8.881 |
| 3540 | CYS447 | N | −9.2914 | −0.1215 | 10.3135 |
| 3541 | CYS447 | CA | −9.3604 | −1.5071 | 10.7405 |
| 3542 | CYS447 | C | −10.7781 | −1.9128 | 11.0309 |

TABLE IV-continued

| Atom No | Residue | Atom name | x coord | y coord | z coord |
|---|---|---|---|---|---|
| 3543 | CYS447 | O | -11.6868 | -1.1019 | 10.9439 |
| 3544 | CYS447 | CB | -8.4782 | -1.7215 | 11.9838 |
| 3545 | CYS447 | SG | -6.7617 | -1.8849 | 11.4129 |
| 3546 | GLN448 | N | -10.9572 | -3.2019 | 11.3776 |
| 3547 | GLN448 | CA | -12.2997 | -3.6777 | 11.6568 |
| 3548 | GLN448 | C | -12.3559 | -4.3087 | 13.021 |
| 3549 | GLN448 | O | -11.3584 | -4.3311 | 13.7248 |
| 3550 | GLN448 | CB | -12.6929 | -4.7019 | 10.576 |
| 3551 | GLN448 | CG | -14.2214 | -4.8842 | 10.5841 |
| 3552 | GLN448 | CD | -14.5629 | -6.3446 | 10.5964 |
| 3553 | GLN448 | OE1 | -15.2139 | -6.8123 | 9.6784 |
| 3554 | GLN448 | NE2 | -14.1306 | -7.0806 | 11.6362 |
| 3555 | GLY449 | N | -13.5408 | -4.8271 | 13.3986 |
| 3556 | GLY449 | CA | -13.6521 | -5.4298 | 14.7135 |
| 3557 | GLY449 | C | -14.9421 | -6.1864 | 14.8275 |
| 3558 | GLY449 | O | -15.9341 | -5.6338 | 15.2739 |
| 3559 | ILE450 | N | -14.9096 | -7.4713 | 14.4265 |
| 3560 | ILE450 | CA | -16.0878 | -8.305 | 14.5969 |
| 3561 | ILE450 | C | -16.2627 | -8.6601 | 16.0492 |
| 3562 | ILE450 | O | -15.3354 | -8.5252 | 16.8306 |
| 3563 | ILE450 | CB | -15.9326 | -9.5842 | 13.7436 |
| 3564 | ILE450 | CG1 | -16.9995 | -10.6372 | 14.115 |
| 3565 | ILE450 | CG2 | -14.5118 | -10.1605 | 13.8955 |
| 3566 | ILE450 | CD1 | -16.6492 | -12.0235 | 13.5415 |
| 3567 | LEU451 | N | -17.4745 | -9.1269 | 16.4041 |
| 3568 | LEU451 | CA | -17.6792 | -9.6277 | 17.7517 |
| 3569 | LEU451 | C | -18.6535 | -10.7714 | 17.7146 |
| 3570 | LEU451 | O | -19.1634 | -11.1042 | 16.6561 |
| 3571 | LEU451 | CB | -18.2011 | -8.5351 | 18.7037 |
| 3572 | LEU451 | CG | -17.1039 | -7.5035 | 19.0253 |
| 3573 | LEU451 | CD1 | -17.0986 | -6.4004 | 17.9498 |
| 3574 | LEU451 | CD2 | -17.4062 | -6.8647 | 20.3934 |
| 3575 | ALA452 | N | -18.914 | -11.3855 | 18.8851 |
| 3576 | ALA452 | CA | -19.811 | -12.5274 | 18.8843 |
| 3577 | ALA452 | C | -20.4078 | -12.7727 | 20.2417 |
| 3578 | ALA452 | O | -20.1361 | -12.0456 | 21.1807 |
| 3579 | ALA452 | CB | -19.0467 | -13.7711 | 18.3944 |
| 3580 | LEU453 | N | -21.2402 | -13.8306 | 20.3318 |
| 3581 | LEU453 | CA | -21.8105 | -14.1816 | 21.6185 |
| 3582 | LEU453 | C | -22.2269 | -15.6259 | 21.5694 |
| 3583 | LEU453 | O | -22.9677 | -16.0119 | 20.6803 |
| 3584 | LEU453 | CB | -23.0163 | -13.2979 | 21.9873 |
| 3585 | LEU453 | CG | -23.0743 | -13.0848 | 23.5134 |
| 3586 | LEU453 | CD1 | -24.2561 | -12.1686 | 23.8721 |
| 3587 | LEU453 | CD2 | -23.2629 | -14.4276 | 24.2404 |
| 3588 | LEU454 | N | -21.7179 | -16.4119 | 22.538 |
| 3589 | LEU454 | CA | -22.0031 | -17.8374 | 22.5715 |
| 3590 | LEU454 | C | -21.7649 | -18.549 | 21.2663 |
| 3591 | LEU454 | O | -20.6473 | -18.9583 | 20.9962 |
| 3592 | LEU454 | CB | -23.3365 | -18.2012 | 23.258 |
| 3593 | LEU454 | CG | -24.5355 | -17.7682 | 22.3939 |
| 3594 | LEU454 | CD1 | -25.5516 | -18.9204 | 22.3016 |
| 3595 | LEU454 | CD2 | -25.1978 | -16.5096 | 22.9825 |
| 3596 | ASP455 | N | -22.8361 | -18.7049 | 20.4641 |
| 3597 | ASP455 | CA | -22.7111 | -19.4269 | 19.2122 |
| 3598 | ASP455 | C | -23.9693 | -19.2033 | 18.4191 |
| 3599 | ASP455 | O | -24.6883 | -20.1354 | 18.0977 |
| 3600 | ASP455 | CB | -22.4065 | -20.918 | 19.468 |
| 3601 | ASP455 | CG | -23.4556 | -21.5473 | 20.3398 |
| 3602 | ASP455 | OD1 | -23.4766 | -21.2391 | 21.5615 |
| 3603 | ASP455 | OD2 | -24.2562 | -22.3595 | 19.8046 |
| 3604 | LEU456 | N | -24.2256 | -17.9188 | 18.1067 |
| 3605 | LEU456 | CA | -25.4488 | -17.5741 | 17.4012 |
| 3606 | LEU456 | C | -25.4177 | -18.0274 | 15.967 |
| 3607 | LEU456 | O | -24.4079 | -18.5308 | 15.5021 |
| 3608 | LEU456 | CB | -25.7189 | -16.0568 | 17.4969 |
| 3609 | LEU456 | CG | -25.2245 | -15.4804 | 18.8418 |
| 3610 | LEU456 | CD1 | -25.6259 | -14.0019 | 18.9853 |
| 3611 | LEU456 | CD2 | -25.8085 | -16.2725 | 20.0232 |
| 3612 | ASN457 | N | -26.5491 | -17.8556 | 15.2576 |
| 3613 | ASN457 | CA | -26.6035 | -18.3511 | 13.894 |
| 3614 | ASN457 | C | -26.5348 | -17.2364 | 12.8876 |
| 3615 | ASN457 | O | -25.5467 | -17.5147 | 11.6988 |
| 3616 | ASN457 | CB | -27.8819 | -19.1935 | 13.7129 |
| 3617 | ASN457 | CG | -27.8633 | -19.9255 | 12.4013 |
| 3618 | ASN457 | OD1 | -28.7526 | -19.734 | 11.5886 |
| 3619 | ASN457 | ND2 | -26.8431 | -20.773 | 12.1774 |
| 3620 | ALA458 | N | -26.4576 | -15.9721 | 13.3534 |
| 3621 | ALA458 | CA | -26.3819 | -14.8723 | 12.4045 |
| 3622 | ALA458 | C | -25.196 | -15.0739 | 11.5085 |
| 3623 | ALA458 | O | -25.3624 | -15.2125 | 10.3077 |
| 3624 | ALA458 | CB | -26.2713 | -13.5328 | 13.1531 |
| 3625 | SER459 | N | -23.9936 | -15.1232 | 12.1096 |
| 3626 | SER459 | CA | -22.8526 | -15.5511 | 11.3264 |
| 3627 | SER459 | C | -22.8258 | -17.0523 | 11.3748 |
| 3628 | SER459 | O | -22.1743 | -17.633 | 12.2275 |
| 3629 | SER459 | CB | -21.5611 | -14.9004 | 11.8587 |
| 3630 | SER459 | OG | -21.5207 | -14.9551 | 13.2861 |
| 3631 | GLY460 | N | -23.5545 | -17.6907 | 10.4395 |
| 3632 | GLY460 | CA | -23.5731 | -19.1412 | 10.4551 |
| 3633 | GLY460 | C | -24.3729 | -19.7103 | 9.3209 |
| 3634 | GLY460 | O | -24.3669 | -20.9183 | 9.1474 |
| 3635 | THR461 | N | -25.0651 | -18.8512 | 8.5476 |
| 3636 | THR461 | CA | -25.8776 | -19.3898 | 7.4721 |
| 3637 | THR461 | C | -25.8192 | -18.4964 | 6.2644 |
| 3638 | THR461 | O | -25.8752 | -17.2885 | 6.42 |
| 3639 | THR461 | CB | -27.332 | -19.5874 | 7.9424 |
| 3640 | THR461 | OG1 | -27.3496 | -20.3788 | 9.1335 |
| 3641 | THR461 | CG2 | -28.1507 | -20.3002 | 6.8495 |
| 3642 | MET462 | N | -25.7015 | -19.054 | 5.0422 |
| 3643 | MET462 | CA | -25.6916 | -20.5014 | 4.9115 |
| 3644 | MET462 | C | -24.3543 | -21.0862 | 5.2649 |
| 3645 | MET462 | O | -24.2089 | -21.6013 | 6.3617 |
| 3646 | MET462 | CB | -26.1399 | -20.9827 | 3.5177 |
| 3647 | MET462 | CG | -27.1016 | -19.9726 | 2.8654 |
| 3648 | MET462 | SD | -26.0964 | -18.9071 | 1.7923 |
| 3649 | MET462 | CE | -26.8403 | -17.3145 | 2.2498 |
| 3650 | SER463 | N | -23.3742 | -21.0232 | 4.3405 |
| 3651 | SER463 | CA | -22.0933 | -21.625 | 4.6622 |
| 3652 | SER463 | C | -20.9364 | -21.0807 | 3.872 |
| 3653 | SER463 | O | -21.1103 | -20.3086 | 2.9427 |
| 3654 | SER463 | CB | -22.1673 | -23.1539 | 4.4857 |
| 3655 | SER463 | OG | -22.2279 | -23.478 | 3.0943 |
| 3656 | ILE464 | N | -19.7303 | -21.5325 | 4.2705 |
| 3657 | ILE464 | CA | -18.5404 | -21.2112 | 3.5042 |
| 3658 | ILE464 | C | -18.6579 | -21.8491 | 2.1149 |
| 3659 | ILE464 | O | -18.1781 | -21.2911 | 1.1766 |
| 3660 | ILE464 | CB | -17.2947 | -21.7419 | 4.2472 |
| 3661 | ILE464 | CG1 | -16.0361 | -21.5244 | 3.3814 |
| 3662 | ILE464 | CG2 | -17.4593 | -23.237 | 4.5853 |
| 3663 | ILE464 | CD1 | -14.7779 | -22.0522 | 4.0959 |
| 3664 | GLN465 | N | -19.3259 | -23.0197 | 2.1078 |
| 3665 | GLN465 | CA | -19.5831 | -23.6643 | 0.8319 |
| 3666 | GLN465 | C | -20.3295 | -22.7182 | -0.0651 |
| 3667 | GLN465 | O | -20.1229 | -22.7443 | -1.2678 |
| 3668 | GLN465 | CB | -20.444 | -24.9165 | 1.0837 |
| 3669 | GLN465 | CG | -19.7163 | -25.8538 | 2.0665 |
| 3670 | GLN465 | CD | -20.3202 | -25.7168 | 3.434 |
| 3671 | GLN465 | OE1 | -19.6984 | -25.1588 | 4.3229 |
| 3672 | GLN465 | NE2 | -21.5492 | -26.2327 | 3.6147 |
| 3673 | GLU466 | N | -21.1788 | -21.8589 | 0.5345 |
| 3674 | GLU466 | CA | -21.8194 | -20.8295 | -0.2637 |
| 3675 | GLU466 | C | -20.8655 | -19.7025 | -0.5599 |
| 3676 | GLU466 | O | -21.2575 | -18.5461 | -0.5642 |
| 3677 | GLU466 | CB | -23.1093 | -20.3379 | 0.4195 |
| 3678 | GLU466 | CG | -24.3071 | -21.0682 | -0.2163 |
| 3679 | GLU466 | CD | -25.0033 | -20.9491 | 0.7812 |
| 3680 | GLU466 | OE1 | -26.2538 | -22.0654 | 0.6838 |
| 3681 | GLU466 | OE2 | -24.3149 | -22.5175 | 1.6704 |
| 3682 | PHE467 | N | -19.5915 | -20.0647 | -0.8145 |
| 3683 | PHE467 | CA | -18.6057 | -19.0773 | -1.2217 |
| 3684 | PHE467 | C | -18.4992 | -17.9348 | -0.2519 |
| 3685 | PHE467 | O | -18.7028 | -16.7913 | -0.6279 |
| 3686 | PHE467 | CB | -18.8775 | -18.6158 | -2.6665 |
| 3687 | PHE467 | CG | -18.8007 | -19.8306 | -3.5833 |
| 3688 | PHE467 | CD1 | -19.9284 | -20.6341 | -3.7711 |
| 3689 | PHE467 | CD2 | -17.6019 | -20.1412 | -4.2302 |
| 3690 | PHE467 | CE1 | -19.8486 | -21.7681 | -4.5831 |
| 3691 | PHE467 | CE2 | -17.5246 | -21.272 | -5.0471 |
| 3692 | PHE467 | CZ | -18.6458 | -22.0883 | -5.2185 |
| 3693 | ARG468 | N | -18.1687 | -18.2613 | 1.013 |
| 3694 | ARG468 | CA | -18.1013 | -17.2092 | 2.0099 |
| 3695 | ARG468 | C | -17.3189 | -17.6414 | 3.219 |
| 3696 | ARG468 | O | -17.2096 | -18.8309 | 3.4638 |

TABLE IV-continued

| Atom No | Residue | Atom name | x coord | y coord | z coord |
|---|---|---|---|---|---|
| 3697 | ARG468 | CB | −19.5391 | −16.8 | 2.3619 |
| 3698 | ARG468 | CG | −19.9077 | −15.5407 | 1.5629 |
| 3699 | ARG468 | CD | −21.3668 | −15.6322 | 1.0869 |
| 3700 | ARG468 | NE | −21.6434 | −14.468 | 0.2675 |
| 3701 | ARG468 | CZ | −22.7141 | −13.7518 | 0.4496 |
| 3702 | ARG468 | NH1 | −22.9115 | −12.7039 | −0.2936 |
| 3703 | ARG468 | NH2 | −23.5889 | −14.0641 | 1.3599 |
| 3704 | ASP469 | N | −16.745 | −16.6834 | 3.9761 |
| 3705 | ASP469 | CA | −15.8373 | −17.0925 | 5.037 |
| 3706 | ASP469 | C | −16.05 | −16.3696 | 6.3396 |
| 3707 | ASP469 | O | −16.7493 | −15.3712 | 6.3862 |
| 3708 | ASP469 | CB | −14.3729 | −16.9777 | 4.571 |
| 3709 | ASP469 | CG | −13.9302 | −18.2086 | 3.8302 |
| 3710 | ASP469 | OD1 | −12.8642 | −18.7671 | 4.199 |
| 3711 | ASP469 | OD2 | −14.6368 | −18.6322 | 2.8782 |
| 3712 | LEU470 | N | −15.4321 | −16.918 | 7.4061 |
| 3713 | LEU470 | CA | −15.6036 | −16.3798 | 8.7478 |
| 3714 | LEU470 | C | −14.9378 | −15.0526 | 8.9918 |
| 3715 | LEU470 | O | −14.3951 | −14.435 | 8.0894 |
| 3716 | LEU470 | CB | −17.0618 | −16.4526 | 9.2636 |
| 3717 | LEU470 | CG | −17.5558 | −15.1004 | 9.8279 |
| 3718 | LEU470 | CD1 | −17.8156 | −14.1091 | 8.6845 |
| 3719 | LEU470 | CD2 | −18.8011 | −15.2192 | 10.7218 |
| 3720 | TRP471 | N | −15.0438 | −14.6356 | 10.2697 |
| 3721 | TRP471 | CA | −14.7445 | −13.2703 | 10.6552 |
| 3722 | TRP471 | C | −13.4505 | −13.1482 | 11.3955 |
| 3723 | TRP471 | O | −12.402 | −13.4452 | 10.8476 |
| 3724 | TRP471 | CB | −15.0216 | −12.1778 | 9.6047 |
| 3725 | TRP471 | CG | −15.8341 | −11.0716 | 10.2105 |
| 3726 | TRP471 | CD1 | −15.4677 | −9.7868 | 10.3272 |
| 3727 | TRP471 | CD2 | −17.2153 | −11.191 | 10.7969 |
| 3728 | TRP471 | NE1 | −16.4268 | −9.0953 | 10.8891 |
| 3729 | TRP471 | CE2 | −17.4766 | −9.8896 | 11.18 |
| 3730 | TRP471 | CE3 | −18.1224 | −12.2308 | 10.9936 |
| 3731 | TRP471 | CZ2 | −18.6801 | −9.5302 | 11.7862 |
| 3732 | TRP471 | CZ3 | −19.3127 | −11.8885 | 11.647 |
| 3733 | TRP471 | CH2 | −19.5898 | −10.5671 | 12.0256 |
| 3734 | LYS472 | N | −13.5592 | −12.7134 | 12.6662 |
| 3735 | LYS472 | CA | −12.3709 | −12.5281 | 13.4815 |
| 3736 | LYS472 | C | −11.6523 | −11.2652 | 13.091 |
| 3737 | LYS472 | O | −11.6137 | −10.9442 | 11.9143 |
| 3738 | LYS472 | CB | −11.4541 | −13.7677 | 13.4882 |
| 3739 | LYS472 | CG | −10.8259 | −13.9547 | 14.8805 |
| 3740 | LYS472 | CD | −9.2936 | −13.8414 | 14.7855 |
| 3741 | LYS472 | CE | −8.8943 | −12.4087 | 14.3892 |
| 3742 | LYS472 | NZ | −7.4446 | −12.2088 | 14.5154 |
| 3743 | GLN473 | N | −11.084 | −10.5054 | 14.0493 |
| 3744 | GLN473 | CA | −11.1305 | −10.9221 | 15.4406 |
| 3745 | GLN473 | C | −12.4414 | −10.5471 | 16.0684 |
| 3746 | GLN473 | O | −12.6715 | −9.3793 | 16.3395 |
| 3747 | GLN473 | CB | −9.9771 | −10.2204 | 16.1819 |
| 3748 | GLN473 | CG | −9.5473 | −11.0699 | 17.3916 |
| 3749 | GLN473 | CD | −8.0631 | −11.2939 | 17.3549 |
| 3750 | GLN473 | OE1 | −7.6174 | −12.4275 | 17.289 |
| 3751 | GLN473 | NE2 | −7.2768 | −10.2035 | 17.398 |
| 3752 | LEU474 | N | −13.3061 | −11.5517 | 16.3078 |
| 3753 | LEU474 | CA | −14.5666 | −11.2333 | 16.9532 |
| 3754 | LEU474 | C | −14.5097 | −11.4497 | 18.434 |
| 3755 | LEU474 | O | −13.7945 | −12.319 | 18.9057 |
| 3756 | LEU474 | CB | −15.7761 | −11.9997 | 16.3893 |
| 3757 | LEU474 | CG | −15.5066 | −13.5144 | 16.358 |
| 3758 | LEU474 | CD1 | −16.8462 | −14.2616 | 16.2372 |
| 3759 | LEU474 | CD2 | −14.6256 | −13.8496 | 15.1415 |
| 3760 | LYS475 | N | −15.2938 | −10.6362 | 19.1639 |
| 3761 | LYS475 | CA | −15.3764 | −10.8467 | 20.594 |
| 3762 | LYS475 | C | −16.4623 | −11.8534 | 20.8451 |
| 3763 | LYS475 | O | −17.5127 | −11.5008 | 21.3576 |
| 3764 | LYS475 | CB | −15.6919 | −9.5072 | 21.2876 |
| 3765 | LYS475 | CG | −14.3884 | −8.7313 | 21.5514 |
| 3766 | LYS475 | CD | −14.1716 | −7.6716 | 20.455 |
| 3767 | LYS475 | CE | −13.5279 | −8.3139 | 19.2124 |
| 3768 | LYS475 | NZ | −13.2432 | −7.2662 | 18.2213 |
| 3769 | LEU476 | N | −16.2048 | −13.1274 | 20.4849 |
| 3770 | LEU476 | CA | −17.2074 | −14.1368 | 20.7723 |
| 3771 | LEU476 | C | −17.3598 | −14.2772 | 22.2538 |
| 3772 | LEU476 | O | −16.3956 | −14.5589 | 22.9461 |
| 3773 | LEU476 | CB | −16.9055 | −15.5044 | 20.1284 |
| 3774 | LEU476 | CG | −17.8622 | −16.6139 | 20.6251 |
| 3775 | LEU476 | CD1 | −17.4057 | −17.2144 | 21.9679 |
| 3776 | LEU476 | CD2 | −19.3105 | −16.1055 | 20.7499 |
| 3777 | SER477 | N | −18.6041 | −14.0714 | 22.7157 |
| 3778 | SER477 | CA | −18.8438 | −14.1521 | 24.1395 |
| 3779 | SER477 | C | −18.8661 | −15.576 | 24.6074 |
| 3780 | SER477 | O | −19.5043 | −16.4165 | 23.9951 |
| 3781 | SER477 | CB | −20.1921 | −13.484 | 24.4527 |
| 3782 | SER477 | OG | −20.1822 | −12.1688 | 23.8963 |
| 3783 | GLN478 | N | −18.1605 | −15.8375 | 25.7225 |
| 3784 | GLN478 | CA | −18.2964 | −17.1389 | 26.3477 |
| 3785 | GLN478 | C | −19.6603 | −17.184 | 26.9769 |
| 3786 | GLN478 | O | −20.2313 | −18.2527 | 27.1221 |
| 3787 | GLN478 | CB | −17.1909 | −17.314 | 27.4078 |
| 3788 | GLN478 | CG | −15.7783 | −17.1447 | 26.8039 |
| 3789 | GLN478 | CD | −15.6896 | −17.5401 | 25.3558 |
| 3790 | GLN478 | OE1 | −15.394 | −16.7066 | 24.5156 |
| 3791 | GLN478 | NE2 | −15.947 | −18.8243 | 25.0503 |
| 3792 | LYS479 | N | −20.1891 | −15.989 | 27.3126 |
| 3793 | LYS479 | CA | −21.5695 | −15.9001 | 27.7579 |
| 3794 | LYS479 | C | −22.518 | −16.3006 | 26.6601 |
| 3795 | LYS479 | O | −22.093 | −16.6819 | 25.5809 |
| 3796 | LYS479 | CB | −21.9024 | −14.4684 | 28.2308 |
| 3797 | LYS479 | CG | −21.1271 | −13.4064 | 27.4257 |
| 3798 | LYS479 | CD | −19.8093 | −13.0884 | 28.158 |
| 3799 | LYS479 | CE | −18.6074 | −13.3679 | 27.239 |
| 3800 | LYS479 | NZ | −18.3823 | −12.2219 | 26.3474 |
| 3801 | VAL480 | N | −23.8296 | −16.2161 | 26.9525 |
| 3802 | VAL480 | CA | −24.8025 | −16.6796 | 25.9789 |
| 3803 | VAL480 | C | −25.9383 | −15.6936 | 25.8977 |
| 3804 | VAL480 | O | −25.7435 | −14.5235 | 26.1871 |
| 3805 | VAL480 | CB | −25.2777 | −18.0865 | 26.4048 |
| 3806 | VAL480 | CG1 | −26.1324 | −18.7344 | 25.2995 |
| 3807 | VAL480 | CG2 | −24.0673 | −18.9988 | 26.6815 |
| 3808 | PHE481 | N | −27.1361 | −16.1703 | 25.5011 |
| 3809 | PHE481 | CA | −28.2686 | −15.2688 | 25.3871 |
| 3810 | PHE481 | C | −28.5777 | −14.6108 | 26.6995 |
| 3811 | PHE481 | O | −28.5512 | −15.2663 | 27.7289 |
| 3812 | PHE481 | CB | −29.5093 | −16.0464 | 24.9095 |
| 3813 | PHE481 | CG | −30.6455 | −15.1135 | 24.4987 |
| 3814 | PHE481 | CD1 | −30.405 | −13.7648 | 24.2231 |
| 3815 | PHE481 | CD2 | −31.9427 | −15.622 | 24.3969 |
| 3816 | PHE481 | CE1 | −31.4575 | −12.979 | 23.8457 |
| 3817 | PHE481 | CE2 | −32.9913 | −14.7928 | 23.9908 |
| 3818 | PHE481 | CZ | −32.7463 | −13.4484 | 23.7008 |
| 3819 | HIS482 | N | −28.8647 | −13.2949 | 26.6425 |
| 3820 | HIS482 | CA | −29.1666 | −12.5712 | 27.8657 |
| 3821 | HIS482 | C | −28.0142 | −12.6683 | 28.827 |
| 3822 | HIS482 | O | −28.2101 | −12.9102 | 30.0076 |
| 3823 | HIS482 | CB | −30.4761 | −13.0913 | 28.4932 |
| 3824 | HIS482 | CG | −31.6535 | −12.8039 | 27.6078 |
| 3825 | HIS482 | ND1 | −32.6249 | −13.674 | 27.4567 |
| 3826 | HIS482 | CD2 | −31.8465 | −11.6717 | 26.9044 |
| 3827 | HIS482 | CE1 | −33.4945 | −13.1446 | 26.6562 |
| 3828 | HIS482 | NE2 | −33.1102 | −12.0025 | 26.3046 |
| 3829 | LYS483 | N | −26.7884 | −12.4904 | 28.299 |
| 3830 | LYS483 | CA | −25.6324 | −12.6329 | 29.1636 |
| 3831 | LYS483 | C | −24.6189 | −11.5883 | 28.8083 |
| 3832 | LYS483 | O | −24.1628 | −11.5435 | 27.6766 |
| 3833 | LYS483 | CB | −25.0266 | −14.0442 | 29.0363 |
| 3834 | LYS483 | CG | −26.1005 | −15.0942 | 29.3754 |
| 3835 | LYS483 | CD | −25.5128 | −16.5103 | 29.2494 |
| 3836 | LYS483 | CE | −26.6608 | −17.5359 | 29.2614 |
| 3837 | LYS483 | NZ | −26.1029 | −18.8953 | 29.2265 |
| 3838 | GLN484 | N | −24.2798 | −10.7423 | 29.8014 |
| 3839 | GLN484 | CA | −23.3352 | −9.6715 | 29.5338 |
| 3840 | GLN484 | C | −22.0236 | −10.2252 | 29.0607 |
| 3841 | GLN484 | O | −21.606 | −11.2796 | 29.5116 |
| 3842 | GLN484 | CB | −23.0998 | −8.8037 | 30.7839 |
| 3843 | GLN484 | CG | −24.4469 | −8.3374 | 31.367 |
| 3844 | GLN484 | CD | −24.5187 | −8.7226 | 32.8162 |
| 3845 | GLN484 | OE1 | −25.3451 | −9.5393 | 33.1882 |
| 3846 | GLN484 | NE2 | −23.647 | −8.1311 | 33.6529 |
| 3847 | ASP485 | N | −21.3878 | −9.501 | 28.1225 |
| 3848 | ASP485 | CA | −20.1652 | −10.0221 | 27.5422 |
| 3849 | ASP485 | C | −18.9649 | −9.6997 | 28.3851 |
| 3850 | ASP485 | O | −19.0926 | −9.0979 | 29.4395 |

TABLE IV-continued

| Atom No | Residue | Atom name | x coord | y coord | z coord |
|---|---|---|---|---|---|
| 3851 | ASP485 | CB | −20.0082 | −9.4693 | 26.1131 |
| 3852 | ASP485 | CG | −21.1396 | −9.9172 | 25.2301 |
| 3853 | ASP485 | OD1 | −21.3088 | −9.3015 | 24.1442 |
| 3854 | ASP485 | OD2 | −21.8672 | −10.8755 | 25.6106 |
| 3855 | ARG486 | N | −17.7821 | −10.1222 | 27.8996 |
| 3856 | ARG486 | CA | −16.5738 | −9.915 | 28.6768 |
| 3857 | ARG486 | C | −15.3703 | −10.2696 | 27.8524 |
| 3858 | ARG486 | O | −15.4489 | −11.148 | 27.0082 |
| 3859 | ARG486 | CB | −16.5904 | −10.7773 | 29.9554 |
| 3860 | ARG486 | CG | −16.9669 | −12.2259 | 29.5918 |
| 3861 | ARG486 | CD | −16.9507 | −13.1163 | 30.8459 |
| 3862 | ARG486 | NE | −16.4438 | −14.423 | 30.4703 |
| 3863 | ARG486 | CZ | −15.4104 | −14.941 | 31.0681 |
| 3864 | ARG486 | NH1 | −14.9709 | −16.1035 | 30.6875 |
| 3865 | ARG486 | NH2 | −14.8105 | −14.3159 | 32.0383 |
| 3866 | GLY487 | N | −14.2495 | −9.5658 | 28.1093 |
| 3867 | GLY487 | CA | −13.0384 | −9.848 | 27.3574 |
| 3868 | GLY487 | C | −12.5891 | −11.2554 | 27.6213 |
| 3869 | GLY487 | O | −12.254 | −11.9666 | 26.6877 |
| 3870 | SER488 | N | −12.6035 | −11.6512 | 28.91 |
| 3871 | SER488 | CA | −12.2732 | −13.0265 | 29.2428 |
| 3872 | SER488 | C | −13.2361 | −13.9456 | 28.5477 |
| 3873 | SER488 | O | −12.8507 | −15.0267 | 28.1324 |
| 3874 | SER488 | CB | −12.4306 | −13.2055 | 30.7638 |
| 3875 | SER488 | OG | −11.5098 | −12.3537 | 31.45 |
| 3876 | GLY489 | N | −14.4953 | −13.4891 | 28.4056 |
| 3877 | GLY489 | CA | −15.4658 | −14.2927 | 27.6778 |
| 3878 | GLY489 | C | −15.3005 | −14.0949 | 26.1974 |
| 3879 | GLY489 | O | −16.3031 | −13.9565 | 25.519 |
| 3880 | TYR490 | N | −14.0514 | −14.0902 | 25.6914 |
| 3881 | TYR490 | CA | −13.8643 | −13.9993 | 24.2515 |
| 3882 | TYR490 | C | −12.8647 | −15.0311 | 23.8046 |
| 3883 | TYR490 | O | −12.3326 | −15.7491 | 24.6367 |
| 3884 | TYR490 | CB | −13.3901 | −12.5919 | 23.8351 |
| 3885 | TYR490 | CG | −14.4754 | −11.5416 | 24.0603 |
| 3886 | TYR490 | CD1 | −14.1148 | −10.2607 | 24.4856 |
| 3887 | TYR490 | CD2 | −15.8226 | −11.8443 | 23.8463 |
| 3888 | TYR490 | CE1 | −15.0993 | −9.2996 | 24.7292 |
| 3889 | TYR490 | CE2 | −16.8117 | −10.8964 | 24.1178 |
| 3890 | TYR490 | CZ | −16.4483 | −9.6229 | 24.562 |
| 3891 | TYR490 | OH | −17.4285 | −8.6779 | 24.8375 |
| 3892 | LEU491 | N | −12.6034 | −15.1172 | 22.4831 |
| 3893 | LEU491 | CA | −11.6638 | −16.129 | 22.0245 |
| 3894 | LEU491 | C | −11.252 | −15.9456 | 20.5902 |
| 3895 | LEU491 | O | −12.0934 | −15.9191 | 19.7064 |
| 3896 | LEU491 | CB | −12.1723 | −17.5602 | 22.3026 |
| 3897 | LEU491 | CG | −13.3597 | −17.9456 | 21.3964 |
| 3898 | LEU491 | CD1 | −13.8683 | −19.3391 | 21.8069 |
| 3899 | LEU491 | CD2 | −14.5076 | −16.9305 | 21.5416 |
| 3900 | ASN492 | N | −9.9258 | −15.8234 | 20.3828 |
| 3901 | ASN492 | CA | −9.4009 | −15.6758 | 19.0336 |
| 3902 | ASN492 | C | −7.9853 | −16.1958 | 19.0018 |
| 3903 | ASN492 | O | −7.4131 | −16.4041 | 20.0593 |
| 3904 | ASN492 | CB | −9.4086 | −14.1987 | 18.5951 |
| 3905 | ASN492 | CG | −10.7986 | −13.6329 | 18.5686 |
| 3906 | ASN492 | OD1 | −11.1194 | −12.7871 | 19.3868 |
| 3907 | ASN492 | ND2 | −11.639 | −14.0921 | 17.6246 |
| 3908 | TRP493 | N | −7.3666 | −16.4405 | 17.8269 |
| 3909 | TRP493 | CA | −8.033 | −16.1681 | 16.5662 |
| 3910 | TRP493 | C | −6.9975 | −15.7789 | 15.5421 |
| 3911 | TRP493 | O | −6.647 | −14.6114 | 15.4916 |
| 3912 | TRP493 | CB | −8.8914 | −17.3508 | 16.0732 |
| 3913 | TRP493 | CG | −9.8756 | −17.8632 | 17.0855 |
| 3914 | TRP493 | CD1 | −11.2065 | −17.7072 | 17.0457 |
| 3915 | TRP493 | CD2 | −9.5666 | −18.6484 | 18.3321 |
| 3916 | TRP493 | NE1 | −11.7642 | −18.2709 | 18.0878 |
| 3917 | TRP493 | CE2 | −10.8239 | −18.8265 | 18.8777 |
| 3918 | TRP493 | CE3 | −8.4064 | −19.1398 | 18.9289 |
| 3919 | TRP493 | CZ2 | −11.0102 | −19.4955 | 20.0863 |
| 3920 | TRP493 | CZ3 | −8.5843 | −19.8107 | 20.1447 |
| 3921 | TRP493 | CH2 | −9.8554 | −19.9779 | 20.7139 |
| 3922 | GLU494 | N | −6.4974 | −16.7269 | 14.7194 |
| 3923 | GLU494 | CA | −5.4994 | −16.3438 | 13.7304 |
| 3924 | GLU494 | C | −5.5057 | −17.2435 | 12.5255 |
| 3925 | GLU494 | O | −5.0583 | −18.3768 | 12.5985 |
| 3926 | GLU494 | CB | −4.0923 | −16.2476 | 14.3499 |
| 3927 | GLU494 | CG | −3.7763 | −14.7825 | 14.7135 |
| 3928 | GLU494 | CD | −4.102 | −13.8467 | 13.5824 |
| 3929 | GLU494 | OE1 | −4.7641 | −12.8096 | 13.8511 |
| 3930 | GLU494 | OE2 | −3.7091 | −14.1469 | 12.4229 |
| 3931 | GLN495 | N | −6.0364 | −16.7035 | 11.4097 |
| 3932 | GLN495 | CA | −6.304 | −17.5166 | 10.2357 |
| 3933 | GLN495 | C | −7.2692 | −16.8182 | 9.3166 |
| 3934 | GLN495 | O | −7.338 | −15.5996 | 9.3254 |
| 3935 | GLN495 | CB | −5.0369 | −17.9776 | 9.493 |
| 3936 | GLN495 | CG | −4.8209 | −19.4876 | 9.7211 |
| 3937 | GLN495 | CD | −6.0634 | −20.2775 | 9.4157 |
| 3938 | GLN495 | OE1 | −6.5357 | −21.0175 | 10.2627 |
| 3939 | GLN495 | NE2 | −6.6081 | −20.1267 | 8.195 |
| 3940 | LEU496 | N | −8.0384 | −17.6007 | 8.5327 |
| 3941 | LEU496 | CA | −9.0582 | −16.9857 | 7.6964 |
| 3942 | LEU496 | C | −10.3289 | −17.7858 | 7.7509 |
| 3943 | LEU496 | O | −10.2675 | −18.9972 | 7.8842 |
| 3944 | LEU496 | CB | −8.595 | −16.8349 | 6.2352 |
| 3945 | LEU496 | CG | −7.3993 | −15.8684 | 6.14 |
| 3946 | LEU496 | CD1 | −6.9522 | −15.7636 | 4.6704 |
| 3947 | LEU496 | CD2 | −7.801 | −14.4732 | 6.6533 |
| 3948 | HIS497 | N | −11.4883 | −17.0996 | 7.6701 |
| 3949 | HIS497 | CA | −12.7528 | −17.7812 | 7.9109 |
| 3950 | HIS497 | C | −12.8025 | −18.1945 | 9.3541 |
| 3951 | HIS497 | O | −12.5097 | −19.3358 | 9.6708 |
| 3952 | HIS497 | CB | −12.9863 | −18.9953 | 6.9865 |
| 3953 | HIS497 | CG | −14.3988 | −19.4985 | 7.1136 |
| 3954 | HIS497 | ND1 | −14.9898 | −19.6536 | 8.2769 |
| 3955 | HIS497 | CD2 | −15.1943 | −19.8347 | 6.0807 |
| 3956 | HIS497 | CE1 | −16.1873 | −20.0931 | 8.0516 |
| 3957 | HIS497 | NE2 | −16.3672 | −20.2202 | 6.8162 |
| 3958 | ALA498 | N | −13.1814 | −17.2429 | 10.2272 |
| 3959 | ALA498 | CA | −13.1595 | −17.515 | 11.6542 |
| 3960 | ALA498 | C | −14.0791 | −18.6291 | 12.0738 |
| 3961 | ALA498 | O | −14.7686 | −19.2061 | 11.248 |
| 3962 | ALA498 | CB | −13.566 | −16.215 | 12.3713 |
| 3963 | ALA499 | N | −14.0686 | −18.913 | 13.3931 |
| 3964 | ALA499 | CA | −14.9678 | −19.9106 | 13.9554 |
| 3965 | ALA499 | C | −14.5838 | −20.2116 | 15.3775 |
| 3966 | ALA499 | O | −13.7636 | −19.5168 | 15.957 |
| 3967 | ALA499 | CB | −14.9691 | −21.2336 | 13.1688 |
| 3968 | MET500 | N | −15.1933 | −21.276 | 15.9393 |
| 3969 | MET500 | CA | −14.9391 | −21.6046 | 17.3319 |
| 3970 | MET500 | C | −15.426 | −20.4754 | 18.1944 |
| 3971 | MET500 | O | −14.7312 | −20.0207 | 19.0888 |
| 3972 | MET500 | CB | −13.4583 | −21.9532 | 17.5791 |
| 3973 | MET500 | CG | −13.3701 | −22.9759 | 18.7261 |
| 3974 | MET500 | SD | −12.7965 | −22.1232 | 20.2218 |
| 3975 | MET500 | CE | −12.6583 | −23.5784 | 21.2996 |
| 3976 | ARG501 | N | −16.6523 | −20.0177 | 17.8795 |
| 3977 | ARG501 | CA | −17.1808 | −18.8494 | 18.5571 |
| 3978 | ARG501 | C | −18.6731 | −18.8256 | 18.3681 |
| 3979 | ARG501 | O | −19.2805 | −19.8657 | 18.1664 |
| 3980 | ARG501 | CB | −16.5623 | −17.6128 | 17.8727 |
| 3981 | ARG501 | CG | −15.1516 | −17.3417 | 18.4288 |
| 3982 | ARG501 | CD | −14.67 | −15.9651 | 17.9376 |
| 3983 | ARG501 | NE | −13.573 | −16.1153 | 16.9993 |
| 3984 | ARG501 | CZ | −13.7607 | −16.5824 | 15.7985 |
| 3985 | ARG501 | NH1 | −12.7489 | −16.6829 | 14.9893 |
| 3986 | ARG501 | NH2 | −14.9398 | −16.9495 | 15.3919 |
| 3987 | GLU502 | N | −19.2645 | −17.6149 | 18.4157 |
| 3988 | GLU502 | CA | −20.6847 | −17.4904 | 18.1419 |
| 3989 | GLU502 | C | −20.9358 | −18.0166 | 16.7604 |
| 3990 | GLU502 | O | −21.946 | −18.6548 | 16.5213 |
| 3991 | GLU502 | CB | −21.034 | −15.992 | 18.1823 |
| 3992 | GLU502 | CG | −22.4733 | −15.7624 | 17.6882 |
| 3993 | GLU502 | CD | −22.4706 | −15.3281 | 16.2512 |
| 3994 | GLU502 | OE1 | −23.0568 | −16.062 | 15.4118 |
| 3995 | GLU502 | OE2 | −21.886 | −14.2506 | 15.958 |
| 3996 | ALA503 | N | −19.9852 | −17.7542 | 15.8483 |
| 3997 | ALA503 | CA | −20.1081 | −18.3485 | 14.5355 |
| 3998 | ALA503 | C | −19.1648 | −19.5142 | 14.4331 |
| 3999 | ALA503 | O | −18.1384 | −19.5231 | 15.095 |
| 4000 | ALA503 | CB | −19.7811 | −17.2624 | 13.5006 |
| 4001 | GLY504 | N | −19.5234 | −20.5169 | 13.6078 |
| 4002 | GLY504 | CA | −18.6468 | −21.6697 | 13.4978 |
| 4003 | GLY504 | C | −19.42 | −22.9573 | 13.4308 |
| 4004 | GLY504 | O | −20.6152 | −22.9529 | 13.1838 |

TABLE IV-continued

| Atom No | Residue | Atom name | x coord | y coord | z coord | Atom No | Residue | Atom name | x coord | y coord | z coord |
|---|---|---|---|---|---|---|---|---|---|---|---|
| 4005 | ARG505 | N | −18.7084 | −24.0801 | 13.6488 | 4082 | HIS514 | N | −29.9612 | −13.1856 | 19.2758 |
| 4006 | ARG505 | CA | −19.3631 | −25.3686 | 13.5231 | 4083 | HIS514 | CA | −30.3937 | −11.8433 | 19.6082 |
| 4007 | ARG505 | C | −20.074 | −25.7173 | 14.7992 | 4084 | HIS514 | C | −29.7979 | −11.4447 | 20.9308 |
| 4008 | ARG505 | O | −19.5131 | −26.3771 | 15.6597 | 4085 | HIS514 | O | −30.5143 | −11.0878 | 21.8524 |
| 4009 | ARG505 | CB | −18.3277 | −26.4418 | 13.1353 | 4086 | HIS514 | CB | −31.9352 | −11.8143 | 19.6557 |
| 4010 | ARG505 | CG | −19.0675 | −27.7271 | 12.72 | 4087 | HIS514 | CG | −32.5477 | −12.2504 | 18.3549 |
| 4011 | ARG505 | CD | −18.0544 | −28.8431 | 12.4085 | 4088 | HIS514 | ND1 | −33.8314 | −12.5101 | 18.2644 |
| 4012 | ARG505 | NE | −17.7481 | −28.8403 | 10.9898 | 4089 | HIS514 | CD2 | −31.8956 | −12.4211 | 17.188 |
| 4013 | ARG505 | CZ | −16.5174 | −28.8541 | 10.5667 | 4090 | HIS514 | CE1 | −34.0697 | −12.8611 | 17.0406 |
| 4014 | ARG505 | NH1 | −16.2831 | −28.843 | 9.2882 | 4091 | HIS514 | NE2 | −33.0067 | −12.8313 | 16.3739 |
| 4015 | ARG505 | NH2 | −15.5188 | −28.8751 | 11.4002 | 4092 | THR515 | N | −28.4557 | −11.5005 | 21.0224 |
| 4016 | HIS506 | N | −21.3392 | −25.2707 | 14.9051 | 4093 | THR515 | CA | −27.8194 | −11.0067 | 22.2293 |
| 4017 | HIS506 | CA | −22.0972 | −25.5838 | 16.103 | 4094 | THR515 | C | −26.3531 | −10.7594 | 22.0257 |
| 4018 | HIS506 | C | −23.5704 | −25.4112 | 15.8649 | 4095 | THR515 | O | −25.697 | −11.4658 | 21.2771 |
| 4019 | HIS506 | O | −23.9709 | −24.8666 | 14.8481 | 4096 | THR515 | CB | −28.1139 | −11.8416 | 23.4938 |
| 4020 | HIS506 | CB | −21.6667 | −24.6447 | 17.2475 | 4097 | THR515 | OG1 | −27.8485 | −11.0635 | 24.664 |
| 4021 | HIS506 | CG | −21.8326 | −23.2214 | 16.8002 | 4098 | THR515 | CG2 | −27.2537 | −13.119 | 23.5284 |
| 4022 | HIS506 | ND1 | −20.8661 | −22.5673 | 16.199 | 4099 | ARG516 | N | −25.8659 | −9.7201 | 22.7263 |
| 4023 | HIS506 | CD2 | −22.9533 | −22.4907 | 16.9519 | 4100 | ARG516 | CA | −24.4561 | −9.3847 | 22.6753 |
| 4024 | HIS506 | CE1 | −21.3155 | −21.3829 | 15.9318 | 4101 | ARG516 | C | −24.1989 | −8.6831 | 23.9778 |
| 4025 | HIS506 | NE2 | −22.4991 | −21.2742 | 16.3357 | 4102 | ARG516 | O | −24.063 | −7.4704 | 24.0149 |
| 4026 | ARG507 | N | −24.3781 | −25.8767 | 16.8381 | 4103 | ARG516 | CB | −24.1919 | −8.4614 | 21.4679 |
| 4027 | ARG507 | CA | −25.8061 | −25.6307 | 16.7529 | 4104 | ARG516 | CG | −24.1308 | −9.2883 | 20.1698 |
| 4028 | ARG507 | C | −26.0315 | −24.1818 | 17.0795 | 4105 | ARG516 | CD | −22.8747 | −10.1783 | 20.1863 |
| 4029 | ARG507 | O | −26.2062 | −23.8255 | 18.2343 | 4106 | ARG516 | NE | −23.2084 | −11.5089 | 19.7188 |
| 4030 | ARG507 | CB | −26.5313 | −26.5302 | 17.7719 | 4107 | ARG516 | CZ | −22.8227 | −11.9319 | 18.5506 |
| 4031 | ARG507 | CG | −26.5793 | −27.9768 | 17.2479 | 4108 | ARG516 | NH1 | −23.1216 | −13.1413 | 18.1896 |
| 4032 | ARG507 | CD | −27.4735 | −28.8176 | 18.177 | 4109 | ARG516 | NH2 | −22.1438 | −11.1823 | 17.7344 |
| 4033 | ARG507 | NE | −27.5376 | −30.1818 | 17.6859 | 4110 | ALA517 | N | −24.1631 | −9.4895 | 25.0588 |
| 4034 | ARG507 | CZ | −27.1634 | −31.1823 | 18.4298 | 4111 | ALA517 | CA | −24.1682 | −8.9339 | 26.4027 |
| 4035 | ARG507 | NH1 | −27.2354 | −32.3908 | 17.9563 | 4112 | ALA517 | C | −25.5826 | −8.5546 | 26.7308 |
| 4036 | ARG507 | NH2 | −26.7191 | −30.9953 | 19.6381 | 4113 | ALA517 | O | −26.1868 | −9.1632 | 27.5994 |
| 4037 | LYS508 | N | −26.0164 | −23.3389 | 16.03 | 4114 | ALA517 | CB | −23.1864 | −7.7643 | 26.6139 |
| 4038 | LYS508 | CA | −26.1133 | −21.911 | 16.2711 | 4115 | GLY518 | N | −26.1113 | −7.5522 | 26.0026 |
| 4039 | LYS508 | C | −27.4339 | −21.5158 | 16.8629 | 4116 | GLY518 | CA | −27.5232 | −7.2444 | 26.1371 |
| 4040 | LYS508 | O | −28.4323 | −21.1882 | 16.6601 | 4117 | GLY518 | C | −28.2821 | −7.9608 | 25.0554 |
| 4041 | LYS508 | CB | −25.8432 | −21.1072 | 14.9894 | 4118 | GLY518 | O | −27.716 | −8.263 | 24.0173 |
| 4042 | LYS508 | CG | −24.5525 | −21.6192 | 14.3297 | 4119 | CYS519 | N | −29.5766 | −8.2345 | 25.3095 |
| 4043 | LYS508 | CD | −24.0293 | −20.5702 | 13.3357 | 4120 | CYS519 | CA | −30.3711 | −8.9519 | 24.3259 |
| 4044 | LYS508 | CE | −22.737 | −21.1133 | 12.7056 | 4121 | CYS519 | C | −30.5352 | −8.1275 | 23.0777 |
| 4045 | LYS508 | NZ | −23.0643 | −22.1664 | 11.7337 | 4122 | CYS519 | O | −31.4697 | −7.3499 | 22.9756 |
| 4046 | SER509 | N | −27.4122 | −20.4063 | 17.6226 | 4123 | CYS519 | CB | −31.7408 | −9.2363 | 24.9747 |
| 4047 | SER509 | CA | −28.6287 | −19.9826 | 18.289 | 4124 | CYS519 | SG | −32.8006 | −10.1165 | 23.7893 |
| 4048 | SER509 | C | −29.2901 | −18.8631 | 17.5368 | 4125 | THR520 | N | −29.6209 | −8.3119 | 22.1069 |
| 4049 | SER509 | O | −28.8376 | −18.4787 | 16.4708 | 4126 | THR520 | CA | −29.7507 | −7.5622 | 20.8694 |
| 4050 | SER509 | CB | −28.2766 | −19.5319 | 19.7192 | 4127 | THR520 | C | −30.8517 | −8.1256 | 20.0101 |
| 4051 | SER509 | OG | −27.1009 | −18.72 | 19.6917 | 4128 | THR520 | O | −31.5034 | −9.0805 | 20.3994 |
| 4052 | TRP510 | N | −30.3851 | −18.3351 | 18.1135 | 4129 | THR520 | CB | −28.394 | −7.5683 | 20.1334 |
| 4053 | TRP510 | CA | −31.0793 | −17.2525 | 17.4436 | 4130 | THR520 | OG1 | −28.4296 | −6.678 | 19.0149 |
| 4054 | TRP510 | C | −31.6712 | −16.3401 | 18.4731 | 4131 | THR520 | CG2 | −28.0242 | −8.9858 | 19.6561 |
| 4055 | TRP510 | O | −31.5666 | −15.1336 | 18.328 | 4132 | LEU521 | N | −31.0527 | −7.5245 | 18.8205 |
| 4056 | TRP510 | CB | −32.1576 | −17.8213 | 16.506 | 4133 | LEU521 | CA | −31.9831 | −8.0999 | 17.8603 |
| 4057 | TRP510 | CG | −31.5471 | −17.9643 | 15.1431 | 4134 | LEU521 | C | −33.3511 | −8.3288 | 18.4454 |
| 4058 | TRP510 | CD1 | −31.6121 | −19.0333 | 14.3346 | 4135 | LEU521 | O | −33.9048 | −9.4088 | 18.3106 |
| 4059 | TRP510 | CD2 | −30.7387 | −16.9143 | 14.4302 | 4136 | LEU521 | CB | −31.4089 | −9.3888 | 17.2327 |
| 4060 | TRP510 | NE1 | −30.9688 | −18.7879 | 13.2198 | 4137 | LEU521 | CG | −29.882 | −9.2979 | 17.0395 |
| 4061 | TRP510 | CE2 | −30.4479 | −17.5436 | 13.235 | 4138 | LEU521 | CD1 | −29.3723 | −10.6018 | 16.3999 |
| 4062 | TRP510 | CE3 | −30.3098 | −15.6237 | 14.7371 | 4139 | LEU521 | CD2 | −29.53 | −8.1117 | 16.1223 |
| 4063 | TRP510 | CZ2 | −29.7138 | −16.9085 | 12.2337 | 4140 | ILE522 | N | −33.8974 | −7.2926 | 19.1103 |
| 4064 | TRP510 | CZ3 | −29.5691 | −14.98 | 13.7383 | 4141 | ILE522 | CA | −35.2004 | −7.4612 | 19.7307 |
| 4065 | TRP510 | CH2 | −29.298 | −15.6002 | 12.5096 | 4142 | ILE522 | C | −35.9061 | −6.1378 | 19.7926 |
| 4066 | SER511 | N | −32.2648 | −16.9216 | 19.5345 | 4143 | ILE522 | O | −37.0732 | −6.0582 | 19.4452 |
| 4067 | SER511 | CA | −32.6247 | −16.0935 | 20.6714 | 4144 | ILE522 | CB | −35.056 | −8.0071 | 21.1669 |
| 4068 | SER511 | C | −31.3371 | −15.569 | 21.239 | 4145 | ILE522 | CG1 | −34.1288 | −7.105 | 22.0053 |
| 4069 | SER511 | O | −31.1914 | −14.3694 | 21.4039 | 4146 | ILE522 | CG2 | −34.5223 | −9.4518 | 21.1494 |
| 4070 | SER511 | CB | −33.3761 | −16.9395 | 21.7181 | 4147 | ILE522 | CD1 | −34.4094 | −7.314 | 23.5048 |
| 4071 | SER511 | OG | −32.5848 | −18.0604 | 22.1239 | 4148 | ARG523 | N | −35.1764 | −5.0996 | 20.246 |
| 4072 | CYS512 | N | −30.3893 | −16.4931 | 21.4971 | 4149 | ARG523 | CA | −35.7994 | −3.8012 | 20.4375 |
| 4073 | CYS512 | CA | −29.054 | −16.0688 | 21.8787 | 4150 | ARG523 | C | −36.2561 | −3.1922 | 19.1412 |
| 4074 | CYS512 | C | −28.4923 | −15.2338 | 20.7654 | 4151 | ARG523 | O | −35.9804 | −3.7237 | 18.0772 |
| 4075 | CYS512 | O | −27.8063 | −14.2613 | 21.0336 | 4152 | ARG523 | CB | −34.7842 | −2.8678 | 21.1238 |
| 4076 | CYS512 | CB | −28.1483 | −17.3054 | 22.0288 | 4153 | ARG523 | CG | −34.2737 | −3.5234 | 22.4214 |
| 4077 | CYS512 | SG | −28.9325 | −18.5393 | 23.1075 | 4154 | ARG523 | CD | −32.8623 | −2.9969 | 22.7386 |
| 4078 | GLY513 | N | −28.8125 | −15.6145 | 19.5098 | 4155 | ARG523 | NE | −32.2864 | −3.7696 | 23.8244 |
| 4079 | GLY513 | CA | −28.404 | −14.7965 | 18.3796 | 4156 | ARG523 | CZ | −31.2373 | −4.5175 | 23.6371 |
| 4080 | GLY513 | C | −28.8091 | −13.3673 | 18.6036 | 4157 | ARG523 | NH1 | −30.746 | −5.1887 | 24.6364 |
| 4081 | GLY513 | O | −28.0983 | −12.4604 | 18.202 | 4158 | ARG523 | NH2 | −30.6715 | −4.607 | 22.4691 |

TABLE IV-continued

| Atom No | Residue | Atom name | x coord | y coord | z coord |
|---|---|---|---|---|---|
| 4159 | GLN524 | N | −36.9758 | −2.0581 | 19.2423 |
| 4160 | GLN524 | CA | −37.4924 | −1.4475 | 18.0298 |
| 4161 | GLN524 | C | −37.3061 | 0.0429 | 18.0658 |
| 4162 | GLN524 | O | −36.8246 | 0.5916 | 19.0436 |
| 4163 | GLN524 | CB | −38.9918 | −1.7647 | 17.8648 |
| 4164 | GLN524 | CG | −39.2516 | −3.2706 | 18.0637 |
| 4165 | GLN524 | CD | −39.684 | −3.5165 | 19.4805 |
| 4166 | GLN524 | OE1 | −38.9756 | −4.1667 | 20.231 |
| 4167 | GLN524 | NE2 | −40.8636 | −2.9935 | 19.8606 |

TABLE V

| Atom No | Residue | Atom name | x coord | y coord | z coord |
|---|---|---|---|---|---|
| 1 | LYS12 | CA | −26.781 | 19.61 | −5.574 |
| 2 | LYS12 | C | −27.853 | 18.529 | −5.301 |
| 3 | LYS12 | N | −27.307 | 20.9 | −5.159 |
| 4 | LYS12 | O | −27.815 | 17.778 | −4.324 |
| 5 | LYS12 | CB | −25.462 | 19.387 | −4.819 |
| 6 | LYS12 | CG | −24.469 | 18.447 | −5.526 |
| 7 | LYS12 | CD | −24.861 | 16.966 | −5.511 |
| 8 | LYS12 | CE | −23.82 | 16.057 | −6.165 |
| 9 | LYS12 | NZ | −22.573 | 16.005 | −5.369 |
| 10 | LEU13 | N | −28.901 | 18.567 | −6.21 |
| 11 | LEU13 | CA | −30.014 | 17.612 | −6.169 |
| 12 | LEU13 | C | −29.844 | 16.617 | −7.329 |
| 13 | LEU13 | O | −29.62 | 15.424 | −7.12 |
| 14 | LEU13 | CB | −31.372 | 18.325 | −6.222 |
| 15 | LEU13 | CG | −31.708 | 19.142 | −4.957 |
| 16 | LEU13 | CD1 | −33.003 | 19.928 | −5.179 |
| 17 | LEU13 | CD2 | −31.852 | 18.264 | −3.713 |
| 18 | ALA14 | N | −29.896 | 17.156 | −8.611 |
| 19 | ALA14 | CA | −30.062 | 16.233 | −9.738 |
| 20 | ALA14 | C | −28.974 | 15.148 | −9.82 |
| 21 | ALA14 | O | −29.304 | 13.976 | −10.052 |
| 22 | ALA14 | CB | −30.199 | 16.966 | −11.065 |
| 23 | PRO15 | N | −27.648 | 15.468 | −9.615 |
| 24 | PRO15 | CA | −26.614 | 14.433 | −9.739 |
| 25 | PRO15 | C | −26.577 | 13.384 | −8.613 |
| 26 | PRO15 | O | −25.683 | 12.59 | −8.564 |
| 27 | PRO15 | CB | −25.291 | 15.205 | −9.757 |
| 28 | PRO15 | CG | −25.689 | 16.611 | −10.179 |
| 29 | PRO15 | CD | −27.049 | 16.79 | −9.529 |
| 30 | ARG16 | N | −27.611 | 13.432 | −7.698 |
| 31 | ARG16 | CA | −27.889 | 12.313 | −6.808 |
| 32 | ARG16 | C | −28.719 | 11.222 | −7.523 |
| 33 | ARG16 | O | −28.811 | 10.092 | −7.04 |
| 34 | ARG16 | CB | −28.669 | 12.759 | −5.565 |
| 35 | ARG16 | CG | −27.969 | 13.889 | −4.779 |
| 36 | ARG16 | CD | −28.841 | 14.271 | −3.563 |
| 37 | ARG16 | NE | −28.553 | 15.641 | −3.125 |
| 38 | ARG16 | CZ | −28.879 | 16.152 | −1.919 |
| 39 | ARG16 | NH1 | −28.571 | 17.443 | −1.675 |
| 40 | ARG16 | NH2 | −29.498 | 15.43 | −0.966 |
| 41 | TYR17 | N | −29.447 | 11.628 | −8.629 |
| 42 | TYR17 | CA | −30.387 | 10.734 | −9.307 |
| 43 | TYR17 | C | −30.365 | 10.753 | −10.847 |
| 44 | TYR17 | O | −30.892 | 9.844 | −11.493 |
| 45 | TYR17 | CB | −31.82 | 10.861 | −8.763 |
| 46 | TYR17 | CG | −32.42 | 12.247 | −8.83 |
| 47 | TYR17 | CD1 | −33.026 | 12.713 | −10.005 |
| 48 | TYR17 | CD2 | −32.399 | 13.079 | −7.7 |
| 49 | TYR17 | CE1 | −33.605 | 13.985 | −10.05 |
| 50 | TYR17 | CE2 | −32.976 | 14.348 | −7.743 |
| 51 | TYR17 | CZ | −33.575 | 14.791 | −8.915 |
| 52 | TYR17 | OH | −34.113 | 16.045 | −8.919 |
| 53 | SER18 | N | −29.786 | 11.842 | −11.463 |
| 54 | SER18 | CA | −29.362 | 11.756 | −12.86 |
| 55 | SER18 | C | −28.037 | 10.969 | −12.906 |
| 56 | SER18 | O | −27.418 | 10.622 | −11.898 |
| 57 | SER18 | CB | −29.251 | 13.135 | −13.513 |
| 58 | SER18 | OG | −28.18 | 13.894 | −12.961 |
| 59 | ARG19 | N | −27.608 | 10.612 | −14.178 |
| 60 | ARG19 | CA | −26.407 | 9.799 | −14.302 |
| 61 | ARG19 | C | −25.186 | 10.715 | −14.173 |
| 62 | ARG19 | O | −25.093 | 11.798 | −14.749 |
| 63 | ARG19 | CB | −26.36 | 9.052 | −15.639 |
| 64 | ARG19 | CG | −27.385 | 7.915 | −15.684 |
| 65 | ARG19 | CD | −27.352 | 7.176 | −17.017 |
| 66 | ARG19 | NE | −28.229 | 5.993 | −17.009 |
| 67 | ARG19 | CZ | −29.584 | 6.014 | −17.06 |
| 68 | ARG19 | NH1 | −30.264 | 4.849 | −17.011 |
| 69 | ARG19 | NH2 | −30.28 | 7.164 | −17.165 |
| 70 | ARG20 | N | −24.137 | 10.172 | −13.44 |
| 71 | ARG20 | CA | −23.074 | 11.059 | −12.946 |
| 72 | ARG20 | C | −22.105 | 11.601 | −14.025 |
| 73 | ARG20 | O | −21.196 | 12.384 | −13.749 |
| 74 | ARG20 | CB | −22.298 | 10.391 | −11.796 |
| 75 | ARG20 | CG | −21.451 | 9.183 | −12.222 |
| 76 | ARG20 | CD | −21.741 | 7.92 | −11.41 |
| 77 | ARG20 | NE | −21.225 | 7.976 | −10.034 |
| 78 | ARG20 | CZ | −21.316 | 6.918 | −9.177 |
| 79 | ARG20 | NH1 | −20.707 | 6.953 | −7.974 |
| 80 | ARG20 | NH2 | −22.006 | 5.801 | −9.504 |
| 81 | ALA21 | N | −22.342 | 11.167 | −15.311 |
| 82 | ALA21 | CA | −21.702 | 11.786 | −16.466 |
| 83 | ALA21 | C | −22.401 | 13.094 | −16.884 |
| 84 | ALA21 | O | −21.802 | 13.973 | −17.513 |
| 85 | ALA21 | CB | −21.7 | 10.815 | −17.638 |
| 86 | SER22 | N | −23.748 | 13.189 | −16.596 |
| 87 | SER22 | CA | −24.595 | 14.209 | −17.204 |
| 88 | SER22 | C | −24.187 | 15.655 | −16.886 |
| 89 | SER22 | O | −24.338 | 16.517 | −17.76 |
| 90 | SER22 | CB | −26.076 | 14.009 | −16.861 |
| 91 | SER22 | OG | −26.564 | 12.755 | −17.346 |
| 92 | PRO23 | N | −23.727 | 15.993 | −15.627 |
| 93 | PRO23 | CA | −23.271 | 17.363 | −15.354 |
| 94 | PRO23 | C | −21.806 | 17.591 | −15.778 |
| 95 | PRO23 | O | −21.311 | 18.716 | −15.797 |
| 96 | PRO23 | CB | −23.413 | 17.512 | −13.839 |
| 97 | PRO23 | CG | −23.201 | 16.095 | −13.327 |
| 98 | PRO23 | CD | −23.881 | 15.239 | −14.385 |
| 99 | GLN24 | N | −21.082 | 16.438 | −16.016 |
| 100 | GLN24 | CA | −19.678 | 16.471 | −16.414 |
| 101 | GLN24 | C | −19.544 | 16.633 | −17.939 |
| 102 | GLN24 | O | −18.62 | 17.275 | −18.441 |
| 103 | GLN24 | CB | −18.95 | 15.209 | −15.942 |
| 104 | GLN24 | CG | −18.96 | 15.085 | −14.417 |
| 105 | GLN24 | CD | −18.096 | 13.933 | −13.964 |
| 106 | GLN24 | OE1 | −16.973 | 14.097 | −13.504 |
| 107 | GLN24 | NE2 | −18.651 | 12.698 | −14.155 |
| 108 | GLN25 | N | −20.485 | 15.967 | −18.706 |
| 109 | GLN25 | CA | −20.388 | 15.96 | −20.167 |
| 110 | GLN25 | C | −20.253 | 17.391 | −20.748 |
| 111 | GLN25 | O | −19.364 | 17.623 | −21.581 |
| 112 | GLN25 | CB | −21.577 | 15.23 | −20.803 |
| 113 | GLN25 | CG | −21.36 | 13.719 | −20.86 |
| 114 | GLN25 | CD | −22.653 | 13.001 | −21.172 |
| 115 | GLN25 | OE1 | −23.272 | 12.342 | −20.342 |
| 116 | GLN25 | NE2 | −23.097 | 13.155 | −22.455 |
| 117 | PRO26 | N | −21.115 | 18.387 | −20.32 |
| 118 | PRO26 | CA | −20.991 | 19.766 | −20.799 |
| 119 | PRO26 | C | −19.946 | 20.596 | −20.02 |
| 120 | PRO26 | O | −20.004 | 21.825 | −19.936 |
| 121 | PRO26 | CB | −22.395 | 20.35 | −20.632 |
| 122 | PRO26 | CG | −22.91 | 19.622 | −19.398 |
| 123 | PRO26 | CD | −22.368 | 18.214 | −19.591 |
| 124 | GLN27 | N | −18.849 | 19.895 | −19.569 |
| 125 | GLN27 | CA | −17.613 | 20.528 | −19.115 |
| 126 | GLN27 | C | −16.463 | 19.898 | −19.929 |
| 127 | GLN27 | O | −15.331 | 19.73 | −19.484 |
| 128 | GLN27 | CB | −17.416 | 20.396 | −17.603 |
| 129 | GLN27 | CG | −18.523 | 21.051 | −16.774 |
| 130 | GLN27 | CD | −18.442 | 22.561 | −16.807 |
| 131 | GLN27 | OE1 | −17.735 | 23.205 | −16.038 |
| 132 | GLN27 | NE2 | −19.197 | 23.17 | −17.767 |
| 133 | GLN28 | N | −16.808 | 19.71 | −21.262 |
| 134 | GLN28 | CA | −15.945 | 19.054 | −22.232 |
| 135 | GLN28 | C | −16.691 | 18.924 | −23.579 |
| 136 | GLN28 | O | −16.447 | 19.642 | −24.544 |
| 137 | GLN28 | CB | −14.567 | 19.723 | −22.419 |

TABLE V-continued

| Atom No | Residue | Atom name | x coord | y coord | z coord |
|---|---|---|---|---|---|
| 138 | GLN28 | CG | −14.595 | 21.247 | −22.555 |
| 139 | GLN28 | CD | −13.26 | 21.765 | −23.043 |
| 140 | GLN28 | OE1 | −13.065 | 22.155 | −24.189 |
| 141 | GLN28 | NE2 | −12.242 | 21.746 | −22.12 |
| 142 | ASP29 | N | −17.633 | 17.907 | −23.602 |
| 143 | ASP29 | CA | −18.243 | 17.418 | −24.852 |
| 144 | ASP29 | C | −17.114 | 16.809 | −25.738 |
| 145 | ASP29 | O | −15.94 | 16.761 | −25.373 |
| 146 | ASP29 | CB | −19.095 | 18.476 | −25.541 |
| 147 | ASP29 | CG | −20.157 | 17.743 | −26.352 |
| 148 | ASP29 | OD1 | −21.32 | 17.755 | −25.873 |
| 149 | ASP29 | OD2 | −19.723 | 17.189 | −27.416 |
| 150 | PHE30 | N | −17.515 | 16.262 | −26.934 |
| 151 | PHE30 | CA | −16.585 | 15.682 | −27.911 |
| 152 | PHE30 | C | −17.336 | 15.656 | −29.244 |
| 153 | PHE30 | O | −16.883 | 16.173 | −30.268 |
| 154 | PHE30 | CB | −16.091 | 14.297 | −27.475 |
| 155 | PHE30 | CG | −15.177 | 13.595 | −28.452 |
| 156 | PHE30 | CD1 | −13.793 | 13.795 | −28.41 |
| 157 | PHE30 | CD2 | −15.69 | 12.688 | −29.387 |
| 158 | PHE30 | CE1 | −12.94 | 13.077 | −29.25 |
| 159 | PHE30 | CE2 | −14.838 | 11.962 | −30.221 |
| 160 | PHE30 | CZ | −13.461 | 12.156 | −30.153 |
| 161 | GLU31 | N | −18.571 | 15.047 | −29.206 |
| 162 | GLU31 | CA | −19.371 | 14.861 | −30.403 |
| 163 | GLU31 | C | −19.84 | 16.233 | −30.919 |
| 164 | GLU31 | O | −19.914 | 16.467 | −32.129 |
| 165 | GLU31 | CB | −20.581 | 13.945 | −30.146 |
| 166 | GLU31 | CG | −20.204 | 12.473 | −29.906 |
| 167 | GLU31 | CD | −19.422 | 12.179 | −28.631 |
| 168 | GLU31 | OE1 | −18.905 | 11.018 | −28.535 |
| 169 | GLU31 | OE2 | −19.275 | 13.143 | −27.826 |
| 170 | ALA32 | N | −20.23 | 17.156 | −29.959 |
| 171 | ALA32 | CA | −20.695 | 18.481 | −30.361 |
| 172 | ALA32 | C | −19.529 | 19.381 | −30.805 |
| 173 | ALA32 | O | −19.719 | 20.395 | −31.476 |
| 174 | ALA32 | CB | −21.475 | 19.175 | −29.256 |
| 175 | LEU33 | N | −18.285 | 19.002 | −30.336 |
| 176 | LEU33 | CA | −17.064 | 19.644 | −30.808 |
| 177 | LEU33 | C | −16.734 | 19.113 | −32.211 |
| 178 | LEU33 | O | −16.436 | 19.883 | −33.13 |
| 179 | LEU33 | CB | −15.891 | 19.427 | −29.85 |
| 180 | LEU33 | CG | −16.068 | 20.121 | −28.484 |
| 181 | LEU33 | CD1 | −14.97 | 19.656 | −27.528 |
| 182 | LEU33 | CD2 | −16.034 | 21.645 | −28.603 |
| 183 | LEU34 | N | −16.806 | 17.743 | −32.408 |
| 184 | LEU34 | CA | −16.484 | 17.2 | −33.728 |
| 185 | LEU34 | C | −17.468 | 17.783 | −34.767 |
| 186 | LEU34 | O | −17.124 | 18.027 | −35.925 |
| 187 | LEU34 | CB | −16.582 | 15.672 | −33.798 |
| 188 | LEU34 | CG | −15.405 | 14.894 | −33.178 |
| 189 | LEU34 | CD1 | −15.661 | 13.393 | −33.352 |
| 190 | LEU34 | CD2 | −14.056 | 15.246 | −33.805 |
| 191 | ALA35 | N | −18.765 | 17.953 | −34.31 |
| 192 | ALA35 | CA | −19.818 | 18.481 | −35.163 |
| 193 | ALA35 | C | −19.724 | 20.006 | −35.38 |
| 194 | ALA35 | O | −20.487 | 20.59 | −36.158 |
| 195 | ALA35 | CB | −21.195 | 18.145 | −34.609 |
| 196 | GLU36 | N | −18.78 | 20.682 | −34.645 |
| 197 | GLU36 | CA | −18.303 | 22.015 | −35.021 |
| 198 | GLU36 | C | −17.186 | 21.785 | −36.053 |
| 199 | GLU36 | O | −17.234 | 22.262 | −37.192 |
| 200 | GLU36 | CB | −17.861 | 22.801 | −33.778 |
| 201 | GLU36 | CG | −17.443 | 24.24 | −34.073 |
| 202 | GLU36 | CD | −16.03 | 24.44 | −34.627 |
| 203 | GLU36 | OE1 | −15.172 | 23.573 | −34.311 |
| 204 | GLU36 | OE2 | −15.902 | 25.463 | −35.368 |
| 205 | CYS37 | N | −16.146 | 20.978 | −35.621 |
| 206 | CYS37 | CA | −14.854 | 21.039 | −36.301 |
| 207 | CYS37 | C | −14.982 | 20.521 | −37.736 |
| 208 | CYS37 | O | −14.408 | 21.084 | −38.67 |
| 209 | CYS37 | CB | −13.796 | 20.222 | −35.56 |
| 210 | CYS37 | SG | −13.318 | 20.986 | −33.971 |
| 211 | LEU38 | N | −15.724 | 19.365 | −37.893 |
| 212 | LEU38 | CA | −15.839 | 18.71 | −39.193 |
| 213 | LEU38 | C | −16.86 | 19.396 | −40.122 |
| 214 | LEU38 | O | −16.939 | 19.086 | −41.311 |
| 215 | LEU38 | CB | −16.189 | 17.219 | −39.063 |
| 216 | LEU38 | CG | −14.967 | 16.304 | −38.849 |
| 217 | LEU38 | CD1 | −14.173 | 16.629 | −37.586 |
| 218 | LEU38 | CD2 | −15.421 | 14.844 | −38.807 |
| 219 | ARG39 | N | −17.699 | 20.323 | −39.529 |
| 220 | ARG39 | CA | −18.489 | 21.215 | −40.371 |
| 221 | ARG39 | C | −17.655 | 22.435 | −40.786 |
| 222 | ARG39 | O | −17.723 | 22.893 | −41.927 |
| 223 | ARG39 | CB | −19.765 | 21.696 | −39.67 |
| 224 | ARG39 | CG | −20.879 | 20.645 | −39.722 |
| 225 | ARG39 | CD | −22.192 | 21.193 | −39.164 |
| 226 | ARG39 | NE | −22.073 | 21.461 | −37.731 |
| 227 | ARG39 | CZ | −22.814 | 22.311 | −37 |
| 228 | ARG39 | NH1 | −22.502 | 22.479 | −35.699 |
| 229 | ARG39 | NH2 | −23.855 | 22.991 | −37.519 |
| 230 | ASN40 | N | −16.956 | 23.056 | −39.765 |
| 231 | ASN40 | CA | −16.365 | 24.376 | −39.99 |
| 232 | ASN40 | C | −15.001 | 24.28 | −40.69 |
| 233 | ASN40 | O | −14.541 | 25.23 | −41.324 |
| 234 | ASN40 | CB | −16.187 | 25.141 | −38.682 |
| 235 | ASN40 | CG | −17.481 | 25.764 | −38.204 |
| 236 | ASN40 | OD1 | −18.559 | 25.676 | −38.782 |
| 237 | ASN40 | ND2 | −17.346 | 26.478 | −37.045 |
| 238 | GLY41 | N | −14.267 | 23.143 | −40.414 |
| 239 | GLY41 | CA | −12.89 | 23.005 | −40.854 |
| 240 | GLY41 | C | −11.898 | 23.611 | −39.86 |
| 241 | GLY41 | O | −10.739 | 23.874 | −40.176 |
| 242 | CYS42 | N | −12.38 | 23.728 | −38.571 |
| 243 | CYS42 | CA | −11.519 | 24.131 | −37.462 |
| 244 | CYS42 | C | −10.8 | 22.878 | −36.938 |
| 245 | CYS42 | O | −11.253 | 21.744 | −37.079 |
| 246 | CYS42 | CB | −12.322 | 24.733 | −36.301 |
| 247 | CYS42 | SG | −13.088 | 26.325 | −36.732 |
| 248 | LEU43 | N | −9.636 | 23.151 | −36.236 |
| 249 | LEU43 | CA | −9.096 | 22.166 | −35.302 |
| 250 | LEU43 | C | −9.601 | 22.594 | −33.916 |
| 251 | LEU43 | O | −9.9 | 23.761 | −33.659 |
| 252 | LEU43 | CB | −7.562 | 22.161 | −35.29 |
| 253 | LEU43 | CG | −6.909 | 21.736 | −36.619 |
| 254 | LEU43 | CD1 | −5.39 | 21.902 | −36.521 |
| 255 | LEU43 | CD2 | −7.243 | 20.293 | −36.997 |
| 256 | PHE44 | N | −9.616 | 21.585 | −32.979 |
| 257 | PHE44 | CA | −10.012 | 21.847 | −31.602 |
| 258 | PHE44 | C | −8.796 | 22.437 | −30.875 |
| 259 | PHE44 | O | −7.718 | 21.842 | −30.797 |
| 260 | PHE44 | CB | −10.433 | 20.557 | −30.896 |
| 261 | PHE44 | CG | −10.682 | 20.72 | −29.416 |
| 262 | PHE44 | CD1 | −11.728 | 21.521 | −28.942 |
| 263 | PHE44 | CD2 | −9.854 | 20.066 | −28.491 |
| 264 | PHE44 | CE1 | −11.942 | 21.656 | −27.57 |
| 265 | PHE44 | CE2 | −10.09 | 20.179 | −27.123 |
| 266 | PHE44 | CZ | −11.134 | 20.973 | −26.663 |
| 267 | GLU45 | N | −9.013 | 23.684 | −30.325 |
| 268 | GLU45 | CA | −8.117 | 24.256 | −29.33 |
| 269 | GLU45 | C | −8.867 | 24.183 | −27.994 |
| 270 | GLU45 | O | −10.022 | 24.587 | −27.87 |
| 271 | GLU45 | CB | −7.785 | 25.72 | −29.653 |
| 272 | GLU45 | CG | −6.759 | 25.864 | −30.78 |
| 273 | GLU45 | CD | −5.434 | 25.234 | −30.385 |
| 274 | GLU45 | OE1 | −4.99 | 25.529 | −29.227 |
| 275 | GLU45 | OE2 | −4.95 | 24.381 | −31.195 |
| 276 | ASP46 | N | −8.134 | 23.636 | −26.957 |
| 277 | ASP46 | CA | −8.68 | 23.586 | −25.607 |
| 278 | ASP46 | C | −8.389 | 24.957 | −24.968 |
| 279 | ASP46 | O | −7.252 | 25.424 | −24.869 |
| 280 | ASP46 | CB | −8.053 | 22.452 | −24.808 |
| 281 | ASP46 | CG | −8.813 | 22.241 | −23.517 |
| 282 | ASP46 | OD1 | −8.966 | 23.266 | −22.785 |
| 283 | ASP46 | OD2 | −9.206 | 21.058 | −23.267 |
| 284 | THR47 | N | −9.545 | 25.589 | −24.549 |
| 285 | THR47 | CA | −9.557 | 26.883 | −23.87 |
| 286 | THR47 | C | −9.369 | 26.703 | −22.354 |
| 287 | THR47 | O | −9.032 | 27.646 | −21.638 |
| 288 | THR47 | CB | −10.923 | 27.57 | −24.096 |
| 289 | THR47 | OG1 | −11.445 | 27.165 | −25.369 |
| 290 | THR47 | CG2 | −10.813 | 29.09 | −24.071 |
| 291 | SER48 | N | −9.771 | 25.476 | −21.842 |

TABLE V-continued

| Atom No | Residue | Atom name | x coord | y coord | z coord |
|---|---|---|---|---|---|
| 292 | SER48 | CA | −9.616 | 25.195 | −20.406 |
| 293 | SER48 | C | −8.158 | 24.878 | −20.053 |
| 294 | SER48 | O | −7.708 | 25.08 | −18.927 |
| 295 | SER48 | CB | −10.481 | 23.997 | −20.005 |
| 296 | SER48 | OG | −11.808 | 24.115 | −20.522 |
| 297 | PHE49 | N | −7.444 | 24.246 | −21.05 |
| 298 | PHE49 | CA | −6.033 | 23.891 | −20.932 |
| 299 | PHE49 | C | −5.262 | 24.642 | −22.045 |
| 300 | PHE49 | O | −4.968 | 24.108 | −23.124 |
| 301 | PHE49 | CB | −5.884 | 22.358 | −21.029 |
| 302 | PHE49 | CG | −4.649 | 21.869 | −20.32 |
| 303 | PHE49 | CD1 | −4.611 | 21.823 | −18.919 |
| 304 | PHE49 | CD2 | −3.528 | 21.454 | −21.044 |
| 305 | PHE49 | CE1 | −3.482 | 21.342 | −18.255 |
| 306 | PHE49 | CE2 | −2.404 | 20.966 | −20.375 |
| 307 | PHE49 | CZ | −2.382 | 20.901 | −18.983 |
| 308 | PRO50 | N | −4.967 | 25.977 | −21.797 |
| 309 | PRO50 | CA | −4.379 | 26.826 | −22.826 |
| 310 | PRO50 | C | −2.846 | 26.69 | −22.873 |
| 311 | PRO50 | O | −2.174 | 26.135 | −22.003 |
| 312 | PRO50 | CB | −4.778 | 28.243 | −22.411 |
| 313 | PRO50 | CG | −4.787 | 28.153 | −20.889 |
| 314 | PRO50 | CD | −5.383 | 26.774 | −20.646 |
| 315 | ALA51 | N | −2.291 | 27.32 | −23.972 |
| 316 | ALA51 | CA | −0.862 | 27.308 | −24.27 |
| 317 | ALA51 | C | −0.137 | 28.512 | −23.632 |
| 318 | ALA51 | O | 0.623 | 29.243 | −24.266 |
| 319 | ALA51 | CB | −0.667 | 27.281 | −25.782 |
| 320 | THR52 | N | −0.343 | 28.652 | −22.272 |
| 321 | THR52 | CA | 0.396 | 29.632 | −21.46 |
| 322 | THR52 | C | 1.448 | 28.845 | −20.633 |
| 323 | THR52 | O | 1.924 | 27.777 | −21.027 |
| 324 | THR52 | CB | −0.56 | 30.482 | −20.595 |
| 325 | THR52 | OG1 | −1.056 | 29.691 | −19.513 |
| 326 | THR52 | CG2 | −1.734 | 31.065 | −21.37 |
| 327 | LEU53 | N | 1.866 | 29.437 | −19.452 |
| 328 | LEU53 | CA | 2.574 | 28.681 | −18.418 |
| 329 | LEU53 | C | 1.6 | 28.189 | −17.317 |
| 330 | LEU53 | O | 1.975 | 27.466 | −16.389 |
| 331 | LEU53 | CB | 3.658 | 29.545 | −17.754 |
| 332 | LEU53 | CG | 4.727 | 30.104 | −18.714 |
| 333 | LEU53 | CD1 | 5.702 | 30.996 | −17.939 |
| 334 | LEU53 | CD2 | 5.501 | 29 | −19.432 |
| 335 | SER54 | N | 0.291 | 28.613 | −17.427 |
| 336 | SER54 | CA | −0.681 | 28.479 | −16.33 |
| 337 | SER54 | C | −1.097 | 27.015 | −16.162 |
| 338 | SER54 | O | −1.541 | 26.751 | −15.109 |
| 339 | SER54 | CB | −1.966 | 29.285 | −16.585 |
| 340 | SER54 | OG | −1.692 | 30.559 | −17.187 |
| 341 | SER55 | N | −1.042 | 26.303 | −17.334 |
| 342 | SER55 | CA | −1.355 | 24.887 | −17.495 |
| 343 | SER55 | C | −0.139 | 24.005 | −17.146 |
| 344 | SER55 | O | −0.226 | 22.783 | −17.014 |
| 345 | SER55 | CB | −1.784 | 24.668 | −18.951 |
| 346 | SER55 | OG | −1.052 | 25.563 | −19.803 |
| 347 | ILE56 | N | 1.066 | 24.675 | −17.053 |
| 348 | ILE56 | CA | 2.278 | 24.001 | −16.601 |
| 349 | ILE56 | C | 2.33 | 24.124 | −15.072 |
| 350 | ILE56 | O | 2.39 | 23.12 | −14.359 |
| 351 | ILE56 | CB | 3.557 | 24.544 | −17.287 |
| 352 | ILE56 | CG1 | 3.357 | 24.643 | −18.815 |
| 353 | ILE56 | CG2 | 4.77 | 23.668 | −16.944 |
| 354 | ILE56 | CD1 | 4.592 | 25.09 | −19.577 |
| 355 | GLY57 | N | 2.367 | 25.424 | −14.596 |
| 356 | GLY57 | CA | 2.7 | 25.698 | −13.211 |
| 357 | GLY57 | C | 4.2 | 25.489 | −12.997 |
| 358 | GLY57 | O | 4.879 | 24.744 | −13.702 |
| 359 | SER58 | N | 4.733 | 26.171 | −11.92 |
| 360 | SER58 | CA | 6.169 | 26.079 | −11.675 |
| 361 | SER58 | C | 6.538 | 26.776 | −10.355 |
| 362 | SER58 | O | 6.339 | 27.974 | −10.161 |
| 363 | SER58 | CB | 6.996 | 26.674 | −12.826 |
| 364 | SER58 | OG | 6.453 | 27.908 | −13.297 |
| 365 | GLY59 | N | 7.11 | 25.938 | −9.41 |
| 366 | GLY59 | CA | 7.488 | 26.438 | −8.1 |
| 367 | GLY59 | C | 8.997 | 26.684 | −7.979 |
| 368 | GLY59 | O | 9.805 | 25.782 | −7.739 |
| 369 | SER60 | N | 9.412 | 27.977 | −8.223 |
| 370 | SER60 | CA | 10.761 | 28.487 | −7.965 |
| 371 | SER60 | C | 11.834 | 27.742 | −8.76 |
| 372 | SER60 | O | 12.293 | 28.182 | −9.813 |
| 373 | SER60 | CB | 11.133 | 28.6 | −6.484 |
| 374 | SER60 | OG | 12.351 | 29.365 | −6.324 |
| 375 | LEU61 | N | 12.211 | 26.514 | −8.255 |
| 376 | LEU61 | CA | 13.268 | 25.74 | −8.903 |
| 377 | LEU61 | C | 12.877 | 25.429 | −10.352 |
| 378 | LEU61 | O | 13.704 | 25.396 | −11.26 |
| 379 | LEU61 | CB | 13.547 | 24.434 | −8.149 |
| 380 | LEU61 | CG | 14.084 | 24.624 | −6.716 |
| 381 | LEU61 | CD1 | 14.196 | 23.264 | −6.022 |
| 382 | LEU61 | CD2 | 15.443 | 25.326 | −6.691 |
| 383 | LEU62 | N | 11.543 | 25.141 | −10.533 |
| 384 | LEU62 | CA | 11.016 | 24.696 | −11.813 |
| 385 | LEU62 | C | 10.583 | 25.875 | −12.708 |
| 386 | LEU62 | O | 10.123 | 25.694 | −13.835 |
| 387 | LEU62 | CB | 9.873 | 23.701 | −11.583 |
| 388 | LEU62 | CG | 10.292 | 22.481 | −10.728 |
| 389 | LEU62 | CD1 | 9.07 | 21.645 | −10.371 |
| 390 | LEU62 | CD2 | 11.333 | 21.609 | −11.429 |
| 391 | GLN63 | N | 10.796 | 27.141 | −12.19 |
| 392 | GLN63 | CA | 10.621 | 28.352 | −12.999 |
| 393 | GLN63 | C | 11.905 | 28.667 | −13.786 |
| 394 | GLN63 | O | 11.905 | 29.443 | −14.74 |
| 395 | GLN63 | CB | 10.28 | 29.576 | −12.132 |
| 396 | GLN63 | CG | 8.901 | 29.468 | −11.493 |
| 397 | GLN63 | CD | 8.643 | 30.538 | −10.459 |
| 398 | GLN63 | OE1 | 8.52 | 30.29 | −9.262 |
| 399 | GLN63 | NE2 | 8.574 | 31.811 | −10.947 |
| 400 | LYS64 | N | 13.058 | 28.134 | −13.247 |
| 401 | LYS64 | CA | 14.394 | 28.557 | −13.668 |
| 402 | LYS64 | C | 14.973 | 27.615 | −14.741 |
| 403 | LYS64 | O | 15.964 | 27.927 | −15.399 |
| 404 | LYS64 | CB | 15.316 | 28.621 | −12.437 |
| 405 | LYS64 | CG | 14.863 | 29.702 | −11.435 |
| 406 | LYS64 | CD | 15.239 | 29.355 | −9.991 |
| 407 | LYS64 | CE | 14.471 | 30.217 | −8.988 |
| 408 | LYS64 | NZ | 14.487 | 29.568 | −7.652 |
| 409 | LEU65 | N | 14.366 | 26.377 | −14.827 |
| 410 | LEU65 | CA | 14.828 | 25.348 | −15.748 |
| 411 | LEU65 | C | 14.299 | 25.454 | −17.198 |
| 412 | LEU65 | O | 15.052 | 25.083 | −18.109 |
| 413 | LEU65 | CB | 14.562 | 23.925 | −15.22 |
| 414 | LEU65 | CG | 15.32 | 23.551 | −13.931 |
| 415 | LEU65 | CD1 | 14.885 | 22.157 | −13.472 |
| 416 | LEU65 | CD2 | 16.838 | 23.581 | −14.107 |
| 417 | PRO66 | N | 12.985 | 25.815 | −17.464 |
| 418 | PRO66 | CA | 12.437 | 25.65 | −18.822 |
| 419 | PRO66 | C | 12.087 | 26.965 | −19.575 |
| 420 | PRO66 | O | 10.97 | 27.132 | −20.083 |
| 421 | PRO66 | CB | 11.167 | 24.841 | −18.536 |
| 422 | PRO66 | CG | 10.629 | 25.517 | −17.279 |
| 423 | PRO66 | CD | 11.893 | 25.854 | −16.493 |
| 424 | PRO67 | N | 13.064 | 27.918 | −19.775 |
| 425 | PRO67 | CA | 12.782 | 29.095 | −20.588 |
| 426 | PRO67 | C | 12.822 | 28.72 | −22.081 |
| 427 | PRO67 | O | 13.391 | 27.717 | −22.509 |
| 428 | PRO67 | CB | 13.909 | 30.063 | −20.243 |
| 429 | PRO67 | CG | 15.085 | 29.13 | −19.974 |
| 430 | PRO67 | CD | 14.441 | 27.918 | −19.309 |
| 431 | ARG68 | N | 12.179 | 29.621 | −22.908 |
| 432 | ARG68 | CA | 12.145 | 29.51 | −24.371 |
| 433 | ARG68 | C | 11.217 | 28.398 | −24.898 |
| 434 | ARG68 | O | 11.203 | 28.074 | −26.089 |
| 435 | ARG68 | CB | 13.525 | 29.367 | −25.038 |
| 436 | ARG68 | CG | 14.512 | 30.474 | −24.677 |
| 437 | ARG68 | CD | 15.852 | 30.291 | −25.393 |
| 438 | ARG68 | NE | 16.958 | 30.148 | −24.436 |
| 439 | ARG68 | CZ | 17.252 | 29.02 | −23.743 |
| 440 | ARG68 | NH1 | 18.155 | 29.105 | −22.735 |
| 441 | ARG68 | NH2 | 16.701 | 27.826 | −23.987 |
| 442 | LEU69 | N | 10.338 | 27.861 | −23.97 |
| 443 | LEU69 | CA | 9.584 | 26.677 | −24.351 |
| 444 | LEU69 | C | 8.561 | 27.022 | −25.444 |
| 445 | LEU69 | O | 8.092 | 28.147 | −25.609 |

TABLE V-continued

| Atom No | Residue | Atom name | x coord | y coord | z coord |
|---|---|---|---|---|---|
| 446 | LEU69 | CB | 8.961 | 25.93 | −23.163 |
| 447 | LEU69 | CG | 8.04 | 26.719 | −22.211 |
| 448 | LEU69 | CD1 | 6.717 | 27.144 | −22.848 |
| 449 | LEU69 | CD2 | 7.734 | 25.845 | −20.99 |
| 450 | GLN70 | N | 8.218 | 25.944 | −26.234 |
| 451 | GLN70 | CA | 7.169 | 26.042 | −27.225 |
| 452 | GLN70 | C | 6.106 | 25.004 | −26.851 |
| 453 | GLN70 | O | 6.376 | 23.939 | −26.294 |
| 454 | GLN70 | CB | 7.673 | 25.793 | −28.652 |
| 455 | GLN70 | CG | 8.902 | 26.625 | −29.028 |
| 456 | GLN70 | CD | 10.18 | 25.816 | −28.919 |
| 457 | GLN70 | OE1 | 10.366 | 24.784 | −29.564 |
| 458 | GLN70 | NE2 | 11.135 | 26.334 | −28.095 |
| 459 | TRP71 | N | 4.834 | 25.353 | −27.245 |
| 460 | TRP71 | CA | 3.735 | 24.391 | −27.223 |
| 461 | TRP71 | C | 3.541 | 24.022 | −28.697 |
| 462 | TRP71 | O | 3.381 | 24.894 | −29.553 |
| 463 | TRP71 | CB | 2.456 | 25.02 | −26.68 |
| 464 | TRP71 | CG | 2.454 | 25.224 | −25.191 |
| 465 | TRP71 | CD1 | 2.869 | 26.355 | −24.508 |
| 466 | TRP71 | CD2 | 1.907 | 24.336 | −24.212 |
| 467 | TRP71 | NE1 | 2.537 | 26.21 | −23.186 |
| 468 | TRP71 | CE2 | 1.903 | 25.006 | −22.992 |
| 469 | TRP71 | CE3 | 1.334 | 23.052 | −24.262 |
| 470 | TRP71 | CZ2 | 1.291 | 24.491 | −21.846 |
| 471 | TRP71 | CZ3 | 0.686 | 22.535 | −23.136 |
| 472 | TRP71 | CH2 | 0.656 | 23.252 | −21.947 |
| 473 | LYS72 | N | 3.624 | 22.679 | −28.983 |
| 474 | LYS72 | CA | 3.494 | 22.16 | −30.348 |
| 475 | LYS72 | C | 2.42 | 21.068 | −30.347 |
| 476 | LYS72 | O | 2.092 | 20.469 | −29.321 |
| 477 | LYS72 | CB | 4.83 | 21.592 | −30.849 |
| 478 | LYS72 | CG | 5.858 | 22.692 | −31.13 |
| 479 | LYS72 | CD | 7.126 | 22.114 | −31.759 |
| 480 | LYS72 | CE | 8.191 | 23.186 | −31.926 |
| 481 | LYS72 | NZ | 9.428 | 22.568 | −32.457 |
| 482 | ARG73 | N | 1.871 | 20.801 | −31.584 |
| 483 | ARG73 | CA | 1.094 | 19.583 | −31.812 |
| 484 | ARG73 | C | 2.115 | 18.449 | −32.15 |
| 485 | ARG73 | O | 3.335 | 18.648 | −32.191 |
| 486 | ARG73 | CB | 0.057 | 19.819 | −32.924 |
| 487 | ARG73 | CG | −1 | 20.889 | −32.607 |
| 488 | ARG73 | CD | −2.153 | 20.364 | −31.751 |
| 489 | ARG73 | NE | −3.204 | 21.384 | −31.608 |
| 490 | ARG73 | CZ | −4.491 | 21.125 | −31.262 |
| 491 | ARG73 | NH1 | −4.929 | 19.909 | −30.901 |
| 492 | ARG73 | NH2 | −5.372 | 22.129 | −31.273 |
| 493 | PRO74 | N | 1.613 | 17.176 | −32.386 |
| 494 | PRO74 | CA | 2.532 | 16.075 | −32.691 |
| 495 | PRO74 | C | 3.204 | 16.037 | −34.08 |
| 496 | PRO74 | O | 4.339 | 15.537 | −34.178 |
| 497 | PRO74 | CB | 1.692 | 14.815 | −32.46 |
| 498 | PRO74 | CG | 0.722 | 15.264 | −31.377 |
| 499 | PRO74 | CD | 0.364 | 16.664 | −31.838 |
| 500 | PRO75 | N | 2.518 | 16.432 | −35.214 |
| 501 | PRO75 | CA | 3.119 | 16.245 | −36.536 |
| 502 | PRO75 | C | 4.309 | 17.176 | −36.837 |
| 503 | PRO75 | O | 5.012 | 17.021 | −37.836 |
| 504 | PRO75 | CB | 1.974 | 16.435 | −37.528 |
| 505 | PRO75 | CG | 1.003 | 17.338 | −36.786 |
| 506 | PRO75 | CD | 1.147 | 16.902 | −35.335 |
| 507 | GLU76 | N | 4.55 | 18.16 | −35.895 |
| 508 | GLU76 | CA | 5.745 | 18.993 | −35.974 |
| 509 | GLU76 | C | 6.967 | 18.157 | −35.531 |
| 510 | GLU76 | O | 8.116 | 18.48 | −35.833 |
| 511 | GLU76 | CB | 5.704 | 20.206 | −35.021 |
| 512 | GLU76 | CG | 4.624 | 21.241 | −35.323 |
| 513 | GLU76 | CD | 3.326 | 20.806 | −34.659 |
| 514 | GLU76 | OE1 | 2.924 | 21.524 | −33.694 |
| 515 | GLU76 | OE2 | 2.825 | 19.744 | −35.135 |
| 516 | LEU77 | N | 6.674 | 17.174 | −34.601 |
| 517 | LEU77 | CA | 7.698 | 16.407 | −33.913 |
| 518 | LEU77 | C | 7.993 | 15.098 | −34.656 |
| 519 | LEU77 | O | 9.151 | 14.751 | −34.894 |
| 520 | LEU77 | CB | 7.281 | 16.104 | −32.465 |
| 521 | LEU77 | CG | 7.016 | 17.359 | −31.608 |
| 522 | LEU77 | CD1 | 6.472 | 16.945 | −30.239 |
| 523 | LEU77 | CD2 | 8.274 | 18.211 | −31.436 |
| 524 | HIS78 | N | 6.902 | 14.283 | −34.897 |
| 525 | HIS78 | CA | 7.056 | 12.996 | −35.577 |
| 526 | HIS78 | C | 6.321 | 13.054 | −36.919 |
| 527 | HIS78 | O | 5.266 | 13.665 | −37.072 |
| 528 | HIS78 | CB | 6.494 | 11.831 | −34.748 |
| 529 | HIS78 | CG | 7.297 | 11.485 | −33.533 |
| 530 | HIS78 | ND1 | 6.849 | 10.582 | −32.599 |
| 531 | HIS78 | CD2 | 8.531 | 11.874 | −33.051 |
| 532 | HIS78 | CE1 | 7.78 | 10.503 | −31.605 |
| 533 | HIS78 | NE2 | 8.817 | 11.265 | −31.855 |
| 534 | SER79 | N | 6.896 | 12.292 | −37.918 |
| 535 | SER79 | CA | 6.39 | 12.314 | −39.296 |
| 536 | SER79 | C | 5.22 | 11.341 | −39.492 |
| 537 | SER79 | O | 4.445 | 11.438 | −40.442 |
| 538 | SER79 | CB | 7.51 | 11.959 | −40.277 |
| 539 | SER79 | OG | 8.239 | 10.828 | −39.793 |
| 540 | ASN80 | N | 5.183 | 10.301 | −38.59 |
| 541 | ASN80 | CA | 4.117 | 9.304 | −38.557 |
| 542 | ASN80 | C | 3.642 | 9.227 | −37.097 |
| 543 | ASN80 | O | 4.05 | 8.344 | −36.336 |
| 544 | ASN80 | CB | 4.652 | 7.957 | −39.044 |
| 545 | ASN80 | CG | 3.555 | 6.92 | −39.15 |
| 546 | ASN80 | OD1 | 2.364 | 7.137 | −38.952 |
| 547 | ASN80 | ND2 | 4.004 | 5.678 | −39.506 |
| 548 | PRO81 | N | 2.793 | 10.222 | −36.654 |
| 549 | PRO81 | CA | 2.231 | 10.173 | −35.311 |
| 550 | PRO81 | C | 1.077 | 9.157 | −35.31 |
| 551 | PRO81 | O | 0.264 | 9.064 | −36.229 |
| 552 | PRO81 | CB | 1.737 | 11.592 | −35.063 |
| 553 | PRO81 | CG | 1.329 | 12.074 | −36.452 |
| 554 | PRO81 | CD | 2.346 | 11.41 | −37.374 |
| 555 | GLN82 | N | 1.042 | 8.343 | −34.196 |
| 556 | GLN82 | CA | 0.079 | 7.257 | −34.071 |
| 557 | GLN82 | C | −0.393 | 7.201 | −32.612 |
| 558 | GLN82 | O | 0.262 | 7.684 | −31.692 |
| 559 | GLN82 | CB | 0.687 | 5.91 | −34.478 |
| 560 | GLN82 | CG | 1.026 | 5.81 | −35.967 |
| 561 | GLN82 | CD | −0.208 | 5.864 | −36.841 |
| 562 | GLN82 | OE1 | −1.346 | 5.673 | −36.422 |
| 563 | GLN82 | NE2 | 0.056 | 6.091 | −38.163 |
| 564 | PHE83 | N | −1.617 | 6.574 | −32.457 |
| 565 | PHE83 | CA | −2.289 | 6.467 | −31.154 |
| 566 | PHE83 | C | −2.105 | 5.038 | −30.619 |
| 567 | PHE83 | O | −1.725 | 4.817 | −29.472 |
| 568 | PHE83 | CB | −3.772 | 6.838 | −31.314 |
| 569 | PHE83 | CG | −4.503 | 7.095 | −30.019 |
| 570 | PHE83 | CD1 | −4.162 | 8.191 | −29.213 |
| 571 | PHE83 | CD2 | −5.58 | 6.284 | −29.64 |
| 572 | PHE83 | CE1 | −4.89 | 8.472 | −28.055 |
| 573 | PHE83 | CE2 | −6.306 | 6.572 | −28.483 |
| 574 | PHE83 | CZ | −5.965 | 7.666 | −27.693 |
| 575 | TYR84 | N | −2.472 | 4.037 | −31.493 |
| 576 | TYR84 | CA | −2.292 | 2.612 | −31.215 |
| 577 | TYR84 | C | −2.348 | 1.943 | −32.592 |
| 578 | TYR84 | O | −3.064 | 2.387 | −33.49 |
| 579 | TYR84 | CB | −3.419 | 2.024 | −30.349 |
| 580 | TYR84 | CG | −3.01 | 1.729 | −28.926 |
| 581 | TYR84 | CD1 | −3.451 | 2.547 | −27.877 |
| 582 | TYR84 | CD2 | −2.2 | 0.621 | −28.633 |
| 583 | TYR84 | CE1 | −3.109 | 2.253 | −26.556 |
| 584 | TYR84 | CE2 | −1.846 | 0.336 | −27.314 |
| 585 | TYR84 | CZ | −2.305 | 1.151 | −26.286 |
| 586 | TYR84 | OH | −1.942 | 0.839 | −25.008 |
| 587 | PHE85 | N | −1.583 | 0.803 | −32.722 |
| 588 | PHE85 | CA | −1.557 | 0.054 | −33.976 |
| 589 | PHE85 | C | −1.018 | −1.353 | −33.675 |
| 590 | PHE85 | O | 0.157 | −1.675 | −33.809 |
| 591 | PHE85 | CB | −0.869 | 0.752 | −35.162 |
| 592 | PHE85 | CG | 0.567 | 1.2 | −35.04 |
| 593 | PHE85 | CD1 | 1.526 | 0.717 | −35.943 |
| 594 | PHE85 | CD2 | 0.952 | 2.184 | −34.122 |
| 595 | PHE85 | CE1 | 2.828 | 1.22 | −35.939 |
| 596 | PHE85 | CE2 | 2.257 | 2.675 | −34.109 |
| 597 | PHE85 | CZ | 3.192 | 2.205 | −35.026 |
| 598 | ALA86 | N | −2.007 | −2.183 | −33.163 |
| 599 | ALA86 | CA | −1.777 | −3.512 | −32.605 |

TABLE V-continued

| Atom No | Residue | Atom name | x coord | y coord | z coord |
|---|---|---|---|---|---|
| 600 | ALA86 | C | −1.378 | −3.41 | −31.12 |
| 601 | ALA86 | O | −1.093 | −2.352 | −30.564 |
| 602 | ALA86 | CB | −0.813 | −4.383 | −33.405 |
| 603 | LYS87 | N | −1.392 | −4.628 | −30.458 |
| 604 | LYS87 | CA | −1.132 | −4.726 | −29.017 |
| 605 | LYS87 | C | 0.379 | −4.824 | −28.732 |
| 606 | LYS87 | O | 0.853 | −4.568 | −27.626 |
| 607 | LYS87 | CB | −1.863 | −5.937 | −28.42 |
| 608 | LYS87 | CG | −3.355 | −5.643 | −28.213 |
| 609 | LYS87 | CD | −4.1 | −6.829 | −27.594 |
| 610 | LYS87 | CE | −5.384 | −6.375 | −26.912 |
| 611 | LYS87 | NZ | −6.065 | −7.531 | −26.331 |
| 612 | ALA88 | N | 1.123 | −5.333 | −29.781 |
| 613 | ALA88 | CA | 2.584 | −5.318 | −29.775 |
| 614 | ALA88 | C | 3.128 | −6.294 | −28.7 |
| 615 | ALA88 | O | 2.602 | −7.389 | −28.494 |
| 616 | ALA88 | CB | 3.115 | −3.89 | −29.745 |
| 617 | LYS89 | N | 4.291 | −5.911 | −28.057 |
| 618 | LYS89 | CA | 4.945 | −6.782 | −27.079 |
| 619 | LYS89 | C | 5.754 | −5.89 | −26.126 |
| 620 | LYS89 | O | 5.385 | −5.663 | −24.971 |
| 621 | LYS89 | CB | 5.825 | −7.83 | −27.788 |
| 622 | LYS89 | CG | 6.606 | −8.738 | −26.825 |
| 623 | LYS89 | CD | 7.485 | −9.72 | −27.607 |
| 624 | LYS89 | CE | 8.029 | −10.844 | −26.742 |
| 625 | LYS89 | NZ | 9.338 | −10.527 | −26.142 |
| 626 | ARG90 | N | 6.881 | −5.351 | −26.721 |
| 627 | ARG90 | CA | 7.917 | −4.637 | −25.989 |
| 628 | ARG90 | C | 7.456 | −3.225 | −25.613 |
| 629 | ARG90 | O | 6.494 | −2.665 | −26.128 |
| 630 | ARG90 | CB | 9.216 | −4.573 | −26.818 |
| 631 | ARG90 | CG | 10.046 | −5.857 | −26.712 |
| 632 | ARG90 | CD | 10.86 | −5.887 | −25.426 |
| 633 | ARG90 | NE | 11.405 | −7.218 | −25.152 |
| 634 | ARG90 | CZ | 12.701 | −7.569 | −25.276 |
| 635 | ARG90 | NH1 | 13.526 | −6.914 | −26.122 |
| 636 | ARG90 | NH2 | 13.203 | −8.576 | −24.542 |
| 637 | LEU91 | N | 8.235 | −2.676 | −24.617 |
| 638 | LEU91 | CA | 7.904 | −1.434 | −23.919 |
| 639 | LEU91 | C | 9.226 | −0.664 | −23.931 |
| 640 | LEU91 | O | 10.235 | −1.123 | −23.392 |
| 641 | LEU91 | CB | 7.475 | −1.815 | −22.498 |
| 642 | LEU91 | CG | 6.487 | −0.843 | −21.846 |
| 643 | LEU91 | CD1 | 5.945 | −1.465 | −20.56 |
| 644 | LEU91 | CD2 | 7.114 | 0.509 | −21.527 |
| 645 | ASP92 | N | 9.214 | 0.48 | −24.704 |
| 646 | ASP92 | CA | 10.404 | 1.319 | −24.881 |
| 647 | ASP92 | C | 11.496 | 0.478 | −25.612 |
| 648 | ASP92 | O | 11.245 | −0.57 | −26.213 |
| 649 | ASP92 | CB | 10.877 | 1.95 | −23.572 |
| 650 | ASP92 | CG | 9.809 | 2.796 | −22.89 |
| 651 | ASP92 | OD1 | 9.046 | 3.441 | −23.668 |
| 652 | ASP92 | OD2 | 9.837 | 2.781 | −21.626 |
| 653 | LEU93 | N | 12.768 | 1.028 | −25.618 |
| 654 | LEU93 | CA | 13.922 | 0.28 | −26.105 |
| 655 | LEU93 | C | 14.741 | −0.175 | −24.876 |
| 656 | LEU93 | O | 14.723 | −1.344 | −24.474 |
| 657 | LEU93 | CB | 14.753 | 1.108 | −27.099 |
| 658 | LEU93 | CG | 14.023 | 1.446 | −28.416 |
| 659 | LEU93 | CD1 | 14.893 | 2.381 | −29.261 |
| 660 | LEU93 | CD2 | 13.669 | 0.2 | −29.23 |
| 661 | CYS94 | N | 15.447 | 0.831 | −24.233 |
| 662 | CYS94 | CA | 16.324 | 0.577 | −23.09 |
| 663 | CYS94 | C | 16.131 | 1.7 | −22.062 |
| 664 | CYS94 | O | 15.357 | 1.583 | −21.113 |
| 665 | CYS94 | CB | 17.803 | 0.423 | −23.481 |
| 666 | CYS94 | SG | 18.154 | −1.146 | −24.337 |
| 667 | GLN95 | N | 16.809 | 2.875 | −22.309 |
| 668 | GLN95 | CA | 16.828 | 3.977 | −21.343 |
| 669 | GLN95 | C | 15.595 | 4.88 | −21.519 |
| 670 | GLN95 | O | 15.666 | 6.101 | −21.667 |
| 671 | GLN95 | CB | 18.128 | 4.782 | −21.468 |
| 672 | GLN95 | CG | 19.35 | 3.971 | −21.037 |
| 673 | GLN95 | CD | 20.631 | 4.716 | −21.332 |
| 674 | GLN95 | OE1 | 21.398 | 4.387 | −22.23 |
| 675 | GLN95 | NE2 | 20.868 | 5.796 | −20.532 |
| 676 | GLY96 | N | 14.387 | 4.241 | −21.336 |
| 677 | GLY96 | CA | 13.113 | 4.941 | −21.412 |
| 678 | GLY96 | C | 12.794 | 5.775 | −20.17 |
| 679 | GLY96 | O | 11.648 | 5.904 | −19.733 |
| 680 | ILE97 | N | 13.836 | 6.527 | −19.667 |
| 681 | ILE97 | CA | 13.733 | 7.329 | −18.442 |
| 682 | ILE97 | C | 13.041 | 8.673 | −18.791 |
| 683 | ILE97 | O | 13.56 | 9.771 | −18.609 |
| 684 | ILE97 | CB | 15.122 | 7.531 | −17.772 |
| 685 | ILE97 | CG1 | 15.926 | 6.211 | −17.692 |
| 686 | ILE97 | CG2 | 14.949 | 8.124 | −16.362 |
| 687 | ILE97 | CD1 | 17.34 | 6.378 | −17.148 |
| 688 | VAL98 | N | 11.751 | 8.517 | −19.265 |
| 689 | VAL98 | CA | 10.927 | 9.621 | −19.757 |
| 690 | VAL98 | C | 9.429 | 9.286 | −19.558 |
| 691 | VAL98 | O | 8.531 | 9.843 | −20.19 |
| 692 | VAL98 | CB | 11.221 | 9.994 | −21.234 |
| 693 | VAL98 | CG1 | 12.475 | 10.859 | −21.382 |
| 694 | VAL98 | CG2 | 11.335 | 8.767 | −22.145 |
| 695 | GLY99 | N | 9.185 | 8.415 | −18.514 |
| 696 | GLY99 | CA | 7.875 | 7.865 | −18.235 |
| 697 | GLY99 | C | 7.657 | 7.649 | −16.74 |
| 698 | GLY99 | O | 8.578 | 7.612 | −15.928 |
| 699 | ASP100 | N | 6.324 | 7.452 | −16.42 |
| 700 | ASP100 | CA | 5.893 | 7.06 | −15.077 |
| 701 | ASP100 | C | 5.918 | 5.515 | −15.027 |
| 702 | ASP100 | O | 5.893 | 4.805 | −16.031 |
| 703 | ASP100 | CB | 4.487 | 7.593 | −14.83 |
| 704 | ASP100 | CG | 4.12 | 7.565 | −13.351 |
| 705 | ASP100 | OD1 | 3.671 | 8.643 | −12.877 |
| 706 | ASP100 | OD2 | 4.264 | 6.429 | −12.793 |
| 707 | CYS101 | N | 5.865 | 4.992 | −13.749 |
| 708 | CYS101 | CA | 5.769 | 3.556 | −13.534 |
| 709 | CYS101 | C | 4.373 | 3.044 | −13.937 |
| 710 | CYS101 | O | 4.226 | 1.887 | −14.348 |
| 711 | CYS101 | CB | 6.133 | 3.221 | −12.089 |
| 712 | CYS101 | SG | 6.148 | 1.438 | −11.724 |
| 713 | TRP102 | N | 3.29 | 3.904 | −13.831 |
| 714 | TRP102 | CA | 1.957 | 3.399 | −14.203 |
| 715 | TRP102 | C | 1.878 | 3.08 | −15.714 |
| 716 | TRP102 | O | 1.076 | 2.263 | −16.17 |
| 717 | TRP102 | CB | 0.751 | 4.239 | −13.763 |
| 718 | TRP102 | CG | 0.781 | 5.685 | −14.133 |
| 719 | TRP102 | CD1 | 1.058 | 6.715 | −13.259 |
| 720 | TRP102 | CD2 | 0.498 | 6.294 | −15.401 |
| 721 | TRP102 | NE1 | 1.069 | 7.893 | −13.955 |
| 722 | TRP102 | CE2 | 0.713 | 7.668 | −15.262 |
| 723 | TRP102 | CE3 | 0.088 | 5.808 | −16.661 |
| 724 | TRP102 | CZ2 | 0.584 | 8.568 | −16.325 |
| 725 | TRP102 | CZ3 | −0.042 | 6.694 | −17.735 |
| 726 | TRP102 | CH2 | 0.205 | 8.052 | −17.567 |
| 727 | PHE103 | N | 2.748 | 3.808 | −16.5 |
| 728 | PHE103 | CA | 2.834 | 3.674 | −17.967 |
| 729 | PHE103 | C | 3.477 | 2.303 | −18.263 |
| 730 | PHE103 | O | 3.184 | 1.626 | −19.246 |
| 731 | PHE103 | CB | 3.697 | 4.823 | −18.521 |
| 732 | PHE103 | CG | 3.647 | 5.182 | −19.989 |
| 733 | PHE103 | CD1 | 2.98 | 4.439 | −20.966 |
| 734 | PHE103 | CD2 | 4.345 | 6.338 | −20.391 |
| 735 | PHE103 | CE1 | 3.011 | 4.843 | −22.306 |
| 736 | PHE103 | CE2 | 4.371 | 6.743 | −21.725 |
| 737 | PHE103 | CZ | 3.701 | 5.994 | −22.684 |
| 738 | LEU104 | N | 4.471 | 1.954 | −17.371 |
| 739 | LEU104 | CA | 5.153 | 0.669 | −17.416 |
| 740 | LEU104 | C | 4.232 | −0.452 | −16.89 |
| 741 | LEU104 | O | 4.292 | −1.604 | −17.331 |
| 742 | LEU104 | CB | 6.453 | 0.729 | −16.608 |
| 743 | LEU104 | CG | 7.691 | 1.153 | −17.425 |
| 744 | LEU104 | CD1 | 7.519 | 2.468 | −18.183 |
| 745 | LEU104 | CD2 | 8.893 | 1.266 | −16.486 |
| 746 | ALA105 | N | 3.406 | −0.101 | −15.834 |
| 747 | ALA105 | CA | 2.56 | −1.101 | −15.193 |
| 748 | ALA105 | C | 1.429 | −1.517 | −16.151 |
| 749 | ALA105 | O | 1.062 | −2.692 | −16.237 |
| 750 | ALA105 | CB | 1.951 | −0.585 | −13.898 |
| 751 | ALA106 | N | 0.819 | −0.484 | −16.85 |
| 752 | ALA106 | CA | −0.432 | −0.724 | −17.57 |
| 753 | ALA106 | C | −0.204 | −1.675 | −18.754 |

TABLE V-continued

| Atom No | Residue | Atom name | x coord | y coord | z coord |
|---|---|---|---|---|---|
| 754 | ALA106 | O | −1.054 | −2.479 | −19.141 |
| 755 | ALA106 | CB | −1.013 | 0.582 | −18.097 |
| 756 | LEU107 | N | 1.009 | −1.53 | −19.398 |
| 757 | LEU107 | CA | 1.321 | −2.176 | −20.673 |
| 758 | LEU107 | C | 1.718 | −3.678 | −20.575 |
| 759 | LEU107 | O | 2.258 | −4.293 | −21.501 |
| 760 | LEU107 | CB | 2.384 | −1.374 | −21.433 |
| 761 | LEU107 | CG | 1.878 | −0.061 | −22.059 |
| 762 | LEU107 | CD1 | 3.035 | 0.663 | −22.753 |
| 763 | LEU107 | CD2 | 0.74 | −0.303 | −23.051 |
| 764 | GLN108 | N | 1.244 | −4.303 | −19.443 |
| 765 | GLN108 | CA | 1.063 | −5.742 | −19.321 |
| 766 | GLN108 | C | −0.337 | −6.131 | −19.827 |
| 767 | GLN108 | O | −0.557 | −7.222 | −20.355 |
| 768 | GLN108 | CB | 1.183 | −6.173 | −17.853 |
| 769 | GLN108 | CG | 2.621 | −6.422 | −17.41 |
| 770 | GLN108 | CD | 3.582 | −5.274 | −17.628 |
| 771 | GLN108 | OE1 | 4.64 | −5.424 | −18.24 |
| 772 | GLN108 | NE2 | 3.248 | −4.089 | −17.05 |
| 773 | ALA109 | N | −1.359 | −5.255 | −19.525 |
| 774 | ALA109 | CA | −2.772 | −5.614 | −19.668 |
| 775 | ALA109 | C | −3.291 | −5.495 | −21.117 |
| 776 | ALA109 | O | −4.39 | −5.022 | −21.399 |
| 777 | ALA109 | CB | −3.596 | −4.765 | −18.713 |
| 778 | LEU110 | N | −2.462 | −6.089 | −22.051 |
| 779 | LEU110 | CA | −2.756 | −6.142 | −23.476 |
| 780 | LEU110 | C | −2.279 | −7.502 | −24.017 |
| 781 | LEU110 | O | −1.669 | −7.63 | −25.075 |
| 782 | LEU110 | CB | −2.121 | −5.001 | −24.287 |
| 783 | LEU110 | CG | −2.629 | −3.591 | −23.935 |
| 784 | LEU110 | CD1 | −1.731 | −2.934 | −22.892 |
| 785 | LEU110 | CD2 | −2.658 | −2.71 | −25.186 |
| 786 | ALA111 | N | −2.72 | −8.579 | −23.265 |
| 787 | ALA111 | CA | −2.753 | −9.915 | −23.857 |
| 788 | ALA111 | C | −4.101 | −10.024 | −24.608 |
| 789 | ALA111 | O | −4.773 | −9.031 | −24.91 |
| 790 | ALA111 | CB | −2.558 | −10.955 | −22.762 |
| 791 | LEU112 | N | −4.465 | −11.29 | −25.015 |
| 792 | LEU112 | CA | −5.86 | −11.58 | −25.354 |
| 793 | LEU112 | C | −6.414 | −12.161 | −24.046 |
| 794 | LEU112 | O | −5.918 | −13.188 | −23.572 |
| 795 | LEU112 | CB | −5.952 | −12.64 | −26.461 |
| 796 | LEU112 | CG | −5.261 | −12.256 | −27.785 |
| 797 | LEU112 | CD1 | −5.34 | −13.427 | −28.769 |
| 798 | LEU112 | CD2 | −5.866 | −11.005 | −28.417 |
| 799 | HIS113 | N | −7.43 | −11.444 | −23.451 |
| 800 | HIS113 | CA | −7.821 | −11.611 | −22.048 |
| 801 | HIS113 | C | −6.923 | −10.665 | −21.229 |
| 802 | HIS113 | O | −5.785 | −10.341 | −21.566 |
| 803 | HIS113 | CB | −7.778 | −13.012 | −21.426 |
| 804 | HIS113 | CG | −8.611 | −14.02 | −22.134 |
| 805 | HIS113 | ND1 | −8.095 | −14.823 | −23.122 |
| 806 | HIS113 | CD2 | −9.929 | −14.406 | −22.032 |
| 807 | HIS113 | CE1 | −9.092 | −15.645 | −23.555 |
| 808 | HIS113 | NE2 | −10.212 | −15.424 | −22.906 |
| 809 | GLN114 | N | −7.504 | −10.22 | −20.054 |
| 810 | GLN114 | CA | −6.884 | −9.215 | −19.194 |
| 811 | GLN114 | C | −6.983 | −7.797 | −19.8 |
| 812 | GLN114 | O | −6.316 | −6.849 | −19.385 |
| 813 | GLN114 | CB | −5.444 | −9.521 | −18.747 |
| 814 | GLN114 | CG | −5.258 | −10.965 | −18.283 |
| 815 | GLN114 | CD | −4.009 | −11.203 | −17.462 |
| 816 | GLN114 | OE1 | −4.009 | −11.949 | −16.481 |
| 817 | GLN114 | NE2 | −2.866 | −10.614 | −17.913 |
| 818 | ASP115 | N | −7.986 | −7.644 | −20.739 |
| 819 | ASP115 | CA | −8.063 | −6.457 | −21.592 |
| 820 | ASP115 | C | −8.661 | −5.284 | −20.776 |
| 821 | ASP115 | O | −9.86 | −5.006 | −20.77 |
| 822 | ASP115 | CB | −8.938 | −6.751 | −22.812 |
| 823 | ASP115 | CG | −8.176 | −7.678 | −23.745 |
| 824 | ASP115 | OD1 | −8.126 | −8.901 | −23.421 |
| 825 | ASP115 | OD2 | −7.654 | −7.126 | −24.764 |
| 826 | ILE116 | N | −7.728 | −4.588 | −20.009 |
| 827 | ILE116 | CA | −8.165 | −3.488 | −19.133 |
| 828 | ILE116 | C | −8.463 | −2.254 | −20.018 |
| 829 | ILE116 | O | −9.325 | −1.423 | −19.726 |
| 830 | ILE116 | CB | −7.086 | −3.125 | −18.066 |
| 831 | ILE116 | CG1 | −6.977 | −4.238 | −16.998 |
| 832 | ILE116 | CG2 | −7.362 | −1.775 | −17.38 |
| 833 | ILE116 | CD1 | −5.89 | −3.988 | −15.958 |
| 834 | LEU117 | N | −7.566 | −2.046 | −21.058 |
| 835 | LEU117 | CA | −7.268 | −0.678 | −21.504 |
| 836 | LEU117 | C | −8.491 | 0.028 | −22.113 |
| 837 | LEU117 | O | −8.609 | 1.255 | −22.1 |
| 838 | LEU117 | CB | −6.122 | −0.667 | −22.53 |
| 839 | LEU117 | CG | −4.72 | −0.396 | −21.943 |
| 840 | LEU117 | CD1 | −4.559 | 1.055 | −21.489 |
| 841 | LEU117 | CD2 | −4.346 | −1.348 | −20.81 |
| 842 | SER118 | N | −9.408 | −0.805 | −22.71 |
| 843 | SER118 | CA | −10.624 | −0.306 | −23.348 |
| 844 | SER118 | C | −11.65 | 0.289 | −22.366 |
| 845 | SER118 | O | −12.654 | 0.877 | −22.767 |
| 846 | SER118 | CB | −11.286 | −1.413 | −24.169 |
| 847 | SER118 | OG | −11.43 | −2.584 | −23.363 |
| 848 | ARG119 | N | −11.355 | 0.143 | −21.025 |
| 849 | ARG119 | CA | −12.143 | 0.802 | −19.988 |
| 850 | ARG119 | C | −11.707 | 2.275 | −19.855 |
| 851 | ARG119 | O | −12.455 | 3.127 | −19.381 |
| 852 | ARG119 | CB | −11.894 | 0.161 | −18.62 |
| 853 | ARG119 | CG | −12.335 | −1.297 | −18.522 |
| 854 | ARG119 | CD | −11.739 | −1.974 | −17.293 |
| 855 | ARG119 | NE | −12.298 | −1.457 | −16.042 |
| 856 | ARG119 | CZ | −11.803 | −0.482 | −15.244 |
| 857 | ARG119 | NH1 | −10.711 | 0.247 | −15.555 |
| 858 | ARG119 | NH2 | −12.452 | −0.258 | −14.089 |
| 859 | VAL120 | N | −10.362 | 2.488 | −20.094 |
| 860 | VAL120 | CA | −9.706 | 3.779 | −19.884 |
| 861 | VAL120 | C | −9.694 | 4.555 | −21.214 |
| 862 | VAL120 | O | −9.932 | 5.766 | −21.253 |
| 863 | VAL120 | CB | −8.269 | 3.569 | −19.347 |
| 864 | VAL120 | CG1 | −7.529 | 4.896 | −19.144 |
| 865 | VAL120 | CG2 | −8.281 | 2.797 | −18.023 |
| 866 | VAL121 | N | −9.242 | 3.824 | −22.299 |
| 867 | VAL121 | CA | −8.985 | 4.393 | −23.615 |
| 868 | VAL121 | C | −10.137 | 3.956 | −24.546 |
| 869 | VAL121 | O | −10.169 | 2.831 | −25.059 |
| 870 | VAL121 | CB | −7.629 | 3.889 | −24.177 |
| 871 | VAL121 | CG1 | −7.284 | 4.624 | −25.476 |
| 872 | VAL121 | CG2 | −6.481 | 4.066 | −23.177 |
| 873 | PRO122 | N | −11.151 | 4.858 | −24.793 |
| 874 | PRO122 | CA | −12.257 | 4.516 | −25.681 |
| 875 | PRO122 | C | −11.727 | 4.64 | −27.122 |
| 876 | PRO122 | O | −11.655 | 5.707 | −27.736 |
| 877 | PRO122 | CB | −13.34 | 5.54 | −25.351 |
| 878 | PRO122 | CG | −12.56 | 6.749 | −24.854 |
| 879 | PRO122 | CD | −11.376 | 6.132 | −24.132 |
| 880 | LEU123 | N | −11.265 | 3.444 | −27.648 |
| 881 | LEU123 | CA | −10.478 | 3.372 | −28.894 |
| 882 | LEU123 | C | −11.285 | 3.658 | −30.198 |
| 883 | LEU123 | O | −11.001 | 3.142 | −31.278 |
| 884 | LEU123 | CB | −9.802 | 1.984 | −29.007 |
| 885 | LEU123 | CG | −8.58 | 1.794 | −28.085 |
| 886 | LEU123 | CD1 | −8.246 | 0.307 | −27.948 |
| 887 | LEU123 | CD2 | −7.356 | 2.544 | −28.613 |
| 888 | ASN124 | N | −12.211 | 4.68 | −30.117 |
| 889 | ASN124 | CA | −12.829 | 5.29 | −31.3 |
| 890 | ASN124 | C | −12.104 | 6.607 | −31.619 |
| 891 | ASN124 | O | −12.689 | 7.68 | −31.747 |
| 892 | ASN124 | CB | −14.341 | 5.477 | −31.162 |
| 893 | ASN124 | CG | −14.79 | 6.026 | −29.825 |
| 894 | ASN124 | OD1 | −14.992 | 7.218 | −29.597 |
| 895 | ASN124 | ND2 | −14.98 | 5.078 | −28.858 |
| 896 | GLN125 | N | −10.738 | 6.468 | −31.766 |
| 897 | GLN125 | CA | −9.826 | 7.606 | −31.832 |
| 898 | GLN125 | C | −8.631 | 7.22 | −32.717 |
| 899 | GLN125 | O | −8.277 | 6.051 | −32.867 |
| 900 | GLN125 | CB | −9.337 | 7.976 | −30.426 |
| 901 | GLN125 | CG | −10.449 | 8.556 | −29.557 |
| 902 | GLN125 | CD | −9.954 | 8.892 | −28.177 |
| 903 | GLN125 | OE1 | −9.565 | 10.014 | −27.87 |
| 904 | GLN125 | NE2 | −9.96 | 7.87 | −27.275 |
| 905 | SER126 | N | −7.977 | 8.292 | −33.292 |
| 906 | SER126 | CA | −6.903 | 8.121 | −34.272 |
| 907 | SER126 | C | −6.247 | 9.491 | −34.529 |

TABLE V-continued

| Atom No | Residue | Atom name | x coord | y coord | z coord |
|---|---|---|---|---|---|
| 908 | SER126 | O | -6.72 | 10.537 | -34.089 |
| 909 | SER126 | CB | -7.434 | 7.571 | -35.601 |
| 910 | SER126 | OG | -6.393 | 7.517 | -36.579 |
| 911 | PHE127 | N | -5.107 | 9.413 | -35.315 |
| 912 | PHE127 | CA | -4.435 | 10.605 | -35.843 |
| 913 | PHE127 | C | -4.861 | 10.96 | -37.282 |
| 914 | PHE127 | O | -4.327 | 11.876 | -37.907 |
| 915 | PHE127 | CB | -2.908 | 10.456 | -35.78 |
| 916 | PHE127 | CG | -2.362 | 10.971 | -34.47 |
| 917 | PHE127 | CD1 | -2.161 | 10.109 | -33.388 |
| 918 | PHE127 | CD2 | -2.091 | 12.334 | -34.312 |
| 919 | PHE127 | CE1 | -1.653 | 10.589 | -32.181 |
| 920 | PHE127 | CE2 | -1.612 | 12.819 | -33.096 |
| 921 | PHE127 | CZ | -1.378 | 11.946 | -32.035 |
| 922 | THR128 | N | -5.945 | 10.264 | -37.77 |
| 923 | THR128 | CA | -6.502 | 10.531 | -39.093 |
| 924 | THR128 | C | -8.034 | 10.544 | -38.983 |
| 925 | THR128 | O | -8.707 | 11.526 | -39.309 |
| 926 | THR128 | CB | -5.992 | 9.555 | -40.178 |
| 927 | THR128 | OG1 | -5.571 | 8.303 | -39.635 |
| 928 | THR128 | CG2 | -4.785 | 10.13 | -40.915 |
| 929 | GLU129 | N | -8.608 | 9.393 | -38.494 |
| 930 | GLU129 | CA | -10.035 | 9.112 | -38.601 |
| 931 | GLU129 | C | -10.811 | 10.009 | -37.614 |
| 932 | GLU129 | O | -11.205 | 9.625 | -36.517 |
| 933 | GLU129 | CB | -10.335 | 7.629 | -38.31 |
| 934 | GLU129 | CG | -9.759 | 6.652 | -39.339 |
| 935 | GLU129 | CD | -8.271 | 6.311 | -39.226 |
| 936 | GLU129 | OE1 | -7.929 | 5.198 | -39.697 |
| 937 | GLU129 | OE2 | -7.53 | 7.208 | -38.687 |
| 938 | LYS130 | N | -11.005 | 11.296 | -38.003 |
| 939 | LYS130 | CA | -11.731 | 12.34 | -37.373 |
| 940 | LYS130 | C | -10.877 | 12.95 | -36.242 |
| 941 | LYS130 | O | -11.355 | 13.334 | -35.177 |
| 942 | LYS130 | CB | -13.126 | 11.929 | -36.873 |
| 943 | LYS130 | CG | -13.995 | 11.284 | -37.956 |
| 944 | LYS130 | CD | -15.417 | 11.04 | -37.448 |
| 945 | LYS130 | CE | -16.274 | 10.388 | -38.522 |
| 946 | LYS130 | NZ | -17.636 | 10.16 | -37.984 |
| 947 | TYR131 | N | -9.562 | 13.204 | -36.609 |
| 948 | TYR131 | CA | -8.563 | 13.568 | -35.589 |
| 949 | TYR131 | C | -8.9 | 14.925 | -34.947 |
| 950 | TYR131 | O | -8.836 | 15.109 | -33.729 |
| 951 | TYR131 | CB | -7.175 | 13.608 | -36.26 |
| 952 | TYR131 | CG | -6.046 | 14.306 | -35.541 |
| 953 | TYR131 | CD1 | -5.831 | 14.159 | -34.166 |
| 954 | TYR131 | CD2 | -5.155 | 15.104 | -36.281 |
| 955 | TYR131 | CE1 | -4.787 | 14.844 | -33.54 |
| 956 | TYR131 | CE2 | -4.101 | 15.77 | -35.655 |
| 957 | TYR131 | CZ | -3.927 | 15.641 | -34.285 |
| 958 | TYR131 | OH | -2.881 | 16.305 | -33.712 |
| 959 | ALA132 | N | -9.049 | 15.977 | -35.833 |
| 960 | ALA132 | CA | -9.562 | 17.291 | -35.428 |
| 961 | ALA132 | C | -8.797 | 18.069 | -34.324 |
| 962 | ALA132 | O | -9.201 | 19.152 | -33.891 |
| 963 | ALA132 | CB | -11.05 | 17.221 | -35.103 |
| 964 | GLY133 | N | -7.619 | 17.503 | -33.892 |
| 965 | GLY133 | CA | -6.856 | 18.065 | -32.802 |
| 966 | GLY133 | C | -7.431 | 17.783 | -31.41 |
| 967 | GLY133 | O | -7.144 | 18.54 | -30.47 |
| 968 | ILE134 | N | -8.174 | 16.624 | -31.274 |
| 969 | ILE134 | CA | -8.908 | 16.289 | -30.044 |
| 970 | ILE134 | C | -8.793 | 14.785 | -29.724 |
| 971 | ILE134 | O | -8.765 | 13.926 | -30.603 |
| 972 | ILE134 | CB | -10.397 | 16.728 | -30.16 |
| 973 | ILE134 | CG1 | -11.124 | 16.686 | -28.801 |
| 974 | ILE134 | CG2 | -11.169 | 15.94 | -31.224 |
| 975 | ILE134 | CD1 | -12.511 | 17.313 | -28.847 |
| 976 | PHE135 | N | -8.83 | 14.489 | -28.371 |
| 977 | PHE135 | CA | -8.833 | 13.117 | -27.856 |
| 978 | PHE135 | C | -9.685 | 13.073 | -26.568 |
| 979 | PHE135 | O | -10.012 | 14.085 | -25.944 |
| 980 | PHE135 | CB | -7.413 | 12.624 | -27.534 |
| 981 | PHE135 | CG | -6.553 | 12.377 | -28.746 |
| 982 | PHE135 | CD1 | -5.529 | 13.267 | -29.088 |
| 983 | PHE135 | CD2 | -6.777 | 11.255 | -29.554 |
| 984 | PHE135 | CE1 | -4.741 | 13.032 | -30.215 |
| 985 | PHE135 | CE2 | -6.003 | 11.033 | -30.691 |
| 986 | PHE135 | CZ | -4.989 | 11.924 | -31.023 |
| 987 | ARG136 | N | -10.009 | 11.798 | -26.139 |
| 988 | ARG136 | CA | -10.796 | 11.546 | -24.941 |
| 989 | ARG136 | C | -10.416 | 10.231 | -24.233 |
| 990 | ARG136 | O | -9.984 | 9.248 | -24.834 |
| 991 | ARG136 | CB | -12.308 | 11.593 | -25.207 |
| 992 | ARG136 | CG | -12.821 | 10.558 | -26.217 |
| 993 | ARG136 | CD | -14.35 | 10.528 | -26.238 |
| 994 | ARG136 | NE | -14.865 | 9.659 | -27.303 |
| 995 | ARG136 | CZ | -16.136 | 9.742 | -27.779 |
| 996 | ARG136 | NH1 | -16.503 | 8.988 | -28.829 |
| 997 | ARG136 | NH2 | -17.054 | 10.552 | -27.241 |
| 998 | PHE137 | N | -10.687 | 10.254 | -22.871 |
| 999 | PHE137 | CA | -10.321 | 9.168 | -21.959 |
| 1000 | PHE137 | C | -11.354 | 9.108 | -20.824 |
| 1001 | PHE137 | O | -11.947 | 10.111 | -20.421 |
| 1002 | PHE137 | CB | -8.944 | 9.385 | -21.316 |
| 1003 | PHE137 | CG | -7.793 | 9.34 | -22.287 |
| 1004 | PHE137 | CD1 | -7.236 | 10.527 | -22.776 |
| 1005 | PHE137 | CD2 | -7.258 | 8.117 | -22.706 |
| 1006 | PHE137 | CE1 | -6.147 | 10.489 | -23.643 |
| 1007 | PHE137 | CE2 | -6.162 | 8.083 | -23.57 |
| 1008 | PHE137 | CZ | -5.604 | 9.269 | -24.035 |
| 1009 | TRP138 | N | -11.51 | 7.859 | -20.254 |
| 1010 | TRP138 | CA | -12.345 | 7.665 | -19.064 |
| 1011 | TRP138 | C | -11.447 | 7.497 | -17.827 |
| 1012 | TRP138 | O | -10.396 | 6.86 | -17.86 |
| 1013 | TRP138 | CB | -13.233 | 6.421 | -19.182 |
| 1014 | TRP138 | CG | -14.47 | 6.651 | -19.997 |
| 1015 | TRP138 | CD1 | -14.621 | 6.385 | -21.343 |
| 1016 | TRP138 | CD2 | -15.731 | 7.146 | -19.529 |
| 1017 | TRP138 | NE1 | -15.902 | 6.7 | -21.705 |
| 1018 | TRP138 | CE2 | -16.607 | 7.155 | -20.616 |
| 1019 | TRP138 | CE3 | -16.213 | 7.579 | -18.276 |
| 1020 | TRP138 | CZ2 | -17.942 | 7.566 | -20.511 |
| 1021 | TRP138 | CZ3 | -17.545 | 7.994 | -18.155 |
| 1022 | TRP138 | CH2 | -18.395 | 7.984 | -19.257 |
| 1023 | PHE139 | N | -11.973 | 8.052 | -16.675 |
| 1024 | PHE139 | CA | -11.306 | 7.973 | -15.369 |
| 1025 | PHE139 | C | -12.384 | 7.696 | -14.306 |
| 1026 | PHE139 | O | -13.538 | 8.118 | -14.423 |
| 1027 | PHE139 | CB | -10.641 | 9.3 | -14.98 |
| 1028 | PHE139 | CG | -9.331 | 9.613 | -15.658 |
| 1029 | PHE139 | CD1 | -9.286 | 10.091 | -16.972 |
| 1030 | PHE139 | CD2 | -8.136 | 9.507 | -14.936 |
| 1031 | PHE139 | CE1 | -8.072 | 10.481 | -17.539 |
| 1032 | PHE139 | CE2 | -6.928 | 9.916 | -15.495 |
| 1033 | PHE139 | CZ | -6.896 | 10.405 | -16.798 |
| 1034 | TRP140 | N | -11.939 | 7.013 | -13.188 |
| 1035 | TRP140 | CA | -12.701 | 7.014 | -11.929 |
| 1036 | TRP140 | C | -12.057 | 8.105 | -11.072 |
| 1037 | TRP140 | O | -10.834 | 8.217 | -11.006 |
| 1038 | TRP140 | CB | -12.571 | 5.667 | -11.208 |
| 1039 | TRP140 | CG | -13.383 | 5.54 | -9.948 |
| 1040 | TRP140 | CD1 | -14.64 | 4.977 | -9.842 |
| 1041 | TRP140 | CD2 | -12.984 | 5.899 | -8.615 |
| 1042 | TRP140 | NE1 | -14.998 | 4.949 | -8.521 |
| 1043 | TRP140 | CE2 | -14.019 | 5.533 | -7.753 |
| 1044 | TRP140 | CE3 | -11.825 | 6.474 | -8.053 |
| 1045 | TRP140 | CZ2 | -13.959 | 5.73 | -6.367 |
| 1046 | TRP140 | CZ3 | -11.752 | 6.684 | -6.671 |
| 1047 | TRP140 | CH2 | -12.806 | 6.317 | -5.841 |
| 1048 | HIS141 | N | -12.917 | 8.884 | -10.331 |
| 1049 | HIS141 | CA | -12.408 | 9.837 | -9.352 |
| 1050 | HIS141 | C | -13.458 | 10.025 | -8.248 |
| 1051 | HIS141 | O | -14.635 | 10.302 | -8.48 |
| 1052 | HIS141 | CB | -12.141 | 11.23 | -9.934 |
| 1053 | HIS141 | CG | -11.032 | 11.334 | -10.919 |
| 1054 | HIS141 | ND1 | -9.75 | 10.877 | -10.725 |
| 1055 | HIS141 | CD2 | -11.005 | 11.901 | -12.174 |
| 1056 | HIS141 | CE1 | -9.024 | 11.237 | -11.83 |
| 1057 | HIS141 | NE2 | -9.754 | 11.864 | -12.721 |
| 1058 | TYR142 | N | -12.985 | 9.871 | -6.958 |
| 1059 | TYR142 | CA | -13.632 | 10.526 | -5.814 |
| 1060 | TYR142 | C | -15.113 | 10.164 | -5.57 |
| 1061 | TYR142 | O | -15.861 | 10.868 | -4.883 |

TABLE V-continued

| Atom No | Residue | Atom name | x coord | y coord | z coord |
|---|---|---|---|---|---|
| 1062 | TYR142 | CB | −13.428 | 12.057 | −5.844 |
| 1063 | TYR142 | CG | −11.989 | 12.464 | −5.617 |
| 1064 | TYR142 | CD1 | −11.292 | 13.263 | −6.54 |
| 1065 | TYR142 | CD2 | −11.335 | 12.063 | −4.448 |
| 1066 | TYR142 | CE1 | −9.96 | 13.636 | −6.306 |
| 1067 | TYR142 | CE2 | −10.014 | 12.428 | −4.224 |
| 1068 | TYR142 | CZ | −9.338 | 13.215 | −5.142 |
| 1069 | TYR142 | OH | −8.073 | 13.56 | −4.798 |
| 1070 | GLY143 | N | −15.476 | 8.919 | −6.043 |
| 1071 | GLY143 | CA | −16.832 | 8.412 | −5.971 |
| 1072 | GLY143 | C | −17.655 | 8.645 | −7.241 |
| 1073 | GLY143 | O | −18.883 | 8.482 | −7.266 |
| 1074 | ASN144 | N | −16.955 | 8.951 | −8.384 |
| 1075 | ASN144 | CA | −17.596 | 9.151 | −9.681 |
| 1076 | ASN144 | C | −16.688 | 8.618 | −10.801 |
| 1077 | ASN144 | O | −15.464 | 8.573 | −10.704 |
| 1078 | ASN144 | CB | −17.922 | 10.63 | −9.913 |
| 1079 | ASN144 | CG | −19.33 | 11.081 | −9.576 |
| 1080 | ASN144 | OD1 | −19.774 | 12.166 | −9.944 |
| 1081 | ASN144 | ND2 | −20.118 | 10.253 | −8.821 |
| 1082 | TRP145 | N | −17.387 | 8.237 | −11.939 |
| 1083 | TRP145 | CA | −16.681 | 8.01 | −13.204 |
| 1084 | TRP145 | C | −16.708 | 9.355 | −13.94 |
| 1085 | TRP145 | O | −17.634 | 10.157 | −13.793 |
| 1086 | TRP145 | CB | −17.356 | 6.938 | −14.068 |
| 1087 | TRP145 | CG | −16.948 | 5.548 | −13.681 |
| 1088 | TRP145 | CD1 | −17.601 | 4.704 | −12.805 |
| 1089 | TRP145 | CD2 | −15.793 | 4.843 | −14.152 |
| 1090 | TRP145 | NE1 | −16.89 | 3.535 | −12.723 |
| 1091 | TRP145 | CE2 | −15.768 | 3.603 | −13.515 |
| 1092 | TRP145 | CE3 | −14.756 | 5.154 | −15.056 |
| 1093 | TRP145 | CZ2 | −14.741 | 2.671 | −13.713 |
| 1094 | TRP145 | CZ3 | −13.723 | 4.237 | −15.269 |
| 1095 | TRP145 | CH2 | −13.715 | 3.018 | −14.599 |
| 1096 | VAL146 | N | −15.638 | 9.562 | −14.788 |
| 1097 | VAL146 | CA | −15.39 | 10.871 | −15.385 |
| 1098 | VAL146 | C | −14.852 | 10.644 | −16.812 |
| 1099 | VAL146 | O | −13.837 | 9.963 | −17.003 |
| 1100 | VAL146 | CB | −14.358 | 11.689 | −14.569 |
| 1101 | VAL146 | CG1 | −14.207 | 13.097 | −15.155 |
| 1102 | VAL146 | CG2 | −14.719 | 11.766 | −13.081 |
| 1103 | PRO147 | N | −15.549 | 11.254 | −17.843 |
| 1104 | PRO147 | CA | −15.043 | 11.286 | −19.215 |
| 1105 | PRO147 | C | −14.214 | 12.571 | −19.39 |
| 1106 | PRO147 | O | −14.723 | 13.693 | −19.373 |
| 1107 | PRO147 | CB | −16.31 | 11.349 | −20.067 |
| 1108 | PRO147 | CG | −17.313 | 12.106 | −19.2 |
| 1109 | PRO147 | CD | −16.917 | 11.758 | −17.771 |
| 1110 | VAL148 | N | −12.848 | 12.386 | −19.479 |
| 1111 | VAL148 | CA | −11.973 | 13.532 | −19.714 |
| 1112 | VAL148 | C | −11.758 | 13.62 | −21.235 |
| 1113 | VAL148 | O | −11.456 | 12.641 | −21.92 |
| 1114 | VAL148 | CB | −10.63 | 13.404 | −18.97 |
| 1115 | VAL148 | CG1 | −9.735 | 14.62 | −19.234 |
| 1116 | VAL148 | CG2 | −10.856 | 13.273 | −17.459 |
| 1117 | VAL149 | N | −11.918 | 14.896 | −21.747 |
| 1118 | VAL149 | CA | −11.758 | 15.208 | −23.164 |
| 1119 | VAL149 | C | −10.691 | 16.306 | −23.249 |
| 1120 | VAL149 | O | −10.646 | 17.256 | −22.459 |
| 1121 | VAL149 | CB | −13.078 | 15.659 | −23.809 |
| 1122 | VAL149 | CG1 | −12.86 | 15.9 | −25.303 |
| 1123 | VAL149 | CG2 | −14.181 | 14.618 | −23.583 |
| 1124 | ILE150 | N | −9.774 | 16.139 | −24.272 |
| 1125 | ILE150 | CA | −8.459 | 16.763 | −24.18 |
| 1126 | ILE150 | C | −7.864 | 16.991 | −25.584 |
| 1127 | ILE150 | O | −8.123 | 16.277 | −26.552 |
| 1128 | ILE150 | CB | −7.579 | 15.931 | −23.204 |
| 1129 | ILE150 | CG1 | −7.164 | 14.539 | −23.729 |
| 1130 | ILE150 | CG2 | −6.394 | 16.721 | −22.679 |
| 1131 | ILE150 | CD1 | −5.892 | 14.481 | −24.561 |
| 1132 | ASP151 | N | −7.006 | 18.07 | −25.645 |
| 1133 | ASP151 | CA | −6.201 | 18.426 | −26.811 |
| 1134 | ASP151 | C | −4.805 | 17.775 | −26.706 |
| 1135 | ASP151 | O | −4.388 | 17.224 | −25.683 |
| 1136 | ASP151 | CB | −6.032 | 19.945 | −26.887 |
| 1137 | ASP151 | CG | −5.19 | 20.42 | −25.713 |
| 1138 | ASP151 | OD1 | −4.284 | 21.264 | −25.964 |
| 1139 | ASP151 | OD2 | −5.384 | 19.863 | −24.585 |
| 1140 | ASP152 | N | −4.025 | 17.991 | −27.816 |
| 1141 | ASP152 | CA | −2.677 | 17.478 | −27.987 |
| 1142 | ASP152 | C | −1.662 | 18.603 | −28.256 |
| 1143 | ASP152 | O | −0.641 | 18.39 | −28.91 |
| 1144 | ASP152 | CB | −2.65 | 16.414 | −29.084 |
| 1145 | ASP152 | CG | −3.094 | 16.94 | −30.439 |
| 1146 | ASP152 | OD1 | −2.806 | 16.218 | −31.441 |
| 1147 | ASP152 | OD2 | −3.733 | 18.037 | −30.439 |
| 1148 | ARG153 | N | −1.855 | 19.793 | −27.564 |
| 1149 | ARG153 | CA | −0.747 | 20.739 | −27.456 |
| 1150 | ARG153 | C | 0.246 | 20.139 | −26.438 |
| 1151 | ARG153 | O | −0.025 | 20.021 | −25.241 |
| 1152 | ARG153 | CB | −1.151 | 22.137 | −26.954 |
| 1153 | ARG153 | CG | −1.674 | 23.084 | −28.031 |
| 1154 | ARG153 | CD | −3.156 | 22.953 | −28.326 |
| 1155 | ARG153 | NE | −3.946 | 24.076 | −27.803 |
| 1156 | ARG153 | CZ | −4.465 | 24.31 | −26.588 |
| 1157 | ARG153 | NH1 | −4.293 | 23.508 | −25.537 |
| 1158 | ARG153 | NH2 | −5.257 | 25.397 | −26.457 |
| 1159 | LEU154 | N | 1.429 | 19.688 | −26.982 |
| 1160 | LEU154 | CA | 2.505 | 19.144 | −26.165 |
| 1161 | LEU154 | C | 3.541 | 20.264 | −25.943 |
| 1162 | LEU154 | O | 3.869 | 21.026 | −26.862 |
| 1163 | LEU154 | CB | 3.194 | 17.955 | −26.85 |
| 1164 | LEU154 | CG | 2.267 | 16.758 | −27.143 |
| 1165 | LEU154 | CD1 | 3.043 | 15.674 | −27.891 |
| 1166 | LEU154 | CD2 | 1.648 | 16.167 | −25.875 |
| 1167 | PRO155 | N | 4.111 | 20.347 | −24.685 |
| 1168 | PRO155 | CA | 5.113 | 21.362 | −24.364 |
| 1169 | PRO155 | C | 6.512 | 20.815 | −24.687 |
| 1170 | PRO155 | O | 6.887 | 19.688 | −24.347 |
| 1171 | PRO155 | CB | 4.968 | 21.566 | −22.858 |
| 1172 | PRO155 | CG | 4.548 | 20.186 | −22.366 |
| 1173 | PRO155 | CD | 3.654 | 19.668 | −23.481 |
| 1174 | VAL156 | N | 7.327 | 21.709 | −25.354 |
| 1175 | VAL156 | CA | 8.68 | 21.349 | −25.743 |
| 1176 | VAL156 | C | 9.633 | 22.52 | −25.452 |
| 1177 | VAL156 | O | 9.287 | 23.695 | −25.577 |
| 1178 | VAL156 | CB | 8.788 | 20.883 | −27.216 |
| 1179 | VAL156 | CG1 | 7.781 | 19.785 | −27.562 |
| 1180 | VAL156 | CG2 | 8.635 | 22.013 | −28.231 |
| 1181 | ASN157 | N | 10.914 | 22.138 | −25.11 |
| 1182 | ASN157 | CA | 12.032 | 23.084 | −25.07 |
| 1183 | ASN157 | C | 12.942 | 22.663 | −26.224 |
| 1184 | ASN157 | O | 13.399 | 21.524 | −26.322 |
| 1185 | ASN157 | CB | 12.82 | 23.005 | −23.768 |
| 1186 | ASN157 | CG | 12.778 | 24.303 | −22.999 |
| 1187 | ASN157 | OD1 | 12.36 | 24.37 | −21.846 |
| 1188 | ASN157 | ND2 | 13.288 | 25.39 | −23.643 |
| 1189 | GLU158 | N | 13.114 | 23.635 | −27.193 |
| 1190 | GLU158 | CA | 14.111 | 23.471 | −28.257 |
| 1191 | GLU158 | C | 13.939 | 22.143 | −29.043 |
| 1192 | GLU158 | O | 14.864 | 21.58 | −29.619 |
| 1193 | GLU158 | CB | 15.539 | 23.711 | −27.735 |
| 1194 | GLU158 | CG | 15.875 | 25.194 | −27.503 |
| 1195 | GLU158 | CD | 15.163 | 25.954 | −26.384 |
| 1196 | GLU158 | OE1 | 14.01 | 25.532 | −26.053 |
| 1197 | GLU158 | OE2 | 15.803 | 26.929 | −25.881 |
| 1198 | ALA159 | N | 12.617 | 21.738 | −29.135 |
| 1199 | ALA159 | CA | 12.147 | 20.492 | −29.732 |
| 1200 | ALA159 | C | 12.26 | 19.213 | −28.87 |
| 1201 | ALA159 | O | 11.813 | 18.139 | −29.278 |
| 1202 | ALA159 | CB | 12.681 | 20.249 | −31.14 |
| 1203 | GLY160 | N | 12.833 | 19.347 | −27.627 |
| 1204 | GLY160 | CA | 12.798 | 18.281 | −26.635 |
| 1205 | GLY160 | C | 11.549 | 18.465 | −25.774 |
| 1206 | GLY160 | O | 11.176 | 19.573 | −25.389 |
| 1207 | GLN161 | N | 10.863 | 17.298 | −25.497 |
| 1208 | GLN161 | CA | 9.536 | 17.315 | −24.877 |
| 1209 | GLN161 | C | 9.627 | 17.448 | −23.346 |
| 1210 | GLN161 | O | 10.562 | 16.979 | −22.701 |
| 1211 | GLN161 | CB | 8.748 | 16.054 | −25.271 |
| 1212 | GLN161 | CG | 8.339 | 16.079 | −26.748 |
| 1213 | GLN161 | CD | 7.893 | 14.73 | −27.264 |
| 1214 | GLN161 | OE1 | 6.724 | 14.462 | −27.521 |
| 1215 | GLN161 | NE2 | 8.897 | 13.818 | −27.434 |

TABLE V-continued

| Atom No | Residue | Atom name | x coord | y coord | z coord |
|---|---|---|---|---|---|
| 1216 | LEU162 | N | 8.539 | 18.094 | −22.773 |
| 1217 | LEU162 | CA | 8.479 | 18.432 | −21.343 |
| 1218 | LEU162 | C | 7.22 | 17.826 | −20.681 |
| 1219 | LEU162 | O | 6.667 | 18.336 | −19.709 |
| 1220 | LEU162 | CB | 8.471 | 19.955 | −21.132 |
| 1221 | LEU162 | CG | 9.695 | 20.714 | −21.671 |
| 1222 | LEU162 | CD1 | 9.416 | 22.218 | −21.608 |
| 1223 | LEU162 | CD2 | 10.961 | 20.379 | −20.884 |
| 1224 | VAL163 | N | 6.852 | 16.608 | −21.195 |
| 1225 | VAL163 | CA | 5.733 | 15.782 | −20.703 |
| 1226 | VAL163 | C | 6.309 | 14.359 | −20.709 |
| 1227 | VAL163 | O | 7.323 | 14.092 | −21.364 |
| 1228 | VAL163 | CB | 4.505 | 16.045 | −21.609 |
| 1229 | VAL163 | CG1 | 3.751 | 14.822 | −22.116 |
| 1230 | VAL163 | CG2 | 3.528 | 16.978 | −20.898 |
| 1231 | PHE164 | N | 5.641 | 13.412 | −19.96 |
| 1232 | PHE164 | CA | 6.097 | 12.023 | −19.996 |
| 1233 | PHE164 | C | 5.696 | 11.42 | −21.353 |
| 1234 | PHE164 | O | 4.599 | 11.614 | −21.871 |
| 1235 | PHE164 | CB | 5.51 | 11.16 | −18.874 |
| 1236 | PHE164 | CG | 6.08 | 11.364 | −17.485 |
| 1237 | PHE164 | CD1 | 5.246 | 11.166 | −16.374 |
| 1238 | PHE164 | CD2 | 7.433 | 11.648 | −17.25 |
| 1239 | PHE164 | CE1 | 5.739 | 11.272 | −15.071 |
| 1240 | PHE164 | CE2 | 7.928 | 11.755 | −15.947 |
| 1241 | PHE164 | CZ | 7.081 | 11.568 | −14.858 |
| 1242 | VAL165 | N | 6.676 | 10.652 | −21.956 |
| 1243 | VAL165 | CA | 6.617 | 10.292 | −23.37 |
| 1244 | VAL165 | C | 7.345 | 8.961 | −23.613 |
| 1245 | VAL165 | O | 8.126 | 8.471 | −22.805 |
| 1246 | VAL165 | CB | 7.223 | 11.381 | −24.302 |
| 1247 | VAL165 | CG1 | 6.328 | 12.612 | −24.414 |
| 1248 | VAL165 | CG2 | 8.64 | 11.794 | −23.892 |
| 1249 | SER166 | N | 7.079 | 8.398 | −24.848 |
| 1250 | SER166 | CA | 7.919 | 7.347 | −25.421 |
| 1251 | SER166 | C | 7.498 | 7.205 | −26.902 |
| 1252 | SER166 | O | 6.799 | 8.053 | −27.462 |
| 1253 | SER166 | CB | 7.877 | 6.045 | −24.628 |
| 1254 | SER166 | OG | 8.632 | 5.033 | −25.298 |
| 1255 | SER167 | N | 8.079 | 6.144 | −27.575 |
| 1256 | SER167 | CA | 8.464 | 6.287 | −28.98 |
| 1257 | SER167 | C | 8.573 | 4.942 | −29.715 |
| 1258 | SER167 | O | 9.355 | 4.741 | −30.642 |
| 1259 | SER167 | CB | 9.76 | 7.099 | −29.116 |
| 1260 | SER167 | OG | 10.789 | 6.523 | −28.311 |
| 1261 | THR168 | N | 7.578 | 4.041 | −29.385 |
| 1262 | THR168 | CA | 7.352 | 2.822 | −30.159 |
| 1263 | THR168 | C | 5.861 | 2.433 | −30.103 |
| 1264 | THR168 | O | 4.999 | 3.146 | −29.584 |
| 1265 | THR168 | CB | 8.308 | 1.676 | −29.773 |
| 1266 | THR168 | OG1 | 8.098 | 0.575 | −30.674 |
| 1267 | THR168 | CG2 | 8.139 | 1.18 | −28.343 |
| 1268 | TYR169 | N | 5.555 | 1.224 | −30.708 |
| 1269 | TYR169 | CA | 4.235 | 0.981 | −31.326 |
| 1270 | TYR169 | C | 3.133 | 0.935 | −30.247 |
| 1271 | TYR169 | O | 1.952 | 1.171 | −30.479 |
| 1272 | TYR169 | CB | 4.186 | −0.38 | −32.048 |
| 1273 | TYR169 | CG | 4.901 | −0.542 | −33.373 |
| 1274 | TYR169 | CD1 | 5.939 | 0.286 | −33.819 |
| 1275 | TYR169 | CD2 | 4.514 | −1.623 | −34.188 |
| 1276 | TYR169 | CE1 | 6.569 | 0.048 | −35.046 |
| 1277 | TYR169 | CE2 | 5.137 | −1.86 | −35.414 |
| 1278 | TYR169 | CZ | 6.16 | −1.023 | −35.835 |
| 1279 | TYR169 | OH | 6.741 | −1.283 | −37.041 |
| 1280 | LYS170 | N | 3.604 | 0.444 | −29.05 |
| 1281 | LYS170 | CA | 2.798 | 0.211 | −27.851 |
| 1282 | LYS170 | C | 2.744 | 1.483 | −26.973 |
| 1283 | LYS170 | O | 1.97 | 1.612 | −26.026 |
| 1284 | LYS170 | CB | 3.513 | −0.903 | −27.078 |
| 1285 | LYS170 | CG | 2.592 | −1.758 | −26.213 |
| 1286 | LYS170 | CD | 3.445 | −2.788 | −25.473 |
| 1287 | LYS170 | CE | 2.645 | −3.746 | −24.614 |
| 1288 | LYS170 | NZ | 3.578 | −4.381 | −23.651 |
| 1289 | ASN171 | N | 3.768 | 2.368 | −27.234 |
| 1290 | ASN171 | CA | 4.157 | 3.465 | −26.36 |
| 1291 | ASN171 | C | 3.766 | 4.86 | −26.88 |
| 1292 | ASN171 | O | 3.772 | 5.831 | −26.123 |
| 1293 | ASN171 | CB | 5.673 | 3.426 | −26.177 |
| 1294 | ASN171 | CG | 6.106 | 2.591 | −24.996 |
| 1295 | ASN171 | OD1 | 6.751 | 1.552 | −25.119 |
| 1296 | ASN171 | ND2 | 5.736 | 3.079 | −23.775 |
| 1297 | LEU172 | N | 3.56 | 4.976 | −28.242 |
| 1298 | LEU172 | CA | 3.524 | 6.295 | −28.877 |
| 1299 | LEU172 | C | 2.334 | 7.141 | −28.378 |
| 1300 | LEU172 | O | 1.156 | 6.825 | −28.533 |
| 1301 | LEU172 | CB | 3.413 | 6.16 | −30.41 |
| 1302 | LEU172 | CG | 4.79 | 6.179 | −31.103 |
| 1303 | LEU172 | CD1 | 4.705 | 5.551 | −32.493 |
| 1304 | LEU172 | CD2 | 5.329 | 7.605 | −31.219 |
| 1305 | PHE173 | N | 2.709 | 8.282 | −27.695 |
| 1306 | PHE173 | CA | 1.821 | 9.402 | −27.38 |
| 1307 | PHE173 | C | 0.666 | 9.132 | −26.405 |
| 1308 | PHE173 | O | 0.273 | 10.019 | −25.637 |
| 1309 | PHE173 | CB | 1.276 | 10.121 | −28.626 |
| 1310 | PHE173 | CG | 2.341 | 10.844 | −29.423 |
| 1311 | PHE173 | CD1 | 2.506 | 10.572 | −30.787 |
| 1312 | PHE173 | CD2 | 3.148 | 11.827 | −28.829 |
| 1313 | PHE173 | CE1 | 3.466 | 11.258 | −31.533 |
| 1314 | PHE173 | CE2 | 4.118 | 12.501 | −29.574 |
| 1315 | PHE173 | CZ | 4.274 | 12.219 | −30.927 |
| 1316 | TRP174 | N | 0.023 | 7.916 | −26.48 |
| 1317 | TRP174 | CA | −1.29 | 7.75 | −25.846 |
| 1318 | TRP174 | C | −1.183 | 8.012 | −24.328 |
| 1319 | TRP174 | O | −2.097 | 8.524 | −23.68 |
| 1320 | TRP174 | CB | −1.927 | 6.381 | −26.136 |
| 1321 | TRP174 | CG | −1.211 | 5.23 | −25.501 |
| 1322 | TRP174 | CD1 | −0.168 | 4.507 | −26.045 |
| 1323 | TRP174 | CD2 | −1.461 | 4.683 | −24.201 |
| 1324 | TRP174 | NE1 | 0.247 | 3.582 | −25.124 |
| 1325 | TRP174 | CE2 | −0.482 | 3.72 | −23.964 |
| 1326 | TRP174 | CE3 | −2.406 | 4.949 | −23.187 |
| 1327 | TRP174 | CZ2 | −0.367 | 3.063 | −22.735 |
| 1328 | TRP174 | CZ3 | −2.329 | 4.256 | −21.975 |
| 1329 | TRP174 | CH2 | −1.31 | 3.34 | −21.745 |
| 1330 | GLY175 | N | 0.002 | 7.587 | −23.752 |
| 1331 | GLY175 | CA | 0.236 | 7.682 | −22.325 |
| 1332 | GLY175 | C | 0.629 | 9.101 | −21.926 |
| 1333 | GLY175 | O | 0.44 | 9.536 | −20.791 |
| 1334 | ALA176 | N | 1.254 | 9.821 | −22.928 |
| 1335 | ALA176 | CA | 1.572 | 11.239 | −22.756 |
| 1336 | ALA176 | C | 0.261 | 12.029 | −22.715 |
| 1337 | ALA176 | O | 0.075 | 12.979 | −21.955 |
| 1338 | ALA176 | CB | 2.429 | 11.734 | −23.913 |
| 1339 | LEU177 | N | −0.676 | 11.617 | −23.645 |
| 1340 | LEU177 | CA | −1.98 | 12.249 | −23.72 |
| 1341 | LEU177 | C | −2.785 | 11.896 | −22.451 |
| 1342 | LEU177 | O | −3.58 | 12.7 | −21.959 |
| 1343 | LEU177 | CB | −2.706 | 11.834 | −25 |
| 1344 | LEU177 | CG | −2.049 | 12.401 | −26.277 |
| 1345 | LEU177 | CD1 | −2.554 | 11.649 | −27.507 |
| 1346 | LEU177 | CD2 | −2.312 | 13.898 | −26.435 |
| 1347 | LEU178 | N | −2.592 | 10.625 | −21.934 |
| 1348 | LEU178 | CA | −3.28 | 10.202 | −20.707 |
| 1349 | LEU178 | C | −2.707 | 10.975 | −19.493 |
| 1350 | LEU178 | O | −3.431 | 11.346 | −18.565 |
| 1351 | LEU178 | CB | −3.153 | 8.688 | −20.509 |
| 1352 | LEU178 | CG | −3.953 | 8.098 | −19.331 |
| 1353 | LEU178 | CD1 | −5.449 | 8.386 | −19.425 |
| 1354 | LEU178 | CD2 | −3.751 | 6.582 | −19.292 |
| 1355 | GLU179 | N | −1.337 | 11.179 | −19.493 |
| 1356 | GLU179 | CA | −0.666 | 11.977 | −18.452 |
| 1357 | GLU179 | C | −1.269 | 13.394 | −18.502 |
| 1358 | GLU179 | O | −1.645 | 13.991 | −17.49 |
| 1359 | GLU179 | CB | 0.855 | 11.976 | −18.681 |
| 1360 | GLU179 | CG | 1.656 | 12.821 | −17.692 |
| 1361 | GLU179 | CD | 2.28 | 14.011 | −18.424 |
| 1362 | GLU179 | OE1 | 3.48 | 13.853 | −18.808 |
| 1363 | GLU179 | OE2 | 1.514 | 15.003 | −18.568 |
| 1364 | LYS180 | N | −1.378 | 13.922 | −19.776 |
| 1365 | LYS180 | CA | −1.856 | 15.282 | −19.97 |
| 1366 | LYS180 | C | −3.353 | 15.369 | −19.581 |
| 1367 | LYS180 | O | −3.847 | 16.402 | −19.118 |
| 1368 | LYS180 | CB | −1.6 | 15.696 | −21.418 |
| 1369 | LYS180 | CG | −2.039 | 17.119 | −21.728 |

TABLE V-continued

| Atom No | Residue | Atom name | x coord | y coord | z coord |
|---|---|---|---|---|---|
| 1370 | LYS180 | CD | −1.673 | 17.5 | −23.169 |
| 1371 | LYS180 | CE | −2.371 | 18.765 | −23.644 |
| 1372 | LYS180 | NZ | −3.814 | 18.529 | −23.623 |
| 1373 | ALA181 | N | −4.117 | 14.246 | −19.843 |
| 1374 | ALA181 | CA | −5.532 | 14.194 | −19.486 |
| 1375 | ALA181 | C | −5.69 | 14.205 | −17.958 |
| 1376 | ALA181 | O | −6.638 | 14.765 | −17.406 |
| 1377 | ALA181 | CB | −6.199 | 12.946 | −20.04 |
| 1378 | TYR182 | N | −4.741 | 13.478 | −17.262 |
| 1379 | TYR182 | CA | −4.747 | 13.443 | −15.796 |
| 1380 | TYR182 | C | −4.457 | 14.878 | −15.312 |
| 1381 | TYR182 | O | −5.095 | 15.396 | −14.394 |
| 1382 | TYR182 | CB | −3.706 | 12.448 | −15.261 |
| 1383 | TYR182 | CG | −3.807 | 11.985 | −13.822 |
| 1384 | TYR182 | CD1 | −2.727 | 11.247 | −13.3 |
| 1385 | TYR182 | CD2 | −4.931 | 12.18 | −13.008 |
| 1386 | TYR182 | CE1 | −2.776 | 10.707 | −12.013 |
| 1387 | TYR182 | CE2 | −4.982 | 11.63 | −11.721 |
| 1388 | TYR182 | CZ | −3.915 | 10.88 | −11.242 |
| 1389 | TYR182 | OH | −3.965 | 10.288 | −10.012 |
| 1390 | ALA183 | N | −3.434 | 15.531 | −15.988 |
| 1391 | ALA183 | CA | −3.038 | 16.884 | −15.608 |
| 1392 | ALA183 | C | −4.202 | 17.867 | −15.839 |
| 1393 | ALA183 | O | −4.4 | 18.834 | −15.1 |
| 1394 | ALA183 | CB | −1.832 | 17.348 | −16.408 |
| 1395 | LYS184 | N | −4.981 | 17.64 | −16.97 |
| 1396 | LYS184 | CA | −5.99 | 18.628 | −17.348 |
| 1397 | LYS184 | C | −7.037 | 18.763 | −16.233 |
| 1398 | LYS184 | O | −7.581 | 19.841 | −15.989 |
| 1399 | LYS184 | CB | −6.679 | 18.274 | −18.681 |
| 1400 | LYS184 | CG | −7.882 | 19.184 | −18.979 |
| 1401 | LYS184 | CD | −8.472 | 18.994 | −20.377 |
| 1402 | LYS184 | CE | −9.794 | 19.745 | −20.487 |
| 1403 | LYS184 | NZ | −10.324 | 19.656 | −21.85 |
| 1404 | LEU185 | N | −7.438 | 17.54 | −15.652 |
| 1405 | LEU185 | CA | −8.502 | 17.579 | −14.661 |
| 1406 | LEU185 | C | −7.993 | 18.015 | −13.276 |
| 1407 | LEU185 | O | −8.758 | 18.521 | −12.443 |
| 1408 | LEU185 | CB | −9.19 | 16.216 | −14.574 |
| 1409 | LEU185 | CG | −10.637 | 16.334 | −14.048 |
| 1410 | LEU185 | CD1 | −11.596 | 16.865 | −15.116 |
| 1411 | LEU185 | CD2 | −11.116 | 14.98 | −13.546 |
| 1412 | SER186 | N | −6.679 | 17.712 | −12.974 |
| 1413 | SER186 | CA | −6.082 | 18.2 | −11.73 |
| 1414 | SER186 | C | −5.982 | 19.731 | −11.809 |
| 1415 | SER186 | O | −6.408 | 20.446 | −10.901 |
| 1416 | SER186 | CB | −4.744 | 17.544 | −11.396 |
| 1417 | SER186 | OG | −3.726 | 17.894 | −12.319 |
| 1418 | GLY187 | N | −5.389 | 20.215 | −12.954 |
| 1419 | GLY187 | CA | −5.295 | 21.628 | −13.244 |
| 1420 | GLY187 | C | −4.073 | 21.958 | −14.088 |
| 1421 | GLY187 | O | −4.101 | 22.845 | −14.942 |
| 1422 | SER188 | N | −2.929 | 21.274 | −13.737 |
| 1423 | SER188 | CA | −1.635 | 21.633 | −14.299 |
| 1424 | SER188 | C | −0.634 | 20.464 | −14.245 |
| 1425 | SER188 | O | −0.86 | 19.395 | −13.679 |
| 1426 | SER188 | CB | −1.08 | 22.931 | −13.683 |
| 1427 | SER188 | OG | −1.317 | 23.08 | −12.285 |
| 1428 | TYR189 | N | 0.559 | 20.686 | −14.923 |
| 1429 | TYR189 | CA | 1.584 | 19.634 | −14.924 |
| 1430 | TYR189 | C | 2.307 | 19.583 | −13.564 |
| 1431 | TYR189 | O | 2.837 | 18.545 | −13.161 |
| 1432 | TYR189 | CB | 2.64 | 19.809 | −16.024 |
| 1433 | TYR189 | CG | 2.104 | 19.641 | −17.427 |
| 1434 | TYR189 | CD1 | 2.367 | 20.614 | −18.397 |
| 1435 | TYR189 | CD2 | 1.388 | 18.501 | −17.808 |
| 1436 | TYR189 | CE1 | 1.864 | 20.5 | −19.69 |
| 1437 | TYR189 | CE2 | 0.894 | 18.376 | −19.107 |
| 1438 | TYR189 | CZ | 1.125 | 19.379 | −20.036 |
| 1439 | TYR189 | OH | 0.641 | 19.22 | −21.301 |
| 1440 | GLU190 | N | 2.384 | 20.786 | −12.876 |
| 1441 | GLU190 | CA | 3.168 | 20.899 | −11.632 |
| 1442 | GLU190 | C | 2.609 | 19.903 | −10.583 |
| 1443 | GLU190 | O | 3.317 | 19.387 | −9.715 |
| 1444 | GLU190 | CB | 3.086 | 22.345 | −11.112 |
| 1445 | GLU190 | CG | 3.854 | 22.683 | −9.83 |
| 1446 | GLU190 | CD | 5.371 | 22.781 | −9.988 |
| 1447 | GLU190 | OE1 | 5.914 | 21.822 | −10.607 |
| 1448 | GLU190 | OE2 | 5.92 | 23.794 | −9.457 |
| 1449 | ASP191 | N | 1.247 | 19.682 | −10.688 |
| 1450 | ASP191 | CA | 0.426 | 19.049 | −9.662 |
| 1451 | ASP191 | C | 0.887 | 17.614 | −9.366 |
| 1452 | ASP191 | O | 0.648 | 17.058 | −8.296 |
| 1453 | ASP191 | CB | −1.033 | 18.939 | −10.123 |
| 1454 | ASP191 | CG | −1.597 | 20.089 | −10.935 |
| 1455 | ASP191 | OD1 | −2.749 | 19.891 | −11.438 |
| 1456 | ASP191 | OD2 | −0.842 | 21.096 | −11.106 |
| 1457 | LEU192 | N | 1.439 | 16.958 | −10.45 |
| 1458 | LEU192 | CA | 1.598 | 15.508 | −10.482 |
| 1459 | LEU192 | C | 2.801 | 15.062 | −9.63 |
| 1460 | LEU192 | O | 2.951 | 13.901 | −9.246 |
| 1461 | LEU192 | CB | 1.795 | 15.005 | −11.92 |
| 1462 | LEU192 | CG | 0.622 | 15.292 | −12.882 |
| 1463 | LEU192 | CD1 | 0.972 | 14.781 | −14.281 |
| 1464 | LEU192 | CD2 | −0.69 | 14.659 | −12.415 |
| 1465 | GLN193 | N | 3.748 | 16.036 | −9.4 |
| 1466 | GLN193 | CA | 4.968 | 15.752 | −8.659 |
| 1467 | GLN193 | C | 4.574 | 15.629 | −7.176 |
| 1468 | GLN193 | O | 4.262 | 16.607 | −6.498 |
| 1469 | GLN193 | CB | 5.987 | 16.876 | −8.833 |
| 1470 | GLN193 | CG | 6.408 | 17.051 | −10.293 |
| 1471 | GLN193 | CD | 6.947 | 18.435 | −10.567 |
| 1472 | GLN193 | OE1 | 8.067 | 18.62 | −11.029 |
| 1473 | GLN193 | NE2 | 6.061 | 19.431 | −10.274 |
| 1474 | SER194 | N | 4.539 | 14.329 | −6.718 |
| 1475 | SER194 | CA | 3.995 | 13.858 | −5.439 |
| 1476 | SER194 | C | 2.514 | 13.433 | −5.505 |
| 1477 | SER194 | O | 1.863 | 13.182 | −4.484 |
| 1478 | SER194 | CB | 4.308 | 14.701 | −4.189 |
| 1479 | SER194 | OG | 3.332 | 15.722 | −3.907 |
| 1480 | GLY195 | N | 2.041 | 13.202 | −6.782 |
| 1481 | GLY195 | CA | 1.101 | 12.127 | −7.04 |
| 1482 | GLY195 | C | 1.928 | 10.845 | −7.219 |
| 1483 | GLY195 | O | 3.15 | 10.857 | −7.377 |
| 1484 | GLN196 | N | 1.186 | 9.688 | −7.163 |
| 1485 | GLN196 | CA | 1.797 | 8.377 | −7.026 |
| 1486 | GLN196 | C | 0.965 | 7.331 | −7.793 |
| 1487 | GLN196 | O | −0.253 | 7.41 | −7.969 |
| 1488 | GLN196 | CB | 1.808 | 7.923 | −5.553 |
| 1489 | GLN196 | CG | 2.661 | 8.755 | −4.601 |
| 1490 | GLN196 | CD | 2.095 | 8.793 | −3.196 |
| 1491 | GLN196 | OE1 | 1.964 | 9.849 | −2.572 |
| 1492 | GLN196 | NE2 | 1.777 | 7.59 | −2.63 |
| 1493 | VAL197 | N | 1.681 | 6.168 | −8.084 |
| 1494 | VAL197 | CA | 1.01 | 5.06 | −8.774 |
| 1495 | VAL197 | C | −0.116 | 4.492 | −7.891 |
| 1496 | VAL197 | O | −1.095 | 3.91 | −8.354 |
| 1497 | VAL197 | CB | 1.965 | 3.914 | −9.166 |
| 1498 | VAL197 | CG1 | 2.893 | 4.344 | −10.297 |
| 1499 | VAL197 | CG2 | 2.792 | 3.356 | −8.003 |
| 1500 | SER198 | N | 0.102 | 4.647 | −6.537 |
| 1501 | SER198 | CA | −0.789 | 4.109 | −5.523 |
| 1502 | SER198 | C | −2.164 | 4.782 | −5.597 |
| 1503 | SER198 | O | −3.17 | 4.207 | −5.178 |
| 1504 | SER198 | CB | −0.199 | 4.308 | −4.12 |
| 1505 | SER198 | OG | 0.213 | 5.664 | −3.897 |
| 1506 | GLU199 | N | −2.127 | 6.1 | −6.024 |
| 1507 | GLU199 | CA | −3.344 | 6.848 | −6.325 |
| 1508 | GLU199 | C | −3.753 | 6.559 | −7.786 |
| 1509 | GLU199 | O | −4.916 | 6.304 | −8.108 |
| 1510 | GLU199 | CB | −3.127 | 8.357 | −6.167 |
| 1511 | GLU199 | CG | −2.568 | 8.791 | −4.805 |
| 1512 | GLU199 | CD | −1.449 | 9.818 | −4.893 |
| 1513 | GLU199 | OE1 | −0.876 | 9.96 | −6.007 |
| 1514 | GLU199 | OE2 | −1.141 | 10.415 | −3.814 |
| 1515 | ALA200 | N | −2.74 | 6.657 | −8.734 |
| 1516 | ALA200 | CA | −3.103 | 6.771 | −10.149 |
| 1517 | ALA200 | C | −3.797 | 5.49 | −10.633 |
| 1518 | ALA200 | O | −4.67 | 5.494 | −11.502 |
| 1519 | ALA200 | CB | −1.874 | 7.023 | −11.007 |
| 1520 | LEU201 | N | −3.322 | 4.319 | −10.067 |
| 1521 | LEU201 | CA | −3.888 | 3.038 | −10.447 |
| 1522 | LEU201 | C | −5.325 | 2.882 | −9.906 |
| 1523 | LEU201 | O | −6.103 | 2.079 | −10.432 |

TABLE V-continued

| Atom No | Residue | Atom name | x coord | y coord | z coord |
|---|---|---|---|---|---|
| 1524 | LEU201 | CB | -3.011 | 1.864 | -9.998 |
| 1525 | LEU201 | CG | -1.642 | 1.78 | -10.709 |
| 1526 | LEU201 | CD1 | -0.767 | 0.732 | -10.018 |
| 1527 | LEU201 | CD2 | -1.779 | 1.433 | -12.193 |
| 1528 | VAL202 | N | -5.667 | 3.646 | -8.801 |
| 1529 | VAL202 | CA | -7.065 | 3.737 | -8.368 |
| 1530 | VAL202 | C | -7.818 | 4.513 | -9.456 |
| 1531 | VAL202 | O | -8.867 | 4.067 | -9.927 |
| 1532 | VAL202 | CB | -7.246 | 4.416 | -6.992 |
| 1533 | VAL202 | CG1 | -8.72 | 4.645 | -6.65 |
| 1534 | VAL202 | CG2 | -6.578 | 3.6 | -5.892 |
| 1535 | ASP203 | N | -7.254 | 5.713 | -9.85 |
| 1536 | ASP203 | CA | -8.006 | 6.652 | -10.692 |
| 1537 | ASP203 | C | -8.397 | 5.992 | -12.047 |
| 1538 | ASP203 | O | -9.411 | 6.314 | -12.673 |
| 1539 | ASP203 | CB | -7.187 | 7.906 | -10.97 |
| 1540 | ASP203 | CG | -7.174 | 8.932 | -9.842 |
| 1541 | ASP203 | OD1 | -8.293 | 9.338 | -9.338 |
| 1542 | ASP203 | OD2 | -6.035 | 9.446 | -9.607 |
| 1543 | PHE204 | N | -7.478 | 5.086 | -12.557 |
| 1544 | PHE204 | CA | -7.72 | 4.42 | -13.845 |
| 1545 | PHE204 | C | -8.653 | 3.196 | -13.671 |
| 1546 | PHE204 | O | -9.343 | 2.734 | -14.585 |
| 1547 | PHE204 | CB | -6.418 | 3.901 | -14.479 |
| 1548 | PHE204 | CG | -5.392 | 4.96 | -14.801 |
| 1549 | PHE204 | CD1 | -5.721 | 6.123 | -15.505 |
| 1550 | PHE204 | CD2 | -4.062 | 4.771 | -14.4 |
| 1551 | PHE204 | CE1 | -4.747 | 7.093 | -15.756 |
| 1552 | PHE204 | CE2 | -3.099 | 5.749 | -14.641 |
| 1553 | PHE204 | CZ | -3.439 | 6.913 | -15.318 |
| 1554 | THR205 | N | -8.498 | 2.525 | -12.471 |
| 1555 | THR205 | CA | -9.181 | 1.26 | -12.237 |
| 1556 | THR205 | C | -10.57 | 1.499 | -11.629 |
| 1557 | THR205 | O | -11.559 | 0.925 | -12.094 |
| 1558 | THR205 | CB | -8.375 | 0.292 | -11.355 |
| 1559 | THR205 | OG1 | -7.023 | 0.205 | -11.813 |
| 1560 | THR205 | OG2 | -8.953 | -1.117 | -11.399 |
| 1561 | GLY206 | N | -10.57 | 2.248 | -10.471 |
| 1562 | GLY206 | CA | -11.736 | 2.417 | -9.612 |
| 1563 | GLY206 | C | -11.773 | 1.408 | -8.46 |
| 1564 | GLY206 | O | -12.704 | 1.354 | -7.66 |
| 1565 | GLY207 | N | -10.674 | 0.575 | -8.411 |
| 1566 | GLY207 | CA | -10.481 | -0.4 | -7.359 |
| 1567 | GLY207 | C | -9.701 | 0.191 | -6.19 |
| 1568 | GLY207 | O | -9.342 | 1.364 | -6.144 |
| 1569 | VAL208 | N | -9.446 | -0.722 | -5.185 |
| 1570 | VAL208 | CA | -8.721 | -0.33 | -3.977 |
| 1571 | VAL208 | C | -7.241 | -0.71 | -4.177 |
| 1572 | VAL208 | O | -6.892 | -1.808 | -4.614 |
| 1573 | VAL208 | CB | -9.326 | -1.027 | -2.736 |
| 1574 | VAL208 | CG1 | -8.569 | -0.683 | -1.451 |
| 1575 | VAL208 | CG2 | -10.802 | -0.645 | -2.557 |
| 1576 | THR209 | N | -6.341 | 0.271 | -3.793 |
| 1577 | THR209 | CA | -4.903 | -0.012 | -3.717 |
| 1578 | THR209 | C | -4.681 | -0.655 | -2.348 |
| 1579 | THR209 | O | -5.049 | -0.111 | -1.308 |
| 1580 | THR209 | CB | -4.045 | 1.266 | -3.824 |
| 1581 | THR209 | OG1 | -4.047 | 1.727 | -5.178 |
| 1582 | THR209 | CG2 | -2.587 | 1.029 | -3.45 |
| 1583 | MET210 | N | -4.037 | -1.872 | -2.386 |
| 1584 | MET210 | CA | -3.614 | -2.558 | -1.167 |
| 1585 | MET210 | C | -2.079 | -2.547 | -1.22 |
| 1586 | MET210 | O | -1.446 | -3.248 | -2.012 |
| 1587 | MET210 | CB | -4.185 | -3.983 | -1.139 |
| 1588 | MET210 | CG | -4.994 | -4.283 | 0.122 |
| 1589 | MET210 | SD | -3.932 | -4.483 | 1.581 |
| 1590 | MET210 | CE | -5.23 | -4.677 | 2.828 |
| 1591 | THR211 | N | -1.497 | -1.595 | -0.405 |
| 1592 | THR211 | CA | -0.058 | -1.513 | -0.171 |
| 1593 | THR211 | C | 0.329 | -2.517 | 0.925 |
| 1594 | THR211 | O | -0.404 | -2.788 | 1.874 |
| 1595 | THR211 | CB | 0.362 | -0.109 | 0.315 |
| 1596 | THR211 | OG1 | -0.653 | 0.417 | 1.181 |
| 1597 | THR211 | CG2 | 0.568 | 0.868 | -0.834 |
| 1598 | ILE212 | N | 1.606 | -3.032 | 0.784 |
| 1599 | ILE212 | CA | 2.161 | -3.992 | 1.731 |
| 1600 | ILE212 | C | 3.653 | -3.623 | 1.842 |
| 1601 | ILE212 | O | 4.439 | -3.679 | 0.89 |
| 1602 | ILE212 | CB | 1.996 | -5.467 | 1.269 |
| 1603 | ILE212 | CG1 | 0.544 | -5.787 | 0.842 |
| 1604 | ILE212 | CG2 | 2.459 | -6.409 | 2.391 |
| 1605 | ILE212 | CD1 | 0.323 | -7.224 | 0.389 |
| 1606 | ASN213 | N | 4.051 | -3.196 | 3.097 |
| 1607 | ASN213 | CA | 5.445 | -2.852 | 3.377 |
| 1608 | ASN213 | C | 6.198 | -4.176 | 3.565 |
| 1609 | ASN213 | O | 6.374 | -4.712 | 4.655 |
| 1610 | ASN213 | CB | 5.591 | -1.95 | 4.597 |
| 1611 | ASN213 | CG | 5.543 | -0.495 | 4.194 |
| 1612 | ASN213 | OD1 | 4.56 | 0.217 | 4.374 |
| 1613 | ASN213 | ND2 | 6.679 | -0.011 | 3.606 |
| 1614 | LEU214 | N | 6.631 | -4.743 | 2.372 |
| 1615 | LEU214 | CA | 6.849 | -6.196 | 2.257 |
| 1616 | LEU214 | C | 7.948 | -6.786 | 3.164 |
| 1617 | LEU214 | O | 8.071 | -8 | 3.325 |
| 1618 | LEU214 | CB | 7.21 | -6.524 | 0.797 |
| 1619 | LEU214 | CG | 6.781 | -7.924 | 0.322 |
| 1620 | LEU214 | CD1 | 5.264 | -8.091 | 0.35 |
| 1621 | LEU214 | CD2 | 7.299 | -8.169 | -1.097 |
| 1622 | ALA215 | N | 8.799 | -5.866 | 3.743 |
| 1623 | ALA215 | CA | 9.746 | -6.28 | 4.771 |
| 1624 | ALA215 | C | 9.004 | -6.749 | 6.035 |
| 1625 | ALA215 | O | 9.443 | -7.658 | 6.743 |
| 1626 | ALA215 | CB | 10.69 | -5.138 | 5.114 |
| 1627 | GLU216 | N | 7.856 | -6.051 | 6.362 |
| 1628 | GLU216 | CA | 6.965 | -6.512 | 7.432 |
| 1629 | GLU216 | C | 6.126 | -7.656 | 6.824 |
| 1630 | GLU216 | O | 4.964 | -7.535 | 6.437 |
| 1631 | GLU216 | CB | 6.095 | -5.354 | 7.928 |
| 1632 | GLU216 | CG | 5.351 | -5.703 | 9.216 |
| 1633 | GLU216 | CD | 4.479 | -4.568 | 9.76 |
| 1634 | GLU216 | OE1 | 4.149 | -4.705 | 10.973 |
| 1635 | GLU216 | OE2 | 4.185 | -3.649 | 8.948 |
| 1636 | ALA217 | N | 6.837 | -8.845 | 6.702 |
| 1637 | ALA217 | CA | 6.304 | -9.929 | 5.891 |
| 1638 | ALA217 | C | 5.088 | -10.522 | 6.619 |
| 1639 | ALA217 | O | 5.13 | -10.958 | 7.768 |
| 1640 | ALA217 | CB | 7.341 | -11.017 | 5.666 |
| 1641 | HIS218 | N | 3.921 | -10.47 | 5.876 |
| 1642 | HIS218 | CA | 2.657 | -10.92 | 6.446 |
| 1643 | HIS218 | C | 2.558 | -12.444 | 6.27 |
| 1644 | HIS218 | O | 3.016 | -13.043 | 5.297 |
| 1645 | HIS218 | CB | 1.464 | -10.242 | 5.762 |
| 1646 | HIS218 | CG | 1.262 | -8.812 | 6.152 |
| 1647 | HIS218 | ND1 | 2.268 | -7.905 | 6.403 |
| 1648 | HIS218 | CD2 | 0.101 | -8.086 | 6.327 |
| 1649 | HIS218 | CE1 | 1.678 | -6.716 | 6.736 |
| 1650 | HIS218 | NE2 | 0.368 | -6.792 | 6.683 |
| 1651 | GLY219 | N | 1.808 | -13.081 | 7.253 |
| 1652 | GLY219 | CA | 1.951 | -14.522 | 7.447 |
| 1653 | GLY219 | C | 1.238 | -15.416 | 6.431 |
| 1654 | GLY219 | O | 1.25 | -16.64 | 6.533 |
| 1655 | ASN220 | N | 0.606 | -14.742 | 5.413 |
| 1656 | ASN220 | CA | -0.097 | -15.41 | 4.321 |
| 1657 | ASN220 | C | 0.08 | -14.582 | 3.033 |
| 1658 | ASN220 | O | -0.798 | -14.425 | 2.188 |
| 1659 | ASN220 | CB | -1.55 | -15.706 | 4.677 |
| 1660 | ASN220 | CG | -2.411 | -14.472 | 4.791 |
| 1661 | ASN220 | OD1 | -3.291 | -14.195 | 3.978 |
| 1662 | ASN220 | ND2 | -2.161 | -13.678 | 5.875 |
| 1663 | LEU221 | N | 1.381 | -14.127 | 2.838 |
| 1664 | LEU221 | CA | 1.657 | -13.17 | 1.758 |
| 1665 | LEU221 | C | 1.537 | -13.871 | 0.395 |
| 1666 | LEU221 | O | 1.097 | -13.298 | -0.603 |
| 1667 | LEU221 | CB | 3.045 | -12.546 | 1.961 |
| 1668 | LEU221 | CG | 3.463 | -11.398 | 1.019 |
| 1669 | LEU221 | CD1 | 4.053 | -11.903 | -0.296 |
| 1670 | LEU221 | CD2 | 2.349 | -10.38 | 0.782 |
| 1671 | TRP222 | N | 2.049 | -15.157 | 0.345 |
| 1672 | TRP222 | CA | 1.983 | -15.898 | -0.921 |
| 1673 | TRP222 | C | 0.519 | -16.115 | -1.317 |
| 1674 | TRP222 | O | 0.144 | -16.108 | -2.489 |
| 1675 | TRP222 | CB | 2.717 | -17.243 | -0.832 |
| 1676 | TRP222 | CG | 3.702 | -17.433 | -1.948 |
| 1677 | TRP222 | CD1 | 3.681 | -18.413 | -2.923 |

TABLE V-continued

| Atom No | Residue | Atom name | x coord | y coord | z coord | | Atom No | Residue | Atom name | x coord | y coord | z coord |
|---|---|---|---|---|---|---|---|---|---|---|---|---|
| 1678 | TRP222 | CD2 | 4.845 | −16.612 | −2.211 | | 1755 | ASN231 | CG | −9.222 | −10.039 | −8.619 |
| 1679 | TRP222 | NE1 | 4.778 | −18.245 | −3.728 | | 1756 | ASN231 | OD1 | −8.789 | −8.888 | −8.614 |
| 1680 | TRP222 | CE2 | 5.502 | −17.153 | −3.312 | | 1757 | ASN231 | ND2 | −10.546 | −10.28 | −8.837 |
| 1681 | TRP222 | CE3 | 5.376 | −15.448 | −1.617 | | 1758 | ARG232 | N | −6.507 | −11.647 | −10.936 |
| 1682 | TRP222 | CZ2 | 6.677 | −16.608 | −3.831 | | 1759 | ARG232 | CA | −5.833 | −11 | −12.059 |
| 1683 | TRP222 | CZ3 | 6.521 | −14.861 | −2.163 | | 1760 | ARG232 | C | −5.824 | −9.478 | −11.843 |
| 1684 | TRP222 | CH2 | 7.167 | −15.439 | −3.249 | | 1761 | ARG232 | O | −6.255 | −8.671 | −12.672 |
| 1685 | ASP223 | N | −0.329 | −16.336 | −0.26 | | 1762 | ARG232 | CB | −6.345 | −11.407 | −13.448 |
| 1686 | ASP223 | CA | −1.732 | −16.674 | −0.436 | | 1763 | ARG232 | CG | −6.11 | −12.893 | −13.724 |
| 1687 | ASP223 | C | −2.439 | −15.457 | −1.071 | | 1764 | ARG232 | CD | −6.664 | −13.312 | −15.077 |
| 1688 | ASP223 | O | −3.327 | −15.585 | −1.915 | | 1765 | ARG232 | NE | −6.351 | −14.717 | −15.369 |
| 1689 | ASP223 | CB | −2.365 | −17.05 | 0.899 | | 1766 | ARG232 | CZ | −5.132 | −15.175 | −15.748 |
| 1690 | ASP223 | CG | −1.492 | −17.936 | 1.793 | | 1767 | ARG232 | NH1 | −4.95 | −16.509 | −15.884 |
| 1691 | ASP223 | OD1 | −2.122 | −18.723 | 2.549 | | 1768 | ARG232 | NH2 | −4.091 | −14.362 | −16.01 |
| 1692 | ASP223 | OD2 | −0.241 | −17.716 | 1.707 | | 1769 | THR233 | N | −5.206 | −9.094 | −10.668 |
| 1693 | ILE224 | N | −2.011 | −14.218 | −0.61 | | 1770 | THR233 | CA | −4.818 | −7.708 | −10.41 |
| 1694 | ILE224 | CA | −2.557 | −12.964 | −1.141 | | 1771 | THR233 | C | −3.502 | −7.41 | −11.169 |
| 1695 | ILE224 | C | −2.205 | −12.885 | −2.64 | | 1772 | THR233 | O | −2.874 | −8.268 | −11.79 |
| 1696 | ILE224 | O | −3.014 | −12.473 | −3.475 | | 1773 | THR233 | CB | −4.613 | −7.455 | −8.905 |
| 1697 | ILE224 | CB | −2.02 | −11.714 | −0.388 | | 1774 | THR233 | OG1 | −3.54 | −8.265 | −8.436 |
| 1698 | ILE224 | CG1 | −2.573 | −11.676 | 1.05 | | 1775 | THR233 | CG2 | −5.843 | −7.771 | −8.071 |
| 1699 | ILE224 | CG2 | −2.385 | −10.409 | −1.116 | | 1776 | LEU234 | N | −3.086 | −6.084 | −11.103 |
| 1700 | ILE224 | CD1 | −1.906 | −10.642 | 1.947 | | 1777 | LEU234 | CA | −1.673 | −5.76 | −11.307 |
| 1701 | LEU225 | N | −0.9 | −13.202 | −2.961 | | 1778 | LEU234 | C | −1.027 | −5.808 | −9.904 |
| 1702 | LEU225 | CA | −0.423 | −13.139 | −4.339 | | 1779 | LEU234 | O | −1.659 | −5.515 | −8.885 |
| 1703 | LEU225 | C | −1.047 | −14.261 | −5.206 | | 1780 | LEU234 | CB | −1.478 | −4.37 | −11.924 |
| 1704 | LEU225 | O | −1.184 | −14.141 | −6.428 | | 1781 | LEU234 | CG | −2.119 | −4.193 | −13.316 |
| 1705 | LEU225 | CB | 1.105 | −13.173 | −4.41 | | 1782 | LEU234 | CD1 | −1.98 | −2.738 | −13.772 |
| 1706 | LEU225 | CG | 1.79 | −11.79 | −4.36 | | 1783 | LEU234 | CD2 | −1.502 | −5.121 | −14.364 |
| 1707 | LEU225 | CD1 | 1.338 | −10.9 | −3.204 | | 1784 | ILE235 | N | 0.303 | −6.192 | −9.912 |
| 1708 | LEU225 | CD2 | 3.308 | −11.981 | −4.304 | | 1785 | ILE235 | CA | 1.03 | −6.564 | −8.693 |
| 1709 | ILE226 | N | −1.398 | −15.419 | −4.543 | | 1786 | ILE235 | C | 2.451 | −6.001 | −8.879 |
| 1710 | ILE226 | CA | −2.158 | −16.482 | −5.211 | | 1787 | ILE235 | O | 3.222 | −6.474 | −9.721 |
| 1711 | ILE226 | C | −3.569 | −15.908 | −5.494 | | 1788 | ILE235 | CB | 1.117 | −8.11 | −8.538 |
| 1712 | ILE226 | O | −4.099 | −16.024 | −6.603 | | 1789 | ILE235 | CG1 | −0.254 | −8.808 | −8.634 |
| 1713 | ILE226 | CB | −2.153 | −17.799 | −4.401 | | 1790 | ILE235 | CG2 | 1.846 | −8.473 | −7.234 |
| 1714 | ILE226 | CG1 | −0.769 | −18.483 | −4.52 | | 1791 | ILE235 | CD1 | −0.173 | −10.328 | −8.602 |
| 1715 | ILE226 | CG2 | −3.251 | −18.76 | −4.869 | | 1792 | GLY236 | N | 2.759 | −4.917 | −8.08 |
| 1716 | ILE226 | CD1 | −0.545 | −19.602 | −3.512 | | 1793 | GLY236 | CA | 4.011 | −4.19 | −8.235 |
| 1717 | GLU227 | N | −4.195 | −15.25 | −4.447 | | 1794 | GLY236 | C | 4.421 | −3.56 | −6.91 |
| 1718 | GLU227 | CA | −5.531 | −14.679 | −4.634 | | 1795 | GLY236 | O | 3.603 | −3.04 | −6.148 |
| 1719 | GLU227 | C | −5.479 | −13.627 | −5.764 | | 1796 | CYS237 | N | 5.725 | −3.547 | −6.529 |
| 1720 | GLU227 | O | −6.373 | −13.499 | −6.603 | | 1797 | CYS237 | CA | 6.857 | −4.283 | −7.087 |
| 1721 | GLU227 | CB | −6.066 | −13.998 | −3.364 | | 1798 | CYS237 | C | 8.063 | −3.78 | −6.284 |
| 1722 | GLU227 | CG | −7.271 | −14.723 | −2.779 | | 1799 | CYS237 | O | 7.91 | −3.319 | −5.153 |
| 1723 | GLU227 | CD | −6.902 | −15.919 | −1.909 | | 1800 | CYS237 | CB | 6.703 | −5.791 | −6.864 |
| 1724 | GLU227 | OE1 | −6.286 | −15.606 | −0.837 | | 1801 | CYS237 | SG | 7.471 | −6.738 | −8.199 |
| 1725 | GLU227 | OE2 | −7.305 | −17.042 | −2.336 | | 1802 | GLN238 | N | 9.292 | −3.94 | −6.884 |
| 1726 | ALA228 | N | −4.374 | −12.795 | −5.728 | | 1803 | GLN238 | CA | 10.552 | −3.904 | −6.105 |
| 1727 | ALA228 | CA | −4.271 | −11.646 | −6.618 | | 1804 | GLN238 | C | 11.444 | −4.893 | −6.899 |
| 1728 | ALA228 | C | −4.181 | −12.118 | −8.08 | | 1805 | GLN238 | O | 10.903 | −5.735 | −7.626 |
| 1729 | ALA228 | O | −4.639 | −11.458 | −9.016 | | 1806 | GLN238 | CB | 11.161 | −2.511 | −5.884 |
| 1730 | ALA228 | CB | −3.029 | −10.841 | −6.274 | | 1807 | GLN238 | CG | 10.422 | −1.538 | −4.952 |
| 1731 | THR229 | N | −3.461 | −13.284 | −8.258 | | 1808 | GLN238 | CD | 10.355 | −1.958 | −3.489 |
| 1732 | THR229 | CA | −3.262 | −13.877 | −9.57 | | 1809 | GLN238 | OE1 | 11.034 | −1.48 | −2.583 |
| 1733 | THR229 | C | −4.478 | −14.672 | −10.083 | | 1810 | GLN238 | NE2 | 9.443 | −2.924 | −3.213 |
| 1734 | THR229 | O | −4.599 | −14.866 | −11.298 | | 1811 | THR239 | N | 12.807 | −4.866 | −6.7 |
| 1735 | THR229 | CB | −1.972 | −14.717 | −9.672 | | 1812 | THR239 | CA | 13.655 | −5.762 | −7.512 |
| 1736 | THR229 | OG1 | −1.776 | −15.533 | −8.52 | | 1813 | THR239 | C | 13.612 | −7.169 | −6.901 |
| 1737 | THR229 | CG2 | −0.729 | −13.851 | −9.858 | | 1814 | THR239 | O | 13.197 | −8.155 | −7.508 |
| 1738 | TYR230 | N | −5.375 | −15.178 | −9.154 | | 1815 | THR239 | CB | 15.092 | −5.205 | −7.588 |
| 1739 | TYR230 | CA | −6.665 | −15.726 | −9.594 | | 1816 | THR239 | OG1 | 14.982 | −3.829 | −7.972 |
| 1740 | TYR230 | C | −7.839 | −14.716 | −9.578 | | 1817 | THR239 | CG2 | 15.953 | −5.988 | −8.57 |
| 1741 | TYR230 | O | −8.954 | −15.009 | −10.022 | | 1818 | HIS240 | N | 14.09 | −7.248 | −5.61 |
| 1742 | TYR230 | CB | −7.009 | −17.12 | −9.043 | | 1819 | HIS240 | CA | 14.281 | −8.527 | −4.914 |
| 1743 | TYR230 | CG | −7.495 | −17.25 | −7.62 | | 1820 | HIS240 | C | 12.978 | −8.912 | −4.203 |
| 1744 | TYR230 | CD1 | −6.708 | −17.904 | −6.661 | | 1821 | HIS240 | O | 12.88 | −9.04 | −2.985 |
| 1745 | TYR230 | CD2 | −8.779 | −16.824 | −7.252 | | 1822 | HIS240 | CB | 15.458 | −8.418 | −3.936 |
| 1746 | TYR230 | CE1 | −7.187 | −18.111 | −5.364 | | 1823 | HIS240 | CG | 16.743 | −8.341 | −4.684 |
| 1747 | TYR230 | CE2 | −9.252 | −17.022 | −5.955 | | 1824 | HIS240 | ND1 | 17.417 | −9.453 | −5.129 |
| 1748 | TYR230 | CZ | −8.453 | −17.658 | −5.02 | | 1825 | HIS240 | CD2 | 17.479 | −7.272 | −5.144 |
| 1749 | TYR230 | OH | −8.933 | −17.814 | −3.747 | | 1826 | HIS240 | CE1 | 18.495 | −9.005 | −5.838 |
| 1750 | ASN231 | N | −7.53 | −13.45 | −9.12 | | 1827 | HIS240 | NE2 | 18.56 | −7.693 | −5.865 |
| 1751 | ASN231 | CA | −8.366 | −12.287 | −9.435 | | 1828 | SER241 | N | 11.916 | −9.112 | −5.071 |
| 1752 | ASN231 | C | −7.876 | −11.655 | −10.756 | | 1829 | SER241 | CA | 10.542 | −9.313 | −4.607 |
| 1753 | ASN231 | O | −8.659 | −11.094 | −11.523 | | 1830 | SER241 | C | 10.161 | −10.799 | −4.555 |
| 1754 | ASN231 | CB | −8.348 | −11.242 | −8.326 | | 1831 | SER241 | O | 9.027 | −11.208 | −4.801 |

TABLE V-continued

| Atom No | Residue | Atom name | x coord | y coord | z coord |
|---|---|---|---|---|---|
| 1832 | SER241 | CB | 9.546 | −8.498 | −5.441 |
| 1833 | SER241 | OG | 8.59 | −7.843 | −4.604 |
| 1834 | GLY242 | N | 11.138 | −11.604 | −4.005 |
| 1835 | GLY242 | CA | 10.886 | −12.991 | −3.685 |
| 1836 | GLY242 | C | 11.518 | −13.984 | −4.646 |
| 1837 | GLY242 | O | 11.058 | −15.12 | −4.768 |
| 1838 | GLU243 | N | 12.701 | −13.574 | −5.222 |
| 1839 | GLU243 | CA | 13.646 | −14.531 | −5.795 |
| 1840 | GLU243 | C | 14.662 | −14.811 | −4.652 |
| 1841 | GLU243 | O | 14.268 | −14.833 | −3.474 |
| 1842 | GLU243 | CB | 14.083 | −14.032 | −7.179 |
| 1843 | GLU243 | CG | 12.878 | −14.115 | −8.149 |
| 1844 | GLU243 | CD | 13.078 | −14.26 | −9.661 |
| 1845 | GLU243 | OE1 | 13.914 | −13.477 | −10.185 |
| 1846 | GLU243 | OE2 | 12.38 | −15.174 | −10.223 |
| 1847 | LYS244 | N | 15.967 | −15.146 | −4.963 |
| 1848 | LYS244 | CA | 16.915 | −15.495 | −3.891 |
| 1849 | LYS244 | C | 18.043 | −14.481 | −3.601 |
| 1850 | LYS244 | O | 18.714 | −14.546 | −2.563 |
| 1851 | LYS244 | CB | 17.58 | −16.87 | −4.126 |
| 1852 | LYS244 | CG | 16.585 | −18.033 | −4.084 |
| 1853 | LYS244 | CD | 17.202 | −19.34 | −3.557 |
| 1854 | LYS244 | CE | 16.229 | −20.489 | −3.773 |
| 1855 | LYS244 | NZ | 16.694 | −21.744 | −3.179 |
| 1856 | ILE245 | N | 18.33 | −13.6 | −4.621 |
| 1857 | ILE245 | CA | 19.704 | −13.1 | −4.817 |
| 1858 | ILE245 | C | 20.105 | −12.091 | −3.705 |
| 1859 | ILE245 | O | 19.301 | −11.591 | −2.912 |
| 1860 | ILE245 | CB | 19.866 | −12.645 | −6.297 |
| 1861 | ILE245 | CG1 | 19.798 | −13.898 | −7.213 |
| 1862 | ILE245 | CG2 | 21.135 | −11.843 | −6.591 |
| 1863 | ILE245 | CD1 | 19.972 | −13.612 | −8.696 |
| 1864 | LEU246 | N | 21.47 | −11.909 | −3.553 |
| 1865 | LEU246 | CA | 22.04 | −11.035 | −2.526 |
| 1866 | LEU246 | C | 21.875 | −9.555 | −2.918 |
| 1867 | LEU246 | O | 21.604 | −9.188 | −4.057 |
| 1868 | LEU246 | CB | 23.526 | −11.357 | −2.297 |
| 1869 | LEU246 | CG | 23.787 | −12.752 | −1.695 |
| 1870 | LEU246 | CD1 | 25.282 | −13.077 | −1.762 |
| 1871 | LEU246 | CD2 | 23.311 | −12.848 | −0.244 |
| 1872 | GLU247 | N | 22.06 | −8.689 | −1.856 |
| 1873 | GLU247 | CA | 21.764 | −7.257 | −1.941 |
| 1874 | GLU247 | C | 22.653 | −6.574 | −0.877 |
| 1875 | GLU247 | O | 23.403 | −7.203 | −0.125 |
| 1876 | GLU247 | CB | 20.257 | −7.031 | −1.687 |
| 1877 | GLU247 | CG | 19.585 | −6.072 | −2.672 |
| 1878 | GLU247 | CD | 19.777 | −4.615 | −2.3 |
| 1879 | GLU247 | OE1 | 18.747 | −3.984 | −1.931 |
| 1880 | GLU247 | OE2 | 20.979 | −4.202 | −2.313 |
| 1881 | ASN248 | N | 22.551 | −5.209 | −0.847 |
| 1882 | ASN248 | CA | 23.218 | −4.331 | 0.109 |
| 1883 | ASN248 | C | 22.391 | −3.063 | 0.424 |
| 1884 | ASN248 | O | 22.479 | −2.526 | 1.53 |
| 1885 | ASN248 | CB | 24.616 | −3.956 | −0.38 |
| 1886 | ASN248 | CG | 25.697 | −4.59 | 0.469 |
| 1887 | ASN248 | OD1 | 26.558 | −3.934 | 1.047 |
| 1888 | ASN248 | ND2 | 25.696 | −5.956 | 0.515 |
| 1889 | GLY249 | N | 21.675 | −2.496 | −0.615 |
| 1890 | GLY249 | CA | 20.704 | −1.458 | −0.326 |
| 1891 | GLY249 | C | 19.996 | −0.918 | −1.571 |
| 1892 | GLY249 | O | 20.588 | −0.612 | −2.604 |
| 1893 | LEU250 | N | 18.631 | −0.761 | −1.405 |
| 1894 | LEU250 | CA | 17.733 | −0.144 | −2.382 |
| 1895 | LEU250 | C | 17.442 | −1.024 | −3.615 |
| 1896 | LEU250 | O | 16.294 | −1.159 | −4.043 |
| 1897 | LEU250 | CB | 18.165 | 1.266 | −2.829 |
| 1898 | LEU250 | CG | 18.419 | 2.269 | −1.685 |
| 1899 | LEU250 | CD1 | 18.916 | 3.597 | −2.264 |
| 1900 | LEU250 | CD2 | 17.174 | 2.512 | −0.832 |
| 1901 | VAL251 | N | 18.555 | −1.5 | −4.273 |
| 1902 | VAL251 | CA | 18.487 | −2.051 | −5.63 |
| 1903 | VAL251 | C | 18.664 | −0.876 | −6.614 |
| 1904 | VAL251 | O | 19.193 | 0.189 | −6.286 |
| 1905 | VAL251 | CB | 19.538 | −3.173 | −5.802 |
| 1906 | VAL251 | CG1 | 20.982 | −2.666 | −5.845 |
| 1907 | VAL251 | CG2 | 19.264 | −4.06 | −7.016 |
| 1908 | GLU252 | N | 18.244 | −1.121 | −7.904 |
| 1909 | GLU252 | CA | 18.313 | −0.099 | −8.931 |
| 1910 | GLU252 | C | 17.064 | 0.805 | −8.898 |
| 1911 | GLU252 | O | 16.015 | 0.521 | −8.32 |
| 1912 | GLU252 | CB | 18.559 | −0.724 | −10.313 |
| 1913 | GLU252 | CG | 17.381 | −1.462 | −10.947 |
| 1914 | GLU252 | CD | 16.937 | −2.788 | −10.337 |
| 1915 | GLU252 | OE1 | 16.583 | −3.673 | −11.176 |
| 1916 | GLU252 | OE2 | 16.902 | −2.853 | −9.067 |
| 1917 | GLY253 | N | 17.189 | 1.972 | −9.635 |
| 1918 | GLY253 | CA | 16.143 | 2.98 | −9.629 |
| 1919 | GLY253 | C | 15.005 | 2.579 | −10.561 |
| 1920 | GLY253 | O | 14.857 | 3.072 | −11.678 |
| 1921 | HIS254 | N | 14.186 | 1.593 | −10.045 |
| 1922 | HIS254 | CA | 13.164 | 0.948 | −10.863 |
| 1923 | HIS254 | C | 12.181 | 0.227 | −9.928 |
| 1924 | HIS254 | O | 12.461 | −0.07 | −8.768 |
| 1925 | HIS254 | CB | 13.814 | −0.05 | −11.838 |
| 1926 | HIS254 | CG | 13.022 | −0.295 | −13.075 |
| 1927 | HIS254 | ND1 | 12.803 | 0.665 | −14.031 |
| 1928 | HIS254 | CD2 | 12.416 | −1.427 | −13.576 |
| 1929 | HIS254 | CE1 | 12.073 | 0.088 | −15.029 |
| 1930 | HIS254 | NE2 | 11.843 | −1.182 | −14.795 |
| 1931 | ALA255 | N | 10.976 | −0.101 | −10.519 |
| 1932 | ALA255 | CA | 10.04 | −1.017 | −9.884 |
| 1933 | ALA255 | C | 9.562 | −1.974 | −10.98 |
| 1934 | ALA255 | O | 9.432 | −1.627 | −12.151 |
| 1935 | ALA255 | CB | 8.88 | −0.293 | −9.228 |
| 1936 | TYR256 | N | 9.353 | −3.256 | −10.524 |
| 1937 | TYR256 | CA | 9.061 | −4.376 | −11.419 |
| 1938 | TYR256 | C | 7.558 | −4.671 | −11.306 |
| 1939 | TYR256 | O | 6.814 | −4.032 | −10.559 |
| 1940 | TYR256 | CB | 9.918 | −5.601 | −11.046 |
| 1941 | TYR256 | CG | 11.385 | −5.477 | −11.403 |
| 1942 | TYR256 | CD1 | 12.185 | −4.472 | −10.843 |
| 1943 | TYR256 | CD2 | 11.987 | −6.408 | −12.262 |
| 1944 | TYR256 | CE1 | 13.533 | −4.357 | −11.178 |
| 1945 | TYR256 | CE2 | 13.343 | −6.305 | −12.583 |
| 1946 | TYR256 | CZ | 14.104 | −5.269 | −12.053 |
| 1947 | TYR256 | OH | 15.418 | −5.186 | −12.413 |
| 1948 | THR257 | N | 7.096 | −5.697 | −12.106 |
| 1949 | THR257 | CA | 5.751 | −6.245 | −11.912 |
| 1950 | THR257 | C | 5.882 | −7.767 | −11.761 |
| 1951 | THR257 | O | 6.862 | −8.39 | −12.172 |
| 1952 | THR257 | CB | 4.785 | −5.826 | −13.033 |
| 1953 | THR257 | OG1 | 3.438 | −6.226 | −12.762 |
| 1954 | THR257 | CG2 | 5.178 | −6.346 | −14.404 |
| 1955 | LEU258 | N | 4.796 | −8.365 | −11.156 |
| 1956 | LEU258 | CA | 4.758 | −9.801 | −10.82 |
| 1957 | LEU258 | C | 3.657 | −10.421 | −11.703 |
| 1958 | LEU258 | O | 2.578 | −9.849 | −11.876 |
| 1959 | LEU258 | CB | 4.477 | −9.917 | −9.316 |
| 1960 | LEU258 | CG | 5.035 | −11.17 | −8.621 |
| 1961 | LEU258 | CD1 | 5.351 | −10.838 | −7.159 |
| 1962 | LEU258 | CD2 | 4.036 | −12.324 | −8.672 |
| 1963 | THR259 | N | 3.969 | −11.634 | −12.313 |
| 1964 | THR259 | CA | 3.099 | −12.191 | −13.367 |
| 1965 | THR259 | C | 2.945 | −13.737 | −13.36 |
| 1966 | THR259 | O | 2.503 | −14.372 | −14.326 |
| 1967 | THR259 | CB | 3.424 | −11.686 | −14.802 |
| 1968 | THR259 | OG1 | 4.665 | −12.213 | −15.307 |
| 1969 | THR259 | CG2 | 3.491 | −10.171 | −14.94 |
| 1970 | GLY260 | N | 3.177 | −14.344 | −12.141 |
| 1971 | GLY260 | CA | 3.017 | −15.778 | −11.933 |
| 1972 | GLY260 | C | 3.617 | −16.24 | −10.601 |
| 1973 | GLY260 | O | 4.34 | −15.515 | −9.914 |
| 1974 | ILE261 | N | 3.277 | −17.542 | −10.254 |
| 1975 | ILE261 | CA | 3.485 | −18.055 | −8.884 |
| 1976 | ILE261 | C | 3.328 | −19.605 | −8.878 |
| 1977 | ILE261 | O | 2.85 | −20.201 | −9.849 |
| 1978 | ILE261 | CB | 2.487 | −17.336 | −7.933 |
| 1979 | ILE261 | CG1 | 2.935 | −17.375 | −6.465 |
| 1980 | ILE261 | CG2 | 1.049 | −17.849 | −8.094 |
| 1981 | ILE261 | CD1 | 2.357 | −16.213 | −5.673 |
| 1982 | ARG262 | N | 3.751 | −20.227 | −7.708 |
| 1983 | ARG262 | CA | 3.281 | −21.535 | −7.183 |
| 1984 | ARG262 | C | 4.264 | −22.043 | −6.083 |
| 1985 | ARG262 | O | 5.187 | −21.344 | −5.659 |

TABLE V-continued

| Atom No | Residue | Atom name | x coord | y coord | z coord |
|---|---|---|---|---|---|
| 1986 | ARG262 | CB | 3.005 | −22.6 | −8.255 |
| 1987 | ARG262 | CG | 4.269 | −23.015 | −9.005 |
| 1988 | ARG262 | CD | 3.951 | −23.82 | −10.255 |
| 1989 | ARG262 | NE | 3.381 | −22.955 | −11.296 |
| 1990 | ARG262 | CZ | 3.328 | −23.325 | −12.598 |
| 1991 | ARG262 | NH1 | 2.901 | −22.461 | −13.537 |
| 1992 | ARG262 | NH2 | 3.705 | −24.548 | −13.015 |
| 1993 | LYS263 | N | 4.005 | −23.303 | −5.575 |
| 1994 | LYS263 | CA | 4.937 | −24.024 | −4.693 |
| 1995 | LYS263 | C | 5.465 | −25.246 | −5.468 |
| 1996 | LYS263 | O | 4.778 | −25.813 | −6.32 |
| 1997 | LYS263 | CB | 4.195 | −24.458 | −3.421 |
| 1998 | LYS263 | CG | 5.102 | −25.081 | −2.357 |
| 1999 | LYS263 | CD | 4.339 | −25.363 | −1.061 |
| 2000 | LYS263 | CE | 5.27 | −25.934 | 0 |
| 2001 | LYS263 | NZ | 4.644 | −25.802 | 1.335 |
| 2002 | VAL264 | N | 6.718 | −25.681 | −5.083 |
| 2003 | VAL264 | CA | 7.326 | −26.916 | −5.581 |
| 2004 | VAL264 | C | 8.106 | −27.592 | −4.428 |
| 2005 | VAL264 | O | 8.335 | −27.036 | −3.352 |
| 2006 | VAL264 | CB | 8.248 | −26.692 | −6.807 |
| 2007 | VAL264 | CG1 | 7.47 | −26.229 | −8.04 |
| 2008 | VAL264 | CG2 | 9.396 | −25.727 | −6.504 |
| 2009 | THR265 | N | 8.554 | −28.869 | −4.72 |
| 2010 | THR265 | CA | 9.554 | −29.535 | −3.884 |
| 2011 | THR265 | C | 10.787 | −29.809 | −4.756 |
| 2012 | THR265 | O | 10.694 | −30.025 | −5.965 |
| 2013 | THR265 | CB | 8.991 | −30.793 | −3.206 |
| 2014 | THR265 | OG1 | 9.877 | −31.233 | −2.175 |
| 2015 | THR265 | CG2 | 8.73 | −31.956 | −4.153 |
| 2016 | CYS266 | N | 11.978 | −29.812 | −4.061 |
| 2017 | CYS266 | CA | 13.284 | −29.87 | −4.714 |
| 2018 | CYS266 | C | 14.097 | −30.88 | −3.895 |
| 2019 | CYS266 | O | 14.691 | −30.581 | −2.86 |
| 2020 | CYS266 | CB | 13.989 | −28.509 | −4.7 |
| 2021 | CYS266 | SG | 13.206 | −27.305 | −5.819 |
| 2022 | LYS267 | N | 13.961 | −32.195 | −4.31 |
| 2023 | LYS267 | CA | 14.689 | −33.299 | −3.673 |
| 2024 | LYS267 | C | 14.286 | −33.478 | −2.192 |
| 2025 | LYS267 | O | 15.01 | −34.029 | −1.367 |
| 2026 | LYS267 | CB | 16.213 | −33.232 | −3.892 |
| 2027 | LYS267 | CG | 16.663 | −34.184 | −5.011 |
| 2028 | LYS267 | CD | 18.157 | −34.036 | −5.317 |
| 2029 | LYS267 | CE | 18.571 | −34.928 | −6.481 |
| 2030 | LYS267 | NZ | 20.005 | −34.709 | −6.786 |
| 2031 | HIS268 | N | 12.97 | −33.132 | −1.95 |
| 2032 | HIS268 | CA | 12.274 | −33.231 | −0.667 |
| 2033 | HIS268 | C | 12.482 | −32.006 | 0.241 |
| 2034 | HIS268 | O | 11.993 | −31.959 | 1.37 |
| 2035 | HIS268 | CB | 12.498 | −34.526 | 0.134 |
| 2036 | HIS268 | CG | 12.281 | −35.759 | −0.675 |
| 2037 | HIS268 | ND1 | 13.322 | −36.468 | −1.223 |
| 2038 | HIS268 | CD2 | 11.152 | −36.446 | −1.061 |
| 2039 | HIS268 | CE1 | 12.789 | −37.516 | −1.915 |
| 2040 | HIS268 | NE2 | 11.478 | −37.53 | −1.837 |
| 2041 | ARG269 | N | 13.176 | −30.951 | −0.316 |
| 2042 | ARG269 | CA | 13.144 | −29.618 | 0.276 |
| 2043 | ARG269 | C | 12.021 | −28.86 | −0.454 |
| 2044 | ARG269 | O | 12.043 | −28.758 | −1.688 |
| 2045 | ARG269 | CB | 14.46 | −28.861 | 0.046 |
| 2046 | ARG269 | CG | 15.662 | −29.559 | 0.684 |
| 2047 | ARG269 | CD | 16.953 | −28.794 | 0.405 |
| 2048 | ARG269 | NE | 18.104 | −29.474 | 1.018 |
| 2049 | ARG269 | CZ | 19.385 | −29.046 | 0.903 |
| 2050 | ARG269 | NH1 | 20.373 | −29.744 | 1.502 |
| 2051 | ARG269 | NH2 | 19.706 | −27.938 | 0.204 |
| 2052 | PRO270 | N | 11.014 | −28.293 | 0.298 |
| 2053 | PRO270 | CA | 9.987 | −27.465 | −0.337 |
| 2054 | PRO270 | C | 10.563 | −26.091 | −0.7 |
| 2055 | PRO270 | O | 11.354 | −25.501 | 0.037 |
| 2056 | PRO270 | CB | 8.9 | −27.291 | 0.729 |
| 2057 | PRO270 | CG | 9.144 | −28.441 | 1.697 |
| 2058 | PRO270 | CD | 10.654 | −28.613 | 1.67 |
| 2059 | GLU271 | N | 10.059 | −25.54 | −1.864 |
| 2060 | GLU271 | CA | 10.405 | −24.182 | −2.273 |
| 2061 | GLU271 | C | 9.161 | −23.549 | −2.941 |
| 2062 | GLU271 | O | 8.302 | −24.202 | −3.534 |
| 2063 | GLU271 | CB | 11.647 | −24.106 | −3.183 |
| 2064 | GLU271 | CG | 12.953 | −24.496 | −2.481 |
| 2065 | GLU271 | CD | 14.184 | −24.134 | −3.291 |
| 2066 | GLU271 | OE1 | 14.842 | −23.104 | −2.938 |
| 2067 | GLU271 | OE2 | 14.491 | −24.885 | −4.272 |
| 2068 | TYR272 | N | 9.087 | −22.177 | −2.79 |
| 2069 | TYR272 | CA | 7.922 | −21.389 | −3.21 |
| 2070 | TYR272 | C | 8.368 | −20.54 | −4.407 |
| 2071 | TYR272 | O | 9.278 | −19.715 | −4.286 |
| 2072 | TYR272 | CB | 7.46 | −20.467 | −2.073 |
| 2073 | TYR272 | CG | 6.69 | −21.185 | −0.988 |
| 2074 | TYR272 | CD1 | 7.353 | −21.902 | 0.018 |
| 2075 | TYR272 | CD2 | 5.289 | −21.136 | −0.972 |
| 2076 | TYR272 | CE1 | 6.629 | −22.565 | 1.011 |
| 2077 | TYR272 | CE2 | 4.562 | −21.773 | 0.033 |
| 2078 | TYR272 | CZ | 5.241 | −22.492 | 1.008 |
| 2079 | TYR272 | OH | 4.541 | −23.204 | 1.947 |
| 2080 | LEU273 | N | 7.728 | −20.835 | −5.606 |
| 2081 | LEU273 | CA | 8.076 | −20.123 | −6.831 |
| 2082 | LEU273 | C | 7.317 | −18.786 | −6.864 |
| 2083 | LEU273 | O | 6.155 | −18.677 | −6.464 |
| 2084 | LEU273 | CB | 7.669 | −20.839 | −8.137 |
| 2085 | LEU273 | CG | 8.109 | −22.294 | −8.354 |
| 2086 | LEU273 | CD1 | 7.859 | −22.713 | −9.808 |
| 2087 | LEU273 | CD2 | 9.577 | −22.515 | −8.047 |
| 2088 | VAL274 | N | 8.026 | −17.773 | −7.475 |
| 2089 | VAL274 | CA | 7.432 | −16.492 | −7.872 |
| 2090 | VAL274 | C | 7.657 | −16.369 | −9.387 |
| 2091 | VAL274 | O | 8.406 | −17.132 | −9.998 |
| 2092 | VAL274 | CB | 8.092 | −15.34 | −7.081 |
| 2093 | VAL274 | CG1 | 7.194 | −14.107 | −6.99 |
| 2094 | VAL274 | CG2 | 9.471 | −14.952 | −7.61 |
| 2095 | LYS275 | N | 7.044 | −15.285 | −9.983 |
| 2096 | LYS275 | CA | 7.464 | −14.86 | −11.304 |
| 2097 | LYS275 | C | 7.322 | −13.332 | −11.429 |
| 2098 | LYS275 | O | 6.235 | −12.753 | −11.4 |
| 2099 | LYS275 | CB | 6.633 | −15.505 | −12.406 |
| 2100 | LYS275 | CG | 7.255 | −15.212 | −13.764 |
| 2101 | LYS275 | CD | 6.224 | −15.112 | −14.878 |
| 2102 | LYS275 | CE | 6.828 | −14.538 | −16.146 |
| 2103 | LYS275 | NZ | 7.123 | −13.098 | −16.004 |
| 2104 | LEU276 | N | 8.531 | −12.693 | −11.629 |
| 2105 | LEU276 | CA | 8.634 | −11.276 | −11.95 |
| 2106 | LEU276 | C | 8.444 | −11.093 | −13.474 |
| 2107 | LEU276 | O | 8.563 | −12.011 | −14.289 |
| 2108 | LEU276 | CB | 10.025 | −10.736 | −11.562 |
| 2109 | LEU276 | CG | 10.275 | −10.475 | −10.064 |
| 2110 | LEU276 | CD1 | 9.462 | −9.29 | −9.559 |
| 2111 | LEU276 | CD2 | 10.031 | −11.687 | −9.173 |
| 2112 | ARG277 | N | 8.207 | −9.79 | −13.855 |
| 2113 | ARG277 | CA | 8.528 | −9.281 | −15.18 |
| 2114 | ARG277 | C | 9.232 | −7.926 | −14.936 |
| 2115 | ARG277 | O | 8.825 | −7.1 | −14.115 |
| 2116 | ARG277 | CB | 7.289 | −9.089 | −16.071 |
| 2117 | ARG277 | CG | 7.647 | −8.941 | −17.558 |
| 2118 | ARG277 | CD | 6.742 | −7.976 | −18.331 |
| 2119 | ARG277 | NE | 7.367 | −7.619 | −19.624 |
| 2120 | ARG277 | CZ | 7.335 | −6.381 | −20.171 |
| 2121 | ARG277 | NH1 | 6.551 | −5.395 | −19.697 |
| 2122 | ARG277 | NH2 | 8.113 | −6.055 | −21.217 |
| 2123 | ASN278 | N | 10.335 | −7.719 | −15.749 |
| 2124 | ASN278 | CA | 10.937 | −6.394 | −15.894 |
| 2125 | ASN278 | C | 10.093 | −5.697 | −16.971 |
| 2126 | ASN278 | O | 9.954 | −6.213 | −18.087 |
| 2127 | ASN278 | CB | 12.38 | −6.516 | −16.379 |
| 2128 | ASN278 | CG | 12.947 | −5.17 | −16.753 |
| 2129 | ASN278 | OD1 | 13.081 | −4.819 | −17.922 |
| 2130 | ASN278 | ND2 | 13.226 | −4.345 | −15.705 |
| 2131 | PRO279 | N | 9.541 | −4.466 | −16.682 |
| 2132 | PRO279 | CA | 8.574 | −3.868 | −17.602 |
| 2133 | PRO279 | C | 9.153 | −3.581 | −18.99 |
| 2134 | PRO279 | O | 8.444 | −3.571 | −19.998 |
| 2135 | PRO279 | CB | 8.162 | −2.571 | −16.921 |
| 2136 | PRO279 | CG | 8.254 | −2.911 | −15.445 |
| 2137 | PRO279 | CD | 9.464 | −3.83 | −15.371 |
| 2138 | TRP280 | N | 10.496 | −3.269 | −18.983 |
| 2139 | TRP280 | CA | 11.252 | −2.927 | −20.181 |

TABLE V-continued

| Atom No | Residue | Atom name | x coord | y coord | z coord |
|---|---|---|---|---|---|
| 2140 | TRP280 | C | 11.773 | −4.151 | −20.963 |
| 2141 | TRP280 | O | 12.441 | −4.014 | −21.997 |
| 2142 | TRP280 | CB | 12.425 | −1.995 | −19.834 |
| 2143 | TRP280 | CG | 12.051 | −0.559 | −19.634 |
| 2144 | TRP280 | CD1 | 11.011 | 0.111 | −20.238 |
| 2145 | TRP280 | CD2 | 12.756 | 0.413 | −18.852 |
| 2146 | TRP280 | NE1 | 11.062 | 1.433 | −19.885 |
| 2147 | TRP280 | CE2 | 12.088 | 1.633 | −18.993 |
| 2148 | TRP280 | CE3 | 13.913 | 0.373 | −18.044 |
| 2149 | TRP280 | CZ2 | 12.486 | 2.793 | −18.323 |
| 2150 | TRP280 | CZ3 | 14.341 | 1.535 | −17.391 |
| 2151 | TRP280 | CH2 | 13.626 | 2.723 | −17.518 |
| 2152 | GLY281 | N | 11.411 | −5.382 | −20.457 |
| 2153 | GLY281 | CA | 11.425 | −6.582 | −21.268 |
| 2154 | GLY281 | C | 12.714 | −7.392 | −21.278 |
| 2155 | GLY281 | O | 12.875 | −8.304 | −22.095 |
| 2156 | LYS282 | N | 13.616 | −7.04 | −20.301 |
| 2157 | LYS282 | CA | 14.908 | −7.695 | −20.115 |
| 2158 | LYS282 | C | 14.766 | −8.868 | −19.119 |
| 2159 | LYS282 | O | 13.791 | −9.007 | −18.381 |
| 2160 | LYS282 | CB | 15.966 | −6.676 | −19.648 |
| 2161 | LYS282 | CG | 16.466 | −5.772 | −20.791 |
| 2162 | LYS282 | CD | 15.559 | −4.566 | −21.044 |
| 2163 | LYS282 | CE | 15.714 | −4.002 | −22.451 |
| 2164 | LYS282 | NZ | 14.659 | −2.99 | −22.664 |
| 2165 | VAL283 | N | 15.825 | −9.754 | −19.149 |
| 2166 | VAL283 | CA | 15.911 | −10.959 | −18.324 |
| 2167 | VAL283 | C | 17.177 | −10.793 | −17.449 |
| 2168 | VAL283 | O | 17.109 | −10.559 | −16.244 |
| 2169 | VAL283 | CB | 15.921 | −12.225 | −19.213 |
| 2170 | VAL283 | CG1 | 15.998 | −13.494 | −18.366 |
| 2171 | VAL283 | CG2 | 14.674 | −12.299 | −20.104 |
| 2172 | GLU284 | N | 18.379 | −10.886 | −18.141 |
| 2173 | GLU284 | CA | 19.583 | −10.233 | −17.632 |
| 2174 | GLU284 | C | 20.03 | −10.638 | −16.205 |
| 2175 | GLU284 | O | 20.417 | −9.814 | −15.373 |
| 2176 | GLU284 | CB | 19.515 | −8.702 | −17.837 |
| 2177 | GLU284 | CG | 19.846 | −8.253 | −19.27 |
| 2178 | GLU284 | CD | 18.886 | −8.593 | −20.412 |
| 2179 | GLU284 | OE1 | 18.035 | −9.506 | −20.171 |
| 2180 | GLU284 | OE2 | 19.025 | −7.906 | −21.459 |
| 2181 | TRP285 | N | 20.155 | −12.004 | −15.985 |
| 2182 | TRP285 | CA | 20.932 | −12.497 | −14.842 |
| 2183 | TRP285 | C | 21.761 | −13.735 | −15.237 |
| 2184 | TRP285 | O | 21.657 | −14.301 | −16.323 |
| 2185 | TRP285 | CB | 20.117 | −12.623 | −13.545 |
| 2186 | TRP285 | CG | 19.575 | −13.984 | −13.239 |
| 2187 | TRP285 | CD1 | 20.1 | −14.89 | −12.334 |
| 2188 | TRP285 | CD2 | 18.396 | −14.581 | −13.783 |
| 2189 | TRP285 | NE1 | 19.303 | −16.003 | −12.321 |
| 2190 | TRP285 | CE2 | 18.241 | −15.827 | −13.175 |
| 2191 | TRP285 | CE3 | 17.431 | −14.167 | −14.72 |
| 2192 | TRP285 | CZ2 | 17.159 | −16.669 | −13.441 |
| 2193 | TRP285 | CZ3 | 16.37 | −15.024 | −15.03 |
| 2194 | TRP285 | CH2 | 16.238 | −16.257 | −14.401 |
| 2195 | LYS286 | N | 22.694 | −14.106 | −14.287 |
| 2196 | LYS286 | CA | 23.764 | −15.067 | −14.54 |
| 2197 | LYS286 | C | 23.324 | −16.517 | −14.251 |
| 2198 | LYS286 | O | 23.999 | −17.284 | −13.562 |
| 2199 | LYS286 | CB | 24.995 | −14.701 | −13.688 |
| 2200 | LYS286 | CG | 25.529 | −13.29 | −13.965 |
| 2201 | LYS286 | CD | 26.7 | −12.953 | −13.039 |
| 2202 | LYS286 | CE | 27.191 | −11.531 | −13.271 |
| 2203 | LYS286 | NZ | 28.293 | −11.237 | −12.323 |
| 2204 | GLY287 | N | 22.185 | −16.93 | −14.91 |
| 2205 | GLY287 | CA | 21.742 | −18.311 | −14.832 |
| 2206 | GLY287 | C | 20.289 | −18.461 | −15.26 |
| 2207 | GLY287 | O | 19.729 | −17.631 | −15.971 |
| 2208 | ASP288 | N | 19.681 | −19.612 | −14.781 |
| 2209 | ASP288 | CA | 18.234 | −19.828 | −14.932 |
| 2210 | ASP288 | C | 17.649 | −20.449 | −13.637 |
| 2211 | ASP288 | O | 16.602 | −21.088 | −13.602 |
| 2212 | ASP288 | CB | 17.889 | −20.638 | −16.168 |
| 2213 | ASP288 | CG | 16.404 | −20.537 | −16.444 |
| 2214 | ASP288 | OD1 | 15.815 | −21.581 | −16.865 |
| 2215 | ASP288 | OD2 | 15.809 | −19.437 | −16.223 |
| 2216 | TRP289 | N | 18.357 | −20.074 | −12.511 |
| 2217 | TRP289 | CA | 17.877 | −20.166 | −11.129 |
| 2218 | TRP289 | C | 19.03 | −19.498 | −10.338 |
| 2219 | TRP289 | O | 19.797 | −18.685 | −10.878 |
| 2220 | TRP289 | CB | 17.536 | −21.597 | −10.681 |
| 2221 | TRP289 | CG | 16.279 | −21.693 | −9.854 |
| 2222 | TRP289 | CD1 | 15.892 | −20.886 | −8.8 |
| 2223 | TRP289 | CD2 | 15.271 | −22.707 | −9.975 |
| 2224 | TRP289 | NE1 | 14.706 | −21.358 | −8.3 |
| 2225 | TRP289 | CE2 | 14.29 | −22.451 | −9.016 |
| 2226 | TRP289 | CE3 | 15.125 | −23.852 | −10.78 |
| 2227 | TRP289 | CZ2 | 13.16 | −23.26 | −8.852 |
| 2228 | TRP289 | CZ3 | 14.018 | −24.69 | −10.599 |
| 2229 | TRP289 | CH2 | 13.041 | −24.39 | −9.659 |
| 2230 | SER290 | N | 19.145 | −19.799 | −9.004 |
| 2231 | SER290 | CA | 20.299 | −19.398 | −8.195 |
| 2232 | SER290 | C | 20.188 | −20.151 | −6.87 |
| 2233 | SER290 | O | 19.141 | −20.146 | −6.229 |
| 2234 | SER290 | CB | 20.369 | −17.892 | −7.938 |
| 2235 | SER290 | OG | 20.955 | −17.227 | −9.058 |
| 2236 | ASP291 | N | 21.338 | −20.833 | −6.53 |
| 2237 | ASP291 | CA | 21.456 | −21.969 | −5.601 |
| 2238 | ASP291 | C | 22.001 | −23.178 | −6.401 |
| 2239 | ASP291 | O | 22.889 | −23.913 | −5.967 |
| 2240 | ASP291 | CB | 20.238 | −22.329 | −4.751 |
| 2241 | ASP291 | CG | 19.008 | −22.859 | −5.469 |
| 2242 | ASP291 | OD1 | 17.956 | −22.999 | −4.741 |
| 2243 | ASP291 | OD2 | 19.125 | −23.137 | −6.697 |
| 2244 | SER292 | N | 21.344 | −23.438 | −7.59 |
| 2245 | SER292 | CA | 21.699 | −24.591 | −8.422 |
| 2246 | SER292 | C | 20.931 | −24.457 | −9.74 |
| 2247 | SER292 | O | 19.801 | −24.911 | −9.91 |
| 2248 | SER292 | CB | 21.375 | −25.923 | −7.735 |
| 2249 | SER292 | OG | 22.418 | −26.301 | −6.832 |
| 2250 | SER293 | N | 21.606 | −23.736 | −10.724 |
| 2251 | SER293 | CA | 20.846 | −23.111 | −11.818 |
| 2252 | SER293 | C | 20.023 | −24.1 | −12.653 |
| 2253 | SER293 | O | 19.033 | −23.732 | −13.285 |
| 2254 | SER293 | CB | 21.757 | −22.335 | −12.787 |
| 2255 | SER293 | OG | 21.239 | −21.017 | −13.017 |
| 2256 | SER294 | N | 20.552 | −25.369 | −12.751 |
| 2257 | SER294 | CA | 19.9 | −26.41 | −13.529 |
| 2258 | SER294 | C | 18.95 | −27.304 | −12.721 |
| 2259 | SER294 | O | 18.437 | −28.308 | −13.229 |
| 2260 | SER294 | CB | 20.925 | −27.265 | −14.275 |
| 2261 | SER294 | OG | 21.73 | −27.996 | −13.353 |
| 2262 | LYS295 | N | 18.479 | −26.832 | −11.502 |
| 2263 | LYS295 | CA | 17.627 | −27.699 | −10.671 |
| 2264 | LYS295 | C | 16.164 | −27.847 | −11.19 |
| 2265 | LYS295 | O | 15.295 | −28.434 | −10.547 |
| 2266 | LYS295 | CB | 17.676 | −27.362 | −9.169 |
| 2267 | LYS295 | CG | 16.925 | −26.088 | −8.807 |
| 2268 | LYS295 | CD | 16.949 | −25.757 | −7.309 |
| 2269 | LYS295 | CE | 16.153 | −24.479 | −7.118 |
| 2270 | LYS295 | NZ | 16.053 | −24.049 | −5.734 |
| 2271 | TRP296 | N | 15.972 | −27.431 | −12.491 |
| 2272 | TRP296 | CA | 14.872 | −27.88 | −13.336 |
| 2273 | TRP296 | C | 15.035 | −29.371 | −13.716 |
| 2274 | TRP296 | O | 14.133 | −29.981 | −14.29 |
| 2275 | TRP296 | CB | 14.8 | −27.078 | −14.65 |
| 2276 | TRP296 | CG | 14.669 | −25.595 | −14.468 |
| 2277 | TRP296 | CD1 | 15.671 | −24.659 | −14.644 |
| 2278 | TRP296 | CD2 | 13.501 | −24.875 | −14.057 |
| 2279 | TRP296 | NE1 | 15.173 | −23.419 | −14.334 |
| 2280 | TRP296 | CE2 | 13.856 | −23.529 | −13.95 |
| 2281 | TRP296 | CE3 | 12.188 | −25.254 | −13.707 |
| 2282 | TRP296 | CZ2 | 12.979 | −22.546 | −13.477 |
| 2283 | TRP296 | CZ3 | 11.306 | −24.286 | −13.215 |
| 2284 | TRP296 | CH2 | 11.7 | −22.956 | −13.095 |
| 2285 | GLU297 | N | 16.247 | −29.961 | −13.388 |
| 2286 | GLU297 | CA | 16.539 | −31.354 | −13.743 |
| 2287 | GLU297 | C | 15.677 | −32.306 | −12.884 |
| 2288 | GLU297 | O | 15.277 | −33.393 | −13.297 |
| 2289 | GLU297 | CB | 18.004 | −31.703 | −13.427 |
| 2290 | GLU297 | CG | 19.007 | −31.221 | −14.472 |
| 2291 | GLU297 | CD | 20.397 | −31.304 | −13.831 |
| 2292 | GLU297 | OE1 | 20.987 | −30.192 | −13.67 |
| 2293 | GLU297 | OE2 | 20.785 | −32.465 | −13.524 |

TABLE V-continued

| Atom No | Residue | Atom name | x coord | y coord | z coord |
|---|---|---|---|---|---|
| 2294 | LEU298 | N | 15.589 | −31.926 | −11.556 |
| 2295 | LEU298 | CA | 14.981 | −32.77 | −10.54 |
| 2296 | LEU298 | C | 13.519 | −32.377 | −10.28 |
| 2297 | LEU298 | O | 13.091 | −31.231 | −10.421 |
| 2298 | LEU298 | CB | 15.78 | −32.784 | −9.222 |
| 2299 | LEU298 | CG | 16.265 | −31.396 | −8.743 |
| 2300 | LEU298 | CD1 | 15.964 | −31.174 | −7.264 |
| 2301 | LEU298 | CD2 | 17.769 | −31.245 | −8.989 |
| 2302 | LEU299 | N | 12.717 | −33.443 | −9.879 |
| 2303 | LEU299 | CA | 11.365 | −33.264 | −9.327 |
| 2304 | LEU299 | C | 10.5 | −32.443 | −10.305 |
| 2305 | LEU299 | O | 9.686 | −31.581 | −9.965 |
| 2306 | LEU299 | CB | 11.374 | −32.701 | −7.897 |
| 2307 | LEU299 | CG | 11.447 | −33.753 | −6.767 |
| 2308 | LEU299 | CD1 | 10.173 | −34.597 | −6.679 |
| 2309 | LEU299 | CD2 | 12.675 | −34.655 | −6.851 |
| 2310 | SER300 | N | 10.666 | −32.827 | −11.626 |
| 2311 | SER300 | CA | 10.223 | −31.96 | −12.711 |
| 2312 | SER300 | C | 9.831 | −32.797 | −13.923 |
| 2313 | SER300 | O | 10.551 | −32.865 | −14.918 |
| 2314 | SER300 | CB | 11.302 | −30.919 | −13.047 |
| 2315 | SER300 | OG | 11.474 | −30.005 | −11.938 |
| 2316 | PRO301 | N | 8.614 | −33.454 | −13.838 |
| 2317 | PRO301 | CA | 8.076 | −34.181 | −14.985 |
| 2318 | PRO301 | C | 7.562 | −33.163 | −16.023 |
| 2319 | PRO301 | O | 7.523 | −31.942 | −15.833 |
| 2320 | PRO301 | CB | 6.982 | −35.058 | −14.38 |
| 2321 | PRO301 | CG | 6.479 | −34.227 | −13.206 |
| 2322 | PRO301 | CD | 7.752 | −33.593 | −12.669 |
| 2323 | LYS302 | N | 7.147 | −33.74 | −17.215 |
| 2324 | LYS302 | CA | 6.877 | −32.868 | −18.363 |
| 2325 | LYS302 | C | 5.645 | −31.983 | −18.078 |
| 2326 | LYS302 | O | 5.484 | −30.869 | −18.57 |
| 2327 | LYS302 | CB | 6.672 | −33.716 | −19.625 |
| 2328 | LYS302 | CG | 7.287 | −33.047 | −20.856 |
| 2329 | LYS302 | CD | 7.05 | −33.874 | −22.119 |
| 2330 | LYS302 | CE | 7.704 | −33.225 | −23.329 |
| 2331 | LYS302 | NZ | 7.445 | −34.06 | −24.526 |
| 2332 | GLU303 | N | 4.738 | −32.591 | −17.247 |
| 2333 | GLU303 | CA | 3.395 | −32.129 | −16.953 |
| 2334 | GLU303 | C | 3.494 | −30.92 | −16.005 |
| 2335 | GLU303 | O | 2.6 | −30.081 | −15.915 |
| 2336 | GLU303 | CB | 2.6 | −33.255 | −16.265 |
| 2337 | GLU303 | CG | 2.426 | −34.527 | −17.11 |
| 2338 | GLU303 | CD | 3.625 | −35.48 | −17.279 |
| 2339 | GLU303 | OE1 | 4.772 | −34.963 | −17.076 |
| 2340 | GLU303 | OE2 | 3.337 | −36.652 | −17.636 |
| 2341 | LYS304 | N | 4.62 | −30.928 | −15.189 |
| 2342 | LYS304 | CA | 4.963 | −29.757 | −14.397 |
| 2343 | LYS304 | C | 5.639 | −28.73 | −15.32 |
| 2344 | LYS304 | O | 5.311 | −27.541 | −15.299 |
| 2345 | LYS304 | CB | 5.895 | −30.123 | −13.229 |
| 2346 | LYS304 | CG | 5.971 | −29.01 | −12.169 |
| 2347 | LYS304 | CD | 7.075 | −29.248 | −11.128 |
| 2348 | LYS304 | CE | 8.442 | −28.814 | −11.643 |
| 2349 | LYS304 | NZ | 9.501 | −29.237 | −10.709 |
| 2350 | ILE305 | N | 6.707 | −29.199 | −16.076 |
| 2351 | ILE305 | CA | 7.642 | −28.242 | −16.673 |
| 2352 | ILE305 | C | 7.027 | −27.482 | −17.864 |
| 2353 | ILE305 | O | 7.481 | −26.394 | −18.219 |
| 2354 | ILE305 | CB | 9.006 | −28.894 | −17.018 |
| 2355 | ILE305 | CG1 | 10.144 | −27.856 | −16.892 |
| 2356 | ILE305 | CG2 | 9.013 | −29.558 | −18.397 |
| 2357 | ILE305 | CD1 | 11.534 | −28.452 | −17.059 |
| 2358 | LEU306 | N | 5.999 | −28.115 | −18.541 |
| 2359 | LEU306 | CA | 5.39 | −27.484 | −19.715 |
| 2360 | LEU306 | C | 4.473 | −26.329 | −19.282 |
| 2361 | LEU306 | O | 4.199 | −25.396 | −20.035 |
| 2362 | LEU306 | CB | 4.555 | −28.471 | −20.543 |
| 2363 | LEU306 | CG | 5.396 | −29.398 | −21.441 |
| 2364 | LEU306 | CD1 | 4.513 | −30.523 | −21.988 |
| 2365 | LEU306 | CD2 | 6.043 | −28.646 | −22.606 |
| 2366 | LEU307 | N | 3.896 | −26.466 | −18.035 |
| 2367 | LEU307 | CA | 3.011 | −25.447 | −17.465 |
| 2368 | LEU307 | C | 3.873 | −24.476 | −16.624 |
| 2369 | LEU307 | O | 3.586 | −24.139 | −15.471 |
| 2370 | LEU307 | CB | 1.901 | −26.13 | −16.649 |
| 2371 | LEU307 | CG | 0.531 | −25.423 | −16.742 |
| 2372 | LEU307 | CD1 | −0.532 | −26.257 | −16.022 |
| 2373 | LEU307 | CD2 | 0.541 | −24.005 | −16.174 |
| 2374 | LEU308 | N | 4.949 | −23.941 | −17.302 |
| 2375 | LEU308 | CA | 6.035 | −23.215 | −16.647 |
| 2376 | LEU308 | C | 6.876 | −22.584 | −17.768 |
| 2377 | LEU308 | O | 7.035 | −23.144 | −18.85 |
| 2378 | LEU308 | CB | 6.897 | −24.178 | −15.807 |
| 2379 | LEU308 | CG | 6.948 | −23.815 | −14.312 |
| 2380 | LEU308 | CD1 | 7.362 | −25.033 | −13.486 |
| 2381 | LEU308 | CD2 | 7.91 | −22.662 | −14.059 |
| 2382 | ARG309 | N | 7.444 | −21.368 | −17.44 |
| 2383 | ARG309 | CA | 8.209 | −20.556 | −18.396 |
| 2384 | ARG309 | C | 7.215 | −20.097 | −19.499 |
| 2385 | ARG309 | O | 7.211 | −20.57 | −20.633 |
| 2386 | ARG309 | CB | 9.475 | −21.225 | −18.956 |
| 2387 | ARG309 | CG | 10.305 | −22.098 | −18.003 |
| 2388 | ARG309 | CD | 10.578 | −21.562 | −16.604 |
| 2389 | ARG309 | NE | 11.464 | −20.401 | −16.533 |
| 2390 | ARG309 | CZ | 12.822 | −20.438 | −16.568 |
| 2391 | ARG309 | NH1 | 13.482 | −21.55 | −16.944 |
| 2392 | ARG309 | NH2 | 13.489 | −19.33 | −16.193 |
| 2393 | LYS310 | N | 6.259 | −19.194 | −19.052 |
| 2394 | LYS310 | CA | 4.947 | −19.081 | −19.688 |
| 2395 | LYS310 | C | 4.447 | −17.723 | −20.214 |
| 2396 | LYS310 | O | 3.452 | −17.693 | −20.947 |
| 2397 | LYS310 | CB | 3.872 | −19.736 | −18.785 |
| 2398 | LYS310 | CG | 3.685 | −19.061 | −17.42 |
| 2399 | LYS310 | CD | 2.648 | −17.934 | −17.42 |
| 2400 | LYS310 | CE | 2.777 | −17.078 | −16.165 |
| 2401 | LYS310 | NZ | 2.02 | −15.832 | −16.318 |
| 2402 | ASP311 | N | 5.044 | −16.569 | −19.735 |
| 2403 | ASP311 | CA | 4.74 | −15.299 | −20.408 |
| 2404 | ASP311 | C | 5.793 | −15.231 | −21.565 |
| 2405 | ASP311 | O | 6.162 | −16.217 | −22.208 |
| 2406 | ASP311 | CB | 4.787 | −14.092 | −19.465 |
| 2407 | ASP311 | CG | 3.902 | −13.966 | −18.244 |
| 2408 | ASP311 | OD1 | 4.261 | −13.082 | −17.402 |
| 2409 | ASP311 | OD2 | 2.909 | −14.74 | −18.122 |
| 2410 | ASN312 | N | 6.275 | −13.977 | −21.862 |
| 2411 | ASN312 | CA | 7.564 | −13.796 | −22.526 |
| 2412 | ASN312 | C | 8.052 | −12.481 | −21.892 |
| 2413 | ASN312 | O | 7.388 | −11.907 | −21.023 |
| 2414 | ASN312 | CB | 7.365 | −13.694 | −24.032 |
| 2415 | ASN312 | CG | 8.686 | −13.81 | −24.752 |
| 2416 | ASN312 | OD1 | 9.415 | −12.829 | −24.929 |
| 2417 | ASN312 | ND2 | 9.044 | −15.07 | −25.117 |
| 2418 | ASP313 | N | 9.252 | −11.973 | −22.353 |
| 2419 | ASP313 | CA | 9.486 | −10.538 | −22.209 |
| 2420 | ASP313 | C | 9.702 | −10.172 | −20.729 |
| 2421 | ASP313 | O | 9.242 | −9.152 | −20.219 |
| 2422 | ASP313 | CB | 8.356 | −9.744 | −22.863 |
| 2423 | ASP313 | CG | 9.03 | −8.547 | −23.469 |
| 2424 | ASP313 | OD1 | 8.905 | −7.459 | −22.843 |
| 2425 | ASP313 | OD2 | 9.677 | −8.778 | −24.555 |
| 2426 | GLY314 | N | 10.58 | −11.035 | −20.099 |
| 2427 | GLY314 | CA | 10.855 | −10.98 | −18.679 |
| 2428 | GLY314 | C | 10.158 | −12.165 | −18.019 |
| 2429 | GLY314 | O | 9.038 | −12.091 | −17.509 |
| 2430 | GLU315 | N | 10.88 | −13.349 | −18.127 |
| 2431 | GLU315 | CA | 10.289 | −14.613 | −17.709 |
| 2432 | GLU315 | C | 10.687 | −14.949 | −16.262 |
| 2433 | GLU315 | O | 9.83 | −15.216 | −15.422 |
| 2434 | GLU315 | CB | 10.576 | −15.729 | −18.718 |
| 2435 | GLU315 | CG | 9.7 | −16.972 | −18.527 |
| 2436 | GLU315 | CD | 8.191 | −16.747 | −18.473 |
| 2437 | GLU315 | OE1 | 7.717 | −15.846 | −19.212 |
| 2438 | GLU315 | OE2 | 7.517 | −17.508 | −17.705 |
| 2439 | PHE316 | N | 12.03 | −15.012 | −15.961 |
| 2440 | PHE316 | CA | 12.47 | −15.188 | −14.559 |
| 2441 | PHE316 | C | 12.08 | −16.622 | −14.073 |
| 2442 | PHE316 | O | 12.298 | −17.599 | −14.803 |
| 2443 | PHE316 | CB | 12.074 | −14.002 | −13.659 |
| 2444 | PHE316 | CG | 12.736 | −12.706 | −14.072 |
| 2445 | PHE316 | CD1 | 12.085 | −11.8 | −14.916 |
| 2446 | PHE316 | CD2 | 14.029 | −12.408 | −13.619 |
| 2447 | PHE316 | CE1 | 12.726 | −10.628 | −15.319 |

TABLE V-continued

| Atom No | Residue | Atom name | x coord | y coord | z coord |
|---|---|---|---|---|---|
| 2448 | PHE316 | CE2 | 14.666 | −11.235 | −14.021 |
| 2449 | PHE316 | CZ | 14.015 | −10.347 | −14.874 |
| 2450 | TRP317 | N | 11.496 | −16.719 | −12.823 |
| 2451 | TRP317 | CA | 11.006 | −17.943 | −12.169 |
| 2452 | TRP317 | C | 12.038 | −18.518 | −11.196 |
| 2453 | TRP317 | O | 12.339 | −19.713 | −11.19 |
| 2454 | TRP317 | CB | 10.477 | −19.098 | −13.034 |
| 2455 | TRP317 | CG | 9.177 | −18.858 | −13.717 |
| 2456 | TRP317 | CD1 | 9.014 | −18.346 | −14.977 |
| 2457 | TRP317 | CD2 | 7.867 | −19.138 | −13.223 |
| 2458 | TRP317 | NE1 | 7.687 | −18.372 | −15.307 |
| 2459 | TRP317 | CE2 | 6.957 | −18.85 | −14.244 |
| 2460 | TRP317 | CE3 | 7.371 | −19.616 | −11.994 |
| 2461 | TRP317 | CZ2 | 5.578 | −19.027 | −14.082 |
| 2462 | TRP317 | CZ3 | 5.996 | −19.79 | −11.817 |
| 2463 | TRP317 | CH2 | 5.113 | −19.497 | −12.85 |
| 2464 | MET318 | N | 12.499 | −17.644 | −10.234 |
| 2465 | MET318 | CA | 13.197 | −18.156 | −9.071 |
| 2466 | MET318 | C | 12.185 | −18.312 | −7.905 |
| 2467 | MET318 | O | 10.996 | −18.594 | −8.078 |
| 2468 | MET318 | CB | 14.469 | −17.368 | −8.77 |
| 2469 | MET318 | CG | 15.331 | −17.18 | −10.014 |
| 2470 | MET318 | SD | 16.964 | −16.506 | −9.576 |
| 2471 | MET318 | CE | 16.727 | −14.789 | −10.107 |
| 2472 | THR319 | N | 12.757 | −18.296 | −6.644 |
| 2473 | THR319 | CA | 12.098 | −18.913 | −5.49 |
| 2474 | THR319 | C | 12.337 | −18.067 | −4.244 |
| 2475 | THR319 | O | 13.343 | −17.371 | −4.135 |
| 2476 | THR319 | CB | 12.703 | −20.312 | −5.228 |
| 2477 | THR319 | OG1 | 14.001 | −20.424 | −5.84 |
| 2478 | THR319 | CG2 | 11.866 | −21.415 | −5.826 |
| 2479 | LEU320 | N | 11.403 | −18.247 | −3.239 |
| 2480 | LEU320 | CA | 11.304 | −17.264 | −2.158 |
| 2481 | LEU320 | C | 12.534 | −17.265 | −1.231 |
| 2482 | LEU320 | O | 12.769 | −18.16 | −0.422 |
| 2483 | LEU320 | CB | 10.046 | −17.551 | −1.315 |
| 2484 | LEU320 | CG | 9.838 | −16.663 | −0.069 |
| 2485 | LEU320 | CD1 | 9.894 | −15.167 | −0.371 |
| 2486 | LEU320 | CD2 | 8.505 | −17.02 | 0.596 |
| 2487 | GLN321 | N | 13.316 | −16.124 | −1.361 |
| 2488 | GLN321 | CA | 14.259 | −15.744 | −0.311 |
| 2489 | GLN321 | C | 14.594 | −14.23 | −0.308 |
| 2490 | GLN321 | O | 15.433 | −13.779 | 0.472 |
| 2491 | GLN321 | CB | 15.548 | −16.59 | −0.36 |
| 2492 | GLN321 | CG | 15.855 | −17.306 | 0.958 |
| 2493 | GLN321 | CD | 16.904 | −16.635 | 1.819 |
| 2494 | GLN321 | OE1 | 17.909 | −17.223 | 2.211 |
| 2495 | GLN321 | NE2 | 16.654 | −15.35 | 2.201 |
| 2496 | ASP322 | N | 13.848 | −13.446 | −1.164 |
| 2497 | ASP322 | CA | 14.248 | −12.103 | −1.611 |
| 2498 | ASP322 | C | 14.249 | −10.983 | −0.562 |
| 2499 | ASP322 | O | 14.875 | −9.931 | −0.719 |
| 2500 | ASP322 | CB | 15.535 | −12.116 | −2.438 |
| 2501 | ASP322 | CG | 15.34 | −11.89 | −3.933 |
| 2502 | ASP322 | OD1 | 14.15 | −11.758 | −4.35 |
| 2503 | ASP322 | OD2 | 16.426 | −11.883 | −4.604 |
| 2504 | PHE323 | N | 13.365 | −11.161 | 0.484 |
| 2505 | PHE323 | CA | 12.822 | −10.018 | 1.237 |
| 2506 | PHE323 | C | 13.889 | −9.399 | 2.172 |
| 2507 | PHE323 | O | 13.821 | −9.433 | 3.397 |
| 2508 | PHE323 | CB | 11.584 | −10.422 | 2.054 |
| 2509 | PHE323 | CG | 10.362 | −10.884 | 1.285 |
| 2510 | PHE323 | CD1 | 9.301 | −11.438 | 2.022 |
| 2511 | PHE323 | CD2 | 10.212 | −10.75 | −0.103 |
| 2512 | PHE323 | CE1 | 8.125 | −11.847 | 1.393 |
| 2513 | PHE323 | CE2 | 9.041 | −11.175 | −0.733 |
| 2514 | PHE323 | CZ | 7.997 | −11.712 | 0.016 |
| 2515 | LYS324 | N | 14.906 | −8.775 | 1.479 |
| 2516 | LYS324 | CA | 16.059 | −8.143 | 2.097 |
| 2517 | LYS324 | C | 15.945 | −6.647 | 1.722 |
| 2518 | LYS324 | O | 15.583 | −5.78 | 2.514 |
| 2519 | LYS324 | CB | 17.384 | −8.77 | 1.596 |
| 2520 | LYS324 | CG | 17.441 | −10.305 | 1.664 |
| 2521 | LYS324 | CD | 18.492 | −10.874 | 0.693 |
| 2522 | LYS324 | CE | 18.146 | −12.301 | 0.28 |
| 2523 | LYS324 | NZ | 19.058 | −12.75 | −0.782 |
| 2524 | THR325 | N | 16.254 | −6.375 | 0.404 |
| 2525 | THR325 | CA | 16.294 | −5.05 | −0.205 |
| 2526 | THR325 | C | 14.889 | −4.694 | −0.708 |
| 2527 | THR325 | O | 14.517 | −5.055 | −1.83 |
| 2528 | THR325 | CB | 17.024 | −3.925 | 0.565 |
| 2529 | THR325 | OG1 | 17.428 | −2.899 | −0.365 |
| 2530 | THR325 | CG2 | 18.294 | −4.377 | 1.287 |
| 2531 | HIS326 | N | 14.032 | −4.082 | 0.182 |
| 2532 | HIS326 | CA | 12.651 | −3.745 | −0.185 |
| 2533 | HIS326 | C | 12.125 | −2.627 | 0.715 |
| 2534 | HIS326 | O | 12.506 | −2.495 | 1.878 |
| 2535 | HIS326 | CB | 11.71 | −4.964 | −0.039 |
| 2536 | HIS326 | CG | 11.237 | −5.489 | −1.35 |
| 2537 | HIS326 | ND1 | 12.091 | −5.768 | −2.384 |
| 2538 | HIS326 | CD2 | 9.99 | −5.805 | −1.841 |
| 2539 | HIS326 | CE1 | 11.334 | −6.159 | −3.442 |
| 2540 | HIS326 | NE2 | 10.057 | −6.237 | −3.142 |
| 2541 | PHE327 | N | 11.119 | −1.865 | 0.135 |
| 2542 | PHE327 | CA | 10.379 | −0.87 | 0.91 |
| 2543 | PHE327 | C | 8.879 | −1.214 | 0.924 |
| 2544 | PHE327 | O | 8.273 | −1.356 | 1.992 |
| 2545 | PHE327 | CB | 10.648 | 0.554 | 0.401 |
| 2546 | PHE327 | CG | 9.97 | 1.626 | 1.224 |
| 2547 | PHE327 | CD1 | 10.239 | 1.762 | 2.594 |
| 2548 | PHE327 | CD2 | 9.058 | 2.506 | 0.626 |
| 2549 | PHE327 | CE1 | 9.585 | 2.734 | 3.353 |
| 2550 | PHE327 | CE2 | 8.404 | 3.477 | 1.386 |
| 2551 | PHE327 | CZ | 8.663 | 3.588 | 2.75 |
| 2552 | VAL328 | N | 8.241 | −1.278 | −0.304 |
| 2553 | VAL328 | CA | 6.78 | −1.405 | −0.381 |
| 2554 | VAL328 | C | 6.367 | −2.087 | −1.695 |
| 2555 | VAL328 | O | 6.835 | −1.75 | −2.78 |
| 2556 | VAL328 | CB | 6.081 | −0.035 | −0.188 |
| 2557 | VAL328 | CG1 | 6.279 | 0.921 | −1.369 |
| 2558 | VAL328 | CG2 | 4.586 | −0.186 | 0.103 |
| 2559 | LEU329 | N | 5.431 | −3.088 | −1.541 |
| 2560 | LEU329 | CA | 4.722 | −3.699 | −2.671 |
| 2561 | LEU329 | C | 3.282 | −3.186 | −2.586 |
| 2562 | LEU329 | O | 2.749 | −2.915 | −1.507 |
| 2563 | LEU329 | CB | 4.817 | −5.23 | −2.55 |
| 2564 | LEU329 | CG | 4.055 | −6.055 | −3.609 |
| 2565 | LEU329 | CD1 | 4.816 | −7.344 | −3.94 |
| 2566 | LEU329 | CD2 | 2.655 | −6.451 | −3.126 |
| 2567 | LEU330 | N | 2.607 | −3.134 | −3.785 |
| 2568 | LEU330 | CA | 1.18 | −2.918 | −3.839 |
| 2569 | LEU330 | C | 0.517 | −3.852 | −4.863 |
| 2570 | LEU330 | O | 1.06 | −4.232 | −5.901 |
| 2571 | LEU330 | CB | 0.768 | −1.455 | −4.071 |
| 2572 | LEU330 | CG | 1.329 | −0.785 | −5.344 |
| 2573 | LEU330 | CD1 | 0.345 | 0.266 | −5.863 |
| 2574 | LEU330 | CD2 | 2.677 | −0.104 | −5.08 |
| 2575 | VAL331 | N | −0.782 | −4.176 | −4.512 |
| 2576 | VAL331 | CA | −1.727 | −4.683 | −5.49 |
| 2577 | VAL331 | C | −2.826 | −3.621 | −5.632 |
| 2578 | VAL331 | O | −3.195 | −2.922 | −4.684 |
| 2579 | VAL331 | CB | −2.31 | −6.064 | −5.13 |
| 2580 | VAL331 | CG1 | −1.224 | −7.136 | −5.153 |
| 2581 | VAL331 | CG2 | −3.01 | −6.103 | −3.774 |
| 2582 | ILE332 | N | −3.381 | −3.556 | −6.897 |
| 2583 | ILE332 | CA | −4.589 | −2.77 | −7.148 |
| 2584 | ILE332 | C | −5.721 | −3.807 | −7.228 |
| 2585 | ILE332 | O | −5.873 | −4.569 | −8.182 |
| 2586 | ILE332 | CB | −4.423 | −1.846 | −8.371 |
| 2587 | ILE332 | CG1 | −5.382 | −0.638 | −8.329 |
| 2588 | ILE332 | CG2 | −4.482 | −2.546 | −9.731 |
| 2589 | ILE332 | CD1 | −6.855 | −0.957 | −8.158 |
| 2590 | CYS333 | N | −6.476 | −3.899 | −6.073 |
| 2591 | CYS333 | CA | −7.589 | −4.832 | −5.976 |
| 2592 | CYS333 | C | −8.783 | −4.185 | −6.689 |
| 2593 | CYS333 | O | −9.295 | −3.132 | −6.309 |
| 2594 | CYS333 | CB | −7.977 | −5.116 | −4.53 |
| 2595 | CYS333 | SG | −6.842 | −6.3 | −3.743 |
| 2596 | LYS334 | N | −9.182 | −4.88 | −7.816 |
| 2597 | LYS334 | CA | −10.111 | −4.323 | −8.792 |
| 2598 | LYS334 | C | −11.546 | −4.279 | −8.235 |
| 2599 | LYS334 | O | −11.95 | −5.048 | −7.365 |
| 2600 | LYS334 | CB | −10.11 | −5.186 | −10.065 |
| 2601 | LYS334 | CG | −8.863 | −4.966 | −10.925 |

TABLE V-continued

| Atom No | Residue | Atom name | x coord | y coord | z coord |
|---|---|---|---|---|---|
| 2602 | LYS334 | CD | −8.707 | −6.065 | −11.976 |
| 2603 | LYS334 | CE | −7.611 | −5.715 | −12.971 |
| 2604 | LYS334 | NZ | −7.367 | −6.877 | −13.845 |
| 2605 | LEU335 | N | −12.355 | −3.345 | −8.864 |
| 2606 | LEU335 | CA | −13.81 | −3.365 | −8.711 |
| 2607 | LEU335 | C | −14.436 | −4.308 | −9.769 |
| 2608 | LEU335 | O | −13.753 | −4.987 | −10.536 |
| 2609 | LEU335 | CB | −14.404 | −1.947 | −8.725 |
| 2610 | LEU335 | CG | −14.005 | −0.994 | −9.87 |
| 2611 | LEU335 | CD1 | −14.051 | −1.609 | −11.257 |
| 2612 | LEU335 | CD2 | −14.918 | 0.238 | −9.852 |
| 2613 | THR336 | N | −15.823 | −4.328 | −9.782 |
| 2614 | THR336 | CA | −16.561 | −5.327 | −10.569 |
| 2615 | THR336 | C | −16.279 | −5.158 | −12.078 |
| 2616 | THR336 | O | −15.707 | −6.075 | −12.687 |
| 2617 | THR336 | CB | −18.053 | −5.318 | −10.19 |
| 2618 | THR336 | OG1 | −18.175 | −5.305 | −8.755 |
| 2619 | THR336 | CG2 | −18.802 | −6.527 | −10.736 |
| 2620 | PRO337 | N | −16.567 | −3.978 | −12.736 |
| 2621 | PRO337 | CA | −16.139 | −3.762 | −14.13 |
| 2622 | PRO337 | C | −14.623 | −3.439 | −14.198 |
| 2623 | PRO337 | O | −14.151 | −2.408 | −14.688 |
| 2624 | PRO337 | CB | −17.009 | −2.603 | −14.62 |
| 2625 | PRO337 | CG | −17.292 | −1.815 | −13.346 |
| 2626 | PRO337 | CD | −17.465 | −2.912 | −12.306 |
| 2627 | GLY338 | N | −13.819 | −4.463 | −13.734 |
| 2628 | GLY338 | CA | −12.369 | −4.376 | −13.653 |
| 2629 | GLY338 | C | −11.676 | −4.999 | −14.864 |
| 2630 | GLY338 | O | −10.467 | −4.881 | −15.049 |
| 2631 | LEU339 | N | −12.517 | −5.75 | −15.649 |
| 2632 | LEU339 | CA | −12.165 | −6.392 | −16.909 |
| 2633 | LEU339 | C | −13.452 | −6.384 | −17.749 |
| 2634 | LEU339 | O | −14.556 | −6.131 | −17.257 |
| 2635 | LEU339 | CB | −11.709 | −7.847 | −16.695 |
| 2636 | LEU339 | CG | −10.31 | −8 | −16.073 |
| 2637 | LEU339 | CD1 | −10.003 | −9.479 | −15.823 |
| 2638 | LEU339 | CD2 | −9.234 | −7.392 | −16.971 |
| 2639 | LEU340 | N | −13.287 | −6.756 | −19.068 |
| 2640 | LEU340 | CA | −14.439 | −6.983 | −19.944 |
| 2641 | LEU340 | C | −14.996 | −8.379 | −19.597 |
| 2642 | LEU340 | O | −14.778 | −9.384 | −20.267 |
| 2643 | LEU340 | CB | −14.015 | −6.863 | −21.414 |
| 2644 | LEU340 | CG | −15.167 | −6.977 | −22.434 |
| 2645 | LEU340 | CD1 | −16.231 | −5.895 | −22.245 |
| 2646 | LEU340 | CD2 | −14.603 | −6.904 | −23.856 |
| 2647 | SER341 | N | −15.653 | −8.423 | −18.375 |
| 2648 | SER341 | CA | −16.715 | −9.391 | −18.078 |
| 2649 | SER341 | C | −16.338 | −10.882 | −18.154 |
| 2650 | SER341 | O | −17.186 | −11.77 | −18.227 |
| 2651 | SER341 | CB | −18.025 | −9.094 | −18.827 |
| 2652 | SER341 | OG | −17.834 | −9.05 | −20.236 |
| 2653 | GLN342 | N | −14.988 | −11.143 | −17.948 |
| 2654 | GLN342 | CA | −14.489 | −12.484 | −18.241 |
| 2655 | GLN342 | C | −15.049 | −13.524 | −17.241 |
| 2656 | GLN342 | O | −15.217 | −13.291 | −16.038 |
| 2657 | GLN342 | CB | −12.955 | −12.548 | −18.112 |
| 2658 | GLN342 | CG | −12.195 | −11.889 | −19.267 |
| 2659 | GLN342 | CD | −10.69 | −11.852 | −19.048 |
| 2660 | GLN342 | OE1 | −9.978 | −10.911 | −19.398 |
| 2661 | GLN342 | NE2 | −10.135 | −12.963 | −18.478 |
| 2662 | GLU343 | N | −15.17 | −14.791 | −17.779 |
| 2663 | GLU343 | CA | −15.785 | −15.89 | −17.033 |
| 2664 | GLU343 | C | −14.716 | −16.454 | −16.084 |
| 2665 | GLU343 | O | −14.982 | −16.976 | −15.005 |
| 2666 | GLU343 | CB | −16.253 | −17.031 | −17.956 |
| 2667 | GLU343 | CG | −17.318 | −16.631 | −18.981 |
| 2668 | GLU343 | CD | −16.779 | −15.923 | −20.232 |
| 2669 | GLU343 | OE1 | −17.457 | −16.091 | −21.28 |
| 2670 | GLU343 | OE2 | −15.72 | −15.245 | −20.048 |
| 2671 | ALA344 | N | −13.443 | −16.438 | −16.632 |
| 2672 | ALA344 | CA | −12.281 | −16.858 | −15.876 |
| 2673 | ALA344 | C | −11.844 | −15.727 | −14.926 |
| 2674 | ALA344 | O | −12.048 | −14.533 | −15.162 |
| 2675 | ALA344 | CB | −11.13 | −17.223 | −16.802 |
| 2676 | ALA345 | N | −11.171 | −16.198 | −13.811 |
| 2677 | ALA345 | CA | −10.751 | −15.378 | −12.674 |
| 2678 | ALA345 | C | −11.96 | −14.979 | −11.811 |
| 2679 | ALA345 | O | −13.024 | −14.585 | −12.3 |
| 2680 | ALA345 | CB | −9.926 | −14.16 | −13.056 |
| 2681 | GLN346 | N | −11.726 | −15.069 | −10.444 |
| 2682 | GLN346 | CA | −12.774 | −14.685 | −9.503 |
| 2683 | GLN346 | C | −12.841 | −13.153 | −9.405 |
| 2684 | GLN346 | O | −11.88 | −12.418 | −9.633 |
| 2685 | GLN346 | CB | −12.573 | −15.264 | −8.103 |
| 2686 | GLN346 | CG | −12.839 | −16.767 | −8.015 |
| 2687 | GLN346 | CD | −13.021 | −17.178 | −6.565 |
| 2688 | GLN346 | OE1 | −13.722 | −16.548 | −5.776 |
| 2689 | GLN346 | NE2 | −12.378 | −18.327 | −6.205 |
| 2690 | LYS347 | N | −14.088 | −12.681 | −9.037 |
| 2691 | LYS347 | CA | −14.468 | −11.268 | −9.084 |
| 2692 | LYS347 | C | −15.517 | −11.068 | −7.972 |
| 2693 | LYS347 | O | −15.975 | −12.017 | −7.333 |
| 2694 | LYS347 | CB | −15.011 | −10.884 | −10.479 |
| 2695 | LYS347 | CG | −14.023 | −11.248 | −11.595 |
| 2696 | LYS347 | CD | −14.491 | −10.939 | −13.015 |
| 2697 | LYS347 | CE | −13.508 | −11.511 | −14.04 |
| 2698 | LYS347 | NZ | −13.675 | −12.969 | −14.176 |
| 2699 | TRP348 | N | −15.889 | −9.76 | −7.745 |
| 2700 | TRP348 | CA | −16.666 | −9.383 | −6.56 |
| 2701 | TRP348 | C | −17.466 | −8.095 | −6.815 |
| 2702 | TRP348 | O | −17.235 | −7.335 | −7.758 |
| 2703 | TRP348 | CB | −15.803 | −9.263 | −5.289 |
| 2704 | TRP348 | CG | −14.525 | −8.481 | −5.421 |
| 2705 | TRP348 | CD1 | −14.24 | −7.437 | −6.28 |
| 2706 | TRP348 | CD2 | −13.347 | −8.677 | −4.623 |
| 2707 | TRP348 | NE1 | −12.934 | −7.071 | −6.103 |
| 2708 | TRP348 | CE2 | −12.359 | −7.828 | −5.115 |
| 2709 | TRP348 | CE3 | −13.023 | −9.513 | −3.536 |
| 2710 | TRP348 | CZ2 | −11.051 | −7.818 | −4.623 |
| 2711 | TRP348 | CZ3 | −11.735 | −9.471 | −2.99 |
| 2712 | TRP348 | CH2 | −10.755 | −8.653 | −3.544 |
| 2713 | THR349 | N | −18.461 | −7.859 | −5.885 |
| 2714 | THR349 | CA | −19.45 | −6.792 | −6.055 |
| 2715 | THR349 | C | −18.885 | −5.466 | −5.521 |
| 2716 | THR349 | O | −18.407 | −5.345 | −4.393 |
| 2717 | THR349 | CB | −20.729 | −7.127 | −5.256 |
| 2718 | THR349 | OG1 | −20.996 | −8.532 | −5.384 |
| 2719 | THR349 | CG2 | −21.937 | −6.338 | −5.745 |
| 2720 | TYR350 | N | −19.048 | −4.388 | −6.376 |
| 2721 | TYR350 | CA | −18.566 | −3.041 | −6.011 |
| 2722 | TYR350 | C | −19.482 | −2.397 | −4.937 |
| 2723 | TYR350 | O | −20.094 | −1.341 | −5.106 |
| 2724 | TYR350 | CB | −18.5 | −2.155 | −7.273 |
| 2725 | TYR350 | CG | −17.919 | −0.767 | −7.101 |
| 2726 | TYR350 | CD1 | −16.742 | −0.538 | −6.376 |
| 2727 | TYR350 | CD2 | −18.552 | 0.325 | −7.718 |
| 2728 | TYR350 | CE1 | −16.227 | 0.755 | −6.246 |
| 2729 | TYR350 | CE2 | −18.041 | 1.618 | −7.586 |
| 2730 | TYR350 | CZ | −16.891 | 1.825 | −6.839 |
| 2731 | TYR350 | OH | −16.434 | 3.104 | −6.694 |
| 2732 | THR351 | N | −19.482 | −3.031 | −3.709 |
| 2733 | THR351 | CA | −20.34 | −2.593 | −2.598 |
| 2734 | THR351 | C | −19.646 | −1.44 | −1.834 |
| 2735 | THR351 | O | −19.535 | −1.419 | −0.609 |
| 2736 | THR351 | CB | −20.687 | −3.766 | −1.655 |
| 2737 | THR351 | OG1 | −21.089 | −4.902 | −2.437 |
| 2738 | THR351 | CG2 | −21.844 | −3.438 | −0.709 |
| 2739 | MET352 | N | −19.26 | −0.379 | −2.635 |
| 2740 | MET352 | CA | −18.829 | 0.901 | −2.074 |
| 2741 | MET352 | C | −20.09 | 1.772 | −1.929 |
| 2742 | MET352 | O | −21.078 | 1.635 | −2.649 |
| 2743 | MET352 | CB | −17.791 | 1.551 | −3 |
| 2744 | MET352 | CG | −17.031 | 2.699 | −2.336 |
| 2745 | MET352 | SD | −15.698 | 3.301 | −3.427 |
| 2746 | MET352 | CE | −14.9 | 4.439 | −2.265 |
| 2747 | ARG353 | N | −20.012 | 2.736 | −0.941 |
| 2748 | ARG353 | CA | −21.065 | 3.727 | −0.741 |
| 2749 | ARG353 | C | −20.409 | 5.118 | −0.686 |
| 2750 | ARG353 | O | −19.193 | 5.265 | −0.578 |
| 2751 | ARG353 | CB | −21.866 | 3.44 | 0.534 |
| 2752 | ARG353 | CG | −22.613 | 2.105 | 0.469 |
| 2753 | ARG353 | CD | −23.63 | 1.995 | 1.594 |
| 2754 | ARG353 | NE | −24.282 | 0.679 | 1.613 |
| 2755 | ARG353 | CZ | −23.829 | −0.389 | 2.309 |

TABLE V-continued

| Atom No | Residue | Atom name | x coord | y coord | z coord |
|---|---|---|---|---|---|
| 2756 | ARG353 | NH1 | −24.598 | −1.488 | 2.418 |
| 2757 | ARG353 | NH2 | −22.633 | −0.385 | 2.934 |
| 2758 | GLU354 | N | −21.313 | 6.159 | −0.787 |
| 2759 | GLU354 | CA | −20.907 | 7.561 | −0.682 |
| 2760 | GLU354 | C | −21.009 | 8.025 | 0.787 |
| 2761 | GLU354 | O | −21.52 | 7.333 | 1.669 |
| 2762 | GLU354 | CB | −21.795 | 8.418 | −1.607 |
| 2763 | GLU354 | CG | −21.021 | 8.966 | −2.806 |
| 2764 | GLU354 | CD | −19.941 | 9.964 | −2.419 |
| 2765 | GLU354 | OE1 | −19.803 | 10.212 | −1.187 |
| 2766 | GLU354 | OE2 | −19.268 | 10.453 | −3.384 |
| 2767 | GLY355 | N | −20.49 | 9.288 | 1.024 |
| 2768 | GLY355 | CA | −20.444 | 9.829 | 2.368 |
| 2769 | GLY355 | C | −20.044 | 11.301 | 2.472 |
| 2770 | GLY355 | O | −19.549 | 11.947 | 1.552 |
| 2771 | ARG356 | N | −20.278 | 11.835 | 3.732 |
| 2772 | ARG356 | CA | −19.973 | 13.22 | 4.076 |
| 2773 | ARG356 | C | −19.435 | 13.261 | 5.517 |
| 2774 | ARG356 | O | −19.822 | 12.473 | 6.377 |
| 2775 | ARG356 | CB | −21.22 | 14.11 | 4.019 |
| 2776 | ARG356 | CG | −21.71 | 14.391 | 2.6 |
| 2777 | ARG356 | CD | −23.015 | 15.181 | 2.591 |
| 2778 | ARG356 | NE | −24.15 | 14.34 | 3.001 |
| 2779 | ARG356 | CZ | −24.814 | 14.395 | 4.183 |
| 2780 | ARG356 | NH1 | −25.871 | 13.564 | 4.361 |
| 2781 | ARG356 | NH2 | −24.496 | 15.216 | 5.191 |
| 2782 | TRP357 | N | −18.54 | 14.291 | 5.734 |
| 2783 | TRP357 | CA | −17.903 | 14.556 | 7.028 |
| 2784 | TRP357 | C | −17.788 | 16.092 | 7.12 |
| 2785 | TRP357 | O | −16.762 | 16.695 | 6.804 |
| 2786 | TRP357 | CB | −16.508 | 13.905 | 7.125 |
| 2787 | TRP357 | CG | −16.539 | 12.489 | 7.622 |
| 2788 | TRP357 | CD1 | −16.376 | 12.093 | 8.934 |
| 2789 | TRP357 | CD2 | −16.724 | 11.29 | 6.859 |
| 2790 | TRP357 | NE1 | −16.508 | 10.732 | 9.009 |
| 2791 | TRP357 | CE2 | −16.721 | 10.216 | 7.753 |
| 2792 | TRP357 | CE3 | −16.909 | 11.018 | 5.486 |
| 2793 | TRP357 | CZ2 | −16.913 | 8.891 | 7.346 |
| 2794 | TRP357 | CZ3 | −17.121 | 9.701 | 5.064 |
| 2795 | TRP357 | CH2 | −17.119 | 8.656 | 5.983 |
| 2796 | GLU358 | N | −18.962 | 16.734 | 7.473 |
| 2797 | GLU358 | CA | −19.026 | 18.171 | 7.728 |
| 2798 | GLU358 | C | −18.992 | 18.415 | 9.253 |
| 2799 | GLU358 | O | −19.324 | 17.567 | 10.083 |
| 2800 | GLU358 | CB | −20.231 | 18.902 | 7.101 |
| 2801 | GLU358 | CG | −21.012 | 18.159 | 6.019 |
| 2802 | GLU358 | CD | −22.066 | 17.165 | 6.495 |
| 2803 | GLU358 | OE1 | −22.758 | 16.626 | 5.577 |
| 2804 | GLU358 | OE2 | −22.149 | 16.952 | 7.747 |
| 2805 | LYS359 | N | −18.551 | 19.678 | 9.621 |
| 2806 | LYS359 | CA | −18.467 | 20.053 | 11.028 |
| 2807 | LYS359 | C | −19.789 | 20.701 | 11.473 |
| 2808 | LYS359 | O | −20.366 | 21.552 | 10.792 |
| 2809 | LYS359 | CB | −17.316 | 21.036 | 11.288 |
| 2810 | LYS359 | CG | −15.946 | 20.357 | 11.18 |
| 2811 | LYS359 | CD | −14.806 | 21.321 | 11.516 |
| 2812 | LYS359 | CE | −13.46 | 20.611 | 11.454 |
| 2813 | LYS359 | NZ | −12.388 | 21.56 | 11.839 |
| 2814 | ARG360 | N | −20.185 | 20.303 | 12.74 |
| 2815 | ARG360 | CA | −21.453 | 20.645 | 13.397 |
| 2816 | ARG360 | C | −22.571 | 19.638 | 13.049 |
| 2817 | ARG360 | O | −23.753 | 19.862 | 13.306 |
| 2818 | ARG360 | CB | −21.969 | 22.07 | 13.156 |
| 2819 | ARG360 | CG | −20.949 | 23.176 | 13.424 |
| 2820 | ARG360 | CD | −21.441 | 24.49 | 12.83 |
| 2821 | ARG360 | NE | −20.344 | 25.336 | 12.347 |
| 2822 | ARG360 | CZ | −19.678 | 25.135 | 11.181 |
| 2823 | ARG360 | NH1 | −18.825 | 26.093 | 10.748 |
| 2824 | ARG360 | NH2 | −19.827 | 24.028 | 10.422 |
| 2825 | SER361 | N | −22.132 | 18.433 | 12.534 |
| 2826 | SER361 | CA | −23.092 | 17.492 | 11.962 |
| 2827 | SER361 | C | −22.527 | 16.07 | 12.006 |
| 2828 | SER361 | O | −23.052 | 15.2 | 12.699 |
| 2829 | SER361 | CB | −23.45 | 17.878 | 10.521 |
| 2830 | SER361 | OG | −22.244 | 18.109 | 9.793 |
| 2831 | THR362 | N | −21.427 | 15.849 | 11.197 |
| 2832 | THR362 | CA | −20.967 | 14.494 | 10.88 |
| 2833 | THR362 | C | −19.496 | 14.261 | 11.248 |
| 2834 | THR362 | O | −19.07 | 13.144 | 11.557 |
| 2835 | THR362 | CB | −21.194 | 14.156 | 9.395 |
| 2836 | THR362 | OG1 | −20.74 | 15.237 | 8.575 |
| 2837 | THR362 | CG2 | −22.654 | 13.848 | 9.079 |
| 2838 | ALA363 | N | −18.642 | 15.337 | 11.141 |
| 2839 | ALA363 | CA | −17.212 | 15.227 | 11.413 |
| 2840 | ALA363 | C | −17 | 15.136 | 12.933 |
| 2841 | ALA363 | O | −16.552 | 16.058 | 13.607 |
| 2842 | ALA363 | CB | −16.435 | 16.394 | 10.824 |
| 2843 | GLY364 | N | −17.37 | 13.903 | 13.457 |
| 2844 | GLY364 | CA | −17.585 | 13.743 | 14.883 |
| 2845 | GLY364 | C | −16.35 | 13.324 | 15.673 |
| 2846 | GLY364 | O | −16.398 | 13.133 | 16.887 |
| 2847 | GLY365 | N | −15.212 | 13.151 | 14.922 |
| 2848 | GLY365 | CA | −13.952 | 12.741 | 15.498 |
| 2849 | GLY365 | C | −13.734 | 11.229 | 15.406 |
| 2850 | GLY365 | O | −14.527 | 10.457 | 14.872 |
| 2851 | GLN366 | N | −12.522 | 10.847 | 15.957 |
| 2852 | GLN366 | CA | −12.075 | 9.46 | 16.036 |
| 2853 | GLN366 | C | −12.217 | 9.004 | 17.5 |
| 2854 | GLN366 | O | −12.316 | 9.799 | 18.438 |
| 2855 | GLN366 | CB | −10.612 | 9.339 | 15.598 |
| 2856 | GLN366 | CG | −10.4 | 9.744 | 14.14 |
| 2857 | GLN366 | CD | −8.968 | 9.503 | 13.72 |
| 2858 | GLN366 | OE1 | −8.143 | 10.402 | 13.608 |
| 2859 | GLN366 | NE2 | −8.653 | 8.196 | 13.472 |
| 2860 | ARG367 | N | −12.109 | 7.634 | 17.701 |
| 2861 | ARG367 | CA | −12.65 | 7.006 | 18.916 |
| 2862 | ARG367 | C | −11.849 | 7.197 | 20.228 |
| 2863 | ARG367 | O | −11.982 | 6.425 | 21.184 |
| 2864 | ARG367 | CB | −12.905 | 5.498 | 18.688 |
| 2865 | ARG367 | CG | −11.635 | 4.631 | 18.755 |
| 2866 | ARG367 | CD | −11.779 | 3.48 | 19.753 |
| 2867 | ARG367 | NE | −10.476 | 3.073 | 20.296 |
| 2868 | ARG367 | CZ | −9.887 | 3.665 | 21.366 |
| 2869 | ARG367 | NH1 | −10.429 | 4.7 | 22.025 |
| 2870 | ARG367 | NH2 | −8.69 | 3.226 | 21.806 |
| 2871 | GLN368 | N | −11.05 | 8.313 | 20.291 |
| 2872 | GLN368 | CA | −10.37 | 8.732 | 21.509 |
| 2873 | GLN368 | C | −10.05 | 10.237 | 21.513 |
| 2874 | GLN368 | O | −9.328 | 10.743 | 22.375 |
| 2875 | GLN368 | CB | −9.092 | 7.906 | 21.735 |
| 2876 | GLN368 | CG | −8.796 | 7.688 | 23.221 |
| 2877 | GLN368 | CD | −7.888 | 6.49 | 23.4 |
| 2878 | GLN368 | OE1 | −8.313 | 5.334 | 23.354 |
| 2879 | GLN368 | NE2 | −6.565 | 6.78 | 23.545 |
| 2880 | LEU369 | N | −10.702 | 11.007 | 20.568 |
| 2881 | LEU369 | CA | −10.55 | 12.461 | 20.559 |
| 2882 | LEU369 | C | −11.611 | 13.036 | 21.509 |
| 2883 | LEU369 | O | −12.578 | 13.703 | 21.135 |
| 2884 | LEU369 | CB | −10.684 | 13.044 | 19.146 |
| 2885 | LEU369 | CG | −9.617 | 12.561 | 18.142 |
| 2886 | LEU369 | CD1 | −9.783 | 13.301 | 16.811 |
| 2887 | LEU369 | CD2 | −8.184 | 12.745 | 18.645 |
| 2888 | LEU370 | N | −11.352 | 12.814 | 22.853 |
| 2889 | LEU370 | CA | −12.372 | 12.994 | 23.897 |
| 2890 | LEU370 | C | −12.689 | 14.478 | 24.253 |
| 2891 | LEU370 | O | −13.159 | 14.812 | 25.339 |
| 2892 | LEU370 | CB | −12.003 | 12.227 | 25.183 |
| 2893 | LEU370 | CG | −11.831 | 10.701 | 25.034 |
| 2894 | LEU370 | CD1 | −11.47 | 10.087 | 26.39 |
| 2895 | LEU370 | CD2 | −13.076 | 10.017 | 24.47 |
| 2896 | GLN371 | N | −12.58 | 15.354 | 23.193 |
| 2897 | GLN371 | CA | −13.322 | 16.61 | 23.121 |
| 2898 | GLN371 | C | −14.711 | 16.324 | 22.524 |
| 2899 | GLN371 | O | −15.701 | 16.945 | 22.907 |
| 2900 | GLN371 | CB | −12.536 | 17.591 | 22.228 |
| 2901 | GLN371 | CG | −13.169 | 18.976 | 22.049 |
| 2902 | GLN371 | CD | −14.262 | 19.089 | 20.995 |
| 2903 | GLN371 | OE1 | −15.348 | 19.606 | 21.238 |
| 2904 | GLN371 | NE2 | −13.921 | 18.669 | 19.739 |
| 2905 | ASP372 | N | −14.704 | 15.511 | 21.402 |
| 2906 | ASP372 | CA | −15.799 | 15.527 | 20.44 |
| 2907 | ASP372 | C | −16.76 | 14.328 | 20.615 |
| 2908 | ASP372 | O | −16.66 | 13.492 | 21.511 |
| 2909 | ASP372 | CB | −15.203 | 15.594 | 19.035 |

TABLE V-continued

| Atom No | Residue | Atom name | x coord | y coord | z coord |
|---|---|---|---|---|---|
| 2910 | ASP372 | CG | −16.111 | 16.58 | 18.31 |
| 2911 | ASP372 | OD1 | −17.287 | 16.145 | 18.107 |
| 2912 | ASP372 | OD2 | −15.588 | 17.709 | 18.076 |
| 2913 | THR373 | N | −17.792 | 14.315 | 19.688 |
| 2914 | THR373 | CA | −18.977 | 13.493 | 19.86 |
| 2915 | THR373 | C | −18.777 | 12.024 | 19.482 |
| 2916 | THR373 | O | −19.582 | 11.178 | 19.884 |
| 2917 | THR373 | CB | −20.195 | 14.049 | 19.085 |
| 2918 | THR373 | OG1 | −21.431 | 13.373 | 19.431 |
| 2919 | THR373 | CG2 | −20.056 | 13.997 | 17.571 |
| 2920 | PHE374 | N | −17.84 | 11.738 | 18.522 |
| 2921 | PHE374 | CA | −17.508 | 10.392 | 18.051 |
| 2922 | PHE374 | C | −18.642 | 9.76 | 17.217 |
| 2923 | PHE374 | O | −18.488 | 9.453 | 16.032 |
| 2924 | PHE374 | CB | −17.011 | 9.462 | 19.177 |
| 2925 | PHE374 | CG | −16.836 | 8.017 | 18.764 |
| 2926 | PHE374 | CD1 | −16.167 | 7.669 | 17.583 |
| 2927 | PHE374 | CD2 | −17.375 | 6.996 | 19.561 |
| 2928 | PHE374 | CE1 | −16.096 | 6.336 | 17.182 |
| 2929 | PHE374 | CE2 | −17.284 | 5.66 | 19.166 |
| 2930 | PHE374 | CZ | −16.653 | 5.331 | 17.97 |
| 2931 | TRP375 | N | −19.817 | 9.514 | 17.898 |
| 2932 | TRP375 | CA | −20.82 | 8.557 | 17.424 |
| 2933 | TRP375 | C | −21.755 | 9.084 | 16.323 |
| 2934 | TRP375 | O | −22.61 | 8.367 | 15.804 |
| 2935 | TRP375 | CB | −21.629 | 7.912 | 18.564 |
| 2936 | TRP375 | CG | −22.331 | 8.872 | 19.483 |
| 2937 | TRP375 | CD1 | −21.851 | 9.306 | 20.704 |
| 2938 | TRP375 | CD2 | −23.628 | 9.464 | 19.323 |
| 2939 | TRP375 | NE1 | −22.769 | 10.151 | 21.262 |
| 2940 | TRP375 | CE2 | −23.867 | 10.263 | 20.444 |
| 2941 | TRP375 | CE3 | −24.638 | 9.38 | 18.341 |
| 2942 | TRP375 | CZ2 | −25.054 | 10.984 | 20.627 |
| 2943 | TRP375 | CZ3 | −25.831 | 10.092 | 18.509 |
| 2944 | TRP375 | CH2 | −26.035 | 10.881 | 19.638 |
| 2945 | LYS376 | N | −21.516 | 10.383 | 15.928 |
| 2946 | LYS376 | CA | −22.219 | 11.011 | 14.814 |
| 2947 | LYS376 | C | −21.41 | 10.936 | 13.501 |
| 2948 | LYS376 | O | −21.746 | 11.557 | 12.494 |
| 2949 | LYS376 | CB | −22.584 | 12.47 | 15.123 |
| 2950 | LYS376 | CG | −23.353 | 12.625 | 16.44 |
| 2951 | LYS376 | CD | −23.905 | 14.043 | 16.608 |
| 2952 | LYS376 | CE | −24.52 | 14.269 | 17.983 |
| 2953 | LYS376 | NZ | −23.482 | 14.625 | 18.973 |
| 2954 | ASN377 | N | −20.364 | 10.027 | 13.505 |
| 2955 | ASN377 | CA | −19.79 | 9.578 | 12.237 |
| 2956 | ASN377 | C | −20.838 | 8.658 | 11.589 |
| 2957 | ASN377 | O | −21.536 | 7.917 | 12.289 |
| 2958 | ASN377 | CB | −18.536 | 8.733 | 12.44 |
| 2959 | ASN377 | CG | −17.282 | 9.556 | 12.579 |
| 2960 | ASN377 | OD1 | −16.574 | 9.835 | 11.614 |
| 2961 | ASN377 | ND2 | −16.991 | 9.935 | 13.859 |
| 2962 | PRO378 | N | −20.903 | 8.629 | 10.213 |
| 2963 | PRO378 | CA | −21.896 | 7.798 | 9.54 |
| 2964 | PRO378 | C | −21.427 | 6.334 | 9.541 |
| 2965 | PRO378 | O | −20.324 | 5.978 | 9.129 |
| 2966 | PRO378 | CB | −21.965 | 8.358 | 8.118 |
| 2967 | PRO378 | CG | −20.59 | 8.984 | 7.909 |
| 2968 | PRO378 | CD | −20.246 | 9.536 | 9.283 |
| 2969 | GLN379 | N | −22.355 | 5.455 | 10.063 |
| 2970 | GLN379 | CA | −22.13 | 4.02 | 10.099 |
| 2971 | GLN379 | C | −22.575 | 3.441 | 8.742 |
| 2972 | GLN379 | O | −23.457 | 3.955 | 8.053 |
| 2973 | GLN379 | CB | −22.913 | 3.342 | 11.236 |
| 2974 | GLN379 | CG | −22.593 | 3.905 | 12.627 |
| 2975 | GLN379 | CD | −23.27 | 5.236 | 12.913 |
| 2976 | GLN379 | OE1 | −24.062 | 5.774 | 12.145 |
| 2977 | GLN379 | NE2 | −22.924 | 5.779 | 14.122 |
| 2978 | PHE380 | N | −21.936 | 2.265 | 8.383 |
| 2979 | PHE380 | CA | −22.185 | 1.634 | 7.09 |
| 2980 | PHE380 | C | −22.63 | 0.18 | 7.295 |
| 2981 | PHE380 | O | −22.198 | −0.546 | 8.188 |
| 2982 | PHE380 | CB | −20.949 | 1.658 | 6.181 |
| 2983 | PHE380 | CG | −20.569 | 3.043 | 5.716 |
| 2984 | PHE380 | CD1 | −19.357 | 3.616 | 6.122 |
| 2985 | PHE380 | CD2 | −21.416 | 3.779 | 4.873 |
| 2986 | PHE380 | CE1 | −19.001 | 4.896 | 5.693 |
| 2987 | PHE380 | CE2 | −21.056 | 5.057 | 4.443 |
| 2988 | PHE380 | CZ | −19.848 | 5.615 | 4.853 |
| 2989 | LEU381 | N | −23.534 | −0.249 | 6.338 |
| 2990 | LEU381 | CA | −24.25 | −1.514 | 6.46 |
| 2991 | LEU381 | C | −23.534 | −2.548 | 5.567 |
| 2992 | LEU381 | O | −23.838 | −2.741 | 4.388 |
| 2993 | LEU381 | CB | −25.714 | −1.298 | 6.037 |
| 2994 | LEU381 | CG | −26.653 | −2.459 | 6.414 |
| 2995 | LEU381 | CD1 | −26.929 | −2.494 | 7.92 |
| 2996 | LEU381 | CD2 | −27.978 | −2.326 | 5.66 |
| 2997 | LEU382 | N | −22.46 | −3.169 | 6.173 |
| 2998 | LEU382 | CA | −21.835 | −4.382 | 5.63 |
| 2999 | LEU382 | C | −22.284 | −5.561 | 6.522 |
| 3000 | LEU382 | O | −22.899 | −5.375 | 7.577 |
| 3001 | LEU382 | CB | −20.31 | −4.248 | 5.591 |
| 3002 | LEU382 | CG | −19.805 | −3.112 | 4.675 |
| 3003 | LEU382 | CD1 | −18.293 | −2.95 | 4.834 |
| 3004 | LEU382 | CD2 | −20.143 | −3.357 | 3.203 |
| 3005 | SER383 | N | −21.988 | −6.824 | 6.048 |
| 3006 | SER383 | CA | −22.588 | −8.052 | 6.617 |
| 3007 | SER383 | C | −21.629 | −9.25 | 6.398 |
| 3008 | SER383 | O | −20.671 | −9.146 | 5.623 |
| 3009 | SER383 | CB | −23.949 | −8.315 | 5.955 |
| 3010 | SER383 | OG | −24.973 | −7.4 | 6.396 |
| 3011 | VAL384 | N | −21.83 | −10.37 | 7.195 |
| 3012 | VAL384 | CA | −21.372 | −11.751 | 6.842 |
| 3013 | VAL384 | C | −22.079 | −12.761 | 7.821 |
| 3014 | VAL384 | O | −22.425 | −12.38 | 8.942 |
| 3015 | VAL384 | CB | −19.837 | −11.888 | 6.772 |
| 3016 | VAL384 | CG1 | −19.229 | −12.214 | 8.117 |
| 3017 | VAL384 | CG2 | −19.373 | −12.917 | 5.744 |
| 3018 | TRP385 | N | −22.278 | −14.06 | 7.353 |
| 3019 | TRP385 | CA | −22.723 | −15.189 | 8.229 |
| 3020 | TRP385 | C | −21.53 | −16.149 | 8.431 |
| 3021 | TRP385 | O | −20.479 | −15.995 | 7.81 |
| 3022 | TRP385 | CB | −24.005 | −15.93 | 7.763 |
| 3023 | TRP385 | CG | −23.947 | −16.867 | 6.581 |
| 3024 | TRP385 | CD1 | −23.168 | −18.003 | 6.451 |
| 3025 | TRP385 | CD2 | −24.804 | −16.854 | 5.419 |
| 3026 | TRP385 | NE1 | −23.438 | −18.598 | 5.247 |
| 3027 | TRP385 | CE2 | −24.405 | −17.891 | 4.578 |
| 3028 | TRP385 | CE3 | −25.913 | −16.085 | 5.006 |
| 3029 | TRP385 | CZ2 | −24.963 | −18.119 | 3.313 |
| 3030 | TRP385 | CZ3 | −26.5 | −16.301 | 3.754 |
| 3031 | TRP385 | CH2 | −26.014 | −17.294 | 2.91 |
| 3032 | ARG386 | N | −21.73 | −17.184 | 9.335 |
| 3033 | ARG386 | CA | −20.636 | −18.069 | 9.763 |
| 3034 | ARG386 | C | −21.064 | −19.578 | 9.786 |
| 3035 | ARG386 | O | −21.971 | −19.986 | 10.516 |
| 3036 | ARG386 | CB | −20.162 | −17.568 | 11.128 |
| 3037 | ARG386 | CG | −19.024 | −18.381 | 11.725 |
| 3038 | ARG386 | CD | −18.422 | −17.636 | 12.911 |
| 3039 | ARG386 | NE | −17.243 | −16.862 | 12.502 |
| 3040 | ARG386 | CZ | −17.023 | −15.559 | 12.755 |
| 3041 | ARG386 | NH1 | −15.887 | −14.992 | 12.315 |
| 3042 | ARG386 | NH2 | −17.891 | −14.792 | 13.442 |
| 3043 | PRO387 | N | −20.383 | −20.443 | 8.926 |
| 3044 | PRO387 | CA | −20.892 | −21.788 | 8.578 |
| 3045 | PRO387 | C | −20.298 | −22.971 | 9.395 |
| 3046 | PRO387 | O | −19.435 | −22.831 | 10.267 |
| 3047 | PRO387 | CB | −20.461 | −21.931 | 7.113 |
| 3048 | PRO387 | CG | −19.113 | −21.221 | 7.091 |
| 3049 | PRO387 | CD | −19.383 | −20.011 | 7.958 |
| 3050 | GLU388 | N | −20.764 | −24.221 | 9.005 |
| 3051 | GLU388 | CA | −20.389 | −25.505 | 9.623 |
| 3052 | GLU388 | C | −19.082 | −26.127 | 9.012 |
| 3053 | GLU388 | O | −18.926 | −27.349 | 8.891 |
| 3054 | GLU388 | CB | −21.524 | −26.521 | 9.497 |
| 3055 | GLU388 | CG | −22.909 | −26.148 | 10.003 |
| 3056 | GLU388 | CD | −23.108 | −26.087 | 11.515 |
| 3057 | GLU388 | OE1 | −22.765 | −27.093 | 12.197 |
| 3058 | GLU388 | OE2 | −23.571 | −24.979 | 11.934 |
| 3059 | GLU389 | N | −18.033 | −25.254 | 8.789 |
| 3060 | GLU389 | CA | −16.664 | −25.697 | 8.397 |
| 3061 | GLU389 | C | −15.987 | −26.349 | 9.647 |
| 3062 | GLU389 | O | −16.605 | −26.566 | 10.696 |
| 3063 | GLU389 | CB | −15.93 | −24.498 | 7.763 |

TABLE V-continued

| Atom No | Residue | Atom name | x coord | y coord | z coord |
|---|---|---|---|---|---|
| 3064 | GLU389 | CG | −14.713 | −24.819 | 6.884 |
| 3065 | GLU389 | CD | −13.399 | −24.46 | 7.563 |
| 3066 | GLU389 | OE1 | −12.701 | −23.533 | 7.064 |
| 3067 | GLU389 | OE2 | −13.124 | −25.121 | 8.61 |
| 3068 | GLY390 | N | −14.681 | −26.751 | 9.516 |
| 3069 | GLY390 | CA | −14.027 | −27.553 | 10.53 |
| 3070 | GLY390 | C | −13.423 | −26.714 | 11.662 |
| 3071 | GLY390 | O | −14.015 | −25.771 | 12.195 |
| 3072 | ARG391 | N | −12.162 | −27.162 | 12.036 |
| 3073 | ARG391 | CA | −11.427 | −26.628 | 13.18 |
| 3074 | ARG391 | C | −10.954 | −25.21 | 12.832 |
| 3075 | ARG391 | O | −10.327 | −24.927 | 11.809 |
| 3076 | ARG391 | CB | −10.224 | −27.531 | 13.497 |
| 3077 | ARG391 | CG | −9.386 | −27.126 | 14.715 |
| 3078 | ARG391 | CD | −10.134 | −27.236 | 16.041 |
| 3079 | ARG391 | NE | −9.223 | −26.995 | 17.173 |
| 3080 | ARG391 | CZ | −9.596 | −27.072 | 18.477 |
| 3081 | ARG391 | NH1 | −8.666 | −26.907 | 19.442 |
| 3082 | ARG391 | NH2 | −10.872 | −27.303 | 18.843 |
| 3083 | ARG392 | N | −11.331 | −24.267 | 13.785 |
| 3084 | ARG392 | CA | −11.305 | −22.854 | 13.436 |
| 3085 | ARG392 | C | −10.846 | −21.965 | 14.609 |
| 3086 | ARG392 | O | −11.058 | −20.753 | 14.675 |
| 3087 | ARG392 | CB | −12.647 | −22.412 | 12.835 |
| 3088 | ARG392 | CG | −12.793 | −22.794 | 11.36 |
| 3089 | ARG392 | CD | −14.19 | −22.585 | 10.807 |
| 3090 | ARG392 | NE | −15.126 | −23.597 | 11.318 |
| 3091 | ARG392 | CZ | −16.472 | −23.486 | 11.233 |
| 3092 | ARG392 | NH1 | −17.268 | −24.443 | 11.732 |
| 3093 | ARG392 | NH2 | −17.067 | −22.445 | 10.617 |
| 3094 | SER393 | N | −9.984 | −22.596 | 15.478 |
| 3095 | SER393 | CA | −9.333 | −21.934 | 16.611 |
| 3096 | SER393 | C | −7.956 | −21.336 | 16.252 |
| 3097 | SER393 | O | −7.059 | −21.28 | 17.093 |
| 3098 | SER393 | CB | −9.151 | −22.928 | 17.767 |
| 3099 | SER393 | OG | −8.707 | −22.282 | 18.955 |
| 3100 | LEU394 | N | −7.851 | −20.775 | 14.996 |
| 3101 | LEU394 | CA | −6.568 | −20.364 | 14.404 |
| 3102 | LEU394 | C | −6.794 | −19.764 | 12.993 |
| 3103 | LEU394 | O | −6.362 | −20.323 | 11.985 |
| 3104 | LEU394 | CB | −5.522 | −21.52 | 14.394 |
| 3105 | LEU394 | CG | −5.762 | −22.791 | 13.539 |
| 3106 | LEU394 | CD1 | −4.561 | −23.734 | 13.699 |
| 3107 | LEU394 | CD2 | −7.04 | −23.555 | 13.868 |
| 3108 | ARG395 | N | −7.593 | −18.622 | 12.89 |
| 3109 | ARG395 | CA | −8.21 | −18.3 | 11.586 |
| 3110 | ARG395 | C | −8.701 | −16.782 | 11.178 |
| 3111 | ARG395 | O | −9.874 | −16.525 | 10.892 |
| 3112 | ARG395 | CB | −9.39 | −19.275 | 11.375 |
| 3113 | ARG395 | CG | −9.286 | −20.806 | 11.46 |
| 3114 | ARG395 | CD | −8.562 | −21.618 | 10.391 |
| 3115 | ARG395 | NE | −9.305 | −21.658 | 9.128 |
| 3116 | ARG395 | CZ | −10.205 | −22.574 | 8.688 |
| 3117 | ARG395 | NH1 | −10.593 | −23.658 | 9.402 |
| 3118 | ARG395 | NH2 | −10.761 | −22.39 | 7.476 |
| 3119 | PRO396 | N | −7.74 | −15.79 | 11.005 |
| 3120 | PRO396 | CA | −7.983 | −14.407 | 10.506 |
| 3121 | PRO396 | C | −8.425 | −14.105 | 9.049 |
| 3122 | PRO396 | O | −8.923 | −14.954 | 8.312 |
| 3123 | PRO396 | CB | −6.609 | −13.747 | 10.679 |
| 3124 | PRO396 | CG | −5.993 | −14.423 | 11.868 |
| 3125 | PRO396 | CD | −6.711 | −15.746 | 11.993 |
| 3126 | CYS397 | N | −8.274 | −12.755 | 8.692 |
| 3127 | CYS397 | CA | −8.72 | −12.15 | 7.421 |
| 3128 | CYS397 | C | −8.328 | −10.621 | 7.371 |
| 3129 | CYS397 | O | −7.924 | −10.054 | 8.394 |
| 3130 | CYS397 | CB | −10.208 | −12.41 | 7.221 |
| 3131 | CYS397 | SG | −11.279 | −11.876 | 8.582 |
| 3132 | SER398 | N | −8.423 | −9.94 | 6.157 |
| 3133 | SER398 | CA | −8.182 | −8.484 | 6.024 |
| 3134 | SER398 | C | −9.232 | −7.657 | 5.24 |
| 3135 | SER398 | O | −9.673 | −7.98 | 4.142 |
| 3136 | SER398 | CB | −6.83 | −8.139 | 5.399 |
| 3137 | SER398 | OG | −6.54 | −6.747 | 5.627 |
| 3138 | VAL399 | N | −9.546 | −6.441 | 5.84 |
| 3139 | VAL399 | CA | −10.484 | −5.489 | 5.229 |
| 3140 | VAL399 | C | −9.877 | −4.905 | 3.935 |
| 3141 | VAL399 | O | −8.669 | −4.858 | 3.714 |
| 3142 | VAL399 | CB | −10.915 | −4.399 | 6.256 |
| 3143 | VAL399 | CG1 | −12.368 | −4.572 | 6.703 |
| 3144 | VAL399 | CG2 | −10.719 | −2.942 | 5.827 |
| 3145 | LEU400 | N | −10.855 | −4.406 | 3.088 |
| 3146 | LEU400 | CA | −10.577 | −3.844 | 1.768 |
| 3147 | LEU400 | C | −11.708 | −2.838 | 1.468 |
| 3148 | LEU400 | O | −12.448 | −2.909 | 0.491 |
| 3149 | LEU400 | CB | −10.524 | −4.964 | 0.726 |
| 3150 | LEU400 | CG | −10.008 | −4.493 | −0.644 |
| 3151 | LEU400 | CD1 | −8.493 | −4.301 | −0.627 |
| 3152 | LEU400 | CD2 | −10.408 | −5.497 | −1.721 |
| 3153 | VAL401 | N | −11.801 | −1.835 | 2.407 |
| 3154 | VAL401 | CA | −12.723 | −0.702 | 2.301 |
| 3155 | VAL401 | C | −11.844 | 0.483 | 2.736 |
| 3156 | VAL401 | O | −10.856 | 0.309 | 3.454 |
| 3157 | VAL401 | CB | −13.959 | −0.896 | 3.208 |
| 3158 | VAL401 | CG1 | −14.994 | 0.218 | 3.018 |
| 3159 | VAL401 | CG2 | −14.649 | −2.245 | 2.967 |
| 3160 | SER402 | N | −12.241 | 1.72 | 2.284 |
| 3161 | SER402 | CA | −11.36 | 2.883 | 2.401 |
| 3162 | SER402 | C | −12.157 | 4.151 | 2.745 |
| 3163 | SER402 | O | −13.38 | 4.229 | 2.642 |
| 3164 | SER402 | CB | −10.56 | 3.073 | 1.105 |
| 3165 | SER402 | OG | −11.443 | 3.091 | −0.023 |
| 3166 | LEU403 | N | −11.356 | 5.198 | 3.161 |
| 3167 | LEU403 | CA | −11.854 | 6.504 | 3.597 |
| 3168 | LEU403 | C | −10.857 | 7.561 | 3.072 |
| 3169 | LEU403 | O | −10.423 | 8.519 | 3.706 |
| 3170 | LEU403 | CB | −12.133 | 6.514 | 5.096 |
| 3171 | LEU403 | CG | −12.702 | 7.82 | 5.681 |
| 3172 | LEU403 | CD1 | −13.726 | 8.51 | 4.783 |
| 3173 | LEU403 | CD2 | −13.325 | 7.552 | 7.053 |
| 3174 | LEU404 | N | −10.668 | 7.373 | 1.714 |
| 3175 | LEU404 | CA | −9.941 | 8.264 | 0.812 |
| 3176 | LEU404 | C | −10.818 | 9.529 | 0.723 |
| 3177 | LEU404 | O | −12.024 | 9.486 | 0.474 |
| 3178 | LEU404 | CB | −9.801 | 7.527 | −0.53 |
| 3179 | LEU404 | CG | −8.834 | 8.136 | −1.553 |
| 3180 | LEU404 | CD1 | −8.581 | 7.127 | −2.68 |
| 3181 | LEU404 | CD2 | −9.37 | 9.432 | −2.147 |
| 3182 | GLN405 | N | −10.159 | 10.714 | 1.016 |
| 3183 | GLN405 | CA | −10.916 | 11.95 | 1.155 |
| 3184 | GLN405 | C | −11.398 | 12.498 | −0.194 |
| 3185 | GLN405 | O | −10.848 | 12.242 | −1.26 |
| 3186 | GLN405 | CB | −10.152 | 13.044 | 1.92 |
| 3187 | GLN405 | CG | −8.982 | 13.679 | 1.17 |
| 3188 | GLN405 | CD | −8.409 | 14.848 | 1.941 |
| 3189 | GLN405 | OE1 | −8.517 | 16.01 | 1.558 |
| 3190 | GLN405 | NE2 | −7.772 | 14.524 | 3.104 |
| 3191 | LYS406 | N | −12.457 | 13.383 | −0.088 |
| 3192 | LYS406 | CA | −12.778 | 14.302 | −1.177 |
| 3193 | LYS406 | C | −12.141 | 15.635 | −0.743 |
| 3194 | LYS406 | O | −12.518 | 16.183 | 0.306 |
| 3195 | LYS406 | CB | −14.292 | 14.496 | −1.302 |
| 3196 | LYS406 | CG | −15.033 | 13.227 | −1.744 |
| 3197 | LYS406 | CD | −16.543 | 13.452 | −1.659 |
| 3198 | LYS406 | CE | −17.366 | 12.198 | −1.9 |
| 3199 | LYS406 | NZ | −17.498 | 11.909 | −3.337 |
| 3200 | PRO407 | N | −11.126 | 16.161 | −1.511 |
| 3201 | PRO407 | CA | −10.416 | 17.373 | −1.111 |
| 3202 | PRO407 | C | −11.214 | 18.633 | −1.495 |
| 3203 | PRO407 | O | −12.201 | 18.619 | −2.226 |
| 3204 | PRO407 | CB | −9.092 | 17.307 | −1.875 |
| 3205 | PRO407 | CG | −9.469 | 16.556 | −3.147 |
| 3206 | PRO407 | CD | −10.478 | 15.53 | −2.653 |
| 3207 | ARG408 | N | −10.711 | 19.793 | −0.93 |
| 3208 | ARG408 | CA | −11.226 | 21.121 | −1.276 |
| 3209 | ARG408 | C | −10.01 | 21.966 | −1.669 |
| 3210 | ARG408 | O | −8.867 | 21.71 | −1.273 |
| 3211 | ARG408 | CB | −11.946 | 21.751 | −0.075 |
| 3212 | ARG408 | CG | −13.319 | 21.114 | 0.167 |
| 3213 | ARG408 | CD | −13.694 | 21.058 | 1.65 |
| 3214 | ARG408 | NE | −14.581 | 19.919 | 1.947 |
| 3215 | ARG408 | CZ | −14.228 | 18.617 | 1.777 |
| 3216 | ARG408 | NH1 | −12.974 | 18.264 | 1.444 |
| 3217 | ARG408 | NH2 | −15.149 | 17.647 | 1.94 |

TABLE V-continued

| Atom No | Residue | Atom name | x coord | y coord | z coord |
|---|---|---|---|---|---|
| 3218 | HIS409 | N | -10.29 | 23.114 | -2.386 |
| 3219 | HIS409 | CA | -9.225 | 23.894 | -3.039 |
| 3220 | HIS409 | C | -8.423 | 24.827 | -2.092 |
| 3221 | HIS409 | O | -7.786 | 25.794 | -2.516 |
| 3222 | HIS409 | CB | -9.749 | 24.675 | -4.261 |
| 3223 | HIS409 | CG | -10.004 | 23.779 | -5.431 |
| 3224 | HIS409 | ND1 | -11.239 | 23.595 | -6 |
| 3225 | HIS409 | CD2 | -9.152 | 23.013 | -6.2 |
| 3226 | HIS409 | CE1 | -11.089 | 22.715 | -7.037 |
| 3227 | HIS409 | NE2 | -9.837 | 22.33 | -7.181 |
| 3228 | ARG410 | N | -8.27 | 24.332 | -0.808 |
| 3229 | AHG410 | CA | -7.107 | 24.629 | 0.028 |
| 3230 | ARG410 | C | -5.953 | 23.707 | -0.422 |
| 3231 | ARG410 | O | -4.786 | 24.104 | -0.504 |
| 3232 | ARG410 | CB | -7.462 | 24.385 | 1.5 |
| 3233 | ARG410 | CG | -6.329 | 24.746 | 2.464 |
| 3234 | ARG410 | CD | -6.767 | 24.581 | 3.916 |
| 3235 | ARG410 | NE | -5.679 | 24.889 | 4.856 |
| 3236 | ARG410 | CZ | -4.671 | 24.047 | 5.193 |
| 3237 | ARG410 | NH1 | -4.554 | 22.815 | 4.655 |
| 3238 | ARG410 | NH2 | -3.751 | 24.446 | 6.098 |
| 3239 | CYS411 | N | -6.287 | 22.387 | -0.683 |
| 3240 | CYS411 | CA | -5.272 | 21.47 | -1.206 |
| 3241 | CYS411 | C | -4.915 | 21.959 | -2.62 |
| 3242 | CYS411 | O | -5.71 | 22.596 | -3.317 |
| 3243 | CYS411 | CB | -5.753 | 20.019 | -1.281 |
| 3244 | CYS411 | SG | -6.127 | 19.345 | 0.368 |
| 3245 | ARG412 | N | -3.614 | 21.698 | -3.013 |
| 3246 | ARG412 | CA | -3.076 | 22.247 | -4.266 |
| 3247 | ARG412 | C | -3.132 | 21.185 | -5.377 |
| 3248 | ARG412 | O | -3.331 | 21.488 | -6.55 |
| 3249 | ARG412 | CB | -1.624 | 22.739 | -4.093 |
| 3250 | ARG412 | CG | -1.472 | 24.264 | -3.936 |
| 3251 | ARG412 | CD | -1.97 | 24.831 | -2.609 |
| 3252 | ARG412 | NE | -3.426 | 24.817 | -2.508 |
| 3253 | ARG412 | CZ | -4.289 | 25.563 | -3.227 |
| 3254 | ARG412 | NH1 | -3.925 | 26.701 | -3.841 |
| 3255 | ARG412 | NH2 | -5.553 | 25.134 | -3.334 |
| 3256 | LYS413 | N | -2.775 | 19.912 | -4.979 |
| 3257 | LYS413 | CA | -2.423 | 18.864 | -5.94 |
| 3258 | LYS413 | C | -3.566 | 17.87 | -6.208 |
| 3259 | LYS413 | O | -3.417 | 16.89 | -6.934 |
| 3260 | LYS413 | CB | -1.2 | 18.077 | -5.447 |
| 3261 | LYS413 | CG | 0.061 | 18.939 | -5.336 |
| 3262 | LYS413 | CD | 1.276 | 18.072 | -5.005 |
| 3263 | LYS413 | CE | 2.534 | 18.909 | -4.838 |
| 3264 | LYS413 | NZ | 3.687 | 18.012 | -4.683 |
| 3265 | ARG414 | N | -4.745 | 18.116 | -5.519 |
| 3266 | ARG414 | CA | -5.96 | 17.328 | -5.776 |
| 3267 | ARG414 | C | -5.757 | 15.849 | -5.368 |
| 3268 | ARG414 | O | -6.423 | 14.935 | -5.854 |
| 3269 | ARG414 | CB | -6.46 | 17.417 | -7.226 |
| 3270 | ARG414 | CG | -6.939 | 18.805 | -7.644 |
| 3271 | ARG414 | CD | -8.386 | 19.082 | -7.238 |
| 3272 | ARG414 | NE | -8.988 | 20.13 | -8.069 |
| 3273 | ARG414 | CZ | -9.199 | 20.038 | -9.405 |
| 3274 | ARG414 | NH1 | -9.55 | 21.142 | -10.09 |
| 3275 | ARG414 | NH2 | -9.091 | 18.866 | -10.056 |
| 3276 | LYS415 | N | -4.876 | 15.685 | -4.308 |
| 3277 | LYS415 | CA | -4.204 | 14.401 | -4.077 |
| 3278 | LYS415 | C | -5.175 | 13.385 | -3.436 |
| 3279 | LYS415 | O | -5.764 | 13.646 | -2.38 |
| 3280 | LYS415 | CB | -3.002 | 14.629 | -3.139 |
| 3281 | LYS415 | CG | -2.124 | 13.386 | -2.95 |
| 3282 | LYS415 | CD | -0.881 | 13.715 | -2.115 |
| 3283 | LYS415 | CE | -0.054 | 12.499 | -1.707 |
| 3284 | LYS415 | NZ | 0.445 | 11.776 | -2.873 |
| 3285 | PRO416 | N | -5.289 | 12.137 | -4.035 |
| 3286 | PRO416 | CA | -6.208 | 11.119 | -3.493 |
| 3287 | PRO416 | C | -5.699 | 10.44 | -2.2 |
| 3288 | PRO416 | O | -5.502 | 9.229 | -2.116 |
| 3289 | PRO416 | CB | -6.379 | 10.111 | -4.639 |
| 3290 | PRO416 | CG | -6.094 | 10.922 | -5.889 |
| 3291 | PRO416 | CD | -4.993 | 11.863 | -5.44 |
| 3292 | LEU417 | N | -5.558 | 11.296 | -1.119 |
| 3293 | LEU417 | CA | -5.151 | 10.828 | 0.207 |
| 3294 | LEU417 | C | -6.354 | 10.546 | 1.155 |
| 3295 | LEU417 | O | -7.531 | 10.596 | 0.797 |
| 3296 | LEU417 | CB | -4.029 | 11.711 | 0.793 |
| 3297 | LEU417 | CG | -4.428 | 12.987 | 1.563 |
| 3298 | LEU417 | CD1 | -3.186 | 13.579 | 2.241 |
| 3299 | LEU417 | CD2 | -5.07 | 14.051 | 0.682 |
| 3300 | LEU418 | N | -5.985 | 10.162 | 2.433 |
| 3301 | LEU418 | CA | -6.93 | 9.736 | 3.481 |
| 3302 | LEU418 | C | -7.686 | 10.961 | 4.037 |
| 3303 | LEU418 | O | -7.214 | 12.1 | 4.002 |
| 3304 | LEU418 | CB | -6.102 | 9.081 | 4.61 |
| 3305 | LEU418 | CG | -6.88 | 8.332 | 5.706 |
| 3306 | LEU418 | CD1 | -7.557 | 7.083 | 5.159 |
| 3307 | LEU418 | CD2 | -5.933 | 7.937 | 6.844 |
| 3308 | ALA419 | N | -8.902 | 10.672 | 4.638 |
| 3309 | ALA419 | CA | -9.558 | 11.629 | 5.528 |
| 3310 | ALA419 | C | -9.125 | 11.34 | 6.98 |
| 3311 | ALA419 | O | -8.25 | 12 | 7.538 |
| 3312 | ALA419 | CB | -11.072 | 11.637 | 5.361 |
| 3313 | ILE420 | N | -9.751 | 10.262 | 7.572 |
| 3314 | ILE420 | CA | -9.394 | 9.73 | 8.889 |
| 3315 | ILE420 | C | -9.594 | 8.204 | 8.777 |
| 3316 | ILE420 | O | -10.033 | 7.702 | 7.74 |
| 3317 | ILE420 | CB | -10.195 | 10.35 | 10.062 |
| 3318 | ILE420 | CG1 | -11.716 | 10.074 | 10.052 |
| 3319 | ILE420 | CG2 | -9.889 | 11.838 | 10.256 |
| 3320 | ILE420 | CD1 | -12.536 | 10.817 | 9.009 |
| 3321 | GLY421 | N | -9.242 | 7.453 | 9.882 |
| 3322 | GLY421 | CA | -9.545 | 6.029 | 9.923 |
| 3323 | GLY421 | C | -10.876 | 5.785 | 10.639 |
| 3324 | GLY421 | O | -11.293 | 6.56 | 11.506 |
| 3325 | PHE422 | N | -11.516 | 4.611 | 10.28 |
| 3326 | PHE422 | CA | -12.881 | 4.271 | 10.723 |
| 3327 | PHE422 | C | -12.978 | 2.908 | 11.459 |
| 3328 | PHE422 | O | -12.03 | 2.131 | 11.58 |
| 3329 | PHE422 | CB | -13.905 | 4.426 | 9.586 |
| 3330 | PHE422 | CG | -13.725 | 3.469 | 8.435 |
| 3331 | PHE422 | CD1 | -14.505 | 2.311 | 8.335 |
| 3332 | PHE422 | CD2 | -12.772 | 3.732 | 7.443 |
| 3333 | PHE422 | CE1 | -14.332 | 1.436 | 7.261 |
| 3334 | PHE422 | CE2 | -12.596 | 2.855 | 6.375 |
| 3335 | PHE422 | CZ | -13.376 | 1.708 | 6.286 |
| 3336 | TYR423 | N | -14.215 | 2.649 | 12.042 |
| 3337 | TYR423 | CA | -14.36 | 1.647 | 13.112 |
| 3338 | TYR423 | C | -15.679 | 0.909 | 12.861 |
| 3339 | TYR423 | O | -16.769 | 1.43 | 13.102 |
| 3340 | TYR423 | CB | -14.392 | 2.292 | 14.525 |
| 3341 | TYR423 | CG | -13.436 | 3.454 | 14.663 |
| 3342 | TYR423 | CD1 | -13.908 | 4.752 | 14.408 |
| 3343 | TYR423 | CD2 | -12.065 | 3.241 | 14.853 |
| 3344 | TYR423 | CE1 | -13.014 | 5.801 | 14.239 |
| 3345 | TYR423 | CE2 | -11.166 | 4.292 | 14.683 |
| 3346 | TYR423 | CZ | -11.652 | 5.542 | 14.327 |
| 3347 | TYR423 | OH | -10.774 | 6.499 | 13.905 |
| 3348 | LEU424 | N | -15.555 | -0.326 | 12.252 |
| 3349 | LEU424 | CA | -16.735 | -1.139 | 11.976 |
| 3350 | LEU424 | C | -17.057 | -2.062 | 13.172 |
| 3351 | LEU424 | O | -16.209 | -2.733 | 13.761 |
| 3352 | LEU424 | CB | -16.547 | -2.012 | 10.728 |
| 3353 | LEU424 | CG | -16.532 | -1.242 | 9.395 |
| 3354 | LEU424 | CD1 | -16.122 | -2.192 | 8.266 |
| 3355 | LEU424 | CD2 | -17.888 | -0.613 | 9.07 |
| 3356 | TYR425 | N | -18.407 | -2.132 | 13.465 |
| 3357 | TYR425 | CA | -18.935 | -2.946 | 14.562 |
| 3358 | TYR425 | C | -20.066 | -3.78 | 13.949 |
| 3359 | TYR425 | O | -21.154 | -3.292 | 13.65 |
| 3360 | TYR425 | CB | -19.461 | -2.075 | 15.711 |
| 3361 | TYR425 | CG | -18.348 | -1.351 | 16.436 |
| 3362 | TYR425 | CD1 | -18.103 | 0.007 | 16.184 |
| 3363 | TYR425 | CD2 | -17.52 | -2.037 | 17.337 |
| 3364 | TYR425 | CE1 | -17.053 | 0.67 | 16.823 |
| 3365 | TYR425 | CE2 | -16.465 | -1.376 | 17.97 |
| 3366 | TYR425 | CZ | -16.239 | -0.029 | 17.709 |
| 3367 | TYR425 | OH | -15.195 | 0.579 | 18.343 |
| 3368 | ARG426 | N | -19.7 | -5.072 | 13.62 |
| 3369 | ARG426 | CA | -20.619 | -5.985 | 12.935 |
| 3370 | ARG426 | C | -21.328 | -6.886 | 13.962 |
| 3371 | ARG426 | O | -20.791 | -7.22 | 15.016 |

TABLE V-continued

| Atom No | Residue | Atom name | x coord | y coord | z coord |
|---|---|---|---|---|---|
| 3372 | ARG426 | CB | -19.831 | -6.833 | 11.928 |
| 3373 | ARG426 | CG | -19.498 | -6.044 | 10.651 |
| 3374 | ARG426 | CD | -18.185 | -6.492 | 10.014 |
| 3375 | ARG426 | NE | -18.271 | -6.602 | 8.552 |
| 3376 | ARG426 | CZ | -18.851 | -7.644 | 7.904 |
| 3377 | ARG426 | NH1 | -18.874 | -7.652 | 6.555 |
| 3378 | ARG426 | NH2 | -19.409 | -8.672 | 8.574 |
| 3379 | MET427 | N | -22.589 | -7.326 | 13.584 |
| 3380 | MET427 | CA | -23.458 | -8.081 | 14.497 |
| 3381 | MET427 | C | -24.524 | -8.836 | 13.668 |
| 3382 | MET427 | O | -25.435 | -8.232 | 13.105 |
| 3383 | MET427 | CB | -24.21 | -7.149 | 15.474 |
| 3384 | MET427 | CG | -23.321 | -6.538 | 16.555 |
| 3385 | MET427 | SD | -24.334 | -5.591 | 17.739 |
| 3386 | MET427 | CE | -23.003 | -4.993 | 18.809 |
| 3387 | ASN428 | N | -24.345 | -10.21 | 13.56 |
| 3388 | ASN428 | CA | -25.495 | -11.121 | 13.342 |
| 3389 | ASN428 | C | -26.198 | -10.914 | 11.983 |
| 3390 | ASN428 | O | -27.267 | -10.315 | 11.873 |
| 3391 | ASN428 | CB | -26.504 | -11.046 | 14.496 |
| 3392 | ASN428 | CG | -25.841 | -11.268 | 15.835 |
| 3393 | ASN428 | OD1 | -25.592 | -10.354 | 16.617 |
| 3394 | ASN428 | ND2 | -25.496 | -12.557 | 16.116 |
| 3395 | LYS429 | N | -25.502 | -11.41 | 10.89 |
| 3396 | LYS429 | CA | -25.762 | -10.926 | 9.529 |
| 3397 | LYS429 | C | -25.484 | -12.015 | 8.456 |
| 3398 | LYS429 | O | -25.267 | -13.184 | 8.767 |
| 3399 | LYS429 | CB | -24.914 | -9.658 | 9.352 |
| 3400 | LYS429 | CG | -25.731 | -8.384 | 9.563 |
| 3401 | LYS429 | CD | -24.844 | -7.196 | 9.938 |
| 3402 | LYS429 | CE | -25.496 | -5.884 | 9.55 |
| 3403 | LYS429 | NZ | -25.222 | -5.639 | 8.124 |
| 3404 | GLU430 | N | -25.568 | -11.583 | 7.132 |
| 3405 | GLU430 | CA | -25.522 | -12.497 | 5.971 |
| 3406 | GLU430 | C | -24.303 | -12.271 | 5.033 |
| 3407 | GLU430 | O | -23.738 | -11.184 | 4.938 |
| 3408 | GLU430 | CB | -26.789 | -12.36 | 5.12 |
| 3409 | GLU430 | CG | -28.058 | -12.739 | 5.875 |
| 3410 | GLU430 | CD | -29.177 | -12.747 | 4.838 |
| 3411 | GLU430 | OE1 | -29.853 | -11.683 | 4.78 |
| 3412 | GLU430 | OE2 | -29.261 | -13.809 | 4.158 |
| 3413 | MET431 | N | -23.937 | -13.375 | 4.265 |
| 3414 | MET431 | CA | -22.64 | -13.472 | 3.578 |
| 3415 | MET431 | C | -22.448 | -12.481 | 2.41 |
| 3416 | MET431 | O | -23.38 | -11.916 | 1.837 |
| 3417 | MET431 | CB | -22.355 | -14.908 | 3.081 |
| 3418 | MET431 | CG | -21.332 | -15.608 | 3.982 |
| 3419 | MET431 | SD | -21.075 | -17.319 | 3.462 |
| 3420 | MET431 | CE | -19.889 | -17.834 | 4.72 |
| 3421 | THR432 | N | -21.117 | -12.353 | 2.026 |
| 3422 | THR432 | CA | -20.633 | -11.428 | 1 |
| 3423 | THR432 | C | -20.416 | -12.185 | -0.332 |
| 3424 | THR432 | O | -21.316 | -12.297 | -1.171 |
| 3425 | THR432 | CB | -19.345 | -10.708 | 1.456 |
| 3426 | THR432 | OG1 | -18.337 | -11.689 | 1.747 |
| 3427 | THR432 | CG2 | -19.559 | -9.846 | 2.692 |
| 3428 | TRP433 | N | -19.203 | -12.821 | -0.466 |
| 3429 | TRP433 | CA | -18.684 | -13.334 | -1.741 |
| 3430 | TRP433 | C | -17.643 | -14.447 | -1.47 |
| 3431 | TRP433 | O | -17.445 | -14.869 | -0.33 |
| 3432 | TRP433 | CB | -18.203 | -12.196 | -2.66 |
| 3433 | TRP433 | CG | -17.287 | -11.209 | -2.005 |
| 3434 | TRP433 | CD1 | -16.045 | -11.47 | -1.461 |
| 3435 | TRP433 | CD2 | -17.527 | -9.805 | -1.836 |
| 3436 | TRP433 | NE1 | -15.553 | -10.308 | -0.933 |
| 3437 | TRP433 | CE2 | -16.424 | -9.273 | -1.171 |
| 3438 | TRP433 | CE3 | -18.578 | -8.933 | -2.188 |
| 3439 | TRP433 | CZ2 | -16.306 | -7.916 | -0.848 |
| 3440 | TRP433 | CZ3 | -18.473 | -7.572 | -1.876 |
| 3441 | TRP433 | CH2 | -17.352 | -7.072 | -1.22 |
| 3442 | SER434 | N | -17.074 | -14.988 | -2.607 |
| 3443 | SER434 | CA | -16.302 | -16.251 | -2.675 |
| 3444 | SER434 | C | -14.816 | -16.052 | -2.31 |
| 3445 | SER434 | O | -14.388 | -15.017 | -1.798 |
| 3446 | SER434 | CB | -16.474 | -16.814 | -4.092 |
| 3447 | SER434 | OG | -16.026 | -15.858 | -5.058 |
| 3448 | SER435 | N | -13.978 | -17.125 | -2.611 |
| 3449 | SER435 | CA | -12.701 | -17.345 | -1.906 |
| 3450 | SER435 | C | -11.638 | -16.241 | -1.942 |
| 3451 | SER435 | O | -10.671 | -16.273 | -1.174 |
| 3452 | SER435 | CB | -12.027 | -18.653 | -2.353 |
| 3453 | SER435 | OG | -11.566 | -18.579 | -3.706 |
| 3454 | LEU436 | N | -11.87 | -15.187 | -2.797 |
| 3455 | LEU436 | CA | -11.111 | -13.952 | -2.65 |
| 3456 | LEU436 | C | -11.359 | -13.328 | -1.26 |
| 3457 | LEU436 | O | -10.531 | -12.606 | -0.705 |
| 3458 | LEU436 | CB | -11.517 | -12.903 | -3.684 |
| 3459 | LEU436 | CG | -11.315 | -13.279 | -5.154 |
| 3460 | LEU436 | CD1 | -11.864 | -12.154 | -6.032 |
| 3461 | LEU436 | CD2 | -9.846 | -13.513 | -5.489 |
| 3462 | GLY437 | N | -12.62 | -13.556 | -0.747 |
| 3463 | GLY437 | CA | -13.039 | -13.084 | 0.547 |
| 3464 | GLY437 | C | -12.719 | -14.037 | 1.689 |
| 3465 | GLY437 | O | -13.079 | -13.791 | 2.842 |
| 3466 | SER438 | N | -11.88 | -15.091 | 1.39 |
| 3467 | SER438 | CA | -11.446 | -16.058 | 2.416 |
| 3468 | SER438 | C | -10.602 | -15.312 | 3.458 |
| 3469 | SER438 | O | -10.428 | -15.716 | 4.604 |
| 3470 | SER438 | CB | -10.628 | -17.205 | 1.821 |
| 3471 | SER438 | OG | -9.526 | -16.709 | 1.058 |
| 3472 | ARG439 | N | -10.038 | -14.168 | 2.939 |
| 3473 | ARG439 | CA | -9.286 | -13.194 | 3.686 |
| 3474 | ARG439 | C | -10.124 | -11.915 | 3.874 |
| 3475 | ARG439 | O | -9.563 | -10.825 | 3.969 |
| 3476 | ARG439 | CB | -7.99 | -12.932 | 2.92 |
| 3477 | ARG439 | CG | -6.867 | -12.299 | 3.739 |
| 3478 | ARG439 | CD | -5.585 | -12.165 | 2.925 |
| 3479 | ARG439 | NE | -5.069 | -13.475 | 2.519 |
| 3480 | ARG439 | CZ | -5.407 | -14.133 | 1.391 |
| 3481 | ARG439 | NH1 | -5.1 | -15.423 | 1.213 |
| 3482 | ARG439 | NH2 | -6.106 | -13.565 | 0.399 |
| 3483 | GLN440 | N | -11.463 | -12.096 | 4.166 |
| 3484 | GLN440 | CA | -12.465 | -11.035 | 4.403 |
| 3485 | GLN440 | C | -12.178 | -10.022 | 5.552 |
| 3486 | GLN440 | O | -11.043 | -9.693 | 5.896 |
| 3487 | GLN440 | CB | -12.943 | -10.352 | 3.108 |
| 3488 | GLN440 | CG | -11.864 | -9.689 | 2.259 |
| 3489 | GLN440 | CD | -12.414 | -9.178 | 0.948 |
| 3490 | GLN440 | OE1 | -13.474 | -9.548 | 0.455 |
| 3491 | GLN440 | NE2 | -11.597 | -8.285 | 0.317 |
| 3492 | PRO441 | N | -13.239 | -9.428 | 6.202 |
| 3493 | PRO441 | CA | -13.036 | -8.136 | 6.862 |
| 3494 | PRO441 | C | -12.416 | -8.117 | 8.287 |
| 3495 | PRO441 | O | -13.114 | -7.991 | 9.295 |
| 3496 | PRO441 | CB | -14.447 | -7.52 | 6.857 |
| 3497 | PRO441 | CG | -15.365 | -8.731 | 6.917 |
| 3498 | PRO441 | CD | -14.652 | -9.738 | 6.038 |
| 3499 | PHE442 | N | -11.029 | -8.153 | 8.366 |
| 3500 | PHE442 | CA | -10.332 | -7.805 | 9.62 |
| 3501 | PHE442 | C | -9.083 | -6.896 | 9.496 |
| 3502 | PHE442 | O | -9.206 | -5.679 | 9.672 |
| 3503 | PHE442 | CB | -10.116 | -8.98 | 10.59 |
| 3504 | PHE442 | CG | -9.39 | -8.563 | 11.855 |
| 3505 | PHE442 | CD1 | -9.915 | -7.563 | 12.689 |
| 3506 | PHE442 | CD2 | -8.13 | -9.099 | 12.155 |
| 3507 | PHE442 | CE1 | -9.175 | -7.076 | 13.767 |
| 3508 | PHE442 | CE2 | -7.399 | -8.621 | 13.245 |
| 3509 | PHE442 | CZ | -7.914 | -7.601 | 14.042 |
| 3510 | PHE443 | N | -7.864 | -7.47 | 9.167 |
| 3511 | PHE443 | CA | -6.592 | -6.816 | 9.559 |
| 3512 | PHE443 | C | -6.519 | -5.329 | 9.168 |
| 3513 | PHE443 | O | -6.065 | -4.502 | 9.956 |
| 3514 | PHE443 | CB | -5.35 | -7.501 | 8.958 |
| 3515 | PHE443 | CG | -4.915 | -8.78 | 9.632 |
| 3516 | PHE443 | CD1 | -4.499 | -8.779 | 10.97 |
| 3517 | PHE443 | CD2 | -4.845 | -9.977 | 8.906 |
| 3518 | PHE443 | CE1 | -4.053 | -9.956 | 11.575 |
| 3519 | PHE443 | CE2 | -4.392 | -11.152 | 9.509 |
| 3520 | PHE443 | CZ | -4.002 | -11.141 | 10.845 |
| 3521 | SER444 | N | -6.944 | -5.024 | 7.889 |
| 3522 | SER444 | CA | -7.273 | -3.663 | 7.462 |
| 3523 | SER444 | C | -6.103 | -2.826 | 6.927 |
| 3524 | SER444 | O | -4.948 | -2.922 | 7.329 |
| 3525 | SER444 | CB | -8.006 | -2.808 | 8.523 |

TABLE V-continued

| Atom No | Residue | Atom name | x coord | y coord | z coord |
|---|---|---|---|---|---|
| 3526 | SER444 | OG | −9.277 | −3.34 | 8.873 |
| 3527 | LEU445 | N | −6.519 | −1.872 | 6.004 |
| 3528 | LEU445 | CA | −5.909 | −0.544 | 5.962 |
| 3529 | LEU445 | C | −7.064 | 0.398 | 6.361 |
| 3530 | LEU445 | O | −8.241 | 0.056 | 6.242 |
| 3531 | LEU445 | CB | −5.414 | −0.178 | 4.561 |
| 3532 | LEU445 | CG | −4.232 | −1.026 | 4.061 |
| 3533 | LEU445 | CD1 | −3.967 | −0.717 | 2.587 |
| 3534 | LEU445 | CD2 | −2.959 | −0.783 | 4.872 |
| 3535 | GLU446 | N | −6.68 | 1.619 | 6.875 |
| 3536 | GLU446 | CA | −7.618 | 2.736 | 7.041 |
| 3537 | GLU446 | C | −8.712 | 2.552 | 8.119 |
| 3538 | GLU446 | O | −9.611 | 3.382 | 8.283 |
| 3539 | GLU446 | CB | −8.281 | 3.187 | 5.724 |
| 3540 | GLU446 | CG | −7.293 | 3.445 | 4.588 |
| 3541 | GLU446 | CD | −7.919 | 4.079 | 3.345 |
| 3542 | GLU446 | OE1 | −7.238 | 3.967 | 2.289 |
| 3543 | GLU446 | OE2 | −9.047 | 4.637 | 3.496 |
| 3544 | ALA447 | N | −8.607 | 1.443 | 8.935 |
| 3545 | ALA447 | CA | −9.769 | 1.048 | 9.716 |
| 3546 | ALA447 | C | −9.445 | 0.063 | 10.841 |
| 3547 | ALA447 | O | −8.421 | −0.612 | 10.864 |
| 3548 | ALA447 | CB | −10.827 | 0.409 | 8.815 |
| 3549 | CYS448 | N | −10.472 | −0.034 | 11.766 |
| 3550 | CYS448 | CA | −10.613 | −1.163 | 12.675 |
| 3551 | CYS448 | C | −11.992 | −1.8 | 12.41 |
| 3552 | CYS448 | O | −12.953 | −1.175 | 11.954 |
| 3553 | CYS448 | CB | −10.567 | −0.751 | 14.15 |
| 3554 | CYS448 | SG | −8.969 | −0.041 | 14.652 |
| 3555 | GLN449 | N | −12.101 | −3.113 | 12.828 |
| 3556 | GLN449 | CA | −13.353 | −3.852 | 12.697 |
| 3557 | GLN449 | C | −13.478 | −4.789 | 13.901 |
| 3558 | GLN449 | O | −12.505 | −5.372 | 14.383 |
| 3559 | GLN449 | CB | −13.392 | −4.607 | 11.36 |
| 3560 | GLN449 | CG | −14.686 | −5.391 | 11.114 |
| 3561 | GLN449 | CD | −14.77 | −6.726 | 11.827 |
| 3562 | GLN449 | OE1 | −15.787 | −7.134 | 12.383 |
| 3563 | GLN449 | NE2 | −13.64 | −7.486 | 11.733 |
| 3564 | GLY450 | N | −14.782 | −4.982 | 14.336 |
| 3565 | GLY450 | CA | −15.039 | −5.922 | 15.4 |
| 3566 | GLY450 | C | −16.488 | −6.393 | 15.59 |
| 3567 | GLY450 | O | −17.472 | −5.878 | 15.069 |
| 3568 | ILE451 | N | −16.545 | −7.431 | 16.511 |
| 3569 | ILE451 | CA | −17.782 | −7.967 | 17.084 |
| 3570 | ILE451 | C | −17.402 | −8.498 | 18.495 |
| 3571 | ILE451 | O | −16.283 | −8.969 | 18.747 |
| 3572 | ILE451 | CB | −18.431 | −9.052 | 16.18 |
| 3573 | ILE451 | CG1 | −19.753 | −9.581 | 16.776 |
| 3574 | ILE451 | CG2 | −17.474 | −10.212 | 15.914 |
| 3575 | ILE451 | CD1 | −20.564 | −10.47 | 15.844 |
| 3576 | LEU452 | N | −18.429 | −8.406 | 19.42 |
| 3577 | LEU452 | CA | −18.457 | −9.171 | 20.67 |
| 3578 | LEU452 | C | −19.38 | −10.365 | 20.366 |
| 3579 | LEU452 | O | −20.564 | −10.223 | 20.049 |
| 3580 | LEU452 | CB | −19.03 | −8.361 | 21.838 |
| 3581 | LEU452 | CG | −17.969 | −7.553 | 22.614 |
| 3582 | LEU452 | CD1 | −17.285 | −6.489 | 21.757 |
| 3583 | LEU452 | CD2 | −18.613 | −6.897 | 23.838 |
| 3584 | ALA453 | N | −18.72 | −11.575 | 20.334 |
| 3585 | ALA453 | CA | −19.368 | −12.823 | 19.955 |
| 3586 | ALA453 | C | −19.845 | −13.573 | 21.207 |
| 3587 | ALA453 | O | −19.208 | −13.543 | 22.263 |
| 3588 | ALA453 | CB | −18.397 | −13.666 | 19.146 |
| 3589 | LEU454 | N | −20.992 | −14.335 | 21.039 |
| 3590 | LEU454 | CA | −21.678 | −14.884 | 22.218 |
| 3591 | LEU454 | C | −22.532 | −16.117 | 21.838 |
| 3592 | LEU454 | O | −23.352 | −16.077 | 20.924 |
| 3593 | LEU454 | CB | −22.578 | −13.791 | 22.84 |
| 3594 | LEU454 | CG | −22.179 | −13.341 | 24.254 |
| 3595 | LEU454 | CD1 | −23.059 | −12.174 | 24.702 |
| 3596 | LEU454 | CD2 | −22.264 | −14.459 | 25.287 |
| 3597 | LEU455 | N | −22.303 | −17.232 | 22.626 |
| 3598 | LEU455 | CA | −23.037 | −18.504 | 22.562 |
| 3599 | LEU455 | C | −22.923 | −19.278 | 21.221 |
| 3600 | LEU455 | O | −21.809 | −19.515 | 20.749 |
| 3601 | LEU455 | CB | −24.366 | −18.564 | 23.336 |
| 3602 | LEU455 | CG | −25.471 | −17.604 | 22.881 |
| 3603 | LEU455 | CD1 | −26.844 | −18.245 | 23.061 |
| 3604 | LEU455 | CD2 | −25.453 | −16.307 | 23.685 |
| 3605 | ASP456 | N | −24.08 | −19.73 | 20.622 |
| 3606 | ASP456 | CA | −24.079 | −20.807 | 19.612 |
| 3607 | ASP456 | C | −25.142 | −20.552 | 18.52 |
| 3608 | ASP456 | O | −25.977 | −21.383 | 18.16 |
| 3609 | ASP456 | CB | −24.277 | −22.157 | 20.297 |
| 3610 | ASP456 | CG | −25.561 | −22.276 | 21.117 |
| 3611 | ASP456 | OD1 | −25.678 | −23.357 | 21.757 |
| 3612 | ASP456 | OD2 | −26.351 | −21.282 | 21.082 |
| 3613 | LEU457 | N | −25.039 | −19.315 | 17.918 |
| 3614 | LEU457 | CA | −26.163 | −18.744 | 17.205 |
| 3615 | LEU457 | C | −26.23 | −19.102 | 15.711 |
| 3616 | LEU457 | O | −25.275 | −18.996 | 14.942 |
| 3617 | LEU457 | CB | −26.152 | −17.21 | 17.303 |
| 3618 | LEU457 | CG | −26.172 | −16.655 | 18.737 |
| 3619 | LEU457 | CD1 | −26.215 | −15.13 | 18.687 |
| 3620 | LEU457 | CD2 | −27.342 | −17.195 | 19.553 |
| 3621 | ASN458 | N | −27.517 | −19.404 | 15.283 |
| 3622 | ASN458 | CA | −27.869 | −19.553 | 13.868 |
| 3623 | ASN458 | C | −28.119 | −18.161 | 13.271 |
| 3624 | ASN458 | O | −28.082 | −17.963 | 12.057 |
| 3625 | ASN458 | CB | −29.094 | −20.438 | 13.704 |
| 3626 | ASN458 | CG | −29.345 | −20.88 | 12.281 |
| 3627 | ASN458 | OD1 | −30.369 | −20.599 | 11.654 |
| 3628 | ASN458 | ND2 | −28.395 | −21.678 | 11.711 |
| 3629 | ALA459 | N | −28.339 | −17.149 | 14.183 |
| 3630 | ALA459 | CA | −28.623 | −15.775 | 13.76 |
| 3631 | ALA459 | C | −27.383 | −15.129 | 13.104 |
| 3632 | ALA459 | O | −27.454 | −14.087 | 12.457 |
| 3633 | ALA459 | CB | −29.048 | −14.929 | 14.952 |
| 3634 | SER460 | N | −26.191 | −15.771 | 13.377 |
| 3635 | SER460 | CA | −24.923 | −15.423 | 12.737 |
| 3636 | SER460 | C | −24.465 | −16.523 | 11.762 |
| 3637 | SER460 | O | −23.307 | −16.571 | 11.336 |
| 3638 | SER460 | CB | −23.826 | −15.211 | 13.796 |
| 3639 | SER460 | OG | −24.097 | −14.046 | 14.573 |
| 3640 | GLY461 | N | −25.421 | −17.425 | 11.328 |
| 3641 | GLY461 | CA | −24.972 | −18.751 | 10.942 |
| 3642 | GLY461 | C | −26.015 | −19.652 | 10.301 |
| 3643 | GLY461 | O | −26.07 | −20.852 | 10.568 |
| 3644 | THR462 | N | −26.747 | −19.036 | 9.319 |
| 3645 | THR462 | CA | −27.6 | −19.729 | 8.332 |
| 3646 | THR462 | C | −27.351 | −18.909 | 7.069 |
| 3647 | THR462 | O | −27.307 | −17.676 | 7.15 |
| 3648 | THR462 | CB | −29.076 | −19.719 | 8.781 |
| 3649 | THR462 | OG1 | −29.416 | −21.025 | 9.273 |
| 3650 | THR462 | CG2 | −30.111 | −19.384 | 7.717 |
| 3651 | MET463 | N | −27.18 | −19.512 | 5.856 |
| 3652 | MET463 | CA | −27.327 | −20.912 | 5.478 |
| 3653 | MET463 | C | −26.033 | −21.723 | 5.745 |
| 3654 | MET463 | O | −25.904 | −22.367 | 6.789 |
| 3655 | MET463 | CB | −27.787 | −21.064 | 4.019 |
| 3656 | MET463 | CG | −29.23 | −20.624 | 3.748 |
| 3657 | MET463 | SD | −29.329 | −19.017 | 2.886 |
| 3658 | MET463 | CE | −29.982 | −17.973 | 4.209 |
| 3659 | SER464 | N | −25.026 | −21.675 | 4.795 |
| 3660 | SER464 | CA | −23.925 | −22.653 | 4.837 |
| 3661 | SER464 | C | −22.64 | −22.062 | 4.223 |
| 3662 | SER464 | O | −22.496 | −20.845 | 4.081 |
| 3663 | SER464 | CB | −24.372 | −23.959 | 4.164 |
| 3664 | SER464 | OG | −24.026 | −24.012 | 2.783 |
| 3665 | ILE465 | N | −21.628 | −22.979 | 3.953 |
| 3666 | ILE465 | CA | −20.496 | −22.62 | 3.087 |
| 3667 | ILE465 | C | −20.695 | −23.153 | 1.652 |
| 3668 | ILE465 | O | −19.948 | −22.821 | 0.73 |
| 3669 | ILE465 | CB | −19.145 | −23.079 | 3.699 |
| 3670 | ILE465 | CG1 | −17.945 | −22.428 | 2.976 |
| 3671 | ILE465 | CG2 | −19 | −24.602 | 3.768 |
| 3672 | ILE465 | CD1 | −16.65 | −22.488 | 3.777 |
| 3673 | GLN466 | N | −21.729 | −24.05 | 1.464 |
| 3674 | GLN466 | CA | −21.953 | −24.678 | 0.166 |
| 3675 | GLN466 | C | −22.583 | −23.712 | −0.858 |
| 3676 | GLN466 | O | −22.796 | −24.041 | −2.023 |
| 3677 | GLN466 | CB | −22.784 | −25.961 | 0.289 |
| 3678 | GLN466 | CG | −22.141 | −26.997 | 1.216 |
| 3679 | GLN466 | CD | −22.575 | −26.832 | 2.658 |

TABLE V-continued

| Atom No | Residue | Atom name | x coord | y coord | z coord |
|---|---|---|---|---|---|
| 3680 | GLN466 | OE1 | −21.911 | −26.247 | 3.509 |
| 3681 | GLN466 | NE2 | −23.792 | −27.386 | 2.948 |
| 3682 | GLU467 | N | −22.787 | −22.432 | −0.379 |
| 3683 | GLU467 | CA | −23.107 | −21.313 | −1.25 |
| 3684 | GLU467 | C | −21.82 | −20.77 | −1.92 |
| 3685 | GLU467 | O | −21.881 | −19.958 | −2.844 |
| 3686 | GLU467 | CB | −23.776 | −20.18 | −0.456 |
| 3687 | GLU467 | CG | −25.224 | −20.493 | −0.071 |
| 3688 | GLU467 | CD | −25.479 | −21.591 | 0.957 |
| 3689 | GLU467 | OE1 | −26.685 | −21.909 | 1.125 |
| 3690 | GLU467 | OE2 | −24.462 | −22.076 | 1.549 |
| 3691 | PHE468 | N | −20.625 | −21.177 | −1.354 |
| 3692 | PHE468 | CA | −19.297 | −20.857 | −1.887 |
| 3693 | PHE468 | C | −18.973 | −19.378 | −1.635 |
| 3694 | PHE468 | O | −18.508 | −18.641 | −2.502 |
| 3695 | PHE468 | CB | −19.081 | −21.242 | −3.361 |
| 3696 | PHE468 | CG | −19.031 | −22.735 | −3.584 |
| 3697 | PHE468 | CD1 | −20.188 | −23.444 | −3.925 |
| 3698 | PHE468 | CD2 | −17.824 | −23.433 | −3.437 |
| 3699 | PHE468 | CE1 | −20.141 | −24.826 | −4.118 |
| 3700 | PHE468 | CE2 | −17.777 | −24.814 | −3.637 |
| 3701 | PHE468 | CZ | −18.935 | −25.51 | −3.977 |
| 3702 | ARG469 | N | −19.176 | −18.978 | −0.326 |
| 3703 | ARG469 | CA | −18.955 | −17.606 | 0.138 |
| 3704 | ARG469 | C | −18.233 | −17.68 | 1.516 |
| 3705 | ARG469 | O | −18.179 | −18.736 | 2.152 |
| 3706 | ARG469 | CB | −20.289 | −16.841 | 0.146 |
| 3707 | ARG469 | CG | −20.949 | −16.705 | −1.238 |
| 3708 | ARG469 | CD | −22.418 | −16.286 | −1.154 |
| 3709 | ARG469 | NE | −22.576 | −14.835 | −1.038 |
| 3710 | ARG469 | CZ | −23.571 | −14.191 | −0.388 |
| 3711 | ARG469 | NH1 | −23.577 | −12.85 | −0.416 |
| 3712 | ARG469 | NH2 | −24.531 | −14.828 | 0.309 |
| 3713 | ASP470 | N | −17.645 | −16.493 | 1.966 |
| 3714 | ASP470 | CA | −16.41 | −16.571 | 2.797 |
| 3715 | ASP470 | C | −16.38 | −15.736 | 4.16 |
| 3716 | ASP470 | O | −17.401 | −15.304 | 4.688 |
| 3717 | ASP470 | CB | −15.244 | −16.262 | 1.861 |
| 3718 | ASP470 | CG | −14.765 | −17.549 | 1.208 |
| 3719 | ASP470 | OD1 | −13.791 | −18.098 | 1.798 |
| 3720 | ASP470 | OD2 | −15.341 | −17.873 | 0.133 |
| 3721 | LEU471 | N | −15.118 | −15.643 | 4.759 |
| 3722 | LEU471 | CA | −14.762 | −15.476 | 6.201 |
| 3723 | LEU471 | C | −15.071 | −14.186 | 7.029 |
| 3724 | LEU471 | O | −15.89 | −13.351 | 6.66 |
| 3725 | LEU471 | CB | −15.013 | −16.798 | 6.953 |
| 3726 | LEU471 | CG | −15.999 | −16.857 | 8.125 |
| 3727 | LEU471 | CD1 | −17.41 | −16.426 | 7.758 |
| 3728 | LEU471 | CD2 | −16.021 | −18.296 | 8.651 |
| 3729 | TRP472 | N | −14.336 | −14.066 | 8.234 |
| 3730 | TRP472 | CA | −14.807 | −13.29 | 9.424 |
| 3731 | TRP472 | C | −13.809 | −13.453 | 10.645 |
| 3732 | TRP472 | O | −13.539 | −14.592 | 11.04 |
| 3733 | TRP472 | CB | −15.274 | −11.864 | 9.136 |
| 3734 | TRP472 | CG | −16.065 | −11.203 | 10.232 |
| 3735 | TRP472 | CD1 | −15.809 | −9.925 | 10.672 |
| 3736 | TRP472 | CD2 | −17.245 | −11.631 | 10.929 |
| 3737 | TRP472 | NE1 | −16.69 | −9.598 | 11.66 |
| 3738 | TRP472 | CE2 | −17.645 | −10.577 | 11.759 |
| 3739 | TRP472 | CE3 | −18.065 | −12.779 | 10.891 |
| 3740 | TRP472 | CZ2 | −18.831 | −10.599 | 12.5 |
| 3741 | TRP472 | CZ3 | −19.274 | −12.8 | 11.599 |
| 3742 | TRP472 | CH2 | −19.649 | −11.725 | 12.395 |
| 3743 | LYS473 | N | −13.317 | −12.328 | 11.277 |
| 3744 | LYS473 | CA | −12.528 | −12.244 | 12.559 |
| 3745 | LYS473 | C | −12.555 | −10.73 | 12.919 |
| 3746 | LYS473 | O | −13.222 | −9.962 | 12.208 |
| 3747 | LYS473 | CB | −11.089 | −12.779 | 12.405 |
| 3748 | LYS473 | CG | −10.658 | −13.618 | 13.62 |
| 3749 | LYS473 | CD | −9.176 | −13.615 | 14.033 |
| 3750 | LYS473 | CE | −8.406 | −12.325 | 13.805 |
| 3751 | LYS473 | NZ | −7.253 | −12.238 | 14.705 |
| 3752 | GLN474 | N | −11.902 | −10.125 | 13.948 |
| 3753 | GLN474 | CA | −11.485 | −10.565 | 15.29 |
| 3754 | GLN474 | C | −12.758 | −10.505 | 16.136 |
| 3755 | GLN474 | O | −13.294 | −9.445 | 16.479 |
| 3756 | GLN474 | CB | −10.453 | −9.581 | 15.879 |
| 3757 | GLN474 | CG | −10.067 | −9.819 | 17.345 |
| 3758 | GLN474 | CD | −8.796 | −10.613 | 17.546 |
| 3759 | GLN474 | OE1 | −8.217 | −11.236 | 16.662 |
| 3760 | GLN474 | NE2 | −8.339 | −10.619 | 18.834 |
| 3761 | LEU475 | N | −13.276 | −11.753 | 16.425 |
| 3762 | LEU475 | CA | −14.466 | −11.861 | 17.241 |
| 3763 | LEU475 | C | −14.037 | −12.156 | 18.68 |
| 3764 | LEU475 | O | −13.301 | −13.098 | 18.97 |
| 3765 | LEU475 | CB | −15.503 | −12.844 | 16.703 |
| 3766 | LEU475 | CG | −15.106 | −14.314 | 16.529 |
| 3767 | LEU475 | CD1 | −16.382 | −15.157 | 16.439 |
| 3768 | LEU475 | CD2 | −14.241 | −14.554 | 15.294 |
| 3769 | LYS476 | N | −14.52 | −11.229 | 19.594 |
| 3770 | LYS476 | CA | −14.296 | −11.408 | 21.023 |
| 3771 | LYS476 | C | −15.403 | −12.373 | 21.456 |
| 3772 | LYS476 | O | −16.557 | −11.986 | 21.643 |
| 3773 | LYS476 | CB | −14.448 | −10.084 | 21.787 |
| 3774 | LYS476 | CG | −13.182 | −9.226 | 21.871 |
| 3775 | LYS476 | CD | −13.144 | −8.045 | 20.896 |
| 3776 | LYS476 | CE | −12.76 | −8.445 | 19.483 |
| 3777 | LYS476 | NZ | −13.864 | −8.18 | 18.544 |
| 3778 | LEU477 | N | −15.034 | −13.706 | 21.475 |
| 3779 | LEU477 | CA | −15.975 | −14.735 | 21.911 |
| 3780 | LEU477 | C | −16.033 | −14.625 | 23.426 |
| 3781 | LEU477 | O | −15.074 | −14.88 | 24.151 |
| 3782 | LEU477 | CB | −15.534 | −16.129 | 21.469 |
| 3783 | LEU477 | CG | −16.481 | −17.3 | 21.82 |
| 3784 | LEU477 | CD1 | −16.3 | −17.827 | 23.24 |
| 3785 | LEU477 | CD2 | −17.957 | −17.001 | 21.566 |
| 3786 | SER478 | N | −17.236 | −14.142 | 23.884 |
| 3787 | SER478 | CA | −17.475 | −13.916 | 25.289 |
| 3788 | SER478 | C | −17.836 | −15.275 | 25.896 |
| 3789 | SER478 | O | −18.871 | −15.882 | 25.619 |
| 3790 | SER478 | CB | −18.596 | −12.9 | 25.497 |
| 3791 | SER478 | OG | −18.322 | −12.077 | 26.646 |
| 3792 | GLN479 | N | −16.886 | −15.779 | 26.773 |
| 3793 | GLN479 | CA | −17.03 | −17.108 | 27.39 |
| 3794 | GLN479 | C | −18.077 | −16.997 | 28.527 |
| 3795 | GLN479 | O | −17.791 | −17.049 | 29.722 |
| 3796 | GLN479 | CB | −15.688 | −17.598 | 27.959 |
| 3797 | GLN479 | CG | −14.69 | −18.011 | 26.879 |
| 3798 | GLN479 | CD | −14.908 | −19.453 | 26.483 |
| 3799 | GLN479 | OE1 | −15.734 | −19.8 | 25.647 |
| 3800 | GLN479 | NE2 | −14.156 | −20.36 | 27.173 |
| 3801 | LYS480 | N | −19.356 | −16.773 | 28.067 |
| 3802 | LYS480 | CA | −20.517 | −16.487 | 28.906 |
| 3803 | LYS480 | C | −21.77 | −16.665 | 28.014 |
| 3804 | LYS480 | O | −21.677 | −17.136 | 26.877 |
| 3805 | LYS480 | CB | −20.356 | −15.172 | 29.687 |
| 3806 | LYS480 | CG | −19.899 | −13.945 | 28.877 |
| 3807 | LYS480 | CD | −18.895 | −13.069 | 29.654 |
| 3808 | LYS480 | CE | −17.427 | −13.47 | 29.478 |
| 3809 | LYS480 | NZ | −16.768 | −12.661 | 28.431 |
| 3810 | VAL481 | N | −22.997 | −16.427 | 28.604 |
| 3811 | VAL481 | CA | −24.229 | −17.002 | 28.043 |
| 3812 | VAL481 | C | −25.429 | −16.015 | 28.09 |
| 3813 | VAL481 | O | −25.351 | −14.874 | 28.538 |
| 3814 | VAL481 | CB | −24.567 | −18.365 | 28.717 |
| 3815 | VAL481 | CG1 | −23.517 | −19.439 | 28.415 |
| 3816 | VAL481 | CG2 | −24.767 | −18.237 | 30.229 |
| 3817 | PHE482 | N | −26.597 | −16.56 | 27.571 |
| 3818 | PHE482 | CA | −27.802 | −15.775 | 27.256 |
| 3819 | PHE482 | C | −28.301 | −14.989 | 28.477 |
| 3820 | PHE482 | O | −28.668 | −15.532 | 29.517 |
| 3821 | PHE482 | CB | −28.909 | −16.748 | 26.797 |
| 3822 | PHE482 | CG | −30.248 | −16.149 | 26.442 |
| 3823 | PHE482 | CD1 | −30.36 | −15.064 | 25.568 |
| 3824 | PHE482 | CD2 | −31.424 | −16.738 | 26.933 |
| 3825 | PHE482 | CE1 | −31.614 | −14.568 | 25.206 |
| 3826 | PHE482 | CE2 | −32.678 | −16.249 | 26.563 |
| 3827 | PHE482 | CZ | −32.773 | −15.165 | 25.696 |
| 3828 | HIS483 | N | −28.23 | −13.613 | 28.311 |
| 3829 | HIS483 | CA | −28.735 | −12.668 | 29.304 |
| 3830 | HIS483 | C | −27.97 | −12.722 | 30.637 |
| 3831 | HIS483 | C | −28.45 | −12.283 | 31.683 |
| 3832 | HIS483 | CB | −30.254 | −12.74 | 29.528 |
| 3833 | HIS483 | CG | −31.073 | −12.26 | 28.373 |

TABLE V-continued

| Atom No | Residue | Atom name | x coord | y coord | z coord |
|---|---|---|---|---|---|
| 3834 | HIS483 | ND1 | −32.394 | −12.607 | 28.232 |
| 3835 | HIS483 | CD2 | −30.826 | −11.421 | 27.306 |
| 3836 | HIS483 | CE1 | −32.878 | −11.963 | 27.13 |
| 3837 | HIS483 | NE2 | −31.948 | −11.251 | 26.535 |
| 3838 | LYS484 | N | −26.657 | −13.133 | 30.533 |
| 3839 | LYS484 | CA | −25.685 | −12.862 | 31.58 |
| 3840 | LYS484 | C | −24.653 | −11.904 | 30.972 |
| 3841 | LYS484 | C | −24.407 | −11.865 | 29.767 |
| 3842 | LYS484 | CB | −25.05 | −14.143 | 32.123 |
| 3843 | LYS484 | CG | −26.115 | −15.069 | 32.724 |
| 3844 | LYS484 | CD | −25.513 | −16.271 | 33.448 |
| 3845 | LYS484 | CE | −26.619 | −17.214 | 33.907 |
| 3846 | LYS484 | NZ | −26.018 | −18.377 | 34.601 |
| 3847 | GLN485 | N | −24.023 | −11.091 | 31.9 |
| 3848 | GLN485 | CA | −23.392 | −9.862 | 31.435 |
| 3849 | GLN485 | C | −22.075 | −10.171 | 30.7 |
| 3850 | GLN485 | O | −21.35 | −11.127 | 30.976 |
| 3851 | GLN485 | CB | −23.103 | −8.888 | 32.593 |
| 3852 | GLN485 | CG | −24.353 | −8.174 | 33.122 |
| 3853 | GLN485 | CD | −25.272 | −9.063 | 33.935 |
| 3854 | GLN485 | OE1 | −25.095 | −10.268 | 34.093 |
| 3855 | GLN485 | NE2 | −26.344 | −8.412 | 34.475 |
| 3856 | ASP486 | N | −21.755 | −9.213 | 29.744 |
| 3857 | ASP486 | CA | −20.474 | −9.264 | 29.055 |
| 3858 | ASP486 | C | −19.431 | −8.63 | 29.985 |
| 3859 | ASP486 | O | −19.696 | −7.757 | 30.808 |
| 3860 | ASP486 | CB | −20.494 | −8.536 | 27.718 |
| 3861 | ASP486 | CG | −20.864 | −9.533 | 26.626 |
| 3862 | ASP486 | OD1 | −21.919 | −9.27 | 25.974 |
| 3863 | ASP486 | OD2 | −20.035 | −10.491 | 26.497 |
| 3864 | ARG487 | N | −18.167 | −9.147 | 29.798 |
| 3865 | ARG487 | CA | −17.035 | −8.814 | 30.649 |
| 3866 | ARG487 | C | −15.801 | −9.489 | 30.029 |
| 3867 | ARG487 | O | −15.896 | −10.495 | 29.316 |
| 3868 | ARG487 | CB | −17.223 | −9.265 | 32.114 |
| 3869 | ARG487 | CG | −17.552 | −10.755 | 32.235 |
| 3870 | ARG487 | CD | −17.844 | −11.202 | 33.664 |
| 3871 | ARG487 | NE | −18.195 | −12.636 | 33.704 |
| 3872 | ARG487 | CZ | −17.357 | −13.643 | 33.349 |
| 3873 | ARG487 | NH1 | −17.852 | −14.883 | 33.153 |
| 3874 | ARG487 | NH2 | −16.047 | −13.438 | 33.161 |
| 3875 | GLY488 | N | −14.596 | −8.926 | 30.413 |
| 3876 | GLY488 | CA | −13.358 | −9.294 | 29.739 |
| 3877 | GLY488 | C | −12.713 | −10.564 | 30.276 |
| 3878 | GLY488 | O | −11.803 | −11.146 | 29.685 |
| 3879 | SER489 | N | −13.197 | −10.993 | 31.488 |
| 3880 | SER489 | CA | −12.728 | −12.203 | 32.159 |
| 3881 | SER489 | C | −13.311 | −13.449 | 31.456 |
| 3882 | SER489 | O | −14.069 | −14.252 | 32.002 |
| 3883 | SER489 | CB | −13.068 | −12.139 | 33.651 |
| 3884 | SER489 | OG | −14.433 | −11.726 | 33.865 |
| 3885 | GLY490 | N | −12.87 | −13.583 | 30.151 |
| 3886 | GLY490 | CA | −13.229 | −14.693 | 29.3 |
| 3887 | GLY490 | C | −13.465 | −14.203 | 27.871 |
| 3888 | GLY490 | O | −14.604 | −13.942 | 27.472 |
| 3889 | TYR491 | N | −12.286 | −14.06 | 27.158 |
| 3890 | TYR491 | CA | −12.146 | −13.768 | 25.722 |
| 3891 | TYR491 | C | −10.925 | −14.598 | 25.239 |
| 3892 | TYR491 | O | −10.081 | −15.004 | 26.04 |
| 3893 | TYR491 | CB | −11.825 | −12.287 | 25.44 |
| 3894 | TYR491 | CG | −12.903 | −11.243 | 25.626 |
| 3895 | TYR491 | CD1 | −12.514 | −9.911 | 25.86 |
| 3896 | TYR491 | CD2 | −14.265 | −11.515 | 25.474 |
| 3897 | TYR491 | CE1 | −13.461 | −8.888 | 25.963 |
| 3898 | TYR491 | CE2 | −15.218 | −10.499 | 25.599 |
| 3899 | TYR491 | CZ | −14.811 | −9.194 | 25.84 |
| 3900 | TYR491 | OH | −15.774 | −8.234 | 25.938 |
| 3901 | LEU492 | N | −10.827 | −14.786 | 23.871 |
| 3902 | LEU492 | CA | −9.715 | −15.511 | 23.231 |
| 3903 | LEU492 | C | −9.789 | −15.324 | 21.697 |
| 3904 | LEU492 | O | −10.873 | −15.114 | 21.145 |
| 3905 | LEU492 | CB | −9.668 | −17.007 | 23.602 |
| 3906 | LEU492 | CG | −10.781 | −17.923 | 23.041 |
| 3907 | LEU492 | CD1 | −10.571 | −19.357 | 23.543 |
| 3908 | LEU492 | CD2 | −12.197 | −17.488 | 23.413 |
| 3909 | ASN493 | N | −8.603 | −15.444 | 20.997 |
| 3910 | ASN493 | CA | −8.429 | −15.381 | 19.514 |
| 3911 | ASN493 | C | −6.895 | −15.31 | 19.247 |
| 3912 | ASN493 | O | −6.15 | −14.752 | 20.061 |
| 3913 | ASN493 | CB | −9.05 | −14.117 | 18.881 |
| 3914 | ASN493 | CG | −10.391 | −14.229 | 18.165 |
| 3915 | ASN493 | OD1 | −10.682 | −13.55 | 17.18 |
| 3916 | ASN493 | ND2 | −11.348 | −15.029 | 18.73 |
| 3917 | TRP494 | N | −6.359 | −15.716 | 18.044 |
| 3918 | TRP494 | CA | −6.597 | −17.008 | 17.376 |
| 3919 | TRP494 | C | −6.2 | −16.972 | 15.869 |
| 3920 | TRP494 | O | −7.085 | −17.043 | 15.008 |
| 3921 | TRP494 | CB | −5.864 | −18.162 | 18.077 |
| 3922 | TRP494 | CG | −6.493 | −18.602 | 19.362 |
| 3923 | TRP494 | CD1 | −7.744 | −19.168 | 19.512 |
| 3924 | TRP494 | CD2 | −5.893 | −18.577 | 20.663 |
| 3925 | TRP494 | NE1 | −7.895 | −19.543 | 20.819 |
| 3926 | TRP494 | CE2 | −6.784 | −19.19 | 21.546 |
| 3927 | TRP494 | CE3 | −4.659 | −18.117 | 21.169 |
| 3928 | TRP494 | CZ2 | −6.494 | −19.381 | 22.902 |
| 3929 | TRP494 | CZ3 | −4.361 | −18.287 | 22.526 |
| 3930 | TRP494 | CH2 | −5.266 | −18.913 | 23.378 |
| 3931 | GLU495 | N | −4.845 | −16.903 | 15.565 |
| 3932 | GLU495 | CA | −4.323 | −16.498 | 14.235 |
| 3933 | GLU495 | C | −4.049 | −17.662 | 13.21 |
| 3934 | GLU495 | O | −3.999 | −18.834 | 13.572 |
| 3935 | GLU495 | CB | −3.105 | −15.573 | 14.392 |
| 3936 | GLU495 | CG | −3.338 | −14.37 | 15.316 |
| 3937 | GLU495 | CD | −4.475 | −13.47 | 14.863 |
| 3938 | GLU495 | OE1 | −5.652 | −13.786 | 15.24 |
| 3939 | GLU495 | OE2 | −4.185 | −12.479 | 14.142 |
| 3940 | GLN496 | N | −3.91 | −17.286 | 11.867 |
| 3941 | GLN496 | CA | −4.128 | −18.198 | 10.691 |
| 3942 | GLN496 | C | −5.056 | −17.459 | 9.649 |
| 3943 | GLN496 | O | −4.914 | −16.249 | 9.455 |
| 3944 | GLN496 | CB | −2.773 | −18.562 | 10.06 |
| 3945 | GLN496 | CG | −2.739 | −19.971 | 9.465 |
| 3946 | GLN496 | CD | −3.606 | −20.099 | 8.236 |
| 3947 | GLN496 | OE1 | −4.785 | −20.438 | 8.302 |
| 3948 | GLN496 | NE2 | −3.013 | −19.72 | 7.067 |
| 3949 | LEU497 | N | −6.036 | −18.212 | 9 |
| 3950 | LEU497 | CA | −7.082 | −17.633 | 8.107 |
| 3951 | LEU497 | C | −8.492 | −18.334 | 8.207 |
| 3952 | LEU497 | O | −8.592 | −19.564 | 8.188 |
| 3953 | LEU497 | CB | −6.683 | −17.756 | 6.624 |
| 3954 | LEU497 | CG | −5.572 | −16.816 | 6.133 |
| 3955 | LEU497 | CD1 | −5.241 | −17.167 | 4.678 |
| 3956 | LEU497 | CD2 | −5.983 | −15.347 | 6.229 |
| 3957 | HIS498 | N | −9.613 | −17.501 | 8.234 |
| 3958 | HIS498 | CA | −11.051 | −17.916 | 8.02 |
| 3959 | HIS498 | C | −11.841 | −18.503 | 9.278 |
| 3960 | HIS498 | O | −12.191 | −19.685 | 9.35 |
| 3961 | HIS498 | CB | −11.123 | −18.798 | 6.747 |
| 3962 | HIS498 | CG | −12.453 | −19.296 | 6.297 |
| 3963 | HIS498 | ND1 | −13.171 | −20.239 | 6.994 |
| 3964 | HIS498 | CD2 | −13.177 | −19.116 | 5.137 |
| 3965 | HIS498 | CE1 | −14.275 | −20.556 | 6.265 |
| 3966 | HIS498 | NE2 | −14.325 | −19.868 | 5.15 |
| 3967 | ALA499 | N | −12.13 | −17.598 | 10.312 |
| 3968 | ALA499 | CA | −12.588 | −18.068 | 11.649 |
| 3969 | ALA499 | C | −14.09 | −18.292 | 11.984 |
| 3970 | ALA499 | O | −15.033 | −17.654 | 11.517 |
| 3971 | ALA499 | CB | −12.103 | −17.133 | 12.772 |
| 3972 | ALA500 | N | −14.242 | −19.215 | 13.024 |
| 3973 | ALA500 | CA | −15.505 | −19.589 | 13.67 |
| 3974 | ALA500 | C | −15.146 | −20.461 | 14.896 |
| 3975 | ALA500 | O | −14.092 | −20.275 | 15.507 |
| 3976 | ALA500 | CB | −16.39 | −20.34 | 12.698 |
| 3977 | MET501 | N | −16.081 | −21.397 | 15.283 |
| 3978 | MET501 | CA | −15.902 | −22.298 | 16.434 |
| 3979 | MET501 | C | −15.979 | −21.489 | 17.736 |
| 3980 | MET501 | O | −15.297 | −21.742 | 18.725 |
| 3981 | MET501 | CB | −14.634 | −23.153 | 16.353 |
| 3982 | MET501 | CG | −14.778 | −24.434 | 17.177 |
| 3983 | MET501 | SD | −13.151 | −25.163 | 17.543 |
| 3984 | MET501 | CE | −12.736 | −24.159 | 18.999 |
| 3985 | ARG502 | N | −16.942 | −20.505 | 17.697 |
| 3986 | ARG502 | CA | −17.038 | −19.447 | 18.694 |
| 3987 | ARG502 | C | −18.557 | −19.172 | 18.805 |

TABLE V-continued

| Atom No | Residue | Atom name | x coord | y coord | z coord |
|---|---|---|---|---|---|
| 3988 | ARG502 | O | −19.316 | −20.076 | 19.158 |
| 3989 | ARG502 | CB | −16.146 | −18.28 | 18.257 |
| 3990 | ARG502 | CG | −14.626 | −18.523 | 18.409 |
| 3991 | ARG502 | CD | −13.871 | −17.382 | 17.745 |
| 3992 | ARG502 | NE | −12.409 | −17.446 | 17.791 |
| 3993 | ARG502 | CZ | −11.63 | −18.186 | 16.968 |
| 3994 | ARG502 | NH1 | −10.307 | −17.933 | 16.92 |
| 3995 | ARG3502 | NH2 | −12.109 | −19.143 | 16.165 |
| 3996 | GLU503 | N | −19.034 | −17.964 | 18.301 |
| 3997 | GLU503 | CA | −20.488 | −17.651 | 18.368 |
| 3998 | GLU503 | C | −21.257 | −18.617 | 17.459 |
| 3999 | GLU503 | O | −22.454 | −18.869 | 17.584 |
| 4000 | GLU503 | CB | −20.749 | −16.219 | 17.876 |
| 4001 | GLU503 | CG | −22.228 | −15.886 | 17.704 |
| 4002 | GLU503 | CD | −22.439 | −14.387 | 17.63 |
| 4003 | GLU503 | OE1 | −22.748 | −13.938 | 16.486 |
| 4004 | GLU503 | OE2 | −22.316 | −13.748 | 18.729 |
| 4005 | ALA504 | N | −20.506 | −19.008 | 16.372 |
| 4006 | ALA504 | CA | −20.935 | −20.061 | 15.492 |
| 4007 | ALA504 | C | −19.729 | −20.986 | 15.274 |
| 4008 | ALA504 | O | −18.558 | −20.607 | 15.372 |
| 4009 | ALA504 | CB | −21.442 | −19.471 | 14.191 |
| 4010 | GLY505 | N | −20.091 | −22.262 | 14.917 |
| 4011 | GLY505 | CA | −19.139 | −23.332 | 14.703 |
| 4012 | GLY505 | C | −19.814 | −24.4 | 13.856 |
| 4013 | GLY505 | O | −20.725 | −24.12 | 13.072 |
| 4014 | ARG506 | N | −19.264 | −25.662 | 14.004 |
| 4015 | ARG506 | CA | −19.955 | −26.86 | 13.504 |
| 4016 | ARG506 | C | −20.693 | −27.446 | 14.714 |
| 4017 | ARG506 | O | −20.065 | −27.881 | 15.68 |
| 4018 | ARG506 | CB | −18.946 | −27.862 | 12.938 |
| 4019 | ARG506 | CG | −19.611 | −29.153 | 12.447 |
| 4020 | ARG506 | CD | −18.652 | −30.027 | 11.642 |
| 4021 | ARG506 | NE | −18.39 | −29.446 | 10.322 |
| 4022 | ARG506 | CZ | −17.684 | −30.031 | 9.334 |
| 4023 | ARG506 | NH1 | −17.591 | −29.385 | 8.157 |
| 4024 | ARG506 | NH2 | −17.083 | −31.226 | 9.486 |
| 4025 | HIS507 | N | −22.069 | −27.325 | 14.683 |
| 4026 | HIS507 | CA | −22.898 | −27.667 | 15.848 |
| 4027 | HIS507 | C | −24.408 | −27.458 | 15.594 |
| 4028 | H1S507 | O | −24.865 | −26.798 | 14.664 |
| 4029 | HIS507 | CB | −22.481 | −26.938 | 17.157 |
| 4030 | HIS507 | CG | −22.311 | −25.457 | 17.051 |
| 4031 | HIS507 | ND1 | −21.963 | −24.674 | 18.126 |
| 4032 | HIS507 | CD2 | −22.406 | −24.57 | 16.004 |
| 4033 | HIS507 | CE1 | −21.806 | −23.393 | 17.674 |
| 4034 | HIS507 | NE2 | −22.047 | −23.299 | 16.384 |
| 4035 | ARG508 | N | −25.233 | −28.045 | 16.547 |
| 4036 | ARG508 | CA | −26.681 | −27.836 | 16.521 |
| 4037 | ARG508 | C | −26.953 | −26.425 | 17.074 |
| 4038 | ARG508 | O | −27.094 | −26.198 | 18.273 |
| 4039 | ARG508 | CB | −27.41 | −28.873 | 17.387 |
| 4040 | ARG508 | CG | −27.241 | −30.306 | 16.881 |
| 4041 | ARG508 | CD | −28.092 | −31.273 | 17.698 |
| 4042 | ARG508 | NE | −27.858 | −32.671 | 17.307 |
| 4043 | ARG508 | CZ | −26.814 | −33.431 | 17.719 |
| 4044 | ARG508 | NH1 | −26.724 | −34.713 | 17.302 |
| 4045 | ARG508 | NH2 | −25.855 | −32.95 | 18.538 |
| 4046 | LYS509 | N | −26.933 | −25.445 | 16.096 |
| 4047 | LYS509 | CA | −26.969 | −24.029 | 16.467 |
| 4048 | LYS509 | C | −28.345 | −23.634 | 17.061 |
| 4049 | LYS509 | O | −29.398 | −24.176 | 16.727 |
| 4050 | LYS509 | CB | −26.716 | −23.15 | 15.232 |
| 4051 | LYS509 | CG | −25.253 | −23.169 | 14.785 |
| 4052 | LYS509 | CD | −25.024 | −22.297 | 13.551 |
| 4053 | LYS509 | CE | −23.562 | −21.957 | 13.328 |
| 4054 | LYS509 | NZ | −22.88 | −22.921 | 12.47 |
| 4055 | SER510 | N | −28.295 | −22.573 | 17.952 |
| 4056 | SER510 | CA | −29.498 | −22.004 | 18.563 |
| 4057 | SER510 | C | −30.006 | −20.796 | 17.746 |
| 4058 | SER510 | O | −29.321 | −20.221 | 16.898 |
| 4059 | SER510 | CB | −29.268 | −21.629 | 20.032 |
| 4060 | SER510 | OG | −28.392 | −20.517 | 20.163 |
| 4061 | TRP511 | N | −31.309 | −20.407 | 18.039 |
| 4062 | TRP511 | CA | −31.959 | −19.289 | 17.34 |
| 4063 | TRP511 | C | −32.482 | −18.271 | 18.358 |
| 4064 | TRP511 | O | −32.101 | −17.099 | 18.366 |
| 4065 | TRP511 | CB | −33.115 | −19.757 | 16.431 |
| 4066 | TRP511 | CG | −32.941 | −19.317 | 15.011 |
| 4067 | TRP511 | CD1 | −32.722 | −20.154 | 13.938 |
| 4068 | TRP511 | CD2 | −32.94 | −17.976 | 14.5 |
| 4069 | TRP511 | NE1 | −32.51 | −19.383 | 12.827 |
| 4070 | TRP511 | CE2 | −32.641 | −18.051 | 13.138 |
| 4071 | TRP511 | CE3 | −33.131 | −16.699 | 15.07 |
| 4072 | TRP511 | CZ2 | −32.5 | −16.919 | 12.326 |
| 4073 | TRP511 | CZ3 | −33.004 | −15.557 | 14.271 |
| 4074 | TRP511 | CH2 | −32.69 | −15.668 | 12.919 |
| 4075 | SER512 | N | −33.435 | −18.746 | 19.244 |
| 4076 | SER512 | CA | −34.294 | −17.813 | 19.992 |
| 4077 | SER512 | C | −33.484 | −16.939 | 20.958 |
| 4078 | SER512 | O | −33.897 | −15.859 | 21.378 |
| 4079 | SER512 | CB | −35.369 | −18.565 | 20.78 |
| 4080 | SER512 | OG | −34.785 | −19.668 | 21.473 |
| 4081 | CYS513 | N | −32.281 | −17.495 | 21.329 |
| 4082 | CYS513 | CA | −31.384 | −16.86 | 22.278 |
| 4083 | CYS513 | C | −30.615 | −15.692 | 21.628 |
| 4084 | CYS513 | O | −29.947 | −14.898 | 22.298 |
| 4085 | CYS513 | CB | −30.354 | −17.852 | 22.818 |
| 4086 | CYS513 | SG | −31.115 | −19.286 | 23.643 |
| 4087 | GLY514 | N | −30.674 | −15.588 | 20.256 |
| 4088 | GLY514 | CA | −29.821 | −14.695 | 19.484 |
| 4089 | GLY514 | C | −30.244 | −13.23 | 19.509 |
| 4090 | GLY514 | O | −30.297 | −12.547 | 18.49 |
| 4091 | HIS515 | N | −30.4 | −12.719 | 20.783 |
| 4092 | HIS515 | CA | −31.066 | −11.438 | 21.038 |
| 4093 | HIS515 | C | −30.372 | −10.761 | 22.233 |
| 4094 | HIS515 | O | −30.942 | −9.978 | 22.991 |
| 4095 | HIS515 | CB | −32.567 | −11.643 | 21.32 |
| 4096 | HIS515 | CG | −33.314 | −12.194 | 20.15 |
| 4097 | HIS515 | ND1 | −33.83 | −13.466 | 20.107 |
| 4098 | HIS515 | CD2 | −33.647 | −11.648 | 18.927 |
| 4099 | HIS515 | CE1 | −34.429 | −13.627 | 18.887 |
| 4100 | HIS515 | NE2 | −34.34 | −12.543 | 18.154 |
| 4101 | THR516 | N | −29.009 | −10.996 | 22.305 |
| 4102 | THR516 | CA | −28.221 | −10.644 | 23.488 |
| 4103 | THR516 | C | −26.824 | −10.167 | 23.058 |
| 4104 | THR516 | O | −26.179 | −10.748 | 22.183 |
| 4105 | THR516 | CB | −28.127 | −11.847 | 24.46 |
| 4106 | THR516 | OG1 | −27.657 | −11.48 | 25.761 |
| 4107 | THR516 | CG2 | −27.272 | −12.999 | 23.942 |
| 4108 | ARG517 | N | −26.341 | −9.092 | 23.773 |
| 4109 | ARG517 | CA | −24.985 | −8.515 | 23.652 |
| 4110 | ARG517 | C | −24.85 | −7.641 | 24.913 |
| 4111 | ARG517 | O | −25.456 | −6.566 | 24.999 |
| 4112 | ARG517 | CB | −24.819 | −7.564 | 22.45 |
| 4113 | ARG517 | CG | −24.775 | −8.14 | 21.035 |
| 4114 | ARG517 | CD | −23.657 | −9.149 | 20.771 |
| 4115 | ARG517 | NE | −24.174 | −10.51 | 20.9 |
| 4116 | ARG517 | CZ | −23.72 | −11.583 | 20.231 |
| 4117 | ARG517 | NH1 | −24.407 | −12.739 | 20.281 |
| 4118 | ARG517 | NH2 | −22.586 | −11.579 | 19.529 |
| 4119 | ALA518 | N | −24.215 | −8.205 | 25.999 |
| 4120 | ALA518 | CA | −24.204 | −7.553 | 27.314 |
| 4121 | ALA518 | C | −25.608 | −7.517 | 27.958 |
| 4122 | ALA518 | O | −25.869 | −8.139 | 28.986 |
| 4123 | ALA518 | CB | −23.545 | −6.175 | 27.309 |
| 4124 | GLY519 | N | −26.512 | −6.701 | 27.309 |
| 4125 | GLY519 | CA | −27.93 | −6.718 | 27.587 |
| 4126 | GLY519 | C | −28.688 | −7.409 | 26.449 |
| 4127 | GLY519 | O | −28.14 | −8.03 | 25.539 |
| 4128 | GYS520 | N | −30.062 | −7.253 | 26.577 |
| 4129 | GYS520 | CA | −30.985 | −7.773 | 25.539 |
| 4130 | CYS520 | C | −31.014 | −6.765 | 24.375 |
| 4131 | GYS520 | O | −30.996 | −5.539 | 24.549 |
| 4132 | GYS520 | CB | −32.391 | −7.922 | 26.13 |
| 4133 | GYS520 | SG | −33.538 | −8.817 | 25.043 |
| 4134 | THR521 | N | −31.107 | −7.334 | 23.121 |
| 4135 | THR521 | CA | −31.076 | −6.541 | 21.899 |
| 4136 | THR521 | C | −31.737 | −7.262 | 20.707 |
| 4137 | THR521 | O | −32.218 | −8.387 | 20.775 |
| 4138 | THR521 | CB | −29.655 | −6.04 | 21.56 |
| 4139 | THR521 | OG1 | −29.725 | −5.151 | 20.433 |
| 4140 | THR521 | CG2 | −28.67 | −7.165 | 21.268 |
| 4141 | LEU522 | N | −31.81 | −6.461 | 19.576 |

TABLE V-continued

| Atom No | Residue | Atom name | x coord | y coord | z coord |
|---|---|---|---|---|---|
| 4142 | LEU522 | CA | −32.287 | −6.938 | 18.274 |
| 4143 | LEU522 | C | −33.808 | −7.211 | 18.26 |
| 4144 | LEU522 | O | −34.349 | −7.886 | 17.388 |
| 4145 | LEU522 | CB | −31.478 | −8.115 | 17.702 |
| 4146 | LEU522 | CG | −30 | −7.79 | 17.401 |
| 4147 | LEU522 | CD1 | −29.235 | −9.081 | 17.093 |
| 4148 | LEU522 | CD2 | −29.848 | −6.812 | 16.235 |
| 4149 | ILE523 | N | −34.516 | −6.48 | 19.199 |
| 4150 | ILE523 | CA | −35.973 | −6.535 | 19.323 |
| 4151 | ILE523 | C | −36.545 | −5.152 | 19.708 |
| 4152 | ILE523 | O | −37.73 | −4.987 | 20 |
| 4153 | ILE523 | CB | −36.474 | −7.617 | 20.317 |
| 4154 | ILE523 | CG1 | −35.954 | −7.381 | 21.752 |
| 4155 | ILE523 | CG2 | −36.139 | −9.03 | 19.829 |
| 4156 | ILE523 | CD1 | −36.643 | −8.264 | 22.785 |
| 4157 | ARG524 | N | −35.627 | −4.116 | 19.641 |
| 4158 | ARG524 | CA | −36.041 | −2.731 | 19.862 |
| 4159 | ARG524 | C | −36.617 | −2.156 | 18.555 |
| 4160 | ARG524 | O | −36.56 | −2.757 | 17.481 |
| 4161 | ARG524 | CB | −34.864 | −1.887 | 20.374 |
| 4162 | ARG524 | CG | −34.488 | −2.249 | 21.814 |
| 4163 | ARG524 | CD | −33.444 | −1.292 | 22.384 |
| 4164 | ARG524 | NE | −33.203 | −1.547 | 23.815 |
| 4165 | ARG524 | CZ | −32.502 | −2.592 | 24.316 |
| 4166 | ARG524 | NH1 | −32.437 | −2.773 | 25.651 |
| 4167 | ARG524 | NH2 | −31.859 | −3.466 | 23.526 |
| 4168 | GLN525 | N | −37.257 | −0.95 | 18.72 |
| 4169 | GLN525 | CA | −37.785 | −0.124 | 17.626 |
| 4170 | GLN525 | CB | −39.314 | −0.234 | 17.512 |
| 4171 | GLN525 | CG | −39.806 | −1.609 | 17.056 |
| 4172 | GLN525 | CD | −39.88 | −2.607 | 18.192 |
| 4173 | GLN525 | OE1 | −40.549 | −2.433 | 19.205 |
| 4174 | GLN525 | NE2 | −39.152 | −3.75 | 17.988 |
| 4175 | GLN525 | C | −37.468 | 1.347 | 17.904 |
| 4176 | GLN525 | O | −36.858 | 1.67 | 18.923 |
| 4177 | GLN525 | OXT | −37.884 | 2.231 | 16.996 |

---

SEQUENCE LISTING

<160> NUMBER OF SEQ ID NOS: 145

<210> SEQ ID NO 1
<211> LENGTH: 4584
<212> TYPE: DNA
<213> ORGANISM: Homo sapiens
<220> FEATURE:
<221> NAME/KEY: CDS
<222> LOCATION: (114)..(1397)
<220> FEATURE:
<221> NAME/KEY: CDS
<222> LOCATION: (1537)..(1995)

<400> SEQUENCE: 1

```
gaaaaatcca tgctgaagga ccccaggacc agcaccagtt cctgagcatc tttcccgggc      60
tgagcagcag agactcctca ggaagactca ctggactgta cccaccacct gcc atg       116
                                                              Met
                                                                1 tct ctg tgg cca cct ttc cga tgc aga tgg aag ctg gcg cca agg tac      164
Ser Leu Trp Pro Pro Phe Arg Cys Arg Trp Lys Leu Ala Pro Arg Tyr
        5                  10                  15 tct agg agg gcg tct cca cag caa ccc caa cag gac ttt gag gcc ctg      212
Ser Arg Arg Ala Ser Pro Gln Gln Pro Gln Gln Asp Phe Glu Ala Leu
     20                  25                  30 ctg gca gag tgc ctg agg aat ggc tgc ctc ttt gaa gac acc agc ttc      260
Leu Ala Glu Cys Leu Arg Asn Gly Cys Leu Phe Glu Asp Thr Ser Phe
 35                  40                  45 ccg gcc acc ctg agc tcc atc ggc agt ggc tcc ctg ctg cag aag ctg      308
Pro Ala Thr Leu Ser Ser Ile Gly Ser Gly Ser Leu Leu Gln Lys Leu
50                  55                  60                  65
```

-continued

| | |
|---|---|
| cca ccc cgc ctg cag tgg aag agg ccc ccg gag ctg cac agc aat ccc<br>Pro Pro Arg Leu Gln Trp Lys Arg Pro Pro Glu Leu His Ser Asn Pro<br>                70                      75                80 | 356 |
| cag ttt tat ttt gcc aag gcc aaa agg ctg gat ctg tgc cag ggg ata<br>Gln Phe Tyr Phe Ala Lys Ala Lys Arg Leu Asp Leu Cys Gln Gly Ile<br>                     85                   90                95 | 404 |
| gta gga gac tgc tgg ttc ttg gct gct ttg caa gct ctg gcc ttg cac<br>Val Gly Asp Cys Trp Phe Leu Ala Ala Leu Gln Ala Leu Ala Leu His<br>                 100                105               110 | 452 |
| cag gac atc ctg agc cgg gtt gtt ccc ctg aat cag agt ttc act gag<br>Gln Asp Ile Leu Ser Arg Val Val Pro Leu Asn Gln Ser Phe Thr Glu<br>115                   120                125 | 500 |
| aag tat gct ggc atc ttc cgg ttc tgg ttc tgg cac tat ggg aac tgg<br>Lys Tyr Ala Gly Ile Phe Arg Phe Trp Phe Trp His Tyr Gly Asn Trp<br>130                   135                140               145 | 548 |
| gtt cct gtg gtg atc gat gac cgt ctg cct gtg aat gag gct ggc cag<br>Val Pro Val Val Ile Asp Asp Arg Leu Pro Val Asn Glu Ala Gly Gln<br>                 150                155               160 | 596 |
| ctg gtc ttt gtc tcc tcc acc tat aag aac ttg ttc tgg gga gca ctt<br>Leu Val Phe Val Ser Ser Thr Tyr Lys Asn Leu Phe Trp Gly Ala Leu<br>                 165                170               175 | 644 |
| ctg gaa aag gcc tat gcc aag ctc tct ggt tcc tat gaa gac ttg cag<br>Leu Glu Lys Ala Tyr Ala Lys Leu Ser Gly Ser Tyr Glu Asp Leu Gln<br>            180                185               190 | 692 |
| tca gga cag gtg tct gaa gcc ctt gta gac ttc act gga ggg gtg aca<br>Ser Gly Gln Val Ser Glu Ala Leu Val Asp Phe Thr Gly Gly Val Thr<br>195                   200                205 | 740 |
| atg acc atc aac ctg gca gaa gcc cat ggc aac ctc tgg gac atc ctc<br>Met Thr Ile Asn Leu Ala Glu Ala His Gly Asn Leu Trp Asp Ile Leu<br>210                   215                220             225 | 788 |
| atc gaa gcc acc tac aac aga acc ctc att ggc tgc cag acc cac tca<br>Ile Glu Ala Thr Tyr Asn Arg Thr Leu Ile Gly Cys Gln Thr His Ser<br>                 230                235               240 | 836 |
| ggg aag att ctg gag aat ggg ctg gtg gaa ggc cat gcc tat act ctc<br>Gly Lys Ile Leu Glu Asn Gly Leu Val Glu Gly His Ala Tyr Thr Leu<br>                 245                250               255 | 884 |
| aca gga atc agg aag gtg acc tgc aaa cat aga cct gaa tat ctc gtc<br>Thr Gly Ile Arg Lys Val Thr Cys Lys His Arg Pro Glu Tyr Leu Val<br>            260                265               270 | 932 |
| aag cta cgg aac ccc tgg gga aag gtg gaa tgg aaa gga gac tgg agt<br>Lys Leu Arg Asn Pro Trp Gly Lys Val Glu Trp Lys Gly Asp Trp Ser<br>275                   280                285 | 980 |
| gac agt tca agt aaa tgg gag ctg ctg agc ccc aag gag aag att ctg<br>Asp Ser Ser Ser Lys Trp Glu Leu Leu Ser Pro Lys Glu Lys Ile Leu<br>290                   295                300             305 | 1028 |
| ctt ctg agg aaa gac aat gac gga gaa ttc tgg atg acg ctg cag gac<br>Leu Leu Arg Lys Asp Asn Asp Gly Glu Phe Trp Met Thr Leu Gln Asp<br>                 310                315               320 | 1076 |
| ttt aaa aca cat ttc gtg ctc ctg gtt atc tgt aaa ctg acc cca ggc<br>Phe Lys Thr His Phe Val Leu Leu Val Ile Cys Lys Leu Thr Pro Gly<br>            325                330               335 | 1124 |
| ctg ttg agc cag gag gcg gcc cag aag tgg acg tac acc atg cgg gag<br>Leu Leu Ser Gln Glu Ala Ala Gln Lys Trp Thr Tyr Thr Met Arg Glu<br>            340                345               350 | 1172 |
| ggg aga tgg gag aag cgg agc aca gct ggt ggc cag agg cag ttg ctg<br>Gly Arg Trp Glu Lys Arg Ser Thr Ala Gly Gly Gln Arg Gln Leu Leu<br>355                   360                365 | 1220 |
| cag gac aca ttt tgg aag aac ccg cag ttc ctg ctg tct gtc tgg agg<br>Gln Asp Thr Phe Trp Lys Asn Pro Gln Phe Leu Leu Ser Val Trp Arg<br>370                   375                380             385 | 1268 |

```
ccc gag gag ggc agg aga tcc ctg agg ccc tgc agc gtg ctg gtg tcc      1316
Pro Glu Glu Gly Arg Arg Ser Leu Arg Pro Cys Ser Val Leu Val Ser
            390                 395                 400 ctg ctc cag aag ccc agg cac agg tgc cgc aag cgg aag cct ctc ctc      1364
Leu Leu Gln Lys Pro Arg His Arg Cys Arg Lys Arg Lys Pro Leu Leu
        405                 410                 415 gcc att ggc ttc tac ctc tat agg atg aac aag tgaaattggc agcaattctg    1417
Ala Ile Gly Phe Tyr Leu Tyr Arg Met Asn Lys
    420                 425 gtgtcgtctt ctcaaaggag atagaagacc aaaatgaaag gcaggatgaa ttcttcacca    1477
aattctttga aaagcatcca gagattaatg cagttcaact tcagaacctc ctgaaccag     1536 atg acc tgg tca agt ctg ggg agc aga cag ccc ttc ttt agc ctg gaa      1584
Met Thr Trp Ser Ser Leu Gly Ser Arg Gln Pro Phe Phe Ser Leu Glu
        430                 435                 440 gcc tgc cag ggg atc ctg gcc tta ctg gac ctt aat gca tca ggt act      1632
Ala Cys Gln Gly Ile Leu Ala Leu Leu Asp Leu Asn Ala Ser Gly Thr
445                 450                 455                 460 atg agc atc cag gaa ttc agg gac ctg tgg aag cag ctg aag ctc tct      1680
Met Ser Ile Gln Glu Phe Arg Asp Leu Trp Lys Gln Leu Lys Leu Ser
                465                 470                 475 cag aag gtt ttc cac aag caa gac cgt ggg tca gga tac ctg aac tgg      1728
Gln Lys Val Phe His Lys Gln Asp Arg Gly Ser Gly Tyr Leu Asn Trp
            480                 485                 490 gag cag ctg cac gct gcc atg agg gag gca ggt agg cac agg aag agc      1776
Glu Gln Leu His Ala Ala Met Arg Glu Ala Gly Arg His Arg Lys Ser
        495                 500                 505 tgg agc tgt ggg cac aca cgg gca ggg tgc aca ctc atc agg cag agg      1824
Trp Ser Cys Gly His Thr Arg Ala Gly Cys Thr Leu Ile Arg Gln Arg
    510                 515                 520 aga ggg gat gtg tgg cat gct gaa gta act cta ata cgc agt gtt act      1872
Arg Gly Asp Val Trp His Ala Glu Val Thr Leu Ile Arg Ser Val Thr
525                 530                 535                 540 ctc aaa gac gta gat ctg cag tca act cca aca ttt ttt atg att gtc      1920
Leu Lys Asp Val Asp Leu Gln Ser Thr Pro Thr Phe Phe Met Ile Val
                545                 550                 555 cct gtg atc cta gcc aac att gat gga ggg gtg gca cat tca act tct      1968
Pro Val Ile Leu Ala Asn Ile Asp Gly Gly Val Ala His Ser Thr Ser
            560                 565                 570 tat tta atc ttc aac acc acc ttg tta taatcctcac ttcacagagg            2015
Tyr Leu Ile Phe Asn Thr Thr Leu Leu
        575                 580 aagaaattga agctcaattg cctggggttt aaattcagga ctgccgggct cccaagcagg    2075
tacttttgag cacttagcag actgcctcct tcattgaagg ctggtaacat acttgatgaa    2135
aacagcctca tgctggttgc cttaacagac agggtgaag agtagggatt aaataaaata    2195
aattggttaa acaattaaac cattcaaaat gaaccctata aaagaagatt tccatgctat    2255
caggattcag gtccctaaac tggagggaca tttgaagggg ccttgagcag gagggagct    2315 gggtgcaagc ccccaatacc cacagcagga gcttgtgctc aatgcaggaa tcatgctcag    2375
tgatgacgtc tgtcagctga tgctcatccg ctacggcggc ccccgcctcc agatggactt    2435
tgtcagtttc atccacttga tgctgcgtgt agagaacatg gagggtaagc tggcggaag    2495 ctggggaggg ccaggtcttc ctctgctgcc ccatgacttc ccacctgtcc ctagtttaag    2555
cacaagggag acagccgcc atcccagaaa cagcagacca gggaagctgt ggggaccctcc   2615 agccaagtgc ctgtgaaccc tggctgcaga tatccaaact catcttttcc tgacttgttc   2675
```

-continued

```
cagagacaaa ggcttgaagt ggctcactta tcatagatgt ggctgcgtgt ggtcacatgt      2735
aggctgacac tgggttccct cacgttttca gaatggatgt ggttaaggtg agacatatgg      2795
gaggaactaa ttcataatgt ttccaataga cacattagct gtattccttt ctgctgcatt      2855
ttcacagatg tcttccaaaa cttaacccaa gatggcaaag ggatatacct ccagaagcca      2915
gagtggatga tgatggcact gtactcctga gaaggctgag tctcacctgc cctcactgaa      2975
gactctgcat gtggcccaag agcagccttt ggctgagacc aacccatgcc caccctactt      3035
actgatcttc aggacagcct cactagccgt caccttctca gctgggaagg tttctcttct      3095
gcagccctcc ccgtgcatgg ccagcatgca gaaagggaag ggaggaagta aagattacat      3155
cagatttgta aaagctagcc atccttccct gaggccacaa ccttgtcaca agcggagatg      3215
ttacctgaca tggcctaagc attctgactc cagagctggt gtggttagcc tccatacaac      3275
actgcctctg tggctgcaaa ctcaagtgac tttagacatg ccacatgttc tcacatggtg      3335
gggtaatcat ctaggtttta aggtctgaaa tgggaatgat atatccttag acatttagtc      3395
ccagcatctg caaattgata gagacatagg ctaagtttca gctgtttggg gatggggtca      3455
gggatatagt gggcttttcag aaacacagac agtaagagaa ttggcagagt ccaggtgggg      3515
tgggctggct ctggcatctg aggtcatggg gtagtcttct tctgacaata tctccgtatg      3575
attggatctg gggcaaccta gtagatttaa acacctgag ttctcaaagg gcttcctgct      3635
tgtgacaggt gtgtctattt gcttgatata tagactatca gatccatttc aaatctgtcc      3695
agaaattctc tgtctatcta cttcaaagga caaaaacaaa cccatgctaa attatagagt      3755
caatcagtgg gtggttggta tatctgattt tttgaactac catgaaacac cttgtttatg      3815
tcatccctct caaccaagaa tacaggtgca aaaccagaac aatggccttt ttccaaagtc      3875
tatgcaattt attcataagt tagcacctca gagccattta ttactacagg ttgagcatcc      3935
caaatctgaa aaccccaaat ctgaaatact ccaaaatcta aaatttctga gagtagacat      3995
gaaactcaaa ggaaatagg gcattttgga ttttgaattt ttggggtttga ggtgttcaac      4055 tgacaagtct ataatgcaga tatcctgaaa tctgaaacac ttctggtccc aagcatttta      4115
gttaagagat agtcaacctg tattctattt aatcttaatt tacaaacaat tctaacaaac      4175
atggctgttt gatttccaac tccatagcag actcaggaag gaagctgaat gaagagataa      4235
aagtgtgtcc attggcagag gactaaagga gatttgagca cctgtcagat gggtactgta      4295
ccagaagaaa ggagcacttt gaaagcgtag cttatggggt aggaaagtat tttatttagg      4355
aaaaaaaacc cttcatttat tccaaatgat aaaatgtaaa atgggtttcc ataaagtgcc      4415
agatacatga gatgttgttg attttataaa tgatgatcat gtatttacag ccttttacag      4475 tttttttatat ccattgactt atttgtgtct ttgtctttaa aatctgccat tgcaaatagc      4535
tgttttaata aaccaatttt gccttggccc ctgaaaaaaa aaaaaaaa                   4584
```

<210> SEQ ID NO 2
<211> LENGTH: 428
<212> TYPE: PRT
<213> ORGANISM: Homo sapiens

<400> SEQUENCE: 2

```
Met Ser Leu Trp Pro Pro Phe Arg Cys Arg Trp Lys Leu Ala Pro Arg
1               5                   10                  15

Tyr Ser Arg Arg Ala Ser Pro Gln Gln Pro Gln Gln Asp Phe Glu Ala
            20                  25                  30
```

```
Leu Leu Ala Glu Cys Leu Arg Asn Gly Cys Leu Phe Glu Asp Thr Ser
         35                  40                  45
Phe Pro Ala Thr Leu Ser Ser Ile Gly Ser Gly Ser Leu Leu Gln Lys
     50                  55                  60
Leu Pro Pro Arg Leu Gln Trp Lys Arg Pro Pro Glu Leu His Ser Asn
 65                  70                  75                  80
Pro Gln Phe Tyr Phe Ala Lys Ala Lys Arg Leu Asp Leu Cys Gln Gly
                 85                  90                  95
Ile Val Gly Asp Cys Trp Phe Leu Ala Ala Leu Gln Ala Leu Ala Leu
             100                 105                 110
His Gln Asp Ile Leu Ser Arg Val Val Pro Leu Asn Gln Ser Phe Thr
         115                 120                 125
Glu Lys Tyr Ala Gly Ile Phe Arg Phe Trp Phe Trp His Tyr Gly Asn
     130                 135                 140
Trp Val Pro Val Val Ile Asp Asp Arg Leu Pro Val Asn Glu Ala Gly
145                 150                 155                 160
Gln Leu Val Phe Val Ser Ser Thr Tyr Lys Asn Leu Phe Trp Gly Ala
                 165                 170                 175
Leu Leu Glu Lys Ala Tyr Ala Lys Leu Ser Gly Ser Tyr Glu Asp Leu
             180                 185                 190
Gln Ser Gly Gln Val Ser Glu Ala Leu Val Asp Phe Thr Gly Gly Val
         195                 200                 205
Thr Met Thr Ile Asn Leu Ala Glu Ala His Gly Asn Leu Trp Asp Ile
     210                 215                 220
Leu Ile Glu Ala Thr Tyr Asn Arg Thr Leu Ile Gly Cys Gln Thr His
225                 230                 235                 240
Ser Gly Lys Ile Leu Glu Asn Gly Leu Val Glu Gly His Ala Tyr Thr
                 245                 250                 255
Leu Thr Gly Ile Arg Lys Val Thr Cys Lys His Arg Pro Glu Tyr Leu
             260                 265                 270
Val Lys Leu Arg Asn Pro Trp Gly Lys Val Glu Trp Lys Gly Asp Trp
         275                 280                 285
Ser Asp Ser Ser Ser Lys Trp Glu Leu Leu Ser Pro Lys Glu Lys Ile
     290                 295                 300
Leu Leu Leu Arg Lys Asp Asn Asp Gly Glu Phe Trp Met Thr Leu Gln
305                 310                 315                 320
Asp Phe Lys Thr His Phe Val Leu Leu Val Ile Cys Lys Leu Thr Pro
                 325                 330                 335
Gly Leu Leu Ser Gln Glu Ala Ala Gln Lys Trp Thr Tyr Thr Met Arg
             340                 345                 350
Glu Gly Arg Trp Glu Lys Arg Ser Thr Ala Gly Gly Gln Arg Gln Leu
         355                 360                 365
Leu Gln Asp Thr Phe Trp Lys Asn Pro Gln Phe Leu Leu Ser Val Trp
     370                 375                 380
Arg Pro Glu Glu Gly Arg Arg Ser Leu Arg Pro Cys Ser Val Leu Val
385                 390                 395                 400
Ser Leu Leu Gln Lys Pro Arg His Arg Cys Arg Lys Arg Lys Pro Leu
                 405                 410                 415
Leu Ala Ile Gly Phe Tyr Leu Tyr Arg Met Asn Lys
             420                 425

<210> SEQ ID NO 3
<211> LENGTH: 153
```

```
<212> TYPE: PRT
<213> ORGANISM: Homo sapiens

<400> SEQUENCE: 3

Met Thr Trp Ser Ser Leu Gly Ser Arg Gln Pro Phe Ser Leu Glu
1               5                   10                  15

Ala Cys Gln Gly Ile Leu Ala Leu Leu Asp Leu Asn Ala Ser Gly Thr
                20                  25                  30

Met Ser Ile Gln Glu Phe Arg Asp Leu Trp Lys Gln Leu Lys Leu Ser
        35                  40                  45

Gln Lys Val Phe His Lys Gln Asp Arg Gly Ser Gly Tyr Leu Asn Trp
50                  55                  60

Glu Gln Leu His Ala Ala Met Arg Glu Ala Gly Arg His Arg Lys Ser
65                  70                  75                  80

Trp Ser Cys Gly His Thr Arg Ala Gly Cys Thr Leu Ile Arg Gln Arg
                85                  90                  95

Arg Gly Asp Val Trp His Ala Glu Val Thr Leu Ile Arg Ser Val Thr
                100                 105                 110

Leu Lys Asp Val Asp Leu Gln Ser Thr Pro Thr Phe Phe Met Ile Val
        115                 120                 125

Pro Val Ile Leu Ala Asn Ile Asp Gly Gly Val Ala His Ser Thr Ser
        130                 135                 140

Tyr Leu Ile Phe Asn Thr Thr Leu Leu
145                 150

<210> SEQ ID NO 4
<211> LENGTH: 671
<212> TYPE: PRT
<213> ORGANISM: Homo sapiens

<400> SEQUENCE: 4

Met Arg Ala Gly Arg Gly Ala Thr Pro Ala Arg Glu Leu Phe Arg Asp
1               5                   10                  15

Ala Ala Phe Pro Ala Ala Asp Ser Ser Leu Phe Cys Asp Leu Ser Thr
                20                  25                  30

Pro Leu Ala Gln Phe Arg Glu Asp Ile Thr Trp Arg Pro Gln Glu
        35                  40                  45

Ile Cys Ala Thr Pro Arg Leu Phe Pro Asp Pro Arg Glu Gly Gln
    50                  55                  60

Val Lys Gln Gly Leu Leu Gly Asp Cys Trp Phe Leu Cys Ala Cys Ala
65                  70                  75                  80

Ala Leu Gln Lys Ser Arg His Leu Leu Asp Gln Val Ile Pro Pro Gly
                85                  90                  95

Gln Pro Ser Trp Ala Asp Gln Glu Tyr Arg Gly Ser Phe Thr Cys Arg
                100                 105                 110

Ile Trp Gln Phe Gly Arg Trp Val Glu Val Thr Thr Asp Asp Arg Leu
        115                 120                 125

Pro Cys Leu Ala Gly Arg Leu Cys Phe Ser Arg Cys Gln Arg Glu Asp
        130                 135                 140

Val Phe Trp Leu Pro Leu Leu Glu Lys Val Tyr Ala Lys Val His Gly
145                 150                 155                 160

Ser Tyr Glu His Leu Trp Ala Gly Gln Val Ala Asp Ala Leu Val Asp
                165                 170                 175

Leu Thr Gly Gly Leu Ala Glu Arg Trp Asn Leu Lys Gly Val Ala Gly
                180                 185                 190
```

```
Ser Gly Gly Gln Gln Asp Arg Pro Gly Arg Trp Glu His Arg Thr Cys
        195                 200                 205

Arg Gln Leu Leu His Leu Lys Asp Gln Cys Leu Ile Ser Cys Cys Val
210                 215                 220

Leu Ser Pro Arg Ala Gly Ala Arg Glu Leu Gly Glu Phe His Ala Phe
225                 230                 235                 240

Ile Val Ser Asp Leu Arg Glu Leu Gln Gly Gln Ala Gly Gln Cys Ile
            245                 250                 255

Leu Leu Leu Arg Ile Gln Asn Pro Trp Gly Arg Arg Cys Trp Gln Gly
        260                 265                 270

Leu Trp Arg Glu Gly Gly Glu Gly Trp Ser Gln Val Asp Ala Ala Val
    275                 280                 285

Ala Ser Glu Leu Leu Ser Gln Leu Gln Glu Gly Glu Phe Trp Val Glu
290                 295                 300

Glu Glu Glu Phe Leu Arg Glu Phe Asp Glu Leu Thr Val Gly Tyr Pro
305                 310                 315                 320

Val Thr Glu Ala Gly His Leu Gln Ser Leu Tyr Thr Glu Arg Leu Leu
            325                 330                 335

Cys His Thr Arg Ala Leu Pro Gly Ala Trp Val Lys Gly Gln Ser Ala
        340                 345                 350

Gly Gly Cys Arg Asn Asn Ser Gly Phe Pro Ser Asn Pro Lys Phe Trp
    355                 360                 365

Leu Arg Val Ser Glu Pro Ser Glu Val Tyr Ile Ala Val Leu Gln Arg
370                 375                 380

Ser Arg Leu His Ala Ala Asp Trp Ala Gly Arg Ala Arg Ala Leu Val
385                 390                 395                 400

Gly Asp Ser His Thr Ser Trp Ser Pro Ala Ser Ile Pro Gly Lys His
            405                 410                 415

Tyr Gln Ala Val Gly Leu His Leu Trp Lys Val Glu Lys Arg Arg Val
        420                 425                 430

Asn Leu Pro Arg Val Leu Ser Met Pro Pro Val Ala Gly Thr Ala Cys
        435                 440                 445

His Ala Tyr Asp Arg Glu Val His Leu Arg Cys Glu Leu Ser Pro Gly
        450                 455                 460

Tyr Tyr Leu Ala Val Pro Ser Thr Phe Leu Lys Asp Ala Pro Gly Glu
465                 470                 475                 480

Phe Leu Leu Arg Val Phe Ser Thr Gly Arg Val Ser Leu Ser Ala Ile
            485                 490                 495

Arg Ala Val Ala Lys Asn Thr Thr Pro Gly Ala Ala Leu Pro Ala Gly
        500                 505                 510

Glu Trp Gly Thr Val Gln Leu Arg Gly Ser Trp Arg Val Gly Gln Thr
    515                 520                 525

Ala Gly Gly Ser Arg Asn Phe Ala Ser Tyr Pro Thr Asn Pro Cys Phe
530                 535                 540

Pro Phe Ser Val Pro Glu Gly Pro Gly Pro Arg Cys Val Arg Ile Thr
545                 550                 555                 560

Leu His Gln His Cys Arg Pro Ser Asp Thr Glu Phe His Pro Ile Gly
            565                 570                 575

Phe His Ile Phe Gln Val Pro Glu Gly Gly Arg Ser Gln Asp Ala Pro
        580                 585                 590

Pro Leu Leu Leu Gln Glu Phe Leu Leu Ser Cys Val Pro His Arg Tyr
    595                 600                 605
```

```
Ala Gln Glu Val Ser Arg Leu Cys Leu Leu Pro Ala Gly Thr Tyr Lys
    610                 615                 620

Val Val Pro Ser Thr Tyr Leu Pro Asp Thr Glu Gly Ala Phe Thr Val
625                 630                 635                 640

Thr Ile Ala Thr Arg Ile Asp Pro Ser Ile His Ser Gln Glu Met Leu
                645                 650                 655

Gly Gln Phe Leu Gln Glu Val Ser Val Met Ala Val Met Lys Thr
                660                 665                 670

<210> SEQ ID NO 5
<211> LENGTH: 639
<212> TYPE: PRT
<213> ORGANISM: Homo sapiens

<400> SEQUENCE: 5

Met Phe Ser Cys Val Lys Pro Tyr Glu Asp Gln Asn Tyr Ser Ala Leu
1               5                   10                  15

Arg Gln Asp Cys Arg Arg Lys Val Leu Phe Glu Asp Pro Leu Phe
            20                  25                  30

Pro Ala Thr Asp Asp Ser Leu Tyr Tyr Lys Gly Thr Pro Gly Pro Ala
            35                  40                  45

Val Arg Trp Lys Arg Pro Lys Gly Ile Cys Glu Asp Pro Arg Leu Phe
50                  55                  60

Val Asp Gly Ile Ser Ser His Asp Leu His Gln Gly Gln Val Gly Asn
65                  70                  75                  80

Cys Trp Phe Val Ala Ala Cys Ser Ser Leu Ala Ser Arg Glu Ser Leu
                85                  90                  95

Trp Gln Lys Val Ile Pro Asp Trp Lys Glu Gln Glu Trp Asp Pro Arg
            100                 105                 110

Lys Ala Gln Ala Tyr Ala Gly Ile Phe His Phe His Phe Trp Arg Leu
            115                 120                 125

Gly Met Val Asp Val Val Ile Asp Glu Arg Leu Pro Thr Val Asn Asn
130                 135                 140

Gln Leu Ile Tyr Cys His Ser Asn Ser Arg Asn Glu Phe Trp Cys Ala
145                 150                 155                 160

Leu Val Glu Lys Ala Tyr Ala Lys Leu Ala Gly Cys Tyr Gln Ala Leu
                165                 170                 175

Asp Gly Gly Asn Thr Ala Asp Ala Leu Val Asp Phe Thr Gly Gly Val
            180                 185                 190

Ser Glu Pro Ile Asp Leu Thr Glu Gly Asp Phe Ala Asn Asp Glu Thr
            195                 200                 205

Lys Arg Asn Gln Leu Phe Glu Arg Met Leu Lys Val His Ser Arg Gly
            210                 215                 220

Gly Leu Ile Ser Ala Ser Ile Lys Ala Val Thr Ala Ala Asp Met Glu
225                 230                 235                 240

Ala Arg Leu Ala Cys Gly Leu Val Lys Gly His Ala Tyr Ala Val Thr
                245                 250                 255

Asp Val Arg Lys Val Arg Leu Gly His Gly Leu Leu Ala Phe Phe Lys
            260                 265                 270

Ser Glu Lys Leu Asp Met Ile Arg Leu Arg Asn Pro Trp Gly Glu Arg
            275                 280                 285

Glu Trp Asn Gly Pro Trp Ser Asp Thr Ser Glu Glu Trp Gln Lys Val
            290                 295                 300

Ser Lys Ser Glu Arg Glu Lys Met Gly Val Thr Val Gln Asp Asp Gly
305                 310                 315                 320
```

-continued

```
Glu Phe Trp Met Thr Phe Glu Asp Val Cys Arg Tyr Phe Thr Asp Ile
            325                 330                 335

Ile Lys Cys Arg Val Ile Asn Thr Ser His Leu Ser Ile His Lys Thr
        340                 345                 350

Trp Glu Glu Ala Arg Leu His Gly Ala Trp Thr Leu His Glu Asp Pro
    355                 360                 365

Arg Gln Asn Arg Gly Gly Gly Cys Ile Asn His Lys Asp Thr Phe Phe
370                 375                 380

Gln Asn Pro Gln Tyr Ile Phe Glu Val Lys Lys Pro Glu Asp Glu Val
385                 390                 395                 400

Leu Ile Cys Ile Gln Gln Arg Pro Lys Arg Ser Thr Arg Arg Glu Gly
                405                 410                 415

Lys Gly Glu Asn Leu Ala Ile Gly Phe Asp Ile Tyr Lys Val Glu Glu
            420                 425                 430

Asn Arg Gln Tyr Arg Met His Ser Leu Gln His Lys Ala Ala Ser Ser
        435                 440                 445

Ile Tyr Ile Asn Ser Arg Ser Val Phe Leu Arg Thr Asp Gln Pro Glu
    450                 455                 460

Gly Arg Tyr Val Ile Pro Thr Thr Phe Glu Pro Gly His Thr Gly
465                 470                 475                 480

Glu Phe Leu Leu Arg Val Phe Thr Asp Val Pro Ser Asn Cys Arg Glu
                485                 490                 495

Leu Arg Leu Asp Lys Pro Pro His Thr Cys Trp Ser Ser Leu Cys Gly
            500                 505                 510

Tyr Pro Gln Leu Val Thr Gln Val His Val Leu Gly Ala Ala Gly Leu
        515                 520                 525

Lys Asp Ser Pro Thr Gly Ala Asn Ser Tyr Val Ile Ile Lys Cys Glu
    530                 535                 540

Gly Asp Lys Val Arg Ser Ala Val Gln Lys Gly Thr Ser Thr Pro Glu
545                 550                 555                 560

Tyr Asn Val Lys Gly Ile Phe Tyr Arg Lys Lys Leu Ser Gln Pro Ile
                565                 570                 575

Thr Val Gln Val Trp Asn His Arg Val Leu Lys Asp Glu Phe Leu Gly
            580                 585                 590

Gln Val His Leu Lys Ala Asp Pro Asp Asn Leu Gln Ala Leu His Thr
        595                 600                 605

Leu His Leu Arg Asp Arg Asn Ser Arg Gln Pro Ser Asn Leu Pro Gly
    610                 615                 620

Thr Val Ala Val His Ile Leu Ser Ser Thr Ser Leu Met Ala Val
625                 630                 635

<210> SEQ ID NO 6
<211> LENGTH: 714
<212> TYPE: PRT
<213> ORGANISM: Homo sapiens

<400> SEQUENCE: 6

Met Ser Glu Glu Ile Ile Thr Pro Val Tyr Cys Thr Gly Val Ser Ala
1               5                   10                  15

Gln Val Gln Lys Gln Arg Ala Arg Glu Leu Gly Leu Gly Arg His Glu
            20                  25                  30

Asn Ala Ile Lys Tyr Leu Gly Gln Asp Tyr Glu Gln Leu Arg Val Arg
        35                  40                  45

Cys Leu Gln Ser Gly Thr Leu Phe Arg Asp Glu Ala Phe Pro Pro Val
    50                  55                  60
```

-continued

```
Pro Gln Ser Leu Gly Tyr Lys Asp Leu Gly Pro Asn Ser Ser Lys Thr
 65                  70                  75                  80

Tyr Gly Ile Lys Trp Lys Arg Pro Thr Glu Leu Leu Ser Asn Pro Gln
                 85                  90                  95

Phe Ile Val Asp Gly Ala Thr Arg Thr Asp Ile Cys Gln Gly Ala Leu
            100                 105                 110

Gly Asp Cys Trp Leu Leu Ala Ala Ile Ala Ser Leu Thr Leu Asn Asp
        115                 120                 125

Thr Leu Leu His Arg Val Val Pro His Gly Gln Ser Phe Gln Asn Gly
    130                 135                 140

Tyr Ala Gly Ile Phe His Phe Gln Leu Trp Gln Phe Gly Glu Trp Val
145                 150                 155                 160

Asp Val Val Val Asp Asp Leu Leu Pro Ile Lys Asp Gly Lys Leu Val
                165                 170                 175

Phe Val His Ser Ala Glu Gly Asn Glu Phe Trp Ser Ala Leu Leu Glu
            180                 185                 190

Lys Ala Tyr Ala Lys Val Asn Gly Ser Tyr Glu Ala Leu Ser Gly Gly
        195                 200                 205

Ser Thr Ser Glu Gly Phe Glu Asp Phe Thr Gly Gly Val Thr Glu Trp
    210                 215                 220

Tyr Glu Leu Arg Lys Ala Pro Ser Asp Leu Tyr Gln Ile Ile Leu Lys
225                 230                 235                 240

Ala Leu Glu Arg Gly Ser Leu Leu Gly Cys Ser Ile Asp Ile Ser Ser
                245                 250                 255

Val Leu Asp Met Glu Ala Ile Thr Phe Lys Lys Leu Val Lys Gly His
            260                 265                 270

Ala Tyr Ser Val Thr Gly Ala Lys Gln Val Asn Tyr Arg Gly Gln Val
        275                 280                 285

Val Ser Leu Ile Arg Met Arg Asn Pro Trp Gly Glu Val Glu Trp Thr
    290                 295                 300

Gly Ala Trp Ser Asp Ser Ser Ser Glu Trp Asn Asn Val Asp Pro Tyr
305                 310                 315                 320

Glu Arg Asp Gln Leu Arg Val Lys Met Glu Asp Gly Glu Phe Trp Met
                325                 330                 335

Ser Phe Arg Asp Phe Met Arg Glu Phe Thr Arg Leu Glu Ile Cys Asn
            340                 345                 350

Leu Thr Pro Asp Ala Leu Lys Ser Arg Thr Ile Arg Lys Trp Asn Thr
        355                 360                 365

Thr Leu Tyr Glu Gly Thr Trp Arg Arg Gly Ser Thr Ala Gly Gly Cys
    370                 375                 380

Arg Asn Tyr Pro Ala Thr Phe Trp Val Asn Pro Gln Phe Lys Ile Arg
385                 390                 395                 400

Leu Asp Glu Thr Asp Asp Pro Asp Asp Tyr Gly Asp Arg Glu Ser Gly
                405                 410                 415

Cys Ser Phe Val Leu Ala Leu Met Gln Lys His Arg Arg Arg Glu Arg
            420                 425                 430

Arg Phe Gly Arg Asp Met Glu Thr Ile Gly Phe Ala Val Tyr Glu Val
        435                 440                 445

Pro Pro Glu Leu Val Gly Gln Pro Ala Val His Leu Lys Arg Asp Phe
    450                 455                 460

Phe Leu Ala Asn Ala Ser Arg Ala Arg Ser Glu Gln Phe Ile Asn Leu
465                 470                 475                 480
```

-continued

```
Arg Glu Val Ser Thr Arg Phe Arg Leu Pro Pro Gly Glu Tyr Val Val
            485                 490                 495

Val Pro Ser Thr Phe Glu Pro Asn Lys Glu Gly Asp Phe Val Leu Arg
        500                 505                 510

Phe Phe Ser Glu Lys Ser Ala Gly Thr Val Glu Leu Asp Asp Gln Ile
    515                 520                 525

Gln Ala Asn Leu Pro Asp Glu Gln Val Leu Ser Glu Glu Ile Asp
530                 535                 540

Glu Asn Phe Lys Ala Leu Phe Arg Gln Leu Ala Gly Glu Asp Met Glu
545                 550                 555                 560

Ile Ser Val Lys Glu Leu Arg Thr Ile Leu Asn Arg Ile Ile Ser Lys
                565                 570                 575

His Lys Asp Leu Arg Thr Lys Gly Phe Ser Leu Glu Ser Cys Arg Ser
            580                 585                 590

Met Val Asn Leu Met Asp Arg Asp Gly Asn Gly Lys Leu Gly Leu Val
        595                 600                 605

Glu Phe Asn Ile Leu Trp Asn Arg Ile Arg Asn Tyr Leu Ser Ile Phe
    610                 615                 620

Arg Lys Phe Asp Leu Asp Lys Ser Gly Ser Met Ser Ala Tyr Glu Met
625                 630                 635                 640

Arg Met Ala Ile Glu Ser Ala Gly Phe Lys Leu Asn Lys Lys Leu Tyr
                645                 650                 655

Glu Leu Ile Ile Thr Arg Tyr Ser Glu Pro Asp Leu Ala Val Asp Phe
            660                 665                 670

Asp Asn Phe Val Cys Cys Leu Val Arg Leu Glu Thr Met Phe Arg Phe
        675                 680                 685

Phe Lys Thr Leu Asp Thr Asp Leu Asp Gly Val Val Thr Phe Asp Leu
    690                 695                 700

Phe Lys Trp Leu Gln Leu Thr Met Phe Ala
705                 710

<210> SEQ ID NO 7
<211> LENGTH: 821
<212> TYPE: PRT
<213> ORGANISM: Homo sapiens

<400> SEQUENCE: 7

Met Pro Thr Val Ile Ser Ala Ser Val Ala Pro Arg Thr Ala Ala Glu
1               5                   10                  15

Pro Arg Ser Pro Gly Pro Val Pro His Pro Ala Gln Ser Lys Ala Thr
            20                  25                  30

Glu Ala Gly Gly Gly Asn Pro Ser Gly Ile Tyr Ser Ala Ile Ile Ser
        35                  40                  45

Arg Asn Phe Pro Ile Ile Gly Val Lys Glu Lys Thr Phe Glu Gln Leu
    50                  55                  60

His Lys Lys Cys Leu Glu Lys Lys Val Leu Tyr Val Asp Pro Glu Phe
65                  70                  75                  80

Pro Pro Asp Glu Thr Ser Leu Phe Tyr Ser Gln Lys Phe Pro Ile Gln
                85                  90                  95

Phe Val Trp Lys Arg Pro Pro Glu Ile Cys Glu Asn Pro Arg Phe Ile
            100                 105                 110

Ile Asp Gly Ala Asn Arg Thr Asp Ile Cys Gln Gly Glu Leu Gly Asp
        115                 120                 125

Cys Trp Phe Leu Ala Ala Ile Ala Cys Leu Thr Leu Asn Gln His Leu
    130                 135                 140
```

-continued

```
Leu Phe Arg Val Ile Pro His Asp Gln Ser Phe Ile Glu Asn Tyr Ala
145                 150                 155                 160

Gly Ile Phe His Phe Gln Phe Trp Arg Tyr Gly Glu Trp Val Asp Val
            165                 170                 175

Val Ile Asp Asp Cys Leu Pro Thr Tyr Asn Asn Gln Leu Val Phe Thr
        180                 185                 190

Lys Ser Asn His Arg Asn Glu Phe Trp Ser Ala Leu Leu Glu Lys Ala
            195                 200                 205

Tyr Ala Lys Leu His Gly Ser Tyr Glu Ala Leu Lys Gly Gly Asn Thr
    210                 215                 220

Thr Glu Ala Met Glu Asp Phe Thr Gly Gly Val Ala Glu Phe Phe Glu
225                 230                 235                 240

Ile Arg Asp Ala Pro Ser Asp Met Tyr Lys Ile Met Lys Lys Ala Ile
                245                 250                 255

Glu Arg Gly Ser Leu Met Gly Cys Ser Ile Asp Asp Gly Thr Asn Met
                260                 265                 270

Thr Tyr Gly Thr Ser Pro Ser Gly Leu Asn Met Gly Glu Leu Ile Ala
    275                 280                 285

Arg Met Val Arg Asn Met Asp Asn Ser Leu Leu Gln Asp Ser Asp Leu
290                 295                 300

Asp Pro Arg Gly Ser Asp Glu Arg Pro Thr Arg Thr Ile Ile Pro Val
305                 310                 315                 320

Gln Tyr Glu Thr Arg Met Ala Cys Gly Leu Val Arg Gly His Ala Tyr
                325                 330                 335

Ser Val Thr Gly Leu Asp Glu Val Pro Phe Lys Gly Glu Lys Val Lys
                340                 345                 350

Leu Val Arg Leu Arg Asn Pro Trp Gly Gln Val Glu Trp Asn Gly Ser
                355                 360                 365

Trp Ser Asp Arg Trp Lys Asp Trp Ser Phe Val Asp Lys Asp Glu Lys
370                 375                 380

Ala Arg Leu Gln His Gln Val Thr Glu Asp Gly Glu Phe Trp Met Ser
385                 390                 395                 400

Tyr Glu Asp Phe Ile Tyr His Phe Thr Lys Leu Glu Ile Cys Asn Leu
                405                 410                 415

Thr Ala Asp Ala Leu Gln Ser Asp Lys Leu Gln Thr Trp Thr Val Ser
                420                 425                 430

Val Asn Glu Gly Arg Trp Val Arg Gly Cys Ser Ala Gly Gly Cys Arg
            435                 440                 445

Asn Phe Pro Asp Thr Phe Trp Thr Asn Pro Gln Tyr Arg Leu Lys Leu
450                 455                 460

Leu Glu Glu Asp Asp Asp Pro Asp Asp Ser Glu Val Ile Cys Ser Phe
465                 470                 475                 480

Leu Val Ala Leu Met Gln Lys Asn Arg Arg Lys Asp Arg Lys Leu Gly
                485                 490                 495

Ala Ser Leu Phe Thr Ile Gly Phe Ala Ile Tyr Glu Val Pro Lys Glu
                500                 505                 510

Met His Gly Asn Lys Gln His Leu Gln Lys Asp Phe Phe Leu Tyr Asn
                515                 520                 525

Ala Ser Lys Ala Arg Ser Lys Thr Tyr Ile Asn Met Arg Glu Val Ser
                530                 535                 540

Gln Arg Phe Arg Leu Pro Pro Ser Glu Tyr Val Ile Val Pro Ser Thr
545                 550                 555                 560
```

-continued

```
Tyr Glu Pro His Gln Glu Gly Glu Phe Ile Leu Arg Val Phe Ser Glu
                565                 570                 575

Lys Arg Asn Leu Ser Glu Glu Val Glu Asn Thr Ile Ser Val Asp Arg
            580                 585                 590

Pro Val Lys Lys Lys Thr Lys Pro Ile Ile Phe Val Ser Asp Arg
        595                 600                 605

Ala Asn Ser Asn Lys Glu Leu Gly Val Asp Gln Glu Ser Glu Glu Gly
    610                 615                 620

Lys Gly Lys Thr Ser Pro Asp Lys Gln Lys Gln Ser Pro Gln Pro Gln
625                 630                 635                 640

Pro Gly Ser Ser Asp Gln Glu Ser Glu Gln Gln Phe Arg Asn
                645                 650                 655

Ile Phe Lys Gln Ile Ala Gly Asp Asp Met Glu Ile Cys Ala Asp Glu
                660                 665                 670

Leu Lys Lys Val Leu Asn Thr Val Asn Lys His Lys Asp Leu Lys
        675                 680                 685

Thr His Gly Phe Thr Leu Glu Ser Cys Arg Ser Met Ile Ala Leu Met
    690                 695                 700

Asp Thr Asp Gly Ser Gly Lys Leu Asn Leu Gln Glu Phe His His Leu
705                 710                 715                 720

Trp Asn Lys Ile Lys Ala Trp Gln Lys Ile Phe Lys His Tyr Asp Thr
                725                 730                 735

Asp Gln Ser Gly Thr Ile Asn Ser Tyr Glu Met Arg Asn Ala Val Asn
                740                 745                 750

Asp Ala Gly Phe His Leu Asn Asn Gln Leu Tyr Asp Ile Ile Thr Met
        755                 760                 765

Arg Tyr Ala Asp Lys His Met Asn Ile Asp Phe Asp Ser Phe Ile Cys
770                 775                 780

Cys Phe Val Arg Leu Glu Gly Met Phe Arg Ala Phe His Ala Phe Asp
785                 790                 795                 800

Lys Asp Gly Asp Gly Ile Ile Lys Leu Asn Val Leu Glu Trp Leu Gln
                805                 810                 815

Leu Thr Met Tyr Ala
            820

<210> SEQ ID NO 8
<211> LENGTH: 713
<212> TYPE: PRT
<213> ORGANISM: Mus musculus

<400> SEQUENCE: 8

Met Thr Glu Glu Leu Ile Thr Pro Val Tyr Cys Thr Gly Val Ser Ala
1               5                   10                  15

Gln Val Gln Lys Lys Arg Asp Lys Glu Leu Gly Leu Gly Arg His Glu
            20                  25                  30

Asn Ala Ile Lys Tyr Leu Gly Gln Asp Tyr Glu Thr Leu Arg Ala Arg
        35                  40                  45

Cys Leu Gln Ser Gly Val Leu Phe Gln Asp Glu Ala Phe Pro Pro Val
    50                  55                  60

Ser His Ser Leu Gly Phe Lys Glu Leu Gly Pro His Ser Ser Lys Thr
65                  70                  75                  80

Tyr Gly Ile Lys Trp Lys Arg Pro Thr Glu Leu Met Ser Asn Pro Gln
                85                  90                  95

Phe Ile Val Asp Gly Ala Thr Arg Thr Asp Ile Cys Gln Gly Ala Leu
            100                 105                 110
```

-continued

```
Gly Asp Cys Trp Leu Leu Ala Ala Ile Ala Ser Leu Thr Leu Asn Glu
        115                 120                 125

Thr Ile Leu His Arg Val Val Pro Tyr Gly Gln Ser Phe Gln Asp Gly
    130                 135                 140

Tyr Ala Gly Ile Phe His Phe Gln Leu Trp Gln Phe Gly Glu Trp Val
145                 150                 155                 160

Asp Val Val Ile Asp Asp Leu Leu Pro Thr Lys Asp Gly Lys Leu Val
                165                 170                 175

Phe Val His Ser Ala Gln Gly Asn Glu Phe Trp Ser Ala Leu Leu Glu
            180                 185                 190

Lys Ala Tyr Ala Lys Val Asn Gly Ser Tyr Glu Ala Leu Ser Gly Gly
        195                 200                 205

Cys Thr Ser Glu Ala Phe Glu Asp Phe Thr Gly Gly Val Thr Glu Trp
    210                 215                 220

Tyr Asp Leu Gln Lys Ala Pro Ser Asp Leu Tyr Gln Ile Ile Leu Lys
225                 230                 235                 240

Ala Leu Glu Arg Gly Ser Leu Leu Gly Cys Ser Ile Asn Ile Ser Asp
                245                 250                 255

Ile Arg Asp Leu Glu Ala Ile Thr Phe Lys Asn Leu Val Arg Gly His
            260                 265                 270

Ala Tyr Ser Val Thr Gly Ala Lys Gln Val Thr Tyr Gln Gly Gln Arg
        275                 280                 285

Val Asn Leu Ile Arg Met Arg Asn Pro Trp Gly Glu Val Glu Trp Lys
    290                 295                 300

Gly Pro Trp Ser Asp Ser Ser Tyr Glu Trp Asn Lys Val Asp Pro Tyr
305                 310                 315                 320

Glu Arg Glu Gln Leu Arg Val Lys Met Glu Asp Gly Glu Phe Trp Met
                325                 330                 335

Ser Phe Arg Asp Phe Ile Arg Glu Phe Thr Lys Leu Glu Ile Cys Asn
            340                 345                 350

Leu Thr Pro Asp Ala Leu Lys Ser Arg Thr Leu Arg Asn Trp Asn Thr
        355                 360                 365

Thr Phe Tyr Glu Gly Thr Trp Arg Arg Gly Ser Thr Ala Gly Gly Cys
    370                 375                 380

Arg Asn Tyr Pro Ala Thr Phe Trp Val Asn Pro Gln Phe Lys Ile Arg
385                 390                 395                 400

Leu Glu Glu Val Asp Asp Ala Asp Asp Tyr Asp Asn Arg Glu Ser Gly
                405                 410                 415

Cys Ser Phe Leu Leu Ala Leu Met Gln Lys His Arg Arg Arg Glu Arg
            420                 425                 430

Arg Phe Gly Arg Asp Met Glu Thr Ile Gly Phe Ala Val Tyr Gln Val
        435                 440                 445

Pro Arg Glu Leu Ala Gly Gln Pro Val His Leu Lys Arg Asp Phe Phe
    450                 455                 460

Leu Ala Asn Ala Ser Arg Ala Gln Ser Glu His Phe Ile Asn Leu Arg
465                 470                 475                 480

Glu Val Ser Asn Arg Ile Arg Leu Pro Pro Gly Glu Tyr Ile Val Val
                485                 490                 495

Pro Ser Thr Phe Glu Pro Asn Lys Glu Gly Asp Phe Leu Leu Arg Phe
            500                 505                 510

Phe Ser Glu Lys Lys Ala Gly Thr Gln Glu Leu Asp Asp Gln Ile Gln
        515                 520                 525
```

```
Ala Asn Leu Pro Asp Glu Lys Val Leu Ser Glu Glu Ile Asp Asp
    530                 535                 540

Asn Phe Lys Thr Leu Phe Ser Lys Leu Ala Gly Asp Asp Met Glu Ile
545                 550                 555                 560

Ser Val Lys Glu Leu Gln Thr Ile Leu Asn Arg Ile Ile Ser Lys His
                565                 570                 575

Lys Asp Leu Arg Thr Asn Gly Phe Ser Leu Glu Ser Cys Arg Ser Met
            580                 585                 590

Val Asn Leu Met Asp Arg Asp Gly Asn Gly Lys Leu Gly Leu Val Glu
        595                 600                 605

Phe Asn Ile Leu Trp Asn Arg Ile Arg Asn Tyr Leu Thr Ile Phe Arg
610                 615                 620

Lys Phe Asp Leu Asp Lys Ser Gly Ser Met Ser Ala Tyr Glu Met Arg
625                 630                 635                 640

Met Ala Ile Glu Ala Ala Gly Phe Lys Leu Asn Lys Lys Leu His Glu
                645                 650                 655

Leu Ile Ile Thr Arg Tyr Ser Glu Pro Asp Leu Ala Val Asp Phe Asp
            660                 665                 670

Asn Phe Val Cys Cys Leu Val Arg Leu Glu Thr Met Phe Arg Phe Phe
        675                 680                 685

Lys Leu Leu Asp Thr Asp Leu Asp Gly Val Val Thr Phe Asp Leu Phe
690                 695                 700

Lys Trp Leu Gln Leu Thr Met Phe Ala
705                 710

<210> SEQ ID NO 9
<211> LENGTH: 709
<212> TYPE: PRT
<213> ORGANISM: Homo sapiens

<400> SEQUENCE: 9

Met Pro Tyr Leu Leu Pro Gly Phe Phe Cys Asp Arg Val Ile Arg Glu
1               5                   10                  15

Arg Asp Arg Arg Asn Gly Glu Gly Thr Val Ser Gln Pro Leu Lys Phe
            20                  25                  30

Glu Gly Gln Asp Phe Val Val Leu Lys Gln Arg Cys Leu Ala Gln Lys
        35                  40                  45

Cys Leu Phe Glu Asp Arg Val Phe Pro Ala Gly Val Gln Ala Leu Gly
    50                  55                  60

Ser His Glu Leu Ser Gln Lys Ala Lys Met Lys Ala Ile Thr Trp Lys
65                  70                  75                  80

Lys Pro Lys Glu Ile Cys Glu Asn Pro Gly Phe Ile Ile Gly Gly Ala
                85                  90                  95

Asn Arg Thr Asp Ile Cys Gln Gly Asp Leu Gly Asp Cys Trp Phe Leu
            100                 105                 110

Ala Ala Ile Ala Cys Leu Thr Leu Asn Glu Arg Leu Leu Phe Arg Val
        115                 120                 125

Ile Pro His Asp Gln Ser Phe Thr Glu Asn Tyr Ala Gly Ile Phe His
    130                 135                 140

Phe Gln Phe Trp Arg Tyr Gly Asp Trp Val Asp Val Ile Asp Asp
145                 150                 155                 160

Cys Leu Pro Thr Tyr Asn Asn Gln Leu Val Phe Thr Lys Ser Asn His
                165                 170                 175

Arg Asn Glu Phe Trp Ser Ala Leu Leu Glu Lys Ala Tyr Ala Lys Leu
            180                 185                 190
```

-continued

His Gly Ser Tyr Glu Ala Leu Lys Gly Gly Asn Thr Thr Glu Ala Met
            195                 200                 205

Glu Asp Phe Thr Gly Val Thr Glu Phe Glu Ile Lys Asp Ala
210                 215                 220

Pro Ser Asp Met Tyr Lys Ile Met Arg Lys Ala Ile Glu Arg Gly Ser
225                 230                 235                 240

Leu Met Gly Cys Ser Ile Asp Thr Ile Val Pro Val Gln Tyr Glu Thr
                245                 250                 255

Arg Met Ala Cys Gly Leu Val Lys Gly His Ala Tyr Ser Val Thr Gly
            260                 265                 270

Leu Glu Glu Ala Leu Phe Lys Gly Glu Lys Val Lys Leu Val Arg Leu
        275                 280                 285

Arg Asn Pro Trp Gly Gln Val Glu Trp Asn Gly Ser Trp Ser Asp Gly
        290                 295                 300

Trp Lys Asp Trp Ser Phe Val Asp Lys Asp Glu Lys Ala Arg Leu Gln
305                 310                 315                 320

His Gln Val Thr Glu Asp Gly Glu Phe Trp Met Ser Tyr Asp Asp Phe
                325                 330                 335

Val Tyr His Phe Thr Lys Leu Glu Ile Cys Asn Leu Thr Ala Asp Ala
            340                 345                 350

Leu Glu Ser Asp Lys Leu Gln Thr Trp Thr Val Ser Val Asn Glu Gly
        355                 360                 365

Arg Trp Val Arg Gly Cys Ser Ala Gly Gly Cys Arg Asn Phe Pro Asp
    370                 375                 380

Thr Phe Trp Thr Asn Pro Gln Tyr Arg Leu Lys Leu Leu Lys Glu Asp
385                 390                 395                 400

Asp Asp Pro Glu Asp Ser Glu Val Ile Cys Ser Phe Leu Val Ala Leu
                405                 410                 415

Met Gln Lys Asp Arg Arg Lys Asp Arg Lys Leu Gly Ala Asn Leu Phe
            420                 425                 430

Thr Ile Gly Phe Ala Ile Tyr Glu Val Pro Lys Glu Met His Gly Asn
        435                 440                 445

Lys Gln His Leu Gln Lys Asp Phe Phe Leu Tyr Asn Ala Ser Lys Ala
450                 455                 460

Arg Ser Lys Thr Tyr Ile Asn Met Arg Glu Val Ser Gln Arg Phe Arg
465                 470                 475                 480

Leu Pro Pro Ser Glu Tyr Val Ile Val Pro Ser Thr Tyr Glu Pro His
                485                 490                 495

Gln Glu Gly Glu Phe Ile Leu Arg Val Phe Ser Glu Lys Arg Asn Leu
            500                 505                 510

Ser Glu Glu Ala Glu Asn Thr Ile Ser Val Asp Arg Pro Val Pro Arg
        515                 520                 525

Pro Gly His Thr Asp Gln Glu Ser Glu Glu Gln Gln Phe Arg Asn
        530                 535                 540

Ile Phe Arg Gln Ile Ala Gly Asp Asp Met Glu Ile Cys Ala Asp Glu
545                 550                 555                 560

Leu Lys Asn Val Leu Asn Thr Val Val Asn Lys His Lys Asp Leu Lys
                565                 570                 575

Thr Gln Gly Phe Thr Leu Glu Ser Cys Arg Ser Met Ile Ala Leu Met
            580                 585                 590

Asp Thr Asp Gly Ser Gly Arg Leu Asn Leu Gln Glu Phe His His Leu
        595                 600                 605

-continued

Trp Lys Lys Ile Lys Ala Trp Gln Lys Ile Phe Lys His Tyr Asp Thr
610             615                 620

Asp His Ser Gly Thr Ile Asn Ser Tyr Glu Met Arg Asn Ala Val Asn
625                 630                 635                 640

Asp Ala Gly Phe His Leu Asn Ser Gln Leu Tyr Asp Ile Ile Thr Met
            645                 650                 655

Arg Tyr Ala Asp Lys His Met Asn Ile Asp Phe Asp Ser Phe Ile Cys
                660                 665                 670

Cys Phe Val Arg Leu Glu Gly Met Phe Arg Ala Phe Asn Ala Phe Asp
        675                 680                 685

Lys Asp Gly Asp Gly Ile Ile Lys Leu Asn Val Leu Glu Trp Leu Gln
690                 695                 700

Leu Thr Met Tyr Ala
705

<210> SEQ ID NO 10
<211> LENGTH: 647
<212> TYPE: PRT
<213> ORGANISM: Homo sapiens

<400> SEQUENCE: 10

Met Ala Ala Leu Ala Ala Gly Val Ser Lys Gln Arg Ala Val Ala Glu
1               5                   10                  15

Gly Leu Gly Ser Asn Gln Asn Ala Val Lys Tyr Leu Gly Gln Asp Phe
            20                  25                  30

Glu Thr Leu Arg Lys Gln Cys Leu Asn Ser Gly Val Leu Phe Lys Asp
        35                  40                  45

Pro Glu Phe Pro Ala Cys Pro Ser Ala Leu Gly Tyr Lys Asp Leu Gly
50                  55                  60

Pro Gly Ser Pro Asp Thr Gln Gly Ile Val Trp Lys Arg Pro Thr Glu
65                  70                  75                  80

Leu Cys Pro Asn Pro Gln Phe Ile Val Gly Ala Thr Arg Thr Asp
                85                  90                  95

Ile Arg Gln Gly Gly Leu Gly Asp Cys Trp Leu Leu Ala Ala Ile Ala
            100                 105                 110

Ser Leu Thr Leu Asn Glu Lys Leu Leu Tyr Arg Val Leu Pro Arg Asp
        115                 120                 125

Gln Ser Phe Gln Lys Asp Tyr Ala Gly Ile Phe His Phe Gln Phe Trp
130                 135                 140

Gln Tyr Gly Glu Trp Val Glu Val Ile Asp Asp Arg Leu Pro Thr
145                 150                 155                 160

Lys Asn Gly Gln Leu Leu Phe Leu His Ser Glu Glu Gly Asn Glu Phe
                165                 170                 175

Trp Ser Ala Leu Leu Glu Lys Ala Tyr Ala Lys Leu Asn Gly Ser Tyr
            180                 185                 190

Glu Ala Leu Val Gly Gly Ser Thr Ile Glu Gly Phe Glu Asp Phe Thr
        195                 200                 205

Gly Gly Ile Ser Glu Phe Tyr Asp Leu Lys Lys Pro Pro Glu Asn Leu
210                 215                 220

Tyr Tyr Ile Ile Gln Lys Ala Leu Arg Lys Gly Ser Leu Leu Gly Cys
225                 230                 235                 240

Ser Ile Asp Val Ser Thr Ala Ala Glu Ala Glu Ala Thr Thr Arg Gln
                245                 250                 255

Lys Leu Val Lys Gly His Ala Tyr Ser Val Thr Gly Val Glu Glu Val
            260                 265                 270

```
Asn Phe His Gly Arg Pro Glu Lys Leu Ile Arg Leu Arg Asn Pro Trp
            275                 280                 285

Gly Glu Val Glu Trp Ser Gly Ala Trp Ser Asp Asn Ala Pro Glu Trp
        290                 295                 300

Asn Tyr Ile Asp Pro Arg Arg Lys Glu Glu Leu Asp Lys Lys Ala Glu
305                 310                 315                 320

Asp Gly Glu Phe Trp Met Ser Phe Ser Asp Phe Leu Lys Gln Tyr Ser
            325                 330                 335

Arg Leu Glu Ile Cys Asn Leu Ser Pro Asp Ser Leu Ser Ser Glu Glu
        340                 345                 350

Ile His Lys Trp Asn Leu Val Leu Phe Asn Gly Arg Trp Thr Arg Gly
            355                 360                 365

Ser Thr Ala Gly Gly Cys Leu Asn Tyr Pro Gly Thr Tyr Trp Thr Asn
        370                 375                 380

Pro Gln Phe Lys Ile His Leu Asp Glu Val Asp Glu Asp Gln Glu Glu
385                 390                 395                 400

Gly Thr Ser Glu Pro Cys Cys Thr Val Leu Leu Gly Leu Met Gln Lys
            405                 410                 415

Asn Arg Arg Arg Gln Lys Arg Ile Gly Gln Gly Met Leu Ala Ile Gly
        420                 425                 430

Phe Asp Ile Tyr Lys Val Glu Glu Asn Arg Gln Tyr Arg Met His Ser
            435                 440                 445

Leu Gln His Lys Ala Ala Ser Ser Ile Tyr Ile Asn Ser Arg Ser Val
        450                 455                 460

Phe Leu Arg Thr Asp Gln Pro Glu Gly Arg Tyr Val Ile Ile Pro Thr
465                 470                 475                 480

Thr Phe Glu Pro Gly His Thr Gly Glu Phe Leu Leu Arg Val Phe Thr
            485                 490                 495

Asp Val Pro Ser Asn Cys Arg Glu Leu Arg Leu Asp Lys Pro Pro His
        500                 505                 510

Thr Cys Trp Ser Ser Leu Cys Gly Tyr Pro Gln Leu Val Thr Gln Val
            515                 520                 525

His Val Leu Gly Ala Ala Gly Leu Lys Asp Ser Pro Thr Gly Ala Asn
        530                 535                 540

Ser Tyr Val Ile Ile Lys Cys Glu Gly Asp Lys Val Arg Ser Ala Val
545                 550                 555                 560

Gln Lys Gly Thr Ser Thr Pro Glu Tyr Asn Val Lys Gly Ile Phe Tyr
            565                 570                 575

Arg Lys Lys Leu Ser Gln Pro Ile Thr Val Gln Val Trp Asn His Arg
        580                 585                 590

Val Leu Lys Asp Glu Phe Leu Gly Gln Val His Leu Lys Ala Asp Pro
            595                 600                 605

Asp Asn Leu Gln Ala Leu His Thr Leu His Leu Arg Asp Arg Asn Ser
        610                 615                 620

Arg Gln Pro Ser Asn Leu Pro Gly Thr Val Ala Val His Ile Leu Ser
625                 630                 635                 640

Ser Thr Ser Leu Met Ala Val
            645

<210> SEQ ID NO 11
<211> LENGTH: 702
<212> TYPE: PRT
<213> ORGANISM: Homo sapiens
```

```
<400> SEQUENCE: 11

Met Val Ala His Ile Asn Asn Ser Arg Leu Lys Ala Lys Gly Val Gly
  1               5                  10                  15

Gln His Asp Asn Ala Gln Asn Phe Gly Asn Gln Ser Phe Glu Glu Leu
             20                  25                  30

Arg Ala Ala Cys Leu Arg Lys Gly Glu Leu Phe Glu Asp Pro Leu Phe
         35                  40                  45

Pro Ala Glu Pro Ser Ser Leu Gly Phe Lys Asp Leu Gly Pro Asn Ser
 50                  55                  60

Lys Asn Val Gln Asn Ile Ser Trp Gln Arg Pro Lys Asp Ile Ile Asn
 65                  70                  75                  80

Asn Pro Leu Phe Ile Met Asp Gly Ile Ser Pro Thr Asp Ile Cys Gln
                 85                  90                  95

Gly Ile Leu Gly Asp Cys Trp Leu Leu Ala Ala Ile Gly Ser Leu Thr
                100                 105                 110

Thr Cys Pro Lys Leu Leu Tyr Arg Val Pro Arg Gly Gln Ser Phe
                115                 120                 125

Lys Lys Asn Tyr Ala Gly Ile Phe His Phe Gln Ile Trp Gln Phe Gly
130                 135                 140

Gln Trp Val Asn Val Val Asp Asp Arg Leu Pro Thr Lys Asn Asp
145                 150                 155                 160

Lys Leu Val Phe Val His Ser Thr Glu Arg Ser Glu Phe Trp Ser Ala
                165                 170                 175

Leu Leu Glu Lys Ala Tyr Ala Lys Leu Ser Gly Ser Tyr Glu Ala Leu
                180                 185                 190

Ser Gly Gly Ser Thr Met Glu Gly Leu Glu Asp Phe Thr Gly Val
                195                 200                 205

Ala Gln Ser Phe Gln Leu Gln Arg Pro Pro Gln Asn Leu Leu Arg Leu
            210                 215                 220

Leu Arg Lys Ala Val Glu Arg Ser Ser Leu Met Gly Cys Ser Ile Glu
225                 230                 235                 240

Val Thr Ser Asp Ser Glu Leu Glu Ser Met Thr Asp Lys Met Leu Val
                245                 250                 255

Arg Gly His Ala Tyr Ser Val Thr Gly Leu Gln Asp Val His Tyr Arg
                260                 265                 270

Gly Lys Met Glu Thr Leu Ile Arg Val Arg Asn Pro Trp Gly Arg Ile
                275                 280                 285

Glu Trp Asn Gly Ala Trp Ser Asp Ser Ala Arg Glu Trp Glu Val
            290                 295                 300

Ala Ser Asp Ile Gln Met Gln Leu Leu His Lys Thr Glu Asp Gly Glu
305                 310                 315                 320

Phe Trp Met Ser Tyr Gln Asp Phe Leu Asn Asn Phe Thr Leu Leu Glu
                325                 330                 335

Ile Cys Asn Leu Thr Pro Asp Thr Leu Ser Gly Asp Tyr Lys Ser Tyr
                340                 345                 350

Trp His Thr Thr Phe Tyr Glu Gly Ser Trp Arg Arg Gly Ser Ser Ala
            355                 360                 365

Gly Gly Cys Arg Asn His Pro Gly Thr Phe Trp Thr Asn Pro Gln Phe
370                 375                 380

Lys Ile Ser Leu Pro Glu Gly Asp Pro Glu Asp Ala Glu Gly
385                 390                 395                 400

Asn Val Val Cys Thr Cys Leu Val Ala Leu Met Gln Lys Asn Trp
                405                 410                 415
```

```
Arg His Ala Arg Gln Gln Gly Ala Gln Leu Gln Thr Ile Gly Phe Val
            420                 425                 430

Leu Tyr Ala Val Pro Lys Glu Phe Gln Asn Ile Gln Asp Val His Leu
        435                 440                 445

Lys Lys Glu Phe Phe Thr Lys Tyr Gln Asp His Gly Phe Ser Glu Ile
450                 455                 460

Phe Thr Asn Ser Arg Glu Val Ser Ser Gln Leu Arg Leu Pro Pro Gly
465                 470                 475                 480

Glu Tyr Ile Ile Ile Pro Ser Thr Phe Glu Pro His Arg Asp Ala Asp
                485                 490                 495

Phe Leu Leu Arg Val Phe Thr Glu Lys His Ser Glu Ser Trp Glu Leu
            500                 505                 510

Asp Glu Val Asn Tyr Ala Glu Gln Leu Gln Glu Lys Val Ser Glu
        515                 520                 525

Asp Asp Met Asp Gln Asp Phe Leu His Leu Phe Lys Ile Val Ala Gly
530                 535                 540

Glu Gly Lys Glu Ile Gly Val Tyr Glu Leu Gln Arg Leu Leu Asn Arg
545                 550                 555                 560

Met Ala Ile Lys Phe Lys Ser Phe Lys Thr Lys Gly Phe Gly Leu Asp
                565                 570                 575

Ala Cys Arg Cys Met Ile Asn Leu Met Asp Lys Asp Gly Ser Gly Lys
            580                 585                 590

Leu Gly Leu Leu Glu Phe Lys Ile Leu Trp Lys Lys Leu Lys Lys Trp
        595                 600                 605

Met Asp Ile Phe Arg Glu Cys Asp Gln Asp His Ser Gly Thr Leu Asn
610                 615                 620

Ser Tyr Glu Met Arg Leu Val Ile Glu Lys Ala Gly Ile Lys Leu Asn
625                 630                 635                 640

Asn Lys Val Met Gln Val Leu Val Ala Arg Tyr Ala Asp Asp Asp Leu
                645                 650                 655

Ile Ile Asp Phe Asp Ser Phe Ile Ser Cys Phe Leu Arg Leu Lys Thr
            660                 665                 670

Met Phe Thr Phe Phe Leu Thr Met Asp Pro Lys Asn Thr Gly His Ile
        675                 680                 685

Cys Leu Ser Leu Glu Gln Trp Leu Gln Met Thr Met Trp Gly
690                 695                 700

<210> SEQ ID NO 12
<211> LENGTH: 700
<212> TYPE: PRT
<213> ORGANISM: Homo sapiens

<400> SEQUENCE: 12

Met Ala Gly Ile Ala Ala Lys Leu Ala Lys Asp Arg Glu Ala Ala Glu
1               5                   10                  15

Gly Leu Gly Ser His Glu Arg Ala Ile Lys Tyr Leu Asn Gln Asp Tyr
                20                  25                  30

Glu Ala Leu Arg Asn Glu Cys Leu Glu Ala Gly Thr Leu Phe Gln Asp
            35                  40                  45

Pro Ser Phe Pro Ala Ile Pro Ser Ala Leu Gly Phe Lys Glu Leu Gly
        50                  55                  60

Pro Tyr Ser Ser Lys Thr Arg Gly Met Arg Trp Lys Arg Pro Thr Glu
65                  70                  75                  80

Ile Cys Ala Asp Pro Gln Phe Ile Ile Gly Gly Ala Thr Arg Thr Asp
                85                  90                  95
```

```
Ile Cys Gln Gly Ala Leu Gly Asp Cys Trp Leu Leu Ala Ala Ile Ala
            100                 105                 110

Ser Leu Thr Leu Asn Glu Glu Ile Leu Ala Arg Val Val Pro Leu Asn
        115                 120                 125

Gln Ser Phe Gln Glu Asn Tyr Ala Gly Ile Phe His Phe Gln Phe Trp
    130                 135                 140

Gln Tyr Gly Glu Trp Val Glu Val Val Asp Asp Arg Leu Pro Thr
145                 150                 155                 160

Lys Asp Gly Glu Leu Leu Phe Val His Ser Ala Glu Gly Ser Glu Phe
                165                 170                 175

Trp Ser Ala Leu Leu Glu Lys Ala Tyr Ala Lys Ile Asn Gly Cys Tyr
            180                 185                 190

Glu Ala Leu Ser Gly Gly Ala Thr Glu Gly Phe Glu Asp Phe Thr
        195                 200                 205

Gly Gly Ile Ala Glu Trp Tyr Glu Leu Lys Lys Pro Pro Asn Leu
210                 215                 220

Phe Lys Ile Ile Gln Lys Ala Leu Gln Lys Gly Ser Leu Leu Gly Cys
225                 230                 235                 240

Ser Ile Asp Ile Thr Ser Ala Ala Asp Ser Glu Ala Ile Thr Phe Gln
            245                 250                 255

Lys Leu Val Lys Gly His Ala Tyr Ser Val Thr Gly Ala Glu Glu Val
        260                 265                 270

Glu Ser Asn Gly Ser Leu Gln Lys Leu Ile Arg Ile Arg Asn Pro Trp
    275                 280                 285

Gly Glu Val Glu Trp Thr Gly Arg Trp Asn Asp Asn Cys Pro Ser Trp
290                 295                 300

Asn Thr Ile Asp Pro Glu Glu Arg Glu Arg Leu Thr Arg Arg His Glu
305                 310                 315                 320

Asp Gly Glu Phe Trp Met Ser Phe Ser Asp Phe Leu Arg His Tyr Ser
            325                 330                 335

Arg Leu Glu Ile Cys Asn Leu Thr Pro Asp Thr Leu Thr Ser Asp Thr
        340                 345                 350

Tyr Lys Lys Trp Lys Leu Thr Lys Met Asp Gly Asn Trp Arg Arg Gly
    355                 360                 365

Ser Thr Ala Gly Gly Cys Arg Asn Tyr Pro Asn Thr Phe Trp Met Asn
370                 375                 380

Pro Gln Tyr Leu Ile Lys Leu Glu Glu Glu Asp Glu Asp Glu Glu Asp
385                 390                 395                 400

Gly Glu Ser Gly Cys Thr Phe Leu Val Gly Leu Ile Gln Lys His Arg
            405                 410                 415

Arg Arg Gln Arg Lys Met Gly Glu Asp Met His Thr Ile Gly Phe Gly
        420                 425                 430

Ile Tyr Glu Val Pro Glu Glu Leu Ser Gly Gln Thr Asn Ile His Leu
    435                 440                 445

Ser Lys Asn Phe Phe Leu Thr Asn Arg Ala Arg Glu Arg Ser Asp Thr
450                 455                 460

Phe Ile Asn Leu Arg Glu Val Leu Asn Arg Phe Lys Leu Pro Pro Gly
465                 470                 475                 480

Glu Tyr Ile Leu Val Pro Ser Thr Phe Glu Pro Asn Lys Asp Gly Asp
            485                 490                 495

Phe Cys Ile Arg Val Phe Ser Glu Lys Lys Ala Asp Tyr Gln Ala Val
        500                 505                 510
```

-continued

```
Asp Asp Glu Ile Glu Ala Asn Leu Glu Glu Phe Asp Ile Ser Glu Asp
        515                 520                 525
Asp Ile Asp Asp Gly Val Arg Arg Leu Phe Ala Gln Leu Ala Gly Glu
    530                 535                 540
Asp Ala Glu Ile Ser Ala Phe Glu Leu Gln Thr Ile Leu Arg Arg Val
545                 550                 555                 560
Leu Ala Lys Arg Gln Asp Ile Lys Ser Asp Gly Phe Ser Ile Glu Thr
                565                 570                 575
Cys Lys Ile Met Val Asp Met Leu Asp Ser Asp Gly Ser Gly Lys Leu
            580                 585                 590
Gly Leu Lys Glu Phe Tyr Ile Leu Trp Thr Lys Ile Gln Lys Tyr Gln
        595                 600                 605
Lys Ile Tyr Arg Glu Ile Asp Val Asp Arg Ser Gly Thr Met Asn Ser
    610                 615                 620
Tyr Glu Met Arg Lys Ala Leu Glu Glu Ala Gly Phe Lys Met Pro Cys
625                 630                 635                 640
Gln Leu His Gln Val Ile Val Ala Arg Phe Ala Asp Asp Gln Leu Ile
                645                 650                 655
Ile Asp Phe Asp Asn Phe Val Arg Cys Leu Val Arg Leu Glu Thr Leu
            660                 665                 670
Phe Lys Ile Phe Lys Gln Leu Asp Pro Glu Asn Thr Gly Thr Ile Glu
        675                 680                 685
Leu Asp Leu Ile Ser Trp Leu Cys Phe Ser Val Leu
    690                 695                 700

<210> SEQ ID NO 13
<211> LENGTH: 690
<212> TYPE: PRT
<213> ORGANISM: Homo sapiens

<400> SEQUENCE: 13

Met Pro Tyr Leu Tyr Arg Ala Pro Gly Pro Gln Ala His Pro Val Pro
1               5                   10                  15
Lys Asp Ala Arg Ile Thr His Ser Ser Gly Gln Ser Phe Glu Gln Met
            20                  25                  30
Arg Gln Glu Cys Leu Gln Arg Gly Thr Leu Phe Glu Asp Ala Asp Phe
        35                  40                  45
Pro Ala Ser Asn Ser Ser Leu Phe Tyr Ser Glu Arg Pro Gln Ile Pro
    50                  55                  60
Phe Val Trp Lys Arg Pro Gly Glu Ile Val Lys Asn Pro Glu Phe Ile
65                  70                  75                  80
Leu Gly Gly Ala Thr Arg Thr Asp Ile Cys Gln Gly Glu Leu Gly Asp
                85                  90                  95
Cys Trp Leu Leu Ala Ala Ile Ala Ser Leu Thr Leu Asn Gln Lys Ala
            100                 105                 110
Leu Ala Arg Val Ile Pro Gln Asp Gln Ser Phe Gly Pro Gly Tyr Ala
        115                 120                 125
Gly Ile Phe His Phe Gln Phe Trp Gln His Ser Glu Trp Leu Asp Val
    130                 135                 140
Val Ile Asp Asp Arg Leu Pro Thr Phe Arg Asp Arg Leu Val Phe Leu
145                 150                 155                 160
His Ser Ala Asp His Asn Glu Phe Trp Ser Ala Leu Leu Glu Lys Ala
                165                 170                 175
Tyr Ala Lys Leu Asn Gly Ser Tyr Glu Ala Leu Lys Gly Gly Ser Ala
            180                 185                 190
```

```
Ile Glu Ala Met Glu Asp Phe Thr Gly Gly Val Ala Glu Thr Phe Gln
            195                 200                 205

Thr Lys Glu Ala Pro Glu Asn Phe Tyr Glu Ile Leu Glu Lys Ala Leu
        210                 215                 220

Lys Arg Gly Ser Leu Leu Gly Cys Phe Ile Asp Thr Arg Ser Ala Ala
225                 230                 235                 240

Glu Ser Glu Ala Arg Thr Pro Phe Gly Leu Ile Lys Gly His Ala Tyr
                245                 250                 255

Ser Val Thr Gly Ile Asp Gln Val Ser Phe Arg Gly Gln Arg Ile Glu
            260                 265                 270

Leu Ile Arg Ile Arg Asn Pro Trp Gly Gln Val Glu Trp Asn Gly Ser
        275                 280                 285

Trp Ser Asp Ser Ser Pro Glu Trp Arg Ser Val Gly Pro Ala Glu Gln
        290                 295                 300

Lys Arg Leu Cys His Thr Ala Leu Asp Asp Gly Glu Phe Trp Met Ala
305                 310                 315                 320

Phe Lys Asp Phe Lys Ala His Phe Asp Lys Val Glu Ile Cys Asn Leu
                325                 330                 335

Thr Pro Asp Ala Leu Glu Glu Asp Ala Ile His Lys Trp Glu Val Thr
            340                 345                 350

Val His Gln Gly Ser Trp Val Arg Gly Ser Thr Ala Gly Gly Cys Arg
        355                 360                 365

Asn Phe Leu Asp Thr Phe Trp Thr Asn Pro Gln Ile Lys Leu Ser Leu
        370                 375                 380

Thr Glu Lys Asp Glu Gly Gln Glu Glu Cys Ser Phe Leu Val Ala Leu
385                 390                 395                 400

Met Gln Lys Asp Arg Arg Lys Leu Lys Arg Phe Gly Ala Asn Val Leu
                405                 410                 415

Thr Ile Gly Tyr Ala Ile Tyr Glu Cys Pro Asp Lys Asp Glu His Leu
            420                 425                 430

Asn Lys Asp Phe Phe Arg Tyr His Ala Ser Arg Ala Arg Ser Lys Thr
        435                 440                 445

Phe Ile Asn Leu Arg Glu Val Ser Asp Arg Phe Lys Leu Pro Pro Gly
450                 455                 460

Glu Tyr Ile Leu Ile Pro Ser Thr Phe Glu Pro His Gln Glu Ala Asp
465                 470                 475                 480

Phe Cys Leu Arg Ile Phe Ser Glu Lys Lys Ala Ile Thr Arg Asp Met
                485                 490                 495

Asp Gly Asn Val Asp Ile Asp Leu Pro Glu Pro Lys Pro Thr Pro
            500                 505                 510

Pro Asp Gln Glu Thr Glu Glu Gln Arg Phe Arg Ala Leu Phe Glu
        515                 520                 525

Gln Val Ala Gly Glu Asp Met Glu Val Thr Ala Glu Glu Leu Glu Tyr
        530                 535                 540

Val Leu Asn Ala Val Leu Gln Lys Lys Asp Ile Lys Phe Lys
545                 550                 555                 560

Leu Ser Leu Ile Ser Cys Lys Asn Ile Ile Ser Leu Met Asp Thr Ser
                565                 570                 575

Gly Asn Gly Lys Leu Glu Phe Asp Glu Phe Lys Val Phe Trp Asp Lys
            580                 585                 590

Leu Lys Gln Trp Ile Asn Leu Phe Leu Arg Phe Asp Ala Asp Lys Ser
        595                 600                 605
```

```
Gly Thr Met Ser Thr Tyr Glu Leu Arg Thr Ala Leu Lys Ala Ala Gly
    610                 615                 620

Phe Gln Leu Ser Ser His Leu Leu Gln Leu Ile Val Leu Arg Tyr Ala
625                 630                 635                 640

Asp Glu Glu Leu Gln Leu Asp Phe Asp Asp Phe Leu Asn Cys Leu Val
                645                 650                 655

Arg Leu Glu Asn Ala Ser Arg Val Phe Gln Ala Leu Ser Thr Lys Asn
            660                 665                 670

Lys Glu Phe Ile His Leu Asn Ile Asn Glu Phe Ile His Leu Thr Met
        675                 680                 685

Asn Ile
    690

<210> SEQ ID NO 14
<211> LENGTH: 792
<212> TYPE: DNA
<213> ORGANISM: Homo sapiens

<400> SEQUENCE: 14
caggactttg aggccctgct ggcagagtgc ctgaggaatg ctgcctcttt tgaagacacc      60
agcttcccgg ccaccctgag ctccatcggc agtggctccc tgctgcagaa gctgccaccc     120
cgcctgcagt ggaagaggcc cccggagctg cacagcaatc cccagttttt ttttgccaag     180
gccaaaaggc tggatctgtg ccaggggata gtaggagact gctggttctt ggctgctttg     240
caagctctgg ccttgcacca ggacatcctg agccgggttg ttcccctgaa tcagagtttc     300
actgagaagt atgctggcat cttccggttc tggttctggc actatgggaa ctgggttcct     360
gtggtgatcg atgaccgtct gcctgtgaat gaggctggcc agctggtctt tgtctcctcc     420
acctataaga acttgttctg gggagcactt ctggaaaagg cctatgccaa gctctctggt     480
tcctatgaag acttgcagtc aggacaggtg tctgaagccc ttgtagactt cactggaggg     540
gtgacaatga ccatcaacct ggcagaagcc catggcaacc tctgggacat cctcatcgaa     600
gccacctaca acagaaccct cattggctgc cagaccccact cagggagaa gattctggag     660 aatgggctgg tggaaggcca tgcctatact ctcacaggaa tcaggaaggt gacctgcaaa     720
catagacctg aatatctcgt caagctacgg aacccctggg aaaggtggaa atggaaagga     780
gactggagtg ac                                                          792

<210> SEQ ID NO 15
<211> LENGTH: 543
<212> TYPE: DNA
<213> ORGANISM: Homo sapiens

<400> SEQUENCE: 15
atgacgctgc aggactttaa aacacatttc gtgctcctgg ttatctgtaa actgaccccca     60 ggcctgttga gccaggaggc ggcccagaag tggacgtaca ccatgcggga ggggagatgg     120
gagaagcgga gcacagctgg tggccagagg cagttgctgc aggacacatt ttggaagaac     180
ccgcagttcc tgctgtctgt ctggaggccc gaggagggca ggagatccct gaggccctgc     240
agcgtgctgg tgtccctgct ccagaagccc aggcacaggt gccgcaagcg aagcctctc      300 ctcgccattg gcttctacct gtatagggta gccataaaat ggaaggcaca gggacattcc     360
tcacatcatt tagtgctggt gttgtttttta agaaacactc ctctgagcca gcctgatagg     420
tttctcaagg agaaagaagt gagtcaggag ctgtgtctgg aaccagggac gtacctcatc     480
```

```
gtgccctgca tattggaggc ccaccagaag tcagagttcg tcctcagggt cttctccagg      540
aag                                                                    543

<210> SEQ ID NO 16
<211> LENGTH: 66
<212> TYPE: DNA
<213> ORGANISM: Homo sapiens

<400> SEQUENCE: 16
aaatgggaac tctttagaat agatggatcc ttgaggcaca caagtactca aatgtcagca       60
aggaat                                                                  66

<210> SEQ ID NO 17
<211> LENGTH: 51
<212> TYPE: DNA
<213> ORGANISM: Homo sapiens

<400> SEQUENCE: 17
ttccaatacc atacccatcc tgaatggctc cagctggtgg tcatagataa a                51

<210> SEQ ID NO 18
<211> LENGTH: 39
<212> TYPE: DNA
<213> ORGANISM: Homo sapiens

<400> SEQUENCE: 18
gagtggttcc ttctgaaagc tccaaggaag aacctattt                              39

<210> SEQ ID NO 19
<211> LENGTH: 77
<212> TYPE: DNA
<213> ORGANISM: Homo sapiens

<400> SEQUENCE: 19
agggagccac tgccgatgga gctcagggtg gccgggaagc tggtgtcttc aaagaggcag       60
ccattcctca ggcactc                                                     77

<210> SEQ ID NO 20
<211> LENGTH: 18
<212> TYPE: DNA
<213> ORGANISM: Homo sapiens

<400> SEQUENCE: 20
gactttgagg ccctgctg                                                    18

<210> SEQ ID NO 21
<211> LENGTH: 20
<212> TYPE: DNA
<213> ORGANISM: Homo sapiens

<400> SEQUENCE: 21
acaggaaccc agttcccata                                                  20

<210> SEQ ID NO 22
<211> LENGTH: 19
<212> TYPE: DNA
<213> ORGANISM: Homo sapiens

<400> SEQUENCE: 22
cacctgccat gtctctgtg                                                   19
```

<210> SEQ ID NO 23
<211> LENGTH: 25
<212> TYPE: DNA
<213> ORGANISM: Homo sapiens

<400> SEQUENCE: 23
gattataaca aggtggtgtt gaaga                                          25

<210> SEQ ID NO 24
<211> LENGTH: 1287
<212> TYPE: DNA
<213> ORGANISM: Homo sapiens

<400> SEQUENCE: 24
atgtctctgt ggccaccttt ccgatgcaga tggaagctgg cgccaaggta ctctaggagg    60
gcgtctccac agcaacccca acaggacttt gaggccctgc tggcagagtg cctgaggaat   120
ggctgcctct ttgaagacac cagcttcccg gccaccctga gctccatcgg cagtggctcc   180
ctgctgcaga agctgccacc ccgcctgcag tggaagaggc cccggagct gcacagcaat    240
ccccagtttt attttgccaa ggccaaaagg ctggatctgt gccaggggat agtaggagac   300
tgctggttct tggctgcttt gcaagctctg gccttgcacc aggacatcct gagccgggtt   360
gttcccctga atcagagttt cactgagaag tatgctggca tcttccggtt ctggttctgg   420
cactatggga actgggttcc tgtggtgatc gatgaccgtc tgcctgtgaa tgaggctggc   480
cagctggtct ttgtctcctc cacctataag aacttgttct ggggagcact tctggaaaag   540
gcctatgcca agctctctgg ttcctatgaa gacttgcagt caggacaggt gtctgaagcc   600
cttgtagact tcactggagg ggtgacaatg accatcaacc tggcagaagc ccatggcaac   660
ctctgggaca tcctcatcga agccacctac aacagaaccc tcattggctg ccagacccac   720
tcagggaaga ttctggagaa tgggctggtg aaggccatg cctatactct cacaggaatc    780
aggaaggtga cctgcaaaca tagacctgaa tatctcgtca agctacgaaa cccctgggga   840
aaggtggaat ggaaaggaga ctggagtgac agttcaagta atgggagct gctgagcccc    900
aaggagaaga ttctgcttct gaggaaagac aatgacggag aattctggat gacgctgcag   960
gactttaaaa cacatttcgt gctcctggtt atctgtaaac tgaccccagg cctgttgagc  1020
caggaggcgg cccagaagtg gacgtacacc atgcgggagg ggagatggga gaagcggagc  1080
acagctggtg gccagaggca gttgctgcag gacacatttt ggaagaaccc gcagttcctg  1140
ctgtctgtct ggaggcccga ggagggcagg agatccctga ggccctgcag cgtgctggtg  1200
tccctgctcc agaagcccag gcacaggtgc cgcaagcgga agcctctcct cgccattggc  1260
ttctacctct ataggatgaa caagtga                                       1287

<210> SEQ ID NO 25
<211> LENGTH: 428
<212> TYPE: PRT
<213> ORGANISM: Homo sapiens

<400> SEQUENCE: 25

Met Ser Leu Trp Pro Pro Phe Arg Cys Arg Trp Lys Leu Ala Pro Arg
1               5                   10                  15

Tyr Ser Arg Arg Ala Ser Pro Gln Gln Pro Gln Gln Asp Phe Glu Ala
            20                  25                  30

Leu Leu Ala Glu Cys Leu Arg Asn Gly Cys Leu Phe Glu Asp Thr Ser
        35                  40                  45

```
Phe Pro Ala Thr Leu Ser Ser Ile Gly Ser Gly Ser Leu Leu Gln Lys
     50                  55                  60

Leu Pro Pro Arg Leu Gln Trp Lys Arg Pro Pro Glu Leu His Ser Asn
 65                  70                  75                  80

Pro Gln Phe Tyr Phe Ala Lys Ala Lys Arg Leu Asp Leu Cys Gln Gly
                 85                  90                  95

Ile Val Gly Asp Cys Trp Phe Leu Ala Ala Leu Gln Ala Leu Ala Leu
            100                 105                 110

His Gln Asp Ile Leu Ser Arg Val Val Pro Leu Asn Gln Ser Phe Thr
        115                 120                 125

Glu Lys Tyr Ala Gly Ile Phe Arg Phe Trp Phe Trp His Tyr Gly Asn
    130                 135                 140

Trp Val Pro Val Val Ile Asp Asp Arg Leu Pro Val Asn Glu Ala Gly
145                 150                 155                 160

Gln Leu Val Phe Val Ser Ser Thr Tyr Lys Asn Leu Phe Trp Gly Ala
                165                 170                 175

Leu Leu Glu Lys Ala Tyr Ala Lys Leu Ser Gly Ser Tyr Glu Asp Leu
            180                 185                 190

Gln Ser Gly Gln Val Ser Glu Ala Leu Val Asp Phe Thr Gly Gly Val
        195                 200                 205

Thr Met Thr Ile Asn Leu Ala Glu Ala His Gly Asn Leu Trp Asp Ile
    210                 215                 220

Leu Ile Glu Ala Thr Tyr Asn Arg Thr Leu Ile Gly Cys Gln Thr His
225                 230                 235                 240

Ser Gly Lys Ile Leu Glu Asn Gly Leu Val Glu Gly His Ala Tyr Thr
                245                 250                 255

Leu Thr Gly Ile Arg Lys Val Thr Cys Lys His Arg Pro Glu Tyr Leu
            260                 265                 270

Val Lys Leu Arg Asn Pro Trp Gly Lys Val Glu Trp Lys Gly Asp Trp
        275                 280                 285

Ser Asp Ser Ser Lys Trp Glu Leu Leu Ser Pro Lys Glu Lys Ile
    290                 295                 300

Leu Leu Leu Arg Lys Asp Asn Asp Gly Glu Phe Trp Met Thr Leu Gln
305                 310                 315                 320

Asp Phe Lys Thr His Phe Val Leu Leu Val Ile Cys Lys Leu Thr Pro
                325                 330                 335

Gly Leu Leu Ser Gln Glu Ala Ala Gln Lys Trp Thr Tyr Thr Met Arg
            340                 345                 350

Glu Gly Arg Trp Glu Lys Arg Ser Thr Ala Gly Gly Gln Arg Gln Leu
        355                 360                 365

Leu Gln Asp Thr Phe Trp Lys Asn Pro Gln Phe Leu Leu Ser Val Trp
    370                 375                 380

Arg Pro Glu Glu Gly Arg Arg Ser Leu Arg Pro Cys Ser Val Leu Val
385                 390                 395                 400

Ser Leu Leu Gln Lys Pro Arg His Arg Cys Arg Lys Arg Lys Pro Leu
                405                 410                 415

Leu Ala Ile Gly Phe Tyr Leu Tyr Arg Met Asn Lys
            420                 425

<210> SEQ ID NO 26
<211> LENGTH: 153
<212> TYPE: PRT
<213> ORGANISM: Homo sapiens
```

<400> SEQUENCE: 26

Met Thr Trp Ser Ser Leu Gly Ser Arg Gln Pro Phe Phe Ser Leu Glu
1               5                   10                  15

Ala Cys Gln Gly Ile Leu Ala Leu Leu Asp Leu Asn Ala Ser Gly Thr
            20                  25                  30

Met Ser Ile Gln Glu Phe Arg Asp Leu Trp Lys Gln Leu Lys Leu Ser
        35                  40                  45

Gln Lys Val Phe His Lys Gln Asp Arg Gly Ser Gly Tyr Leu Asn Trp
    50                  55                  60

Glu Gln Leu His Ala Ala Met Arg Glu Ala Gly Arg His Arg Lys Ser
65                  70                  75                  80

Trp Ser Cys Gly His Thr Arg Ala Gly Cys Thr Leu Ile Arg Gln Arg
                85                  90                  95

Arg Gly Asp Val Trp His Ala Glu Val Thr Leu Ile Arg Ser Val Thr
            100                 105                 110

Leu Lys Asp Val Asp Leu Gln Ser Thr Pro Thr Phe Phe Met Ile Val
            115                 120                 125

Pro Val Ile Leu Ala Asn Ile Asp Gly Gly Val Ala His Ser Thr Ser
130                 135                 140

Tyr Leu Ile Phe Asn Thr Thr Leu Leu
145                 150

<210> SEQ ID NO 27
<211> LENGTH: 1203
<212> TYPE: DNA
<213> ORGANISM: Homo sapiens

<400> SEQUENCE: 27
caggactttg aggccctgct ggcagagtgc ctgaggaatg gctgcctctt tgaagacacc      60
agcttcccgg ccaccctgag ctccatcggc agtggctccc tgctgcagaa gctgccaccc    120
cgcctgcagt ggaagaggcc cccggagctg cacagcaatc cccagtttta ttttgccaag    180
gccaaaaggc tggatctgtg ccaggggata gtaggagact gctggttctt ggctgctttg    240
caagctctgg ccttgcacca ggacatcctg agccgggttg ttcccctgaa tcagagtttc    300
actgagaagt atgctggcat cttccggttc tggttctggc actatgggaa ctgggttcct    360
gtggtgatcg atgaccgtct gcctgtgaat gaggctggcc agctggtctt tgtctcctcc    420
acctataaga acttgttctg gggagcactt ctggaaaagg cctatgccaa gctctctggt    480
tcctatgaag acttgcagtc aggacaggtg tctgaagccc ttgtagactt cactggaggg    540
gtgacaatga ccatcaacct ggcagaagcc catggcaacc tctgggacat cctcatcgaa    600
gccacctaca cagaaccct cattggctgc agacccact cagggaagat tctggagaat    660
gggctggtgg aaggccatgc ctatactctc acaggaatca ggaaggtgac ctgcaaacat    720
agacctgaat atctcgtcaa gctacggaac ccctggggaa agtggaatg aaaggagac    780 tggagtgaca gttcaagtaa atgggagctg ctgagcccca aggagaagat tctgcttctg    840
aggaaagaca atgacggaga attctggatg acgctgcagg actttaaaac acatttcgtg    900
ctcctggtta tctgtaaact gaccccaggc ctgttgagcc aggaggcggc ccagaagtgg    960
acgtacacca tgcgggaggg gagatgggag aagcggagca cagctggtgg ccagaggcag   1020
ttgctgcagg acacattttg gaagaacccg cagttcctgc tgtctgtctg gagggccgag   1080
gagggcagga gatccctgag gccctgcagc gtgctggtgt ccctgctcca gaagcccagg   1140

```
cacaggtgcc gcaagcggaa gcctctcctc gccattggct tctacctcta taggatgaac   1200
aag                                                                 1203
```

<210> SEQ ID NO 28
<211> LENGTH: 13
<212> TYPE: PRT
<213> ORGANISM: Homo sapiens

<400> SEQUENCE: 28

```
Leu Ala Pro Arg Tyr Ser Arg Arg Ala Ser Pro Gln Gln
1               5                   10
```

<210> SEQ ID NO 29
<211> LENGTH: 13
<212> TYPE: PRT
<213> ORGANISM: Homo sapiens

<400> SEQUENCE: 29

```
Leu Asn Gln Ser Phe Thr Glu Lys Tyr Ala Gly Ile Phe
1               5                   10
```

<210> SEQ ID NO 30
<211> LENGTH: 13
<212> TYPE: PRT
<213> ORGANISM: Homo sapiens

<400> SEQUENCE: 30

```
Val Phe Val Ser Ser Thr Tyr Lys Asn Leu Phe Trp Gly
1               5                   10
```

<210> SEQ ID NO 31
<211> LENGTH: 13
<212> TYPE: PRT
<213> ORGANISM: Homo sapiens

<400> SEQUENCE: 31

```
Gly Cys Gln Thr His Ser Gly Lys Ile Leu Glu Asn Gly
1               5                   10
```

<210> SEQ ID NO 32
<211> LENGTH: 13
<212> TYPE: PRT
<213> ORGANISM: Homo sapiens

<400> SEQUENCE: 32

```
Gly Ile Arg Lys Val Thr Cys Lys His Arg Pro Glu Tyr
1               5                   10
```

<210> SEQ ID NO 33
<211> LENGTH: 13
<212> TYPE: PRT
<213> ORGANISM: Homo sapiens

<400> SEQUENCE: 33

```
Asp Trp Ser Asp Ser Ser Ser Lys Trp Glu Leu Leu Ser
1               5                   10
```

<210> SEQ ID NO 34
<211> LENGTH: 13
<212> TYPE: PRT
<213> ORGANISM: Homo sapiens

```
<400> SEQUENCE: 34

Lys Trp Glu Leu Leu Ser Pro Lys Glu Lys Ile Leu Leu
1               5                   10

<210> SEQ ID NO 35
<211> LENGTH: 13
<212> TYPE: PRT
<213> ORGANISM: Homo sapiens

<400> SEQUENCE: 35

Gln Lys Trp Thr Tyr Thr Met Arg Glu Gly Arg Trp Glu
1               5                   10

<210> SEQ ID NO 36
<211> LENGTH: 13
<212> TYPE: PRT
<213> ORGANISM: Homo sapiens

<400> SEQUENCE: 36

Glu Glu Gly Arg Arg Ser Leu Arg Pro Cys Ser Val Leu
1               5                   10

<210> SEQ ID NO 37
<211> LENGTH: 13
<212> TYPE: PRT
<213> ORGANISM: Homo sapiens

<400> SEQUENCE: 37

Lys Gln Leu Lys Leu Ser Gln Lys Val Phe His Lys Gln
1               5                   10

<210> SEQ ID NO 38
<211> LENGTH: 13
<212> TYPE: PRT
<213> ORGANISM: Homo sapiens

<400> SEQUENCE: 38

Leu Ile Arg Ser Val Thr Leu Lys Asp Val Asp Leu Gln
1               5                   10

<210> SEQ ID NO 39
<211> LENGTH: 14
<212> TYPE: PRT
<213> ORGANISM: Homo sapiens

<400> SEQUENCE: 39

Arg Val Val Pro Leu Asn Gln Ser Phe Thr Glu Lys Tyr Ala
1               5                   10

<210> SEQ ID NO 40
<211> LENGTH: 14
<212> TYPE: PRT
<213> ORGANISM: Homo sapiens

<400> SEQUENCE: 40

Ile Glu Ala Thr Tyr Asn Arg Thr Leu Ile Gly Cys Gln Thr
1               5                   10

<210> SEQ ID NO 41
<211> LENGTH: 14
<212> TYPE: PRT
<213> ORGANISM: Homo sapiens
```

-continued

```
<400> SEQUENCE: 41

Ala Leu Leu Asp Leu Asn Ala Ser Gly Thr Met Ser Ile Gln
1               5                   10

<210> SEQ ID NO 42
<211> LENGTH: 10
<212> TYPE: PRT
<213> ORGANISM: Homo sapiens

<400> SEQUENCE: 42

Ser Tyr Leu Ile Phe Asn Thr Thr Leu Leu
1               5                   10

<210> SEQ ID NO 43
<211> LENGTH: 14
<212> TYPE: PRT
<213> ORGANISM: Homo sapiens

<400> SEQUENCE: 43

Val Trp Arg Pro Glu Glu Gly Arg Arg Ser Leu Arg Pro Cys
1               5                   10

<210> SEQ ID NO 44
<211> LENGTH: 23
<212> TYPE: PRT
<213> ORGANISM: Homo sapiens

<400> SEQUENCE: 44

Ile Leu Ala Leu Leu Asp Leu Asn Ala Ser Gly Thr Met Ser Ile Gln
1               5                   10                  15

Glu Phe Arg Asp Leu Trp Lys
            20

<210> SEQ ID NO 45
<211> LENGTH: 22
<212> TYPE: PRT
<213> ORGANISM: Homo sapiens

<400> SEQUENCE: 45

Arg Leu Asp Leu Cys Gln Gly Ile Val Gly Asp Cys Trp Phe Leu Ala
1               5                   10                  15

Ala Leu Gln Ala Leu Ala
            20

<210> SEQ ID NO 46
<211> LENGTH: 241
<212> TYPE: PRT
<213> ORGANISM: homo sapiens

<400> SEQUENCE: 46

Arg Leu Asp Leu Cys Gln Gly Ile Val Gly Asp Cys Trp Phe Leu Ala
1               5                   10                  15

Ala Leu Gln Ala Leu Ala Leu His Gln Asp Ile Leu Ser Arg Val Val
            20                  25                  30

Pro Leu Asn Gln Ser Phe Thr Glu Lys Tyr Ala Gly Ile Phe Arg Phe
        35                  40                  45

Trp Phe Trp His Tyr Gly Asn Trp Val Pro Val Ile Asp Asp Arg
    50                  55                  60

Leu Pro Val Asn Glu Ala Gly Gln Leu Val Phe Val Ser Ser Thr Tyr
65                  70                  75                  80
```

-continued

```
Lys Asn Leu Phe Trp Gly Ala Leu Leu Glu Lys Ala Tyr Ala Lys Leu
                 85                  90                  95
Ser Gly Ser Tyr Glu Asp Leu Gln Ser Gly Gln Val Ser Glu Ala Leu
            100                 105                 110
Val Asp Phe Thr Gly Gly Val Thr Met Thr Ile Asn Leu Ala Glu Ala
        115                 120                 125
His Gly Asn Leu Trp Asp Ile Leu Ile Glu Ala Thr Tyr Asn Arg Thr
130                 135                 140
Leu Ile Gly Cys Gln Thr His Ser Gly Lys Ile Leu Glu Asn Gly Leu
145                 150                 155                 160
Val Glu Gly His Ala Tyr Thr Leu Thr Gly Ile Arg Lys Val Thr Cys
                165                 170                 175
Lys His Arg Pro Glu Tyr Leu Val Lys Leu Arg Asn Pro Trp Gly Lys
            180                 185                 190
Val Glu Trp Lys Gly Asp Trp Ser Asp Ser Ser Lys Trp Glu Leu
        195                 200                 205
Leu Ser Pro Lys Glu Lys Ile Leu Leu Arg Lys Asp Asn Asp Gly
    210                 215                 220
Glu Phe Trp Met Thr Leu Gln Asp Phe Lys Thr His Phe Val Leu Leu
225                 230                 235                 240
Val
```

<210> SEQ ID NO 47
<211> LENGTH: 8
<212> TYPE: PRT
<213> ORGANISM: bacteriophage T7

<400> SEQUENCE: 47

```
Asp Tyr Lys Asp Asp Asp Asp Lys
1               5
```

<210> SEQ ID NO 48
<211> LENGTH: 733
<212> TYPE: DNA
<213> ORGANISM: homo sapiens

<400> SEQUENCE: 48

```
gggatccgga gcccaaatct tctgacaaaa ctcacacatg cccaccgtgc ccagcacctg      60
aattcgaggg tgcaccgtca gtcttcctct tccccccaaa acccaaggac accctcatga     120
tctcccggac tcctgaggtc acatgcgtgg tggtggacgt aagccacgaa gaccctgagg     180
tcaagttcaa ctggtacgtg gacggcgtgg aggtgcataa tgccaagaca aagccgcggg     240
aggagcagta caacagcacg taccgtgtgg tcagcgtcct caccgtcctg caccaggact     300
ggctgaatgg caaggagtac aagtgcaagg tctccaacaa agccctccca accccatcg     360
agaaaaccat ctccaaagcc aaagggcagc ccgagaacc acaggtgtac accctgcccc     420
catcccggga tgagctgacc aagaaccagg tcagcctgac ctgcctggtc aaaggcttct     480
atccaagcga catcgccgtg gagtgggaga gcaatgggca gccggagaac aactacaaga     540
ccacgcctcc cgtgctggac tccgacggct ccttcttcct ctacagcaag ctcaccgtgg     600
acaagagcag gtggcagcag gggaacgtct tctcatgctc cgtgatgcat gaggctctgc     660
acaaccacta cacgcagaag agcctctccc tgtctccggg taaatgagtg cgacggccgc     720
gactctagag gat                                                        733
```

```
<210> SEQ ID NO 49
<211> LENGTH: 39
<212> TYPE: DNA
<213> ORGANISM: Homo sapiens

<400> SEQUENCE: 49
gcagcagcgg ccgcccacag caaccccaac aggactttg                              39

<210> SEQ ID NO 50
<211> LENGTH: 37
<212> TYPE: DNA
<213> ORGANISM: Homo sapiens

<400> SEQUENCE: 50
gcagcagtcg actaacaagg tggtgttgaa gattaaa                                37

<210> SEQ ID NO 51
<211> LENGTH: 37
<212> TYPE: DNA
<213> ORGANISM: Homo sapiens

<400> SEQUENCE: 51
gcagcagcgg ccgcatgtct ctgtggccac ctttccg                                37

<210> SEQ ID NO 52
<211> LENGTH: 36
<212> TYPE: DNA
<213> ORGANISM: Homo sapiens

<400> SEQUENCE: 52
gcagcagtcg acgaggtaga agccaatggc gaggag                                 36

<210> SEQ ID NO 53
<211> LENGTH: 2095
<212> TYPE: DNA
<213> ORGANISM: Homo sapiens
<220> FEATURE:
<221> NAME/KEY: CDS
<222> LOCATION: (9)..(2090)

<400> SEQUENCE: 53
```

| | | | | | | | | | | | | | | | |
|---|---|---|---|---|---|---|---|---|---|---|---|---|---|---|---|
| cacctgcc | atg | tct | ctg | tgg | cca | cct | ttc | cga | tgc | aga | tgg | aag | ctg | gcg | 50 |
| | Met | Ser | Leu | Trp | Pro | Pro | Phe | Arg | Cys | Arg | Trp | Lys | Leu | Ala | |
| | 1 | | | 5 | | | | | 10 | | | | | | |
| cca | agg | tac | tct | agg | agg | gcg | tct | cca | cag | caa | ccc | caa | cag | gac | ttt | 98 |
| Pro | Arg | Tyr | Ser | Arg | Arg | Ala | Ser | Pro | Gln | Gln | Pro | Gln | Gln | Asp | Phe | |
| 15 | | | | 20 | | | | | 25 | | | | | 30 | | |
| gag | gcc | ctg | ctg | gca | gag | tgc | ctg | agg | aat | ggc | tgc | ctc | ttt | gaa | gac | 146 |
| Glu | Ala | Leu | Leu | Ala | Glu | Cys | Leu | Arg | Asn | Gly | Cys | Leu | Phe | Glu | Asp | |
| | | | 35 | | | | | 40 | | | | | 45 | | | |
| acc | agc | ttc | ccg | gcc | acc | ctg | agc | tcc | atc | ggc | agt | ggc | tcc | ctg | ctg | 194 |
| Thr | Ser | Phe | Pro | Ala | Thr | Leu | Ser | Ser | Ile | Gly | Ser | Gly | Ser | Leu | Leu | |
| | 50 | | | | | 55 | | | | | 60 | | | | | |
| cag | aag | ctg | cca | ccc | cgc | ctg | cag | tgg | aag | agg | ccc | cgg | gag | ctg | cac | 242 |
| Gln | Lys | Leu | Pro | Pro | Arg | Leu | Gln | Trp | Lys | Arg | Pro | Pro | Glu | Leu | His | |
| 65 | | | | | 70 | | | | | 75 | | | | | | |
| agc | aat | ccc | cag | ttt | tat | ttt | gcc | aag | gcc | aaa | agg | ctg | gat | ctg | tgc | 290 |
| Ser | Asn | Pro | Gln | Phe | Tyr | Phe | Ala | Lys | Ala | Lys | Arg | Leu | Asp | Leu | Cys | |
| | 80 | | | | 85 | | | | | 90 | | | | | | |
| cag | ggg | ata | gta | gga | gac | tgc | tgg | ttc | ttg | gct | gct | ttg | caa | gct | ctg | 338 |
| Gln | Gly | Ile | Val | Gly | Asp | Cys | Trp | Phe | Leu | Ala | Ala | Leu | Gln | Ala | Leu | |
| 95 | | | | 100 | | | | | 105 | | | | | 110 | | |

-continued

| | | |
|---|---|---|
| gcc ttg cac cag gac atc ctg agc cgg gtt gtt ccc ctg aat cag agt<br>Ala Leu His Gln Asp Ile Leu Ser Arg Val Val Pro Leu Asn Gln Ser<br>        115        120       125 | | 386 |
| ttc act gag aag tat gct ggc atc ttc cgg ttc tgg ttc tgg cac tat<br>Phe Thr Glu Lys Tyr Ala Gly Ile Phe Arg Phe Trp Phe Trp His Tyr<br>    130         135        140 | | 434 |
| ggg aac tgg gtt cct gtg gtg atc gat gac cgt ctg cct gtg aat gag<br>Gly Asn Trp Val Pro Val Val Ile Asp Asp Arg Leu Pro Val Asn Glu<br>   145        150        155 | | 482 |
| gct ggc cag ctg gtc ttt gtc tcc tcc acc tat aag aac ttg ttc tgg<br>Ala Gly Gln Leu Val Phe Val Ser Ser Thr Tyr Lys Asn Leu Phe Trp<br>160         165        170 | | 530 |
| gga gca ctt ctg gaa aag gcc tat gcc aag ctc tct ggt tcc tat gaa<br>Gly Ala Leu Leu Glu Lys Ala Tyr Ala Lys Leu Ser Gly Ser Tyr Glu<br>175         180        185        190 | | 578 |
| gac ttg cag tca gga cag gtg tct gaa gcc ctt gta gac ttc act gga<br>Asp Leu Gln Ser Gly Gln Val Ser Glu Ala Leu Val Asp Phe Thr Gly<br>        195        200       205 | | 626 |
| ggg gtg aca atg acc atc aac ctg gca gaa gcc cat ggc aac ctc tgg<br>Gly Val Thr Met Thr Ile Asn Leu Ala Glu Ala His Gly Asn Leu Trp<br>        210        215       220 | | 674 |
| gac atc ctc atc gaa gcc acc tac aac aga acc ctc att ggc tgc cag<br>Asp Ile Leu Ile Glu Ala Thr Tyr Asn Arg Thr Leu Ile Gly Cys Gln<br>        225        230       235 | | 722 |
| acc cac tca ggg gag aag att ctg gag aat ggg ctg gtg gaa ggc cat<br>Thr His Ser Gly Glu Lys Ile Leu Glu Asn Gly Leu Val Glu Gly His<br>   240        245        250 | | 770 |
| gcc tat act ctc aca gga atc agg aag gtg acc tgc aaa cat aga cct<br>Ala Tyr Thr Leu Thr Gly Ile Arg Lys Val Thr Cys Lys His Arg Pro<br>255         260        265        270 | | 818 |
| gaa tat ctc gtc aag cta cgg aac ccc tgg gga aag gtg gaa tgg aaa<br>Glu Tyr Leu Val Lys Leu Arg Asn Pro Trp Gly Lys Val Glu Trp Lys<br>        275        280       285 | | 866 |
| gga gac tgg agt gac agt tca agt aaa tgg gag ctg ctg agc ccc aag<br>Gly Asp Trp Ser Asp Ser Ser Ser Lys Trp Glu Leu Leu Ser Pro Lys<br>   290        295        300 | | 914 |
| gag aag att ctg ctt ctg agg aaa gac aat gac gga gaa ttc tgg atg<br>Glu Lys Ile Leu Leu Leu Arg Lys Asp Asn Asp Gly Glu Phe Trp Met<br>        305        310       315 | | 962 |
| acg ctg cag gac ttt aaa aca cat ttc gtg ctc ctg gtt atc tgt aaa<br>Thr Leu Gln Asp Phe Lys Thr His Phe Val Leu Leu Val Ile Cys Lys<br>   320        325        330 | | 1010 |
| ctg acc cca ggc ctg ttg agc cag gag gcg gcc cag aag tgg acg tac<br>Leu Thr Pro Gly Leu Leu Ser Gln Glu Ala Ala Gln Lys Trp Thr Tyr<br>335         340        345        350 | | 1058 |
| acc atg cgg gag ggg aga tgg gag aag cgg agc aca gct ggt ggc cag<br>Thr Met Arg Glu Gly Arg Trp Glu Lys Arg Ser Thr Ala Gly Gly Gln<br>        355        360       365 | | 1106 |
| agg cag ttg ctg cag gac aca ttt tgg aag aac ccg cag ttc ctg ctg<br>Arg Gln Leu Leu Gln Asp Thr Phe Trp Lys Asn Pro Gln Phe Leu Leu<br>        370        375       380 | | 1154 |
| tct gtc tgg agg ccc gag gag ggc agg aga tcc ctg agg ccc tgc agc<br>Ser Val Trp Arg Pro Glu Glu Gly Arg Arg Ser Leu Arg Pro Cys Ser<br>   385        390        395 | | 1202 |
| gtg ctg gtg tcc ctg ctc cag aag ccc agg cac agg tgc cgc aag cgg<br>Val Leu Val Ser Leu Leu Gln Lys Pro Arg His Arg Cys Arg Lys Arg<br>400         405        410 | | 1250 |
| aag cct ctc ctc gcc att ggc ttc tac ctc tat agg tac cat gat gac<br>Lys Pro Leu Leu Ala Ile Gly Phe Tyr Leu Tyr Arg Tyr His Asp Asp<br>415         420        425        430 | | 1298 |

| | | | | | | | | | | | | | | | | |
|---|---|---|---|---|---|---|---|---|---|---|---|---|---|---|---|---|
| cag | agg | aga | ctg | ccc | cct | gag | ttc | ttc | cag | aga | aac | act | cct | ctg | agc | 1346 |
| Gln | Arg | Arg | Leu | Pro | Pro | Glu | Phe | Phe | Gln | Arg | Asn | Thr | Pro | Leu | Ser | |
| | | | 435 | | | | | 440 | | | | | 445 | | | |
| cag | cct | gat | agg | ttt | ctc | aag | gag | aaa | gaa | gtg | agt | cag | gag | ctg | tgt | 1394 |
| Gln | Pro | Asp | Arg | Phe | Leu | Lys | Glu | Lys | Glu | Val | Ser | Gln | Glu | Leu | Cys | |
| | | 450 | | | | | 455 | | | | | 460 | | | | |
| ctg | gaa | cca | ggg | acg | tac | ctc | atc | gtg | ccc | tgc | ata | ttg | gag | gcc | cac | 1442 |
| Leu | Glu | Pro | Gly | Thr | Tyr | Leu | Ile | Val | Pro | Cys | Ile | Leu | Glu | Ala | His | |
| | 465 | | | | | 470 | | | | | 475 | | | | | |
| cag | aag | tca | gag | ttc | gtc | ctc | agg | gtc | ttc | tcc | agg | aag | cac | atc | ttt | 1490 |
| Gln | Lys | Ser | Glu | Phe | Val | Leu | Arg | Val | Phe | Ser | Arg | Lys | His | Ile | Phe | |
| 480 | | | | | 485 | | | | | 490 | | | | | | |
| tat | gaa | att | ggc | agc | aat | tct | ggt | gtc | gtc | ttc | tca | aag | gag | ata | gaa | 1538 |
| Tyr | Glu | Ile | Gly | Ser | Asn | Ser | Gly | Val | Val | Phe | Ser | Lys | Glu | Ile | Glu | |
| 495 | | | | | 500 | | | | | 505 | | | | | 510 | |
| gac | caa | aat | gaa | agg | cag | gat | gaa | ttc | ttc | acc | aaa | ttc | ttt | gaa | aag | 1586 |
| Asp | Gln | Asn | Glu | Arg | Gln | Asp | Glu | Phe | Phe | Thr | Lys | Phe | Phe | Glu | Lys | |
| | | | | 515 | | | | | 520 | | | | | 525 | | |
| cat | cca | gag | att | aat | gca | gtt | caa | ctt | cag | aac | ctc | ctg | aac | cag | atg | 1634 |
| His | Pro | Glu | Ile | Asn | Ala | Val | Gln | Leu | Gln | Asn | Leu | Leu | Asn | Gln | Met | |
| | | | 530 | | | | | 535 | | | | | 540 | | | |
| acc | tgg | tca | agt | ctg | ggg | agc | aga | cag | ccc | ttc | ttt | agc | ctg | gaa | gcc | 1682 |
| Thr | Trp | Ser | Ser | Leu | Gly | Ser | Arg | Gln | Pro | Phe | Phe | Ser | Leu | Glu | Ala | |
| | | 545 | | | | | 550 | | | | | 555 | | | | |
| tgc | cag | ggg | atc | ctg | gcc | tta | ctg | gac | ctt | aat | gca | tca | ggt | act | atg | 1730 |
| Cys | Gln | Gly | Ile | Leu | Ala | Leu | Leu | Asp | Leu | Asn | Ala | Ser | Gly | Thr | Met | |
| | 560 | | | | | 565 | | | | | 570 | | | | | |
| agc | atc | cag | gaa | ttc | agg | gac | ctg | tgg | aag | cag | ctg | aag | ctc | tct | cag | 1778 |
| Ser | Ile | Gln | Glu | Phe | Arg | Asp | Leu | Trp | Lys | Gln | Leu | Lys | Leu | Ser | Gln | |
| 575 | | | | | 580 | | | | | 585 | | | | | 590 | |
| aag | gtt | ttc | cac | aag | caa | gac | cgt | ggg | tca | gga | tac | ctg | aac | tgg | gag | 1826 |
| Lys | Val | Phe | His | Lys | Gln | Asp | Arg | Gly | Ser | Gly | Tyr | Leu | Asn | Trp | Glu | |
| | | | | 595 | | | | | 600 | | | | | 605 | | |
| cag | ctg | cac | gct | gcc | atg | agg | gag | gca | ggt | agg | cac | agg | aag | agc | tgg | 1874 |
| Gln | Leu | His | Ala | Ala | Met | Arg | Glu | Ala | Gly | Arg | His | Arg | Lys | Ser | Trp | |
| | | | 610 | | | | | 615 | | | | | 620 | | | |
| agc | tgt | ggg | cac | aca | cgg | gca | ggg | tgc | aca | ctc | atc | agg | cag | agg | aga | 1922 |
| Ser | Cys | Gly | His | Thr | Arg | Ala | Gly | Cys | Thr | Leu | Ile | Arg | Gln | Arg | Arg | |
| | | 625 | | | | | 630 | | | | | 635 | | | | |
| ggg | gat | gtg | tgg | cat | gct | gaa | gta | act | cta | ata | cgc | agt | gtt | act | ctc | 1970 |
| Gly | Asp | Val | Trp | His | Ala | Glu | Val | Thr | Leu | Ile | Arg | Ser | Val | Thr | Leu | |
| | 640 | | | | | 645 | | | | | 650 | | | | | |
| aaa | gac | gta | gat | ctg | cag | tca | act | cca | aca | ttt | ttt | atg | att | gtc | cct | 2018 |
| Lys | Asp | Val | Asp | Leu | Gln | Ser | Thr | Pro | Thr | Phe | Phe | Met | Ile | Val | Pro | |
| 655 | | | | | 660 | | | | | 665 | | | | | 670 | |
| gtg | atc | cta | gcc | aac | att | gat | gga | ggg | gtg | gca | cat | tca | act | tct | tat | 2066 |
| Val | Ile | Leu | Ala | Asn | Ile | Asp | Gly | Gly | Val | Ala | His | Ser | Thr | Ser | Tyr | |
| | | | | 675 | | | | | 680 | | | | | 685 | | |
| tta | atc | ttc | aac | acc | acc | ttg | tta | taatc | | | | | | | | 2095 |
| Leu | Ile | Phe | Asn | Thr | Thr | Leu | Leu | | | | | | | | | |
| | | | 690 | | | | | | | | | | | | | |

<210> SEQ ID NO 54
<211> LENGTH: 694
<212> TYPE: PRT
<213> ORGANISM: Homo sapiens

<400> SEQUENCE: 54

Met Ser Leu Trp Pro Pro Phe Arg Cys Arg Trp Lys Leu Ala Pro Arg
1               5                   10                  15

-continued

```
Tyr Ser Arg Arg Ala Ser Pro Gln Gln Pro Gln Gln Asp Phe Glu Ala
             20                  25                  30
Leu Leu Ala Glu Cys Leu Arg Asn Gly Cys Leu Phe Glu Asp Thr Ser
         35                  40                  45
Phe Pro Ala Thr Leu Ser Ser Ile Gly Ser Gly Ser Leu Leu Gln Lys
 50                  55                  60
Leu Pro Pro Arg Leu Gln Trp Lys Arg Pro Pro Glu Leu His Ser Asn
 65                  70                  75                  80
Pro Gln Phe Tyr Phe Ala Lys Ala Lys Arg Leu Asp Leu Cys Gln Gly
                 85                  90                  95
Ile Val Gly Asp Cys Trp Phe Leu Ala Ala Leu Gln Ala Leu Ala Leu
            100                 105                 110
His Gln Asp Ile Leu Ser Arg Val Val Pro Leu Asn Gln Ser Phe Thr
            115                 120                 125
Glu Lys Tyr Ala Gly Ile Phe Arg Phe Trp Phe Trp His Tyr Gly Asn
130                 135                 140
Trp Val Pro Val Val Ile Asp Asp Arg Leu Pro Val Asn Glu Ala Gly
145                 150                 155                 160
Gln Leu Val Phe Val Ser Ser Thr Tyr Lys Asn Leu Phe Trp Gly Ala
                165                 170                 175
Leu Leu Glu Lys Ala Tyr Ala Lys Leu Ser Gly Ser Tyr Glu Asp Leu
            180                 185                 190
Gln Ser Gly Gln Val Ser Glu Ala Leu Val Asp Phe Thr Gly Gly Val
        195                 200                 205
Thr Met Thr Ile Asn Leu Ala Glu Ala His Gly Asn Leu Trp Asp Ile
    210                 215                 220
Leu Ile Glu Ala Thr Tyr Asn Arg Thr Leu Ile Gly Cys Gln Thr His
225                 230                 235                 240
Ser Gly Glu Lys Ile Leu Glu Asn Gly Leu Val Glu Gly His Ala Tyr
                245                 250                 255
Thr Leu Thr Gly Ile Arg Lys Val Thr Cys Lys His Arg Pro Glu Tyr
            260                 265                 270
Leu Val Lys Leu Arg Asn Pro Trp Gly Lys Val Glu Trp Lys Gly Asp
        275                 280                 285
Trp Ser Asp Ser Ser Lys Trp Glu Leu Leu Ser Pro Lys Glu Lys
    290                 295                 300
Ile Leu Leu Leu Arg Lys Asp Asn Asp Gly Glu Phe Trp Met Thr Leu
305                 310                 315                 320
Gln Asp Phe Lys Thr His Phe Val Leu Leu Val Ile Cys Lys Leu Thr
                325                 330                 335
Pro Gly Leu Leu Ser Gln Glu Ala Ala Gln Lys Trp Thr Tyr Thr Met
            340                 345                 350
Arg Glu Gly Arg Trp Glu Lys Arg Ser Thr Ala Gly Gly Gln Arg Gln
        355                 360                 365
Leu Leu Gln Asp Thr Phe Trp Lys Asn Pro Gln Phe Leu Leu Ser Val
    370                 375                 380
Trp Arg Pro Glu Glu Gly Arg Arg Ser Leu Arg Pro Cys Ser Val Leu
385                 390                 395                 400
Val Ser Leu Leu Gln Lys Pro Arg His Arg Cys Arg Lys Arg Lys Pro
                405                 410                 415
Leu Leu Ala Ile Gly Phe Tyr Leu Tyr Arg Tyr His Asp Asp Gln Arg
            420                 425                 430
```

-continued

```
Arg Leu Pro Pro Glu Phe Phe Gln Arg Asn Thr Pro Leu Ser Gln Pro
        435                 440                 445

Asp Arg Phe Leu Lys Glu Lys Glu Val Ser Gln Glu Leu Cys Leu Glu
    450                 455                 460

Pro Gly Thr Tyr Leu Ile Val Pro Cys Ile Leu Glu Ala His Gln Lys
465                 470                 475                 480

Ser Glu Phe Val Leu Arg Val Phe Ser Arg Lys His Ile Phe Tyr Glu
                485                 490                 495

Ile Gly Ser Asn Ser Gly Val Val Phe Ser Lys Glu Ile Glu Asp Gln
                500                 505                 510

Asn Glu Arg Gln Asp Glu Phe Phe Thr Lys Phe Glu Lys His Pro
            515                 520                 525

Glu Ile Asn Ala Val Gln Leu Gln Asn Leu Leu Asn Gln Met Thr Trp
        530                 535                 540

Ser Ser Leu Gly Ser Arg Gln Pro Phe Phe Ser Leu Glu Ala Cys Gln
545                 550                 555                 560

Gly Ile Leu Ala Leu Leu Asp Leu Asn Ala Ser Gly Thr Met Ser Ile
                565                 570                 575

Gln Glu Phe Arg Asp Leu Trp Lys Gln Leu Lys Leu Ser Gln Lys Val
                580                 585                 590

Phe His Lys Gln Asp Arg Gly Ser Gly Tyr Leu Asn Trp Glu Gln Leu
        595                 600                 605

His Ala Ala Met Arg Glu Ala Gly Arg His Arg Lys Ser Trp Ser Cys
    610                 615                 620

Gly His Thr Arg Ala Gly Cys Thr Leu Ile Arg Gln Arg Arg Gly Asp
625                 630                 635                 640

Val Trp His Ala Glu Val Thr Leu Ile Arg Ser Val Thr Leu Lys Asp
                645                 650                 655

Val Asp Leu Gln Ser Thr Pro Thr Phe Phe Met Ile Val Pro Val Ile
                660                 665                 670

Leu Ala Asn Ile Asp Gly Gly Val Ala His Ser Thr Ser Tyr Leu Ile
        675                 680                 685

Phe Asn Thr Thr Leu Leu
    690

<210> SEQ ID NO 55
<211> LENGTH: 2104
<212> TYPE: DNA
<213> ORGANISM: Homo sapiens
<220> FEATURE:
<221> NAME/KEY: CDS
<222> LOCATION: (9)..(2099)

<400> SEQUENCE: 55 cacctgcc atg tct ctg tgg cca cct ttc cga tgc aga tgg aag ctg gcg        50
         Met Ser Leu Trp Pro Pro Phe Arg Cys Arg Trp Lys Leu Ala
         1               5                   10 cca agg tac tct agg agg gcg tct cca cag caa ccc caa cag gac ttt        98
Pro Arg Tyr Ser Arg Arg Ala Ser Pro Gln Gln Pro Gln Gln Asp Phe
15                  20                  25                  30 gag gcc ctg ctg gca gag tgc ctg agg aat ggc tgc ctc ttt gaa gac       146
Glu Ala Leu Leu Ala Glu Cys Leu Arg Asn Gly Cys Leu Phe Glu Asp
                35                  40                  45 acc agc ttc ccg gcc acc ctg agc tcc atc ggc agt ggc tcc ctg ctg       194
Thr Ser Phe Pro Ala Thr Leu Ser Ser Ile Gly Ser Gly Ser Leu Leu
            50                  55                  60 cag aag ctg cca ccc cgc ctg cag tgg aag agg ccc ccg gag ctg cac       242
```

```
                                                                        -continued Gln Lys Leu Pro Pro Arg Leu Gln Trp Lys Arg Pro Glu Leu His
         65                  70                  75 agc aat ccc cag ttt tat ttt gcc aag gcc aaa agg ctg gat ctg tgc          290
Ser Asn Pro Gln Phe Tyr Phe Ala Lys Ala Lys Arg Leu Asp Leu Cys
     80                  85                  90 cag ggg ata gta gga gac tgc tgg ttc ttg gct gct ttg caa gct ctg          338
Gln Gly Ile Val Gly Asp Cys Trp Phe Leu Ala Ala Leu Gln Ala Leu
 95                 100                 105                 110 gcc ttg cac cag gac atc ctg agc cgg gtt gtt ccc ctg aat cag agt         386
Ala Leu His Gln Asp Ile Leu Ser Arg Val Val Pro Leu Asn Gln Ser
                 115                 120                 125 ttc act gag aag tat gct ggc atc ttc cgg ttc tgg ttc tgg cac tat         434
Phe Thr Glu Lys Tyr Ala Gly Ile Phe Arg Phe Trp Phe Trp His Tyr
             130                 135                 140 ggg aac tgg gtt cct gtg gtg atc gat gac cgt ctg cct gtg aat gag         482
Gly Asn Trp Val Pro Val Val Ile Asp Asp Arg Leu Pro Val Asn Glu
         145                 150                 155 gct ggc cag ctg gtc ttt gtc tcc tcc acc tat aag aac ttg ttc tgg         530
Ala Gly Gln Leu Val Phe Val Ser Ser Thr Tyr Lys Asn Leu Phe Trp
     160                 165                 170 gga gca ctt ctg gaa aag gcc tat gcc aag ctc tct ggt tcc tat gaa         578
Gly Ala Leu Leu Glu Lys Ala Tyr Ala Lys Leu Ser Gly Ser Tyr Glu
175                 180                 185                 190 gac ttg cag tca gga cag gtg tct gaa gcc ctt gta gac ttc act gga         626
Asp Leu Gln Ser Gly Gln Val Ser Glu Ala Leu Val Asp Phe Thr Gly
                 195                 200                 205 ggg gtg aca atg acc atc aac ctg gca gaa gcc cat ggc aac ctc tgg         674
Gly Val Thr Met Thr Ile Asn Leu Ala Glu Ala His Gly Asn Leu Trp
             210                 215                 220 gac atc ctc atc gaa gcc acc tac aac aga acc ctc att ggc tgc cag         722
Asp Ile Leu Ile Glu Ala Thr Tyr Asn Arg Thr Leu Ile Gly Cys Gln
         225                 230                 235 acc cac tca ggg gag aag att ctg gag aat ggg ctg gtg gaa ggc cat         770
Thr His Ser Gly Glu Lys Ile Leu Glu Asn Gly Leu Val Glu Gly His
     240                 245                 250 gcc tat act ctc aca gga atc agg aag gtg acc tgc aaa cat aga cct         818
Ala Tyr Thr Leu Thr Gly Ile Arg Lys Val Thr Cys Lys His Arg Pro
255                 260                 265                 270 gaa tat ctc gtc aag cta cgg aac ccc tgg gga aag gtg gaa tgg aaa         866
Glu Tyr Leu Val Lys Leu Arg Asn Pro Trp Gly Lys Val Glu Trp Lys
                 275                 280                 285 gga gac tgg agt gac agt tca agt aaa tgg gag ctg ctg agc ccc aag         914
Gly Asp Trp Ser Asp Ser Ser Ser Lys Trp Glu Leu Leu Ser Pro Lys
             290                 295                 300 gag aag att ctg ctt ctg agg aaa gac aat gac gga gaa ttc tgg atg         962
Glu Lys Ile Leu Leu Leu Arg Lys Asp Asn Asp Gly Glu Phe Trp Met
         305                 310                 315 acg ctg cag gac ttt aaa aca cat ttc gtg ctc ctg gtt atc tgt aaa        1010
Thr Leu Gln Asp Phe Lys Thr His Phe Val Leu Leu Val Ile Cys Lys
     320                 325                 330 ctg acc cca ggc ctg ttg agc cag gag gcg gcc cag aag tgg acg tac        1058
Leu Thr Pro Gly Leu Leu Ser Gln Glu Ala Ala Gln Lys Trp Thr Tyr
335                 340                 345                 350 acc atg cgg gag ggg aga tgg gag aag cgg agc aca gct ggt ggc cag        1106
Thr Met Arg Glu Gly Arg Trp Glu Lys Arg Ser Thr Ala Gly Gly Gln
                 355                 360                 365 agg cag ttg ctg cag gac aca ttt tgg aag aac ccg cag ttc ctg ctg        1154
Arg Gln Leu Leu Gln Asp Thr Phe Trp Lys Asn Pro Gln Phe Leu Leu
             370                 375                 380
```

-continued

```
tct gtc tgg agg ccc gag gag ggc agg aga tcc ctg agg ccc tgc agc    1202
Ser Val Trp Arg Pro Glu Glu Gly Arg Arg Ser Leu Arg Pro Cys Ser
        385                 390                 395 gtg ctg gtg tcc ctg ctc cag aag ccc agg cac agg tgc cgc aag cgg    1250
Val Leu Val Ser Leu Leu Gln Lys Pro Arg His Arg Cys Arg Lys Arg
400                 405                 410 aag cct ctc ctc gcc att ggc ttc tac ctc tat agg atg aac aag tac    1298
Lys Pro Leu Leu Ala Ile Gly Phe Tyr Leu Tyr Arg Met Asn Lys Tyr
415                 420                 425                 430 cat gat gac cag agg aga ctg ccc cct gag ttc ttc cag aga aac act    1346
His Asp Asp Gln Arg Arg Leu Pro Pro Glu Phe Phe Gln Arg Asn Thr
                435                 440                 445 cct ctg agc cag cct gat agg ttt ctc aag gag aaa gaa gtg agt cag    1394
Pro Leu Ser Gln Pro Asp Arg Phe Leu Lys Glu Lys Glu Val Ser Gln
        450                 455                 460 gag ctg tgt ctg gaa cca ggg acg tac ctc atc gtg ccc tgc ata ttg    1442
Glu Leu Cys Leu Glu Pro Gly Thr Tyr Leu Ile Val Pro Cys Ile Leu
        465                 470                 475 gag gcc cac cag aag tca gag ttc gtc ctc agg gtc ttc tcc agg aag    1490
Glu Ala His Gln Lys Ser Glu Phe Val Leu Arg Val Phe Ser Arg Lys
480                 485                 490 cac atc ttt tat gaa att ggc agc aat tct ggt gtc gtc ttc tca aag    1538
His Ile Phe Tyr Glu Ile Gly Ser Asn Ser Gly Val Val Phe Ser Lys
495                 500                 505                 510 gag ata gaa gac caa aat gaa agg cag gat gaa ttc ttc acc aaa ttc    1586
Glu Ile Glu Asp Gln Asn Glu Arg Gln Asp Glu Phe Phe Thr Lys Phe
                515                 520                 525 ttt gaa aag cat cca gag att aat gca gtt caa ctt cag aac ctc ctg    1634
Phe Glu Lys His Pro Glu Ile Asn Ala Val Gln Leu Gln Asn Leu Leu
        530                 535                 540 aac cag atg acc tgg tca agt ctg ggg agc aga cag ccc ttc ttt agc    1682
Asn Gln Met Thr Trp Ser Ser Leu Gly Ser Arg Gln Pro Phe Phe Ser
        545                 550                 555 ctg gaa gcc tgc cag ggg atc ctg gcc tta ctg gac ctt aat gca tca    1730
Leu Glu Ala Cys Gln Gly Ile Leu Ala Leu Leu Asp Leu Asn Ala Ser
560                 565                 570 ggt act atg agc atc cag gaa ttc agg gac ctg tgg aag cag ctg aag    1778
Gly Thr Met Ser Ile Gln Glu Phe Arg Asp Leu Trp Lys Gln Leu Lys
575                 580                 585                 590 ctc tct cag aag gtt ttc cac aag caa gac cgt ggg tca gga tac ctg    1826
Leu Ser Gln Lys Val Phe His Lys Gln Asp Arg Gly Ser Gly Tyr Leu
                595                 600                 605 aac tgg gag cag ctg cac gct gcc atg agg gag gca ggt agg cac agg    1874
Asn Trp Glu Gln Leu His Ala Ala Met Arg Glu Ala Gly Arg His Arg
        610                 615                 620 aag agc tgg agc tgt ggg cac aca cgg gca ggg tgc aca ctc atc agg    1922
Lys Ser Trp Ser Cys Gly His Thr Arg Ala Gly Cys Thr Leu Ile Arg
        625                 630                 635 cag agg aga ggg gat gtg tgg cat gct gaa gta act cta ata cgc agt    1970
Gln Arg Arg Gly Asp Val Trp His Ala Glu Val Thr Leu Ile Arg Ser
640                 645                 650 gtt act ctc aaa gac gta gat ctg cag tca act cca aca ttt ttt atg    2018
Val Thr Leu Lys Asp Val Asp Leu Gln Ser Thr Pro Thr Phe Phe Met
655                 660                 665                 670 att gtc cct gtg atc cta gcc aac att gat gga ggg gtg gca cat tca    2066
Ile Val Pro Val Ile Leu Ala Asn Ile Asp Gly Gly Val Ala His Ser
                675                 680                 685 act tct tat tta atc ttc aac acc acc ttg tta taatc              2104
Thr Ser Tyr Leu Ile Phe Asn Thr Thr Leu Leu
                690                 695
```

<210> SEQ ID NO 56
<211> LENGTH: 697
<212> TYPE: PRT
<213> ORGANISM: Homo sapiens

<400> SEQUENCE: 56

```
Met Ser Leu Trp Pro Pro Phe Arg Cys Arg Trp Lys Leu Ala Pro Arg
1               5                   10                  15
Tyr Ser Arg Arg Ala Ser Pro Gln Gln Pro Gln Gln Asp Phe Glu Ala
            20                  25                  30
Leu Leu Ala Glu Cys Leu Arg Asn Gly Cys Leu Phe Glu Asp Thr Ser
        35                  40                  45
Phe Pro Ala Thr Leu Ser Ser Ile Gly Ser Gly Ser Leu Leu Gln Lys
    50                  55                  60
Leu Pro Pro Arg Leu Gln Trp Lys Arg Pro Glu Leu His Ser Asn
65                  70                  75                  80
Pro Gln Phe Tyr Phe Ala Lys Ala Lys Arg Leu Asp Leu Cys Gln Gly
                85                  90                  95
Ile Val Gly Asp Cys Trp Phe Leu Ala Ala Leu Gln Ala Leu Ala Leu
            100                 105                 110
His Gln Asp Ile Leu Ser Arg Val Val Pro Leu Asn Gln Ser Phe Thr
        115                 120                 125
Glu Lys Tyr Ala Gly Ile Phe Arg Phe Trp Phe Trp His Tyr Gly Asn
    130                 135                 140
Trp Val Pro Val Val Ile Asp Asp Arg Leu Pro Val Asn Glu Ala Gly
145                 150                 155                 160
Gln Leu Val Phe Val Ser Ser Thr Tyr Lys Asn Leu Phe Trp Gly Ala
                165                 170                 175
Leu Leu Glu Lys Ala Tyr Ala Lys Leu Ser Gly Ser Tyr Glu Asp Leu
            180                 185                 190
Gln Ser Gly Gln Val Ser Glu Ala Leu Val Asp Phe Thr Gly Gly Val
        195                 200                 205
Thr Met Thr Ile Asn Leu Ala Glu Ala His Gly Asn Leu Trp Asp Ile
    210                 215                 220
Leu Ile Glu Ala Thr Tyr Asn Arg Thr Leu Ile Gly Cys Gln Thr His
225                 230                 235                 240
Ser Gly Glu Lys Ile Leu Glu Asn Gly Leu Val Glu Gly His Ala Tyr
                245                 250                 255
Thr Leu Thr Gly Ile Arg Lys Val Thr Cys Lys His Arg Pro Glu Tyr
            260                 265                 270
Leu Val Lys Leu Arg Asn Pro Trp Gly Lys Val Glu Trp Lys Gly Asp
        275                 280                 285
Trp Ser Asp Ser Ser Lys Trp Glu Leu Leu Ser Pro Lys Glu Lys
    290                 295                 300
Ile Leu Leu Leu Arg Lys Asp Asn Asp Gly Glu Phe Trp Met Thr Leu
305                 310                 315                 320
Gln Asp Phe Lys Thr His Phe Val Leu Val Ile Cys Lys Leu Thr
                325                 330                 335
Pro Gly Leu Leu Ser Gln Glu Ala Ala Gln Lys Trp Thr Tyr Thr Met
            340                 345                 350
Arg Glu Gly Arg Trp Glu Lys Arg Ser Thr Ala Gly Gly Gln Arg Gln
        355                 360                 365
Leu Leu Gln Asp Thr Phe Trp Lys Asn Pro Gln Phe Leu Leu Ser Val
    370                 375                 380
```

```
Trp Arg Pro Glu Glu Gly Arg Arg Ser Leu Arg Pro Cys Ser Val Leu
385                 390                 395                 400

Val Ser Leu Leu Gln Lys Pro Arg His Arg Cys Arg Lys Arg Lys Pro
            405                 410                 415

Leu Leu Ala Ile Gly Phe Tyr Leu Tyr Arg Met Asn Lys Tyr His Asp
            420                 425                 430

Asp Gln Arg Arg Leu Pro Pro Glu Phe Phe Gln Arg Asn Thr Pro Leu
            435                 440                 445

Ser Gln Pro Asp Arg Phe Leu Lys Glu Lys Glu Val Ser Gln Glu Leu
            450                 455                 460

Cys Leu Glu Pro Gly Thr Tyr Leu Ile Val Pro Cys Ile Leu Glu Ala
465                 470                 475                 480

His Gln Lys Ser Glu Phe Val Leu Arg Val Phe Ser Arg Lys His Ile
                485                 490                 495

Phe Tyr Glu Ile Gly Ser Asn Ser Gly Val Val Phe Ser Lys Glu Ile
                500                 505                 510

Glu Asp Gln Asn Glu Arg Gln Asp Glu Phe Phe Thr Lys Phe Phe Glu
            515                 520                 525

Lys His Pro Glu Ile Asn Ala Val Gln Leu Gln Asn Leu Leu Asn Gln
530                 535                 540

Met Thr Trp Ser Ser Leu Gly Ser Arg Gln Pro Phe Phe Ser Leu Glu
545                 550                 555                 560

Ala Cys Gln Gly Ile Leu Ala Leu Leu Asp Leu Asn Ala Ser Gly Thr
                565                 570                 575

Met Ser Ile Gln Glu Phe Arg Asp Leu Trp Lys Gln Leu Lys Leu Ser
                580                 585                 590

Gln Lys Val Phe His Lys Gln Asp Arg Gly Ser Gly Tyr Leu Asn Trp
            595                 600                 605

Glu Gln Leu His Ala Ala Met Arg Glu Ala Gly Arg His Arg Lys Ser
            610                 615                 620

Trp Ser Cys Gly His Thr Arg Ala Gly Cys Thr Leu Ile Arg Gln Arg
625                 630                 635                 640

Arg Gly Asp Val Trp His Ala Glu Val Thr Leu Ile Arg Ser Val Thr
                645                 650                 655

Leu Lys Asp Val Asp Leu Gln Ser Thr Pro Thr Phe Phe Met Ile Val
                660                 665                 670

Pro Val Ile Leu Ala Asn Ile Asp Gly Gly Val Ala His Ser Thr Ser
            675                 680                 685

Tyr Leu Ile Phe Asn Thr Thr Leu Leu
    690                 695

<210> SEQ ID NO 57
<211> LENGTH: 13
<212> TYPE: PRT
<213> ORGANISM: Homo sapiens

<400> SEQUENCE: 57

Leu Ala Pro Arg Tyr Ser Arg Arg Ala Ser Pro Gln Gln
1               5                   10

<210> SEQ ID NO 58
<211> LENGTH: 13
<212> TYPE: PRT
<213> ORGANISM: Homo sapiens
```

-continued

<400> SEQUENCE: 58

Leu Asn Gln Ser Phe Thr Glu Lys Tyr Ala Gly Ile Phe
1               5                   10

<210> SEQ ID NO 59
<211> LENGTH: 13
<212> TYPE: PRT
<213> ORGANISM: Homo sapiens

<400> SEQUENCE: 59

Val Phe Val Ser Ser Thr Tyr Lys Asn Leu Phe Trp Gly
1               5                   10

<210> SEQ ID NO 60
<211> LENGTH: 13
<212> TYPE: PRT
<213> ORGANISM: Homo sapiens

<400> SEQUENCE: 60

Gly Ile Arg Lys Val Thr Cys Lys His Arg Pro Glu Tyr
1               5                   10

<210> SEQ ID NO 61
<211> LENGTH: 13
<212> TYPE: PRT
<213> ORGANISM: Homo sapiens

<400> SEQUENCE: 61

Asp Trp Ser Asp Ser Ser Ser Lys Trp Glu Leu Leu Ser
1               5                   10

<210> SEQ ID NO 62
<211> LENGTH: 13
<212> TYPE: PRT
<213> ORGANISM: Homo sapiens

<400> SEQUENCE: 62

Lys Trp Glu Leu Leu Ser Pro Lys Glu Lys Ile Leu Leu
1               5                   10

<210> SEQ ID NO 63
<211> LENGTH: 13
<212> TYPE: PRT
<213> ORGANISM: Homo sapiens

<400> SEQUENCE: 63

Gln Lys Trp Thr Tyr Thr Met Arg Glu Gly Arg Trp Glu
1               5                   10

<210> SEQ ID NO 64
<211> LENGTH: 13
<212> TYPE: PRT
<213> ORGANISM: Homo sapiens

<400> SEQUENCE: 64

Glu Glu Gly Arg Arg Ser Leu Arg Pro Cys Ser Val Leu
1               5                   10

<210> SEQ ID NO 65
<211> LENGTH: 13
<212> TYPE: PRT
<213> ORGANISM: Homo sapiens

<400> SEQUENCE: 65

Val Leu Arg Val Phe Ser Arg Lys His Ile Phe Tyr Glu
1               5                   10

<210> SEQ ID NO 66
<211> LENGTH: 13
<212> TYPE: PRT
<213> ORGANISM: Homo sapiens

<400> SEQUENCE: 66

Lys Gln Leu Lys Leu Ser Gln Lys Val Phe His Lys Gln
1               5                   10

<210> SEQ ID NO 67
<211> LENGTH: 13
<212> TYPE: PRT
<213> ORGANISM: Homo sapiens

<400> SEQUENCE: 67

Leu Ile Arg Ser Val Thr Leu Lys Asp Val Asp Leu Gln
1               5                   10

<210> SEQ ID NO 68
<211> LENGTH: 14
<212> TYPE: PRT
<213> ORGANISM: Homo sapiens

<400> SEQUENCE: 68

Arg Val Val Pro Leu Asn Gln Ser Phe Thr Glu Lys Tyr Ala
1               5                   10

<210> SEQ ID NO 69
<211> LENGTH: 14
<212> TYPE: PRT
<213> ORGANISM: Homo sapiens

<400> SEQUENCE: 69

Ile Glu Ala Thr Tyr Asn Arg Thr Leu Ile Gly Cys Gln Thr
1               5                   10

<210> SEQ ID NO 70
<211> LENGTH: 14
<212> TYPE: PRT
<213> ORGANISM: Homo sapiens

<400> SEQUENCE: 70

Ala Leu Leu Asp Leu Asn Ala Ser Gly Thr Met Ser Ile Gln
1               5                   10

<210> SEQ ID NO 71
<211> LENGTH: 10
<212> TYPE: PRT
<213> ORGANISM: Homo sapiens

<400> SEQUENCE: 71

Ser Tyr Leu Ile Phe Asn Thr Thr Leu Leu
1               5                   10

<210> SEQ ID NO 72
<211> LENGTH: 14
<212> TYPE: PRT
<213> ORGANISM: Homo sapiens -continued

```
<400> SEQUENCE: 72

Val Trp Arg Pro Glu Glu Gly Arg Arg Ser Leu Arg Pro Cys
1               5                   10

<210> SEQ ID NO 73
<211> LENGTH: 13
<212> TYPE: PRT
<213> ORGANISM: Homo sapiens

<400> SEQUENCE: 73

Leu Ile Arg Gln Arg Arg Gly Asp Val Trp His Ala Glu
1               5                   10

<210> SEQ ID NO 74
<211> LENGTH: 23
<212> TYPE: PRT
<213> ORGANISM: Homo sapiens

<400> SEQUENCE: 74

Ile Leu Ala Leu Leu Asp Leu Asn Ala Ser Gly Thr Met Ser Ile Gln
1               5                   10                  15

Glu Phe Arg Asp Leu Trp Lys
            20

<210> SEQ ID NO 75
<211> LENGTH: 22
<212> TYPE: PRT
<213> ORGANISM: Homo sapiens

<400> SEQUENCE: 75

Arg Leu Asp Leu Cys Gln Gly Ile Val Gly Asp Cys Trp Phe Leu Ala
1               5                   10                  15

Ala Leu Gln Ala Leu Ala
            20

<210> SEQ ID NO 76
<211> LENGTH: 13
<212> TYPE: PRT
<213> ORGANISM: Homo sapiens

<400> SEQUENCE: 76

Leu Ala Pro Arg Tyr Ser Arg Arg Ala Ser Pro Gln Gln
1               5                   10

<210> SEQ ID NO 77
<211> LENGTH: 13
<212> TYPE: PRT
<213> ORGANISM: Homo sapiens

<400> SEQUENCE: 77

Leu Asn Gln Ser Phe Thr Glu Lys Tyr Ala Gly Ile Phe
1               5                   10

<210> SEQ ID NO 78
<211> LENGTH: 13
<212> TYPE: PRT
<213> ORGANISM: Homo sapiens

<400> SEQUENCE: 78

Val Phe Val Ser Ser Thr Tyr Lys Asn Leu Phe Trp Gly
1               5                   10
```

```
<210> SEQ ID NO 79
<211> LENGTH: 13
<212> TYPE: PRT
<213> ORGANISM: Homo sapiens

<400> SEQUENCE: 79

Gly Ile Arg Lys Val Thr Cys Lys His Arg Pro Glu Tyr
1               5                   10

<210> SEQ ID NO 80
<211> LENGTH: 13
<212> TYPE: PRT
<213> ORGANISM: Homo sapiens

<400> SEQUENCE: 80

Asp Trp Ser Asp Ser Ser Lys Trp Glu Leu Leu Ser
1               5                   10

<210> SEQ ID NO 81
<211> LENGTH: 13
<212> TYPE: PRT
<213> ORGANISM: Homo sapiens

<400> SEQUENCE: 81

Lys Trp Glu Leu Leu Ser Pro Lys Glu Lys Ile Leu Leu
1               5                   10

<210> SEQ ID NO 82
<211> LENGTH: 13
<212> TYPE: PRT
<213> ORGANISM: Homo sapiens

<400> SEQUENCE: 82

Gln Lys Trp Thr Tyr Thr Met Arg Glu Gly Arg Trp Glu
1               5                   10

<210> SEQ ID NO 83
<211> LENGTH: 13
<212> TYPE: PRT
<213> ORGANISM: Homo sapiens

<400> SEQUENCE: 83

Glu Glu Gly Arg Arg Ser Leu Arg Pro Cys Ser Val Leu
1               5                   10

<210> SEQ ID NO 84
<211> LENGTH: 13
<212> TYPE: PRT
<213> ORGANISM: Homo sapiens

<400> SEQUENCE: 84

Val Leu Arg Val Phe Ser Arg Lys His Ile Phe Tyr Glu
1               5                   10

<210> SEQ ID NO 85
<211> LENGTH: 13
<212> TYPE: PRT
<213> ORGANISM: Homo sapiens

<400> SEQUENCE: 85

Lys Gln Leu Lys Leu Ser Gln Lys Val Phe His Lys Gln
1               5                   10

<210> SEQ ID NO 86
<211> LENGTH: 13
```

```
<212> TYPE: PRT
<213> ORGANISM: Homo sapiens

<400> SEQUENCE: 86

Leu Ile Arg Ser Val Thr Leu Lys Asp Val Asp Leu Gln
1               5                   10

<210> SEQ ID NO 87
<211> LENGTH: 14
<212> TYPE: PRT
<213> ORGANISM: Homo sapiens

<400> SEQUENCE: 87

Arg Val Val Pro Leu Asn Gln Ser Phe Thr Glu Lys Tyr Ala
1               5                   10

<210> SEQ ID NO 88
<211> LENGTH: 14
<212> TYPE: PRT
<213> ORGANISM: Homo sapiens

<400> SEQUENCE: 88

Val Trp Arg Pro Glu Glu Gly Arg Arg Ser Leu Arg Pro Cys
1               5                   10

<210> SEQ ID NO 89
<211> LENGTH: 13
<212> TYPE: PRT
<213> ORGANISM: Homo sapiens

<400> SEQUENCE: 89

Leu Ile Arg Gln Arg Arg Gly Asp Val Trp His Ala Glu
1               5                   10

<210> SEQ ID NO 90
<211> LENGTH: 23
<212> TYPE: PRT
<213> ORGANISM: Homo sapiens

<400> SEQUENCE: 90

Ile Leu Ala Leu Leu Asp Leu Asn Ala Ser Gly Thr Met Ser Ile Gln
1               5                   10                  15

Glu Phe Arg Asp Leu Trp Lys
                20

<210> SEQ ID NO 91
<211> LENGTH: 22
<212> TYPE: PRT
<213> ORGANISM: Homo sapiens

<400> SEQUENCE: 91

Arg Leu Asp Leu Cys Gln Gly Ile Val Gly Asp Cys Trp Phe Leu Ala
1               5                   10                  15

Ala Leu Gln Ala Leu Ala
                20

<210> SEQ ID NO 92
<211> LENGTH: 242
<212> TYPE: PRT
<213> ORGANISM: Homo sapiens

<400> SEQUENCE: 92

Arg Leu Asp Leu Cys Gln Gly Ile Val Gly Asp Cys Trp Phe Leu Ala
1               5                   10                  15
```

```
Ala Leu Gln Ala Leu Ala Leu His Gln Asp Ile Leu Ser Arg Val Val
            20                  25                  30

Pro Leu Asn Gln Ser Phe Thr Glu Lys Tyr Ala Gly Ile Phe Arg Phe
        35                  40                  45

Trp Phe Trp His Tyr Gly Asn Trp Val Pro Val Ile Asp Asp Arg
 50                  55                  60

Leu Pro Val Asn Glu Ala Gly Gln Leu Val Phe Ser Ser Thr Tyr
65                  70                  75                  80

Lys Asn Leu Phe Trp Gly Ala Leu Leu Glu Lys Ala Tyr Ala Lys Leu
                85                  90                  95

Ser Gly Ser Tyr Glu Asp Leu Gln Ser Gly Gln Val Ser Glu Ala Leu
            100                 105                 110

Val Asp Phe Thr Gly Gly Val Thr Met Thr Ile Asn Leu Ala Glu Ala
            115                 120                 125

His Gly Asn Leu Trp Asp Ile Leu Ile Glu Ala Thr Tyr Asn Arg Thr
130                 135                 140

Leu Ile Gly Cys Gln Thr His Ser Gly Glu Lys Ile Leu Glu Asn Gly
145                 150                 155                 160

Leu Val Glu Gly His Ala Tyr Thr Leu Thr Gly Ile Arg Lys Val Thr
                165                 170                 175

Cys Lys His Arg Pro Glu Tyr Leu Val Lys Leu Arg Asn Pro Trp Gly
            180                 185                 190

Lys Val Glu Trp Lys Gly Asp Trp Ser Asp Ser Ser Lys Trp Glu
            195                 200                 205

Leu Leu Ser Pro Lys Glu Lys Ile Leu Leu Arg Lys Asp Asn Asp
        210                 215                 220

Gly Glu Phe Trp Met Thr Leu Gln Asp Phe Lys Thr His Phe Val Leu
225                 230                 235                 240

Leu Val

<210> SEQ ID NO 93
<211> LENGTH: 242
<212> TYPE: PRT
<213> ORGANISM: Homo sapiens

<400> SEQUENCE: 93

Arg Leu Asp Leu Cys Gln Gly Ile Val Gly Asp Cys Trp Phe Leu Ala
1               5                   10                  15

Ala Leu Gln Ala Leu Ala Leu His Gln Asp Ile Leu Ser Arg Val Val
            20                  25                  30

Pro Leu Asn Gln Ser Phe Thr Glu Lys Tyr Ala Gly Ile Phe Arg Phe
        35                  40                  45

Trp Phe Trp His Tyr Gly Asn Trp Val Pro Val Ile Asp Asp Arg
 50                  55                  60

Leu Pro Val Asn Glu Ala Gly Gln Leu Val Phe Ser Ser Thr Tyr
65                  70                  75                  80

Lys Asn Leu Phe Trp Gly Ala Leu Leu Glu Lys Ala Tyr Ala Lys Leu
                85                  90                  95

Ser Gly Ser Tyr Glu Asp Leu Gln Ser Gly Gln Val Ser Glu Ala Leu
            100                 105                 110

Val Asp Phe Thr Gly Gly Val Thr Met Thr Ile Asn Leu Ala Glu Ala
            115                 120                 125

His Gly Asn Leu Trp Asp Ile Leu Ile Glu Ala Thr Tyr Asn Arg Thr
130                 135                 140
```

-continued

```
Leu Ile Gly Cys Gln Thr His Ser Gly Glu Lys Ile Leu Glu Asn Gly
145                 150                 155                 160

Leu Val Glu Gly His Ala Tyr Thr Leu Thr Gly Ile Arg Lys Val Thr
                165                 170                 175

Cys Lys His Arg Pro Glu Tyr Leu Val Lys Leu Arg Asn Pro Trp Gly
            180                 185                 190

Lys Val Glu Trp Lys Gly Asp Trp Ser Asp Ser Ser Lys Trp Glu
        195                 200                 205

Leu Leu Ser Pro Lys Glu Lys Ile Leu Leu Arg Lys Asp Asn Asp
    210                 215                 220

Gly Glu Phe Trp Met Thr Leu Gln Asp Phe Lys Thr His Phe Val Leu
225                 230                 235                 240

Leu Val
```

<210> SEQ ID NO 94
<211> LENGTH: 39
<212> TYPE: DNA
<213> ORGANISM: Homo sapiens

<400> SEQUENCE: 94
gcagcagcgg ccgcaggctg gatctgtgcc aggggatag                    39

<210> SEQ ID NO 95
<211> LENGTH: 31
<212> TYPE: DNA
<213> ORGANISM: Homo sapiens

<400> SEQUENCE: 95
gcagcagtcg actaacaagg tggtgttgaa g                            31

<210> SEQ ID NO 96
<211> LENGTH: 37
<212> TYPE: DNA
<213> ORGANISM: Homo sapiens

<400> SEQUENCE: 96
gcagcagcgg ccgcatgtct ctgtggccac ctttccg                      37

<210> SEQ ID NO 97
<211> LENGTH: 37
<212> TYPE: DNA
<213> ORGANISM: Homo sapiens

<400> SEQUENCE: 97
gcagcagtcg acccccctggc aggcttccag gctaaag                     37

<210> SEQ ID NO 98
<211> LENGTH: 39
<212> TYPE: DNA
<213> ORGANISM: Homo sapiens

<400> SEQUENCE: 98
gcagcagcgg ccgcaggctg gatctgtgcc aggggatag                    39

<210> SEQ ID NO 99
<211> LENGTH: 31
<212> TYPE: DNA
<213> ORGANISM: Homo sapiens

<400> SEQUENCE: 99
gcagcagtcg actaacaagg tggtgttgaa g    31

<210> SEQ ID NO 100
<211> LENGTH: 37
<212> TYPE: DNA
<213> ORGANISM: Homo sapiens

<400> SEQUENCE: 100
gcagcagcgg ccgcatgtct ctgtggccac ctttccg    37

<210> SEQ ID NO 101
<211> LENGTH: 37
<212> TYPE: DNA
<213> ORGANISM: Homo sapiens

<400> SEQUENCE: 101
gcagcagtcg accccctggc aggcttccag gctaaag    37

<210> SEQ ID NO 102
<211> LENGTH: 14
<212> TYPE: PRT
<213> ORGANISM: Homo sapiens

<400> SEQUENCE: 102

Ile Glu Ala Thr Tyr Asn Arg Thr Leu Ile Gly Cys Gln Thr
1               5                   10

<210> SEQ ID NO 103
<211> LENGTH: 14
<212> TYPE: PRT
<213> ORGANISM: Homo sapiens

<400> SEQUENCE: 103

Ala Leu Leu Asp Leu Asn Ala Ser Gly Thr Met Ser Ile Gln
1               5                   10

<210> SEQ ID NO 104
<211> LENGTH: 10
<212> TYPE: PRT
<213> ORGANISM: Homo sapiens

<400> SEQUENCE: 104

Ser Tyr Leu Ile Phe Asn Thr Thr Leu Leu
1               5                   10

<210> SEQ ID NO 105
<211> LENGTH: 23
<212> TYPE: DNA
<213> ORGANISM: Homo sapiens

<400> SEQUENCE: 105
caggtgcagc tggtgcagtc tgg    23

<210> SEQ ID NO 106
<211> LENGTH: 23
<212> TYPE: DNA
<213> ORGANISM: Homo sapiens

<400> SEQUENCE: 106
caggtcaact taagggagtc tgg    23

```
<210> SEQ ID NO 107
<211> LENGTH: 23
<212> TYPE: DNA
<213> ORGANISM: Homo sapiens

<400> SEQUENCE: 107
gaggtgcagc tggtggagtc tgg                                    23

<210> SEQ ID NO 108
<211> LENGTH: 23
<212> TYPE: DNA
<213> ORGANISM: Homo sapiens

<400> SEQUENCE: 108
caggtgcagc tgcaggagtc ggg                                    23

<210> SEQ ID NO 109
<211> LENGTH: 23
<212> TYPE: DNA
<213> ORGANISM: Homo sapiens

<400> SEQUENCE: 109
gaggtgcagc tgttgcagtc tgc                                    23

<210> SEQ ID NO 110
<211> LENGTH: 23
<212> TYPE: DNA
<213> ORGANISM: Homo sapiens

<400> SEQUENCE: 110
caggtacagc tgcagcagtc agg                                    23

<210> SEQ ID NO 111
<211> LENGTH: 24
<212> TYPE: DNA
<213> ORGANISM: Homo sapiens

<400> SEQUENCE: 111
tgaggagacg gtgaccaggg tgcc                                   24

<210> SEQ ID NO 112
<211> LENGTH: 24
<212> TYPE: DNA
<213> ORGANISM: Homo sapiens

<400> SEQUENCE: 112
tgaagagacg gtgaccattg tccc                                   24

<210> SEQ ID NO 113
<211> LENGTH: 24
<212> TYPE: DNA
<213> ORGANISM: Homo sapiens

<400> SEQUENCE: 113
tgaggagacg gtgaccaggg ttcc                                   24

<210> SEQ ID NO 114
<211> LENGTH: 24
<212> TYPE: DNA
<213> ORGANISM: Homo sapiens

<400> SEQUENCE: 114
tgaggagacg gtgaccgtgg tccc                                   24
```

```
<210> SEQ ID NO 115
<211> LENGTH: 23
<212> TYPE: DNA
<213> ORGANISM: Homo sapiens

<400> SEQUENCE: 115
gacatccaga tgacccagtc tcc                                           23

<210> SEQ ID NO 116
<211> LENGTH: 23
<212> TYPE: DNA
<213> ORGANISM: Homo sapiens

<400> SEQUENCE: 116
gatgttgtga tgactcagtc tcc                                           23

<210> SEQ ID NO 117
<211> LENGTH: 23
<212> TYPE: DNA
<213> ORGANISM: Homo sapiens

<400> SEQUENCE: 117
gatattgtga tgactcagtc tcc                                           23

<210> SEQ ID NO 118
<211> LENGTH: 23
<212> TYPE: DNA
<213> ORGANISM: Homo sapiens

<400> SEQUENCE: 118
gaaattgtgt tgacgcagtc tcc                                           23

<210> SEQ ID NO 119
<211> LENGTH: 23
<212> TYPE: DNA
<213> ORGANISM: Homo sapiens

<400> SEQUENCE: 119
gacatcgtga tgacccagtc tcc                                           23

<210> SEQ ID NO 120
<211> LENGTH: 23
<212> TYPE: DNA
<213> ORGANISM: Homo sapiens

<400> SEQUENCE: 120
gaaacgacac tcacgcagtc tcc                                           23

<210> SEQ ID NO 121
<211> LENGTH: 23
<212> TYPE: DNA
<213> ORGANISM: Homo sapiens

<400> SEQUENCE: 121
gaaattgtgc tgactcagtc tcc                                           23

<210> SEQ ID NO 122
<211> LENGTH: 23
<212> TYPE: DNA
<213> ORGANISM: Homo sapiens

<400> SEQUENCE: 122
cagtctgtgt tgacgcagcc gcc                                           23
```

```
<210> SEQ ID NO 123
<211> LENGTH: 23
<212> TYPE: DNA
<213> ORGANISM: Homo sapiens

<400> SEQUENCE: 123
cagtctgccc tgactcagcc tgc                                              23

<210> SEQ ID NO 124
<211> LENGTH: 23
<212> TYPE: DNA
<213> ORGANISM: Homo sapiens

<400> SEQUENCE: 124
tcctatgtgc tgactcagcc acc                                              23

<210> SEQ ID NO 125
<211> LENGTH: 23
<212> TYPE: DNA
<213> ORGANISM: Homo sapiens

<400> SEQUENCE: 125
tcttctgagc tgactcagga ccc                                              23

<210> SEQ ID NO 126
<211> LENGTH: 23
<212> TYPE: DNA
<213> ORGANISM: Homo sapiens

<400> SEQUENCE: 126
cacgttatac tgactcaacc gcc                                              23

<210> SEQ ID NO 127
<211> LENGTH: 23
<212> TYPE: DNA
<213> ORGANISM: Homo sapiens

<400> SEQUENCE: 127
caggctgtgc tcactcagcc gtc                                              23

<210> SEQ ID NO 128
<211> LENGTH: 23
<212> TYPE: DNA
<213> ORGANISM: Homo sapiens

<400> SEQUENCE: 128
aattttatgc tgactcagcc cca                                              23

<210> SEQ ID NO 129
<211> LENGTH: 24
<212> TYPE: DNA
<213> ORGANISM: Homo sapiens

<400> SEQUENCE: 129
acgtttgatt tccaccttgg tccc                                             24

<210> SEQ ID NO 130
<211> LENGTH: 24
<212> TYPE: DNA
<213> ORGANISM: Homo sapiens

<400> SEQUENCE: 130
acgtttgatc tccagcttgg tccc                                             24
```

```
<210> SEQ ID NO 131
<211> LENGTH: 24
<212> TYPE: DNA
<213> ORGANISM: Homo sapiens

<400> SEQUENCE: 131
acgtttgata tccactttgg tccc                                          24

<210> SEQ ID NO 132
<211> LENGTH: 24
<212> TYPE: DNA
<213> ORGANISM: Homo sapiens

<400> SEQUENCE: 132
acgtttgatc tccaccttgg tccc                                          24

<210> SEQ ID NO 133
<211> LENGTH: 24
<212> TYPE: DNA
<213> ORGANISM: Homo sapiens

<400> SEQUENCE: 133
acgtttaatc tccagtcgtg tccc                                          24

<210> SEQ ID NO 134
<211> LENGTH: 23
<212> TYPE: DNA
<213> ORGANISM: Homo sapiens

<400> SEQUENCE: 134
cagtctgtgt tgacgcagcc gcc                                           23

<210> SEQ ID NO 135
<211> LENGTH: 23
<212> TYPE: DNA
<213> ORGANISM: Homo sapiens

<400> SEQUENCE: 135
cagtctgccc tgactcagcc tgc                                           23

<210> SEQ ID NO 136
<211> LENGTH: 23
<212> TYPE: DNA
<213> ORGANISM: Homo sapiens

<400> SEQUENCE: 136
tcctatgtgc tgactcagcc acc                                           23

<210> SEQ ID NO 137
<211> LENGTH: 23
<212> TYPE: DNA
<213> ORGANISM: Homo sapiens

<400> SEQUENCE: 137
tcttctgagc tgactcagga ccc                                           23

<210> SEQ ID NO 138
<211> LENGTH: 23
<212> TYPE: DNA
<213> ORGANISM: Homo sapiens
```

-continued

```
<400> SEQUENCE: 138
cacgttatac tgactcaacc gcc                                              23

<210> SEQ ID NO 139
<211> LENGTH: 23
<212> TYPE: DNA
<213> ORGANISM: Homo sapiens

<400> SEQUENCE: 139
caggctgtgc tcactcagcc gtc                                              23

<210> SEQ ID NO 140
<211> LENGTH: 23
<212> TYPE: DNA
<213> ORGANISM: Homo sapiens

<400> SEQUENCE: 140
aattttatgc tgactcagcc cca                                              23

<210> SEQ ID NO 141
<211> LENGTH: 10
<212> TYPE: PRT
<213> ORGANISM: Homo sapiens

<400> SEQUENCE: 141

Ala Leu Leu Glu Lys Ala Tyr Ala Lys Leu
 1               5                  10

<210> SEQ ID NO 142
<211> LENGTH: 15
<212> TYPE: PRT
<213> ORGANISM: Homo sapiens

<400> SEQUENCE: 142

Ala Leu Leu Glu Lys Ala Tyr Ala Lys Leu Ser Gly Ser Tyr Glu
 1               5                  10                  15

<210> SEQ ID NO 143
<211> LENGTH: 19
<212> TYPE: DNA
<213> ORGANISM: Homo sapiens

<400> SEQUENCE: 143
tcgtgccctg catattgga                                                   19

<210> SEQ ID NO 144
<211> LENGTH: 24
<212> TYPE: DNA
<213> ORGANISM: Homo sapiens

<400> SEQUENCE: 144
aaaagatgtg cttcctggag aaga                                             24

<210> SEQ ID NO 145
<211> LENGTH: 28
<212> TYPE: DNA
<213> ORGANISM: Homo sapiens

<400> SEQUENCE: 145
cccaccagaa gtcagagttc gtcctcag                                         28
```

The invetion claimed is:

1. An isolated nucleic acid molecule comprising a polynucleotide sequence selected from the group consisting of:
   (a) an isolated polynucleotide encoding a polypeptide comprising amino acids 1 to 697 of SEQ ID NO:56; and
   (b) an isolated polynucleotide encoding a polypeptide comprising amino acids 2 to 697 of SEQ ID NO:56.

2. The isolated nucleic acid molecule of claim 1, wherein said polynucleotide is (a).

3. The isolated nucleic acid molecule of claim 2, wherein said polynucleotide comprises nucleotides 9 to 2099 of SEQ ID NO:55.

4. The isolated nucleic acid molecule of claim 1, wherein said polynucleotide is (b).

5. The isolated nucleic acid molecule of claim 4, wherein said polynucleotide comprises nucleotides 12 to 2099 of SEQ ID NO:55.

6. An isolated nucleic acid molecule comprising a polynucleotide sequence selected from the group consisting of:
   (a) an isolated polynucleotide encoding a polypeptide comprising amino acids 1 to 694 of SEQ ID NO:54; and
   (b) an isolated polynucleotide encoding a polypeptide comprising amino acids 2 to 694 of SEQ ID NO:54.

7. The isolated nucleic acid molecule of claim 6, wherein said polynucleotide is (a).

8. The isolated nucleic acid molecule of claim 7, wherein said polynucleotide comprises nucleotides 9 to 2090 of SEQ ID NO:53.

9. The isolated nucleic acid molecule of claim 6, wherein said polynucleotide is (b).

10. The isolated nucleic acid molecule of claim 9, wherein said polynucleotide comprises nucleotides 12 to 2090 of SEQ ID NO:53.

11. An isolated nucleic acid molecule comprising a polynucleotide encoding a polypeptide comprising the sequence of amino acids from position 1 through position 587 of SEQ ID NO:56, wherein said polypeptide has calcium-dependent cysteine protease activity.

12. The isolated nucleic acid molecule of claim 11, wherein said polynucleotide comprises the sequence of nucleotides from position 9 through position 1769 of SEQ ID NO:55.

13. An isolated nucleic acid comprising a polynucleotide encoding a polypeptide comprising the sequence of amino acids from position 1 through position 584 of SEQ ID NO:54, wherein said polypeptide has calcium-dependent cysteine protease activity.

14. The isolated nucleic acid molecule of claim 13, wherein said polynucleotide comprises the sequence of nucleotides from position 9 through position 1760 of SEQ ID NO:53.

15. An isolated nucleic acid comprising a polynucleotide encoding the CAN-12v1 polypeptide or the CAN-12v2 polypeptide as encoded by a cDNA clone contained in ATCC Deposit No: PTA-3434.

16. A recombinant vector comprising the isolated nucleic acid molecule of claim 1.

17. An isolated recombinant host cell comprising the vector of claim 16.

18. A method of making an isolated polypeptide comprising:
   (a) culturing the recombinant host cell of claim 17 under conditions such that said polypeptide is expressed; and
   (b) recovering said polypeptide.

* * * * *

UNITED STATES PATENT AND TRADEMARK OFFICE
CERTIFICATE OF CORRECTION

PATENT NO. : 7,186,564 B2
APPLICATION NO. : 10/116519
DATED : March 6, 2007
INVENTOR(S) : Jian Chen et al.

It is certified that error appears in the above-identified patent and that said Letters Patent is hereby corrected as shown below:

Column 17, Line 13
 Add description for Figure 7 which should read:
 --Figure 7 provides the nucleotide sequences of the predicted CAN-12 exons (SEQ ID NO:13, 14, 15, 16, 17, and 26) based upon the genomic sequence from bac AC015980.--

Column 28, line 28
 Substitute "gene." with --gene,--

Column 64, line 23
 Replace "6" with --12--

Column 64, line 32
 Replace "andior" with --and/or--

Column 64, line 22, 24, 26, 28 and 30
 After "CAN-12" add --v1 and CAN-12v2--

Column 64, line 22 through 37 should now read:
 --Expanded analysis of CAN-12v1 and CAN-12v2 expression levels by TAQMAN$^{TM}$ quantitative PCR (see Figure 12) confirmed that the CAN-12v1 and CAN-12v2 polypeptide is expressed in the lymph gland. However, the TAQMAN$^{TM}$ quantitative PCR determined that the CAN-12v1 and CAN-12v2 polypeptides are primarily expressed in the esophagus. In fact, with the exception of the lymph gland, the steady state mRNA level of CAN-12v1 and CAN-12v2 was approximately 2700 times higher in the esophagus than in all other tissues tested. These data suggest modulators of the CAN-12v1 and CAN-12v2 polynucleotides and polypeptides may be useful for the treatment, detection, and/or amelioration of the following, non-limiting diseases and disorders associated with the esophagus: dysphagia, cricoharyngeal incoordination, esophageal carcinoma, esophageal webs, achalasia, symptomatic diffuse esophageal spasm, gastroesophageal reflux, and/or corrosive esophagitis.--

Column 101, line 8
 Substitute "gene." with --gene,--

Column 253, line 22
 Substitute "AMPLITAQ GOLDu" with --AMPLITAQ GOLD$^{TM}$--

Column 255, line 15 and 16
 Append "calpain" after "CAN-12."

UNITED STATES PATENT AND TRADEMARK OFFICE
CERTIFICATE OF CORRECTION

PATENT NO.       : 7,186,564 B2
APPLICATION NO.  : 10/116519
DATED            : March 6, 2007
INVENTOR(S)      : Jian Chen et al.

It is certified that error appears in the above-identified patent and that said Letters Patent is hereby corrected as shown below:

Column 427 and 428 - Sequence Listing
    <160> substitute "145" with --150--
    <160> should now read --NUMBER OF SEQ ID NOS: 150--

Column 533, Following
    <400> SEQUENCE: 145
    cccaccagaa gtcagagttc gtcctcag Add in its entirety:

--
<210> 146
<211> 4
<212> PRT
<213> Artificial

<220>
<223> Amidation Consensus Sequence.

<220>
<221> misc_feature
<222> (1)..(1)
<223> Xaa can be any naturally occurring amino acid <220>
<221> MISC_FEATURE
<222> (3)..(4)
<223> wherein "x" equals either "R" or "K".

<400> 146

Xaa Gly Xaa Xaa
1

<210> 147
<211> 13
<212> PRT
<213> Artificial

<220>
<223> EF hand calcium binding consensus sequence.

UNITED STATES PATENT AND TRADEMARK OFFICE
CERTIFICATE OF CORRECTION

PATENT NO.       : 7,186,564 B2
APPLICATION NO.  : 10/116519
DATED            : March 6, 2007
INVENTOR(S)      : Jian Chen et al.

It is certified that error appears in the above-identified patent and that said Letters Patent is hereby corrected as shown below:

<220>
<221> misc_feature
<222> (2)..(2)
<223> Xaa can be any naturally occurring amino acid <220>
<221> MISC_FEATURE
<222> (3)..(3)
<223> wherein "x" equals either D, N, or S.

<220>
<221> MISC_FEATURE
<222> (4)..(4)
<223> wherein "x" equals any naturally occuring amino acid except I, L, V, F, Y, or W.

<220>
<221> MISC_FEATURE
<222> (5)..(5)
<223> wherein "x" equals either D, E, N, S, T, or G.

<220>
<221> MISC_FEATURE
<222> (6)..(6)
<223> wherein "x" equals either D, N, Q, G, H, R, or K.

<220>
<221> MISC_FEATURE
<222> (7)..(7)
<223> wherein "x" equals any naturally occuring amino acid except G, or P.

<220>
<221> MISC_FEATURE
<222> (8)..(8)
<223> wherein "x" equals either L, I, V, M, or C.

<220>
<221> MISC_FEATURE
<222> (9)..(9)
<223> wherein "x" equals either D, E, N, Q, S, T, A, G, or C.

UNITED STATES PATENT AND TRADEMARK OFFICE
CERTIFICATE OF CORRECTION

PATENT NO. : 7,186,564 B2
APPLICATION NO. : 10/116519
DATED : March 6, 2007
INVENTOR(S) : Jian Chen et al.

It is certified that error appears in the above-identified patent and that said Letters Patent is hereby corrected as shown below:

<220>
<221> misc_feature
<222> (10)..(11)
<223> Xaa can be any naturally occurring amino acid <220>
<221> MISC_FEATURE
<222> (12)..(12)
<223> wherein "x" equals either D or E.

<220>
<221> MISC_FEATURE
<222> (13)..(13)
<223> wherein "x" equals either L, I, V, M, F, Y, or W.

<400> 147

Asp Xaa Xaa Xaa Xaa Xaa Xaa Xaa Xaa Xaa Xaa Xaa Xaa
1               5                   10

<210> 148
<211> 12
<212> PRT
<213> Artificial

<220>
<223> Eukaryotic thiol (cysteine) protease active site consensus
      sequence.

<220>
<221> misc_feature
<222> (2)..(4)
<223> Xaa can be any naturally occurring amino acid <220>
<221> MISC_FEATURE
<222> (5)..(5)
<223> where "x" is either G or E.

UNITED STATES PATENT AND TRADEMARK OFFICE
CERTIFICATE OF CORRECTION

PATENT NO. : 7,186,564 B2
APPLICATION NO. : 10/116519
DATED : March 6, 2007
INVENTOR(S) : Jian Chen et al.

It is certified that error appears in the above-identified patent and that said Letters Patent is hereby corrected as shown below:

<220>
<221> misc_feature
<222> (6)..(6)
<223> Xaa can be any naturally occurring amino acid <220>
<221> MISC_FEATURE
<222> (8)..(8)
<223> where "x" is either Y or W.

<220>
<221> misc_feature
<222> (9)..(10)
<223> Xaa can be any naturally occurring amino acid <220>
<221> MISC_FEATURE
<222> (11)..(11)
<223> where "x" is either S, T, A, G, or C.

<220>
<221> MISC_FEATURE
<222> (12)..(12)
<223> where "x" is either S, T, A, G, C, or V.

<400> 148

Gin Xaa Xaa Xaa Xaa Cys Xaa Xaa Xaa Xaa Xaa
1               5                   10

<210> 149
<211> 11
<212> PRT
<213> Artificial

<220>
<223> Alternative eukaryotic thiol (cysteine) protease active site consensus sequence.

UNITED STATES PATENT AND TRADEMARK OFFICE
CERTIFICATE OF CORRECTION

| | |
|---|---|
| PATENT NO. | : 7,186,564 B2 |
| APPLICATION NO. | : 10/116519 |
| DATED | : March 6, 2007 |
| INVENTOR(S) | : Jian Chen et al. |

It is certified that error appears in the above-identified patent and that said Letters Patent is hereby corrected as shown below:

```
<220>
<221> MISC_FEATURE
<222> (1)..(1)
<223> wherein "x" equals either L, I, V, M, G, S, T, A, or N.

<220>
<221> misc_feature
<222> (2)..(2)
<223> Xaa can be any naturally occurring amino acid <220>
<221> MISC_FEATURE
<222> (4)..(4)
<223> wherein "x" equals either G, S, A, C, or E.

<220>
<221> MISC_FEATURE
<222> (5)..(5)
<223> wherein "x" equals either L, I, V, or M.

<220>
<221> misc_feature
<222> (6)..(6)
<223> Xaa can be any naturally occurring amino acid <220>
<221> MISC_FEATURE
<222> (7)..(8)
<223> wherein "x" equals either L, I, V, M, A, or T.

<220>
<221> misc_feature
<222> (10)..(10)
<223> Xaa can be any naturally occurring amino acid <220>
<221> MISC_FEATURE
<222> (11)..(11)
<223> wherein "x" equals either G, S, A, D, N, or H.
```

UNITED STATES PATENT AND TRADEMARK OFFICE
CERTIFICATE OF CORRECTION

PATENT NO. : 7,186,564 B2
APPLICATION NO. : 10/116519
DATED : March 6, 2007
INVENTOR(S) : Jian Chen et al.

It is certified that error appears in the above-identified patent and that said Letters Patent is hereby corrected as shown below:

<400> 149

Xaa Xaa His Xaa Xaa Xaa Xaa Xaa Gly Xaa Xaa
1               5                   10

<210> 150
<211> 20
<212> PRT
<213> Artificial

<220>
<223> Alternative eukaryotic thiol (cysteine) protease active site
      consensus sequence.

<220>
<221> MISC_FEATURE
<222> (1)..(1)
<223> wherein "x" equals either F, Y, C, or H.

<220>
<221> MISC_FEATURE
<222> (2)..(2)
<223> wherein "x" equals either W or I.

<220>
<221> MISC_FEATURE
<222> (3)..(3)
<223> wherein "x" equals either L, I, V, or T.

<220>
<221> misc_feature
<222> (4)..(4)
<223> Xaa can be any naturally occurring amino acid <220>
<221> MISC_FEATURE
<222> (5)..(5)
<223> wherein "x" equals either K, R, Q, A, or G.

UNITED STATES PATENT AND TRADEMARK OFFICE
CERTIFICATE OF CORRECTION

PATENT NO.      : 7,186,564 B2
APPLICATION NO. : 10/116519
DATED           : March 6, 2007
INVENTOR(S)     : Jian Chen et al.

It is certified that error appears in the above-identified patent and that said Letters Patent is hereby corrected as shown below:

<220>
    <221> MISC_FEATURE
    <222> (7)..(7)
    <223> wherein "x" equals either S or T.

<220>
    <221> misc_feature
    <222> (9)..(11)
    <223> Xaa can be any naturally occurring amino acid <220>
    <221> MISC_FEATURE
    <222> (12)..(12)
    <223> wherein "x" equals either F, Y, or W.

<220>
    <221> misc_feature
    <222> (14)..(15)
    <223> Xaa can be any naturally occurring amino acid <220>
    <221> MISC_FEATURE
    <222> (17)..(17)
    <223> wherein "x" equals either L, F, Y, or W.

<220>
    <221> MISC_FEATURE
    <222> (18)..(18)
    <223> wherein "x" equals either L, I, V, M, F, Y, or G.

<220>
    <221> misc_feature
    <222> (19)..(19)
    <223> Xaa can be any naturally occurring amino acid <220>
    <221> MISC_FEATURE
    <222> (20)..(20)
    <223> wherein "x" equals either L, I, V, M, or F.

UNITED STATES PATENT AND TRADEMARK OFFICE
CERTIFICATE OF CORRECTION

PATENT NO. : 7,186,564 B2
APPLICATION NO. : 10/116519
DATED : March 6, 2007
INVENTOR(S) : Jian Chen et al.

It is certified that error appears in the above-identified patent and that said Letters Patent is hereby corrected as shown below:

<400> 150

Xaa Xaa Xaa Xaa Xaa Asn Xaa Trp Xaa Xaa Xaa Xaa Gly Xaa Xaa Gly
1               5                   10                  15

Xaa Xaa Xaa Xaa
        20 --

Signed and Sealed this

Tenth Day of July, 2007

JON W. DUDAS
*Director of the United States Patent and Trademark Office*